US010647698B2

(12) United States Patent
Crew et al.

(10) Patent No.: US 10,647,698 B2
(45) Date of Patent: May 12, 2020

(54) TETRAHYDRONAPHTHALENE AND TETRAHYDROISOQUINOLINE DERIVATIVES AS ESTROGEN RECEPTOR DEGRADERS

(71) Applicant: Arvinas, Inc., New Haven, CT (US)

(72) Inventors: Andrew P. Crew, Guilford, CT (US);
Yimin Qian, Plainsboro, NJ (US);
Hanqing Dong, Madison, CT (US);
Jing Wang, Milford, CT (US)

(73) Assignee: Arvinas Operations, Inc., New Haven, CT (US)

( * ) Notice: Subject to any disclaimer, the term of this patent is extended or adjusted under 35 U.S.C. 154(b) by 60 days.

(21) Appl. No.: 15/829,541

(22) Filed: Dec. 1, 2017

(65) Prior Publication Data
US 2018/0155322 A1 Jun. 7, 2018

Related U.S. Application Data

(60) Provisional application No. 62/540,049, filed on Aug. 1, 2017, provisional application No. 62/429,041, filed on Dec. 1, 2016.

(51) Int. Cl.
| | | |
|---|---|---|
| *C07D 401/14* | (2006.01) |
| *A61K 47/54* | (2017.01) |
| *A61P 15/00* | (2006.01) |
| *A61P 35/00* | (2006.01) |
| *A61K 31/454* | (2006.01) |
| *A61K 31/4545* | (2006.01) |
| *A61K 31/4725* | (2006.01) |
| *A61K 31/496* | (2006.01) |
| *A61K 31/497* | (2006.01) |
| *A61K 31/501* | (2006.01) |
| *A61K 31/519* | (2006.01) |
| *A61K 31/5386* | (2006.01) |
| *A61K 31/551* | (2006.01) |
| *A61K 38/05* | (2006.01) |
| *A61K 38/06* | (2006.01) |
| *A61K 45/06* | (2006.01) |
| *C07D 401/04* | (2006.01) |
| *C07D 471/04* | (2006.01) |
| *C07D 471/10* | (2006.01) |
| *C07D 487/04* | (2006.01) |
| *C07D 487/08* | (2006.01) |
| *C07D 487/10* | (2006.01) |
| *C07D 498/10* | (2006.01) |
| *C07K 5/078* | (2006.01) |

(Continued)

(52) U.S. Cl.
CPC .......... *C07D 401/14* (2013.01); *A61K 31/454* (2013.01); *A61K 31/4545* (2013.01); *A61K 31/4725* (2013.01); *A61K 31/496* (2013.01); *A61K 31/497* (2013.01); *A61K 31/501* (2013.01); *A61K 31/519* (2013.01); *A61K 31/5386* (2013.01); *A61K 31/551* (2013.01); *A61K 38/05* (2013.01); *A61K 38/06* (2013.01); *A61K 45/06* (2013.01); *A61K 47/54* (2017.08); *A61K 47/545* (2017.08); *A61P 15/00* (2018.01); *A61P 35/00* (2018.01); *C07D 401/04* (2013.01); *C07D 471/04* (2013.01); *C07D 471/10* (2013.01); *C07D 487/04* (2013.01); *C07D 487/08* (2013.01); *C07D 487/10* (2013.01); *C07D 498/10* (2013.01); *C07K 5/06165* (2013.01); *C07K 5/0806* (2013.01); *C07K 5/06034* (2013.01)

(58) Field of Classification Search
CPC .................................................. C07D 401/14
See application file for complete search history.

(56) References Cited

U.S. PATENT DOCUMENTS 5,492,922 A    2/1996  Palkowitz et al.
5,681,835 A   10/1997  Willson
             (Continued)

FOREIGN PATENT DOCUMENTS

CN    1844118 A    10/2006
CN   102477033      5/2012
             (Continued)

OTHER PUBLICATIONS

Abraham, R.T., "Phosphatidylinositol 3-kinase related kinases", (1996), Current Opinion in Immunology. 8 (3) 412-418.
(Continued)

*Primary Examiner* — Matthew P Coughlin
(74) *Attorney, Agent, or Firm* — Cooley LLP; Ivor R. Elrifi; Thomas J. Paxton

(57) ABSTRACT

The present disclosure relates to bifunctional compounds, which find utility as modulators of estrogen receptor (target protein). In particular, the present disclosure is directed to bifunctional compounds, which contain on one end at least one of a Von Hippel-Lindau ligand, a cereblon ligand, Inhibitors of Apoptosis Proteins ligand, mouse double-minute homolog 2 ligand, or a combination thereof, which binds to the respective E3 ubiquitin ligase, and on the other end a moiety which binds the target protein, such that the target protein is placed in proximity to the ubiquitin ligase to effect degradation (and inhibition) of target protein. The present disclosure exhibits a broad range of pharmacological activities associated with degradation/inhibition of target protein. Diseases or disorders that result from aggregation or accumulation of the target protein are treated or prevented with compounds and compositions of the present disclosure.

6 Claims, 249 Drawing Sheets

(51) Int. Cl.
*C07K 5/083* (2006.01)
*C07K 5/062* (2006.01)

(56) References Cited

U.S. PATENT DOCUMENTS

| | | | |
|---|---|---|---|
| 5,877,219 | A | 3/1999 | Willson |
| 6,207,716 | B1 | 3/2001 | Willson |
| 6,306,663 | B1 | 10/2001 | Kenten et al. |
| 6,670,348 | B1 | 12/2003 | Rosen et al. |
| 7,030,141 | B2 | 4/2006 | Bigge et al. |
| 7,041,298 | B2 | 5/2006 | Deshaies et al. |
| 7,208,157 | B2 | 4/2007 | Sakamoto et al. |
| 7,244,851 | B2 | 7/2007 | Cohen et al. |
| 7,345,081 | B2 | 3/2008 | Cohen et al. |
| 7,419,975 | B2 | 9/2008 | Palermo et al. |
| 7,517,906 | B2 | 4/2009 | Condon et al. |
| 7,915,293 | B2 | 3/2011 | Ramesh |
| 9,500,653 | B2 | 11/2016 | Crews et al. |
| 9,632,089 | B2 | 4/2017 | Crews et al. |
| 2006/0128632 | A1 | 6/2006 | Sharma et al. |
| 2008/0051432 | A1 | 2/2008 | Zhang |
| 2008/0214501 | A1 | 9/2008 | Pan et al. |
| 2008/0269140 | A1 | 10/2008 | Wang et al. |
| 2010/0203012 | A1 | 8/2010 | Laurent et al. |
| 2011/0195043 | A1 | 8/2011 | Sun et al. |
| 2011/0230457 | A1* | 9/2011 | Berghausen .......... C07D 217/24 514/210.02 |
| 2012/0270800 | A1 | 10/2012 | Verdine et al. |
| 2014/0235629 | A1 | 8/2014 | Bartberger et al. |
| 2014/0243372 | A1 | 8/2014 | Rew |
| 2014/0302523 | A1 | 10/2014 | Crews et al. |
| 2014/0356322 | A1 | 12/2014 | Crews et al. |
| 2015/0119435 | A1 | 4/2015 | Crews et al. |
| 2015/0291562 | A1* | 10/2015 | Crew .................. C07D 401/14 424/94.3 |
| 2015/0344473 | A1 | 10/2015 | Du et al. |
| 2016/0022642 | A1 | 1/2016 | Crews et al. |
| 2016/0045607 | A1 | 2/2016 | Crew et al. |
| 2016/0058872 | A1 | 3/2016 | Crew et al. |
| 2016/0136230 | A1 | 5/2016 | Campos et al. |
| 2016/0214972 | A1 | 7/2016 | Jin et al. |
| 2016/0243247 | A1 | 8/2016 | Bradner et al. |
| 2016/0272639 | A1 | 9/2016 | Crew et al. |
| 2016/0368911 | A1 | 12/2016 | Campos et al. |
| 2017/0008904 | A1 | 1/2017 | Crew et al. |
| 2017/0037004 | A1 | 2/2017 | Crew et al. |
| 2017/0065719 | A1 | 3/2017 | Qian et al. |
| 2017/0121321 | A1 | 5/2017 | Crews et al. |
| 2017/0281784 | A1 | 10/2017 | Wang et al. |
| 2017/0307614 | A1 | 10/2017 | Crews et al. |
| 2017/0327469 | A1 | 11/2017 | Crew et al. |
| 2018/0015087 | A1 | 1/2018 | Liu et al. |
| 2018/0072711 | A1 | 3/2018 | Crew et al. |
| 2018/0099940 | A1 | 4/2018 | Crew et al. |
| 2018/0125821 | A1 | 5/2018 | Crew et al. |
| 2018/0147202 | A1 | 5/2018 | Crew et al. |
| 2018/0155322 | A1 | 6/2018 | Crew et al. |
| 2018/0177750 | A1 | 6/2018 | Crew et al. |
| 2018/0179183 | A1 | 6/2018 | Crew et al. |
| 2018/0193470 | A1 | 7/2018 | Crew et al. |
| 2018/0215731 | A1 | 8/2018 | Crew et al. |
| 2018/0228907 | A1 | 8/2018 | Crew et al. |
| 2018/0237418 | A1 | 8/2018 | Crew et al. |
| 2018/0256586 | A1 | 9/2018 | Crew et al. |

FOREIGN PATENT DOCUMENTS

| | | |
|---|---|---|
| CN | 103688176 A | 3/2014 |
| EP | 2985285 | 2/2016 |
| JP | A 2004-525889 | 8/2004 |
| JP | A 2010-502627 | 1/2010 |
| RU | 2008112221 A | 10/2009 |
| RU | 2448101 C2 | 4/2012 |
| RU | 2011121567 A | 10/2012 |
| RU | 2012138709 A | 3/2014 |
| WO | WO 1998/003502 | 1/1998 |
| WO | WO 1998/045287 | 10/1998 |
| WO | WO 1999/015521 | 4/1999 |
| WO | WO 2000/066119 | 11/2000 |
| WO | WO 2002/066512 | 8/2002 |
| WO | WO 2002/100845 | 12/2002 |
| WO | WO 2005/097791 | 10/2005 |
| WO | WO 2006/069063 | 6/2006 |
| WO | WO 2006/113942 | 10/2006 |
| WO | WO 2007/101347 | 9/2007 |
| WO | WO 2007/106670 | 9/2007 |
| WO | WO 2007/130626 | 11/2007 |
| WO | WO 2008/011392 | 1/2008 |
| WO | WO 2008/014236 | 1/2008 |
| WO | WO 2008/109057 | 9/2008 |
| WO | WO 2008/128121 | 10/2008 |
| WO | WO 2008/128171 | 10/2008 |
| WO | WO 2008/134679 | 11/2008 |
| WO | WO 2009/015254 | 1/2009 |
| WO | WO 2009/060292 | 5/2009 |
| WO | WO 2010/107485 | 9/2010 |
| WO | WO 2010/141805 | 12/2010 |
| WO | WO 2011/008260 | 1/2011 |
| WO | WO 2012/003281 | 1/2012 |
| WO | WO 2012/040527 | 3/2012 |
| WO | WO 2012/078559 | 6/2012 |
| WO | WO 2012/090104 | 7/2012 |
| WO | WO 2013/071035 | 5/2013 |
| WO | WO 2013/071039 | 5/2013 |
| WO | WO 2013/106643 | 7/2013 |
| WO | WO 2013/106646 | 7/2013 |
| WO | WO 2013/170147 | 11/2013 |
| WO | WO 2013/175417 | 11/2013 |
| WO | WO 2013/178570 | 12/2013 |
| WO | WO 2014/011712 | 1/2014 |
| WO | WO 2014/020502 | 2/2014 |
| WO | WO 2014/025759 | 2/2014 |
| WO | WO 2014/038606 | 3/2014 |
| WO | WO 2014/047024 | 3/2014 |
| WO | WO 2014/055461 | 4/2014 |
| WO | WO 2014/074658 | 5/2014 |
| WO | WO 2014/100065 | 6/2014 |
| WO | WO 2014/100071 | 6/2014 |
| WO | WO 2014/107713 | 7/2014 |
| WO | WO 2014/108452 | 7/2014 |
| WO | WO 2014/123418 | 8/2014 |
| WO | WO 2014/134201 | 9/2014 |
| WO | WO 2014/151863 | 9/2014 |
| WO | WO 2015/000867 | 1/2015 |
| WO | WO 2015/000868 | 1/2015 |
| WO | WO 2015/006524 | 1/2015 |
| WO | WO 2015/160845 | 10/2015 |
| WO | WO 2016/105518 | 6/2016 |
| WO | WO 2016/118666 | 7/2016 |
| WO | WO 2016/146985 | 9/2016 |
| WO | WO 2016/169989 | 10/2016 |
| WO | WO 2016/172134 | 10/2016 |
| WO | WO 2016/197114 | 12/2016 |
| WO | WO 2017/011590 | 1/2017 |
| WO | WO 2017/024318 A1 | 2/2017 |
| WO | WO 2017/024319 A1 | 2/2017 |
| WO | WO 2017/030814 | 2/2017 |
| WO | WO 2017/046036 | 3/2017 |
| WO | WO 2017/079267 | 5/2017 |
| WO | WO 2017/161119 | 9/2017 |
| WO | WO 2017/185036 | 10/2017 |
| WO | WO 2017/197051 | 11/2017 |

OTHER PUBLICATIONS

Ahn, et al., "HIF-1alpha peptide derivatives with modifications at the hydroxyproline residue as activators of HIF-1alpha", Bioorg Med Chem Lett. 19(15), 2009, 4403-4405.

Ali, S. et al. Molecular mechanisms and mode of tamoxifen resistance in breast cancer. Bioinformation 12, 135-139 (2016).

Ardecky, RJ, et al., "Design, synthesis and evaluation of inhibitor of apoptosis protein (IAP) antagonists that are highly selective for the

(56) References Cited

OTHER PUBLICATIONS

BIR2 domain of XIAP", Bioorg. Med. Chem., 23(14): 4253-4257 (2013).
Asano M, et al., "Design, sterioselective synthesis, and biological evaluation of novel tri-cyclic compounds as inhibitor of apoptosis proteins (IAP) antagonists", Bioorg. Med. Chem., 21(18): 5725-5737 (2013).
Bargagna-Mohan, et al., "Use of PROTACS as molecular probes of angiogenesis", Bioorg Med Chem Lett. 15(11) 2005, 2724-2727.
Battista, M. J. & Schmidt, M. Fulvestrant for the treatment of endometrial cancer. Expert Opin Investig Drugs 25, 475-483 (2016).
Bondeson, et al., (2017) "Targeted Protein Degradation by Small Molecules." *Annu Rev Pharmacol Toxicol* 57:107-123.
Bondeson, et al., "Catalytic in vivo protein knockdown by small-molecule PROTACS", National Chem Biol. 11(8) Aug. 2015, 611-617.
Buckley, et al., "HaloPROTACS: use of small molecule PROTACS to induce degradation of HaloTag fusion proteins", ACS Chem Biol. 10(8), 2015, 1831-1837.
Buckley, et al., "Small-molecule inhibitors of the interaction between the E3 ligase VHL and HIF1a", Angew Chem Int Ed Engl.51(46), Nov. 12, 2012, 11463-11467.
Buckley, et al., "Targeting the von Hippel-Lindau E3 ubiquitin ligase using small molecules to disrupt the VHL/HIF-1α interaction", Journal of the American Chemical Society, Feb. 27, 2012, 134(10): 4465-4468.
Burke, et al., "Design, Synthesis and Biological Evaluation of Doxorubicin-Formaldehyde Conjugates Targeted to Breast Cancer Cells", Journal of Medicinal Chemistry, Jan. 24, 2004, vol. 47, No. 5, pp. 1193-1206.
Burslem, et al., (2017) "Small-Molecule Modulation of Protein Homeostasis." *Chem Rev* 117(17):11269-11301.
Capitosti, S., et al., "Thalidomide analogues demonstrate dual inhibition of both angiogenesis and prostate cancer", Bioorganic & Medicinal Chemistry 12, (2004) 327-336.
Carmony, KC, et al., "PROTAC-Induced Proteolytic Targeting", Methods Mol. Biol., 2012, vol. 832, pp. 627-638.
CAS Registry No. 1004933-70-3, which entered STN on Feb. 21, 2008.
CAS Registry No. 871986-52-6 entered STN Jan. 16, 2006.
Chene, P., et al., "Inhibiting the p53-MDM2 interaction: an important target for cancer therapy" Nat. Rev. Cancer (2003), 3, 102-109.
Cheng-Gen, Feng, et al., "Progress in Antiestrogens for the Treatment of Breast Cancer", Chinese Journal of New Drugs, vol. 15., No. 13, pp. 1051-1057, Dec. 31, 2006 (With Abstract).
Cohen, F, et al., "Orally bioavailable antagonists of inhibitor of apoptosis proteins based on an azabicyclooctane scaffold", J. Med. Chem., 52(6), 1723-1730 (2009).
Cohen, F. et al., "Antagonists of inhibitors of apoptosis proteins based on thiazole amide isosteres", Bioorg. Med. Chem. Lett., 20(7), 2229-2233 (2010).
Connor, C.E., et al., "Circumventing tamoxifen resistance in breast cancers using antiestrogens that induce unique conformational changes in the estrogen receptor", Cancer Res. 61: 2917-2922 (2001).
Contino-Pepin, Christiane, et al., "Preliminary biological evaluations of new thalidomide analogues for multiple sclerosis application", Bioorganic & Medicinal Chemistry Letter 19 (2009), 878-881.
Corson, et al., "Design and applications of bifunctional small molecules: why two heads are better than one", ACS Chemical Biology vol. 3 No. 11, pp. 677-692; Nov. 21, 2008.
Crews, C. M., "Targeting the undruggable proteome: the small molecules of my dreams", *Chem Biol* 17, 551-555, doi:S1074-5521(10)00196-1 [pii] 10.1016/j.chembiol.2010.05.011 (2010).
Cromm, et al., (2017) "Targeted Protein Degradation: from Chemical Biology to Drug Discovery." *Cell Chem Biol* 24(9):1181-1190.
Cyrus, et al., "Jostling for position: optimizing linker location in the design of estrogen receptor-targeting PROTACs", Chem Med Chem. 5(7), Jul. 5, 2010, 979-985.
Cyrus, K. et al, "Impact of Linker Length on the Activity of PROTACs," Mol. Biosyst., 2011, vol. 7, No. 2, pp. 359-364.
Cyrus, K. et al, "Two-Headed PROTAC: An Effective New Tool for Targeted Protein Degradation," Chembiochem., 2010, vol. 11, pp. 1531-1534.
Deroo, B.J., et al., "Estrogen receptors and human disease", Journal of Clinical Investigation, (2006), vol. 116(3), pp. 561-570.
Di, J et al. "Reactivation of p53 by inhibiting Mdm2 E3 Ligase: a novel antitumor approach", Current Cancer Drug Targets (2011), 11(8), 987-994.
Ding, Q, et al., "Discovery of RG7388, a potent and selective p53-MDM2 inhibitor in clinical development", J Med Chem. Jul. 25, 2013; 56(14):5979-83. doi: 10.1021/jm400487c. Epub Jul. 16, 2013. PubMed PMID: 23808545 (J. Med. Chem. (2013) 56, 5979-5983 Ding, et al).
Dixon, S. J. et al., "Identifying druggable disease-modifying gene products",. *Curr Opin Chem Biol* 13, 549-555, doi:S1367-5931(09)00107-0 [pii] 10.1016/j.cbpa.2009.08.003 (2009).
Fischer, et al., "Structure of the DDB1-DRBN E3 Ubiquitin ligase in complex with thalidomide", Nature, vol. 000, pp. 1-5 (2014).
Flygare, J.A., et al. "Small-molecule pan-IAP antagonists: a patent review", Expert Opin. Ther. Pat., 20 (2), 251-267 ( 2010).
Gadd, M.S., et al., "Structural basis of PROTAC cooperative recognition for selective protein degradation", Nat Chem Biol 13, 514-521 (2017).
Galdeano, et al., "Structure-guided design and optimization of small molecules targeting the protein-protein interaction between the von hippel-lindau (VHL) E3 ubiquitin ligase and the Hypoxia inducible factor (HIF) alpha subunit with in vitro nanomolar affinities", Journal Med Chem, Aug. 2014, vol. 57, pp. 8657-8663.
Garner, F., Shomali, M., Paquin, D., Lyttle, C. R. & Hattersley, G. RAD1901: a novel, orally bioavailable selective estrogen receptor degrader that demonstrates antitumor activity in breast cancer xenograft models. Anticancer Drugs 26, 948-956 (2015).
Golub, et al., "Molecular classification of cancer: class discovery and class prediction by gene expression monitoring", Science 286, 531-537 (1991).
Gosink, M et al., "Redirecting the specificity of ubiquitination by modifying ubiquitin-conjugating enzymes", Pro. Natl. Acad Sci, vol. 92, pp. 9117-9121, 1995.
Haupt, Y. et al., "Mdm2 promotes the rapid degradation of p53", Nature 387, 296-299 (1997).
Heldring, et al., "Estrogen Receptors: How Do They Signal and What are Their Targets", Physiological Reviews (2007), vol. 87, pp. 905-931.
Hennessy, EJ, et al., "Discovery of aminopiperidine-based Smac mimetics as IAP antagonists", Bioorg. Med. Chem. Lett., 22(4), 1690-1694 (2012).
Hines, J., et al., "Posttranslational protein knockdown coupled to receptor tyrosine kinase activation with phosphoPROTACs", Proc Natl Acad Sci USA 110, 8942-8947 (2013).
Hird, AW, et al., "Structure-based design and synthesis of tricyclic IAP (Inhibitors of Apoptosis Proteins) inhibitors", Bioorg. Med. Chem. Lett., 24(7): 1820-1824 (2014).
Hoffmann, J. et al. Characterization of New Estrogen Receptor Destabilizing Compounds: Effects on Estrogen-Sensitive and Tamoxifen-Resistant Breast Cancer. JNCI Journal of the National Cancer Institute 96, 210-218 (2004).
Hon, et al., "Structural basis for the recognition of hydroxyproline in Hlf-1 alpha by pVHL", Nature 417, Jun. 27, 2002, 975-978.
Huang, et al., (2016) "Drugging the undruggables: exploring the ubiquitin system for drug development." *Cell Res* 26(4):484-498.
Hughes, et al., (2017) "Molecular recognition of ternary complexes: a new dimension in the structure-guided design of chemical degraders." *Essays Biochem* 61(5):505-516.
Ivan, M., et al., "HIFa Targeted for VHL-Mediated Destruction by Proline Hydroxylation: Implications for O2 Sensing", Science, vol. 292, No. 5516, pp. 464-468, 2001.
Jang, E.R. et al., "Targeted Degradation of Proteins by PROTACs," Curr. Protoc. Chem. Biol., 2010, vol. 2, No. 2, pp. 71-87.
Jiang, et al., "Synthesis of 7alpha-substituted derivatives of 17beta-estradiol", Steroids 71(5), May 2006, 334-342 (Abstract).

(56) References Cited

OTHER PUBLICATIONS

Jordan, V.C. et al., "A monohydroxylated metabolite of tamoxifen with potent antioestrogenic activity", Endocrinol 75: 305-316 (1977).
Kim, K.S., "Discovery of tetrahydroisoquinoline-based bivalent heterodimeric IAP antagonists", Bioorg. Med. Chem. Lett. 24(21), 5022-5029 (2014).
Knott, Edward (1955). "Compounds containing sulphur chromophores. Part I. The action of bases on heterocyclic sulphide quarternary salts", Journal of The Chemical Society (resumed). 10.1039/jr9550000916. 949-954.
Kronke, et al, "Lenalidomide Causes Selective Degradation of IKZF1 and IKZF3 in Multiple Myeloma Cells", Science 343, 301-305 (2014).
Lai, A. et al. Identification of GDC-0810 (ARN-810), an Orally Bioavailable Selective Estrogen Receptor Degrader (SERD) that Demonstrates Robust Activity in Tamoxifen-Resistant Breast Cancer Xenografts. J. Med. Chem. 58, 4888-4904 (2015).
Lai, A.C., et al., "Modular PROTAC Design for the Degradation of Oncogenic BCR-ABL", Angew Chem Int Ed Engl 55, 807-810 (2016).
Lai, et al., (2017) "Induced protein degradation: an emerging drug discovery paradigm." *Nat Rev Drug Discov* 16(2):101-114.
Lala, et al., "Role of nitric oxide in tumor progression: Lessons from experimental tumors", Cancer and Metastasis Reviews 17:91-106 (1998).
Lebraud, H., et al., "Protein Degradation by In-Cell Self-Assembly of Proteolysis Targeting Chimeras", ACS Central Science, 2, 927-934 (2016).
Lee, et al., "Targeted Degradation of the Aryl Hydrocarbon Receptor by the PROTAC Approach: A Useful Chemical Genetic Tool", ChemBioChem vol. 8, Issue 17, pp. 2058-2062, Nov. 23, 2007.
Levine, et al., Targeting the androgen receptor with steroid conjugates, J. Med. Chem., vol. 57., No. 20. pp. 8224-8237, (2014).
Li, Yan, et al., "Single polymer-drug conjugate carrying two drugs for fixed-dose co-delivery", Medicinal Chemistry, 2014, vol. 4(10): 676-683.
Liu, Hong, et al., "Bioactivation of the selective estrogen receptor modulator desmethylated arzoxifene to quinoids: 4'-fluoro substitution prevents quinoid formation", Chem. Res. Toxicol. 2005, 18, 162-173.
Liu, K., et al., "Design and biological characterization of hybrid compounds of curcumin and thalidomide for multiple myeloma", Org. Biomol. Chem. 2013, 11, 4757-4763.
Lopez-Girona, A. et al., Cereblon is a direct protein target for immunomodulatory and antiproliferative activities of lenalidomide and pomalidomide, Leukemia 26: 2326-2335, 2012.
Lu, et al., "Hijacking the E3 ubiquitin ligase cereblon to efficiently target BRD4", Chem Biol 22(6), 2015, 755-763.
Lu, et al., "The myeloma drug lenalidomide promotes the cereblon-dependent destruction of ikaros proteins", Science 343, 305-309 (2014).
Mahalingam, D., et al., "Targeting HSP90 for cancer therapy", Br J Cancer 100, 1523-1529 (2009).
Maniaci C, et al. (2017) "Homo-PROTACs: bivalent small-molecule dimerizers of the VHL E3 ubiquitin ligase to induce self-degradation." *Nat Commun* 8(1):830 1-13.
Mannhold, R., et al., "IAP antagonists: promising candidates for cancer therapy", Drug Discov. Today, 15 (5-6), 210-219 (2010).
Mcguire, et al., "Taxol: A unique antineoplastic agent with significant activity in advanced ovarian epithelial neoplasms", Ann. Intem, Med., 111:273, 1989.
Medline Plus Trusted Health Information for You, www.nlm.nih.gov/medlineplus/cancer.html pp. 1-10, (2007).
Min, Jung-hyun, et al., "Structure of an HIV-1-alpha—pVHL complex: hydroxyproline recognition in signaling", Jun. 7, 2002, 296: 1886-1889.
Miyazaki, M., et al., "Discovery of DS-5272 as a promising candidate: a potent and orally active p53-MDM2 interaction inhibitor", Bioorg. Med. Chem. Lett. (2015) 23, 2360-2367.
Muller, G., et al., "Amino-Substituted Thalodomide Analogs: Potent Inhibitors of TNF-α Production", Bioorganic & Medicinal Chemistry Letters 9 (1999) 1625-1630.
Ndubaku, C, et al., "Antagonism of c-IAP and XIAP proteins is required for efficient induction of cell death by small-molecule IAP antagonists", ACS Chem Biol. Jul. 17, 2009;4(7):557-566.
Neklesa, T.K., et al., "Chemical biology: Greasy tags for protein removal", Nature 487, 308-309 (2012).
Neklesa, Targeted protein degradation by PROTACs. Pharmacology & Therapeutics 174, 138-144 (2017).
Nikolovska-Coleska, et al., "Interaction of a cyclic, Bivalent Smac Mimetic with the X-linked inhibitor of apoptosis protein", Biochemistry, 2008, 47(37), pp. 9811-9824.
Ohoka, N. et al. SNIPER(TACC3) induces cytoplasmic vacuolization and sensitizes cancer cells to Bortezomib. Cancer Sci. 108, 1032-1041 (2017).
Oost, T.K. et al., "Discovery of potent antagonists of the antiapoptotic protein XIAP for the treatment of cancer", Journal of Medicinal Chemistry 2004, 47, 4417-4426.
Ottis P, et al. (2017) "Assessing Different E3 Ligases for Small Molecule Induced Protein Ubiquitination and Degradation." *ACS Chem Biol* 12(10):2570-2578.
Ottis, et al., (2017) "Proteolysis-Targeting Chimeras: Induced Protein Degradation as a Therapeutic Strategy." *ACS Chem Biol* 12(4):892-898.
Perez, HL,"Discovery of potent heterodimeric antagonists of inhibitor of apoptosis proteins (IAPs) with sustained antitumor activity", J. Med. Chem. 58(3), 1556-1562 (2015).
Poutiainen, PK, et. al., "Design, synthesis, and biological evaluation of nonsteroidal cycloalkane[d]isoxazole-containing androgen receptor modulators", J. Med. Chem. 55, 6316-6327 (2012).
Puppala, D. et al., "Development of an Aryl Hydrocarbon Receptor Antagonist Using the Proteolysis-Targeting chimeric Molecules Approach: A Potential Tool for Chemoprevention," Mol. Pharmacol., 2008, vol. 73, No. 4, pp. 1064-1071.
Qin, Zhihui, et al., "Benzothiophene selective estrogen receptor modulators with modulated oxidative activity and receptor affinity", J. Med Chem 2007, 50, 2682-2692.
Raina, et al., (2017) "Targeted protein knockdown using small molecule degraders." *Curr Opin Chem Biol* 39:46-53.
Raina, K., et al., "PROTAC-induced BET protein degradation as a therapy for castration-resistant prostate cancer", Proc Natl Acad Sci USA 113, 7124-7129 (2016).
Remillard D, et al. (2017) "Degradation of the BAF Complex Factor BRD9 by Heterobifunctional Ligands." *Angew Chem Int Ed Engl* 56(21):5738-5743.
Rew, Y, et al., "Discovery of AM-7209, a potent and selective 4-amidobenzoic acid inhibitor of the MDM2-p53 interaction", J Med Chem. Dec. 26, 2014;57(24):10499-10511. doi: 10.1021/jm501550p. Epub Dec. 4, 2014. PubMed PMID: 25384157.
Robertson, J. F. R. Fulvestrant (Faslodex)—how to make a good drug better. Oncologist 12, 774-784 (2007).
Rodriguez-Gonzalez, et al., "Targeting steroid hormone receptors for ubiquitination and degradation in breast and prostate cancer", Oncogene. 27(57), Dec. 4, 2008, 7201-7211.
Rotili, D., et al., "Photoactivable peptides for identifying enzyme-substrate and protein-protein interactions", Chem Commun (Carob) 47(5), Feb. 2011, 1488-1490.
Ruchelman, A., et al., "Isosteric analogs of lenalidominde and pomalidomide: Synthesis and biological activity", Bioorganic & Medicinal Chemistry Letters 23 (2013) 360-365.
Sakamoto, et al., "Development of Protacs to target cancer-promoting proteins for ubiquitination and degradation", Mol Cell Proteomics. 2(12), Dec. 2003, 1350-1358.
Sakamoto, et al., "Protacs: chimeric molecules that target proteins to the Skp 1-Cullin-F box complex for ubiquitination and degradation", Proc Natl Acad Sci U S A.98(15), Jul. 17, 2001, 8554-8559.
Salami, J. & Crews, C. M. Waste disposal—An attractive strategy for cancer therapy. Science 355, 1163-1167 (2017).
Schiedel, M., et al., "Chemically Induced Degradation of Sirtuin 2 (Sirt2) by a Proteolysis Targeting Chimera (PROTAC) Based on Sirtuin Rearranging Ligands (SirReals)", J Med Chem. (2017), 61:482-491.

(56) References Cited

OTHER PUBLICATIONS

Schneekloth, et al., "Chemical Genetic Control of Protein Levels: Selective in Vivo Targeted Degradation", J Am Chem Soc. 126(12), Mar. 31, 2004, 3748-3754.
Schneekloth, et al., Targeted intracellular protein degradation induced by a small molecule: En route to chemical proteomics, Bioorg. Med. Chem. Lett. 18 (2008) 5904-5908.
Smith, et al., "Targeted Intracellular Protein Degradation Induced by a Small Molecule: En Route to Chemical Proteomics", Bioorg Med Chem Lett. 18(22), Nov. 15, 2008, 5904-5908.
Stewart, Scott G., et al., "Efforts toward elucidating Thalidomide's molecular target: An Expedient Synthesis of the first Thalidomide Biotin Analogue" Org. Biomol., Chem., 2010, 8, 4059-4062.
STN transcript excerpt Nov. 24, 2017 "Compounds containing sulfur Chromophores v. Complex cyanines".
Stoppler, Melissa Conrad., Endometriosis [online], "Endometriosis Definition and Facts" URL http://www.medicinenet.com/endometriosis/article.htm, retrieved on Apr. 5, 2017.
Stoppler, Melissa Conrad., Endometriosis [online], "What about surgery for Endometriosis?" URL http://www.medicinenet.com/endometriosis/article.htm, retrieved on Apr. 5, 2017.
Suh, N. et al. Arzoxifene, a new selective estrogen receptor modulator for chemoprevention of experimental breast cancer. Cancer Res. 61, 8412-8415 (2001).
Sun, D, et al., "Discovery of AMG 232, a potent, selective, and orally bioavailable MDM2-p53 inhibitor in clinical development", J Med Chem. Feb. 27, 2014;57(4):1454-72. doi: 10.1021/jm401753e. Epub Feb. 5, 2014. PubMed PMID: 24456472.
Sun, et al., "Potent bivalent Smac mimetics: effect of the linker on binding to inhibitor apoptosis proteins (IAPs) and anticancer activity", J. Med. Chem. 53, 3306-3318 (2011).
Toure, et al., (2016) "Small-Molecule PROTACS: New Approaches to Protein Degradation." *Angew Chem Int Ed Engl* 55(6):1966-1973.
Trewartha D, Carter K. "Advances in prostate cancer treatment", Nat Rev Drug Discov. Nov. 2013;12(11):823-824. doi: 10.1038/nrd4068. PubMed PMID: 24172327.
Turk, B. E., "Binding of thalidomide to alpha1-acid glycoprotein may be involved in its inhibition of tumor necrosis factor alpha production", Proc. Natl. Acad. Sci. U.S.A. 1996, 93, 7552-7556.
Vamos M., et al., "Expedient synthesis of highly potent antagonists of inhibitor of apoptosis proteins (IAPs) with unique selectivity for ML-IAP", ACS Chem. Biol., 8(4), 725-732 (2013).
Van Molle, et al., "Dissecting fragment-based lead discovery at the von Hippel-Lindau protein:hypoxia inducible factor 1a protein-protein interface", Chem Biol. 19(10), Oct. 26, 2012, 1300-1312.
Vassilev, et al., "In vivo activation of the p53 pathway by small-molecule antagonists of MDM2", Science 303, Feb. 6, 2004, 844-848.
Vazquez, A. et al., "The genetics of the p53 pathway, apoptosis and cancer therapy", Nat. Rev. Drug. Dis., 7, 979-982 (2008).
Vu, B. et al. "Discovery of RG7112: a small-molecule MDM2 inhibitor in clinical development", ACS Med. Chem. Lett. (2013) 4, 466-469.
Wang J, et al., "Discovery of novel second mitochondrial-derived activator of caspase mimetics as selective inhibitor or apoptosis protein inhibitors", J. Pharmacol. Exp. Ther., 349(2): 319-29 (2014).
Wang, C. et al. Estrogen induces c-myc gene expression via an upstream enhancer activated by the estrogen receptor and the AP-1 transcription factor. Mol. Endocrinol. 25, 1527-1538 (2011).
Wang, S., et al. "Small-molecule inhibitors of the MDM2-p53 protein-protein interaction (MDM2 inhibitors) in clinical trials for cancer treatment", J. Med. Chem. (2015) 58, 1038-1052.
Wang, S., et al. "Temporal activation of p53 by a specific MDM2 inhibitor is selectively toxic to tumors and leads to complete tumor growth inhabitation", PNAS USA (2008) 105, 3933-3938.
Weir, H. M. et al. AZD9496: An Oral Estrogen Receptor Inhibitor That Blocks the Growth of ER-Positive and ESR1-Mutant Breast Tumors in Preclinical Models. Cancer Res. 76, 3307-3318 (2016).
Willson, T.M. et al., "3-[4-(1,2-Diphenylbut-1-Enyl)Phenyl] Acrylic Acid: A non-steroidal estrogen with functional selectivity for bone over uterus in rats", Journal of Medicinal Chemistry, American Chemical Society, US May 25, 1994, vol. 37 No. 11, pp. 1550-1552.
Winter, et al., "Phthalimide Conjugation as a strategy for in vivo target protein degradation", Science, 2015 vol. 348 (6241), pp. 1376-1381 [Pub online: May 21, 2015].
Yu, F. & Bender, W. The mechanism of tamoxifen in breast cancer prevention. Breast Cancer Research 3, A74 (2001).
Zengerle, et al., "Selective Small Molecule Induced Degradation of the BET Bromodomain Protein BRD4" ACS Chemical Biology, Jun. 2, 2015, vol. 10, pp. 1770-1777.
Zhang B.et al., "Small-molecule MDM2-p53 inhibitors: recent advances", Future Med. Chem. (2015) 7, 631-645.
Zhang, D. et al., "Targeted Degradation of Proteins by Small Molecules: A Novel Tool for Functional Proteomics," comb Chem. High Throughput Screen., 2004, vol. 7, No. 7, pp. 689-697.
Zhong, H. et al, "Modulation of Hypoxia-inducible Factor 1α Expression by the Epidermal Growth Factor/Phosphatidylinositol 3-Kinase/PTEN/AKT/FRAP Pathway in Human Prostate Cancer Cells: Implications for Tumor Angiogenesis and Therapeutics", Cancer res, (2000) 60(6), 1541-1545.
Zhou, B., et al. "Discovery of a Small-Molecule Degrader of Bromodomain and Extra-Terminal (BET) Proteins with Picomolar Cellular Potencies and Capable of Achieving Tumor Regression", J Med Chem. 61(2), 462-481 (2018) (DOI:10.1021/acs.jmedchem.6b01816) (2017).

\* cited by examiner

FIG. 5
Table 1: Activity, synthetic methods and characterization of ER PROTACs
| Example # | Structure | ERE Luciferase IC$_{50}$ [nM] | MW | Observed [M+H]/z | Synthetic Method |
|---|---|---|---|---|---|
| 1 | 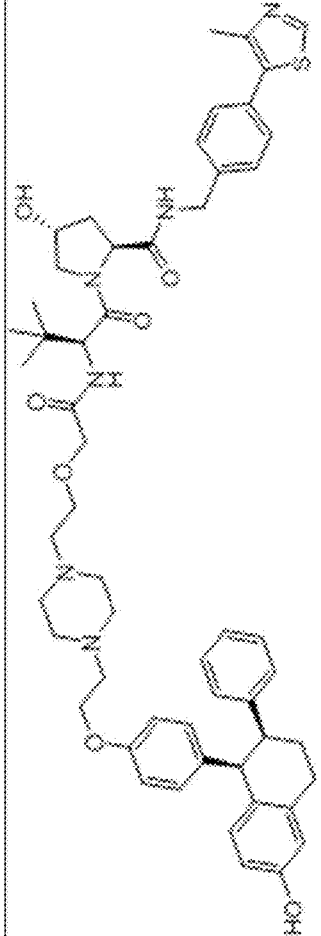 | 0.35 | 943.22 | 943.4 | Scheme 3-1, 3-2 |
| 2 | 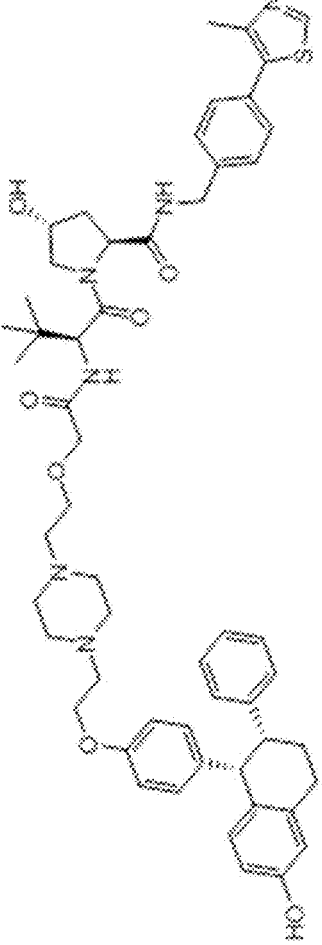 | 192 | 943.22 | 943.4 | Scheme 3-1, 3-2 |

FIG. 5 Continued
| Example # | Structure | ERE Luciferase IC$_{50}$ [nM] | MW | Observed [M+H]/z | Synthetic Method |
|---|---|---|---|---|---|
| 3 | 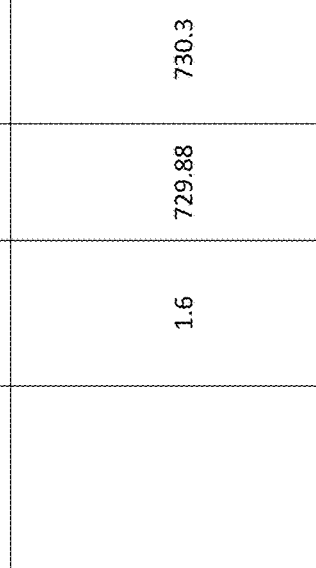 | 1.6 | 729.88 | 730.3 | Scheme 3-3 |
| 4 | 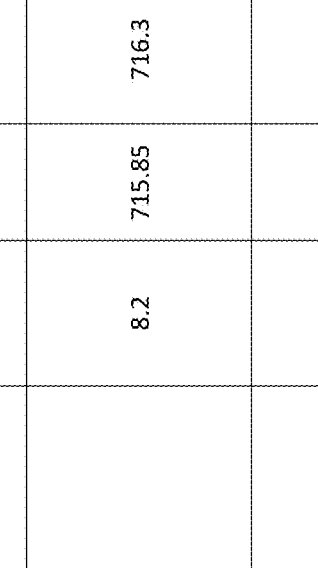 | 8.2 | 715.85 | 716.3 | Scheme 3-3 |
| 5 | 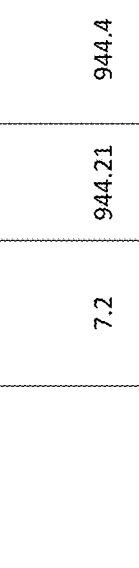 | 7.2 | 944.21 | 944.4 | Scheme 3-4 |

FIG. 5 Continued

| Example # | Structure | ERE Luciferase IC$_{50}$ [nM] | MW | Observed [M+H]/z | Synthetic Method |
|---|---|---|---|---|---|
| 6 | 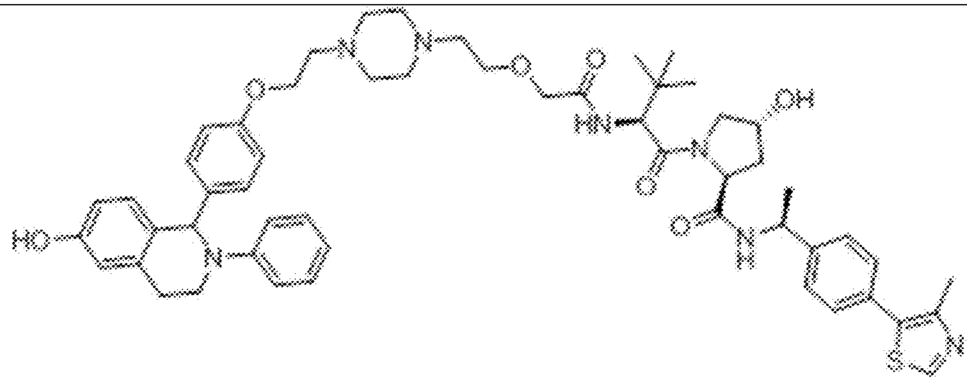 | 4.3 | 958.23 | 958.4 | Scheme 3-4 |
| 7 | 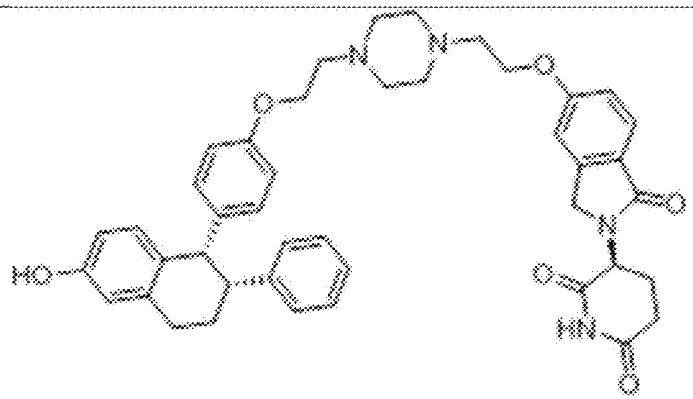 | 8.1 | 714.86 | 715.3 | Scheme 3-5 |

FIG. 5 Continued

| Example # | Structure | ERE Luciferase IC$_{50}$ [nM] | MW | Observed [M+H]/z | Synthetic Method |
|---|---|---|---|---|---|
| 8 | 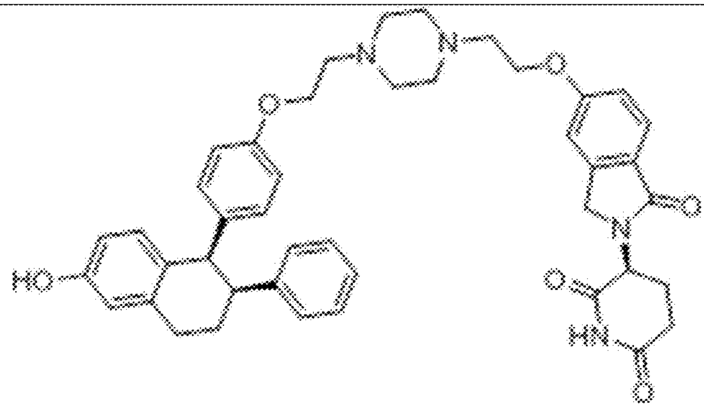 | 0.3 | 714.86 | 715.3 | Scheme 3-5 |
| 9 | 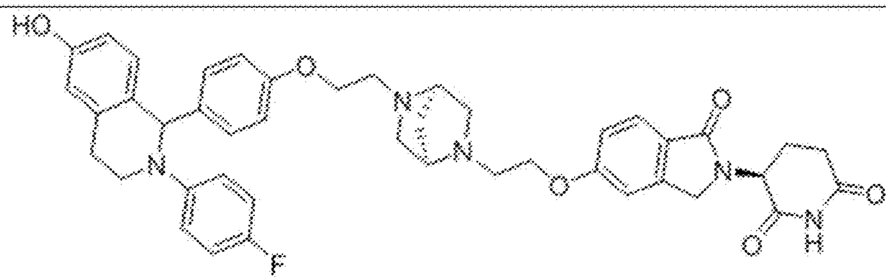 | 0.6 | 745.85 | 746.3 | Scheme 3-6 |

FIG. 5 Continued

| Example # | Structure | ERE Luciferase IC$_{50}$ [nM] | MW | Observed [M+H]/z | Synthetic Method |
|---|---|---|---|---|---|
| 10 | 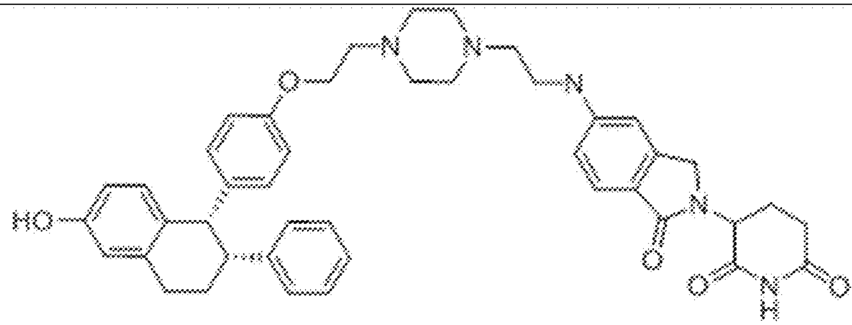 | 7 | 713.88 | 714.3 | Scheme 3-7 |
| 11 | 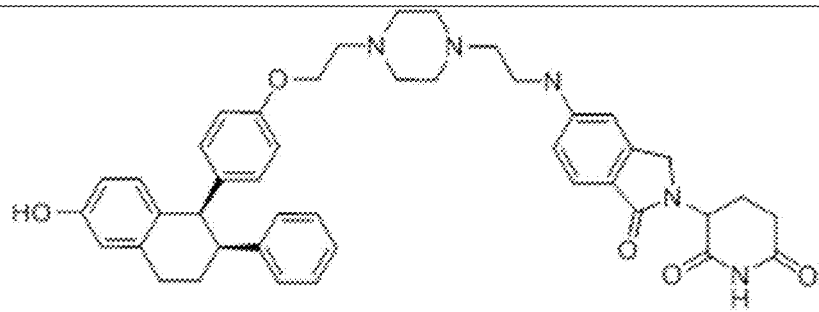 | 0.2 | 713.88 | 714.3 | Scheme 3-7 |
| 12 | 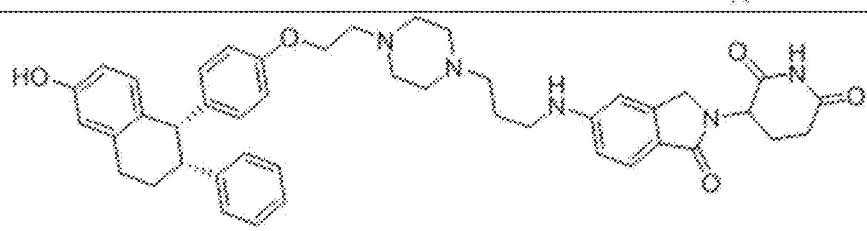 | 11 | 727.91 | 728.3 | Scheme 3-7 |

FIG. 5 Continued

| Example # | Structure | ERE Luciferase IC$_{50}$ [nM] | MW | Observed [M+H]/z | Synthetic Method |
|---|---|---|---|---|---|
| 13 | 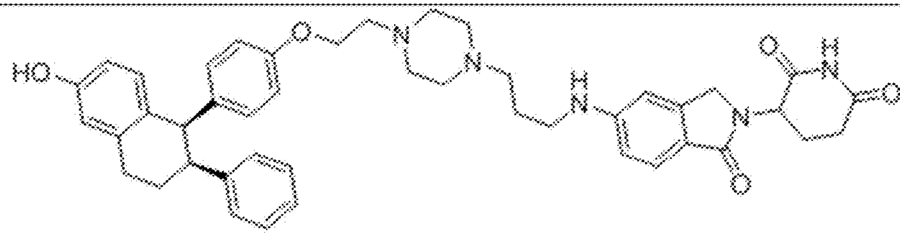 | 0.4 | 727.91 | 728.3 | Scheme 3-7 |
| 14 | 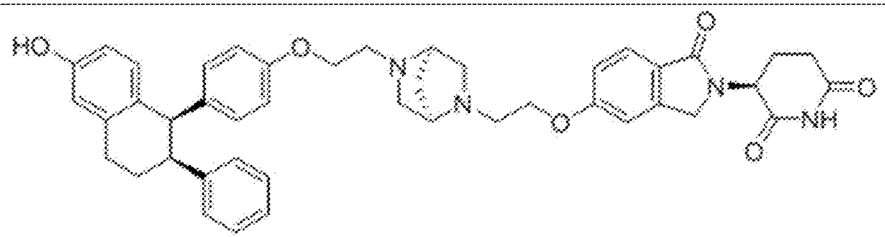 | 0.2 | 726.87 | 727.3 | Scheme 3-5 |
| 15 | 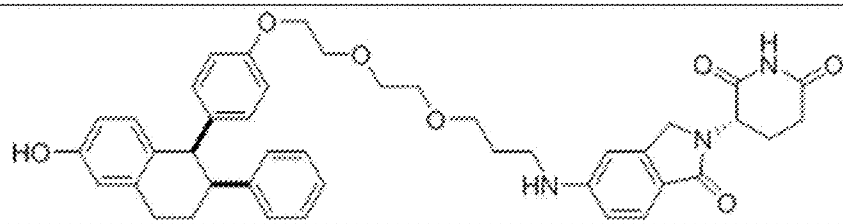 | 1.4 | 703.84 | 704.3 | Scheme 3-8 |
| 16 | 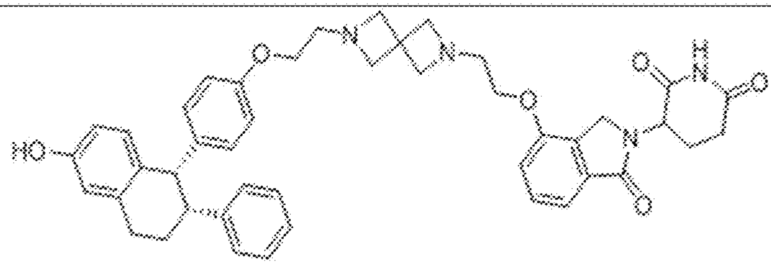 | >300 | 726.87 | 727.3 | Scheme 3-9 |

FIG. 5 Continued

| Example # | Structure | ERE Luciferase IC$_{50}$ [nM] | MW | Observed [M+H]/z | Synthetic Method |
|---|---|---|---|---|---|
| 17 | 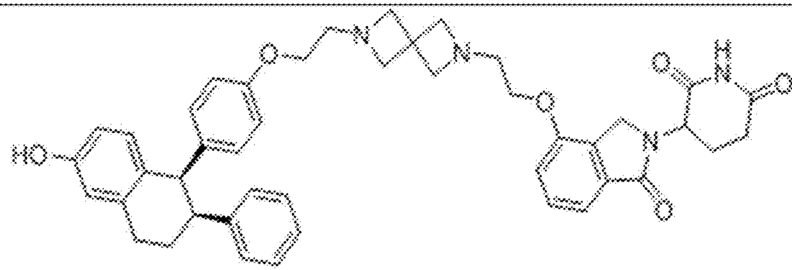 | 3 | 726.87 | 727.3 | Scheme 3-9 |
| 18 | 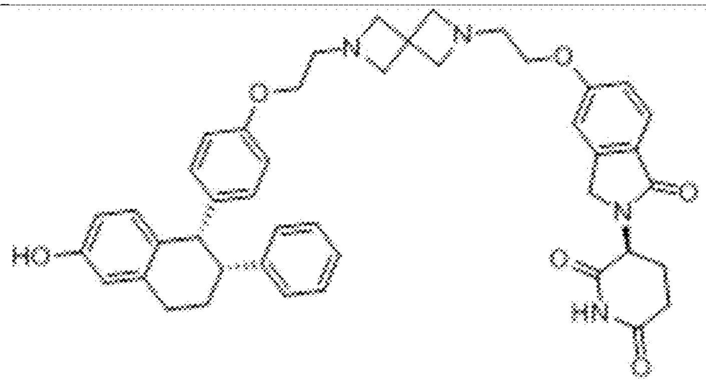 | >100 | 726.87 | 727.3 | Scheme 3-9 |

FIG. 5 Continued

| Example # | Structure | ERE Luciferase IC₅₀ [nM] | MW | Observed [M+H]/z | Synthetic Method |
|---|---|---|---|---|---|
| 19 | 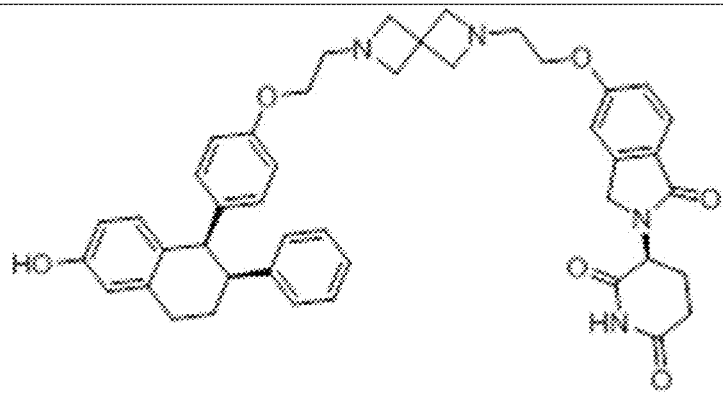 | 0.8 | 726.87 | 727.3 | Scheme 3-9 |
| 20 | 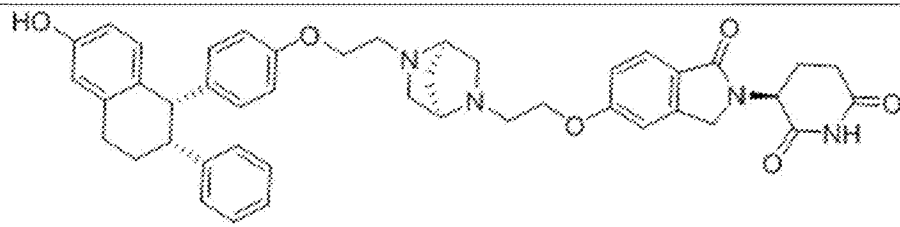 | 10 | 726.87 | 727.3 | Scheme 3-5 |
| 21 | 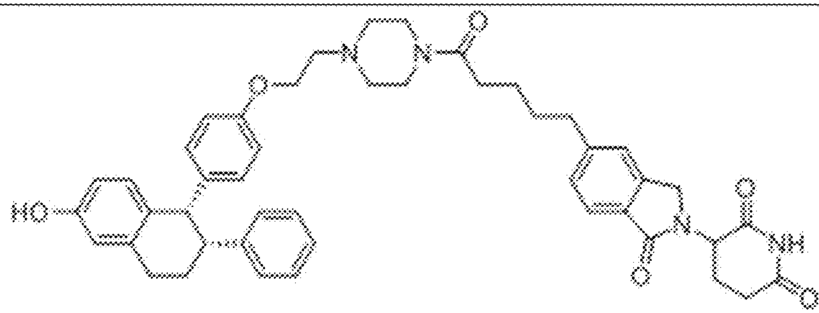 | 32 | 754.93 | 755.3 | Scheme 3-12 |

FIG. 5 Continued
| Example # | Structure | ERE Luciferase IC$_{50}$ [nM] | MW | Observed [M+H]/z | Synthetic Method |
|---|---|---|---|---|---|
| 22 | 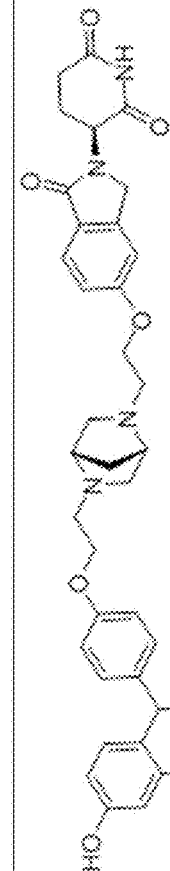 | 0.5 | 745.85 | 746.3 | Scheme 3-6 |
| 23 | 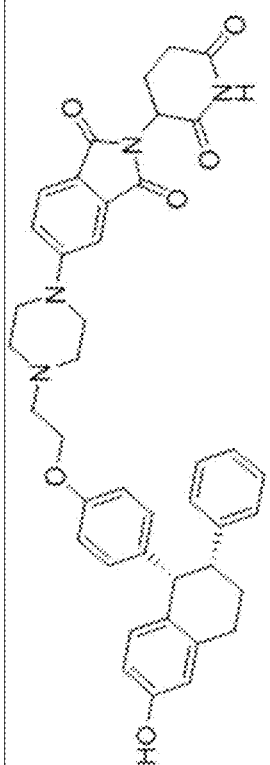 | >300 | 684.79 | 685.2 | Scheme 3-10 |
| 24 | 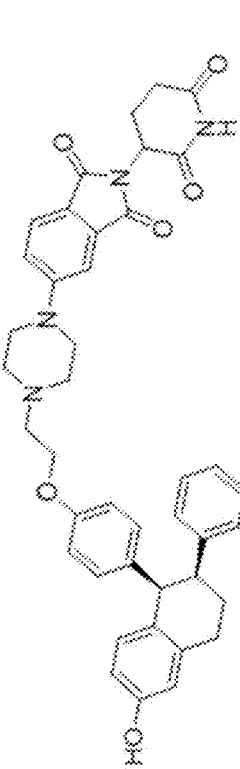 | 2 | 684.79 | 685.2 | Scheme-3-10 |

FIG. 5 Continued

| Example # | Structure | ERE Luciferase IC$_{50}$ [nM] | MW | Observed [M+H]/z | Synthetic Method |
|---|---|---|---|---|---|
| 25 | 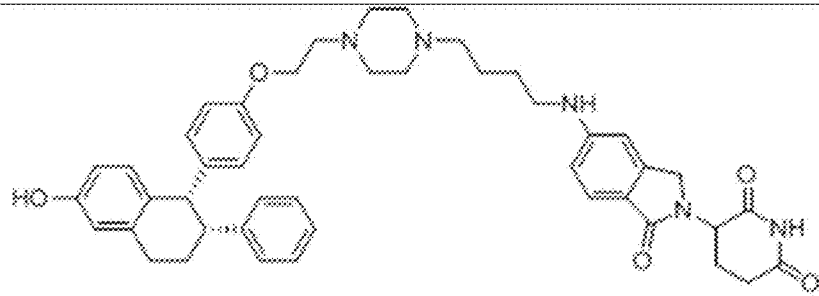 | >100 | 741.93 | 742.3 | Scheme 3-11 |
| 26 | 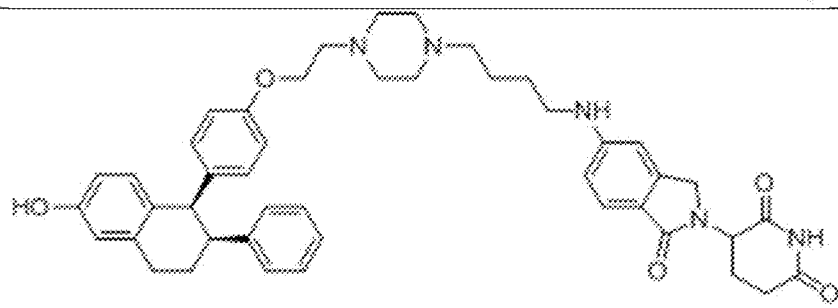 | 0.2 | 741.93 | 742.3 | Scheme 3-11 |
| 27 | 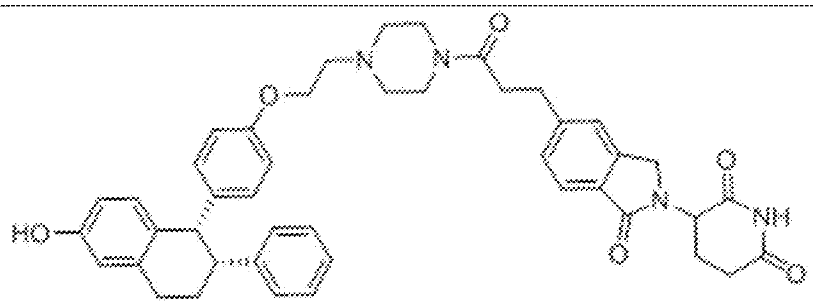 | 21.5 | 726.87 | 727.3 | Scheme 3-12 |

FIG. 5 Continued

| Example # | Structure | ERE Luciferase IC$_{50}$ [nM] | MW | Observed [M+H]/z | Synthetic Method |
|---|---|---|---|---|---|
| 28 | 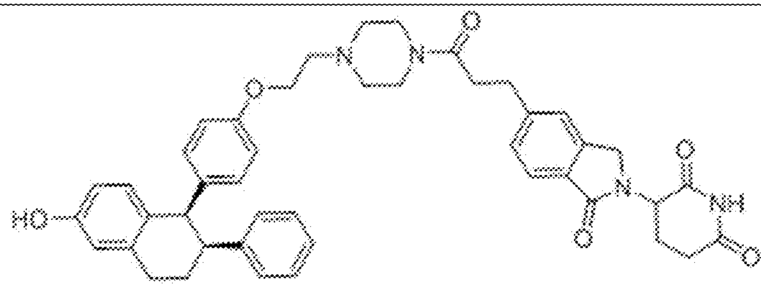 | 0.5 | 726.87 | 727.3 | Scheme 3-12 |
| 29 | 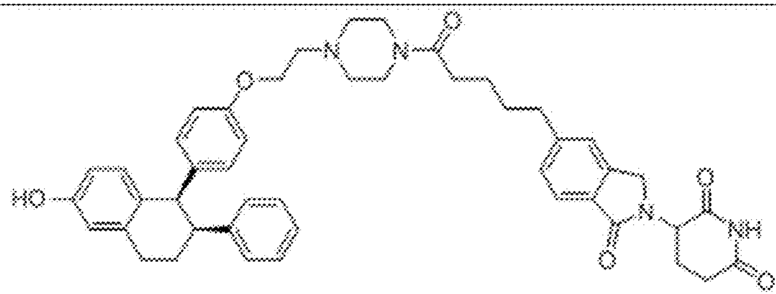 | 0.3 | 754.93 | 755.3 | Scheme 3-12 |
| 30 | 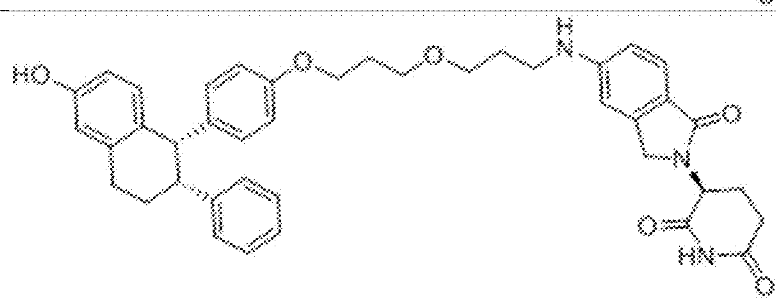 | >300 | 673.81 | 674.2 | Scheme 3-8 |

FIG. 5 Continued

| Example # | Structure | ERE Luciferase IC$_{50}$ [nM] | MW | Observed [M+H]/z | Synthetic Method |
|---|---|---|---|---|---|
| 31 | 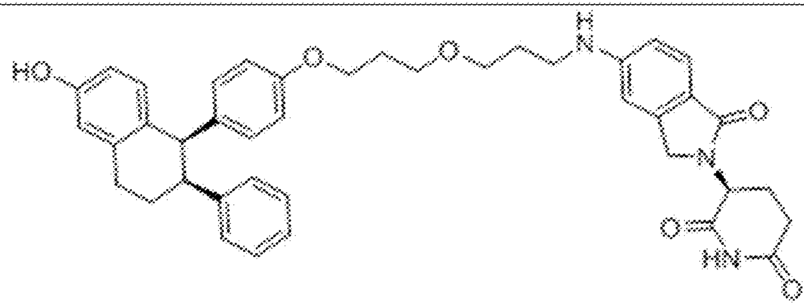 | 1.1 | 673.81 | 674.2 | Scheme 3-8 |
| 32 | 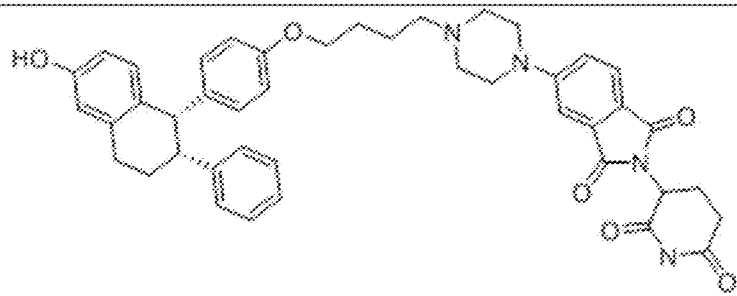 | >300 | 712.85 | 713.2 | Scheme 3-10 |
| 33 | 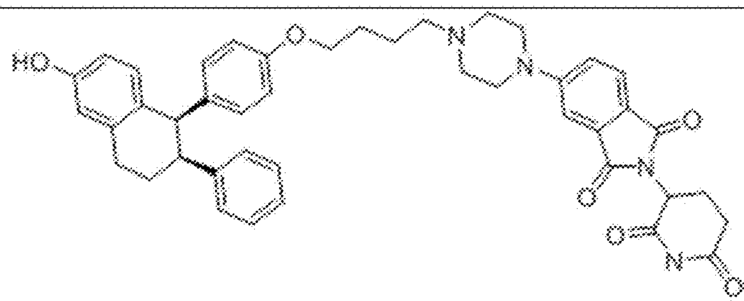 | 0.6 | 712.85 | 713.2 | Scheme 3-10 |

FIG. 5 Continued
| Example # | Structure | ERE Luciferase IC₅₀ [nM] | MW | Observed [M+H]/z | Synthetic Method |
|---|---|---|---|---|---|
| 34 | 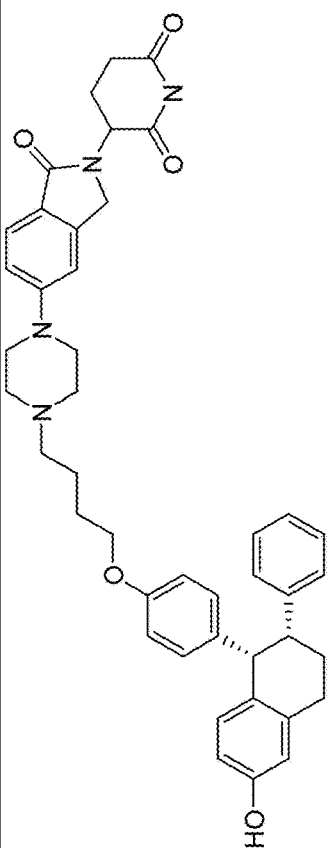 | >100 | 698.86 | 699.26 | Scheme 3-10 |
| 35 | 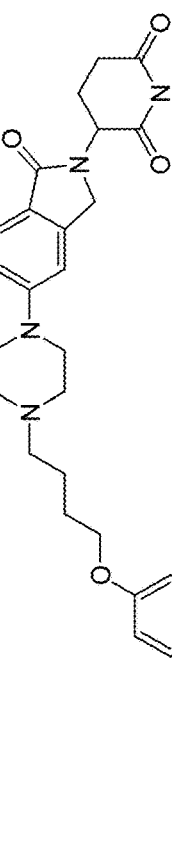 | 0.3 | 698.86 | 699.3 | Scheme 3-10 |
| 36 | 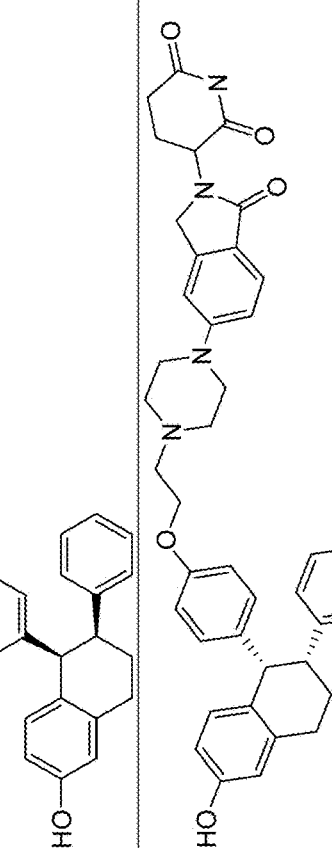 | >100 | 670.81 | 671.2 | Scheme 3-10 |

FIG. 5 Continued

| Example # | Structure | ERE Luciferase IC$_{50}$ [nM] | MW | Observed [M+H]/z | Synthetic Method |
|---|---|---|---|---|---|
| 37 | 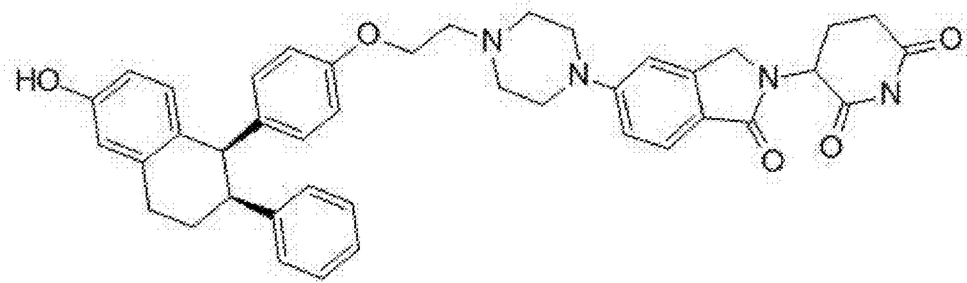 | 0.3 | 670.81 | 671.2 | Scheme 3-10 |
| 38 | 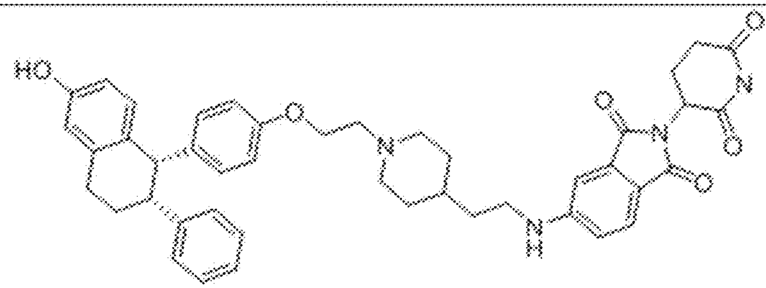 | >100 | 726.87 | 727.3 | Scheme 3-13 |
| 39 | 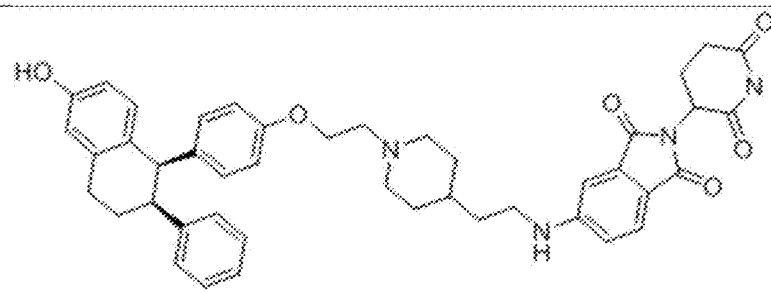 | 0.4 | 726.87 | 727.3 | Scheme 3-13 |

FIG. 5 Continued

| Example # | Structure | ERE Luciferase IC$_{50}$ [nM] | MW | Observed [M+H]/Z | Synthetic Method |
|---|---|---|---|---|---|
| 40 | 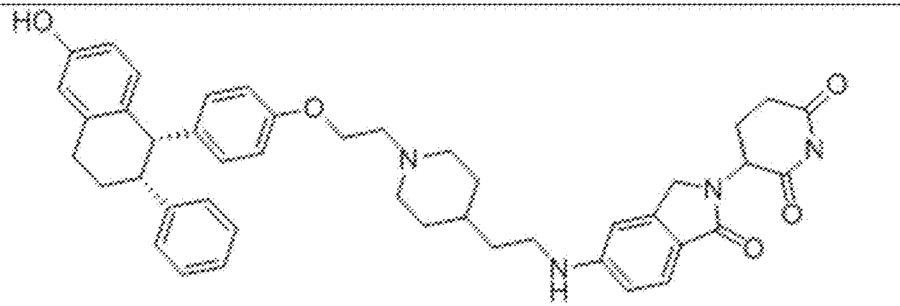 | 71.1 | 712.89 | 713.3 | Scheme 3-13 |
| 41 | 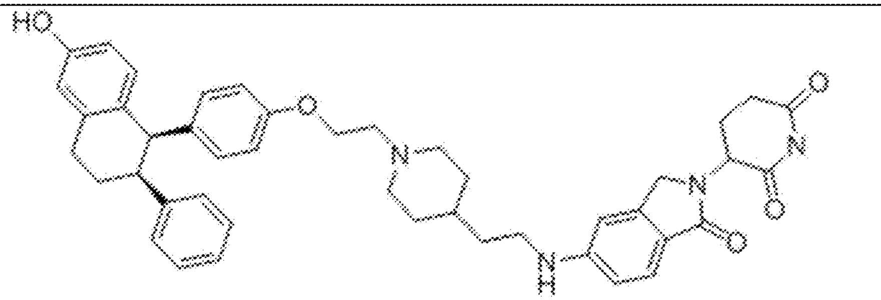 | 0.1 | 712.89 | 713.3 | Scheme 3-13 |
| 42 | 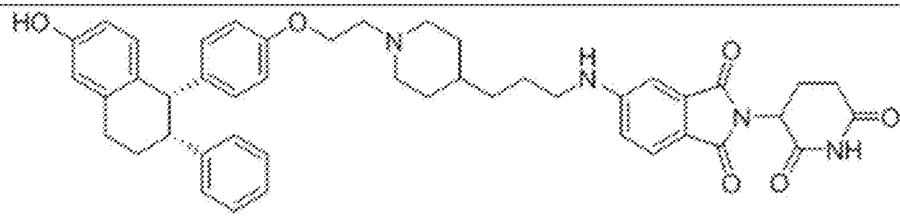 | 111.3 | 740.9 | 741.3 | Scheme 3-13 |

FIG. 5 Continued

| Example # | Structure | ERE Luciferase IC$_{50}$ [nM] | MW | Observed [M+H]/z | Synthetic Method |
|---|---|---|---|---|---|
| 43 | 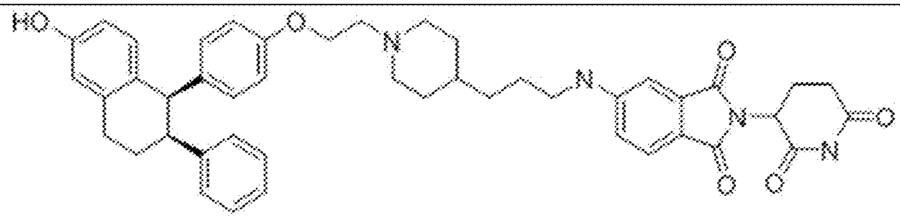 | 0.4 | 740.9 | 741.3 | Scheme 3-13 |
| 44 | 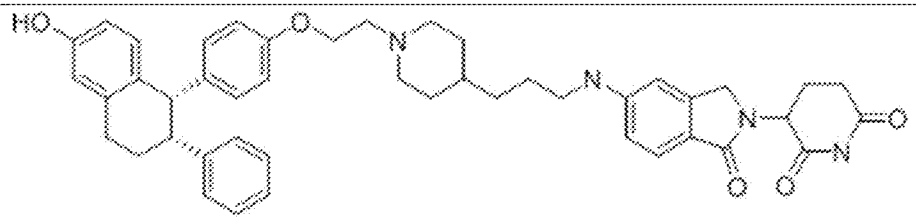 | >50 | 726.92 | 727.6 | Scheme 3-13 |
| 45 | 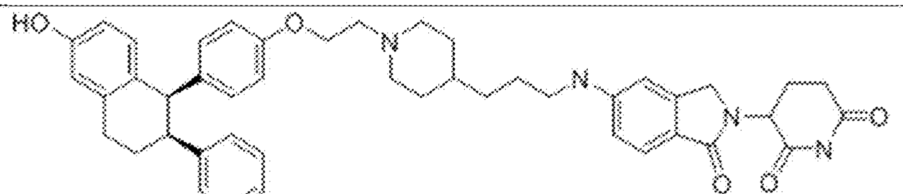 | 0.2 | 726.92 | 727.3 | Scheme 3-13 |
| 46 | 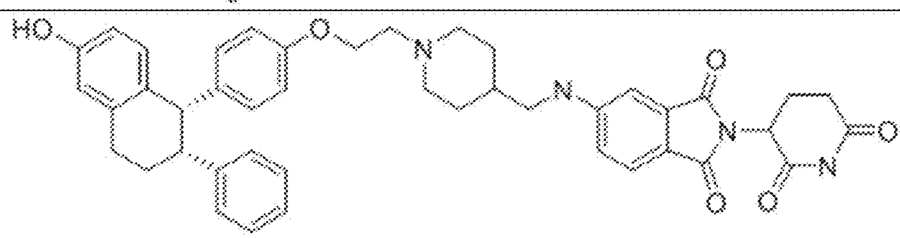 | >100 | 712.85 | 713.2 | Scheme 3-13 |

FIG. 5 Continued

| Example # | Structure | ERE Luciferase IC$_{50}$ [nM] | MW | Observed [M+H]/z | Synthetic Method |
|---|---|---|---|---|---|
| 47 | 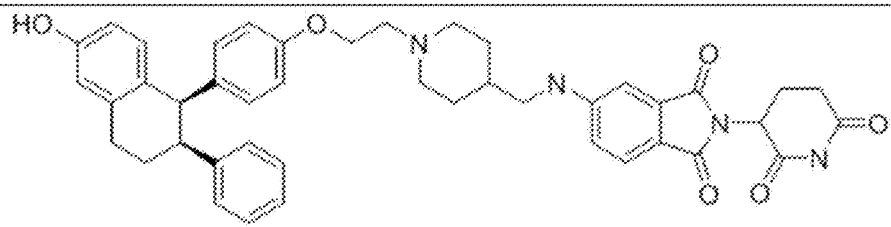 | 0.2 | 712.85 | 713.2 | Scheme 3-13 |
| 48 | 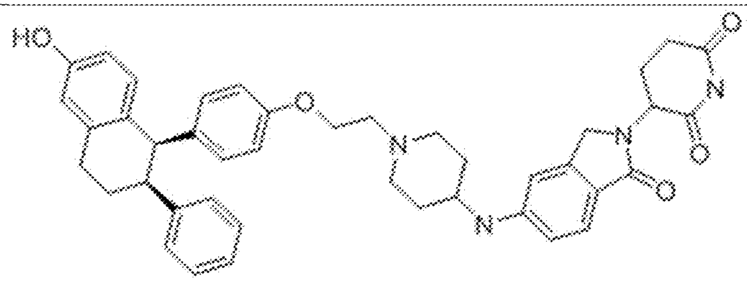 | 0.5 | 684.84 | 685.3 | Scheme 3-14 |
| 49 | 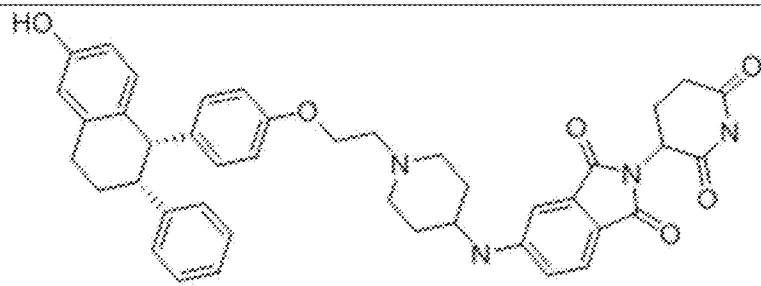 | > 300 | 698.82 | 699.2 | Scheme 3-13 |

FIG. 5 Continued
| Example # | Structure | ERE Luciferase IC$_{50}$ [nM] | MW | Observed [M+H]/z | Synthetic Method |
|---|---|---|---|---|---|
| 50 | 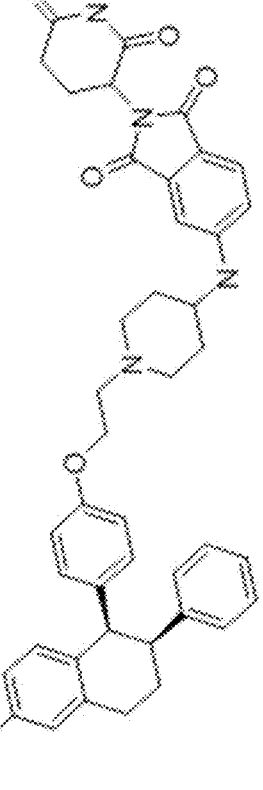 | 0.4 | 698.82 | 699.2 | Scheme 3-13 |
| 51 | 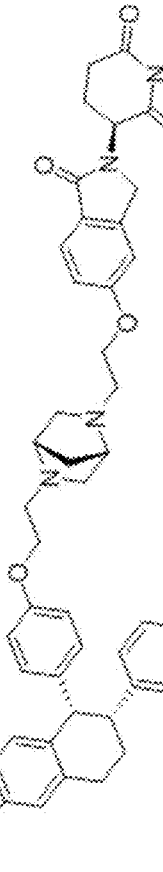 | >25 | 726.87 | 727.3 | Scheme 3-5 |
| 52 | 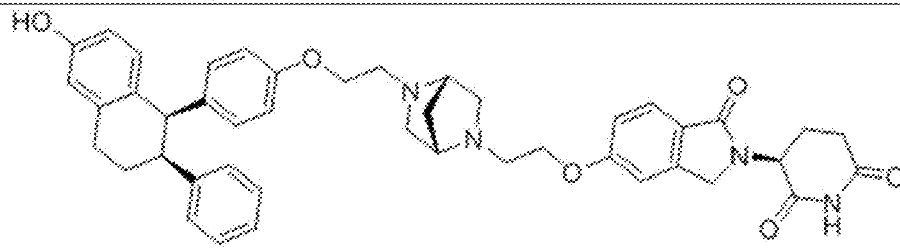 | 0.1 | 726.87 | 727.3 | Scheme 3-5 |

FIG. 5 Continued

| Example # | Structure | ERE Luciferase IC$_{50}$ [nM] | MW | Observed [M+H]/z | Synthetic Method |
|---|---|---|---|---|---|
| 53 | 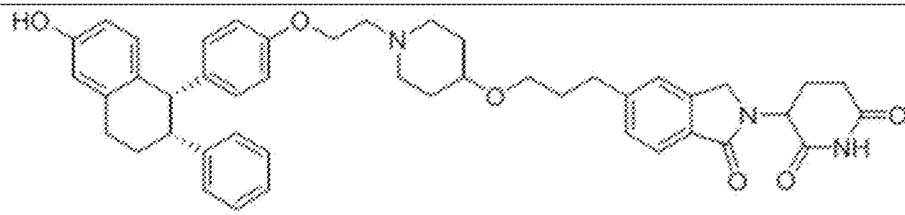 | >50 | 727.9 | 728.3 | Scheme 3-15 |
| 54 | 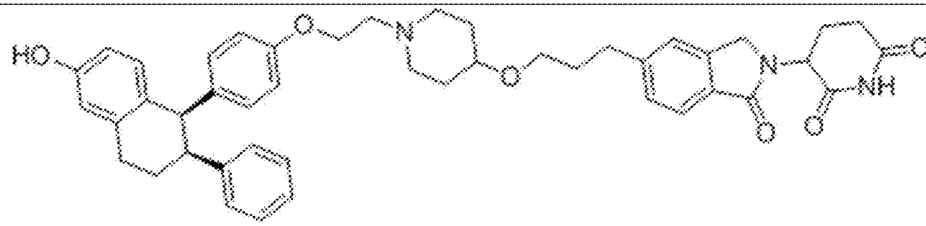 | 0.1 | 727.9 | 728.3 | Scheme 3-15 |
| 55 | 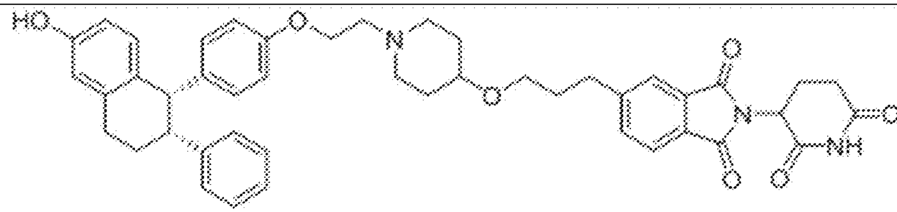 | >75 | 741.89 | 742.3 | Scheme 3-15 |
| 56 | 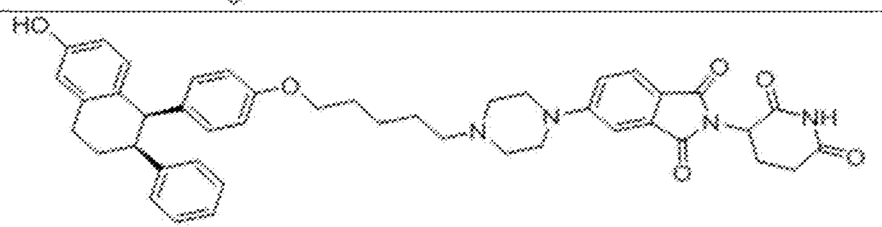 | >50 | 698.86 | 699.3 | Scheme 3-15 |

FIG. 5 Continued

| Example # | Structure | ERE Luciferase IC$_{50}$ [nM] | MW | Observed [M+H]/z | Synthetic Method |
|---|---|---|---|---|---|
| 57 | 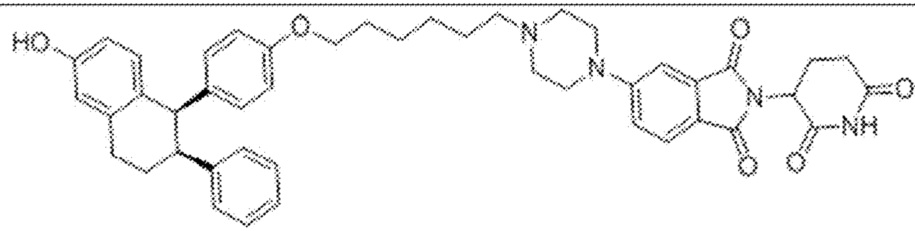 | 0.1 | 698.86 | 699.3 | Scheme 3-10 |
| 58 | 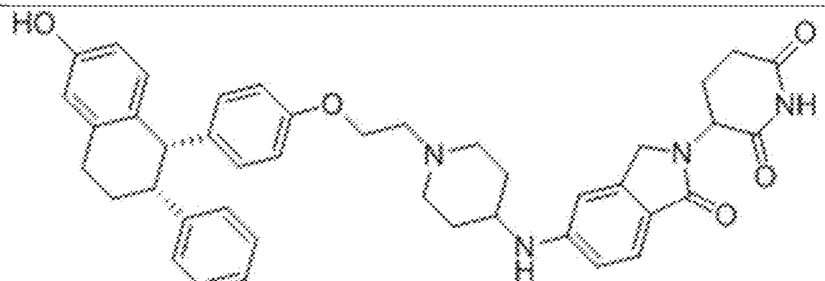 | >70 | 684.84 | 685.3 | Scheme 3-14 |
| 59 | 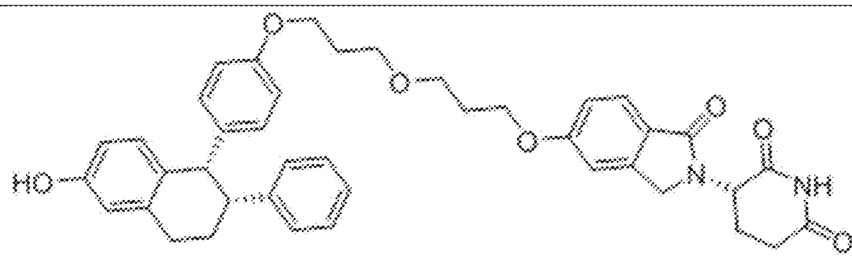 | >300 | 674.79 | 675.2 | Scheme 3-16 |

FIG. 5 Continued

| Example # | Structure | ERE Luciferase IC$_{50}$ [nM] | MW | Observed [M+H]/z | Synthetic Method |
|---|---|---|---|---|---|
| 60 | 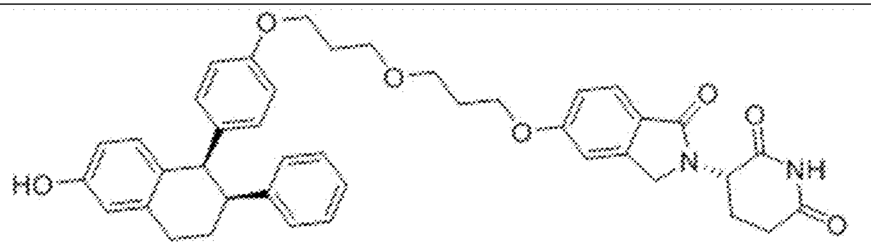 | 1.62 | 674.79 | 675.2 | Scheme 3-16 |
| 61 | 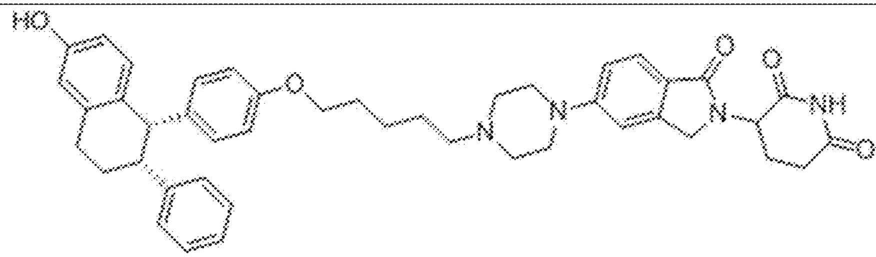 | 107.04 | 712.89 | 713.6 | Scheme-3-10 |
| 62 | 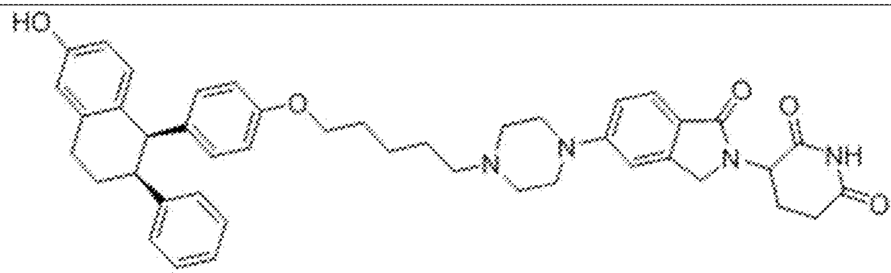 | 0.99 | 712.89 | 713.5 | Scheme 3-10 |

FIG. 5 Continued

| Example # | Structure | ERE Luciferase IC$_{50}$ [nM] | MW | Observed [M+H]/z | Synthetic Method |
|---|---|---|---|---|---|
| 63 | 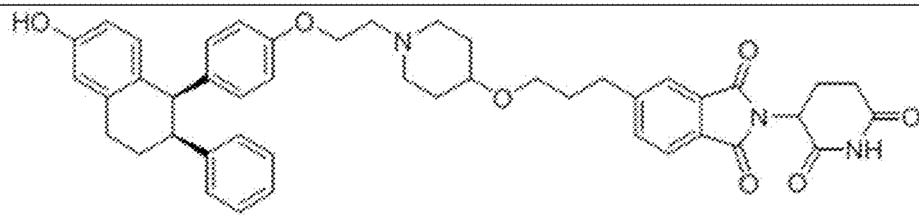 | 0.32 | 741.89 | 742.3 | Scheme 3-15 |
| 64 | 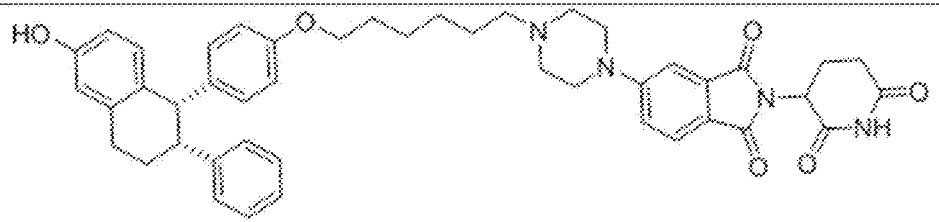 | >300 | 740.9 | 741.3 | Scheme 3-10 |
| 65 | 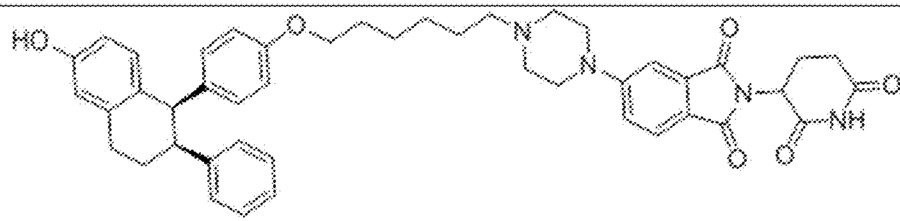 | 1.97 | 740.9 | 741.3 | Scheme 3-10 |
| 66 | 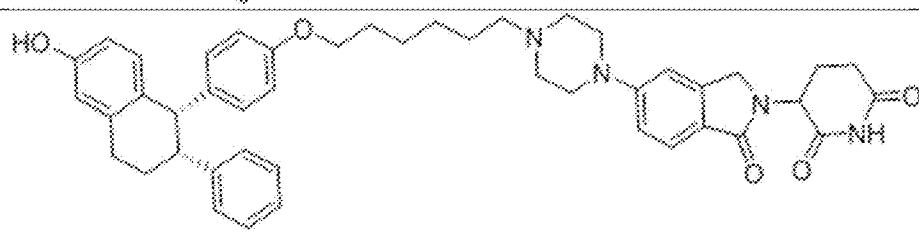 | >300 | 726.92 | 727.3 | Scheme 3-10 |

FIG. 5 Continued

| Example # | Structure | ERE Luciferase IC$_{50}$ [nM] | MW | Observed [M+H]/z | Synthetic Method |
|---|---|---|---|---|---|
| 67 | 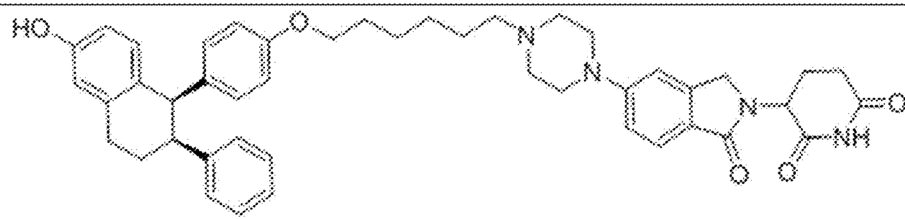 | 0.7 | 726.92 | 727.3 | Scheme 3-10 |
| 68 | 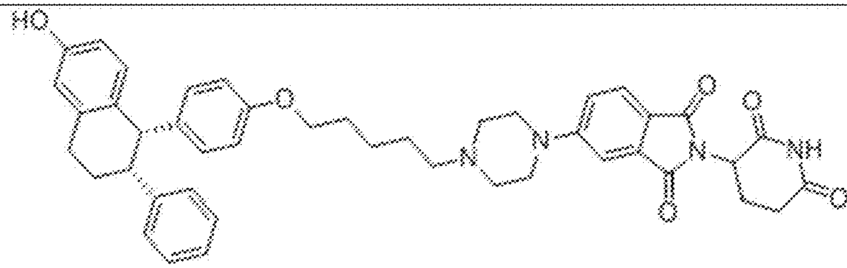 | >300 | 726.87 | 727.3 | Scheme 3-10 |
| 69 | 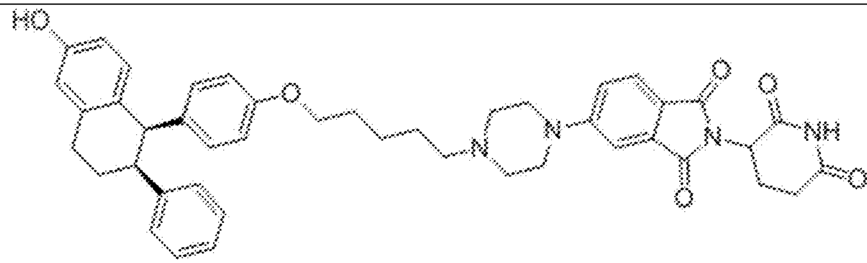 | 2.21 | 726.87 | 727.3 | Scheme 3-10 |

FIG. 5 Continued

| Example # | Structure | ERE Luciferase IC₅₀ [nM] | MW | Observed [M+H]/z | Synthetic Method |
|---|---|---|---|---|---|
| 70 | 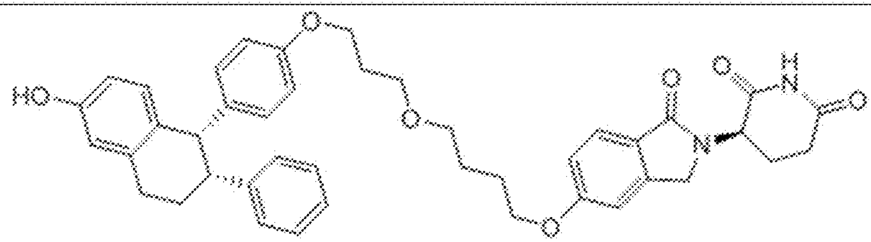 | >300 | 688.82 | 689.3 | Scheme 3-16 |
| 71 | 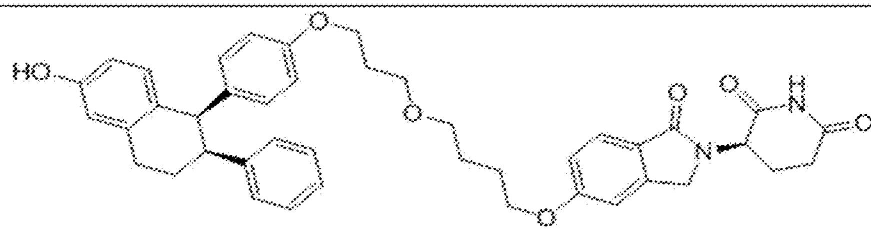 | 2.1 | 688.82 | 689.3 | Scheme 3-16 |
| 72 | 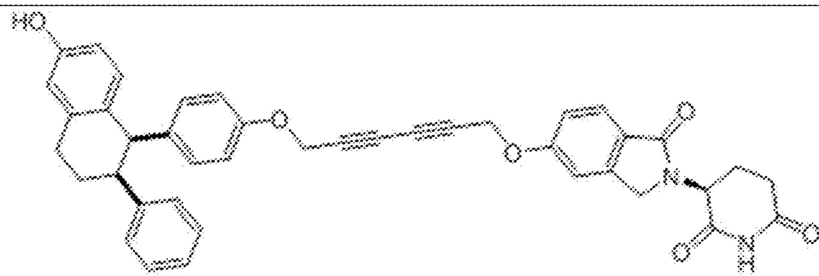 | 9.5 | 650.73 | 651.2 | Scheme 3-17 |

FIG. 5 Continued

| Example # | Structure | ERE Luciferase IC$_{50}$ [nM] | MW | Observed [M+H]/z | Synthetic Method |
|---|---|---|---|---|---|
| 73 | 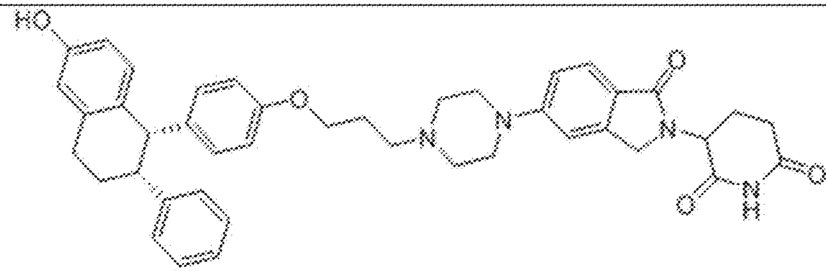 | 157 | 684.84 | 685.3 | Scheme 3-10 |
| 74 | 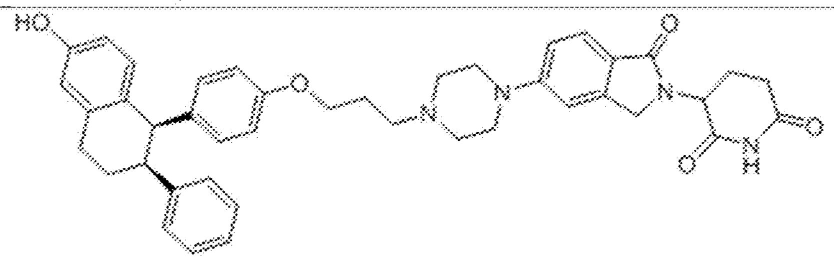 | 0.4 | 684.84 | 685.3 | Scheme 3-10 |
| 75 | 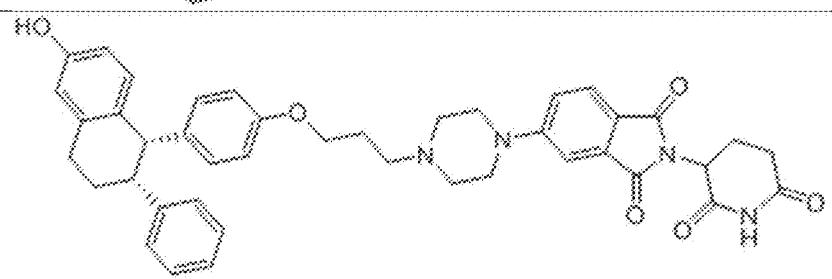 | >300 | 698.82 | 699.3 | Scheme 3-10 |

FIG. 5 Continued

| Example # | Structure | ERE Luciferase IC$_{50}$ [nM] | MW | Observed [M+H]/z | Synthetic Method |
|---|---|---|---|---|---|
| 76 | 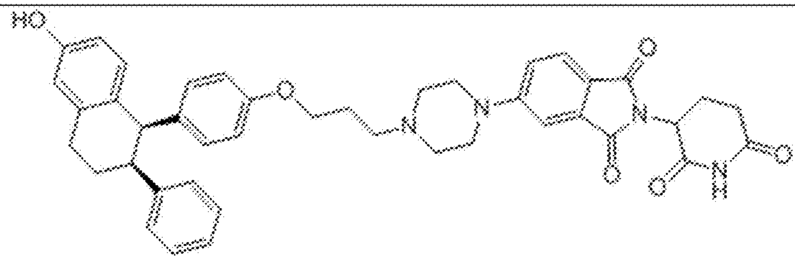 | 1.8 | 698.82 | 699.3 | Scheme 3-10 |
| 77 | 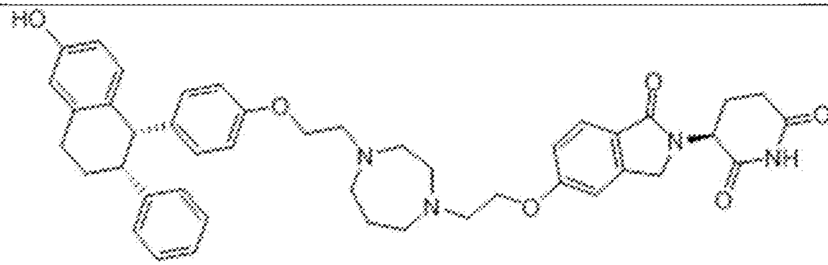 | 57 | 728.89 | 729.4 | Scheme 3-5 |
| 78 | 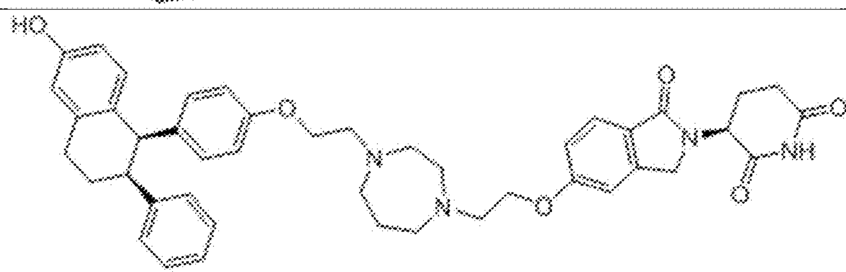 | 0.2 | 728.89 | 729.4 | Scheme 3-5 |

FIG. 5 Continued

| Example # | Structure | ERE Luciferase IC$_{50}$ [nM] | MW | Observed [M+H]/Z | Synthetic Method |
|---|---|---|---|---|---|
| 79 | 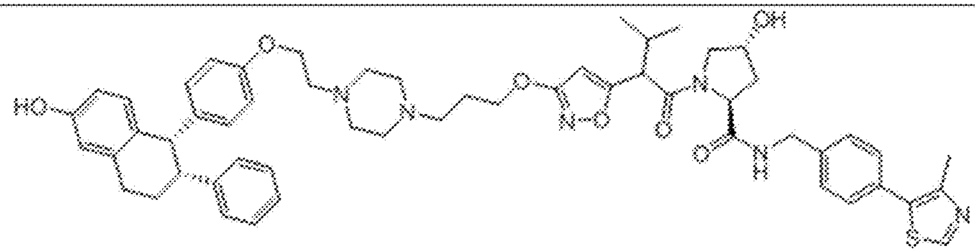 | >300 | 953.21 | 953.4 | Scheme 3-18 |
| 80 | 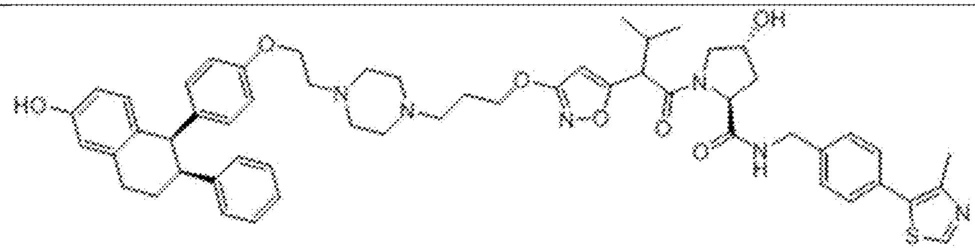 | 0.46 | 953.21 | 953.4 | Scheme 3-18 |
| 81 | 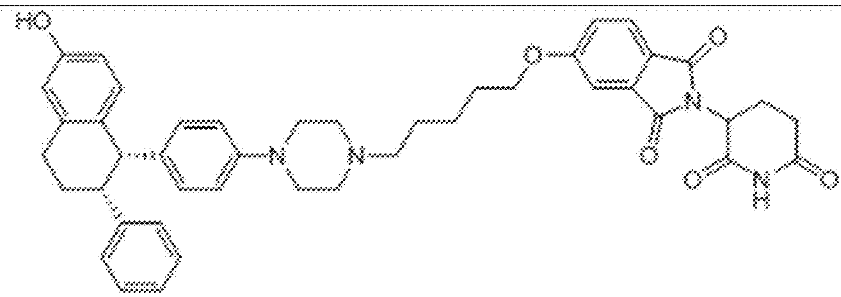 | >300 | 726.87 | 727.3 | Scheme 3-21 |

FIG. 5 Continued

| Example # | Structure | ERE Luciferase IC$_{50}$ [nM] | MW | Observed [M+H]/z | Synthetic Method |
|---|---|---|---|---|---|
| 82 | 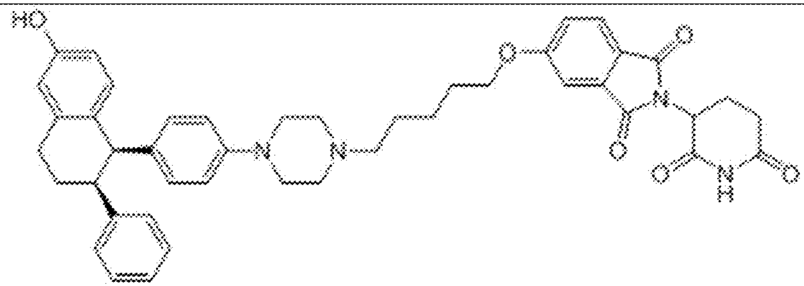 | 0.41 | 726.87 | 727.3 | Scheme 3-21 |
| 83 | 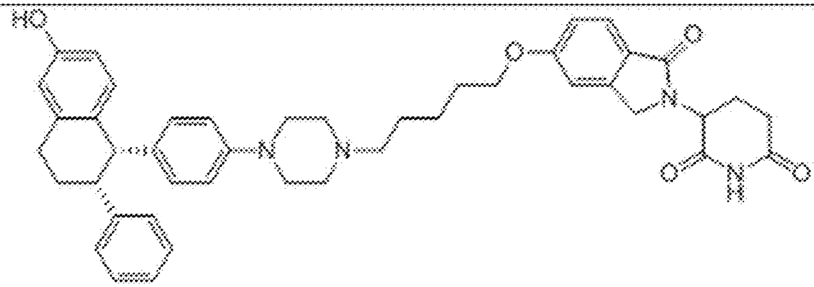 | >300 | 712.89 | 713.4 | Scheme 3-19 |
| 84 | 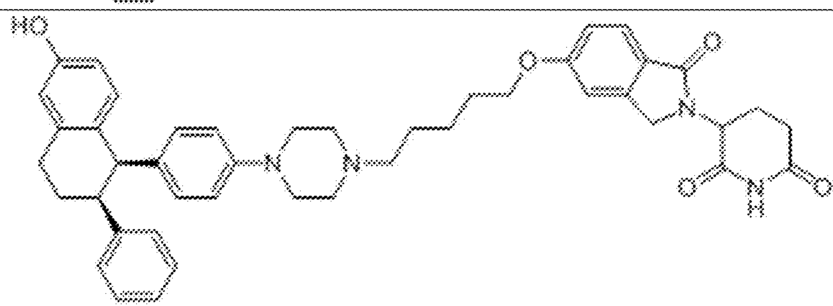 | | 712.89 | 713.4 | Scheme 3-19 |

FIG. 5 Continued

| Example # | Structure | ERE Luciferase IC$_{50}$ [nM] | MW | Observed [M+H]/z | Synthetic Method |
|---|---|---|---|---|---|
| 85 | 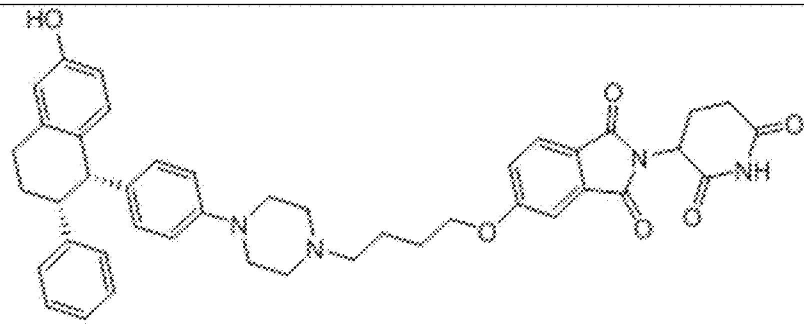 | >300 | 712.85 | 713.3 | Scheme 3-21 |
| 86 | 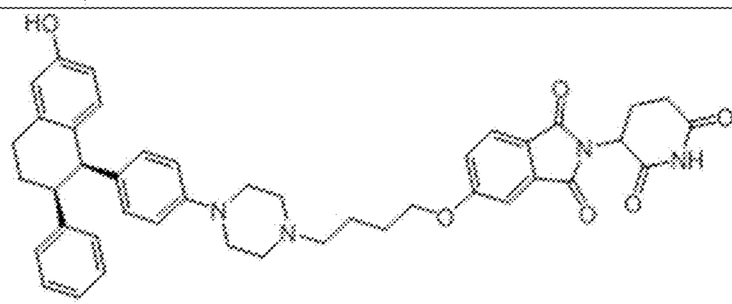 | 0.27 | 712.85 | 713.3 | Scheme 3-21 |
| 87 | 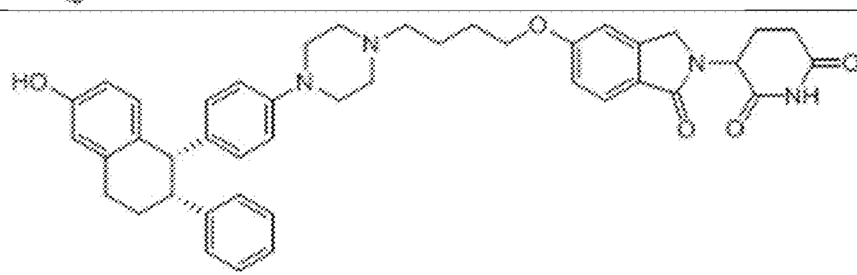 | | 698.86 | 699.3 | Scheme 3-19 |

FIG. 5 Continued
| Example # | Structure | ERE Luciferase IC$_{50}$ [nM] | MW | Observed [M+H]/z | Synthetic Method |
|---|---|---|---|---|---|
| 88 | 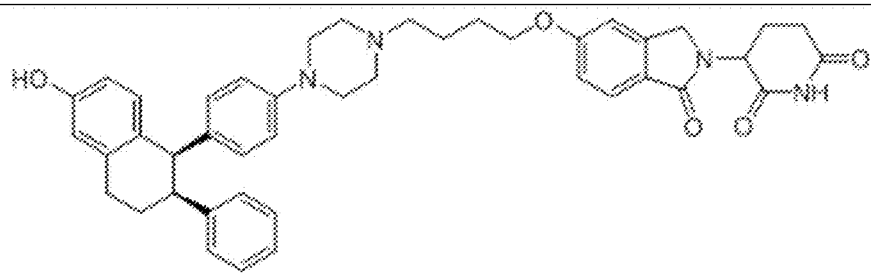 | 0.1 | 698.86 | 699.3 | Scheme 3-19 |
| 89 | 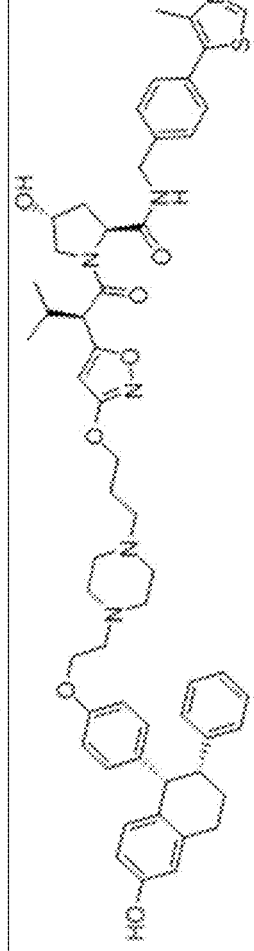 | >300 | 953.21 | 953.4 | Scheme 3-18 |
| 90 | 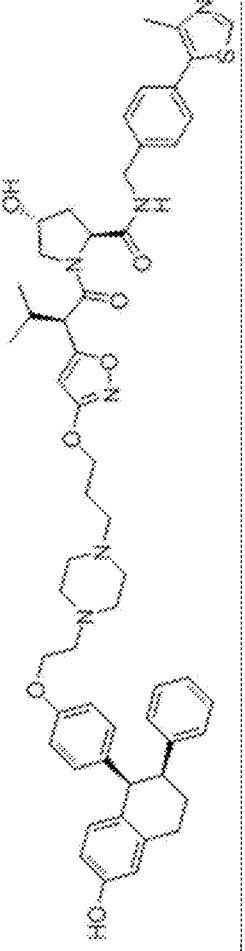 | 2 | 953.21 | 953.4 | Scheme 3-18 |

FIG. 5 Continued

| Example # | Structure | ERE Luciferase IC$_{50}$ [nM] | MW | Observed [M+H]/z | Synthetic Method |
|---|---|---|---|---|---|
| 91 | 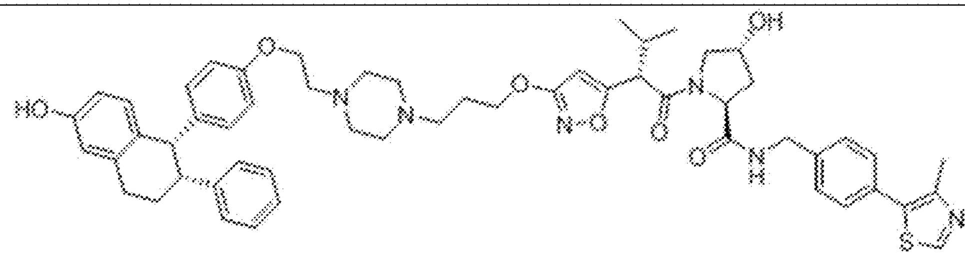 | >300 | 953.21 | 953.4 | Scheme 3-18 |
| 92 | 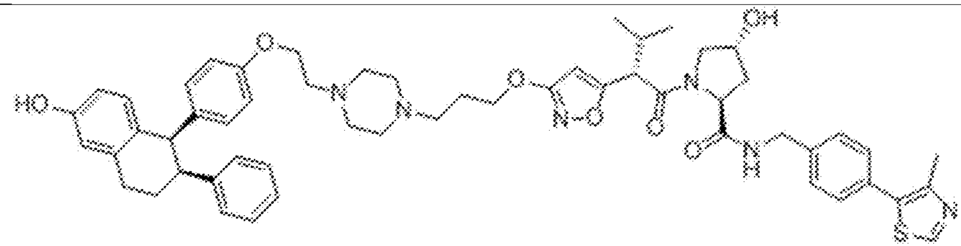 | 1.1 | 953.21 | 953.4 | Scheme 3-18 |
| 93 | 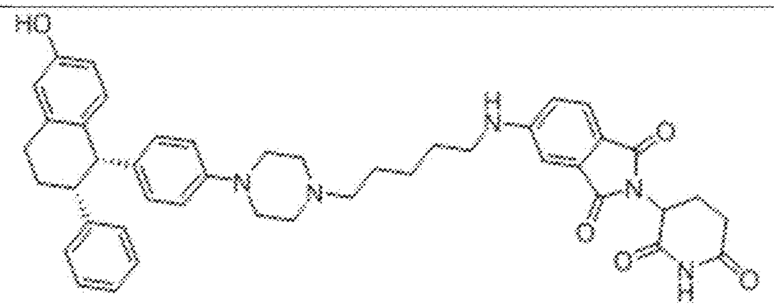 | >300 | 725.89 | 726.3 | Scheme 3-20 |

FIG. 5 Continued

| Example # | Structure | ERE Luciferase IC₅₀ [nM] | MW | Observed [M+H]/z | Synthetic Method |
|---|---|---|---|---|---|
| 94 | 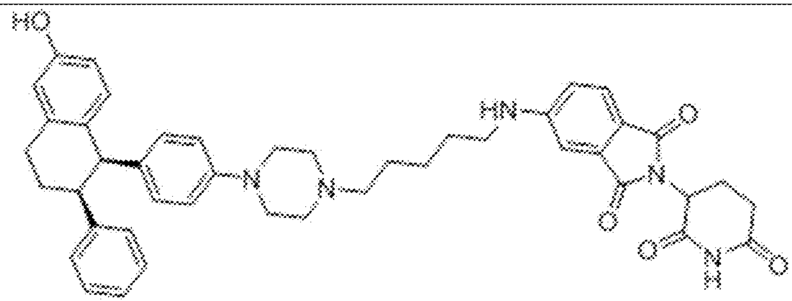 | 1.1 | 725.89 | 726.3 | Scheme 3-20 |
| 95 | 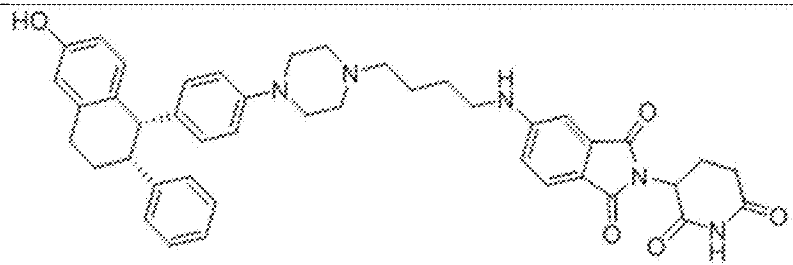 | >300 | 711.86 | 712.3 | Scheme 3-20 |
| 96 | 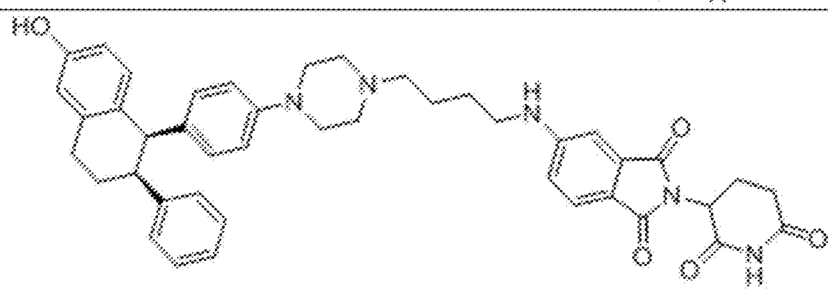 | 0.58 | 711.86 | 712.3 | Scheme 3-20 |

FIG. 5 Continued

| Example # | Structure | ERE Luciferase IC$_{50}$ [nM] | MW | Observed [M+H]/z | Synthetic Method |
|---|---|---|---|---|---|
| 97 | 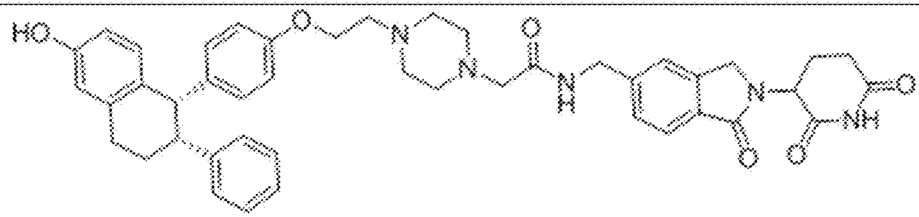 | >300 | 741.89 | 742.3 | Scheme 3-22 |
| 98 | 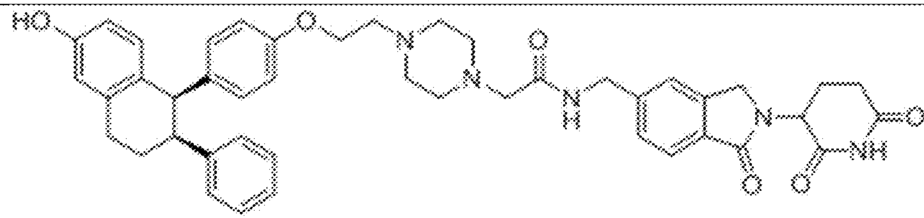 | 0.55 | 741.89 | 742.3 | Scheme 3-22 |
| 99 | 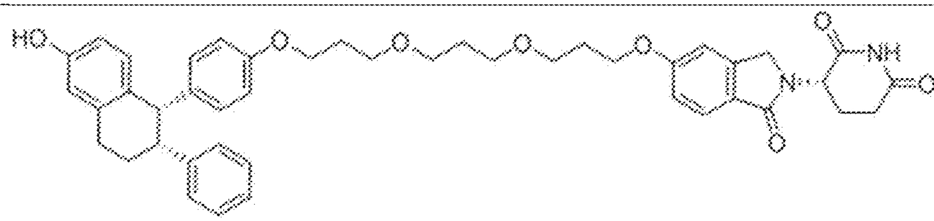 | >300 | 732.87 | 733.3 | Scheme 3-16 |
| 100 | 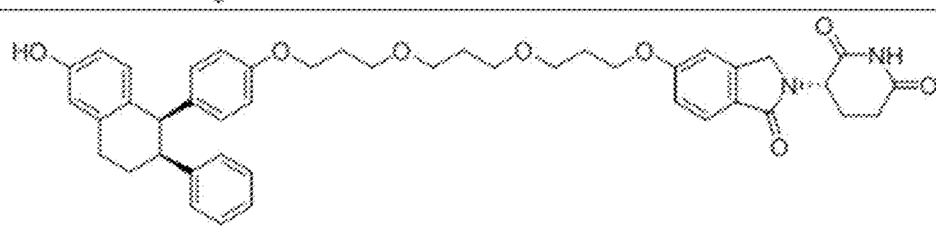 | 3.19 | 732.87 | 733.3 | Scheme 3-16 |

FIG. 5 Continued
| Example # | Structure | ERE Luciferase IC$_{50}$ [nM] | MW | Observed [M+H]/z | Synthetic Method |
|---|---|---|---|---|---|
| 101 | 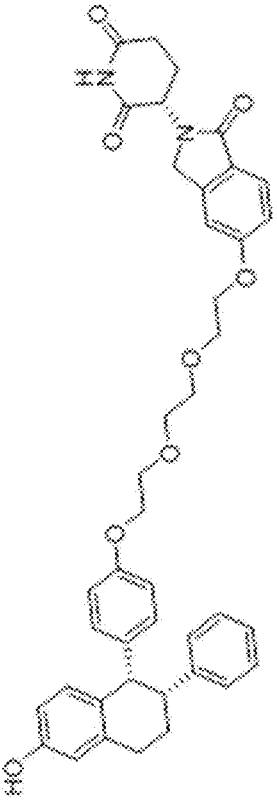 | >300 | 690.79 | 691.3 | Scheme 3-16 |
| 102 | 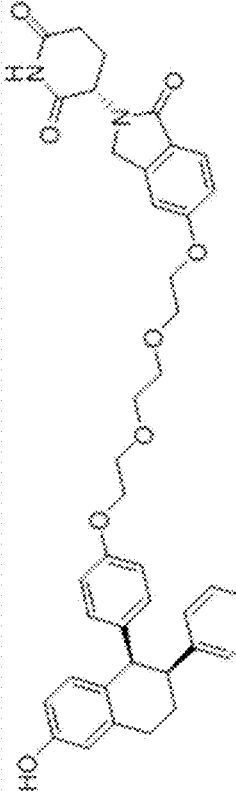 | 1.26 | 690.79 | 691.3 | Scheme 3-16 |
| 103 | 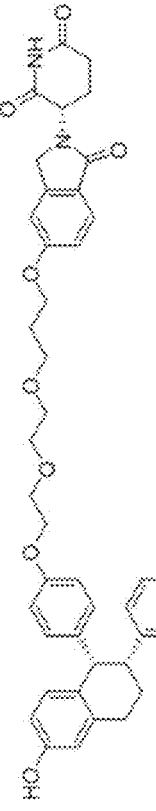 | >300 | 704.82 | 705.3 | Scheme 3-16 |
| 104 | 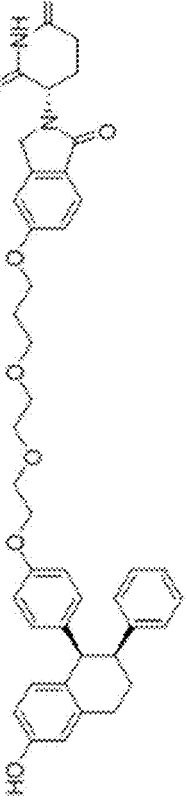 | 1.56 | 704.82 | 705.3 | Scheme 3-16 |

FIG. 5 Continued
| Example # | Structure | ERE Luciferase IC$_{50}$ [nM] | MW | Observed [M+H]/z | Synthetic Method |
|---|---|---|---|---|---|
| 105 | 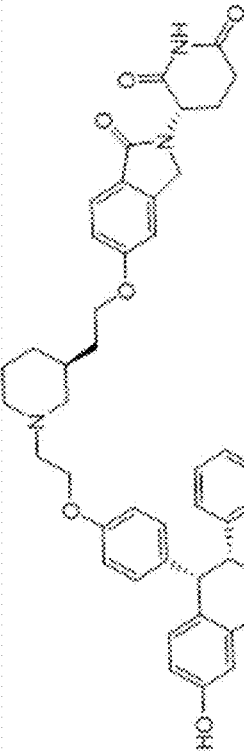 | 82 | 713.88 | 714.3 | Scheme 3-23 |
| 106 | 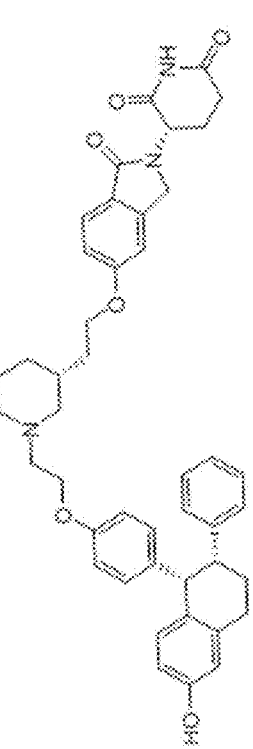 | 59 | 713.88 | 714.3 | Scheme 3-23 |
| 107 | 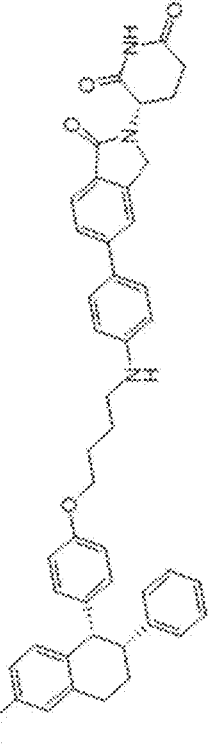 | >300 | 705.86 | 706.3 | Scheme 3-8 |

FIG. 5 Continued

| Example # | Structure | ERE Luciferase IC$_{50}$ [nM] | MW | Observed [M+H]/z | Synthetic Method |
|---|---|---|---|---|---|
| 108 | 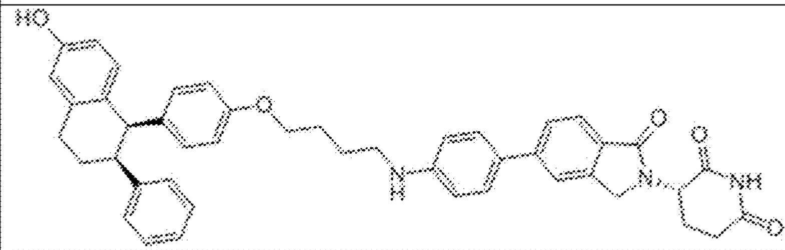 | 5.8 | 705.86 | 706.3 | Scheme 3-8 |
| 109 | 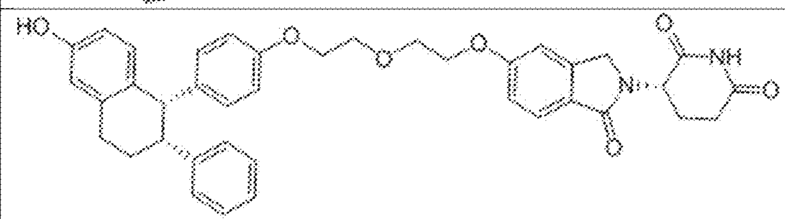 | 6.8 | 646.74 | 647.2 | Scheme 3-16 |
| 110 | 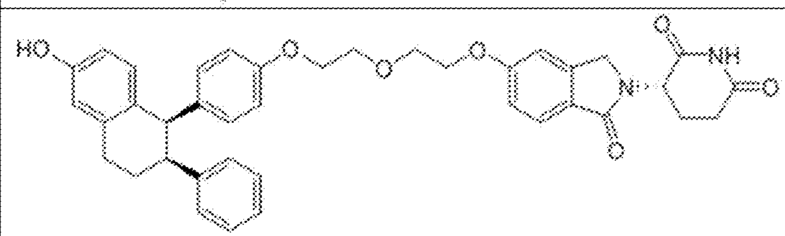 | 1.1 | 646.74 | 647.2 | Scheme 3-16 |

FIG. 5 Continued

| Example # | Structure | ERE Luciferase IC$_{50}$ [nM] | MW | Observed [M+H]/z | Synthetic Method |
|---|---|---|---|---|---|
| 111 | 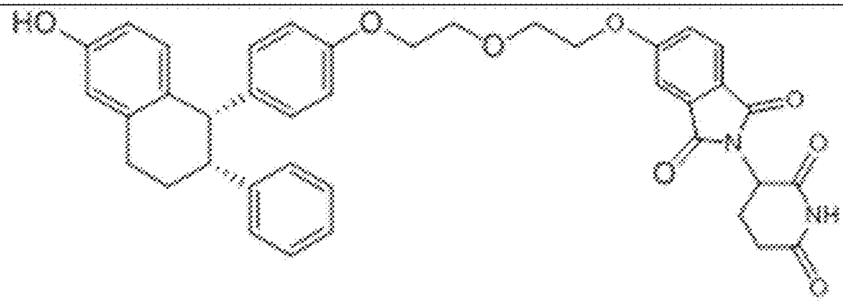 | >300 | 660.72 | 661.2 | Scheme 3-25 |
| 112 | 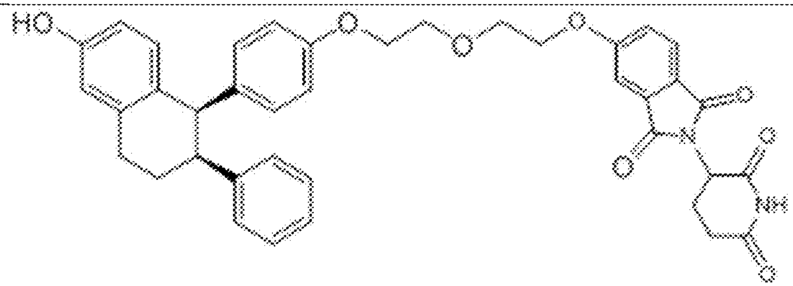 | 1.9 | 660.72 | 661.2 | Scheme 3-25 |
| 113 | 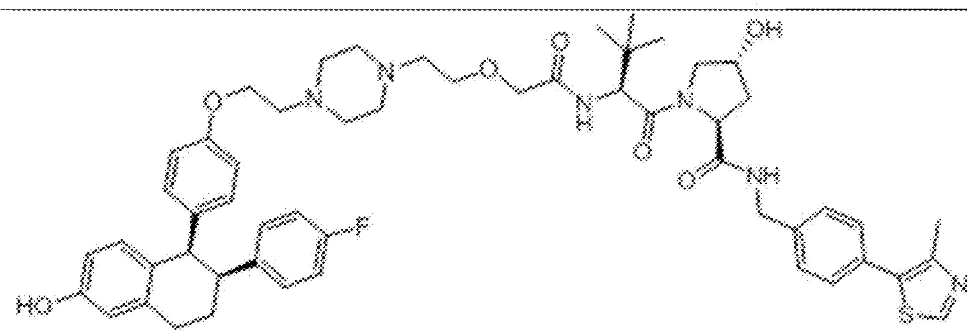 | | 961.21 | | |

FIG. 5 Continued

| Example # | Structure | ERE Luciferase IC$_{50}$ [nM] | MW | Observed [M+H]/z | Synthetic Method |
|---|---|---|---|---|---|
| 114 | 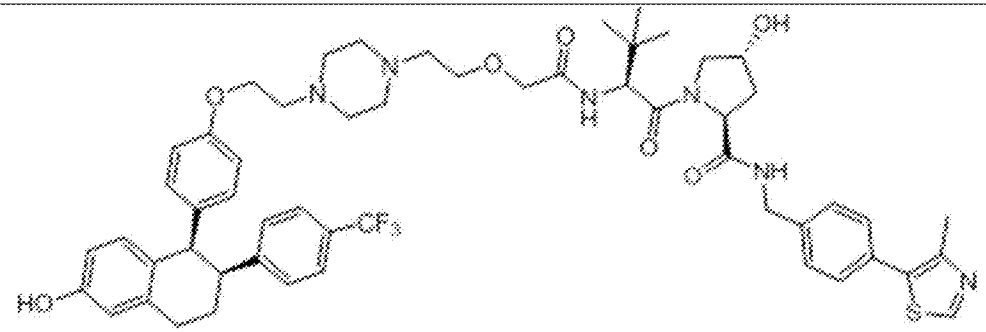 | | 1011.22 | | |
| 115 | 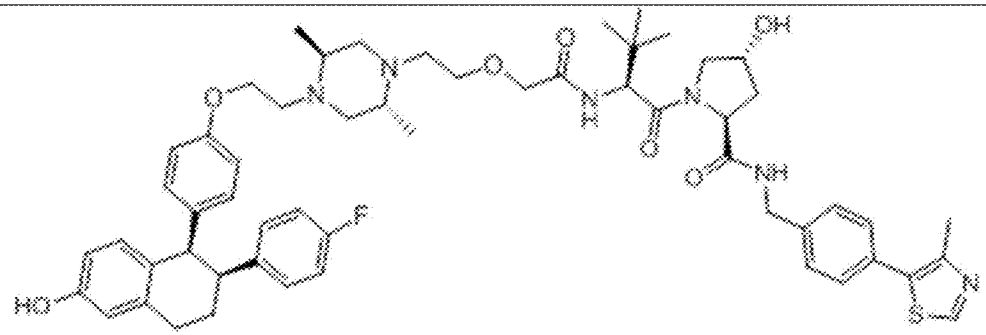 | | 989.26 | | |
| 116 | 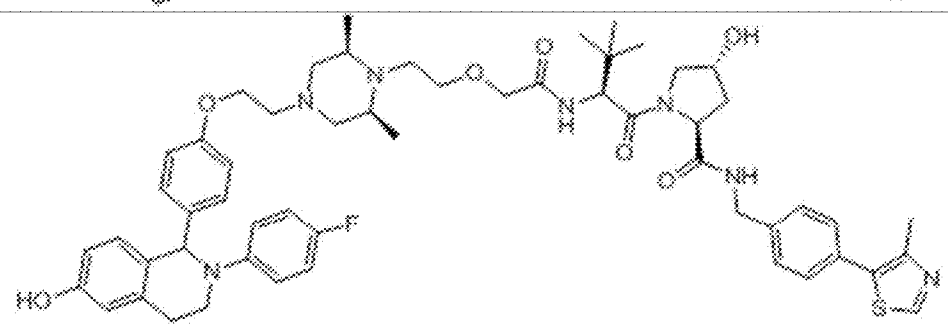 | | 990.25 | | |

FIG. 5 Continued

| Example # | Structure | ERE Luciferase IC$_{50}$ [nM] | MW | Observed [M+H]/z | Synthetic Method |
|---|---|---|---|---|---|
| 117 | 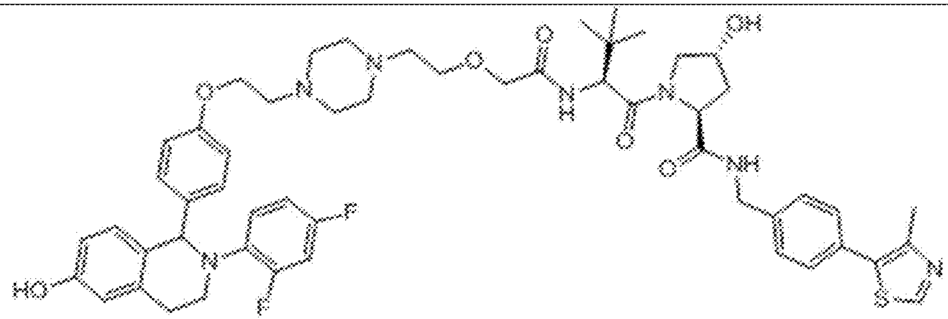 | | 980.19 | | |
| 118 | 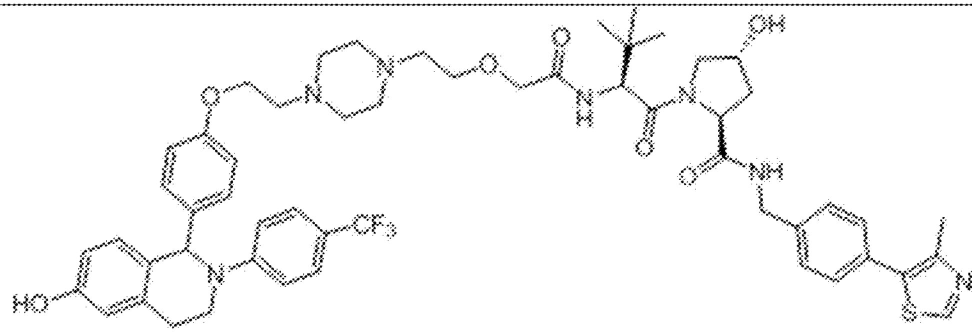 | | 1012.2 | | |
| 119 | 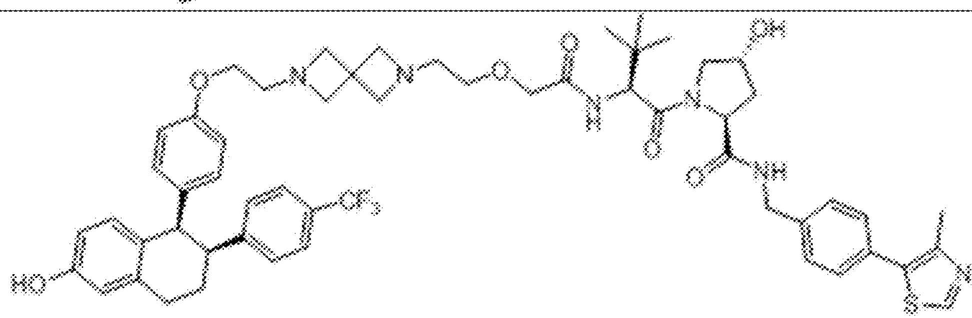 | | 1023.23 | | |

FIG. 5 Continued

| Example # | Structure | ERE Luciferase IC$_{50}$ [nM] | MW | Observed [M+H]/z | Synthetic Method |
|---|---|---|---|---|---|
| 120 | 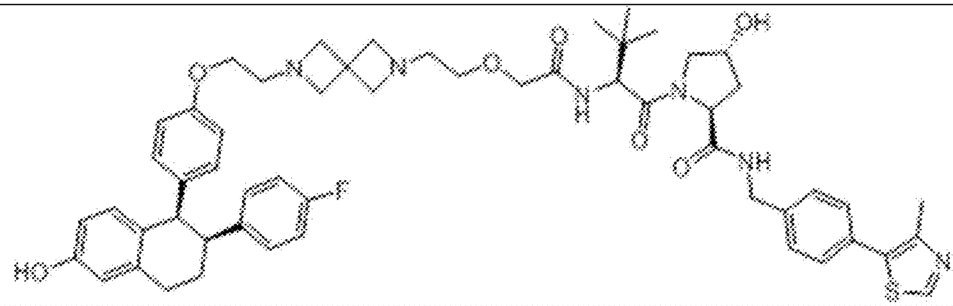 | | 973.22 | | |
| 121 | 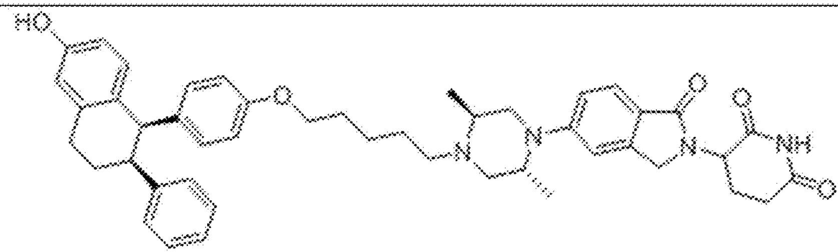 | 1.1 | 740.95 | 741.6 | Scheme 2-5, 3-10 |
| 122 | 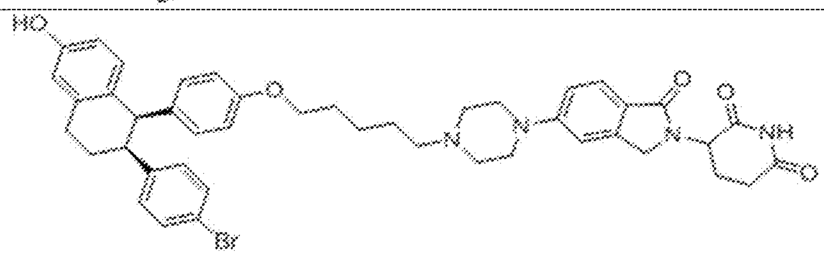 | | 791.79 | | |

FIG. 5 Continued

| Example # | Structure | ERE Luciferase IC$_{50}$ [nM] | MW | Observed [M+H]/z | Synthetic Method |
|---|---|---|---|---|---|
| 123 | 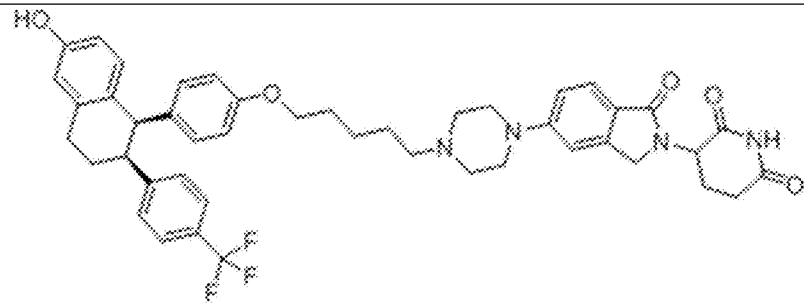 | 5.8 | 780.89 | 781.3 | Scheme 3-10 |
| 124 | 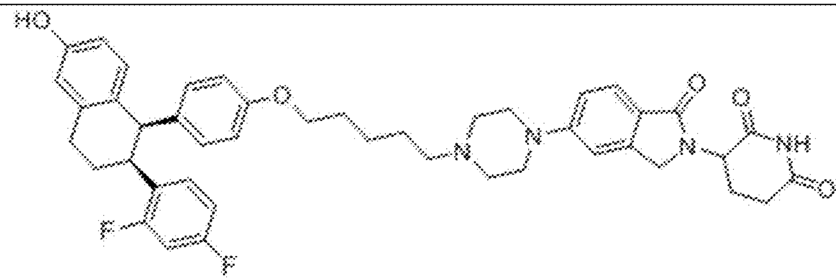 | 2.0 | 748.87 | 749.3 | Scheme 3-10 |
| 125 | 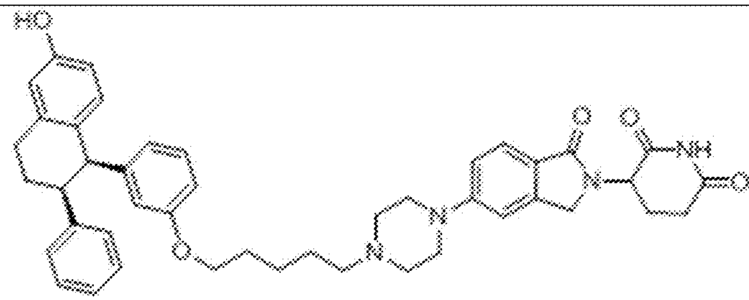 | | 712.89 | | |

FIG. 5 Continued

| Example # | Structure | ERE Luciferase IC$_{50}$ [nM] | MW | Observed [M+H]/z | Synthetic Method |
|---|---|---|---|---|---|
| 126 | 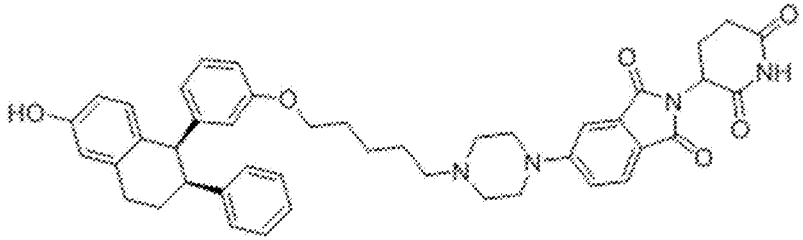 | | 726.87 | | |
| 127 | 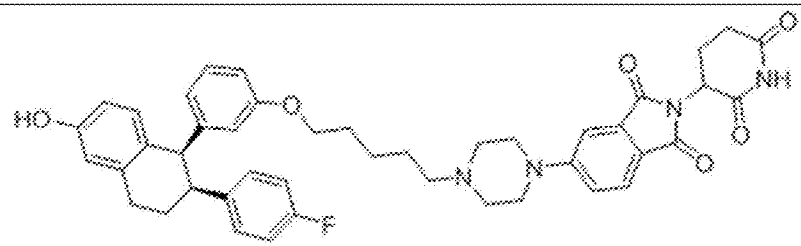 | | 744.86 | | |
| 128 | 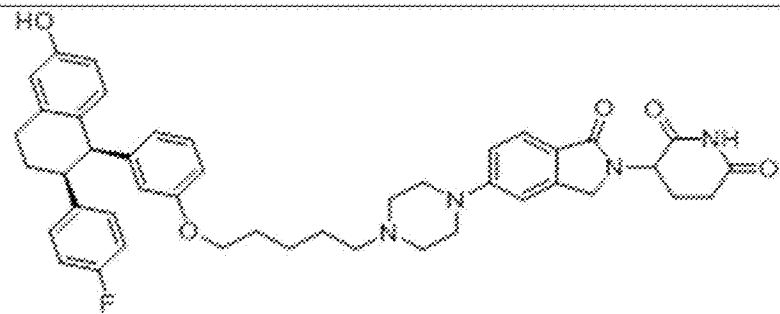 | 4.6 | 730.88 | 731.3 | Scheme 1-14, 3-26 |

FIG. 5 Continued

| Example # | Structure | ERE Luciferase IC$_{50}$ [nM] | MW | Observed [M+H]/z | Synthetic Method |
|---|---|---|---|---|---|
| 129 | 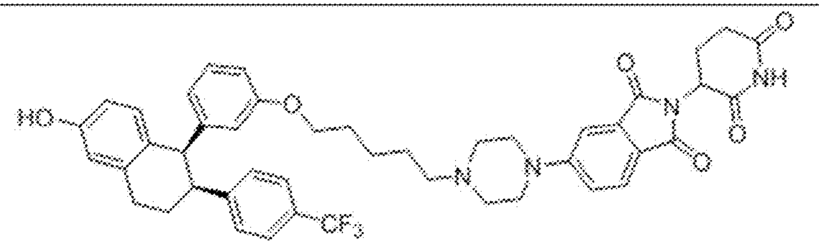 | | 794.87 | | |
| 130 | 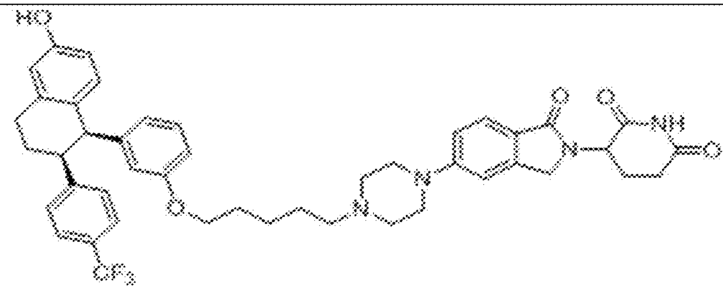 | 6.5 | 780.89 | 781.3 | Scheme 1-14, 3-26 |
| 131 | 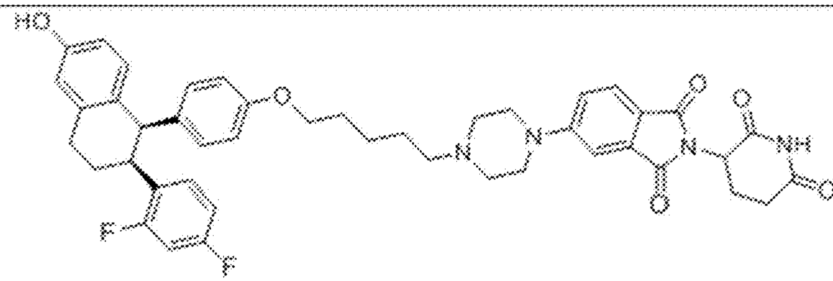 | 3.6 | 762.85 | 763.3 | Scheme 3-26 |

FIG. 5 Continued

| Example # | Structure | ERE Luciferase IC$_{50}$ [nM] | MW | Observed [M+H]/z | Synthetic Method |
|---|---|---|---|---|---|
| 132 | 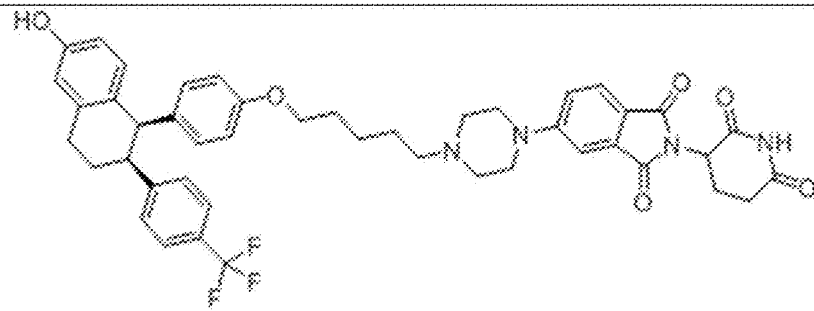 | 6.8 | 794.9 | 795.3 | Scheme 3-26 |
| 133 | 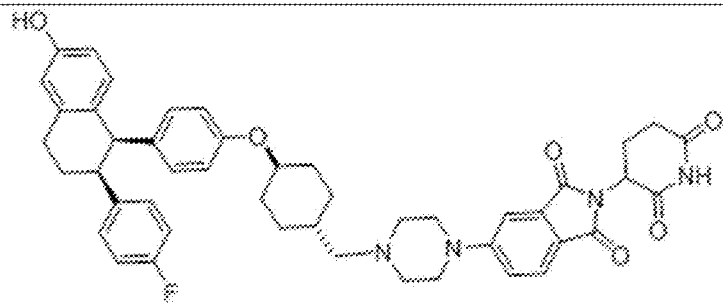 | 3.3 | 770.9 | 771.3 | Scheme 1-25, 3-10 |
| 134 | 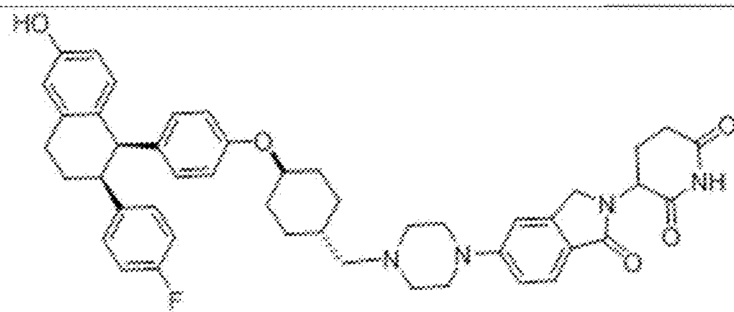 | 1.1 | 756.92 | 757.4 | Scheme 1-25, 3-10 |

FIG. 5 Continued

| Example # | Structure | ERE Luciferase IC$_{50}$ [nM] | MW | Observed [M+H]/z | Synthetic Method |
|---|---|---|---|---|---|
| 135 | 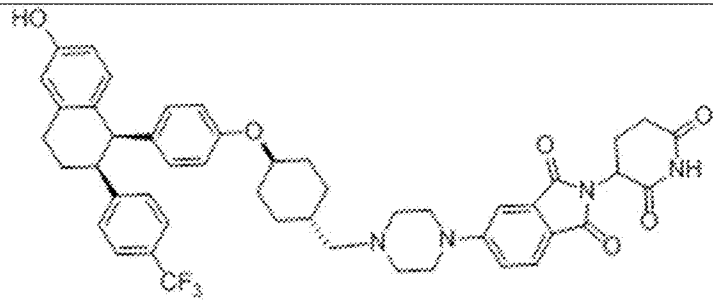 | 13.61 | 820.91 | 821.2 | Scheme 1-25, 3-10 |
| 136 | 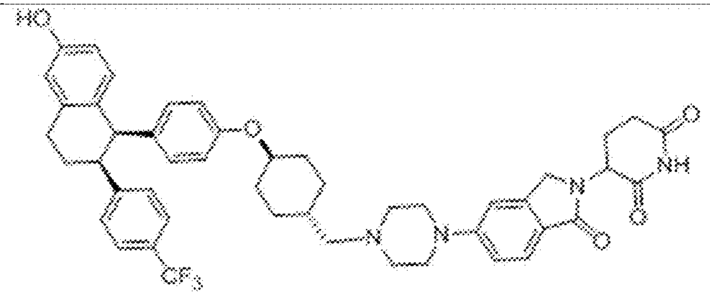 | 3.1 | 806.93 | 807.3 | Scheme 1-25, 3-10 |
| 137 | 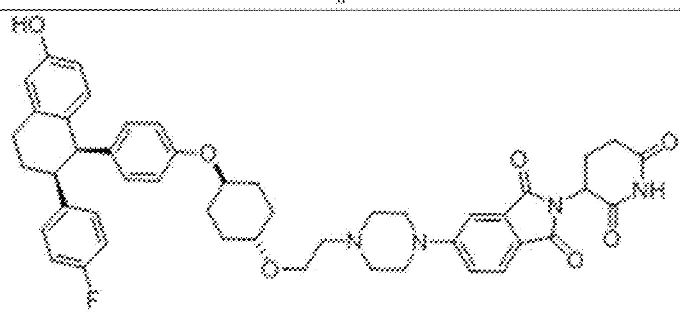 | | 800.93 | | |

FIG. 5 Continued

| Example # | Structure | ERE Luciferase IC$_{50}$ [nM] | MW | Observed [M+H]/z | Synthetic Method |
|---|---|---|---|---|---|
| 138 | 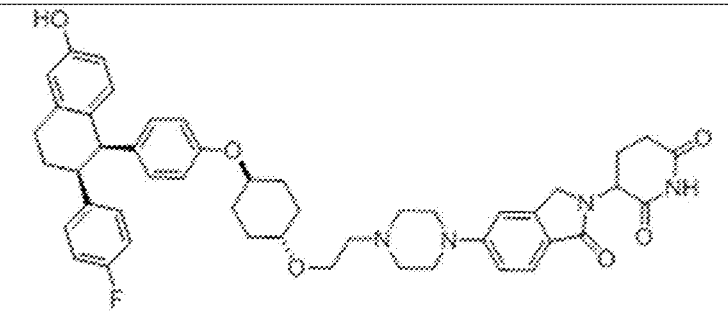 | | 786.95 | | |
| 139 | 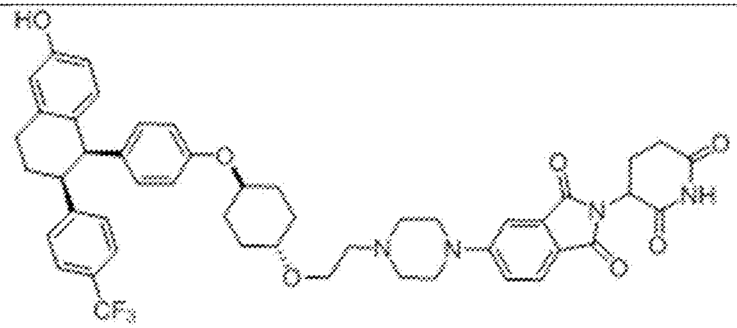 | | 850.94 | | |
| 140 | 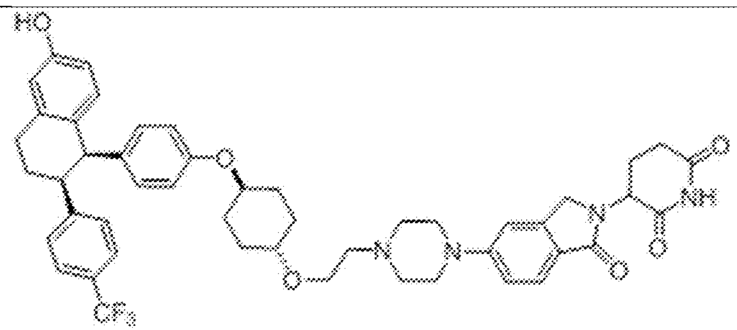 | | 836.95 | | |

FIG. 5 Continued

| Example # | Structure | ERE Luciferase IC$_{50}$ [nM] | MW | Observed [M+H]/z | Synthetic Method |
|---|---|---|---|---|---|
| 141 | 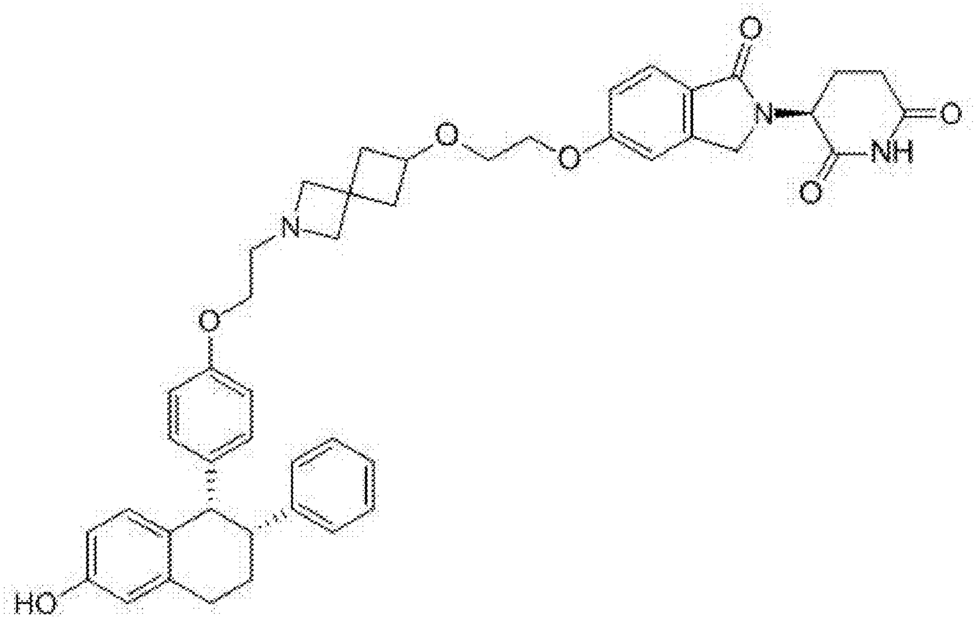 | 33 | 741.89 | 742.2 | Scheme 3-5 |
| 142 | 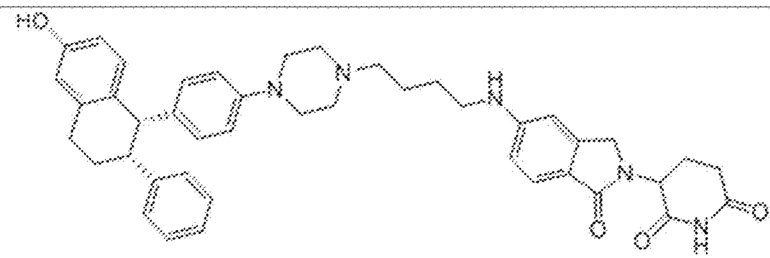 | 50 | 697.88 | 698.2 | Scheme 3-20 |

FIG. 5 Continued

| Example # | Structure | ERE Luciferase IC$_{50}$ [nM] | MW | Observed [M+H]/z | Synthetic Method |
|---|---|---|---|---|---|
| 143 | 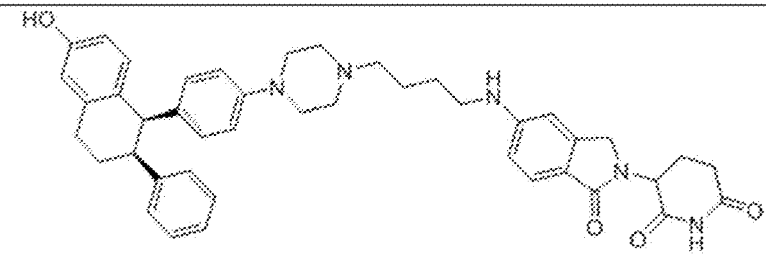 | 0.2 | 697.88 | 698.2 | Scheme 3-20 |
| 144 | 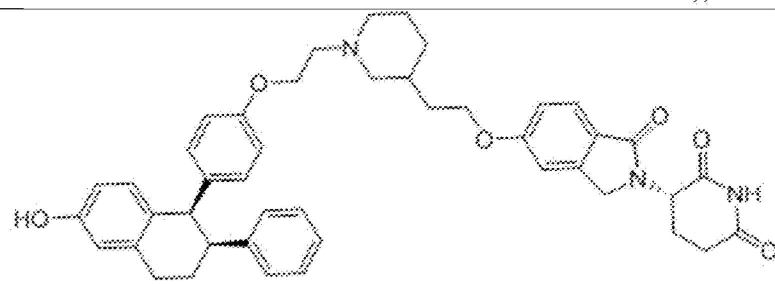 | 0.3 | 713.88 | 714.2 | Scheme 3-23 |
| 145 | 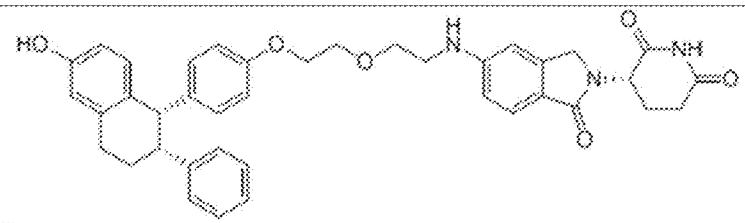 | 31 | 645.76 | 646.0 | Scheme 3-8 |
| 146 | 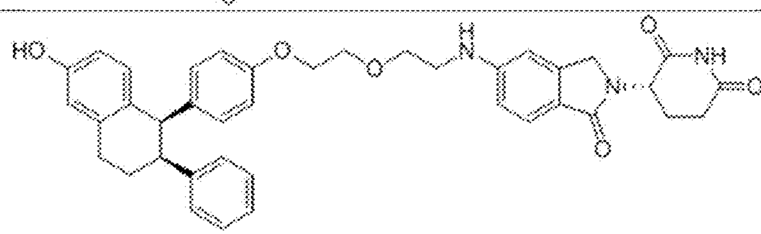 | 0.6 | 645.76 | 646.1 | Scheme 3-8 |

FIG. 5 Continued

| Example # | Structure | ERE Luciferase IC$_{50}$ [nM] | MW | Observed [M+H]/z | Synthetic Method |
|---|---|---|---|---|---|
| 147 | 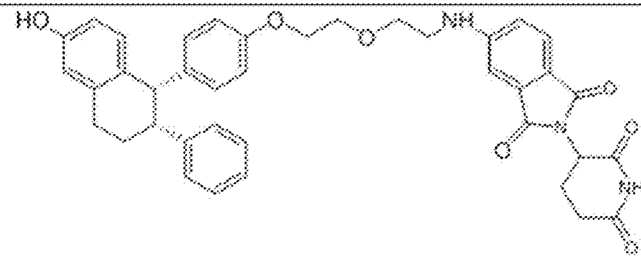 | >300 | 659.74 | 660.1 | Scheme 3-8 |
| 148 | 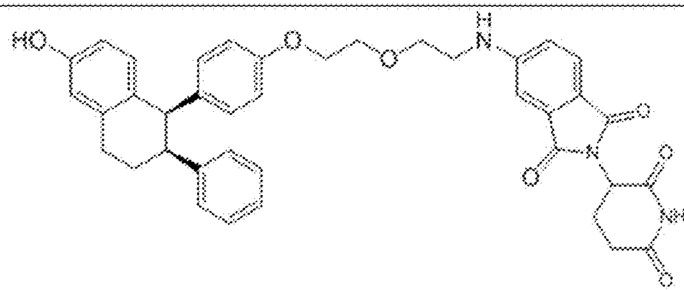 | 1.0 | 659.74 | 660.1 | Scheme 3-8 |
| 149 | 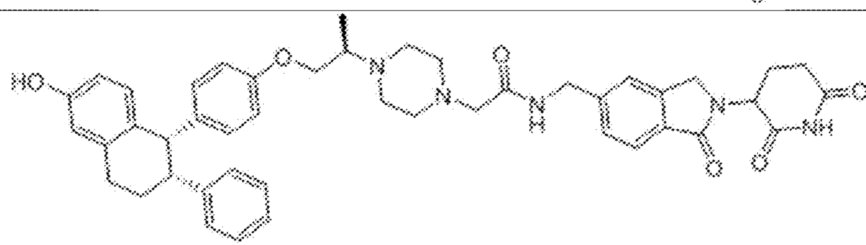 | >300 | 755.92 | 756.2 | Scheme 3-28 |

FIG. 5 Continued

| Example # | Structure | ERE Luciferase IC$_{50}$ [nM] | MW | Observed [M+H]/z | Synthetic Method |
|---|---|---|---|---|---|
| 150 | 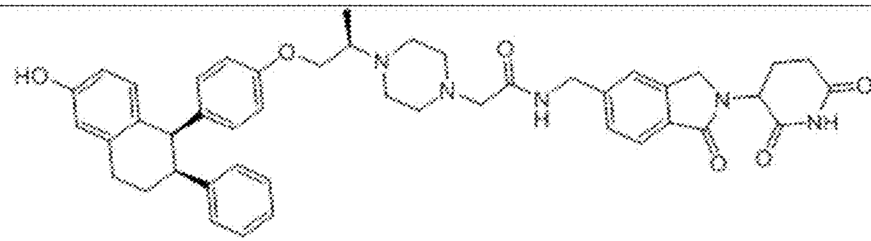 | 0.8 | 755.92 | 756.2 | Scheme 3-28 |
| 151 | 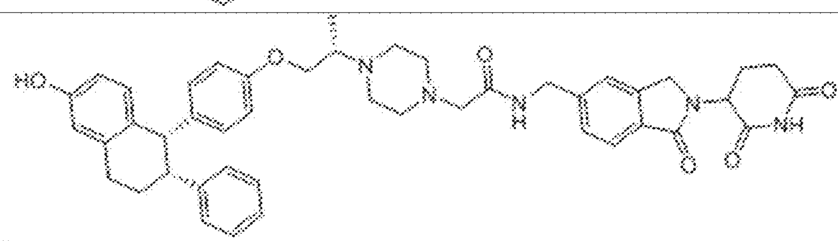 | >300 | 755.92 | 756.2 | Scheme 3-28 |
| 152 | 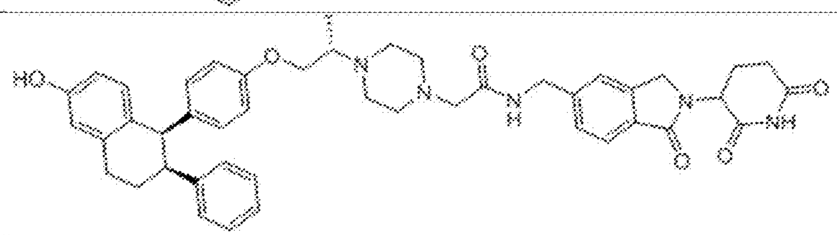 | 0.2 | 755.92 | 756.2 | Scheme 3-28 |

FIG. 5 Continued

| Example # | Structure | ERE Luciferase IC$_{50}$ [nM] | MW | Observed [M+H]/z | Synthetic Method |
|---|---|---|---|---|---|
| 153 | 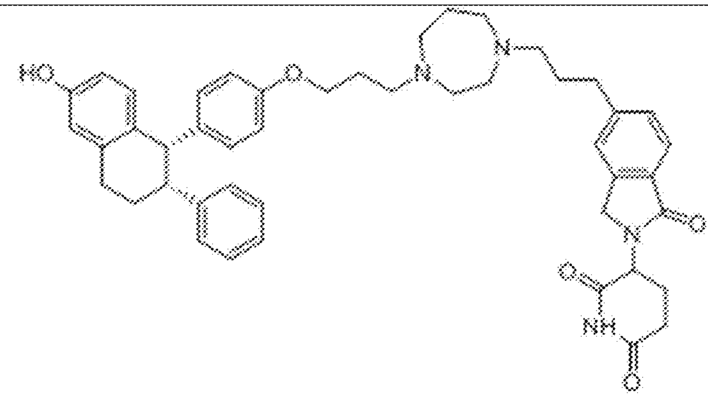 | >300 | 740.95 | 741.3 | Scheme 2-36, 3-10 |
| 154 | 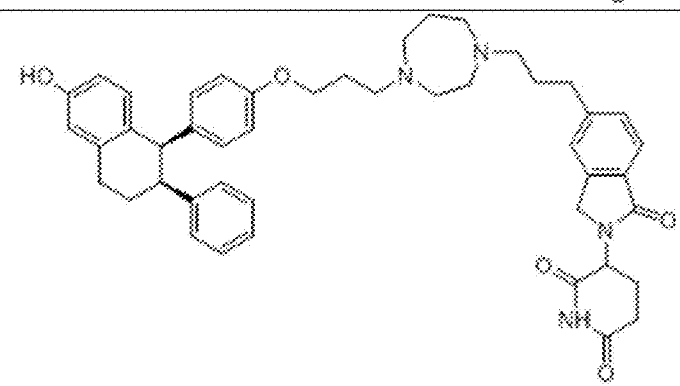 | 0.7 | 740.95 | 741.3 | Scheme 2-36, 3-10 |

FIG. 5 Continued
| Example # | Structure | ERE Luciferase IC$_{50}$ [nM] | MW | Observed [M+H]/z | Synthetic Method |
|---|---|---|---|---|---|
| 155 | 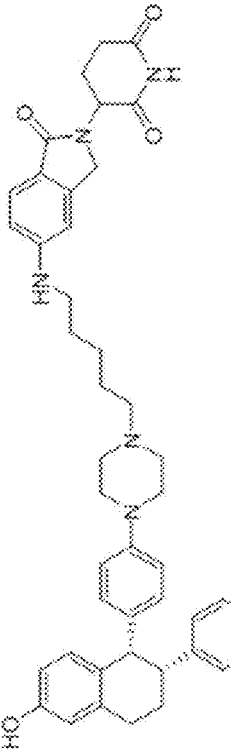 | 73 | 711.91 | 712.6 | Scheme 3-20 |
| 156 | 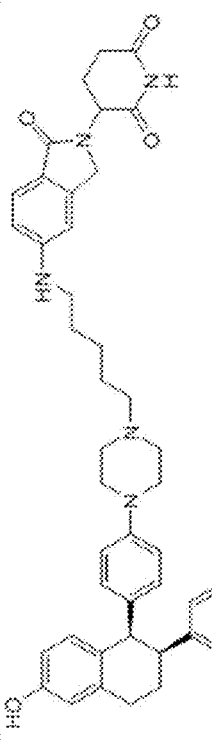 | 0.4 | 711.91 | 712.6 | Scheme 3-20 |
| 157 | 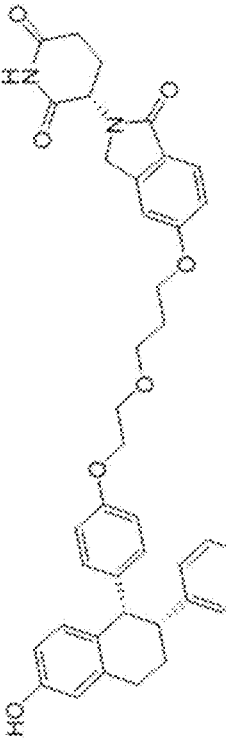 | 23 | 660.77 | 661.5 | Scheme 3-10 |

FIG. 5 Continued
| Example # | Structure | ERE Luciferase IC₅₀ [nM] | MW | Observed [M+H]/z | Synthetic Method |
|---|---|---|---|---|---|
| 158 | 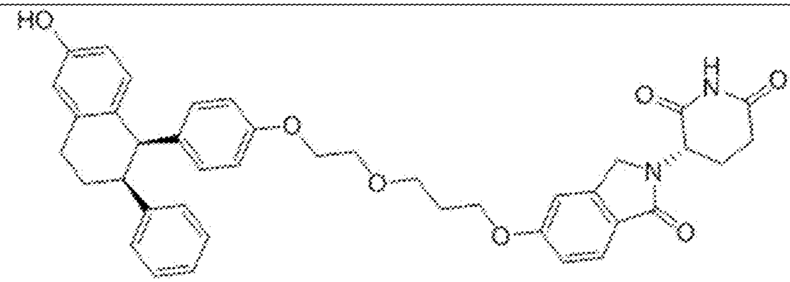 | 2.2 | 660.77 | 661.5 | Scheme 3-16 |
| 159 | 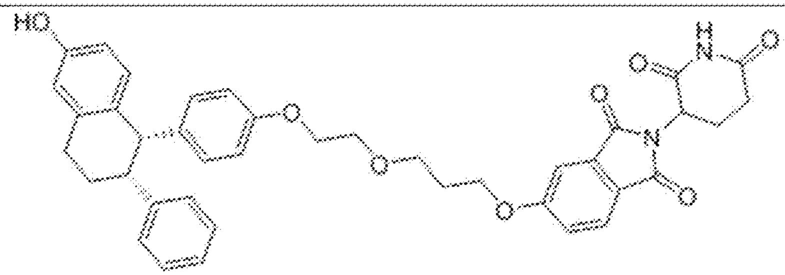 | >300 | 674.75 | 675.5 | Scheme 3-16 |
| 160 | 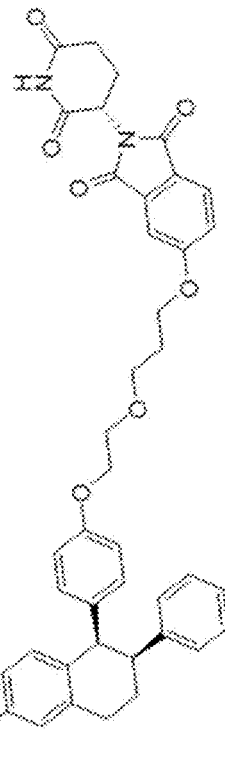 | 2.8 | 674.75 | 675.5 | Scheme 3-16 |

FIG. 5 Continued

| Example # | Structure | ERE Luciferase IC$_{50}$ [nM] | MW | Observed [M+H]/z | Synthetic Method |
|---|---|---|---|---|---|
| 161 | 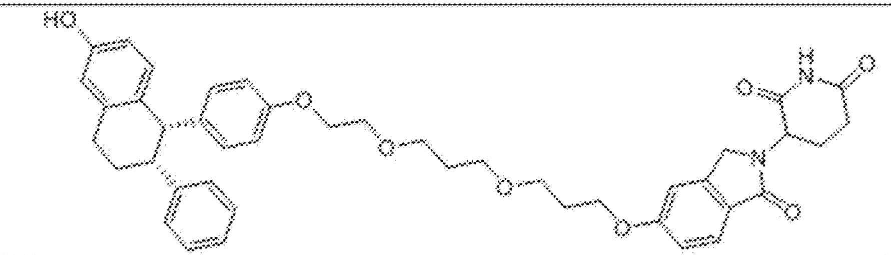 | >300 | 718.85 | 719.5 | Scheme 3-16 |
| 162 | 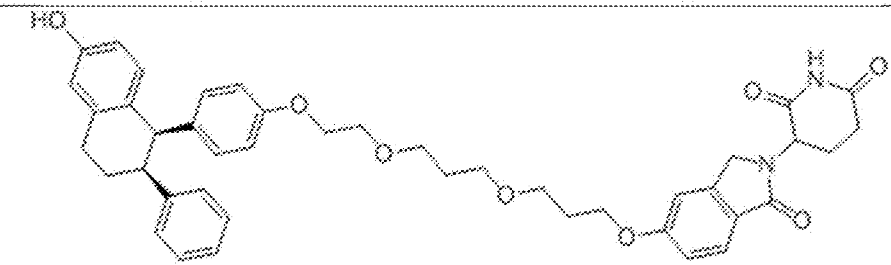 | 1.8 | 718.85 | 719.5 | Scheme 1-16 |
| 163 | 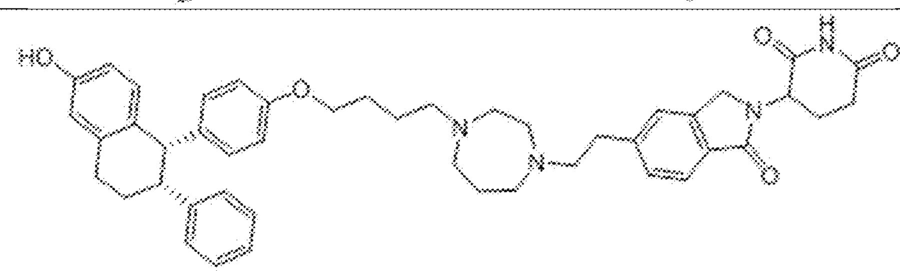 | >300 | 740.95 | 741.6 | Scheme 3-29 |

FIG. 5 Continued

| Example # | Structure | ERE Luciferase IC$_{50}$ [nM] | MW | Observed [M+H]/Z | Synthetic Method |
|---|---|---|---|---|---|
| 164 | 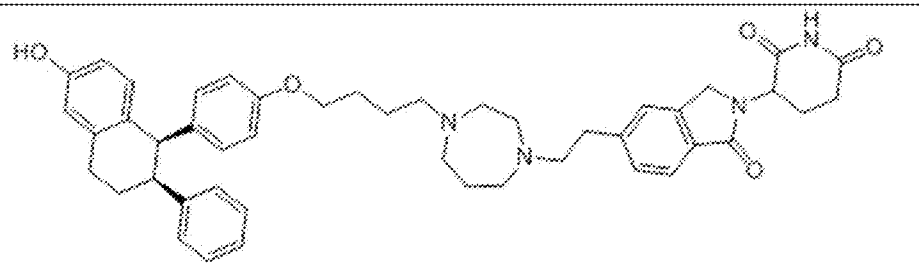 | 1.2 | 740.95 | 741.4 | Scheme 3-29 |
| 165 | 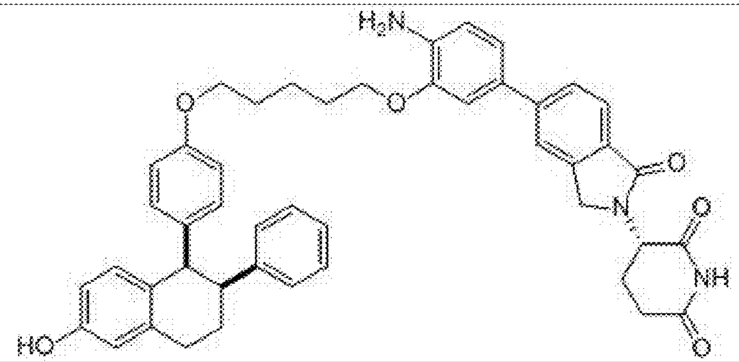 | 9.4 | 735.88 | 736.6 | Scheme 3-30 |
| 166 | 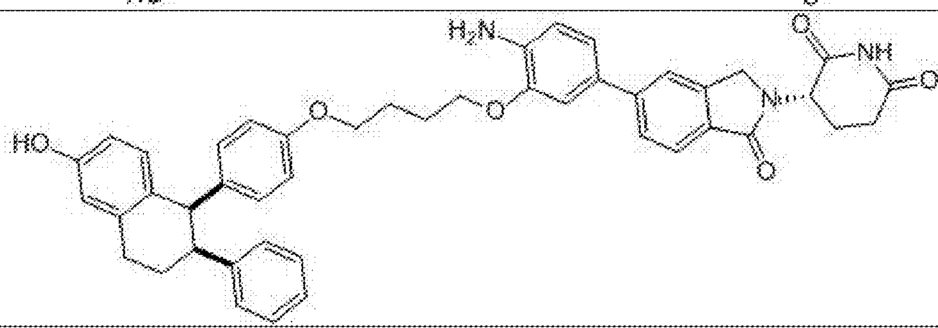 | 6.1 | 721.85 | 722.5 | Scheme 3-30 |

FIG. 5 Continued

| Example # | Structure | ERE Luciferase IC$_{50}$ [nM] | MW | Observed [M+H]/z | Synthetic Method |
|---|---|---|---|---|---|
| 167 | 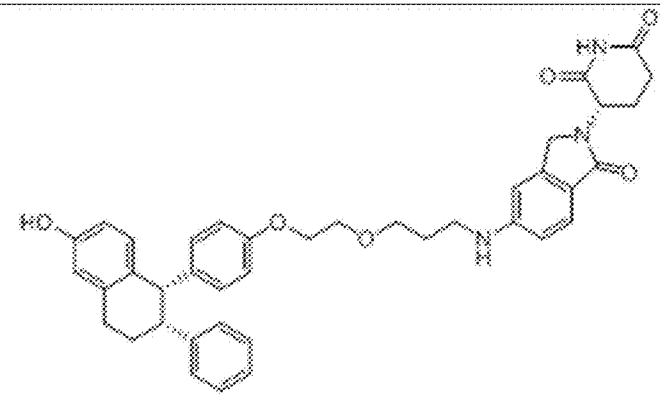 | 25 | 659.78 | 660.0 | Scheme 3-8 |
| 168 | 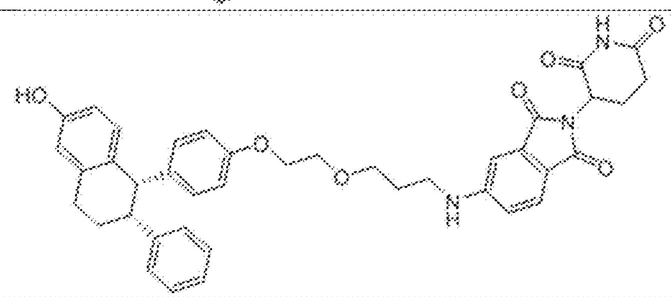 | >300 | 673.77 | 674.3 | Scheme 3-8 |

FIG. 5 Continued

| Example # | Structure | ERE Luciferase IC$_{50}$ [nM] | MW | Observed [M+H]/z | Synthetic Method |
|---|---|---|---|---|---|
| 169 | 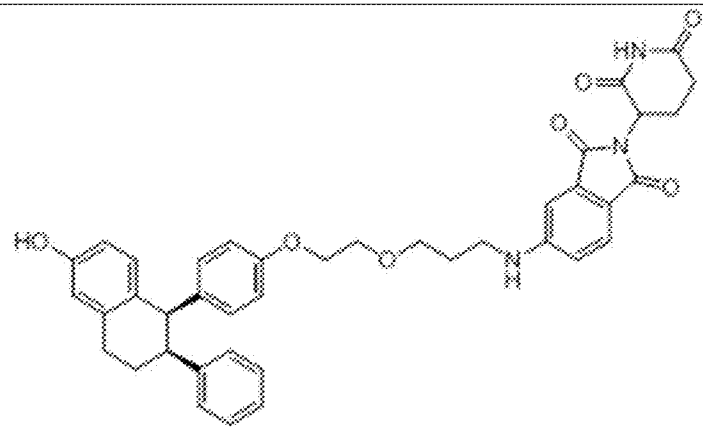 | 3.5 | 673.77 | 674.3 | Scheme 3-8 |
| 170 | 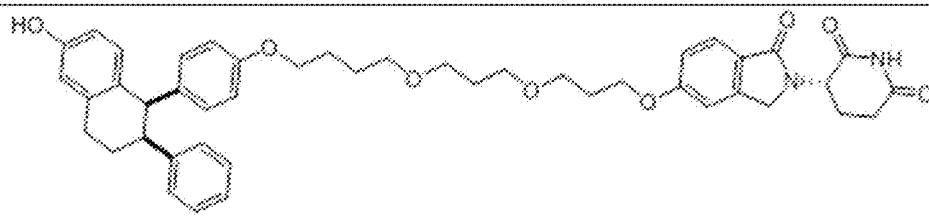 | 5.1 | 746.9 | 747.3 | Scheme 3-8 |
| 171 | 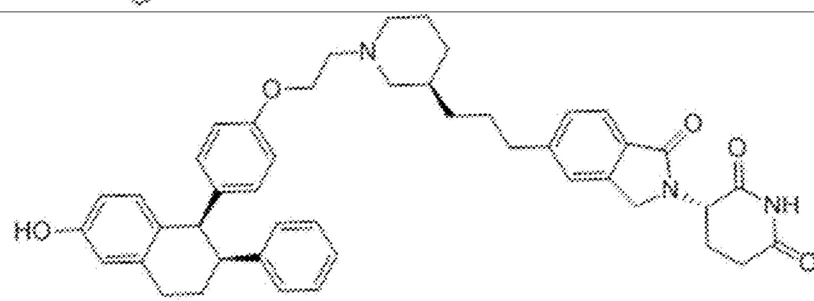 | 0.4 | 711.9 | 712.3 | Scheme 3-31 |

FIG. 5 Continued

| Example # | Structure | ERE Luciferase IC$_{50}$ [nM] | MW | Observed [M+H]/z | Synthetic Method |
|---|---|---|---|---|---|
| 172 | 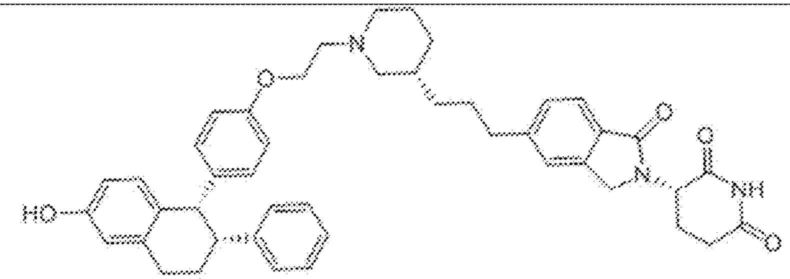 | 44 | 711.9 | 712.4 | Scheme 3-31 |
| 173 | 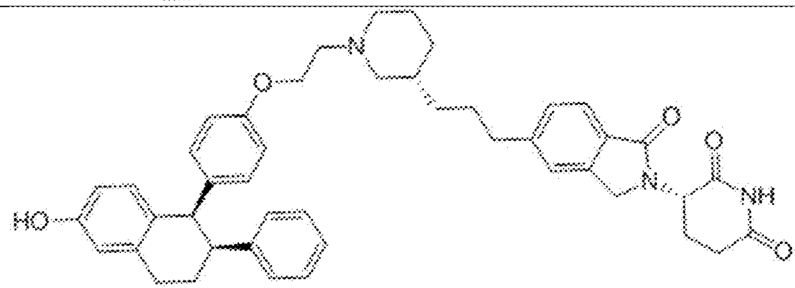 | 0.5 | 711.9 | 712.4 | Scheme 3-31 |
| 174 | 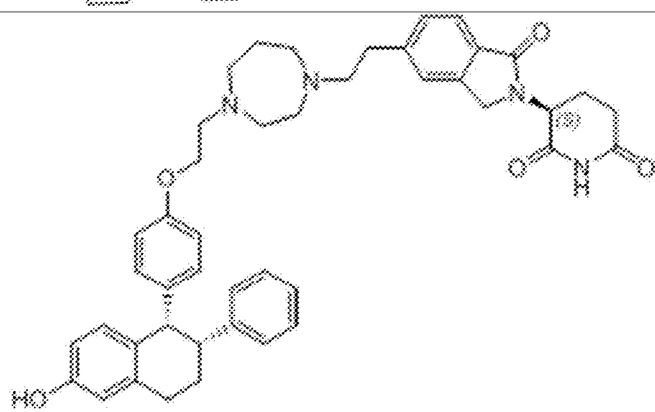 | 94 | 712.89 | 713.3 | Scheme 3-29 |

FIG. 5 Continued

| Example # | Structure | ERE Luciferase IC$_{50}$ [nM] | MW | Observed [M+H]/z | Synthetic Method |
|---|---|---|---|---|---|
| 175 | 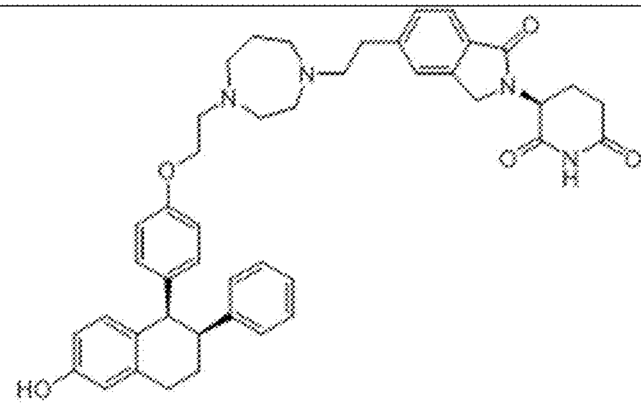 | 0.6 | 712.89 | 713.3 | Scheme 3-29 |
| 176 | 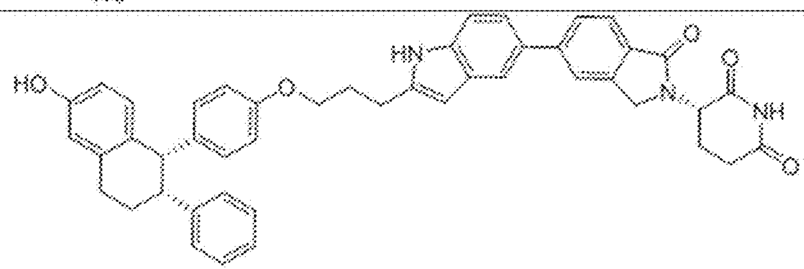 | >300 | 715.85 | 716.3 | Scheme 3-32 |
| 177 | 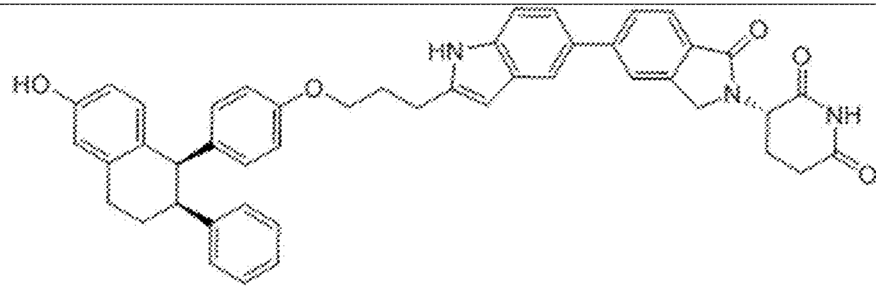 | 9.1 | 715.85 | 716.3 | Scheme 3-32 |

FIG. 5 Continued

| Example # | Structure | ERE Luciferase IC$_{50}$ [nM] | MW | Observed [M+H]/z | Synthetic Method |
|---|---|---|---|---|---|
| 178 | 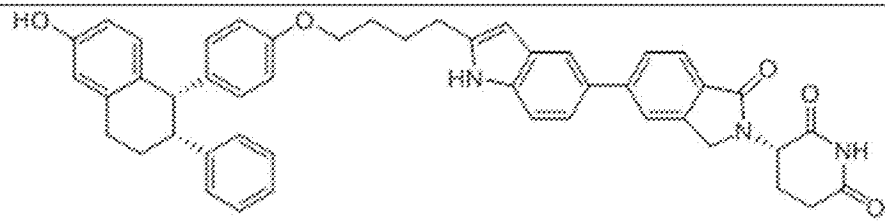 | >300 | 729.88 | 730.3 | Scheme 3-32 |
| 179 | 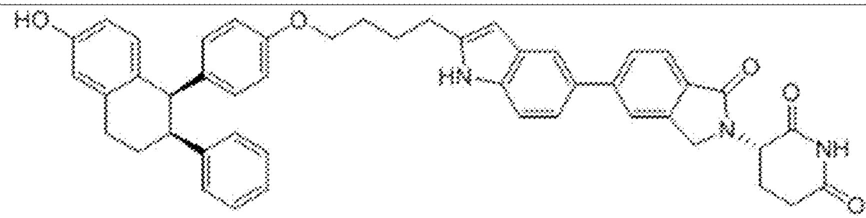 | 9.9 | 729.88 | 730.3 | Scheme 3-32 |
| 180 | 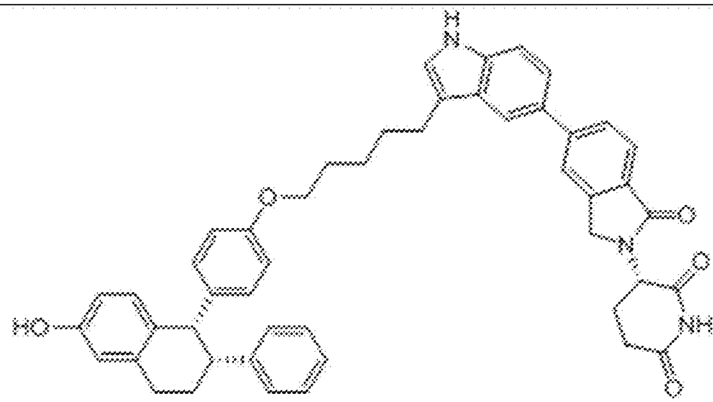 | >300 | 743.9 | 744.3 | Scheme 3-33 |

FIG. 5 Continued
| Example # | Structure | ERE Luciferase IC$_{50}$ [nM] | MW | Observed [M+H]/z | Synthetic Method |
|---|---|---|---|---|---|
| 181 | 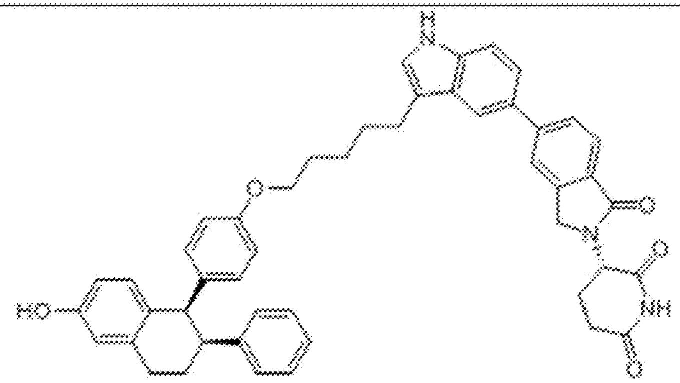 | 10 | 743.9 | 744.3 | Scheme 3-33 |
| 182 | 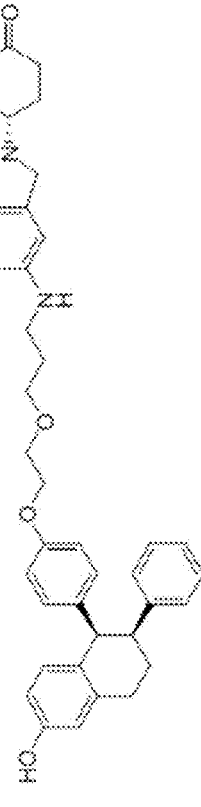 | 1.5 | 659.78 | 660.3 | Scheme 3-8 |

FIG. 5 Continued
| Example # | Structure | ERE Luciferase IC$_{50}$ [nM] | MW | Observed [M+H]/z | Synthetic Method |
|---|---|---|---|---|---|
| 183 | 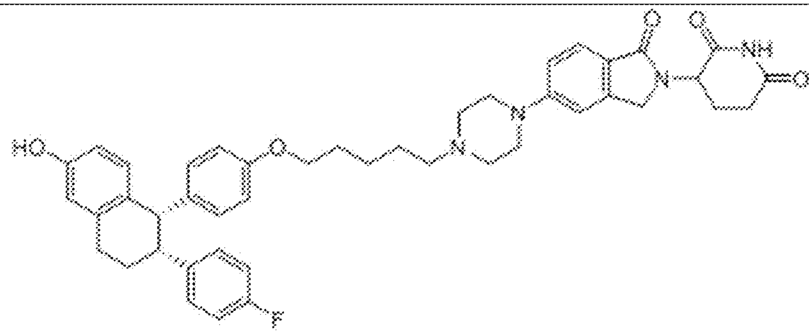 | >300 | 730.88 | 731.3 | Scheme 3-10 |
| 184 | 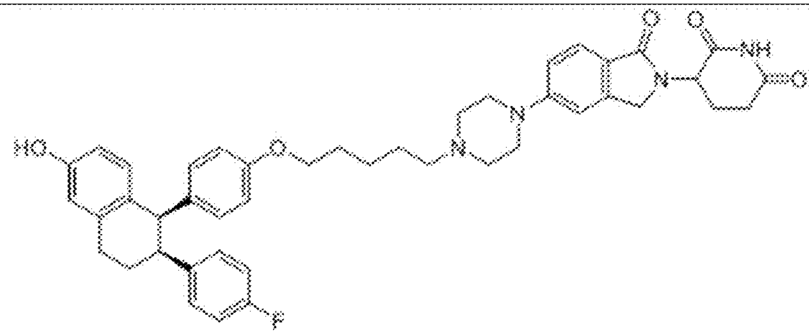 | 1.8 | 730.88 | 731.3 | Scheme 3-10 |
| 185 | 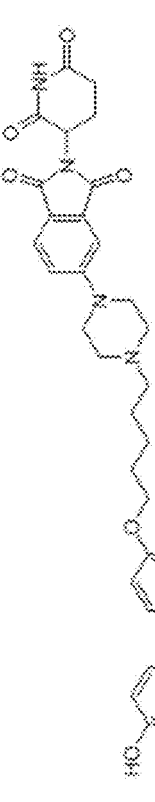 | >300 | 744.86 | 745.3 | Scheme 3-10 |

FIG. 5 Continued

| Example # | Structure | ERE Luciferase IC$_{50}$ [nM] | MW | Observed [M+H]/z | Synthetic Method |
|---|---|---|---|---|---|
| 186 | 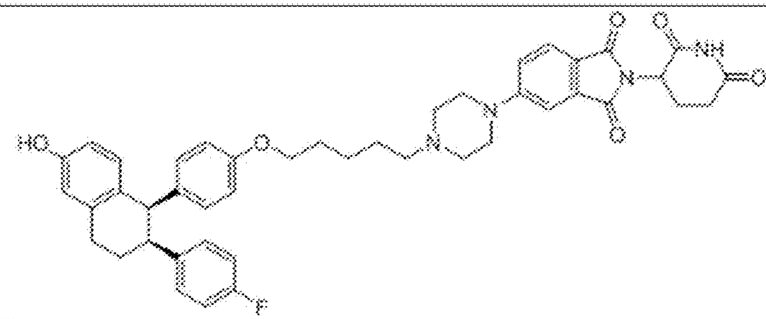 | 3.9 | 744.86 | 745.3 | Scheme 3-10 |
| 187 | 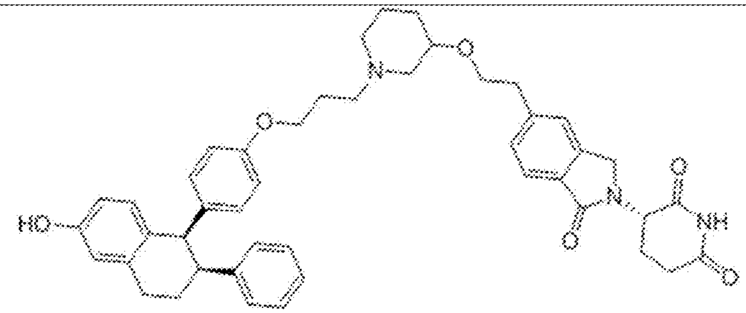 | 0.15 | 727.9 | 728.3 | Scheme 3-34 |
| 188 | 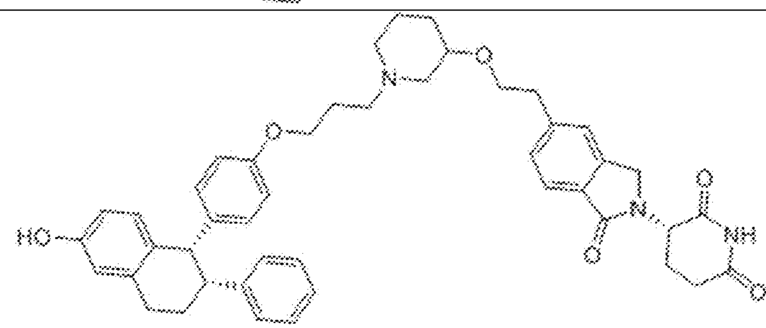 | 20.8 | 727.9 | 728.3 | Scheme 3-34 |

FIG. 5 Continued

| Example # | Structure | ERE Luciferase IC$_{50}$ [nM] | MW | Observed [M+H]/z | Synthetic Method |
|---|---|---|---|---|---|
| 189 | 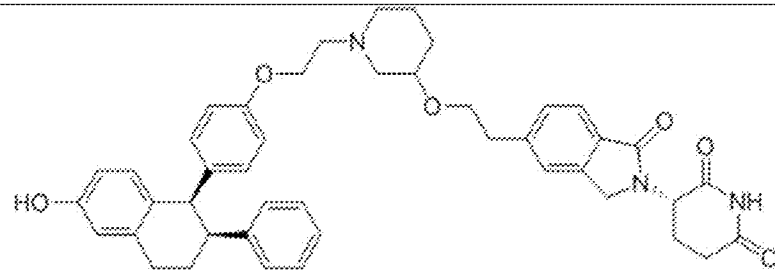 | 0.38 | 713.88 | 714.3 | Scheme 3-34 |
| 190 | 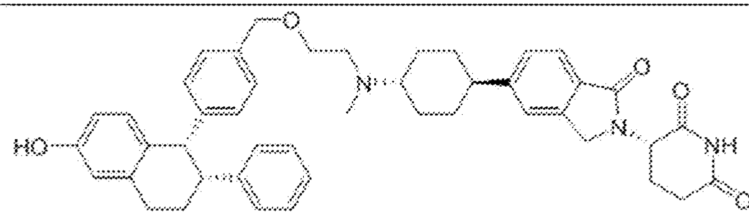 | >300 | 711.91 | 712.3 | Scheme 3-35 |
| 191 | 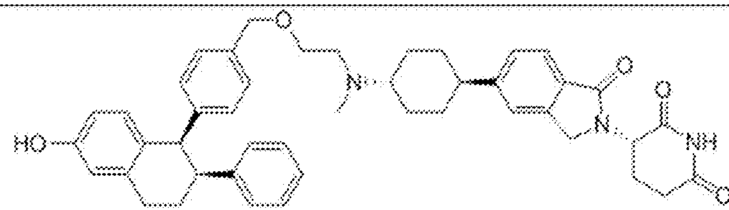 | 0.87 | 711.91 | 712.3 | Scheme 3-35 |
| 192 | 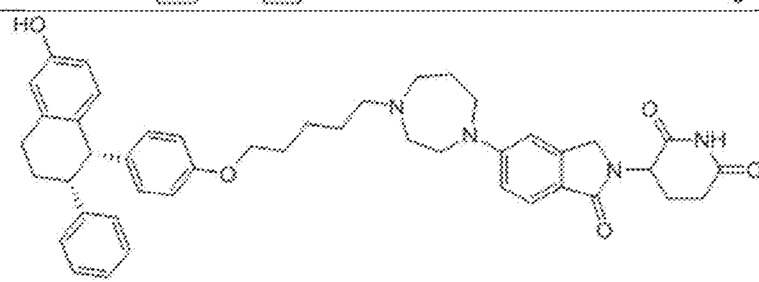 | >300 | 726.92 | 727.3 | Scheme 2-32, 3-10 |

FIG. 5 Continued

| Example # | Structure | ERE Luciferase IC$_{50}$ [nM] | MW | Observed [M+H]/z | Synthetic Method |
|---|---|---|---|---|---|
| 193 | 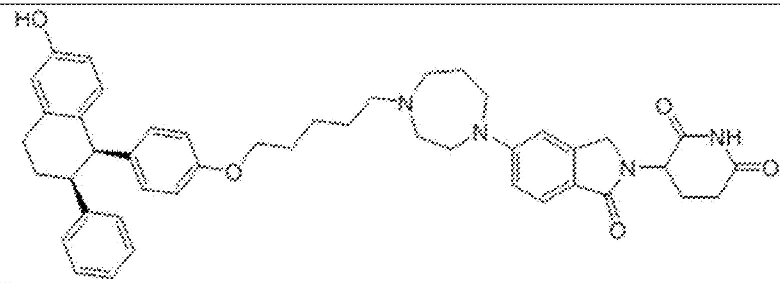 | 0.5 | 726.92 | 727.3 | Scheme 2-32, 3-10 |
| 194 | 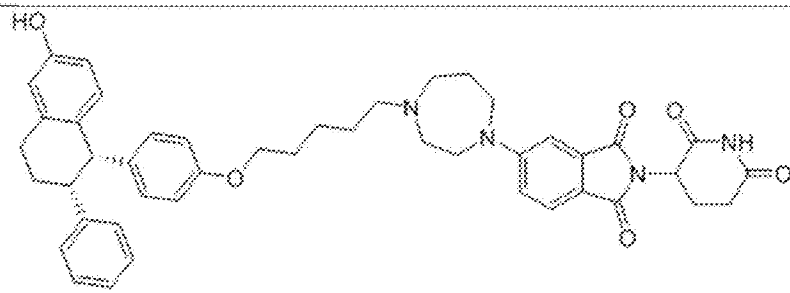 | >300 | 740.9 | 741.3 | Scheme 2-32, 3-10 |
| 195 | 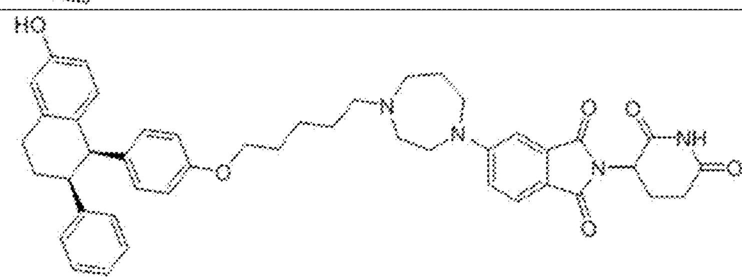 | 0.8 | 740.9 | 741.3 | Scheme 2-32, 3-10 |

FIG. 5 Continued

| Example # | Structure | ERE Luciferase IC$_{50}$ [nM] | MW | Observed [M+H]/z | Synthetic Method |
|---|---|---|---|---|---|
| 196 | 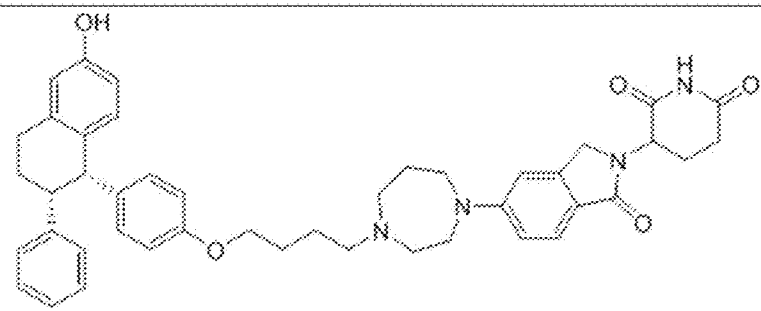 | >300 | 712.89 | 713.3 | Schme 2-32, 3-10 |
| 197 | 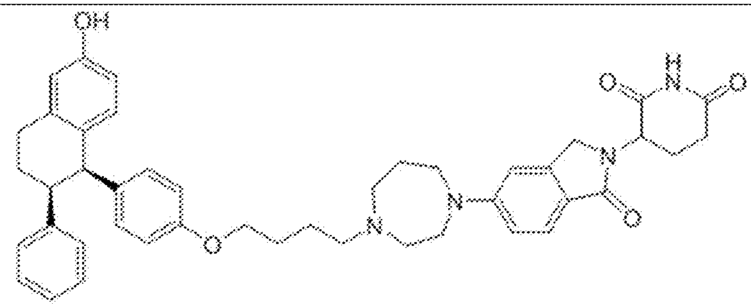 | 0.2 | 712.89 | 713.3 | Scheme 2-32, 3-10 |
| 198 | 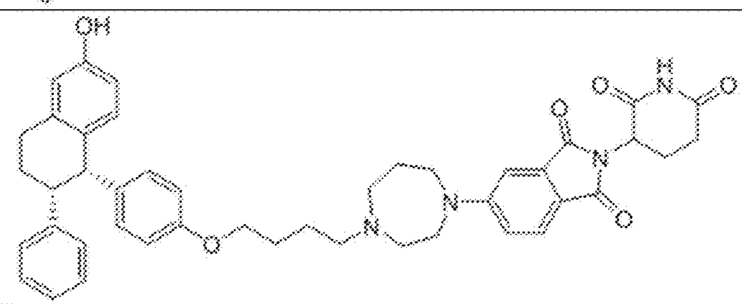 | >300 | 726.87 | 727.3 | Scheme 2-32, 3-10 |

FIG. 5 Continued
| Example # | Structure | ERE Luciferase IC$_{50}$ [nM] | MW | Observed [M+H]/z | Synthetic Method |
|---|---|---|---|---|---|
| 199 | 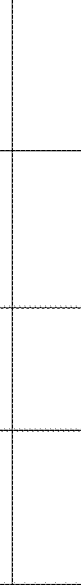 | 0.63 | 726.87 | 727.3 | Scheme 2-32, 3-10 |
| 200 | 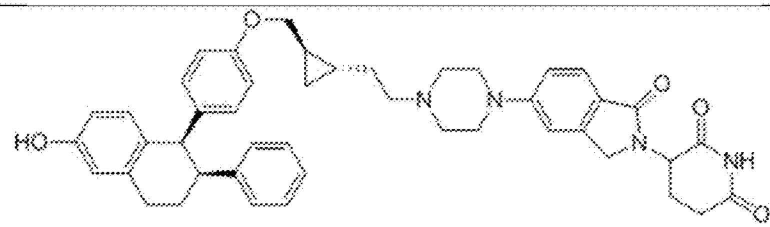 | 0.72 | 724.9 | 725.3 | Scheme 3-36 |
| 201 | 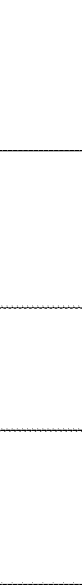 | 1.98 | 738.89 | 739.2 | Scheme 3-36 |

FIG. 5 Continued

| Example # | Structure | ERE Luciferase IC$_{50}$ [nM] | MW | Observed [M+H]/z | Synthetic Method |
|---|---|---|---|---|---|
| 202 | 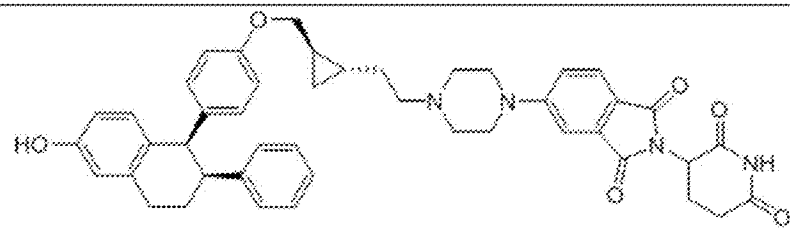 | 1.91 | 738.89 | 739.2 | Scheme 3-36 |
| 203 | 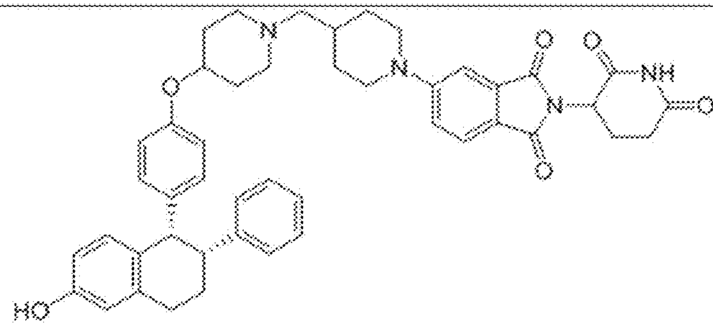 | >300 | 752.91 | 753.2 | Scheme 3-37 |
| 204 | 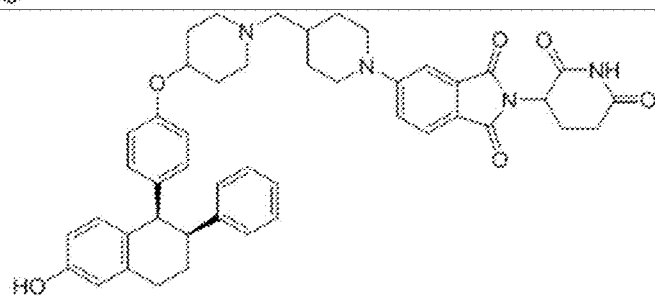 | 0.26 | 752.91 | 753.2 | Scheme 3-37 |

FIG. 5 Continued

| Example # | Structure | ERE Luciferase IC$_{50}$ [nM] | MW | Observed [M+H]/z | Synthetic Method |
|---|---|---|---|---|---|
| 205 | 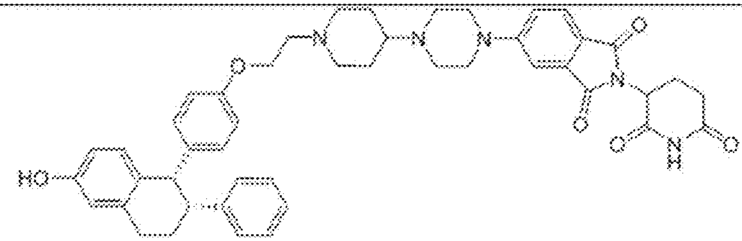 | 61.5 | 767.93 | 768.3 | Scheme 3-27 |
| 206 | 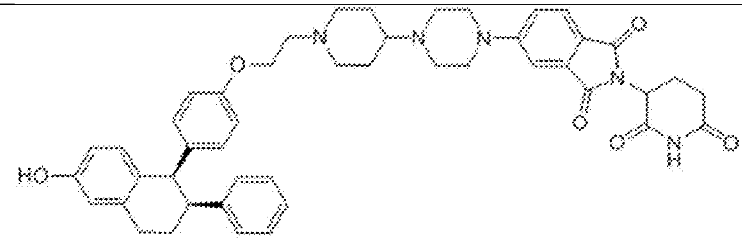 | 0.27 | 767.93 | 768.3 | Scheme 3-27 |
| 207 | 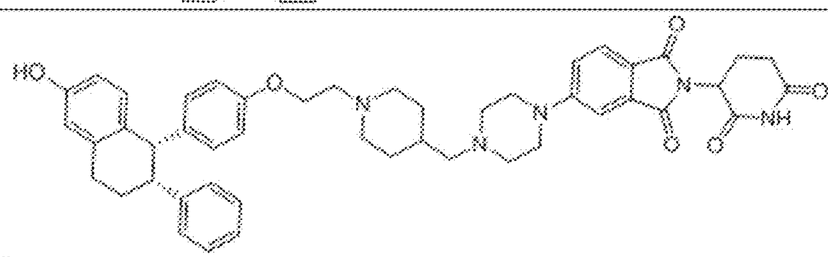 | 110.4 | 781.95 | 782.3 | Scheme 2-33, 3-10 |
| 208 | 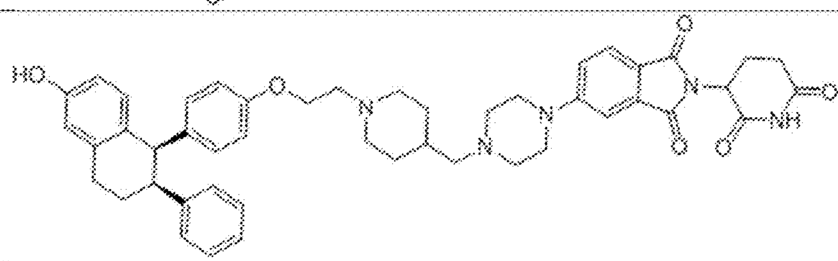 | 0.85 | 781.95 | 782.3 | Scheme 2-33, 3-10 |

FIG. 5 Continued
| Example # | Structure | ERE Luciferase IC$_{50}$ [nM] | MW | Observed [M+H]/z | Synthetic Method |
|---|---|---|---|---|---|
| 209 | 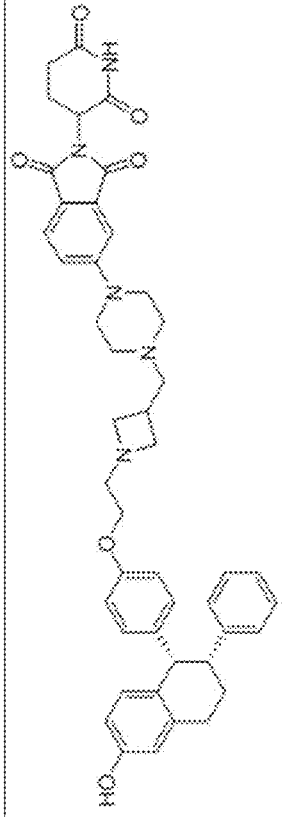 | 68.3 | 753.9 | 754.3 | Scheme 3-39 |
| 210 | 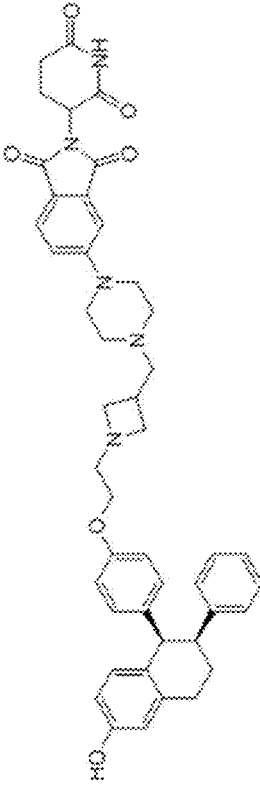 | 0.36 | 753.9 | 754.3 | Scheme 3-39 |
| 211 | 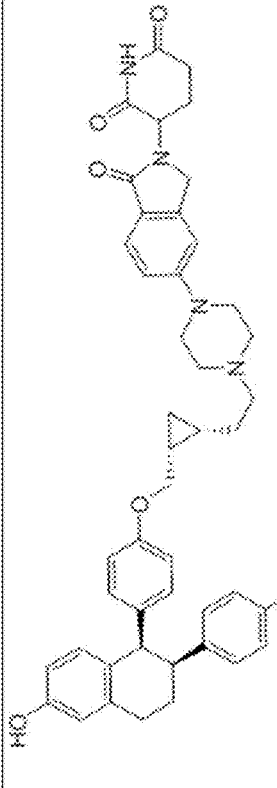 | 2.03 | 742.89 | 743.3 | Scheme 3-36 |

FIG. 5 Continued
| Example # | Structure | ERE Luciferase IC$_{50}$ [nM] | MW | Observed [M+H]/z | Synthetic Method |
|---|---|---|---|---|---|
| 212 | 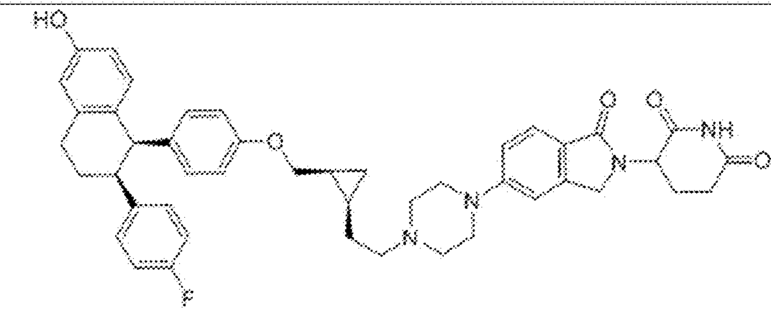 | 1.6 | 742.89 | 743.3 | Scheme 3-36 |
| 213 | 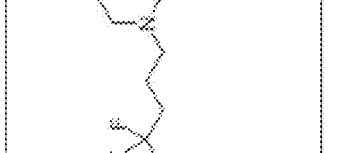 | >300 | 748.87 | 749.2 | Scheme 3-40 |
| 214 | 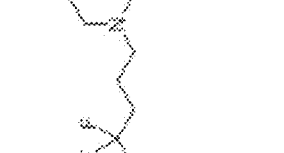 | 1.29 | 748.87 | 749.2 | Scheme 3-40 |

FIG. 5 Continued

| Example # | Structure | ERE Luciferase IC$_{50}$ [nM] | MW | Observed [M+H]/z | Synthetic Method |
|---|---|---|---|---|---|
| 215 | 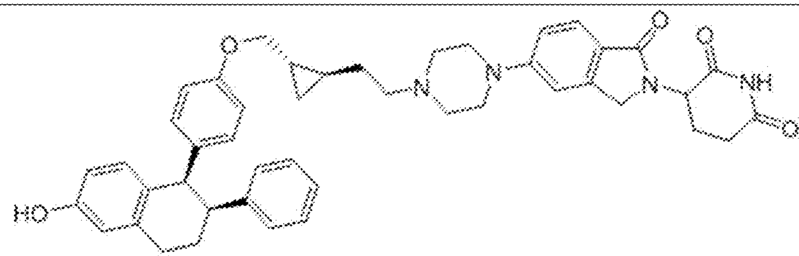 | 0.95 | 724.9 | 725.3 | Scheme 3-36 |
| 216 | 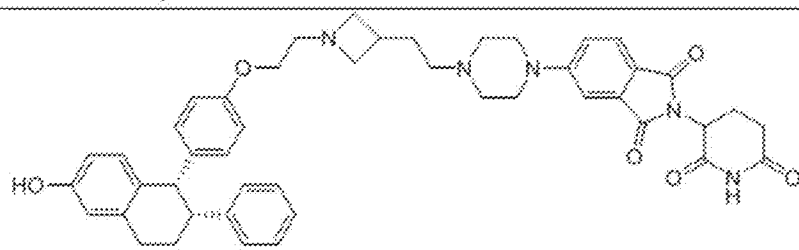 | >300 | 767.93 | 768.6 | Scheme 3-39 |
| 217 | 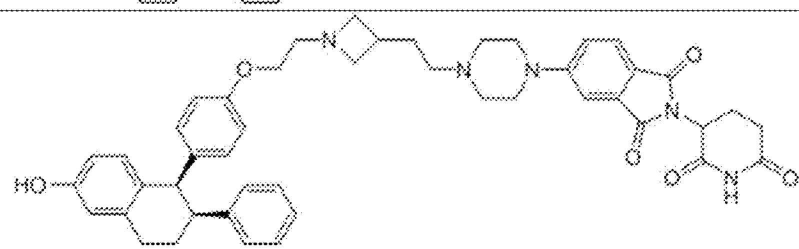 | | 767.93 | 768.6 | Scheme 3-39 |
| 218 | 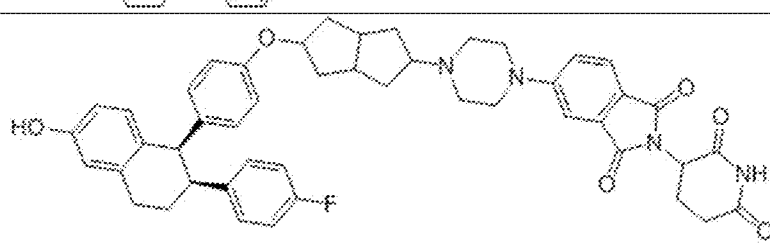 | 4.6 | 782.91 | 783.6 | Scheme 3-41 |

FIG. 5 Continued

| Example # | Structure | ERE Luciferase IC$_{50}$ [nM] | MW | Observed [M+H]/z | Synthetic Method |
|---|---|---|---|---|---|
| 219 | 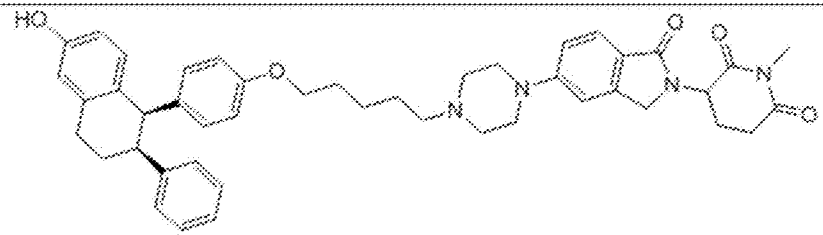 | 1.1 | 726.92 | 727.6 | Scheme 2-28, 3-10 |
| 220 | 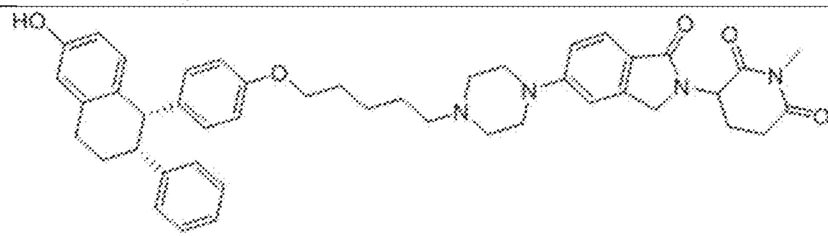 | >300 | 726.92 | 727.6 | Scheme 2-28, 3-10 |
| 221 | 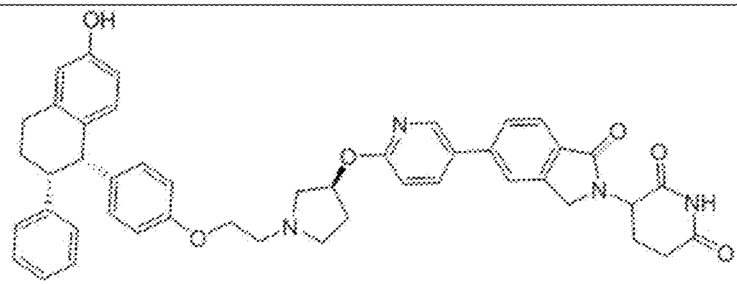 | 34.5 | 748.88 | 749.5 | Scheme 3-42 |

FIG. 5 Continued

| Example # | Structure | ERE Luciferase IC$_{50}$ [nM] | MW | Observed [M+H]/z | Synthetic Method |
|---|---|---|---|---|---|
| 222 | 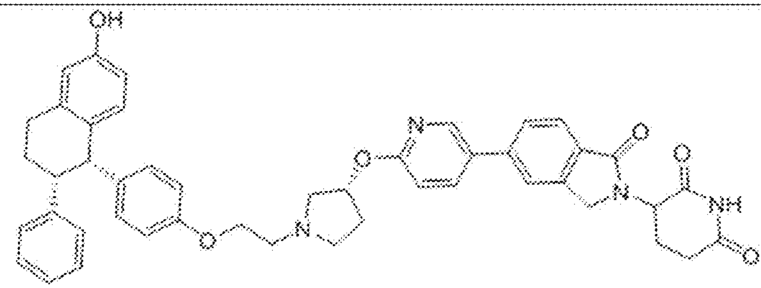 | 67.2 | 748.88 | 749.5 | Scheme 3-42 |
| 223 | 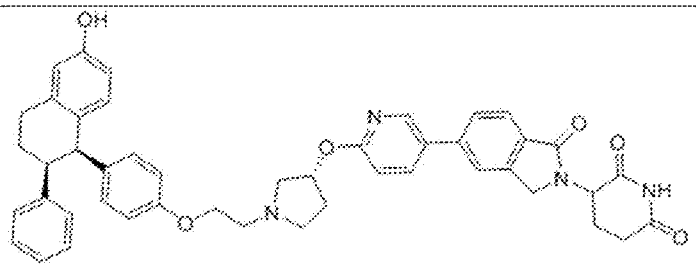 | 0.37 | 748.88 | 749.5 | Scheme 3-42 |
| 224 | 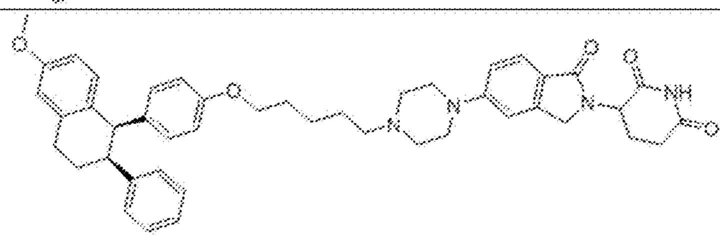 | 16.1 | 726.92 | 727.6 | Scheme 3-10 |

FIG. 5 Continued

| Example # | Structure | ERE Luciferase IC$_{50}$ [nM] | MW | Observed [M+H]/z | Synthetic Method |
|---|---|---|---|---|---|
| 225 | 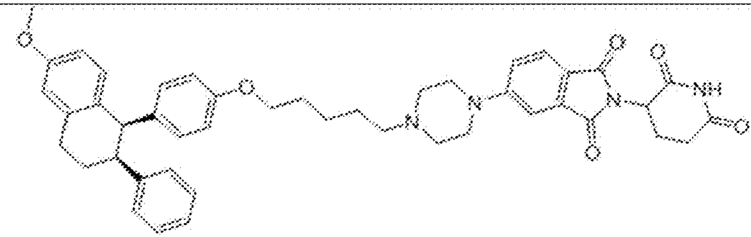 | 106.1 | 740.9 | 741.6 | Scheme 3-10 |
| 226 | 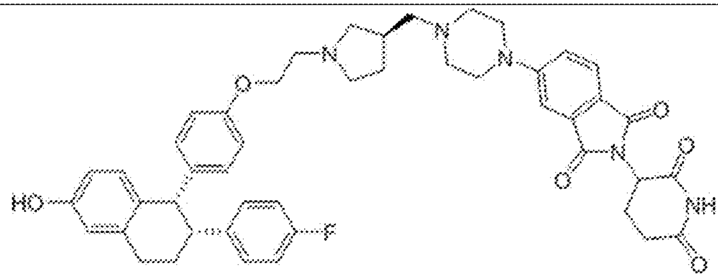 | >300 | 785.92 | 786.6 | Scheme 3-43 |
| 227 | 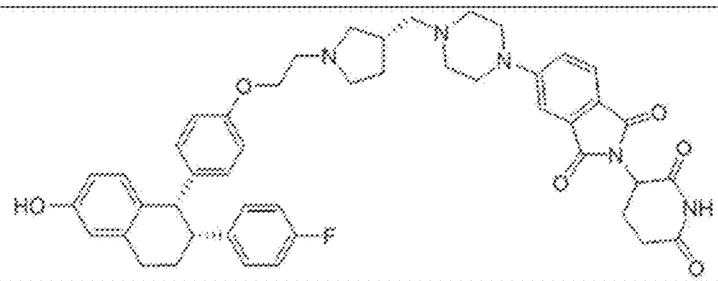 | >300 | 785.92 | 786.6 | Scheme 3-43 |

FIG. 5 Continued

| Example # | Structure | ERE Luciferase IC$_{50}$ [nM] | MW | Observed [M+H]/z | Synthetic Method |
|---|---|---|---|---|---|
| 228 | 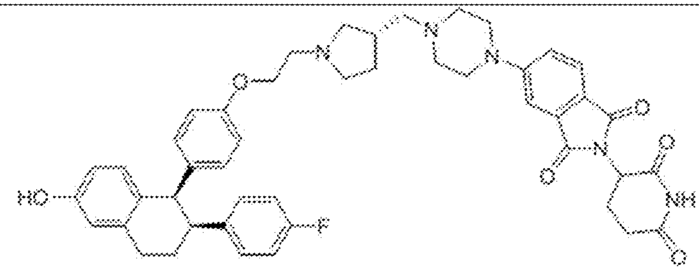 | 0.26 | 785.92 | 786.6 | Scheme 3-43 |
| 229 | 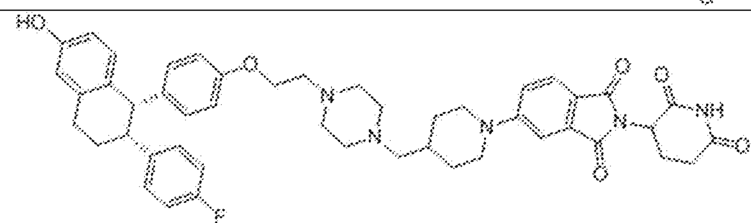 | >300 | 799.94 | 800.6 | Scheme 2-34, 3-10 |
| 230 | 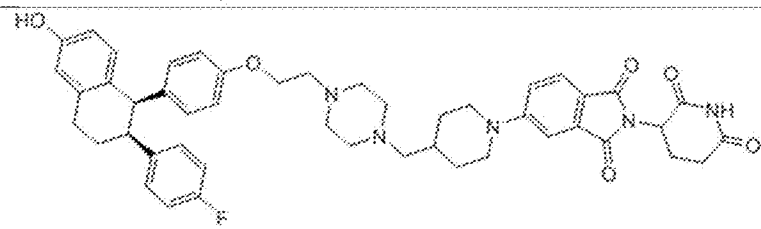 | 0.59 | 799.94 | 800.6 | Scheme 2-34, 3-10 |
| 231 | 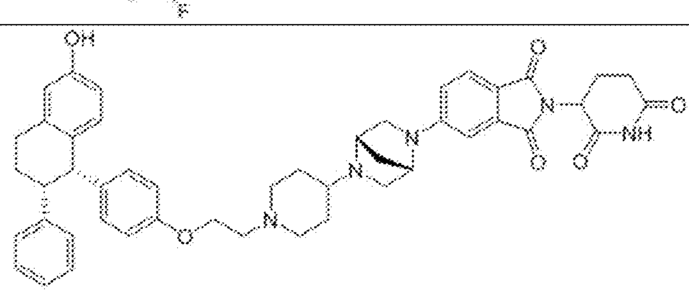 | >300 | 779.94 | 780.6 | Scheme 3-27 |

FIG. 5 Continued

| Example # | Structure | ERE Luciferase IC$_{50}$ [nM] | MW | Observed [M+H]/z | Synthetic Method |
|---|---|---|---|---|---|
| 232 | 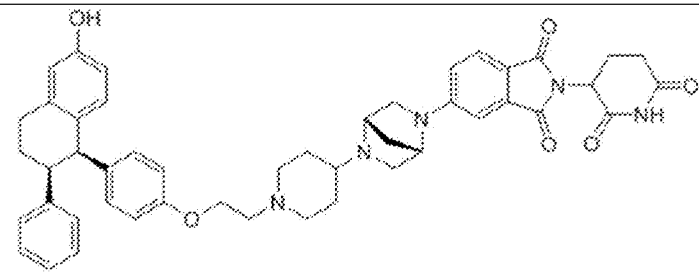 | 1.5 | 779.94 | 780.6 | Scheme 3-27 |
| 233 | 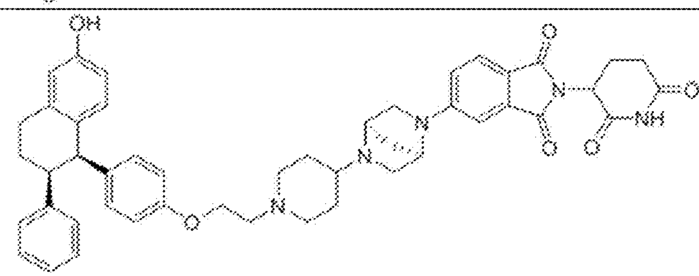 | 0.47 | 779.94 | 780.6 | Scheme 3-27 |
| 234 | 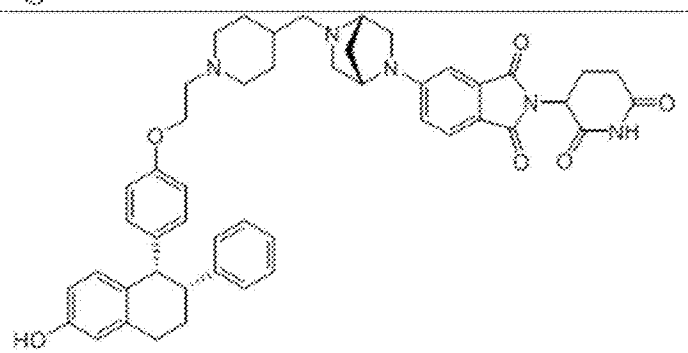 | >300 | 793.97 | 794.6 | Scheme 2-33, 3-10 |

FIG. 5 Continued

| Example # | Structure | ERE Luciferase IC$_{50}$ [nM] | MW | Observed [M+H]/z | Synthetic Method |
|---|---|---|---|---|---|
| 235 | 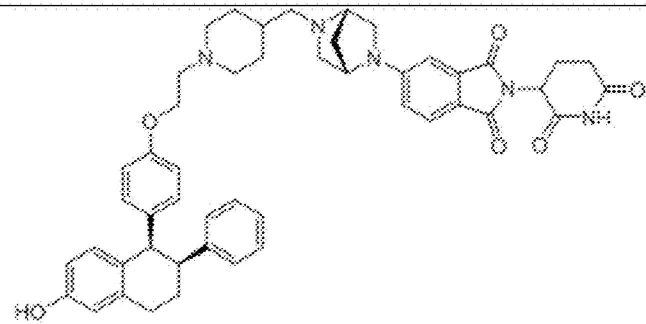 | 1.7 | 793.97 | 794.6 | Scheme 2-33, 3-10 |
| 236 | 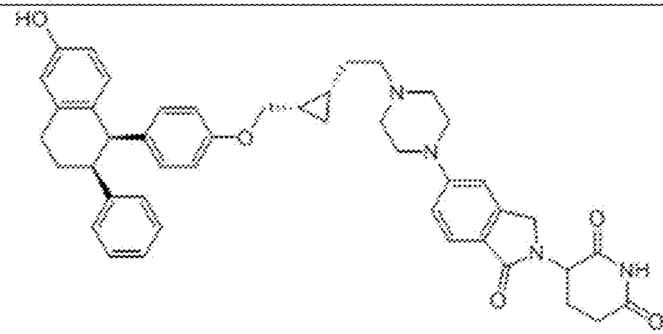 | 1.3 | 724.91 | 725.6 | Scheme 3-36 |
| 237 | 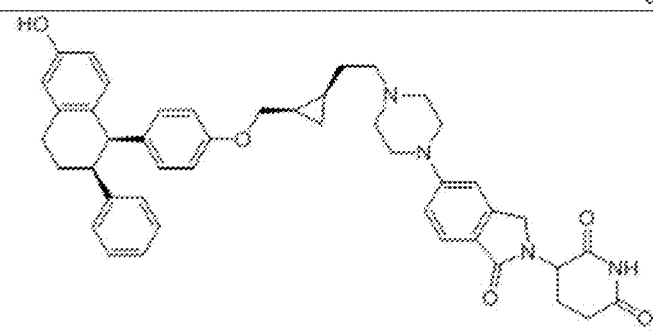 | 0.17 | 724.91 | 725.6 | Scheme 3-36 |

FIG. 5 Continued

| Example # | Structure | ERE Luciferase IC$_{50}$ [nM] | MW | Observed [M+H]/Z | Synthetic Method |
|---|---|---|---|---|---|
| 238 | 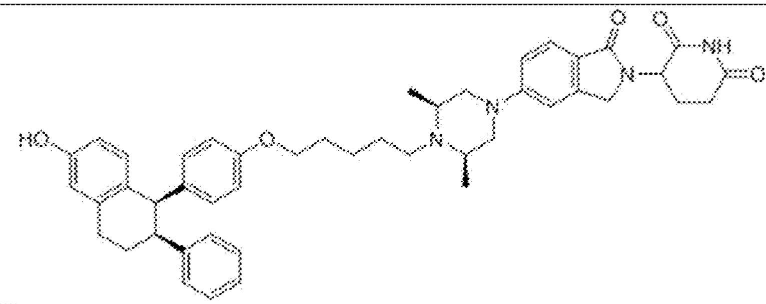 | 7.7 | 740.95 | 741.6 | Scheme 2-35, 3-44 |
| 239 | 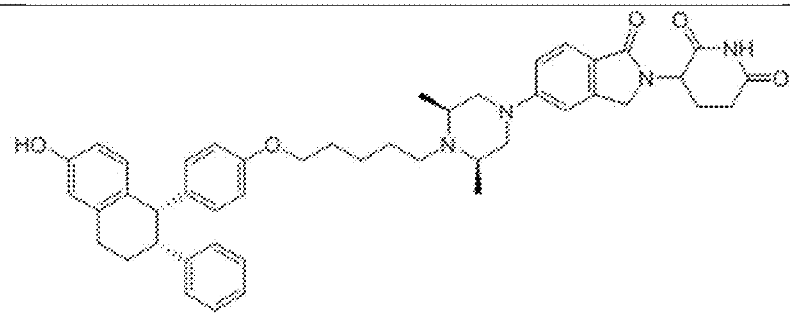 | >300 | 740.95 | 741.6 | Scheme 2-35, 3-44 |
| 240 | 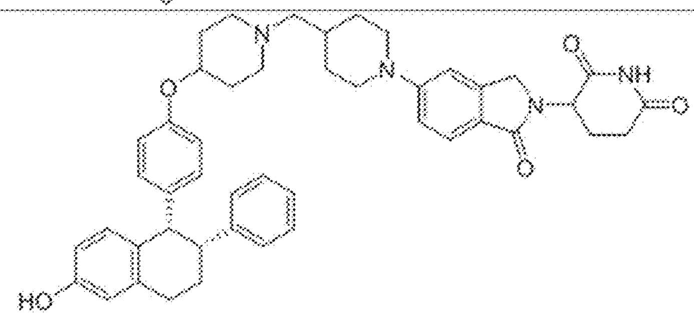 | 2.9 | 738.93 | 739.6 | Scheme 3-38 |

FIG. 5 Continued
| Example # | Structure | ERE Luciferase IC$_{50}$ [nM] | MW | Observed [M+H]/z | Synthetic Method |
|---|---|---|---|---|---|
| 241 | 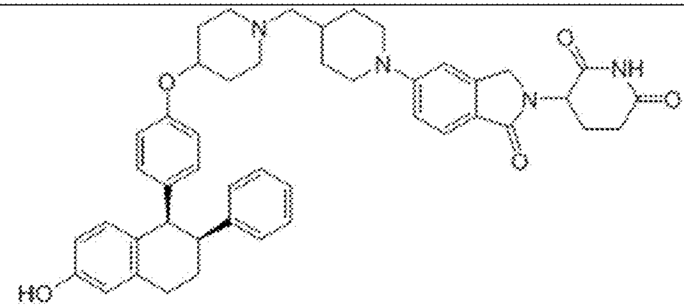 | 0.92 | 738.93 | 739.6 | Scheme 3-38 |
| 242 | 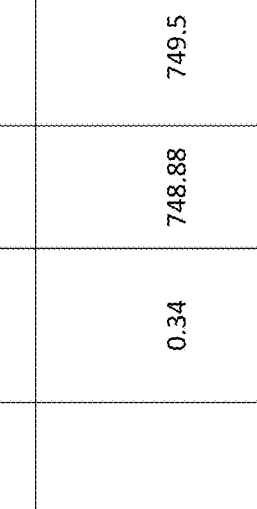 | 0.34 | 748.88 | 749.5 | Scheme 3-42 |
| 243 | 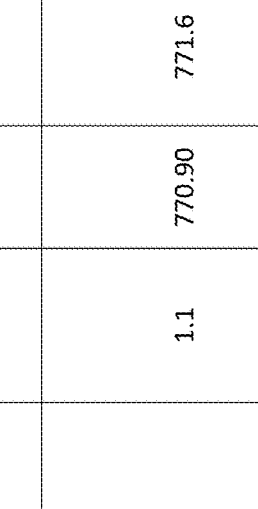 | 1.1 | 770.90 | 771.6 | Scheme 2-8, 3-10 |

FIG. 5 Continued

| Example # | Structure | ERE Luciferase IC$_{50}$ [nM] | MW | Observed [M+H]/z | Synthetic Method |
|---|---|---|---|---|---|
| 244 | 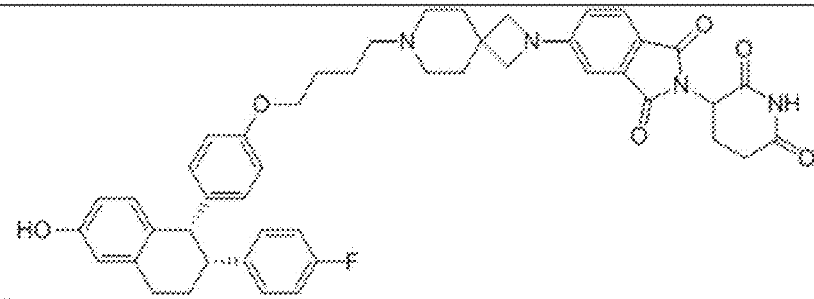 | 69.2 | 770.90 | 771.6 | Scheme 2-8, 3-10 |
| 245 | 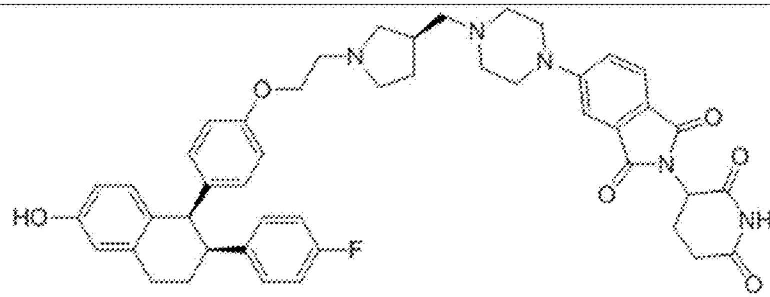 | 1.1 | 785.92 | 786.6 | Scheme 1-24, 3-10 |
| 246 | 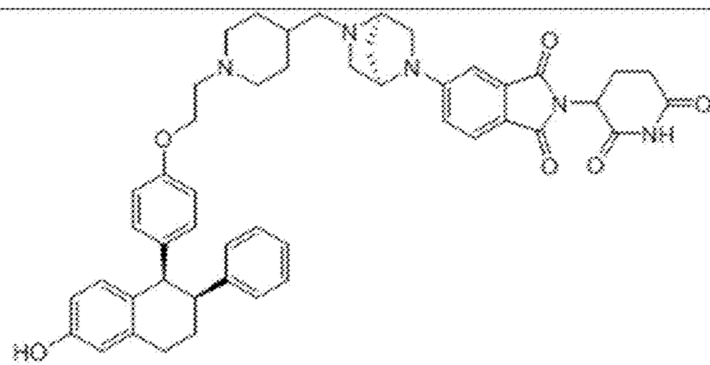 | 5.6 | 793.97 | 794.6 | Scheme 2-33, 3-10 |

FIG. 5 Continued

| Example # | Structure | ERE Luciferase IC$_{50}$ [nM] | MW | Observed [M+H]/Z | Synthetic Method |
|---|---|---|---|---|---|
| 247 | 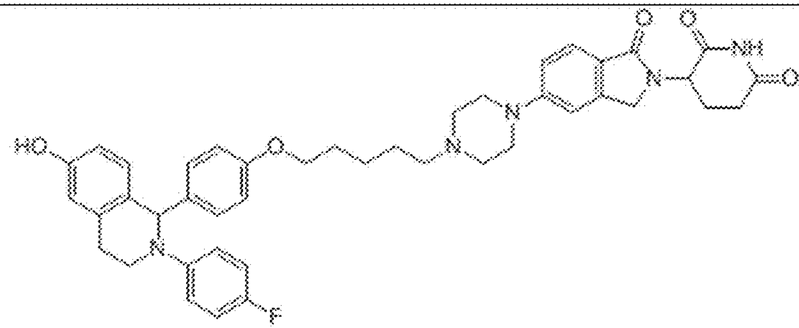 | 2.4 | 731.87 | 732.6 | Scheme 1-26, 3-10 |
| 248 | 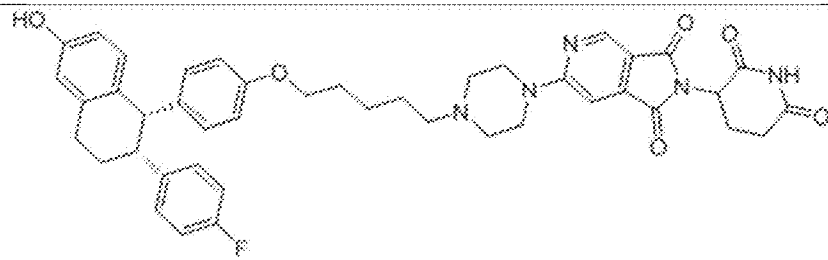 | >300 | 745.85 | 746.5 | Scheme 2-6, 3-10 |
| 249 | 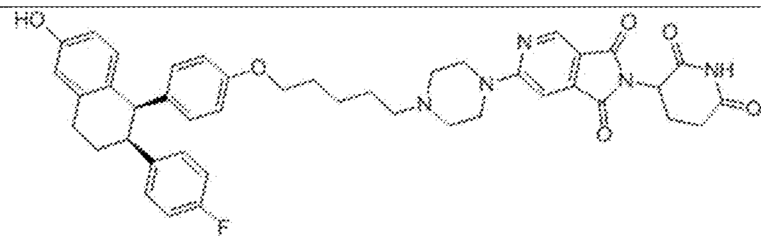 | 4.7 | 745.85 | 746.5 | Scheme 2-6, 3-10 |

FIG. 5 Continued

| Example # | Structure | ERE Luciferase IC$_{50}$ [nM] | MW | Observed [M+H]/Z | Synthetic Method |
|---|---|---|---|---|---|
| 250 | 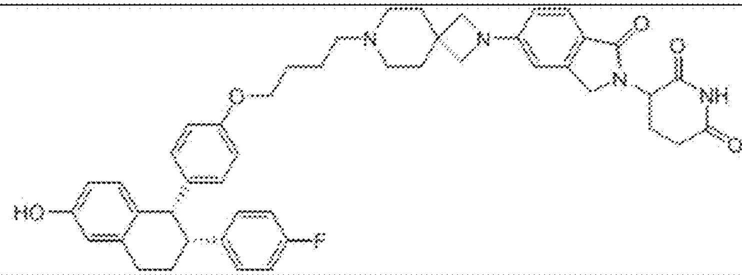 | 51.8 | 756.37 | 757.6 | Scheme 2-8, 3-10 |
| 251 | 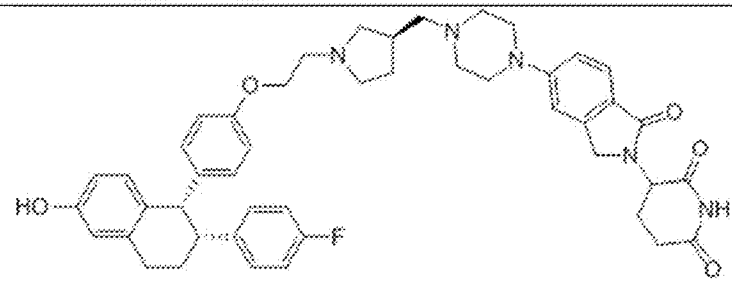 | 88.9 | 771.93 | 772.6 | Scheme 3-43 |
| 252 | 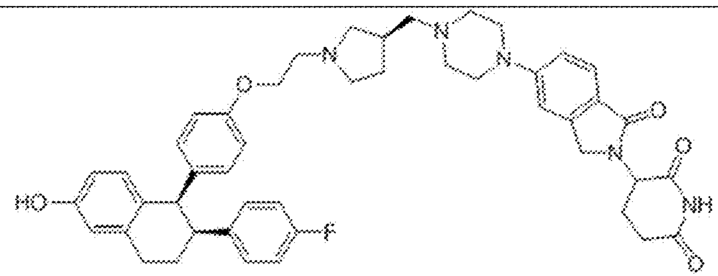 | 0.76 | 771.93 | 772.6 | Scheme 3-43 |

FIG. 5 Continued
| Example # | Structure | ERE Luciferase IC$_{50}$ [nM] | MW | Observed [M+H]/z | Synthetic Method |
|---|---|---|---|---|---|
| 253 | 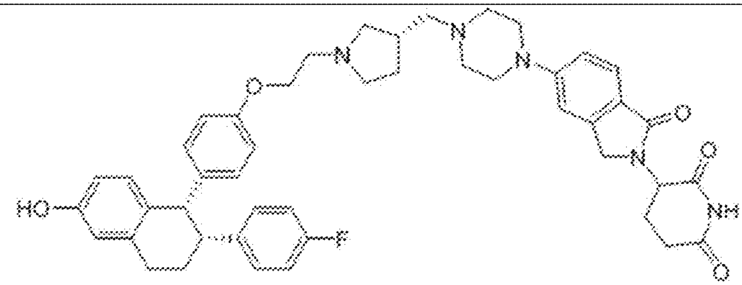 | 64.1 | 771.93 | 772.6 | Scheme 3-43 |
| 254 | 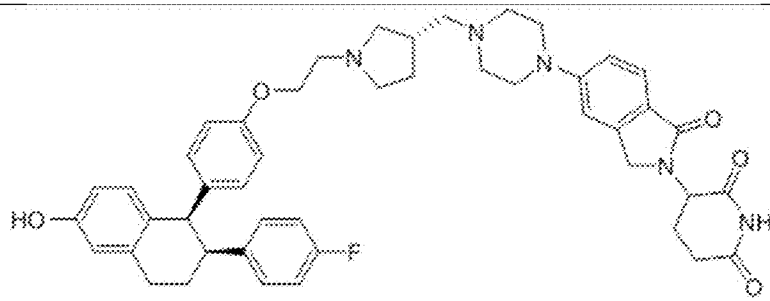 | 0.7 | 771.93 | 772.6 | Scheme 3-43 |
| 255 | 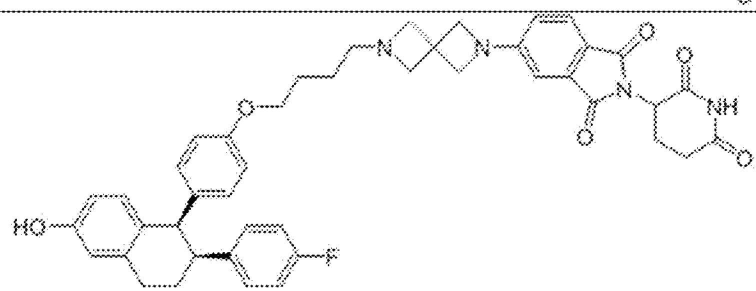 | 0.16 | 742.85 | 743.5 | Scheme 2-37, 3-10 |

FIG. 5 Continued
| Example # | Structure | ERE Luciferase IC$_{50}$ [nM] | MW | Observed [M+H]/Z | Synthetic Method |
|---|---|---|---|---|---|
| 256 | 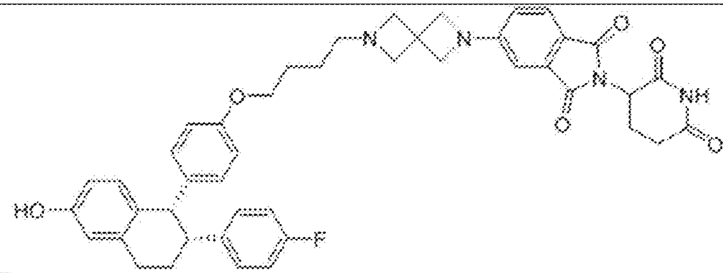 | 30.7 | 742.85 | 743.5 | Scheme 2-37, 3-10 |
| 257 | 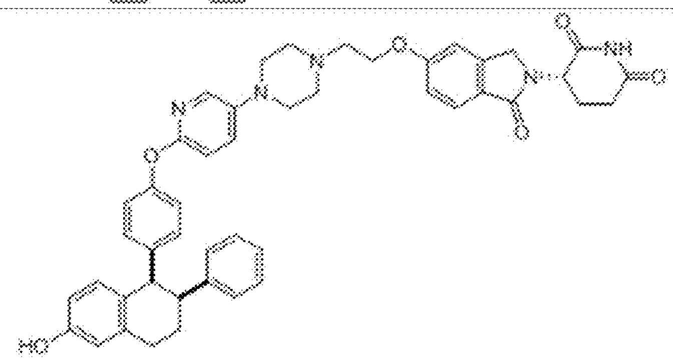 | 3.4 | 763.9 | 764.6 | Scheme 1-27, 2-38 |
| 258 | 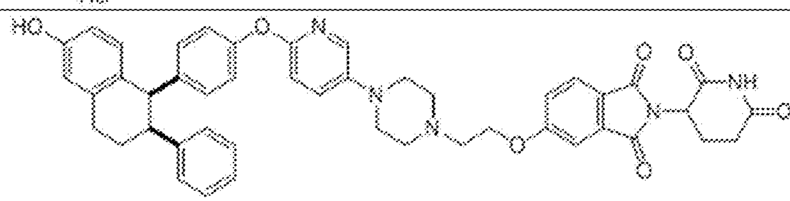 | 10.7 | 777.88 | 778.5 | Scheme 3-45 |

FIG. 5 Continued

| Example # | Structure | ERE Luciferase IC$_{50}$ [nM] | MW | Observed [M+H]/z | Synthetic Method |
|---|---|---|---|---|---|
| 259 | 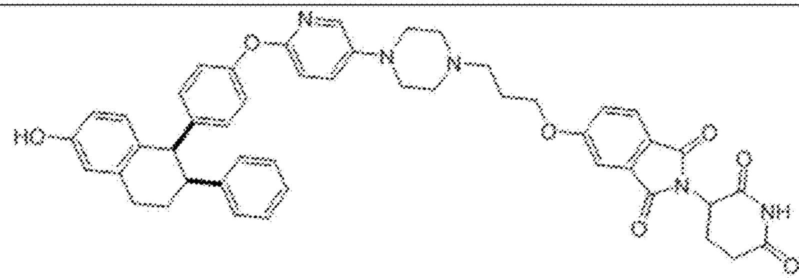 | 6.3 | 791.91 | 792.6 | Scheme 3-45 |
| 260 | 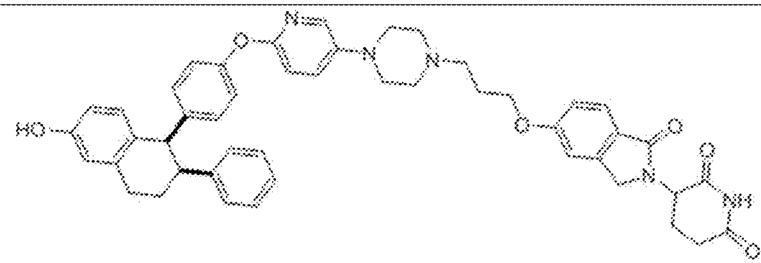 | 2.5 | 777.92 | 778.6 | Scheme 3-45 |
| 261 | 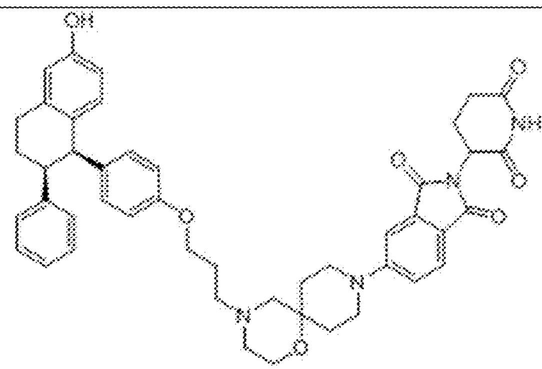 | 4.6 | 768.91 | 769.6 | Scheme 3-46 |

FIG. 5 Continued

| Example # | Structure | ERE Luciferase IC$_{50}$ [nM] | MW | Observed [M+H]/z | Synthetic Method |
|---|---|---|---|---|---|
| 262 | 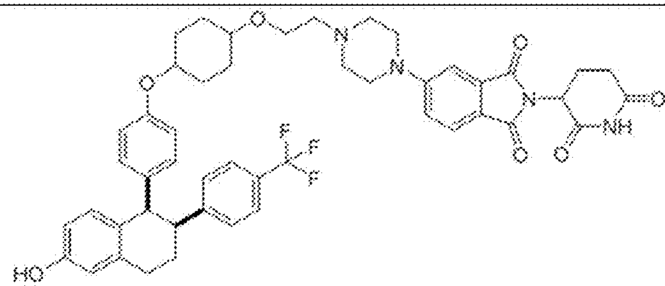 | 9 | 850.94 | 851.6 | Scheme 3-47 |
| 263 | 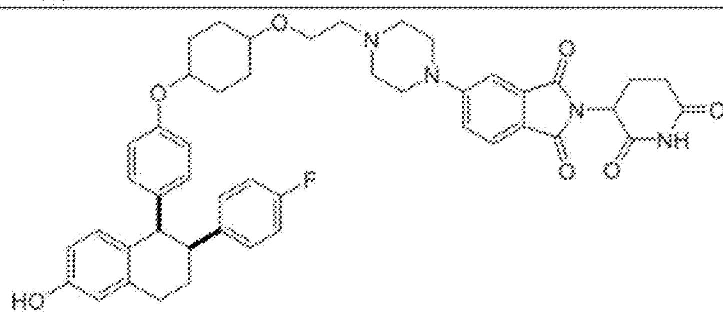 | 5.9 | 800.93 | 801.6 | Scheme 3-47 |
| 264 | 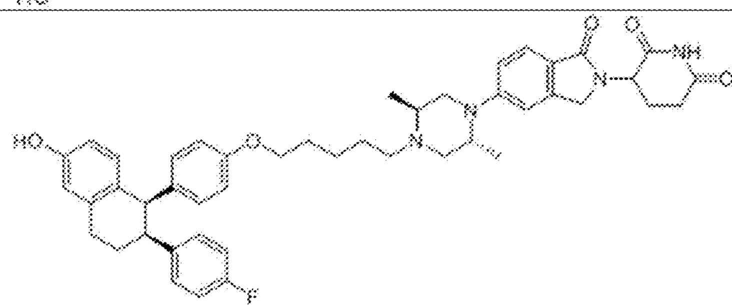 | 1.72 | 758.94 | 759.6 | Scheme 2-5, 3-10 |

FIG. 5 Continued

| Example # | Structure | ERE Luciferase IC$_{50}$ [nM] | MW | Observed [M+H]/z | Synthetic Method |
|---|---|---|---|---|---|
| 265 | 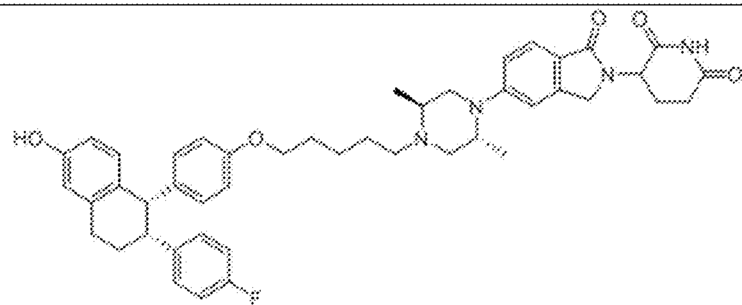 | >300 | 758.94 | 759.6 | Scheme 2-5, 3-10 |
| 266 | 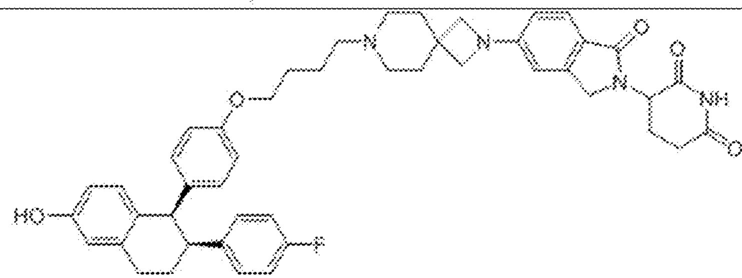 | 0.2 | 756.92 | 757.6 | Scheme 2-8, 3-10 |
| 267 | 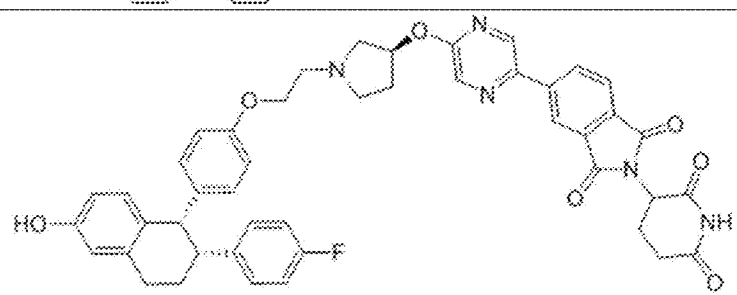 | 135.8 | 781.84 | 782.5 | Scheme 3-48 |

FIG. 5 Continued

| Example # | Structure | ERE Luciferase IC$_{50}$ [nM] | MW | Observed [M+H]/z | Synthetic Method |
|---|---|---|---|---|---|
| 268 | 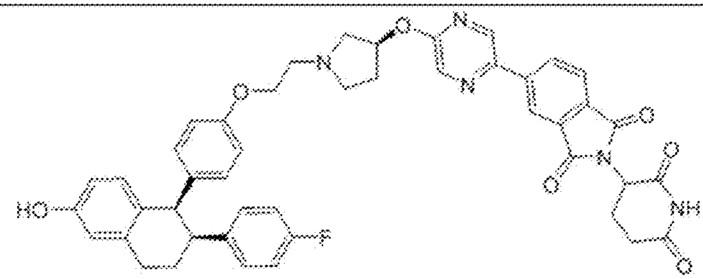 | 1.5 | 781.84 | 782.5 | Scheme 3-48 |
| 269 | 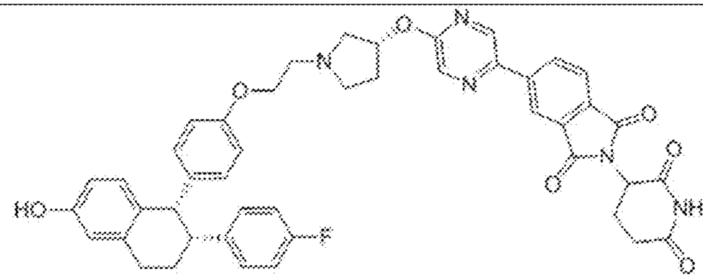 | 68.2 | 781.84 | 782.5 | Scheme 3-48 |
| 270 | 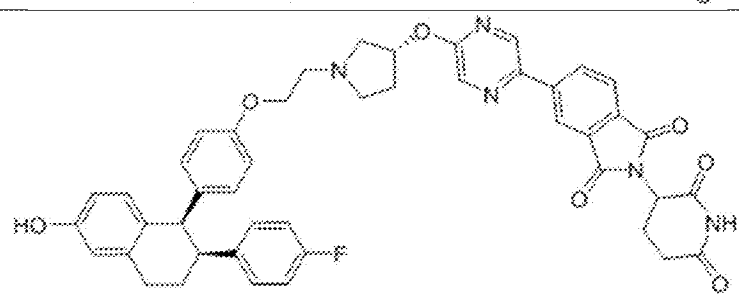 | 1.3 | 781.84 | 782.5 | Scheme 3-48 |

FIG. 5 Continued
| Example # | Structure | ERE Luciferase IC$_{50}$ [nM] | MW | Observed [M+H]/Z | Synthetic Method |
|---|---|---|---|---|---|
| 271 | 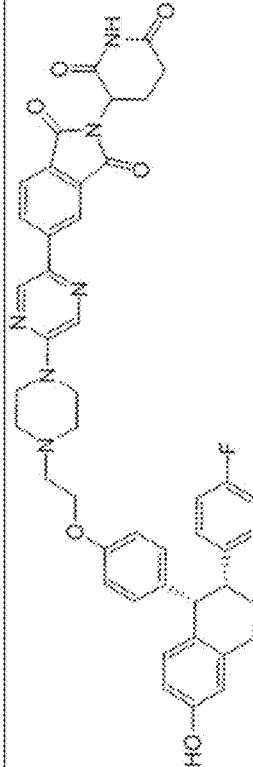 | >300 | 780.86 | 781.5 | Scheme 3-48 |
| 272 | 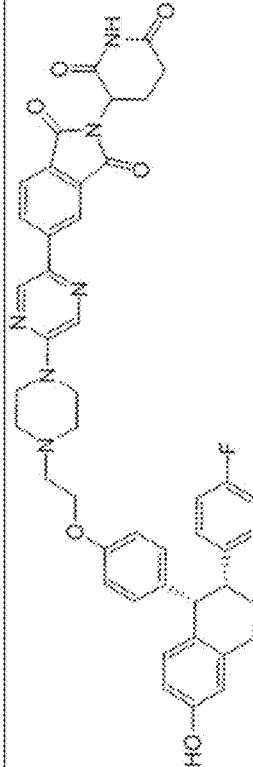 | 2.5 | 780.86 | 781.5 | Scheme 3-48 |
| 273 | 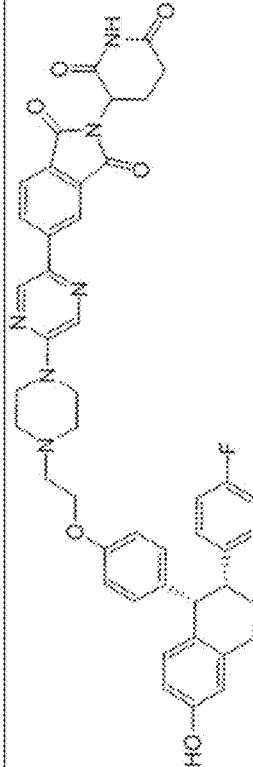 | 57.6 | 781.84 | 782.5 | Scheme 3-48 |

FIG. 5 Continued

| Example # | Structure | ERE Luciferase IC$_{50}$ [nM] | MW | Observed [M+H]/z | Synthetic Method |
|---|---|---|---|---|---|
| 274 | 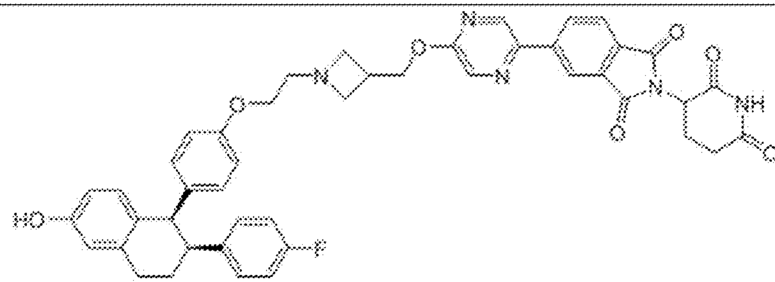 | 0.17 | 781.84 | 782.5 | Scheme 3-48 |
| 275 | 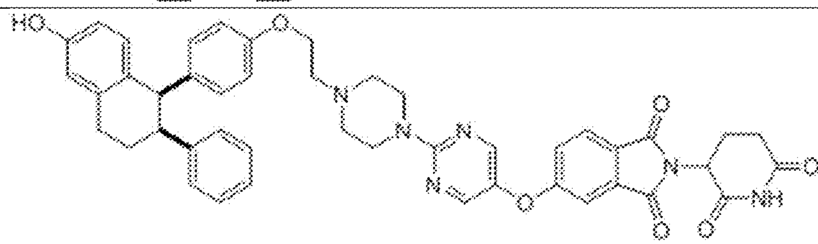 | 4 | 778.87 | 779.5 | Scheme 3-49 |
| 276 | 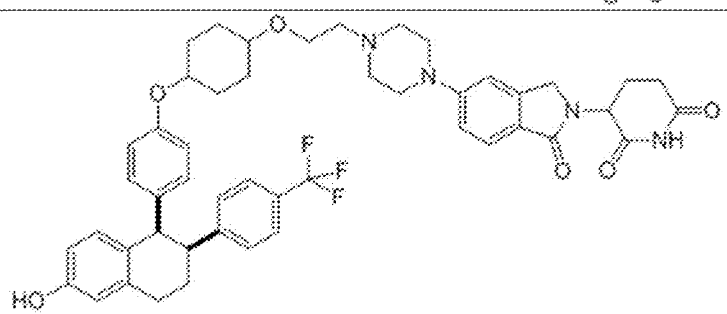 | 4.5 | 836.95 | 837.6 | Scheme 3-47 |

FIG. 5 Continued

| Example # | Structure | ERE Luciferase IC$_{50}$ [nM] | MW | Observed [M+H]/Z | Synthetic Method |
|---|---|---|---|---|---|
| 277 | 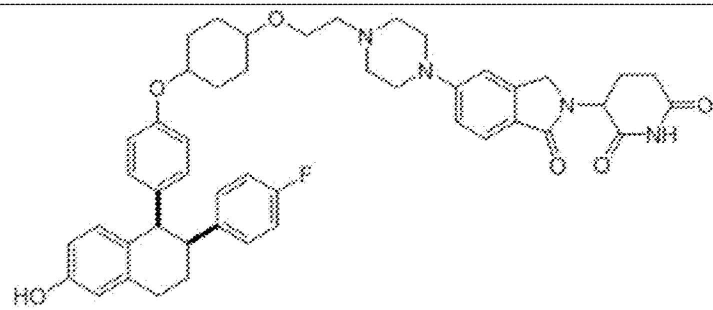 | 2 | 786.95 | 787.6 | Scheme 3-47 |
| 278 | 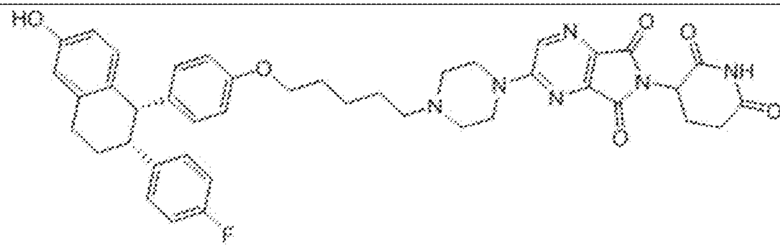 | 40.1 | 746.84 | 747.5 | Scheme 2-9, 3-48 |
| 279 | 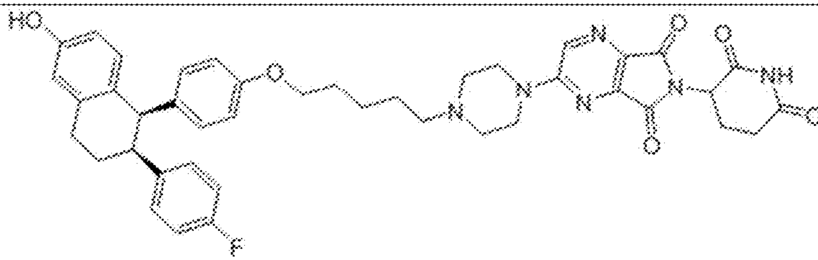 | 1.3 | 746.84 | 747.5 | Scheme 2-9, 3-48 |

FIG. 5 Continued

| Example # | Structure | ERE Luciferase IC$_{50}$ [nM] | MW | Observed [M+H]/z | Synthetic Method |
|---|---|---|---|---|---|
| 280 | 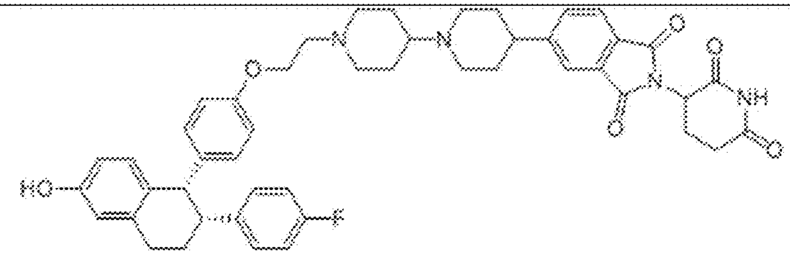 | >300 | 784.93 | 785.6 | Scheme 3-50 |
| 281 | 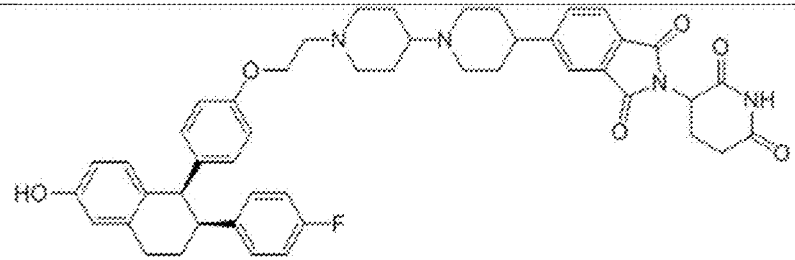 | 2 | 784.93 | 785.6 | Scheme 3-50 |
| 282 | 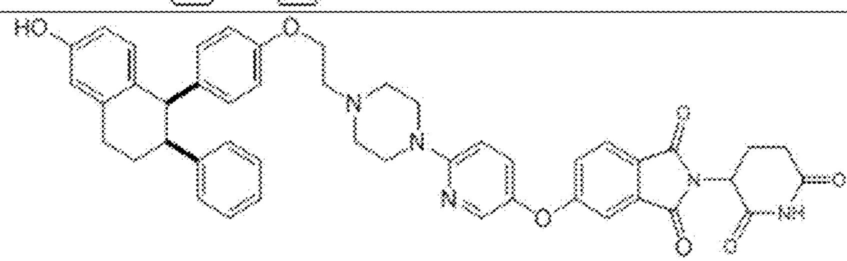 | 4.4 | 777.88 | 778.5 | Scheme 3-49 |

FIG. 5 Continued

| Example # | Structure | ERE Luciferase IC$_{50}$ [nM] | MW | Observed [M+H]/z | Synthetic Method |
|---|---|---|---|---|---|
| 283 | 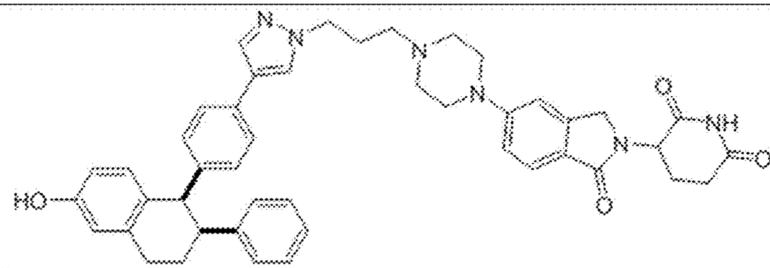 | 0.8 | 734.90 | 735.6 | Scheme 3-51 |
| 284 | 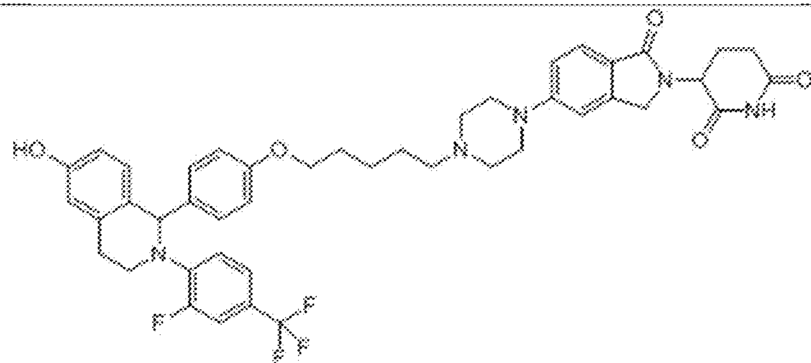 | 4.1 | 799.87 | 800.6 | Scheme 1-26, 3-10 |
| 285 | 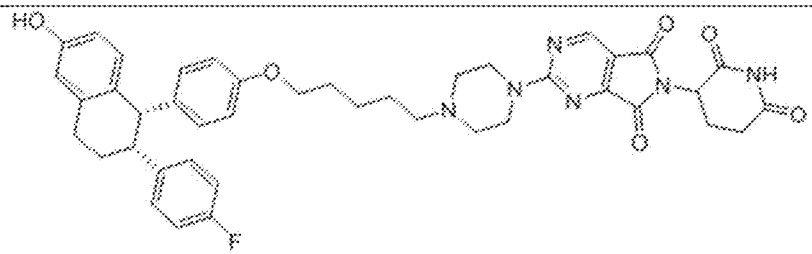 | 125.9 | 746.84 | 747.5 | Scheme 2-10, 3-48 |

FIG. 5 Continued
| Example # | Structure | ERE Luciferase IC$_{50}$ [nM] | MW | Observed [M+H]/z | Synthetic Method |
|---|---|---|---|---|---|
| 286 | 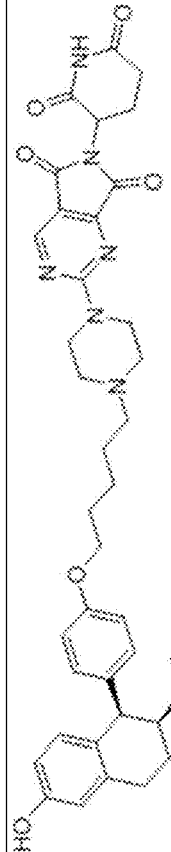 | 13.1 | 746.84 | 747.5 | Scheme 2-10, 3-48 |
| 287 | 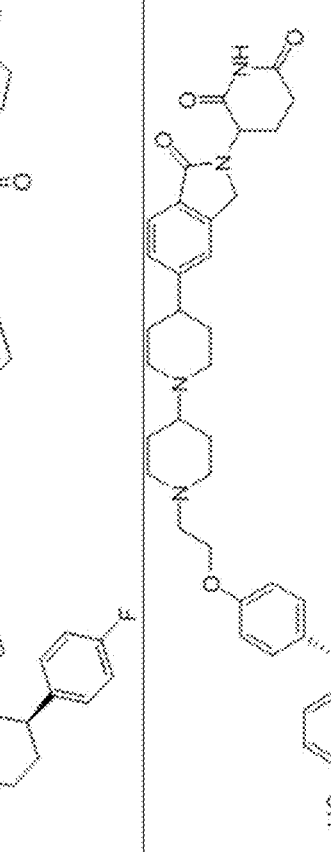 | 98 | 770.95 | 771.6 | Scheme 3-50 |
| 288 | 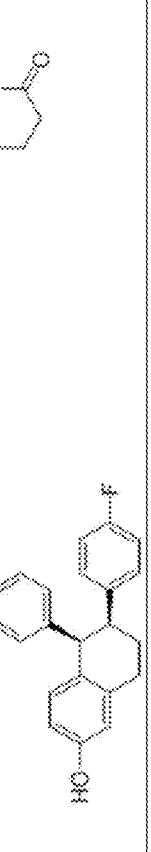 | 1.6 | 770.95 | 771.6 | Scheme 3-50 |

FIG. 5 Continued
| Example # | Structure | ERE Luciferase IC$_{50}$ [nM] | MW | Observed [M+H]/z | Synthetic Method |
|---|---|---|---|---|---|
| 289 | 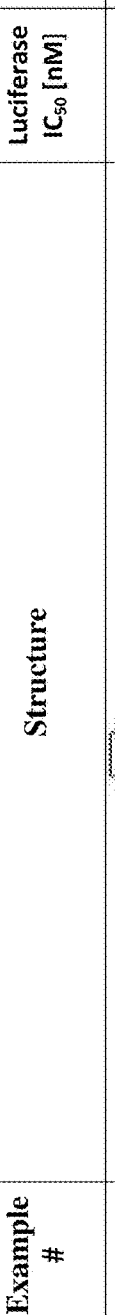 | 0.61 | 767.93 | 768.6 | Scheme 3-52 |
| 290 | 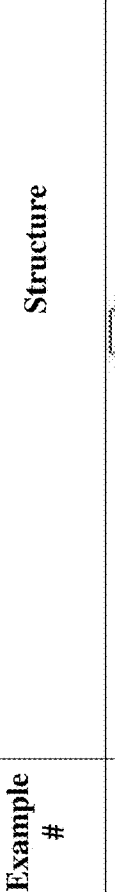 | 0.32 | 737.95 | 738.6 | Scheme 1-28, 2-39 |
| 291 | 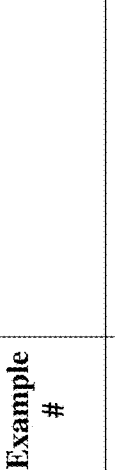 | 0.24 | 751.93 | 752.6 | Scheme 1-28, 2-39 |

FIG. 5 Continued

| Example # | Structure | ERE Luciferase IC$_{50}$ [nM] | MW | Observed [M+H]/z | Synthetic Method |
|---|---|---|---|---|---|
| 292 | 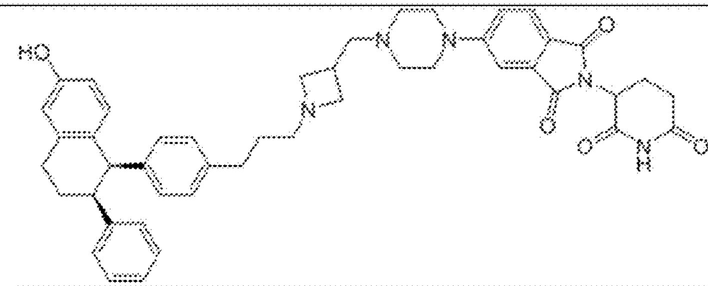 | 0.19 | 751.93 | 752.6 | Scheme 1-28, 2-33 |
| 293 | 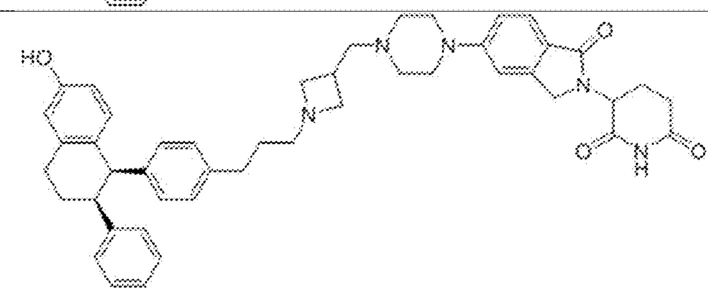 | 1.2 | 737.95 | 738.6 | Scheme 1-28, 2-33 |
| 294 | 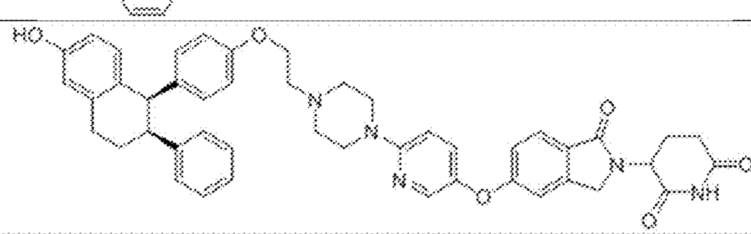 | 1.6 | 763.90 | 764.6 | Scheme 3-53 |

FIG. 5 Continued

| Example # | Structure | ERE Luciferase IC$_{50}$ [nM] | MW | Observed [M+H]/z | Synthetic Method |
|---|---|---|---|---|---|
| 295 | 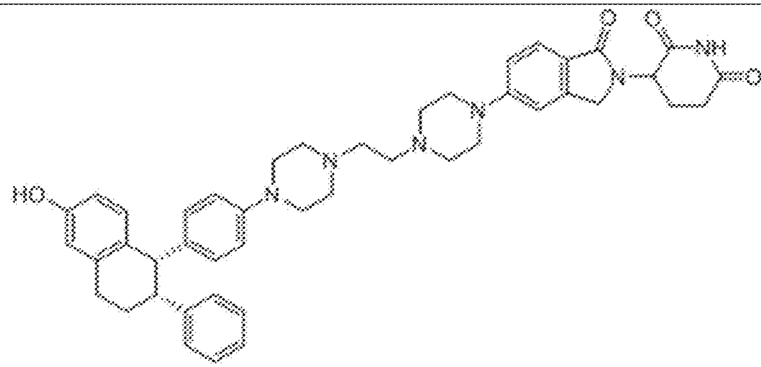 | 137.5 | 738.93 | 739.6 | Scheme 1-4, 3-54 |
| 296 | 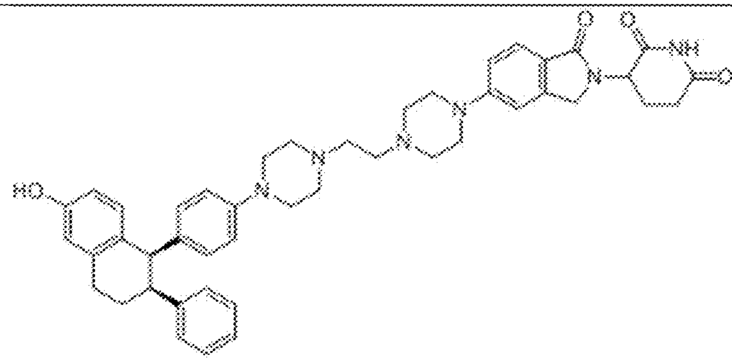 | 0.55 | 738.93 | 739.6 | Scheme 1-4, 3-54 |

FIG. 5 Continued

| Example # | Structure | ERE Luciferase IC$_{50}$ [nM] | MW | Observed [M+H]/z | Synthetic Method |
|---|---|---|---|---|---|
| 297 | 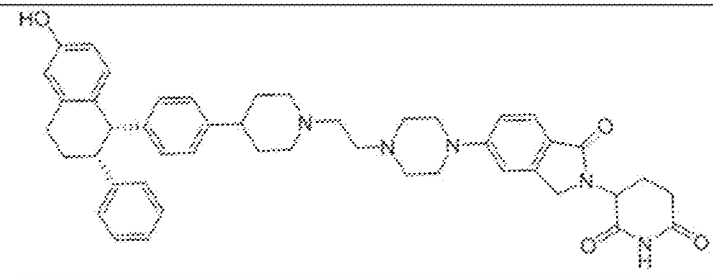 | 69.8 | 737.95 | 738.6 | Scheme 3-54 |
| 298 | 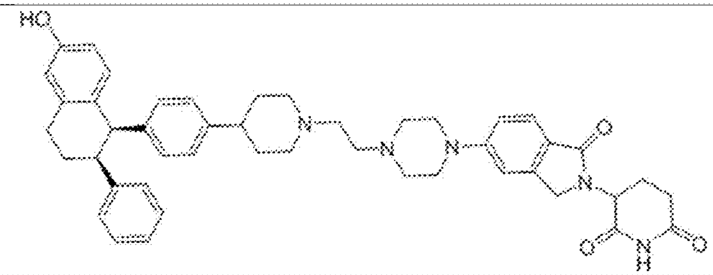 | 0.32 | 737.95 | 738.6 | Scheme 3-54 |
| 299 | 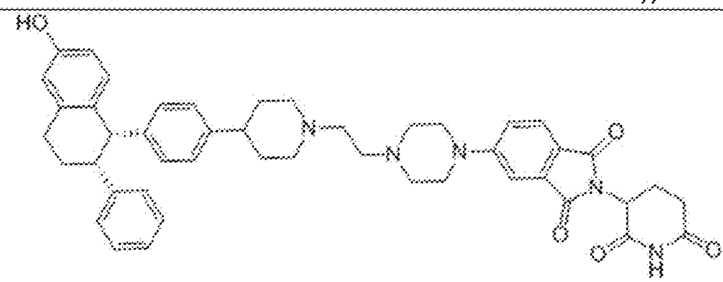 | >100 | 751.93 | 752.6 | Scheme 3-52, 3-54 |

FIG. 5 Continued
| Example # | Structure | ERE Luciferase IC$_{50}$ [nM] | MW | Observed [M+H]/z | Synthetic Method |
|---|---|---|---|---|---|
| 300 | 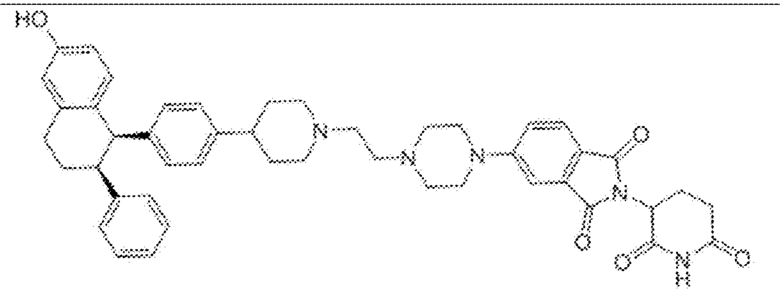 | 0.45 | 751.93 | 752.6 | Scheme 3-52, 3-54 |
| 301 | 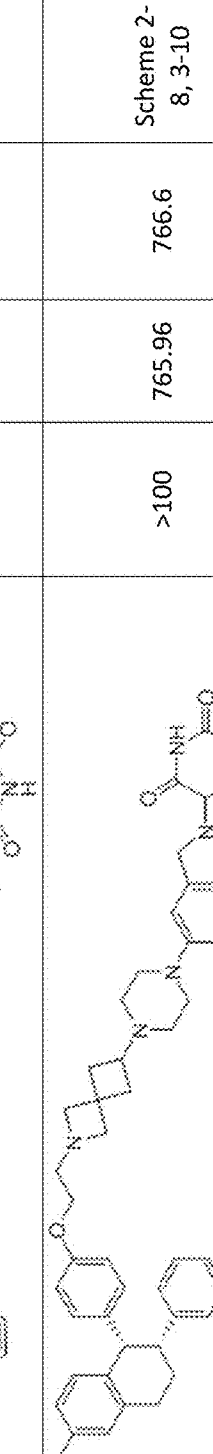 | >100 | 765.96 | 766.6 | Scheme 2-8, 3-10 |
| 302 | 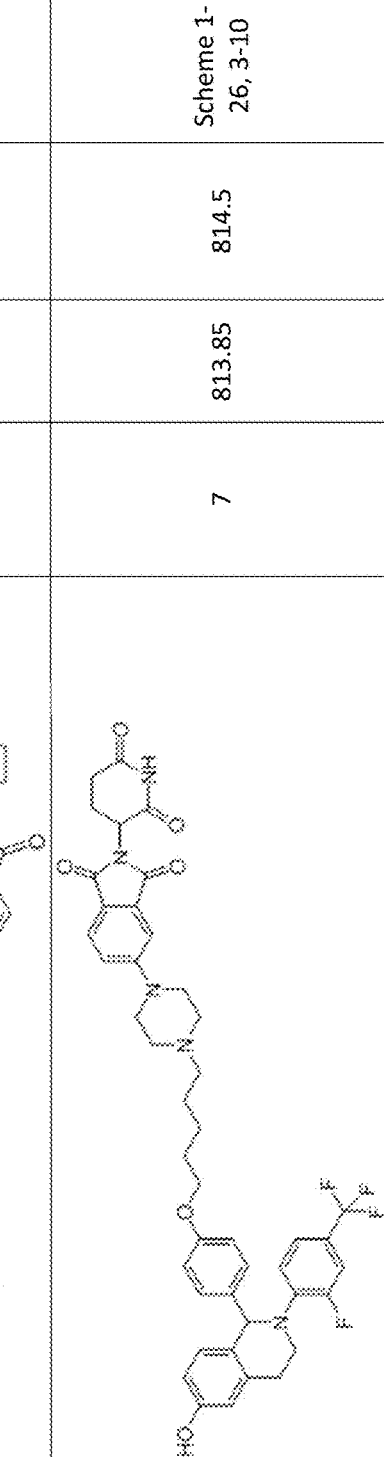 | 7 | 813.85 | 814.5 | Scheme 1-26, 3-10 |

FIG. 5 Continued

| Example # | Structure | ERE Luciferase IC$_{50}$ [nM] | MW | Observed [M+H]/z | Synthetic Method |
|---|---|---|---|---|---|
| 303 | 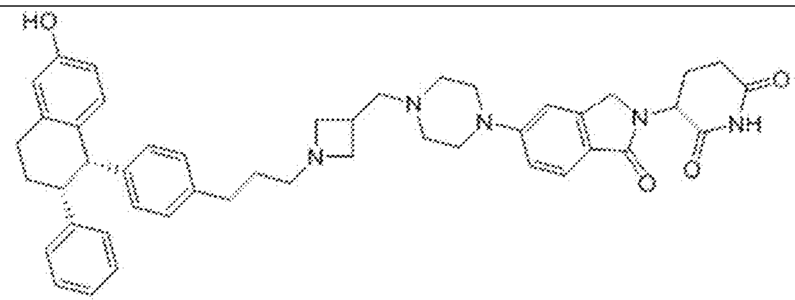 | 66.3 | 737.95 | 738.6 | Scheme 1-28, 2-33 |
| 304 | 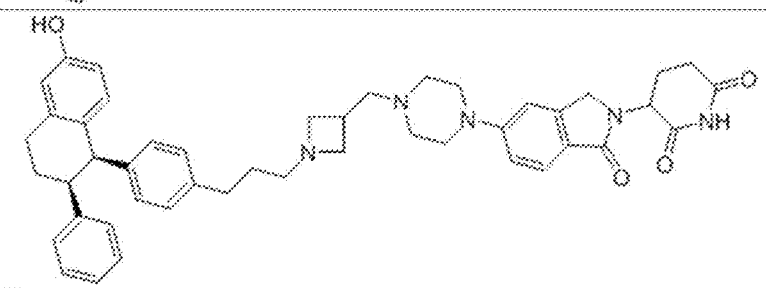 | 0.64 | 737.95 | 738.6 | Scheme 1-28, 2-33 |
| 305 | 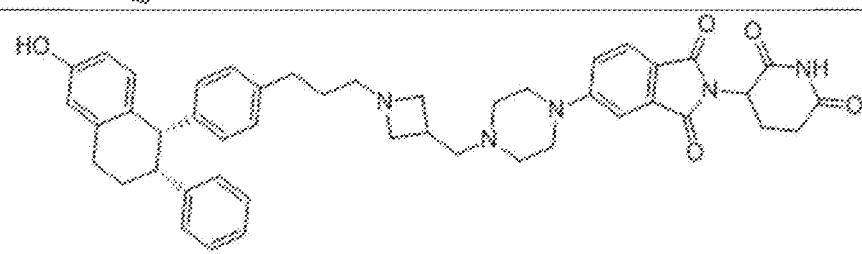 | 32.8 | 751.93 | 752.6 | Scheme 1-28, 2-33 |

FIG. 5 Continued

| Example # | Structure | ERE Luciferase IC$_{50}$ [nM] | MW | Observed [M+H]/Z | Synthetic Method |
|---|---|---|---|---|---|
| 306 | 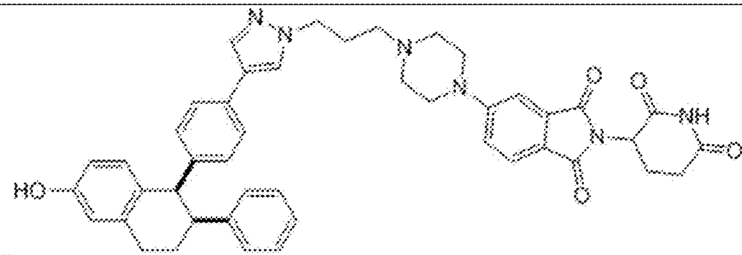 | 1.2 | 748.88 | 749.5 | Scheme 3-51 |
| 307 | 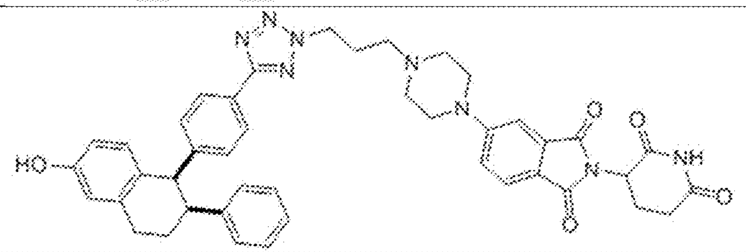 | 2 | 750.86 | 751.5 | Scheme 1-29, 2-1 |
| 308 | 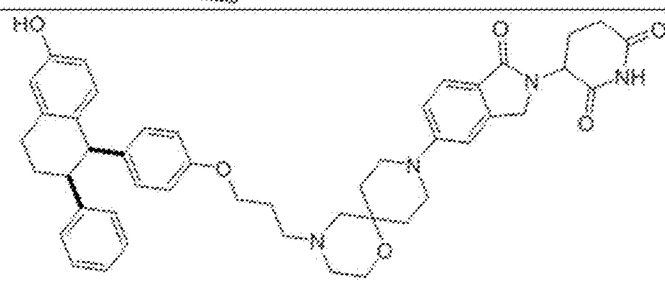 | 3.4 | 754.93 | 755.6 | Scheme 3-55 |
| 309 | 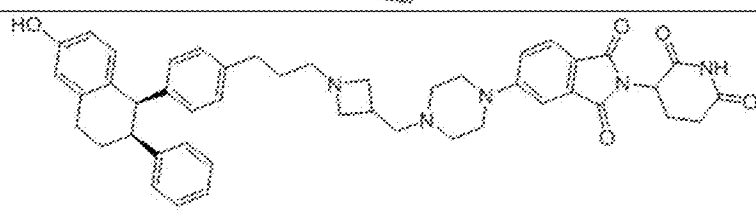 | 0.09 | 751.93 | 752.6 | Scheme 1-28, 2-33 |

FIG. 5 Continued

| Example # | Structure | ERE Luciferase IC$_{50}$ [nM] | MW | Observed [M+H]/z | Synthetic Method |
|---|---|---|---|---|---|
| 310 | 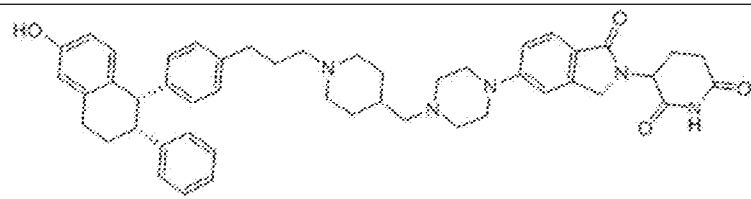 | 117 | 766.00 | 766.6 | Scheme 1-28, 2-33 |
| 311 | 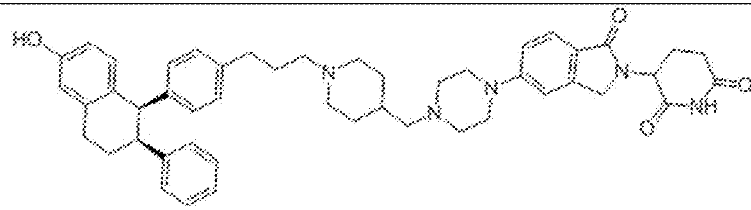 | 2.5 | 766.00 | 766.6 | Scheme 1-28, 2-33 |
| 312 | 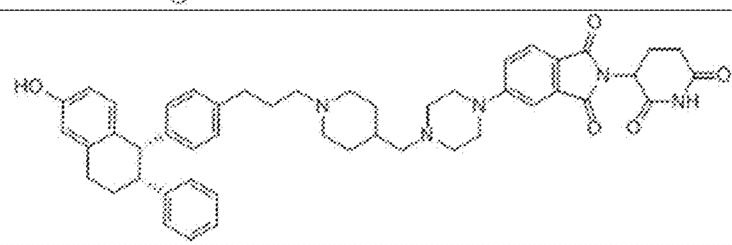 | 102.5 | 779.98 | 780.6 | Scheme 1-28, 2-33 |
| 313 | 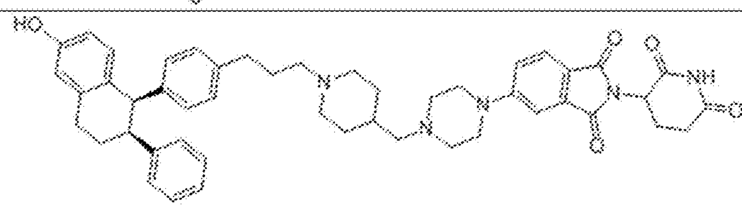 | 1.3 | 779.98 | 780.6 | Scheme 1-28, 2-33 |

FIG. 5 Continued

| Example # | Structure | ERE Luciferase IC$_{50}$ [nM] | MW | Observed [M+H]/Z | Synthetic Method |
|---|---|---|---|---|---|
| 314 | 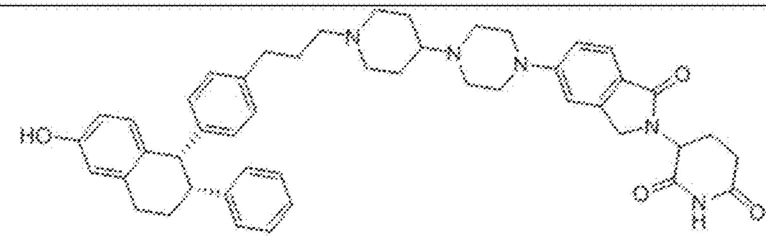 | 57.6 | 751.97 | 752.6 | Scheme 1-28, 3-17 |
| 315 | 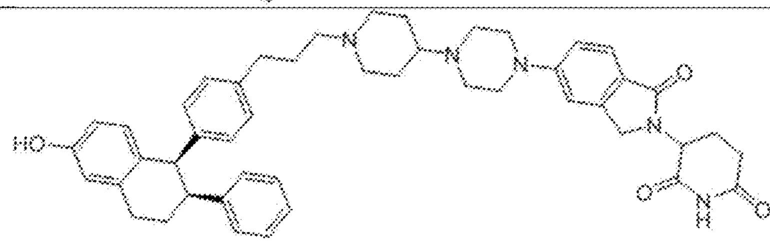 | 0.32 | 751.97 | 752.6 | Scheme 1-28, 3-27 |
| 316 | 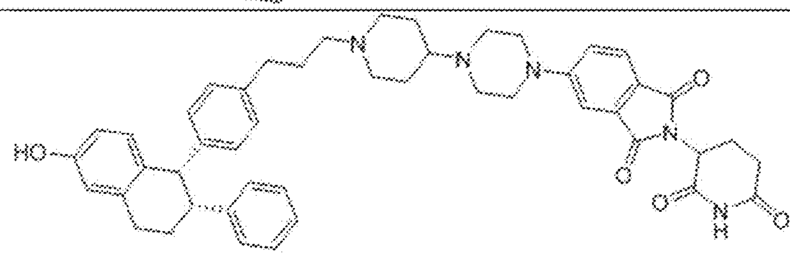 | 12.6 | 765.96 | 766.6 | Scheme 1-28, 3-27 |
| 317 | 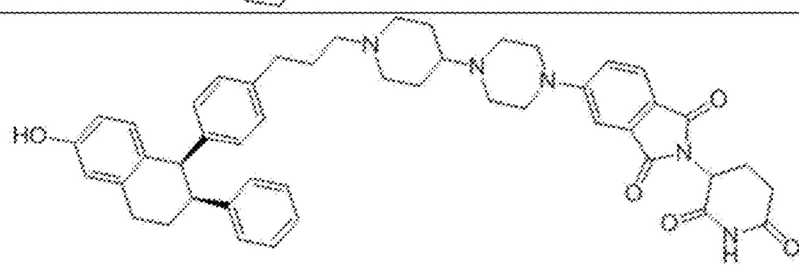 | 0.25 | 765.96 | 766.6 | Scheme 1-28, 3-27 |

FIG. 5 Continued
| Example # | Structure | ERE Luciferase IC$_{50}$ [nM] | MW | Observed [M+H]/z | Synthetic Method |
|---|---|---|---|---|---|
| 318 | 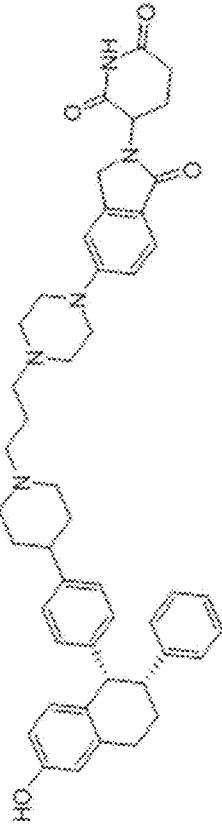 | 62.3 | 751.97 | 752.6 | Scheme 1-5, 3-54 |
| 319 | 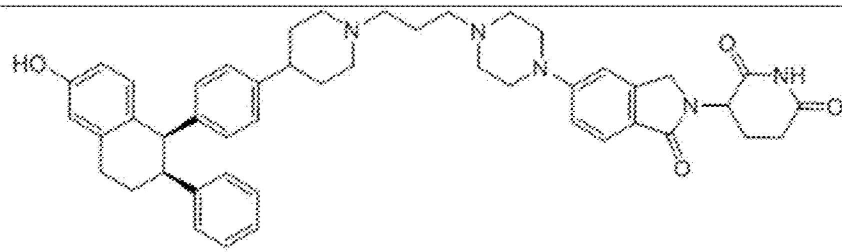 | 1.3 | 751.97 | 752.6 | Scheme 1-5, 3-54 |
| 320 | 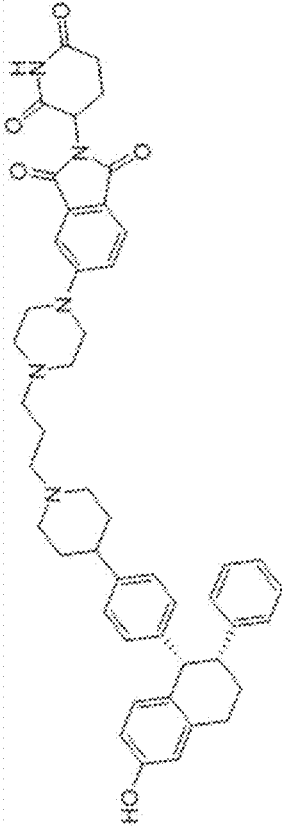 | >300 | 765.96 | 766.6 | Scheme 1-5, 3-52 |

FIG. 5 Continued

| Example # | Structure | ERE Luciferase IC$_{50}$ [nM] | MW | Observed [M+H]/z | Synthetic Method |
|---|---|---|---|---|---|
| 321 | 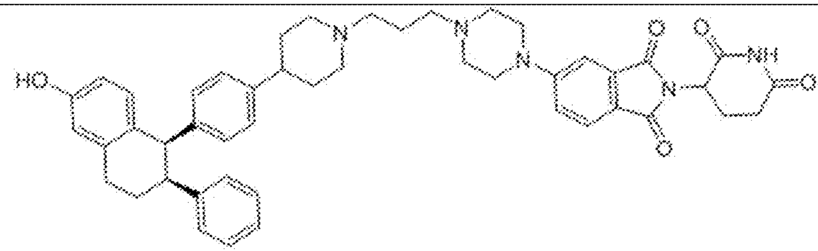 | 1.6 | 765.96 | 766.6 | Scheme 1-5, 3-52 |
| 322 | 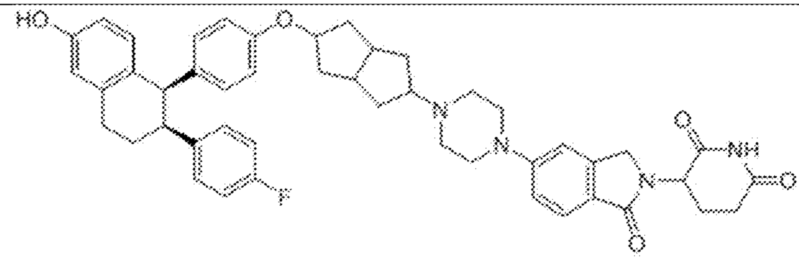 | 1.4 | 768.93 | 769.6 | Scheme 3-41 |
| 323 | 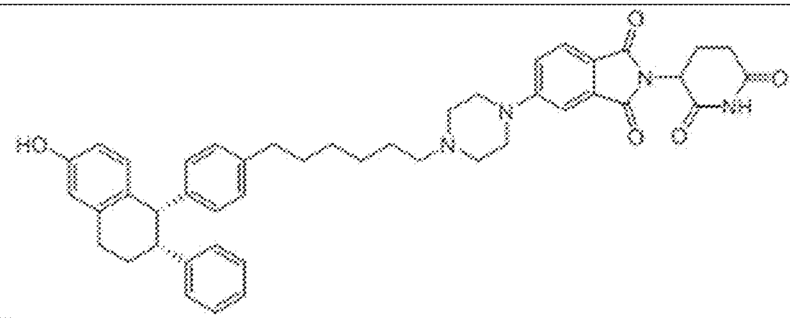 | 161.7 | 724.90 | 725.6 | Scheme 1-28, 3-10 |

FIG. 5 Continued

| Example # | Structure | ERE Luciferase IC$_{50}$ [nM] | MW | Observed [M+H]/z | Synthetic Method |
|---|---|---|---|---|---|
| 324 | 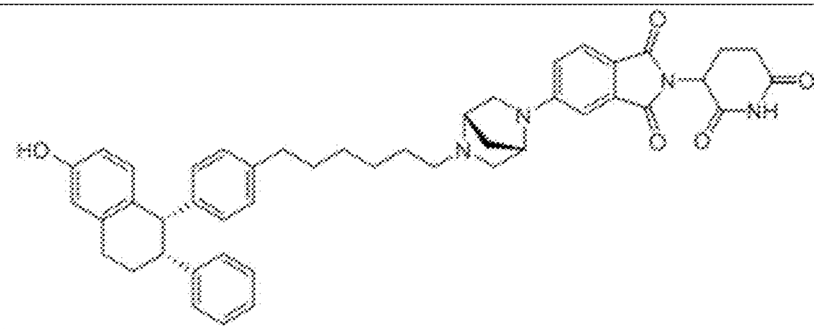 | 79.7 | 736.91 | 737.6 | Scheme 1-28, 3-10 |
| 325 | 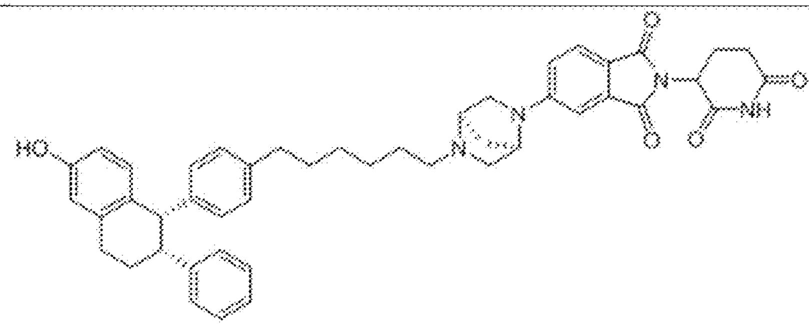 | >300 | 736.91 | 737.6 | Scheme 1-28, 3-10 |
| 326 | 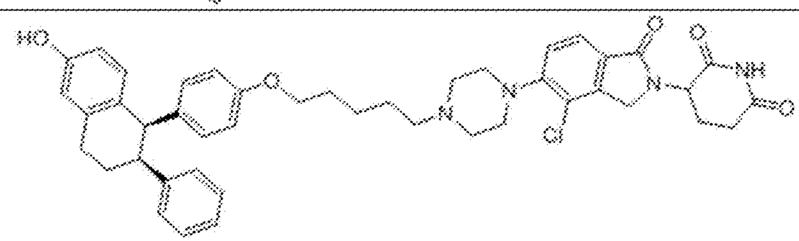 | 0.9 | 747.33 | 747.5 | Scheme 2-41, 3-10 |

FIG. 5 Continued

| Example # | Structure | ERE Luciferase IC$_{50}$ [nM] | MW | Observed [M+H]/Z | Synthetic Method |
|---|---|---|---|---|---|
| 327 | 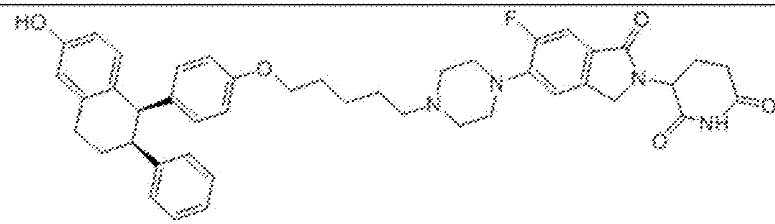 | 0.85 | 730.88 | 731.6 | Scheme 2-11, 3-10 |
| 328 | 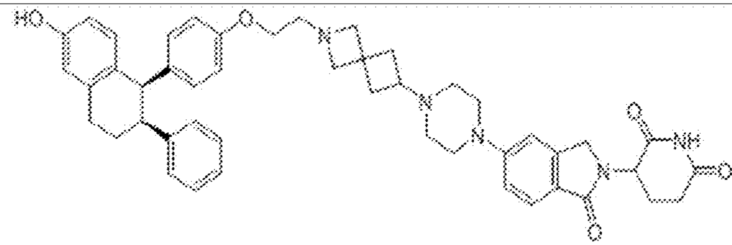 | 1.1 | 765.99 | 766.6 | Scheme 2-13, 3-10 |
| 329 | 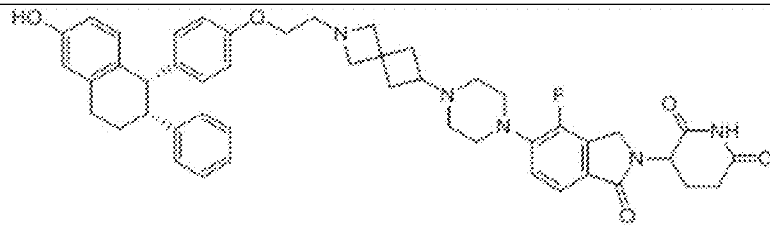 | 115 | 783.95 | 784.6 | Scheme 2-11, 3-10 |
| 330 | 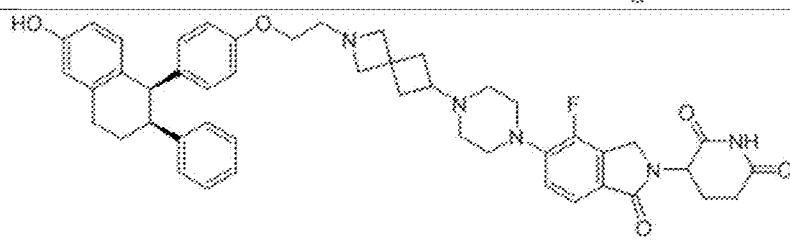 | 0.32 | 783.95 | 784.6 | Scheme 2-11, 3-10 |

FIG. 5 Continued
| Example # | Structure | ERE Luciferase IC$_{50}$ [nM] | MW | Observed [M+H]/z | Synthetic Method |
|---|---|---|---|---|---|
| 331 | 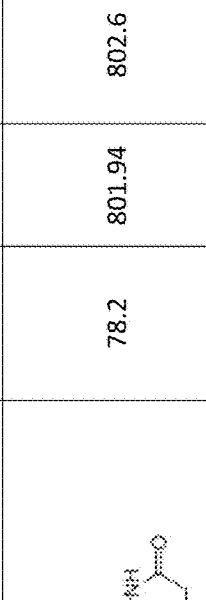 | 78.2 | 801.94 | 802.6 | Scheme 2-12, 3-10 |
| 332 | 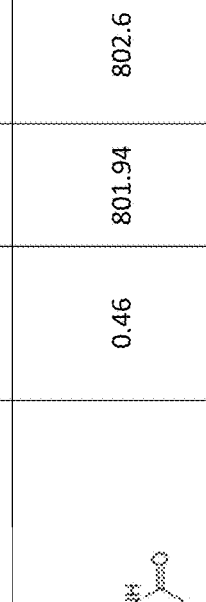 | 0.46 | 801.94 | 802.6 | Scheme 2-12, 3-10 |
| 333 | 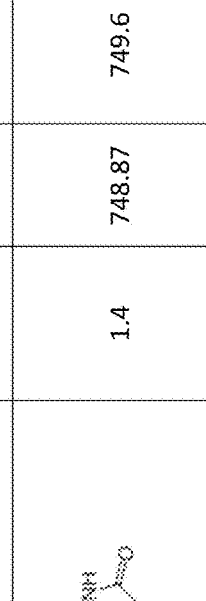 | 1.4 | 748.87 | 749.6 | Scheme 2-12, 3-10 |
| 334 | 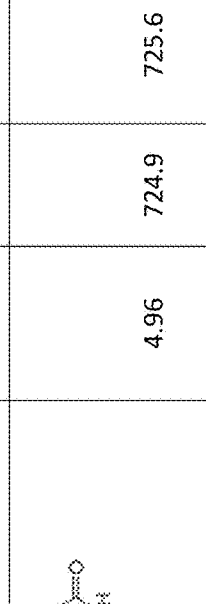 | 4.96 | 724.9 | 725.6 | Scheme 1-28, 2-1 |

FIG. 5 Continued

| Example # | Structure | ERE Luciferase IC$_{50}$ [nM] | MW | Observed [M+H]/z | Synthetic Method |
|---|---|---|---|---|---|
| 335 | 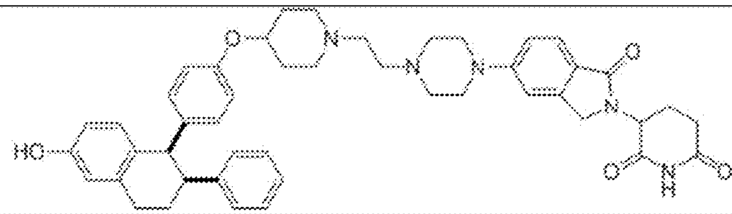 | 0.42 | 753.94 | 754.6 | Scheme 3-52 |
| 336 | 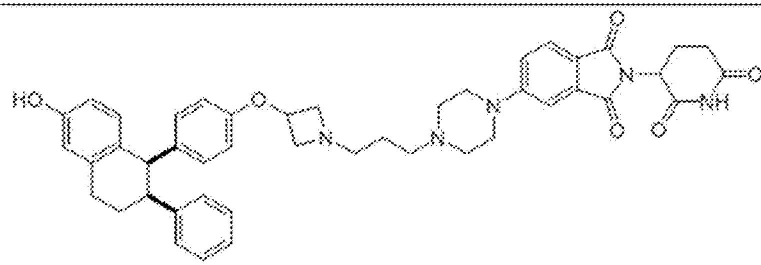 | 1.13 | 753.9 | 754.6 | Scheme 3-57 |
| 337 | 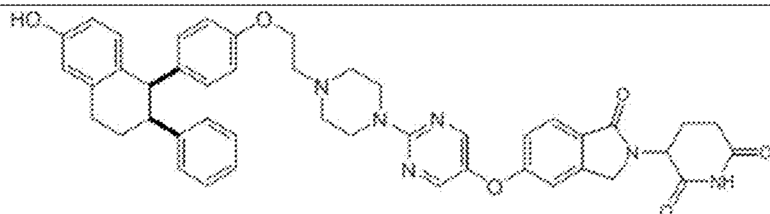 | 2.51 | 764.88 | 765.5 | Scheme 2-42, 3-10 |
| 338 | 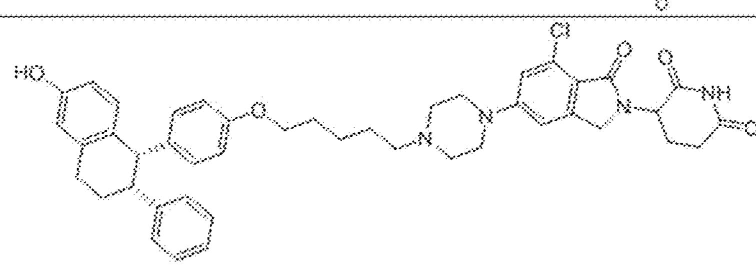 | >300 | 747.33 | 747.5 | Scheme 2-41, 3-10 |

FIG. 5 Continued

| Example # | Structure | ERE Luciferase IC$_{50}$ [nM] | MW | Observed [M+H]/z | Synthetic Method |
|---|---|---|---|---|---|
| 339 | 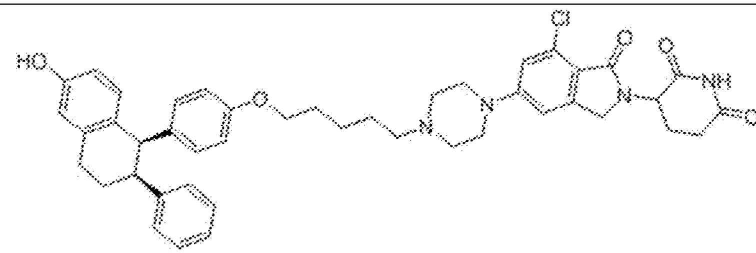 | 2.09 | 747.33 | 747.5 | Scheme 2-41, 3-10 |
| 340 | 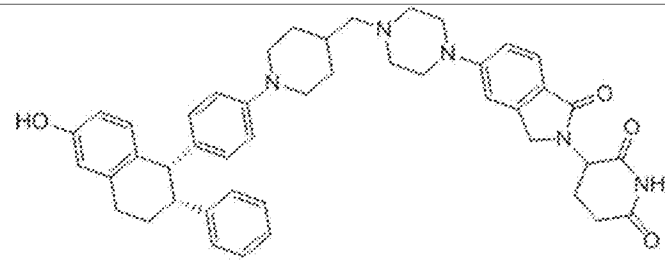 | >300 | 723.92 | 724.6 | Scheme 3-58 |
| 341 | 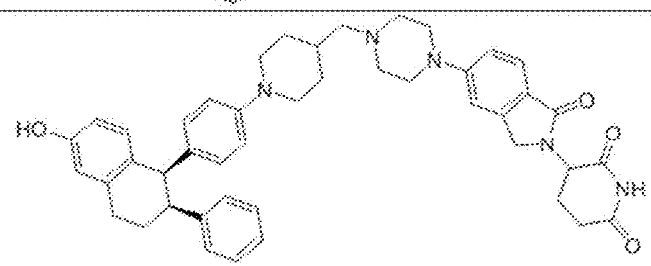 | 1.77 | 723.92 | 724.6 | Scheme 3-58 |

FIG. 5 Continued
| Example # | Structure | ERE Luciferase IC$_{50}$ [nM] | MW | Observed [M+H]/z | Synthetic Method |
|---|---|---|---|---|---|
| 342 | 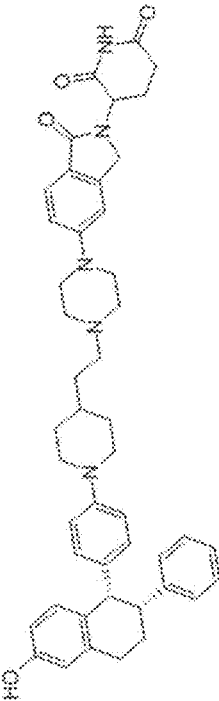 | 114 | 737.95 | 738.6 | Scheme 3-59 |
| 343 | 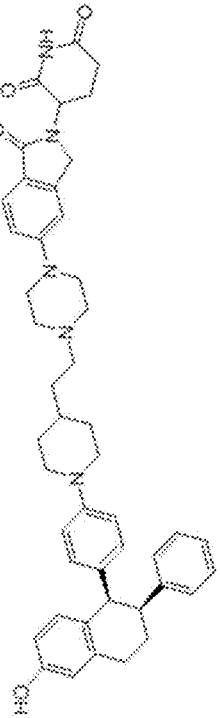 | 1.35 | 737.95 | 738.6 | Scheme 3-59 |
| 344 | 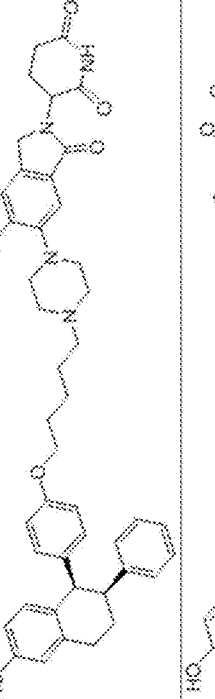 | 1.71 | 730.88 | 731.6 | Scheme 2-43, 3-10 |
| 345 | 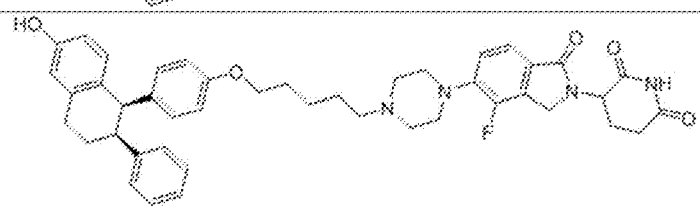 | 1.53 | 730.88 | 731.6 | Scheme 2-11, 3-10 |

FIG. 5 Continued

| Example # | Structure | ERE Luciferase IC$_{50}$ [nM] | MW | Observed [M+H]/z | Synthetic Method |
|---|---|---|---|---|---|
| 346 | 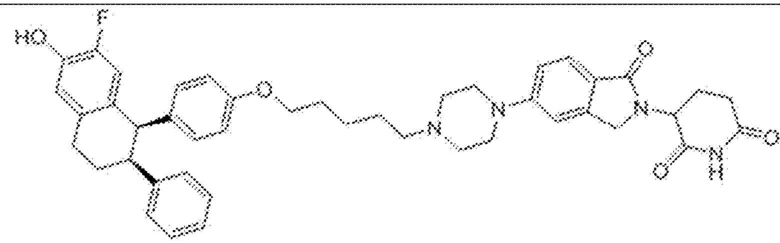 | 1.43 | 730.88 | 731.6 | Scheme 1-30, 3-10 |
| 347 | 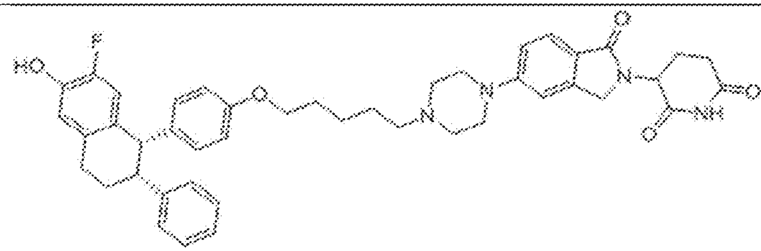 | 106 | 730.88 | 731.6 | Scheme 1-30, 3-10 |
| 348 | 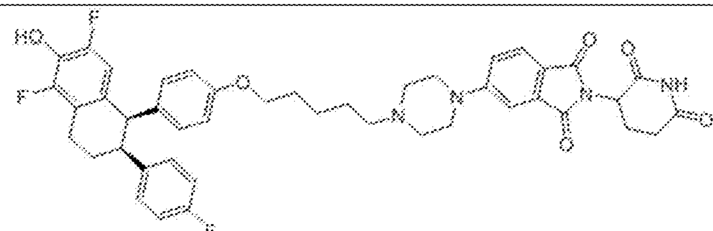 | 8.34 | 780.85 | 781.5 | Scheme 1-31, 3-10 |
| 349 | 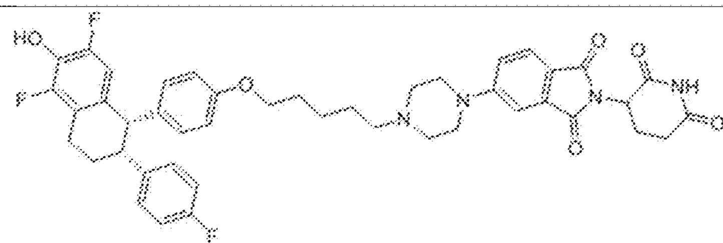 | >300 | 780.85 | 781.5 | Scheme 1-31, 3-10 |

FIG. 5 Continued

| Example # | Structure | ERE Luciferase IC$_{50}$ [nM] | MW | Observed [M+H]/z | Synthetic Method |
|---|---|---|---|---|---|
| 350 | 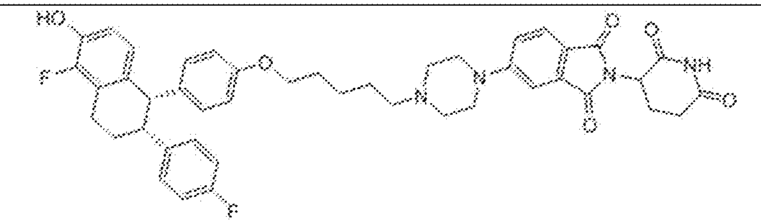 | >300 | 762.85 | 763.5 | Scheme 1-30, 3-10 |
| 351 | 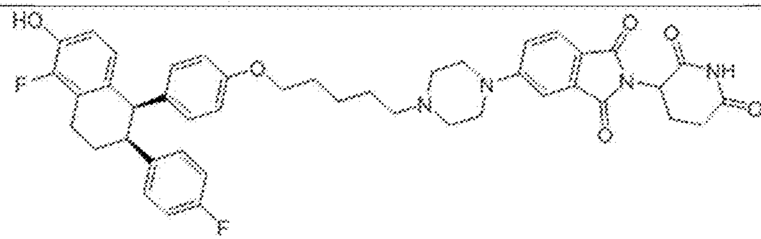 | 3.32 | 762.85 | 763.5 | Scheme 1-30, 3-10 |
| 352 | 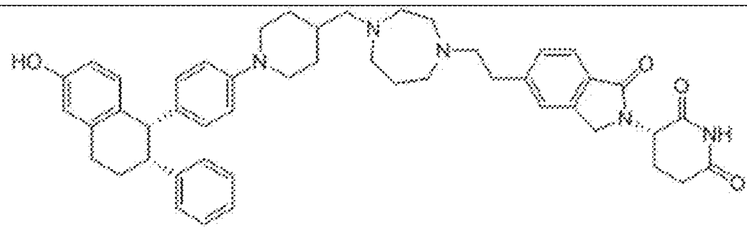 | >300 | 766 | 766.6 | Scheme 1-9, 3-29 |
| 353 | 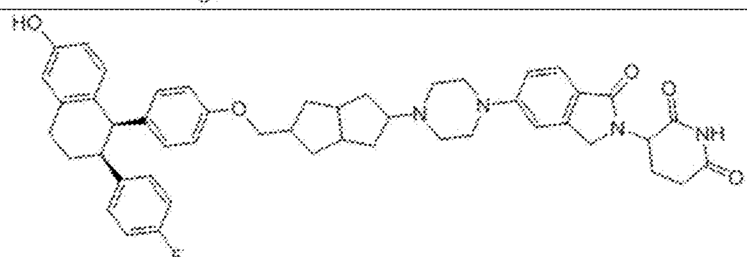 | 2.51 | 782.96 | 783.6 | Scheme 1-32, 2-1 |

FIG. 5 Continued
| Example # | Structure | ERE Luciferase IC$_{50}$ [nM] | MW | Observed [M+H]/z | Synthetic Method |
|---|---|---|---|---|---|
| 354 | 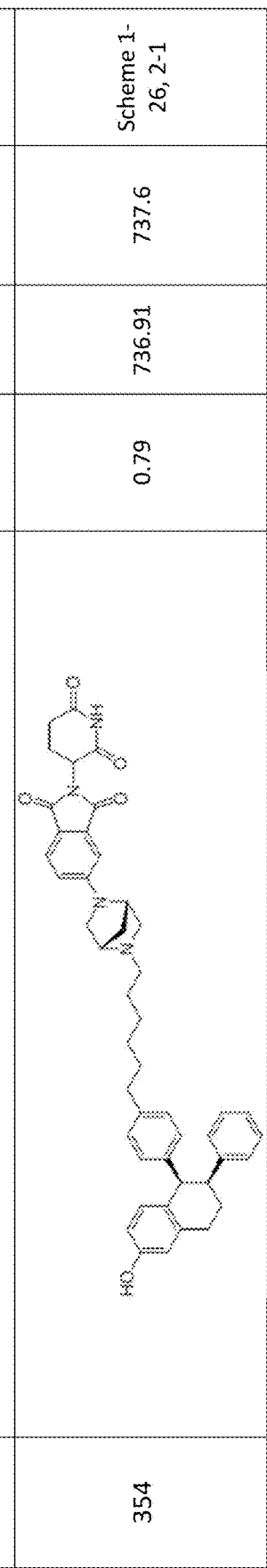 | 0.79 | 736.91 | 737.6 | Scheme 1-26, 2-1 |
| 355 | 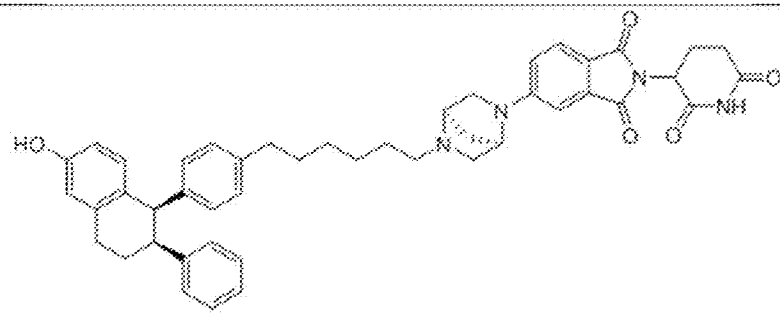 | 2.36 | 736.91 | 737.6 | Scheme 1-26, 2-1 |
| 356 | 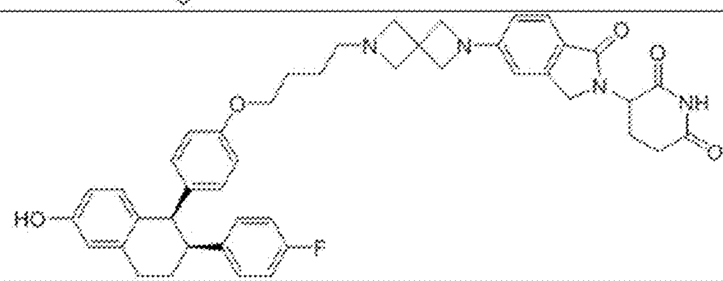 | 0.14 | 728.87 | 729.5 | Scheme 2-1, 3-10 |

FIG. 5 Continued

| Example # | Structure | ERE Luciferase IC$_{50}$ [nM] | MW | Observed [M+H]/z | Synthetic Method |
|---|---|---|---|---|---|
| 357 | 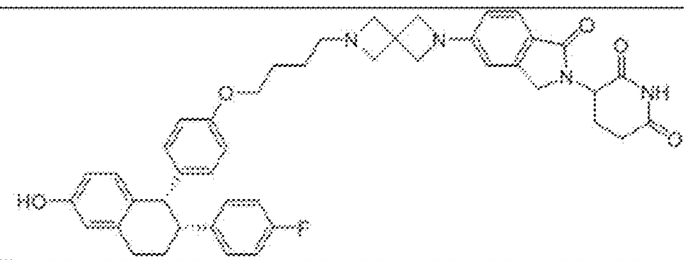 | 114 | 728.87 | 729.5 | Scheme 2-1, 3-10 |
| 358 | 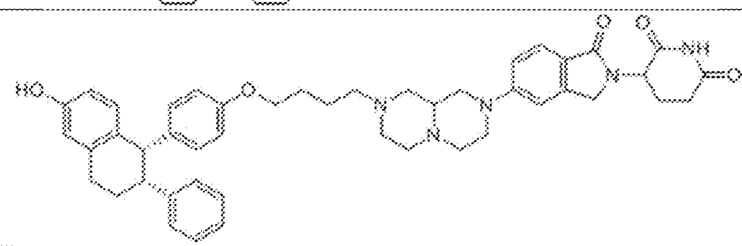 | >300 | 753.94 | 754.6 | Scheme 1-30, 2-44 |
| 359 | 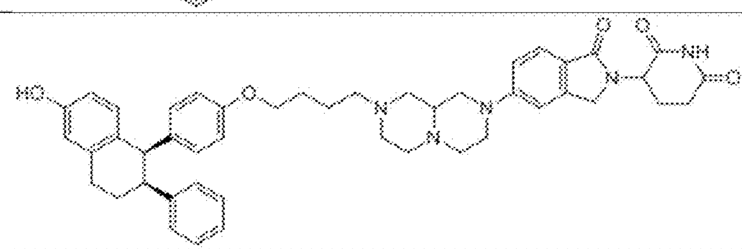 | 0.49 | 753.94 | 754.6 | Scheme 1-30, 2-44 |

FIG. 5 Continued

| Example # | Structure | ERE Luciferase IC₅₀ [nM] | MW | Observed [M+H]/z | Synthetic Method |
|---|---|---|---|---|---|
| 360 | 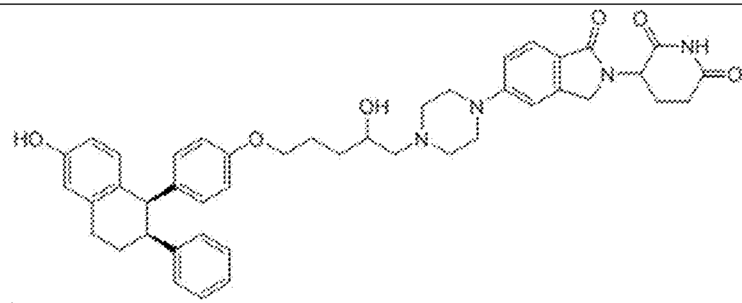 | 0.45 | 728.89 | 729.6 | Scheme 3-60 |
| 361 | 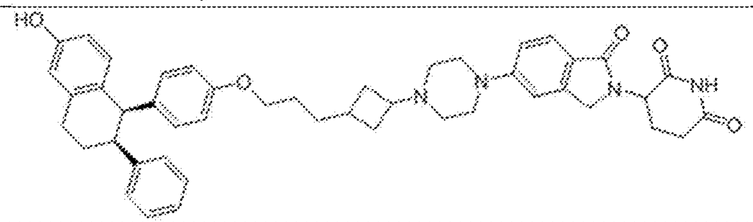 | 1.47 | 738.93 | 739.6 | Scheme 1-33, 2-1 |
| 362 | 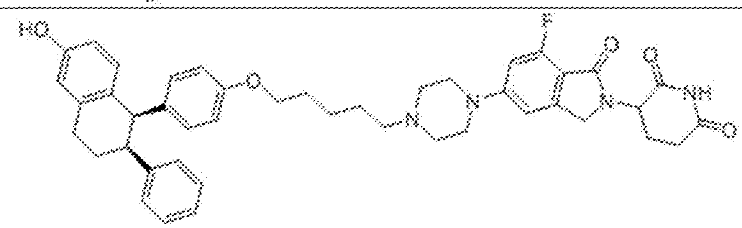 | 0.97 | 730.88 | 731.6 | Scheme 2-11, 3-10 |
| 363 | 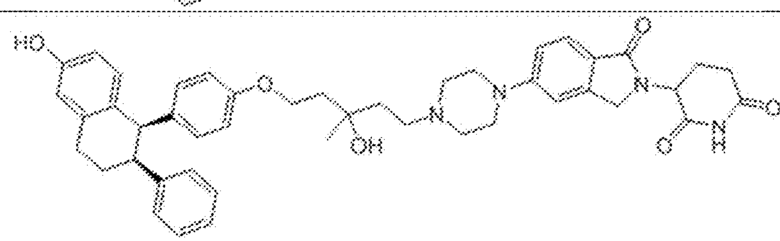 | 0.93 | 742.92 | 743.6 | Scheme 3-61 |

FIG. 5 Continued

| Example # | Structure | ERE Luciferase IC₅₀ [nM] | MW | Observed [M+H]/z | Synthetic Method |
|---|---|---|---|---|---|
| 364 | 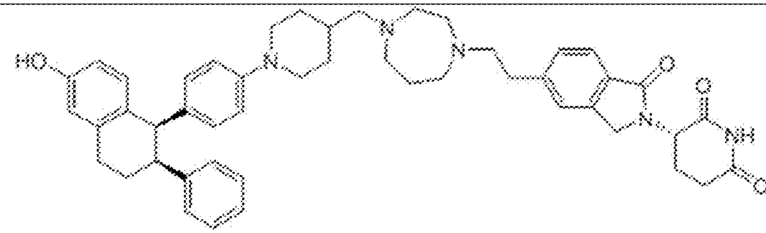 | 1.13 | 766.00 | 766.6 | Scheme 3-29, 3-58 |
| 365 | 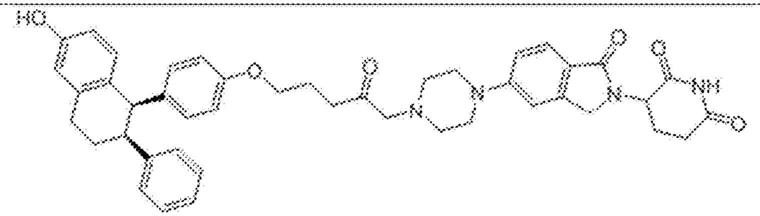 | 1.05 | 726.87 | 727.5 | Scheme 3-62 |
| 366 | 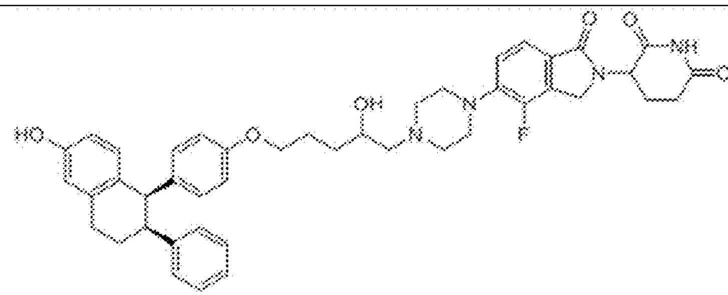 | 1.37 | 746.88 | 747.6 | Scheme 2-11, 3-60 |

FIG. 5 Continued

| Example # | Structure | ERE Luciferase IC$_{50}$ [nM] | MW | Observed [M+H]/z | Synthetic Method |
|---|---|---|---|---|---|
| 367 | 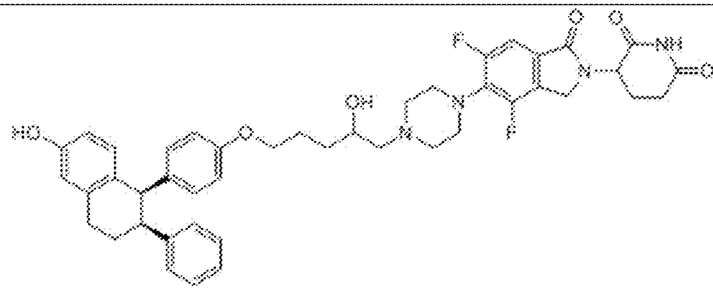 | 1.25 | 764.87 | 765.6 | Scheme 2-12, 3-60 |
| 368 | 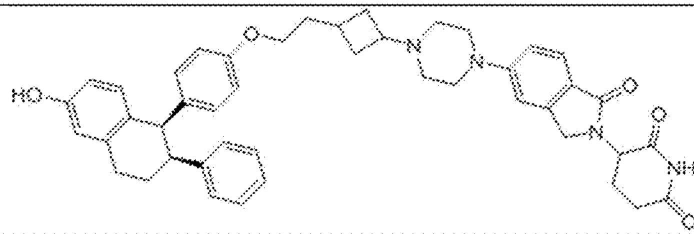 | 1.61 | 724.90 | 725.6 | Scheme 1-33, 3-10 |
| 369 | 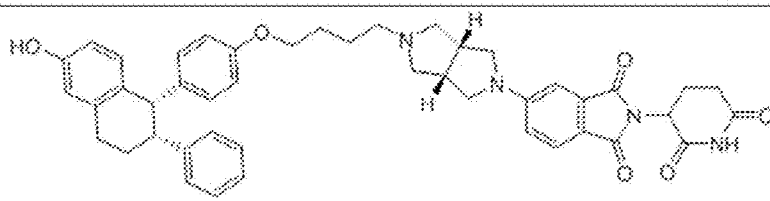 | 75.6 | 738.89 | 739.6 | Scheme 2-1, 3-10 |
| 370 | 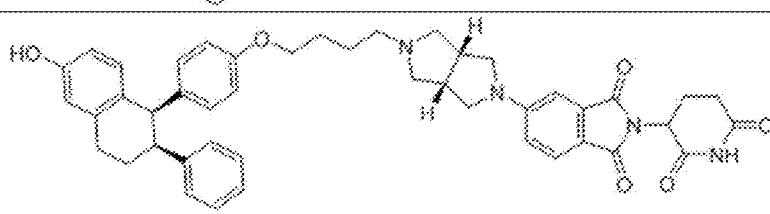 | 0.33 | 738.89 | 739.6 | Scheme 2-1, 3-10 |

FIG. 5 Continued

| Example # | Structure | ERE Luciferase IC$_{50}$ [nM] | MW | Observed [M+H]/z | Synthetic Method |
|---|---|---|---|---|---|
| 371 | 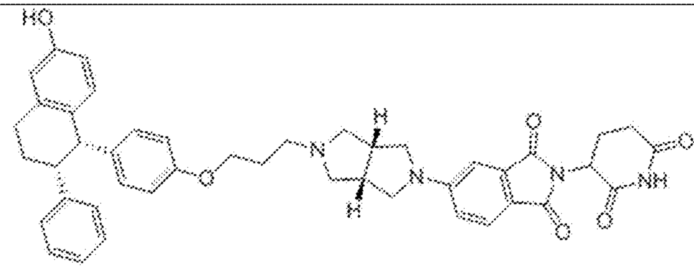 | >300 | 724.86 | 725.5 | Scheme 2-1, 3-10 |
| 372 | 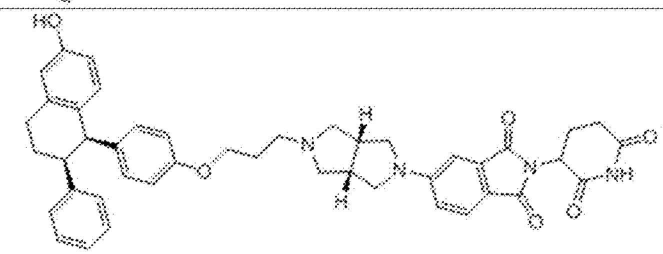 | 0.34 | 724.86 | 725.5 | Scheme 2-1, 3-10 |
| 373 | 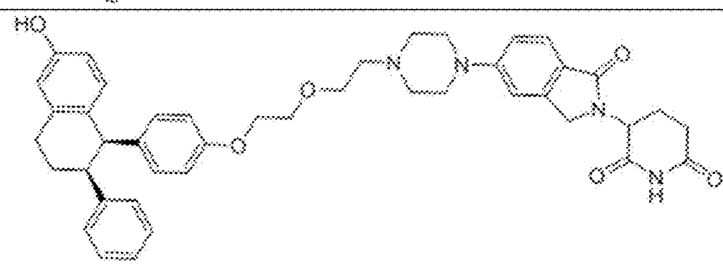 | 0.69 | 714.86 | 715.5 | Scheme 3-8, 3-10 |
| 374 | 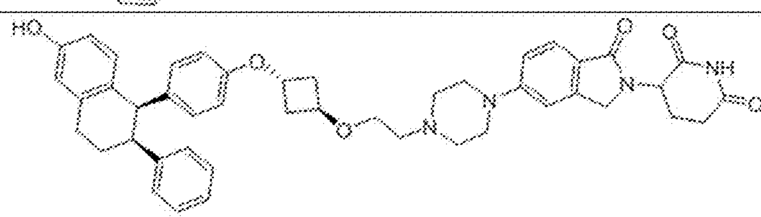 | 1.29 | 740.90 | 741.6 | Scheme 3-63 |

FIG. 5 Continued
| Example # | Structure | ERE Luciferase IC$_{50}$ [nM] | MW | Observed [M+H]/z | Synthetic Method |
|---|---|---|---|---|---|
| 375 | 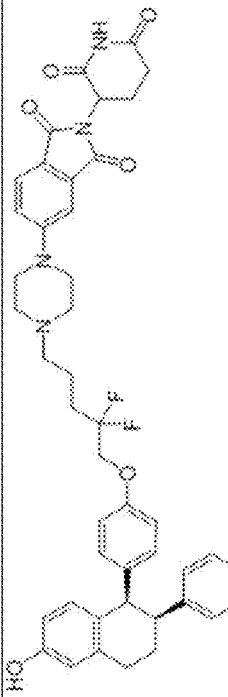 | 5.36 | 762.85 | 763.5 | Scheme 3-40 |
| 376 | 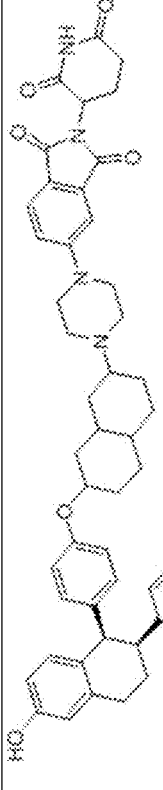 | 26.3 | 810.97 | 811.6 | Scheme 1-34, 2-1 |
| 377 | 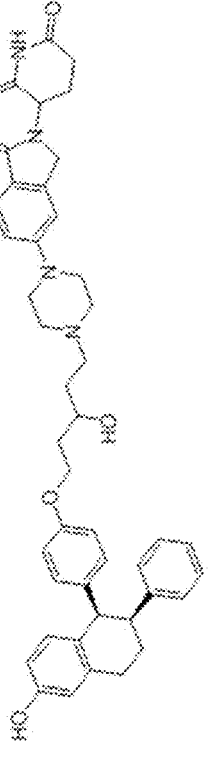 | 0.54 | 728.89 | 729.6 | Scheme 3-64 |

FIG. 5 Continued
| Example # | Structure | ERE Luciferase IC$_{50}$ [nM] | MW | Observed [M+H]/z | Synthetic Method |
|---|---|---|---|---|---|
| 378 | 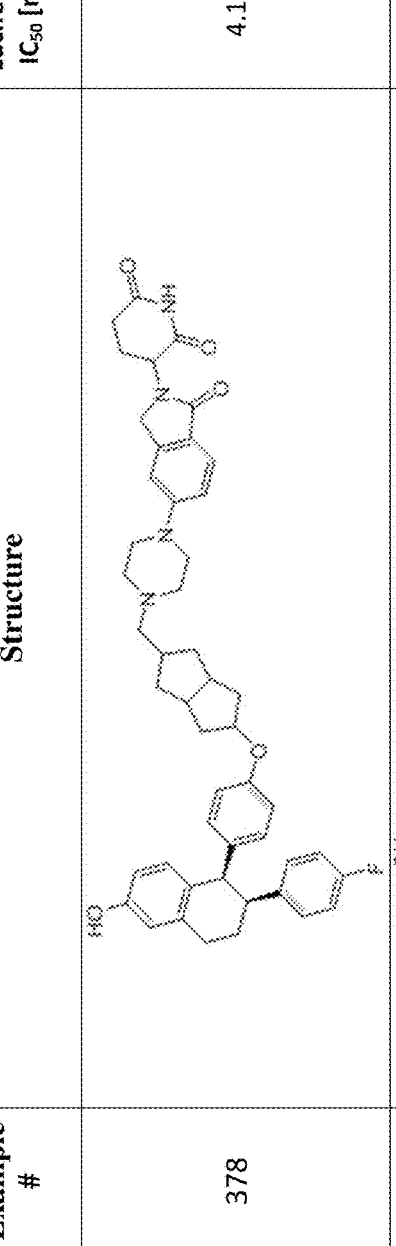 | 4.13 | 782.96 | 783.6 | Scheme 1-35, 2-1 |
| 379 | 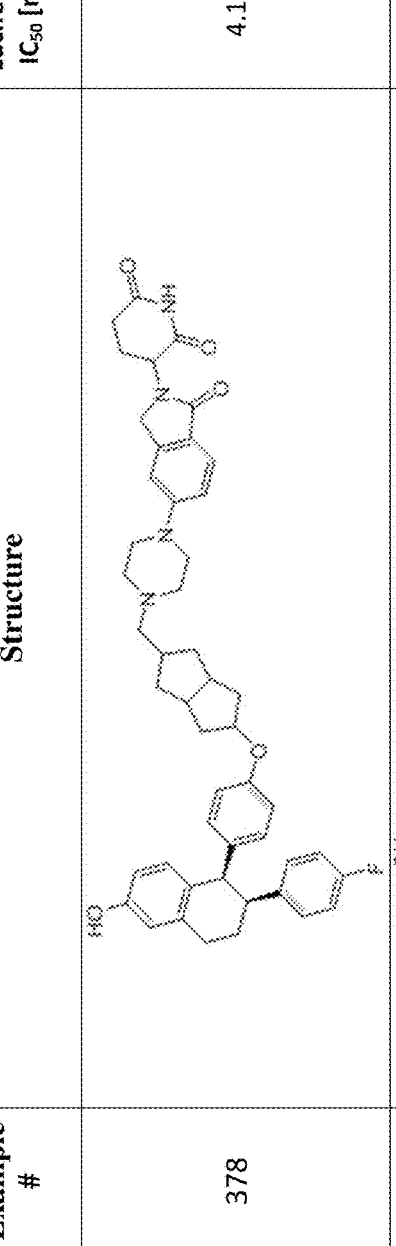 | 7.32 | 818.94 | 819.6 | Scheme 1-35, 2-12 |
| 380 | 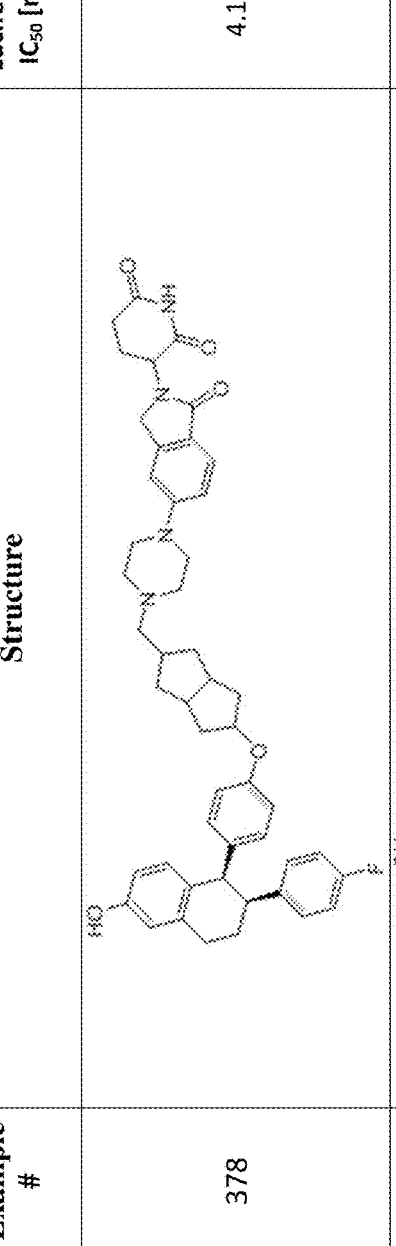 | 1.5 | 738.93 | 739.6 | Scheme 1-36, 2-1 |

FIG. 5 Continued

| Example # | Structure | ERE Luciferase IC$_{50}$ [nM] | MW | Observed [M+H]/z | Synthetic Method |
|---|---|---|---|---|---|
| 381 | 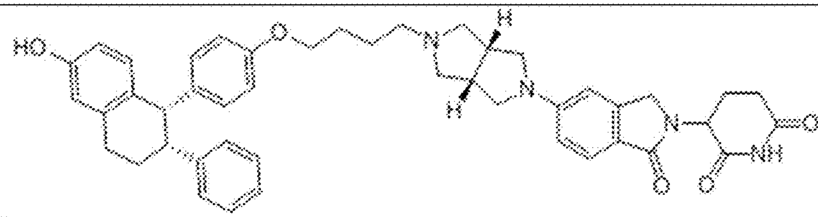 | 41.9 | 724.90 | 725.6 | Scheme 2-1, 3-10 |
| 382 | 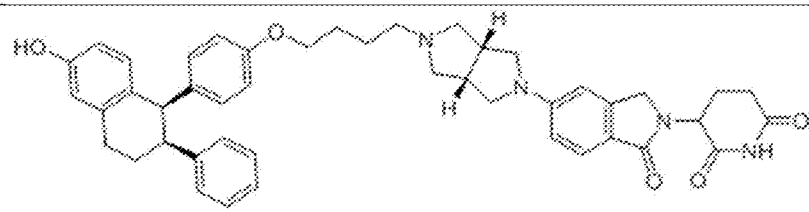 | 0.21 | 724.90 | 725.6 | Scheme 2-1, 3-10 |
| 383 | 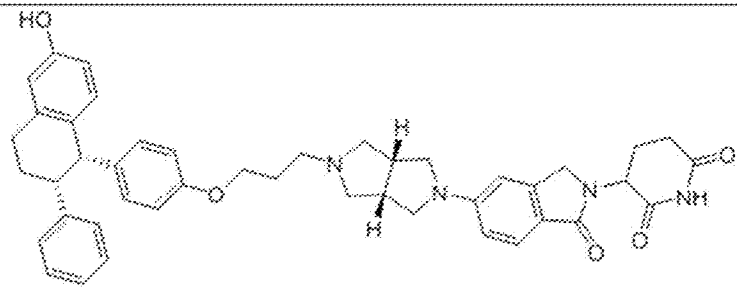 | 54.4 | 710.88 | 711.5 | Scheme 2-1, 3-10 |
| 384 | 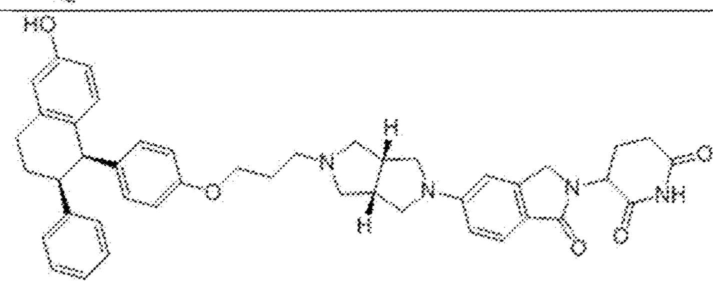 | 0.19 | 710.88 | 711.5 | Scheme 2-1, 3-10 |

FIG. 5 Continued

| Example # | Structure | ERE Luciferase IC$_{50}$ [nM] | MW | Observed [M+H]/z | Synthetic Method |
|---|---|---|---|---|---|
| 385 | 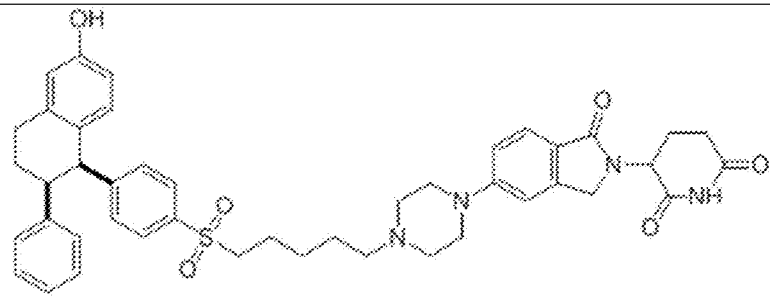 | 6.91 | 760.95 | 761.3 | Scheme 1-37, 2-1 |
| 386 | 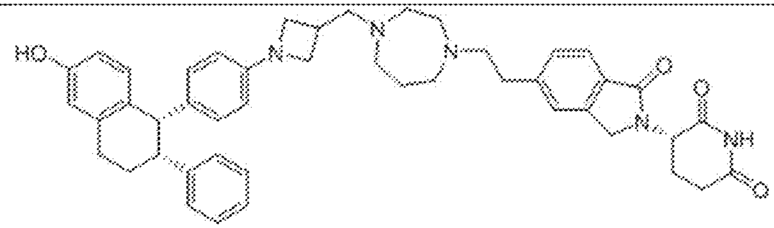 | 101 | 737.95 | 738.6 | Scheme 3-29, 3-58 |
| 387 | 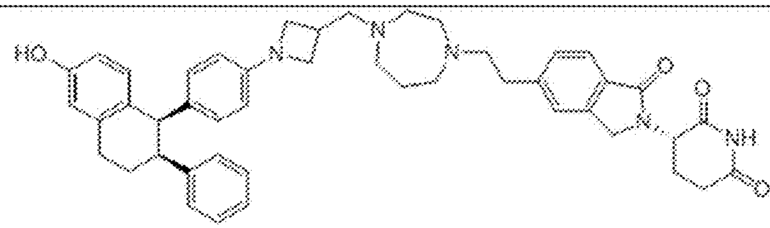 | 1.27 | 737.95 | 738.6 | Scheme 3-65 |
| 388 | 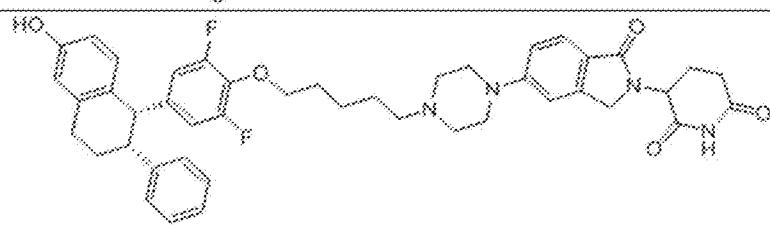 | >300 | 748.87 | 749.6 | Scheme 3-65 |

FIG. 5 Continued

| Example # | Structure | ERE Luciferase IC$_{50}$ [nM] | MW | Observed [M+H]/z | Synthetic Method |
|---|---|---|---|---|---|
| 389 | 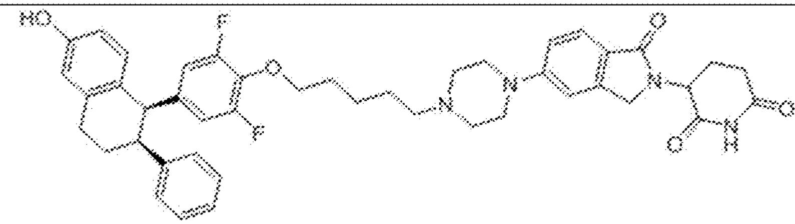 | 3.04 | 748.87 | 749.6 | Scheme 1-1, 2-1 |
| 390 | 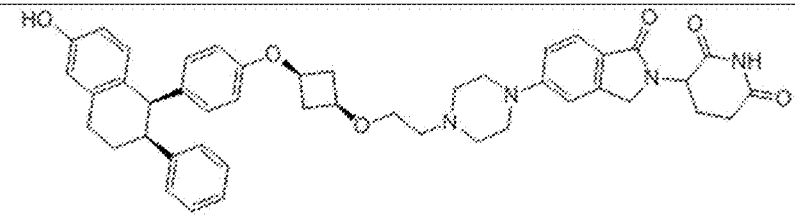 | 1.4 | 740.90 | 741.6 | Scheme 1-38, 3-10 |
| 391 | 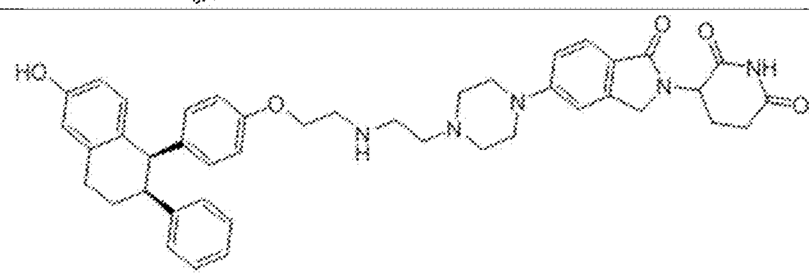 | 0.92 | 713.88 | 714.6 | Scheme 2-45, 3-10 |

FIG. 5 Continued

| Example # | Structure | ERE Luciferase IC$_{50}$ [nM] | MW | Observed [M+H]/z | Synthetic Method |
|---|---|---|---|---|---|
| 392 | 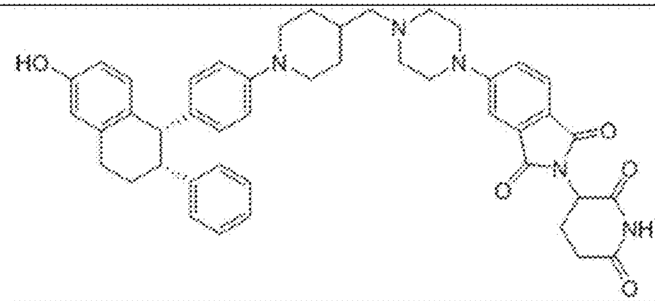 | >300 | 737.90 | 738.6 | Scheme 3-58 |
| 393 | 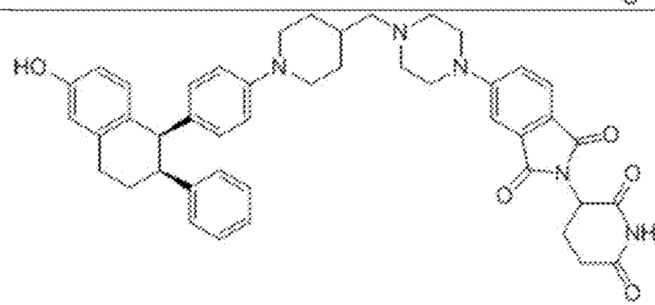 | 11 | 737.90 | 738.6 | Scheme 3-58 |
| 394 | 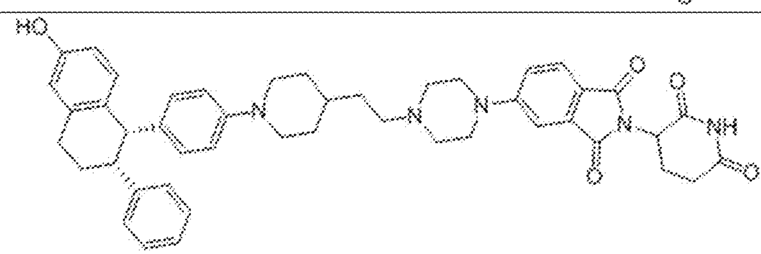 | >300 | 751.93 | 752.6 | Scheme 3-59 |

FIG. 5 Continued

| Example # | Structure | ERE Luciferase IC$_{50}$ [nM] | MW | Observed [M+H]/z | Synthetic Method |
|---|---|---|---|---|---|
| 395 | 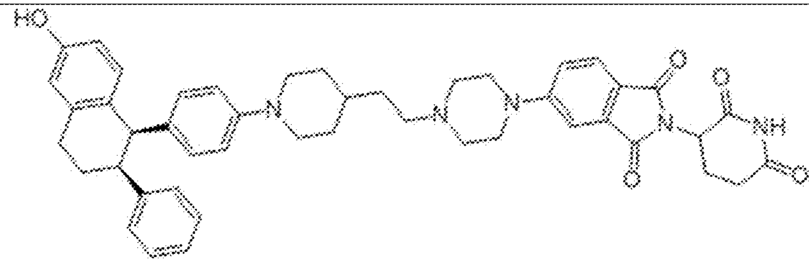 | 11.8 | 751.93 | 752.6 | Scheme 3-59 |
| 396 | 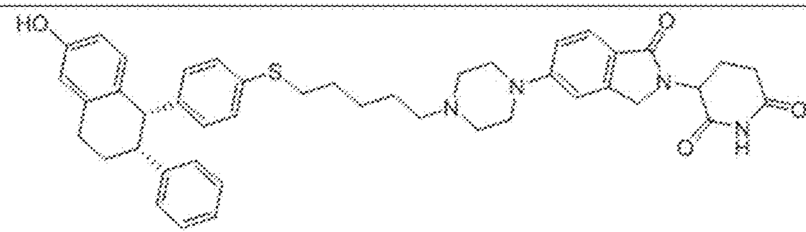 | >300 | 728.95 | 729.5 | Scheme 1-37, 2-1 |
| 397 | 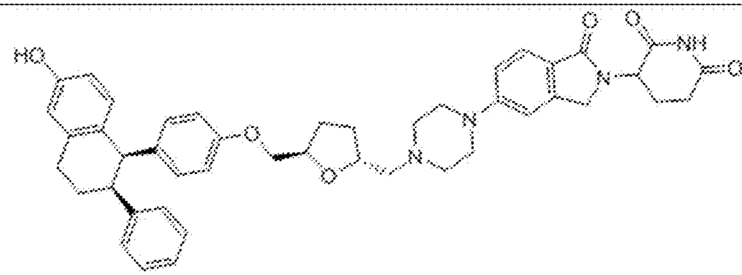 | 1.07 | 740.9 | 741.6 | Scheme 1-15, 3-10 |
| 398 | 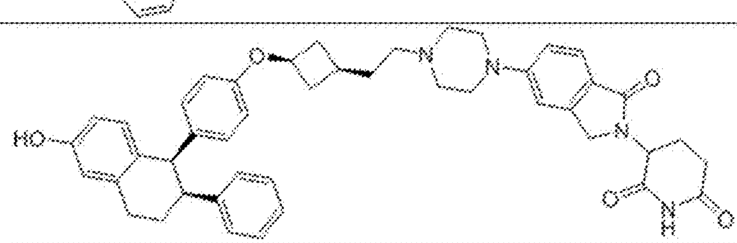 | 2.04 | 724.9 | 725.6 | Scheme 3-66 |

FIG. 5 Continued

| Example # | Structure | ERE Luciferase IC$_{50}$ [nM] | MW | Observed [M+H]/z | Synthetic Method |
|---|---|---|---|---|---|
| 399 | 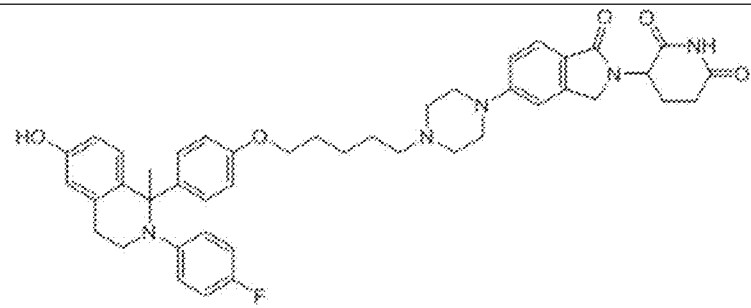 | 4.41 | 745.9 | 746.6 | Scheme 1-26, 2-1 |
| 400 | 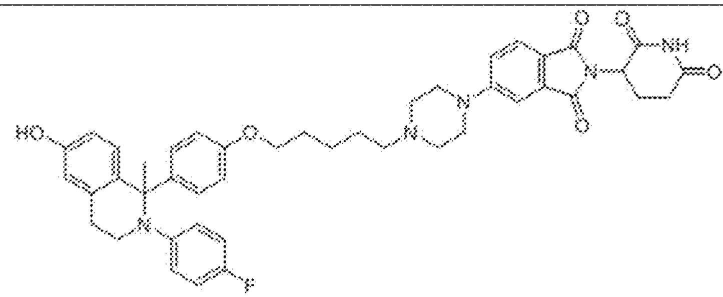 | 9.78 | 759.88 | 760.6 | Scheme 1-26, 2-1 |
| 401 | 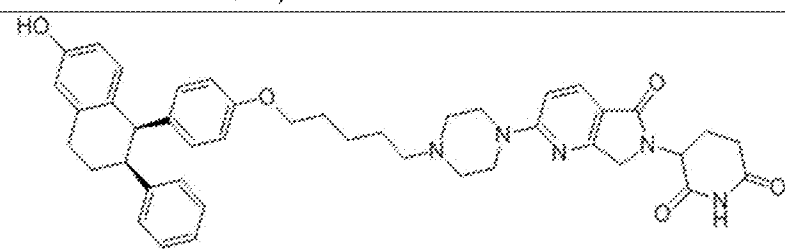 | 1.55 | 713.88 | 714.6 | Scheme 2-3, 3-10 |

FIG. 5 Continued

| Example # | Structure | ERE Luciferase IC$_{50}$ [nM] | MW | Observed [M+H]/Z | Synthetic Method |
|---|---|---|---|---|---|
| 402 | 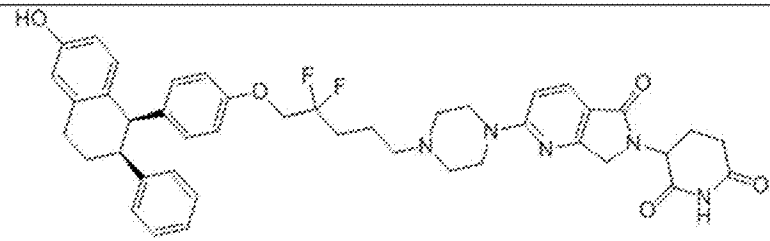 | 2.87 | 749.86 | 750.5 | Scheme 2-3, 3-40 |
| 403 | 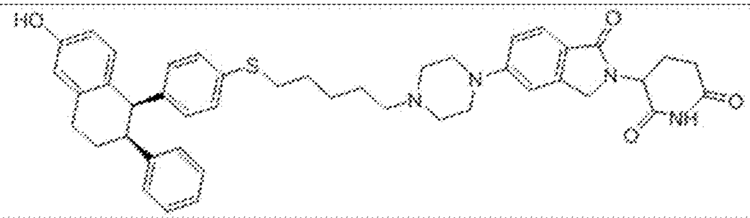 | 1.58 | 728.95 | 729.5 | Scheme 1-37, 2-1 |
| 404 | 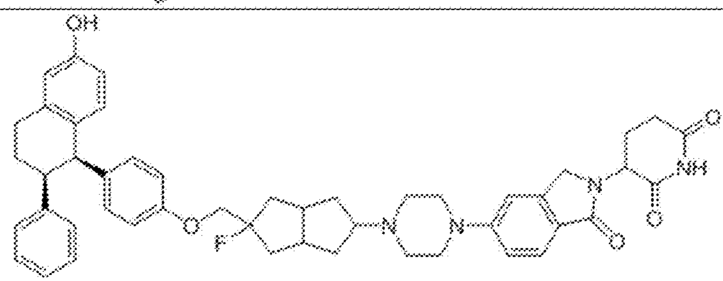 | 0.77 | 782.96 | 783.6 | Scheme 3-67 |
| 405 | 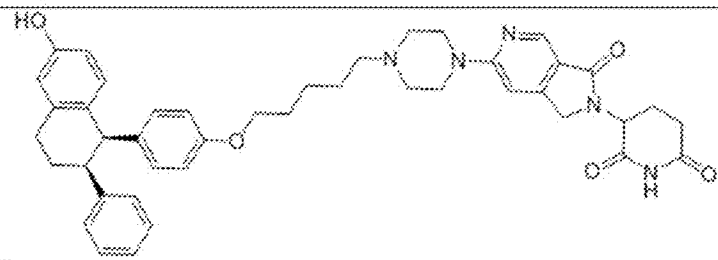 | 1 | 713.88 | 714.6 | Scheme 2-7, 3-10 |

FIG. 5 Continued

| Example # | Structure | ERE Luciferase IC$_{50}$ [nM] | MW | Observed [M+H]/z | Synthetic Method |
|---|---|---|---|---|---|
| 406 | 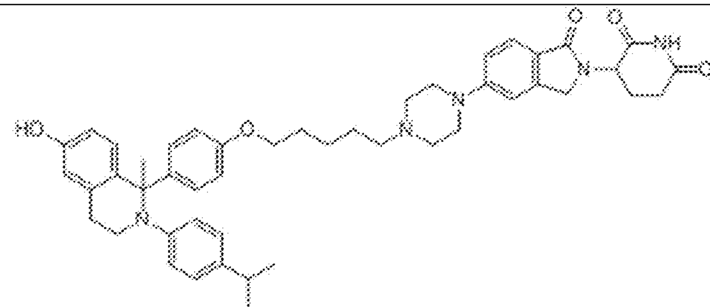 | 5.58 | 769.99 | 770.6 | Scheme 1-26, 2-1 |
| 407 | 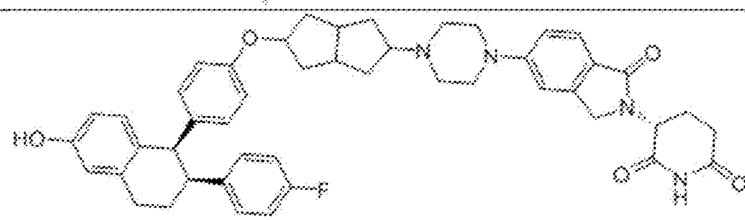 | 1.95 | 768.93 | 769.6 | Scheme 3-41 |
| 408 | 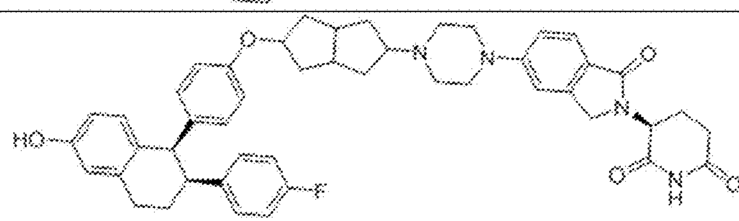 | 1.54 | 768.93 | 769.6 | Scheme 3-41 |

FIG. 5 Continued

| Example # | Structure | ERE Luciferase IC$_{50}$ [nM] | MW | Observed [M+H]/z | Synthetic Method |
|---|---|---|---|---|---|
| 409 | 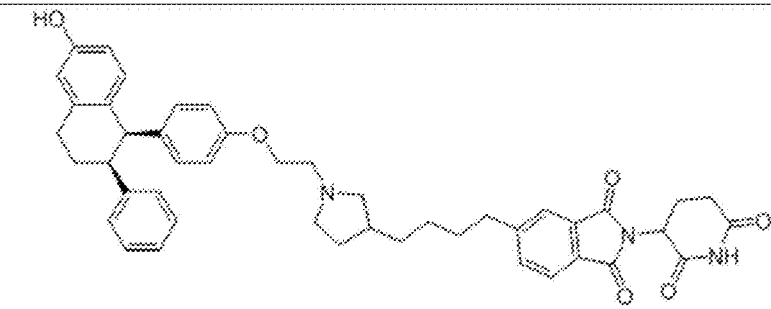 | 0.18 | 725.89 | 726.6 | Scheme 2-18, 3-10 |
| 410 | 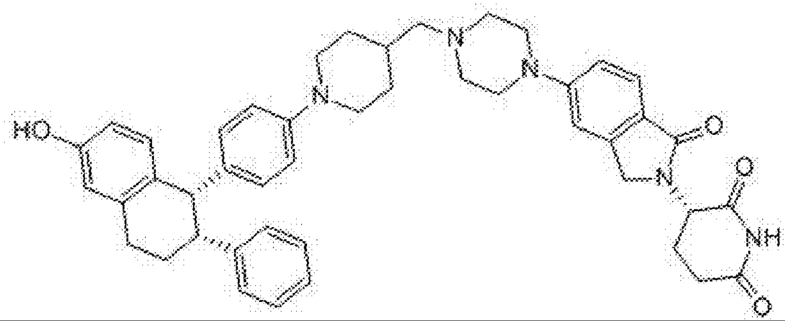 | >300 | 723.92 | 724.6 | Scheme 3-85 |
| 411 | 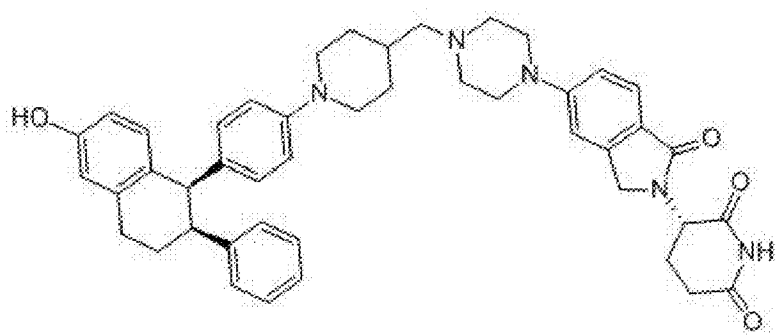 | 1.12 | 723.92 | 724.6 | Scheme 3-85 |

FIG. 5 Continued

| Example # | Structure | ERE Luciferase IC₅₀ [nM] | MW | Observed [M+H]/z | Synthetic Method |
|---|---|---|---|---|---|
| 412 | 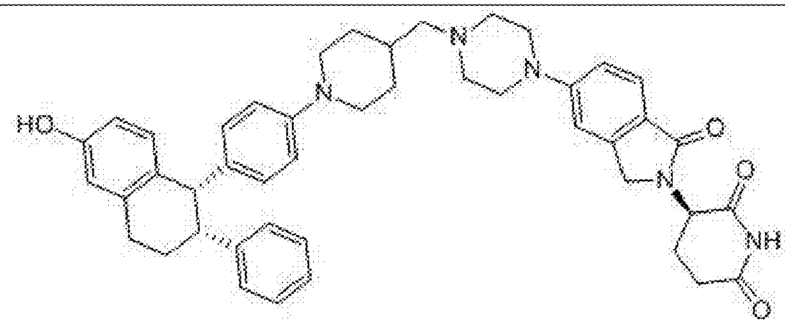 | >300 | 723.92 | 724.6 | Scheme 3-84 |
| 413 | 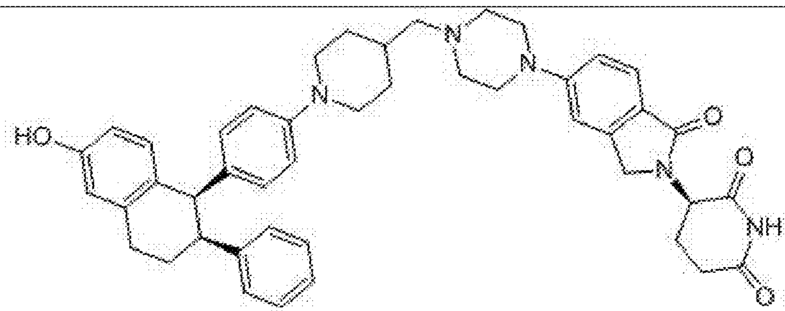 | 2.74 | 723.92 | 724.6 | Scheme 3-84 |
| 414 | 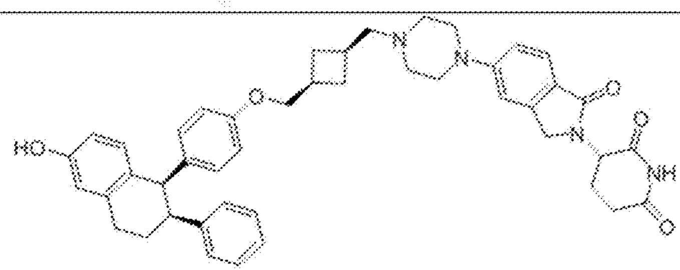 | 0.72 | 724.9 | 725.6 | Scheme 1-40, 2-1 |

FIG. 5 Continued
| Example # | Structure | ERE Luciferase IC$_{50}$ [nM] | MW | Observed [M+H]/z | Synthetic Method |
|---|---|---|---|---|---|
| 415 | 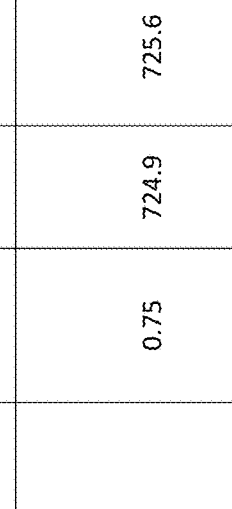 | 0.75 | 724.9 | 725.6 | Scheme 1-40, 2-1 |
| 416 | 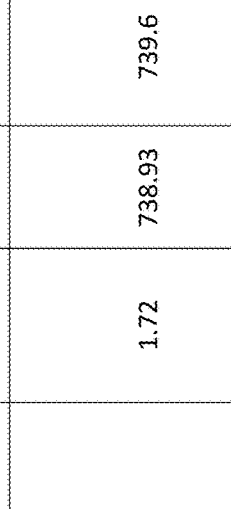 | 1.72 | 738.93 | 739.6 | Scheme 1-39, 2-1 |
| 417 | 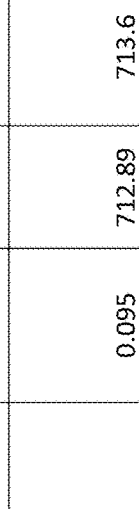 | 0.095 | 712.89 | 713.6 | Scheme 2-18, 3-10 |

FIG. 5 Continued
| Example # | Structure | ERE Luciferase IC$_{50}$ [nM] | MW | Observed [M+H]/z | Synthetic Method |
|---|---|---|---|---|---|
| 418 | 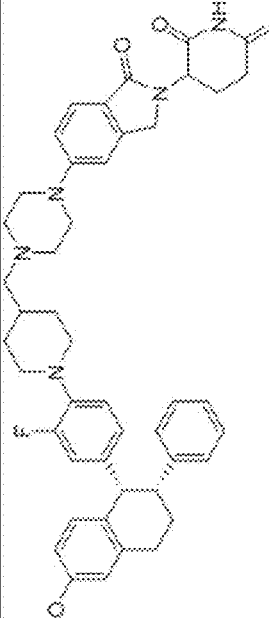 | >300 | 741.91 | 742.6 | Scheme 3-58 |
| 419 | 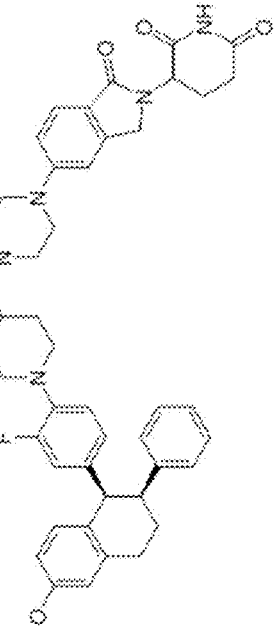 | 2.68 | 741.91 | 742.6 | Scheme 3-58 |
| 420 | 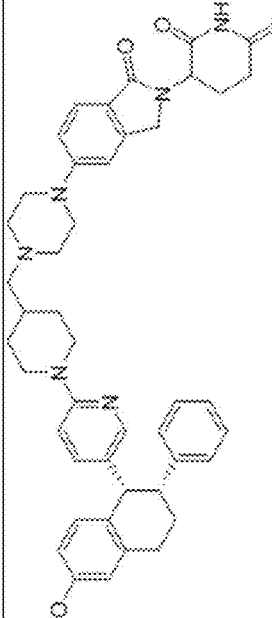 | 93.8 | 724.91 | 725.6 | Scheme 1-41, 2-1 |

FIG. 5 Continued

| Example # | Structure | ERE Luciferase IC$_{50}$ [nM] | MW | Observed [M+H]/z | Synthetic Method |
|---|---|---|---|---|---|
| 421 | 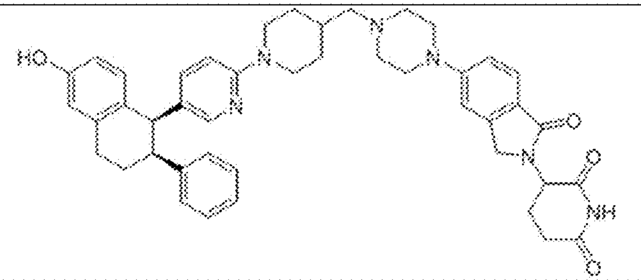 | 4.53 | 724.91 | 725.6 | Scheme 1-41, 2-1 |
| 422 | 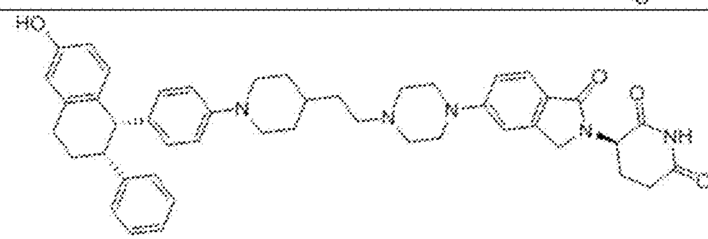 | >300 | 737.95 | 738.6 | Scheme 2-47, 3-59 |
| 423 | 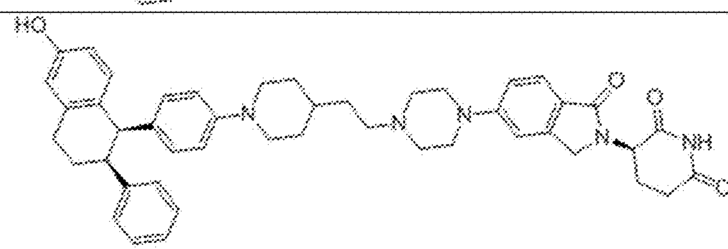 | 1 | 737.95 | 738.6 | Scheme 2-47, 3-59 |

FIG. 5 Continued

| Example # | Structure | ERE Luciferase IC$_{50}$ [nM] | MW | Observed [M+H]/z | Synthetic Method |
|---|---|---|---|---|---|
| 424 | 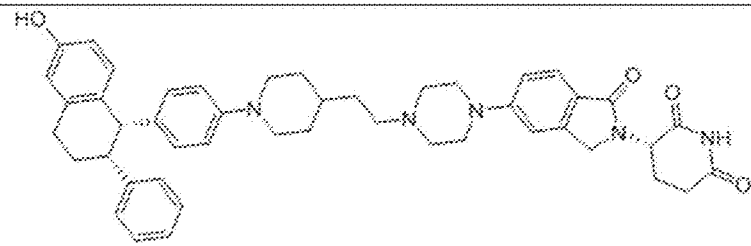 | >300 | 737.95 | 738.6 | Scheme 2-47, 3-59 |
| 425 | 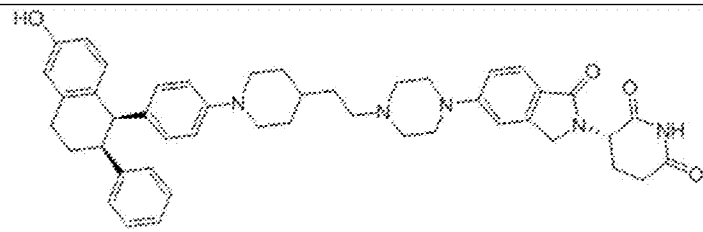 | 2.88 | 737.95 | 738.6 | Scheme 2-47, 3-59 |
| 426 | 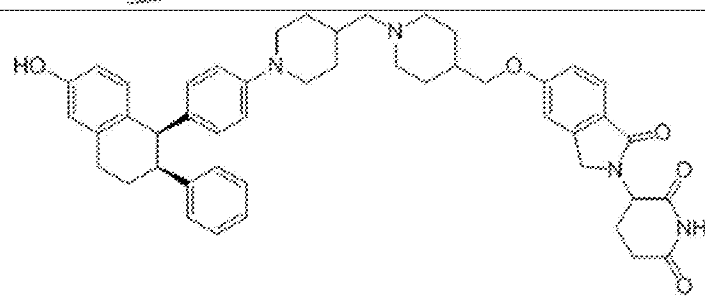 | 0.38 | 752.96 | 753.6 | Scheme 2-20, 3-58 |
| 427 | 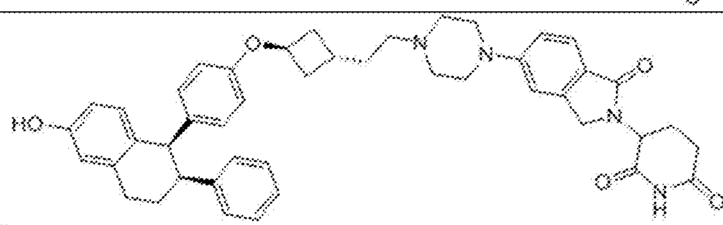 | 0.48 | 724.9 | 725.6 | Scheme 1-16, 2-1 |

FIG. 5 Continued

| Example # | Structure | ERE Luciferase IC$_{50}$ [nM] | MW | Observed [M+H]/z | Synthetic Method |
|---|---|---|---|---|---|
| 428 | 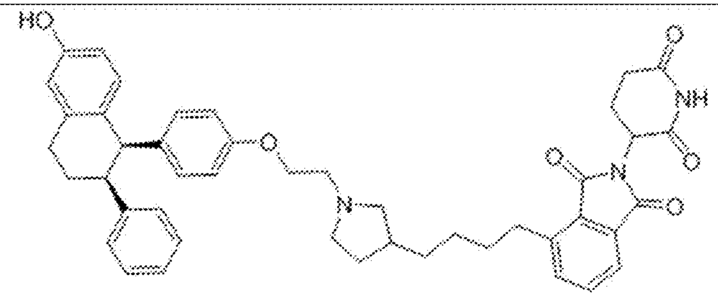 | 0.23 | 725.89 | 726.3 | Scheme 2-18, 3-10 |
| 429 | 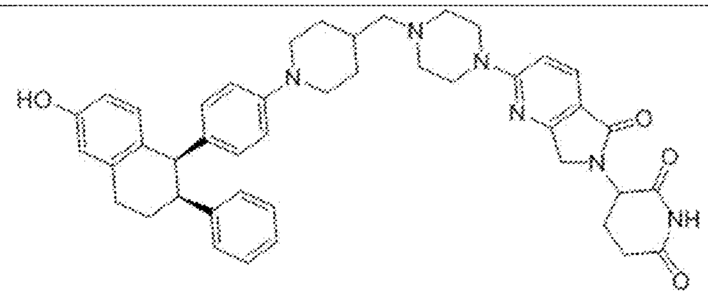 | 1.2 | 724.91 | 725.6 | Scheme 2-3, 3-58 |
| 430 | 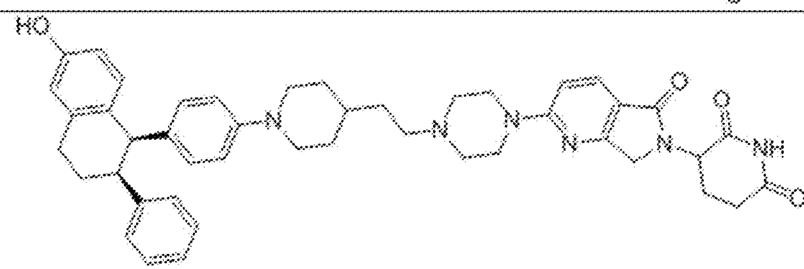 | 0.9 | 738.93 | 739.6 | Scheme 2-3, 3-59 |

FIG. 5 Continued

| Example # | Structure | ERE Luciferase IC$_{50}$ [nM] | MW | Observed [M+H]/z | Synthetic Method |
|---|---|---|---|---|---|
| 431 | 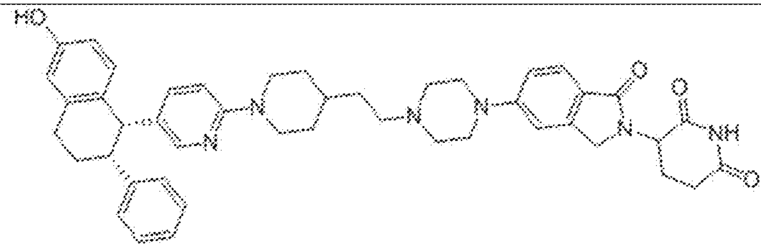 | >300 | 738.93 | 739.6 | Scheme 2-3, 3-59 |
| 432 | 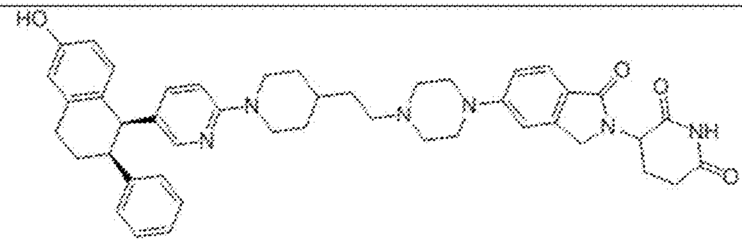 | 1 | 738.93 | 739.6 | Scheme 1-41, 3-59 |
| 433 | 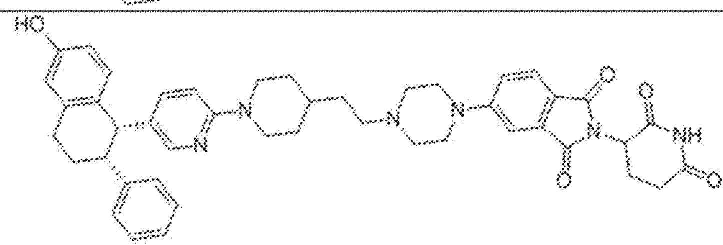 | >300 | 752.92 | 753.6 | Scheme 1-41, 3-59 |
| 434 | 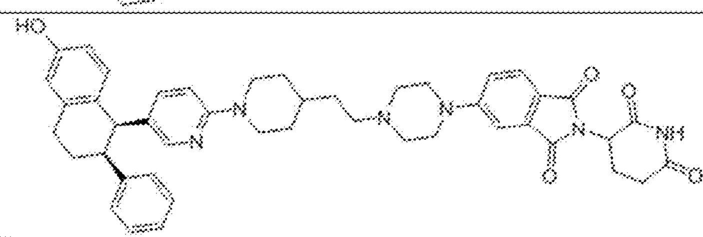 | 7.3 | 752.92 | 753.6 | Scheme 1-41, 3-59 |

FIG. 5 Continued
| Example # | Structure | ERE Luciferase IC$_{50}$ [nM] | MW | Observed [M+H]/z | Synthetic Method |
|---|---|---|---|---|---|
| 435 | 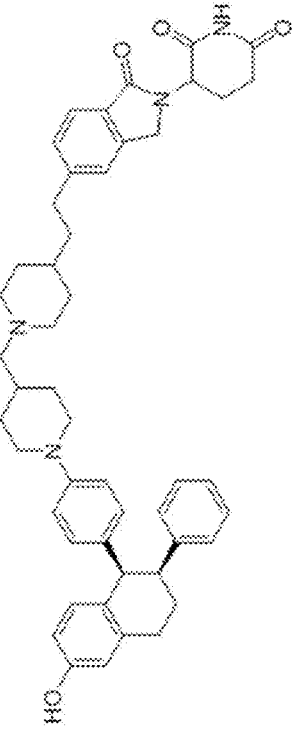 | 0.24 | 750.98 | 751.6 | Scheme 2-17, 3-58 |
| 436 | 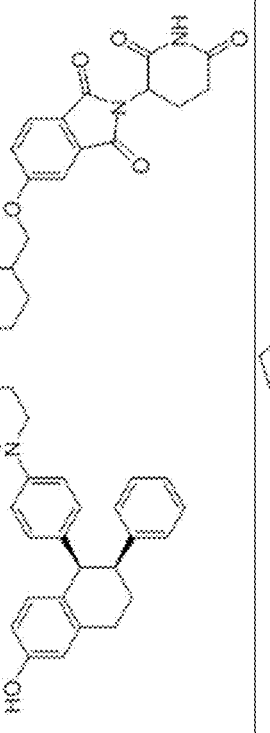 | 0.38 | 766.94 | 767.6 | Scheme 2-17, 3-58 |
| 437 | 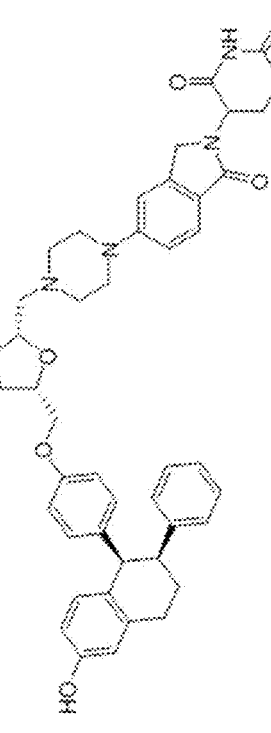 | 0.28 | 740.9 | 741.6 | Scheme 1-15, 2-1 |

FIG. 5 Continued

| Example # | Structure | ERE Luciferase IC$_{50}$ [nM] | MW | Observed [M+H]/z | Synthetic Method |
|---|---|---|---|---|---|
| 438 | 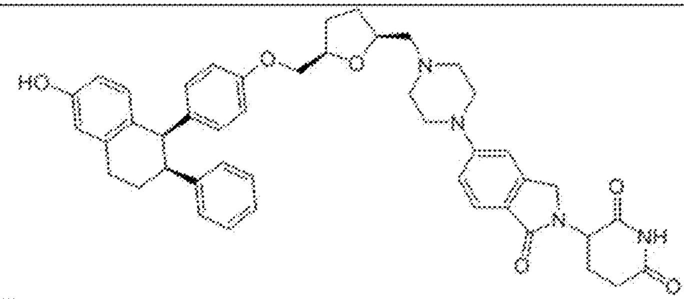 | 0.49 | 740.9 | 741.6 | Scheme 1-15, 2-1 |
| 439 | 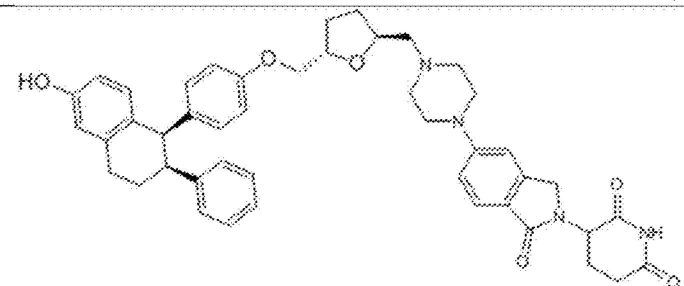 | 0.27 | 740.9 | 741.6 | Scheme 1-15, 2-1 |
| 440 | 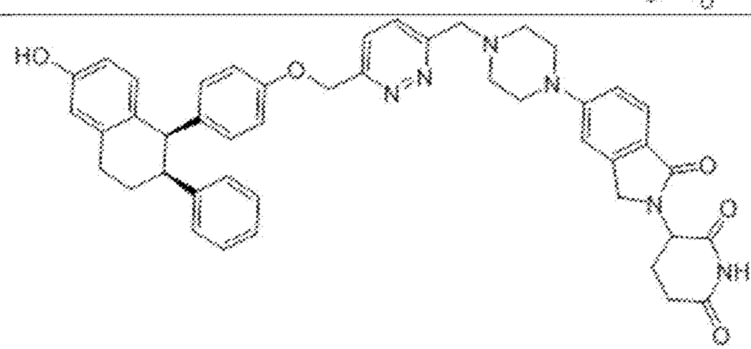 | 1.1 | 748.88 | 749.5 | Scheme 3-68 |

FIG. 5 Continued

| Example # | Structure | ERE Luciferase IC$_{50}$ [nM] | MW | Observed [M+H]/z | Synthetic Method |
|---|---|---|---|---|---|
| 441 | 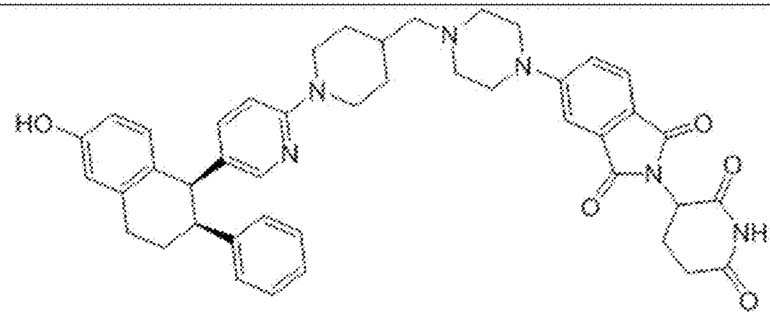 | 13.2 | 738.89 | 739.6 | Scheme 1-41, 2-1 |
| 442 | 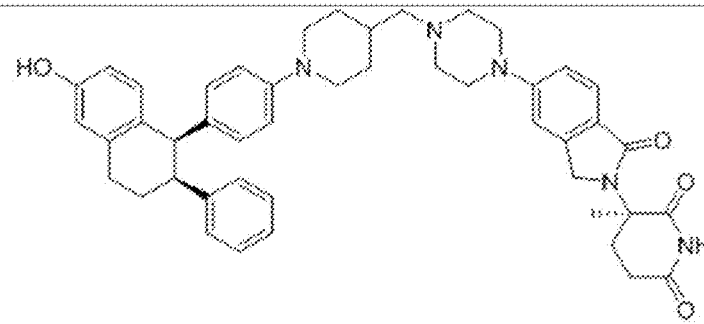 | 2.2 | 737.95 | 738.6 | Scheme 2-29, 3-58 |
| 443 | 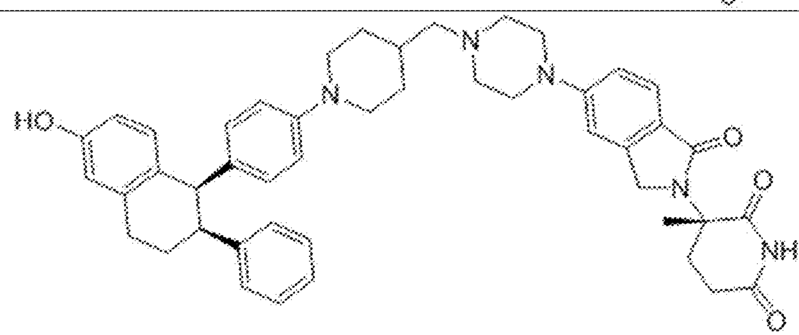 | 1.3 | 737.95 | 738.6 | Scheme 2-29, 3-58 |

FIG. 5 Continued

| Example # | Structure | ERE Luciferase IC$_{50}$ [nM] | MW | Observed [M+H]/z | Synthetic Method |
|---|---|---|---|---|---|
| 444 | 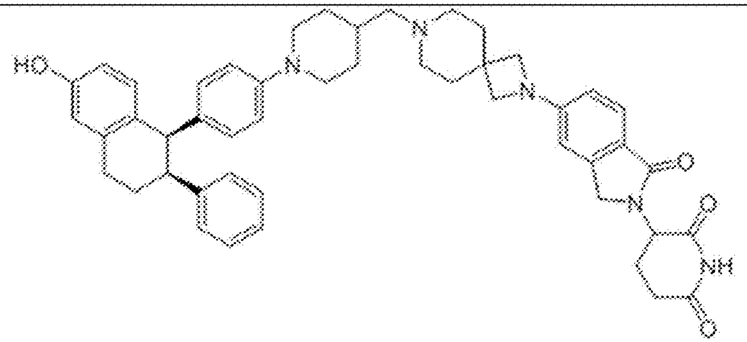 | 0.49 | 763.98 | 764.6 | Scheme 2-8, 3-58 |
| 445 | 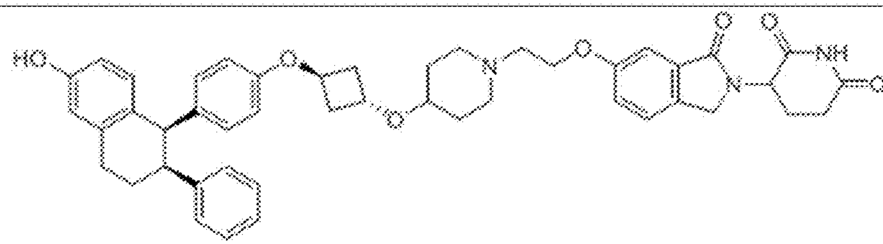 | 0.64 | 755.91 | 756.6 | Scheme 3-69 |
| 446 | 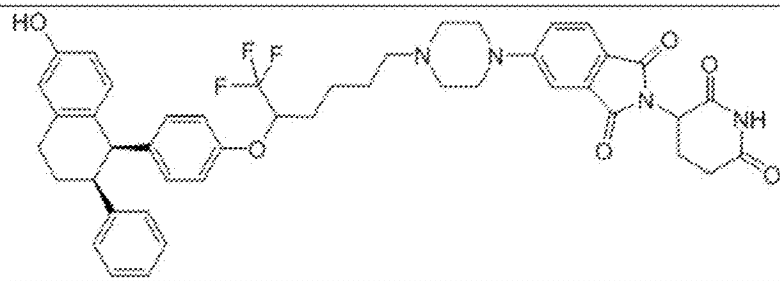 | 14.05 | 794.87 | 795.6 | Scheme 3-70 |

FIG. 5 Continued

| Example # | Structure | ERE Luciferase IC$_{50}$ [nM] | MW | Observed [M+H]/z | Synthetic Method |
|---|---|---|---|---|---|
| 447 | 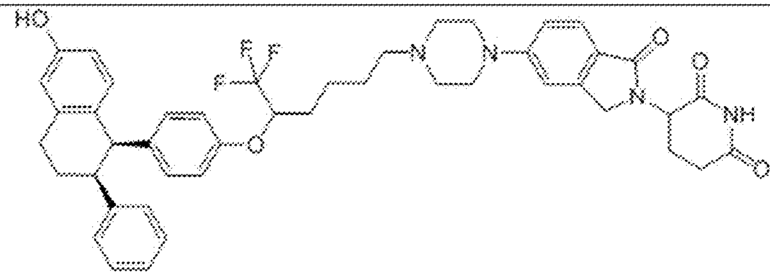 | 4.99 | 780.89 | 781.6 | Scheme 3-70 |
| 448 | 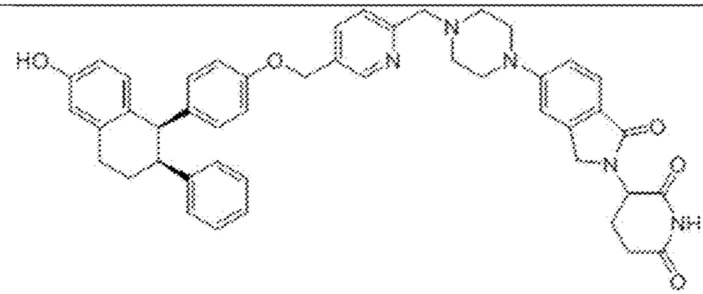 | 1.05 | 747.90 | 748.6 | Scheme 3-71 |
| 449 | 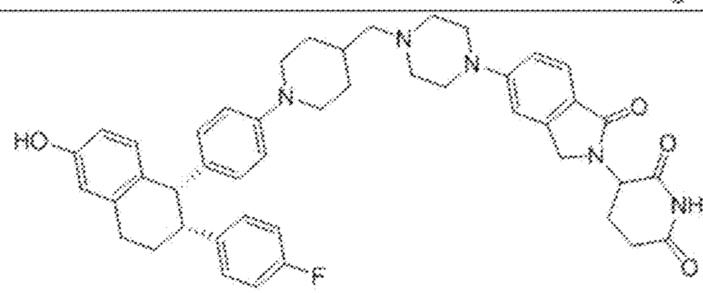 | >300 | 741.91 | 742.6 | Scheme 3-58 |

FIG. 5 Continued

| Example # | Structure | ERE Luciferase IC$_{50}$ [nM] | MW | Observed [M+H]/z | Synthetic Method |
|---|---|---|---|---|---|
| 450 | 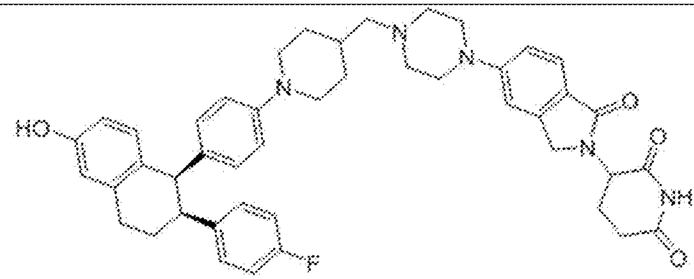 | 1.63 | 741.91 | 742.6 | Scheme 3-58 |
| 451 | 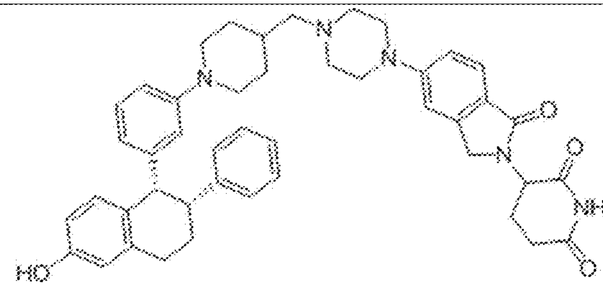 | 75 | 723.92 | 724.6 | Scheme 1-14, 2-1 |
| 452 | 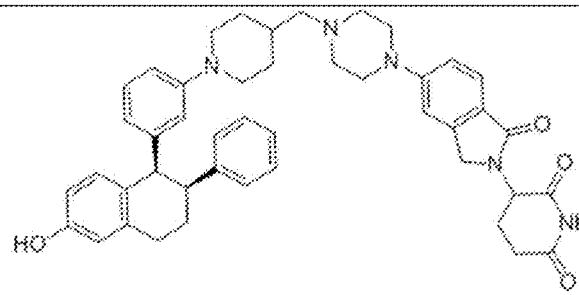 | 26.3 | 723.92 | 724.6 | Scheme 1-14, 2-1 |

FIG. 5 Continued

| Example # | Structure | ERE Luciferase IC$_{50}$ [nM] | MW | Observed [M+H]/z | Synthetic Method |
|---|---|---|---|---|---|
| 453 | 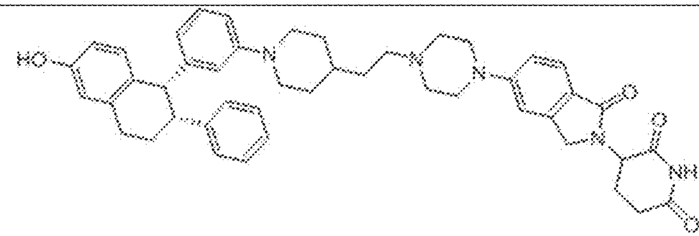 | 66.6 | 737.95 | 738.6 | Scheme 1-14, 2-1 |
| 454 | 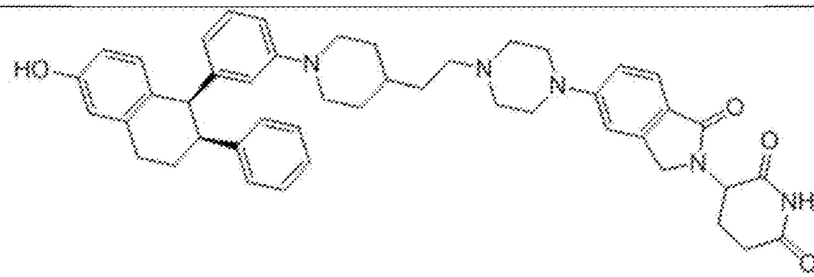 | 3.3 | 737.95 | 738.6 | Scheme 1-14, 2-1 |
| 455 | 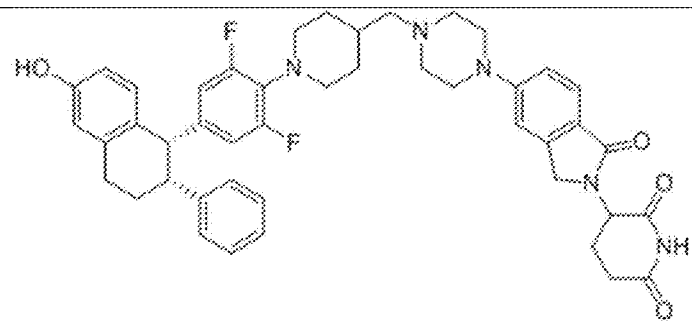 | 14.9 | 759.9 | 760.6 | Scheme 1-13, 2-1 |

FIG. 5 Continued

| Example # | Structure | ERE Luciferase IC$_{50}$ [nM] | MW | Observed [M+H]/z | Synthetic Method |
|---|---|---|---|---|---|
| 456 | 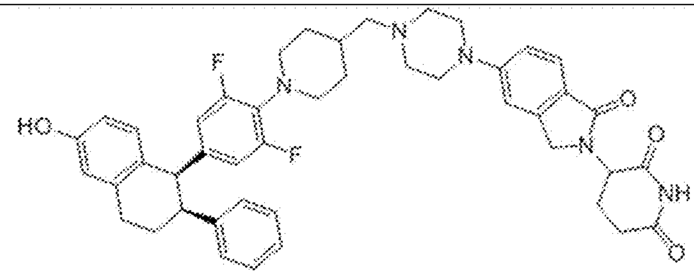 | 4.8 | 759.9 | 760.6 | Scheme 1-13, 2-1 |
| 457 | 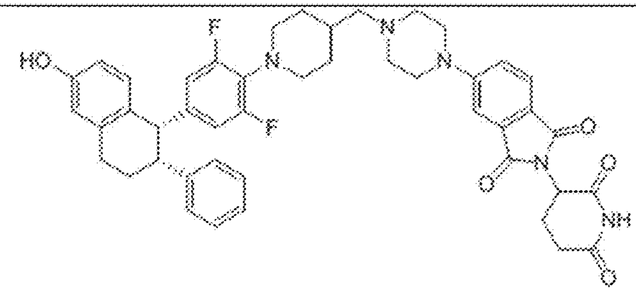 | 92.9 | 773.88 | 774.6 | Scheme 1-13, 2-1 |
| 458 | 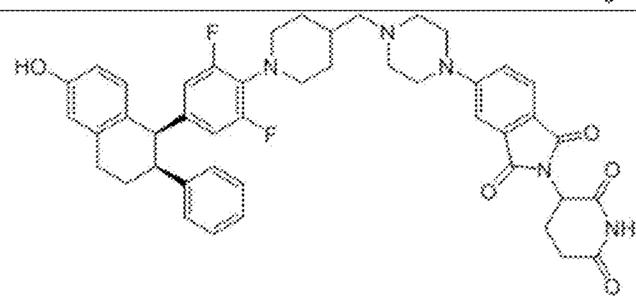 | 23.7 | 773.88 | 774.6 | Scheme 1-13, 2-1 |

FIG. 5 Continued

| Example # | Structure | ERE Luciferase IC₅₀ [nM] | MW | Observed [M+H]/z | Synthetic Method |
|---|---|---|---|---|---|
| 459 | 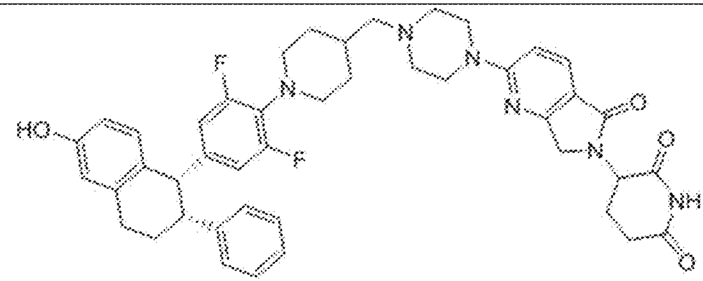 | 19.8 | 760.89 | 761.6 | Scheme 1-13, 2-3 |
| 460 | 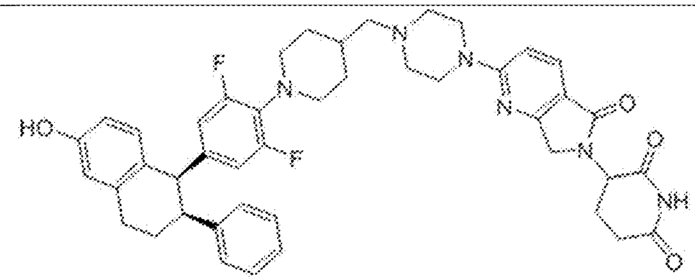 | 4.5 | 760.89 | 761.6 | Scheme 1-13, 2-3 |
| 461 | 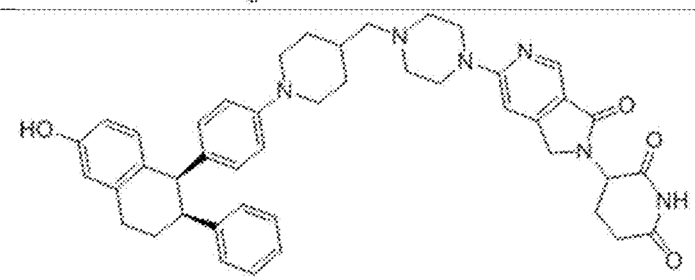 | 1.3 | 724.91 | 725.6 | Scheme 2-7, 3-58 |

FIG. 5 Continued

| Example # | Structure | ERE Luciferase IC$_{50}$ [nM] | MW | Observed [M+H]/z | Synthetic Method |
|---|---|---|---|---|---|
| 462 | 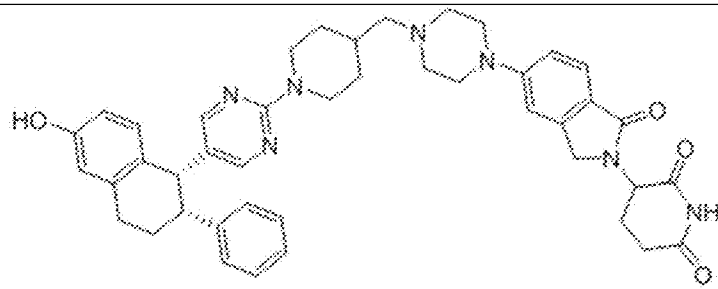 | >300 | 725.89 | 726.6 | Scheme 1-19, 3-58 |
| 463 | 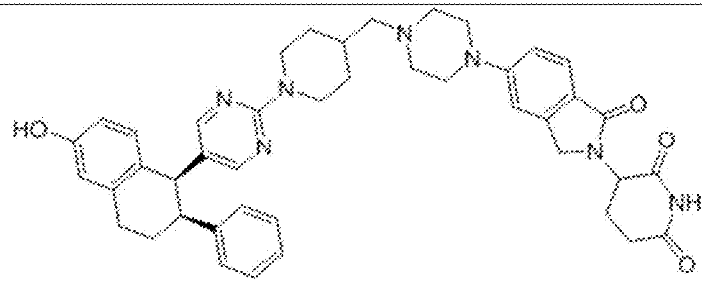 | 3 | 725.89 | 726.6 | Scheme 1-19, 3-58 |
| 464 | 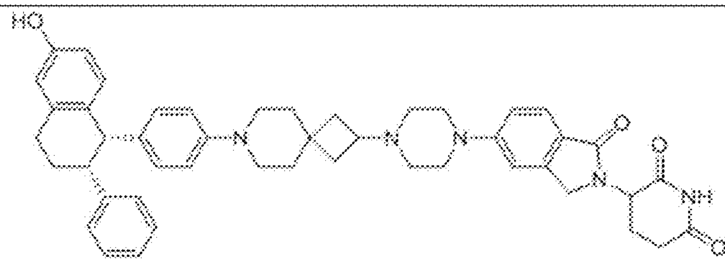 | >300 | 749.96 | 750.6 | Scheme 3-73 |

FIG. 5 Continued

| Example # | Structure | ERE Luciferase IC$_{50}$ [nM] | MW | Observed [M+H]/z | Synthetic Method |
|---|---|---|---|---|---|
| 465 | 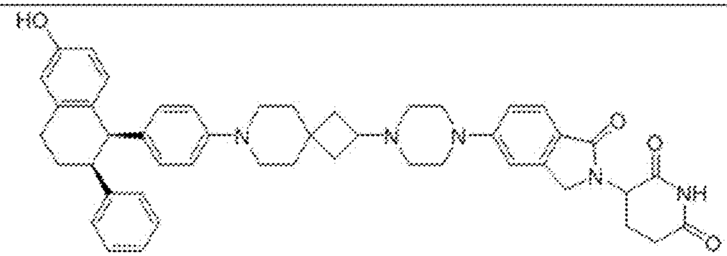 | 2.4 | 749.96 | 750.6 | Scheme 3-73 |
| 466 | 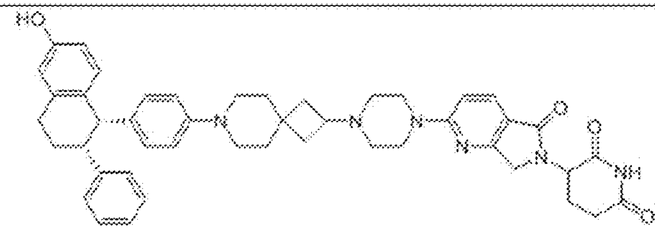 | >300 | 750.94 | 751.6 | Scheme 2-3, 3-73 |
| 467 | 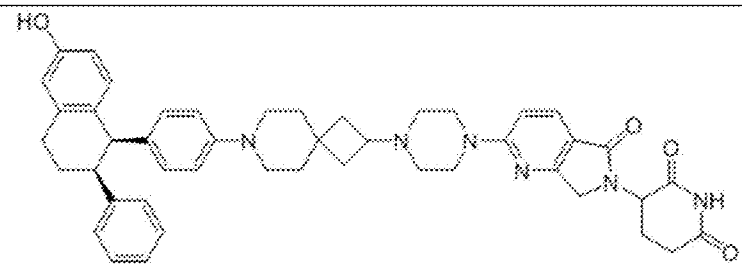 | 2.6 | 750.94 | 751.6 | Scheme 2-3, 3-73 |

FIG. 6

Table 2: Activity, synthetic methods and characterization of ER PROTACs

| Example # | Structure | ERE Luciferase IC$_{50}$ [nM] | MW | Observed [M+H]/Z | Synthetic Method |
|---|---|---|---|---|---|
| 468 | 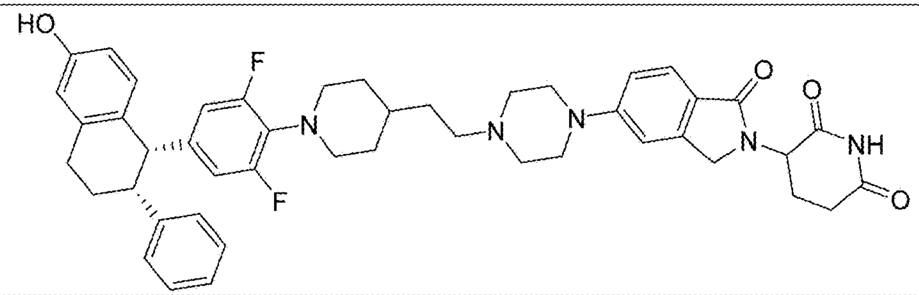 | >300 | 773.93 | 774.6 | Scheme 1-13, 3-59 |
| 469 | 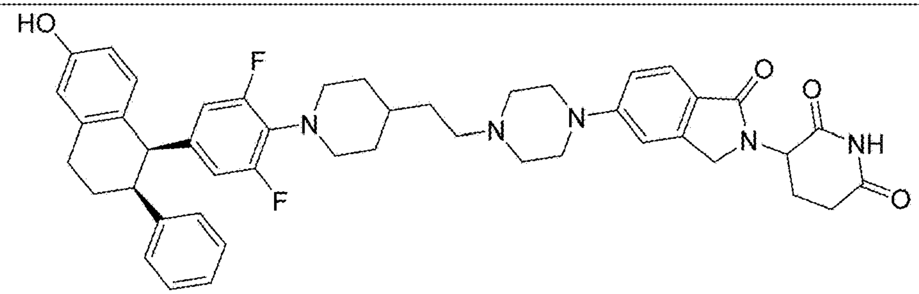 | 6.9 | 773.93 | 774.6 | Scheme 1-13, 3-59 |

FIG. 6 Continued

| Example # | Structure | ERE Luciferase IC$_{50}$ [nM] | MW | Observed [M+H]/z | Synthetic Method |
|---|---|---|---|---|---|
| 470 | 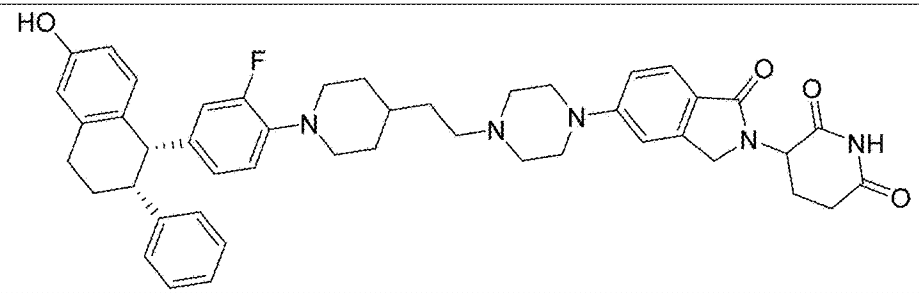 | >300 | 755.94 | 756.6 | Scheme 1-13, 3-59 |
| 471 | 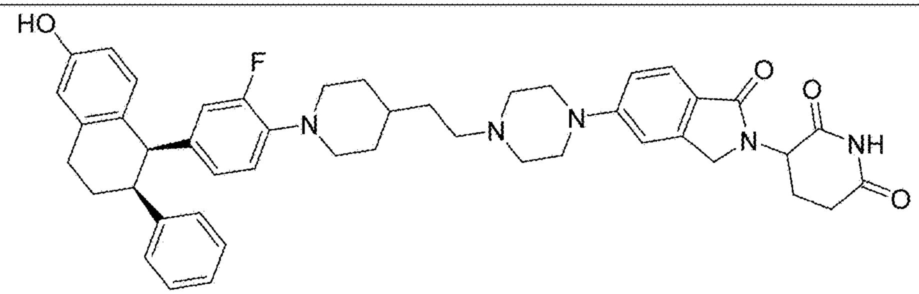 | 2.9 | 755.94 | 756.6 | Scheme 1-13, 3-59 |
| 472 | 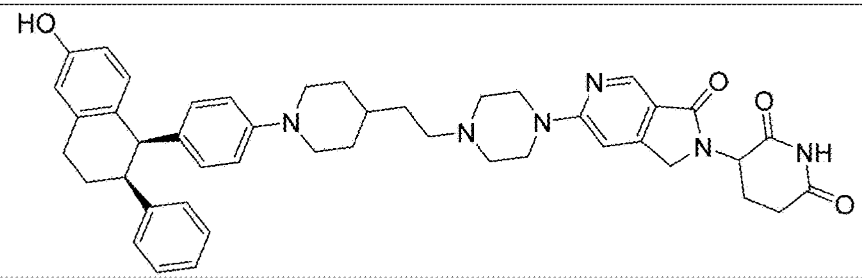 | 1.8 | 738.93 | 739.6 | Scheme 2-7, 3-59 |

FIG. 6 Continued
| Example # | Structure | ERE Luciferase IC$_{50}$ [nM] | MW | Observed [M+H]/z | Synthetic Method |
|---|---|---|---|---|---|
| 473 | 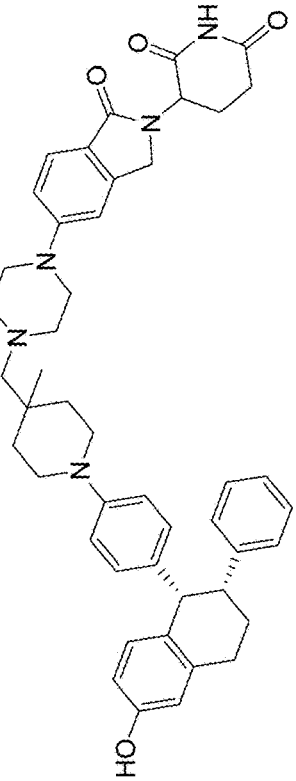 | >300 | 737.95 | 738.6 | Scheme 3-74 |
| 474 | 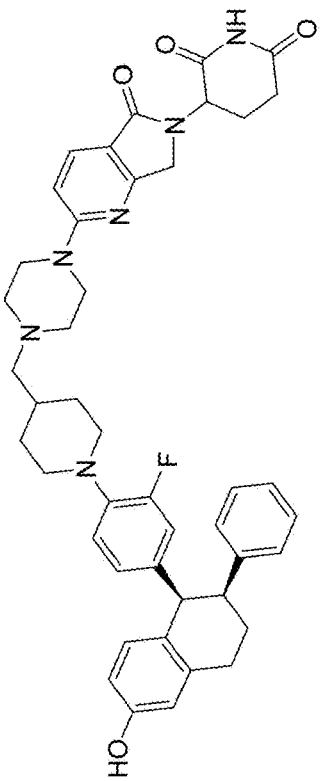 | 2.9 | 742.9 | 743.6 | Scheme 1-13, 2-3 |

FIG. 6 Continued
| Example # | Structure | ERE Luciferase IC$_{50}$ [nM] | MW | Observed [M+H]/z | Synthetic Method |
|---|---|---|---|---|---|
| 475 | 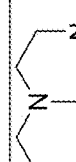 | 224 | 742.9 | 743.6 | Scheme 1-9, 2-3 |
| 476 | 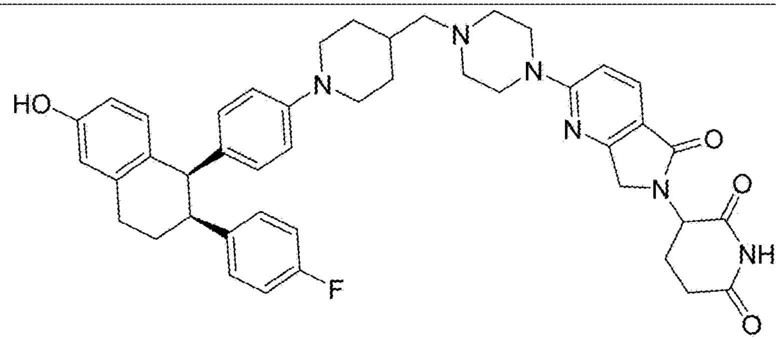 | 2.2 | 742.9 | 743.6 | Scheme 1-9, 2-3 |

FIG. 6 Continued
| Example # | Structure | ERE Luciferase IC$_{50}$ [nM] | MW | Observed [M+H]/z | Synthetic Method |
|---|---|---|---|---|---|
| 477 | 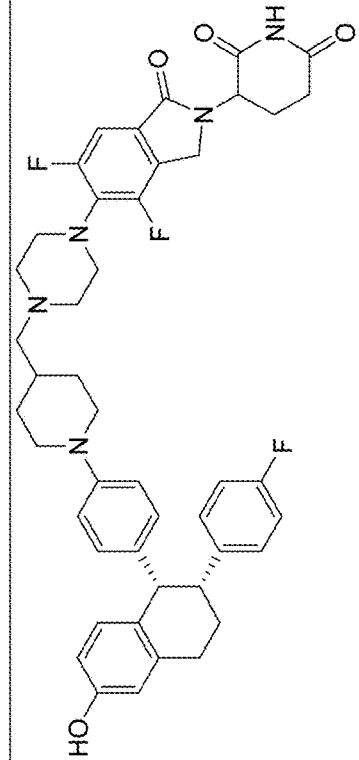 | >300 | 777.89 | 778.6 | Scheme 1-9, 2-12 |
| 478 | 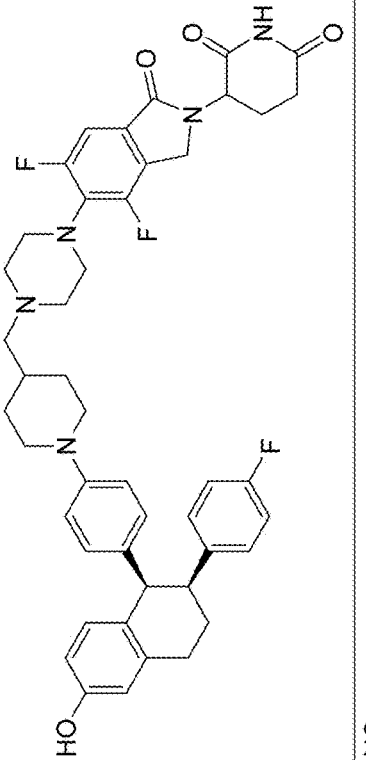 | 3.5 | 777.89 | 778.6 | Scheme 1-9, 2-12 |
| 479 | 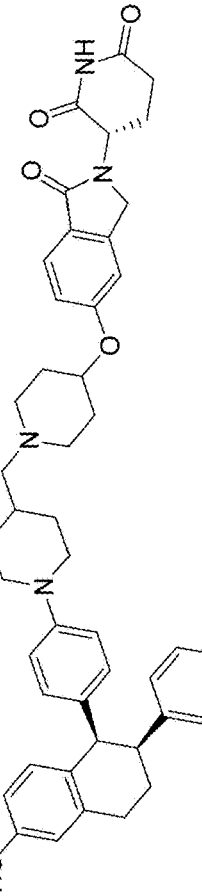 | 0.8 | 738.93 | 739.6 | Scheme 2-20, 3-58 |

FIG. 6 Continued

| Example # | Structure | ERE Luciferase IC$_{50}$ [nM] | MW | Observed [M+H]/z | Synthetic Method |
|---|---|---|---|---|---|
| 480 | 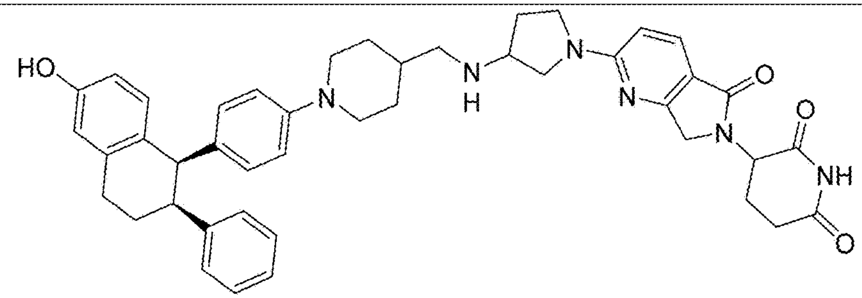 | 0.3 | 724.91 | 725.6 | Scheme 2-19, 3-58 |
| 481 | 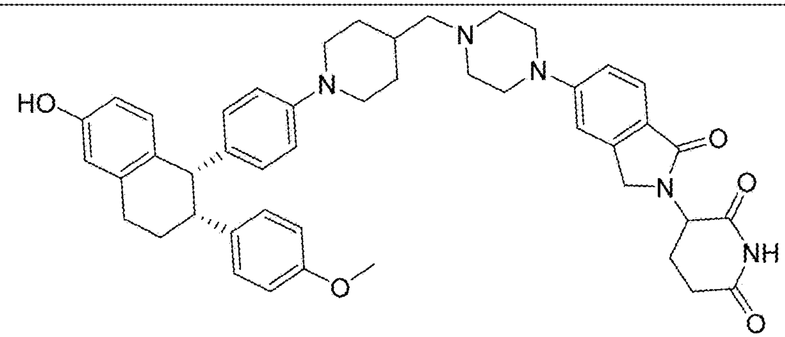 | 143 | 753.94 | 754.6 | Scheme 1-9, 3-58 |
| 482 | 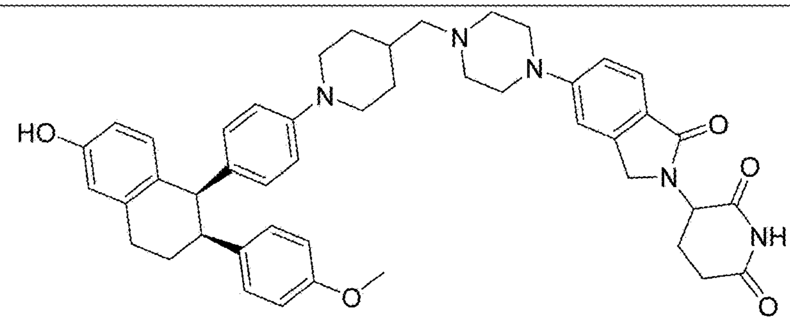 | 0.5 | 753.94 | 754.6 | Scheme 1-9, 3-58 |

FIG. 6 Continued
| Example # | Structure | ERE Luciferase IC$_{50}$ [nM] | MW | Observed [M+H]/Z | Synthetic Method |
|---|---|---|---|---|---|
| 483 | 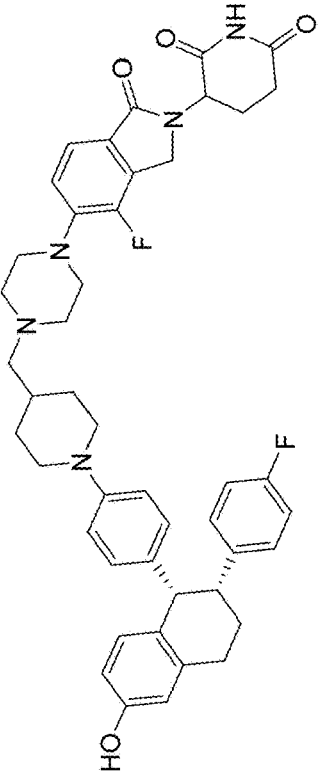 | >300 | 759.9 | 760.6 | Scheme 1-9, 2-11 |
| 484 | 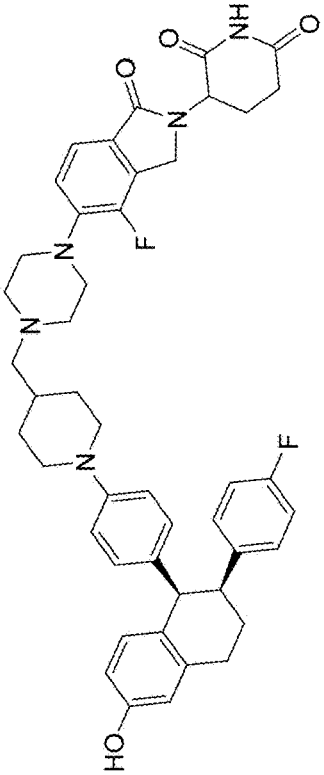 | 2.8 | 759.9 | 760.6 | Scheme 1-9, 2-11 |
| 485 | 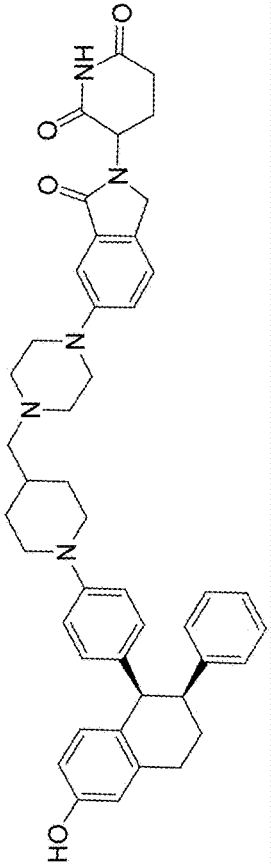 | 1.7 | 723.92 | 724.6 | Scheme 1-9, 2-2 |

FIG. 6 Continued

| Example # | Structure | ERE Luciferase IC₅₀ [nM] | MW | Observed [M+H]/Z | Synthetic Method |
|---|---|---|---|---|---|
| 486 | 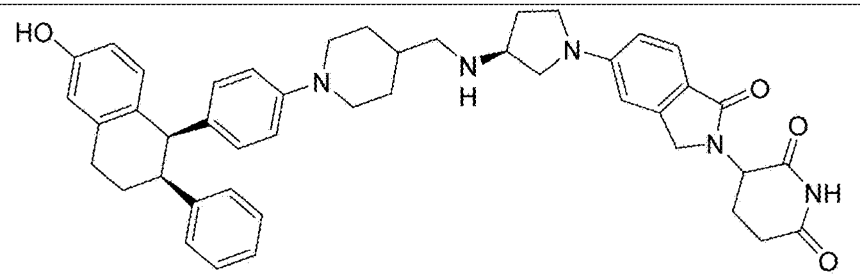 | 0.3 | 723.92 | 724.6 | Scheme 2-19, 3-58 |
| 487 | 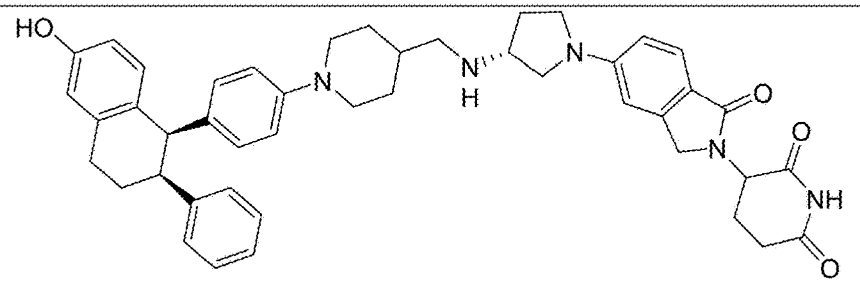 | 0.2 | 723.92 | 724.6 | Scheme 2-19, 3-58 |
| 488 | 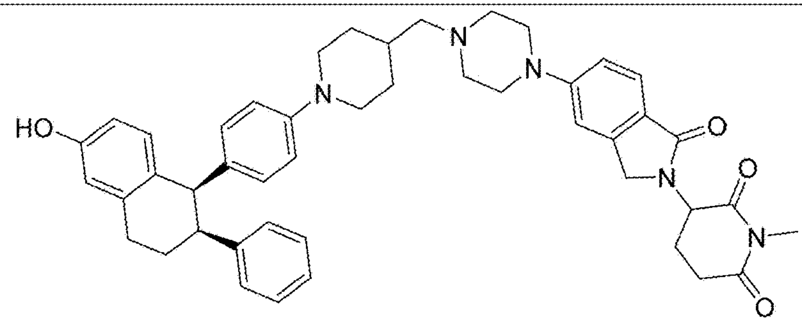 | 1.9 | 737.95 | 738.6 | Scheme 2-28, 3-58 |

FIG. 6 Continued

| Example # | Structure | ERE Luciferase IC$_{50}$ [nM] | MW | Observed [M+H]/Z | Synthetic Method |
|---|---|---|---|---|---|
| 489 | 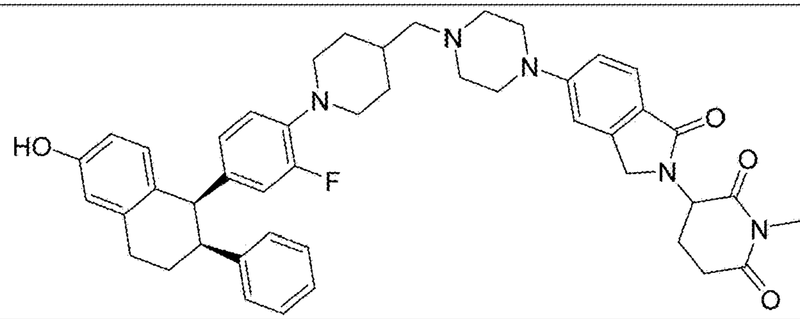 | 3 | 755.94 | 756.6 | Scheme 2-28, 3-58 |
| 490 | 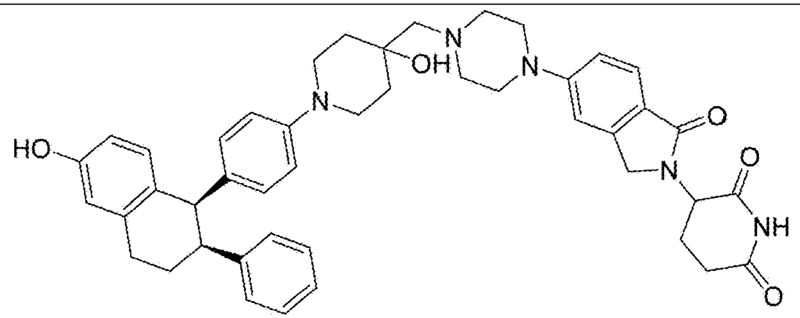 | 1.1 | 739.92 | 740.6 | Scheme 3-75 |
| 491 | 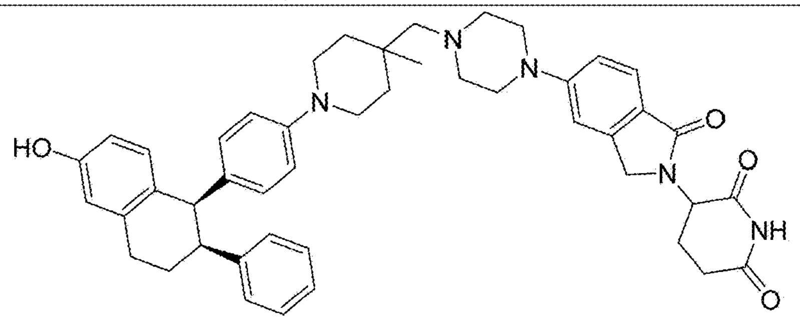 | 4.5 | 737.95 | 738.6 | Scheme 3-74 |

FIG. 6 Continued
| Example # | Structure | ERE Luciferase IC$_{50}$ [nM] | MW | Observed [M+H]/Z | Synthetic Method |
|---|---|---|---|---|---|
| 492 | 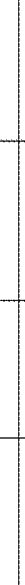 | 1 | 749.96 | 750.6 | Scheme 1-17, 2-1 |
| 493 | 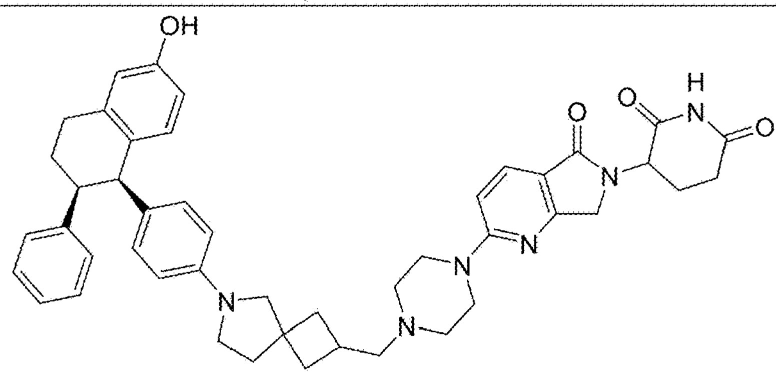 | 0.7 | 750.94 | 751.6 | Scheme 1-17, 2-3 |

FIG. 6 Continued
| Example # | Structure | ERE Luciferase IC$_{50}$ [nM] | MW | Observed [M+H]/Z | Synthetic Method |
|---|---|---|---|---|---|
| 494 | 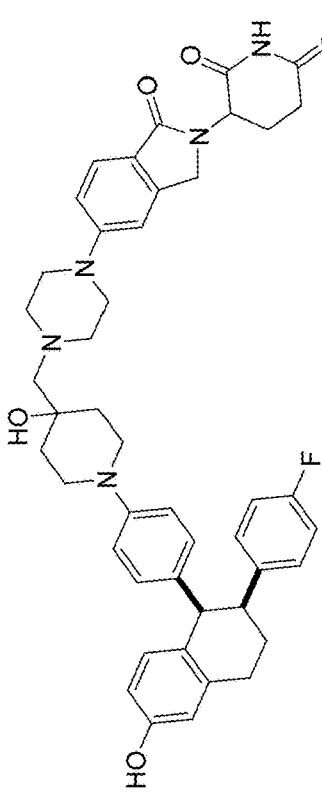 | 1.3 | 757.91 | 758.6 | Scheme 3-75 |
| 495 | 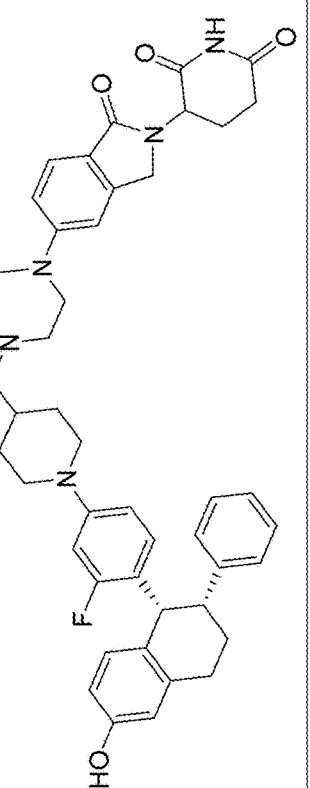 | 183 | 741.91 | 742.6 | Scheme 1-18, 3-58 |

FIG. 6 Continued
| Example # | Structure | ERE Luciferase IC$_{50}$ [nM] | MW | Observed [M+H]/z | Synthetic Method |
|---|---|---|---|---|---|
| 496 | 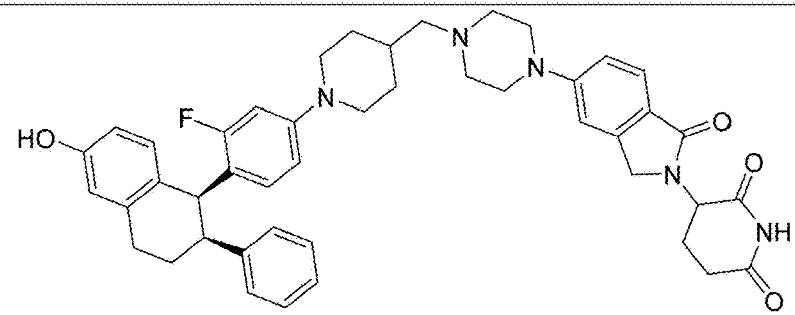 | 0.8 | 741.91 | 742.6 | Scheme 1-18, 3-58 |
| 497 | 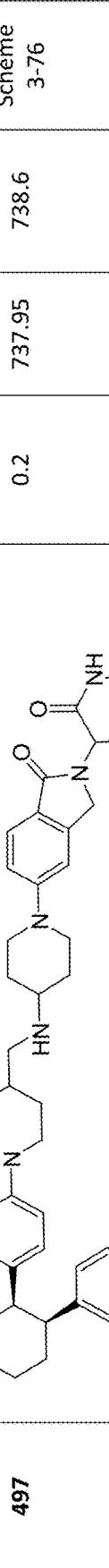 | 0.2 | 737.95 | 738.6 | Scheme 3-76 |
| 498 | 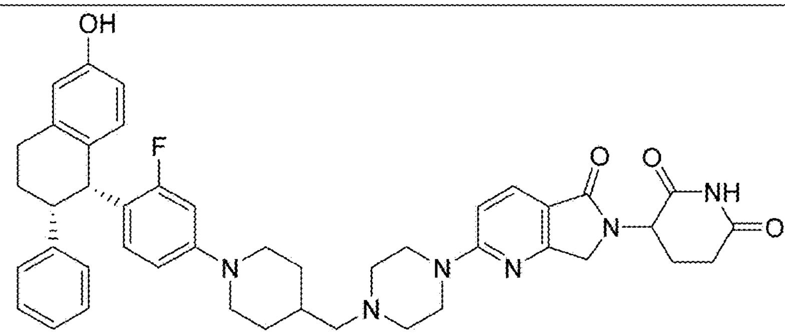 | 140 | 742.9 | 743.6 | Scheme 1-18, 2-3 |

FIG. 6 Continued
| Example # | Structure | ERE Luciferase IC$_{50}$ [nM] | MW | Observed [M+H]/z | Synthetic Method |
|---|---|---|---|---|---|
| 499 | 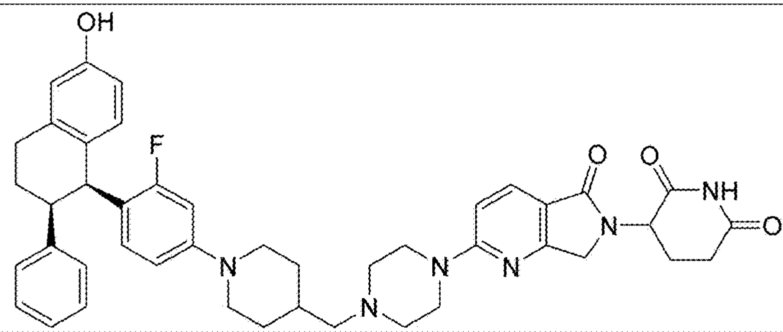 | 0.8 | 742.9 | 743.6 | Scheme 1-18, 2-3 |
| 500 | 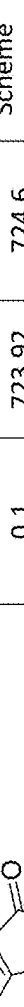 | 0.1 | 723.92 | 724.6 | Scheme 3-76 |

FIG. 6 Continued

| Example # | Structure | ERE Luciferase IC$_{50}$ [nM] | MW | Observed [M+H]/z | Synthetic Method |
|---|---|---|---|---|---|
| 501 | 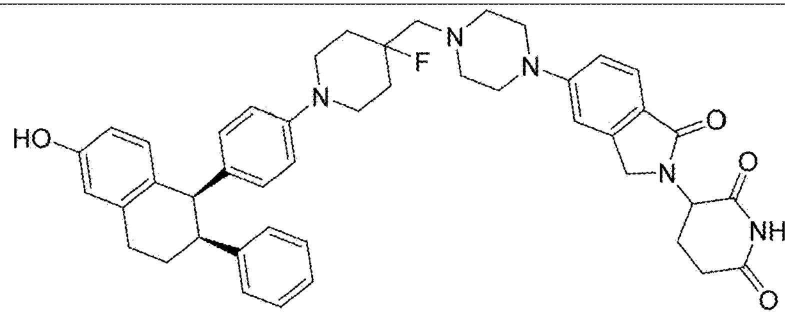 | 2.2 | 741.91 | 742.6 | Scheme 3-77 |
| 502 | 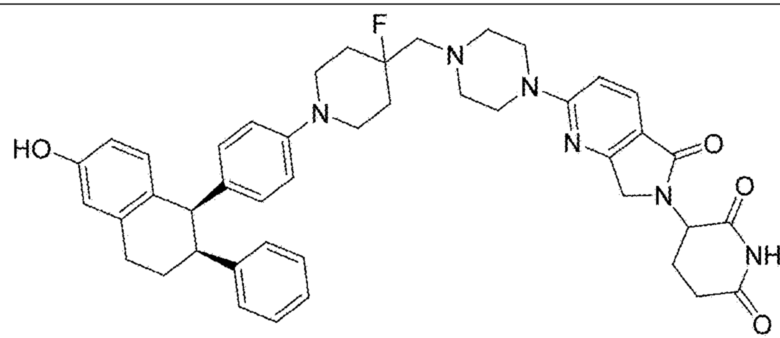 | 1.5 | 742.9 | 743.6 | Scheme 3-77 |
| 503 | 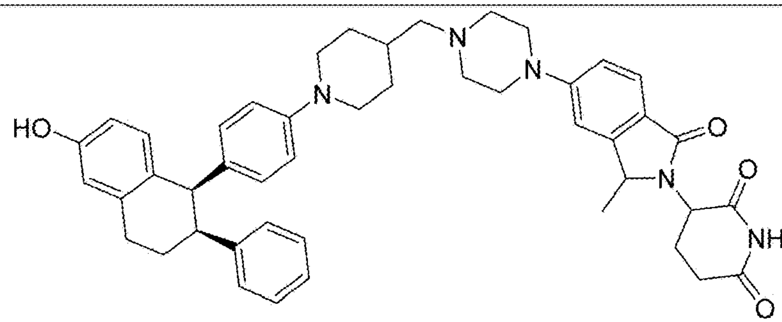 | 2 | 737.95 | 738.6 | Scxheme 2-26, 3-58 |

FIG. 6 Continued
| Example # | Structure | ERE Luciferase IC$_{50}$ [nM] | MW | Observed [M+H]/z | Synthetic Method |
|---|---|---|---|---|---|
| 504 | 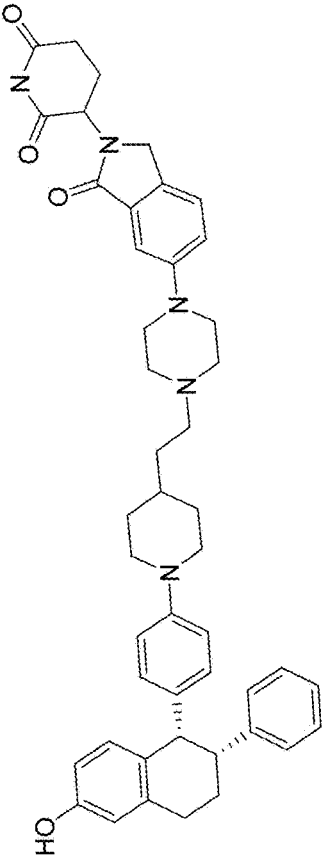 | >300 | 737.95 | 738.6 | Scheme 2-2, 3-59 |
| 505 | 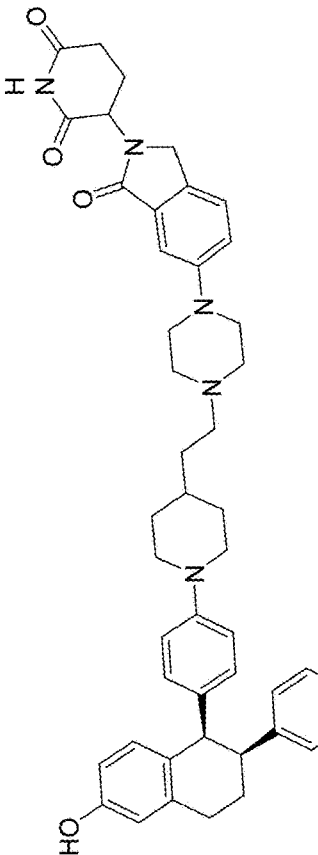 | 1.3 | 737.95 | 738.6 | Scheme 2-2, 3-59 |

FIG. 6 Continued

| Example # | Structure | ERE Luciferase IC50 [nM] | MW | Observed [M+H]/Z | Synthetic Method |
|---|---|---|---|---|---|
| 506 | 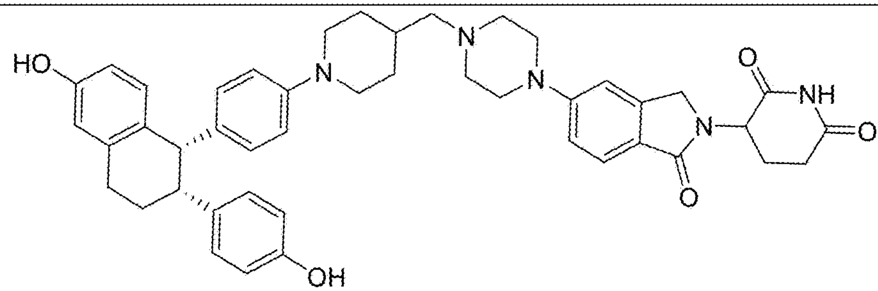 | 101 | 739.92 | 740.6 | Scheme 1-23, 2-1 |
| 507 | 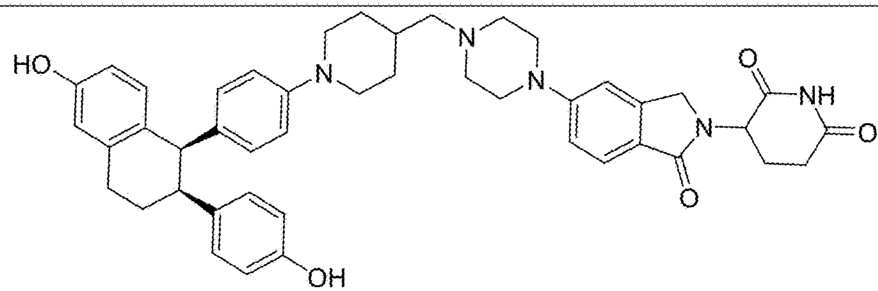 | 0.5 | 739.92 | 740.6 | Scheme 1-23, 2-1 |
| 508 | 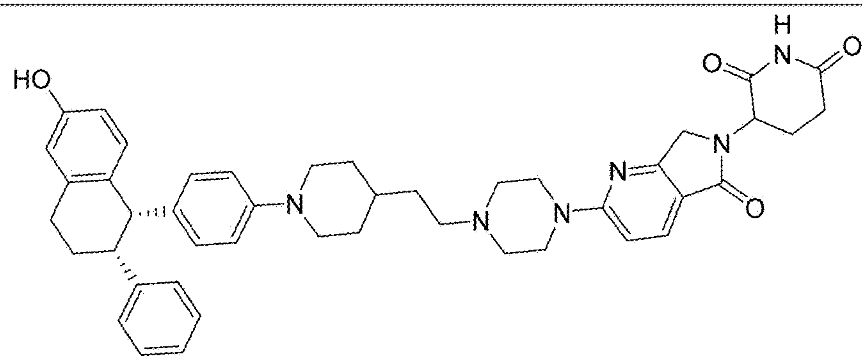 | >300 | 738.93 | 739.6 | Scheme 2-3, 3-59 |

FIG. 6 Continued
| Example # | Structure | ERE Luciferase IC$_{50}$ [nM] | MW | Observed [M+H]/Z | Synthetic Method |
|---|---|---|---|---|---|
| 509 | 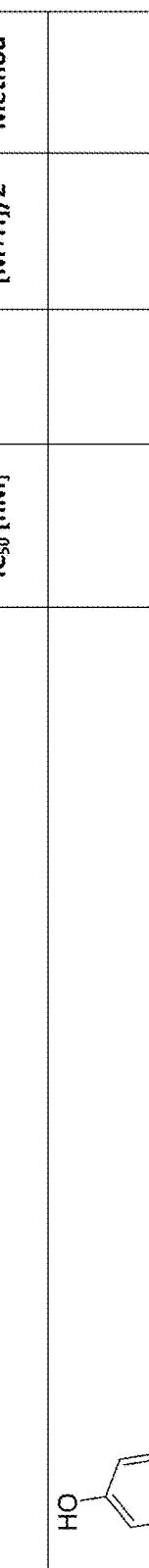 | >300 | 724.91 | 725.6 | Scheme 1-20, 2-3 |
| 510 | 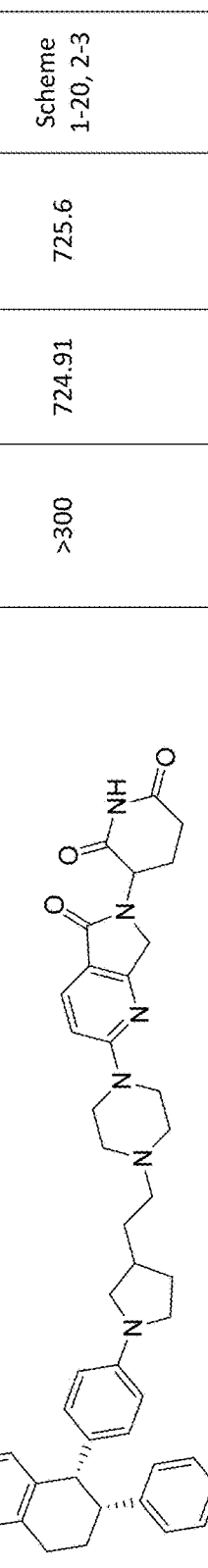 | 2.6 | 724.91 | 725.6 | Scheme 1-20, 2-3 |
| 511 | 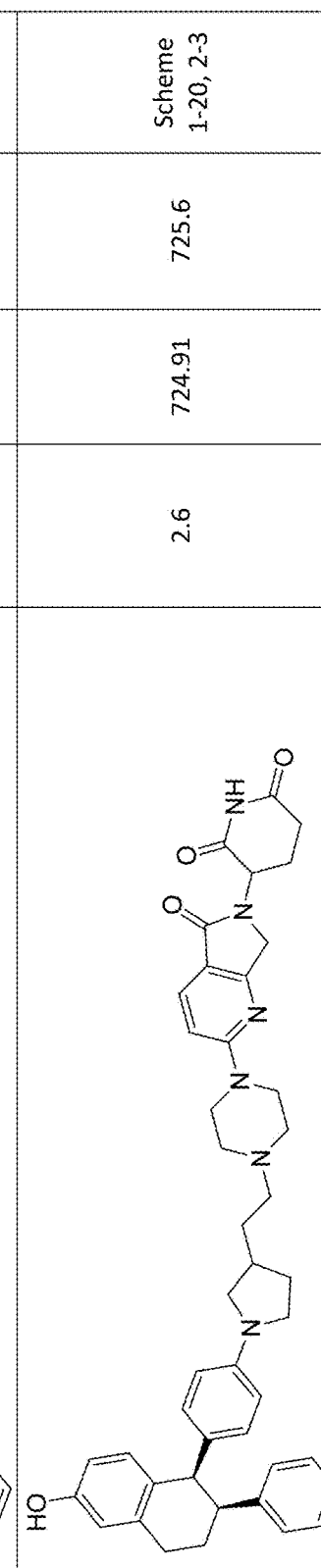 | 4.6 | 755.94 | 756.6 | Scheme 2-26, 3-58 |

FIG. 6 Continued
| Example # | Structure | ERE Luciferase IC$_{50}$ [nM] | MW | Observed [M+H]/z | Synthetic Method |
|---|---|---|---|---|---|
| 512 | 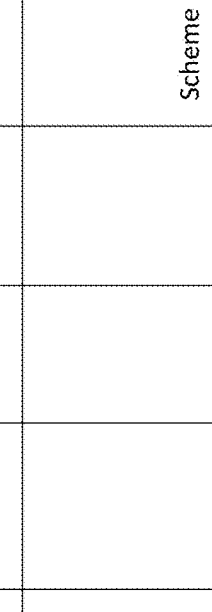 | >300 | 753.94 | 754.6 | Scheme 1-23, 3-59 |
| 513 | 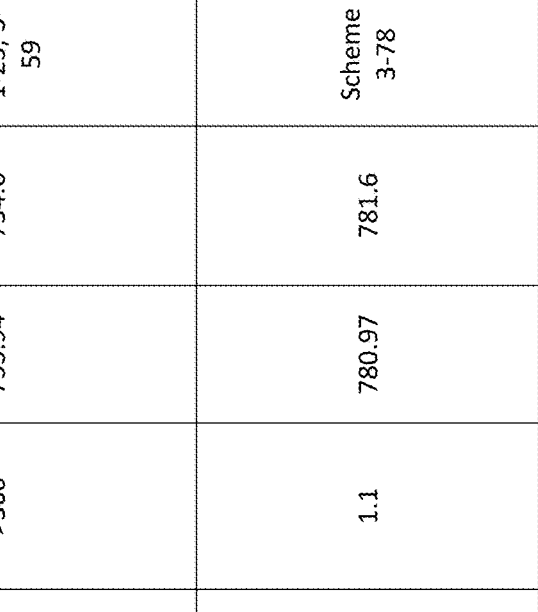 | 1.1 | 780.97 | 781.6 | Scheme 3-78 |

FIG. 6 Continued
| Example # | Structure | ERE Luciferase IC$_{50}$ [nM] | MW | Observed [M+H]/z | Synthetic Method |
|---|---|---|---|---|---|
| 514 | 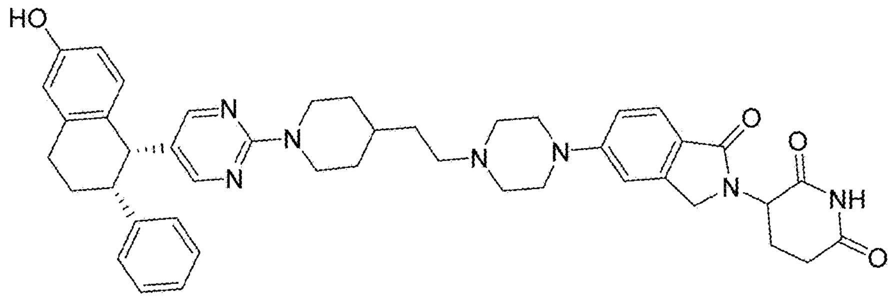 | >300 | 739.92 | 740.6 | Scheme 1-19, 3-59 |
| 515 | 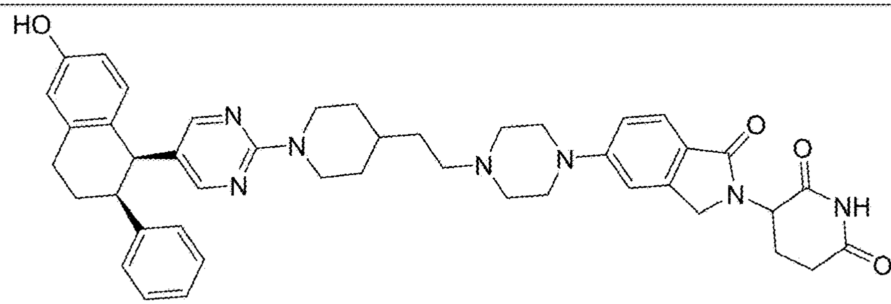 | 1 | 739.92 | 740.6 | Scheme 1-19, 3-59 |
| 516 | 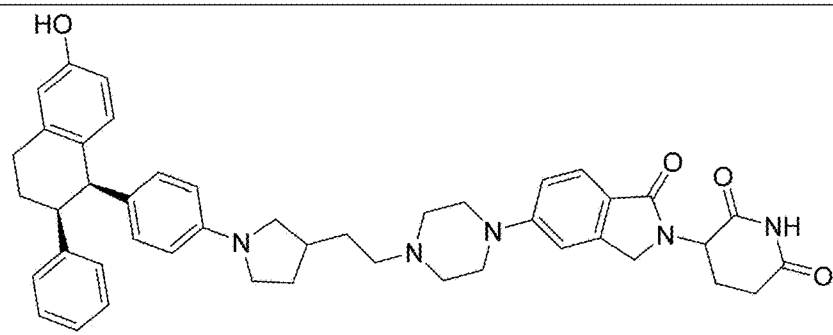 | 1.8 | 723.92 | 724.6 | Scheme 1-20, 2-1 |

FIG. 6 Continued

| Example # | Structure | ERE Luciferase IC$_{50}$ [nM] | MW | Observed [M+H]/z | Synthetic Method |
|---|---|---|---|---|---|
| 517 | 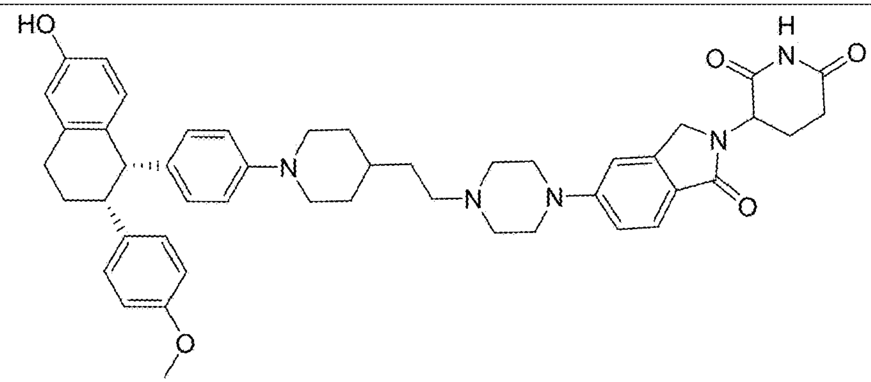 | >300 | 767.97 | 768.6 | Scheme 1-23, 3-59 |
| 518 | 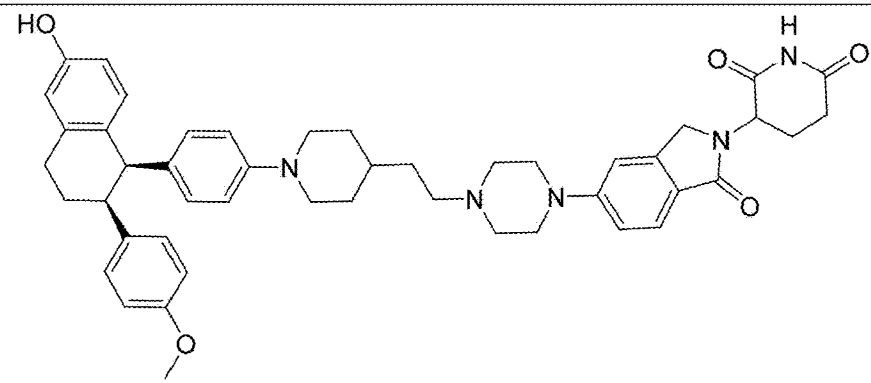 | 0.4 | 767.97 | 768.6 | Scheme 1-23, 3-59 |

FIG. 6 Continued
| Example # | Structure | ERE Luciferase IC$_{50}$ [nM] | MW | Observed [M+H]/z | Synthetic Method |
|---|---|---|---|---|---|
| 519 | 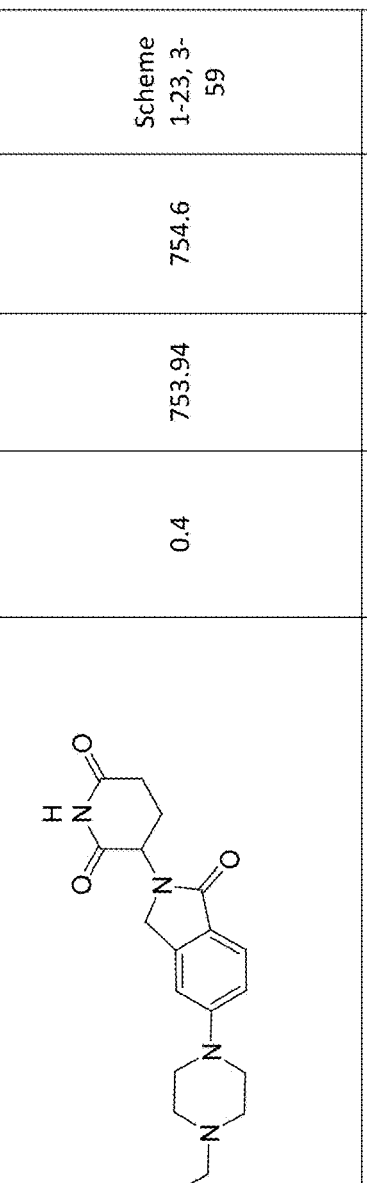 | 0.4 | 753.94 | 754.6 | Scheme 1-23, 3-59 |
| 520 | 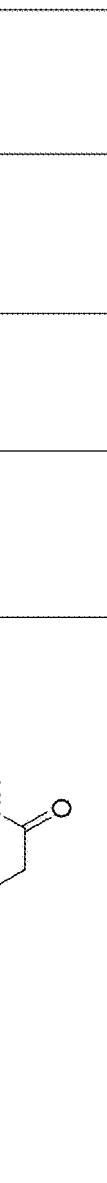 | 0.3 | 766.98 | 767.6 | Scheme 3-80 |

FIG. 6 Continued

| Example # | Structure | ERE Luciferase IC$_{50}$ [nM] | MW | Observed [M+H]/z | Synthetic Method |
|---|---|---|---|---|---|
| 521 | 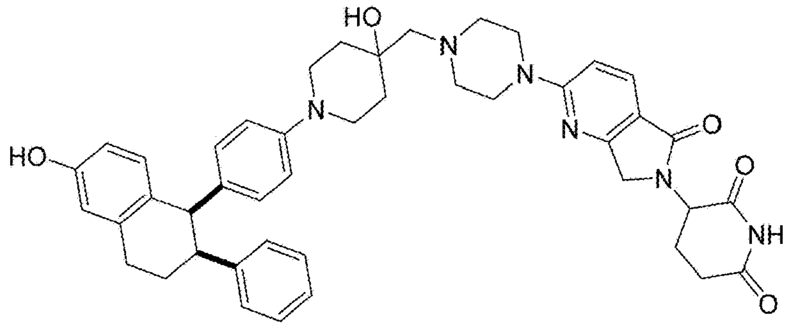 | 4.1 | 740.91 | 741.6 | Scheme 3-81 |
| 522 | 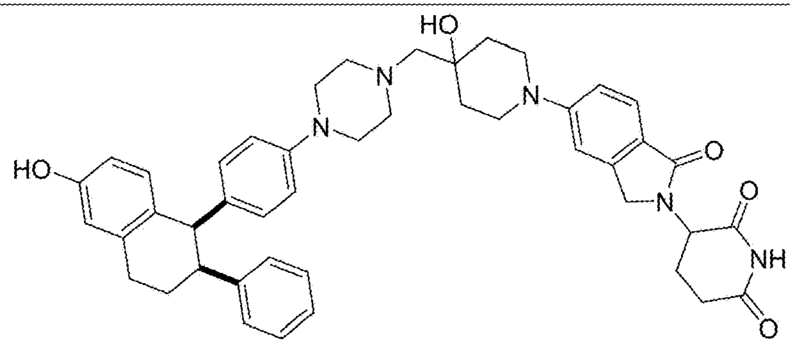 | 1.2 | 739.92 | 740.6 | Scheme 3-82 |
| 523 | 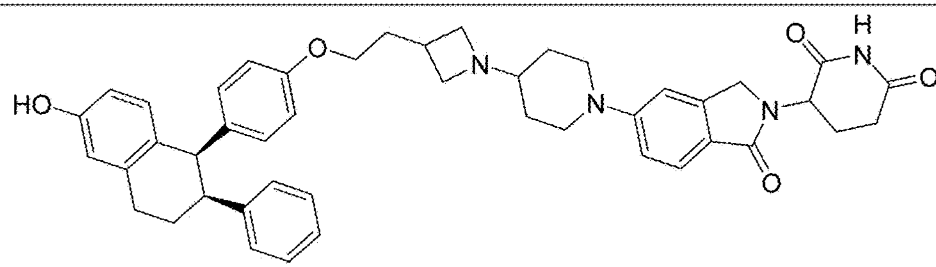 | 0.2 | 724.9 | 725.6 | Scheme 3-83 |

FIG. 6 Continued
| Example # | Structure | ERE Luciferase IC$_{50}$ [nM] | MW | Observed [M+H]/Z | Synthetic Method |
|---|---|---|---|---|---|
| 524 | 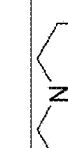 | 1.5 | 741.91 | 742.6 | Scheme 3-85 |
| 525 | 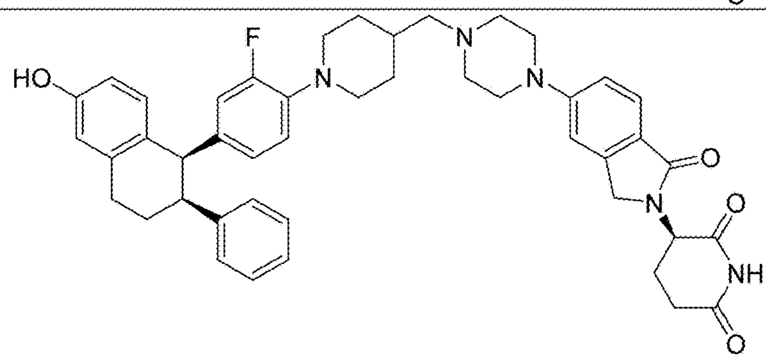 | 1.7 | 741.91 | 742.6 | Scheme 3-84 |

FIG. 6 Continued

| Example # | Structure | ERE Luciferase IC$_{50}$ [nM] | MW | Observed [M+H]/z | Synthetic Method |
|---|---|---|---|---|---|
| 526 | 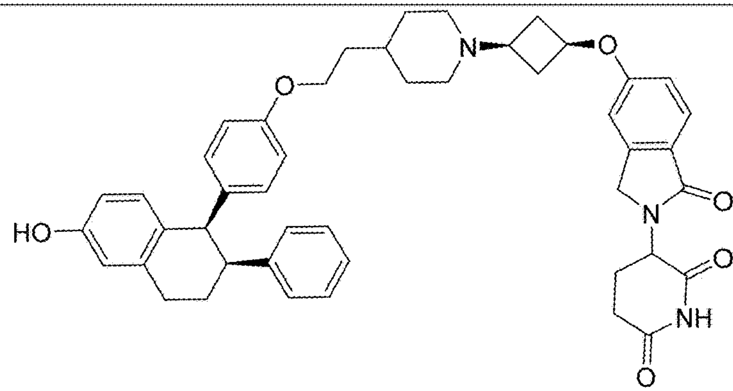 | 0.4 | 739.91 | 740.3 | Scheme 3-86 |
| 527 | 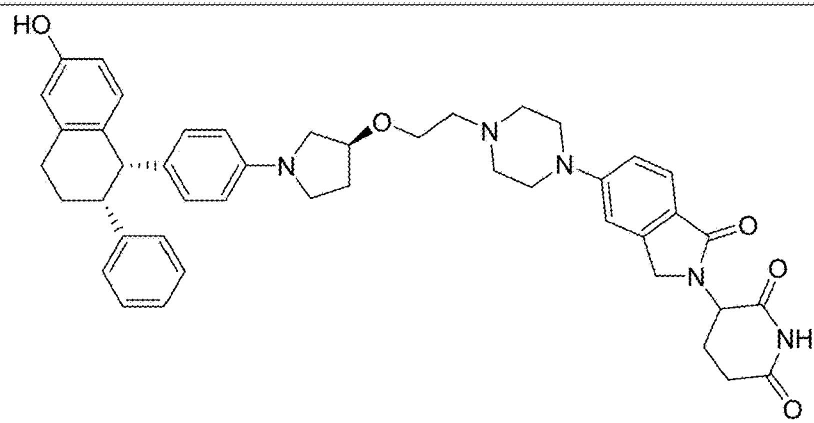 | >300 | 739.92 | 740.3 | Scheme 1-22, 2-1 |

FIG. 6 Continued
| Example # | Structure | ERE Luciferase IC$_{50}$ [nM] | MW | Observed [M+H]/z | Synthetic Method |
|---|---|---|---|---|---|
| 528 | 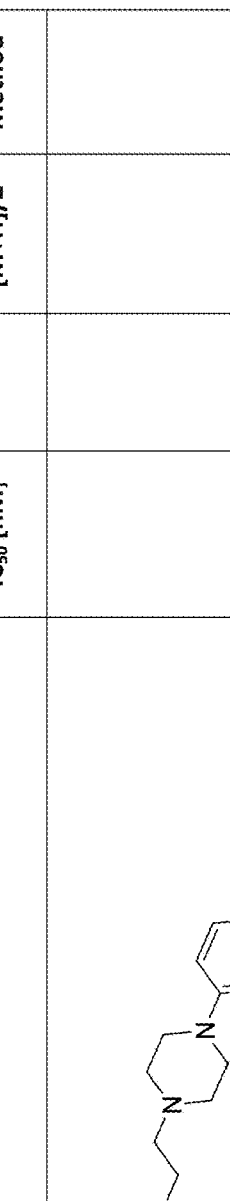 | 1.7 | 739.92 | 740.3 | Scheme 1-22, 2-1 |
| 529 | 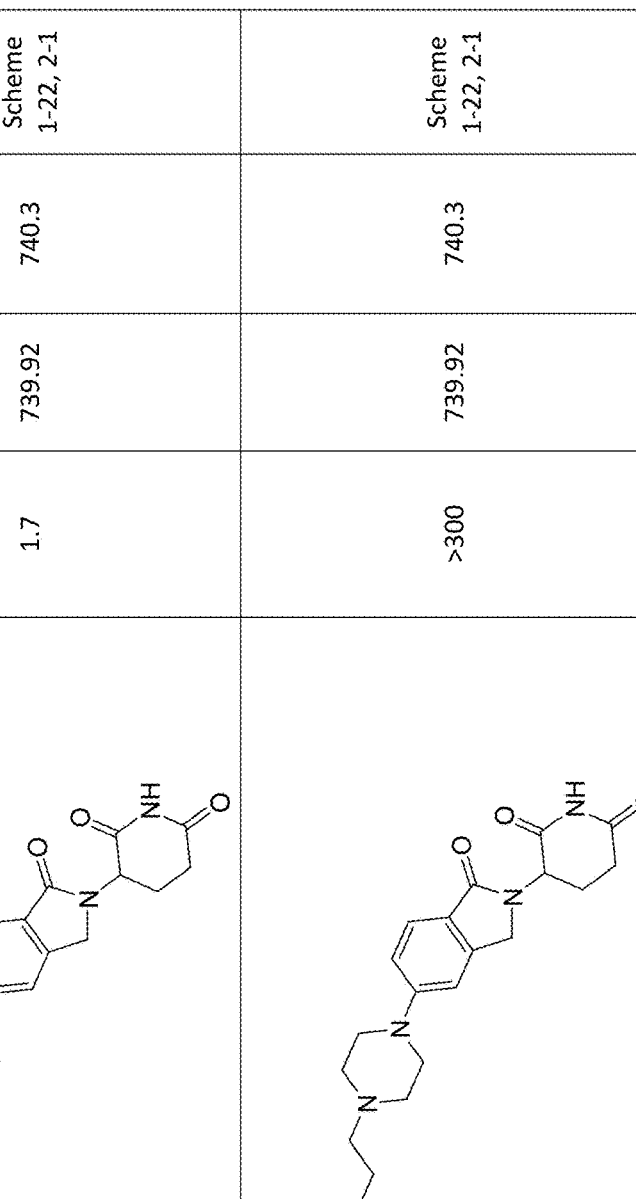 | >300 | 739.92 | 740.3 | Scheme 1-22, 2-1 |

FIG. 6 Continued
| Example # | Structure | ERE Luciferase IC$_{50}$ [nM] | MW | Observed [M+H]/z | Synthetic Method |
|---|---|---|---|---|---|
| 530 | 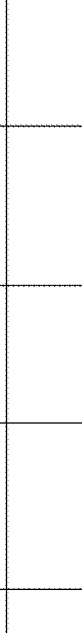 | 1.7 | 739.92 | 740.3 | Scheme 1-22, 2-1 |
| 531 | 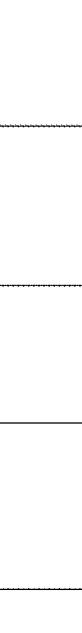 | <0.1 | 725.89 | 726.2 | Scheme 3-87 |

FIG. 6 Continued
| Example # | Structure | ERE Luciferase IC$_{50}$ [nM] | MW | Observed [M+H]/z | Synthetic Method |
|---|---|---|---|---|---|
| 532 | 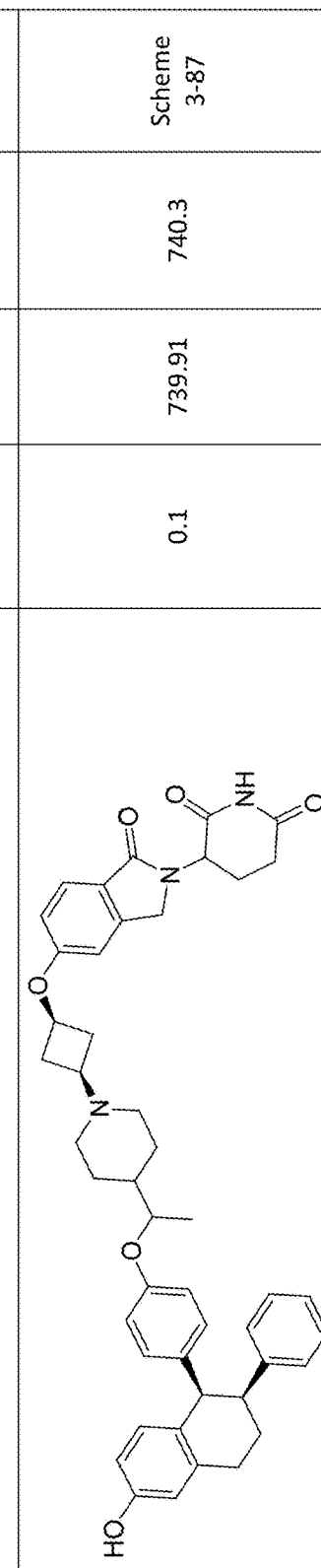 | 0.1 | 739.91 | 740.3 | Scheme 3-87 |
| 533 | 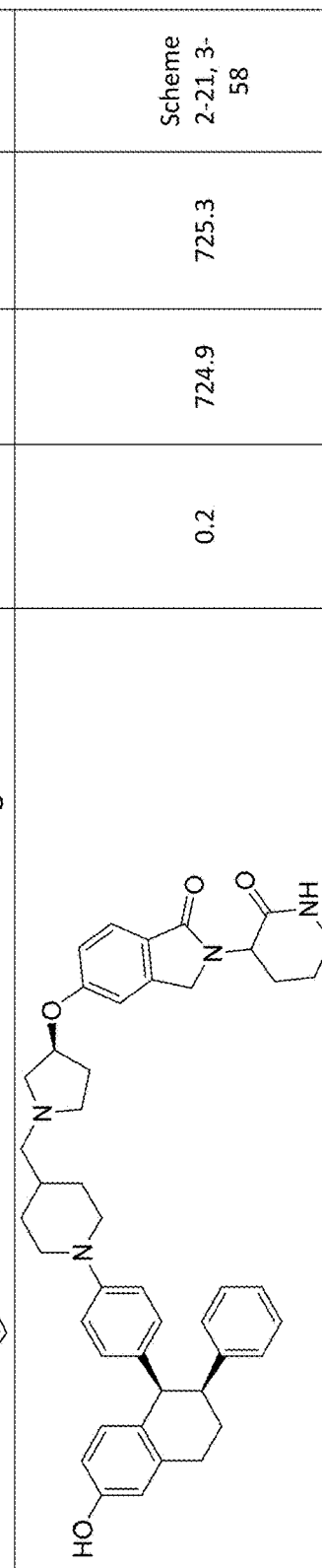 | 0.2 | 724.9 | 725.3 | Scheme 2-21, 3-58 |
| 534 | 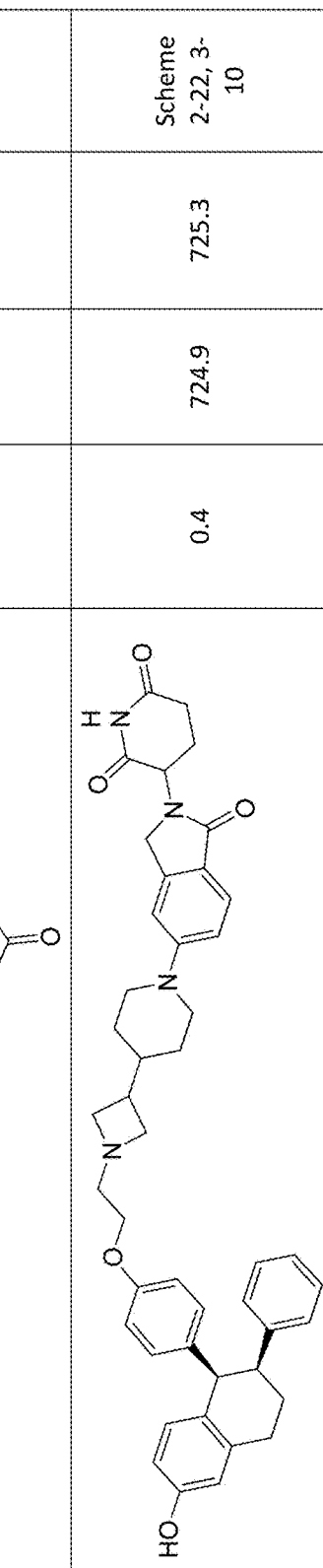 | 0.4 | 724.9 | 725.3 | Scheme 2-22, 3-10 |

FIG. 6 Continued

| Example # | Structure | ERE Luciferase IC$_{50}$ [nM] | MW | Observed [M+H]/Z | Synthetic Method |
|---|---|---|---|---|---|
| 535 | 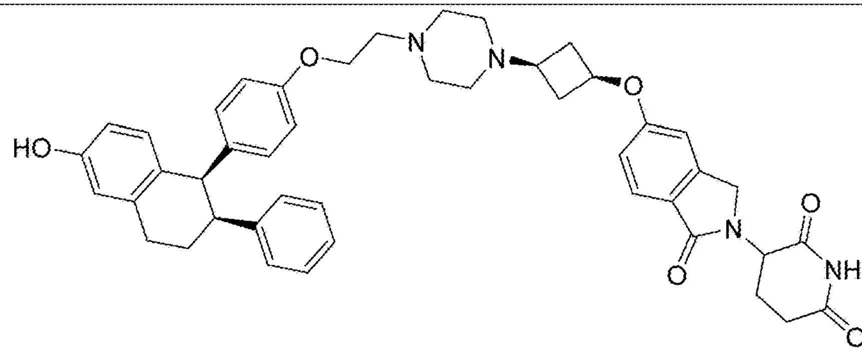 | 0.2 | 740.9 | 741.6 | Scheme 2-23, 3-10 |
| 536 | 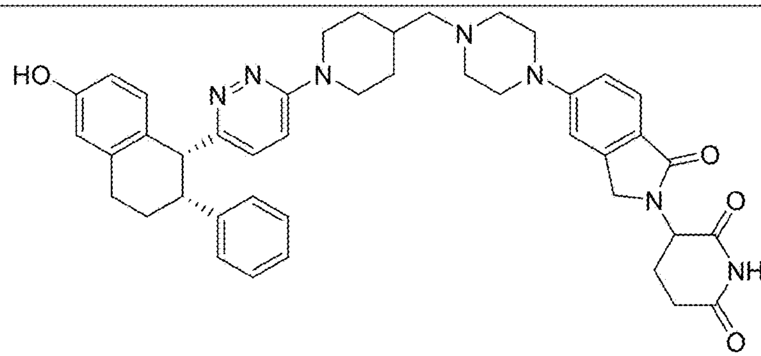 | >300 | 725.89 | 726.6 | Scheme 1-6, 2-1 |

FIG. 6 Continued
| Example # | Structure | ERE Luciferase IC$_{50}$ [nM] | MW | Observed [M+H]/z | Synthetic Method |
|---|---|---|---|---|---|
| 537 | 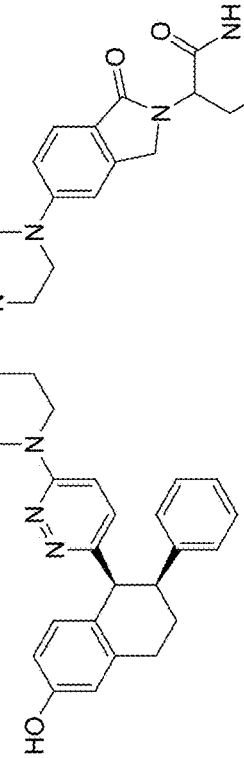 | >300 | 725.89 | 726.6 | Scheme 1-6, 2-1 |
| 538 | 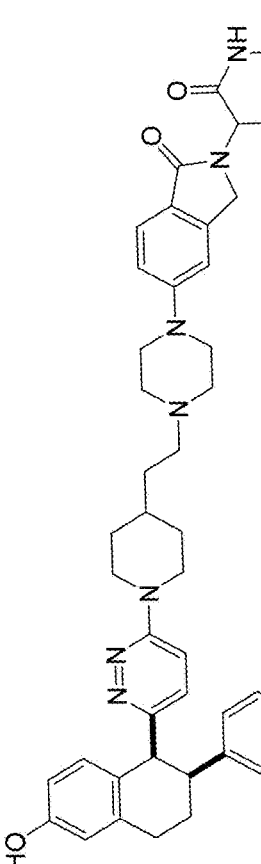 | >300 | 739.92 | 740.6 | Scheme 1-6, 2-1 |

FIG. 6 Continued
| Example # | Structure | ERE Luciferase IC$_{50}$ [nM] | MW | Observed [M+H]/Z | Synthetic Method |
|---|---|---|---|---|---|
| 539 | 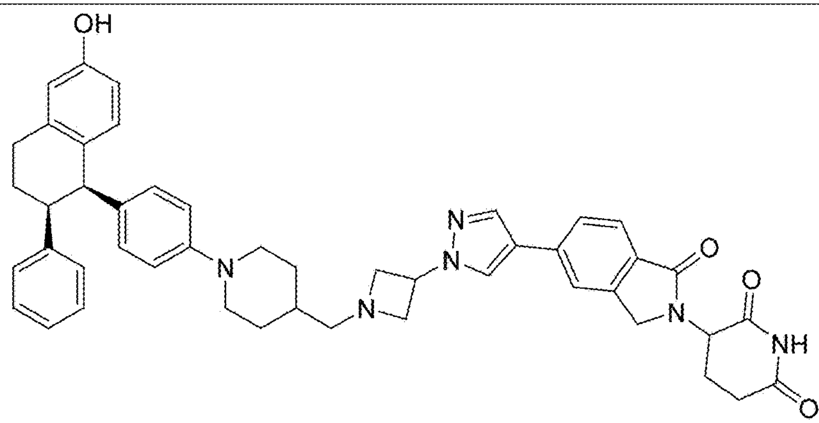 | 0.4 | 760.94 | 761.6 | Scheme 2-24, 3-58 |
| 540 | 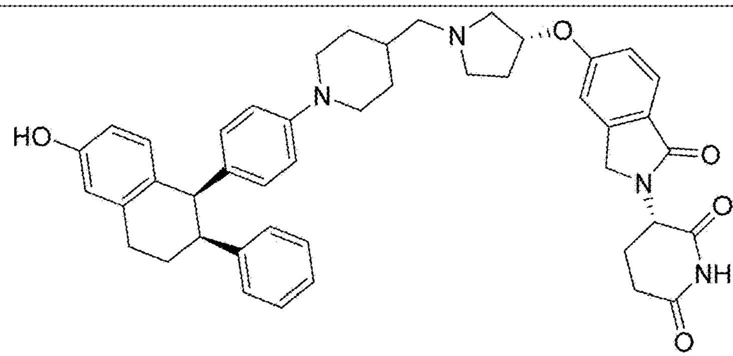 | 0.4 | 724.9 | 725.3 | Scheme 2-21, 3-58 |

FIG. 6 Continued

| Example # | Structure | ERE Luciferase IC₅₀ [nM] | MW | Observed [M+H]/Z | Synthetic Method |
|---|---|---|---|---|---|
| 541 | 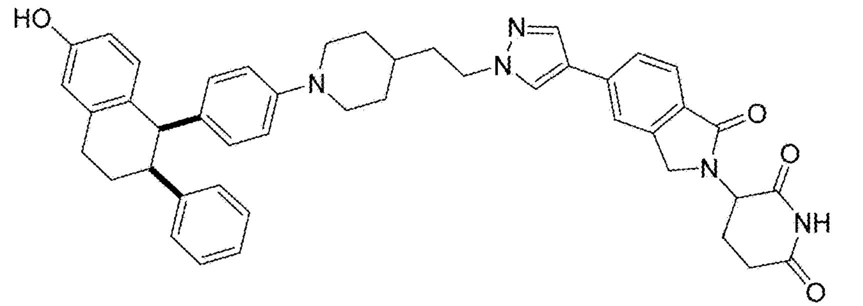 | 12 | 719.89 | 720.3 | Scheme 3-88 |
| 542 | 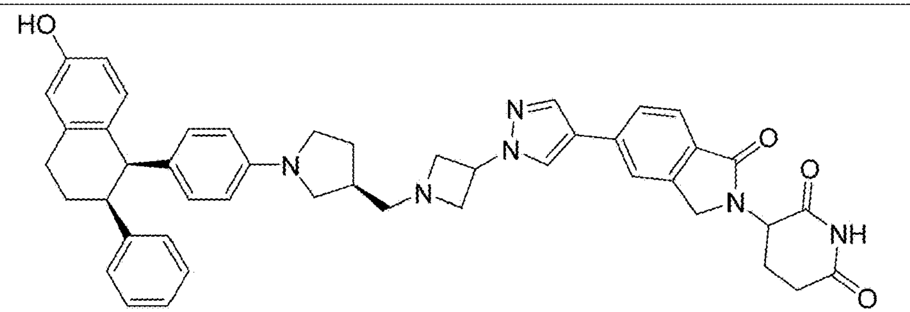 | 1.1 | 746.91 | 747.3 | Scheme 1-24, 2-24 |
| 543 | 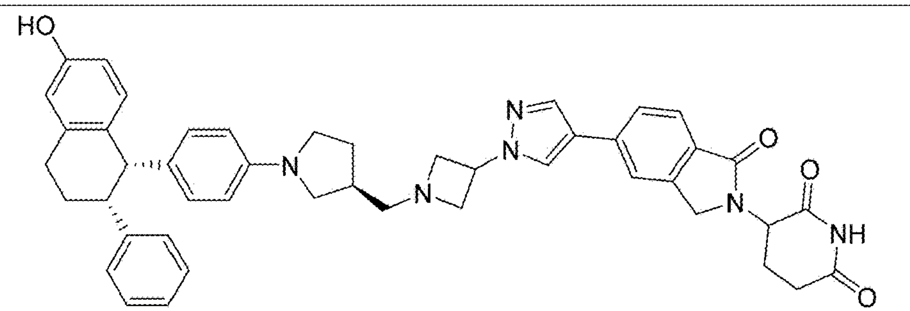 | >300 | 746.91 | 747.3 | Scheme 1-24, 2-24 |

FIG. 6 Continued

| Example # | Structure | ERE Luciferase IC$_{50}$ [nM] | MW | Observed [M+H]/z | Synthetic Method |
|---|---|---|---|---|---|
| 544 | 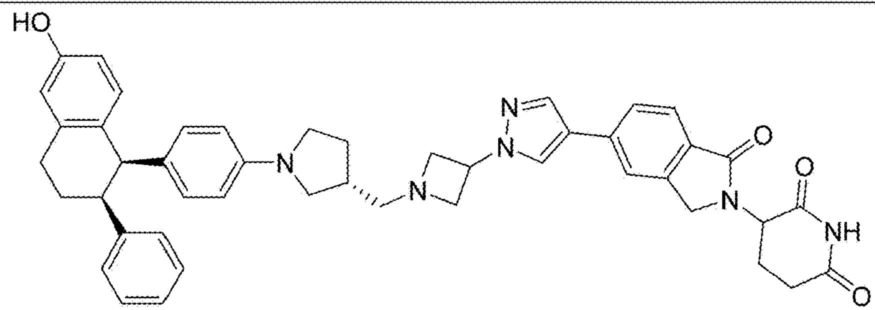 | 0.8 | 746.91 | 747.3 | Scheme 1-24, 2-24 |
| 545 | 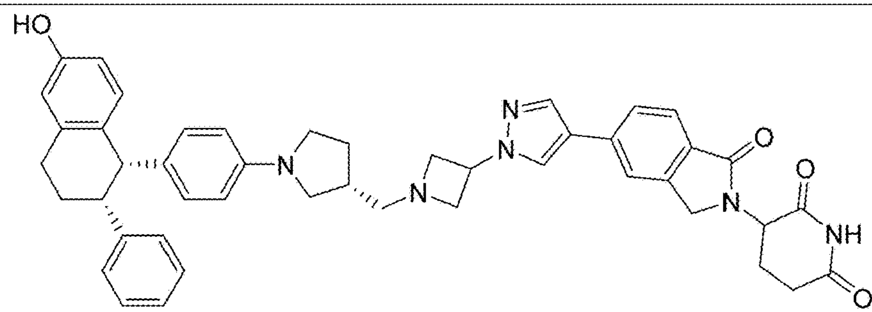 | >300 | 746.91 | 747.3 | Scheme 1-24, 2-24 |
| 546 | 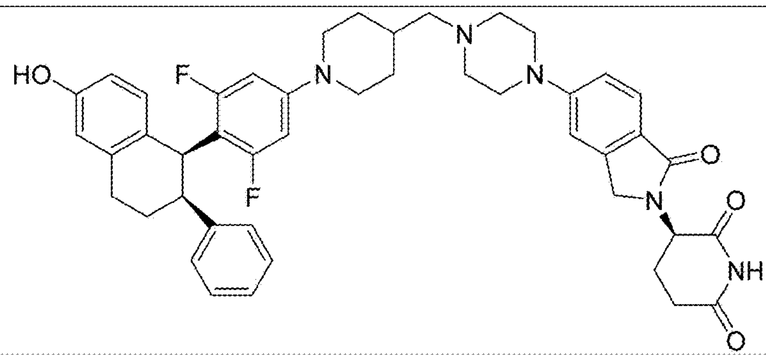 | | 759.9 | 760.3 | Scheme 3-84 |

FIG. 6 Continued

| Example # | Structure | ERE Luciferase IC$_{50}$ [nM] | MW | Observed [M+H]/Z | Synthetic Method |
|---|---|---|---|---|---|
| 547 | 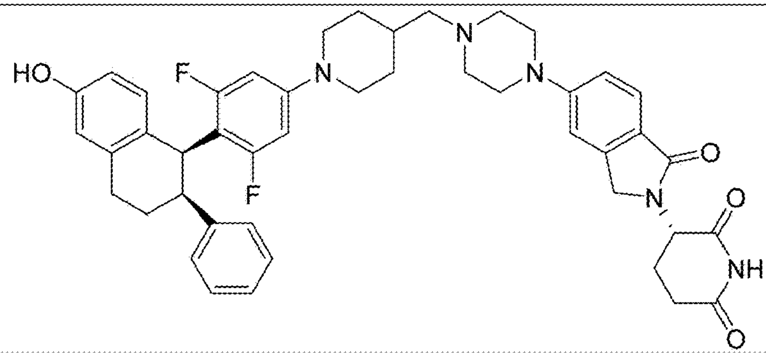 | | 759.9 | 760.3 | Scheme 3-85 |

FIG. 7

Table 3. ERα Degradation Activity, Chemical Name, and NMR Data for Exemplary ER PROTACs

| Example | Stucture Name | DC$_{50}$ (nM)* | D$_{max}$ (%)** | $^1$H-NMR |
|---|---|---|---|---|
| 1 | (2S,4R)-4-hydroxy-1-((S)-2-(2-(2-(4-(2-(4-(4-((1R,2S)-6-hydroxy-2-phenyl-1,2,3,4-tetrahydronaphthalen-1-yl)phenoxy)ethyl)piperazin-1-yl)ethoxy)acetamido)-3,3-dimethylbutanoyl)-N-(4-(4-methylthiazol-5-yl)benzyl)pyrrolidine-2-carboxamide | A | A | δ 9.36 - 9.10 (br, 1H), 8.95 (s, 1H), 8.60 (t, J=5.6 Hz, 1H), 7.39 (m, 5H), 7.16 - 7.12 (m, 3H), 6.82 (d, J= 7.2 Hz, 2H), 6.64 - 6.61 (m, 2H), 6.51 - 6.34 (m, 3H), 6.26 - 6.24 (m, 2H), 5.25 - 5.10 (m, 1H), 4.59 - 4.51 (m, 1H), 4.48 - 4.32 (m, 3H), 4.29 - 4.15 (m, 2H), 3.80 - 3.70 (m, 4H), 3.63 - 3.55 (m, 3H), 3.34 - 3.26 (m, 8H), 3.05 - 2.84 (m, 2H), 2.48 - 2.43 (m, 9H), 2.11 - 2.01 (m, 2H), 1.95 - 1.85 (m, 1H), 1.75 - 1.65 (m, 1H), 0.93 (s, 9H). (DMSO-d6, 400 MHz) |
| 11 | 3-(5-((2-(4-(2-(4-((1R,2S)-6-hydroxy-2- phenyl-1,2,3,4-tetrahydronaphthalen-1-yl)phenoxy)ethyl)piperazin-1-yl)ethyl)amino)-1-oxoisoindolin-2-yl)piperidine-2,6-dione | C | C | δ 10.91 (s, 1H), 9.12 (s, 1H), 7.38 (d, J=8.4 Hz, 1H), 7.18 - 7.08 (m, 3H), 6.83 (d, J=7.2 Hz, 2H), 6.70 - 6.59 (m, 4H), 6.53 (d, J=8.4 Hz, 2H), 6.48 (dd, J=2.4, 8.4 Hz, 1H), 6.26 (d, J=8.4 Hz, 2H), 6.19 (s, 1H), 5.01 (dd, J=5.2, 13.2 Hz, 1H), 4.30 - 4.23 (m, 1H), 4.20 - 4.09 (m, 2H), 3.91 (s, 2H), 3.40 - 3.32 (m, 8H), 3.29 (s, 3H), 3.23 - 3.14 (m, 2H), 2.99 - 2.85 (m, 3H), 2.61 - 2.51 (m, 1H), 2.41 - 2.37 (m, 2H), 2.22 - 2.02 (m, 2H), 1.99 - 1.89 (m, 1H), 1.76 - 1.66 (m, 1H). (DMSO-d6, 400 MHz) |

FIG. 7 Continued

| | | | |
|---|---|---|---|
| 13 | 3-{5-[3-[4-[2-[4-[(1R,2S)-(6-hydroxy-2-phenyl-tetralin-1-yl]phenoxy]ethyl]piperazin-1-yl]propylamino]-1-oxo-isoindolin-2-yl]piperidine-2,6-dione | C | δ 10.91 (s, 1H), 9.11 (s, 1H), 7.37 (d, J=8.4 Hz, 1H), 7.21 - 7.06 (m, 3H), 6.82 (d, J=6.8 Hz, 2H), 6.69 - 6.58 (m, 4H), 6.56 - 6.44 (m, 3H), 6.39 (t, J=5.2 Hz, 1H), 6.26 (d, J=8.6 Hz, 2H), 5.00 (dd, J=5.2, 13.4 Hz, 1H), 4.32 - 4.08 (m, 3H), 3.90 (t, J=5.6 Hz, 2H), 3.30 (s, 1H), 3.10 (q, J=6.4 Hz, 2H), 3.02 - 2.83 (m, 3H), 2.66 - 2.57 (m, 3H), 2.46 - 2.30 (m, 11H), 2.17 - 1.88 (m, 2H), 1.70-1.67 (m, 3H). (DMSO-d6, 400 MHz) |
| 26 | 3-{5-[(4-(4-(2-(4-((1R,2S)-6-hydroxy-2-phenyl-1,2,3,4-tetrahydronaphthalen-1-yl)phenoxy)ethyl)piperazin-1-yl)phenyl)amino)-1-oxoisoindolin-2-yl)piperidine-2,6-dione | A | δ 10.92 (s, 1H), 7.43 - 7.35 (m, 1H), 7.20 - 7.08 (m, 3H), 6.84 (d, J=7.2 Hz, 2H), 6.70 - 6.59 (m, 6H), 6.49 (dd, J=2.4, 8.4 Hz, 1H), 6.30 (d, J=8.4 Hz, 2H), 5.01 (dd, J=5.2, 13.2 Hz, 1H), 4.31 - 4.19 (m, 4H), 4.17 - 4.11 (m, 1H), 3.86 - 3.66 (m, 1H), 3.35 - 3.27 (m, 8H), 3.24 - 3.05 (m, 6H), 3.03 - 2.82 (m, 3H), 2.61 - 2.56 (m, 1H), 2.47 - 2.46 (m, 1H), 2.18 - 2.02 (m, 1H), 1.99 - 1.87 (m, 1H), 1.84 - 1.70 (m, 3H), 1.65 - 1.56 (m, 2H). (DMSO-d6, 400 MHz) |
| 31 | (3S)-3-{5-[3-[4-[(1R,2S)-6-hydroxy-2-phenyl-tetralin-1-yl]phenoxy]propoxy]propylamino]-1-oxo-isoindolin-2-yl)piperidine-2,6-dione | C | δ 10.92 (s, 1H), 9.16 (s, 1H), 7.37 (d, J=8.4 Hz, 1H), 7.15 - 7.08 (m, 3H), 6.81 (d, J=6.8 Hz, 2H), 6.64 - 6.60 (m, 4H), 6.53 - 6.46 (m, 3H), 6.33 (t, J=4.2 Hz, 1H), 6.25 (d, J=8.4 Hz, 2H), 5.00 (dd, J=9.2, 4.8 Hz, 1H), 4.25 (d, J=16.4 Hz, 1H), 4.17 - 4.10 (m, 2H), 3.87 (t, J=6.0 Hz, 2H), 3.49 - 3.33 (m, 4H), 3.28 - 3.27 (m, 1H), 3.13 - 3.08 (m, 2H), 2.97 - 2.89 (m, 3H), 2.59 - 2.58 (m, 1H), 2.40 - 2.27 (m, 1H), 2.11 - 2.03 (m, 1H), 1.94 - 1.84 (m, 3H), 1.80 - 1.68 (m, 3H). (DMSO-d6, 400 MHz) |

FIG. 7 Continued

| 33 | 2-(2,6-dioxo-3-piperidyl)-5-[4- [4-[(1R,2S)-6-hydroxy-2-phenyl-tetralin-1-yl]phenoxy]butyl]piperazin-1-yl]isoindoline-1,3-dione | | C | δ 11.08 (s, 1H), 9.12 (s, 1H), 7.68 (d, J=8.4 Hz, 1H), 7.33 (d, J=2.0 Hz, 1H), 7.28 - 7.23 (m, 1H), 7.18 - 7.10 (m, 3H), 6.82 (d, J=6.8 Hz, 2H), 6.66 - 6.59 (m, 2H), 6.56 - 6.45 (m, 3H), 6.26 (d, J=8.8 Hz, 2H), 5.07 (dd, J=5.2, 12.8 Hz, 1H), 4.18 (d, J=4.8 Hz, 1H), 3.88 - 3.79 (m, 2H), 3.41 (m, 4H), 3.30 (s, 2H), 3.03 - 2.82 (m, 3H), 2.58 - 2.53 (m, 4H), 2.37 - 2.31 (m, 3H), 2.13 - 1.98 (m, 2H), 1.73 - 1.63 (m, 3H), 1.56 (m, 2H). (DMSO-d6, 400 MHz) |
|---|---|---|---|---|
| 35 | 3-[5-[4-[4-[4-[(1R,2S)-6-hydroxy-2-phenyl-tetralin-1-yl]phenoxy]butyl]piperazin-1-yl]-1-oxo-isoindolin-2-yl]piperidine-2,6-dione | A | B | δ 11.06 (s, 1H), 9.10 (s, 1H), 7.65 (d, J=8.4 Hz, 1H), 7.31 (d, J=2.0 Hz, 1H), 7.22 (dd, J=2.0, 8.4 Hz, 1H), 7.15 - 7.07 (m, 3H), 6.80 (d, J=6.8 Hz, 2H), 6.65 - 6.56 (m, 2H), 6.53 - 6.43 (m, 3H), 6.23 (d, J=8.8 Hz, 2H), 5.04 (dd, J=5.2, 13.2 Hz, 1H), 4.15 (d, J=5.2 Hz, 1H), 3.82 (t, J=6.4 Hz, 2H), 3.38 (m, 5H), 3.30 (m, 1H), 2.96 - 2.80 (m, 3H), 2.67 - 2.63 (m, 1H), 2.54 (m, 1H), 2.45 (m, 3H), 2.34 - 2.29 (m, 2H), 2.10 - 1.94 (m, 2H), 1.71 - 1.60 (m, 3H), 1.54 (m,, 2H). (DMSO-d6, 400 MHz) |
| 60 | 3-[(2S)-5-[3-[4-[(1R,2S)-6-hydroxy-2-phenyl-tetralin-1-yl]phenoxy]propoxy]-1-oxo-isoindolin-2-yl]piperidine-2,6-dione | C | C | δ 7.98 (s, 1H), 7.69 (d, J=8 Hz, 1H), 7.21 - 7.09 (m, 3H), 6.95 - 6.72 (m, 6H), 6.61 (dd, J=4, 8 Hz, 1H), 6.53 (d, J=8 Hz, 2H), 6.30 (d, J=8 Hz, 2H), 5.90 - 5.75 (m, 1H), 5.22 (dd, J=4, 12 Hz, 1H), 4.49 - 4.20 (m, 3H), 4.13 - 3.89 (m, 4H), 3.68 - 3.51 (m, 4H), 3.44 - 3.32 (m, 1H), 3.12 - 2.79 (m, 4H), 2.42 - 1.94 (m, 7H), 1.86 - 1.76 (m, 1H). (DMSO-d6, 400 MHz) |

FIG. 7 Continued

| | | | |
|---|---|---|---|
| 62 | 3-(5-(4-{5-(4-[(1R,2S)-6-hydroxy-2-phenyl-1,2,3,4-tetrahydronaphthalen-1-yl]phenoxy}pentyl)piperazin-1-yl)-1-oxoisoindolin-2-yl)piperidine-2,6-dione | A | δ: 10.96 (s, 1H), 10.69 (s, 1H), 9.16 (s, 1H), 7.58 (d, J=8.4 Hz, 1H), 7.23 - 7.08 (m, 5H), 6.83 (d, J=6.4 Hz, 2H), 6.67 - 6.59 (m, 2H), 6.57 - 6.45 (m, 3H), 6.27 (d, J=8.8 Hz, 2H), 5.06 (dd, J=5.2, 13.2 Hz, 1H), 4.40 - 4.31 (m, 1H), 4.28 - 4.14 (m, 2H), 3.99 (d, J=13.2 Hz, 2H), 3.83 (t, J=6.4 Hz, 2H), 3.58 - 3.51 (m, 2H), 3.34 - 3.21 (m, 3H), 3.16 - 3.04 (m, 4H), 3.03 - 2.84 (m, 3H), 2.62 - 2.56 (m, 1H), 2.44 - 2.35 (m, 1H), 2.16 - 2.02 (m, 1H), 2.01 - 1.92 (m, 1H), 1.83 - 1.63 (m, 5H), 1.46 - 1.35 (m, 2H). (DMSO-d6, 400 MHz) |
| 65 | 2-(2,6-dioxo-3-piperidyl)-5-[4-[6-[4-[(1R,2S)-6-hydroxy-2-phenyl-tetralin-1-yl]phenoxy]hexyl]piperazin-1-yl]phenyl]isoindoline-1,3-dione | A | δ 11.08 (s, 1H), 8.31 (s, 1H), 7.67 (d, J=8.4 Hz, 1H), 7.32 (s, 1H), 7.24 (d, J=8.4 Hz, 1H), 7.19 - 7.07 (m, 3H), 6.82 (d, J=6.8 Hz, 2H), 6.68 - 6.57 (m, 2H), 6.56 - 6.43 (m, 3H), 6.25 (d, J=8.4 Hz, 2H), 5.07 (dd, J=5.2, 12.8 Hz, 1H), 4.17 (d, J=4.8 Hz, 1H), 3.80 (t, J=6.4 Hz, 2H), 3.32 (s, 3H), 3.02 - 2.83 (m, 3H), 2.58 (d, J=17.2 Hz, 2H), 2.48 - 2.42 (m, 7H), 2.30 (t, J=7.2 Hz, 2H), 2.14 - 1.96 (m, 2H), 1.74 - 1.57 (m, 3H), 1.50 - 1.26 (m, 6H). (DMSO-d6, 400 MHz) |
| 67 | 3-[5-[4-[6-[4-[(1R,2S)-6-hydroxy-2-phenyl-tetralin-1-yl]phenoxy]hexyl]piperazin-1-yl]-1-oxo-isoindolin-2-yl]piperidine-2,6-dione | A | δ 10.94 (s, 1H), 8.29 (s, 1H), 7.51 (d, J=8.8 Hz, 1H), 7.21 - 7.00 (m, 5H), 6.82 (d, J=6.8 Hz, 2H), 6.67 - 6.57 (m, 2H), 6.55 - 6.45 (m, 3H), 6.25 (d, J=8.4 Hz, 2H), 5.04 (dd, J=5.6, 13.6 Hz, 1H), 4.37 - 4.26 (m, 1H), 4.24 - 4.13 (m, 2H), 3.80 (t, J=6.4 Hz, 2H), 3.26 (s, 3H), 3.04 - 2.84 (m, 3H), 2.63 - 2.52 (m, 2H), 2.46 - 2.34 (m, 7H), 2.32 - 2.26 (m, 2H), 2.08 (dd, J=6.4, 12.8 Hz, 1H), 1.99 - 1.92 (m, 1H), 1.74 - 1.59 (m, 3H), 1.51 - 1.28 (m, 6H). (DMSO-d6, 400 MHz) |

FIG. 7 Continued

| | | | |
|---|---|---|---|
| 69 | 2-(2,6-dioxopiperidin-3-yl)-5-(4-(5-(4-((1R,2S)-6-hydroxy-2-phenyl-1,2,3,4-tetrahydronaphthalen-1-yl)phenoxy)pentyl)piperazin-1-yl)isoindoline-1,3-dione | B | δ 11.10 (s, 1H), 10.14 (s, 1H), 9.14 (s, 1H), 7.76 (d, J=8.4 Hz, 1H), 7.48 (s, 1H), 7.35 (d, J=8.4 Hz, 1H), 7.18 - 7.09 (m, 3H), 6.83 (d, J=6.8 Hz, 2H), 6.66 - 6.59 (m, 2H), 6.53 (d, J=8.8 Hz, 2H), 6.48 (dd, J=2.4, 8.4 Hz, 1H), 6.27 (d, J=8.8 Hz, 2H), 5.09 (dd, J=5.2, 13.2 Hz, 1H), 4.27 - 4.15 (m, 3H), 3.83 (t, J=6.4 Hz, 2H), 3.61 - 2.50 (m, 2H), 3.31 - 3.24 (m, 3H), 3.17 - 3.05 (m, 4H), 3.03 - 2.82 (m, 3H), 2.63 - 2.57 (m, 2H), 2.17 - 1.97 (m, 2H), 1.80 - 1.63 (m, 5H), 1.48 - 1.35 (m, 2H). (DMSO-d6, 400 MHz) |
| 124 | 3-[5-[4-[5-[4-[(1R,2S)-2-(2,4-difluorophenyl)-6-hydroxy-tetralin-1-yl]phenoxy]pentyl]piperazin-1-yl]-1-oxo-isoindolin-2-yl]piperidine-2,6-dione | A | δ 10.96 - 10.94 (m, 2H), 7.58 (d, J= 8.4 Hz, 1H), 7.21 - 7.13 (m, 3H), 6.80 - 6.76 (m, 1H), 6.65 - 6.58 (m, 4H), 6.49 (dd, J= 2.4, 8.0 Hz, 1H), 6.46 - 6.40 (m, 1H), 6.33 (d, J= 8.8 Hz, 2H), 5.06 (dd, J= 5.2, 13.4 Hz, 1H), 4.35 (d, J= 17.2 Hz, 1H), 4.25 - 4.17 (m, 2H), 3.98 (d, J= 13.2 Hz, 2H), 3.84 (t, J= 6.4 Hz, 2H), 3.59 - 3.49 (m, 3H), 3.28 (t, J= 12.4 Hz, 2H), 3.13 - 3.09 (m, 4H), 2.97 - 2.87 (m, 3H), 2.61 - 2.56 (m, 1H), 2.45 - 2.36 (m, 1H), 2.18 - 2.05 (m, 1H), 1.99 - 1.95 (m, 1H), 1.81 - 1.65 (m, 5H), 1.44 - 1.37 (m, 2H). (DMSO-d6, 400 MHz) |
| 128 | 3-[5-[4-[5-[3-[(1R,2S)-2-(4-fluorophenyl)-6-hydroxy-tetralin-1-yl]phenoxy]pentyl]piperazin-1-yl]-1-oxo-isoindolin-2-yl]piperidine-2,6-dione | B | δ 10.96 (s, 1H), 8.28 (s, 1H), 7.52 (d, J=8.8 Hz, 1H), 7.10 - 7.03 (m, 2H), 7.02 - 6.94 (m, 2H), 6.93 - 6.83 (m, 3H), 6.66 (d, J=8.4 Hz, 1H), 6.63 - 6.63 (m, 1H), 6.57 (dd, J=1.9, 8.1 Hz, 1H), 6.49 (dd, J=2.4, 8.4 Hz, 1H), 5.97 (d, J=7.6 Hz, 1H), 5.86 (s, 1H), 5.05 (dd, J=5.2, 13.2 Hz, 1H), 4.36 - 4.29 (m, 1H), 4.24 - 4.16 (m, 2H), 3.74 - 3.66 (m, 2H), 3.59 - 3.48 (m, 1H), 3.42 - 3.31 (m, 2H), 3.30 - 3.24 (m, 4H), 3.06 - 2.81 (m, 3H), 2.64 - 2.56 (m, 1H), 2.47 - 2.27 (m, 5H), 2.15 - 2.00 (m, 1H), 1.99 - 1.88 (m, 1H), 1.77 - 1.65 (m, 1H), 1.64 - 1.52 (m, 2H), 1.52 - 1.39 (m, 2H), 1.38 - 1.27 (m, 2H). (DMSO-d6, 400 MHz) |

FIG. 7 Continued

| | | | |
|---|---|---|---|
| 131 | 5-[4-[5-[4-[(1R,2S)-6-hydroxy-tetralin-1-yl]phenoxy]pentyl]piperazin-1-yl]-2-(2,6-dioxo-3-piperidyl)isoindoline-1,3-dione | A | δ 11.10 (s, 1H), 10.83 (br. s, 1H), 9.19 (br. s, 1H), 7.76 (d, J=8.4 Hz, 1H), 7.48 (d, J=2.0 Hz, 1H), 7.34 (dd, J= 2.0, 8.8 Hz, 1H), 7.22 - 7.16 (m, 1H), 6.80 - 6.75 (m, 1H), 6.65 - 6.57 (m, 4H), 6.49 (dd, J= 2.4, 8.4 Hz, 1H), 6.46 - 6.40 (m, 1H), 6.33 (d, J=8.8 Hz, 2H), 5.09 (dd, J=5.2, 12.8 Hz, 1H), 4.22 - 4.18 (m, 3H), 3.84 (t, J= 6.4 Hz, 2H), 3.57 - 3.46 (m, 3H), 3.31 - 3.28 (m, 2H), 3.11 - 3.05 (m, 4H), 2.97 - 2.86 (m, 3H), 2.61 - 2.52 (m, 2H), 2.13 - 2.01 (m, 2H), 1.75 - 1.65 (m, 5H), 1.44 - 1.39 (m, 2H). (DMSO-d6, 400 MHz) |
| 134 | 3-[5-[4-[4-[(1R,2S)-2-(4-fluorophenyl)-6-hydroxy-tetralin-1-yl]phenoxy]cyclohexyl]methyl]piperazin-1-yl]-1-oxo-isoindolin-2-yl]piperidine-2,6-dione | A | δ 10.95 (s, 1H), 9.14 (s, 1H), 7.51 (d, J=8.8 Hz, 1H), 7.08 - 7.02 (m, 2H), 7.00 - 6.93 (m, 2H), 6.87 - 6.80 (m, 2H), 6.65 (d, J=8.4 Hz, 1H), 6.60 (d, J=2.4 Hz, 1H), 6.55 (d, J=8.8 Hz, 2H), 6.48 (dd, J=2.4, 8.4 Hz, 1H), 6.25 (d, J=8.4 Hz, 2H), 5.04 (dd, J=5.2, 13.2 Hz, 1H), 4.36 - 4.28 (m, 1H), 4.24 - 4.12 (m, 2H), 4.11 - 4.00 (m, 1H), 3.27 - 3.24 (m, 3H), 3.03 - 2.83 (m, 3H), 2.63 - 2.54 (m, 1H), 2.47 - 2.45 (m, 4H), 2.42 - 2.36 (m, 1H), 2.17 - 2.09 (m, 2H), 2.08 - 1.89 (m, 4H), 1.86 - 1.76 (m, 2H), 1.72 - 1.62 (m, 1H), 1.59 - 1.45 (m, 1H), 1.30 - 1.21 (m, 2H), 1.04 - 0.90 (m, 2H). (DMSO-d6, 400 MHz) |
| 135 | 2-(2,6-dioxo-3-piperidyl)-5-[4-[[4-[(1R,2S)-6-hydroxy-2-[4-(trifluoromethyl)phenyl]tetralin-1-yl]phenoxy]cyclohexyl]methyl]piperazin-1-yl]isoindoline-1,3-dione | B | δ 11.10 (s, 1H), 10.32 (s, 1H), 9.20 (s, 1H), 7.76 (d, J=8.4 Hz, 1H), 7.50 (d, J=8.4 Hz, 3H), 7.39 - 7.31 (m, 1H), 7.05 (d, J=8.0 Hz, 2H), 6.66 (d, J=8.4 Hz, 1H), 6.62 (d, J=2.4 Hz, 1H), 6.56 (d, J=8.7 Hz, 2H), 6.50 (dd, J=2.4, 8.4 Hz, 1H), 6.28 (d, J=8.8 Hz, 2H), 5.15 - 5.03 (m, 1H), 5.15 - 5.03 (m, 1H), 5.09 (dd, J=5.2, 13.2 Hz, 1H), 4.26 - 4.03 (m, 4H), 3.61 - 3.54 (m, 2H), 3.53 - 3.47 (m, 3H), 3.17 - 3.05 (m, 2H), 3.03 - 2.81 (m, 5H), 2.62 - 2.53 (m, 2H), 2.21-2.08 (m, 1H), 2.06 - 1.79 (m, 6H), 1.77 - 1.68 (m, 1H), 1.36 - 1.23 (m, 2H), 1.17 – 1.01 (m, 2H). (DMSO-d6, 400 MHz) |

FIG. 7 Continued

| | | | |
|---|---|---|---|
| 156 | 3-[5-({5-(4-(4-{[(1R,2S)-6-hydroxy-2-phenyl-1,2,3,4-tetrahydronaphthalen-1-yl]phenyl}piperazin-1-yl)pentyl]amino)-1-oxoisoindolin-2-yl)piperidine-2,6-dione | A | B | δ 10.92 (s, 1H), 8.22 (s, 1H), 7.37 (d, J=8.0 Hz, 1H), 7.15 - 7.13 (m, 4H), 6.83 (d, J=6.8 Hz, 2H), 6.63 - 6.61 (m, 4H), 6.61 - 6.60 (m, 3H), 6.51 (m, 1H), 6.21 (d, J=8.4 Hz, 2H), 5.09 (dd, J=5.2, 13.6 Hz, 1H), 4.28 - 4.24 (m, 1H), 4.15 - 4.10 (m, 2H), 3.49 - 3.48 (m, 1H), 3.05 - 3.02 (m, 2H), 2.97 - 2.80 (m, 7H), 2.77 - 2.75 (m, 1H), 2.64 - 2.60 (m, 4H), 2.45 - 2.40 (m, 3H), 2.13 - 2.10 (m, 1H), 1.94 - 1.92 (m, 1H), 1.76 - 1.70 (m, 1H), 1.55 - 1.52 (m, 2H), 1.45 - 1.42 (m, 2H), 1.39 - 1.35 (m, 2H). (DMSO-d6, 400 MHz) |
| 164 | 3-[5-[2-[4-[4-[4-{[(1R,2S)-6-hydroxy-2- phenyl- tetralin-1-yl]phenoxy]butyl]-1,4-diazepan-1-yl]ethyl]-1-oxo-isoindolin-2-yl]piperidine-2,6-dione | A | A | δ 10.99 (s, 1H), 8.24 (s, 1H), 7.62 (d, J=8.0 Hz, 1H), 7.44 (s, 1H), 7.36 (d, J=8.0 Hz, 1H), 7.18 - 7.06 (m, 3H), 6.85 - 6.77 (m, 2H), 6.66 - 6.43 (m, 5H), 6.25 (d, J=8.8 Hz, 2H), 5.09 (dd, J=5.2, 13.2 Hz, 1H), 4.44 - 4.23 (m, 2H), 4.16 (d, J=4.8 Hz, 1H), 3.95 - 3.73 (m, 2H), 3.29 (dd, J=4.0, 12.4 Hz, 1H), 3.02 - 2.78 (m, 6H), 2.78 - 2.65 (m, 10H), 2.63 - 2.54 (m, 2H), 2.43 - 2.34 (m, 1H), 2.10 - 1.95 (m, 2H), 1.76 - 1.48 (m, 7H). (DMSO-d6, 400 MHz) |
| 184 | 3-[5-[4-[5-[4-[[(1R,2S)-2-(4-fluorophenyl)-6-hydroxy-tetralin-1-yl]phenoxy]pentyl]piperazin-1-yl]-1-oxo-isoindolin-2-yl]piperidine-2,6-dione | A | A | δ 10.93 (s, 1H), 8.21 (d, J=2.0 Hz, 2H), 7.49 (d, J=8.8 Hz, 1H), 7.05 - 7.00 (m, 2H), 6.95 (t, J=8.8 Hz, 2H), 6.85 - 6.79 (m, 2H), 6.63 - 6.51 (m, 4H), 6.46 (dd, J=2.4, 8.4 Hz, 1H), 6.25 (d, J=8.8 Hz, 2H), 5.02 (dd, J=5.2, 13.2 Hz, 1H), 4.34 - 4.10 (m, 4H), 3.79 (t, J=6.4 Hz, 2H), 3.24 (s, 6H), 2.97 - 2.82 (m, 4H), 2.65 (t, J=2.0 Hz, 1H), 2.32 - 2.27 (m, 4H), 2.06 - 1.92 (m, 2H), 1.68 - 1.60 (m, 3H), 1.49 - 1.34 (m, 4H). (DMSO-d6, 400 MHz) |

FIG. 7 Continued

| 186 | 2-(2,6-dioxo-3-piperidyl)-5-[4-[5-[4-[[(1R, 2S)-2-(4-fluorophenyl)-6-hydroxy-tetralin-1-yl]phenoxy]pentyl]piperazin-1-yl]isoindoline-1,3-dione | A | δ 11.09 (s, 1H), 8.18 (s, 1H), 7.68 (d, J=8.4 Hz, 1H), 7.37 - 7.21 (m, 2H), 7.02 - 6.93 (m, 2H), 6.89 - 6.80 (m, 2H), 6.67 - 6.54 (m, 4H), 6.48 (m, 1H), 6.28 (d, J=8.8 Hz, 2H), 5.07 (m, 1H), 4.16 (d, J=5.2 Hz, 1H), 3.82 (t, J=6.4 Hz, 2H), 3.41 (d, J=4.8 Hz, 5H), 3.35 - 3.29 (m, 2H), 2.99 - 2.83 (m, 3H), 2.62 - 2.56 (m, 1H), 2.48 (s, 3H), 2.36 - 2.28 (m, 2H), 2.10 - 1.98 (m, 2H), 1.72 - 1.61 (m, 3H), 1.54 - 1.44 (m, 2H), 1.43 - 1.35 (m, 2H). (DMSO-d6, 400 MHz) |
| --- | --- | --- | --- |
| 189 | (3S)-3-[5-[2-[[1-[2-[4-[[(1R,2S)-6-hydroxy-2-phenyl-tetralin-1-yl]phenoxy]ethyl]-3-piperidyl]oxy]ethyl]-1-oxo-isoindolin-2-yl]piperidine-2,6-dione | C | δ 11.00 (s, 1H), 9.14 (s, 1H), 7.63 (d, J=8.0 Hz, 1H), 7.47 (s, 1H), 7.38 (d, J=8.0 Hz, 1H), 7.19 - 7.08 (m, 3H), 6.83 (d, J=6.8 Hz, 2H), 6.67 - 6.59 (m, 2H), 6.53 (d, J=8.4 Hz, 2H), 6.49 (dd, J=2.4, 8.4 Hz, 1H), 6.26 (d, J=8.8 Hz, 2H), 5.11 (dd, J=5.2, 13.2 Hz, 1H), 4.45 - 4.37 (m, 1H), 4.31 - 4.24 (m, 1H), 4.18 (d, J=4.8 Hz, 1H), 3.90 (t, J=5.2 Hz, 2H), 3.67 (t, J=6.8 Hz, 2H), 3.33 - 3.15 (m, 3H), 3.03 - 2.85 (m, 6H), 2.64 - 2.56 (m, 3H), 2.43 - 2.36 (m, 1H), 2.15 - 2.05 (m, 1H), 2.03 - 1.92 (m, 2H), 1.90 - 1.81 (m, 2H), 1.75 - 1.66 (m, 1H), 1.64 - 1.55 (m, 1H), 1.44 - 1.30 (m, 1H), 1.11 - 0.97 (m, 1H). (DMSO-d6, 400 MHz) |
| 191 | (3S)-3-[5-[4-[2-[[4-[[(1R,2S)-6-hydroxy-2-phenyl-tetralin-1-yl]phenyl]methoxy]ethyl-methyl-amino]cyclohexyl]-1-oxo-isoindolin-2-yl]piperidine-2,6-dione | A | δ 10.98 (s, 1H), 9.15 (s, 1H), 7.64 (d, J=7.9 Hz, 1H), 7.44 (s, 1H), 7.36 (d, J=8.0 Hz, 1H), 7.18 - 7.05 (m, 3H), 6.94 (d, J=7.2 Hz, 2H), 6.82 (d, J=6.4 Hz, 2H), 6.67 - 6.59 (m, 2H), 6.49 (d, J=2.0 Hz, 1H), 6.37 (d, J=7.6 Hz, 2H), 5.16 - 5.04 (m, 1H), 4.54 - 4.12 (m, 6H), 3.65 - 3.42 (m, 2H), 3.07 - 2.79 (m, 4H), 2.60 (d, J=15.9 Hz, 4H), 2.46 - 2.35 (m, 2H), 2.29 - 2.18 (m, 1H), 2.17 - 2.08 (m, 1H), 2.03 - 1.96 (m, 1H), 1.87 (s, 4H), 1.76 - 1.66 (m, 1H), 1.51 (d, J= 9.0 Hz, 4H). (DMSO-d6, 400 MHz) |

| | | |
|---|---|---|
| 193 | 3-[5-[4-[5-[4-[(1R,2S)-6-hydroxy-2-phenyl-tetralin-1-yl]phenoxy]pentyl]-1,4-diazepan-1-yl]-1-oxo-isoindolin-2-yl]piperidine-2,6-dione | A | δ 10.94 (s, 1H), 8.28 (s, 1H), 7.46 (d, J=8.8 Hz, 1H), 7.14 (d, J=7.2 Hz, 3H), 6.92 - 6.75 (m, 4H), 6.68 - 6.57 (m, 2H), 6.55 - 6.41 (m, 3H), 6.25 (d, J=8.0 Hz, 2H), 5.02 (d, J=8.0 Hz, 1H), 4.33 - 4.23 (m, 1H), 4.21 - 4.13 (m, 2H), 3.77 (s, 2H), 3.40 - 3.36 (m, 4H), 3.05 - 2.82 (m, 4H), 2.70 (s, 2H), 2.60 (s, 2H), 2.44 - 2.27 (m, 4H), 2.07 (s, 1H), 1.94 (d, J=6.4 Hz, 1H), 1.85 (s, 2H), 1.70 (d, J=7.2 Hz, 1H), 1.61 (s, 2H), 1.41 (s, 2H), 1.31 (s, 2H). (DMSO-d6, 400 MHz) |
| 195 | 2-(2,6-dioxopiperidin-3-yl)-5-(4-(5-(4-((1R,2S)-6-hydroxy-2-phenyl-1,2,3,4-tetrahydronaphthalen-1-yl)phenoxy)pentyl)-1,4-diazepan-1-yl)isoindoline-1,3-dione | B | δ 11.10 - 11.05 (s, 1H), 8.34 (s, 2H), 7.61 (d, 1H), 7.18 - 7.08 (m, 4H), 7.04 - 6.98 (d, 1H), 6.82 (d, J=6.4 Hz, 2H), 6.66 - 6.59 (d, 2H), 6.53 - 6.45 (m, 3H), 6.25 (d, J=8.4 Hz, 2H), 5.11 - 5.00 (t, 1H), 4.17 (d, J=4.8 Hz, 1H), 3.77 (t, J=6.3 Hz, 2H), 3.68 - 3.56 (m, 6H), 3.36 - 3.25 (d, 1H), 3.05 - 2.81 (m, 3H), 2.71 (br s, 2H), 2.43 - 2.36 (t, 3H), 2.15 - 1.94 (m, 3H), 1.88 - 1.79 (d, 2H), 1.74 - 1.66 (m, 1H), 1.65 - 1.56 (m, 2H), 1.46 - 1.25 (m, 4H). (DMSO-d6, 400 MHz) |
| 197 | 3-[5-[4-[4-[(1R,2S)-6-hydroxy-2-phenyl-tetralin-1-yl]phenoxy]butyl]-1,4-diazepan-1-yl]-1-oxo-isoindolin-2-yl]piperidine-2,6-dione | C | δ 10.94 (s, 1H), 8.23 (s, 1H), 7.46 (d, J=8.8 Hz, 1H), 7.19 - 7.07 (m, 3H), 6.87 - 6.76 (m, 3H), 6.87 - 6.75 (m, 1H), 6.67 - 6.58 (m, 2H), 6.55 - 6.45 (m, 3H), 6.25 (d, J=8.8 Hz, 2H), 5.02 (dd, J=4.8, 13.2 Hz, 1H), 4.32 - 4.25 (m, 1H), 4.21 - 4.13 (m, 2H), 3.80 (t, J=6.0 Hz, 2H), 3.40 - 3.35 (m, 5H), 3.07 - 2.82 (m, 4H), 2.73 - 2.66 (m, 2H), 2.60 (s, 1H), 2.47 - 2.29 (m, 4H), 2.15 - 2.04 (m, 1H), 1.99 - 1.90 (m, 1H), 1.85 (s, 2H), 1.70 (d, J=6.8 Hz, 1H), 1.65 - 1.56 (m, 2H), 1.54 - 1.43 (m, 2H). (DMSO-d6, 400 MHz) |

FIG. 7 Continued

| | | | |
|---|---|---|---|
| 200 | 3-[5-[4-[2-[[(1S,2R)-2-[[4-[[(1R,2S)-6-hydroxy-2-phenyl-tetralin-1-yl]phenoxy]methyl]cyclopropyl]ethyl]piperazin-1-yl]-1-oxo-isoindolin-2-yl]piperidine-2,6-dione | A | δ 10.96 (s, 1H), 9.14 (s, 1H), 7.51 (d, J=8.4 Hz, 1H), 7.17 - 7.09 (m, 3H), 7.06 - 7.04 (m, 2H), 6.83 - 6.81 (m, 2H), 6.64 - 6.60 (m, 2H), 6.52 - 6.46 (m, 3H), 6.24 (d, J=8.6 Hz, 2H), 5.05 (dd, J=5.4, 12.8 Hz, 1H), 4.34 - 4.30 (m, 1H), 4.20 - 4.16 (m, 2H), 3.67 (d, J=7.2 Hz, 2H), 3.32 - 3.21 (m, 6H), 3.01 - 2.85 (m, 3H), 2.60 - 2.54 (m, 3H), 2.42 - 2.30 (m, 4H), 2.10 - 1.92 (m, 2H), 1.70 - 1.67 (m, 1H), 1.42 - 1.37 (m, 2H), 0.92 - 0.89 (m, 1H), 0.71 - 0.67 (m, 1H), 0.45 - 0.33 (m, 2H). (DMSO-d6, 400 MHz) |
| 201 | 2-(2,6-dioxo-3-piperidyl)-5-[4-[2-[[(1R,2S)- 2-[[4-[[(1R,2S)-6-hydroxy-2-phenyl-tetralin-1-yl]phenoxy]methyl]cyclopropyl]ethyl]piperazin-1-yl]isoindoline-1,3-dione | A | δ 11.09 (s, 1H), 9.13 (s, 1H), 7.67 (d, J=8.4 Hz, 1H), 7.33 (s, 1H), 7.28 - 7.22 (m, 1H), 7.19 - 7.04 (m, 3H), 6.82 (d, J=6.8 Hz, 2H), 6.67 - 6.58 (m, 2H), 6.55 - 6.43 (m, 3H), 6.24 (d, J=8.6 Hz, 2H), 5.07 (dd, J=5.4, 12.8 Hz, 1H), 4.16 (d, J=4.8 Hz, 1H), 3.67 (d, J=7.2 Hz, 2H), 3.41 (s, 4H), 3.28 (s, 2H), 3.07 - 2.81 (m, 3H), 2.65 - 2.53 (m, 2H), 2.47 - 2.28 (m, 5H), 2.15 - 1.92 (m, 2H), 1.69 (d, J=6.8 Hz, 1H), 1.49 - 1.32 (m, 2H), 0.91 (s, 1H), 0.69 (s, 1H), 0.50 - 0.31 (m, 2H). (DMSO-d6, 400 MHz) |
| 202 | 2-(2,6-dioxo-3-piperidyl)-5-[4-[2-[[(1S,2R)-2-[[4-[[(1R,2S)-6-hydroxy-2-phenyl-tetralin-1-yl]phenoxy]methyl]cyclopropyl]ethyl]piperazin-1-yl]isoindoline-1,3-dione | A | δ 11.09 (s, 1H), 9.13 (s, 1H), 7.67 (d, J=8.4 Hz, 1H), 7.33 (s, 1H), 7.28 - 7.22 (m, 1H), 7.16 - 7.09 (m, 3H), 6.82 (d, J=6.8 Hz, 2H), 6.64 - 6.60 (m, 2H), 6.52 - 6.46 (m, 3H), 6.24 (d, J=8.6 Hz, 2H), 5.07 (dd, J=5.4, 12.8 Hz, 1H), 4.16 (d, J=4.8 Hz, 1H), 3.67 (d, J=7.2 Hz, 2H), 3.45 - 3.38 (m, 5H), 3.32 - 3.27 (s, 1H), 2.97 - 2.88 (m, 4H), 2.63 - 2.56 (m, 4H), 2.40 - 2.32 (m, 2H), 2.10 - 1.98 (m, 2H), 1.74 - 1.67 (m, 1H), 1.40 - 1.37 (m, 2H), 0.94 - 0.90 (m, 1H), 0.72 - 0.68 (m, 1H), 0.45 - 0.34 (m, 2H). (DMSO-d6, 400 MHz) |

| | | | |
|---|---|---|---|
| 204 | 3-[5-[4-[[4-[[(1R,2S)-6-hydroxy-2-phenyl-tetralin-1-yl]phenoxy]-1-piperidyl]methyl]-1-piperidyl]-1-oxo-isoindolin-2-yl]piperidine-2,6-dione | C | δ 11.08 (s, 1H), 9.14 (s, 1H), 7.63 (d, J=8.4 Hz, 1H), 7.18 - 7.07 (m, 3H), 6.91 - 6.76 (m, 4H), 6.67 - 6.46 (m, 5H), 6.25 (d, J=8.8 Hz, 2H), 5.05 (dd, J=5.4, 12.9 Hz, 1H), 4.16 (d, J=4.9 Hz, 2H), 3.62 - 3.56 (m, 1H), 3.52 - 3.45 (m, 1H), 3.28 (d, J=3.0 Hz, 1H), 3.04 - 2.81 (m, 4H), 2.67 (dd, J=1.8, 3.6 Hz, 2H), 2.57 - 2.51 (m, 4H), 2.40 - 2.26 (m, 3H), 2.20 - 1.96 (m, 5H), 1.85 (d, J=1.3 Hz, 2H), 1.74 - 1.43 (m, 6H). (DMSO-d6, 400 MHz) |
| 206 | 2-(2,6-dioxo-3-piperidyl)-5-[4-[1-[2-[4-[(1R,2S)-6-hydroxy-2-phenyl-tetralin-1-yl]phenoxy]ethyl]-4-piperidyl]piperazin-1-yl]isoindoline-1,3-dione | A | δ 11.68 (s, 1H), 11.10 (s, 1H), 10.70 (s, 1H), 9.18 (s, 1H), 7.76 (d, J=8.4 Hz, 1H), 7.49 (s, 1H), 7.35 (d, J=8.8 Hz, 1H), 7.20 - 7.10 (m, 3H), 6.85 (d, J=6.8 Hz, 2H), 6.67 - 6.58 (m, 4H), 6.50 (dd, J=2.2, 8.4 Hz, 1H), 6.32 (d, J=8.8 Hz, 2H), 5.10 (dd, J=5.3, 12.8 Hz, 1H), 4.36 - 4.13 (m, 5H), 3.68 (d, J=9.2 Hz, 2H), 3.56 (s, 2H), 3.45 (d, J=12.4 Hz, 5H), 3.32 (s, 1H), 3.25 - 3.01 (m, 4H), 3.00 - 2.83 (m, 3H), 2.64 - 2.53 (m, 2H), 2.43 - 2.33 (m, 2H), 2.21 - 1.96 (m, 4H), 1.73 (d, J=6.4 Hz, 1H). (DMSO-d6, 400 MHz) |
| | | B | |
| 208 | 2-(2,6-dioxo-3-piperidyl)-5-[4-[[1-[2-[4-[(1R,2S)-6-hydroxy-2-phenyl-tetralin-1-yl]phenoxy]ethyl]-4-piperidyl]methyl]piperazin-1-yl]isoindoline-1,3-dione | B | δ 11.10 (s, 1H), 10.95 (s, 1H), 10.48 s, 1H), 9.18 (s, 1H), 7.76 (d, J=8.4 Hz, 1H), 7.49 (s, 1H), 7.35 (d, J=8.8 Hz, 1H), 7.19 - 7.08 (m, 3H), 6.85 (d, J=6.8 Hz, 2H), 6.67 - 6.57 (m, 4H), 6.49 (dd, J=2.4, 8.0 Hz, 1H), 6.31 (d, J=8.4 Hz, 2H), 5.09 (dd, J=5.2, 12.8 Hz, 1H), 4.32 - 4.11 (m, 5H), 3.66 - 3.43 (m, 8H), 3.26 - 3.22 (m, 1H), 3.20 - 2.83 (m, 9H), 2.63 - 2.52 (m, 2H), 2.18 - 1.91 (m, 5H), 1.85 - 1.49 (m, 3H). (DMSO-d6, 400 MHz) |

FIG. 7 Continued

| | | | |
|---|---|---|---|
| 210 | 2-(2,6-dioxo-3-piperidyl)-5-[4-[[1-[2-[4-[(1R,2S)-6-hydroxy-2-phenyl-tetralin-1-yl]phenoxy]ethyl]azetidin-3-yl]methyl]piperazin-1-yl]isoindoline-1,3-dione | A | δ 11.08 (s, 1H), 8.23 (s, 2H), 7.67 (d, J=8.4 Hz, 1H), 7.32 (s, 1H), 7.28 - 7.20 (m, 1H), 7.19 - 7.06 (m, 3H), 6.82 (d, J=6.8 Hz, 2H), 6.67 - 6.57 (m, 2H), 6.54 - 6.45 (m, 3H), 6.26 (d, J=8.8 Hz, 2H), 5.07 (dd, J=5.2, 12.8 Hz, 1H), 4.17 (d, J=5.2 Hz, 1H), 3.75 (d, J=5.6 Hz, 2H), 3.42 -3.37 (m, 7H), 3.30 (d, J=12.0 Hz, 2H), 3.03 - 2.79 (m, 6H), 2.71 - 2.63 (m, 2H), 2.58 - 2.52 (m, 1H), 2.46 - 2.38 (m, 5H), 2.13 - 1.94 (m, 2H), 1.75 - 1.65 (m, 1H). (DMSO-d6, 400 MHz) |
| | | B | |
| 211 | 3-[5-[4-[2-[(1S,2S)-2-[[4-[(1R,2S)-2-(4-fluorophenyl)-6-hydroxy-tetralin-1-yl]phenoxy]methyl]cyclopropyl]ethyl]piperazin-1-yl]-1-oxo-isoindolin-2-yl]piperidine-2,6-dione | A | δ 10.95 (s, 1H), 9.14 (s, 1H), 8.20 (s, 1H), 7.51 (J=8.8 Hz, 1H), 7.05 - 7.01 (m, 2H), 6.99 - 6.93 (m, 2H), 6.87 - 6.81 (m, 2H), 6.66 - 6.55 (m, 4H), 6.47 (d, J=8.0 Hz, 1H), 6.27 (d, J=8.5 Hz, 2H), 5.04 (dd, J=4.8, 13.2 Hz, 1H), 4.35 - 4.28 (m, 1H), 4.23 - 4.13 (m, 2H), 4.01 - 3.92 (m, 1H), 3.75 - 3.65 (m, 2H), 3.24 (s, 3H), 3.02 - 2.82 (m, 5H), 2.59 (s, 4H), 2.40 (t, J=7.2 Hz, 3H), 2.09 - 1.91 (m, 2H), 1.67 (s, 1H), 1.49 (s, 2H), 1.18 (s, 1H), 0.89 (d, J=8.4 Hz, 1H), 0.74 - 0.67 (m, 1H), 0.09 (d, J=4.4 Hz, 1H). (DMSO-d6, 400 MHz) |
| | | B | |
| 212 | 3-[5-[4-[2-[(1R,2R)-2-[[4-[(1R,2S)-6- benzyloxy-2-(4-fluorophenyl)tetralin-1-yl]phenoxy]methyl]cyclopropyl]ethyl]piperazin-1-yl]-1-oxo-isoindolin-2-yl]piperidine-2,6-dione | A | δ 10.95 (s, 1H), 9.14 (s, 1H), 8.21 (s, 1H), 7.51 (d, J=8.8 Hz, 1H), 7.06 - 7.01 (m, 2H), 7.00 - 6.94 (m, 2H), 6.87 - 6.81 (m, 2H), 6.67 - 6.54 (m, 4H), 6.47 (d, J=8.4 Hz, 1H), 6.27 (d, J=8.4 Hz, 2H), 5.04 (dd, J=5.2, 13.2 Hz, 1H), 4.35 - 4.29 (m, 1H), 4.22 - 4.13 (m, 2H), 3.98 (dd, J=6.0, 10.4 Hz, 1H), 3.74 - 3.66 (m, 1H), 3.24 (s, 3H), 3.01 - 2.81 (m, 4H), 2.60 (s, 2H), 2.46 - 2.34 (m, 7H), 2.10 - 1.91 (m, 2H), 1.68 (s, 1H), 1.55 - 1.41 (m, 2H), 1.16 (s, 1H), 0.89 (d, J=6.0 Hz, 1H), 0.75 - 0.65 (m, 1H), 0.09 (d, J=4.8 Hz, 1H). (DMSO-d6, 400 MHz) |

FIG. 7 Continued

| | | | |
|---|---|---|---|
| 214 | 3-[5-[4-[4,4-difluoro-5-[4-[(1R,2S)-6-hydroxy-2-phenyl-tetralin-1-yl]phenoxy]pentyl]piperazin-1-yl]-1-oxo-isoindolin-2-yl]piperidine-2,6-dione | A | δ 10.97 (s, 1H), 10.89 - 10.50 (m, 1H), 9.39 - 8.98 (m, 1H), 7.59 (d, J=8.4 Hz, 1H), 7.29 - 7.03 (m, 5H), 6.84 (d, J=6.8 Hz, 2H), 6.72 - 6.57 (m, 4H), 6.49 (dd, J=2.4, 8.4 Hz, 1H), 6.30 (d, J=8.8 Hz, 2H), 5.06 (dd, J=5.2, 13.2 Hz, 1H), 4.41 - 4.30 (m, 1H), 4.28 - 4.12 (m, 4H), 3.99 (d, J=12.0 Hz, 2H), 3.58 (d, J=12.0 Hz, 1H), 3.54 - 3.52 (m, 1H), 3.35 - 3.29 (m, 1H), 3.29 - 3.07 (m, 6H), 3.04 - 2.84 (m, 3H), 2.59 (d, J=16.8 Hz, 1H), 2.44 - 2.35 (m, 1H), 2.18 - 1.87 (m, 6H), 1.72 (d, J=8.0 Hz, 1H). (DMSO-d6, 400 MHz) |
| 215 | 3-[5-[4-[2-[[(1R,2S)-6-hydroxy- 2-[[4-[(1R,2S)-6-hydroxy-2-phenyl-tetralin-1-yl]phenoxy]methyl]cyclopropyl]ethyl]piperazin-1-yl]-1-oxo- isoindolin-2-yl]piperidine-2,6-dione | A | δ 10.94 (s, 1H), 9.12 (s, 1H), 7.51 (d, J=9.0 Hz, 1H), 7.22 - 7.00 (m, 5H), 6.82 (d, J=6.7 Hz, 2H), 6.68 - 6.57 (m, 2H), 6.55 - 6.44 (m, 3H), 6.24 (d, J=8.7 Hz, 2H), 5.04 (dd, J=5.0, 13.4 Hz, 1H), 4.37 - 4.26 (m, 1H), 4.24 - 4.12 (m, 2H), 3.67 (d, J=6.7 Hz, 2H), 3.26 (s, 7H), 3.05 - 2.83 (m, 3H), 2.58 (d, J=19.8 Hz, 2H), 2.37 (d, J=7.4 Hz, 4H), 2.14 - 1.89 (m, 2H), 1.71 (s, 1H), 1.40 (d, J=7.0 Hz, 2H), 0.91 (s, 1H), 0.69 (s, 1H), 0.47 - 0.28 (m, 2H). (DMSO-d6, 400 MHz) |
| 218 | 2-(2, 6-dioxo-3-piperidyl)-5-[4-[5-[4-[(1R, 2S) – 2 - (4 - fluorophenyl) 6 hydroxyl tetralin 1 yl] phenoxy] - 1, 2, 3, 3a, 4, 5, 6, 6a – octahydropentale 2- yl] piperazin-1-yl]isoindoline-1, 3-dione | A | δ 11.09 (s, 2H), 9.14 (s, 1H), 7.76 (d, J=8.4 Hz, 1H), 7.48 (s, 1H), 7.35 ( d, J=8.6 Hz, 1H), 7.02 - 6.93 (m, 2H), 6.88 - 6.80 (m, 2H), 6.68 - 6.59 (m, 2H), 6.55 (d, J=8.7 Hz, 2H), 6.49 (dd, J=2.4, 8.3 Hz, 1H), 6.27 (d, J=8.6 Hz, 2H), 5.09 (dd, J=5.3, 12.9 Hz, 1H), 4.81 (s, 1H), 4.27 - 4.11 (m, 3H), 3.61 - 3.42 (m, 3H), 3.13 (d, J=11.5 Hz, 2H), 3.09 - 2.71 (m, 4H), 2.67 (d, J=1.8 Hz, 1H), 2.53 (d, J=6.8 Hz, 5H), 2.35 - 2.27 (m, 2H), 2.09 - 1.96 (m, 2H), 1.91 - 1.73 (m, 4H), 1.83 - 1.77 (m, 3H). (DMSO-d6, 400 MHz) |

FIG. 7 Continued

| | | | | |
|---|---|---|---|---|
| 228 | 2-(2,6-dioxo-3-piperidyl)-5-[4-[[(3S)-1-[2-[4-[(1R,2S)-2-(4-fluorophenyl)-6-hydroxy-tetralin-1-yl]phenoxy]ethyl]pyrrolidin-3-yl]methyl]piperazin-1-yl]isoindoline-1,3-dione | | C | δ 11.09 (br s, 1H), 8.24 (br s, 1H), 7.67 (br d, J = 8.5 Hz, 1H), 7.32 (br s, 1H), 7.24 (br d, J = 7.3 Hz, 1H), 6.96 (br d, J = 8.9 Hz, 2H), 6.84 (br s, 2H), 6.65 - 6.54 (m, 4H), 6.48 (br d, J = 5.9 Hz, 1H), 6.27 (br d, J = 8.3 Hz, 2H), 5.12 - 5.00 (m, 1H), 4.15 (br s, 1H), 3.90 (br s, 2H), 3.35 - 3.29 (m, 6H), 2.99 - 2.81 (m, 3H), 2.71 (br s, 5H), 2.37 - 2.32 (m, 1H), 2.35 - 2.24 (m, 2H), 2.02 (br s, 5H), 1.84 (br s, 2H), 1.67 (br s, 2H), 1.39 (br s, 5H). (DMSO-d6, 400 MHz) |
| 242 | 3-[5-[6-[[(3S)-1-[2-[4-[(1R,2S)-6-hydroxy-2-phenyl-tetralin-1-yl]phenoxy]ethyl]pyrrolidin-3-yl]oxy-3-pyridyl]-1-oxo-isoindolin-2-yl]piperidine-2,6-dione | A | B | δ 11.02 (s, 1H), 10.61 - 10.40 (m, 1H), 9.29 - 9.06 (m, 1H), 8.66 - 8.53 (m, 1H), 8.21 - 8.12 (m, 1H), 8.00 - 7.89 (m, 1H), 7.87 - 7.77 (m, 2H), 7.20 - 7.09 (m, 3H), 7.04 - 6.95 (m, 1H), 6.89 - 6.79 (m, 2H), 6.69 - 6.56 (m, 4H), 6.52 - 6.45 (m, 1H), 6.36 - 6.28 (m, 2H), 5.70 - 5.54 (m, 1H), 5.22 - 5.10 (m, 1H), 4.59 - 4.34 (m, 2H), 4.20 (s, 3H), 4.14 - 3.75 (m, 2H), 3.74 - 3.59 (m, 3H), 3.35 - 3.23 (m, 1H), 3.05 - 2.86 (m, 3H), 2.70 - 2.65 (m, 2H), 2.44 (s, 2H), 2.21 - 1.98 (m, 3H), 1.72 (d, J=12.3 Hz, 1H). (DMSO-d6, 400 MHz) |
| 243 | 2-(2,6-dioxo-3-pipetroleumetherridyl)-5-[7-[4-[4-[(1R,2S)-2-(4-fluorophenyl)-6-hydroxy-tetralin-1-yl]phenoxy]butyl]-2,7-diazaspiro[3.5]nonan-2-yl]isoindoline-1,3-dione | A | A | δ 11.09 (s, 1H), 9.12 (s, 1H), 8.25 (s, 1H), 7.65 (s, 1H), 7.05-6.94 (m, 2H), 6.90-6.82 (m, 2H), 6.79 (s, 1H), 6.72-6.69 (m, 3H), 6.65-6.61 (m, 2H), 6.48-6.46 (m, 1H), 6.30-6.25 (m, 2H), 5.08-5.02 (m, 1H), 4.15-4.13 (m, 1H), 3.86-3.80 (m, 2H), 2.94-2.82 (m, 6H), 2.36-2.32 (m, 2H), 2.08-1.94 (m, 3H), 1.78-1.57 (m, 11H). (DMSO-d6, 400 MHz) |

FIG. 7 Continued

| | | | |
|---|---|---|---|
| 245 | 2-(2,6-dioxo-3-piperidyl)-5-[4-[[(3R)-1-[2-[4-[(1R,2S)-2-(4-fluorophenyl)-6-hydroxy-tetralin-1-yl]phenoxy]ethyl]pyrrolidin-3-yl]methyl]piperazin-1-yl]isoindoline-1,3-dione | A | δ 11.18 - 10.65 (m, 3H), 9.19 (s, 1H), 7.78 (d, J = 8.7 Hz, 1H), 7.50 (s, 1H), 7.39 - 7.28 (m, 1H), 7.09 - 6.96 (m, 2H), 6.91 - 6.83 (m, 2H), 6.70 - 6.60 (m, 4H), 6.51-6.48 (m, 1H), 6.34 (d, J = 8.5 Hz, 2H), 5.13-5.08 (m, 1H), 4.30 - 4.12 (m, 5H), 3.62 - 3.43 (m, 9H), 3.31 - 3.07 (m, 5H), 3.01 - 2.84 (m, 4H), 2.65 - 2.56 (m, 5H), 2.13 - 2.01 (m, 2H), 1.71 (d, J = 6.1 Hz, 1H). (DMSO-d6, 400 MHz) |
| 246 | 2-(2,6-dioxo-3-piperidyl)-5-[[(1R,4R)-5-[[1-[2-[4-[(1R,2S)-6-hydroxy-2-phenyl-tetralin-1-yl]phenoxy]ethyl]-4-piperidyl]methyl]-2,5-diazabicyclo[2.2.1]heptan-2-yl]isoindoline-1,3-dione | B | δ 11.13 - 11.01 (m, 1H), 8.22 (s, 2H), 7.61 (d, J=8.4 Hz, 1H), 7.18 - 6.92 (m, 4H), 6.89 - 6.79 (m, 3H), 6.65 - 6.58 (m, 2H), 6.54 - 6.45 (m, 3H), 6.24 (d, J=8.8 Hz, 2H), 5.05 (dd, J=5.2, 12.8 Hz, 1H), 4.66 - 4.56 (m, 1H), 4.16 (d, J=5.2 Hz, 1H), 3.87 (t, J=5.6 Hz, 2H), 3.55 (s, 1H), 3.42 - 3.26 (m, 4H), 2.99 - 2.81 (m, 6H), 2.61 - 2.55 (m, 3H), 2.40 - 2.27 (m, 3H), 2.14 - 1.82 (m, 6H), 1.72 - 1.55 (m, 3H), 1.30 - 1.18 (m, 1H), 1.11 - 0.97 (m, 2H). (DMSO-d6, 400 MHz) |
| 249 | 2-(2,6-dioxo-3-piperidyl)-6-[4-[5-[4-[(1R,2S)-2-(4-fluorophenyl)-6-hydroxy-tetralin-1-yl]phenoxy]pentyl]piperazin-1-yl]pyrrolo[3,4-c]pyridine-1,3-dione | A | δ 11.08 (s, 1H), 8.13 (s, 0.28H), 7.70 (d, J=8.4 Hz, 1H), 7.68 (s, 1H), 7.35 (s, 2H), 7.25 (d, J=7.2 Hz, 1H), 7.23 (s, 1H), 6.98 (d, J=8.8 Hz, 2H), 6.88 (m, 3H), 6.58 (d, J=8.4 Hz, 2H), 6.30 (d, J=8.8 Hz,2H), 5.09 (m, 1H), 4.28 (s, 1H), 3.84 (d, J=6.4 Hz,2H), 3.44 (m, 5H), 2.67 (m, 3H), 2.60 (m, 6H), 2.42 (m, 2H), 1.68 (m, 8H). (DMSO-d6, 400 MHz) |

FIG. 7 Continued

| | | | |
|---|---|---|---|
| 258 | 1,2-cis-2-(2,6-dioxo-3-piperidyl)-5-[2-[4-[6-[4-(6-hydroxy-2-phenyl-tetralin-1-yl)phenoxy]-3-pyridyl]piperazin-1-yl]ethoxy]isoindoline-1,3-dione | C | δ 11.13 (s, 1H), 10.64 (s, 1H), 7.94 - 7.82 (m, 2H), 7.61 - 7.51 (m, 2H), 7.44 (dd, J=2.0, 8.4 Hz, 1H), 7.22 - 7.06 (m, 3H), 6.89 - 6.78 (m, 3H), 6.74 - 6.59 (m, 4H), 6.51 (dd, J=2.4, 8.4Hz, 1H), 6.37 (d, J=8.4 Hz, 2H), 5.14 (dd, J=5.2, 12.8 Hz, 1H), 4.73 - 4.56 (m, 2H), 4.25 (d, J=4.8 Hz, 1H), 3.81 - 3.60 (m, 6H), 3.38 - 3.23 (m, 4H), 3.18 - 3.07 (m, 2H), 3.01 - 2.82 (m, 3H), 2.63 - 2.57 (m, 2H), 2.18 - 1.99 (m, 2H), 1.79 - 1.67 (m, 1H). (DMSO-d6, 400 MHz) |
| 263 | 2-(2,6-dioxo-3-piperidyl)-5-[4-[2-[4-[4-[2-(4-fluoro phenyl)-6-hydroxy-tetralin-1-yl]phenoxy]cyclohexoxy]ethyl]piperazin-1-yl]isoindoline-1,3-dione | B | δ 11.08 (s, 1H), 9.12 (s, 1H), 7.66 (d, J=8.4 Hz, 1H), 7.33 (s, 1H), 7.25 (d, J=8.4 Hz, 1H), 6.99 - 6.91 (m, 2H), 6.85 - 6.78 (m, 2H), 6.65 (d, J=8.4 Hz, 1H), 6.62 - 6.53 (m, 3H), 6.48 (d, J=8.4 Hz, 1H), 6.26 (d, J=8.0 Hz, 2H), 5.07 (dd, J=5.2, 13.2 Hz, 1H), 4.28 - 4.11 (m, 2H), 3.64 - 3.49 (m, 3H), 3.42 (s, 5H), 3.48 - 3.35 (m, 1H), 3.03 - 2.82 (m, 3H), 2.58 - 2.54 (m, 4H), 2.12 - 1.96 (m, 2H), 1.94 - 1.83 (m, 2H), 1.79 - 1.51 (m, 6H), 1.37 - 1.25 (m, 2H). (DMSO-d6, 400 MHz) |
| 270 | 2-(2,6-dioxo-3-piperidyl)-5-[5-[(3R)-1-[2-[4-[(1R,2S)-2-(4-fluorophenyl)-6-hydroxy-tetralin-1-yl]phenoxy]ethyl]pyrrolidin-3-yl]oxypyrazin-2-yl]isoindoline-1,3-dione | C | δ 11.16 (s, 1 H) 10.55 (s, 1 H) 9.03 - 9.26 (m, 2 H) 8.37 - 8.74 (m, 3 H) 8.06 (d, J=8.28 Hz, 1 H) 6.91 - 7.05 (m, 2 H) 6.85 (br s, 2 H) 6.57 - 6.68 (m, 1 H) 6.57 - 6.68 (m, 3 H) 6.48 (br d, J=8.4 Hz, 1 H) 6.32 (br d, J=8.4 Hz, 2 H) 5.42 - 5.82 (m, 1 H) 5.08 - 5.31 (m, 1 H) 4.14 - 4.31 (m, 1 H) 4.14 - 4.26 (m, 1 H) 4.19 (br s, 1 H) 4.08 (s, 1 H) 3.70 - 3.96 (m, 1 H) 3.50 - 3.71 (m, 1 H) 3.42 - 3.95 (m, 1 H) 2.90 - 2.98 (m, 1 H) 2.65 (br s, 1 H) 2.59 (br d, J=7.6 Hz, 2 H) 2.36 - 2.44 (m, 1 H) 2.34 (br s, 2 H) 1.96 - 2.22 (m, 3 H) 1.70 (br s, 1 H). (DMSO-d6, 400 MHz) |

FIG. 7 Continued

| | | | |
|---|---|---|---|
| 272 | 2-(2, 6-dioxo-3-piperidyl)-5-[5-[4-[2-[4-[(1R, 2S)-2-(4-fluorophenyl)-6-hydroxy-tetralin-1-yl]phenoxy] ethyl] piperazin-1-yl] pyrazin-2-yl] isoindoline-1, 3-dione | C | δ 11.14 (s, 1H), 9.13 (s, 1H), 8.93 (s, 1H), 8.48 (m, 3H), 7.98 (d, d = 8.4 Hz, 1H), 6.98 (t, J = 8.8 Hz, 2H), 6.86 (t, J = 5.6 Hz, 2H), 6.65 (m, 4H), 6.45 (m, 1H), 6.30 (d, J = 8.8 Hz, 2H), 5.20 (m, 1H), 4.15 (d, J = 4.8 Hz, 1H), 4.00 (t, J = 5.6 Hz, 1H), 3.68 (t, J = 4.4 Hz, 1H), 2.71 (m, 3H), 2.71 (m, 2H), 2.58 (m, 7H), 2.09 (m, 2H), 1.70 (m, 1H). (DMSO-d6, 400 MHz) |
| 275 | 1,2-cis-2-(2,6-dioxo-3-piperidyl)-5-[2-[4-[2-[4-(6-hydroxy-2-phenyl-tetralin-1-yl)phenoxy]ethyl]piperazin-1-yl]pyrimidin-5-yl]oxy-isoindoline -1,3-dione | C | δ 11.14 (s, 1H), 8.41 (s, 2H), 8.25 (s, 1H), 7.89 (d, J = 7.8 Hz, 1H), 7.49 - 7.34 (m, 2H), 7.26 - 7.05 (m, 3H), 6.83 (d, J = 6.8 Hz, 2H), 6.71 - 6.41 (m, 5H), 6.27 (d, J = 8.6 Hz, 2H), 5.14 (dd, J = 5.2, 13.2 Hz, 1H), 4.18 (d, J = 5.2 Hz, 1H), 3.96 (s, 2H), 3.72 (s, 5H), 3.31 (d, J = 11.8 Hz, 4H), 3.05 - 2.61 (m, 8H), 2.18 - 1.96 (m, 2H), 1.72 (s, 1H). (DMSO-d6, 400 MHz) |
| 289 | 2-(2,6-dioxo-3-piperidyl)-5-[4-[4-(6-hydroxy-2-phenyl-tetralin-1-yl)phenoxy]-1-piperidyl]ethyl]piperazin-1-yl]isoindoline-1,3-dione | A | δ 11.11 (s, 1H), 10.99 (s, 1H), 10.64 - 10.42 (m, 1H), 9.17 (s, 1H), 7.77 (d, J = 8.4 Hz, 1H), 7.56 - 7.49 (m, 1H), 7.37 (d, J = 8.8 Hz, 1H), 7.19 - 7.08 (m, 3H), 6.83 (d, J = 6.8 Hz, 2H), 6.71 - 6.58 (m, 4H), 6.53 - 6.46 (m, 1H), 6.30 (d, J = 8.0 Hz, 2H), 5.10 (dd, J = 5.2, 13.2 Hz, 1H), 4.53 - 4.26 (m, 2H), 4.20 (d, J = 4.8 Hz, 1H), 4.23 - 4.15 (m, 1H), 3.94 - 3.49 (m, 10H), 3.87 - 3.47 (m, 1H), 3.24 - 3.06 (m, 4H), 3.04 - 2.78 (m, 4H), 2.64 - 2.55 (m, 2H), 2.24 - 1.81 (m, 7H), 1.75 - 1.64 (m, 1H). (DMSO-d6, 400 MHz) |

FIG. 7 Continued

| | | | |
|---|---|---|---|
| 296 | 3-[5-[4-[2-[4-[4-[(1R, 2S)-6-hydroxyl-2-phenyl-tetralin-1-yl]phenyl]piperazin-1-yl]ethyl]piperazin-1-yl]-1-oxo-isoindolin-2-yl]piperidine-2,6-dione | A | δ 10.96 (s, 3H), 7.59 (d, J=8.4 Hz, 1H), 7.26 - 7.06 (m, 5H), 6.84 (d, J=7.0 Hz, 2H), 6.68 - 6.59 (m, 4H), 6.49 (dd, J=2.1, 8.3 Hz, 1H), 6.26 (d, J=8.6 Hz, 2H), 5.06 (dd, J=5.0, 13.2 Hz, 1H), 4.41 - 4.30 (m, 1H), 4.27 - 4.03 (m, 4H), 3.70 (s, 8H), 3.43 - 3.08 (m, 8H), 3.08 - 2.81 (m, 5H), 2.58 (d, J=17.7 Hz, 2H), 2.44 - 2.35 (m, 1H), 2.16 - 1.91 (m, 2H), 1.71 (d, J=6.0 Hz, 1H). (DMSO-d6, 400 MHz) |
| 300 | 2-(2,6-dioxopiperidin-3-yl)-5-(4-(2-(4-(4-((1R,2S)-6-hydroxy-2-phenyl-1,2,3,4-tetrahydronaphthalen-1-yl)phenyl)piperazin-1-yl)ethyl)piperazin-1-yl)isoindoline-1,3-dione | A | δ 11.07 (s, 1H), 8.20 (s, 1H), 7.69 - 7.62 (m, 1H), 7.34 - 7.30 (m, 1H), 7.26 - 7.20 (m, 1H), 7.09 (d, J=1.6 Hz, 3H), 6.84 - 6.76 (m, 4H), 6.66 - 6.56 (m, 2H), 6.49 - 6.43 (m, 1H), 6.30 - 6.23 (m, 2H), 5.05 (dd, J=5.2, 15.2 Hz, 1H), 4.21 - 4.15 (d, J=2 Hz 1H), 3.50 - 3.44 (m, 8H), 2.95 (s, 4H), 2.45 (s, 5H), 2.31 (s, 2H), 2.11 - 2.04 (m, 1H), 2.03 - 1.92 (m, 4H), 1.72 - 1.65 (m, 1H), 1.64 - 1.57 (m, 2H), 1.53 - 1.44 (m, 2H). (DMSO-d6, 400 MHz) |
| 302 | 2-(2,6-dioxo-3- piperidyl)-5-[4-[5-[4-[2-[2-fluoro-4-(trifluoromethyl)phenyl]-6-hydroxy-3,4-dihydro-1H-isoquinolin-1-yl]phenoxy]pentyl]piperazin-1-yl]isoindoline-1,3-dione | B | δ 11.09 (s, 1H), 8.19 (s, 1H), 7.67 (d, J = 8.4 Hz, 1H), 7.54 (d, J = 12.4 Hz, 1H), 7.37 - 7.30 (m, 2H), 7.24 (d, J = 8.8 Hz, 1H), 7.08 - 7.00 (m, 1H), 6.92 (d, J = 8.8 Hz, 2H), 6.84 - 6.73 (m, 3H), 6.62 - 6.52 (m, 2H), 5.76 (s, 1H), 5.07 (dd, J = 5.6, 13.2 Hz, 1H), 3.88 (t, J = 6.4 Hz, 2H), 3.17 (br s, 6H), 2.95 - 2.80 (m, 3H), 2.64 - 2.54 (m, 2H), 2.52 (d, J = 2.0 Hz, 2H), 2.46 - 2.42 (m, 2H), 2.32 (d, J = 7.2 Hz, 2H), 2.06 - 1.96 (m, 1H), 1.74 - 1.62 (m, 2H), 1.56 - 1.33 (m, 4H). (DMSO-d6, 400 MHz) |

FIG. 7 Continued

| # | Name | | NMR |
|---|---|---|---|
| 311 | 3-[5-[4-[[1-[3-[4-[[(1R,2S)-6-hydroxy-2-phenyl-tetralin-1-yl]phenyl]propyl]-4-piperidyl]methyl]piperazin-1-yl]-1-oxo-isoindolin-2-yl]piperidine-2,6-dione | A | δ 10.97 (s, 1H), 10.91 (br s, 1H), 10.45 (br s, 1H), 7.59 (d, J = 8.5 Hz, 1H), 7.25 - 7.03 (m, 5H), 6.91 - 6.78 (m, 4H), 6.73 - 6.58 (m, 2H), 6.50 (dd, J = 2.5, 8.3 Hz, 1H), 6.31 (d, J = 8.2 Hz, 2H), 5.07 (dd, J = 5.1, 13.2 Hz, 1H), 4.41 - 4.31 (m, 2H), 4.29 - 4.20 (m, 3H), 3.98 (br d, J = 13.2 Hz, 2H), 3.60 (br d, J = 11.9 Hz, 2H), 3.51 - 3.30 (m, 5H), 3.18 - 3.02 (m, 5H), 3.01 - 2.82 (m, 6H), 2.59 (br d, J = 16.4 Hz, 1H), 2.39 (br dd, J = 4.3, 13.3 Hz, 2H), 2.17 - 2.01 (m, 4H), 1.98 - 1.88 (m, 3H), 1.80 - 1.67 (m, 1H), 1.66 - 1.53 (m, 2H). (DMSO-d6, 400 MHz) |
| 315 | 3-[5-[4-[1-[3-[4-[[(1R,2S)-6-hydroxy-2-phenyl-tetralin-1-yl]phenyl]propyl]-4-piperidyl]piperazin-1-yl]-1-oxo-isoindolin-2-yl]piperidine-2,6-dione | A | δ 11.49 (br s, 1H), 10.97 (s, 1H), 10.57 (br s, 1H), 7.59 (d, J = 8.4 Hz, 1H), 7.21 - 7.08 (m, 5H), 6.90 - 6.78 (m, 4H), 6.68 - 6.59 (m, 2H), 6.49 (dd, J = 2.5, 8.3 Hz, 1H), 6.31 (d, J = 8.2 Hz, 2H), 5.06 (dd, J = 5.1, 13.2 Hz, 1H), 4.36 (br d, J = 17.1 Hz, 1H), 4.28 - 4.21 (m, 3H), 4.02 (br d, J = 13.2 Hz, 2H), 3.66 - 3.54 (m, 4H), 3.46 (br s, 2H), 3.37 - 3.27 (m, 3H), 3.18 (br d, J = 9.2 Hz, 2H), 2.98 - 2.83 (m, 6H), 2.59 (br d, J = 17.2 Hz, 1H), 2.47 - 2.31 (m, 5H), 2.24 - 2.02 (m, 3H), 2.01 - 1.84 (m, 3H), 1.78 - 1.66 (m, 1H). (DMSO-d6, 400 MHz) B |
| 319 | 3-[5-[4-[3-[4-[[(1R,2S)-6-hydroxy-2-phenyl-tetralin-1-yl]phenyl]-1-piperidyl]propyl]piperazin-1-yl]-1-oxo-isoindolin-2-yl]piperidine-2,6-dione | A | δ 10.96 (s, 1H), 9.17 (s, 1H), 7.61 - 7.45 (m, 1H), 7.20 - 7.00 (m, 5H), 6.91 - 6.76 (m, 4H), 6.69 - 6.59 (m, 2H), 6.49 (m, 1H), 6.35 (d, J=8.0 Hz, 2H), 5.06 (m, 1H), 4.39 - 4.15 (m, 3H), 3.57 - 3.42 (m, 6H), 3.24 - 3.00 (m, 7H), 2.61 (s, 6H), 2.18 - 1.69 (m, 10H), 1.26 (d, J=7.2 Hz, 2H). (DMSO-d6, 400 MHz) |

FIG. 7 Continued

| | | | |
|---|---|---|---|
| 321 | 2-(2,6-dioxo-3-piperidyl)-5-[4-[3-[4-[(1R,2S)-6-hydroxy-2-phenyl-tetralin-1-yl]phenyl]-1-piperidyl]propyl]piperazin-1-yl]isoindoline-1,3-dione | A | δ 11.09 (s, 1H), 8.20 (s, 1H), 7.67 (d, J=8.4 Hz, 1H), 7.33 (d, J=2.0 Hz, 1H), 7.25 (m, 1H), 7.17 - 7.08 (m, 3H), 6.86 - 6.76 (m, 4H), 6.68 - 6.59 (m, 2H), 6.48 (m, 1H), 6.29 (d, J=8.0 Hz, 2H), 5.07 (m, 1H), 4.20 (d, J=4.8 Hz, 1H), 3.36 - 3.34 (m, 4H), 3.04 - 2.88 (m, 5H), 2.63 - 2.51 (m, 7H), 2.42 - 2.32 (m, 5H), 2.16 - 1.96 (m, 4H), 1.75 - 1.45 (m, 7H). (DMSO-d6, 400 MHz) |
| 326 | 3-[4-chloro-5-[4-[5-[4-[(1R,2S)-6-hydroxy-2-phenyl-tetralin-1-yl]phenoxy]pentyl]piperazin-1-yl]-1-oxo-isoindolin-2-yl]piperidine-2,6-dione | A | δ 10.94 (s, 1H), 8.28 (s, 1H), 7.46 (d, J=8.8 Hz, 1H), 7.14 (d, J=7.2 Hz, 3H), 6.92 - 6.75 (m, 4H), 6.68 - 6.57 (m, 2H), 6.55 - 6.41 (m, 3H), 6.25 (d, J=8.0 Hz, 2H), 5.02 (d, J=8.0 Hz, 1H), 4.33 - 4.23 (m, 1H), 4.21 - 4.13 (m, 2H), 3.77 (s, 2H), 3.40 - 3.36 (m, 4H), 3.05 - 2.82 (m, 4H), 2.70 (s, 2H), 2.60 (s, 2H), 2.44 - 2.27 (m, 4H), 2.07 (s, 1H), 1.94 (d, J=6.4 Hz, 1H), 1.85 (s, 2H), 1.70 (d, J=7.2 Hz, 1H), 1.61 (s, 2H), 1.41 (s, 2H), 1.31 (s, 2H). (DMSO-d6, 400 MHz) |
| 328 | 3-[5-[4-[2-[2-[4-[(1R,2S)-6-hydroxy-2-phenyl-tetralin-1-yl]phenoxy]ethyl]-2-azaspiro[3.3]heptan-6-yl]piperazin-1-yl]-1-oxo-isoindolin-2-yl]piperidine-2,6-dione | A | δ 10.95 (s, 1H), 8.20 (s, 2H), 7.51 (d, J=8.8 Hz, 2H), 7.17 - 7.09 (m, 3H), 7.05 - 7.03 (m, 2H), 6.83 - 6.82 (m, 2H), 6.64 - 6.60 (m, 2H), 6.51 - 6.47 (m, 3H), 6.26 (d, J=8.4 Hz, 2H), 5.04 (dd, J=5.2, 13.4 Hz, 1H), 4.34 - 4.30 (m, 1H), 4.21 - 4.17 (m, 2H), 3.76 (t, J=5.6 Hz, 2H), 3.32 - 3.17 (m, 7H), 3.02 - 2.84 (m, 4H), 2.70 (t, J=4.8 Hz, 2H), 2.64 - 2.55 (m, 2H), 2.41 - 2.30 (m, 5H), 2.21 - 2.04 (m, 4H), 1.96 - 1.87 (m, 3H), 1.92 - 1.89 (m, 1H). (DMSO-d6, 400 MHz) |

FIG. 7 Continued

| | | | |
|---|---|---|---|
| 330 | 3-[4-fluoro-5-[4-[2-[2-[4-[(1R,2S)-6-hydroxy-2-phenyl-tetralin-1-yl]phenoxy]ethyl]-2-azaspiro[3.3]heptan-6-yl]piperazin-1-yl]-1-oxo-isoindolin-2-yl]piperidine-2,6-dione | A | δ 11.04 - 10.91 (m, 1H), 8.28 - 8.18 (m, 2H), 7.47 (d, J=8.2 Hz, 1H), 7.23 - 7.04 (m, 4H), 6.82 (br d, J=6.7 Hz, 2H), 6.66 - 6.59 (m, 2H), 6.54 - 6.44 (m, 3H), 6.26 (d, J=8.7 Hz, 2H), 5.12 - 5.03 (m, 1H), 4.52 - 4.44 (m, 1H), 4.34 - 4.26 (m, 1H), 4.17 (br d, J=4.9 Hz, 1H), 3.75 (br t, J=5.3 Hz, 1H), 3.23 (br s, 2H), 3.11 (br s, 6H), 3.01 - 2.84 (m, 4H), 2.60 (br t, J=7.3 Hz, 3H), 2.55 - 2.53 (m, 1H), 2.46 - 2.36 (m, 5H), 2.21 - 2.13 (m, 2H), 2.08 (br dd, J=6.8, 12.0 Hz, 1H), 2.01 - 1.95 (m, 1H), 1.91 - 1.84 (m, 2H), 1.75 - 1.66 (m, 1H). (DMSO-d6, 400 MHz) |
| 332 | 3-[4,6-difluoro-5-[4-[2-[2-[4-[(1R,2S)-6- hydroxy-2-phenyl-tetralin-1-yl]phenoxy]ethyl]-2-azaspiro[3.3]heptan-6-yl]piperazin-1-yl]-1-oxo-isoindolin-2-yl]piperidine-2,6-dione | A | δ 10.98 (s, 1H), 8.16 (s, 1H), 7.39 (d, J=10.0 Hz, 1H), 7.20 - 7.06 (m, 3H), 6.83 (d, J=6.8 Hz, 2H), 6.66 - 6.59 (m, 2H), 6.55 - 6.46 (m, 3H), 6.27 (d, J=8.4 Hz, 2H), 5.07 (dd, J=5.2, 13.2 Hz, 1H), 4.47 (d, J=17.2 Hz, 1H), 4.35 - 4.27 (m, 1H), 4.18 (d, J=5.2 Hz, 1H), 3.85 - 3.77 (m, 3H), 3.19 (s, 3H), 3.00 - 2.79 (m, 4H), 2.64 - 2.54 (m, 5H), 2.41 (dd, J=4.4, 12.8 Hz, 2H), 2.37 - 2.29 (m, 5H), 2.20 (dd, J=7.2, 9.2 Hz, 2H), 2.08 (dd, J=6.0, 12.0 Hz, 2H), 2.01 - 1.95 (m, 1H), 1.95 - 1.87 (m, 2H), 1.75 - 1.67 (m, 1H). (DMSO-d6, 400 MHz) |
| 334 | 2-(2,6-dioxopiperidin-3-yl)-5-(4-(6-(4-((1R,2S)-6-hydroxy-2-phenyl-1,2,3,4-tetrahydronaphthalen-1-yl)phenyl)piperazin-1-yl)hexyl)piperazin-1-yl)phenyl)isoindoline-1,3-dione | B | δ 11.09 (s, 1H), 8.22 (s, 1H), 7.67 (d, J = 8.4 Hz, 1H), 7.34-7.31 (m, 1H), 7.26-7.23 (m, 1H), 7.13 - 7.09 (m, 3H), 6.82 - 6.75 (m, 4H), 6.65 (d, J = 8.4 Hz, 1H), 6.61 (d, J = 2.0 Hz, 1H), 6.48 (dd, J = 2.4, 8.4 Hz, 1H), 6.29-6.24 (m, 2H), 5.07 (dd, J = 5.6, 12.4 Hz, 1H), 4.19 (d, J = 4.8 Hz, 1H), 3.28 - 3.16 (m, 4H), 3.04 - 2.82 (m, 4H), 2.62 - 2.52 (m, 2H), 2.46 - 2.38 (m, 6H), 2.28-2.23 (m, 2H), 2.11 - 1.98 (m, 2H), 1.72-1.66 (m, 1H), 1.49-1.37 (m, 4H), 1.30-1.17 (m, 4H). (DMSO-d6, 400 MHz) |

FIG. 7 Continued

| | | | |
|---|---|---|---|
| 335 | 3-[5-[2-[4-[2-[4-(6-hydroxy-2-phenyl-tetralin-1-yl) phenoxy]-1-piperidyl]ethyl]piperazin-1-yl]-1-oxo-isoindolin-2-yl]piperidine-2,6-dione | A | δ 10.95 (s, 1H), 8.20 (s, 1H), 7.51 (d, J=8.8 Hz, 1H), 7.17 - 7.10 (m, 3H), 7.08 - 7.02 (m, 2H), 6.86 - 6.77 (m, 2H), 6.65 (d, J=8.4 Hz, 1H), 6.60 (d, J=2.0 Hz, 1H), 6.54 (d, J=8.8 Hz, 2H), 6.48 (dd, J=2.4, 8.4 Hz, 1H), 6.28 - 6.21 (m, 1H), 6.25 (d, J=8.4 Hz, 1H), 5.04 (dd, J=5.2, 13.2 Hz, 1H), 4.36 - 4.28 (m, 1H), 4.25 - 4.13 (m, 3H), 3.33 - 3.29 (m, 1H), 3.28 - 3.24 (m, 4H), 3.05 - 2.84 (m, 3H), 2.76 - 2.67 (m, 2H), 2.62 - 2.55 (m, 1H), 2.55 - 2.52 (m, 4H), 2.48 - 2.45 (m, 4H), 2.42 - 2.35 (m, 1H), 2.28 - 2.16 (m, 2H), 2.14 - 2.03 (m, 1H), 1.99 - 1.92 (m, 1H), 1.89 - 1.76 (m, 2H), 1.74 - 1.64 (m, 1H), 1.58 - 1.44 (m, 2H). (DMSO-d6, 400 MHz) |
| 336 | 2-(2,6-dioxo-3-piperidyl)-5-[4-[3-[4-(6-hydroxyl-2-phenyl-tetralin-1-yl)phenoxy]azetidin-1-yl]propyl]piperazin-1-yl]isoindoline-1,3-dione | B | δ 11.08 (s, 1H), 8.21 (s, 1H), 7.67 (d, J=8.4 Hz, 1H), 7.32 (d, J=2.0 Hz, 1H), 7.24 (dd, J=2.0, 8.4 Hz, 1H), 7.18 - 7.06 (m, 3H), 6.84 - 6.78 (m, 2H), 6.64 (d, J=8.4 Hz, 1H), 6.60 (d, J=2.4 Hz, 1H), 6.48 (dd, J=2.4, 8.4 Hz, 1H), 6.43 (d, J=8.8 Hz, 2H), 6.25 (d, J=8.8 Hz, 2H), 5.07 (dd, J=5.2, 13.2 Hz, 1H), 4.65 - 4.54 (m, 1H), 4.17 (d, J=4.8 Hz, 1H), 3.72 - 3.60 (m, 2H), 3.42 - 3.39 (m, 4H), 3.34 - 3.26 (m, 3H), 3.04 - 2.80 (m, 5H), 2.63 - 2.53 (m, 2H), 2.47 - 2.44 (m, 4H), 2.33 - 2.27 (m, 2H), 2.15 - 1.97 (m, 2H), 1.75 - 1.62 (m, 1H), 1.53 - 1.35 (m, 2H). (DMSO-d6, 400 MHz) |
| 337 | 3-(5-((2-(4-(4-(2-(4-((1R,2S)-6-hydroxy-2-phenyl-1,2,3,4-tetrahydronaphthalen-1-yl)phenoxy)ethyl)piperazin-1-yl)pyrimidin-5-yl)oxy)-1-oxoisoindolin-2-yl)piperidine-2,6-dione formate | A | δ 10.97 (s, 1H), 8.36 (s, 2H), 8.21 (s, 1H), 7.69 (d, J=8.4 Hz, 1H), 7.24 - 7.07 (m, 5H), 6.83 (d, J=6.8 Hz, 2H), 6.70 - 6.42 (m, 5H), 6.27 (d, J=8.6 Hz, 2H), 5.07 (dd, J=5.0, 13.2 Hz, 1H), 4.46 - 4.11 (m, 3H), 3.96 (t, J=5.6 Hz, 2H), 3.70 (d, J=4.8 Hz, 4H), 3.30 (s, 2H), 3.08 - 2.81 (m, 3H), 2.73 - 2.64 (m, 2H), 2.58 - 2.52 (m, 4H), 2.41 - 2.28 (m, 1H), 2.19 - 1.90 (m, 2H), 1.71 (d, J=7.2 Hz, 1H). (DMSO-d6, 400 MHz) |

FIG. 7 Continued

| | | | |
|---|---|---|---|
| 339 | 3-(5-(4-(5-(4-((1R, 2S)-6-hydroxy-2-phenyl-1,2,3,4-tetrahydronaphthalen-1-yl)phenoxy)pentyl)piperazin-1-yl)phenoxy)pentyl)piperazin-1-yl)phenyl)-7-methoxy-1-oxoisoindolin-2-yl)piperidine-2,6-dione | A | δ 10.97 (s, 1H), 10.61-10.53 (m, 1H), 9.15 (s, 1H), 7.16-7.13 (m, 5H), 6.84-6.83 (m, 2H), 6.62-6.61 (m, 2H), 6.54-6.52 (m, 3H), 6.28-6.26 (m, 2H), 5.04-5.01 (m, 1H), 4.35-4.30 (m, 1H), 4.22-4.17 (m, 2H), 4.06-4.03 (m, 2H), 3.83-3.82 (m, 2H), 3.55-3.51 (m, 2H), 3.35-3.27 (m, 2H), 3.15-3.09 (m, 5H), 2.96-2.80 (m, 2H), 2.60-2.51 (m, 2H), 2.50-2.48 (m, 1H), 2.18-2.10 (m, 1H), 1.97-1.90 (m, 1H), 1.73-1.68 (m, 5H), 1.42-1.40 (m, 2H). (DMSO-d6, 400 MHz). |
| 341 | 3-[5-[4-[[1-[4-[[(1R, 2S)-6-hydroxy-2-phenyl-tetralin-1-yl]phenyl]-4-piperidyl]methyl]piperazin-1-yl]-1-oxo-isoindolin-2-yl]piperidine-2,6-dione | A | δ 10.97 (s, 1H), 10.83 (s, 0.9H, HCl), 7.60 (d, J=8.5 Hz, 1H), 7.40 (br s, 2H), 7.22 – 7.11 (m, 5H), 6.83 (d, J=6.0 Hz, 2H), 6.69 - 6.63 (m, 2H), 6.58 - 6.47 (m, 3H), 5.07 (dd, J=5.2, 13.2 Hz, 1H), 4.41 - 4.30 (m, 2H), 4.28 - 4.21 (m, 1H), 4.00 (d, J=12.7 Hz, 2H), 3.61 (d, J=11.0 Hz, 2H), 3.54 - 3.36 (m, 6H), 3.16 (br s, 4H), 3.06 - 2.84 (m, 3H), 2.76 - 2.53 (m, 1H), 2.43 - 2.33 (m, 1H), 2.27 (br s, 1H), 2.16 - 2.04 (m, 3H), 2.02 – 1.69 (m, 5H). (DMSO-d6, 400 MHz) |
| 343 | 3-[5-[4-[2-[1-[4-[[(1R,2S)-6-hydroxy-2-phenyl-tetralin-1-yl]phenyl]-4-piperidyl]ethyl]piperazin-1-yl]-1-oxo-isoindolin-2-yl]piperidine-2,6-dione | A | δ 11.24 (s, 1H), 10.95 (s, 1H), 7.58 (d, J=8.5 Hz, 1H), 7.48 (d, J=6.8 Hz, 2H), 7.20 – 7.11 (m, 5H), 6.83 (d, J=6.9 Hz, 2H), 6.69 - 6.61 (m, 2H), 6.53 (d, J=7.3 Hz, 3H), 5.06 (dd, J=4.6, 13.2 Hz, 1H), 4.42 - 4.18 (m, 3H), 4.00 (d, J=12.8 Hz, 2H), 3.58 (d, J=10.9 Hz, 2H), 3.47 - 3.27 (m, 6H), 3.23 - 3.03 (m, 4H), 3.02 – 2.84 (m, 3H), 2.71 - 2.52 (m, 1H), 2.39 (d, J=13.7 Hz, 2H), 2.10 – 1.71 (m, 10H). (DMSO-d6, 400 MHz) |

FIG. 7 Continued

| | | | |
|---|---|---|---|
| 344 | 3-[5-fluoro-6-[4-[5-[4-[(1R,2S)-6-hydroxy-2-phenyl-tetralin-1-yl]phenoxy]pentyl]piperazin-1-yl]-1-oxo-isoindolin-2-yl]piperidine-2,6-dione | A | δ 10.98 (s, 1H), 9.12 (s, 1H), 8.13 (s, 1H), 7.46 (d, J=11.6 Hz, 1H), 7.31 (d, J=7.6 Hz, 1H), 7.19 - 7.08 (m, 3H), 6.83 (d, J=6.8 Hz, 2H), 6.66 - 6.58 (m, 2H), 6.56 - 6.44 (m, 4H), 6.26 (d, J=8.4 Hz, 2H), 5.09 (m, 1H), 4.42 - 4.21 (m, 2H), 4.17 (d, J=4.8 Hz, 1H), 3.82 (t, J=6.4 Hz, 2H), 3.30 - 3.25 (m, 2H), 3.11 (s, 4H), 3.01 - 2.86 (m, 4H), 2.59 (d, J=18.0 Hz, 2H), 2.43 - 2.33 (m, 2H), 2.13 - 1.96 (m, 2H), 1.75 - 1.63 (m, 3H), 1.54 (m, 2H), 1.44 - 1.34 (m, 2H). (DMSO-d6, 400 MHz) |
| 345 | 3-[4-fluoro-5-[4-[5-[4-[(1R,2S)-6-hydroxy-2-phenyl-tetralin-1-yl]phenoxy]pentyl]piperazin-1-yl]-1-oxo-isoindolin-2-yl]piperidine-2,6-dione | A | δ 11.12 (s, 1H), 9.26 (s, 1H), 8.26 (s, 1H), 7.62 (d, J=8.0 Hz, 1H), 7.34 - 7.23 (m, 4H), 6.96 (d, J=6.8 Hz, 2H), 6.79 - 6.72 (m, 2H), 6.68 - 6.59 (m, 3H), 6.39 (d, J=8.8 Hz, 2H), 5.21 (dd, J=5.2, 13.6 Hz, 1H), 4.62 (d, J=17.0 Hz, 1H), 4.45 (d, J=17.2 Hz, 1H), 4.31 (d, J=4.8 Hz, 1H), 3.94 (t, J=6.4 Hz, 2H), 3.31 (br s, 2H), 3.16 - 2.98 (m, 4H), 2.74 (br s, 7H), 2.59 - 2.48 (m, 2H), 2.28 - 2.06 (m, 2H), 1.89 - 1.43 (m, 8H). (DMSO-d6, 400 MHz) |
| 346 | 3-[5-[4-[5-[4-[(1R, 2S)-7-fluoro-6-hydroxy-2-phenyl-tetralin-1-yl] phenoxy] pentyl] piperazin-1-yl]-1-oxo-isoindolin-2-yl] piperidine-2, 6-dione | B | δ 10.94 (s, 1H), 9.50 (s, 0.47H), 8.19 (s, 1H), 7.52 (d, J = 8.4 Hz, 1H), 7.15 (m, 5H), 6.83 (m, 3H), 6.56 (m, 3H), 6.27 (d, J=8.0 Hz, 2H), 5.00 (m, 1H), 4.30 (d, J = 8.4 Hz, 2H), 4.18 (d, J=8.8 Hz,2H), 3.83 (m, 2H), 2.90 (m, 4H), 2.67 (s, 1H), 2.50 (m, 7H), 1.68 (m, 3H), 1.49 (m, 4H), 1.38 (m, 5H). (DMSO-d6, 400 MHz) |

FIG. 7 Continued

| | | | |
|---|---|---|---|
| 348 | 3-[5-[4-[5-[4-[(1R,2S)-6-hydroxy-2-phenyl-tetralin-1-yl]phenoxy]pentyl]piperazin-1-yl]-1-oxo-isoindolin-2-yl]piperidine-2,6-dione | B | δ 11.08 (s, 1H), 9.89 (s, 1H), 7.68 (d, J=8.4 Hz, 1H), 7.34 (s, 1H), 7.25 (dd, J=2.0, 8.4 Hz, 1H), 7.03 - 6.94 (m, 2H), 6.84 (dd, J=5.6, 8.4 Hz, 2H), 6.58 (d, J=8.8 Hz, 2H), 6.51 (d, J=11.2 Hz, 1H), 6.29 (d, J=8.8 Hz, 2H), 5.13 - 5.00 (m, 1H), 5.07 (dd, J=5.2, 13.2 Hz, 1H), 4.19 (d, J=4.8 Hz, 1H), 3.83 (t, J=6.4 Hz, 2H), 3.51 - 3.39 (m, 5H), 3.31 - 3.26 (m, 2H), 3.06 (dd, J=5.2, 16.8 Hz, 1H), 2.94 - 2.83 (m, 1H), 2.81 - 2.70 (m, 1H), 2.63 - 2.53 (m, 5H), 2.44 - 2.34 (m, 2H), 2.07 - 1.95 (m, 2H), 1.82 - 1.73 (m, 1H), 1.71 - 1.62 (m, 2H), 1.56 - 1.55 (m, 2H), 1.43 - 1.33 (m, 2H). (DMSO-d6, 400 MHz) |
| 351 | 2-(2,6-dioxo-3-piperidyl)-5-[4-[5-[4-[(1R,2S)-5-fluoro-2-(4-fluorophenyl)-6-hydroxy-tetralin-1-yl] phenoxy] pentyl] piperazin-1-yl] isoindoline-1,3-dione | B | δ 11.08 (s, 1H), 9.50 (s, 0.60H), 8.18 (s, 1H), 7.68 (d, J = 8.4 Hz, 1H), 7.33 (s, 1H), 7.25 (d, J = 7.2 Hz, 1H), 6.96 (m, 2H), 6.86 (m, 2H), 5.09 (m, 1H), 4.20 (d, J = 4.8 Hz, 1H), 3.84 (t, J = 6.4 Hz, 2H), 3.13 (m, 1H), 2.67 (m, 8H), 2.52 (m, 2H), 2.30 (m, 3H), 1.66 (m, 1H), 1.49 (m, 2H), 1.40 (m, 5H). (DMSO-d6, 400 MHz) |
| 355 | 2-(2,6-dioxopiperidin-3-yl)-5-((1R,5S)-6-(6-(4-(((1R,2S)-6-hydroxy-2-phenyl-1,2,3,4-tetrahydronaphthalen-1-yl)phenyl)hexyl)-3,6-diazabicyclo[3.1.1]heptan-3-yl)isoindoline-1,3-dione | B | δ 11.07 (s, 1H), 9.13 (br s, 1H), 8.16 (s, 1H), 7.61 (d, J=8.4 Hz, 1H), 7.15 - 6.96 (m, 4H), 6.88 - 6.70 (m, 5H), 6.67 - 6.58 (m, 2H), 6.47 (dd, J=2.4, 8.4 Hz, 1H), 6.26 (d, J=8.0 Hz, 2H), 5.05 (dd, J=5.2, 12.8 Hz, 1H), 4.61 (br s, 1H), 4.18 (d, J=5.1 Hz, 1H), 3.59 (br s, 1H), 3.44 - 3.37 (m, 2H), 3.02 - 2.83 (m, 4H), 2.61 - 2.51 (m, 4H), 2.43 - 2.35 (m, 4H), 2.16 - 1.94 (m, 2H), 1.90 - 1.77 (m, 2H), 1.69 (br s, 1H), 1.42 (br t, J=7.2 Hz, 2H), 1.34 - 1.11 (m, 6H). (DMSO-d6, 400 MHz) |

FIG. 7 Continued

| | | | |
|---|---|---|---|
| 356 | 3-[5-[6-[4-[(1R,2S)-2-(4-fluorophenyl)-6-hydroxy-tetralin-1-yl]phenoxy]butyl]-2,6-diazaspiro[3.3]heptan-2-yl]-1-oxo-isoindolin-2-yl]piperidine-2,6-dione | A | δ 10.94 (s, 1H), 9.34 - 8.87 (m, 1H), 8.19 (s, 1H), 7.48 (d, J=8.3 Hz, 1H), 7.04 - 6.91 (m, 2H), 6.87 - 6.76 (m, 2H), 6.66 - 6.59 (m, 2H), 6.55 (d, J=8.7 Hz, 2H), 6.52 - 6.44 (m, 3H), 6.27 (d, J=8.7 Hz, 2H), 5.03 (dd, J=5.1, 13.3 Hz, 1H), 4.35 - 4.24 (m, 1H), 4.21 - 4.13 (m, 1H), 4.21 - 4.11 (m, 1H), 3.96 (s, 4H), 3.80 (br t, J=6.5 Hz, 2H), 3.32 (s, 5H), 3.04 - 2.83 (m, 3H), 2.57 (br d, J=16.8 Hz, 1H), 2.45 - 2.34 (m, 3H), 2.13 - 1.90 (m, 2H), 1.73 - 1.56 (m, 3H), 1.42 - 1.30 (m, 2H). (DMSO-d6, 400 MHz) |
| 359 | 3-[5-[8-[4-[4-[(1R,2S)-6-hydroxy-2-phenyl-tetralin-1-yl]phenoxy]butyl]-3,4,6,7,9,9a-hexahydro-1H-pyrazino[1,2-a]pyrazin-2-yl]-1-oxo-isoindolin-2-yl]piperidine-2,6-dione | A | δ 10.95 (s, 1H), 9.13 (s, 1H), 8.13 (s, 1H), 7.53 (d, J=9.2 Hz, 1H), 7.18 - 7.11 (m, 3H), 7.09 - 7.04 (m, 2H), 6.83 (br d, J=7.8 Hz, 2H), 6.66 - 6.58 (m, 2H), 6.54 (d, J=8.7 Hz, 2H), 6.48 (br d, J=8.3 Hz, 1H), 6.26 (br d, J=7.3 Hz, 2H), 5.05 (dd, J=5.3, 13.4 Hz, 1H), 4.36 - 4.13 (m, 3H), 3.87 - 3.72 (m, 4H), 3.12 - 2.76 (m, 9H), 2.58 (br d, J=19.1 Hz, 2H), 2.37 (br dd, J=4.5, 13.4 Hz, 3H), 2.33 - 1.83 (m, 7H), 1.76 - 1.50 (m, 5H). (DMSO-d6, 400 MHz) |
| 360 | 3-[5-[4-[2-hydroxy-5-[4-[(1R,2S)-6-hydroxy-2-phenyl-tetralin-1-yl]phenoxy]pentyl]piperazin-1-yl]-1-oxo-isoindolin-2-yl]piperidine-2,6-dione | A | δ 10.96 (s, 1H), 8.30 (s, 1H), 7.52 (d, J = 8.8 Hz, 1H), 7.18 - 7.03 (m, 5H), 6.83 (d, J = 6.7 Hz, 2H), 6.64 (d, J = 8.0 Hz, 1H), 6.61 (s, 1H), 6.55 - 6.47 (m, 3H), 6.26 (d, J = 8.5 Hz, 2H), 5.05 (dd, J = 5.0, 13.3 Hz, 1H), 4.49 - 4.27 (m, 1H), 4.25 - 4.00 (m, 2H), 3.82 (br t, J = 6.5 Hz, 2H), 3.64 (br d, J = 12.2 Hz, 1H), 3.33 - 3.30 (m, 2H), 3.30 - 3.15 (m, 3H), 3.14 - 2.83 (m, 3H), 2.60 (br d, J = 2.8 Hz, 1H), 2.57 - 2.52 (m, 6H), 2.47 - 2.25 (m, 2H), 2.15 - 2.02 (m, 1H), 2.01 - 1.89 (m, 1H), 1.85 - 1.73 (m, 1H), 1.70 (br d, J = 6.7 Hz, 2H), 1.66 - 1.51 (m, 1H), 1.42 - 1.29 (m, 1H). (DMSO-d6, 400 MHz) |

FIG. 7 Continued

| | | | | |
|---|---|---|---|---|
| 361 | 3-[5-[[6-[4-[2-[4-(6-hydroxy-2-phenyl-tetralin-1-yl)phenoxy]ethyl]piperazin-1-yl]-3-pyridyl]oxy]-1-oxo-isoindolin-2-yl]piperidine-2,6-dione | A | A | δ 10.95 (s, 1H), 9.14 (br s, 1H), 8.15 (s, 1H), 7.52 (d, J= 9.0 Hz, 1H), 7.18 - 7.04 (m, 5H), 6.83 (d, J = 6.7 Hz, 2H), 6.65 (d, J = 8.5 Hz, 1H), 6.61 (s, 1H), 6.54 - 6.47 (m, 3H), 6.26 (d, J = 8.5 Hz, 2H), 5.05 (dd, J = 5.0, 13.3 Hz, 1H), 4.38 - 4.26 (m, 1H), 4.24 - 4.11 (m, 2H), 3.78 (br t, J=6.5 Hz, 2H), 3.54 - 3.31 (m, 5H), 3.03 - 2.83 (m, 3H), 2.62 - 2.52 (m, 2H), 2.47 - 2.31 (m, 5H), 2.21 - 2.04 (m, 3H), 2.01 - 1.87 (m, 2H), 1.71 (br d, J=10.7 Hz, 1H), 1.62 - 1.50 (m, 2H), 1.50 - 1.35 (m, 4H). (DMSO-d6, 400 MHz) |
| 362 | 3-[7-fluoro-5-[4-[5-[4-[(1R,2S)-6-hydroxy-2-phenyl- tetralin-1-yl]phenoxy]pentyl]piperazin-1-yl]-1-oxo-isoindolin-2-yl]piperidine-2,6-dione | A | A | δ 10.97 (s, 1H), 9.14 (s, 1H), 8.14 (s, 1H), 7.19 - 7.08 (m, 3H), 6.94 (s, 1H), 6.90 - 6.78 (m, 3H), 6.67 - 6.59 (m, 2H), 6.55 - 6.47 (m, 3H), 6.27 (d, J=8.8 Hz, 2H), 5.02 (dd, J=5.2, 13.2 Hz, 1H), 4.40 - 4.16 (m, 3H), 3.82 (t, J=6.4 Hz, 2H), 3.30 (s, 2H), 3.07 - 2.80 (m, 6H), 2.41 - 2.32 (m, 1H), 2.17 - 1.90 (m, 2H), 1.77 - 1.53 (m, 5H), 1.45 - 1.32 (m, 2H). (DMSO-d6, 400 MHz) |
| 363 | 3-[5-[4-[3-hydroxy-5-[4-[(1R,2S)-6-hydroxy-2-ph-enyl-tetralin-1-yl]phenoxy]-3-methyl-pentyl]piperazin-1-yl]-1-oxo-isoindolin-2-yl]piperidine-2,6-dione | A | B | δ 10.97 (s, 1H), 8.23 (s, 1H), 7.52 (d, J=8.8 Hz, 1H), 7.18 - 7.10 (m, 3H), 7.08 - 7.03 (m, 2H), 6.82 (br d, J=6.8 Hz, 2H), 6.67 - 6.59 (m, 2H), 6.56 - 6.46 (m, 3H), 6.26 (d, J=8.8 Hz, 2H), 5.13 - 4.98 (m, 1H), 4.38 - 4.13 (m, 3H), 3.93 (br t, J=6.8 Hz, 2H), 3.81 - 3.35 (m, 5H), 3.31 (br s, 1H), 3.10 - 2.80 (m, 4H), 2.69 - 2.59 (m, 1H), 2.53 (br d, J=1.9 Hz, 4H), 2.40 - 2.29 (m, 2H), 2.16 - 2.03 (m, 1H), 2.01 - 1.87 (m, 1H), 1.78 (br t, J=7.2 Hz, 2H), 1.70 (br d, J=7.2 Hz, 1H), 1.60 (br t, J=6.8 Hz, 2H), 1.12 (s, 3H). (DMSO-d6, 400 MHz) |

FIG. 7 Continued

| | | | |
|---|---|---|---|
| 364 | (3S)-3-[5-[2-[4-[[1-[4-[(1R,2S)-6-hydroxy-2-phenyl-tetralin-1-yl]phenyl]-4-piperidyl]methyl]-1,4-diazepan-1-yl]ethyl]-1-oxo-isoindolin-2-yl]piperidine-2,6-dione | A | δ 10.99 (s, 1H), 8.21 (s, 2H), 7.63 (d, J=7.8 Hz, 1H), 7.46 (s, 1H), 7.37 (d, J=8.0 Hz, 1H), 7.17 - 7.09 (m, 3H), 6.83 (d, J=6.3 Hz, 2H), 6.64 (d, J=7.9 Hz, 1H), 6.60 (s, 1H), 6.54 - 6.46 (m, 3H), 6.20 (d, J=8.7 Hz, 2H), 5.10 (dd, J=5.0, 13.3 Hz, 1H), 4.41 (d, J=17.3 Hz, 1H), 4.28 (d, J=17.2 Hz, 1H), 4.12 (br d, J=4.8 Hz, 1H), 3.31 - 3.22 (m, 1H), 3.07 - 2.81 (m, 6H), 2.77 (br d, J=5.9 Hz, 6H), 2.70 - 2.52 (m, 5H), 2.48 - 2.27 (m, 6H), 2.23 - 1.95 (m, 2H), 1.80 - 1.64 (m, 5H), 1.52 (br s, 1H), 1.17 - 1.05 (m, 2H). (DMSO-d6, 400 MHz) | A |
| 365 | 3-[5-[4-[5-[4-[(1R,2S)-6-hydroxy-2-phenyl-tetralin-1-yl]phenoxy]-2-oxo-pentyl]piperazin-1-yl]-1-oxo-isoindolin-2-yl]piperidine-2,6-dione | A | δ 10.97 (br s, 1H), 9.18 (br s, 1H), 7.52 (br d, J = 8.3 Hz, 1H), 7.19 - 7.01 (m, 5H), 6.83 (br d, J = 6.9 Hz, 2H), 6.68 - 6.57 (m, 2H), 6.57 - 6.45 (m, 3H), 6.26 (br d, J = 8.0 Hz, 2H), 5.06 (br dd, J = 4.3, 12.9 Hz, 1H), 4.38 - 4.27 (m, 1H), 4.21 (br d, J = 17.7 Hz, 2H), 3.80 (br s, 1H), 3.31 - 3.22 (m, 4H), 3.17 (br s, 1H), 3.09 - 2.84 (m, 3H), 2.68 (br s, 1H), 2.64 - 2.57 (m, 6H), 2.44 - 2.23 (m, 2H), 2.07 (br s, 1H), 1.97 (br d, J = 5.0 Hz, 1H), 1.91 - 1.79 (m, 2H), 1.71 (br s, 1H). (DMSO-d6, 400 MHz) | A |
| 367 | 3-[4,6-difluoro-5-[4-[2-hydroxy-5-[4-[(1R,2S)-6-hydroxy-2-phenyl-tetralin-1-yl]phenoxy]pentyl]piperazin-1-yl]-1-oxo-isoindolin-2-yl]piperidine-2,6-dione | A | δ 11.02 (br s, 1H), 8.34 (br s, 1H), 7.40 (d, J = 10.0 Hz, 1H), 7.19 - 7.08 (m, 3H), 6.83 (br d, J = 7.0 Hz, 2H), 6.64 (d, J = 8.8 Hz, 1H), 6.61 (s, 1H), 6.57 - 6.46 (m, 3H), 6.26 (d, J = 8.4 Hz, 2H), 5.09 (dd, J = 5.0, 13.3 Hz, 1H), 4.56 - 4.44 (m, 1H), 4.43 - 4.24 (m, 1 H), 4.17 (br d, J = 4.8 Hz, 1H), 3.83 (br t, J = 6.4 Hz, 2H), 3.64 (br s, 1H), 3.30 - 3.25 (m, 2H), 3.21 (br s, 4H), 3.11 - 2.84 (m, 3H), 2.77 - 2.65 (m, 1H), 2.62 (br s, 4 H), 2.45 - 2.23 (m, 3H), 2.20 - 1.91 (m, 2 H), 1.87 - 1.69 (m, 4H), 1.47 - 1.28 (m, 1H). (DMSO-d6, 400 MHz) | B |

FIG. 7 Continued

| | | | |
|---|---|---|---|
| 368 | 3-[5-[4-[3-[2-[4-[(1R,2S)-6-hydroxy-2-phenyl-tetralin-1-yl]phenoxy]ethyl]cyclobutyl]piperazin-1-yl]-1-oxo-isoindolin-2-yl]piperidine-2,6-dione | A | δ 10.95 (s, 1H), 8.16 (s, 1H), 7.51 (d, J=9.2 Hz, 1H), 7.19 - 7.08 (m, 3H), 7.07 - 7.01 (m, 2H), 6.82 (d, J=6.8 Hz, 2H), 6.68 - 6.59 (m, 2H), 6.54 - 6.45 (m, 3H), 6.25 (d, J=8.8 Hz, 2H), 5.04 (dd, J=5.2, 13.2 Hz, 1H), 4.38 - 4.27 (m, 1H), 4.24 - 4.14 (m, 2H), 3.82 - 3.71 (m, 2H), 3.35 - 3.21 (m, 5H), 3.04 - 2.79 (m, 3H), 2.63 - 2.53 (m, 2H), 2.42 - 2.29 (m, 5H), 2.22 - 1.90 (m, 5H), 1.86 - 1.65 (m, 3H), 1.52 - 1.37 (m, 2H). (DMSO-d6, 400 MHz) |
| 373 | 3-[5-[4-[2-[4-[(1R,2S)-6-tert-butoxy-2-phenyl-tetralin-1-yl]phenoxy]ethoxy]ethyl]piperazin-1-yl]-1-oxo-isoindolin-2-yl]piperidine-2,6-dione | A | δ 10.96 (s, 1H), 9.25 - 9.01 (m, 1H), 8.20 (s, 1H), 7.51 (d, J=8.8 Hz, 1H), 7.19 - 7.03 (m, 3H), 6.82 (d, J=6.8 Hz, 2H), 6.66 - 6.59 (m, 2H), 6.55 (d, J=8.8 Hz, 2H), 6.48 (dd, J=2.4, 8.4 Hz, 1H), 6.27 (d, J=8.8 Hz, 2H), 5.05 (dd, J=5.2, 13.2 Hz, 1H), 4.36 - 4.28 (m, 1H), 4.24 - 4.15 (m, 2H), 3.97 - 3.91 (m, 2H), 3.70 - 3.63 (m, 2H), 3.58 (t, J=5.6 Hz, 2H), 3.26 (d, J=3.2 Hz, 6H), 2.99 - 2.84 (m, 3H), 2.62 - 2.53 (m, 6H), 2.38 (d, J=4.4 Hz, 1H), 2.12 - 1.96 (m, 2H), 1.73 - 1.66 (m, 1H). (DMSO-d6, 400 MHz) |
| 374 | 1,3-trans-3-[5-[4-[2-[3-[4-[(1R,2S)-6-hydroxy-2-phenyl-tetralin-1-yl]phenoxy]cyclobutoxy]ethyl]piperazin-1-yl]-1-oxo-isoindolin-2-yl]piperidine-2,6-dione | A | δ 10.95 (s, 1H), 9.14 (s, 1H), 8.20 (s, 1H), 7.51 (d, J=8.8 Hz, 1H), 7.18 - 7.08 (m, 3H), 7.07 - 7.02 (m, 2H), 6.84 - 6.78 (m, 2H), 6.64 (d, J=8.4 Hz, 1H), 6.60 (d, J=2.4 Hz, 1H), 6.48 (dd, J=2.4, 8.4 Hz, 1H), 6.41 (d, J=8.8 Hz, 2H), 6.24 (d, J=8.8 Hz, 2H), 5.04 (dd, J=5.2, 13.2 Hz, 1H), 4.70 - 4.59 (m, 1H), 4.36 - 4.29 (m, 1H), 4.23 - 4.10 (m, 3H), 3.46 - 3.42 (m, 6H), 3.29 - 3.21 (m, 3H), 3.03 - 2.84 (m, 3H), 2.62 - 2.58 (m, 1H), 2.56 - 2.53 (m, 4H), 2.42 - 2.36 (m, 1H), 2.34 - 2.29 (m, 2H), 2.26 - 2.14 (m, 2H), 2.12 - 2.01 (m, 1H), 1.99 - 1.90 (m, 1H), 1.74 - 1.63 (m, 1H). (DMSO-d6, 400 MHz) |

FIG. 7 Continued

| | | | |
|---|---|---|---|
| 376 | 2-(2,6-dioxo-3-piperidyl)-5-[4-[7-[4-[(1R,2S)-2-(4-fluorophenyl)-6-hydroxy-tetralin-1-yl]phenoxy]decalin-2-yl]piperazin-1-yl]isoindoline-1,3-dione | B | δ 11.09 (br d, J=4.9 Hz, 1H), 9.19 (br s, 1H), 8.23 (s, 1H), 7.74 - 7.63 (m, 1H), 7.31 (br s, 1H), 7.27 - 7.14 (m, 1H), 7.02 - 6.89 (m, 2H), 6.88 - 6.74 (m, 2H), 6.71 - 6.53 (m, 4H), 6.49 (br d, J=8.3 Hz, 1H), 6.32 - 6.22 (m, 2H), 5.07 (ddd, J=5.1, 8.2, 13.0 Hz, 1H), 4.52 - 4.07 (m, 2H), 3.45 - 3.42 (m, 4H), 3.30 - 3.27 (m, 1H), 3.07 - 2.80 (m, 3H), 2.60 (br s, 2H), 2.52 (br s, 1H), 2.40 (br s, 1H), 2.23 - 1.94 (m, 4H), 1.92 - 1.16 (m, 12H), 1.14 - 0.76 (m, 4H). (DMSO-d6, 400 MHz) |
| 377 | 3-[5-[4-[3-[2-[4-[(1R,2S)-6-hydroxy-2-phenyl-tetralin-1-yl]phenoxy]ethyl]cyclobutyl]piperazin-1-yl]-1-oxo-isoindolin-2-yl]piperidine-2,6-dione | A | δ 10.97 (s, 1H), 10.69 - 10.26 (m, 1H), 9.18 (s, 1H), 7.58 (d, J=8.4 Hz, 1H), 7.24 - 7.06 (m, 5H), 6.83 (d, J=6.8 Hz, 2H), 6.68 - 6.59 (m, 2H), 6.57 - 6.45 (m, 3H), 6.27 (d, J=8.0 Hz, 2H), 5.06 (dd, J=5.2, 13.6 Hz, 1H), 4.41 - 4.31 (m, 1H), 4.28 - 4.15 (m, 2H), 4.07 - 3.84 (m, 4H), 3.75 - 3.54 (m, 2H), 3.34 - 3.05 (m, 5H), 3.04 - 2.84 (m, 3H), 2.71 - 2.55 (m, 2H), 2.38 (dd, J=3.6, 12.8 Hz, 1H), 2.15 - 2.02 (m, 1H), 2.01 - 1.85 (m, 2H), 1.85 - 1.66 (m, 4H), 1.31 - 1.20 (m, 2H). (DMSO-d6, 400 MHz) |
| 378 | 3-(5-(4-((5-(4-((1R,2S)-2-(4-fluorophenyl)-6-hydroxy-1,2,3,4-tetrahydronaphthalen-1-yl)phenoxy)octahydropentalen-2-yl)methyl)piperazin-1-yl)-1-oxoisoindolin-2-yl)piperidine-2,6-dione | A | δ 10.95 (s, 1H), 8.23 (s, 1H), 7.52-7.50 (m, 1H), 7.05-6.94 (m, 4H), 6.82-6.80 (m, 2H), 6.63-6.60 (m, 2H), 6.53-6.50 (m, 3H), 6.27-6.24 (m, 2H), 5.07-5.02 (m, 1H), 4.75-4.65 (m, 1H), 4.34-4.30 (m, 1H), 4.23-4.13 (m, 2H), 3.32-3.15 (m, 4H), 2.94-2.90 (m, 3H), 2.65-2.60 (m, 2H), 2.48-2.24 (m, 7H), 2.10-1.94 (m, 6H), 1.80-1.70 (m, 4H), 1.68-1.31 (m, 2H), 1.25-1.21 (m, 1H), 0.87-0.86 (m, 1H). (DMSO-d6, 400 MHz) |

FIG. 7 Continued

| | | | |
|---|---|---|---|
| 380 | 3-[5-[4-[3-[2-[4-[(1R,2S)-6-hydroxy-2-phenyl-tetralin-1-yl]phenoxy]ethyl]cyclopentyl]piperazin-1-yl]-1-oxo-isoindolin-2-yl]piperidine-2,6-dione | A | δ 10.93 (s, 1H), 9.12 (s, 0.63H), 8.19 (s, 1H), 7.52 (d, J = 8.8 Hz, 1H), 7.15 (m, 3H), 7.05 (m, 2H), 6.84 (d, J = 7.6 Hz, 2H), 6.53 (m, 2H), 6.51 (m, 3H), 6.27 (d, J = 7.6 Hz, 2H), 5.06 (m, 1H), 4.30 (t, J = 5.6 Hz, 1H), 4.18 (d, J = 4.0 Hz, 2H), 3.81 (t, J = 4.4 Hz, 2H), 3.19 (m, 4H), 2.96 (m, 4H), 2.41 (m, 2H), 2.38 (m, 6H), 1.71 (m, 6H), 1.05 (m, 5H). (DMSO-d6, 400 MHz) |
| | | B | |
| 382 | 3-[5-[[(3aS,6aR)-2-[4-[4-[(1R,2S)-6-hydroxy-2-phenyl-tetralin-1-yl]phenoxy]butyl]-1,3,3a,4,6,6a-hexahydropyrrolo[3,4-c]pyrrol-5-yl]-1-oxo-isoindolin-2-yl]piperidine-2,6-dione | A | δ 10.94 (s, 1H), 8.19 (s, 1H), 7.48 (d, J = 8.8 Hz, 1H), 7.16 - 7.10 (m, 3H), 6.82 - 6.80 (m, 2H), 6.69 - 6.67 (m, 2H), 6.63 - 6.60 (m, 2H), 6.50 - 6.46 (m, 3H), 6.24 - 6.22 (m, 2H), 5.03 (dd, J = 5.2, 13.2 Hz, 1H), 4.32 - 4.28 (m, 1H), 4.20 - 4.16 (m, 2H), 3.79 (t, J = 6.4 Hz, 2H), 3.53 - 3.49 (m, 2H), 3.31 - 3.27 (m, 1H), 3.14 - 3.12 (m, 2H), 3.01 - 2.85 (m, 5H), 2.60 - 2.52 (m, 5H), 2.47 - 2.38 (m, 3H), 2.10 - 1.93 (m, 2H), 1.71 - 1.49 (m, 5H). (DMSO-d6, 400 MHz) |
| | | B | |
| 385 | 3-(5-(4-(5-((4-((1R,2S)-6-hydroxy-2-phenyl-1,2,3,4-tetrahydronaphthalen-1-yl)phenyl)sulfonyl)pentyl)piperazin-1-yl)-1-oxoisoindolin-2-yl)-piperidine-2,6-dione | B | δ 10.96 (s, 1H), 9.26 (br s, 1H), 8.24 (s, 1H), 7.54 - 7.44 (m, 3H), 7.16 - 7.11 (m, 3H), 7.08 - 7.02 (m, 2H), 6.85 - 6.79 (m, 2H), 6.67 - 6.63 (m, 4H), 6.51 (dd, J=2.4, 8.4 Hz, 1H), 5.05 (dd, J=4.8, 13.2 Hz, 1H), 4.39 (d, J=5.6 Hz, 1H), 4.36 - 4.16 (m, 2H), 3.27 - 3.13 (m, 4H), 3.11 - 2.83 (m, 4H), 2.60 (br s, 1H), 2.45 - 2.42 (m, 6H), 2.23 (br t, J=6.8 Hz, 2H), 2.09 (br dd, J=5.6, 12.0 Hz, 2H), 2.00 - 1.90 (m, 1H), 1.75 (br s, 1H), 1.46 - 1.26 (m, 6H). (DMSO-d6, 400 MHz) |
| | | A | |

FIG. 7 Continued

| | | | |
|---|---|---|---|
| 387 | (3S)-3-[5-[2-[4-[[1-[4-[(1R,2S)-6-hydroxy-2-phenyl-tetralin-1-yl]phenyl]azetidin-3-yl]methyl]-1,4-diazepan-1-yl]ethyl]-1-oxo-isoindolin-2-yl]piperidine-2,6-dione | A | δ 10.99 (br s, 1H), 8.30 (s, 2H), 7.62 (d, J=7.9 Hz, 1H), 7.46 (s, 1H), 7.37 (br d, J=7.8 Hz, 1H), 7.20 - 7.08 (m, 3H), 6.82 (br d, J=6.9 Hz, 2H), 6.67 - 6.56 (m, 2H), 6.48 (br d, J=8.0 Hz, 1H), 6.21 - 6.11 (m, J=8.2 Hz, 2H), 6.06 - 5.98 (m, J=8.3 Hz, 2H), 5.10 (br dd, J=5.0, 13.3 Hz, 1H), 4.41 (br d, J=17.3 Hz, 1H), 4.28 (br d, J=17.2 Hz, 1H), 4.10 (br d, J=4.6 Hz, 1H), 3.87 - 3.58 (m, 1H), 3.31 - 3.14 (m, 1H), 2.97 - 2.87 (m, 7H), 2.84 - 2.58 (m, 12H), 2.42 - 2.30 (m, 1H), , 2.09 (br dd, J=6.0, 12.4 Hz, 2H), 2.04 - 1.84 (m, 2H), 1.69 (br s, 4H). (DMSO-d6, 400 MHz) |
| 389 | 3-(5-(4-(5-(2,6-difluoro-4-((1R,2S)-6-hydroxy-2-phenyl-1,2,3,4-tetrahydronaphthalen-1-yl)phenoxy)pentyl)piperazin-1-yl)-1-oxoisoindolin-2-yl)piperidine-2,6-dione | A | δ 10.95 (s, 1H), 9.24 (s, 1H), 8.13 (s, 1H), 7.54 (br d, J = 8.0 Hz, 1H), 7.19 (br d, J = 7.6 Hz, 3H), 7.09 (br s, 2H), 6.88 (d, J = 6.4 Hz, 2H), 6.69 (d, J = 8.4 Hz, 1H), 6.62 (s, 1H), 6.53 (s, 1H), 5.98 (d, J = 9.8 Hz, 2H), 5.09 - 5.02 (m, 1H), 4.37 - 4.30 (m, 1H), 4.26 - 4.18 (m, 2H), 3.96 (t, J = 6.4 Hz, 2H), 3.22 - 2.84 (m, 4H), 2.61 (br s, 1H), 2.53 - 2.52 (m, 6H), 2.38 (br s, 4H), 1.98 (s, 2H), 1.79 - 1.49 (m, 6H), 1.39 (br s, 2H). (DMSO-d6, 400 MHz) |
| 390 | 3-[5-[4-[2-[3-[4-[(1R,2S)-6-hydroxy-2-phenyl-tetralin-1-yl]phenoxy]cyclobutoxy]ethyl]piperazin-1-yl]-1-oxo-isoindolin-2-yl]piperidine-2,6-dione | B | δ 10.95 (s, 1H), 9.19 (s, 1H), 8.16 (s, 1H), 7.51 (d, J=8.8 Hz, 1H), 7.19 - 7.01 (m, 5H), 6.81 (d, J=6.4 Hz, 2H), 6.64 (d, J=8.4 Hz, 1H), 6.60 (d, J=2.4 Hz, 1H), 6.52 - 6.39 (m, 3H), 6.24 (d, J=8.8 Hz, 2H), 5.04 (dd, J=5.2, 13.2 Hz, 1H), 4.37 - 4.27 (m, 1H), 4.25 - 4.12 (m, 3H), 3.72 - 3.62 (m, 1H), 3.43 (t, J=5.6 Hz, 4H), 3.28 - 3.24 (m, 5H), 3.02 - 2.85 (m, 3H), 2.82 - 2.71 (m, 2H), 2.62 - 2.58 (m, 1H), 2.55 - 2.53 (m, 4H), 2.41 - 2.34 (m, 1H), 2.13 - 2.02 (m, 1H), 2.00 - 1.90 (m, 1H), 1.87 - 1.76 (m, 2H), 1.73 - 1.65 (m, 1H). (DMSO-d6, 400 MHz) |

FIG. 7 Continued

| | | | |
|---|---|---|---|
| 391 | 3-[5-[4-[2-[2-[4-[(1R,2S)-6-hydroxy-2-phenyl-tetralin-1-yl]phenoxy]ethylamino]ethyl]piperazin-1-yl]-1-oxo-isoindolin-2-yl]piperidine-2,6-dione | A | δ 10.95 (s, 1H), 8.25 (s, 2H), 7.51 (d, J=8.8 Hz, 1H), 7.17 - 7.08 (m, 3H), 7.07 - 7.01 (m, 2H), 6.81 (d, J=6.5 Hz, 2H), 6.64 - 6.59 (m, 2H), 6.54 (d, J=8.7 Hz, 2H), 6.47 (dd, J=2.4, 8.3 Hz, 1H), 6.26 (d, J=8.5 Hz, 2H), 5.04 (dd, J=5.0, 13.4 Hz, 1H), 4.36 - 4.17 (m, 3H), 3.89 (br s, 2H), 3.27 - 3.20 (m, 2H), 2.97 - 2.85 (m, 5H), 2.73 - 2.67 (m, 2H), 2.52 (br s, 6H), 2.44 - 2.36 (m, 4H), 2.14 - 1.90 (m, 3H), 1.73 - 1.64 (m, 1H). (DMSO-d6, 400 MHz) |
| 393 | 2-(2,6-dioxopiperidin-3-yl)-5-(4-((1-(4-((1R,2S)-6-hydroxy-2-phenyl-1,2,3,4-tetrahydronaphthalen-1-yl)phenyl)piperidin-4-yl)methyl)piperazin-1-yl)isoindoline-1,3-dione | B | δ 11.08 (s, 1H), 9.13 (br s, 1H), 8.19 (s, 1H), 7.67 (d, J = 8.5 Hz, 1H), 7.33 (s, 1H), 7.25 (br d, J = 8.5 Hz, 1H), 7.17 - 7.08 (m, 3H), 6.83 (br d, J = 6.8 Hz, 2H), 6.64 (d, J = 8.3 Hz, 1H), 6.60 (d, J = 2.3 Hz, 1H), 6.53 (d, J = 8.8 Hz, 2H), 6.47 (dd, J = 2.4, 8.2 Hz, 1H), 6.19 (d, J = 8.7 Hz, 2H), 5.07 (dd, J = 5.3, 12.9 Hz, 1H), 4.12 (d, J = 4.5 Hz, 1H), 3.50 - 3.41 (m, 12H), 2.99 - 2.84 (m, 3H), 2.62 - 2.53 (m, 3H), 2.23 - 2.18 (m, 2H), 2.12 - 1.97 (m, 2H), 1.80 - 1.61 (m, 4H), 1.23 - 1.05 (m, 2H). (DMSO-d6, 400 MHz) |
| 395 | 2-(2,6-dioxopiperidin-3-yl)-5-(4-(2-(1-(4-((1R,2S)-6-hydroxy-2-phenyl-1,2,3,4-tetrahydronaphthalen-1-yl)phenyl)piperidin-4-yl)ethyl)piperazin-1-yl)isoindoline-1,3-dione | A | δ 11.08 (s, 1H), 9.10 (s, 1H), 8.15 (s, 1H) 7.68-7.66 (d, 1H), 7.31 (s, 1H), 7.25 (d, 1H), 7.20 – 7.10 (m, 3H), 6.82 (d, 2H), 6.65 – 6.58 (m, 2H), 6.52 – 6.40 (m, 3H), 6.19 (d, 2H), 5.08 - 5.04 (m, 1H), 4.12 - 4.11 (d, J = 4 Hz, 1H), 3.50-3.41 (m 12H), 2.99 – 2.83 (m, 3H), 2.60 – 2.52 (m, 3H), 2.40 - 2.32 (m, 2H), 2.15 – 1.95 (m, 2H), 1.71 (m, 3H), 1.40 (m, 3H), 1.17 (m, 2H). (DMSO-d6, 400 MHz) |

FIG. 7 Continued

| | | | |
|---|---|---|---|
| 397 | 3-[5-[4-[[[(2R,5R)-5-[[4-[[(1R,2S)-6-hydroxy-2-phenyl-tetralin-1-yl]phenoxy]methyl]tetrahydrofuran-2-yl]methyl]piperazin-1-yl]-1-oxo-isoindolin-2-yl]piperidine-2,6-dione | A | δ 10.94 (s, 1H), 9.13 (s, 1H), 8.19 (s, 1H), 7.51 (d, J=8.7 Hz, 1H), 7.20 - 7.09 (m, 3H), 7.07 - 7.02 (m, 2H), 6.83 (d, J=7.2 Hz, 2H), 6.66 - 6.59 (m, 2H), 6.54 (d, J=8.8 Hz, 2H), 6.48 (m, 1H), 6.26 (d, J=8.4 Hz, 2H), 5.04 (m, 1H), 4.38 - 4.10 (m, 5H), 3.77 (d, J=4.4 Hz, 2H), 3.25 (d, J=5.2 Hz, 5H), 3.02 - 2.87 (m, 3H), 2.63 - 2.54 (m, 3H), 2.44 - 2.39 (m, 3H), 2.15 - 1.90 (m, 5H), 1.73 - 1.54 (m, 3H). (DMSO-d6, 400 MHz) |
| 398 | 3-[5-[4-[2-[3-[4-[[(1R,2S)-6-hydroxy-2-phenyl-tetralin-1-yl]phenoxy]cyclobutyl]ethyl]piperazin-1-yl]-1-oxo-isoindolin-2-yl]piperidine-2,6-dione | A | δ 10.96 (s, 1H), 10.17 (s, 1H), 9.14 (s, 1H), 7.59 (d, J=8.4 Hz, 1H), 7.24 - 7.07 (m, 5H), 6.81 (d, J=6.0 Hz, 2H), 6.69 - 6.57 (m, 2H), 6.52 - 6.36 (m, 3H), 6.25 (d, J=8.4 Hz, 2H), 5.06 (dd, J=5.2, 13.2 Hz, 1H), 4.73 - 4.60 (m, 1H), 4.40 - 4.31 (m, 1H), 4.27 - 4.20 (m, 1H), 4.17 (d, J=5.2 Hz, 1H), 4.01 (d, J=12.8 Hz, 2H), 3.58 (d, J=10.4 Hz, 2H), 3.25 - 2.84 (m, 11H), 2.63 - 2.54 (m, 2H), 2.42 - 2.36 (m, 1H), 2.27 - 2.19 (m, 1H), 2.17 - 2.04 (m, 4H), 2.01 - 1.83 (m, 2H), 1.75 - 1.66 (m, 1H). (DMSO-d6, 400 MHz) |
| 399 | 2-(2,6-dioxo-3-piperidyl)-5-[4-[5-[4-[2-(4-fluorophenyl)-6-hydroxy-1-methyl-3,4-dihydroisoquinolin-1-yl]phenoxy]pentyl]piperazin-1-yl]isoindoline-1,3-dione | A | δ 11.08 (s, 1H), 8.22 (s, 1H), 7.68 (d, J=8.5 Hz, 1H), 7.71 - 7.65 (m, 1H), 7.34 (d, J=1.8 Hz, 1H), 7.26 (d, J=7.9 Hz, 1H), 7.07 (d, J=8.8 Hz, 2H), 6.87 (t, J=8.8 Hz, 2H), 6.78 (d, J=8.8 Hz, 2H), 6.60 - 6.43 (m, 5H), 5.07 (dd, J=5.4, 12.8 Hz, 1H), 3.93 (br t, J=6.3 Hz, 2H), 3.33 - 3.15 (m, 11H), 3.09 - 3.00 (m, 1H), 2.95 - 2.84 (m, 1H), 2.78 (br d, J=16.2 Hz, 1H), 2.63 - 2.55 (m, 1H), 2.36 - 2.31 (m, 2H), 2.06 - 1.98 (m, 1H), 1.78 - 1.68 (m, 2H), 1.57 - 1.50 (m, 5H), 1.45 (br d, J=6.8 Hz, 2H). (DMSO-d6, 400 MHz) |

FIG. 7 Continued

| # | Name | | NMR |
|---|------|---|-----|
| 400 | 3-[6-[4-[5-[4-[2-(4-fluorophenyl)-6-hydroxy-1-methyl-3,4-dihydroisoquinolin-1-yl]phenoxy]pentyl]piperazin-1-yl]-1-oxo-isoindolin-2-yl]piperidine-2,6-dione | B | δ 10.95 (s, 1H), 8.20 (s, 1H), 7.52 (d, J=9.0 Hz, 1H), 7.09 - 7.03 (m, 4H), 6.87 (t, J=8.8 Hz, 2H), 6.77 (d, J=8.8 Hz, 2H), 6.60 - 6.49 (m, 4H), 6.48 - 6.43 (m, 1H), 5.05 (dd, J=5.1, 13.3 Hz, 1H), 4.33 (d, J=16.8 Hz, 1H), 4.26 - 4.15 (m, 1H), 3.93 (br t, J=6.3 Hz, 2H), 3.28 (br s, 8H), 3.24 - 3.17 (m, 2H), 3.06 - 2.99 (m, 1H), 2.90 (ddd, J=4.9, 13.1, 17.6 Hz, 1H), 2.78 (br d, J=15.9 Hz, 1H), 2.63 - 2.55 (m, 1H), 2.38 - 2.31 (m, 3H), 2.02 - 1.89 (m, 1H), 1.79 - 1.66 (m, 2H), 1.58 - 1.48 (m, 5H), 1.48 - 1.39 (m, 2H). (DMSO-d6, 400 MHz) |
| 401 | 3-[2-[4-[5-[4-[(1R,2S)-6-hydroxy-2-phenyl-tetralin-1-yl]phenoxy]pentyl]piperazin-1-yl]-5-oxo-7H-pyrrolo[3,4-b]pyridin-6-yl]piperidine-2,6-dione | A | δ 10.96 (s, 1H), 9.13 (br s, 1H), 8.16 (d, J=2.5 Hz, 1H), 7.77 (br d, J=6.7 Hz, 1H), 7.25 - 7.08 (m, 3H), 6.90 (br d, J=7.0 Hz, 1H), 6.83 (br d, J=7.0 Hz, 2H), 6.72 - 6.58 (m, 3H), 6.58 - 6.45 (m, 2H), 6.26 (br d, J=6.7 Hz, 2H), 5.08 (br d, J=10.9 Hz, 1H), 4.27 (br d, J=17.3 Hz, 1H), 4.18 (br s, 1H), 4.10 (br d, J=17.2 Hz, 1H), 3.81 (br s, 2H), 3.71 - 3.52 (m, 4H), 3.25 - 3.21 (m, 1H), 2.91 (s, 3H), 2.68 (br s, 1H), 2.47 - 2.41 (m, 4H), 2.41 - 2.21 (m, 3H), 2.08 (br s, 1H), 1.98 (br s, 1H), 1.67 (br d, J=7.8 Hz, 3H), 1.49 (br s, 2H), 1.39 (br d, J=5.3 Hz, 2H). (DMSO-d6, 400 MHz) |
| 402 | 3-[2-[4-[4,4-difluoro-5-[4-[(1R,2S)-6-hydroxy-2-phenyl-tetralin-1-yl]phenoxy]pentyl]piperazin-1-yl]-5-oxo-7H-pyrrolo[3,4-b]pyridin-6-yl]piperidine-2,6-dione | A | δ 10.96 (s, 1H), 9.18 (br s, 1H), 8.27 (s, 1H), 7.78 (d, J=8.9 Hz, 1H), 7.20 - 7.10 (m, 3H), 6.92 - 6.81 (m, 3H), 6.68 - 6.59 (m, 4H), 6.49 (dd, J=2.5, 8.3 Hz, 1H), 6.30 (d, J=8.7 Hz, 2H), 5.08 (dd, J=5.1, 13.4 Hz, 1H), 4.30 - 4.07 (m, 5H), 3.63 (br s, 4H), 3.04 - 2.86 (m, 4H), 2.76 - 2.64 (m, 1H), 2.57 - 2.53 (m, 4H), 2.46 - 2.30 (m, 3H), 2.18 - 1.93 (m, 4H), 1.72 (br d, J=7.3 Hz, 1H), 1.68 - 1.53 (m, 2H). (DMSO-d6, 400 MHz) |

FIG. 7 Continued

| | | | |
|---|---|---|---|
| 403 | 3-[5-[4-[5-[4-[(1R,2S)-6-hydroxy-2-phenyl-tetralin-1-yl]phenyl]sulfanylpentyl]piperazin-1-yl]-1-oxo-isoindolin-2-yl]piperidine-2,6-dione | A | δ 10.96 (s, 1H), 9.17 (s, 1H), 8.13 (s, 1H), 7.56 (d, J=8.3 Hz, 1H), 7.18 - 7.09 (m, 5H), 6.93 (d, J=8.3 Hz, 2H), 6.87 - 6.80 (m, 2H), 6.69 - 6.58 (m, 2H), 6.54 - 6.48 (m, 1H), 6.32 (d, J=8.3 Hz, 2H), 5.06 (dd, J=5.1, 13.3 Hz, 1H), 4.41 - 4.28 (m, 1H), 4.28 - 4.15 (m, 2H), 3.03 - 2.83 (m, 8H), 2.62 - 2.51 (m, 9H), 2.44 - 2.34 (m, 1H), 2.13 - 2.04 (m, 1H), 2.00 - 1.91 (m, 1H), 1.72 (br d, J=6.7 Hz, 1H), 1.62 - 1.46 (m, 4H), 1.44 - 1.33 (m, 1H), 1.43 - 1.32 (m, 1H). (DMSO-d6, 400 MHz) |
| 404 | 3-[5-[4-[5-fluoro-5-[[4-[(1R,2S)-6-hydroxy-2-p-henyl-tetralin-1-yl]phenoxy]methyl]-2,3,3a,4,6,6a-hexahydro-1H-pentalen-2-yl]piperazin-1-yl]-1-oxo-isoindolin-2-yl]piperidine-2,6-dione | A | δ 10.95 (s, 1H), 9.14 (s, 1H), 8.20 (s, 1H), 7.52 (d, J=9.2 Hz, 1H), 7.22 - 7.10 (m, 3H), 7.07 - 7.00 (m, 2H), 6.85 (br d, J=6.8 Hz, 2H), 6.67 - 6.60 (m, 2H), 6.57 (d, J=8.8 Hz, 2H), 6.49 (dd, J=2.6, 8.3 Hz, 1H), 6.28 (d, J=8.5 Hz, 2H), 5.05 (dd, J=5.2, 13.4 Hz, 1H), 4.39 - 4.15 (m, 3H), 4.01 - 3.87 (m, 2H), 3.27 (br s, 6H), 3.06 - 2.87 (m, 3H), 2.69 - 2.56 (m, 4H), 2.45 - 2.31 (m, 4H), 2.14 (br s, 3H), 2.05 - 1.91 (m, 3H), 1.90 - 1.78 (m, 2H), 1.73 (br s, 1H), 1.38 (br d, J=9.3 Hz, 2H). (DMSO-d6, 400 MHz) |
| 404 (cont) | | B | |
| 405 | 3-(6-(4-(5-(4-((1R,2S)-6-hydroxy-2-phenyl-1,2,3,4-tetrahydronaphthalen-1-yl)phenoxy)pentyl)piperazin-1-yl)-3-oxo-1H-pyrrolo[3,4-c]pyridin-2(3H)-yl)piperidine-2,6-dione | A | δ 11.02 - 10.94 (m, 1H), 11.00 - 10.93 (m, 1H), 10.97 (s, 1H), 8.45 (s, 1H), 8.23 (s, 1H), 7.17 - 7.10 (m, 3H), 6.96 (s, 1H), 7.02 - 6.92 (m, 1H), 6.82 (br d, J = 6.8 Hz, 2H), 6.65 - 6.59 (m, 2H), 6.54 - 6.46 (m, 3H), 6.25 (d, J = 8.4 Hz, 1H), 6.31 - 6.20 (m, 1H), 5.08 - 5.08 (m, 1H), 5.04 (dd, J = 5.2, 13.2 Hz, 1H), 4.41 - 4.13 (m, 3H), 3.82 - 3.80 (m, 1H), 3.60 (br s, 2H), 3.02 - 2.84 (m, 4H), 2.52 (br s, 4H), 2.42 (br s, 4H), 2.29 (br d, J = 7.6 Hz, 2H), 2.08 (br dd, J = 4.8, 12.7 Hz, 1H), 1.99 - 1.90 (m, 1H), 1.71 - 1.62 (m, 3H), 1.50 - 1.35 (m, 3H), 1.54 - 1.30 (m, 1H). (DMSO-d6, 400 MHz) |

FIG. 7 Continued

| | | | |
|---|---|---|---|
| 406 | 3-[5-[4-[5-[4-[6-hydroxy-2-(4-isopropylphenyl)-1-methyl-3,4-dihydroisoquinolin-1-yl]phenoxy]pentyl]piperazin-1-yl]-1-oxo-isoindolin-2-yl]piperidine-2,6-dione | B | δ 10.95 (s, 1H), 9.15 (s, 1H), 8.13 (s, 1H), 7.56 (d, J=8.2 Hz, 1H), 7.13 (br d, J=8.7 Hz, 4H), 6.89 (d, J=8.5 Hz, 2H), 6.78 (d, J=8.8 Hz, 2H), 6.56 - 6.43 (m, 5H), 5.06 (dd, J=5.1, 13.2 Hz, 1H), 4.42 - 4.29 (m, 1H), 4.27 - 4.18 (m, 1H), 3.94 (br t, J=6.1 Hz, 2H), 3.42 (br s, 3H), 3.25 (br s, 4H), 3.09 - 2.83 (m, 5H), 2.81 - 2.65 (m, 3H), 2.59 (br d, J=17.1 Hz, 2H), 2.45 - 2.34 (m, 1H), 2.02 - 1.91 (m, 1H), 1.81 - 1.60 (m, 4H), 1.55 (s, 3H), 1.47 (br d, J=7.2 Hz, 2H), 1.11 (dd, J=1.5, 6.9 Hz, 6H). (DMSO-d6, 400 MHz) |
| 411 | (3S)-3-[5-[4-[5-[4-[[1-[4-[(1R,2S)-6- hydroxy-2-phenyl-tetralin-1-yl]phenyl]-4-piperidyl]methyl]piperazin-1-yl]-1-oxo-isoindolin-2-yl]piperidine-2,6-dione | A | δ 10.93 (s, 1H), 9.09 (s, 1H), 7.51 (d, J=8.8 Hz, 1H), 7.18 - 7.09 (m, 3H), 7.08 - 7.02 (m, 2H), 6.83 (d, J=6.4 Hz, 2H), 6.64 (d, J=8.4 Hz, 1H), 6.60 (d, J=2.0 Hz, 1H), 6.53 (d, J=8.8 Hz, 2H), 6.48 (dd, J=2.4, 8.4 Hz, 1H), 6.20 (d, J=8.8 Hz, 2H), 5.04 (dd, J=5.2, 13.2 Hz, 1H), 4.39 - 4.27 (m, 1H), 4.24 - 4.15 (m, 1H), 4.12 (d, J=4.8 Hz, 1H), 3.51 (d, J=9.6 Hz, 2H), 3.29 - 3.24 (m, 5H), 3.03 - 2.83 (m, 3H), 2.62 - 2.54 (m, 4H), 2.52 (s, 3H), 2.41 - 2.36 (m, 1H), 2.19 (d, J=7.2 Hz, 2H), 2.15 - 2.08 (m, 1H), 2.00 - 1.89 (m, 1H), 1.81 - 1.58 (m, 4H), 1.22 - 1.06 (m, 2H). (DMSO-d6, 400 MHz) |
| 413 | (3R)-3-[5-[4-[5-[4-[[1-[4-[(1R,2S)-6-hydroxy-2- phenyl-tetralin-1-yl]phenyl]-4-piperidyl]methyl]piperazin-1-yl]-1-oxo-isoindolin-2-yl]piperidine-2,6-dione | A | δ 10.93 (s, 1H), 9.09 (s, 1H), 7.51 (d, J=8.8 Hz, 1H), 7.20 - 7.08 (m, 3H), 7.08 - 7.02 (m, 2H), 6.83 (d, J=6.4 Hz, 2H), 6.64 (d, J=8.4 Hz, 1H), 6.60 (d, J=2.4 Hz, 1H), 6.53 (d, J=8.8 Hz, 2H), 6.48 (dd, J=2.4, 8.4 Hz, 1H), 6.20 (d, J=8.8 Hz, 2H), 5.04 (dd, J=5.2, 13.2 Hz, 1H), 4.38 - 4.27 (m, 1H), 4.24 - 4.16 (m, 1H), 4.12 (d, J=4.8 Hz, 1H), 3.51 (d, J=10.0 Hz, 2H), 3.29 - 3.24 (m, 5H), 3.03 - 2.83 (m, 3H), 2.62 - 2.54 (m, 4H), 2.52 (s, 3H), 2.41 - 2.36 (m, 1H), 2.19 (d, J=7.2 Hz, 2H), 2.15 - 2.08 (m, 1H), 2.00 - 1.89 (m, 1H), 1.81 - 1.58 (m, 4H), 1.22 - 1.06 (m, 2H). (DMSO-d6, 400 MHz) |

FIG. 7 Continued

| | | | |
|---|---|---|---|
| 414 | 1,3-cis-3-(5-(4-(((3-(((4-(((1R,2S)-6-hydroxy-2-phenyl-1,2,3,4-tetrahydronaphthalen-1-yl)phenoxy)methyl)cyclobutyl)methyl)piperazin-1-yl)phenoxy)methyl)cyclobutyl)methyl)piperazin-1-yl)-1-oxoisoindolin-2-yl)piperidine-2,6-dione | A | δ 10.94 (s, 1H), 9.14 (s, 1H), 8.18 (s, 1H), 7.50 (d, J=8.9 Hz, 1H), 7.19 - 7.10 (m, 3H), 7.07 - 7.01 (m, 2H), 6.83 (d, J=6.7 Hz, 2H), 6.67 - 6.58 (m, 2H), 6.57 - 6.45 (m, 3H), 6.30 - 6.22 (m, 2H), 5.04 (dd, J=4.8, 12.9 Hz, 1H), 4.37 - 4.14 (m, 3H), 3.90 - 3.71 (m, 2H), 3.90 - 3.69 (m, 1H), 3.25 (s, 8H), 3.05 - 2.82 (m, 3H), 2.60 (s, 2H), 2.43 (s, 5H), 2.18 - 2.09 (m, 2H), 1.98 - 1.67 (m, 4H), 1.46 (d, J=9.5 Hz, 1H). (DMSO-d6, 400 MHz) |
| 415 | 1,3-trans-3-[5-[4-[[-3-[[4-[((1R,2S)-6-hydroxy-2-phenyl-1,2,3,4-tetrahydronaphthalen-1-yl]phenoxy]methyl]cyclobutyl]methyl]piperazin-1-yl]-1-oxoisoindolin-2-yl]piperidine-2,6-dione | A | δ 10.93 (s, 1H), 9.11 (s, 1H), 8.12 (s, 1H), 7.49 (d, J=8.9 Hz, 1H), 7.18 - 7.08 (m, 3H), 7.06 - 6.99 (m, 2H), 6.87 - 6.76 (m, 2H), 6.66 - 6.57 (m, 2H), 6.55 - 6.43 (m, 3H), 6.24 (dd, J=3.4, 8.7 Hz, 2H), 5.02 (dd, J=5.0, 13.2 Hz, 1H), 4.36 - 4.11 (m, 3H), 3.87 - 3.69 (m, 2H), 3.31 - 3.17 (m, 8H), 3.00 - 2.83 (m, 3H), 2.58 (s, 2H), 2.47 - 2.34 (m, 5H), 2.18 - 2.03 (m, 2H), 2.00 - 1.75 (m, 3H), 1.70 (s, 1H), 1.45 (d, J=10.8 Hz, 1H). (DMSO-d6, 400 MHz) |
| 419 | 3-[5-[4-[[1-[2-fluoro-4-[[(1R,2S)-6-hydroxy-2-phenyl-tetralin-1-yl]phenyl]-4-piperidyl]methyl]piperazin-1-yl]-1-oxo-isoindolin-2-yl]piperidine-2,6-dione | A | δ 10.95 (s, 1H), 8.18 (s, 0.9H, formate), 7.51 (d, J= 8.8 Hz, 1H), 7.20 - 7.12 (m, 3H), 7.06 - 7.04 (m, 2H), 6.86 (d, J=6.5 Hz, 2H), 6.67 - 6.61 (m, 3H), 6.49 (dd, J= 2.4, 8.4 Hz, 1H), 6.09 (dd, J= 1.6, 8.0 Hz, 1H), 5.96 (d, J= 14.4 Hz, 1H), 5.04 (dd, J= 5.2, 13.2 Hz, 1H), 4.32 (d, J=17.2 Hz, 1H), 4.22 - 4.17 (m, 2H), 3.34 - 3.11 (m, 13H), 3.00 - 2.87 (m, 3H), 2.60 - 2.54 (m, 1H), 2.43 - 2.35 (m, 1H), 2.20 (d, J= 6.8 Hz, 2H), 2.08 - 1.94 (m, 2H), 1.77 - 1.55 (m, 4H), 1.25 - 1.15 (m, 2H). (DMSO-d6, 400 MHz) |

FIG. 7 Continued

| | | | |
|---|---|---|---|
| 421 | 3-[5-[4-[[1-[5-[(1S,2S)-6-hydroxy-2-phenyl-tetralin-1-yl]-2-pyridyl]-4-piperidyl]methyl]piperazin-1-yl]-1-oxo-isoindolin-2-yl]piperidine-2,6-dione | B | δ 10.95 (s, 1H), 9.15 (s, 1H), 8.13 (s, 1H), 7.53 (d, J=8.4 Hz, 1H), 7.21 - 7.04 (m, 6H), 6.90 (d, J=7.0 Hz, 2H), 6.66 (d, J=8.5 Hz, 1H), 6.60 (s, 1H), 6.56 - 6.44 (m, 4H), 5.05 (dd, J=5.0, 13.3 Hz, 1H), 4.37 - 4.28 (m, 1H), 4.24 - 4.04 (m, 4H), 3.42 -3.23 (m, 10H), 3.03 - 2.77 (m, 3H), 2.65 - 2.57 (m, 2H), 2.56 - 2.52 (m, 1H), 2.46 - 2.21 (m, 2H), 2.19 - 1.92 (m, 2H), 1.72 (br d, J=12.2 Hz, 4H). (DMSO-d6, 400 MHz) |
| 423 | (3R)-3-[5-[4-[2-[1-[4-[(1R,2S)-6-hydroxy-2-phenyl-tetralin-1-yl]phenyl]-4-piperidyl]ethyl]piperazin-1-yl]-1-oxo-isoindolin-2-yl]piperidine-2,6-dione | A | δ 10.94 (s, 1H), 8.24 (s, 1H), 7.51 (d, J=8.8 Hz, 1H), 7.18 - 7.09 (m, 3H), 7.08 - 7.02 (m, 2H), 6.83 (d, J=6.8 Hz, 2H), 6.67 - 6.58 (m, 2H), 6.55 - 6.44 (m, 3H), 6.19 (d, J=8.4 Hz, 2H), 5.04 (m, 1H), 4.38 - 4.28 (m, 1H), 4.23 - 4.16 (m, 1H), 4.12 (d, J=4.5 Hz, 1H), 3.50 (s, 4H), 3.27 (s, 4H), 3.03 - 2.87 (m, 3H), 2.58 (d, J=14.8 Hz, 4H), 2.46 - 2.32 (m, 6H), 2.09 (s, 1H), 2.00 - 1.90 (m, 1H), 1.70 (d, J=12.4 Hz, 3H), 1.45 - 1.36 (m, 3H), 1.26 - 1.14 (m, 2H). (DMSO-d6, 400 MHz) |
| 425 | (3S)-3-[5-[4-[2-[1-[4-[(1R, 2S)-6-hydroxy-2-phenyl-tetralin-1-yl]phenyl]-4-piperidyl]ethyl]piperazin-1-yl]-1-oxo-isoindolin-2-yl]piperidine-2,6-dione | A | δ 10.94 (s, 1H), 9.10 (m, 1H), 8.15 (s, 1H), 7.51 (d, J=8.8 Hz, 1H), 7.21 - 7.04 (m, 5H), 6.83 (d, J=6.4 Hz, 2H), 6.67 - 6.46 (m, 6H), 6.19 (d, J=8.8 Hz, 2H), 5.04 (m, 1H), 4.38 - 4.11 (m, 3H), 3.49 (d, J=10.4 Hz, 2H), 3.29 (s, 6H), 3.00 - 2.83 (m, 3H), 2.60 (s, 4H), 2.47 - 2.32 (m, 6H), 2.14 - 2.04 (m, 1H), 1.99 - 1.90 (m, 1H), 1.70 (d, J=11.6 Hz, 3H), 1.46 - 1.35 (m, 3H), 1.25 - 1.13 (m, 2H). (DMSO-d6, 400 MHz) |

FIG. 7 Continued

| | | | |
|---|---|---|---|
| 426 | 3-[5-[[1-[[1-[4-[(1R,2S)-6-hydroxy-2-phenyl-tetralin-1-yl]phenyl]-4-piperidyl]methyl]-4-piperidyl]methoxy]-1-oxo-isoindolin-2-yl]piperidine-2,6-dione | A | δ 10.96 (s, 1 H) 8.17 (s, 2 H) 7.60 (d, J=8.41 Hz, 1 H) 7.08 - 7.18 (m, 4 H) 6.99 - 7.06 (m, 1 H) 6.83 (br d, J=8.16 Hz, 2 H) 6.63 (d, J=8.28 Hz, 1 H) 6.59 (s, 1 H) 6.47 - 6.55 (m, 3 H) 6.19 (d, J=8.66 Hz, 2 H) 5.06 (dd, J=13.36, 5.08 Hz, 1 H) 4.32 - 4.45 (m, 1 H) 4.20 - 4.30 (m, 1 H) 4.12 (br d, J=4.89 Hz, 1 H) 3.91 (br d, J=5.27 Hz, 3 H) 3.48 (br d, J=9.54 Hz, 2 H) 2.81 - 2.98 (m, 4 H) 2.58 - 2.62 (m, 1 H) 2.12 (br d, J=6.40 Hz, 6 H) 1.88 (br t, J=10.48 Hz, 3 H) 1.68 - 1.74 (m, 5 H) 1.58 (br s, 1 H) 1.30 (br d, J=10.54 Hz, 3 H) 1.06 - 1.19 (m, 3 H). (DMSO-d6, 400 MHz) |
| 427 | 3-[5-[4-[2-[3-[4-[(1R,2S)-6-hydroxy-2-phenyl-tetralin-1-yl]phenoxy]cyclobutyl]ethyl]piperazin-1-yl]-1-oxo-isoindolin-2-yl]piperidine-2,6-dione | A | δ 10.95 (s, 1H), 9.14 (s, 1H), 7.52 (d, J=8.4 Hz, 1H), 7.18 - 7.03 (m, 5H), 6.82 (d, J=6.8 Hz, 2H), 6.68 - 6.59 (m, 2H), 6.51 - 6.41 (m, 3H), 6.24 (d, J=8.8 Hz, 2H), 5.05 (dd, J=5.2, 13.2 Hz, 1H), 4.42 - 4.28 (m, 2H), 4.25 - 4.14 (m, 2H), 3.33 - 3.20 (m, 8H), 3.04 - 2.85 (m, 3H), 2.61 (br s, 2H), 2.45 - 2.34 (m, 2H), 2.24 (t, J=7.2 Hz, 2H), 2.15 - 1.80 (m, 4H), 1.70 (d, J=8.0 Hz, 1H), 1.59 (d, J=7.2 Hz, 4H). (DMSO-d6, 400 MHz) |
| 429 | 3-(2-(4-((1-(4-(4-((1R,2S)-6-hydroxy-2-phenyl-1,2,3,4-tetrahydronaphthalen-1-yl)phenyl)piperidin-4-yl)methyl)piperazin-1-yl)-5-oxo-5H-pyrrolo[3,4-b]pyridin-6(7H)-yl)piperidine-2,6-dione | A | δ 10.95 (s, 1H), 9.11 (br s, 1H), 8.15 (s, 1H), 7.76 (d, J=8.8 Hz, 1H), 7.19 - 7.08 (m, 3H), 6.89 (d, J=9.0 Hz, 1H), 6.83 (br d, J=6.7 Hz, 2H), 6.64 (d, J=8.4 Hz, 1H), 6.60 (d, J=2.3 Hz, 1H), 6.53 (d, J=8.8 Hz, 2H), 6.48 (dd, J=2.5, 8.3 Hz, 1H), 6.20 (d, J=8.7 Hz, 2H), 5.07 (dd, J=5.0, 13.4 Hz, 1H), 4.26 (d, J=17.4 Hz, 1H), 4.15 - 4.05 (m, 2H), 3.64 (br s, 4H), 3.51 (br d, J=10.9 Hz, 2H), 3.27 - 3.21 (m, 2H), 3.04 - 2.83 (m, 3H), 2.60 (br s, 1H), 2.46 - 2.35 (m, 6H), 2.18 (br d, J=7.0 Hz, 2H), 2.13 - 2.01 (m, 1H), 2.00 - 1.89 (m, 1H), 1.80 - 1.55 (m, 4H), 1.24 - 1.07 (m, 2H). (DMSO-d6, 400 MHz) |

FIG. 7 Continued

| | | | |
|---|---|---|---|
| 430 | 3-(2-(4-(2-(1-(4-((1R,2S)-6-hydroxy-2-phenyl-1,2,3,4-tetrahydronaphthalen-1-yl)phenyl)piperidin-4-yl)ethyl)piperazin-1-yl)-5-oxo-5H-pyrrolo[3,4-b]pyridin-6(7H)-yl)piperidine-2,6-dione | A | δ 10.95 (s, 1H), 8.21 (s, 2H), 7.77 (d, J=8.9 Hz, 1H), 7.20 - 7.09 (m, 3H), 6.90 (d, J=8.8 Hz, 1H), 6.84 (br d, J=6.5 Hz, 2H), 6.65 (d, J=8.4 Hz, 1H), 6.60 (d, J=2.3 Hz, 1H), 6.53 (d, J=8.7 Hz, 2H), 6.48 (dd, J=2.3, 8.1 Hz, 1H), 6.20 (d, J=8.7 Hz, 2H), 5.07 (dd, J=5.1, 13.2 Hz, 1H), 4.27 (d, J=17.4 Hz, 1H), 4.16 - 4.06 (m, 2H), 3.64 (br s, 4H), 3.50 (br d, J=12.2 Hz, 2H), 3.29 (br d, J=13.6 Hz, 2H), 3.03 - 2.84 (m, 3H), 2.64 - 2.54 (m, 1H), 2.44 (br s, 5H), 2.40 - 2.34 (m, 3H), 2.18 - 2.04 (m, 1H), 2.02 - 1.89 (m, 1H), 1.71 (br d, J=11.8 Hz, 3H), 1.41 (br s, 3H), 1.28 - 1.10 (m, 2H). (DMSO-d6, 400 MHz) |
| 432 | 3-[5-[4-[2-[1-[5-[(1S,2S)-6-hydroxy-2-phenyl-tetralin-1-yl]-2-pyridyl]-4-piperidyl]ethyl]piperazin-1-yl]-1-oxo-isoindolin-2-yl]piperidine-2,6-dione | A | δ 10.96 (s, 1H), 8.20 (s, 2H), 7.52 (d, J=8.9 Hz, 1H), 7.28 - 7.09 (m, 3H), 7.09 - 7.03 (m, 3H), 6.90 (br d, J=6.9 Hz, 2H), 6.67 (d, J=8.5 Hz, 1H), 6.63 - 6.60 (m, 1H), 6.55 - 6.43 (m, 3H), 5.05 (dd, J=5.1, 13.2 Hz, 1H), 4.33 (br d, J=17.1 Hz, 1H), 4.20 (br d, J=16.9 Hz, 1H), 4.12 (br d, J=4.8 Hz, 1H), 4.07 (br s, 2H), 3.51 (br s, 8H), 3.21 - 2.85 (m, 4H), 2.64 - 2.53 (m, 4H), 2.32 - 2.27 (m, 2H), 2.10 - 1.92 (m, 2H), 1.76 (br d, J=6.8 Hz, 1H), 1.67 (br d, J=11.9 Hz, 2H), 1.47 (br s, 1H), 1.45 - 1.33 (m, 2H), 1.15 - 0.95 (m, 2H). (DMSO-d6, 400 MHz) |
| 434 | 2-(2,6-dioxo-3-piperidyl)-5-[4-[2-[1-[5-[(1S,2S)-6-hydroxy-2-phenyl-tetralin-1-yl]-2-pyridyl]-4-piperidyl]ethyl]piperazin-1-yl]isoindoline-1,3-dione | B | δ 11.08 (s, 1H), 9.17 (s, 1H), 8.17 (s, 1H), 7.68 (d, J=8.4 Hz, 1H), 7.33 (s, 1H), 7.29 - 7.12 (m, 4H), 7.05 (d, J=1.9 Hz, 1H), 6.90 (br d, J=7.0 Hz, 2H), 6.67 (d, J=8.4 Hz, 1H), 6.61 (s, 1H), 6.57 - 6.42 (m, 3H), 5.07 (dd, J=5.3, 12.8 Hz, 1H), 4.13 (br d, J=4.9 Hz, 2H), 4.06 (br s, 2H), 3.26 - 3.04 (m, 8H), 3.02 - 2.84 (m, 5H), 2.64 - 2.52 (m, 4H), 2.30 - 2.20 (m, 1H), 2.02 (br d, J=5.8 Hz, 2H), 1.77 (br s, 1H), 1.67 (br d, J=12.9 Hz, 2H), 1.48 (br s, 1H), 1.39 (br d, J=6.9 Hz, 2H), 1.06 (br d, J=11.8 Hz, 2H). (DMSO-d6, 400 MHz) |

FIG. 7 Continued

| | | | |
|---|---|---|---|
| 436 | 2-(2,6-dioxo-3-piperidyl)-5-[[1-[[1-[4-[(1R,2S)-6-hydroxy-2-phenyl-tetralin-1-yl]phenyl]-4-piperidyl]methyl]-4-piperidyl]methoxy]isoindoline-1,3-dione | A | δ ppm 11.11 (s, 1 H) 8.90 - 9.41 (m, 1 H) 8.20 (s, 1 H) 7.82 (d, J=8.41 Hz, 1 H) 7.39 - 7.45 (m, 1 H) 7.42 (d, J=2.01 Hz, 1 H) 7.06 - 7.19 (m, 3 H) 6.83 (br d, J=6.53 Hz, 2 H) 6.57 - 6.68 (m, 2 H) 6.44 - 6.55 (m, 3 H) 6.19 (d, J=8.53 Hz, 2 H) 5.10 (s, 1 H) 4.12 (d, J=4.64 Hz, 1 H) 4.03 (br d, J=5.77 Hz, 2 H) 3.48 - 3.57 (m, 1 H) 2.80 - 3.00 (m, 5 H) 2.39 - 2.45 (m, 1 H) 2.38 - 2.46 (m, 3 H) 2.38 - 2.45 (m, 2 H) 2.00 - 2.17 (m, 4 H) 1.83 - 1.93 (m, 2 H) 1.65 - 1.78 (m, 6 H) 1.58 (br s, 1 H) 1.31 (br d, J=10.92 Hz, 2 H) 1.11 (br d, J=11.42 Hz, 2 H). (DMSO-d6, 400 MHz) |
| 437 | 3-[5-[4-[[(2R,5S)-5-[[4-[[(1R,2S)-6-hydroxy-2-phenyl-tetralin-1-yl]phenoxy]methyl]tetrahydrofuran-2-yl]methyl]piperazin-1-yl]-1-oxo-isoindolin-2-yl]piperidine-2,6-dione | A | δ 10.96 (s, 1H), 9.14 (s, 1H), 8.17 - 8.11 (m, 1H), 7.56 - 7.50 (m, 1H), 7.19 - 7.04 (m, 5H), 6.87 - 6.81 (m, 2H), 6.66 - 6.46 (m, 5H), 6.30 - 6.24 (m, 2H), 5.10 - 5.01 (m, 1H), 4.36 - 4.15 (m, 5H), 3.83 - 3.76 (m, 2H), 3.05 - 2.84 (m, 4H), 2.53 (br s, 11H), 2.43 - 2.30 (m, 1H), 2.11 - 1.94 (m, 4H), 1.74 - 1.53 (m, 3H). (DMSO-d6, 400 MHz) B |
| 438 | 3-[5-[4-[[(2R,5S)-5-[[4-[[(1R,2S)-6- hydroxy-2-phenyl-tetralin-1-yl]phenoxy]methyl]tetrahydrofuran-2-yl]methyl]piperazin-1-yl]-1-oxo-isoindolin-2-yl]piperidine-2,6-dione | A | δ = 10.96 (s, 1H), 9.14 (d, J=2.8 Hz, 1H), 7.68 - 7.47 (m, 1H), 7.20 - 7.06 (m, 5H), 6.84 (d, J=6.8 Hz, 2H), 6.67 - 6.59 (m, 2H), 6.55 (d, J=8.7 Hz, 2H), 6.48 (dd, J=2.3, 8.2 Hz, 1H), 6.28 (d, J=8.4 Hz, 2H), 5.06 (dd, J=4.9, 13.2 Hz, 1H), 4.41 - 4.11 (m, 5H), 3.90 - 3.80 (m, 2H), 3.09 (s, 4H), 3.03 - 2.86 (m, 4H), 2.64 - 2.52 (m, 5H), 2.47 - 2.34 (m, 2H), 2.20 - 2.01 (m, 3H), 2.00 - 1.90 (m, 1H), 1.81 - 1.65 (m, 2H), 1.63 - 1.51 (m, 1H). (DMSO-d6, 400 MHz) |

FIG. 7 Continued

| | | | |
|---|---|---|---|
| 439 | 3-[5-[4-[[(2S,5S)-5-[[4-[[(1R,2S)-6-hydroxy-2-phenyl-tetralin-1-yl]phenoxy]methyl]tetrahydrofuran-2-yl]methyl]piperazin-1-yl]methyl]piperazin-1-yl]-1-oxo-isoindolin-2-yl]piperidine-2,6-dione | A | δ = 10.96 (s, 1H), 9.15 (s, 1H), 7.56 (d, J=8.4 Hz, 1H), 7.20 - 7.04 (m, 5H), 6.84 (d, J=7.2 Hz, 2H), 6.67 - 6.59 (m, 2H), 6.56 (d, J=8.8 Hz, 2H), 6.48 (dd, J=2.1, 8.4 Hz, 1H), 6.28 (d, J=8.4 Hz, 2H), 5.15 - 4.96 (m, 1H), 5.06 (dd, J=5.2, 13.2 Hz, 1H), 4.41 - 4.09 (m, 5H), 3.84 (s, 2H), 3.30 - 3.08 (m, 5H), 3.03 - 2.80 (m, 4H), 2.59 (d, J=17.6 Hz, 5H), 2.45 - 2.31 (m, 2H), 2.16 - 1.89 (m, 4H), 1.80 - 1.50 (m, 3H). (DMSO-d6, 400 MHz) |
| 440 | 3-[5-[4-[[6-[[4-[[(1R,2S)-6-hydroxy-2-phenyl-tetralin-1-yl]phenoxy]methyl]pyridazin-3-yl]methyl]piperazin-1-yl]-1-oxo-isoindolin-2-yl]piperidine-2,6-dione | A | δ 10.93 (br s, 1H), 9.16 (br s, 1H), 8.40 (s, 1H), 7.77 (q, J=8.7 Hz, 2H), 7.52 (d, J=8.5 Hz, 1H), 7.17 - 7.09 (m, 3H), 7.08 - 7.02 (m, 2H), 6.82 (br d, J=6.5 Hz, 2H), 6.70 - 6.59 (m, 4H), 6.48 (dd, J=2.3, 8.3 Hz, 1H), 6.30 (d, J=8.7 Hz, 2H), 5.24 (s, 2H), 5.04 (dd, J=5.0, 13.4 Hz, 1H), 4.35 - 4.27 (m, 1H), 4.23 - 4.15 (m, 2H), 3.87 (s, 2H), 3.29 (br s, 5H), 3.04 - 2.82 (m, 3H), 2.58 (br s, 5H), 2.39 (br dd, J=4.8, 13.3 Hz, 1H), 2.14 - 2.01 (m, 1H), 1.99 - 1.90 (m, 1H), 1.72 (br s, 1H). (DMSO-d6, 400 MHz) |
| 441 | 2-(2,6-dioxo-3-piperidyl)-5-[4-[[1-[5-[[(1S,2S)-6-hydroxy-2-phenyl-tetralin-1-yl]-2-pyridyl]-4-piperidyl]methyl]piperazin-1-yl]isoindoline-1,3-dione | B | δ 11.08 (s, 1 H) 8.16 (s, 1 H) 7.67 (d, J=8.53 Hz, 1 H) 7.32 (s, 1 H) 7.22 - 7.26 (m, 1 H) 7.12 - 7.21 (m, 3 H) 7.05 (d, J=2.01 Hz, 1 H) 6.89 (br d, J=7.03 Hz, 2 H) 6.66 (d, J=8.41 Hz, 1 H) 6.60 (d, J=2.26 Hz, 1 H) 6.47 - 6.52 (m, 2 H) 6.42 - 6.46 (m, 1 H) 5.06 (dd, J=12.86, 5.33 Hz, 1 H) 4.04 - 4.15 (m, 3 H) 3.51 - 3.58 (m, 8 H) 2.82 - 3.04 (m, 3 H) 2.61 (br d, J=6.02 Hz, 2 H) 2.52 - 2.57 (m, 3 H) 2.16 (br d, J=6.27 Hz, 2 H) 1.97 - 2.08 (m, 2 H) 1.71 (br d, J=11.04 Hz, 4 H) 1.02 (br d, J=11.04 Hz, 2 H). (DMSO-d6, 400 MHz) |

FIG. 7 Continued

| | | | |
|---|---|---|---|
| 442 | (3R)-3-[5-[4-[[1-[4-[[(1R,2S)-6-hydroxy-2-phenyl-tetralin-1-yl]phenyl]-4-piperidyl]methyl]piperazin-1-yl]-1-oxo-isoindolin-2-yl]-3-methyl-piperidine-2,6-dion | C | δ 10.81 (s, 1H), 8.15 (s, 2H), 7.43 (d, J=8.5 Hz, 1H), 7.18 - 7.02 (m, 5H), 6.84 (br d, J=6.7 Hz, 2H), 6.65 (d, J=7.9 Hz, 1H), 6.60 (s, 1H), 6.56 - 6.46 (m, 3H), 6.20 (d, J=8.5 Hz, 2H), 4.63 - 4.44 (m, 2H), 4.13 (br d, J=4.8 Hz, 1H), 3.77 - 3.48 (m, 2H), 3.40 - 3.35 (m, 8H), 3.14 - 2.86 (m, 2H), 2.82 - 2.58 (m, 3H), 2.55 - 2.52 (m, 4H), 2.45 - 2.28 (m, 1H), 2.20 (br d, J=6.9 Hz, 2H), 2.11 (br dd, J=6.1, 12.2 Hz, 1H), 1.96 - 1.80 (m, 1H), 1.75 (br d, J=14.2 Hz, 3H), 1.63 (s, 5H), 1.30 - 1.08 (m, 2H). (DMSO-d6, 400 MHz) |
| 444 | 3-[5-[7-[[1-[4-[[(1R,2S)-6-hydroxy-2-phenyl-tetralin-1-yl]phenyl]-4-piperidyl]methyl]-2,7-diazaspiro[3.5]nonan-2-yl]-1-oxo-isoindolin-2-yl]piperidine-2,6-dione | A | δ 10.93 (s, 1H), 9.12 (s, 1H), 8.20 (s, 1H), 7.47 (d, J=8.3 Hz, 1H), 7.19 - 7.08 (m, 3H), 6.83 (br d, J=6.5 Hz, 2H), 6.64 (d, J=8.4 Hz, 1H), 6.59 (d, J=2.1 Hz, 1H), 6.55 - 6.44 (m, 5H), 6.19 (d, J=8.7 Hz, 2H), 5.02 (dd, J=5.0, 13.2 Hz, 1H), 4.35 - 4.24 (m, 1H), 4.18 (s, 1H), 4.14 - 4.11 (m, 1H), 3.62 (s, 3H), 3.56 - 3.51 (m, 5H), 3.03 - 2.82 (m, 3H), 2.61 - 2.53 (m, 1H), 2.39 - 2.25 (m, 6H), 2.11 (br d, J=6.9 Hz, 3H), 1.98 - 1.91 (m, 1H), 1.78 - 1.66 (m, 7H), 1.58 (br s, 1H), 1.19 - 1.02 (m, 2H). (DMSO-d6, 400 MHz) |
| 448 | 3-[5-[4-[[5-[4-[[(1R,2S)-6-hydroxy-2-phenyl-tetralin-1-yl]phenoxy]methyl]-2-pyridyl]methyl]piperazin-1-yl]-1-oxo-isoindolin-2-yl]piperidine-2,6-dione | A | δ 10.95 (s, 1H), 9.14 (s, 1H), 8.54 (s, 1H), 7.81 (dd, J=1.7, 8.0 Hz, 1H), 7.53 (br d, J=8.5 Hz, 1H), 7.49 (br d, J=8.0 Hz, 1H), 7.20 - 7.03 (m, 5H), 6.84 (br d, J=6.8 Hz, 2H), 6.68 - 6.61 (m, 4H), 6.50 (d, J=8.5 Hz, 1H), 6.30 (d, J=8.7 Hz, 2H), 5.08 - 4.96 (m, 3H), 4.39 - 4.27 (m, 1H), 4.26 - 4.16 (m, 2H), 3.68 (br s, 2H), 3.35 - 3.25 (m, 4H), 3.04 - 2.85 (m, 3H), 2.63 - 2.53 (m, 5H), 2.45 - 2.25 (m, 2H), 2.22 - 2.01 (m, 1H), 2.01 - 1.88 (m, 1H), 1.86 - 1.65 (m, 1H). (DMSO-d6, 400 MHz) |

FIG. 7 Continued

| 450 | 3-[5-[4-[[1-[4-[(1S,2R)-2-(4-fluorophenyl)-6-hydroxy-tetralin-1-yl]phenyl]-4-piperidyl]methyl]piperazin-1-yl]-1-oxo-isoindolin-2-yl]piperidine-2,6-dione | A | δ 10.95 (s, 1H), 9.25 - 8.99 (m, 1H), 8.16 (s, 1H), 7.56 - 7.43 (m, 1H), 7.09 - 7.02 (m, 2H), 7.09 - 7.02 (m, 1H), 7.00 - 6.93 (m, 2H), 6.88 - 6.80 (m, 2H), 6.64 (d, J=8.4 Hz, 1H), 6.61 - 6.53 (m, 3H), 6.50 - 6.45 (m, 1H), 6.21 (d, J=8.4 Hz, 2H), 5.04 (dd, J=5.2, 13.2 Hz, 1H), 4.40 - 4.15 (m, 1H), 4.10 (d, J=4.4 Hz, 1H), 3.69 - 3.59 (m, 1H), 3.29 - 3.28 (m, 4H), 3.00 - 2.84 (m, 4H), 2.63 - 2.53 (m, 5H), 2.45 - 2.36 (m, 3H), 2.18 - 1.91 (m, 4H), 1.88 - 1.53 (m, 4H), 1.23 - 1.10 (m, 2H). (DMSO-d6, 400 MHz) |
| --- | --- | --- | --- |
| 452 | 3-[5-[4-[[1-[3-[(1R,2S)-6-hydroxy-2-phenyl-tetralin-1-yl]phenyl]-4-piperidyl]methyl]piperazin-1-yl]-1-oxo-isoindolin-2-yl]piperidine-2,6-dione | C | δ 10.95 (s, 1H), 9.13 (s, 1H), 7.52 (d, J=8.8 Hz, 1H), 7.19 - 7.03 (m, 5H), 6.88 - 6.81 (m, 3H), 6.68 (d, J=8.4 Hz, 1H), 6.61 (d, J=2.4 Hz, 1H), 6.57 (dd, J=1.6, 8.4 Hz, 1H), 6.49 (dd, J=2.4, 8.2 Hz, 1H), 5.86 (d, J=7.6 Hz, 1H), 5.82 (s, 1H), 5.05 (dd, J=5.2, 13.2 Hz, 1H), 4.38 - 4.28 (m, 1H), 4.24 - 4.13 (m, 2H), 3.33 - 3.26 (m, 6H), 3.21 - 3.10 (m, 2H), 3.04 - 2.84 (m, 3H), 2.63 - 2.56 (m, 1H), 2.52 - 2.51 (m, 2H), 2.43 - 2.30 (m, 3H), 2.29 - 2.23 (m, 1H), 2.19 - 2.04 (m, 3H), 2.00 - 1.91 (m, 1H), 1.76 - 1.54 (m, 4H), 1.17 - 0.95 (m, 2H). (DMSO-d6, 400 MHz) |
| 454 | 3-[5-[4-[2-[1-[3-[(1R,2S)-6-hydroxy-2-phenyl-tetralin-1-yl]phenyl]-4-piperidyl]ethyl]piperazin-1-yl]-1-oxo-isoindolin-2-yl]piperidine-2,6-dione | A | δ 10.95 (s, 1H), 9.12 (s, 1H), 7.52 (d, J=8.8 Hz, 1H), 7.19 - 7.02 (m, 5H), 6.89 - 6.79 (m, 3H), 6.67 (d, J=8.4 Hz, 1H), 6.61 (d, J=2.4 Hz, 1H), 6.58 - 6.53 (m, 1H), 6.49 (dd, J=2.4, 8.4 Hz, 1H), 5.86 (d, J=7.6 Hz, 1H), 5.81 (s, 1H), 5.05 (dd, J=5.2, 13.2 Hz, 1H), 4.37 - 4.28 (m, 1H), 4.25 - 4.13 (m, 2H), 3.32 - 3.24 (m, 6H), 3.14 (t, J=11.6 Hz, 2H), 3.03 - 2.82 (m, 3H), 2.66 - 2.57 (m, 1H), 2.57 - 2.52 (m, 4H), 2.39 - 2.33 (m, 3H), 2.25 (t, J=11.2 Hz, 1H), 2.17 - 2.08 (m, 1H), 2.01 - 1.89 (m, 1H), 1.77 - 1.66 (m, 1H), 1.61 (d, J=12.0 Hz, 2H), 1.46 - 1.26 (m, 3H), 1.19 - 0.96 (m, 2H). (DMSO-d6, 400 MHz) |

FIG. 7 Continued

| | | | |
|---|---|---|---|
| 456 | 3-(5-(4-((1-(2,6-difluoro-4-((1R,2S)-6-hydroxy-2-phenyl-1,2,3,4-tetrahydronaphthalen-1-yl)phenyl)piperidin-4-yl)methyl)piperazin-1-yl)-1-oxoisoindolin-2-yl)piperidine-2,6-dione | A | δ 10.93 (s, 1H), 8.18 (s, 1H), 7.51 (d, J = 8.4 Hz, 1H), 7.23 - 7.13 (m, 3H), 7.08 - 7.02 (m, 2H), 6.90 (br d, J = 7.6 Hz, 2H), 6.68 (d, J = 8.4 Hz, 1H), 6.62 (s, 1H), 6.52 (br d, J = 8.4 Hz, 1H), 5.87 (d, J = 10.8 Hz, 2H), 5.04 (dd, J = 5.2, 13.2 Hz, 1H), 4.36 - 4.16 (m, 3H), 3.26 - 3.19 (m, 7H), 3.07 - 2.83 (m, 9H), 2.19 (br d, J = 6.8 Hz, 3H), 2.00 (br d, J = 18.8 Hz, 3H), 1.81 - 1.56 (m, 5H), 1.16 (br d, J = 9.2 Hz, 2H). (DMSO-d6, 400 MHz) |
| 458 | 5-(4-((1-(2,6-difluoro-4-((1R,2S)-6-hydroxy-2-phenyl-1,2,3,4-tetrahydronaphthalen-1-yl)phenyl)piperidin-4-yl)methyl)piperazin-1-yl)-2-(2,6-dioxopiperidin-3-yl)isoindoline-1,3-dione | B | δ 11.07 (s, 1H), 9.22 (s, 1H), 8.14 (s, 1H), 7.67 (d, J = 8.4 Hz, 1H), 7.33 (s, 1H), 7.26 - 7.16 (m, 4H), 6.90 (d, J = 7.2 Hz, 2H), 6.68 (d, J = 8.4 Hz, 1H), 6.62 (s, 1H), 6.52 (s, 1H), 5.87 (d, J=10.8 Hz, 2H), 5.06 (dd, J = 5.2, 13.2 Hz, 1H), 4.22 (d, J = 4.4 Hz, 1H), 3.47 - 3.39 (m, 1H), 3.03 - 2.86 (m, 6H), 2.52 (br s, 10H), 2.19 (br d, J = 7.2 Hz, 2H), 2.07 - 1.97 (m, 2H), 1.78 - 1.61 (m, 4H), 1.16 (br d, J = 10.8 Hz, 2H). (DMSO-d6, 400 MHz) |
| 460 | 3-(2-(4-((1-(2,6-difluoro-4-((1R,2S)-6-hydroxy-2-phenyl-1,2,3,4-tetrahydronaphthalen-1-yl)phenyl)piperidin-4-yl)methyl)piperazin-1-yl)-5-oxo-5H-pyrrolo[3,4-b]pyridin-6(7H)-yl)piperidine-2,6-dione | A | δ 10.94 (s, 1H), 8.16 (s, 1H), 7.76 (d, J = 8.8 Hz, 1H), 7.23 - 7.12 (m, 3H), 6.92 - 6.87 (m, 3H), 6.68 (d, J = 8.4 Hz, 1H), 6.62 (s, 1H), 6.52 (dd, J = 2.8, 8.4 Hz, 1H), 5.87 (d, J = 10.8 Hz, 2H), 5.06 (dd, J = 5.2, 13.2 Hz, 1H), 4.30 - 4.19 (m, 2H), 4.09 (d, J = 17.2 Hz, 1H), 2.46 - 2.34 (m, 6H), 2.18 (br d, J = 6.4 Hz, 2H), 2.06 - 1.92 (m, 2H), 1.78 - 1.60 (m, 4H), 1.16 (br d, J = 9.6 Hz, 2H). (DMSO-d6, 400 MHz) |

FIG. 7 Continued

| | | | |
|---|---|---|---|
| 461 | 3-[6-[4-[[1-[4-[(1R,2S)-6-hydroxy-2-phenyl-tetralin-1-yl]phenyl]-4-piperidyl]methyl]piperazin-1-yl]-3-oxo-1H-pyrrolo[3,4-c]pyridin-2-yl]piperidine-2,6-dione | A | δ 10.97 (br s, 1H), 9.13 (br s, 1H), 8.45 (br s, 1H), 8.20 (br s, 1H), 7.13 (br s, 3H), 6.96 (br s, 1H), 6.83 (br d, J=4.6 Hz, 2H), 6.67 - 6.58 (m, 2H), 6.56 - 6.44 (m, 3H), 6.19 (br d, J=7.2 Hz, 2H), 5.04 (br d, J=8.9 Hz, 1H), 4.42 - 4.31 (m, 1H), 4.27 - 4.19 (m, 1H), 4.12 (br s, 1H), 3.61 (br s, 6H), 3.00 - 2.85 (m, 4H), 2.63 - 2.57 (m, 2H), 2.42 (br s, 6H), 2.16 (br s, 3H), 1.95 (br s, 1H), 1.79 - 1.61 (m, 4H), 1.14 (br d, J=11.0 Hz, 2H). (DMSO-d6, 400 MHz) |
| 463 | 3-[5-[4-[[1-[5-[(1S,2S)-6-hydroxy-2-phenyl-tetralin-1-yl]pyrimidin-2-yl]-4-piperidyl]methyl]piperazin-1-yl]-1-oxo-isoindolin-2-yl]piperidine-2,6-dione | B | δ 10.94 (s, 1H), 9.19 (s, 1H), 8.14 (s, 1H), 7.51 (d, J=8.4 Hz, 1H), 7.29 - 7.12 (m, 5H), 7.08 - 6.92 (m, 4H), 6.70 (d, J=8.4 Hz, 1H), 6.61 (d, J=2.0 Hz, 1H), 6.56 - 6.49 (m, 1H), 5.04 (dd, J=5.2, 13.2 Hz, 1H), 4.45 (d, J=11.6 Hz, 2H), 4.37 - 4.28 (m, 1H), 4.25 - 4.16 (m, 1H), 4.11 (d, J=4.8 Hz, 1H), 3.31 - 3.19 (s, 7H), 3.04 - 2.84 (m, 3H), 2.80 - 2.54 (m, 4H), 2.43 - 2.30 (m, 2H), 2.22 - 2.13 (m, 2H), 2.06 - 1.91 (m, 2H), 1.84 - 1.66 (m, 4H), 1.04 - 0.87 (m, 2H). (DMSO-d6, 400 MHz) |
| 465 | 3-[5-[4-[7-[4-[(1R,2S)-6-hydroxy-2-phenyl-tetralin-1-yl]phenyl]-7-azaspiro[3.5]nonan-2-yl]piperazin-1-yl]-1-oxo-isoindolin-2-yl]piperidine-2,6-dione | B | δ 10.94 (s, 1H), 9.13 (br s, 1H), 8.14 (s, 1H), 7.52 (d, J=9.0 Hz, 1H), 7.18 - 7.03 (m, 5H), 6.83 (br d, J=6.5 Hz, 2H), 6.67 - 6.57 (m, 2H), 6.57 - 6.45 (m, 3H), 6.20 (br d, J=8.5 Hz, 2H), 5.04 (dd, J=5.0, 13.1 Hz, 1H), 4.39 - 4.28 (m, 1H), 4.26 - 4.16 (m, 1H), 4.12 (br d, J=4.8 Hz, 1H), 3.31 - 3.13 (m, 2H), 3.13 - 2.84 (m, 9H), 2.81 - 2.67 (m, 2H), 2.61 (br s, 1H), 2.40 (br s, 5H), 2.31 - 2.03 (m, 1H), 2.02 - 1.90 (m, 3H), 1.70 (br d, J=6.3 Hz, 1H), 1.65 - 1.48 (m, 6H). (DMSO-d6, 400 MHz) |

FIG. 7 Continued

| 467 | 3-[5-[4-[7-[4-[(1R,2S)-6-hydroxy-2-phenyl-tetralin-1-yl]phenyl]-7-azaspiro[3.5]nonan-2-yl]piperazin-1-yl]-1-oxo-isoindolin-2-yl]piperidine-2,6-dione | A | δ 10.95 (s, 1H), 9.13 (br s, 1H), 8.14 (s, 1H), 7.78 (d, J=8.8 Hz, 1H), 7.19 - 7.07 (m, 3H), 6.91 (br d, J=8.9 Hz, 1H), 6.83 (br d, J=6.7 Hz, 2H), 6.64 (d, J=8.7 Hz, 1H), 6.62 - 6.59 (m, 1H), 6.57 - 6.45 (m, 3H), 6.20 (br d, J=8.5 Hz, 2H), 5.06 (br dd, J=5.0, 13.2 Hz, 1H), 4.27 (br d, J=17.4 Hz, 1H), 4.16 - 3.87 (m, 2H), 3.87 - 3.60 (m, 2H), 2.96 (br s, 5H), 2.89 (br s, 4H), 2.73 (br s, 2H), 2.68 (br s, 1H), 2.45 - 2.26 (m, 5H), 2.23 - 2.02 (m, 1H), 2.02 - 1.85 (m, 3H), 1.70 (br d, J=7.2 Hz, 1H), 1.59 (br s, 4H), 1.53 (br s, 2H). (DMSO-d6, 400 MHz) |
| --- | --- | --- | --- |
| 468 | 3-(5-(4-((1-(2,6-difluoro-4-((1S,2R)-6-hydroxy-2-phenyl-1,2,3,4-tetrahydronaphthalen-1-yl)phenyl)piperidin-4-yl)ethyl)piperazin-1-yl)-1-oxoisoindolin-2-yl)piperidine-2,6-dione | C | δ 10.93 (s, 1H), 8.16 (s, 1H), 7.51 (d, J = 8.4 Hz, 1H), 7.23 - 7.13 (m, 3H), 7.08 - 7.02 (m, 2H), 6.90 (br d, J = 7.6 Hz, 2H), 6.68 (d, J = 8.4 Hz, 1H), 6.62 (s, 1H), 6.52 (br d, J = 8.4 Hz, 1H), 5.87 (d, J = 10.8 Hz, 2H), 5.04 (dd, J = 5.2, 13.2 Hz, 1H), 4.36 - 4.16 (m, 3H), 3.26 - 2.67 (m, 9H), 2.65 - 2.49 (m, 10H), 2.33-2.32(m,2H),2.05-1.75 (m, 2H), 1.65 - 1.56 (m, 3H), 1.41-1.37 (m,2H), 1.21-1.16 (m, 2H). (DMSO-d6, 400 MHz) |
| 469 | 3-(5-(4-((1-(2,6-difluoro-4-((1R,2S)-6-hydroxy-2-phenyl-1,2,3,4-tetrahydronaphthalen-1-yl)phenyl)piperidin-4-yl)ethyl)piperazin-1-yl)-1-oxoisoindolin-2-yl)piperidine-2,6-dione | B | δ 10.93 (s, 1H), 8.16 (s, 1H), 7.51 (d, J = 8.4 Hz, 1H), 7.23 - 7.13 (m, 3H), 7.08 - 7.02 (m, 2H), 6.90 (br d, J = 7.6 Hz, 2H), 6.68 (d, J = 8.4 Hz, 1H), 6.62 (s, 1H), 6.52 (br d, J = 8.4 Hz, 1H), 5.87 (d, J = 10.8 Hz, 2H), 5.04 (dd, J = 5.2, 13.2 Hz, 1H), 4.36 - 4.16 (m, 3H), 3.26 - 2.67 (m, 9H), 2.65 - 2.49 (m, 10H), 2.33-2.32(m,2H),2.05-1.75 (m, 2H), 1.65 - 1.56 (m, 3H), 1.41-1.37 (m,2H), 1.21-1.16 (m, 2H). (DMSO-d6, 400 MHz) |

FIG. 7 Continued

| | | | |
|---|---|---|---|
| 471 | 3-[5-[4-[2-[1-[2-fluoro-4-[(1R,2S)-6-hydroxy-2-phenyl-tetralin-1-yl]phenyl]-4-piperidyl]ethyl]piperazin-1-yl]-1-oxo-isoindolin-2-yl]piperidine-2,6-dione | A | δ 10.93 (s, 1H), 8.16 (s, 1H), 7.51 (d, J= 8.8 Hz, 1H), 7.19 - 7.11 (m, 3H), 7.06 - 7.04 (m, 2H), 6.87 - 6.85 (m, 2H), 6.67 - 6.61 (m, 3H), 6.49 (dd, J= 2.4, 8.4 Hz, 1H), 6.09 (dd, J= 1.6, 8.0 Hz, 1H), 5.96 (dd, J= 1.6, 10.4 Hz, 1H), 5.04 (dd, J= 5.2, 13.2 Hz, 1H), 4.34 - 4.30 (m, 1H), 4.22 - 4.17 (m, 2H), 3.33 - 3.16 (m, 11H), 3.02 - 2.85 (m, 3H), 2.60 - 2.54 (m, 1H), 2.45 - 2.35 (m, 4H), 2.08 - 1.94 (m, 2H), 1.75 - 1.70 (m, 3H), 1.44 - 1.21 (m, 5H). (DMSO-d6, 400 MHz) |
| 472 | 3-[6-[4-[2-[1-[4-[(1R,2S)-6-hydroxy-2-phenyl-tetralin-1-yl]phenyl]-4-piperidyl]ethyl]piperazin-1-yl]-3-oxo-1H-pyrrolo[3,4-c]pyridin-2-yl]piperidine-2,6-dione | B | δ 10.96 (br s, 1H), 9.15 (br s, 1H), 8.45 (br s, 1H), 8.16 (br s, 1H), 7.12 (br s, 3H), 6.99 - 6.78 (m, 3H), 6.61 (br d, J=11.4 Hz, 2H), 6.51 (br s, 3H), 6.20 (br s, 2H), 5.02 (br s, 1H), 4.42 - 4.30 (m, 1H), 4.28 - 4.18 (m, 1H), 4.11 (br s, 1H), 3.60 (br s, 1H), 3.30 - 3.07 (m, 8H), 2.94 (br s, 5H), 2.64 (br s, 5H), 2.35 (br d, J=13.7 Hz, 1H), 2.13 - 1.92 (m, 2H), 1.69 (br s, 3H), 1.40 (br s, 3H), 1.19 (br s, 2H). (DMSO-d6, 400 MHz) |
| 474 | 3-[2-[4-[[1-[2-fluoro-4-[(1R,2S)-6-hydroxy-2-phenyl-tetralin-1-yl]phenyl]-4-piperidyl]methyl]piperazin-1-yl]-5-oxo-7H-pyrrolo[3,4-b]pyridin-6-yl]piperidine-2,6-dione | A | δ 10.91 (s, 1H), 9.12 (s, 1H), 8.13 (s, 1H), 7.74 (d, J=8.8 Hz, 1H), 7.21 - 7.06 (m, 3H), 6.90 - 6.79 (m, 3H), 6.69 - 6.58 (m, 3H), 6.48 (dd, J=2.2, 8.3 Hz, 1H), 6.08 (d, J=8.3 Hz, 1H), 5.95 (d, J=14.3 Hz, 1H), 5.04 (dd, J=5.1, 13.2 Hz, 1H), 4.32 - 4.01 (m, 3H), 3.62 (s, 4H), 3.17 (d, J=9.4 Hz, 3H), 3.01 - 2.82 (m, 3H), 2.67 - 2.52 (m, 1H), 2.45 - 2.29 (m, 7H), 2.17 (d, J=7.2 Hz, 2H), 2.09 - 1.89 (m, 2H), 1.78 - 1.56 (m, 4H), 1.27 - 1.12 (m, 2H). (DMSO-d6, 400 MHz) |

FIG. 7 Continued

| | | | |
|---|---|---|---|
| 476 | 3-[2-[4-[[1-[4-[(1R,2S)-2-(4-fluorophenyl)-6-hydroxy-tetralin-1-yl]phenyl]-4-piperidyl]methyl]piperazin-1-yl]-5-oxo-7H-pyrrolo[3,4-b]pyridin-6-yl]piperidine-2,6-dione | A | δ 10.94 (s, 1H), 8.14 (s, 1H), 7.76 (d, J=8.9 Hz, 1H), 7.01 - 6.93 (m, 2H), 6.92 - 6.79 (m, 3H), 6.64 (d, J=8.4 Hz, 1H), 6.60 - 6.53 (m, 3H), 6.47 (dd, J=2.4, 8.4 Hz, 1H), 6.21 (d, J=8.8 Hz, 2H), 5.06 (dd, J=5.2, 13.2 Hz, 1H), 4.26 (d, J=17.6 Hz, 1H), 4.14 - 4.03 (m, 2H), 3.70 - 3.52 (m, 3H), 3.00 - 2.87 (m, 4H), 2.60 (s, 1H), 2.53 (d, J=7.2 Hz, 5H), 2.43 (s, 5H), 2.37 (d, J=4.0 Hz, 1H), 2.18 (d, J=7.2 Hz, 2H), 2.08 (td, J=6.1, 12.2 Hz, 1H), 1.96 (dd, J=4.8, 10.4 Hz, 1H), 1.77 (s, 1H), 1.76 - 1.56 (m, 4H), 1.24 - 1.06 (m, 2H). (DMSO-d6, 400 MHz) |
| 478 | 3-[4,6-difluoro-5-[4-[[1-[4-[(1R,2S)-2-(4-fluorophenyl)-6-hydroxy-tetralin-1-yl]phenyl]-4-piperidyl]methyl]piperazin-1-yl]-1-oxo-isoindolin-2-yl]piperidine-2,6-dione | B | δ 10.97 (s, 1H), 8.21 (s, 1H), 7.37 (d, J=9.6 Hz, 1H), 6.99 - 6.90 (m, 2H), 6.87 - 6.78 (m, 2H), 6.65 - 6.51 (m, 4H), 6.45 (dd, J=2.0, 8.4 Hz, 1H), 6.19 (d, J=8.4 Hz, 2H), 5.05 (dd, J=5.2, 13.2 Hz, 1H), 4.51 - 4.40 (m, 1H), 4.33 - 4.25 (m, 1H), 4.08 (d, J=4.8 Hz, 1H), 3.49 (d, J=12.0 Hz, 1H), 3.19 (s, 11H), 3.00 - 2.81 (m, 4H), 2.61 - 2.53 (m, 2H), 2.40 - 2.34 (m, 1H), 2.17 (d, J=7.2 Hz, 2H), 2.10 - 1.91 (m, 2H), 1.77 - 1.55 (m, 4H), 1.23 - 1.05 (m, 2H). (DMSO-d6, 400 MHz) |
| 480 | 3-[2-[3-[[1-[4-[(1R,2S)-6-hydroxy-2-phenyl-tetralin-1-yl]phenyl]-4-piperidyl]methylamino]pyrrolidin-1-yl]-5-oxo-7H-pyrrolo[3,4-b]pyridin-6-yl]piperidine-2,6-dione | A | δ 10.94 (s, 1H), 9.12 (s, 1H), 8.38 - 8.08 (m, 1H), 7.72 (d, J=8.7 Hz, 1H), 7.27 - 7.03 (m, 3H), 6.82 (d, J=6.5 Hz, 2H), 6.63 (d, J=8.3 Hz, 1H), 6.59 (d, J=2.3 Hz, 1H), 6.55 - 6.43 (m, 4H), 6.19 (d, J=8.7 Hz, 2H), 5.05 (dd, J=4.9, 13.3 Hz, 1H), 4.24 (d, J=17.3 Hz, 1H), 4.15 - 4.02 (m, 2H), 3.61 (br s, 1H), 3.03 - 2.81 (m, 3H), 2.69 - 2.58 (m, 1H), 2.52 (d, J=1.9 Hz, 5H), 2.48 - 2.41 (m, 5H), 2.37 (br d, J=4.3 Hz, 1H), 2.36 - 2.27 (m, 1H), 2.10 (br d, J=6.4 Hz, 2H), 1.97 - 1.63 (m, 6H), 1.46 (br s, 1H), 1.20 - 1.05 (m, 2H). (DMSO-d6, 400 MHz) |

FIG. 7 Continued

| | | | |
|---|---|---|---|
| 481 | 3-[5-[4-[[1-[4-[((1S,2R)-6-hydroxy-2-(4-methoxyphenyl)tetralin-1-yl]phenyl]-4-piperidyl]methyl]piperazin-1-yl]-1-oxo-isoindolin-2-yl]piperidine-2,6-dione | C | B |
| 482 | 3-[5-[4-[[1-[4-[((1R,2S)-6-hydroxy-2-(4-methoxyphenyl)tetralin-1-yl]phenyl]-4-piperidyl]methyl]piperazin-1-yl]-1-oxo-isoindolin-2-yl]piperidine-2,6-dione | A | B | δ 10.95 (s, 1H), 8.25 (s, 1H), 7.52 (d, J=8.8 Hz, 1H), 7.09 - 7.02 (m, 2H), 6.76 - 6.70 (m, 4H), 6.64 (d, J=8.4 Hz, 1H), 6.60 (d, J=2.3 Hz, 1H), 6.56 (d, J=8.8 Hz, 2H), 6.48 (dd, J=2.4, 8.3 Hz, 1H), 6.23 (d, J=8.7 Hz, 2H), 5.05 (dd, J=5.1, 13.2 Hz, 1H), 4.36 - 4.29 (m, 1H), 4.24 - 4.17 (m, 1H), 4.09 (d, J=4.6 Hz, 1H), 3.69 (s, 3H), 3.38 - 3.17 (m, 13H), 3.03 - 2.82 (m, 3H), 2.60 (br d, J=2.6 Hz, 1H), 2.43 - 2.35 (m, 1H), 2.20 (br d, J=7.2 Hz, 2H), 2.12 - 1.91 (m, 2H), 1.76 (br d, J=12.5 Hz, 2H), 1.66 (br d, J=10.9 Hz, 2H), 1.25 - 1.10 (m, 2H). (DMSO-d6, 400 MHz) |
| 483 | 3-(4-fluoro-5-(4-((1-(4-((1S,2R)-2-(4-fluorophenyl)-6-hydroxy-1,2,3,4-tetrahydronaphthalen-1-yl)phenyl)piperidin-4-yl)methyl)piperazin-1-yl)-1-oxoisoindolin-2-yl)piperidine-2,6-dione | C | A | δ 10.97 (s, 1H), 8.16 (s, 1H), 7.47 (d, J = 8.0 Hz, 1H), 7.15 (t, J = 8.0 Hz, 1H), 7.00 - 6.92 (m, 2H), 6.88 - 6.80 (m, 2H), 6.66 - 6.53 (m, 4H), 6.48 (dd, J = 2.4, 8.4 Hz, 1H), 6.21 (d, J = 8.8 Hz, 2H), 5.07 (dd, J = 5.2, 13.2 Hz, 1H), 4.48 (d, J = 16.8 Hz, 1H), 4.31 (d, J = 16.8 Hz, 1H), 4.10 (br d, J = 4.8 Hz, 1H), 3.13 (br s, 3H), 3.04 - 2.83 (m, 3H), 2.58 (br d, J = 16.8 Hz, 2H), 2.52 (br d, J = 2.0 Hz, 6H), 2.49 - 2.34 (m, 4H), 2.20 (br d, J = 6.8 Hz, 2H), 2.13 - 1.92 (m, 2H), 1.79 - 1.56 (m, 4H), 1.21 - 1.09 (m, 2H). (DMSO-d6, 400 MHz) |

FIG. 7 Continued

| # | Name | | NMR |
|---|---|---|---|
| 484 | 3-[5-(4-{[1-(4-{(1R,2S)-2-(4-fluorophenyl)-6-hydroxy-1,2,3,4-tetrahydronaphthalen-1-yl]phenyl)piperidin-4-yl]methyl}piperazin-1-yl)-1-oxoisoindolin-2-yl)piperidine-2,6-dione | A | δ 10.97 (s, 1H), 8.17 (s, 1H), 7.47 (d, J = 8.0 Hz, 1H), 7.15 (t, J = 8.0 Hz, 1H), 7.01 - 6.91 (m, 2H), 6.87 - 6.80 (m, 2H), 6.65 - 6.54 (m, 4H), 6.48 (dd, J = 2.4, 8.4 Hz, 1H), 6.21 (d, J = 8.4 Hz, 2H), 5.07 (dd, J = 5.2, 13.2 Hz, 1H), 4.48 (d, J = 16.8 Hz, 1H), 4.31 (d, J = 16.8 Hz, 1H), 4.10 (br d, J = 4.8 Hz, 1H), 3.13 (br s, 3H), 3.02 - 2.83 (m, 3H), 2.58 (br d, J = 17.2 Hz, 2H), 2.52 (br d, J = 1.6 Hz, 6H), 2.48 - 2.34 (m, 4H), 2.20 (br d, J = 7.2 Hz, 2H), 2.10 - 1.93 (m, 2H), 1.78 - 1.60 (m, 4H), 1.20 - 1.10 (m, 2H). (DMSO-d6, 400 MHz) |
| 485 | 3-[6-[4-[[1-[4-[(1R,2S)-6-hydroxy-2-phenyl-tetralin-1-yl]phenyl]-4-piperidyl]methyl]piperazin-1-yl]-1-oxoisoindolin-2-yl]piperidine-2,6-dione | B | δ 11.06 - 10.87 (m, 1H), 8.25 (s, 1H), 7.49 - 7.36 (m, 1H), 7.25 (dd, J=2.4, 8.4 Hz, 1H), 7.19 - 7.07 (m, 4H), 6.87 - 6.79 (m, 2H), 6.68 - 6.57 (m, 2H), 6.52 (d, J=8.8 Hz, 2H), 6.47 (dd, J=2.4, 8.4 Hz, 1H), 6.19 (d, J=8.8 Hz, 2H), 5.09 (dd, J=5.2, 13.2 Hz, 1H), 4.39 - 4.27 (m, 1H), 4.24 - 4.15 (m, 1H), 4.12 (d, J=4.8 Hz, 1H), 3.60 - 3.45 (m, 2H), 3.26 (d, J=4.4 Hz, 3H), 3.18 (s, 6H), 2.97 - 2.84 (m, 3H), 2.60 (d, J=2.4 Hz, 2H), 2.44 - 2.34 (m, 2H), 2.27 - 2.13 (m, 3H), 2.12 - 1.96 (m, 2H), 1.80 - 1.61 (m, 4H), 1.20 - 1.05 (m, 2H). (DMSO-d6, 400 MHz) |
| 486 | 3-[5-[(3S)-3-[[1-[4-[(1R,2S)-6-hydroxy-2-phenyl-tetralin-1-yl]phenyl]-4-piperidyl]methylamino]pyrrolidin-1-yl]-1-oxoisoindolin-2-yl]piperidine-2,6-dione | A | δ 10.93 (s, 1H), 9.44 - 8.73 (m, 1H), 8.21 (s, 1H), 7.47 (d, J=9.2 Hz, 1H), 7.18 - 7.08 (m, 3H), 6.82 (d, J=6.4 Hz, 2H), 6.66 - 6.57 (m, 4H), 6.55 - 6.44 (m, 3H), 6.19 (d, J=8.7 Hz, 2H), 5.02 (dd, J=5.2, 13.4 Hz, 1H), 4.35 - 4.24 (m, 1H), 4.21 - 4.08 (m, 2H), 3.55 - 3.45 (m, 1H), 3.32 - 3.30 (m, 4H), 3.10 (br s, 2H), 2.98 - 2.82 (m, 3H), 2.60 (br s, 3H), 2.47 - 2.41 (m, 3H), 2.41 - 2.34 (m, 1H), 2.11 (dt, J=6.3, 12.7 Hz, 2H), 1.98 - 1.65 (m, 6H), 1.46 (br s, 1H), 1.23 - 1.09 (m, 2H). (DMSO-d6, 400 MHz) |

FIG. 7 Continued

| | | | |
|---|---|---|---|
| 487 | 3-[5-[(3R)-3-[[1-[4-[(1R,2S)-6-hydroxy-2-phenyl-tetralin-1-yl]phenyl]-4-piperidyl]methylamino]pyrrolidin-1-yl]-1-oxo-isoindolin-2-yl]piperidine-2,6-dione | A | δ 10.93 (br s, 1H), 9.60 - 8.62 (m, 1H), 8.20 (s, 1H), 7.47 (d, J=9.0 Hz, 1H), 7.18 - 7.07 (m, 3H), 6.82 (d, J=6.5 Hz, 2H), 6.67 - 6.57 (m, 4H), 6.56 - 6.43 (m, 3H), 6.19 (d, J=8.7 Hz, 2H), 5.02 (dd, J=5.0, 13.3 Hz, 1H), 4.36 - 4.24 (m, 1H), 4.20 - 4.08 (m, 2H), 3.48 (br s, 1H), 3.36 - 3.33 (m, 4H), 3.16 - 3.04 (m, 2H), 3.04 - 2.81 (m, 4H), 2.59 (br d, J=3.1 Hz, 1H), 2.52 (br s, 3H), 2.47 - 2.41 (m, 2H), 2.41 - 2.33 (m, 1H), 2.21 - 2.03 (m, 2H), 1.96 - 1.63 (m, 5H), 1.47 (br s, 1H), 1.25 - 1.08 (m, 2H). (DMSO-d6, 400 MHz) |
| 488 | 3-(5-(4-((1-(4-((1R,2S)-6-hydroxy-2-phenyl-1,2,3,4-tetrahydronaphthalen-1-yl)phenyl)piperidin-4-yl)methyl)piperazin-1-yl)-1-oxoisoindolin-2-yl)-1-methylpiperidine-2,6-dione | | δ 7.74 (d, J=8.7 Hz, 1H), 7.22 - 7.12 (m, 3H), 6.99 (br d, J=8.9 Hz, 1H), 6.90 - 6.78 (m, 4H), 6.71 (d, J=2.4 Hz, 1H), 6.63 - 6.55 (m, 3H), 6.29 (d, J=8.5 Hz, 2H), 5.17 (dd, J=5.0, 13.4 Hz, 1H), 4.42 - 4.35 (m, 1H), 4.29 - 4.22 (m, 1H), 4.21 (d, J=4.9 Hz, 1H), 3.57 (br s, 2H), 3.42 - 3.25 (m, 5H), 3.19 (s, 3H), 3.12 - 2.93 (m, 3H), 2.90 - 2.76 (m, 1H), 2.71 - 2.48 (m, 6H), 2.34 - 2.12 (m, 5H), 1.90 - 1.76 (m, 3H), 1.40 - 1.15 (m, 3H). (DMSO-d6, 400 MHz) |
| | | C | |
| 490 | 3-[5-[4-[[4-hydroxy-1-[4-[(1R,2S)-6-hydroxy-2-phenyl-tetralin-1-yl]phenyl]-4-piperidyl]methyl]piperazin-1-yl]-1-oxo-isoindolin-2-yl]piperidine-2,6-dione | A | δ 10.94 (s, 1H), 9.07 (s, 1H), 7.52 (br d, J = 7.8 Hz, 1H), 7.21 - 7.01 (m, 5H), 6.84 (br d, J = 7.0 Hz, 2H), 6.68 - 6.56 (m, 2H), 6.46 (br d, J = 8.0 Hz, 1H), 6.35 - 6.05 (m, 4H), 5.75 (s, 1H), 5.04 (br d, J = 9.8 Hz, 1H), 4.38 - 4.28 (m, 1H), 4.25 - 4.16 (m, 1H), 4.10 (br s, 1H), 3.27 (br s, 8H), 3.23 - 2.74 (m, 8H), 2.63 - 2.57 (m, 2H), 2.40 - 2.28 (m, 1H), 2.24 - 1.38 (m, 8H). (DMSO-d6, 400 MHz) |

FIG. 7 Continued

| | | | |
|---|---|---|---|
| 491 | 3-[5-[4-[[1-[4-[[(1R,2S)-6-hydroxy-2-phenyl-tetralin-1-yl]phenyl]-4-methyl-4-piperidyl]methyl]piperazin-1-yl]-1-oxo-isoindolin-2-yl]piperidine-2,6-dione | A | δ 10.94 (br s, 1H), 9.10 (br s, 1H), 8.28 (s, 1H), 7.52 (d, J=8.5 Hz, 1H), 7.20 - 7.03 (m, 5H), 6.86 (d, J=7.5 Hz, 2H), 6.65 - 6.58 (m, 2H), 6.47 (dd, J=2.4, 8.3 Hz, 1H), 6.20 - 6.08 (m, 4H), 5.04 (dd, J=5.1, 13.2 Hz, 1H), 4.33 (d, J=16.9 Hz, 1H), 4.21 (d, J=16.9 Hz, 1H), 4.10 (br d, J=4.5 Hz, 1H), 3.29 - 3.24 (m, 8H), 3.20 - 3.10 (m, 2H), 3.02 - 2.84 (m, 5H), 2.70 - 2.65 (m, 1H), 2.46 - 2.31 (m, 4H), 2.17 - 2.04 (m, 1H), 2.02 - 1.89 (m, 1H), 1.82 - 1.55 (m, 5H), 1.02 (s, 3H). (DMSO-d6, 400 MHz) |
| 592 | 3-(5-(4-((6-(4-(((1R,2S)-6-hydroxy-2-phenyl-1,2,3,4-tetrahydronaphthalen-1-yl)phenyl)piperazin-1-yl)-6-azaspiro[3.4]octan-2-yl)methyl)piperazin-1-yl)-1-oxoisoindolin-2-yl)piperidine-2,6-dione | A | δ 10.93 (s, 1H), 9.08 (br s, 1H), 8.22 (s, 1H), 7.51 (d, J=8.9 Hz, 1H), 7.20 - 7.09 (m, 3H), 7.07 - 6.97 (m, 2H), 6.85 (br d, J=6.9 Hz, 2H), 6.64 - 6.58 (m, 2H), 6.46 (br d, J=8.3 Hz, 1H), 6.18 - 6.06 (m, 4H), 5.04 (dd, J=4.8, 13.2 Hz, 1H), 4.36 - 4.28 (m, 1H), 4.36 - 4.28 (m, 1H), 4.36 - 4.28 (m, 1H), 4.24 - 4.15 (m, 1H), 4.10 (br s, 1H), 3.25 (br s, 8H), 3.17 - 2.99 (m, 5H), 2.98 - 2.84 (m, 3H), 2.60 (br s, 1H), 2.43 - 2.36 (m, 3H), 2.21 - 1.91 (m, 6H), 1.84 (br t, J=6.8 Hz, 1H), 1.74 - 1.63 (m, 3H). (DMSO-d6, 400 MHz) |
| 493 | 3-(2-(4-((6-(4-(((1R,2S)-6-hydroxy-2-phenyl-1,2,3,4-tetrahydronaphthalen-1-yl)phenyl)piperazin-1-yl)-6-azaspiro[3.4]octan-2-yl)methyl)piperazin-1-yl)-5-oxo-5H-pyrrolo[3,4-b]pyridin-6(7H)-yl)piperidine-2,6-dione | A | δ 10.95 (s, 1H), 8.18 (s, 1H), 7.75 (d, J=8.8 Hz, 1H), 7.21 - 7.07 (m, 1H), 7.21 - 7.07 (m, 2H), 6.92 - 6.81 (m, 3H), 6.64 - 6.57 (m, 2H), 6.46 (br d, J=8.3 Hz, 1H), 6.21 - 6.04 (m, 4H), 5.07 (dd, J=5.1, 13.4 Hz, 1H), 4.26 (d, J=17.4 Hz, 1H), 4.14 - 4.05 (m, 2H), 3.61 (br s, 4H), 3.26 (br d, J=12.8 Hz, 2H), 3.15 (br d, J=3.8 Hz, 1H), 3.11 - 3.03 (m, 2H), 3.00 (br d, J=3.7 Hz, 1H), 2.97 - 2.85 (m, 3H), 2.60 (br s, 1H), 2.42 - 2.36 (m, 6H), 2.16 - 1.91 (m, 6H), 1.83 (br t, J=6.7 Hz, 1H), 1.74 - 1.62 (m, 3H). (DMSO-d6, 400 MHz) |

FIG. 7 Continued

| | | | |
|---|---|---|---|
| 494 | 1,2-cis-3-[5-[4-[[1-[4-[2-(4-fluorophenyl)-6-hydroxy-tetralin-1-yl]phenyl]-4-hydroxy-4-piperidyl]methyl]piperazin-1-yl]-1-oxo-isoindolin-2-yl]piperidine-2,6-dione | A | δ 10.95 (s, 1H), 9.10 (s, 1H), 7.52 (d, J=8.8 Hz, 1H), 7.12 - 7.03 (m, 2H), 6.98 (m, 2H), 6.90 - 6.83 (m, 2H), 6.65 - 6.55 (m, 2H), 6.46 (m, 1H), 6.22 - 6.08 (m, 3H), 6.24 - 6.04 (m, 1H), 5.04 (m, 2H), 4.38 - 4.16 (m, 2H), 4.07 (d, J=4.8 Hz, 1H), 3.29 - 2.89 (m, 12H), 2.63 - 2.54 (m, 7H), 2.10 - 1.63 (m, 8H). (DMSO-d6, 400 MHz) |
| 496 | 3-[5-[4-[[1-[3-fluoro-4-[(1S,2S)-6-hydroxy-2-phenyl-tetralin-1-yl]phenyl]-4-piperidyl]methyl]piperazin-1-yl]-1-oxo-isoindolin-2-yl]piperidine-2,6-dione | A | δ 10.94 (s, 1H, imide), 9.14 (br s, 1H, phenol), 8.20 (s, 0.45H, formate), 7.52 (d, J=8.8 Hz, 1H), 7.08 - 7.03 (m, 5 H), 6.83 (m, 2H), 6.62 (m, 2H), 6.58 - 6.42 (m, 3H), 6.26 (br d, J=13.68 Hz, 1 H), 5.04 (dd, J=13.36, 5.08 Hz, 1H), 4.45 (br d, J=5.02 Hz, 1H), 4.33 (d, J=16.8 Hz, 1H), 4.20 (d, J=16.8 Hz, 1H), 3.63 - 3.50 (m, 2H), 3.29 - 3.21 (m, 9H), 3.03 – 2.84 (m, 3H), 2.60 (br, 3H), 2.40 - 2.35 (m, 1H), 2.19 (br d, J=6.7 Hz, 3H), 2.01 – 1.91 (m, 1H), 1.79 - 1.64 (m, 4H), 1.20 - 1.07 (m, 2H). (DMSO-d6, 400 MHz) |
| 497 | 3-[5-[4-[[1-[4-[(1R,2S)-6-hydroxy-2-phenyl-tetralin-1-yl]phenyl]-4-piperidyl]methylamino]-1-piperidyl]-1-oxo-isoindolin-2-yl]piperidine-2,6-dione | A | δ 10.95 (br s, 1H), 8.30 (s, 1H), 7.50 (br d, J=8.3 Hz, 1H), 7.19 - 7.01 (m, 5H), 6.82 (br d, J=6.7 Hz, 2H), 6.69 - 6.57 (m, 2H), 6.56 - 6.40 (m, 3H), 6.19 (br d, J=8.2 Hz, 2H), 5.03 (br dd, J=4.8, 13.2 Hz, 1H), 4.37 - 4.26 (m, 1H), 4.23 - 4.10 (m, 2H), 3.86 (br d, J=11.8 Hz, 2H), 3.28 (br d, J=12.7 Hz, 2H), 3.04 - 2.77 (m, 7H), 2.69 - 2.54 (m, 5H), 2.40 - 2.28 (m, 2H), 2.17 - 2.03 (m, 1H), 1.94 (br d, J=9.5 Hz, 3H), 1.75 (br d, J=11.9 Hz, 3H), 1.59 - 1.33 (m, 3H), 1.26 - 1.10 (m, 2H). (DMSO-d6, 400 MHz) |

FIG. 7 Continued

| | | | |
|---|---|---|---|
| 499 | 3-[2-[4-[[1-[3-fluoro-4-[[(1S,2S)-6-hydroxy-2-phenyl-tetralin-1-yl]phenyl]-4-piperidyl]methyl]piperazin-1-yl]-5-oxo-7H-pyrrolo[3,4-b]pyridin-6-yl]piperidine-2,6-dione | A | δ 10.95 (s, 1 H), 8.98 - 9.30 (m, 1 H), 8.18 (s, 1 H), 7.77 (d, J=8.91 Hz, 1 H), 7.03 - 7.19 (m, 3 H), 6.90 (d, J=9.03 Hz, 1 H), 6.76 - 6.86 (m, 2 H), 6.58 - 6.65 (m, 2 H), 6.43 - 6.56 (m, 3 H), 6.26 (br d, J=15.56 Hz, 1 H), 5.07 (dd, J=13.11, 5.08 Hz, 1 H), 4.45 (d, J=5.40 Hz, 1 H), 4.27 (d, J=17.44 Hz, 1 H), 4.10 (d, J=17.32 Hz, 1 H), 3.62 - 3.67 (m, 4 H), 3.57 - 3.61 (m, 2 H), 2.84 - 3.04 (m, 5 H), 2.57 - 2.64 (m, 2 H), 2.35 - 2.47 (m, 5 H), 2.12 - 2.23 (m, 3 H), 1.92 - 2.01 (m, 1 H), 1.65 - 1.82 (m, 4 H), 1.06 - 1.21 (m, 2 H). (DMSO-d6, 400 MHz) |
| 500 | 3-[5-[4-[[1-[4-[[(1R,2S)-6-hydroxy-2-phenyl-tetralin-1-yl]phenyl]-4-piperidyl]amino]-1-piperidyl]-1-oxo-isoindolin-2-yl]piperidine-2,6-dione | A | δ 10.93 (br s, 1H), 8.26 (s, 1H), 7.50 (d, J=8.4 Hz, 1H), 7.19 - 7.09 (m, 3H), 7.08 - 7.01 (m, 2H), 6.83 (br d, J=7.2 Hz, 2H), 6.67 - 6.58 (m, 2H), 6.57 - 6.45 (m, 3H), 6.20 (br d, J=8.2 Hz, 2H), 5.03 (dd, J=4.9, 13.3 Hz, 1H), 4.35 - 4.27 (m, 1H), 4.23 - 4.12 (m, 2H), 3.85 (br d, J=12.2 Hz, 2H), 3.40 - 3.38 (m, 2H), 3.04 - 2.80 (m, 8H), 2.69 - 2.53 (m, 4H), 2.40 - 2.28 (m, 1H), 2.18 - 2.01 (m, 1H), 1.99 - 1.80 (m, 5H), 1.71 (br s, 1H), 1.36 (br t, J=10.8 Hz, 4H). (DMSO-d6, 400 MHz) |
| 501 | 3-[5-[4-[[4-fluoro-1-[4-[[(1R,2S)-6-hydroxy-2-p-henyl-tetralin-1-yl]phenyl]-4-piperidyl]methyl]piperazin-1-yl]-1-oxo-isoindolin-2-yl]piperidine-2,6-dione | B | δ 7.92 (br s, 1H), 7.67 (d, J=8.4 Hz, 1H), 7.14 - 7.03 (m, 3H), 6.93 (br d, J=8.8 Hz, 1H), 6.81 (s, 1H), 6.78 - 6.71 (m, 3H), 6.63 (d, J=2.4 Hz, 1H), 6.50 (br d, J=8.4 Hz, 1H), 6.23 - 6.17 (m, 2H), 6.14 - 6.08 (m, 2H), 5.13 (dd, J=5.2, 13.1 Hz, 1H), 5.17 - 5.07 (m, 1H), 4.38 - 4.30 (m, 1H), 4.23 - 4.09 (m, 2H), 3.45 - 3.20 (m, 10H), 3.03 - 2.90 (m, 2H), 2.87 - 2.68 (m, 2H), 2.64 - 2.49 (m, 6H), 2.33 - 1.83 (m, 8H), 1.72 (br d, J=11.6 Hz, 1H). (CDCl3, 400 MHz) |

FIG. 7 Continued

| | | | |
|---|---|---|---|
| 502 | 3-[2-[4-[4-fluoro-1-[4-[(1R,2S)-6-hydroxy-2-phenyl-tetralin-1-yl]phenyl]-4-piperidyl]methyl]piperazin-1-yl]-5-oxo-7H-pyrrolo[3,4-b]pyridin-6-yl]piperidine-2,6-dione | B | δ 7.93 (br s, 1H), 7.79 (d, J=8.8 Hz, 1H), 7.15 - 7.01 (m, 3H), 6.81 - 6.71 (m, 3H), 6.65 - 6.55 (m, 2H), 6.50 (br d, J=8.4 Hz, 1H), 6.25 - 6.16 (m, 2H), 6.15 - 6.06 (m, 2H), 5.13 (dd, J=5.2, 13.2 Hz, 1H), 4.30 - 4.17 (m, 1H), 4.16 - 4.07 (m, 2H), 3.64 (br s, 4H), 3.39 - 3.18 (m, 4H), 3.02 - 2.67 (m, 4H), 2.61 - 2.44 (m, 6H), 2.31 - 1.84 (m, 7H), 1.72 (br d, J=10.8 Hz, 1H), 1.66 - 1.59 (m, 2H). (CDCl3, 400 MHz) |
| 503 | 3-[5-[4-[[1-[4-[(1R,2S)-6-hydroxy-2-phenyl-tetralin-1-yl]phenyl]-4-piperidyl]methyl]piperazin-1-yl]-3-methyl-1-oxo-isoindolin-2-yl]piperidine-2,6-dione | A | δ 1.12 - 1.27 (m, 2H), 1.33 - 1.48 (m, 3H), 1.56 - 1.84 (m, 4H), 1.89 - 2.16 (m, 2H), 2.16 - 2.24 (m, 2H), 2.52 - 2.64 (m, 8H), 2.73 - 3.04 (m, 3H), 3.22 - 3.31 (m, 5H), 3.45 - 3.56 (m, 2H), 4.13 (d, J = 4.4 Hz, 1H), 4.49 - 4.71 (m, 2H), 6.20 (d, J=8.8 Hz, 2H), 6.45 - 6.58 (m, 3H), 6.58 - 6.69 (m, 2H), 6.81-6.86 (m, 2H), 6.99 - 7.04 (m, 1H), 7.07 - 7.20 (m, 4H), 7.42 - 7.49 (m, 1H), 9.14 (br s, 1H), 10.76 - 10.98 (m, 1H). (DMSO-d6, 400 MHz) |
| 505 | 3-(6-(4-(2-(1-(4-((1R,2S)-6-hydroxy-2-phenyl-1,2,3,4-tetrahydronaphthalen-1-yl)phenyl)piperidin-4-yl)ethyl)piperazin-1-yl)-1-oxoisoindolin-2-yl)piperidine-2,6-dione | A | δ 10.97 (s, 1H), 8.21 (s, 1H), 7.40 (d, J=8.8 Hz, 1H), 7.25 (d, J=8 Hz, 1H), 7.12 (m, 2H), 6.8 (d, J=8 Hz, 2H), 6.62 (m, 2H), 6.53 (m, 3H), 6.18 (d, J=8.8 Hz, 1H), 5.08 (d, J=8.8 Hz, 1H), 4.30 (d, J=3.2 Hz, 1H), 4.17 (d, J=3.2 Hz, 1H) 4.11 (d, J=2.4 Hz, 1H),3.53 – 3.47 (m, 5H), 3.47 (m, 3H), 3.17 (m, 5H), 1.68 (d, J=8.8 Hz, 3H), 2.51 (s, 1H), 2.35 – 2.33 (m, 5H), 2.88 (m, 2H), 1.38 (d, J=8.8 Hz, 3H), 1.17 (d, J=8.8 Hz, 2H). (DMSO-d6, 400 MHz) |

FIG. 7 Continued

| | | | |
|---|---|---|---|
| 507 | 3-[5-[4-[[1-[4-[(1R,2S)-6-hydroxy-2-(4-hydroxyphenyl)tetralin-1-yl]phenyl]-4-piperidyl]methyl]piperazin-1-yl]-1-oxo-isoindolin-2-yl]piperidine-2,6-dione | B | δ 10.95 (s, 1H), 8.19 (s, 1H), 7.51 (d, J=9.2 Hz, 1H), 7.09 - 7.02 (m, 2H), 6.65 - 6.51 (m, 8H), 6.49 - 6.44 (m, 1H), 6.21 (d, J=8.8 Hz, 2H), 5.04 (dd, J=4.8, 13.2 Hz, 1H), 4.36 - 4.28 (m, 1H), 4.23 - 4.16 (m, 1H), 4.05 (d, J=4.4 Hz, 1H), 3.66 - 3.48 (m, 2H), 3.18 (s, 7H), 2.91 (d, J=13.2 Hz, 4H), 2.60 (s, 1H), 2.38 (s, 1H), 2.19 (d, J=6.4 Hz, 2H), 1.96 (d, J=5.6 Hz, 3H), 1.83 - 1.56 (m, 5H), 1.26 - 1.05 (m, 3H). (DMSO-d6, 400 MHz) |
| 510 | 3-[2-[4-[2-[1-[4-[(1R,2S)-6-hydroxy-2- phenyl-tetralin-1-yl]phenyl]piperazin-1-yl]ethyl]phenyl]-5-oxo-7H-pyrrolo[3,4-b]pyridin-6-yl]piperidine-2,6-dione | A | δ 10.94 (s, 1H), 9.17 - 8.97 (m, 1H), 8.20 (s, 1H), 7.76 (d, J=8.8 Hz, 1H), 7.18 - 7.09 (m, 1H), 7.19 - 7.09 (m, 2H), 6.93 - 6.82 (m, 3H), 6.65 - 6.57 (m, 2H), 6.47 (dd, J=2.4, 8.0 Hz, 1H), 6.20 - 6.10 (m, 4H), 5.07 (dd, J=4.8, 13.2 Hz, 1H), 4.31 - 4.23 (m, 1H), 4.14 - 4.06 (m, 2H), 3.71 - 3.58 (m, 4H), 3.19 - 3.04 (m, 5H), 2.95 - 2.87 (m, 2H), 2.52 (d, J=2.0 Hz, 5H), 2.27 - 2.15 (m, 2H), 2.14 - 1.92 (m, 4H), 1.75 - 1.50 (m, 5H). (DMSO-d6, 400 MHz) |
| 511 | 3-[5-[4-[[1-[2-fluoro-4-[(1R,2S)-6-hydroxy-2-phenyl-tetralin-1-yl]phenyl]-4-piperidyl]methyl]piperazin-1-yl]-3-methyl-1-oxo-isoindolin-2-yl]piperidine-2,6-dione | B | δ 1.29 - 1.47 (m, 6H), 1.66 - 1.79 (m, 2H), 1.83 - 2.11 (m, 6H), 2.55 - 2.63 (m, 1H), 3.05 - 3.39 (m, 11H), 3.59 - 3.65 (m, 3H), 3.92 - 4.04 (m, 2H), 4.18 - 4.22 (m, 1H), 4.49 - 4.74 (m, 2H), 5.96 - 6.02 (m, 1H), 6.10 - 6.14 (m, 1H), 6.51 (dd, J = 8.0, 2.0 Hz, 1H), 6.62 (d, J=2.0 Hz, 1H), 6.64 - 6.72 (m, 2H), 6.85 - 6.89 (m, 2H), 7.10 - 7.21 (m, 5H), 7.49 - 7.56 (m, 1H), 9.99 (s, 1H), 10.86 - 10.95 (m, 1H). (DMSO-d6, 400 MHz) |

FIG. 7 Continued

| | | | |
|---|---|---|---|
| 515 | 3-[5-[4-[2-[1-[5-[(1S,2S)-6-hydroxy-2-phenyl-tetralin-1-yl]pyrimidin-2-yl]-4-piperidyl]ethyl]piperazin-1-yl]-1-oxo-isoindolin-2-yl]piperidine-2,6-dione | A | δ 10.94 (s, 1H), 8.18 (s, 1H), 7.55 - 7.47 (m, 1H), 7.29 - 7.14 (m, 5H), 7.08 - 7.01 (m, 2H), 6.95 (d, J=7.2 Hz, 2H), 6.70 (d, J=8.4 Hz, 1H), 6.61 (d, J=2.4 Hz, 1H), 6.52 (dd, J=2.4, 8.0 Hz, 1H), 5.04 (dd, J=5.2, 13.2 Hz, 1H), 4.43 (d, J=11.6 Hz, 2H), 4.36 - 4.27 (m, 1H), 4.24 - 4.15 (m, 1H), 4.11 (d, J=4.8 Hz, 1H), 3.36 - 3.23 (m, 4H), 3.04 - 2.83 (m, 4H), 2.77 - 2.65 (m, 3H), 2.63 - 2.52 (m, 2H), 2.40 - 2.29 (m, 4H), 2.06 - 1.90 (m, 3H), 1.86 - 1.74 (m, 1H), 1.66 (d, J=12.0 Hz, 2H), 1.58 - 1.46 (m, 1H), 1.43 - 1.34 (m, 2H), 1.05 - 0.90 (m, 2H). (DMSO-d6, 400 MHz) |
| 516 | 3-[5-[4-[2-[1-[4-[(1R,2S)-6-hydroxy-2- phenyl-tetralin-1-yl]phenyl]pyrrolidin-3-yl]ethyl]piperazin-1-yl]-1-oxo-isoindolin-2-yl]piperidine-2,6-dione | A | δ 10.93 (s, 1H), 9.09 (s, 1H), 8.14 (s, 1H), 7.51 (d, J=8.8 Hz, 1H), 7.18 - 7.02 (m, 5H), 6.84 (d, J=6.8 Hz, 2H), 6.66 - 6.56 (m, 2H), 6.46 (dd, J=2.4, 8.4 Hz, 1H), 6.23 - 6.04 (m, 4H), 5.03 (dd, J=5.2, 13.2 Hz, 1H), 4.36 - 4.29 (m, 1H), 4.24 - 4.17 (m, 1H), 4.12 - 4.08 (m, 1H), 3.28 (br d, J=2.8 Hz, 2H), 3.18 - 3.05 (m, 4H), 2.99 - 2.85 (m, 3H), 2.60 - 2.51 (m, 7H), 2.46 - 2.34 (m, 4H), 2.26 - 2.17 (m, 1H), 2.14 - 1.90 (m, 3H), 1.78 - 1.43 (m, 4H). (DMSO-d6, 400 MHz) |
| 518 | 3-[5-[4-[2-[1-[4-[(1R,2S)-6-hydroxy-2-(4-methoxyphenyl)tetralin-1-yl]phenyl]-4-piperidyl]ethyl]piperazin-1-yl]-1-oxo-isoindolin-2-yl]piperidine-2,6-dione | A | δ 10.94 (s, 1H), 8.14 (s, 1H), 7.50 (d, J=9.2 Hz, 1H), 7.09 - 7.01 (m, 2H), 6.75 - 6.67 (m, 4H), 6.62 (d, J=8.4 Hz, 1H), 6.58 (d, J=2.1 Hz, 1H), 6.53 (d, J=8.8 Hz, 2H), 6.46 (dd, J=2.4, 8.4 Hz, 1H), 6.20 (d, J=8.8 Hz, 2H), 5.03 (dd, J=4.8, 13.2 Hz, 1H), 4.37 - 4.27 (m, 1H), 4.24 - 4.14 (m, 1H), 4.07 (d, J=4.8 Hz, 1H), 3.70 - 3.63 (m, 3H), 3.34 - 3.18 (m, 3H), 2.99 - 2.80 (m, 4H), 2.62 - 2.51 (m, 5H), 2.48 - 2.41 (m, 5H), 2.39 - 2.30 (m, 2H), 2.06 - 1.90 (m, 2H), 1.74 - 1.60 (m, 3H), 1.46 - 1.31 (m, 3H), 1.25 - 1.11 (m, 2H). (DMSO-d6, 400 MHz) |

FIG. 7 Continued

| | | | |
|---|---|---|---|
| 519 | 3-[5-[4-[2-[1-[4-[(1R,2S)-6-hydroxy-2-(4-hydroxyphenyl)tetralin-1-yl]phenyl]-4-piperidyl]ethyl]piperazin-1-yl]-1-oxo-isoindolin-2-yl]piperidine-2,6-dione | A | δ 10.94 (s, 1H), 8.17 (s, 1H), 7.54 - 7.48 (m, 1H), 7.08 - 7.02 (m, 2H), 6.65 - 6.57 (m, 4H), 6.56 - 6.51 (m, 4H), 6.46 (dd, J=2.4, 8.0 Hz, 1H), 6.21 (d, J=8.4 Hz, 2H), 5.04 (dd, J=5.2, 13.2 Hz, 1H), 4.36 - 4.28 (m, 1H), 4.24 - 4.16 (m, 1H), 4.05 (d, J=4.8 Hz, 1H), 3.50 (d, J=9.2 Hz, 2H), 3.27 (s, 4H), 3.15 (d, J=10.4 Hz, 1H), 3.01 - 2.81 (m, 3H), 2.52 (d, J=2.0 Hz, 1H), 2.48 - 2.44 (m, 4H), 2.39 - 2.33 (m, 3H), 2.10 - 1.84 (m, 3H), 1.79 - 1.55 (m, 4H), 1.40 (d, J=6.0 Hz, 3H), 1.25 - 1.15 (m, 2H). (DMSO-d6, 400 MHz) |
| 520 | 3-(5-((1R,3r)-3-(((1-(4-((1R,2S)-6-hydroxy-2-phenyl-1,2,3,4-tetrahydronaphthalen-1-yl)phenyl)piperidin-4-yl)methyl)(isopropyl)amino)cyclobutoxy)-1-oxoisoindolin-2-yl)piperidine-2,6-dione | C | B |
| 523 | 3-[5-[4-[3-[2-[4-[(1R,2S)-6-hydroxy-2-phenyl-tetralin-1-yl]phenoxy]ethyl]azetidin-1-yl]-1-piperidyl]-1-oxo-isoindolin-2-yl]piperidine-2,6-dione | A | δ 10.93 (s, 1H), 8.34 (s, 1H), 7.48 (d, J=8.4 Hz, 1H), 7.20-7.08 (m, 3H), 7.06-6.99 (m, 2H), 6.82 (d, J=6.8 Hz, 2H), 6.66-6.58 (m, 2H), 6.54-6.45 (m, 3H), 6.25 (d, J=8.4 Hz, 2H), 5.03 (dd, J=5.2, 13.6 Hz, 1H), 4.37-4.27 (m, 1H), 4.23-4.15 (m, 2H), 3.78 (t, J=6.0 Hz, 2H), 3.73-3.62 (m, 3H), 3.03-2.82 (m, 6H), 2.75 (t, J=6.4 Hz, 2H), 2.41-2.38 (m, 1H), 2.24-1.91 (m, 5H), 1.88-1.80 (m, 2H), 1.73-1.63 (m, 3H), 1.28-1.12 (m, 3H). (DMSO-d6, 400 MHz) |

FIG. 7 Continued

| | | | |
|---|---|---|---|
| 524 | (3S)-3-[5-[4-[[1-[2-fluoro-4-[(1R,2S)-6-hydroxy-2-phenyl-tetralin-1-yl]phenyl]-4-piperidyl]methyl]piperazin-1-yl]-1-oxo-isoindolin-2-yl]piperidine-2,6-dione | A | δ 10.94 (s, 1H), 9.15 (s, 1H), 7.51 (d, J=8.4 Hz, 1H), 7.23 - 7.10 (m, 3H), 7.09 - 7.01 (m, 2H), 6.86 (d, J=6.8 Hz, 2H), 6.72 - 6.56 (m, 3H), 6.50 (d, J=7.6 Hz, 1H), 6.09 (d, J=8.0 Hz, 1H), 5.97 (d, J=14.0 Hz, 1H), 5.04 (dd, J=4.8, 13.2 Hz, 1H), 4.38 - 4.27 (m, 1H), 4.24 - 4.19 (m, 1H), 4.18 (s, 1H), 3.30 - 3.23 (m, 5H), 3.23 - 3.15 (m, 2H), 3.06 - 2.81 (m, 3H), 2.65 - 2.54 (m, 4H), 2.52 - 2.51 (m, 3H), 2.42 - 2.34 (m, 1H), 2.20 (d, J=7.2 Hz, 2H), 2.13 - 2.01 (m, 1H), 2.00 - 1.91 (m, 1H), 1.84 - 1.70 (m, 3H), 1.68 - 1.54 (m, 1H), 1.24 - 1.11 (m, 2H). (DMSO-d6, 400 MHz) |
| 525 | (3R)-3-[5-[4-[[1-[2-fluoro-4-[(1R,2S)-6-hydroxy-2-phenyl-tetralin-1-yl]phenyl]-4-piperidyl]methyl]piperazin-1-yl]-1-oxo-isoindolin-2-yl]piperidine-2,6-dione | A | δ 10.93 (s, 1H), 9.15 (s, 1H), 7.51 (d, J=8.8 Hz, 1H), 7.23 - 7.09 (m, 3H), 7.08 - 7.01 (m, 2H), 6.86 (d, J=6.4 Hz, 2H), 6.69 - 6.63 (m, 2H), 6.63 - 6.60 (m, 1H), 6.50 (dd, J=2.4, 8.4 Hz, 1H), 6.09 (d, J=8.4 Hz, 1H), 5.97 (d, J=14.0 Hz, 1H), 5.04 (dd, J=5.2, 13.2 Hz, 1H), 4.37 - 4.27 (m, 1H), 4.24 - 4.19 (m, 1H), 4.18 (s, 1H), 3.30 - 3.23 (m, 5H), 3.23 - 3.15 (m, 2H), 3.06 - 2.81 (m, 3H), 2.65 - 2.54 (m, 4H), 2.52 - 2.51 (m, 3H), 2.42 - 2.34 (m, 1H), 2.20 (d, J=7.2 Hz, 2H), 2.13 - 2.01 (m, 1H), 2.00 - 1.91 (m, 1H), 1.84 - 1.70 (m, 3H), 1.68 - 1.54 (m, 1H), 1.24 - 1.11 (m, 2H). (DMSO-d6, 400 MHz) |
| 528 | 3-[5-[4-[2-[(3R)-1-[4-[(1R,2S)-6-hydroxy-2-phenyl-tetralin-1-yl]phenyl]pyrrolidin-3-yl]oxyethyl]piperazin-1-yl]-1-oxo-isoindolin-2-yl]piperidine-2,6-dione | B | δ 10.95 (s, 1H), 9.31 - 8.95 (m, 1H), 8.35 (s, 1H), 7.51 (s, 1H), 7.21 - 7.00 (m, 5H), 6.84 (s, 2H), 6.59 (s, 2H), 6.47 (s, 1H), 6.15 (s, 4H), 5.02 (s, 1H), 4.36 - 3.98 (m, 8H), 3.16 (s, 14H), 2.93 (d, J=16.4 Hz, 2H), 2.34 (s, 1H), 1.99 (s, 3H), 1.69 (s, 1H), 1.29 - 1.09 (m, 2H). (DMSO-d6, 400 MHz) |

FIG. 7 Continued

| | | | |
|---|---|---|---|
| 539 | 3-{5-[1-{1-[4-{[(1R,2S)-6-hydroxy-2- phenyl-tetralin-1-yl]phenyl]-4-piperidyl]methyl]azetidin-3-yl]pyrazol-4-yl]-1-oxo-isoindolin-2-yl]piperidine-2,6-dione | A | δ 10.98 (s, 1H), 9.12 (s, 1H), 8.49 (s, 1H), 8.17 (s, 1H), 8.06 (s, 1H), 7.83 (s, 1H), 7.77 - 7.73 (m, 1H), 7.72 - 7.67 (m, 1H), 7.13 (d, J=7.6 Hz, 3H), 6.82 (d, J=6.4 Hz, 2H), 6.66 - 6.56 (m, 2H), 6.54 - 6.41 (m, 3H), 6.19 (d, J=8.9 Hz, 2H), 5.10 (dd, J=5.2, 13.2 Hz, 1H), 5.02 - 4.93 (m, 1H), 4.50 - 4.43 (m, 1H), 4.33 (d, J=17.2 Hz, 1H), 4.12 (d, J=5.2 Hz, 1H), 2.93 (d, J=13.6 Hz, 2H), 2.54 - 2.52 (m, 7H), 2.41 (d, J=6.4 Hz, 6H), 2.15 - 1.95 (m, 3H), 1.70 (s, 3H), 1.39 (s, 1H), 1.23 - 1.11 (m, 2H). (DMSO-d6, 400 MHz) |
| 540 | (S)-3-(5-(((R)-1-((1-(4-(((1R,2S)-6-hydroxy-2-phenyl-1,2,3,4-tetrahydronaphthalen-1-yl)phenyl)piperidin-4-yl)methyl)pyrrolidin-3-yl)oxy)-1-oxoisoindolin-2-yl)piperidine-2,6-dione | A | B |
| 541 | 3-(5-(1-(2-(1-(4-(((1R,2S)-6-hydroxy-2-phenyl-1,2,3,4-tetrahydronaphthalen-1-yl)phenyl)piperidin-4-yl)ethyl)-1H-pyrazol-4-yl)-1-oxoisoindolin-2-yl)piperidine-2,6-dione | B | B |

FIG. 7 Continued

| | | | |
|---|---|---|---|
| 542 | 3-(5-(1-(1-(((S)-1-(4-((1R,2S)-6-hydroxy-2-phenyl-1,2,3,4-tetrahydronaphthalen-1-yl)phenyl)pyrrolidin-3-yl)methyl)azetidin-3-yl)-1H-pyrazol-4-yl)-1-oxoisoindolin-2-yl)piperidine-2,6-dione | A | A |
| 544 | 3-(5-(1-(1-(((R)-1-(4-((1R,2S)-6-hydroxy-2-phenyl-1,2,3,4-tetrahydronaphthalen-1-yl)phenyl)pyrrolidin-3-yl)methyl)azetidin-3-yl)-1H-pyrazol-4-yl)-1-oxoisoindolin-2-yl)piperidine-2,6-dione | A | A |

*Degradation DC50 range    A: DC50 < 5 nM;   B: 5 nM < DC50 < 50 nM;   C: DC50 > 50 nM

**Degradation Dmax range    A: Dmax > 75%;   B: 50% < Dmax < 75;   C: Dmax < 50%

TETRAHYDRONAPHTHALENE AND TETRAHYDROISOQUINOLINE DERIVATIVES AS ESTROGEN RECEPTOR DEGRADERS

CROSS-REFERENCE TO RELATED APPLICATIONS

The present disclosure claims priority to U.S. Provisional Patent Application No. 62/429,041, filed 1 Dec. 2016 and titled: TETRAHYDRONAPHTHALENE AND TETRAHYDROISOQUINOLINE DERIVATIVES AS ESTROGEN RECEPTOR DEGRADERS, and U.S. Provisional Patent Application No. 62/540,049, filed 1 Aug. 2017 and titled: TETRAHYDRONAPHTHALENE AND TETRAHYDROISOQUINOLINE DERIVATIVES AS ESTROGEN RECEPTOR DEGRADERS, the contents of which are incorporated herein by reference in their entirety for all purposes.

INCORPORATION BY REFERENCE

U.S. patent application Ser. No. 15/230,354, filed on Aug. 5, 2016; and U.S. patent application Ser. No. 15/206,497 filed 11 Jul. 2016; and U.S. patent application Ser. No. 15/209,648 filed 13 Jul. 2016; and U.S. patent application Ser. No. 15/730,728, filed on Oct. 11, 2017; and U.S. patent application Ser. No. 14/686,640, filed on Apr. 14, 2015, published as U.S. Patent Application Publication No. 2015/0291562; and U.S. patent application Ser. No. 14/792,414, filed on Jul. 6, 2015, published as U.S. Patent Application Publication No. 2016/0058872; and U.S. patent application Ser. No. 14/371,956, filed on Jul. 11, 2014, published as U.S. Patent Application Publication No. 2014/0356322; and Patent Application Ser. No. 62/395,228, filed on Sep. 15, 2016, entitled "INDOLE DERIVATIVES AS ESTROGEN RECEPTOR DEGRADERS"; and U.S. patent application Ser. No. 15/074,820, filed on Mar. 18, 2016, published as U.S. Patent Application Publication No. 2016/0272639; and U.S. Provisional Patent Application Ser. No. 62/452,972, filed Jan. 31, 2017; and U.S. Provisional Patent Application Ser. No. 62/429,041, filed Dec. 1, 2016; and International Patent Application No. PCT/US2016/023258, filed Mar. 18, 2016, published as International Patent Application Publication No. WO2016/149668, all of which are incorporated herein by reference in their entirety. Furthermore, all references cited herein are incorporated by reference herein in their entirety.

FIELD OF THE INVENTION

The present disclosure relates to compounds, compositions, and medicaments including the compounds and processes for the preparation thereof. The present disclosure also relates to the use of the compounds, compositions and medicaments, for example, as inhibitors of the activity of the estrogen receptor, including degrading the estrogen receptor, the treatment of diseases and conditions mediated by the estrogen receptor, e.g. the treatment of breast cancer.

BACKGROUND

The estrogen receptor (ER) is a member of the nuclear hormone receptor family and functions as a ligand-activated transcription factor involved with the up and down regulation of gene expression. The natural hormone for the estrogen receptor is 17-beta-estradiol (E2) and closely related metabolites. Binding of estradiol to the estrogen receptor causes a dimerization of the receptor and the dimer in turn binds to estrogen response elements (ERE's) on DNA. The ER-DNA complex recruits other transcription factors responsible for the transcription of DNA downstream from the ERE into mRNA, which is eventually translated into protein. Alternatively, the interaction of ER with DNA may be indirect through the intermediacy of other transcription factors, most notably fos and jun. Since the expression of a large number of genes is regulated by the estrogen receptor and since the estrogen receptor is expressed in many cell types, modulation of the estrogen receptor through binding of either natural hormones or synthetic ER ligands can have profound effects on the physiology and pathophysiology of the organism.

A variety of diseases have their etiology and/or pathology mediated by the ER. Collectively these diseases are called estrogen-dependent diseases. Estrogens are critical for sexual development in females. In addition, estrogens play an important role in maintaining bone density, regulation of blood lipid levels, and appear to have neuroprotective effects. Consequently, decreased estrogen production in post-menopausal women is associated with a number of diseases such as osteoporosis, atherosclerosis, depression and cognitive disorders. Conversely, certain types of proliferative diseases such as breast and uterine cancer and endometriosis are stimulated by estrogens and therefore antiestrogens (i.e. estrogen antagonists) have utility in the prevention and treatment of these types of disorders.

There are two different forms of the estrogen receptor, usually referred to as a and 3, each encoded by a separate gene (ESR1 and ESR2, respectively). Both ERs are widely expressed in different tissue types, but there are some notable differences in their expression patterns. The ERα is found in endometrium, breast cancer cells, ovarian stroma cells, and the hypothalamus. In males, ERα protein is found in the epithelium of the efferent ducts. The expression of the ERβ protein has been documented in kidney, brain, bone, heart, lungs, intestinal mucosa, prostate, and endothelial cells. Development therefore of selective ligands may therefore preserve the beneficial aspects of estrogen.

Breast cancer is the most common malignancy to affect women and the incidence of the disease is increasing worldwide. Estrogens, in particular, act as endocrine growth factors for at least one-third of breast cancers, and depriving the tumor of this stimulus is a recognized therapy for advanced disease in premenopausal women, this is achieved by the ablation of ovarian function through surgical, radio therapeutic, or medical means and, in postmenopausal women, by the use of aromatase inhibitors.

An alternative approach to estrogen withdrawal is to antagonise estrogen with antiestrogens. These are drugs that bind to and compete for estrogen receptors (ER) present in estrogen-responsive tissue. Conventional nonsteroidal antiestrogens, such as tamoxifen, compete efficiently for ER binding but their effectiveness is often limited by the partial agonism they display, which results in an incomplete blockade of estrogen-mediated activity. A specific or "pure" antiestrogen with high affinity for ER and without any agonist effect may have advantages over conventional non-steroidal anti-estrogens in the treatment of estrogen-dependent disease. Fulvestrant is the first of a new class of potent pure anti-estrogens and is completely free of the partial agonist, estrogen-like activity, associated with currently available antiestrogens like tamoxifen.

As such, there is a need for other approaches to antagonise the ER receptor. One approach would be to develop selective ER down regulators or degraders that reduce ER expression at either the transcript or protein level.

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and therefore, are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands which bind to these ligases. For example, since the discovery of nutlins, the first small molecule E3 ligase inhibitors, additional compounds have been reported that target E3 ligases but the field remains underdeveloped. For example, since the discovery of Nutlins, the first small molecule E3 ligase mouse double minute 2 homolog (MDM2) inhibitors, additional compounds have been reported that target MDM2 (i.e., human double minute 2 or HDM2) E3 ligases (J. Di, et al. *Current Cancer Drug Targets* (2011), 11(8), 987-994).

Tumor suppressor gene p53 plays an important role in cell growth arrest and apoptosis in response to DNA damage or stress (A. Vazquez, et al. *Nat. Rev. Drug. Dis.* (2008), 7, 979-982), and inactivation of p53 has been suggested as one of the major pathway for tumor cell survival (A. J. Levine, et al. *Nature* (2000), 408, 307-310). In cancer patients, about 50% were found with p53 mutation (M. Hollstein, et al. *Science* (1991), 233, 49-53), while patients with wild type p53 were often found p53 down regulation by MDM2 through the protein-protein interaction of p53 and MDM2 (P. Chene, et al. *Nat. Rev. Cancer* (2003), 3, 102-109). Under normal cell condition without oncogenic stress signal, MDM2 keeps p53 at low concentration. In response to DNA damage or cellular stress, p53 level increases, and that also causes increase in MDM2 due to the feedback loop from pS3/MDM2 auto regulatory system. In other words, p53 regulates MDM2 at the transcription level, and MDM2 regulates p53 at its activity level (A. J. Levine, et al. *Genes Dev.* (1993) 7, 1126-1132).

Several mechanisms can explain p53 down regulation by MDM2. First, MDM2 binds to N-terminal domain of p53 and blocks expression of p53-responsive genes (J. Momand, et al. *Cell* (1992), 69, 1237-1245). Second, MDM2 shuttles p53 from nucleus to cytoplasm to facilitate proteolytic degradation (J. Roth, et al. *EMBO J.* (1998), 17, 554-564). Lastly, MDM2 carries intrinsic E3 ligase activity of conjugating ubiquitin to p53 for degradation through ubiquitin-dependent 26s proteasome system (UPS) (Y. Haupt, et al. *Nature* (1997) 387, 296-299). As such, because MDM2 functions as E3 ligase, recruiting MDM2 to a disease causing protein and effectuating its ubiquitination and degradation is an approach of high interest for drug discovery.

One E3 ligase with exciting therapeutic potential is the von Hippel-Lindau (VHL) tumor suppressor, the substrate recognition subunit of the E3 ligase complex VCB, which also consists of elongins B and C, Cul2 and Rbx1. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. The first small molecule ligands of Von Hippel Lindau (VHL) to the substrate recognition subunit of the E3 ligase were generated, and crystal structures were obtained confirming that the compound mimics the binding mode of the transcription factor HIF-1α, the major substrate of VHL.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, cereblon ubquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

Inhibitors of Apotosis Proteins (IAPs) are a protein family involved in suppressing apoptosis, i.e. cell death. The human IAP family includes 8 members, and numerous other organisms contain IAP homologs. IAPs contain an E3 ligase specific domain and baculoviral IAP repeat (BIR) domains that recognize substrates, and promote their ubiquitination. IAPs promote ubiquitination and can directly bind and inhibit caspases. Caspases are proteases (e.g. caspase-3, caspase-7 and caspace-9) that implement apoptosis. As such, through the binding of caspases, IAPs inhibit cell death. However, pro-apoptotic stimuli can result in the release of mitochondrial proteins DIABLO (also known as second mitochondria-derived activator of caspases or SMAC) and HTRA2 (also known as Omi). Binding of DIABLO and HTRA2 appears to block TAP activity.

SMAC interacts with essentially all known IAPs including XIAP, c-IAP1, c-IAP2, NIL-IAP, Bruce, and survivin. The first four amino acids (AVPI) of mature SMAC bind to a portion of IAPs, which is believed to be essential for blocking the anti-apoptotic effects of IAPs.

Bifunctional compounds such as those that are described in U.S. Patent Application Publication Nos. 2015-0291562 and 2014-0356322 (incorporated herein by reference), function to recruit endogenous proteins to an E3 ubiquiuin ligase for degradation. In particular, the publications describe bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds.

The present disclosure identifies compounds that are capable of inhibiting estrogen receptor function, including compounds which degrade the estrogen receptor.

SUMMARY

The present disclosure describes bifunctional compounds which function to recruit endogenous proteins to an E3 ubiquitin ligase for degradation, and methods of using the same. In particular, the present disclosure provides bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds as described herein. An advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition, such as cancer, e.g., breast cancer.

As such, in one aspect the disclosure provides bifunctional or PROTAC compounds, which comprise an E3 ubiquitin ligase binding moiety (i.e., a ligand for an E3 ubiquitin ligase or "ULM" group), and a moiety that binds a target protein (i.e., a protein/polypeptide targeting ligand or "PTM" group) such that the target protein/polypeptide is placed in proximity to the ubiquitin ligase to effect degradation (and inhibition) of that protein. In a preferred embodiment, the ULM (ubiquitination ligase modulator) can be Von Hippel-Lindau E3 ubiquitin ligase (VHL) binding moiety (VLM), or a cereblon E3 ubiquitin ligase binding moiety (CLM), or a mouse double minute 2 homolog (MDM2) E3 ubiquitin ligase binding moiety (MLM), or an IAP E3 ubiquitin ligase binding moiety (i.e., a "ILM"). For example, the structure of the bifunctional compound can be depicted as illustrated in FIG. 8a.

The respective positions of the PTM and ULM moieties (e.g., VLM, CLM, MLM, ILM, or a combination thereof) as well as their number as illustrated herein is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as illustrated in FIG. 8b, where PTM is a protein/polypeptide targeting moiety, L is a linker, e.g., a bond or a chemical group coupling PTM to ULM, and ULM is a IAP E3 ubiquitin ligase binding moiety (ILM), or a Von Hippel-Lindau E3 ubiquitin ligase (VHL) binding moiety (VLM), or a cereblon E3 ubiquitin ligase binding moiety (CLM), or a mouse double minute 2 homolog (MDM2) E3 ubiquitin ligase binding moiety (MLM).

For example, the structure of the bifunctional compound can be depicted as illustrated in Figure Sc, wherein: PTM is a protein/polypeptide targeting moiety; "L" is a linker (e.g. a bond or a chemical linker group) coupling the PTM and at least one of VLM, CLM, MLM, ILM, or a combination thereof; VLM is Von Hippel-Lindau E3 ubiquitin ligase binding moiety that binds to VHL E3 ligase; CLM is cereblon E3 ubiquitin ligase binding moiety that binds to cereblon; MLM is an MDM2 E3 ubiquitin ligase binding moiety; and ILM is a IAP binding moiety which binds to IAP.

In an aspect, the present disclosure provides a compound of Formula (I) or (II):

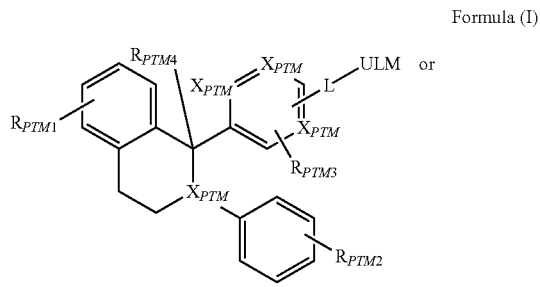

Formula (I)

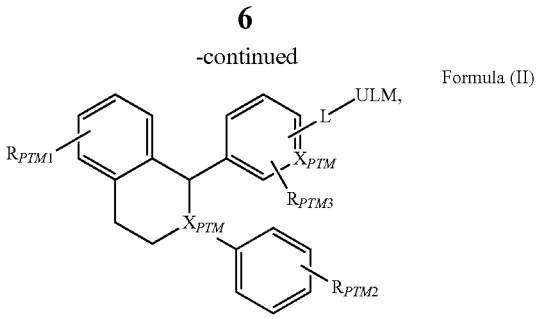

Formula (II)

wherein:
each $X_{PTM}$ is independently CH, N;
ULM is ULM is a ILM, or a VLM, or a CLM, or a MLM;
L is a bond or a linker moiety coupling the tetrahydronaphthalene or tetrahydroisoquinoline moiety and at least one of VLM, CLM, ILM, VLM, or a combination thereof;
each $R_{PTM1}$ is independently OH, halogen, alkoxy (e.g., methoxy or ethoxy), $O(CO)R_{PTM}$, wherein the substitution can be mono-, di- or tri-substituted and $R_{PTM}$ is alkyl or cycloalkyl group with 1 to 6 carbons or aryl groups;
each $R_{PTM2}$ is independently H, halogen, CN, $CF_3$, linear or branched alkyl, alkoxy (e.g., methoxy or ethoxy), wherein the substitution can be mono- or di-substitution;
each $R_{PTM3}$ is independently H, halogen, wherein the substitution can be mono- or di-substitution; and $R_{PTM4}$ is a H, alkyl, methyl, ethyl.

In certain preferred embodiments, the ILM is an AVPI tetrapeptide fragment. As such, in certain additional embodiments, the ILM of the bifunctional compound comprises the amino acids alanine (A), valine (V), proline (P), and isoleucine (1) or their unnatural mimetics, respectively. In additional embodiments, the amino acids of the AVPI tetrapeptide fragment are connected to each other through amide bonds (i.e., —C(O)NH— or —NHC(O)—).

In certain embodiments, the compounds as described herein comprise multiple independently selected ULMs, multiple PTMs, multiple chemical linkers or a combination thereof.

In certain embodiments, ILM comprises chemical moieties such as those described herein.

In additional embodiments, VLM can be hydroxyproline or a derivative thereof. Furthermore, other contemplated VLMs are included in U.S. Patent Application Publication No. 2014/03022523, which as discussed above, is incorporated herein in its entirety.

In an embodiment, the CLM comprises a chemical group derived from an imide, a thioimide, an amide, or a thioamide. In a particular embodiment, the chemical group is a phthalimido group, or an analog or derivative thereof. In a certain embodiment, the CLM is thalidomide, lenalidomide, pomalidomide, analogs thereof, isosteres thereof, or derivatives thereof. Other contemplated CLMs are described in U.S. Patent Application Publication No. 2015/0291562, which is incorporated herein in its entirety.

In certain embodiments, MLM can be nutlin or a derivative thereof. Furthermore, other contemplated MLMs are included in U.S. patent application Ser. No. 15/206,497 filed 11 Jul. 2016, which as discussed above, is incorporated herein in its entirety. In certain additional embodiments, the MLM of the bifunctional compound comprises chemical moieties such as substituted imidazolines, substituted spiroindolinones, substituted pyrrolidines, substituted piperidinones, substituted morpholinones, substituted pyrrolopyrimidines, substituted imidazolopyridines, substituted thiazoloimidazoline, substituted pyrrolopyrrolidinones, and substituted isoquinolinones.

In additional embodiments, the MLM comprises the core structures mentioned above with adjacent bis-aryl substitutions positioned as cis- or trans-configurations.

In certain embodiments, "L" is a bond. In additional embodiments, the linker "L" is a connector with a linear non-hydrogen atom number in the range of 1 to 20. The connector "L" can contain, but not limited to the functional groups such as ether, amide, alkane, alkene, alkyne, ketone, hydroxyl, carboxylic acid, thioether, sulfoxide, and sulfone. The linker can contain aromatic, heteroaromatic, cyclic, bicyclic and tricyclic moieties. Substitution with halogen, such as Cl, F, Br and I can be included in the linker. In the case of fluorine substitution, single or multiple fluorines can be included.

In certain embodiments, VLM is a derivative of trans-3-hydroxyproline, where both nitrogen and carboxylic acid in trans-3-hydroxyproline are functionalized as amides.

In an embodiment, the CLM comprises a chemical group derived from an imide, a thioimide, an amide, or a thioamide. In particular embodiments, the chemical group is a phthalimido group, or an analog or derivative thereof. In certain embodiments, the CLM is thalidomide, lenalidomide, pomalidomide, analogs thereof, isosteres thereof, or derivatives thereof. Other contemplated CLMs are described in U.S. Patent Application Publication US 2015-0291562, which is incorporated herein in its entirety. In some embodiments, the CLM is a derivative of piperidine-2,6-dione, where piperidine-2,6-dione can be substituted at the 3-position, and the 3-substitution can be bicyclic hetero-aromatics with the linkage as C—N bond or C—C bond. Examples of the CLM can be, but not limited to, pomalidomide, lenalidomide and thalidomide and their derivatives.

In certain embodiments, the "L" is a bond. In additional embodiments, the linker "L" is a connector with a linear non-hydrogen atom number in the range of 1 to 20. The connector "L" can contain, but not limited to the functional groups such as ether, amide, alkane, alkene, alkyne, ketone, hydroxyl, carboxylic acid, thioether, sulfoxide, and sulfone. The linker can contain aromatic, heteroaromatic, cyclic, bicyclic and tricyclic moieties. Substitution with halogen, such as Cl, F, Br and I can be included in the linker. In the case of fluorine substitution, single or multiple fluorines can be included.

In an additional aspect, the description provides therapeutic compositions comprising an effective amount of a compound as described herein or salt form thereof, and a pharmaceutically acceptable carrier. The therapeutic compositions modulate protein degradation and/or inhibition in a patient or subject, for example, an animal such as a human, and can be used for treating or ameliorating disease states or conditions which are modulated through the degraded and/or inhibited protein. In certain embodiments, the therapeutic compositions as described herein may be used to effectuate the degradation of proteins of interest for the treatment or amelioration of a disease, e.g., cancer. In certain additional embodiments, the disease is at least one of breast cancer, uterine cancer, ovarian cancer, prostate cancer, endometrial cancer, endometriosis, or a combination thereof. In yet another aspect, the present disclosure provides a method of ubiquitinating/degrading a target protein in a cell. In certain embodiments, the method comprises administering a bifunctional compound as described herein comprising an ILM and a PTM, a PTM and a VLM, or a PTM and a CLM, or a PTM and a MLM, preferably linked through a linker moiety, as otherwise described herein, wherein the VLM/ILM/CLM/MLM is coupled to the PTM through a linker to target protein that binds to PTM for degradation. Similarly, wherein the PTM (e.g., the tetrahydronaphthalene or tetrahydroisoquinoline moiety) is coupled to at least one of VLM, CLM, MLM, ILM, or a combination thereof through a linker to target a protein or polypeptide for degradation. Degradation of the target protein will occur when the target protein is placed in proximity to the E3 ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cells of a patient.

In still another aspect, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable carrier, wherein the composition is effective for treating or ameliorating the disease or disorder or symptom thereof in the subject.

In another aspect, the description provides methods for identifying the effects of the degradation of proteins of interest in a biological system using compounds according to the present disclosure.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional aspects and embodiments are expressly included within the scope of the present disclosure. The publications and other materials used herein to illuminate the background of the disclosure, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating an embodiment of the disclosure and are not to be construed as limiting the disclosure. Further objects, features and advantages of the disclosure will become apparent from the following detailed description taken in conjunction with the accompanying figures showing illustrative embodiments of the disclosure, in which:

FIG. 5. Table 1: Activity, synthetic methods and characterization of exemplary ER PROTACs.

FIG. 6. Table 2: Activity, synthetic methods and characterization of exemplary ER PROTACs.

FIG. 7. Table 3. ERα Degradation Activity, Chemical Name, and NMR Data for Exemplary ER PROTACs. Degradation DC50 ranges: DC50<5 nM (A); 5 nM<DC50<50 nM (B); DC50>50 nM (C); Degradation Dmax ranges: Dmax>75% (A); 50%<Dmax<75 (B); Dmax<50% (C).

DETAILED DESCRIPTION

The following is a detailed description provided to aid those skilled in the art in practicing the present disclosure. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

Figures 1A, 1B:
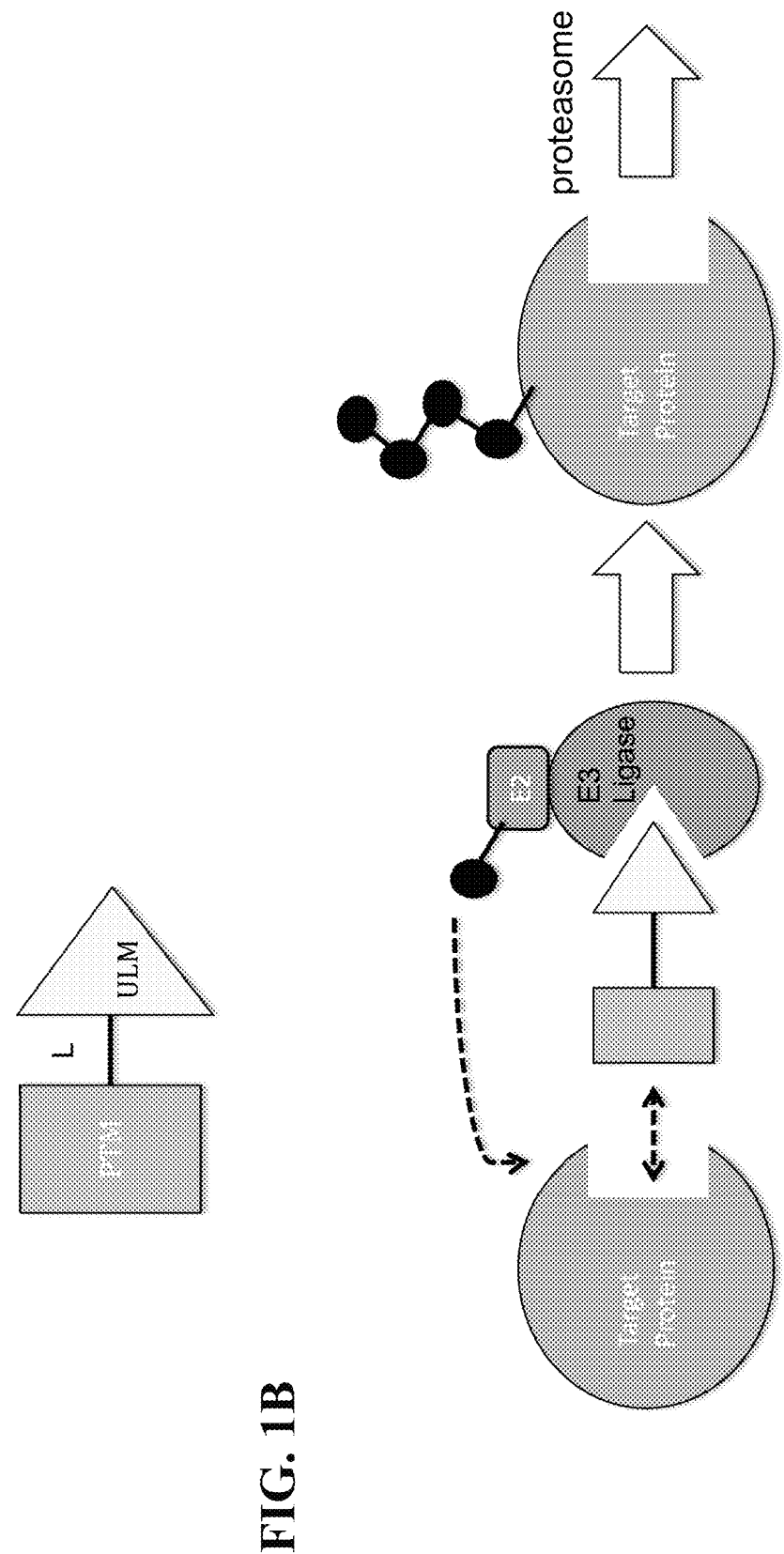
FIG. 1. Illustration of general principle for PROTAC function. (A) Exemplary PROTACs comprise a protein targeting moiety (PTM; darkly shaded rectangle), a ubiquitin ligase binding moiety (ULM; lightly shaded triangle), and optionally a linker moiety (L; black line) coupling or tethering the PTM to the ULM. (B) Illustrates the functional use of the PROTACs as described herein. Briefly, the ULM recognizes and binds to a specific E3 ubiquitin ligase, and the PTM binds and recruits a target protein bringing it into close proximity to the E3 ubiquitin ligase. Typically, the E3 ubiquitin ligase is complexed with an E2 ubiquitin-conjugating protein, and either alone or via the E2 protein catalyzes attachment of ubiquitin (dark circles) to a lysine on the target protein via an isopeptide bond. The poly-ubiquitinated protein (far right) is then targeted for degradation by the proteosomal machinery of the cell.

Presently described are compositions and methods that relate to the surprising and unexpected discovery that an E3 ubiquitin ligase protein (e.g., inhibitors of apoptosis proteins (IAP), a Von Hippel-Lindau E3 ubiquitin ligase (VHL), a cereblon E3 ubiquitin ligase, or a mouse double minute 2 homolog (MDM2) E3 ubiquitin ligase) ubiquitinates a target protein once it and the target protein are placed in proximity by a bifunctional or chimeric construct that binds the E3 ubiquitin ligase protein and the target protein. Accordingly the present disclosure provides such compounds and compositions comprising an E3 ubiquintin ligase binding moiety ("ULM") coupled to a protein target binding moiety ("PTM"), which result in the ubiquitination of a chosen target protein (e., estrogen receptor [ER]), which leads to degradation of the target protein by the proteasome (see FIGS. 1A and 1B). The present disclosure also provides a library of compositions and the use thereof.

In certain aspects, the present disclosure provides compounds which comprise a ligand, e.g., a small molecule ligand (i.e., having a molecular weight of below 2,000, 1,000, 500, or 200 Daltons), which is capable of binding to a E3 ubiquitin ligase, such as IAP, VHL, MDM2, or cereblon, and a moiety that is capable of binding to target protein, in such a way that a target protein (such as ER) is placed in proximity to the E3 ubiquitin ligase to effect degradation (and/or inhibition) of that protein. Small molecule can mean, in addition to the above, that the molecule is non-peptidyl, that is, it is not generally considered a peptide, e.g., comprises fewer than 4, 3, or 2 amino acids. In accordance with the present description, the PTM, ULM or PROTAC molecule can be a small molecule.

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the present disclosure. The upper and lower limits of these smaller ranges may independently be included in the smaller ranges is also encompassed within the present disclosure, subject to any specifically excluded limit in the stated range. Where the stated range includes one or both of the limits, ranges excluding either both of those included limits are also included in the disclosure.

The following terms are used to describe the present disclosure. In instances where a term is not specifically defined herein, that term is given an art-recognized meaning by those of ordinary skill applying that term in context to its use in describing the present disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives, including prodrug and/or deuterated forms thereof where applicable, in context. Deuterated small molecules contemplated are those in which one or more of the hydrogen atoms contained in the drug molecule have been replaced by deuterium.

Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented or understood within the context of the compound shown and well-known rules for valence interactions.

The term "ubiquitin ligase" refers to a family of proteins that facilitate the transfer of ubiquitin to a specific substrate protein, targeting the substrate protein for degradation. For example, IAP an E3 ubiquitin ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

The term "patient" or "subject" is used throughout the specification to describe an animal, preferably a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

Compounds and Compositions

In one aspect, the description provides compounds comprising an E3 ubiquitin ligase binding moiety ("ULM") that is an IAP E3 ubiquitin ligase binding moiety (an "ILM"), a cereblon E3 ubiquitin ligase binding moiety (a "CLM"), a Von Hippel-Lindae E3 ubiquitin ligase (VHL) binding moiety (VLM), and/or a mouse double minute 2 homologue (MDM2) E3 ubiquitin ligase binding moiety (MLM). In an exemplary embodiment, the ULM is coupled to a target protein binding moiety (PTM) via a chemical linker (L) according to the structure:

(A) PTM-L-ULM wherein L is a bond or a chemical linker group, ULM is a E3 ubiquitin ligase binding moiety, and PTM is a target protein binding moiety. The number and/or relative positions of the moieties in the compounds illustrated herein is provided by way of example only. As would be understood by the skilled artisan, compounds described herein can be synthesized with any desired number and/or relative position of the respective functional moieties.

The terms ULM, ILM, VLM, MLM, and CLM are used in their inclusive sense unless the context indicates otherwise. For example, the term ULM is inclusive of all ULMs, including those that bind IAP (i.e., ILMs), MDM2 (i.e., MLM), cereblon (i.e., CLM), and VHL (i.e., VLM). Further, the term ILM is inclusive of all possible IAP E3 ubiquitin ligase binding moieties, the term MLM is inclusive of all possible MDM2 E3 ubiquitin ligase binding moieties, the term VLM is inclusive of all possible VHL binding moieties, and the term CLM is inclusive of all cereblon binding moieties.

In another aspect, the present disclosure provides bifunctional or multifunctional compounds (e.g., PROTACs) useful for regulating protein activity by inducing the degradation of a target protein. In certain embodiments, the compound comprises an ILM or a VLM or a CLM or a MLM coupled, e.g., linked covalently, directly or indirectly, to a moiety that binds a target protein (i.e., a protein targeting moiety or a "PTM"). In certain embodiments, the ILM/VLM/CLM/MLM and PTM are joined or coupled via a chemical linker (L). The ILM binds the IAP E3 ubiquitin ligase, the VLM binds VHL, CLM binds the cereblon E3 ubiquitin ligase, and MLM binds the MDM2 E3 ubiquitin ligase, and the PTM recognizes a target protein and the interaction of the respective moieties with their targets facilitates the degradation of the target protein by placing the target protein in proximity to the ubiquitin ligase protein. An exemplary bifunctional compound can be depicted as:

(B) PTM-ILM
(C) PTM-CLM
(D) PTM-VLM
(E) PTM-MLM

In certain embodiments, the bifunctional compound further comprises a chemical linker ("L"). For example, the bifunctional compound can be depicted as:

(F) PTM-L-ILM
(G) PTM-L-CLM
(H) PTM-L-VLM
(I) PTM-L-MLM wherein the PTM is a protein/polypeptide targeting moiety, the L is a chemical linker, the ILM is a IAP E3 ubiquitin ligase binding moiety, the CLM is a cereblon E3 ubiquitin ligase binding moiety, the VLM is a VHL binding moiety, and the MLM is a MDM2 E3 ubiquitin ligase binding moiety.

In certain embodiments, the ULM (e.g., a ILM, a CLM, a VLM, or a MLM) shows activity or binds to the E3 ubiquitin ligase (e.g., IAP E3 ubiquitin ligase, cereblon E3 ubiquitin ligase, VHL, or MDM2 E3 ubiquitin ligase) with an $IC_{50}$ of less than about 200 μM. The $IC_{50}$ can be determined according to any method known in the art, e.g., a fluorescent polarization assay.

In certain additional embodiments, the bifunctional compounds described herein demonstrate an activity with an $IC_{50}$ of less than about 100, 50, 10, 1, 0.5, 0.1, 0.05, 0.01, 0.005, 0.001 mM, or less than about 100, 50, 10, 1, 0.5, 0.1, 0.05, 0.01, 0.005, 0.001 μM, or less than about 100, 50, 10, 1, 0.5, 0.1, 0.05, 0.01, 0.005, 0.001 nM, or less than about 100, 50, 10, 1, 0.5, 0.1, 0.05, 0.01, 0.005, 0.001 pM.

In certain embodiments, the compounds as described herein comprise multiple PTMs (targeting the same or different protein targets), multiple ULMs, one or more ULMs (i.e., moieties that bind specifically to multiple/different E3 ubiquitin ligase, e.g., VHL, IAP, cereblon, and/or MDM2) or a combination thereof. In any of the aspects or embodiments described herein, the PTMs and ULMs (e.g., ILM, VLM, CLM, and/or MLM) can be coupled directly or via one or more chemical linkers or a combination thereof. In additional embodiments, where a compound has multiple ULMs, the ULMs can be for the same E3 ubiquintin ligase or each respective ULM can bind specifically to a different E3 ubiquitin ligase. In still further embodiments, where a compound has multiple PTMs, the PTMs can bind the same target protein or each respective PTM can bind specifically to a different target protein.

In certain embodiments, where the compound comprises multiple ULMs, the ULMs are identical. In additional embodiments, the compound comprising a plurality of ULMs (e.g., ULM, ULM', etc.), at least one PTM coupled to a ULM directly or via a chemical linker (L) or both. In certain additional embodiments, the compound comprising a plurality of ULMs further comprises multiple PTMs. In still additional embodiments, the PTMs are the same or, optionally, different. In still further embodiments, wherein the PTMs are different, the respective PTMs may bind the same protein target or bind specifically to a different protein target.

In certain embodiments, the compound may comprise a plurality of ULMs and/or a plurality of ULM's. In further embodiments, the compound comprising at least two different ULMs, a plurality of ULMs, and/or a plurality of ULM's further comprises at least one PTM coupled to a ULM or a ULM' directly or via a chemical linker or both. In any of the embodiments described herein, a compound comprising at least two different ULMs can further comprise multiple PTMs. In still additional embodiments, the PTMs are the same or, optionally, different. In still further embodiments, wherein the PTMs are different the respective PTMs may bind the same protein target or bind specifically to a different protein target. In still further embodiments, the PTM itself is a ULM (or ULM'), such as an ILM, a VLM, a CLM, a MLM, an ILM', a VLM', a CLM', and/or a MLM'.

In additional embodiments, the description provides the compounds as described herein including their enantiomers, diastereomers, solvates and polymorphs, including pharmaceutically acceptable salt forms thereof, e.g., acid and base salt forms.

In an aspect, the present disclosure provides a compound of Formula (I) or (II):

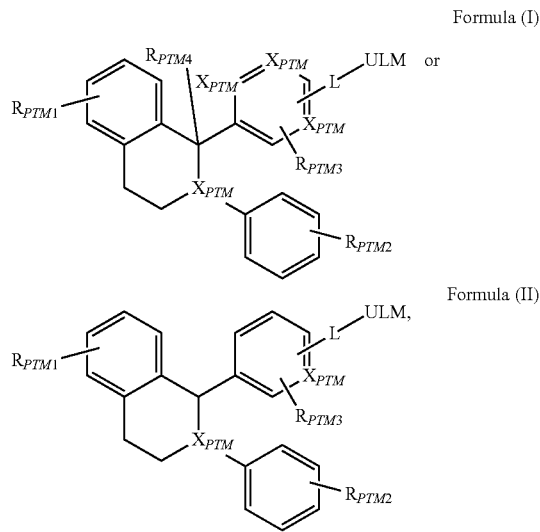

wherein:
- each $X_{PTM}$ is independently CH, N;
- ULM is ULM is a ILM, or a VLM, or a CLM, or a MLM;
- L is a bond or a linker moiety coupling the tetrahydronaphthalene or tetrahydroisoquinoline moiety and at least one of VLM, CLM, ILM, VLM, or a combination thereof;
- each $R_{PTM1}$ is independently OH, halogen, alkoxy (e.g., a methoxy or ethoxy), $O(CO)R_{PTM}$, wherein the substitution can be a mono-, di-, or tri-substitution and $R_{PTM}$ is alkyl or cycloalkyl group with 1 to 6 carbons or aryl groups;
- each $R_{PTM2}$ is independently H, halogen, CN, $CF_3$, linear or branched alkyl, alkoxy (e.g., methoxy or ethoxy), wherein the substitution can be mono- or di-substitution;
- each $R_{PTM3}$ is independently H, halogen, wherein the substitution can be mono- or di-substitution; and
- RPTM4 is a H, alkyl, methyl, ethyl.

The target protein (e.g., estrogen receptor) include oligopeptides and polypeptide sequences of sufficient length that they can bind to a PTM group according to the present disclosure. PTM groups according to the present disclosure include, for example, any moiety which binds to estrogen receptor specifically (binds to a target protein). The compositions described below exemplify some of the members of small molecule target protein binding moieties. Such small molecule target protein binding moieties also include pharmaceutically acceptable salts, enantiomers, solvates and polymorphs of these compositions, as well as other small molecules that may target a protein of interest. These binding moieties are linked to the ubiquitin ligase binding moiety preferably through a linker in order to present a target protein (to which the protein target moiety is bound) in proximity to the ubiquitin ligase for ubiquitination and degradation.

The present disclosure may be used to treat a number of disease states and/or conditions, including any disease state and/or condition in which proteins are dysregulated and where a patient would benefit from the degradation and/or inhibition of proteins.

In an additional aspect, the description provides therapeutic compositions comprising an effective amount of a compound as described herein or salt form thereof, and a pharmaceutically acceptable carrier, additive or excipient, and optionally an additional bioactive agent. The therapeutic compositions modulate protein degradation and/or inhibition in a patient or subject, for example, an animal such as a human, and can be used for treating or ameliorating disease states or conditions which are modulated through the degraded/inhibited protein. In certain embodiments, the therapeutic compositions as described herein may be used to effectuate the degradation of proteins of interest for the treatment or amelioration of a disease, e.g., cancer. In certain additional embodiments, the disease is at least one of breast cancer, uterine cancer, ovarian cancer, prostate cancer, endometrial cancer, endometriosis, or a combination thereof.

In alternative aspects, the present disclosure relates to a method for treating a disease state or ameliorating the symptoms of a disease or condition in a subject in need thereof by degrading a protein or polypeptide through which a disease state or condition is modulated comprising administering to said patient or subject an effective amount, e.g., a therapeutically effective amount, of at least one compound as described hereinabove, optionally in combination with a pharmaceutically acceptable carrier, additive or excipient, and optionally an additional bioactive agent, wherein the composition is effective for treating or ameliorating the disease or disorder or symptom thereof in the subject. The method according to the present disclosure may be used to treat a large number of disease states or conditions including cancer and/or endometriosis, by virtue of the administration of effective amounts of at least one compound described herein. The disease state or condition may be a disease caused by a microbial agent or other exogenous agent such as a virus, bacteria, fungus, protozoa or other microbe or may be a disease state, which is caused by overexpression of a protein, which leads to a disease state and/or condition.

In another aspect, the description provides methods for identifying the effects of the degradation of proteins of interest in a biological system using compounds according to the present disclosure.

The term "target protein" is used to describe a protein or polypeptide, which is a target for binding to a compound according to the present disclosure and degradation by ubiquitin ligase hereunder. Such small molecule target protein binding moieties also include pharmaceutically acceptable salts, enantiomers, solvates and polymorphs of these compositions, as well as other small molecules that may target a protein of interest, such as estrogen receptor. These binding moieties are linked to at least one ULM group (e.g. VLM and/or CLM) through at least one linker group L.

The term "protein target moiety" or PTM is used to describe a small molecule which binds to a target protein or other protein or polypeptide of interest and places/presents that protein or polypeptide in proximity to an ubiquitin ligase such that degradation of the protein or polypeptide by ubiquitin ligase may occur. Non-limiting examples of small molecule target protein binding moieties include selective estrogen receptor modulators, among numerous others. The compositions described below exemplify some of the members of the small molecule target proteins.

The compounds and compositions described herein exemplify some of the members of these types of small molecule target protein binding moieties. Such small molecule target protein binding moieties also include pharmaceutically acceptable salts, enantiomers, solvates and polymorphs of these compositions, as well as other small molecules that may target a protein of interest. References which are cited herein below are incorporated by reference herein in their entirety.

Exemplary ILMs

AVPI tetrapeptide fragments

In any of the compounds described herein, the ILM can comprise an alanine-valine-proline-isoleucine (AVPI) tetrapeptide fragment or an unnatural mimetic thereof. In certain embodiments, the ILM is selected from the group consisting of chemical structures represented by Formulas (I), (II), (III), (IV), and (V):

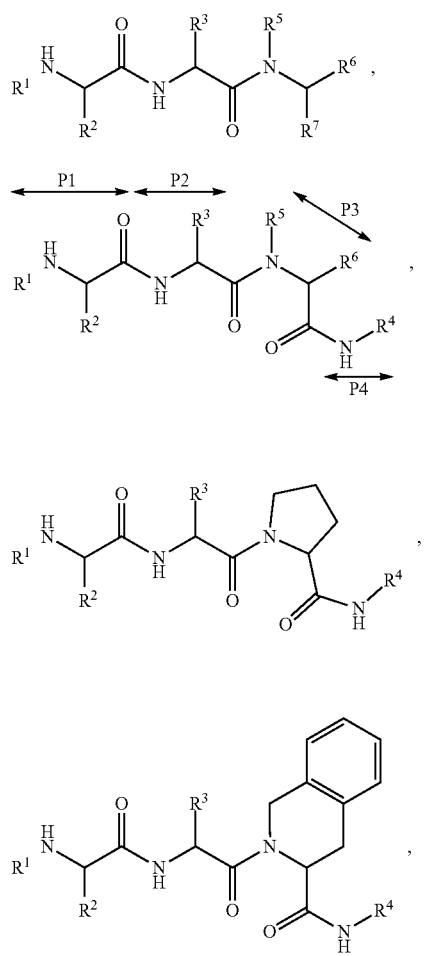

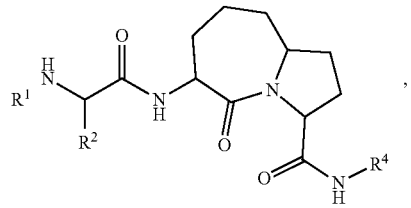

wherein:
R$^1$ for Formulas (I), (II), (III), (IV), and (V) is selected from H or alkyl;
R$^2$ for Formulas (I), (II), (III), (IV), and (V) is selected from H or alkyl;
R$^3$ for Formulas (I), (II), (III), (IV), and (V) is selected from H, or alkyl and heterocycloalkyl;
R$^5$ and R$^6$ for Formulas (I), (II), (III), (IV), and (V) are independently selected from H, alkyl, cycloalkyl, heterocycloalkyl, or more preferably, R$^5$ and R$^6$ taken together for Formulas (I), (II), (III), (IV), and (V) form a pyrrolidine or a piperidine ring further optionally fused to 1-2 cycloalkyl, heterocycloalkyl, aryl or heteroaryl rings, each of which can then be further fused to another cycloalkyl, heterocycloalkyl, aryl or heteroaryl ring;
R$^3$ and R$^5$ for Formulas (I), (II), (III), (IV), and (V) taken together can form a 5-8-membered ring further optionally fused to 1-2 cycloalkyl, heterocycloalkyl, aryl or heteroaryl rings;
R$^7$ for Formulas (I), (II), (III), (IV), and (V) is selected from cycloalkyl, cycloalkylalkyl, heterocycloalkyl, heterocycloalkylalkyl, aryl, arylalkyl, heteroaryl or heteroarylalkyl, each one further optionally substituted with 1-3 substituents selected from halogen, alkyl, haloalkyl, hydroxyl, alkoxy, cyano, (hetero)cycloalkyl or (hetero)aryl, or R$^7$ is —C(O)NH—R$^4$; and
R$^4$ is selected from alkyl, cycloalkyl, heterocycloalkyl, cycloalkylalkyl, heterocycloalkylalkyl, aryl, arylalkyl, heteroaryl, heteroarylalkyl, further optionally substituted with 1-3 substituents as described above.

As shown above, P1, P2, P3, and P4 of Formula (II) correlate with A, V, P, and I, respectively, of the AVPI tetrapeptide fragment or an unnatural mimetic thereof. Similarly, each of Formulas (I) and (III) through (V) have portions correlating with A, V, P, and I of the AVPI tetrapeptide fragment or an unnatural mimetic thereof.

In any of the compounds described herein, the ILM can have the structure of Formula (VI), which is a derivative of IAP antagonists described in WO Pub. No. 2008/014236, or an unnatural mimetic thereof:

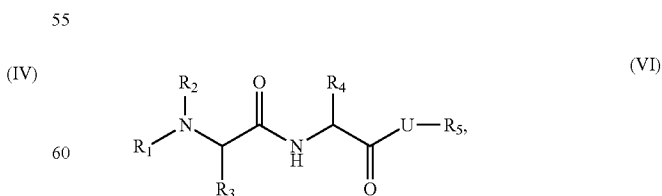

wherein:
R$_1$ of Formula (VI) is, independently selected from H, C$_1$-C$_4$-alkyl, C$_1$-C$_4$-alkenyl, C$_1$-C$_4$-alkynyl or C$_3$-C$_{10}$-cycloalkyl which are unsubstituted or substituted;

$R_2$ of Formula (VI) is, independently selected from H, $C_1$-$C_4$-alkyl, $C_1$-$C_4$-alkenyl, $C_1$-$C_4$-alkynyl or $C_3$-$C_{10}$-cycloalkyl which are unsubstituted or substituted;

$R_3$ of Formula (VI) is, independently selected from H, —$CF_3$, —$C_2H_5$, $C_1$-$C_4$-alkyl, $C_1$-$C_4$-alkenyl, $C_1$-$C_4$-alkynyl, —$CH_2$—Z or any $R_2$ and $R_3$ together form a heterocyclic ring;

each Z of Formula (VI) is, independently selected from H, —OH, F, Cl, —$CH_3$, —$CF_3$, —$CH_2Cl$, —$CH_2F$ or —$CH_2OH$;

$R_4$ of Formula (VI) is, independently selected from $C_1$-$C_{16}$ straight or branched alkyl, $C_1$-$C_{16}$-alkenyl, $C_1$-$C_{16}$-alkynyl, C3-$C_{10}$-cycloalkyl, —$(CH_2)_{0-6}$—$Z_1$. —$(CH_2)_{0-6}$-aryl, and —$(CH_2)_{0-6}$-het, wherein alkyl, cycloalkyl, and phenyl are unsubstituted or substituted;

$R_5$ of Formula (VI) is, independently selected from H, $C_{1-10}$-alkyl, aryl, phenyl, $C_{3-7}$-cycloalkyl, —$(CH_2)_{1-6}$—$C_{3-7}$-cycloalkyl, —$C_{1-10}$-alkyl-aryl, —$(CH_2)_{0-6}$—$C_{3-7}$-cycloalkyl-$(CH_2)_{0-6}$-phenyl, —$(CH_2)_{0-4}$—CH[$(CH_2)_{1-4}$-phenyl]$_2$. indanyl, —C(O)—$C_{1-10}$-alkyl, —C(O)—$(CH_2)_{1-6}$—$C_{3-7}$-cycloalkyl, —C(O)—$(CH_2)_{0-6}$-phenyl, —$(CH_2)_{0-6}$—C(O)-phenyl, —$(CH_2)_{0-6}$-het, —C(O)—$(CH_2)_{1-6}$-het, or $R_5$ is selected from a residue of an amino acid, wherein the alkyl, cycloalkyl, phenyl, and aryl substituents are unsubstituted or substituted;

$Z_1$ of Formula (VI) is, independently selected from —N($R_{10}$)—C(O)—$C_{1-10}$-alkyl, —N($R_{10}$)—C(O)—$(CH_2)_{0-6}$—$C_{3-7}$-cycloalkyl, —N($R_{10}$)—C(O)—$(CH_2)_{0-6}$-phenyl, —N($R_{10}$)—C(O)$(CH_2)_{1-6}$-het, —C(O)—N($R_{11}$)($R_{12}$), —C(O)—O—$C_{1-10}$-alkyl, —C(O)—O—$(CH_2)_{1-6}$—$C_{3-7}$-cycloalkyl, —C(O)—O—$(CH_2)_{0-6}$-phenyl, —C(O)—O—$(CH_2)_{1-6}$-het, —O—C(O)—$C_{1-10}$-alkyl, —O—C(O)—$(CH_2)_{1-6}$—$C_{3-7}$-cycloalkyl, —O—C(O)—$(CH_2)_{0-6}$-phenyl, —O—C(O)—$(CH_2)_{1-6}$-het, wherein alkyl, cycloalkyl, and phenyl are unsubstituted or substituted;

het of Formula (VI) is, independently selected from a 5-7 member heterocyclic ring containing 1-4 heteroatoms selected from N, O, and S, or an 8-12 member fused ring system including at least one 5-7 member heterocyclic ring containing 1, 2, or 3 heteroatoms selected from N, O, and S, which heterocyclic ring or fused ring system is unsubstituted or substituted on a carbon or nitrogen atom; $R_{10}$ of Formula (VI) is selected from H, —$CH_3$. —$CF_3$, —$CH_2OH$, or —$CH_2Cl$; $R_{11}$ and $R_{12}$ of Formula (VI) are independently selected from H, $C_{1-4}$-alkyl, $C_{3-7}$-cycloalkyl, —$(CH_2)_{1-6}$—$C_{3-7}$-cycloakyl, $(CH_2)_{0-6}$-phenyl, wherein alkyl, cycloalkyl, and phenyl are unsubstituted or substituted; or $R_{11}$ and $R_{12}$ together with the nitrogen form het, and U of Formula (VI) is, independently, as shown in Formula (VII):

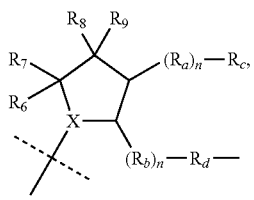

(VII)

wherein:

each n of Formula (VII) is, independently selected from 0 to 5;

X of Formula (VII) is selected from the group —CH and N;

$R_a$ and $R_b$, of Formula (VII) are independently selected from the group O, S, or N atom or $C_{0-8}$-alkyl wherein one or more of the carbon atoms in the alkyl chain are optionally replaced by a heteroatom selected from O, S, or N, and where each alkyl is, independently, either unsubstituted or substituted;

$R_d$ of Formula (VII) is selected from the group Re-Q-($R_f$)$_p$($R_g$)$_q$. and $Ar_1$-D-$Ar_2$;

$R_c$ of Formula (VII) is selected from the group H or any $R_c$ and $R_d$ together form a cycloalkyl or het; where if $R_c$ and $R_d$ form a cycloalkyl or het, $R_5$ is attached to the formed ring at a C or N atom;

p and q of Formula (VII) are independently selected from 0 or 1;

$R_e$ of Formula (VII) is selected from the group $C_{1-8}$-alkyl and alkylidene, and each Re is either unsubstituted or substituted;

Q is selected from the group N, O, S, S(O), and S(O)$_2$;

$Ar_1$ and $Ar_2$ of Formula (VII) are independently selected from the group of substituted or unsubstituted aryl and het;

$R_f$ and $R_g$ of Formula (VII) are independently selected from H, —C1-10-alkyl, $C_{1-10}$-alkylaryl, —OH, —O—$C_{1-10}$-alkyl, —$(CH_2)_{0-6}$—$C_{3-7}$-cycloalkyl, —O—$(CH_2)_{0-6}$-aryl, phenyl, aryl, phenyl-phenyl, —$(CH_2)_{1-6}$-het, —O—$(CH_2)_{1-6}$-het, —$OR_{13}$. —C(0)-$R_{13}$. —C(O)—N($R_{13}$)($R_{14}$), —N($R_{13}$)($R_{14}$), —S—$R_{13}$. —S(O)—$R_{13}$. —S(O)$_2$—$R_{13}$, —S(O)$_2$—$NR_{13}R_{14}$. —$NR_{13}$—S(O)$_2$—$R_{14}$. —S—$C_{t-10}$-alkyl, aryl-$C_{1-4}$-alkyl, or het-$C_{1-4}$-alkyl, wherein alkyl, cycloalkyl, het, and aryl are unsubstituted or substituted, —SO$_2$—$C_{1-2}$-alkyl, —SO$_2$—$C_{1-2}$-alkylphenyl, —O—$C_{1-4}$-alkyl, or any $R_g$ and $R_f$ together form a ring selected from het or aryl; D of Formula (VII) is selected from the group —CO—, —C(O)—$C_{1-7}$-alkylene or arylene, —$CF_2$—, —O—, —S(O), where r is 0-2, 1,3-dioxalane, or $C_{1-7}$-alkyl-OH; where alkyl, alkylene, or arylene are unsubstituted or substituted with one or more halogens, OH, —O—$C_{1-6}$-alkyl, —S—$C_{1-6}$-alkyl, or —$CF_3$; or each D is, independently selected from N($R_h$);

Rh is selected from the group H, unsubstituted or substituted $C_{1-7}$-alkyl, aryl, unsubstituted or substituted —O—($C_{1-7}$-cycloalkyl), —C(O)—$C_{1-10}$-alkyl, —C(O)—$C_{0-10}$-alkyl-aryl, —C—O—$C_{01-10}$-alkyl, —C—O—$C_{0-10}$-alkyl-aryl, —SO$_2$—$C_{1-10}$-alkyl, or —SO$_2$—($C_{0-10}$-alkylaryl);

$R_6$, $R_7$, $R_8$, and $R_9$ of Formula (VII) are, independently, selected from the group H, —$C_{1-10}$-alkyl, —$C_{1-10}$-alkoxy, aryl-$C_{1-10}$— alkoxy, —OH, —O—$C_{1-10}$-alkyl, —$(CH_2)_{0-6}$—$C_{3-7}$-cycloalkyl, —O—$(CH_2)_{0-6}$-aryl, phenyl, —$(CH_2)_{1-6}$-het, —O—$(CH_2)_{1-6}$-het, —$OR_{13}$. —C(O)—$R_3$. —C(O)—N($R_{13}$)($R_{14}$), —N($R_{13}$)($R_{14}$), —S—$R_{13}$. —S(O)—$R_{13}$. —S(O)$_2$—$R_{13}$. —S(O)—$NR_{13}R_{14}$. or —$NR_{13}$—S(O)$_2R_{14}$; wherein each alkyl, cycloalkyl, and aryl is unsubstituted or substituted; and any $R_6$, $R_7$, $R_8$, and $R_9$ optionally together form a ring system;

$R_{13}$ and $R_{14}$ of Formula (VII) are independently selected from the group H, $C_{1-10}$-alkyl, —$(CH_2)_{0-6}$—$C_{3-7}$-cycloalkyl, —$(CH_2)_{0-6}$—$(CH)_{0-1}$-(aryl)$_{1-2}$. —C(O)—$C_{1-10}$-alkyl, —C(O)—$(CH_2)_{1-6}$—$C_{3-7}$-cycloalkyl, —C(O)—O—$(CH_2)_{0-6}$-aryl, —C(O)—$(CH_2)_{0-6}$—O-fluorenyl, —C(O)—NH—$(CH_2)_{0-6}$-aryl, —C(O)—$(CH_2)_{0-6}$-aryl, —C(O)—$(CH_2)_{0-6}$-het, —C(S)—$C_{1-10}$-alkyl, —C(S)—$(CH_2)_{1-6}$—$C_{3-7}$-cycloalkyl, —C(S)—O—$(CH_2)_{0-6}$-aryl, —C(S)—$(CH_2)_{0-6}$—O-fluorenyl, —C(S)—NH—$(CH_2)_{0-6}$-aryl, —C(S)—$(CH_2)_{0-6}$-aryl, or —C(S)—$(CH_2)_{1-6}$-het, wherein each alkyl, cycloalkyl, and aryl is unsubstituted or substituted: or any $R_{13}$ and $R_{14}$ together with a nitrogen atom form het;

wherein alkyl substituents of $R_{13}$ and $R_{14}$ of Formula (VII) are unsubstituted or substituted and when substituted, are substituted by one or more substituents selected from $C_{1-10}$-alkyl, halogen, OH, —O—$C_{1-4}$-alkyl, —S—$C_{1-6}$-alkyl, and —$CF_3$; and substituted phenyl or aryl of $R_{13}$ and $R_{14}$ are substituted by one or more substituents selected from halogen, hydroxyl. $C_{1-4}$-alkyl, $C_{1-4}$-alkoxy, nitro, —CN, —O—C(O)—$C_{1-4}$-alkyl, and —C(O)—O—$C_{1-4}$-aryl; or a pharmaceutically acceptable salt or hydrate thereof.

In certain embodiments, the compound further comprises an independently selected second ILM attached to the ILM of Formula (VI), or an unnatural mimetic thereof, by way of at least one additional independently selected linker group. In an embodiment, the second ILM is a derivative of Formula (VI), or an unnatural mimetic thereof. In a certain embodiment, the at least one additional independently selected linker group comprises two additional independently selected linker groups chemically linking the ILM and the second ILM. In an embodiment, the at least one additional linker group for an ILM of the Formula (VI), or an unnatural mimetic thereof, chemically links groups selected from $R_4$ and $R_5$. For example, an ILM of Formula (VI) and a second ILM of Formula (VI), or an unnatural mimetic thereof, can be linked as shown below:

(A)
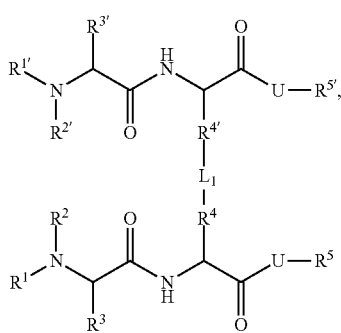

(B)
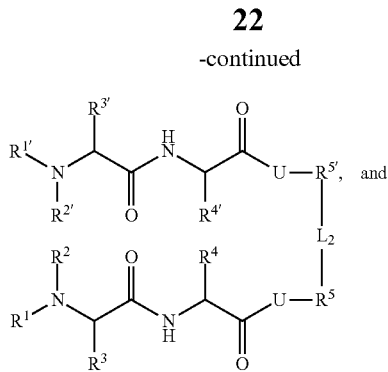

(C)
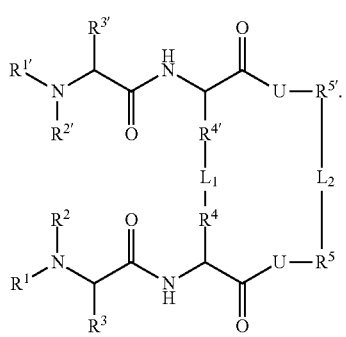

In certain embodiments, the ILM, the at least one additional independently selected linker group L, and the second ILM has a structure selected from the group consisting of:

(A)
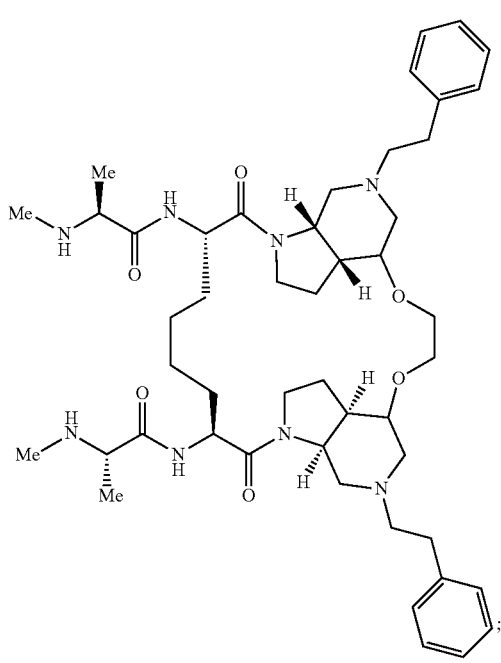

(B)
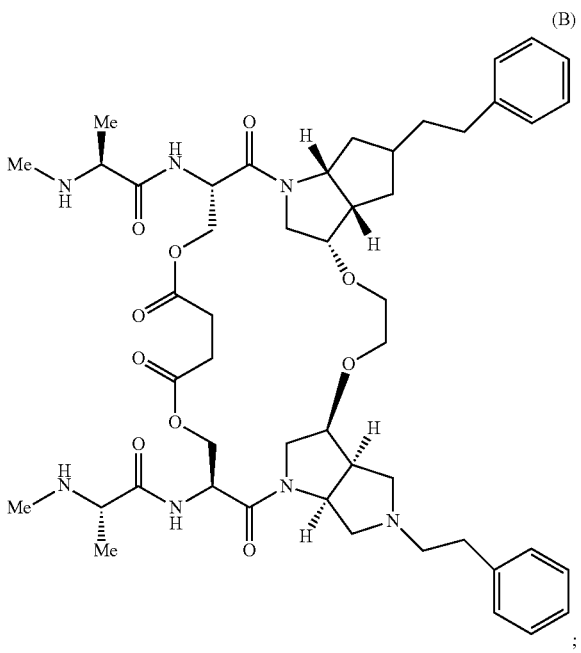

(C)
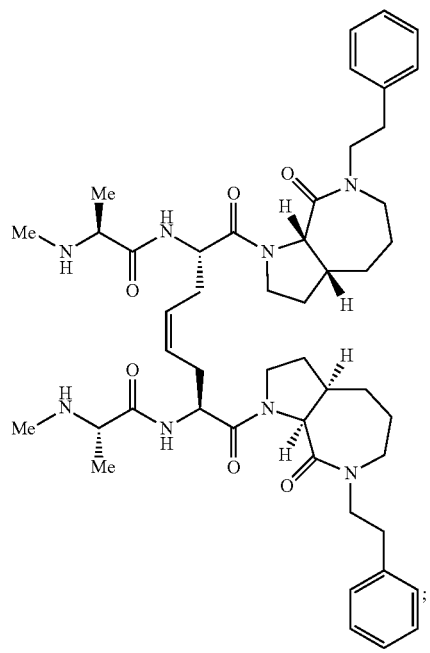
(D)
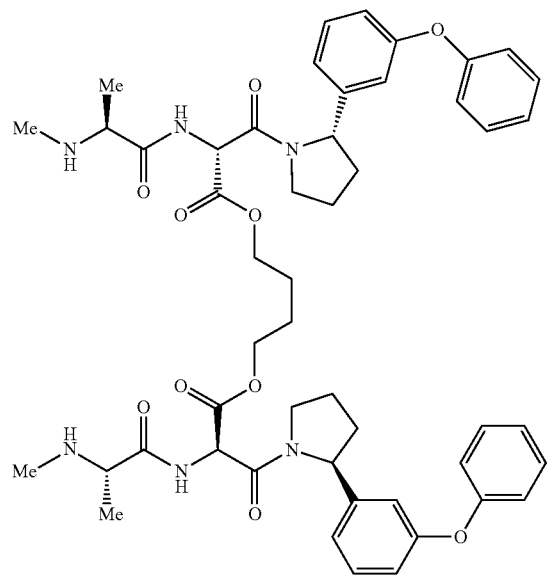
;
(E)
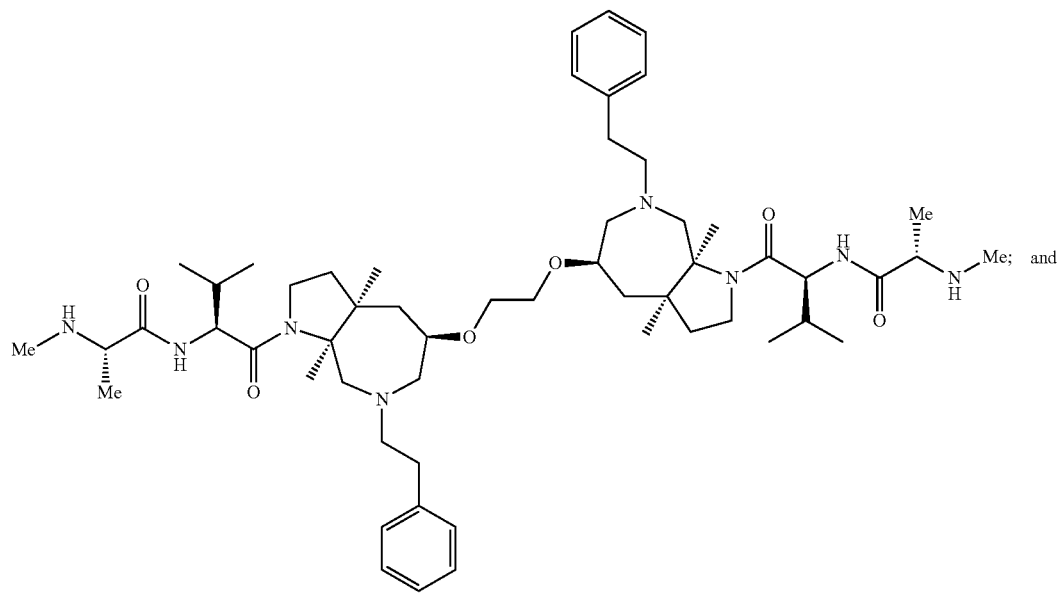
and
(F)
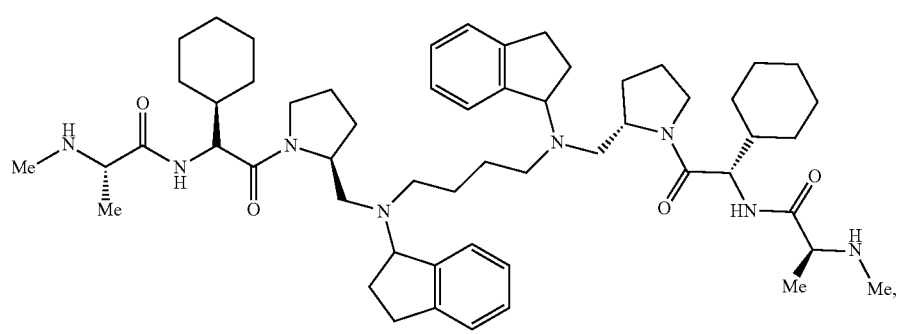
which are derivatives of IAP antagonists described in WO Pub. No. 2008/014236.
In any of the compounds described herein, the ILM can have the structure of Formula (VIII), which is based on the IAP ligands described in Ndubaku, C., et al. Antagonism of c-IAP and XIAP proteins is required for efficient induction of cell death by small-molecule IAP antagonists, *ACS Chem. Biol.*, 557-566, 4 (7) (2009), or an unnatural mimetic thereof:

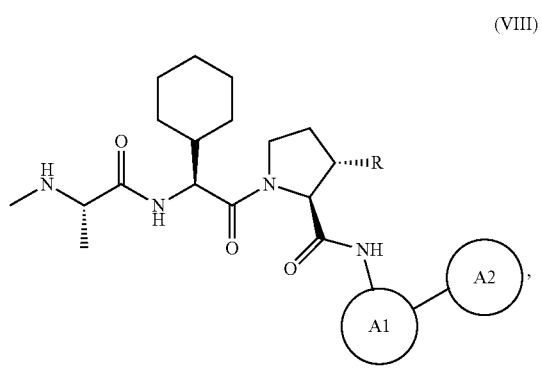

(VIII)

wherein each of A1 and A2 of Formula (VIII) is independently selected from optionally substituted monocyclic, fused rings, aryls and heteroaryls; and R of Formula (VIII) is selected from H or Me.

In a particular embodiment, the linker group L is attached to A1 of Formula (VIII). In another embodiment, the linker group L is attached to A2 of Formula (VIII).

In a particular embodiment, the ILM is selected from the group consisting of

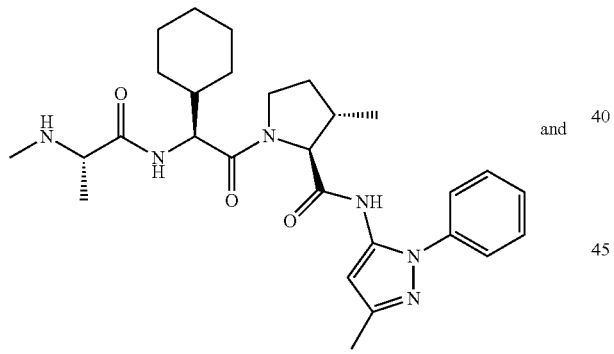

(A)

and

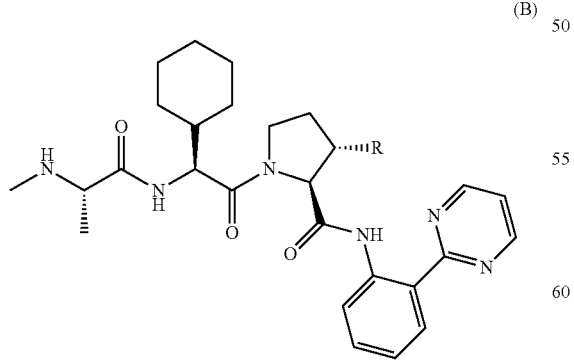

(B)

In any of the compounds described herein, the ILM can have the structure of Formula (IX), which is derived from the chemotypes cross-referenced in Mannhold, R., et al. IAP antagonists: promising candidates for cancer therapy, *Drug Discov. Today*, 15 (5-6), 210-9 (2010), or an unnatural mimetic thereof:

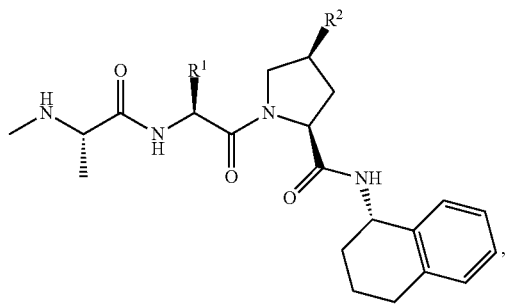

(IX)

wherein $R^1$ is selected from alkyl, cycloalkyl and heterocycloalkyl and, most preferably, from isopropyl, tert-butyl, cyclohexyl and tetrahydropyranyl, and $R^2$ of Formula (IX) is selected from —OPh or H.

In any of the compounds described herein, the ILM can have the structure of Formula (X), which is derived from the chemotypes cross-referenced in Mannhold, R., et al. IAP antagonists: promising candidates for cancer therapy, *Drug Discov. Today*, 15 (5-6), 210-9 (2010), or an unnatural mimetic thereof:

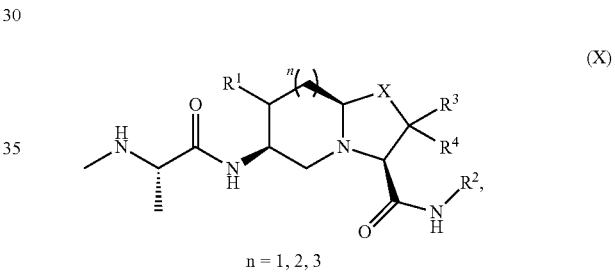

(X)

n = 1, 2, 3 wherein:
$R^1$ of Formula (X) is selected from H, —CH$_2$OH, —CH$_2$CH$_2$OH, —CH$_2$NH$_2$, —CH$_2$CH$_2$NH$_2$; X of Formula (X) is selected from S or CH$_2$;
$R^2$ of Formula (X) is selected from:

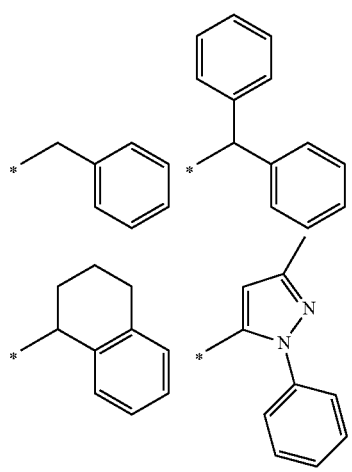

R³ and R⁴ of Formula (X) are independently selected from H or Me

In any of the compounds described herein, the ILM can have the structure of Formula (XI), which is derived from the chemotypes cross-referenced in Mannhold, R., et al. IAP antagonists: promising candidates for cancer therapy, *Drug Discov. Today*, 15 (5-6), 210-9 (2010), or an unnatural mimetic thereof:

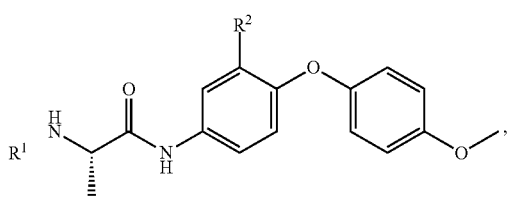

(XI)

wherein R¹ of Formula (XI) is selected from H or Me, and R² of Formula (XI) is selected from H or

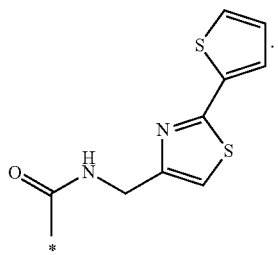

In any of the compounds described herein, the ILM can have the structure of Formula (XII), which is derived from the chemotypes cross-referenced in Mannhold, R., et al. IAP antagonists: promising candidates for cancer therapy, *Drug Discov. Today*, 15 (5-6), 210-9 (2010), or an unnatural mimetic thereof:

(XII)

wherein:
R¹ of Formula (XII) is selected from:

and R² of Formula (XII) is selected from:

In any of the compounds described herein, the IAP E3 ubiquitin ligase binding moiety is selected from the group consisting of:

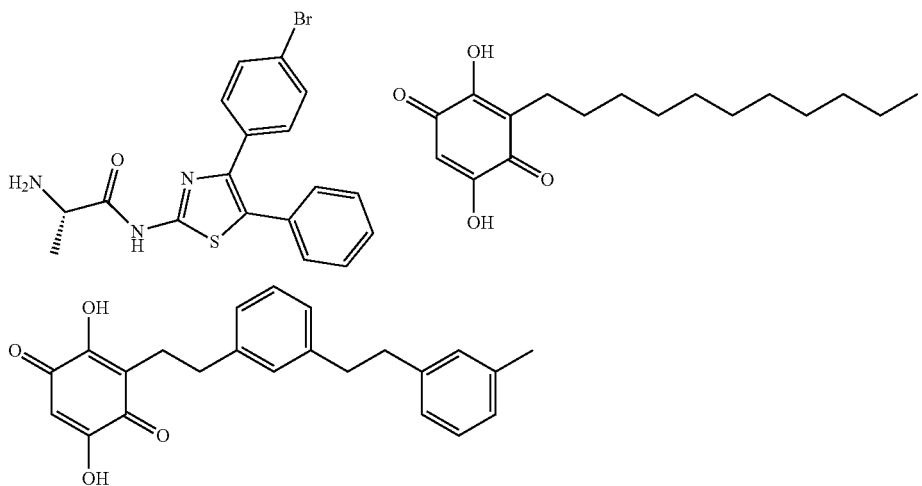

-continued
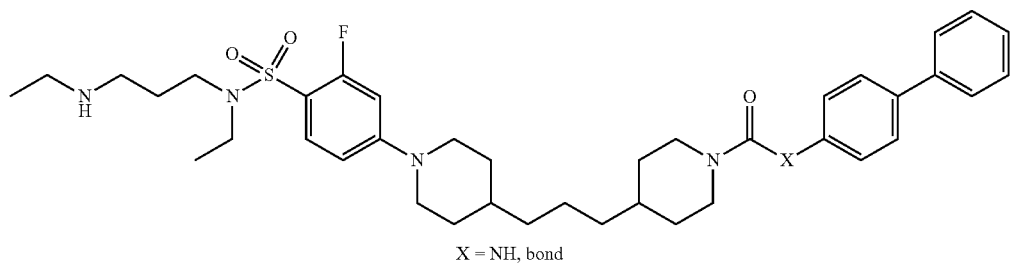
X = NH, bond
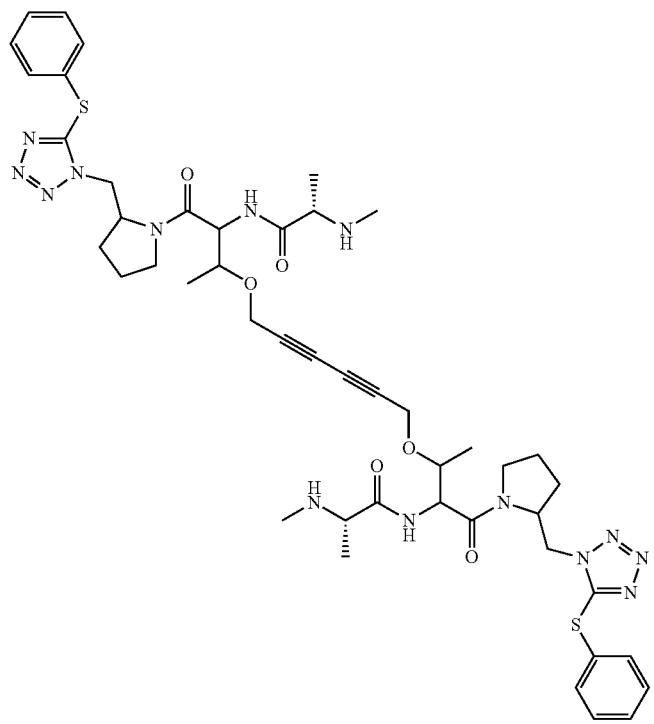
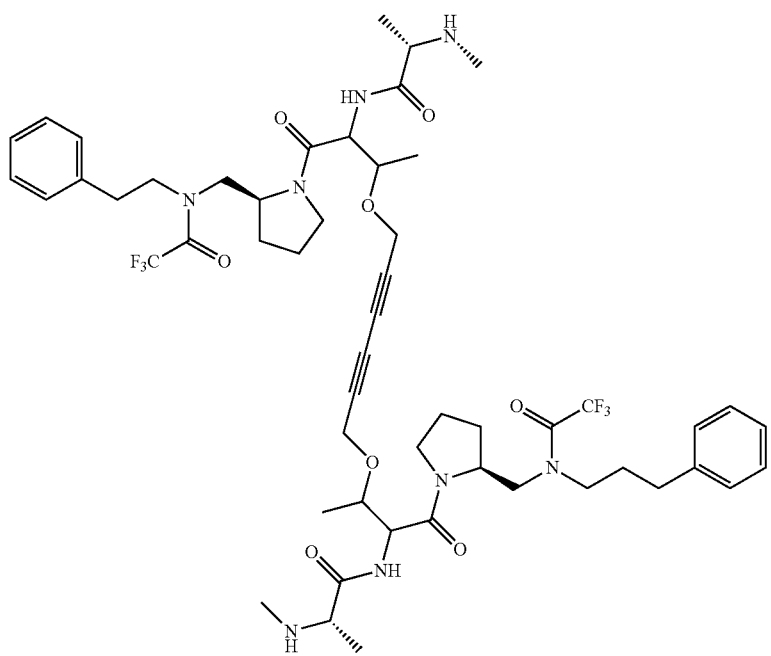

-continued
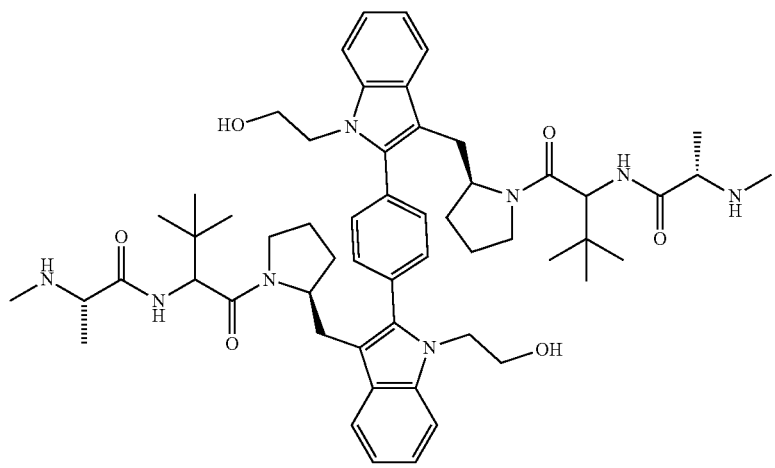
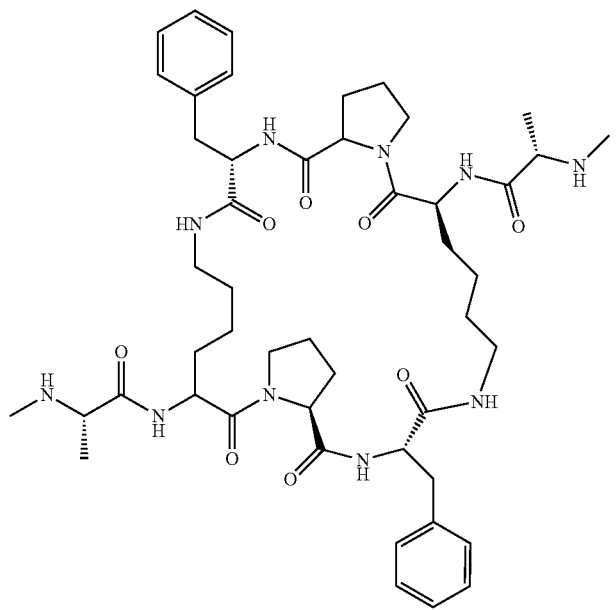
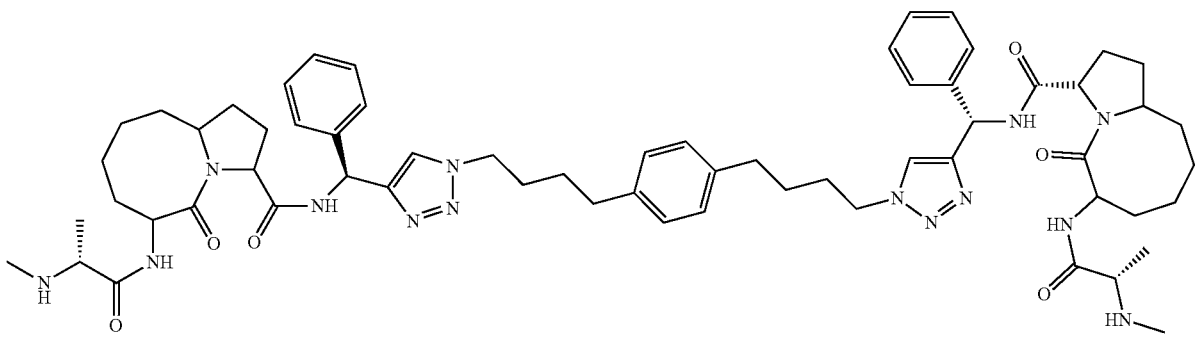

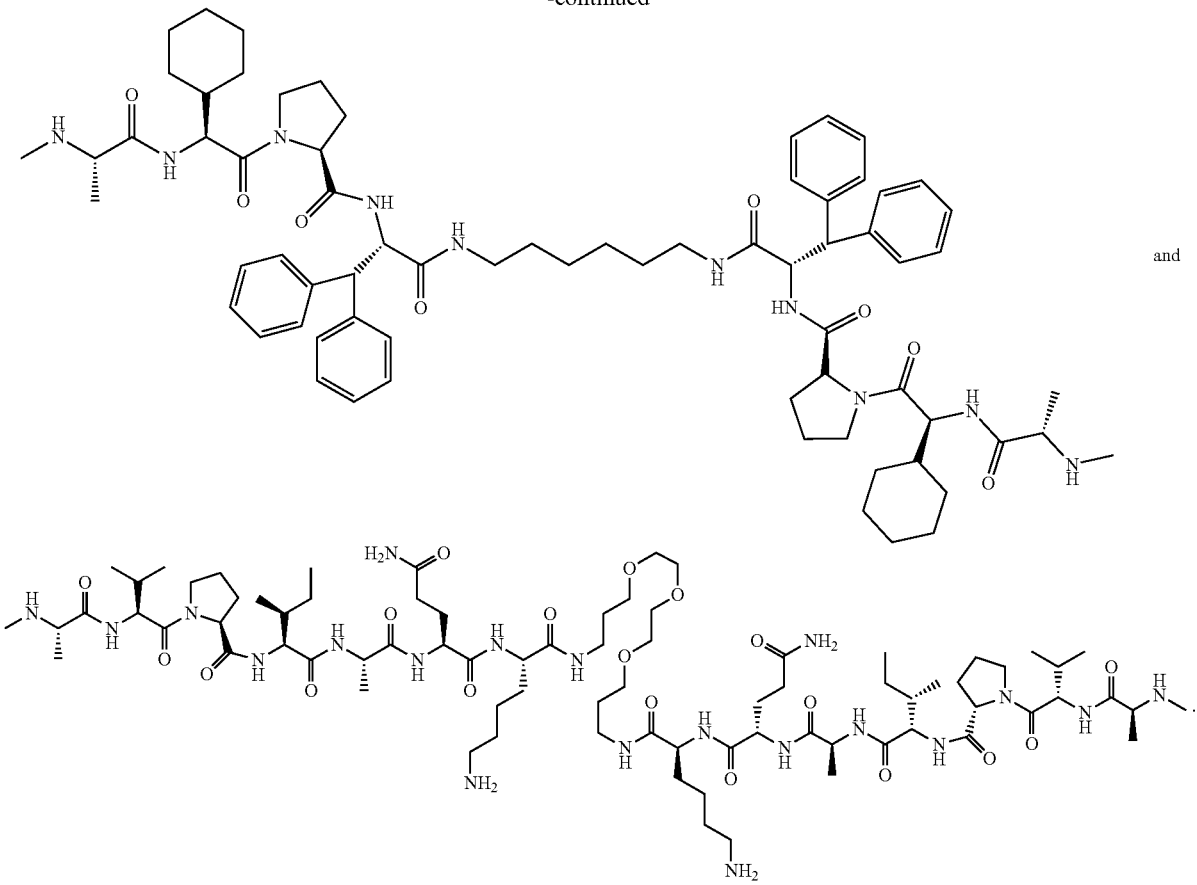

In any of the compounds described herein, the ILM can have the structure of Formula (XIII), which is based on the IAP ligands summarized in Flygare, J. A., et al. Small-molecule pan-IAP antagonists: a patent review, *Expert Opin. Ther. Pat.*, 20 (2), 251-67 (2010), or an unnatural mimetic thereof:

(XIII)

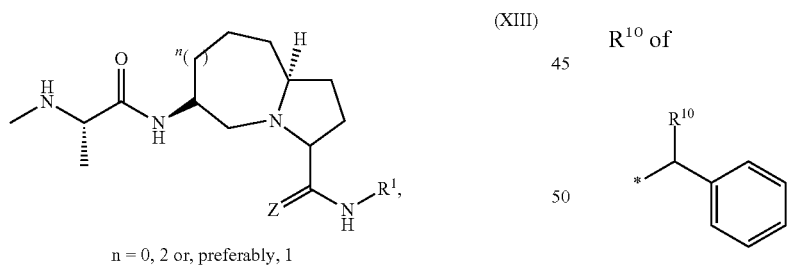

n = 0, 2 or, preferably, 1 wherein:
Z of Formula (XIII) is absent or O;
R$^1$ of Formula (XIII) is selected from:

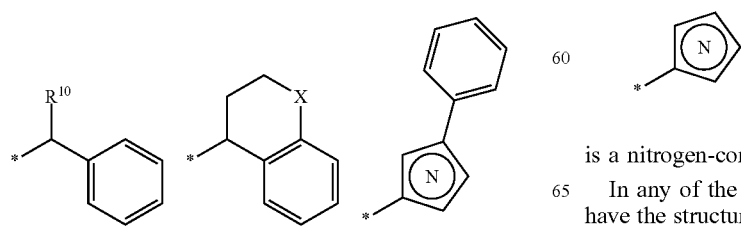

is selected from H, alkyl, or aryl;
X is selected from CH$_2$ and O; and is a nitrogen-containing heteroaryl.

In any of the compounds described herein, the ILM can have the structure of Formula (XIV), which is based on the IAP ligands summarized in Flygare, J. A., et al. Small-molecule pan-IAP antagonists: a patent review, *Expert Opin. Ther. Pat.*, 20 (2), 251-67 (2010), or an unnatural mimetic thereof:

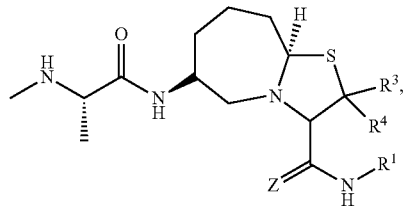
(XIV)

wherein:

Z of Formula (XIV) is absent or O;

R³ and R⁴ of Formula (XIV) are independently selected from H or Me;

R¹ of Formula (XIV) is selected from:

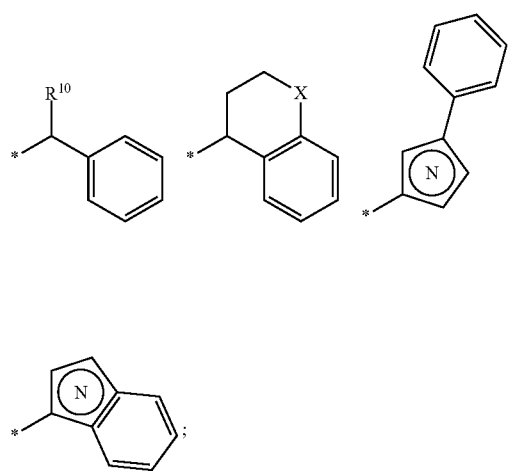

R¹⁰ of

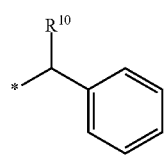

is selected from H, alkyl, or aryl;

X of

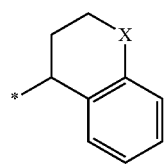

is selected from $CH_2$ and O; and

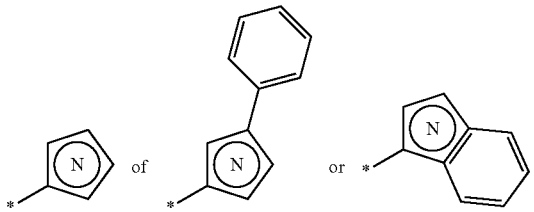

is a nitrogen-containing heteraryl.

In any of the compounds described herein, the ILM is selected from the group consisting of:

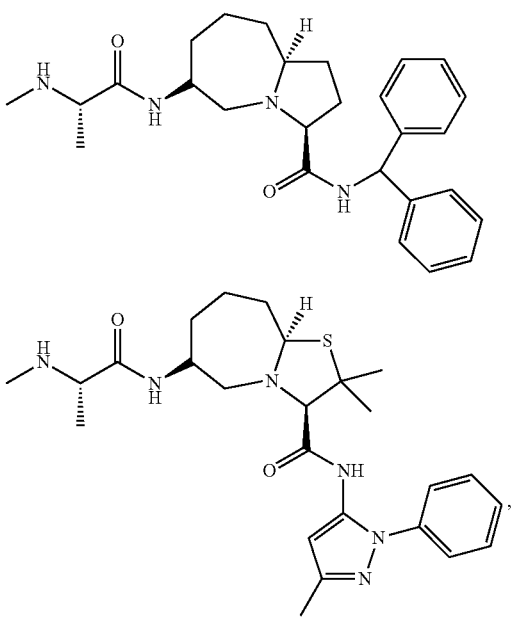

which are derivatives of ligands disclose in US Patent Pub. No. 2008/0269140 and U.S. Pat. No. 7,244,851.

In any of the compounds described herein, the ILM can have the structure of Formula (XV), which was a derivative of the IAP ligand described in WO Pub. No. 2008/128171, or an unnatural mimetic thereof:

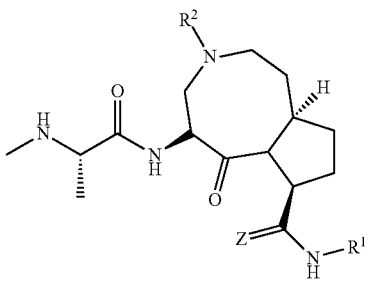
(XV)

wherein:

Z of Formula (XV) is absent or O;

R¹ of Formula (XV) is selected from:

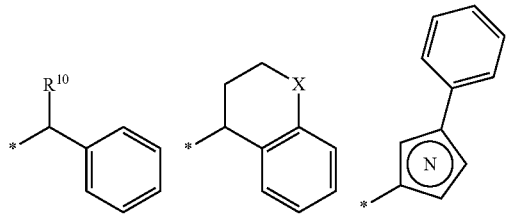

R¹⁰ of

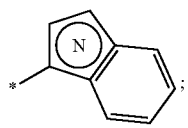

selected from H, alkyl, or aryl;

X of

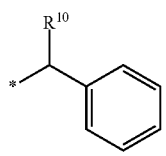

is selected from CH$_2$ and O; and

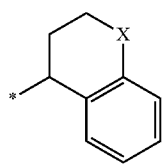

is a nitrogen-containing heteraryl; and R² of Formula (XV) selected from H, alkyl, or acyl;

In a particular embodiment, the ILM has the following structure:

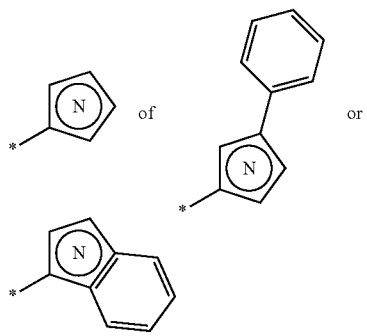

In any of the compounds described herein, the ILM can have the structure of Formula (XVI), which is based on the IAP ligand described in WO Pub. No. 2006/069063, or an unnatural mimetic thereof:

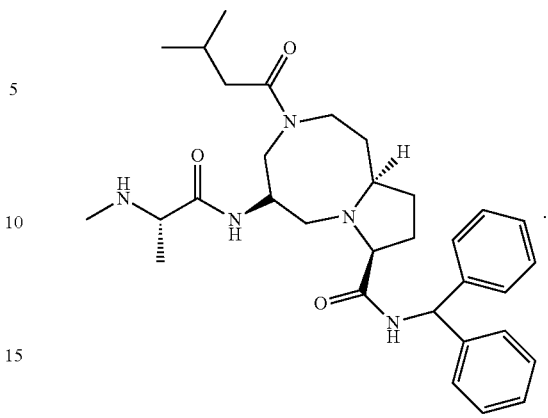

(XVI)

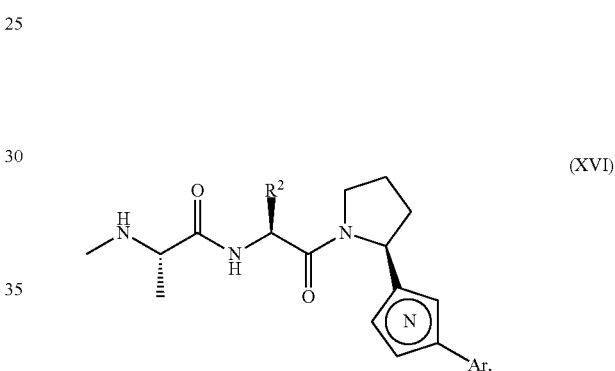

wherein:

R² of Formula (XVI) is selected from alkyl, cycloalkyl and heterocycloalkyl; more preferably, from isopropyl, tert-butyl, cyclohexyl and tetrahydropyranyl, most preferably from cyclohexyl;

of Formula (XVI) is a 5- or 6-membered nitrogen-containing heteroaryl; more preferably, 5-membered nitrogen-containing heteroaryl, and most preferably thiazole; and Ar of Formula (XVI) is an aryl or a heteroaryl.

In any of the compounds described herein, the ILM can have the structure of Formula (XVII), which is based on the IAP ligands described in Cohen, F. et al., Antogonists of inhibitors of apoptosis proteins based on thiazole amide isosteres, Bioorg. Med. Chem. Lett., 20(7), 2229-33 (2010), or an unnatural mimetic thereof:

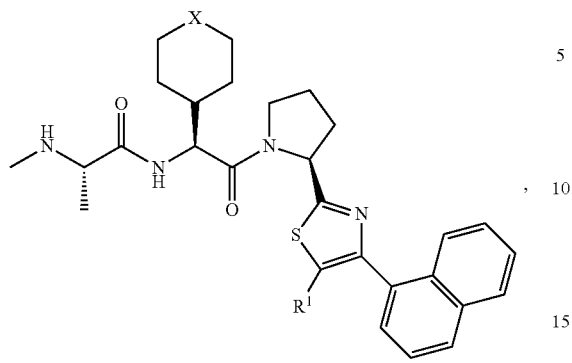
(XVII)

wherein:

R[1] of Formula (XVII) is selected from the group halogen (e.g. fluorine), cyano,

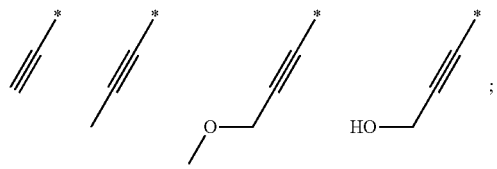
;

X of Formula (XVII) is selected from the group O or CH$_2$.

In any of the compounds described herein, the ILM can have the structure of Formula (XVIII), which is based on the IAP ligands described in Cohen, F. et al., Antogonists of inhibitors of apoptosis proteins based on thiazole amide isosteres, Bioorg. Med. Chem. Lett., 20(7), 2229-33 (2010), or an unnatural mimetic thereof:

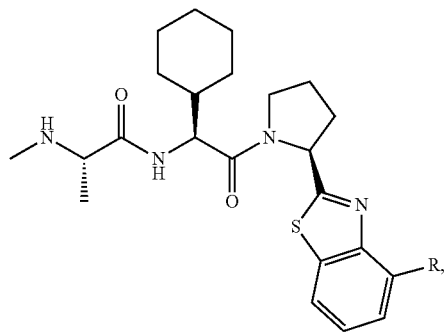
(XVIII)

wherein R of Formula (XVIII) is selected from alkyl, aryl, heteroaryl, arylalkyl, heteroarylalkyl or halogen (in variable substitution position).

In any of the compounds described herein, the ILM can have the structure of Formula (XIX), which is based on the IAP ligands described in Cohen, F. et al., Antogonists of inhibitors of apoptosis proteins based on thiazole amide isosteres, Bioorg. Med. Chem. Lett., 20(7), 2229-33 (2010), or an unnatural mimetic thereof:

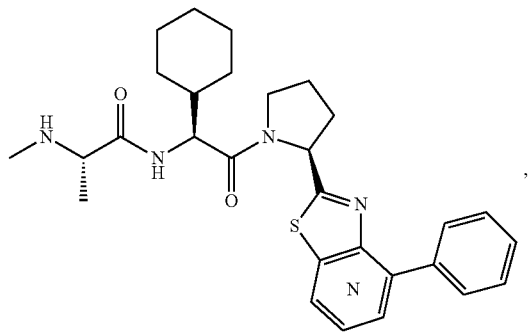
(XIX)

wherein

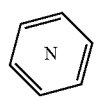

is a 6-member nitrogen heteroaryl.

In a certain embodiment, the ILM of the composition is selected from the group consisting of:

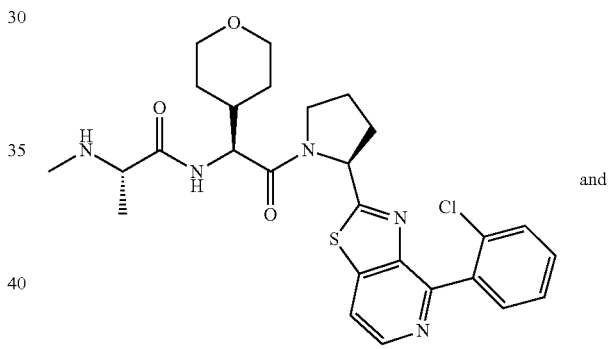
and

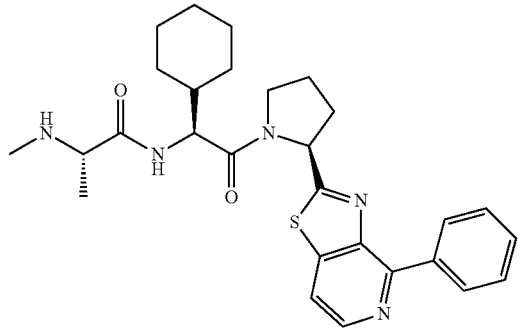

In certain embodiments, the ILM of the composition is selected from the group consisting of:

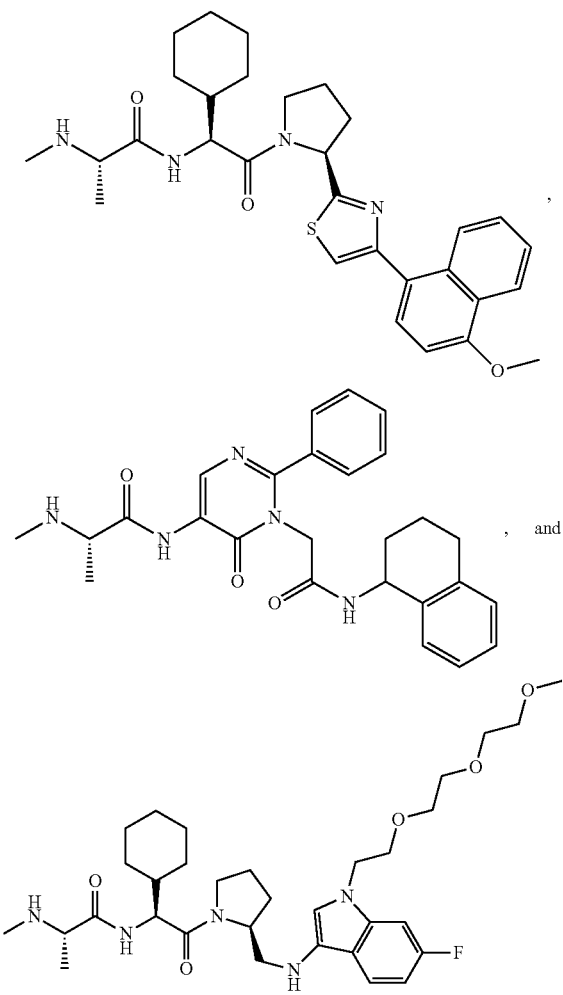

In any of the compounds described herein, the ILM can have the structure of Formula (XX), which is based on the IAP ligands described in WO Pub. No. 2007/101347, or an unnatural mimetic thereof:

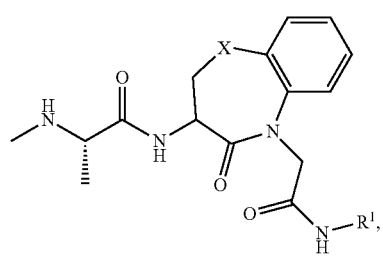
(XX)

wherein X of Formula (XX) is selected from CH$_2$, O, NH, or S.

In any of the compounds described herein, the ILM can have the structure of Formula (XXI), which is based on the IAP ligands described in U.S. Pat. Nos. 7,345,081 and 7,419,975, or an unnatural mimetic thereof:

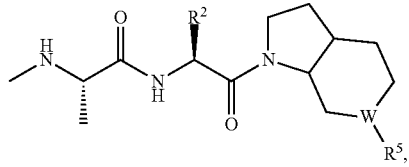
(XXI)

wherein:

R$^2$ of Formula (XXI) is selected from

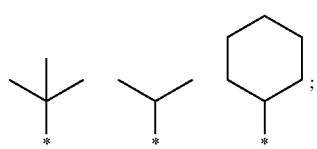

R$^1$ of Formula (XXI) is selected from:

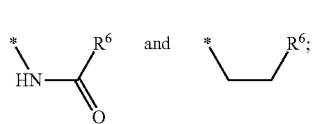

and

W of Formula (XXI) is selected from CH or N; and R$^6$ of

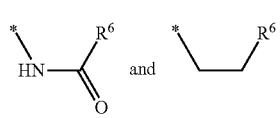

and are independently a mono- or bicyclic fused aryl or heteroaryl.

In certain embodiments, the ILM of the compound is selected from the group consisting of:

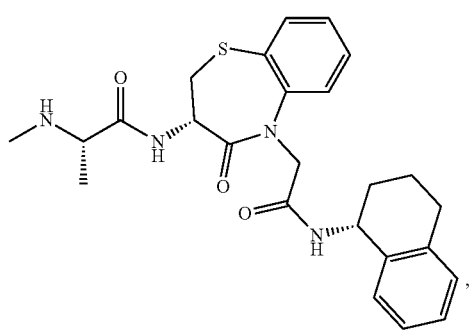

43
-continued
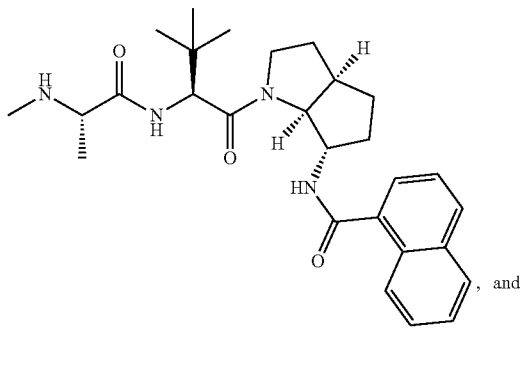
, and
44
-continued
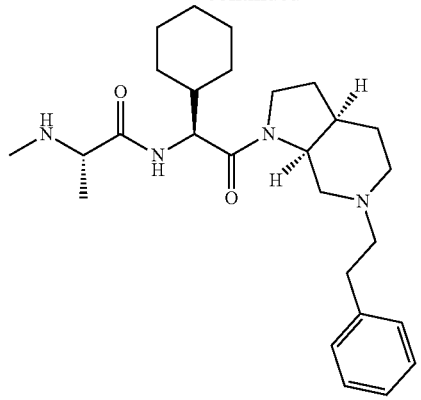
In certain embodiments, the ILM of the compound is selected from the group consisting of:
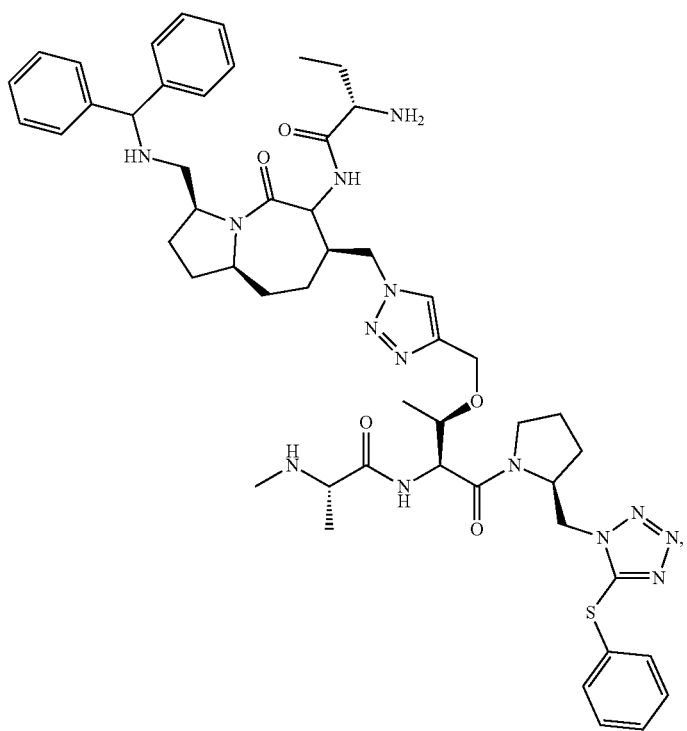

-continued
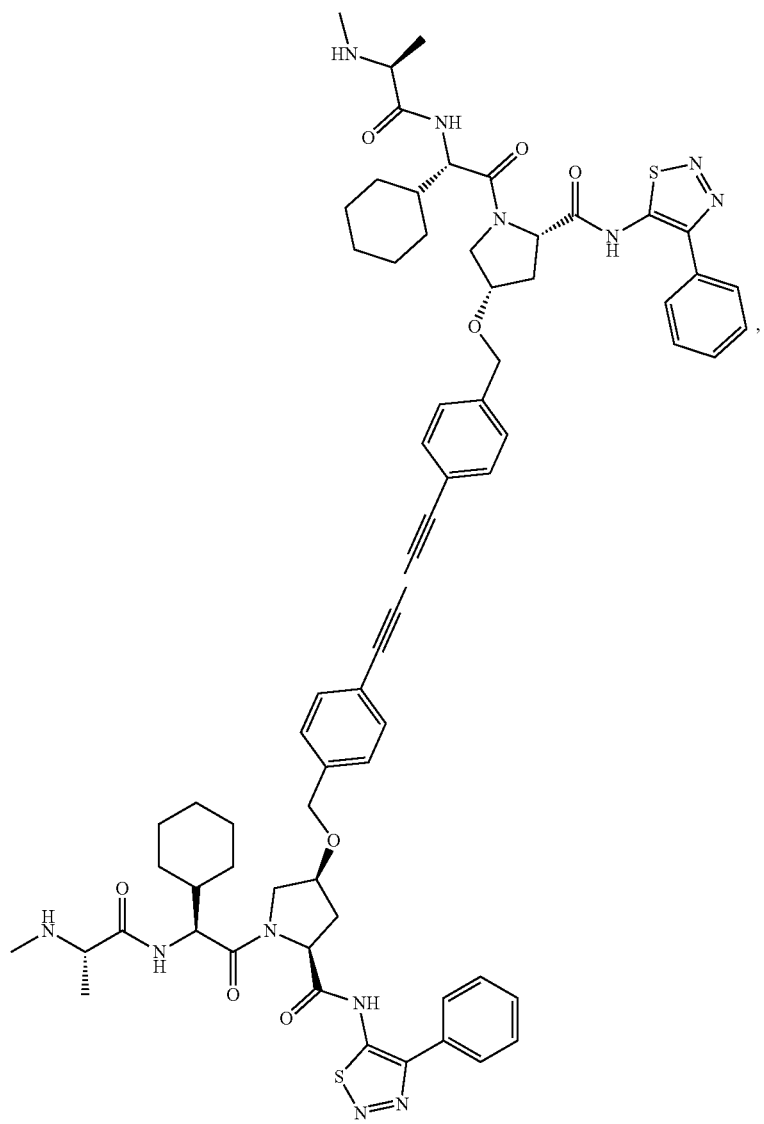
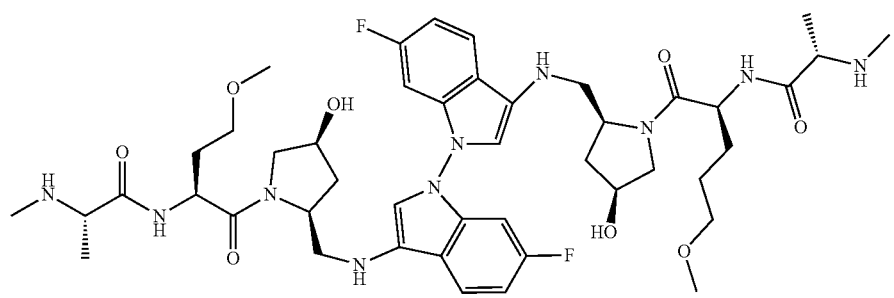

-continued
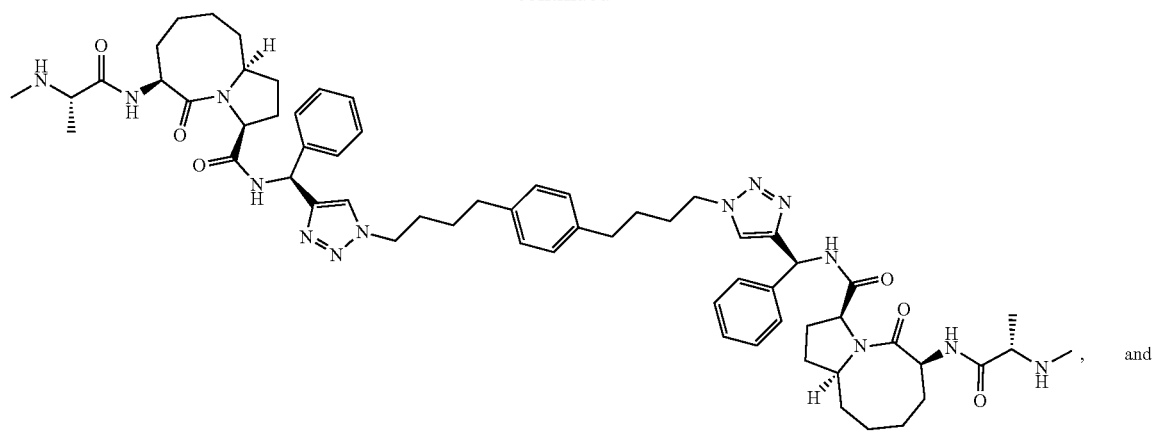
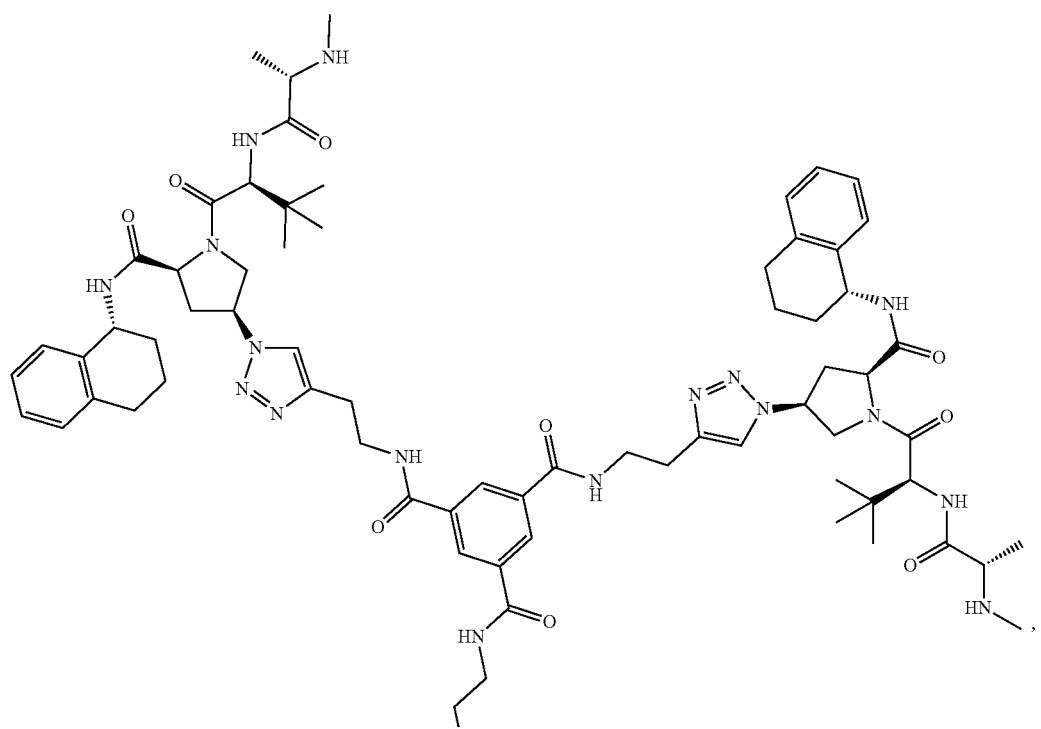

-continued

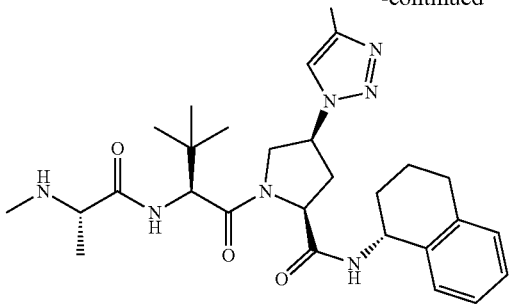

which are described in WO Pub. No. 2009/060292, U.S. Pat. No. 7,517,906, WO Pub. No. 2008/134679, WO Pub. No. 2007/130626, and WO Pub. No. 2008/128121.

In any of the compounds described herein, the ILM can have the structure of Formula (XXII) or (XXIII), which are derived from the IAP ligands described in WO Pub. No. 2015/006524 and Perez H L, *Discovery of potent heterodimeric antagonists of inhibitor of apoptosis proteins (IAPs) with sustained antitumor activity*. J. Med. Chem. 58(3), 1556-62 (2015), or an unnatural mimetic thereof:

(XXII)

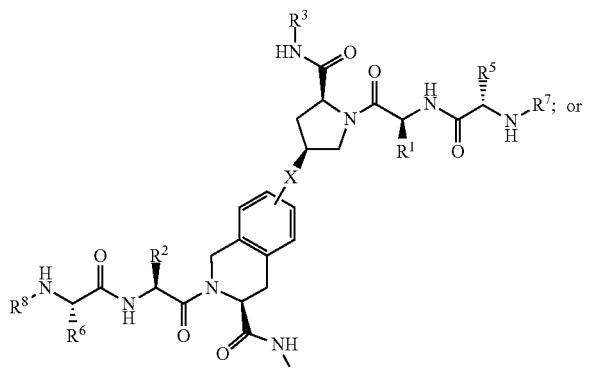

(XXIII)

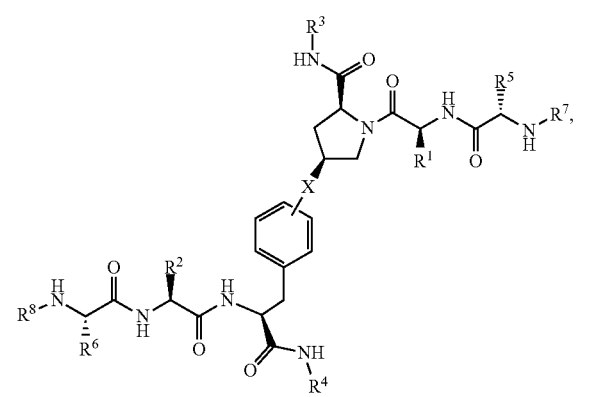

wherein:

$R^1$ of Formula (XXII) or (XXIII) is optionally substituted alkyl, optionally substituted cycloalkyl, optionally substituted cycloalkylalkyl, optionally substituted heterocyclyl, optionally substituted arylalkyl or optionally substituted aryl;

$R^2$ of Formula (XXII) or (XXIII) is optionally substituted alkyl, optionally substituted cycloalkyl, optionally substituted cycloalkylalkyl, optionally substituted heterocyclyl, optionally substituted arylalkyl or optionally substituted aryl;

or alternatively, $R^1$ and $R^2$ of Formula (XXII) or (XXIII) are independently optionally substituted thioalkyl wherein the substituents attached to the S atom of the thioalkyl are optionally substituted alkyl, optionally substituted branched alkyl, optionally substituted heterocyclyl, $-(CH_2)_v COR^{20}$, $-CH_2CHR^{21}COR^{22}$ or $-CH_2R^{23}$;

wherein:

v is an integer from 1-3;

$R^{20}$ and $R^{22}$ of $-(CH_2)COR^{20}$ and $-CH_2R^{23}$ are independently selected from OH, $NR^{24}R^{25}$ or $OR^{26}$;

$R^{20}$ of $-CH_2CHR^{21}COR^2$ is selected from the group $NR^{24}R^{25}$;

$R^{23}$ of $-CH_2R^{23}$ is selected from optionally substituted aryl or optionally substituted heterocyclyl, where the optional substituents include alkyl and halogen;

$R^{24}$ of $NR^{24}R^{25}$ is selected from hydrogen or optionally substituted alkyl;

$R^{25}$ of $NR^{24}R^{25}$ is selected from hydrogen, optionally substituted alkyl, optionally substituted branched alkyl, optionally substituted arylalkyl, optionally substituted heterocyclyl, $-CH_2(OCH_2CH_2O)_m CH_3$, or a polyamine chain, such as spermine or spermidine;

$R^{26}$ of $OR^{26}$ is selected from optionally substituted alkyl, wherein the optional substituents are OH, halogen or $NH_2$; and m is an integer from 1-8;

$R^3$ and $R^4$ of Formula (XXII) or (XXIII) are independently selected from optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

$R^5$, $R^6$, $R^7$ and $R^8$ of Formula (XXII) or (XXIII) are independently selected from hydrogen, optionally substituted alkyl or optionally substituted cycloalkyl; and X is selected from a bond or a chemical linker group, and/or a pharmaceutically acceptable salt, tautomer or stereoisomer thereof.

In certain embodiments, X is a bond or is selected from the group consisting of:

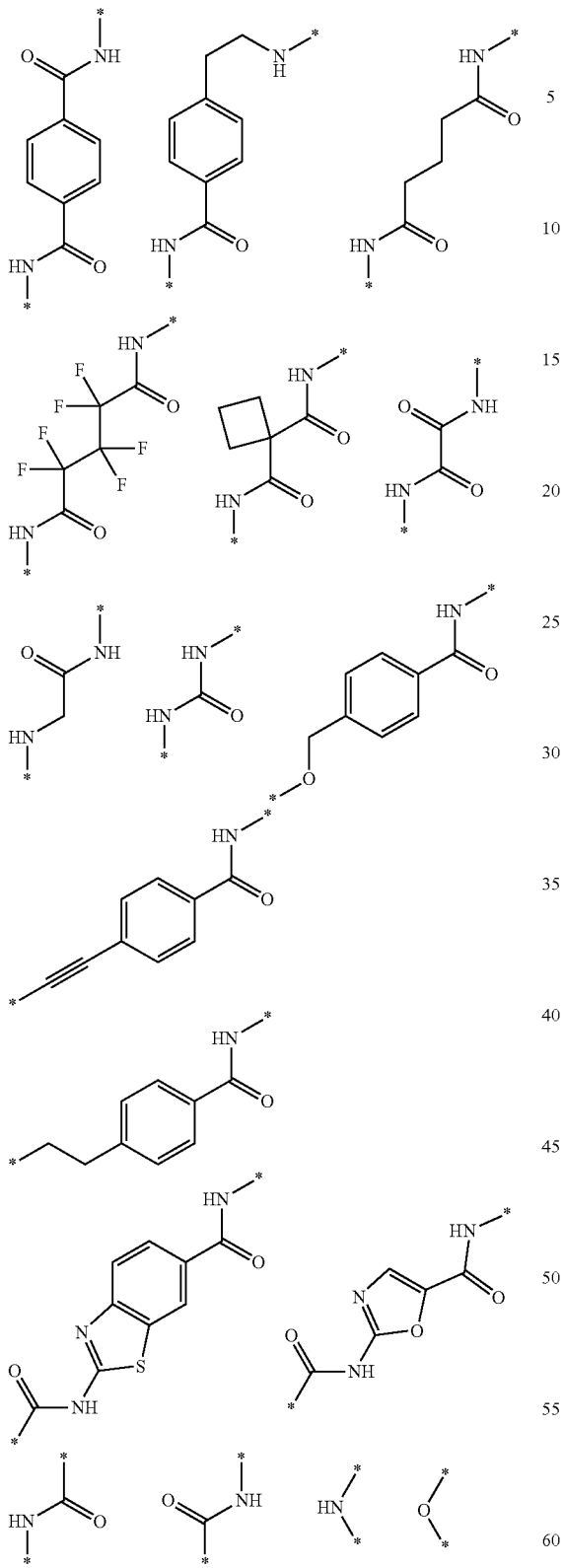

wherein "*" is the point of attachment of a PTM, L or ULM, e.g., an ILM.

In any of the compounds described herein, the ILM can have the structure of Formula (XXIV) or (XXVI), which are derived from the IAP ligands described in WO Pub. No. 2015/006524 and Perez H L, *Discovery of potent heterodimeric antagonists of inhibitor of apoptosis proteins (IAPs) with sustained antitumor activity*. J. Med. Chem. 58(3), 1556-62 (2015), or an unnatural mimetic thereof, and the chemical linker to linker group L as shown:

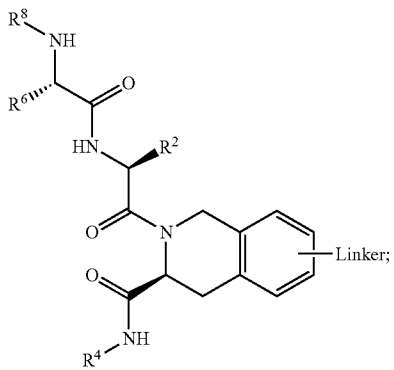

(XXIV)

(XXV)

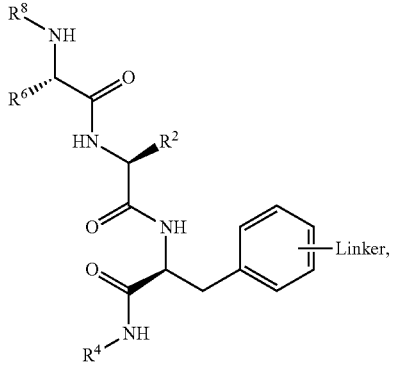

(XXVI)

wherein:
$R^1$ of Formula (XXIV), (XXV) or (XXVI) is selected from optionally substituted alkyl, optionally substituted cycloalkyl, optionally substituted cycloalkylalkyl, optionally substituted heterocyclyl, optionally substituted arylalkyl or optionally substituted aryl;
$R^2$ of Formula (XXIV), (XXV) or (XXVI) is selected from optionally substituted alkyl, optionally substituted cycloalkyl, optionally substituted cycloalkylalkyl, optionally substituted heterocyclyl, optionally substituted arylalkyl or optionally substituted aryl;
or alternatively,
$R^1$ and $R^2$ of Formula (XXIV), (XXV) or (XXVI) are independently selected from optionally substituted thioalkyl wherein the substituents attached to the S atom of the thioalkyl are optionally substituted alkyl, optionally substituted branched alkyl, optionally substituted heterocyclyl, —(CH$_2$)$_v$COR$^{20}$, —CH$_2$CHR$^{21}$COR$^{22}$ or —CH$_2$R$^2$,
wherein:
v is an integer from 1-3;
R$^{20}$ and R$^{21}$ of —(CH$_2$)COR$^{20}$ and —CH$_2$R$^{23}$ are independently selected from OH, NR$^{24}$R$^{25}$ or OR$^{26}$;
R$^{21}$ of —CH$_2$CHR$^{21}$COR$^2$ is selected from NR$^{24}$R$^{25}$;
R$^{23}$ of —CH$_2$R$^{23}$ is selected from optionally substituted aryl or optionally substituted heterocyclyl, wherein the optional substituents include alkyl and halogen;
R$^{24}$ of NR$^{24}$R$^{25}$ is selected from hydrogen or optionally substituted alkyl;
R$^{25}$ of NR$^{24}$R$^{25}$ is selected from hydrogen, optionally substituted alkyl, optionally substituted branched alkyl, optionally substituted arylalkyl, optionally substituted heterocyclyl, —CH$_2$(OCH$_2$CH$_2$O)$_m$CH$_3$, or a polyamine chain, such as spermine or spermidine;
R$^{26}$ of OR$^{2'}$ is selected from optionally substituted alkyl, wherein the optional substituents are OH, halogen or NH$_2$; and
m is an integer from 1-8;
R$^3$ and R$^4$ of Formula (XXIV), (XXV) or (XXVI) are independently optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;
R$^5$, R$^6$, R$^7$ and R$^8$ of Formula (XXIV), (XXV) or (XXVI) are independently hydrogen, optionally substituted alkyl or optionally substituted cycloalkyl; and/or a pharmaceutically acceptable salt, tautomer or stereoisomer thereof.

In a particular embodiment, the ILM according to Formulas (XXII) through (XXVI):
R$^7$ and R$^8$ are selected from the H or Me;
R$^5$ and R$^6$ are selected from the group comprising:

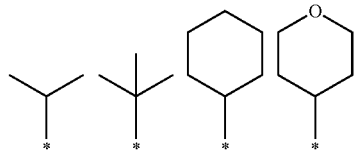

R$^3$ and R$^4$ are selected from the group comprising:

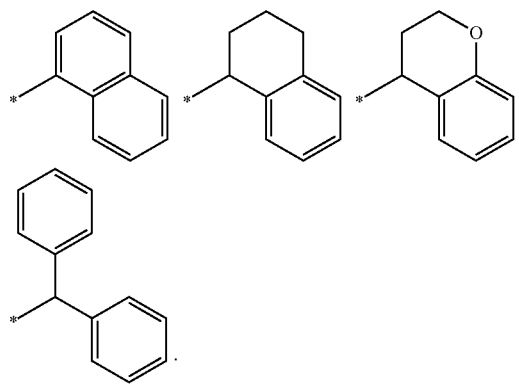

In any of the compounds described herein, the ILM can have the structure of Formula (XXVII) or (XXVII), which are derived from the IAP ligands described in WO Pub. No. 2014/055461 and Kim, K S, *Discovery of tetrahydroisoquinoline-based bivalent heterodimeric IAP antagonists*. Bioorg. Med. Chem. Lett. 24(21), 5022-9 (2014), or an unnatural mimetic thereof:

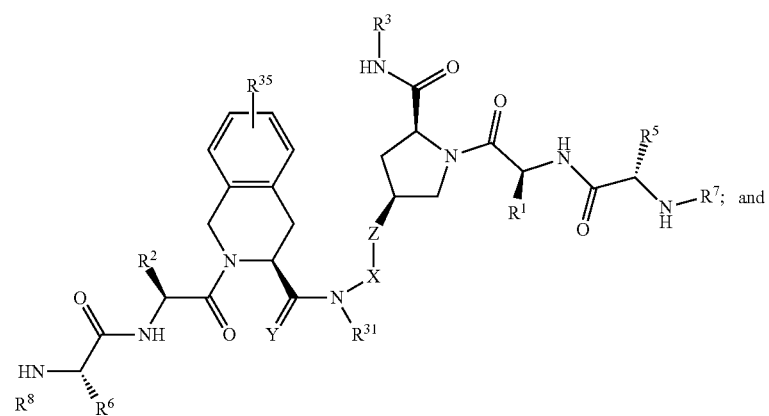

(XXVII)

(XXVIII)

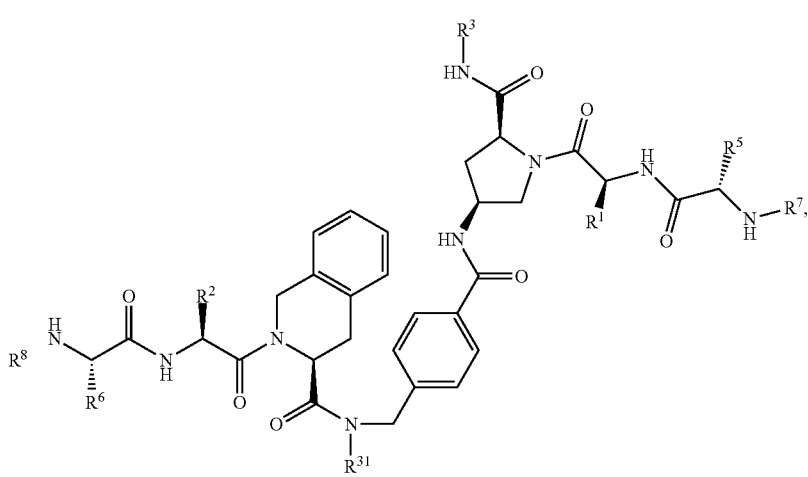

wherein:
- R³ is 1-2 substituents selected from alkyl, halogen, alkoxy, cyano and haloalkoxy;
- R¹ of Formula (XXVII) and (XXVIII) is selected from H or an optionally substituted alkyl, optionally substituted cycloalkyl, optionally substituted cycloalkylalkyl, optionally substituted heterocyclyl, optionally substituted arylalkyl or optionally substituted aryl;
- R² of Formula (XXVII) and (XXVIII) is selected from H or an optionally substituted alkyl, optionally substituted cycloalkyl, optionally substituted cycloalkylalkyl, optionally substituted heterocyclyl, optionally substituted arylalkyl or optionally substituted aryl;

or alternatively,
- R¹ and R² of Formula (XXVII) and (XXVIII) are independently selected from an optionally substituted thioalkyl —CR⁶⁰R⁶¹SR⁷⁰, wherein R⁶⁰ and R⁶¹ are selected from H or methyl, and R⁷ is selected from an optionally substituted alkyl, optionally substituted branched alkyl, optionally substituted heterocyclyl, —(CH₂)ᵥCOR², —CH₂CHR²¹COR²² or —CH₂R²³, wherein:
- v is an integer from 1-3;
- R²⁰ and R²² of —(CH₂)ᵥCOR²⁰ and —CH₂CHR²¹COR²² are independently selected from OH, NR²⁴R²⁵ or OR²⁶;
- R²¹ of —CH₂CHR²¹COR²² is selected from NR²⁴R²⁵;
- R²³ of —CH₂R²³ is selected from an optionally substituted aryl or optionally substituted heterocyclyl, where the optional substituents include alkyl and halogen;
- R²⁴ of NR²⁴R²⁵ is selected from hydrogen or optionally substituted alkyl;
- R²⁵ of NR²⁴R²⁵ is selected from hydrogen, optionally substituted alkyl, optionally substituted branched alkyl, optionally substituted arylalkyl, optionally substituted heterocyclyl, —CH₂CH₂(OCH₂CH₂)ₘCH₃, or a polyamine chain —[CH₂CH₂(CH₂)ψNH]ψCH₂CH₂(CH₂)ω̄NH₂, such as spermine or spermidine;
- wherein δ=0-2, ψ=1-3, ω̄=0-2;
- R²⁶ of OR²⁶ is an optionally substituted alkyl, wherein the optional substituents are OH, halogen or NH₂; and
- m is an integer from 1-8,
- R³ and R⁴ of Formula (XXVII) and (XXVIII) are independently selected from an optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;
- R⁵, R⁶, R⁷ and R⁸ of Formula (XXVII) and (XXVIII) are independently selected from hydrogen, optionally substituted alkyl or optionally substituted cycloalkyl;
- R³¹ of Formulas (XXVII) and (XXVIII) is selected from alkyl, aryl, arylalkyl, heteroaryl or heteroarylalkyl optionally further substituted, preferably selected form the group consisting of:

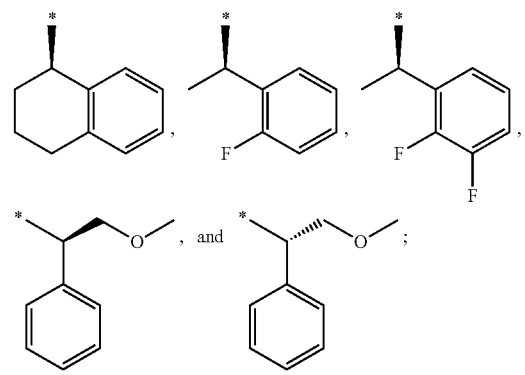

X of Formulas (XXVII) and (XXVIII) is selected from —(CR⁸¹R⁸²)ₘ—, optionally substituted heteroaryl or heterocyclyl,

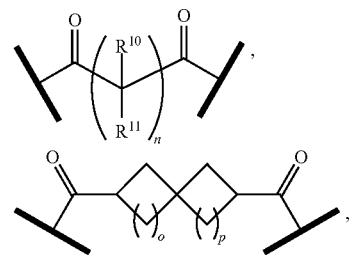

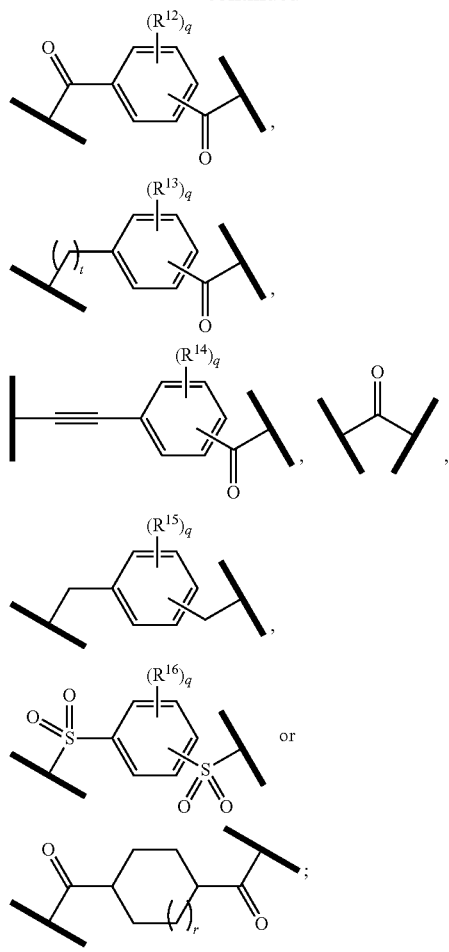

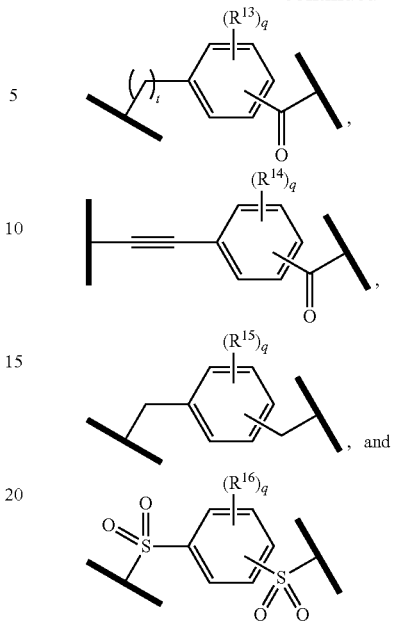

Z of Formulas (XXVII) is selected from C=O, —O—, —NR, —CONH—, —NHCO—, or may be absent;

$R^{81}$ and $R^{82}$ of —$(CR^{81}R^{82})_m$— are independently selected from hydrogen, halogen, alkyl or cycloalkyl, or $R^{81}$ and $R^{82}$ can be taken together to form a carbocyclic ring;

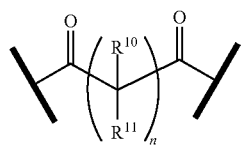

$R^{10}$ and $R^{11}$ of
are independently selected from hydrogen, halogen or alkyl;
$R^{12}$, $R^{13}$, $R^{14}$, $R^{15}$ and $R^{16}$ of

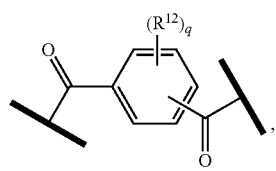

are independently selected from hydrogen, halogen or optionally substituted alkyl or $OR^{17}$;

$R^{17}$ is selected from hydrogen, optionally substituted alkyl or optionally substituted cycloalkyl;

m and n of —$(CR^{21}R^{22})_m$— and

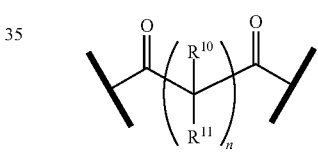

are independently 0, 1, 2, 3, or 4;

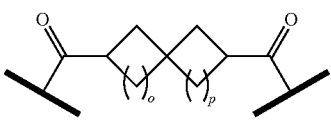

o and p of j are independently 0, 1, 2 or 3;
q and t of

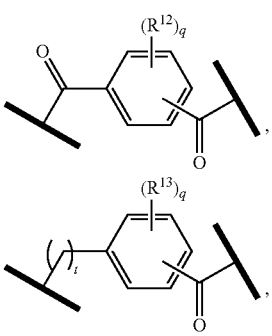

-continued

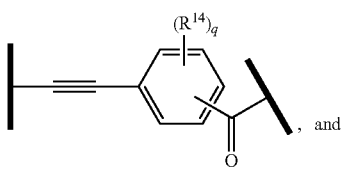
, and

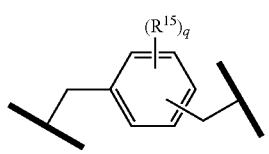

are independently 0, 1, 2, 3, or 4;

r of

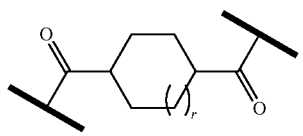

is 0 or 1;

and/or a pharmaceutically acceptable salt, tautomer or stereoisomer thereof.

In any of the compounds described herein, the ILM can have the structure of Formula (XXIX), (XXX), (XXXI), or (XXXII), which are derived from the IAP ligands described in WO Pub. No. 2014/055461 and Kim, K S, *Discovery of tetrahydroisoquinoline-based bivalent heterodimeric IAP antagonists*. Bioorg. Med. Chem. Lett. 24(21), 5022-9 (2014), or an unnatural mimetic thereof, and the chemical linker to linker group L as shown:

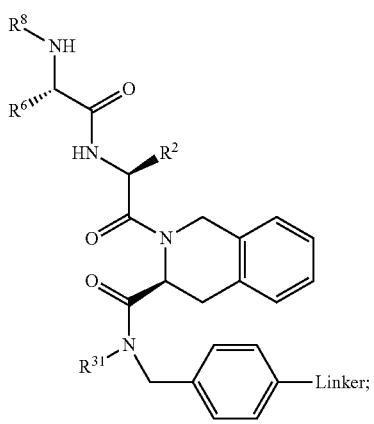
(XXIX)

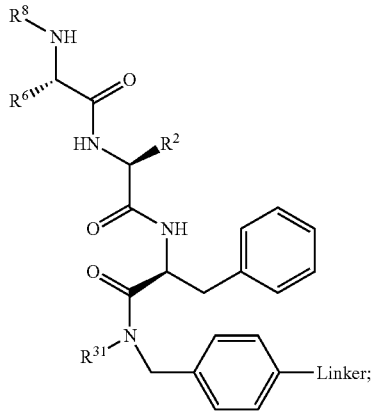
(XXX)

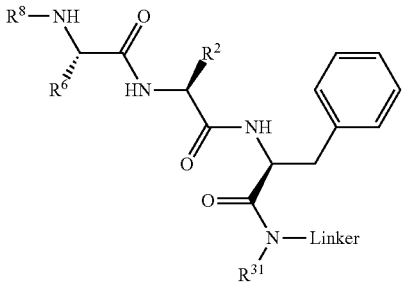
(XXXI); and

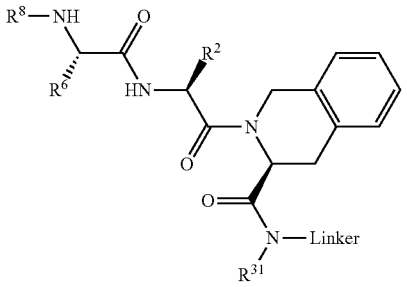
(XXXII), wherein:

$R^2$ of Formula (XXIX) through (XXXII) is selected from H, an optionally substituted alkyl, optionally substituted cycloalkyl, optionally substituted cycloalkylalkyl, optionally substituted heterocyclyl, optionally substituted arylalkyl or optionally substituted aryl; or alternatively;

$R^1$ and $R^2$ of Formula (XXVII) and (XXVIII) are independently selected from H, an optionally substituted thioalkyl —$CR^{60}R^{61}SR^{70}$ wherein $R^{60}$ and $R^{61}$ are selected from H or methyl, and $R^{70}$ is an optionally substituted alkyl, optionally substituted branched alkyl, optionally substituted heterocyclyl, —$(CH_2)_vCOR^{20}$, —$CH_2CHR^{21}COR^{22}$ or —$CH_2R^{23}$;

wherein:

v is an integer from 1-3;

$R^{20}$ and $R^{22}$ of —$(CH_2)_vCOR^{20}$ and —$CH_2CHR^{21}COR^{22}$ are independently selected from OH, $NR^{24}R^{25}$ or $OR^{26}$;

$R^{21}$ of —$CH_2CHR^{21}COR^{22}$ is selected from $NR^{24}R^{23}$;

$R^{23}$ of —$CH_2R^{23}$ is selected from an optionally substituted aryl or optionally substituted heterocyclyl, where the optional substituents include alkyl and halogen;

$R^{24}$ of $NR^{24}R^{25}$ is selected from hydrogen or optionally substituted alkyl;

$R^{25}$ of $NR^{24}R^{25}$ is selected from hydrogen, optionally substituted alkyl, optionally substituted branched alkyl, optionally substituted arylalkyl, optionally substituted heterocyclyl, —$CH_2CH_2(OCH_2CH_2)_mCH_3$, or a polyamine chain —$[CH_2CH_2(CH_2)_\delta NH]_\psi CH_2CH_2(CH_2)\overline{\omega}_rNH_2$, such as spermine or spermidine, wherein $\delta$=0-2, $\psi$=1-3, $\overline{\omega}$=0-2;

$R^{26}$ of $OR^{26}$ is an optionally substituted alkyl, wherein the optional substituents are OH, halogen or $NH_2$, m is an integer from 1-8;

$R^6$ and $R^8$ of Formula (XXIX) through (XXXII) are independently selected from hydrogen, optionally substituted alkyl or optionally substituted cycloalkyl; and $R^{31}$ of Formulas (XXIX) through (XXXII) is selected from alkyl, aryl, arylalkyl, heteroaryl or heteroarylalkyl optionally further substituted, preferably selected form the group consisting of:

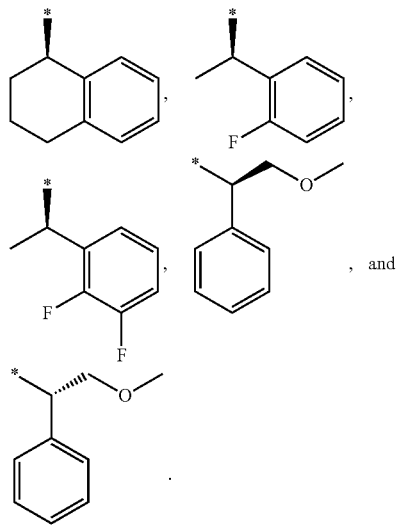

In certain embodiments, the ILM of the compound is:

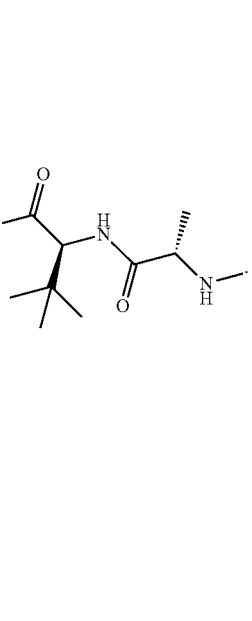

In any of the compounds described herein, the ILM can have the structure of Formula (XXXIII), which are derived from the IAP ligands described in WO Pub. No. 2014/074658 and WO Pub. No. 2013/071035, or an unnatural mimetic thereof:

(XXXIII)

wherein:

$R^2$ of Formula (XXXIII) is selected from H, an optionally substituted alkyl, optionally substituted cycloalkyl, optionally substituted cycloalkylalkyl, optionally substituted heterocyclyl, optionally substituted arylalkyl or optionally substituted aryl;

$R^6$ and $R^8$ of Formula (XXXIII) are independently selected from hydrogen, optionally substituted alkyl or optionally substituted cycloalkyl;

$R^{32}$ of Formula (XXXIII) is selected from ($C_1$-$C_4$ alkylene)-$R^{33}$ wherein $R^{33}$ is selected from hydrogen, aryl, heteroaryl or cycloalkyl optionally further substituted;

X of Formula (XXXIII) is selected from:
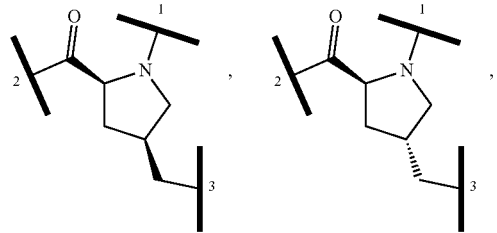
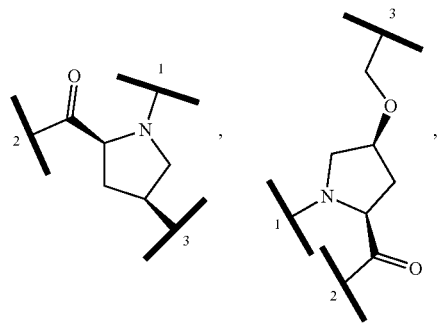
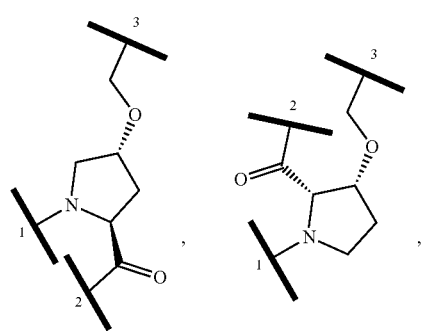
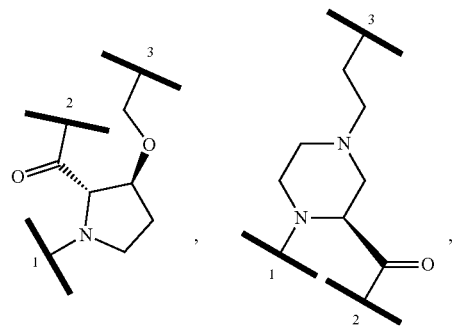
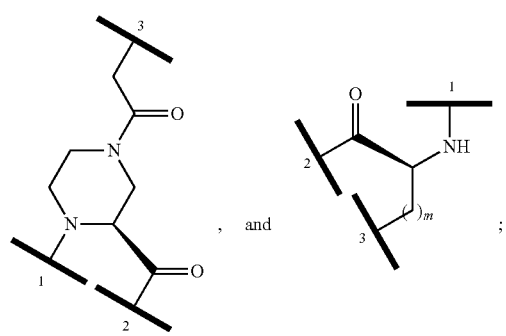
Z and Z' of Formula (XXXIII) are independently selected from:
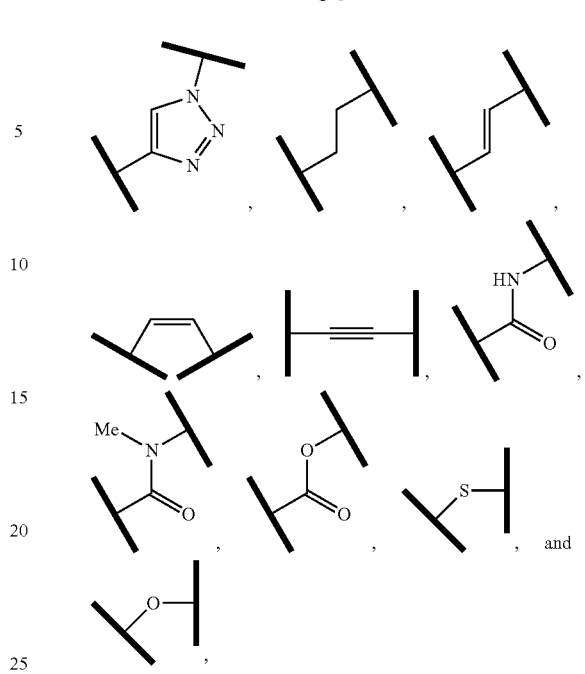
wherein each
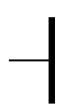
represents a point of attachment to the compound, and Z and Z' cannot both be
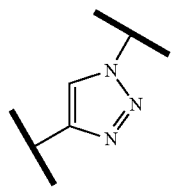
in any given compound;
Y of Formula (XXXIII) is selected from:
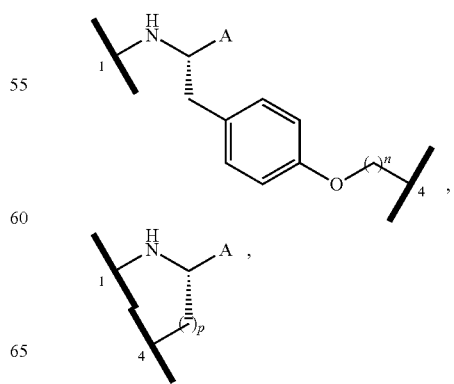

-continued
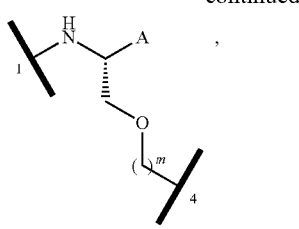
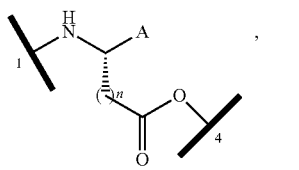
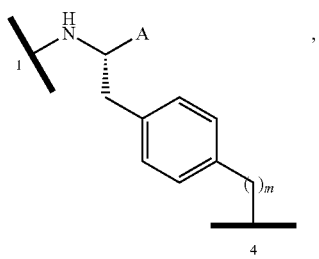
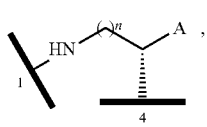
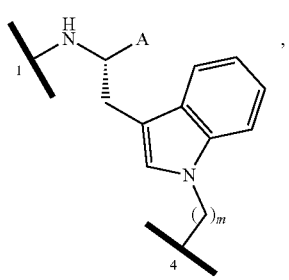
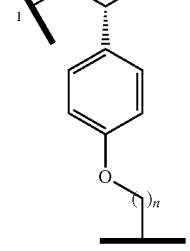
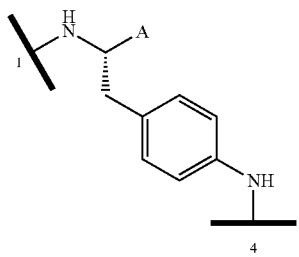
wherein Z and Z' of Formula (XXXIII) are the same and Z is
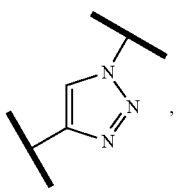
wherein each
represents a point of attachment to the compound, X is selected from:
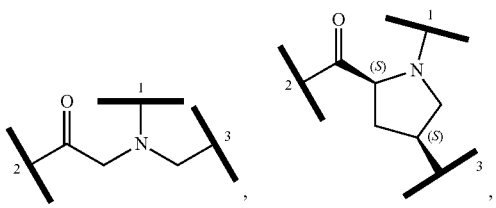
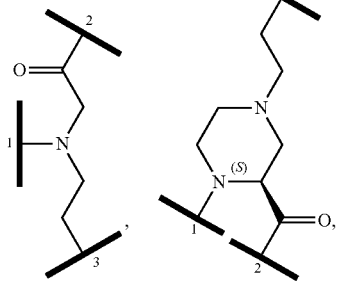
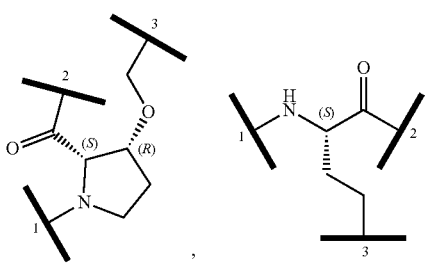
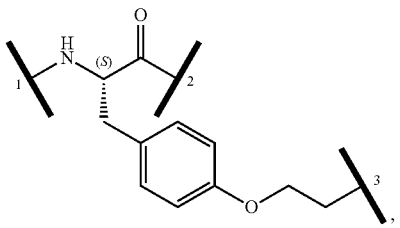

-continued
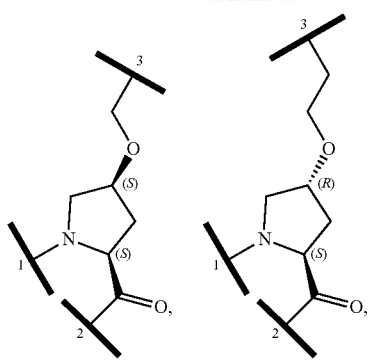
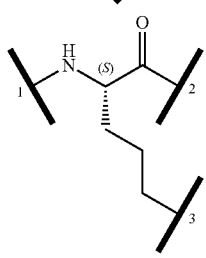
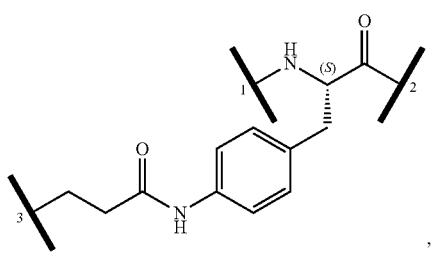
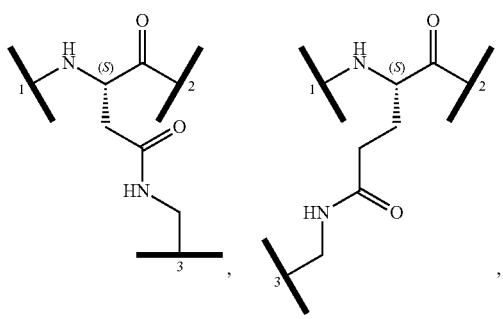
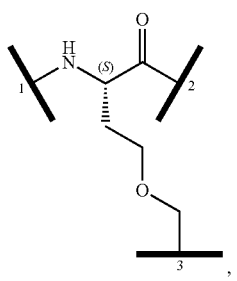
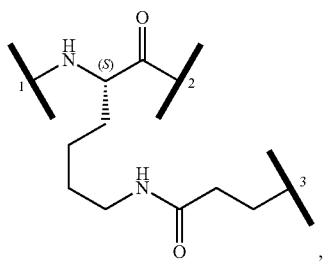
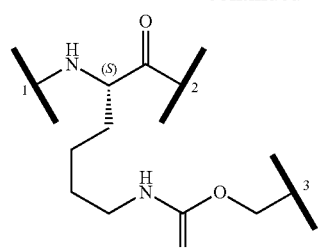
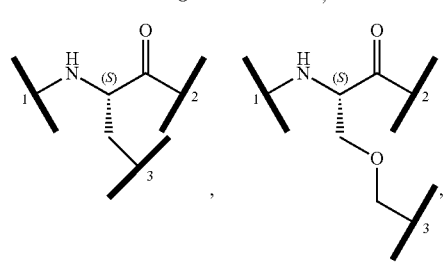
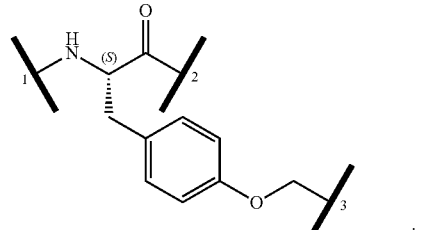, and
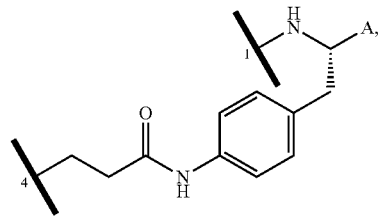, and
Y of Formula (XXXIII) is independently selected from:
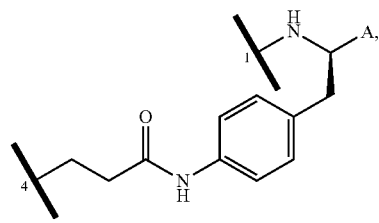
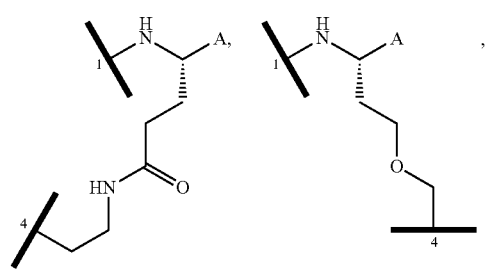

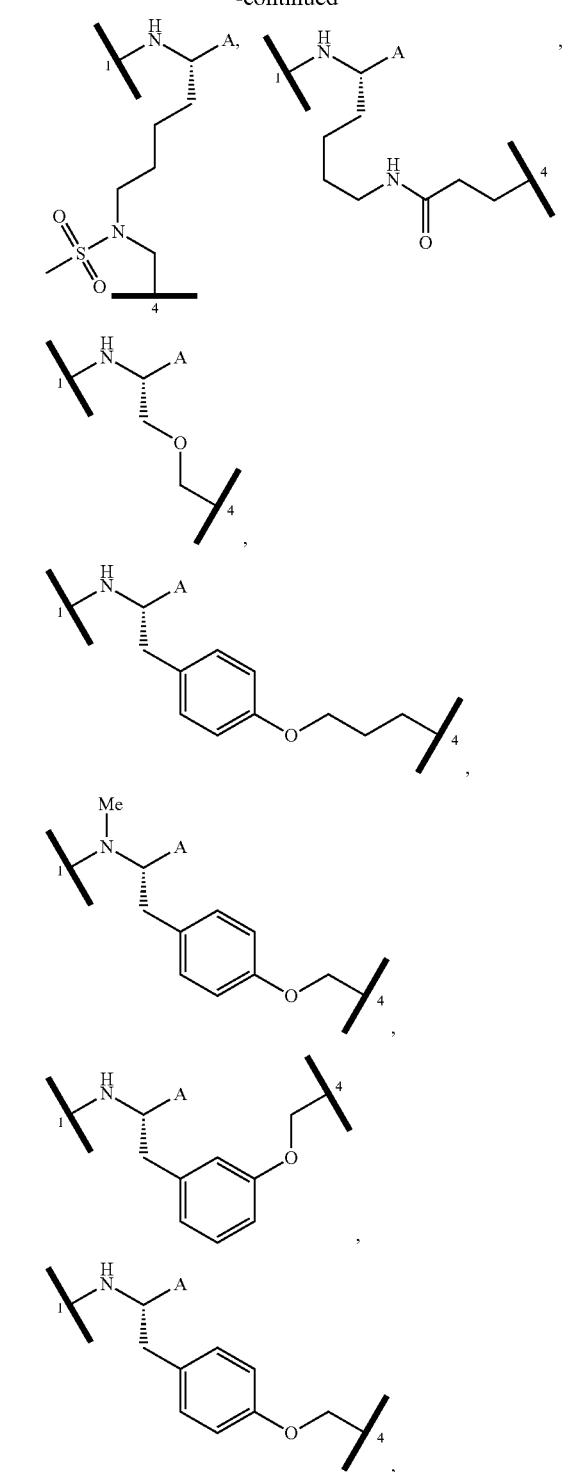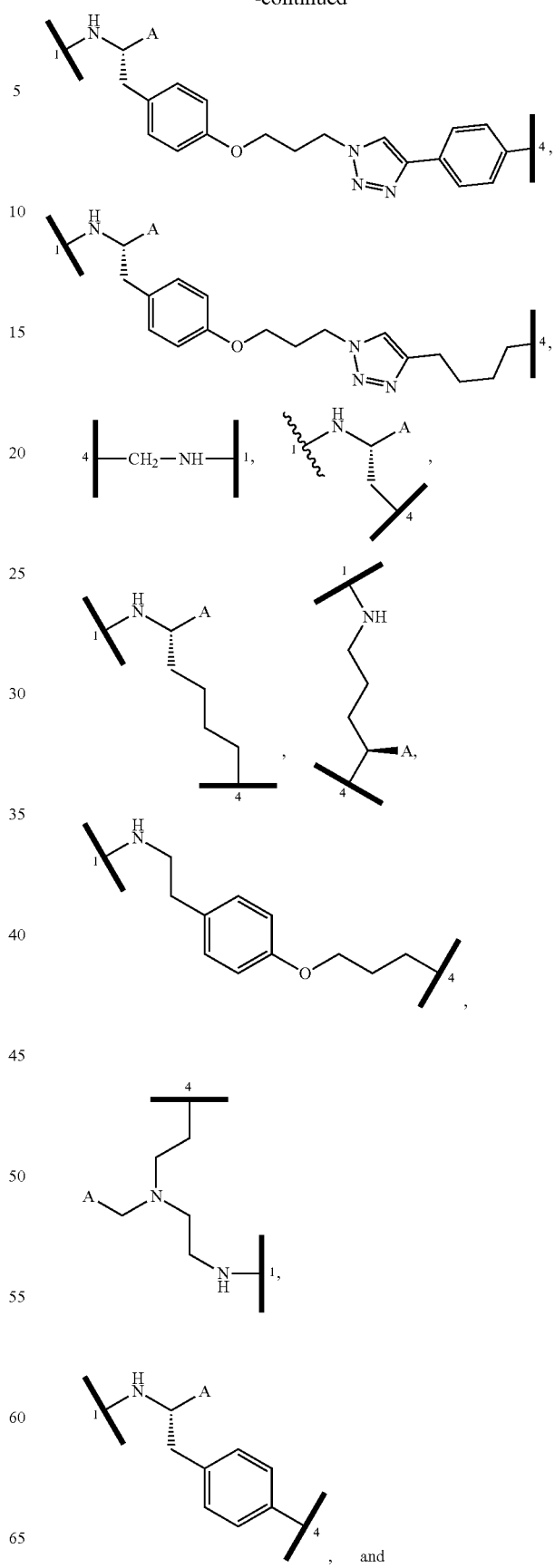

-continued

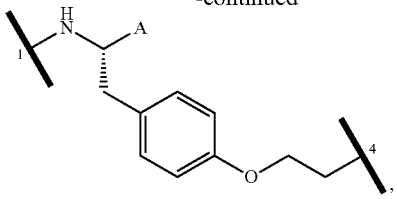

wherein:

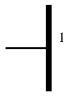

represents a point of attachment to a —C=O portion of the compound;

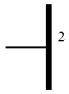

represents a point of attachment to a —NH portion of the compound;

represents a first point of attachment to Z;

represents a second point of attachment to Z;
m is an integer from 0-3;
n is an integer from 1-3;
p is an integer from 0-4; and
A is-C(O)R$^3$;
R$^3$ is selected from —C(O)R$^3$ is OH, NHCN, NHSO$_2$R$^{10}$, NHOR$^{11}$ or N(R$^{12}$)(R$^{13}$);
R$^{10}$ and F$^{11}$ of NHSO$_2$R$^{10}$ and NHOR$^{11}$ are independently selected from hydrogen, optionally substituted —C$_1$-C$_4$ alkyl, cycloalkyl, aryl, heteroaryl, heterocyclyl or heterocycloalkyl;
R$^{12}$ and R$^{13}$ of N(R$^{12}$)(R$^{13}$) are independently selected from hydrogen, —C$_1$-C$_4$ alkyl, —(C$_1$-C$_4$) alkylene)-NH—(C$_1$-C$_4$ alkyl), and —(C$_1$-C$_4$ alkylene)-O—(C$_1$-C$_4$ hydroxyalkyl), or R$^{12}$ and R$^{13}$ taken together with the nitrogen atom to which they are commonly bound to form a saturated heterocyclyl optionally comprising one additional heteroatom selected from N, O and S, and wherein the saturated heterocycle is optionally substituted with methyl.

In any of the compounds described herein, the ILM can have the structure of Formula (XXXIV) or (XXXV), which are derived from the IAP ligands described in WO Pub. No. 2014/047024, or an unnatural mimetic thereof:

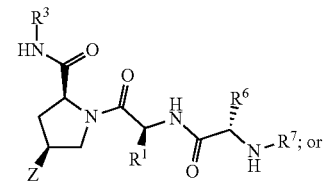

(XXXIV)

(XXXV)

wherein:
X of Formula (XXXIV) or (XXXV) is absent or a group selected from —(CR$^{10}$R$^{11}$)$_m$—, optionally substituted heteroaryl or optionally substituted heterocyclyl,

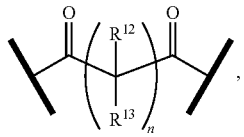

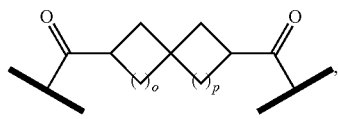

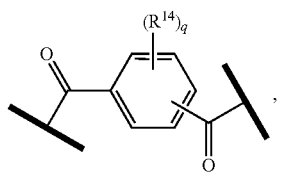

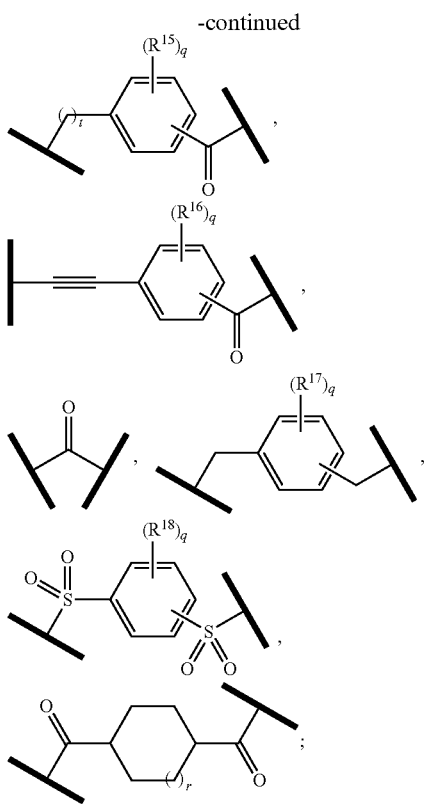

Y and Z of Formula (XXXIV) or (XXXV) are independently selected from C=O, -0-, —NR$^9$—, —CONH—, —NHCO— or may be absent;

R$^1$ and R$^2$ of Formula (XXXIV) or (XXXV) are independently selected from an optionally substituted alkyl, optionally substituted cycloalkyl, optionally substituted cycloalkylalkyl, optionally substituted arylalkyl, optionally substituted aryl, or R$^1$ and R$^2$ of Formula (XXXIV) or (XXXV) are independently selected from optionally substituted thioalkyl wherein the substituents attached to the S atom of the thioalkyl are optionally substituted alkyl, optionally substituted branched alkyl, optionally substituted heterocyclyl, —(CH$_2$)$_v$COR$^{20}$, —CH$_2$CHR$^{21}$COR$^{21}$ or —CH$_2$R$^{23}$; wherein v is an integer from 1-3;

R$^{20}$ and R$^{22}$ of —(CH$_2$)$_v$COR$^{20}$ and —CH$_2$CHR$^{21}$COR$^{22}$ are independently selected from OH, NR$^{24}$R$^{25}$ or OR$^{26}$;

R$^{21}$ of —CH$_2$CHR$^{21}$COR$^{22}$ is selected from NR$^{24}$R$^{25}$;

R$^{23}$ of —CH$_2$R$^{23}$ are selected from an optionally substituted aryl or optionally substituted heterocyclyl, where the optional substituents include alkyl and halogen;

R$^{24}$ of NR$^{24}$R$^{25}$ is selected from hydrogen or optionally substituted alkyl;

R$^{25}$ of NR$^{24}$R$^{25}$ is selected from hydrogen, optionally substituted alkyl, optionally substituted branched alkyl, optionally substituted arylalkyl, optionally substituted heterocyclyl, —CH$_2$(OCH$_2$CH$^{20}$)mCH3, or a polyamine chain;

R$^{26}$ is an optionally substituted alkyl, wherein the optional substituents are OH, halogen or NH$_2$;

m of —(CR$^{10}$R$^{11}$)$_m$— is an integer from 1-8;

R$^3$ and R$^4$ of Formula (XXXIV) or (XXXV) are independently selected from optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

R$^5$, R$^6$, R$^7$ and R$^8$ of Formula (XXXIV) or (XXXV) are independently selected from hydrogen, optionally substituted alkyl or optionally substituted cycloalkyl;

R$^{10}$ and R$^{11}$ of —(CR$^{10}$R$^{11}$)$_m$— are independently selected from hydrogen, halogen or optionally substituted alkyl;

R$^{12}$ and R$^{13}$ of

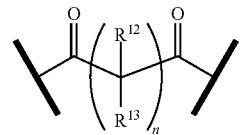

are independently selected from hydrogen, halogen or optionally substituted alkyl, or R$^{12}$ and R$^{13}$ can be taken together to form a carbocyclic ring; R$^{14}$, R$^{15}$, R$^{16}$, R$^{17}$ and R$^{18}$ of

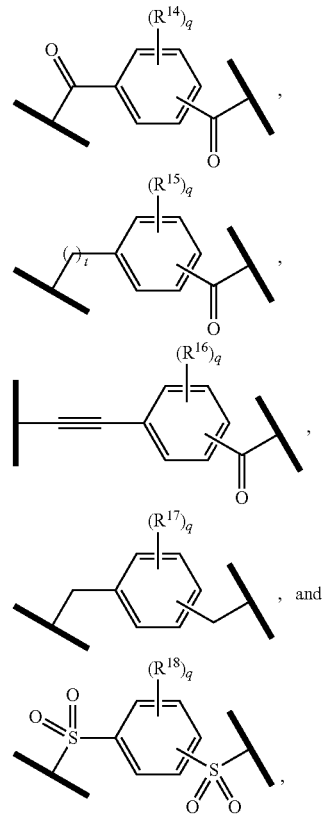

are independently selected from hydrogen, halogen, optionally substituted alkyl or OR$^{19}$;

R$^{19}$ of OR$^{19}$ is selected from hydrogen, optionally substituted alkyl or optionally substituted cycloalkyl;

m and n of —(CR$^{10}$R$^{11}$)$_m$— are independently 0, 1, 2, 3, or 4;

o and p of —(CR$^{10}$R$^{11}$)$_m$— are independently 0, 1, 2 or 3;

q of —(CR$^{10}$R$^{11}$)$_m$— is 0, 1, 2, 3, or 4; r is 0 or 1;

t of —(CR$^{10}$R$^{11}$)$_m$— is 1, 2, or 3; and/or a pharmaceutically acceptable salt, tautomer or stereoisomer thereof.

In any of the compounds described herein, the ILM can have the structure of Formula (XXXVI), which are derived from the IAP ligands described in WO Pub. No. 2014/025759, or an unnatural mimetic thereof:

(XXXVI)

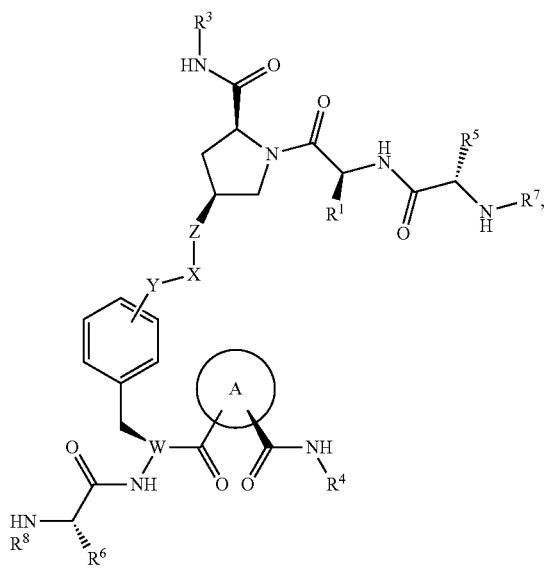

A of Formula (XXXVI) is selected from:

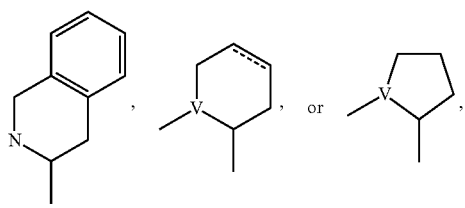

where the dotted line represents an optional double bond;

X of Formula (XXXVI) is selected from: —(CR$^{21}$R$^{22}$)$_m$—,

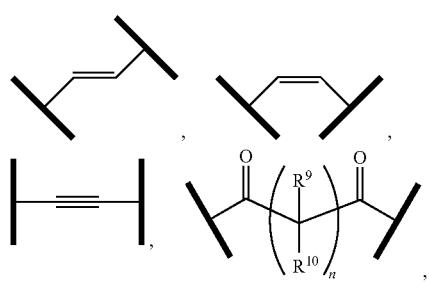


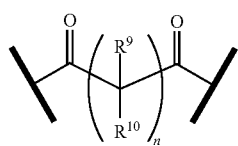

Y and Z of Formula (XXXVI) are independently selected from -O-, —NR$^6$— or are absent;

V of Formula (XXXVI) is selected from —N— or —CH—;

W of Formula (XXXVI) is selected from —CH— or —N—;

R$^1$ of Formula (XXXVI) is selected from an optionally substituted alkyl, optionally substituted cycloalkyl, optionally substituted cycloalkylalkyl, optionally substituted arylalkyl or optionally substituted aryl;

R$^3$ and R$^4$ of Formula (XXXVI) are independently selected from optionally substituted alkyl, optionally substituted cycloalkyl, optionally substituted aryl, optionally substituted heteroaryl, optionally substituted heterocyclyl, optionally substituted arylalkyl, optionally substituted heteroarylalkyl or optionally substituted heterocycloalkyl;

R$^5$, R$^6$, R$^7$ and R$^8$ of Formula (XXIV), (XXV) or (XXVI) are independently selected from hydrogen, optionally substituted alkyl or optionally substituted cycloalkyl, or preferably methyl;

R$^9$ and R$^{10}$ of are independently selected from hydrogen, halogen or optionally substituted alkyl, or $R^9$ and $R^{10}$ can be taken together to form a ring;

$R^{11}$, $R^{12}$, $R^{13}$ and $R^{14}$ of

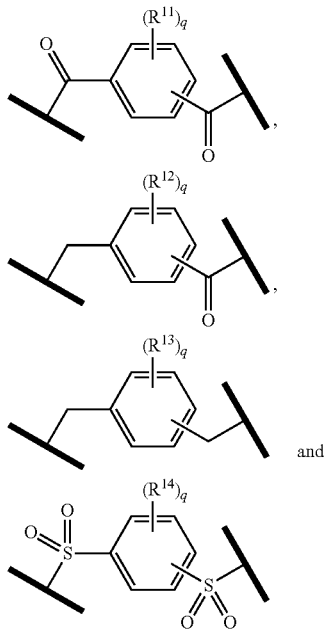

are independently selected from hydrogen, halogen, optionally substituted alkyl or $OR^{15}$;

$R^{15}$ of $OR^{15}$ is selected from hydrogen, optionally substituted alkyl or optionally substituted cycloalkyl;

m and n of —$(CR^{21}R^{22})_m$— and

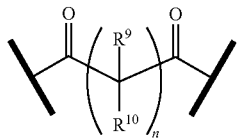

are independently selected from 0, 1, 2, 3, or 4;

o and p of

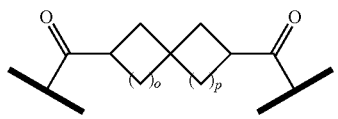

and are independently selected from 0, 1, 2 or 3;

q of

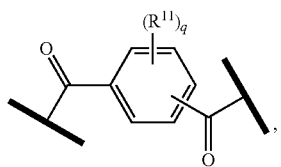

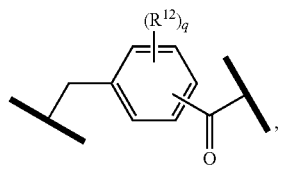

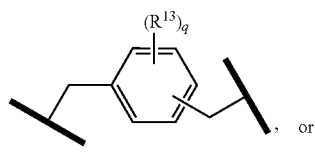

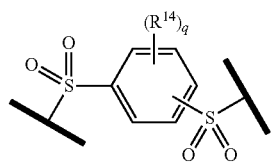

is selected from 0, 1, 2, 3, or 4;

r of

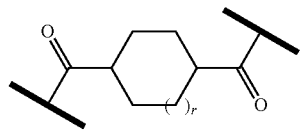

is selected from 0 or 1, and/or or a pharmaceutically acceptable salt, tautomer or stereoisomer thereof.

In any of the compounds described herein, the ILM can have the structure of Formula (XXXVII) or (XXXVIII), which are derived from the IAP ligands described in WO Pub. No. 2014/011712, or an unnatural mimetic thereof:

(XXXVII)

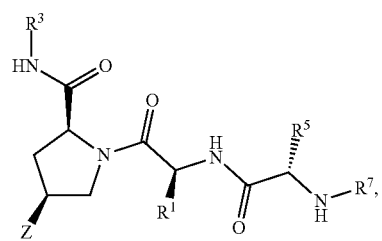

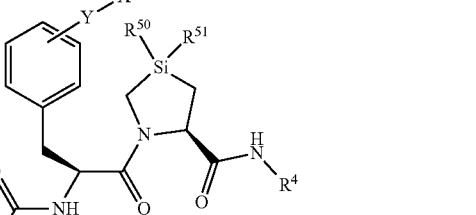

(XXXVIII)

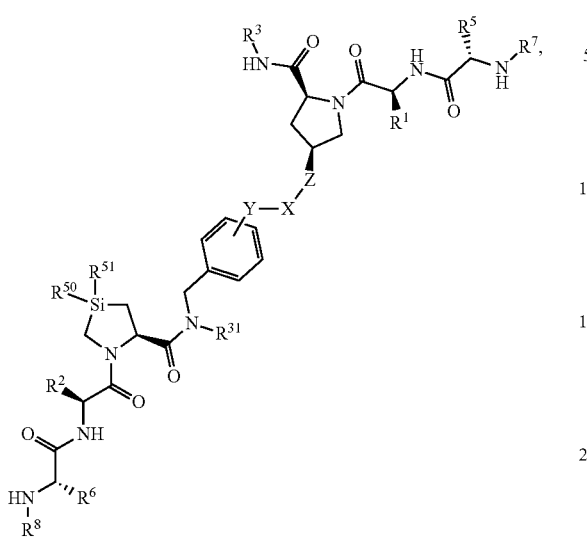

wherein:

X of Formulas (XXXVII) and (XXXVIII) is —(CR$^{16}$R$^{17}$)$_m$—,

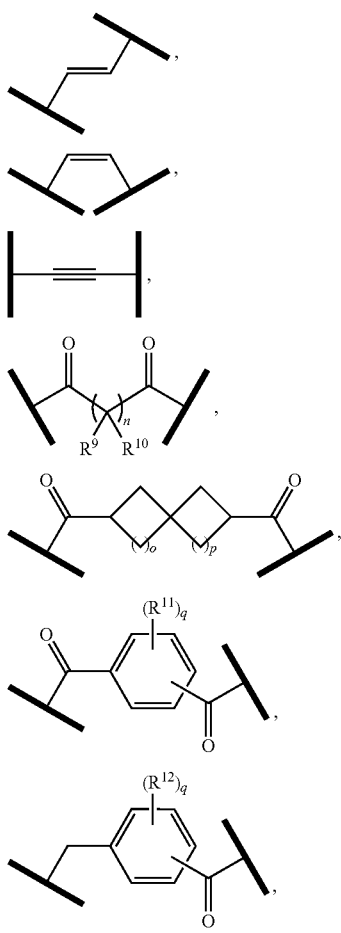

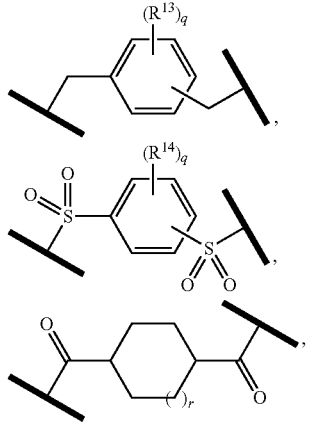

or absent;

Y and Z of Formula (XXXVII) and (XXXVIII) are independently selected from -O-, C=O, NR$^6$ or are absent;

R$^1$ and R$^2$ of Formula (XXXVII) and (XXXVIII) are selected from optionally substituted alkyl, optionally substituted cycloalkyl, optionally substituted alkylaryl or optionally substituted aryl;

R$^3$ and R$^4$ of Formula (XXXVII) and (XXXVIII) are independently selected from optionally substituted alkyl, optionally substituted cycloalkyl, optionally substituted cycloalkylalkyl, optionally substituted arylalkyl or optionally substituted aryl;

R$^5$ and R$^6$ of Formula (XXXVII) and (XXXVIII) are independently selected from optionally substituted alkyl or optionally substituted cycloalkyl;

R$^7$ and R$^8$ of Formula (XXXVII) and (XXXVIII) are independently selected from hydrogen, optionally substituted alkyl or optionally substituted cycloalkyl, or preferably methyl;

R$^9$ and R$^{10}$ of

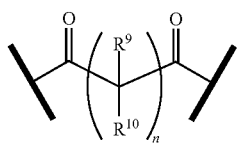

are independently selected from hydrogen, optionally substituted alkyl, or R$^9$ and R$^{10}$ may be taken together to form a ring;

R$^{11}$

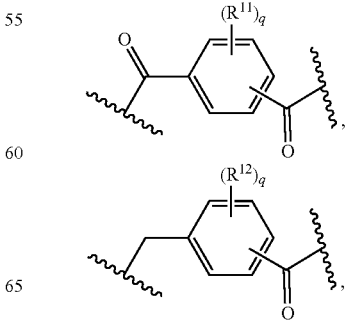

-continued

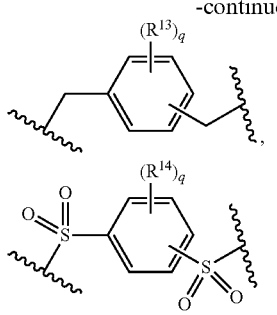

are independently selected from hydrogen, halogen, optionally substituted alkyl or $OR^{15}$;

$R^{15}$ of $OR^{15}$ is selected from hydrogen, optionally substituted alkyl or optionally substituted cycloalkyl;

$R^{16}$ and $R^{17}$ of $-(CR^{16}R^{17})_m-$ are independently selected from hydrogen, halogen or optionally substituted alkyl;

$R^{50}$ and $R^{51}$ of Formula (XXXVII) and (XXXVIII) are independently selected from optionally substituted alkyl, or $R^{50}$ and $R^{51}$ are taken together to form a ring;

m and n of $-(CR^{16}R^{17})_m-$ and

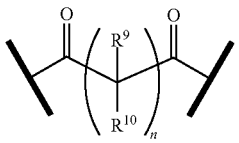

are independently an integer from 0-4;

o and p of

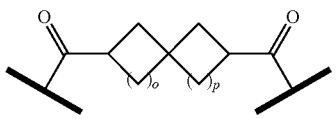

are independently an integer from 0-3;

q of

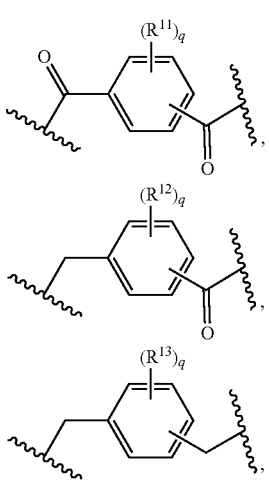

-continued

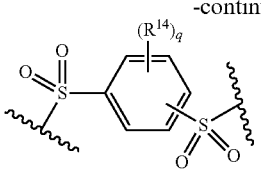

is an integer from 0-4; and r of

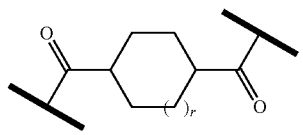

is an integer from 0-1;

or a pharmaceutically acceptable salt, tautomer or stereoisomer thereof.

In an embodiment, $R^1$ and $R^2$ of the ILM of Formula (XXXVII) or (XXXVIII) are t-butyl and $R^3$ and $R^4$ of the ILM of Formula (XXXVII) or (XXXVIII) are tetrahydronaphtalene.

In any of the compounds described herein, the ILM can have the structure of Formula (XXXIX) or (XL), which are derived from the IAP ligands described in WO Pub. No. 2013/071039, or an unnatural mimetic thereof:

(XXXIX)

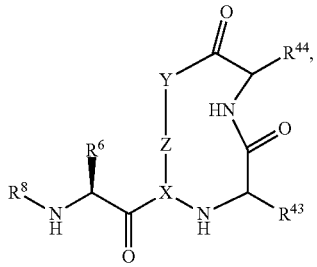

(XL)

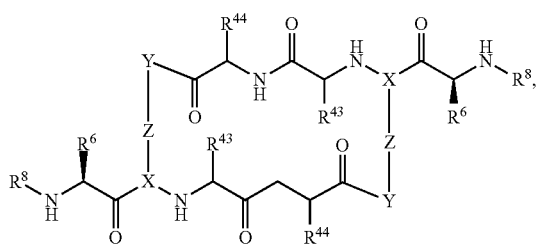

wherein:

$R^{43}$ and $R^{44}$ of Formulas (XXXIX) and (XL) are independently selected from hydrogen, alkyl, aryl, arylalkyl, heteroaryl, heteroarylalkyl, cycloalkyl, cycloalkylalkyl further optionally substituted, and $R^6$ and $R^8$ of Formula (XXXIX) and (XL) are independently selected from hydrogen, optionally substituted alkyl or optionally substituted cycloalkyl.

each X of Formulas (XXXIX) and (XL) is independently selected from:

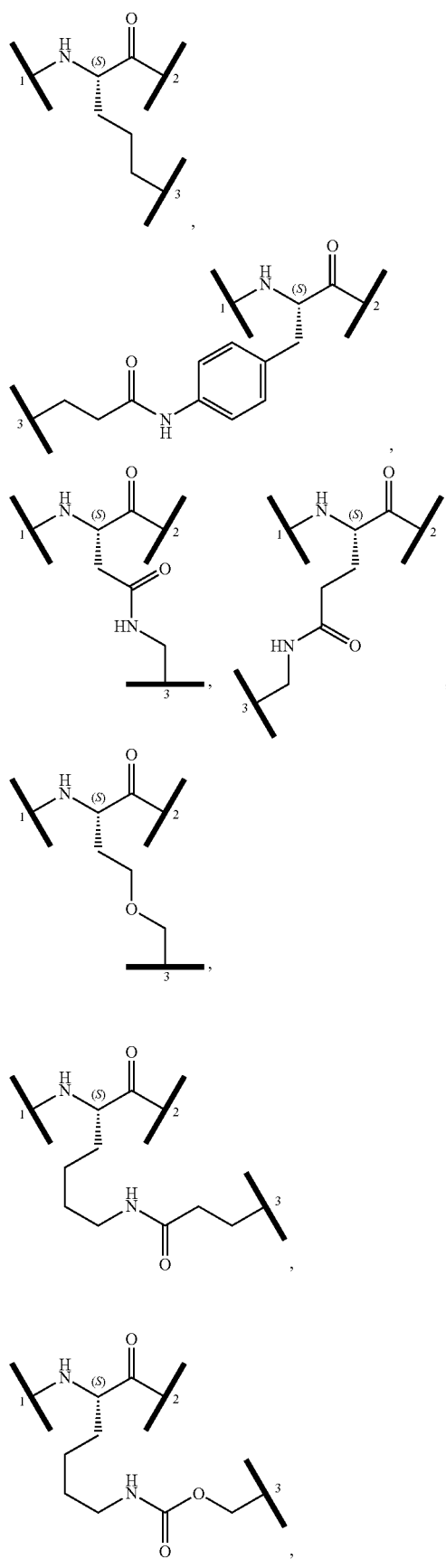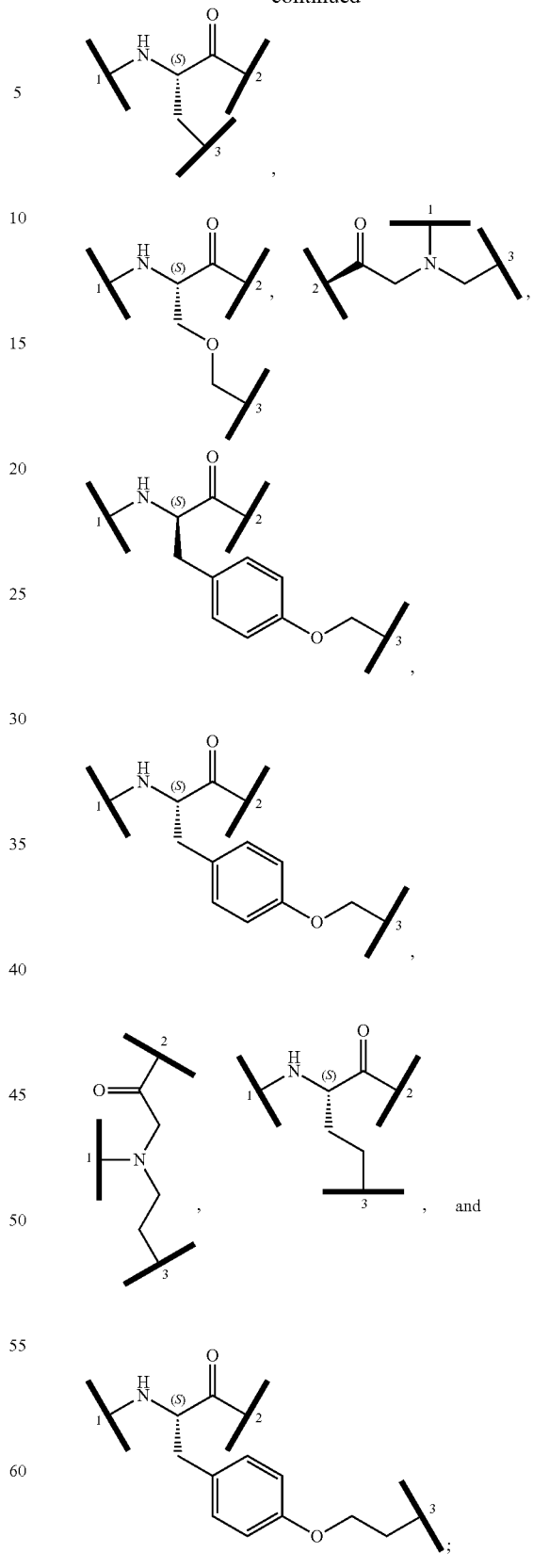
each Z of Formulas (XXXIX) and (XL) is independently selected from

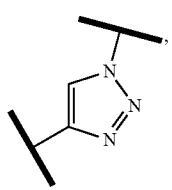
wherein each
represents a point of attachment to the compound; and each Y is selected from:
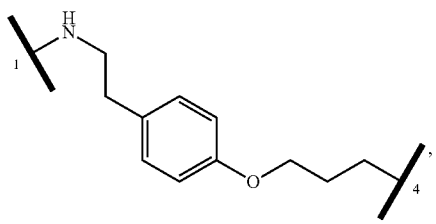
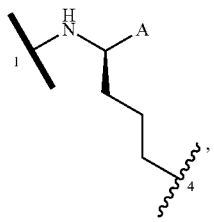
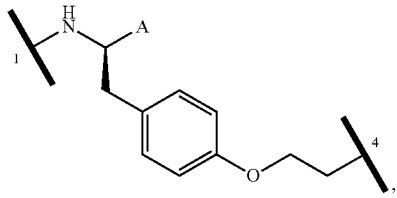
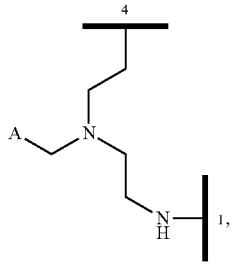
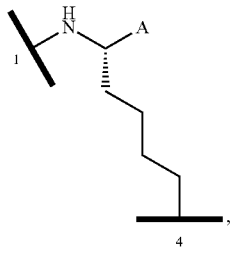
-continued
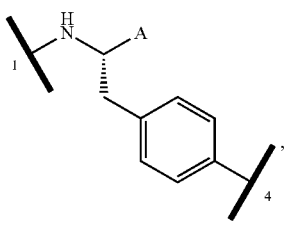
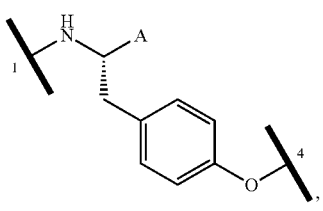
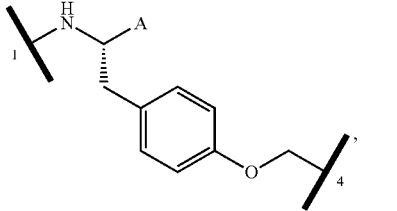
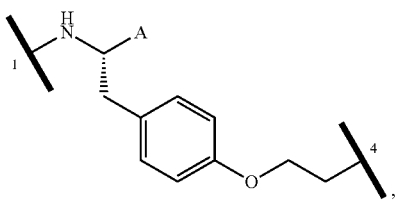
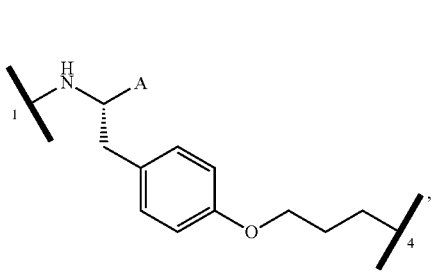
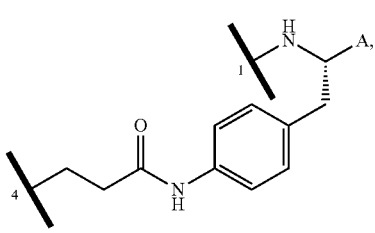
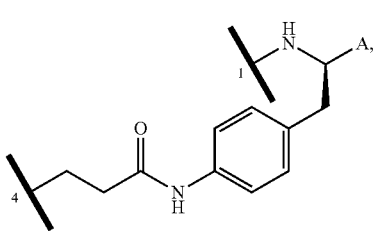

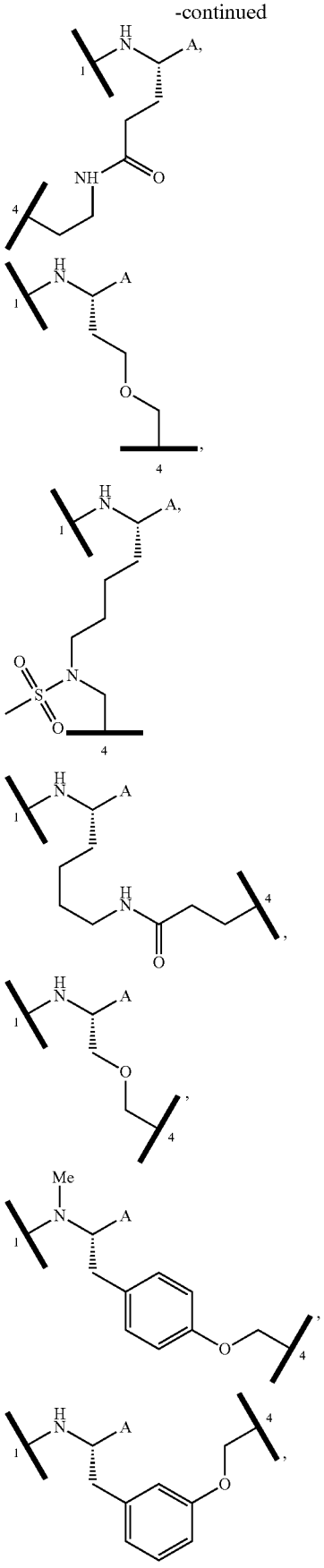
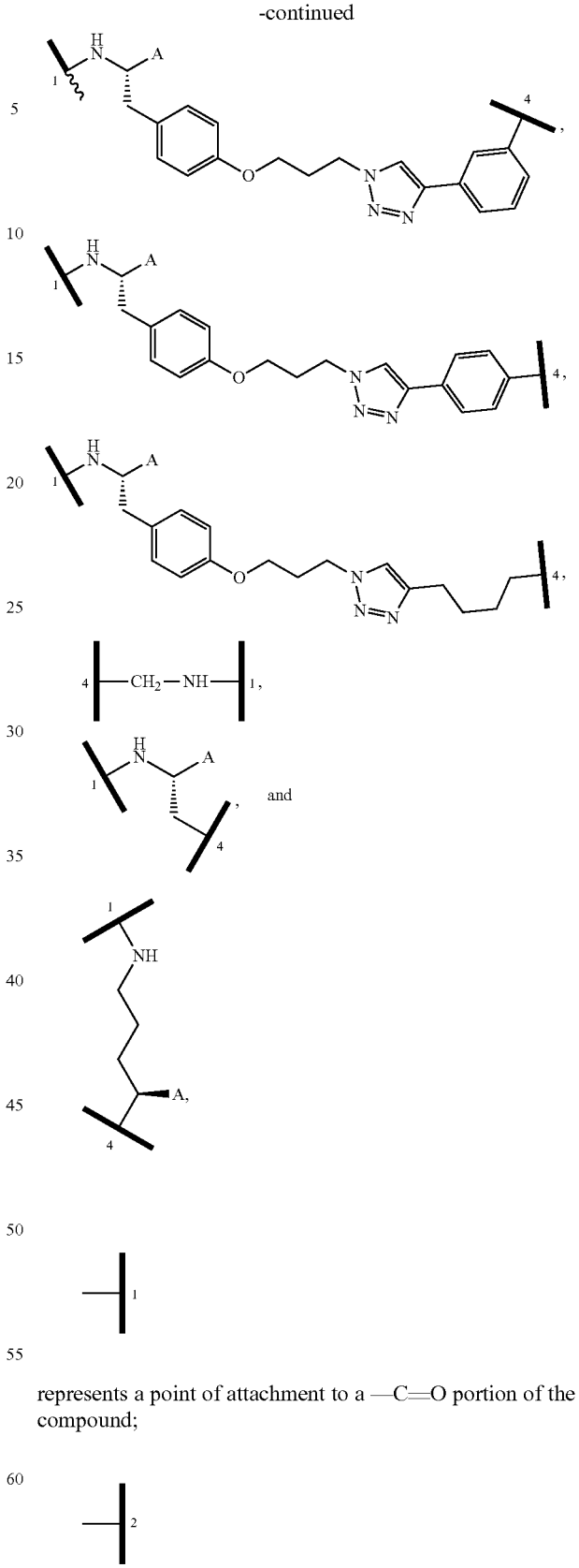
represents a point of attachment to a —C═O portion of the compound;
represents a point of attachment to an amino portion of the compound;

represents a first point of attachment to a Z;

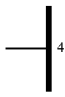

represents a second point of attachment to a Z; and
A is selected from —C(O)R³ or

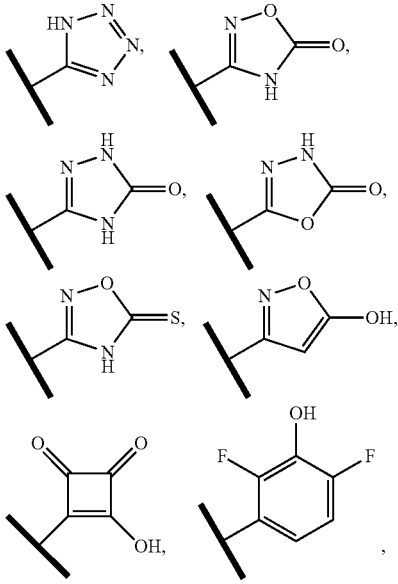

or a tautomeric form of any of the foregoing, wherein:
R³ of —C(O)R³ is selected from OH, NHCN, NHS0₂R¹⁰, NHOR¹¹ or N(R¹²)(R¹³);
R¹⁰ and R¹¹ of NHS0₂R¹⁰ and NHOR¹¹ are independently selected from —C₁-C₄ alkyl, cycloalkyl, aryl, heteroaryl, or heterocycloalkyl, any of which are optionally substituted, and hydrogen;
each of R¹² and R¹³ of N(R¹²)(R¹³) are independently selected from hydrogen, —C₁-C₄ alkyl, —(C₁-C₄ alkylene)-NH—(C₁-C₄ alkyl), benzyl, —(C₁-C₄ alkylene)-C(O)OH,
—(C₁-C₄ alkylene)-C(O)CH₃, —CH(benzyl)-COOH, —C₁-C₄ alkoxy, and
—(C₁-C₄ alkylene)-O—(C₁-C₄ hydroxyalkyl); or R¹² and R¹³ of N(R¹²)(R¹³) are taken together with the nitrogen atom to which they are commonly bound to form a saturated heterocyclyl optionally comprising one additional heteroatom selected from N, O and S, and wherein the saturated heterocycle is optionally substituted with methyl.

In any of the compounds described herein, the ILM can have the structure of Formula (XLI), which are derived from the IAP ligands described in WO Pub. No. 2013/071039, or an unnatural mimetic thereof:

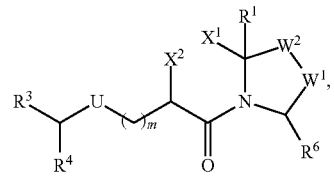

wherein:
W¹ of Formula (XLI) is selected from O, S, N—R^A, or C(R^{8a})(R^{8b});
W² of Formula (XLI) is selected from O, S, N—R^A, or C(R^{8c})(R^{8d}); provided that W¹ and W² are not both O, or both S;
R¹ of Formula (XLI) is selected from H, C₁-C₆alkyl, C₃-C₆cycloalkyl, —C₁-C₆alkyl-(substituted or unsubstituted C₃-C₆cycloalkyl), substituted or unsubstituted aryl, substituted or unsubstituted heteroaryl, —C₁-C₆alkyl-(substituted or unsubstituted aryl), or —C₁-C₆alkyl-(substituted or unsubstituted heteroaryl);
when X¹ is selected from O, N—R^A, S, S(O), or S(O)₂, then X² is C(R^{2a}R^{2b});
or:
X¹ of Formula (XLI) is selected from CR²CR^{2d} and X² is CR^{2a}R^{2b}, and R^{2c} and R^{2d} together form a bond;
or:
X¹ and X² of Formula (XLI) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring;
or:
X¹ of Formula (XLI) is selected from CH₂ and X² is C=O, C=C(R^C)₂, or C=NR^C; where each R^c is independently selected from H, —CN, —OH, alkoxy, substituted or unsubstituted C₁-C₆alkyl, substituted or unsubstituted C₃-C₆cycloalkyl, substituted or unsubstituted C₂-C₅heterocycloalkyl, substituted or unsubstituted aryl, substituted or unsubstituted heteroaryl, —C₁-C₆alkyl-(substituted or unsubstituted C₃-C₆cycloalkyl), —C₁-C₆alkyl-(substituted or unsubstituted C₂-C₅heterocycloalkyl), —C₁-C₆alkyl- (substituted or unsubstituted aryl), or —C₁-C₆alkyl-(substituted or unsubstituted heteroaryl);
R^A of N—R^A is selected from H, C₁-C₆alkyl, —C(=O) C₁-C₂alkyl, substituted or unsubstituted aryl, or substituted or unsubstituted heteroaryl;
R^{2a}, R^{2b}, R^{2c}, R^{2d} of CR^{2c}R^{2d} and CR^{2a}R^{2b} are independently selected from H, substituted or unsubstituted C1-C6alkyl, substituted or unsubstituted C₁-C₆heteroalkyl, substituted or unsubstituted C₃-C₆cycloalkyl, substituted or unsubstituted C₂-C₅heterocycloalkyl, substituted or unsubstituted aryl, substituted or unsubstituted heteroaryl, —C₁-C₆alkyl-(substituted or unsubstituted C₃-C₆cycloalkyl), —C₁-C₆alkyl-(substituted or unsubstituted C₂-C₅heterocycloalkyl), —C₁-C₆alkyl- (substituted or unsubstituted aryl), —C₁-C₆alkyl-(substituted or unsubstituted heteroaryl) and —C(=O)RB;
R^B of —C(=O)R^B is selected from substituted or unsubstituted C₁-C₆alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted C2-$C_5$heterocycloalkyl), —$C_1$-$C_6$alkyl-(substituted or unsubstituted aryl), —$C_1$-$C_6$alkyl-(substituted or unsubstituted heteroaryl), or —$NR^D R^E$;

$R^D$ and $R^E$ of $NR^D R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl- (substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl- (substituted or unsubstituted heteroaryl);

m of Formula (XLI) is selected from 0, 1 or 2;

—U— of Formula (XLI) is selected from —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)NH—;

$R^3$ of Formula (XLI) is selected from $C_1$-$C_3$alkyl, or $C_1$-$C_3$fluoroalkyl;

$R^4$ of Formula (XLI) is selected from —$NHR^5$, —$N(R^5)2$, —$N+(R^5)3$ or —$OR^5$;

each $R^5$ of —$NHR^5$, —$N(R^5)2$, —$N+(R^5)3$ and —$OR^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ of Formula (XLI) together with the atoms to which they are attached form a substituted or unsubstituted 5-7 membered ring;

or:

$R^3$ of Formula (XLI) is bonded to a nitrogen atom of U to form a substituted or unsubstituted 5-7 membered ring;

$R^6$ of Formula (XLI) is selected from —NHC(=O)$R^7$, —C(=O)NH$R^7$, —NHS(=O)$2R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^7$, —($C_1$-$C_3$alkyl)-NHS(=O)$2R^7$, —($C_1$-$C_3$alkyl)-S(=O)2NH$R^7$; —($C_1$-$C_3$alkyl)-NHC(=O)NH$R^7$, —($C_1$-$C_3$alkyl)-NHS(=O)2NH$R^7$, substituted or unsubstituted $C_2$-$C_{10}$heterocycloalkyl, or substituted or unsubstituted heteroaryl;

each $R^7$ of —NHC(=O)$R^7$, —C(=O)NH$R^7$, —NHS(=O)2$R^7$, —S(=O)2NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^7$, —($C_1$-$C_3$alkyl)-NHS(=O)2$R^7$, —($C_1$-$C_3$alkyl)-S(=O)2NH$R^7$; —($C_1$-$C_3$alkyl)-NHC(=O)NH$R^7$, —($C_1$-$C_3$alkyl)-NHS(=O)2NH$R^7$ is independently selected from $C_1$-$C_6$alkyl, $C_1$-$C_6$haloalkyl, $C_1$-$C_6$heteroalkyl, a substituted or unsubstituted C3-C10cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl- (substituted or unsubstituted C2-C10heterocycloalkyl, —$C_1$-$C_6$alkyl-(substituted or unsubstituted aryl), —$C_1$-$C_6$alkyl-(substituted or unsubstituted heteroaryl), —(CH2)p-CH(substituted or unsubstituted aryl)2, —(CH$_2$)$_p$—CH(substituted or unsubstituted heteroaryl)2, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of $R^7$ is selected from 0, 1 or 2;

$R^{8a}$, $R^{8b}$, $R^{8c}$, and $R^{8d}$ of $C(R^{8a})(R^{8b})$ and $C(R^{8c})(R^{8d})$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N; or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8d}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ of $R^{8a}$, $R^{8b}$, $R^{8c}$ and $R^{8d}$ is independently selected from halogen, —OH, —SH, (C=O), CN, $C_1$-$C_4$alkyl, C1-C4fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)$_2$, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH$_2$; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In any of the compounds described herein, the ILM can have the structure of Formula (XLII), which are derived from the IAP ligands described in WO Pub. No. 2013/071039, or an unnatural mimetic thereof:

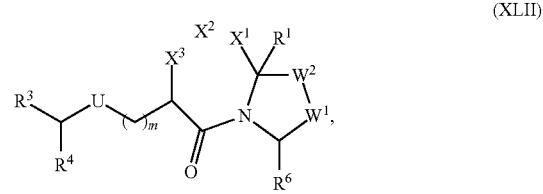

(XLII)

wherein:
$W^1$ of Formula (XLII) is O, S, N—$R^A$, or $C(R^{8a})(R^{8b})$;
$W^2$ of Formula (XLII) is O, S, N—$R^A$, or $C(R^{8c})(R^{8d})$; provided that $W^1$ and $W^2$ are not both O, or both S;
$R^1$ of Formula (XLII) is selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);
when $X^1$ of Formula (XLII) is N—$R^A$, then $X^2$ is C=O, or $CR^{2c}CR^{2d}$, and $X^3$ is $CR^{2a}R^{2b}$;
or:
when $X^1$ of Formula (XLII) is selected from S, S(O), or S(O)2, then $X^2$ is $CR^{2c}R^{2d}$, and $X^3$ is $CR^{2a}R^{2b}$;
or:
when $X^1$ of Formula (XLII) is O, then $X^2$ is $CR^{2c}R^{2d}$ and N—$R^A$ and $X^3$ is $CR^{2a}R^{2b}$; or:
when $X^1$ of Formula (XLII) is $CH_3$, then $X^2$ is selected from O, N—$R^A$, S, S(O), or S(O)$_2$, and $X^3$ is $CR^{2a}R^{2b}$;
when $X^1$ of Formula (XLII) is $CR^{2e}R^{2f}$ and X2 is $CR^{2c}R^{2d}$, and $R^{2e}$ and $R^{2c}$ together form a bond, and $X^3$ of Formula (VLII) is $CR^{2a}R^{2b}$;
or:
$X^1$ and $X^3$ of Formula (XLII) are both $CH_2$ and $X^2$ of Formula (XLII) is C=0, C=C($R^C$)2, or C—$NR^C$; where each $R^C$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_5$alkyl-(substituted or unsubstituted aryl), or —$C_1$-$C_6$alkyl-(substituted or unsubstituted heteroaryl);
or:
$X^1$ and $X^2$ of Formula (XLII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ is $CR^{2a}R^{2b}$;
or:
$X^2$ and $X^3$ of Formula (XLII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ of Formula (VLII) is $CR^{2e}R^{2f}$;
$R^A$ of N—$R^A$ is selected from H, $C_1$-$C_6$alkyl, —C(=O) $C_1$-$C_2$alkyl, substituted or unsubstituted aryl, or substituted or unsubstituted heteroaryl;
$R^{2a}$, $R^{2b}$, $R^{2c}$, $R^{2d}$, $R^{2e}$, and $R^{2f}$ of $CR^{2a}R^{2d}$, $CR^{2a}R^{2b}$ and $CR^{2e}R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_1$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;
$R^B$ of —C(=O)$R^B$ is selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;
$R^D$ and $R^E$ of $NR^DR^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl- (substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl- (substituted or unsubstituted heteroaryl);
m of Formula (XLII) is selected from 0, 1 or 2;
—U— of Formula (XLII) is selected from —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;
$R^3$ of Formula (XLII) is selected from $C_1$-$C_3$alkyl, or $C_1$-$C_3$fluoroalkyl;
$R^4$ of Formula (XLII) is selected from —$NHR^5$, —$N(R^5)_2$, —$N+(R^5)_3$ or —$OR^5$;
each $R^5$ of —$NHR^5$, —$N(R^5)_2$, —$N+(R^5)_3$ and —$OR^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);
or:
$R^3$ and $R^5$ of Formula (XLII) together with the atoms to which they are attached form a substituted or unsubstituted 5-7 membered ring;
or:
$R^3$ of Formula (XLII) is bonded to a nitrogen atom of U to form a substituted or unsubstituted 5-7 membered ring;
$R^6$ of Formula (XLII) is selected from —NHC(=O)$R^7$, —C(=O)NH$R^7$, —NHS(=O)2$R^7$, —S(O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^7$, —($C_1$-$C_3$alkyl)-NHS(=O)$_2$$R^7$, —($C_1$-$C_3$alkyl)-S(=O)$_2$NH$R^7$; —($C_1$-$C_3$alkyl)-NHC(=O)NH$R^7$, —($C_1$-$C_3$alkyl)-NHS(=O)$_2$NH$R^7$, substituted or unsubstituted C2-$C_{10}$heterocycloalkyl, or substituted or unsubstituted heteroaryl;
each $R^7$ of —NHC(=O)$R^7$, —C(=O)NH$R^7$, —NHS(=O)2$R^7$, —S(=O)$_2$NH$R^7$; —NHC(=O)NH$R^7$, —NHS(O)$_2$NH$R^7$, —($C_1$-$C_3$alkyl)-NHC(=O)$R^7$, —($C_1$-$C_3$alkyl)-C(=O)NH$R^7$, —($C_1$-$C_3$alkyl)-NHS(=O)2$R^7$, —($C_1$-$C_3$alkyl)-S(=O)2NH$R^7$; —($C_1$-$C_3$alkyl)-NHC(=O)NH$R^7$, —($C_1$-$C_3$alkyl)-NHS(=O)2NH$R^7$ is independently selected from $C_1$-$C_6$alkyl, $C_1$-$C_6$haloalkyl, $C_1$-$C_6$heteroalkyl, a substituted or unsubstituted C3-C10cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl- (substituted or unsubstituted C2-C10heterocycloalkyl, —C1-C6alkyl-(substituted or unsubstituted aryl), —C$_1$-C$_6$alkyl-(substituted or unsubstituted heteroaryl), —(CH$_2$)p-CH (substituted or unsubstituted aryl)2, —(CH$_2$)$_p$—CH (substituted or unsubstituted heteroaryl)2, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of R$^7$ is selected from 0, 1 or 2;

R$^{8a}$, R$^{8b}$, R$^{8c}$, and R$^{8d}$ of C(R$^{8a}$)(R$^{8b}$) and C(R$^{8c}$)(R$^{8d}$) are independently selected from H, C$_1$-C$_6$alkyl, C$_1$-C$_6$fluoroalkyl, C$_1$-C$_6$ alkoxy, C$_1$-C$_6$heteroalkyl, and substituted or unsubstituted aryl;

or:

R$^{8a}$ and R$^{8d}$ are as defined above, and R$^{8b}$ and R$^{8c}$ together form a bond;

or:

R$^{8a}$ and R$^{8d}$ are as defined above, and R$^{8b}$ and R$^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

R$^{8c}$ and R$^{8d}$ are as defined above, and R$^{8a}$ and R$^{8b}$ together with the atoms to which they are attached form a substituted or unsubstituted saturated, or partially saturated 3-7 membered spirocycle or heterospirocycle comprising 1-3 heteroatoms selected from S, O and N;

or:

R$^{8a}$ and R$^{8b}$ are as defined above, and R$^{8c}$ and R$^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 R$^9$; and each R$^9$ of R$^{8a}$, R$^{8b}$, R$^{8c}$ and R$^{8d}$ is independently selected from halogen, —OH, —SH, (C═O), CN, C$_1$-C$_4$alkyl, C1-C4fluoroalkyl, C$_1$-C$_4$ alkoxy, C$_1$-C$_4$ fluoroalkoxy, —NH$_2$, —NH(C$_1$-C$_4$alkyl), —NH(C$_1$-C$_4$alkyl)$_2$, —C(═O)OH, —C(═0)NH$_2$, —C(═O)C$_1$-C$_3$alkyl, —S(═O)$_2$CH$_3$, —NH(C$_1$-C$_4$alkyl)-OH, —NH(C$_1$-C$_4$alkyl)-O—(C$_1$-C$_4$alkyl), —O(C$_1$-C$_4$alkyl)NH$_2$; —O(C$_1$-C$_4$alkyl)-NH—(C$_1$-C$_4$alkyl), and —O(C$_1$-C$_4$alkyl)-N—(C$_1$-C$_4$alkyl)$_2$, or two R$^9$ together with the atoms to which they are attached form a methylene dioxy or ethylene dioxy ring substituted or unsubstituted with halogen, —OH, or C$_1$-C$_3$alkyl.

In any of the compounds described herein, the ILM can have the structure of Formula (XLIII), which is derived from the IAP ligands described in WO Pub. No. 2013/071039, or an unnatural mimetic thereof:

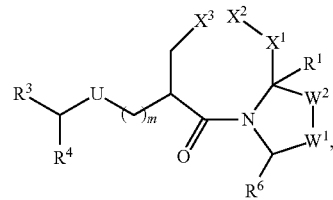

(XLIII)

wherein:

W$^1$ of Formula (XLIII) is selected from O, S, N—R$^A$, or C(R$^{8a}$)(R$^{8b}$);

W$^2$ of Formula (XLIII) is selected from O, S, N—R$^A$, or C(R$^{8c}$)(R$^{8d}$); provided that W$^1$ and W$^2$ are not both O, or both S;

R$^1$ of Formula (XLIII) is selected from H, C$_1$-C$_6$alkyl, C$_3$-C$_6$cycloalkyl, —C$_1$-C$_6$alkyl-(substituted or unsubstituted C$_3$-C$_6$cycloalkyl), substituted or unsubstituted aryl, substituted or unsubstituted heteroaryl, —C$_1$-C$_6$alkyl-(substituted or unsubstituted aryl), or —C$_1$-C$_6$alkyl-(substituted or unsubstituted heteroaryl);

when X$^1$ of Formula (XLIII) is selected from N—R$^A$, S, S(O), or S(O)$_2$, then X$^2$ of Formula (XLIII) is CR$^{2c}$R$^{2d}$, and X$^3$ of Formula (XLIII) is CR$^{2a}$R$^{2b}$;

or:

when X$^1$ of Formula (XLIII) is O, then X$^2$ of Formula (XLIII) is selected from O, N—R$^A$ S, S(O), or S(O)$_2$, and X$^3$ of Formula (XLIII) is CR$^{2a}$R$^{2b}$;

or:

when X$^1$ of Formula (XLIII) is CR$^{2e}$R$^{2f}$ and X$^2$ of Formula (XLIII) is CR$^{2c}$R$^{2d}$, and R$^{2e}$ and R$^{2c}$ together form a bond, and X$^3$ of Formula (XLIII) is CR$^{2a}$R$^{2b}$;

or:

X$^1$ and X$^2$ of Formula (XLIII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and X$^3$ of Formula (XLIII) is CR$^{2a}$R$^{2b}$;

or:

X$^2$ and X$^3$ of Formula (XLIII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and X$^1$ of Formula (VLII) is CR$^{2e}$R$^{2f}$;

R$^A$ of N—R$^A$ is H, C$_1$-C$_6$alkyl, —C(═O)C$_1$-C$_2$alkyl, substituted or unsubstituted aryl, or substituted or unsubstituted heteroaryl;

R$^{2a}$, R$^{2b}$, R$^{2c}$, R$^{2d}$, R$^{2e}$, and R$^{2f}$ of CR$^{2c}$R$^{2d}$, CR$^{2a}$R$^{2b}$ and CR$^{2e}$R$^{2f}$ are independently selected from H, substituted or unsubstituted C$_1$-C$_6$alkyl, substituted or unsubstituted C$_1$-C$_6$heteroalkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-C$_6$alkyl-(substituted or unsubstituted C$_3$-C$_6$cycloalkyl), —C$_1$-C$_6$alkyl-(substituted or unsubstituted C$_2$-C$_5$heterocycloalkyl), —C$_1$-C$_6$alkyl-(substituted or unsubstituted aryl), —$C_1$-$C_6$alkyl-(substituted or unsubstituted heteroaryl) and —C(=O)$R^B$;

$R^B$ of —C(=O)$R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^D R^E$;

$R^D$ and $R^E$ of $NR^D R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl- (substituted or unsubstituted $C_3$-$C_6$cycloalkyl), —$C_1$-$C_6$alkyl-(substituted or unsubstituted $C2$-$C_5$heterocycloalkyl), —$C_1$-$C_6$alkyl-(substituted or unsubstituted aryl), or —$C_1$-$C_6$alkyl- (substituted or unsubstituted heteroaryl);

m of Formula (XLIII) is 0, 1 or 2;

—U— of Formula (XLIII) is —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—; $R^3$ of Formula (XLIII) is $C_1$-$C_3$alkyl, or $C_1$-$C_3$fluoroalkyl;

$R^4$ of Formula (XLIII) is —$NHR^5$, —$N(R^5)_2$, —$N+(R^5)_3$ or —$OR^5$;

each $R^5$ of —$NHR^5$, —$N(R^5)_2$, —$N+(R^5)_3$ and —$OR^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ of Formula (XLIII) together with the atoms to which they are attached form a substituted or unsubstituted 5-7 membered ring;

or:

$R^3$ of Formula (XLIII) is bonded to a nitrogen atom of U to form a substituted or unsubstituted 5-7 membered ring;

$R^6$ of Formula (XLIII) is selected from —NHC(=O)$R^7$, —C(=O)$NHR^7$, —NHS(=O)2$R^7$, —S(=O)$_2NHR^7$; —NHC(=O)$NHR^7$, —NHS(=O)$_2NHR^7$, —($C_1$-$C_3$alkyl)-NHC(=O)$R^7$, —($C_1$-$C_3$alkyl)-C(=O)$NHR^7$, —($C_1$-$C_3$alkyl)-NHS(=O)$_2R^7$, —($C_1$-$C_3$alkyl)-S(=O)$NHR^7$; —($C_1$-$C_3$alkyl)-NHC(=O)$NHR^7$, —($C_1$-$C_3$alkyl)-NHS(=O)$_2NHR^7$, substituted or unsubstituted $C_2$-$C_{10}$heterocycloalkyl, or substituted or unsubstituted heteroaryl;

each $R^7$ of —NHC(=O)$R^7$, —C(=O)$NHR^7$, —NHS(=O)2$R^7$, —S(=O)$_2NHR^7$; —NHC(=O)$NHR^7$, —NHS(=O)2$NHR^7$, —($C_1$-$C_3$alkyl)-NHC(=O)$R^7$, —($C_1$-$C_3$alkyl)-C(=O)$NHR^7$, —($C_1$-$C_3$alkyl)-NHS(=O)2$R^7$, —($C_1$-$C_3$alkyl)-S(=O)2$NHR^7$; —($C_1$-$C_3$alkyl)-NHC(=O)$NHR^7$, —($C_1$-$C_3$alkyl)-NHS(=O)2$NHR^7$ is independently selected from $C_1$-$C_6$alkyl, $C_1$-$C_6$haloalkyl, $C_1$-$C_6$heteroalkyl, a substituted or unsubstituted $C3$-$C10$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl- (substituted or unsubstituted $C_2$-$C_{10}$heterocycloalkyl, —$C_1$-$C_6$alkyl-(substituted or unsubstituted aryl), —C—$C_6$alkyl-(substituted or unsubstituted heteroaryl), —(CH$_2$)p-CH(substituted or unsubstituted aryl)2, —(CH$_2$)$_p$—CH(substituted or unsubstituted heteroaryl)2, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of $R^7$ is 0, 1 or 2;

$R^{8a}$, $R^{8b}$, $R^{8c}$, and $R^{8d}$ of C($R^{8a}$)($R^{8b}$) and C($R^{8c}$)($R^{8d}$) are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ of $R^{8a}$, $R^{8b}$, $R^{8c}$ and $R^{8d}$ is independently selected from halogen, —OH, —SH, (C=O), CN, $C_1$-$C_4$alkyl, $C_1$-$C_4$fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)$_2$, —C(=O)OH, —C(=0)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH2; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In any of the compounds described herein, the ILM can have the structure of Formula (XLIV), which is derived from the IAP ligands described in WO Pub. No. 2013/071039, or an unnatural mimetic thereof:

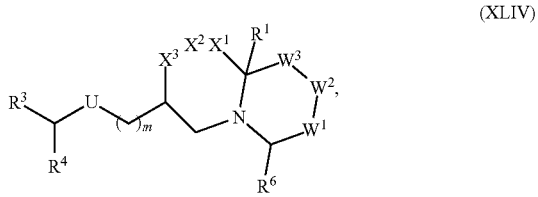

(XLIV)

wherein:
- $W^1$ of Formula (XLIV) is selected from O, S, N—$R^A$, or C($R^{8a}$)($R^{8b}$);
- $W^2$ of Formula (XLIV) is selected from O, S, N—$R^A$, or C($R^{8c}$)($R^{8d}$); provided that $W^1$ and $W^2$ are not both O, or both S;
- $W^3$ of Formula (XLIV) is selected from O, S, N—$R^A$, or C($R^{8e}$)($R^{8d}$), providing that the ring comprising $W^1$, $W^2$, and $W^3$ does not comprise two adjacent oxygen atoms or sulfur atoms;
- $R^1$ of Formula (XLIV) is selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);
- when $X^1$ of Formula (XLIV) is O, then $X^2$ of Formula (XLIV) is selected from $CR^{2c}R^{2d}$ and N—$R^A$, and $X^3$ of Formula (XLIV) is $CR^{2a}R^{2b}$;
  or:
- when $X^1$ of Formula (XLIV) is $CH_2$, then $X^2$ of Formula (XLIV) is selected from O, N—$R^A$, S, S(O), or $S(O)_2$, and $X^3$ of Formula (XLIV) is $CR^{2a}R^{2b}$;
  or:
- when $X^1$ of Formula (XLIV) is $CR^{2e}R^{2f}$ and $X^2$ of Formula (XLIV) is $CR^{2c}R^{2d}$, and $R^{2e}$ and $R^{2c}$ together form a bond, and $X^3$ of Formula (VLIV) is $CR^{2a}R^{2b}$;
  or:
- $X^1$ and $X^3$ of Formula (XLIV) are both $CH_2$ and $X^2$ of Formula (XLII) is C=O, C=C($R^C$)2, or C=$NR^C$; where each $R^C$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_5$alkyl-(substituted or unsubstituted $C_2$-$C_5$heterocycloalkyl), —$C_1$-$C_5$alkyl-(substituted or unsubstituted aryl), or —$C_1$-$C_6$alkyl-(substituted or unsubstituted heteroaryl);
  or:
- $X^1$ and $X^2$ of Formula (XLIV) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ of Formula (XLIV) is $CR^{2a}R^{2b}$; or:
- $X^2$ and $X^3$ of Formula (XLIV) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ of Formula (VLIV) is $CR^{2e}R^{2f}$;
- $R^A$ of N—$R^A$ is selected from H, $C_1$-$C_6$alkyl, —C(=O) $C_1$-$C_2$alkyl, substituted or unsubstituted aryl, or substituted or unsubstituted heteroaryl;
- $R^{2a}$, $R^{2b}$, $R^{2c}$, $R^{2d}$, $R^{2e}$, and $R^{2f}$ of $CR^{2c}R^{2d}$, $CR^{2a}R^{2b}$ and $CR^{2e}R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;
- $R^8$ of —C(=O)$R^B$ is selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;
- $R^D$ and $R^E$ of $NR^DR^E$ are independently selected from H, substituted or unsubstituted $C_1$-$C_6$alkyl, substituted or unsubstituted $C_3$-$C_5$cycloalkyl, substituted or unsubstituted $C_2$-$C_5$heterocycloalkyl, substituted or unsubstituted aryl, substituted or unsubstituted heteroaryl, —$C_1$-$C_6$alkyl- (substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl- (substituted or unsubstituted heteroaryl);
- m of Formula (XLIV) is selected from 0, 1 or 2;
- —U— of Formula (XLIV) is selected from —NHC(=O)—, —C(=O)NH—, —NHS(=O)$_2$—, —S(=O)$_2$NH—, —NHC(=O)NH—, —NHC(=O)O—, —O(C=O)NH—, or —NHS(=O)$_2$NH—;
- $R^3$ of Formula (XLIV) is selected from $C_1$-$C_3$alkyl, or $C_1$-$C_3$fluoroalkyl;
- $R^4$ of Formula (XLIV) is selected from —$NHR^5$, —N($R^5$)$_2$, —N+($R^5$)$_3$ or —$OR^5$;
- each $R^5$ of —$NHR^5$, —N($R^5$)$_2$, —N+($R^5$)$_3$ and —$OR^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);
  or:
- $R^3$ and $R^4$ of Formula (XLIV) together with the atoms to which they are attached form a substituted or unsubstituted 5-7 membered ring;
  or:
- $R^3$ of Formula (XLIII) is bonded to a nitrogen atom of U to form a substituted or unsubstituted 5-7 membered ring;
- $R^6$ of Formula (XLIII) is selected from —NHC(=O)$R^7$, —C(=O)NHR$^7$, —NHS(=O)2$R^7$, —S(=O)$_2$NHR$^7$; —NHC(=O)NHR$^7$, —NHS(=O)$_2$NHR$^7$, —($C_1$-$C_3$alkyl)-NHC(=O)$R^7$, —($C_1$-$C_3$alkyl-C(=O)NHR$^7$, —($C_1$-$C_3$alkyl)-NHS(=O)$_2$R$^7$, —($C_1$-$C_3$alkyl)-S(=O)$_2$NHR$^7$; —($C_1$-$C_3$alkyl)-NHC(=O)NHR$^7$, —(C₁-C₃alkyl)-NHS(=O)₂NHR⁷, substituted or unsubstituted C2-C₁₀heterocycloalkyl, or substituted or unsubstituted heteroaryl;

each R⁷ of —NHC(=O)R⁷, —C(=O)NHR⁷, —NHS(=O)2R⁷, —S(=O)₂NHR⁷; —NHC(=O)NHR⁷, —NHS(=O)2NHR⁷, —(C₁-C₃alkyl)-NHC(=O)R⁷, —(C₁-C₃alkyl)-C(=O)NHR⁷, —(C₁-C₃alkyl)-NHS(=O)2R⁷, —(C₁-C₃alkyl)-S(=O)2NHR⁷; —(C₁-C₃alkyl)-NHC(=O)NHR⁷, —(C₁-C₃alkyl)-NHS(=O)2NHR⁷ is independently selected from C₁-C₆alkyl, C₁-C₆haloalkyl, C₁-C₆heteroalkyl, a substituted or unsubstituted C3-C10cycloalkyl, a substituted or unsubstituted C₂-C₁₀heterocycloalkyl, a substituted or unsubstituted aryl, a substituted or unsubstituted heteroaryl, —C₁-C₆alkyl-(substituted or unsubstituted C₃-C₁₀cycloalkyl), —C₁-C₆alkyl- (substituted or unsubstituted C2-C10heterocycloalkyl, —C1-C6alkyl-(substituted or unsubstituted aryl), —C₁-C₆alkyl-(substituted or unsubstituted heteroaryl), —(CH₂)p-CH(substituted or unsubstituted aryl)2, —(CH₂)$_p$—CH(substituted or unsubstituted heteroaryl)2, —(CH₂)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of R⁷ is selected from 0, 1 or 2;

$R^{8a}$, $R^{8b}$, $R^{8c}$, $R^{8d}$, $R^{8e}$, and $R^{8f}$ of $C(R^{8a})(R^{8b})$, $C(R^{8c})(R^{8d})$ and $C(R^{8e})(R^{8f})$ are independently selected from H, C₁-C₆alkyl, C₁-C₆fluoroalkyl, C₁-C₆ alkoxy, C₁-C₆heteroalkyl, and substituted or unsubstituted aryl;

or:

$R^{8a}$, $R^{8d}$, $R^{8e}$, and $R^{8f}$ of $C(R^{8a})(R^{8b})$, $C(R^{8c})(R^{8d})$ and $C(R^{8e})(R^{8f})$ are as defined above, and $R^{8b}$ and $R^{8c}$ together form a bond;

or:

$R^{8a}$, $R^{8b}$, $R^{8d}$, and $R^{8f}$ of $C(R^{8a})(R^{8b})$, $C(R^{8c})(R^{8d})$ and $C(R^{8e})(R^{8f})$ are as defined above, and $R^{8c}$ and $R^{8e}$ together form a bond;

or:

$R^{8a}$, $R^{8d}$, $R^{8e}$, and $R^{8f}$ of $C(R^{8a})(R^{8b})$, $C(R^{8c})(R^{8d})$ and $C(R^{8e})(R^{8f})$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8a}$, $R^{8b}$, $R^{8d}$, and $R^{8f}$ of $C(R^{8a})(R^{8b})$, $C(R^{8c})(R^{8d})$ and $C(R^{8e})(R^{8f})$ are as defined above, and $R^{8c}$ and $R^{8e}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8a}$, $R^{8b}$, $R^{8d}$, and $R^{8f}$ of $C(R^{8a})(R^{8b})$, $C(R^{8c})(R^{8d})$ and $C(R^{8e})(R^{8f})$ are as defined above, and $R^{8c}$ and $R^{8e}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8d}$, $R^{8e}$, and $R^{8f}$ of $C(R^{8c})(R^{8d})$ and $C(R^{8e})(R^{8f})$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8e}$, and $R^{8f}$ of $C(R^{8a})(R^{8b})$ and $C(R^{8e})(R^{8f})$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

or:

where each substituted alkyl, heteroalkyl, fused ring, spirocycle, heterospirocycle, cycloalkyl, heterocycloalkyl, aryl or heteroaryl is substituted with 1-3 R⁹; and each R⁹ of $R^{8a}$, $R^{8b}$, $R^{8c}$, $R^{8d}$, $R^{8e}$, and $R^{8f}$ is independently selected from halogen, —OH, —SH, (C=O), CN, C₁-C₄alkyl, C1-C4fluoroalkyl, C₁-C₄ alkoxy, C₁-C₄ fluoroalkoxy, —NH₂, —NH(C₁-C₄alkyl), —NH(C₁-C₄alkyl)₂, —C(=O)OH, —C(=0)NH₂, —C(=O)C₁-C₃alkyl, —S(=O)₂CH₃, —NH(C₁-C₄alkyl)-OH, —NH(C₁-C₄alkyl)-O—(C₁-C₄alkyl), —O(C₁-C₄alkyl)-NH2; —O(C₁-C₄alkyl)-NH—(C₁-C₄alkyl), and —O(C₁-C₄alkyl)-N—(C₁-C₄alkyl)₂, or two R⁹ together with the atoms to which they are attached form a methylene dioxy or ethylene dioxy ring substituted or unsubstituted with halogen, —OH, or C₁-C₃alkyl.

In any of the compounds described herein, the ILM can have the structure of Formula (XLV), (XLVI) or (XLVII), which is derived from the IAP ligands described in Vamos, M., et al., *Expedient synthesis of highly potent antagonists of inhibitor of apoptosis proteins (IAPs) with unique selectivity for ML-IAP*, ACS Chem. Biol., 8(4), 725-32 (2013), or an unnatural mimetic thereof:

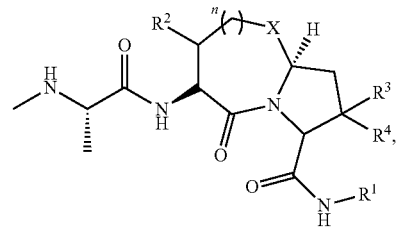

(XLV)

n = 0, 1

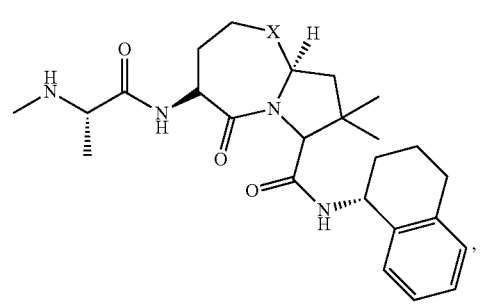

(XLVI)

-continued (XLVII)

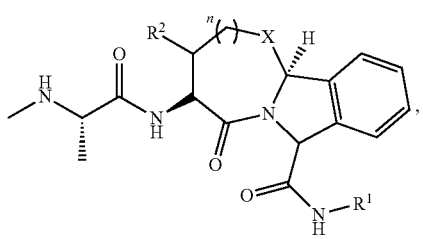

n = 0, 1 wherein:

R², R³ and R⁴ of Formula (XLV) are independently selected from H or ME;

X of Formula (XLV) is independently selected from O or S; and

R¹ of Formula (XLV) is selected from:

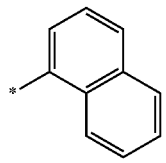 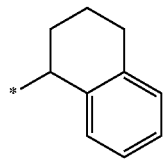 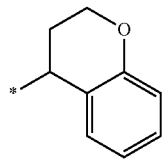

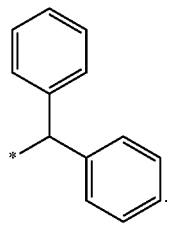

In a particular embodiment, the ILM has a structure according to Formula (XLVIII):

(XLVIII)

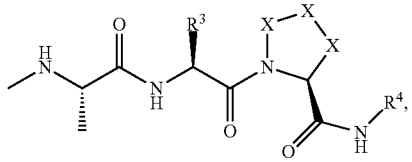

wherein R³ and R⁴ of Formula (XLVIII) are independently selected from H or ME;

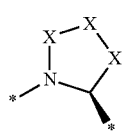

is a 5-member heterocycle selected from:

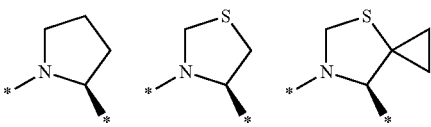

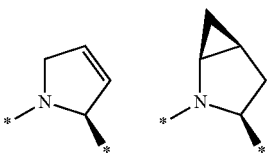

In a particular embodiment, the

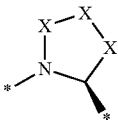

of Formula XLVIII) is

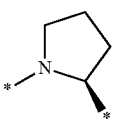 [SMILES: *[C@@H]1CCCN1*]

In a particular embodiment, the ILM has a structure and attached to a linker group L as shown below:

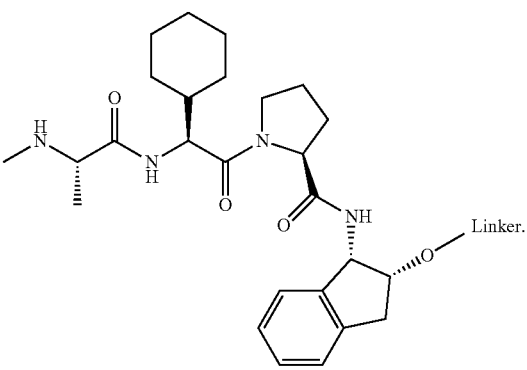

In a particular embodiment, the ILM has a structure according to Formula (XLIX), (L), or (LI):

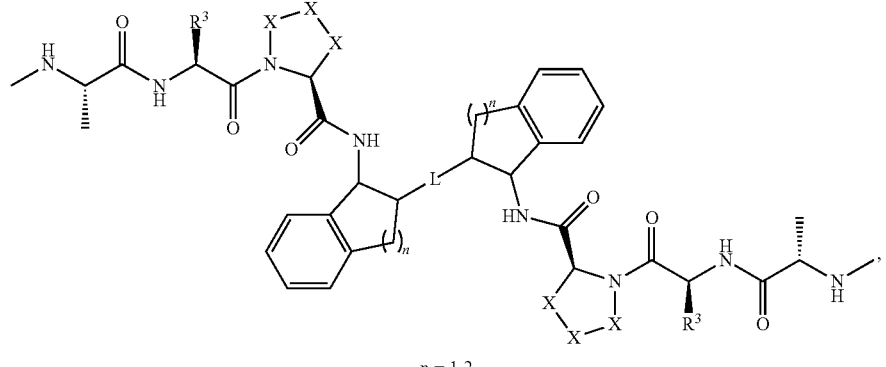
(XLIX)
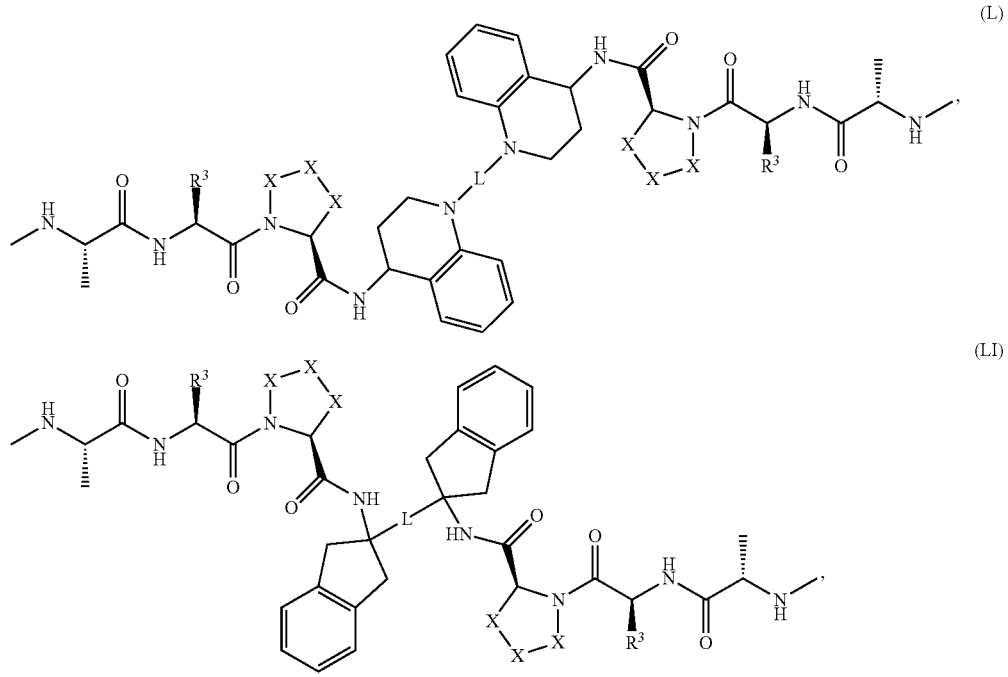
n = 1,2
(L)
(LI)
wherein:
$R^3$ of Formula (XLIX), (L) or (LI) are independently selected from H or ME;
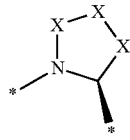
is a 5-member heterocycle selected from:
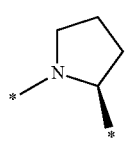 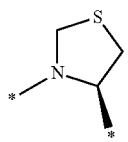 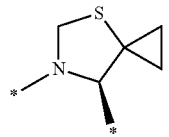
-continued
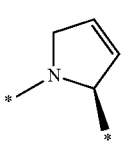 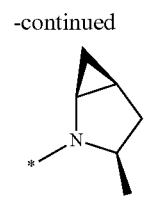
and L of Formula (XLIX), (L) or (LI) is selected from:
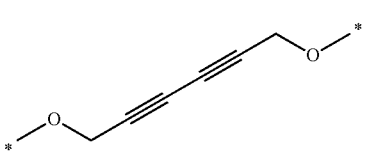

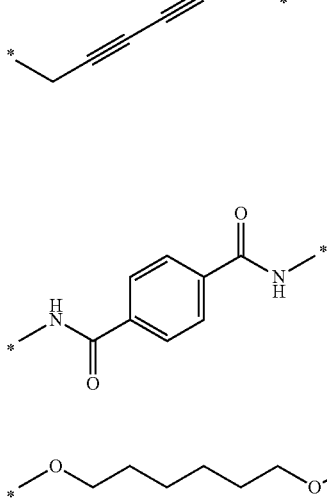
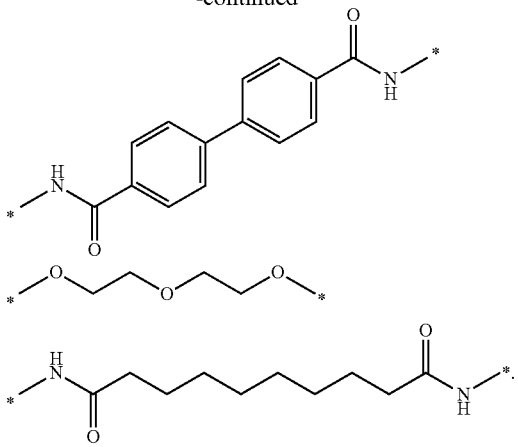
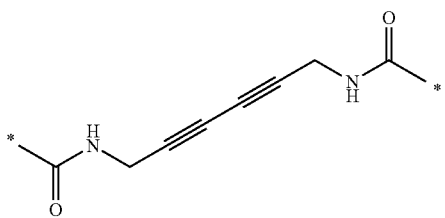
In a particular embodiment, L of Formula (XLIX), (L), or (LI)
In a particular embodiment, the ILM has a structure according to Formula (LII):
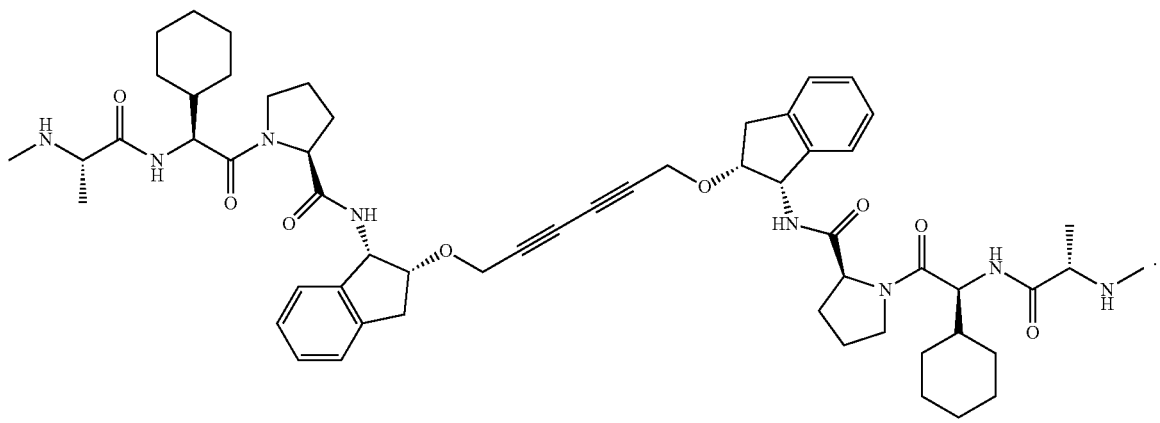
In a particular embodiment, the ILM according to Formula (LII) is chemically linked to the linker group L in the area denoted with

and as shown below:

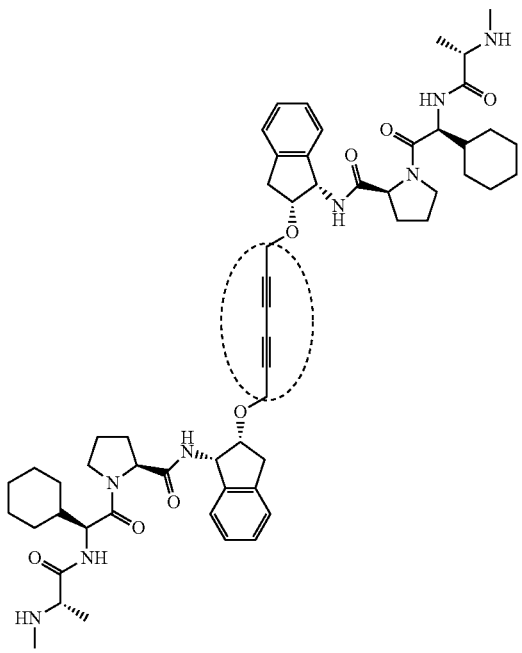 [SMILES: CN[C@@H](C)C(=O)N[C@H](C(=O)N1CCC[C@H]1C(=O)N[C@H]1c2ccccc2C[C@H]1OCC#CC#CCO[C@@H]1Cc2ccccc2[C@@H]1NC(=O)[C@@H]1CCCN1C(=O)[C@@H](NC(=O)[C@H](C)NC)C1CCCCC1)C1CCCCC1]

In any of the compounds described herein, the ILM can have the structure of Formula (LIII) or (LIV), which is based on the IAP ligands described in Hennessy, E J, et al., *Discovery of aminopiperidine-based Smac mimetics as IAP antagonists*, Bioorg. Med. Chem. Lett., 22(4), 1960-4 (2012), or an unnatural mimetic thereof:

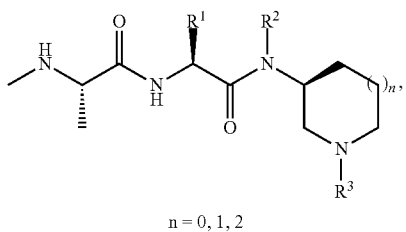

(LIII)

n = 0, 1, 2

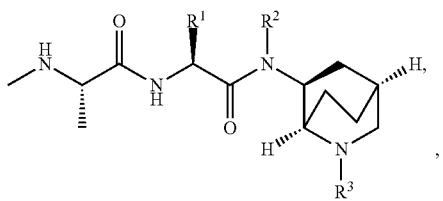

(LIV)

wherein:
R$^1$ of Formulas (LIII) and (LIV) is selected from:

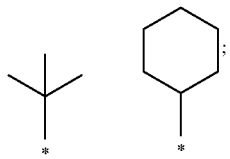

R$^2$ of Formulas (LIII) and (LIV) is selected from H or Me;

R$^3$ of Formulas (LIII) and (LIV) is selected from:

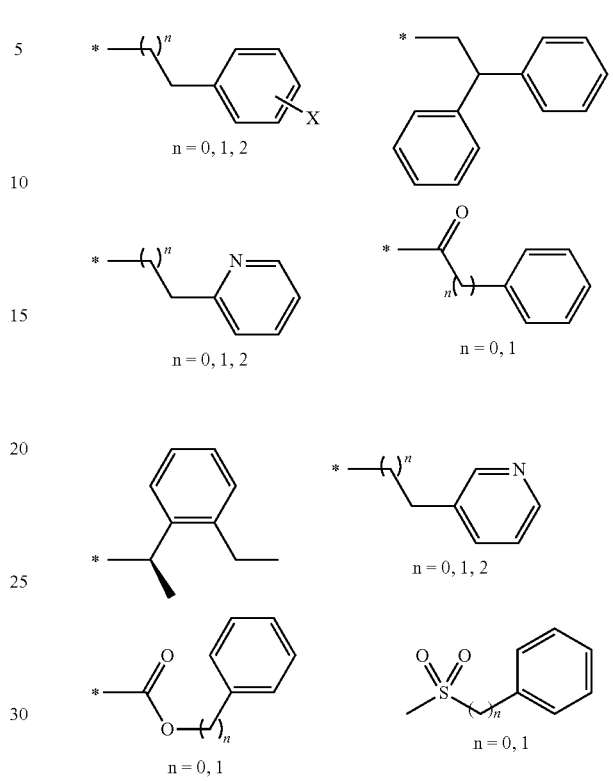

X of is selected from H, halogen, methyl, methoxy, hydroxy, nitro or trifluoromethyl.

In any of the compounds described herein, the ILM can have the structure of and be chemically linked to the linker as shown in Formula (LV) or (LVI), or an unnatural mimetic thereof:

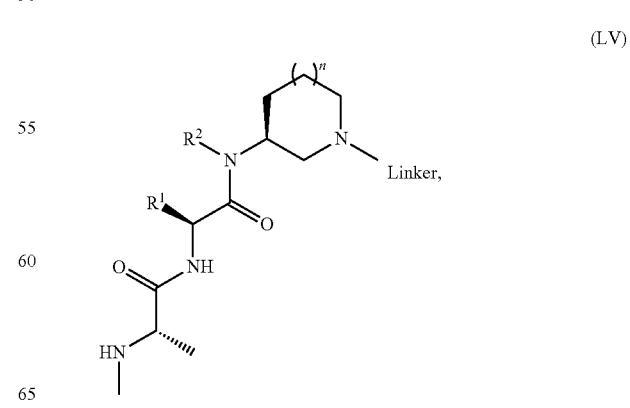

(LV)

-continued (LVI)

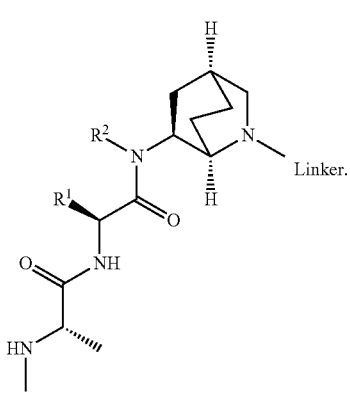

In a particular embodiment, the ILM is represented by the following structure:

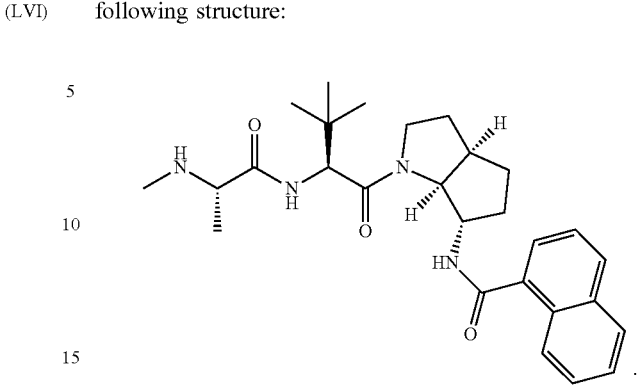

In any of the compounds described herein, the ILM can have the structure of Formula (LVII), which is based on the IAP ligands described in Cohen, F, et al., *Orally bioavailable antagonists of inhibitor of apoptosis proteins based on an azabicyclooctane scaffold*, J. Med. Chem., 52(6), 1723-30 (2009), or an unnatural mimetic thereof:

(LVII)

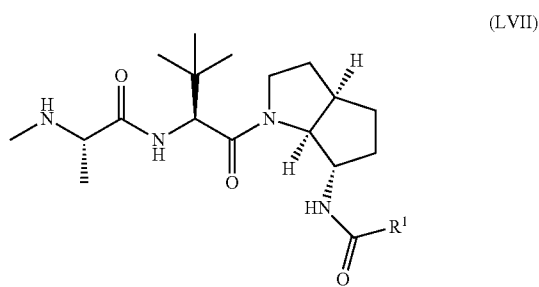

wherein:
R1 of Formulas (LVII) is selected from:

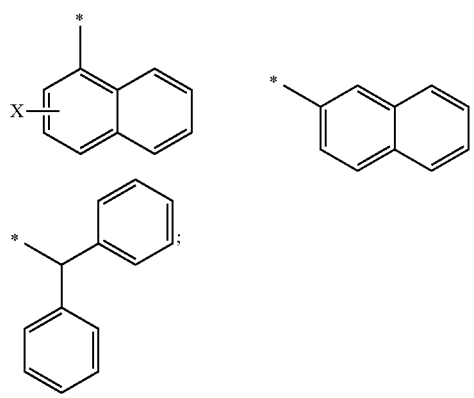

X of

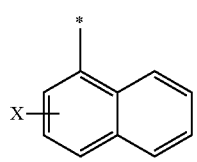

is selected from H, fluoro, methyl or methoxy.

In a particular embodiment, the ILM is selected from the group consisting of, and which the chemical link between the ILM and linker group L is shown:

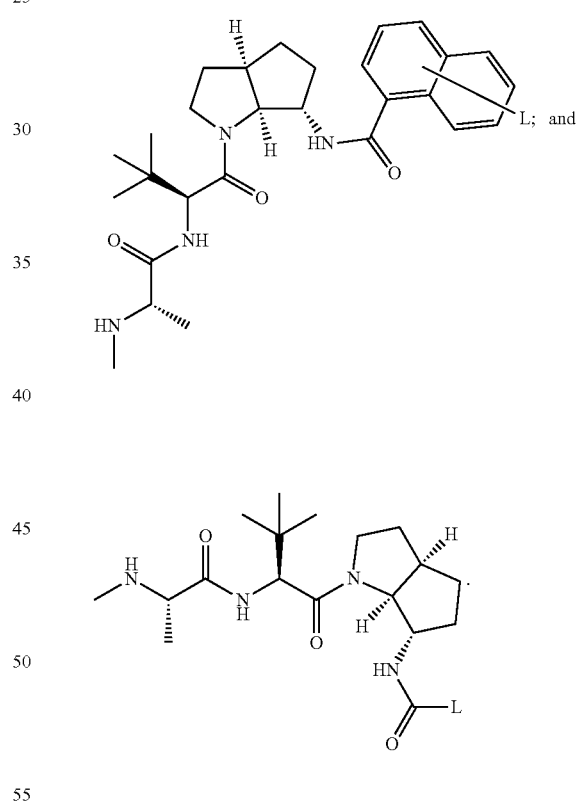

In any of the compounds described herein, the ILM is selected from the group consisting of the structures below, which are based on the IAP ligands described in Asano, M, et al., *Design, stereoselective synthesis, and biological evaluation of novel tri-cyclic compounds as inhibitor of apoptosis proteins (IAP) antagonists*, Bioorg. Med. Chem., 21(18): 5725-37 (2013), or an unnatural mimetic thereof:

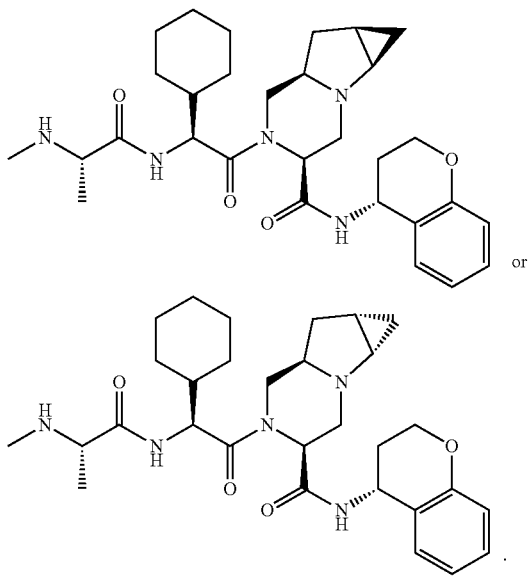

In a particular embodiment, the ILM is selected from the group consisting of, and which the chemical link between the ILM and linker group L is shown:

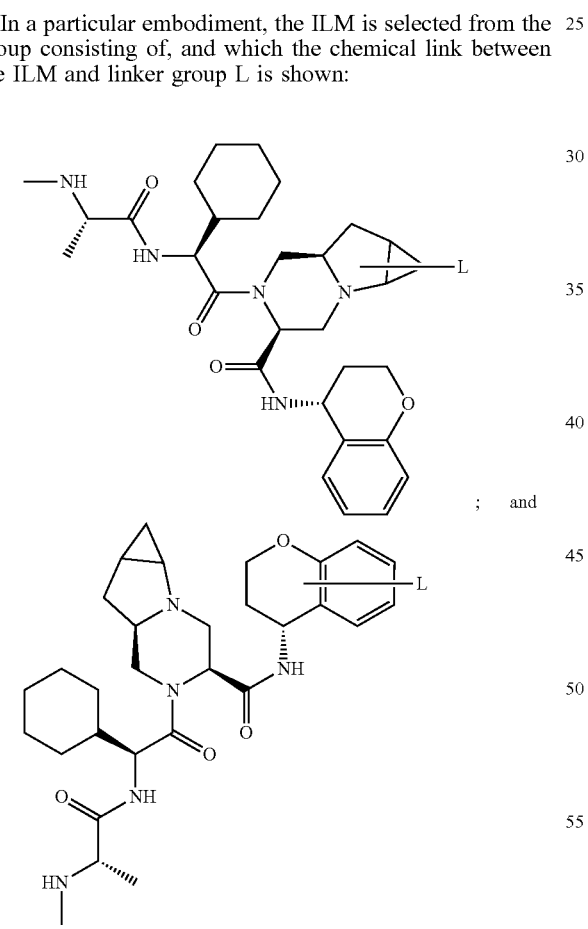

; and

In any of the compounds described herein, the ILM can have the structure of Formula (LVIII), which is based on the IAP ligands described in Asano, M, et al., *Design, stereoselective synthesis, and biological evaluation of novel tricyclic compounds as inhibitor of apoptosis proteins (IAP) antagonists*, Bioorg. Med. Chem., 21(18): 5725-37 (2013), or an unnatural mimetic thereof:

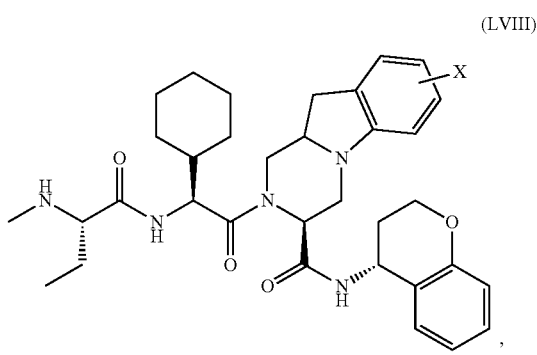

(LVIII)

wherein X of Formula (LVIII) is one or two substituents independently selected from H, halogen or cyano.

In any of the compounds described herein, the ILM can have the structure of and be chemically linked to the linker group L as shown in Formula (LIX) or (LX), or an unnatural mimetic thereof:

(LIX)

or (LX)

wherein X of Formula (LIX) and (LX) is one or two substituents independently selected from H, halogen or cyano, and; and L of Formulas (LIX) and (LX) is a linker group as described herein.

In any of the compounds described herein, the ILM can have the structure of Formula (LXI), which is based on the IAP ligands described in Ardecky, R J, et al., *Design, synthesis and evaluation of inhibitor of apoptosis (IAP)* antagonists that are highly selective for the BIR2 domain of XIAP, Bioorg. Med. Chem., 23(14): 4253-7 (2013), or an unnatural mimetic thereof:

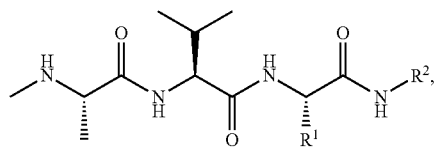
(LXI)

wherein:

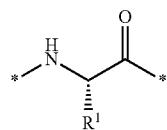

of Formula (LXI) is a natural or unnatural amino acid; and $R^2$ of Formula (LXI) is selected from

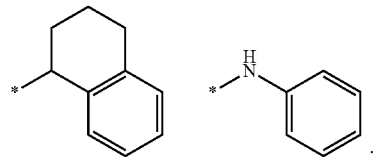

In any of the compounds described herein, the ILM can have the structure of and be chemically linked to the linker group L as shown in Formula (LXII) or (LLXIII), or an unnatural mimetic thereof:

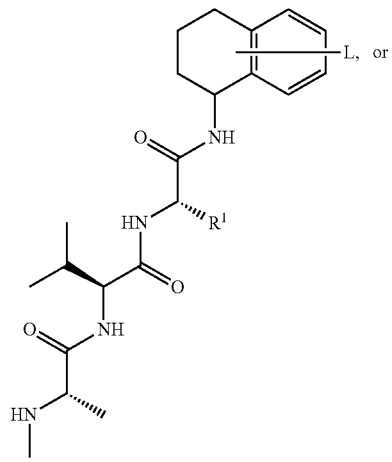
(LXII)

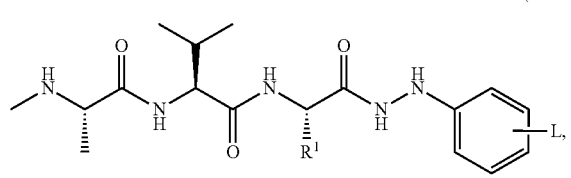
(LXIII)

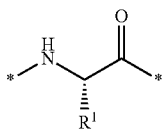

of Formula (LXI) is a natural or unnatural amino acid; and L of Formula (LXI) is a linker group as described herein.

In any of the compounds described herein, the ILM can have the structure selected from the group consisting of, which is based on the IAP ligands described in Wang, J, et al., *Discovery of novel second mitochondrial-derived activator of caspase mimetics as selective inhibitor or apoptosis protein inhibitors*, J. Pharmacol. Exp. Ther., 349(2): 319-29 (2014), or an unnatural mimetic thereof:

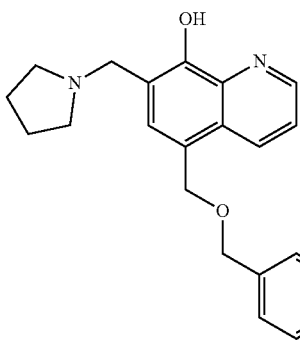
; and

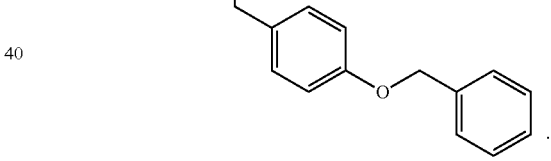

In any of the compounds described herein, the ILM has a structure according to Formula (LXIX), which is based on the IAP ligands described in Hird, A W, et al., Structure-based design and synthesis of tricyclic IAP (*Inhibitors of Apoptosis Proteins*) inhibitors, Bioorg. Med. Chem. Lett., 24(7): 1820-4 (2014), or an unnatural mimetic thereof:

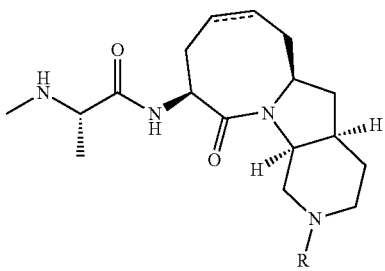
(LXIX)

wherein R of Formula LIX is selected from the group consisting of:

117

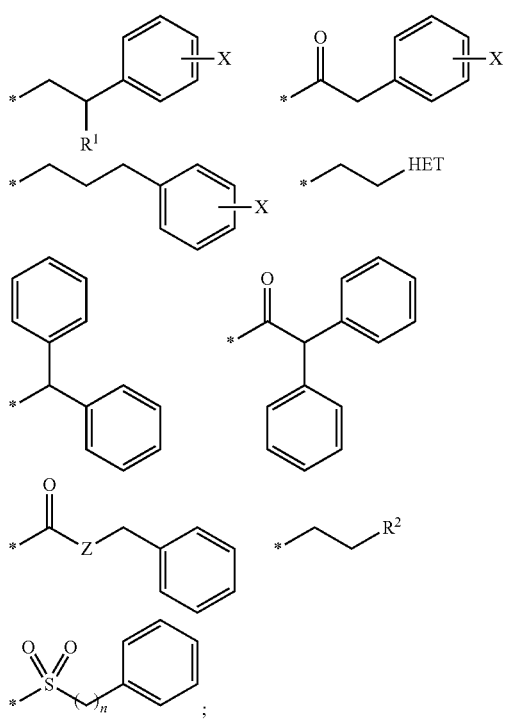

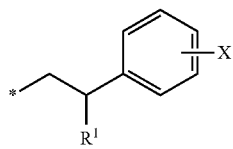

R1 of

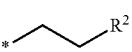

is selected from H or Me;

118

R2 of

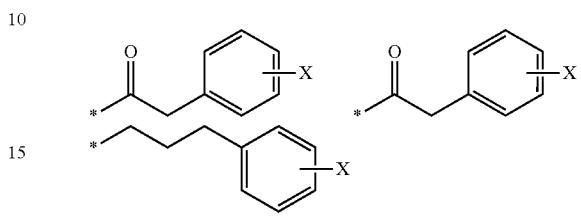

is selected from alkyl or cycloalkyl;
X of

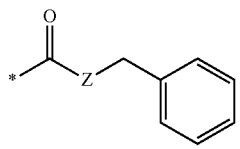

is 1-2 substitutents independently selected from halogen, hydroxy, methoxy, nitro and trifluoromethyl
Z of

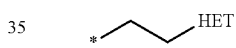

is O or NH;
HET of

*~~HET is mono- or fused bicyclic heteroaryl; and
- - - of Formula (LIX) is an optional double bond.
In a particular embodiment, the ILM of the compound has a chemical structure as represented by:

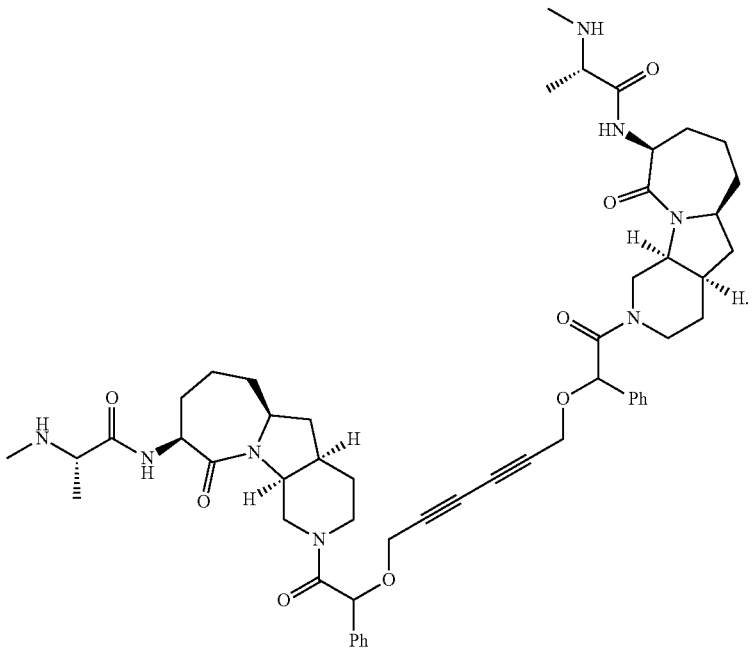

In a particular embodiment, the ILM of the compound has a chemical structure selected from the group consisting of:

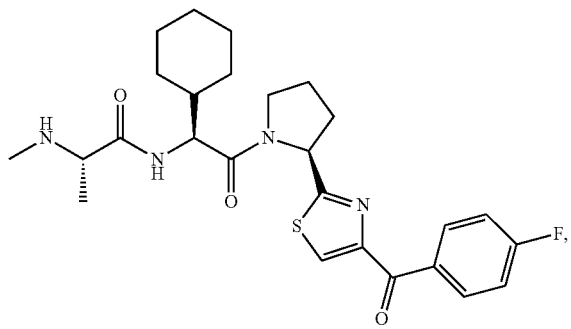

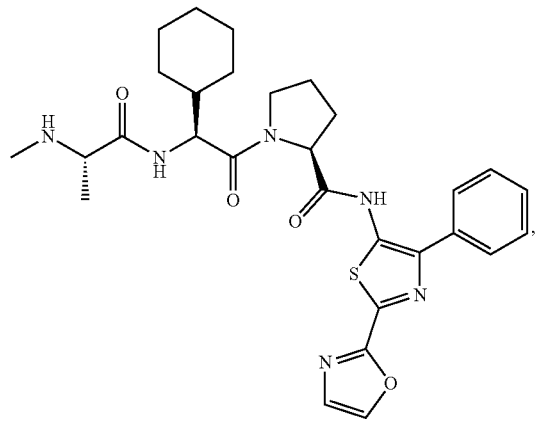

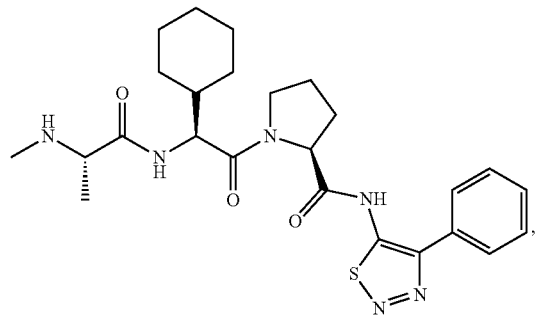

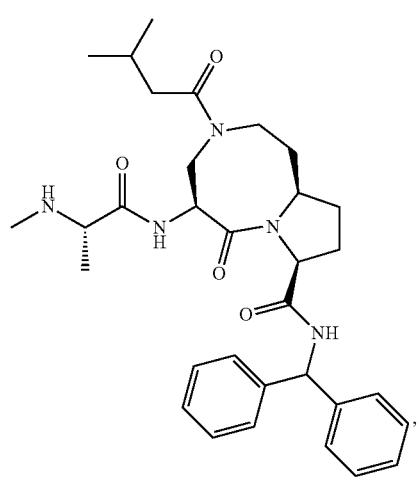

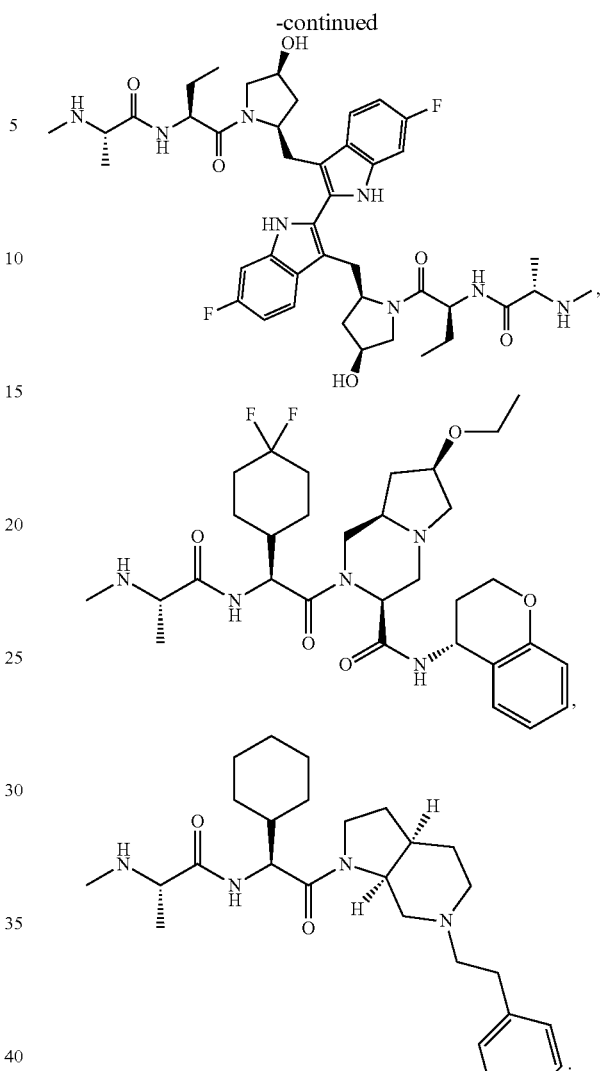

The term "independently" is used herein to indicate that the variable, which is independently applied, varies independently from application to application.

The term "alkyl" shall mean within its context a linear, branch-chained or cyclic fully saturated hydrocarbon radical or alkyl group, preferably a $C_1$-$C_{10}$, more preferably a $C_1$-$C_6$, alternatively a $C_1$-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclo-propylmethyl, cyclobutyl, cyclopentyl, cyclopentylethyl, cyclohexylethyl and cyclohexyl, among others. In certain embodiments, the alkyl group is end-capped with a halogen group (At, Br, Cl, F, or I). In certain preferred embodiments, compounds according to the present disclosure which may be used to covalently bind to dehalogenase enzymes. These compounds generally contain a side chain (often linked through a polyethylene glycol group) which terminates in an alkyl group which has a halogen substituent (often chlorine or bromine) on its distal end which results in covalent binding of the compound containing such a moiety to the protein.

The term "Alkenyl" refers to linear, branch-chained or cyclic $C_2$-$C_{10}$ (preferably $C_2$-$C_6$) hydrocarbon radicals containing at least one C=C bond.

The term "Alkynyl" refers to linear, branch-chained or cyclic $C_2$-$C_{10}$ (preferably $C_2$-$C_6$) hydrocarbon radicals containing at least one C≡C bond.

The term "alkylene" when used, refers to a —$(CH_2)_n$— group (n is an integer generally from 0-6), which may be optionally substituted. When substituted, the alkylene group preferably is substituted on one or more of the methylene groups with a $C_1$-$C_6$ alkyl group (including a cyclopropyl group or a t-butyl group), but may also be substituted with one or more halo groups, preferably from 1 to 3 halo groups or one or two hydroxyl groups, O—($C_1$-$C_6$ alkyl) groups or amino acid sidechains as otherwise disclosed herein. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (often, a methylene) group, may be substituted with an amino acid sidechain group such as a sidechain group of a natural or unnatural amino acid, for example, alanine, 1-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes Co means that carbon is absent and is replaced with H. Thus, a range of carbon atoms which is $C_0$-$C_6$ includes carbons atoms of 1, 2, 3, 4, 5 and 6 and for $C_0$, H stands in place of carbon.

The term "substituted" or "optionally substituted" shall mean independently (i.e., where more than substituent occurs, each substituent is independent of another substituent) one or more substituents (independently up to five substitutents, preferably up to three substituents, often 1 or 2 substituents on a moiety in a compound according to the present disclosure and may include substituents which themselves may be further substituted) at a carbon (or nitrogen) position anywhere on a molecule within context, and includes as substituents hydroxyl, thiol, carboxyl, cyano (CN), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_1$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which is preferably substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present disclosure may include, for example —$SiR_1R_2R_3$ groups where each of $R_1$ and $R_2$ is as otherwise described herein and $R_3$ is H or a $C_1$-$C_6$ alkyl group, preferably $R_1$, $R_2$, $R_3$ in this context is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteraryl moiety) through an optionally substituted —$(CH_2)_m$— or alternatively an optionally substituted —$(OCH_2)_m$—, —$(OCH_2CH_2)_m$— or —$(CH_2CH_2O)_n$— group, which may be substituted with any one or more of the above-described substituents. Alkylene groups —$(CH_2)_m$— or —$(CH_2)_n$— groups or other chains such as ethylene glycol chains, as identified above, may be substituted anywhere on the chain. Preferred substitutents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a sideshain of an amino acid as otherwise described herein and optionally substituted amide (preferably carboxamide substituted as described above) or urethane groups (often with one or two $C_0$-$C_6$ alkyl substitutents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present disclosure, a moiety in a molecule may be optionally substituted with up to five substituents, preferably up to three substituents. Most often, in the present disclosure moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane —O—C(O)—$NR_1R_2$ or —N($R_1$)—C(O)—O—$R_1$, nitro, cyano and amine (especially including a $C_1$-$C_6$ alkylene-$NR_1R_2$, a mono- or di- $C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, —$(CH_2)_m$— (here, m and n are in context, 1, 2, 3, 4, 5 or 6), —S—, —S(O)—, $SO_2$— or —NH—C(O)—NH—, —$(CH_2)_n$OH, —$(CH_2)_n$SH, —$(CH_2)_n$COOH, $C_1$-$C_6$ alkyl, —$(CH_2)_n$O—($C_1$-$C_6$ alkyl), —$(CH_2)_n$C(O)—($C_1$-$C_6$ alkyl), —$(CH_2)_n$OC(O)—($C_1$-$C_6$ alkyl), —$(CH_2)_n$C(O)O—($C_1$-$C_6$ alkyl), —$(CH_2)_n$NHC(O)—$R_1$, —$(CH_2)_n$C(O)—$NR_1R_2$, —$(OCH_2)$OH, —$(CH_2O)_n$COOH, $C_1$-$C_6$ alkyl, —$(OCH_2)_n$O—($C_1$-$C_6$ alkyl), —$(CH_2O)_n$C(O)—($C_1$-$C_6$ alkyl), —$(OCH_2)_n$NHC(O)—$R_1$, —$(CH_2O)_n$C(O)—$NR_1R_2$, —$S(O)_2$—$R_S$, —S(O)—$R_S$ ($R_S$ is $C_1$-$C_6$ alkyl or a —$(CH_2)_m$—$NR_1R_2$ group), $NO_2$, CN or halogen (F, Cl, Br, I, preferably F or Cl), depending on the context of the use of the substituent. $R_1$ and $R_2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(O)—NR$_1$R$_2$ group where R$_1$ and R$_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present disclosure at any available stable position on the ring(s) or as otherwise indicated in the chemical structure presented. Other examples of aryl groups, in context, may include heterocyclic aromatic ring systems, "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, pyrimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: —(CH$_2$)$_n$OH, —(CH$_2$)$_n$—O—(C$_1$-C$_6$)alkyl, —(CH$_2$)$_n$—O—(CH$_2$)$_n$—(C$_1$-C$_6$)alkyl, —(CH$_2$)—C(O)(C$_0$-C$_6$) alkyl, —(CH$_2$)$_n$—C(O)O(C$_0$-C$_6$) alkyl, —(CH$_2$)$_n$—OC(O)(C$_0$-C$_6$)alkyl, amine, mono- or di-(C$_1$-C$_6$ alkyl) amine wherein the alkyl group on the amine is optionally substituted with 1 or 2 hydroxyl groups or up to three halo (preferably F, Cl) groups, OH, COOH, C$_1$-C$_6$ alkyl, preferably CH$_3$, CF$_3$, OMe, OCF$_3$, NO$_2$, or CN group (each of which may be substituted in ortho-, meta- and/or para- positions of the phenyl ring, preferably para-), an optionally substituted phenyl group (the phenyl group itself is preferably connected to a PTM group, including a ULM group, via a linker group), and/or at least one of F, Cl, OH, COOH, CH$_3$, CF$_3$, OMe, OCF$_3$, NO$_2$, or CN group (in ortho-, meta- and/or para- positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo-(preferably, F) or methylsubstituted pyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

"Carboxyl" denotes the group —C(O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

The term "heteroaryl" or "hetaryl" can mean but is in no way limited to an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —(CH$_2$)$_m$—O—C$_1$-C$_6$ alkyl group or an optionally substituted —(CH$_2$)$_m$—C(O)—O—C$_1$-C$_6$ alkyl group), an optionally substituted pyridine (2-, 3, or 4-pyridine) or a group according to the chemical structure:

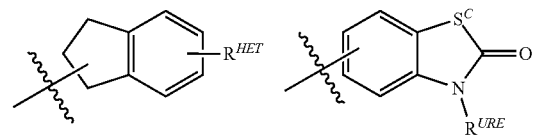

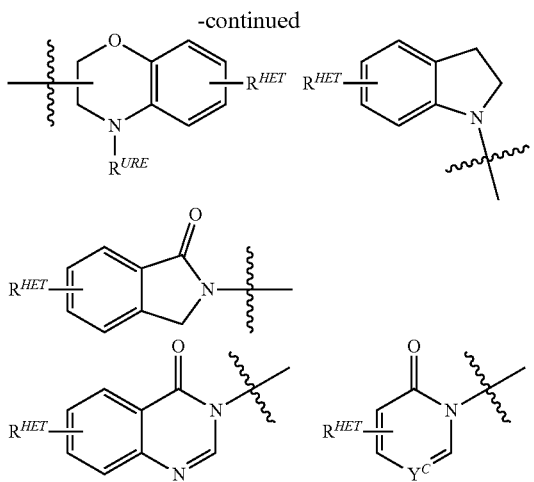

wherein:

$S^c$ is $CHR^{SS}$, $NR^{URE}$, or O;

$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O) ($C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl).

The terms "aralkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

The term "arylalkyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above.

The term "Heterocycle" refers to a cyclic group which contains at least one heteroatom, e.g., N, O or S, and may be aromatic (heteroaryl) or non-aromatic. Thus, the heteroaryl moieties are subsumed under the definition of heterocycle, depending on the context of its use. Exemplary heteroaryl groups are described hereinabove.

Exemplary heterocyclics include: azetidinyl, benzimidazolyl, 1,4- benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolane, 1,3-dioxane, 1,4-dioxane, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO— substituted alkyl, —SOaryl, —SO-heteroaryl, —$SO_2$-alkyl, —$SO_2$-substituted alkyl, —$SO_2$-aryl, oxo (=O), and —$SO_2$-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyl, and the like).

The term "cycloalkyl" can mean but is in no way limited to univalent groups derived from monocyclic or polycyclic alkyl groups or cycloalkanes, as defined herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group in which at least one ring carbon atom of its cyclic structure being replaced with a heteroatom selected from the group consisting of N, O, S or P. "Substituted heterocycloalkyl" refers to a monocyclic or polycyclic alkyl group in which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "independently" is used herein to indicate that the variable, which is independently applied, varies independently from application to application.

The term "lower alkyl" refers to methyl, ethyl or propyl

The term "lower alkoxy" refers to methoxy, ethoxy or propoxy.

In any of the embodiments described herein, the W, X, Y, Z, G, G', R, R', R", Q1-Q4, A, and Rn can independently be covalently coupled to a linker and/or a linker to which is attached one or more PTM, ULM, ILM or ILM' groups.

Exemplary MLMs

In certain additional embodiments, the MLM of the bifunctional compound comprises chemical moieties such as substituted imidazolines, substituted spiro-indolinones, substituted pyrrolidines, substituted piperidinones, substituted morpholinones, substituted pyrrolopyrimidines, substituted imidazolopyridines, substituted thiazoloimidazoline, substituted pyrrolopyrrolidinones, and substituted isoquinolinones.

In additional embodiments, the MLM comprises the core structures mentioned above with adjacent bis-aryl substitutions positioned as cis- or trans-configurations.

In still additional embodiments, the MLM comprises part of structural features as in RG7112, RG7388, SAR405838, AMG-232, AM-7209, DS-5272, MK-8242, and NVP-CGM-097, and analogs or derivatives thereof.

In certain preferred embodiments, MLM is a derivative of substituted imidazoline represented as Formula (A-1), or thiazoloimidazoline represented as Formula (A-2), or spiro indolinone represented as Formula (A-3), or pyrollidone represented as Formula (A-4), or piperidinone/morphinone represented as Formula (A-5), or isoquinolinone represented as Formula (A-6), or pyrollopyrimidine/imidazolopyridine represented as Formula (A-7), or pyrrolopyrrolidinone/imidazolopyrrolidinone represented as Formula (A-8).

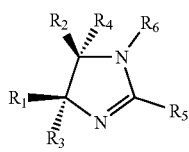

Formula (A-1)

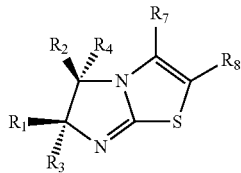

Formula (A-2)

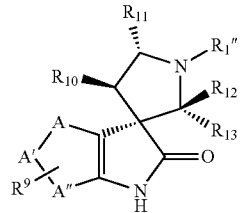

Formula (A-3)

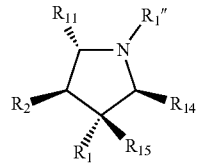

Formula (A-4)

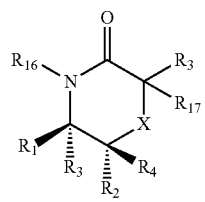

Formula (A-5)

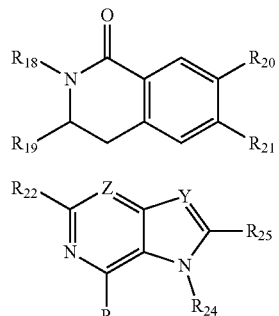

Formula (A-6)

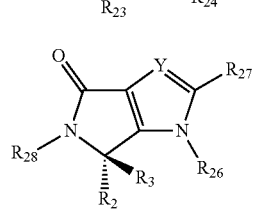

Formula (A-7)

Formula (A-8)

wherein above Formula (A-1) through Formula (A-8),

X of Formula (A-1) through Formula (A-8) is selected from the group consisting of carbon, oxygen, sulfur, sulfoxide, sulfone, and N—$R^a$;

$R^a$ is independently H or an alkyl group with carbon number 1 to 6; Y and Z of Formula (A-1) through Formula (A-8) are independently carbon or nitrogen;

A, A' and A" of Formula (A-1) through Formula (A-8) are independently selected from C, N, O or S, can also be one or two atoms forming a fused bicyclic ring, or a 6,5- and 5,5-fused aromatic bicyclic group;

$R_1$, $R_2$ of Formula (A-1) through Formula (A-8) are independently selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of:

halogen, —CN, C1 to C6 alkyl group, C3 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, and dialkyl amine with 2 to 6 carbons;

$R_3$, $R_4$ of Formula (A-1) through Formula (A-8) are independently selected from the group consisting of H, methyl and C1 to C6 alkyl;

$R_5$ of Formula (A-1) through Formula (A-8) is selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of:

halogen, —CN, C1 to C6 alkyl group, C3 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, dialkyl amine with 2 to 6 carbons, alkyl ether (C2 to C6), alkyl ketone (C3 to C6), morpholinyl, alkyl ester (C3 to C6), alkyl cyanide (C3 to C6);

$R_6$ of Formula (A-1) through Formula (A-8) is H or —C(=O)$R^b$, wherein $R^b$ of Formula (A-1) through Formula (A-8) is selected from the group consisting of alkyl, cycloalkyl, mono-, di- or tri-substituted aryl or heteroaryl, 4-morpholinyl, 1-(3-oxopiperazinyl), 1-piperidinyl, 4-N—$R^c$-morpholinyl, 4-$R^e$-1-piperidinyl, and 3-$R^c$-1-piperidinyl, wherein $R^c$ of Formula (A-1) through Formula (A-8) is selected from the group consisting of alkyl, fluorine substituted alkyl, cyano alkyl, hydroxyl-substituted alkyl, cycloalkyl, alkoxyalkyl, amide alkyl, alkyl sulfone, alkyl sulfoxide, alkyl amide, aryl, heteroaryl, mono-, bis- and tri-substituted aryl or heteroaryl, $CH_2CH_2Rd$, and $CH_2CH_2CH_2Rd$, wherein $R^d$ of Formula (A-1) through Formula (A-8) is selected from the group consisting of alkoxy, alkyl sulfone, alkyl sulfoxide, N-substituted carboxamide, —NHC(O)-alkyl, —NH—$SO_2$-alkyl, aryl, substituted aryl, heteroaryl, substituted heteroaryl;

$R_7$ of Formula (A-1) through Formula (A-8) is selected from the group consisting of H, C1 to C6 alkyl, cyclic alkyl, fluorine substituted alkyl, cyano substituted alkyl, 5- or 6-membered hetero aryl or aryl, substituted 5- or 6-membered hetero aryl or aryl;

$R_8$ of Formula (A-1) through Formula (A-8) is selected from the group consisting of —$R^e$—C(O)—$R^f$, —$R^e$-alkoxy, —$R^e$-aryl, —$R^e$-heteroaryl, and —$R^e$—C(O)—$R^f$—C(O)—$R^g$, wherein:

$R^e$ of Formula (A-1) through Formula (A-8) is an alkylene with 1 to 6 carbons, or a bond;

$R^f$ of Formula (A-1) through Formula (A-8) is a substituted 4- to 7-membered heterocycle;

$R^g$ of Formula (A-1) through Formula (A-8) is selected from the group consisting of aryl, hetero aryl, substituted aryl or heteroaryl, and 4- to 7-membered heterocycle;

$R_9$ of Formula (A-1) through Formula (A-8) is selected from the group consisting of a mono-, bis- or tri-substituent on the fused bicyclic aromatic ring in Formula (A-3), wherein the substitutents are independently selected from the group consisting of halogen, alkene, alkyne, alkyl, unsubstituted or substituted with Cl or F;

$R_{10}$ of Formula (A-1) through Formula (A-8) is selected from the group consisting of an aryl or heteroaryl group, wherein the heteroaryl group can contain one or two heteroatoms as sulfur or nitrogen, aryl or heteroaryl group can be mono-cyclic or bi-cyclic, the aryl or heteroaryl group can be unsubstituted or substituted with one to three substituents, including a halogen, F, Cl, —CN, alkene, alkyne, C1 to C6 alkyl group, C1 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons;

$R_{11}$ of Formula (A-1) through Formula (A-8) is —C(O)—N($R^h$)($R^i$), wherein $R^h$ and $R^i$ are selected from groups consisting of the following:

H, C1 to C6 alkyl, alkoxy substituted alkyl, sulfone substituted alkyl, aryl, heteroaryl aryl, mono-, bis- or tri-substituted aryl or hetero aryl, alkyl carboxylic acid, heteroaryl carboxylic acid, alkyl carboxylic acid, fluorine substituted alkyl carboxylic acid, aryl substituted cycloalkyl, hetero aryl substituted cycloalkyl; wherein $R^h$ and $R^i$ of Formula (A-1) through Formula (A-8) are independently selected from the group consisting of H, connected to form a ring, 4-hydroxycyclohehexane; mono- and di-hydroxy substituted alkyl (C3 to C6); 3-hydroxycyclobutane; phenyl-4-carboxylic acid, and substituted phenyl-4-carboxylic acid;

$R_{12}$ and $R_{13}$ of Formula (A-1) through Formula (A-8) are independently selected from H, lower alkyl (C1 to C6), lower alkenyl (C2 to C6), lower alkynyl (C2 to C6), cycloalkyl (4, 5 and 6-membered ring), substituted cycloalkyl, cycloalkenyl, substituted cycloalkenyl, 5- and 6-membered aryl and heteroaryl, R12 and R13 can be connected to form a 5- and 6-membered ring with or without substitution on the ring;

$R_{14}$ of Formula (A-1) through Formula (A-8) is selected from the group consisting of alkyl, substituted alkyl, alkenyl, substituted alkenyl, aryl, substituted aryl, heteroaryl, substituted heteroaryl, heterocycle, substituted heterocycle, cycloalkyl, substituted cycloalkyl, cycloalkenyl and substituted cycloalkenyl;

$R_{15}$ of Formula (A-1) through Formula (A-8) is CN;

$R_{16}$ of Formula (A-1) through Formula (A-8) is selected from the group consisting of $C_1$-6 alkyl, C1-6 cycloalkyl, C2-6 alkenyl, C1-6 alkyl or C3-6 cycloalkyl with one or multiple hydrogens replaced by fluorine, alkyl or cycloalkyl with one $CH_2$ replaced by S(=O), —S, or —S(=O)$_2$, alkyl or cycloalkyl with terminal $CH_3$ replaced by S(=O)$_2$N(alkyl)(alkyl), —C(=O)N(alkyl)(alkyl), —N(alkyl)S(=O)$_2$(alkyl), —C(=O)2(alkyl), —O(alkyl), C1-6 alkyl or alkyl-cycloalkyl with hydron replaced by hydroxyl group, a 3 to 7 membered cycloalkyl or heterocycloalkyl, optionally containing a —(C=0)- group, or a 5 to 6 membered aryl or heteroaryl group, which heterocycloalkyl or heteroaryl group can contain from one to three heteroatoms independently selected from O, N or S, and the cycloalkyl, heterocycloalkyl, aryl or heteroaryl group can be unsubstituted or substituted with from one to three substituents independently selected from halogen, C1-6 alkyl groups, hydroxylated C1-6 alkyl, C1-6 alkyl containing thioether, ether, sulfone, sulfoxide, fluorine substituted ether or cyano group;

$R_{17}$ of Formula (A-1) through Formula (A-8) is selected from the group consisting of $(CH_2)nC(O)NR^kR^l$, wherein $R^k$ and $R^l$ are independently selected from H, C1-6 alkyl, hydroxylated C1-6 alkyl, C1-6 alkoxy alkyl, C1-6 alkyl with one or multiple hydrogens replaced by fluorine, C1-6 alkyl with one carbon replaced by S(O), S(O)(O), C1-6 alkoxy-alkyl with one or multiple hydrogens replaced by fluorine, C1-6 alkyl with hydrogen replaced by a cyano group, 5 and 6 membered aryl or heteroaryl, alkyl aryl with alkyl group containing 1-6 carbons, and alkyl heteroaryl with alkyl group containing 1-6 carbons, wherein the aryl or heteroaryl group can be further substituted;

$R_{18}$ of Formula (A-1) through Formula (A-8) is selected from the group consisting of substituted aryl, heteroaryl, alkyl, cycloalkyl, the substitution is preferably —N(C1-4 alkyl)(cycloalkyl), —N(C1-4 alkyl)alkyl-cycloalkyl, and —N(C1-4 alkyl)[(alkyl)-(heterocycle-substituted)-cycloalkyl];

$R_{19}$ of Formula (A-1) through Formula (A-8) is selected from the group consisting of aryl, heteroaryl, bicyclic heteroaryl, and these aryl or heteroaryl groups can be substituted with halogen, C1-6 alkyl, C1-6 cycloalkyl, $CF_3$, F, CN, alkyne, alkyl sulfone, the halogen substitution can be mon- bis- or tri-substituted;

$R_{20}$ and $R_{21}$ of Formula (A-1) through Formula (A-8) are independently selected from C1-6 alkyl, C1-6 cycloalkyl, C1-6 alkoxy, hydroxylated C1-6 alkoxy, and fluorine substituted C1-6 alkoxy, wherein $R_{20}$ and $R_{21}$ can further be connected to form a 5, 6 and 7-membered cyclic or heterocyclic ring, which can further be substituted;

$R_{22}$ of Formula (A-1) through Formula (A-8) is selected from the group consisting of H, C1-6 alkyl, C1-6 cycloalkyl, carboxylic acid, carboxylic acid ester, amide, reverse amide, sulfonamide, reverse sulfonamide, N-acyl urea, nitrogen-containing 5-membered heterocycle, the 5-membered heterocycles can be further substituted with C1-6 alkyl, alkoxy, fluorine-substituted alkyl, CN, and alkylsulfone;

$R_{23}$ of Formula (A-1) through Formula (A-8) is selected from aryl, heteroaryl, —O-aryl, —O-heteroaryl, —O—alkyl, —O-alkyl-cycloalkyl, —NH-alkyl, —NH-alkyl-cycloalkyl, —N(H)-aryl, —N(H)-heteroaryl, —N(alkyl)-aryl, —N(alkyl)-heteroaryl, the aryl or heteroaryl groups can be substituted with halogen, C1-6 alkyl, hydroxylated C1-6 alkyl, cycloalkyl, fluorine-substituted C1-6 alkyl, CN, alkoxy, alkyl sulfone, amide and sulfonamide;

$R_{24}$ of Formula (A-1) through Formula (A-8) is selected from the group consisting of —CH2-(C1-6 alkyl), —$CH_2$-cycloalkyl, —$CH_2$-aryl, $CH_2$-heteroaryl, where alkyl, cycloalkyl, aryl and heteroaryl can be substituted with halogen, alkoxy, hydroxylated alkyl, cyano-substituted alkyl, cycloalkyl and substituted cycloalkyl;

$R_{25}$ of Formula (A-1) through Formula (A-8) is selected from the group consisting of C1-6 alkyl, C1-6 alkyl-cycloalkyl, alkoxy-substituted alkyl, hydroxylated alkyl, aryl, heteroaryl, substituted aryl or heteroaryl, 5,6, and 7-membered nitrogen-containing saturated heterocycles, 5,6-fused and 6,6-fused nitrogen-containing saturated heterocycles and these saturated heterocycles can be substituted with C1-6 alkyl, fluorine-substituted C1-6 alkyl, alkoxy, aryl and heteroaryl group;

$R_{26}$ of Formula (A-1) through Formula (A-8) is selected from the group consisting of C1-6 alkyl, C3-6 cycloalkyl, the alkyl or cycloalkyl can be substituted with —OH, alkoxy, fluorine-substituted alkoxy, fluorine-substituted alkyl, —$NH_2$, —NH-alkyl, NH—C(O)alkyl, —NH—S(O)$_2$-alkyl, and —S(O)2-alkyl;

$R_{27}$ of Formula (A-1) through Formula (A-8) is selected from the group consisting of aryl, heteroaryl, bicyclic heteroaryl, wherein the aryl or heteroaryl groups can be substituted with C1-6 alkyl, alkoxy, $NH_2$, NH-alkyl, halogen, or —CN, and the substitution can be independently mono-, bis- and tri-substitution;

$R_{28}$ of Formula (A-1) through Formula (A-8) is selected from the group consisting of aryl, 5 and 6-membered heteroaryl, bicyclic heteroaryl, cycloalkyl, saturated heterocycle such as piperidine, piperidinone, tetrahydropyran, N-acyl-piperidine, wherein the cycloalkyl, saturated heterocycle, aryl or heteroaryl can be further substituted with —OH, alkoxy, mono-, bis- or tri-substitution including halogen, —CN, alkyl sulfone, and fluorine substituted alkyl groups; and $R_{1''}$ of Formula (A-1) through Formula (A-8) is selected from the group consisting of alkyl, aryl substituted alkyl, alkoxy substituted alkyl, cycloalkyl, aryl- substituted cycloalkyl, and alkoxy substituted cycloalkyl.

In certain embodiments, the heterocycles in $R^f$ and $R^g$ of Formula (A-1) through Formula (A-8) are substituted pyrrolidine, substituted piperidine, substituted piperazine.

More specifically, non-limiting examples of MLMs include those shown below as well as those 'hybrid' molecules that arise from the combination of 1 or more of the different features shown in the molecules below.

Using MLM in Formula A-1 through A-8, the following PROTACs can be prepared to target a particular protein for degradation, where "L" is a connector (i.e. a linker group), and "PTM" is a ligand binding to a target protein.

In certain embodiments, the description provides a bifunctional molecule comprising a structure selected from the group consisting of:

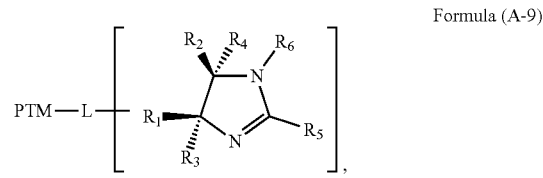

Formula (A-9)

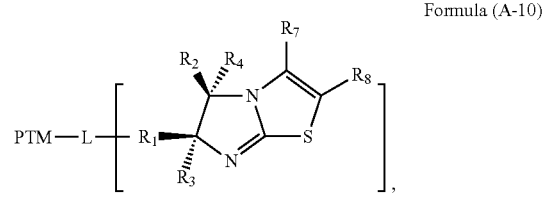

Formula (A-10)

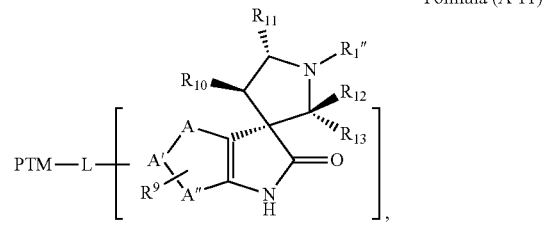

Formula (A-11)

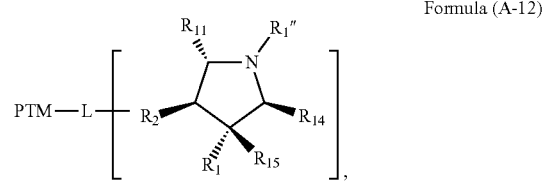

Formula (A-12)

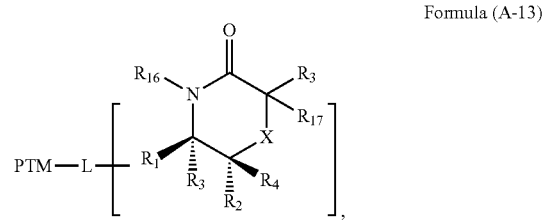

Formula (A-13)

133
-continued

Formula (A-14)

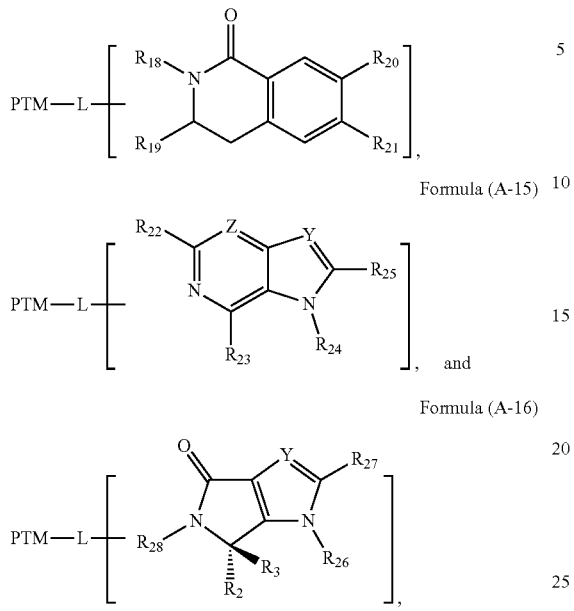

Formula (A-15)

Formula (A-16)

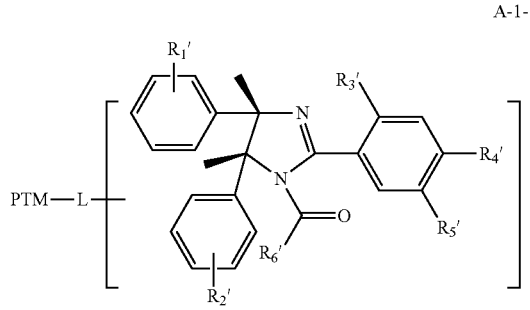

wherein X, $R^a$, Y, Z, A, A', A", $R_1$, $R_2$, $R_3$, $R_4$, $R_5$, $R_6$, $R^b$, $R^c$, $R^d$, $R_7$, $R^e$, $R^f$, $R^g$, $R_9$, $R_{10}$, $R_{11}$, $R_{12}$, $R_{13}$, $R_{14}$, $R_{15}$, $R_{16}$, $R_{17}$, $R^k$, $R^l$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, and $R_{1''}$ are as defined herein with regard to Formulas (A-1) through (A-8).

In certain embodiments, the description provides bifunctional or chimeric molecules with the structure: PTM-L-MLM, wherein PTM is a protein target binding moiety coupled to an MLM by L, wherein L is a bond (i.e., absent) or a chemical linker. In certain embodiments, the MLM has a structure selected from the group consisting of A-1-1, A-1-2, A-1-3, and A-1-4:

A-1-1

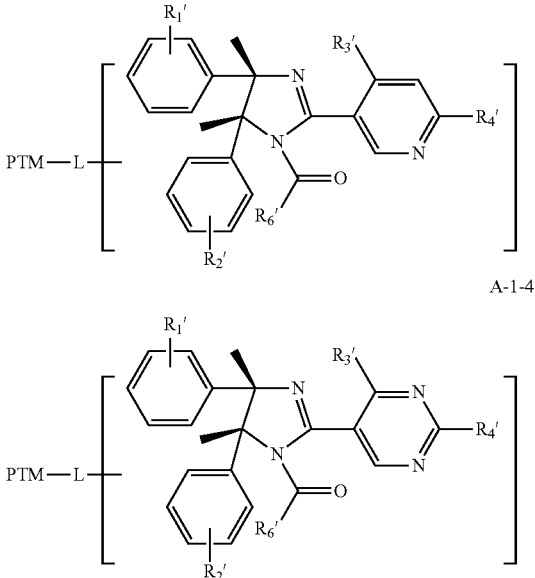

A-1-2

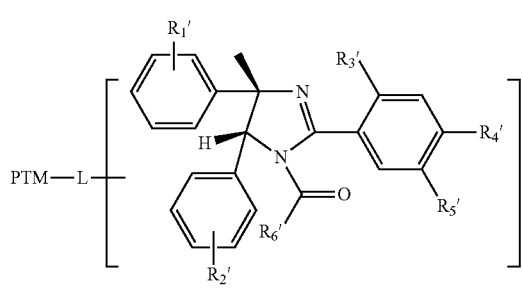

134
-continued

A-1-3

A-1-4 wherein:

R1' and R2' of Formulas A-1-1 throughout A-1-4 (i.e., A-1-1, A-1-2, A-1-3, and A-1-4) are independently selected from the group consisting of F, Cl, Br, I, acetylene, CN, $CF_3$ and $NO_2$;

R3' is selected from the group consisting of —$OCH_3$, —$OCH_2CH_3$, —$OCH_2CH_2F$, —$OCH_2CH_2OCH_3$, and —$OCH(CH_3)_2$;

R4' of Formulas A-1-1 throughout A-1-4 is selected from the group consisting of H, halogen, —$CH_3$, —$CF_3$, —$OCH_3$, —$C(CH_3)_3$, —$CH(CH_3)_2$, -cyclopropyl, —CN, —$C(CH_3)_2OH$, —$C(CH_3)_2CH_2CH_3$, —$C(CH_3)_2CH_2OH$, —$C(CH_3)_2CH_2OCH_2CH_3$, —$C(CH_3)_2CH_2OCH_2CH_2OH$, —$C(CH_3)_2CH_2OCH_2CH_3$, —$C(CH_3)_2CN$, —$C(CH_3)C(O)CH_3$, —$C(CH_3)_2C(O)NHCH_3$, —$C(CH_3)_2C(O)N(CH_3)_2$, —$SCH_3$, —$SCH_2CH_3$, —$S(O)_2CH_3$, —$S(O_2)CH_2CH_3$, —$NHC(CH_3)_3$, —$N(CH_3)_2$, pyrrolidinyl, and 4-morpholinyl;

R5' of Formulas A-1-1 throughout A-1-4 is selected from the group consisting of halogen, -cyclopropyl, —$S(O)_2CH_3$, —$S(O)_2CH_2CH$, 1-pyrrolidinyl, —$NH_2$, —$N(CH_3)_2$, and —$NHC(CH_2)_3$; and R6' of Formulas A-1-4 throughout A-1-4 is selected from the structures presented below where the linker connection point is indicated as "*".

Beside R6' as the point for linker attachment, R4' can also serve as the linker attachment position. In the case that R4' is the linker connection site, linker will be connected to the terminal atom of R4' groups shown above.

In certain embodiments, the linker connection position of Formulas A-1-1 throughout A-1-4 is at least one of R4' or R6' or both.

In certain embodiments, R6' of Formulas A-1-1 throughout A-1-4 is independently selected from the group consisting of H,

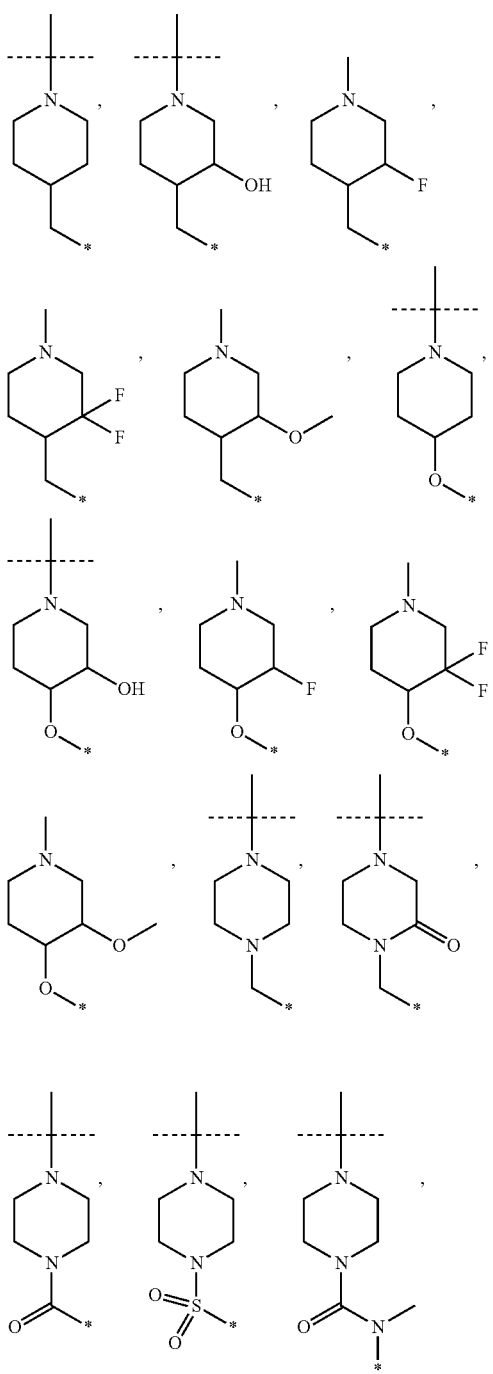
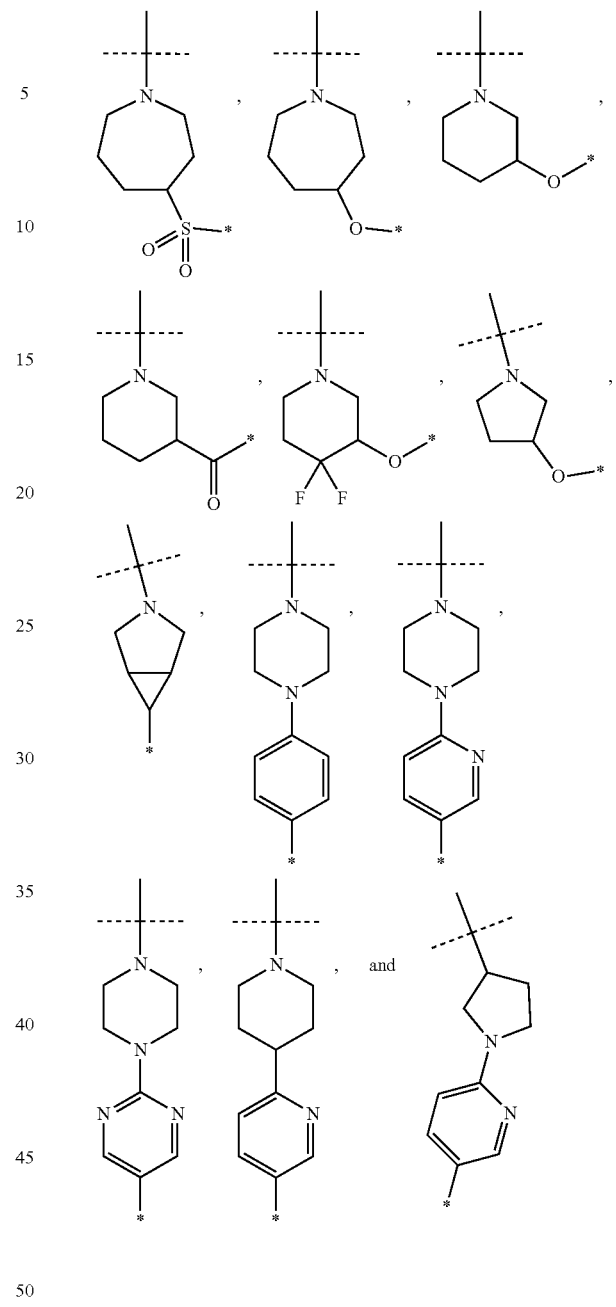
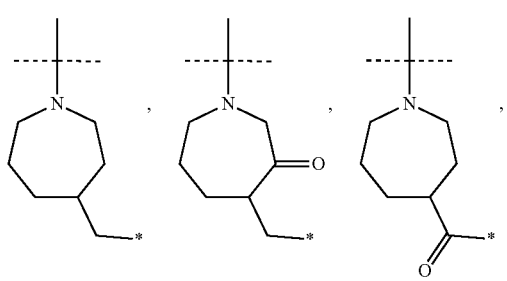

wherein "*" indicates the point of attachment of the linker.

In certain embodiments, the linker of Formula A-4-1 through A-4-6 is attached to at least one of R1', R2', R3', R4', R5', R6', or a combination thereof.

In certain embodiments, the description provides bifunctional or chimeric molecules with the structure: PTM-L-MLM, wherein PTM is a protein target binding moiety coupled to an MLM by L, wherein L is a bond (i.e., absent) or a chemical linker. In certain embodiments, the MLM has a structure selected from the group consisting of A-4-1, A-4-2, A-4-3, A-4-4, A-4-5, and A-4-6:

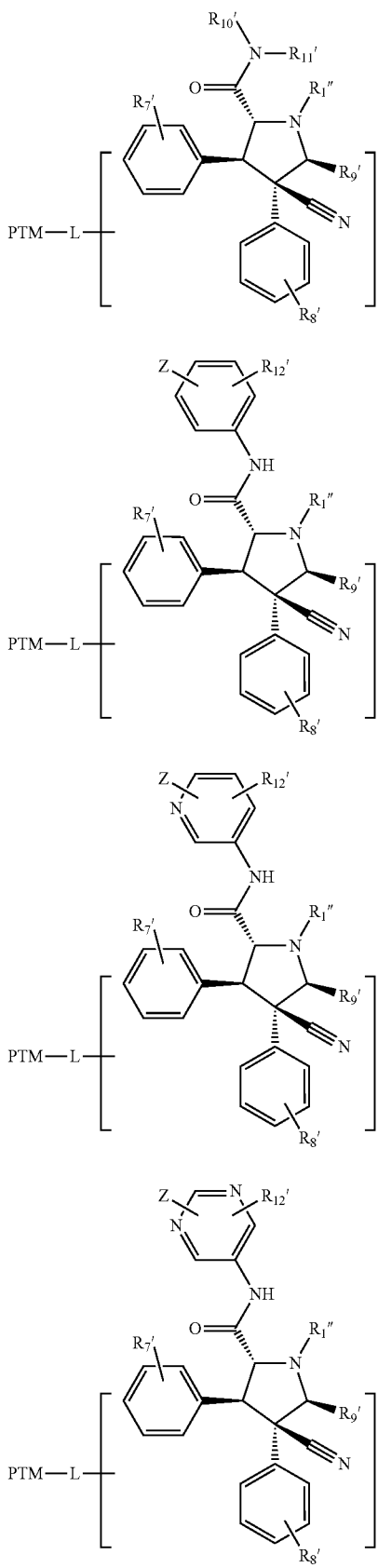
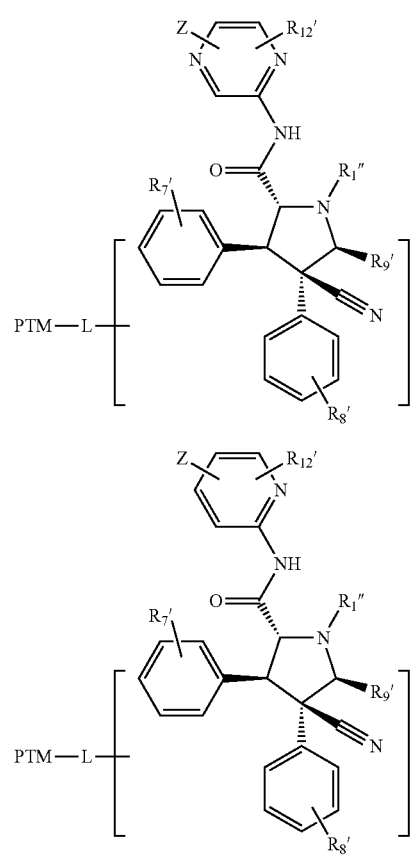

wherein:
R7' of Formula A-4-1 through A-4-6 (i.e., A-4-1, A-4-2, A-4-3, A-4-4, A-4-5, and A-4-6) is a member selected from the group consisting of halogen, mono-, and di- or tri-substituted halogen; R8' of Formula A-4-1 through A-4-6 is selected from the group consisting of H, —F, —Cl, —Br, —I, —CN, —NO$_2$, ethynyl, cyclopropyl, methyl, ethyl, isopropyl, vinyl, methoxy, ethoxy, isopropoxy, —OH, other C1-6 alkyl, other C1-6 alkenyl, and C1-6 alkynyl, mono-, di- or tri-substituted; R9' of Formula A-4-1 through A-4-6 is selected from the group consisting of alkyl, substituted alkyl, alkenyl, substituted alkenyl, alkynyl, substituted alkynyl, aryl, substituted aryl, hetero aryl, substituted heteroaryl, cycloalkyl, substituted cycloalkyl, alkenyl, and substituted cycloalkenyl;
Z of Formula A-4-1 through A-4-6 is selected from the group consisting of H, —OCH$_3$, —OCH$_2$CH$_3$, and halogen;
R10' and R11' of Formula A-4-1 through A-4-6 are each independently selected from the group consisting of H, (CH$_2$)$_n$—R', (CH$_2$)$_n$—NR'R", (CH$_2$)$_n$—NR'COR", (CH$_2$)$_n$—NR'SO$_2$R", (CH$_2$)$_n$—COOH, (CH$_2$)$_n$—COOR', (CH)$_n$—CONR'R", (CH$_2$)$_n$—OR', (CH$_2$)$_n$—SR', (CH$_2$)$_n$—SOR'(CH$_2$)$_n$—CH(OH)—R', (CH$_2$)$_n$—COR', (CH$_2$)$_n$—SO$_2$R', (CH$_2$)$_n$—SONR'R", (CH$_2$)$_n$—SO$_2$NR'R", (CH$_2$CH$_2$O)$_m$—(CH$_2$)$_n$—R', (CH$_2$CH$_2$O)$_m$—(CH$_2$)$_n$—OH, (CH$_2$CH$_2$O)$_m$—(CH$_2$)$_n$—OR', (CH$_2$CH$_2$O)$_m$—(CH$_2$)$_n$—NR'R", (CH$_2$CH$_2$O)$_m$—(CH$_2$)$_n$—NR'COR", (CH$_2$CH$_2$O)$_m$(CH$_2$)$_n$—NR'SO$_2$R", (CH$_2$CH$_2$O)$_m$(CH$_2$)$_n$—COOH, (CH$_2$CH$_2$O)$_m$(CH$_2$)$_n$—COOR', (CH$_2$CH$_2$O)$_m$—(CH2)$_n$—CONR'R", (CH$_2$CH$_2$O)$_m$—(CH$_2$)$_n$—SO$_2$R', (CH$_2$CH$_2$O)$_m$—(CH$_2$)$_n$—COR', (CH$_2$CH$_2$O)$_m$—(CH$_2$)$_n$—SONR'R", (CH$_2$CH$_2$O)$_m$—(CH$_2$)$_n$—SO$_2$NR'R", (CH$_2$)$_p$—

(CH$_2$CH$_2$O)$_m$—(CH$_2$)$_n$R', (CH$_2$)p-(CH$_2$CH$_2$O)$_m$—(CH$_2$)$_n$—OH, (CH$_2$)$_p$—(CH$_2$CH$_2$O)$_m$—(CH$_2$)$_n$—OR', (CH$_2$)$_p$—(CH$_2$CH$_2$O)$_m$—(CH$_2$)$_n$—NR'R", (CH$_2$)$_p$—(CH$_2$CH$_2$O)$_m$—(CH$_2$)$_n$—NR'COR", (CH$_2$)$_p$—(CH$_2$CH$_2$O)$_m$—(CH$_2$)$_n$—NR'SO$_2$R", (CH$_2$)$_p$—(CH$_2$CH$_2$O)$_m$—(CH$_2$)$_n$—COOH, (CH$_2$)$_p$—(CH$_2$CH$_2$O)$_m$—(CH$_2$)$_n$—COOR', (CH$_2$)$_p$—(CH$_2$CH$_2$O)$_m$—(CH$_2$)$_n$—CONR'R", (CH$_2$)p-(CH$_2$CH$_2$O)$_m$—(CH$_2$)$_n$—SO$_2$R', (CH$_2$)$_p$—(CH$_2$CH$_2$O)$_m$—(CH$_2$)$_n$—COR', (CH$_2$)$_p$—(CH$_2$CH$_2$O)$_m$—(CH$_2$)$_n$—SONR'R", (CH$_2$)$_p$—(CH$_2$CH$_2$O)$_m$—(CH$_2$)$_n$—SO$_2$NR'R", Aryl-(CH$_2$)$_n$—COOH, and heteroaryl-alkyl-CO-alkyl-NR'R"m, wherein the alkyl may be substituted with OR', and heteroaryl-(CH$_2$)$_n$-heterocycle wherein the heterocycle may optionally be substituted with alkyl, hydroxyl, COOR' and COR'; wherein R' and R" are selected from H, alkyl, alkyl substituted with halogen, hydroxyl, NH2, NH(alkyl), N(alkyl)$_2$, oxo, carboxy, cycloalkyl and heteroaryl; m, n, and p are independently 0 to 6;

R12' of Formula A-4-1 through A-4-6 is selected from the group consisting of —O-(alkyl), —O-(alkyl)-alkoxy, —C(O)-(alkyl), —C(OH)-alkyl-alkoxy, —C(O)—NH-(alkyl), —C(O)—N-(alkyl)$_2$, —S(O)-(alkyl), S(O)$_2$-(alkyl), —C(O)-(cyclic amine), and —O-aryl-(alkyl), —O-aryl-(alkoxy);

R1" of Formula A-4-1 through A-4-6 is selected from the group consisting of alkyl, aryl substituted alkyl, alkoxy substituted alkyl, cycloalkyl, aryl-substituted cycloalkyl, and alkoxy substituted cycloalkyl.

In any of the aspects or embodiments described herein, the alkyl, alkoxy or the like can be a lower alkyl or lower alkoxy.

In certain embodiments, the linker connection position of Formula A-4-1 through A-4-6 is at least one of Z, R8', R9', R10', R11", R12", or R1".

The method used to design chimeric molecules as presented in A-1-1 through A-1-4, A-4-1 through A-4-6 can be applied to MLM with formula A-2, A-3, A-S, A-6, A-7 and A-8, wherein the solvent exposed area in the MLM can be connected to linker "L" which will be attached to target protein ligand "PTM", to construct PROTACs.

Exemplary MDM2 binding moieties include, but not limited, the following:

1. The HDM2/MDM2 inhibitors identified in Vassilev, et al., In vivo activation of the p53 pathway by small-molecule antagonists of MDM2, *SCIENCE* vol: 303, pag: 844-848 (2004), and Schneekloth, et al., Targeted intracellular protein degradation induced by a small molecule: En route to chemical proteomics, *Bioorg. Med. Chem. Lett.* 18 (2008) 5904-5908, including (or additionally) the compounds nutlin-3, nutlin-2, and nutlin-1 (derivatized) as described below, as well as all derivatives and analogs thereof:

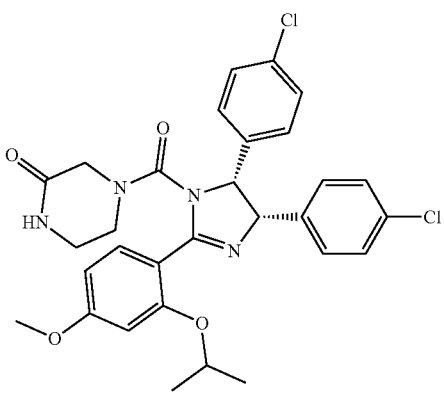 [SMILES: COc1ccc(C2=N[C@@H](c3ccc(Cl)cc3)[C@@H](c3ccc(Cl)cc3)N2C(=O)N2CCNC(=O)C2)c(OC(C)C)c1]

(derivatized where a linker group L or a -(L-MLM) group is attached, for example, at the methoxy group or as a hydroxyl group);

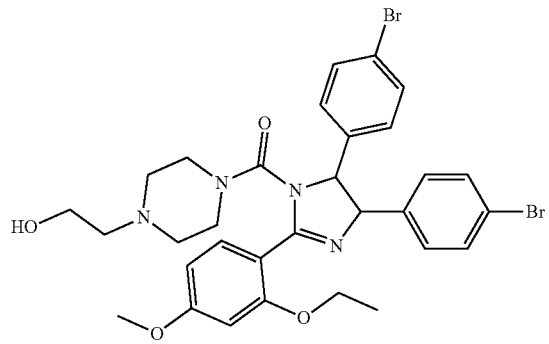 [SMILES: CCOc1cc(OC)ccc1C1=NC(c2ccc(Br)cc2)C(c2ccc(Br)cc2)N1C(=O)N1CCN(CCO)CC1]

(derivatized where a linker group L or a -(L-MLM) group is attached, for example, at the methoxy group or hydroxyl group);

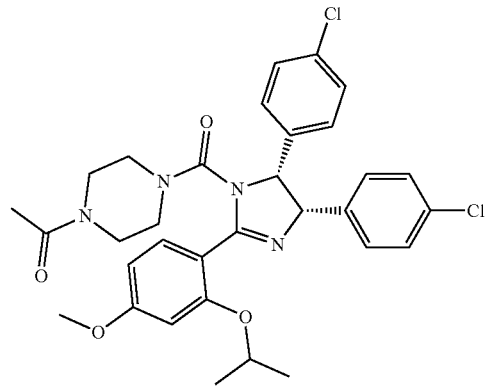 [SMILES: COc1ccc(C2=N[C@@H](c3ccc(Cl)cc3)[C@@H](c3ccc(Cl)cc3)N2C(=O)N2CCN(C(C)=O)CC2)c(OC(C)C)c1]

(derivatized where a linker group L or a -(L-MLM) group is attached, for example, via the methoxy group or as a hydroxyl group); and 2. Trans-4-Iodo-4'-Boranyl-Chalcone

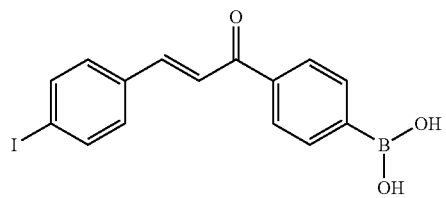 [SMILES: O=C(/C=C/c1ccc(I)cc1)c1ccc(B(O)O)cc1]

(derivatized where a linker group L or a linker group L or a-(L-MLM) group is attached, for example, via a hydroxy group).

Exemplary CLMs

Neo-imide Compounds

In one aspect the description provides compounds useful for binding and/or inhibiting cereblon. In certain embodiments, the compound is selected from the group consisting of chemical structures:

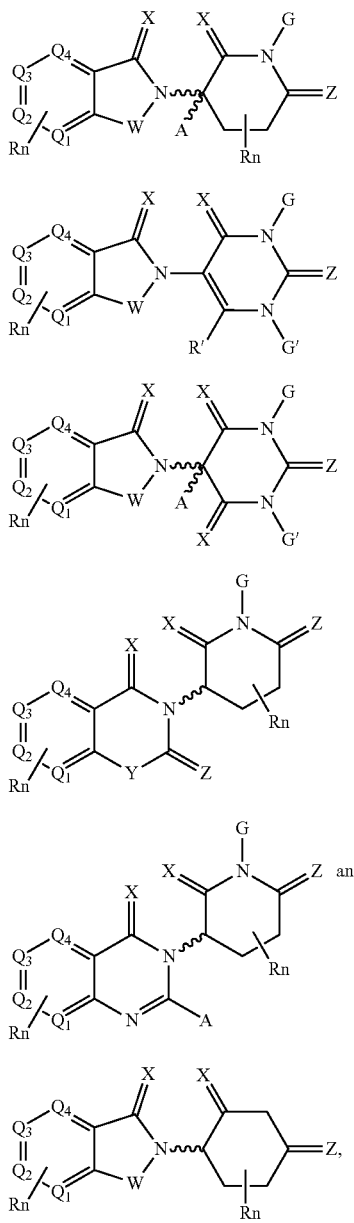

wherein:

W of Formulas (a) through (f) is independently selected from the group CH$_2$, CHR, CO, SO$_2$, NH, and N-alkyl;

X of Formulas (a) through (f) is independently selected from the group O, S and H$_2$;

Y of Formulas (a) through (f) is independently selected from the group CH$_2$, —C=CR', NH, N-alkyl, N-aryl, N-hetaryl, N-cycloalkyl, N-heterocyclyl, O, and S;

Z of Formulas (a) through (f) is independently selected from the group O, and S or H$_2$ except that both X and Z cannot be H$_2$;

G and G' of Formulas (a) through (f) are independently selected from the group H, alkyl (linear, branched, optionally substituted), OH, R'OCOOR, R'OCONRR", CH$_2$-heterocyclyl optionally substituted with R', and benzyl optionally substituted with R';

Q1-Q4 of Formulas (a) through (f) represent a carbon C substituted with a group independently selected from R, R', N or N-oxide;

A of Formulas (a) through (f) is independently selected from the group H, alkyl (linear, branched, optionally substituted), cycloalkyl, Cl and F;

R of Formulas (a) through (f) comprises, but is not limited to: —CONR'R", —OR', —NR'R", —SR', —SO$_2$R', —SO$_2$NR'R", —CR'R"—, —CR'NR'R"—, (—CR'O)$_n$R", -aryl, -hetaryl, -alkyl (linear, branched, optionally substituted), -cycloalkyl, -heterocyclyl, —P(O)(OR')R", —P(O)R'R", —OP(O)(OR')R", —OP(O)R'R", —Cl, —F, —Br, —I, —CF$_3$, —CN, —NR'SO$_2$NR'R", —NR'CONR'R", —CONR'COR", —NR'C(=N—CN)NR'R", —C(=N—CN)NR'R", —NR'C(=N—CN)R", —NR'C(=C—NO$_2$)NR'R", —SO$_2$NR'COR", —NO$_2$, —CO$_2$R', —C(C=N—OR')R", —CR'=CR'R", —CCR', —S(C=O)(C=N—R')R", —SF$_5$ and —OCF$_3$ R' and R" of Formulas (a) through (f) are independently selected from a bond, H, alkyl, cycloalkyl, aryl, heteroaryl, heterocyclic, —C(=O)R, heterocyclyl, each of which is optionally substituted; n of Formulas (a) through (f) is an integer from 1-10 (e.g., 1-4);

∼∼∼ of Formulas (a) through (f) represents a bond that may be stereospecific ((R) or (S)) or non-stereospecific; and R$_n$ of Formulas (a) through (f) comprises 1-4 independent functional groups or atoms.

Exemplary CLMs

In any of the compounds described herein, the CLM comprises a chemical structure selected from the group:

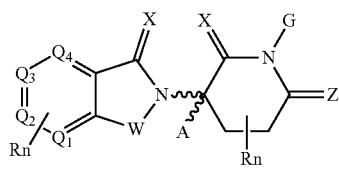

(a)

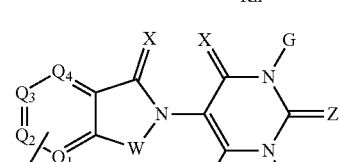

(b)

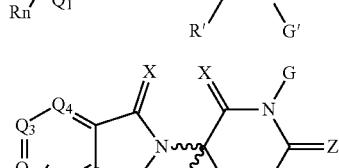

(c)

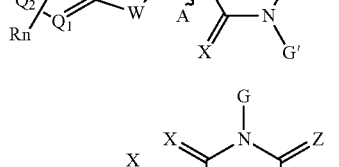

(d)

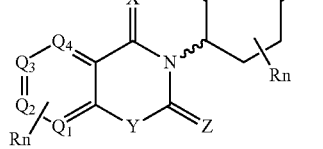

(e)

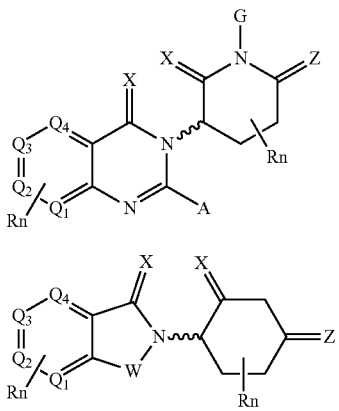

(f)

wherein:
W of Formulas (a) through (f) is independently selected from the group $CH_2$, CHR, C=O, $SO_2$, NH, and N-alkyl;
X of Formulas (a) through (f) is independently selected from the group O, S and H2;
Y of Formulas (a) through (f) is independently selected from the group $CH_2$, —C=CR', NH, N-alkyl, N-aryl, N-hetaryl, N-cycloalkyl, N-heterocyclyl, O, and S;
Z of Formulas (a) through (f) is independently selected from the group O, and S or H2 except that both X and Z cannot be H2;
G and G' of Formulas (a) through (f) are independently selected from the group H, alkyl (linear, ranched, OH, R'OCOOR, R'OCONRR", $CH_2$-heterocyclyl optionally substituted with R', and benzyl optionally substituted with R';
Q1-Q4 of Formulas (a) through (f) represent a carbon C substituted with a group independently selected from R, R', N or N-oxide;
A of Formulas (a) through (f) is independently selected from the group H, alkyl (linear, branched, optionally substituted), cycloalkyl, Cl and F;
R of Formulas (a) through (f) comprises, but is not limited to: —CONR'R", —OR', —NR'R", —SR', —$SO_2$R', —$SO_2$NR'R", —CR'R"—, —CR'NR'R"—, -aryl, -het-aryl, -alkyl, -cycloalkyl, -heterocyclyl, —P(O)(OR')R", —P(O)R'R", —OP(O)(OR')R", —OP(O)R'R", —Cl, —F, —Br, —I, —CF3, —CN, —NR'$SO_2$NR'R", —NR'CONR'R", —CONR'COR", —NR'C(=N—CN)NR'R", —C(=N—CN)NR'R", —NR'C(=N—CN)R", —NR'C(=C—NO2)NR'R", —$SO_2$NR'COR", —NO2, —CO2R', —C(C=N—OR')R", —CR'=CR'R", —CCR', —S(C=O)(C=N—R')R", —SF5 and —OCF3
R' and R" of Formulas (a) through (f) are independently selected from a bond, H, alkyl, cycloalkyl, aryl, heteroaryl, heterocyclic, —C(=O)R, heterocyclyl, each of which is optionally substituted; n of Formulas (a) through (f) is an integer from 1-10 (e.g., 1-4);
⁓ of Formulas (a) through (f) represents a bond that may be stereospecific ((R) or (S)) or non-stereospecific; and
Rn of Formulas (a) through (f) comprises 1-4 independent functional groups or atoms, and optionally, one of which is modified to be covalently joined to a PTM, a chemical linker group (L), a ULM, CLM (or CLM') or combination thereof.

In certain embodiments described herein, the CLM or ULM comprises a chemical structure selected from the group:

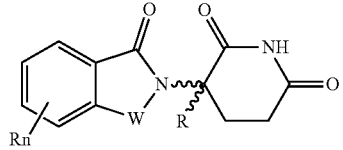

Formula (g)

wherein:
W of Formula (g) is independently selected from the group $CH_2$, C=O, NH, and N-alkyl;
R of Formula (g) is independently selected from a H, methyl, alkyl (e.g., C1-C6 alkyl (linear, branched, optionally substituted));
⁓ of Formula (g) represents a bond that may be stereospecific ((R) or (S)) or non-stereospecific; and
Rn of Formula (g) comprises 1-4 independently selected functional groups or atoms, and optionally, one of which is modified to be covalently joined to a PTM, a chemical linker group (L), a ULM, CLM (or CLM') or combination thereof.

In any of the embodiments described herein, the W, X, Y, Z, G, G', R, R', R", Q1-Q4, A, and Rn of Formulas (a) through (g) can independently be covalently coupled to a linker and/or a linker to which is attached one or more PTM, ULM, CLM or CLM' groups.

More specifically, non-limiting examples of CLMs include those shown below as well as those "hybrid" molecules that arise from the combination of 1 or more of the different features shown in the molecules below.

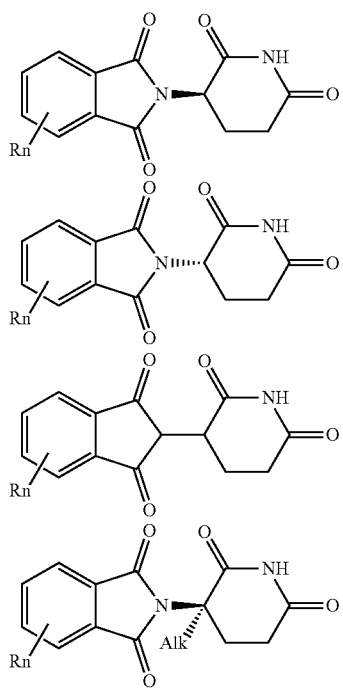

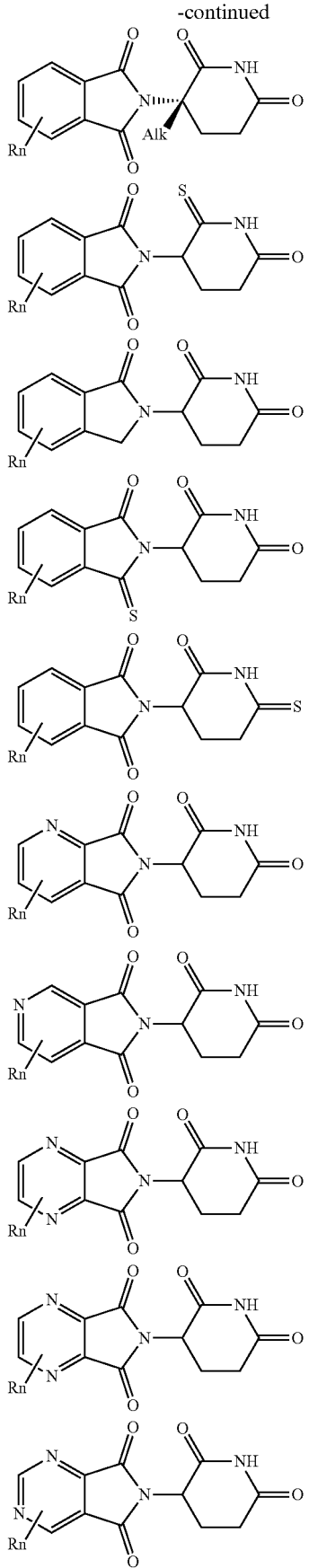
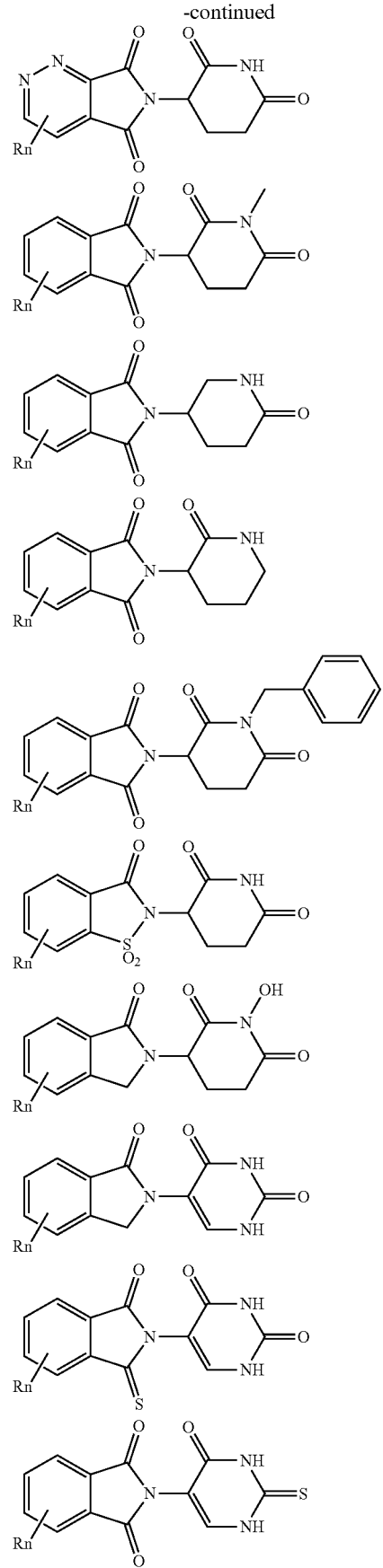

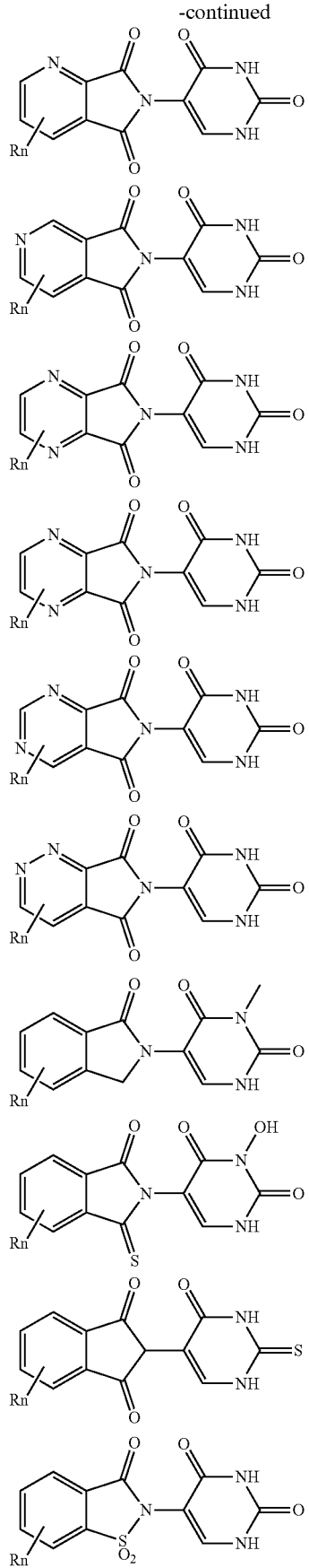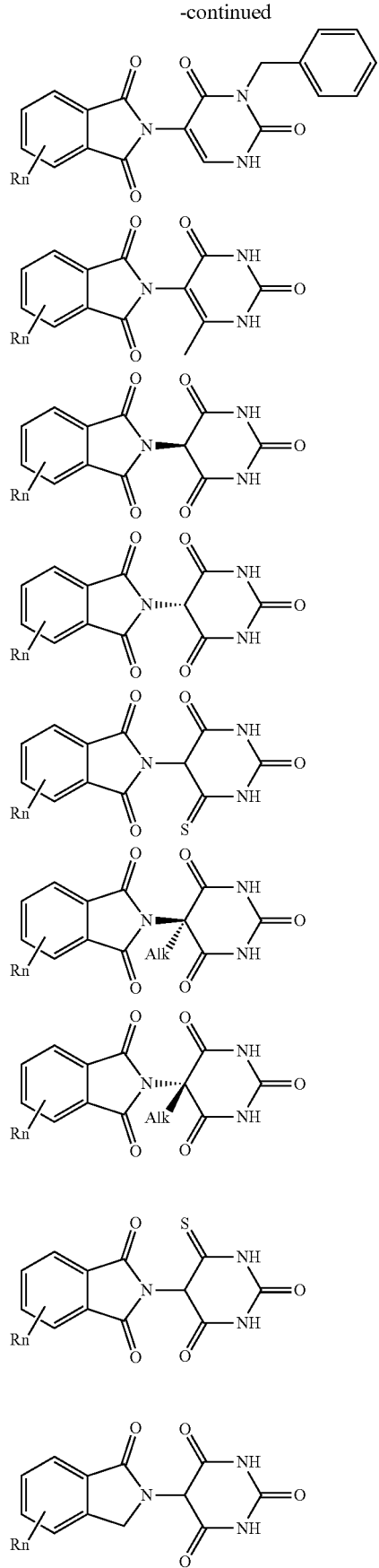

149
-continued
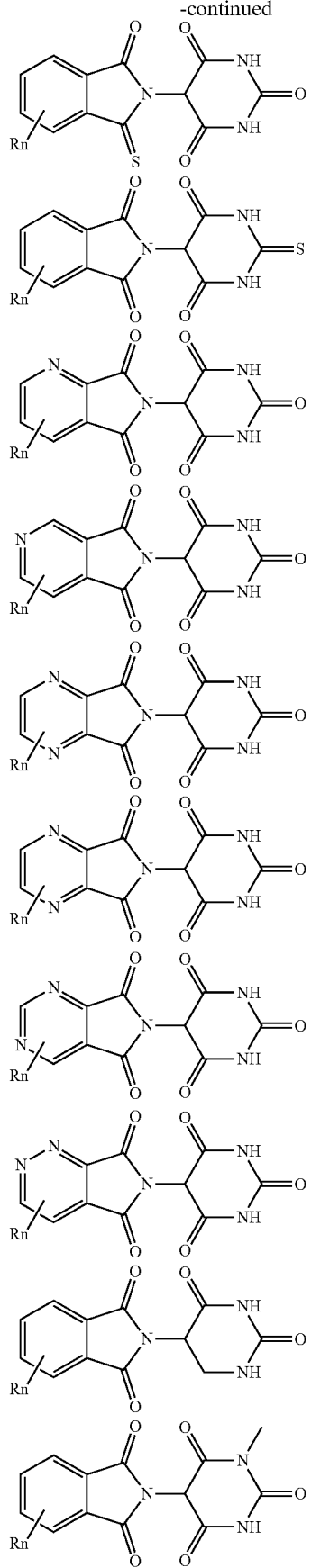
150
-continued
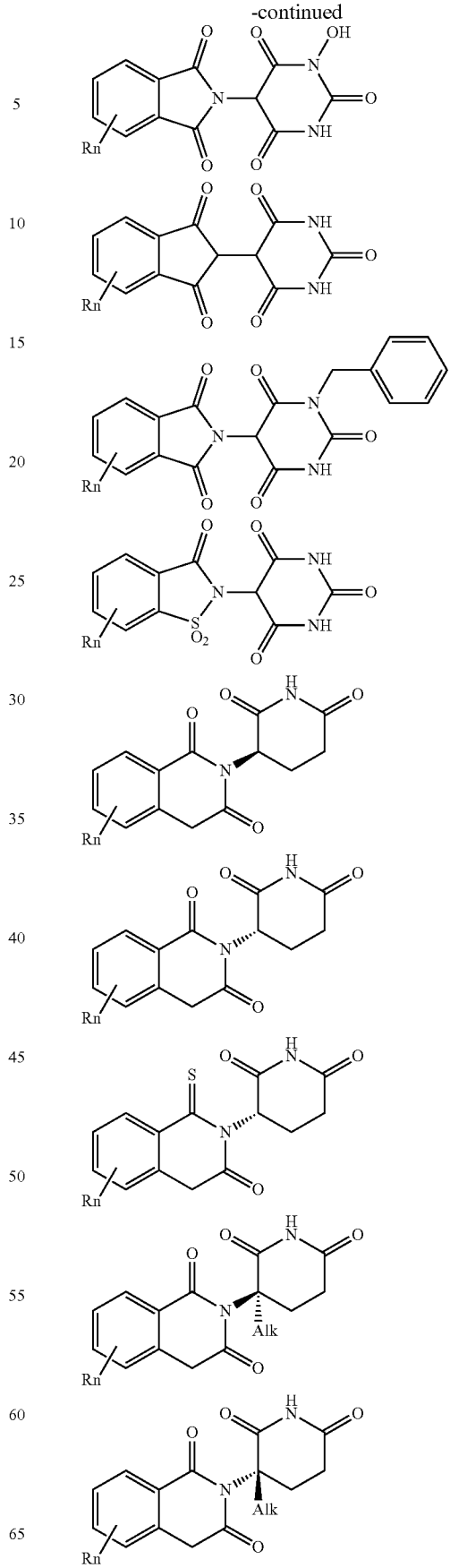

-continued
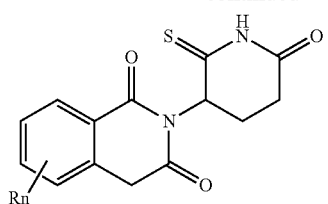
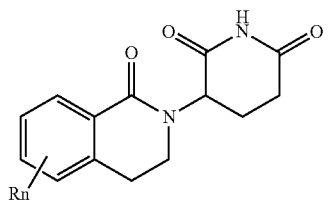
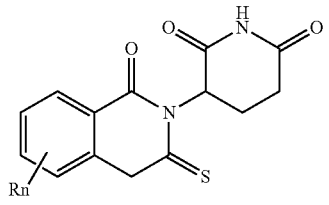
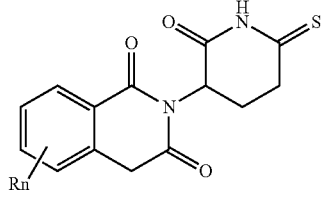
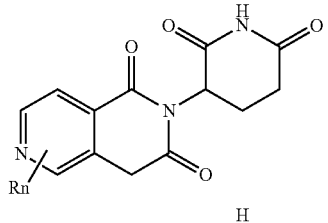
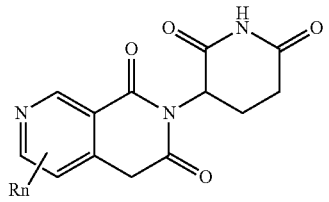
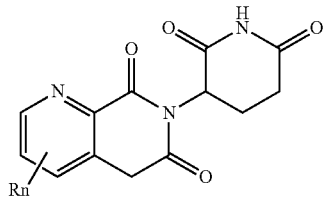
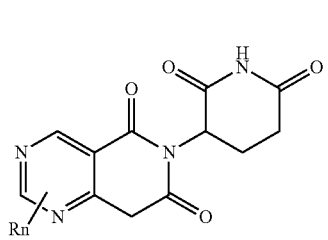
-continued
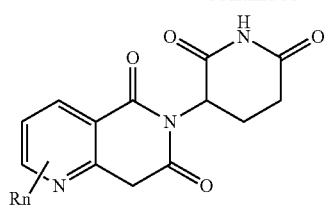
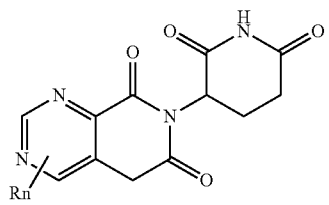
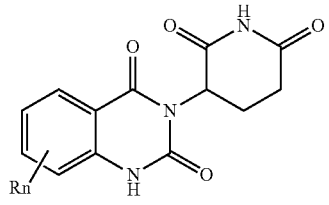
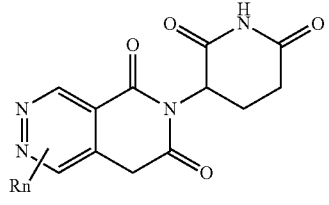
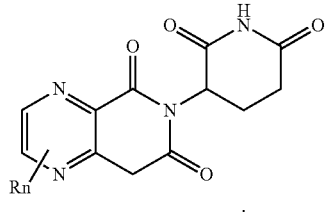
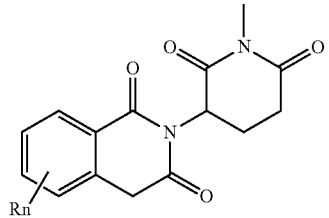
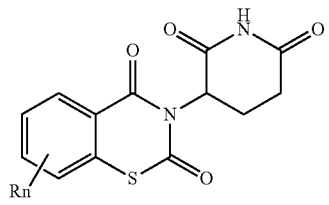
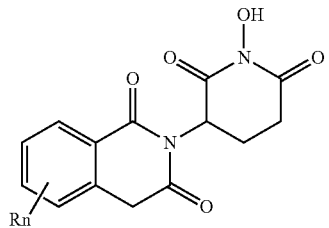

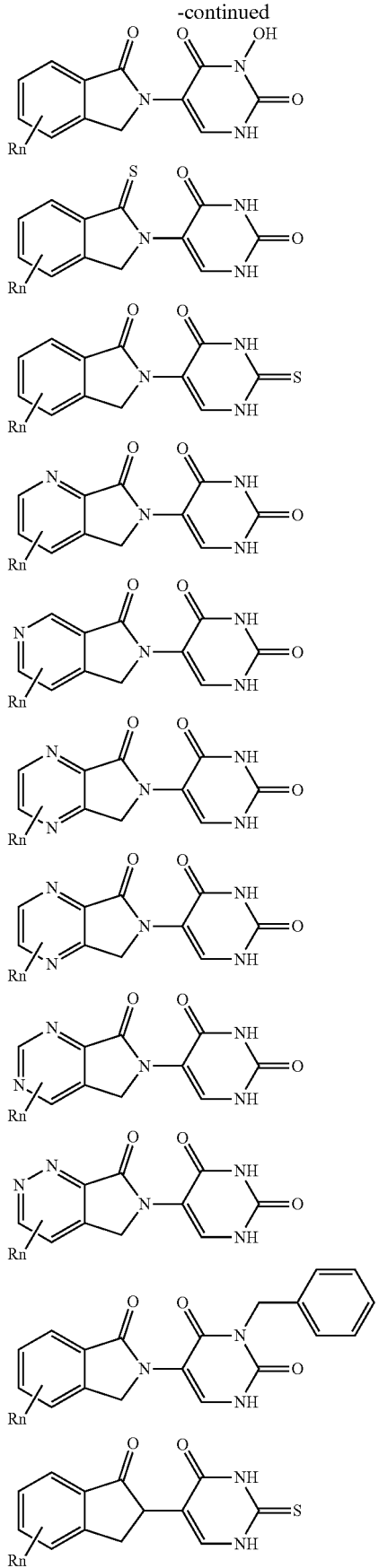
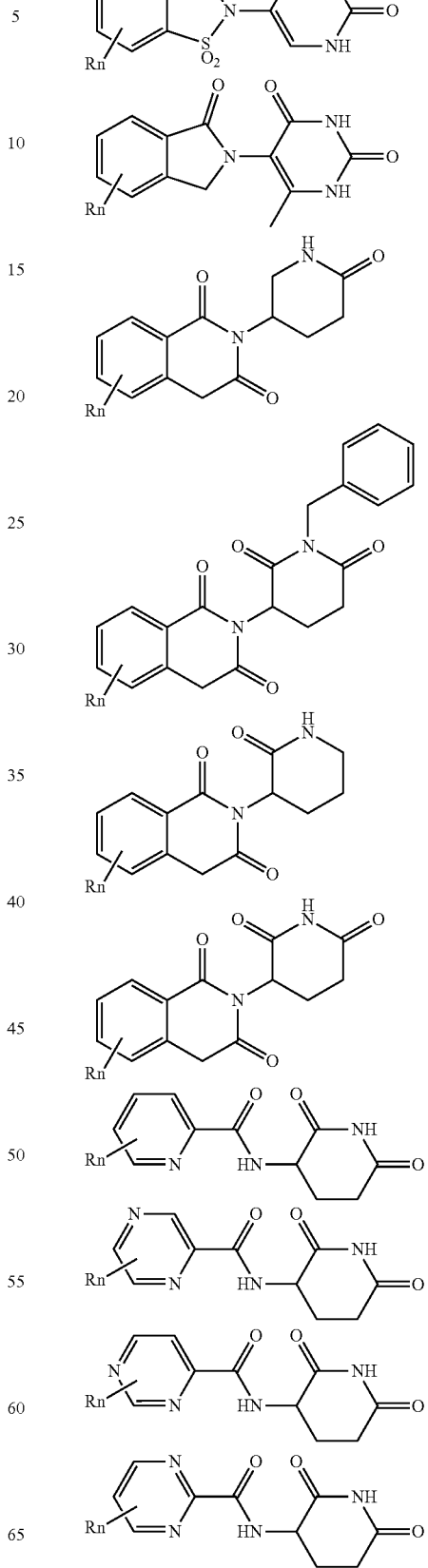

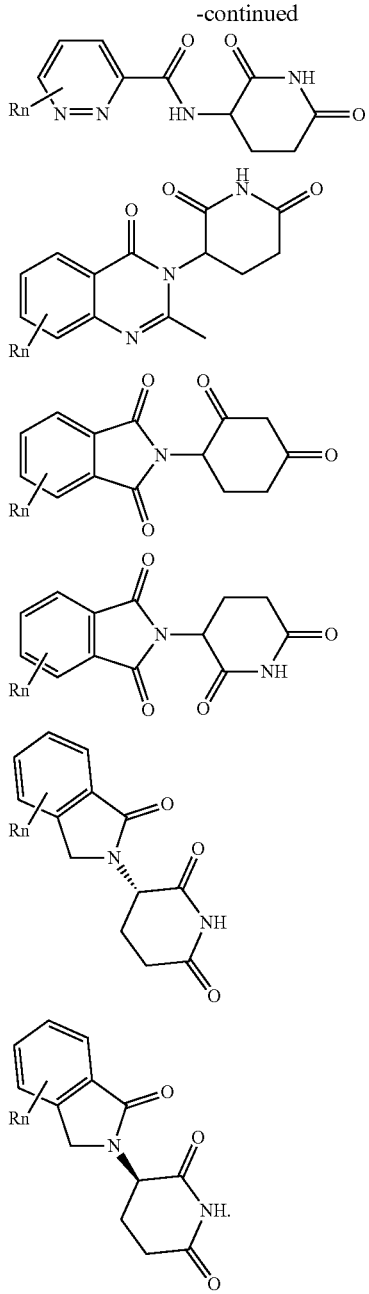
In any of the compounds described herein, the CLM comprises a chemical structure selected from the group:
(h)
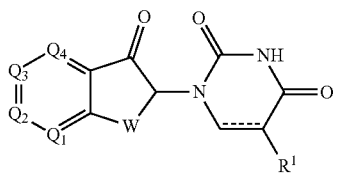
(i)
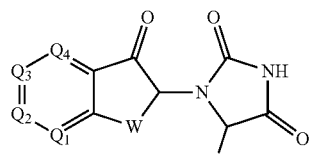
(j)
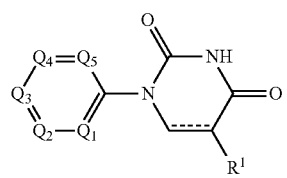
(k)
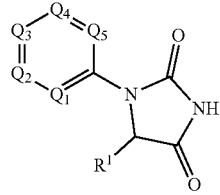
(l)
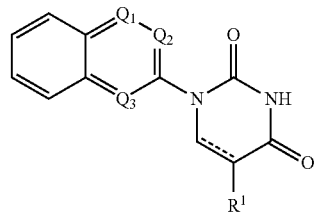
(m)
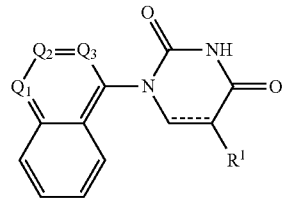
(n)
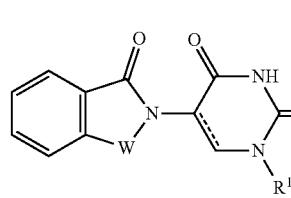
(o)
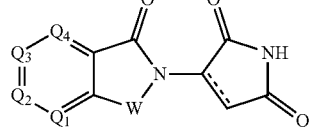
(p)
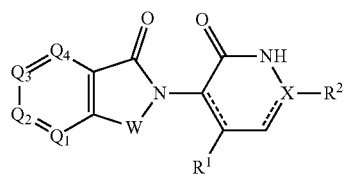

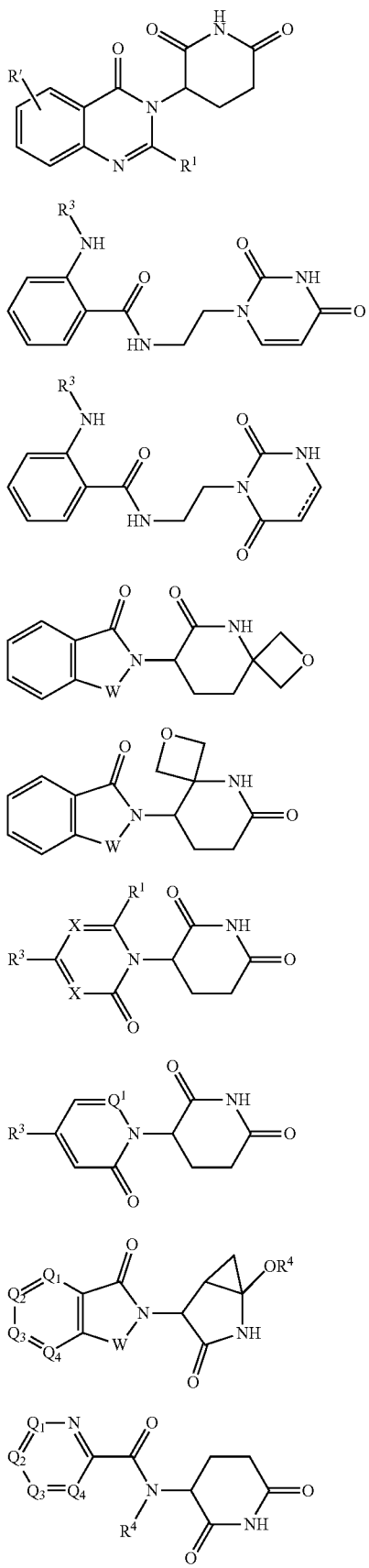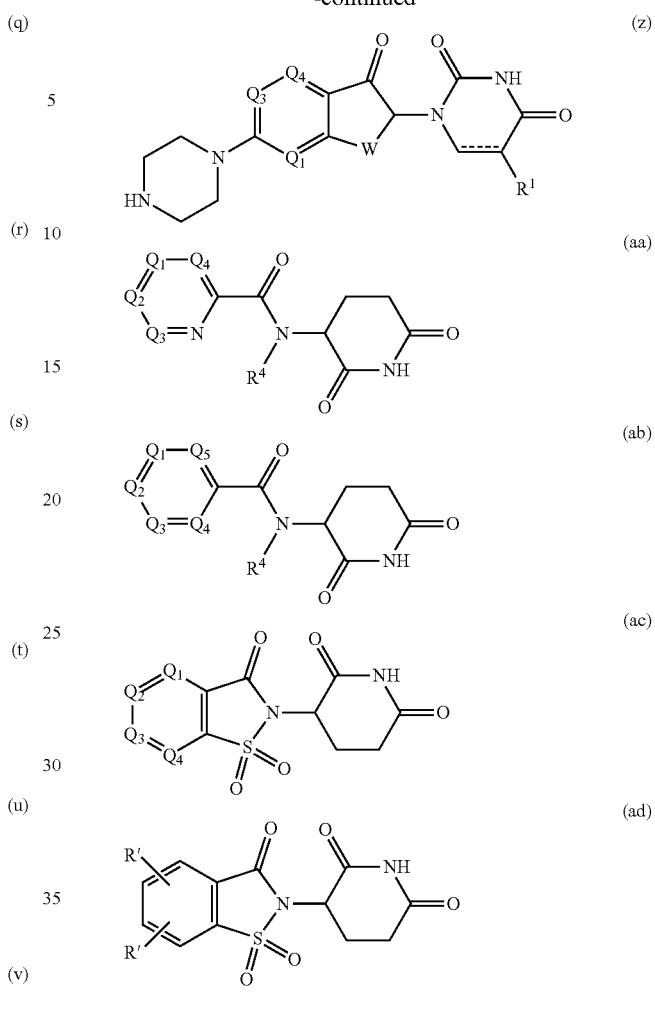

wherein:
W of Formulas (h) through (ad) is independently selected from CH$_2$, CHR, C=O, SO$_2$, NH, and N-alkyl;
Q$_1$, Q$_2$, Q$_3$, Q$_4$, Q$_5$ of Formulas (h) through (ac) are independently represent a carbon C substituted with a group independently selected from R', N or N-oxide;
R$^1$ of Formulas (h) through (ad) is selected from H, CN, C$_1$-C$_3$ alkyl;
R$^2$ of Formulas (h) through (ad) is selected from the group H, CN, C1-C3 alkyl, CHF$_2$, CF$_3$, CHO;
R$^3$ of Formulas (h) through (ad) is selected from H, alkyl, substituted alkyl, alkoxy, substituted alkoxy;
R$^4$ of Formulas (h) through (ad) is selected from H, alkyl, substituted alkyl;
R$^5$ of Formulas (h) through (ad) is H or lower alkyl;
X of Formulas (h) through (ad) is C, CH or N;
R' of Formulas (h) through (ad) is selected from H, halogen, alkyl, substituted alkyl, alkoxy, substituted alkoxy;
R of Formulas (h) through (ad) is H, OH, lower alkyl, lower alkoxy, cyano, halogenated lower alkoxy, or halogenated lower alkyl ⫽ of Formulas (h) through (ad) is a single or double bond; and
the CLM is covalently joined to a PTM, a chemical linker group (L), a ULM, CLM (or CLM') or combination thereof.

In any aspect or embodiment described herein, the CLM or CLM' is covalently joined to a PTM, a chemical linker group (L), a ULM, a CLM, a CLM', or a combination thereof via an R group (such as, R, $R^1$, $R^2$, $R^3$, $R^4$ or R'), W, X, or a Q group (such as, $Q_1$, $Q_2$, $Q_3$, $Q_4$, or $Q_5$) of Formulas (h) through (ad).

In any of the embodiments described herein, the CLM or CLM' is covalently joined to a PTM, a chemical linker group (L), a ULM, a CLM, a CLM', or a combination thereof via W, X, R, $R^1$, $R^2$, $R^3$, $R^4$, $R^5$, R', $Q_1$, $Q_2$, $Q_3$, $Q_4$, and $Q_5$ of Formulas (h) through (ad).

In any of the embodiments described herein, the W, X, $R^1$, $R^2$, $R^3$, $R^4$, R', $Q_1$, $Q_2$, $Q_3$, $Q_4$, and $Q_5$ of Formulas (h) through (ad) can independently be covalently coupled to a linker and/or a linker to which is attached to one or more PTM, ULM, ULM', CLM or CLM' groups.

More specifically, non-limiting examples of CLMs include those shown below as well as "hybrid" molecules or compounds that arise from combining 1 or more features of the following compounds:

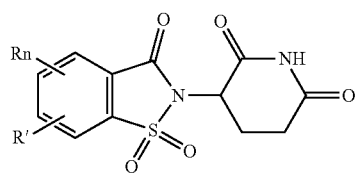
(ae)

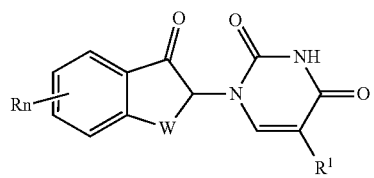
(af)

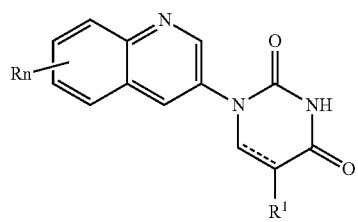
(ag)

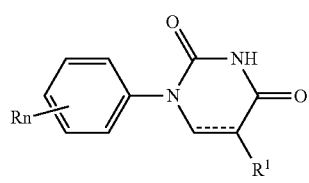
(ah)

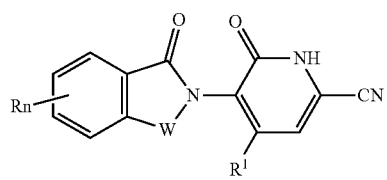
(ai)

-continued

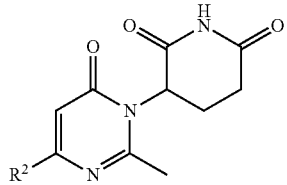
(aj)

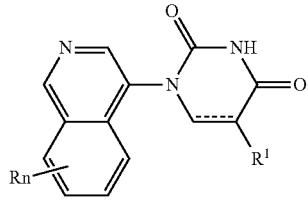
(ak)

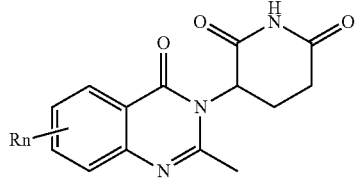
(al)

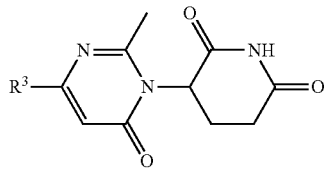
(am)

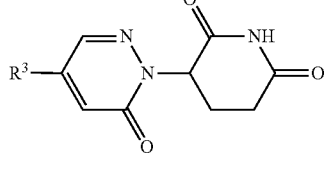
(an)

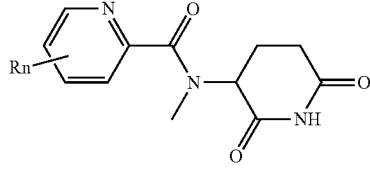
(ao)

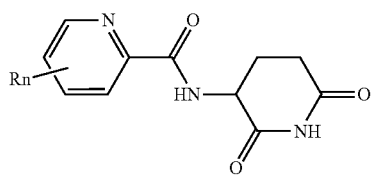
(ap)

wherein:
W of Formulas (ae) through (ap) is independently selected from the group $CH_2$, CHR, C=O, $SO_2$, NH, and N-alkyl;
$R^1$ of Formulas (ae) through (ap) is selected from the group H, CN, $C_1$-$C_3$ alkyl;
$R^3$ of Formulas (ae) through (ap) is selected from H, alkyl, substituted alkyl, alkoxy, substituted alkoxy;
R of Formulas (ae) through (ap) is H;

⌇ is a single or double bond; and
Rn of Formulas (ae) through (ap) comprises a functional group or an atom.

In any of the embodiments described herein, the W, $R^1$, $R^2$, $Q_1$, $Q_2$, $Q_3$, $Q_4$, and Rn of Formulas (ae) through (ap) can independently be covalently coupled to a linker and/or a linker to which is attached one or more PTM, ULM, ULM', CLM or CLM' groups.

In any of the embodiments described herein, the $R^1$, $R^2$, $Q_1$, $Q_2$, $Q_3$, $Q_4$, and Rn of Formulas (ae) through (ap) can independently be covalently coupled to a linker and/or a linker to which is attached one or more PTM, ULM, ULM', CLM or CLM' groups.

In any of the embodiments described herein, the $Q_1$, $Q_2$, $Q_3$, $Q_4$, and Rn of Formulas (ae) through (ap) can independently be covalently coupled to a linker and/or a linker to which is attached one or more PTM, ULM, ULM', CLM or CLM' groups.

In any aspect or embodiment described herein, $R_n$ of Formulas (ae) through (ap) is modified to be covalently joined to the linker group (L), a PTM, a ULM, a second CLM having the same chemical structure as the CLM, a CLM', a second linker, or any multiple or combination thereof.

In any aspect or embodiment described herein, the CLM is selected from:

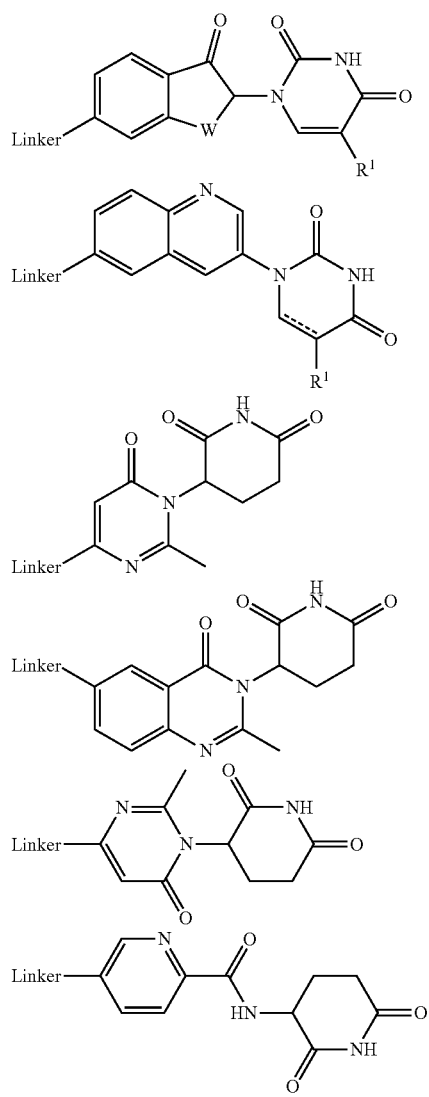

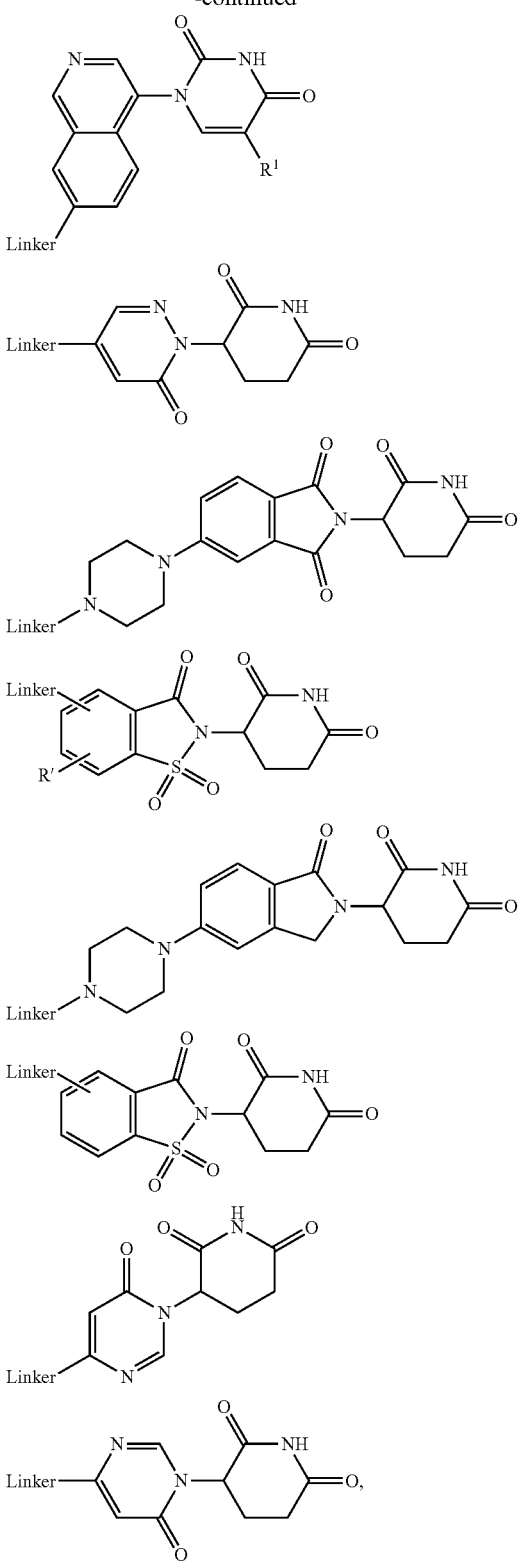

wherein R' is a halogen and R' is as described above with regard to Formulas (h) through (ab) or (ac) through (an).

In certain cases, the CLM can be imides that bind to cereblon E3 ligase. These imides and linker attachment point can be but not limited to the following structures:

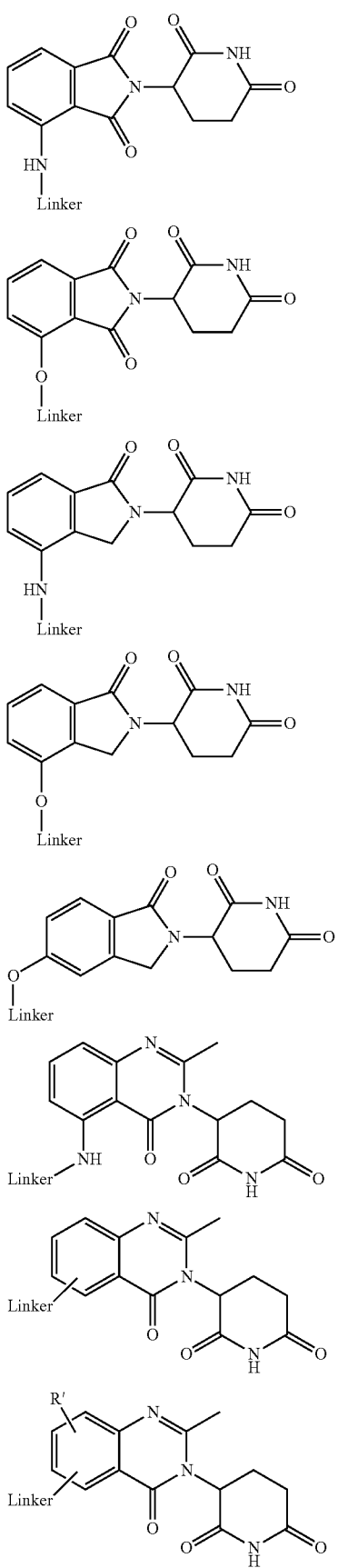
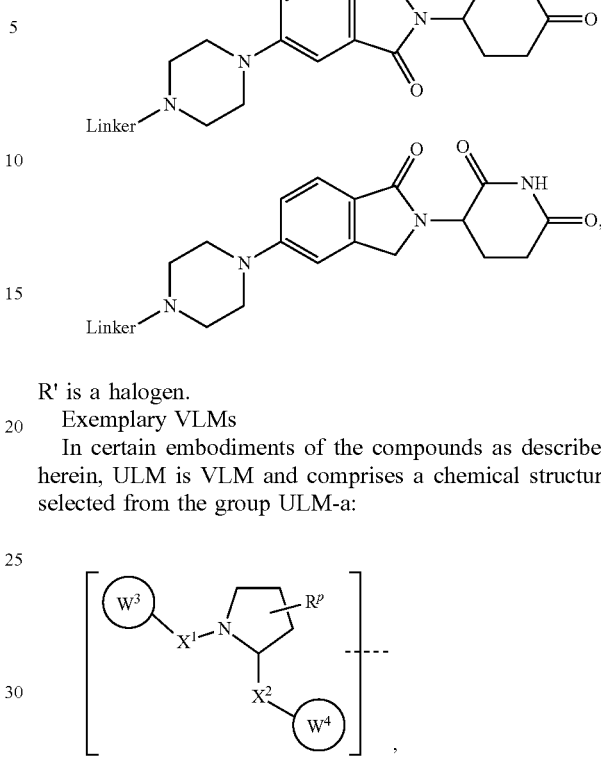

R' is a halogen.

Exemplary VLMs

In certain embodiments of the compounds as described herein, ULM is VLM and comprises a chemical structure selected from the group ULM-a:

wherein
- a dashed line indicates the attachment of at least one PTM, another ULM or VLM or MLM or ILM or CLM (i.e., ULM' or VLM' or CLM' or ILM' or MLM'), or a chemical linker moiety coupling at least one PTM, a ULM' or a VLM' or a CLM' or a ILM' or a MLM' to the other end of the linker;
- $X^1$, $X^2$ of Formula ULM-a are each independently selected from the group of a bond, O, $NR^{Y3}$, $CR^{Y3}R_{Y4}$, C=O, C=S, SO, and $SO_2$;
- $R^{Y3}$, $R^{Y4}$ of Formula ULM-a are each independently selected from the group of H, linear or branched $C_{1-6}$ alkyl, optionally substituted by 1 or more halo, optionally substituted $C_{1-6}$ alkoxyl (e.g., optionally substituted by 0-3 $R^P$ groups);
- $R^P$ of Formula ULM-a is 0, 1, 2, or 3 groups, each independently selected from the group H, halo, —OH, $C_{1-3}$ alkyl, C=O;
- $W^3$ of Formula ULM-a is selected from the group of an optionally substituted -T-N($R^{1a}R^{1b}$)$X^3$, -T-N($R^{1a}R^{1b}$), -T-Aryl, an optionally substituted -T-Heteroaryl, an optionally substituted -T-Heterocycle, an optionally substituted —$NR^1$-T-Aryl, an optionally substituted —$NR^1$-T-Heteroaryl or an optionally substituted —$NR^1$-T-Heterocycle;
- $X^3$ of Formula ULM-a is C=O, $R^1$, $R^{1a}$, $R^{1b}$;
- each of $R^1$, $R^{1a}$, $R^{1b}$ is independently selected from the group consisting of H, linear or branched $C_1$-$C_6$ alkyl group optionally substituted by 1 or more halo or —OH groups, $R^{Y3}$C=O, $R^{Y3}$C=S, $R^{Y3}$SO, $R^{Y3}SO_2$, N($R^{Y3}R^{Y4}$)C=O, N($R^{Y3}R^{Y4}$)C=S, N($R^{Y3}R^{Y4}$)SO, and N($R^{Y3}R^{Y4}$)$SO_2$;
- T of Formula ULM-a is covalently bonded to $X^1$;

$W^4$ of Formula ULM-a is an optionally substituted —$NR^1$-T-Aryl, an optionally substituted —$NR^1$-T-Heteroaryl group or an optionally substituted —$NR^1$-T-Heterocycle, where —$NR^1$ is covalently bonded to $X^2$ and R1 is H or $CH_3$, preferably H.

In any of the embodiments described herein, T is selected from the group of an optionally substituted alkyl, —$(CH_2)_n$— group, wherein each one of the methylene groups is optionally substituted with one or two substituents selected from the group of halogen, methyl, a linear or branched $C_1$-$C_6$ alkyl group optionally substituted by 1 or more halogen or —OH groups or an amino acid side chain optionally substituted; and n is 0 to 6, often 0, 1, 2, or 3, preferably 0 or 1.

In certain embodiments, $W^4$ of Formula ULM-a is

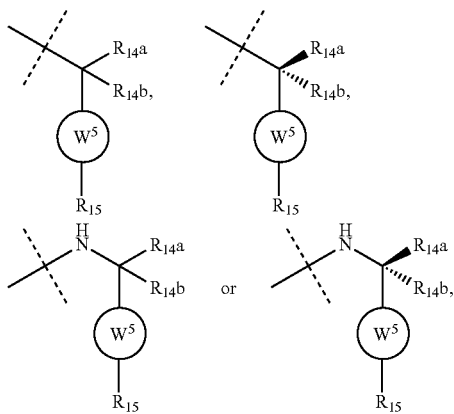

wherein $R_{14a}$, $R_{4b}$, are each independently selected from the group of H, haloalkyl, or optionally substituted alkyl.

In any of the embodiments, $W^5$ of Formula ULM-a is selected from the group of a phenyl or a 5-10 membered heteroaryl, $R_{15}$ of Formula ULM-a is selected from the group of H, halogen, CN, OH, $NO_2$, N $R_{14a}R_{14b}$, $OR_{14}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy; aryl, heteroaryl, cycloalkyl, or cycloheteroalkyl;

In additional embodiments, $W^4$ substituents for use in the present disclosure also include specifically (and without limitation to the specific compound disclosed) the $W^4$ substituents which are found in the identified compounds disclosed herein. Each of these $W^4$ substituents may be used in conjunction with any number of $W^3$ substituents which are also disclosed herein.

In certain additional embodiments, ULM-a, is optionally substituted by 0-3 $R^P$ groups in the pyrrolidine moiety. Each $R^P$ is independently H, halo, —OH, C1-3alkyl, C=O.

In any of the embodiments described herein, the $W^3$, $W^4$ of Formula ULM-a can independently be covalently coupled to a linker which is attached one or more PTM groups.

and wherein the dashed line indicates the site of attachment of at least one PTM, another ULM (ULM') or a chemical linker moiety coupling at least one PTM or a ULM' or both to ULM.

In certain embodiments, ULM is VHL and is represented by the structure:

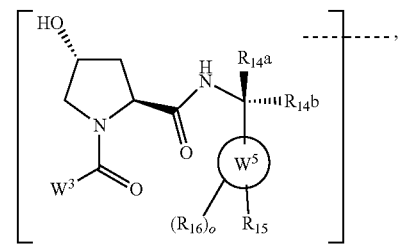

wherein:
$W^3$ of Formula ULM-b is selected from the group of an optionally substituted aryl, optionally substituted heteroaryl, or

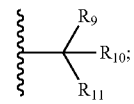

$R_9$ and $R_{10}$ of Formula ULM-b are independently hydrogen, optionally substituted alkyl, optionally substituted cycloalkyl, optionally substituted hydroxyalkyl, optionally substituted heteroaryl, or haloalkyl, or $R_9$, $R_{10}$, and the carbon atom to which they are attached form an optionally substituted cycloalkyl;

$R_{11}$ of Formula ULM-b is selected from the group of an optionally substituted heterocyclic, optionally substituted alkoxy, optionally substituted heteroaryl, optionally substituted aryl,

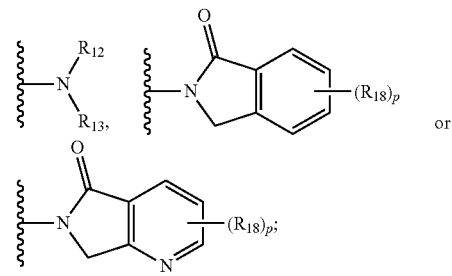

$R_{12}$ of Formula ULM-b is selected from the group of H or optionally substituted alkyl;

$R_{13}$ of Formula ULM-b is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

$R_{14a}$, $R_{14b}$ of Formula ULM-b, are each independently selected from the group of H, haloalkyl, or optionally substituted alkyl;

$W^5$ of Formula ULM-b is selected from the group of a phenyl or a 5-10 membered heteroaryl, $R_{15}$ of Formula ULM-b is selected from the group of H, halogen, CN, OH, $NO_2$, N $R_{14}R_{14b}$, $OR_{14a}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy; aryl, heteroaryl, cycloalkyl, or cycloheteroalkyl (each optionally substituted);

$R_{16}$ of Formula ULM-b is independently selected from the group of halo, optionally substituted alkyl, optionally substituted haloalkyl, hydroxy, or optionally substituted haloalkoxy;

o of Formula ULM-b is 0, 1, 2, 3, or 4;

$R_{18}$ of Formula ULM-b is independently selected from the group of H, halo, optionally substituted alkoxy, cyano, optionally substituted alkyl, haloalkyl, haloalkoxy or a linker; and p of Formula ULM-b is 0, 1, 2, 3, or 4, and wherein the dashed line indicates the site of attachment of at least one PTM, another ULM (ULM') or a chemical linker moiety coupling at least one PTM or a ULM' or both to ULM.

In certain embodiments, $R_{15}$ of Formula ULM-b is

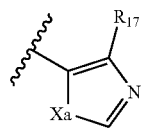

wherein $R_{17}$ is H, halo, optionally substituted $C_{3-6}$cycloalkyl, optionally substituted $C_{1-6}$alkyl, optionally substituted $C_{1-6}$alkenyl, and $C_{1-6}$ haloalkyl; and Xa is S or O.

In certain embodiments, $R_{17}$ of Formula ULM-b is selected from the group methyl, ethyl, isopropyl, and cyclopropyl.

In certain additional embodiments, $R_{15}$ of Formula ULM-b is selected from the group consisting of:

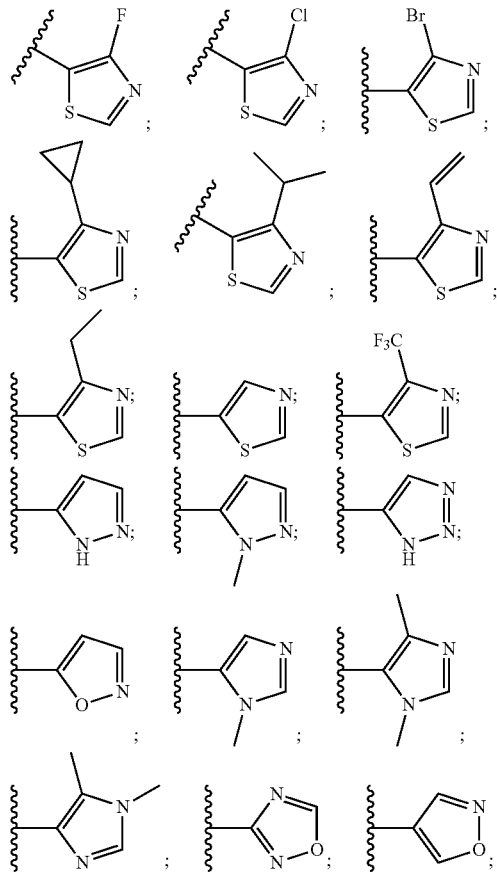

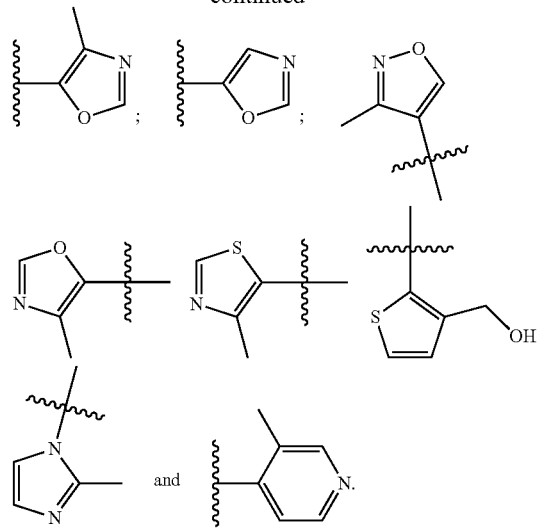

In certain embodiments, $R_{11}$ of Formula ULM-b is selected from the group consisting of:

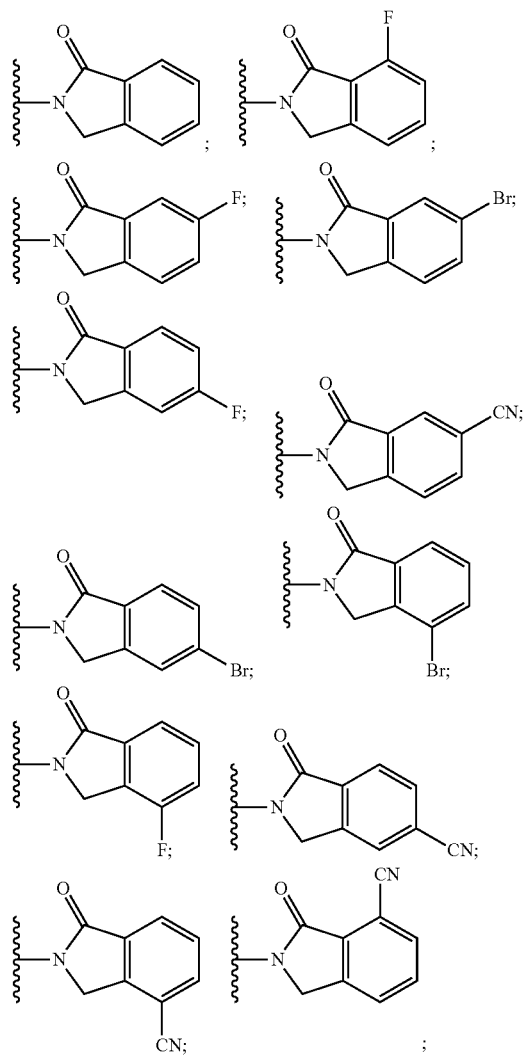

-continued

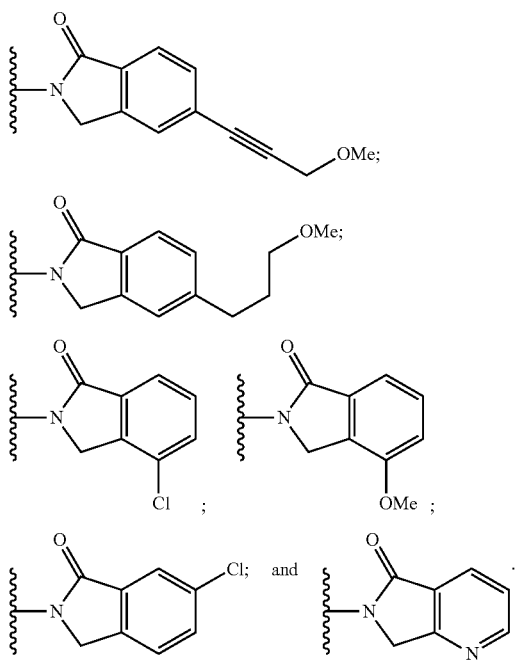

In certain embodiments, ULM has a chemical structure selected from the group of:

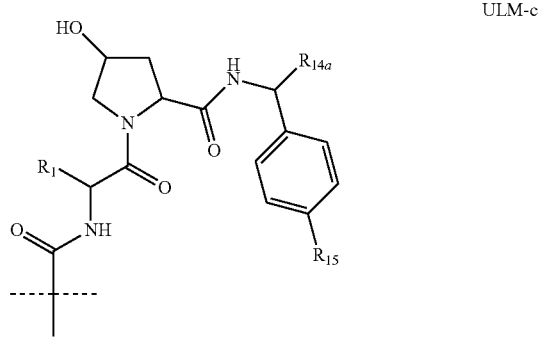

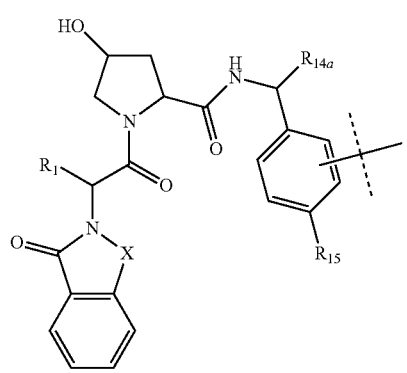

-continued

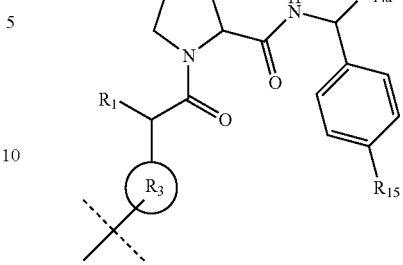

wherein:

R$_1$ of Formulas ULM-c, ULM-d, and ULM-e is H, ethyl, isopropyl, tert-butyl, sec-butyl, cyclopropyl, cyclobutyl, cyclopentyl, or cyclohexyl; optionally substituted alkyl, optionally substituted hydroxyalkyl, optionally substituted heteroaryl, or haloalkyl;

R$_{14a}$ of Formulas ULM-c, ULM-d, and ULM-e is H, haloalkyl, optionally substituted alkyl, methyl, fluoromethyl, hydroxymethyl, ethyl, isopropyl, or cyclopropyl;

R$_{15}$ of Formulas ULM-c, ULM-d, and ULM-e is selected from the group consisting of H, halogen, CN, OH, NO$_2$, optionally substituted heteroaryl, optionally substituted aryl; optionally substituted alkyl, optionally substituted haloalkyl, optionally substituted haloalkoxy, cycloalkyl, or cycloheteroalkyl;

X of Formulas ULM-c, ULM-d, and ULM-e is C or C=O

R$_3$ of Formulas ULM-c, ULM-d, and ULM-e is absent or an optionally substituted 5 or 6 membered heteroaryl; and wherein the dashed line indicates the site of attachment of at least one PTM, another ULM (ULM') or a chemical linker moiety coupling at least one PTM or a ULM' or both to ULM.

In certain embodiments, ULM comprises a group according to the chemical structure:

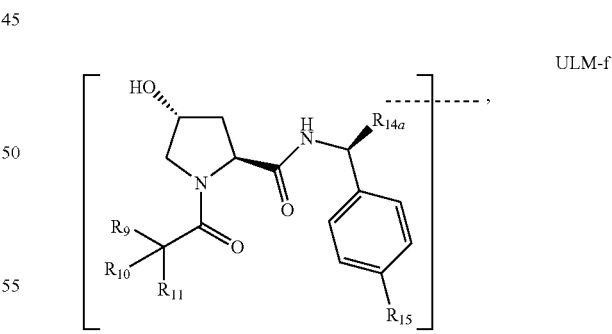

wherein:

R$_{14a}$ of Formula ULM-f is H, haloalkyl, optionally substituted alkyl, methyl, fluoromethyl, hydroxymethyl, ethyl, isopropyl, or cyclopropyl;

R$_9$ of Formula ULM-f is H;

R$_{10}$ of Formula ULM-f is H, ethyl, isopropyl, tert-butyl, sec-butyl, cyclopropyl, cyclobutyl, cyclopentyl, or cyclohexyl;

$R_{11}$ of Formula ULM-f is

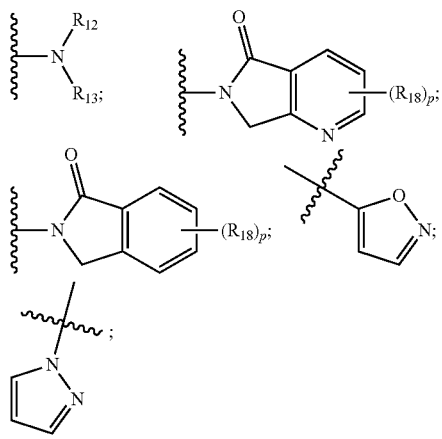

or optionally substituted heteroaryl;
p of Formula ULM-f is 0, 1, 2, 3, or 4;
each $R_{18}$ of Formula ULM-f is independently halo, optionally substituted alkoxy, cyano, optionally substituted alkyl, haloalkyl, haloalkoxy or a linker;
$R_{12}$ of Formula ULM-f is H, C=O;
$R_{13}$ of Formula ULM-f is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl,
$R_{15}$ of Formula ULM-f is selected from the group consisting of H, halogen, Cl, CN, OH, $NO_2$. optionally substituted heteroaryl, optionally substituted aryl;

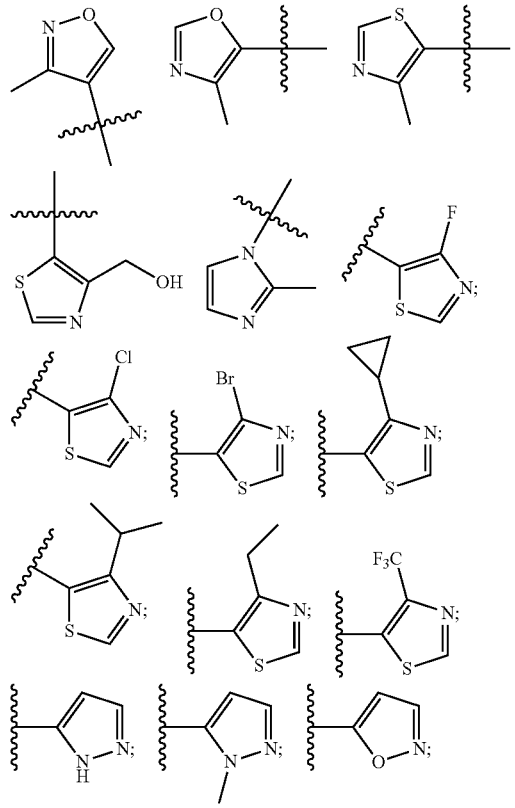

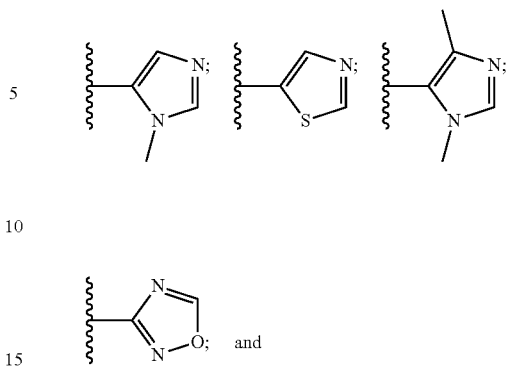

wherein the dashed line of Formula ULM-f indicates the site of attachment of at least one PTM, another ULM (ULM') or a chemical linker moiety coupling at least one PTM or a ULM' or both to ULM.

In certain embodiments, the ULM is selected from the following structures:

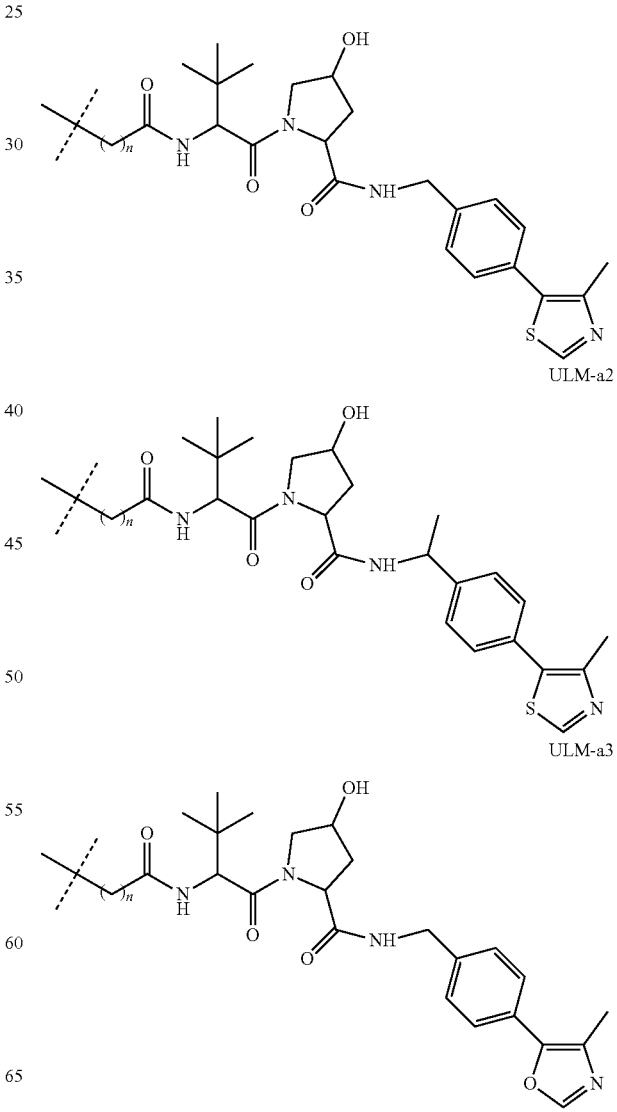

ULM-a4
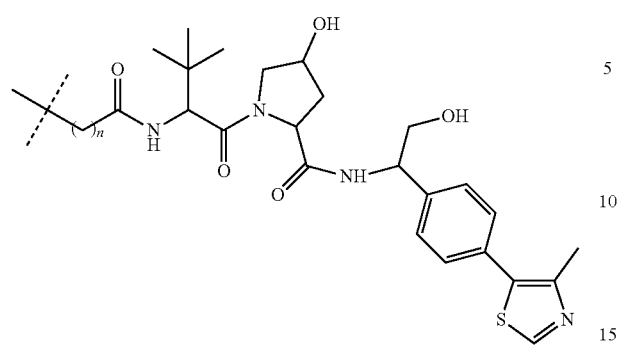
ULM-a8
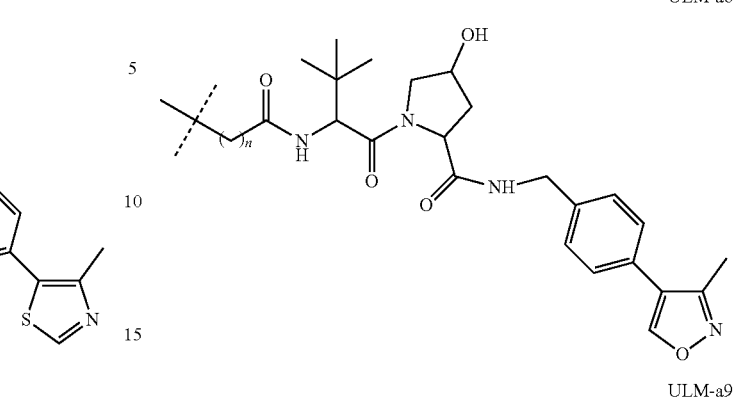
ULM-a5
ULM-a9
ULM-a6
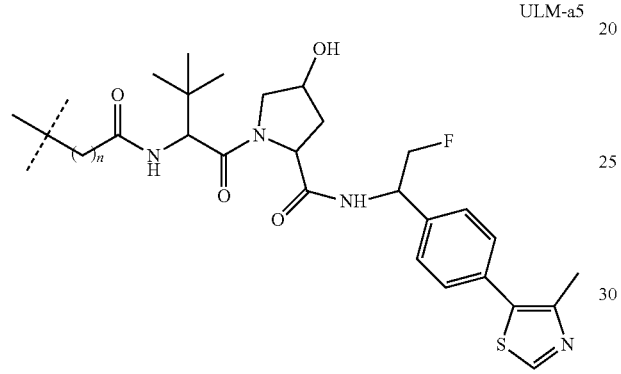
ULM-a10
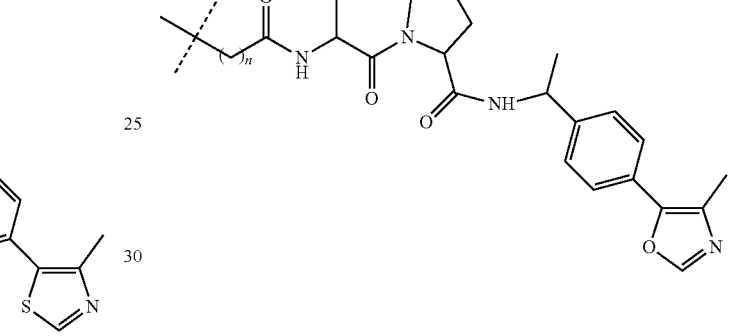
ULM-a7
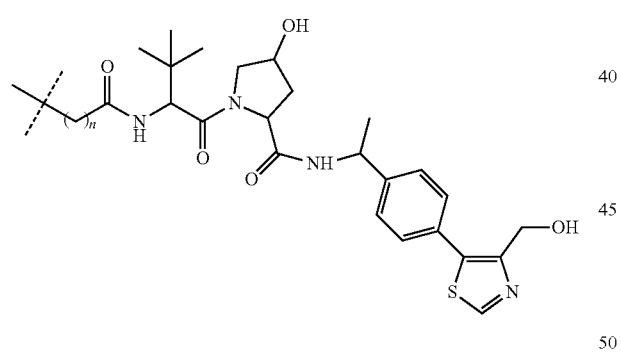
ULM-a11
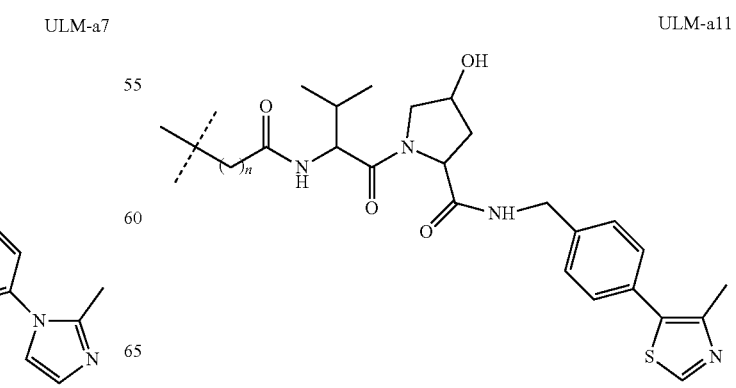

ULM-a12
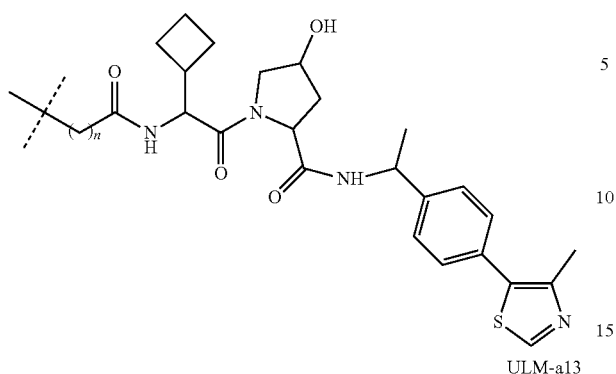
ULM-a13
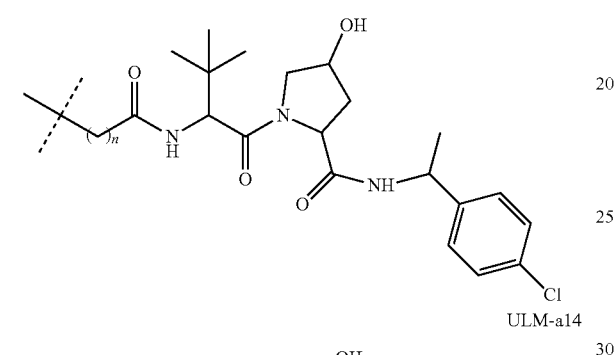
ULM-a14
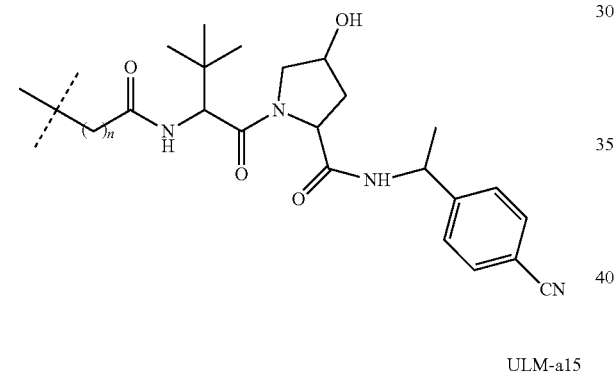
ULM-a15
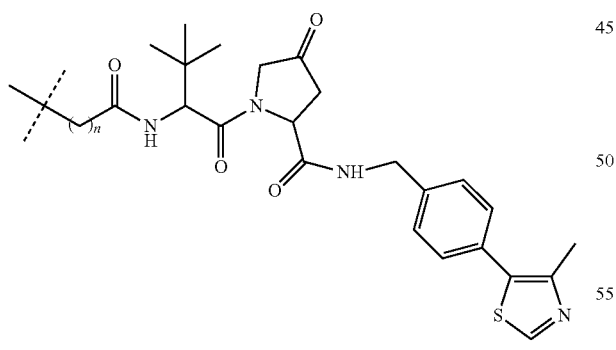
wherein n is 0 or 1.
In certain embodiments, the ULM is selected from the following structures:
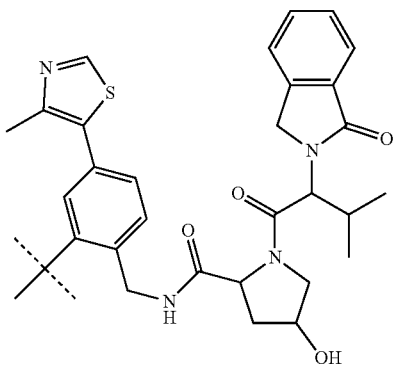
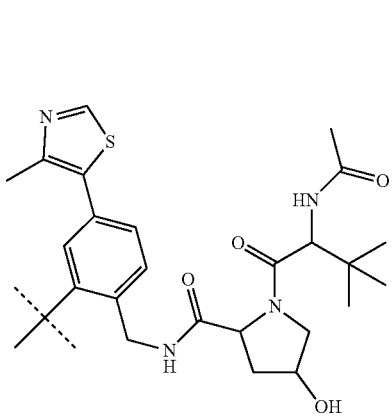
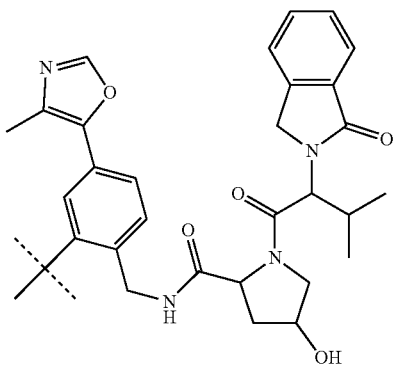
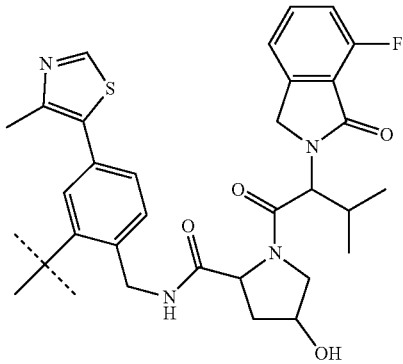

177
-continued
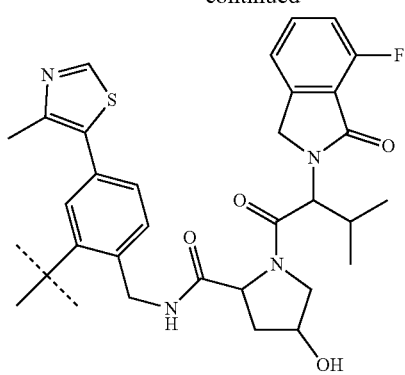
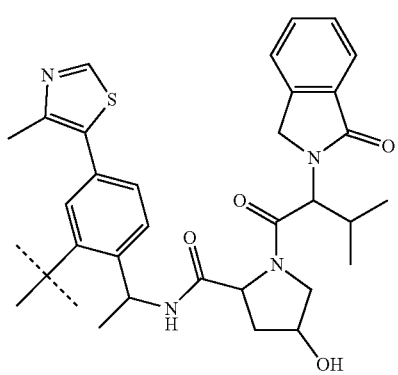
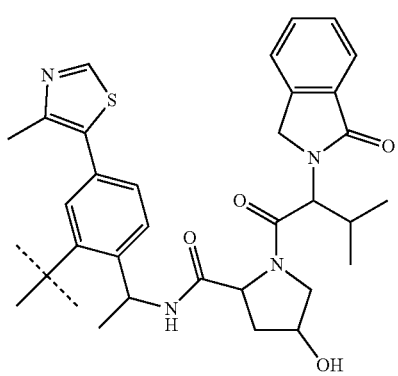
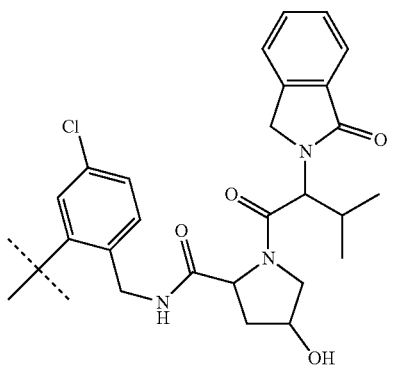
178
-continued
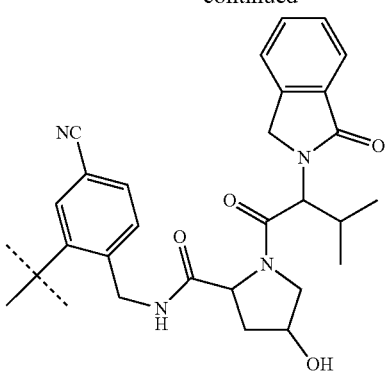
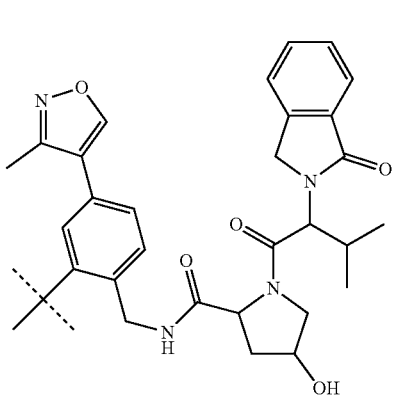
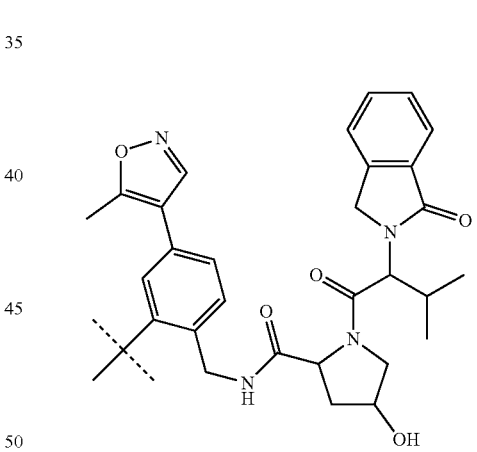
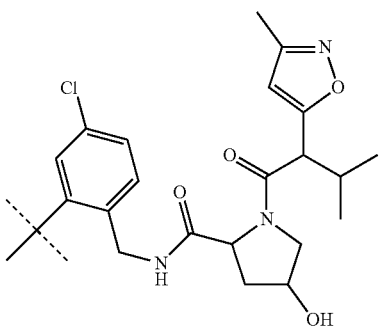

179
-continued
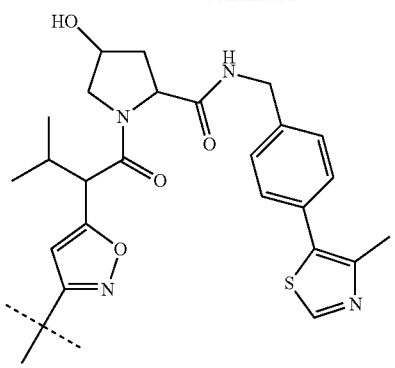
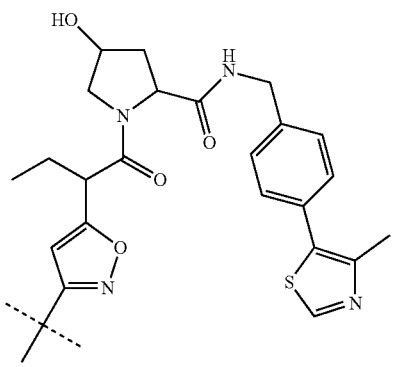
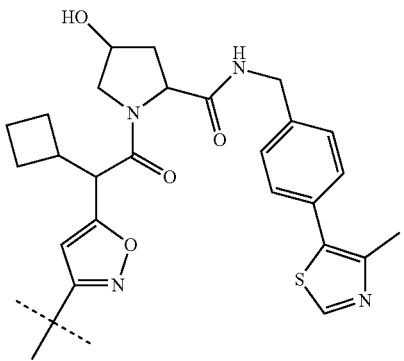
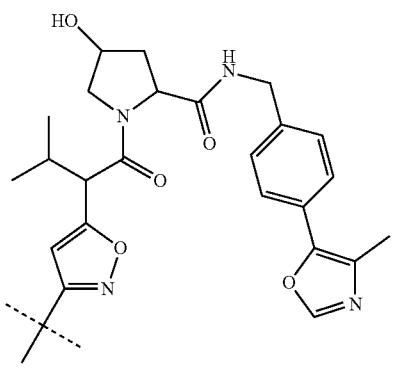
180
-continued
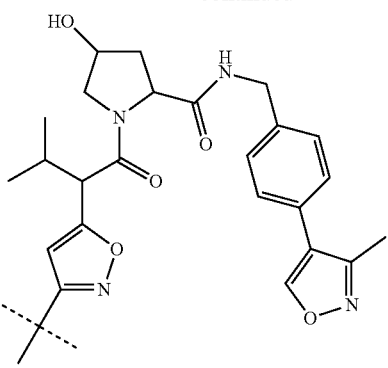
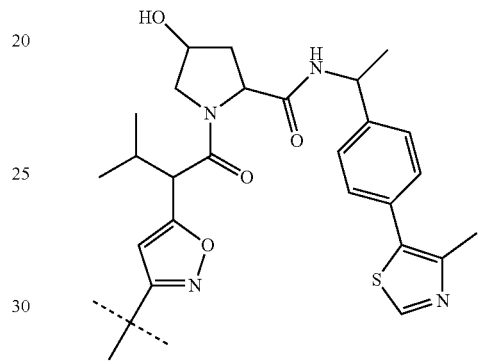
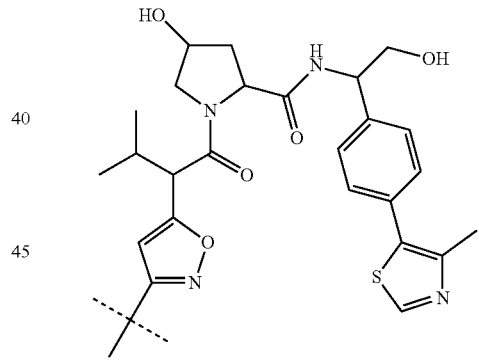
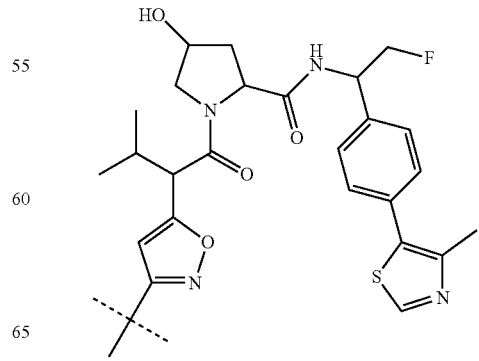

181
-continued
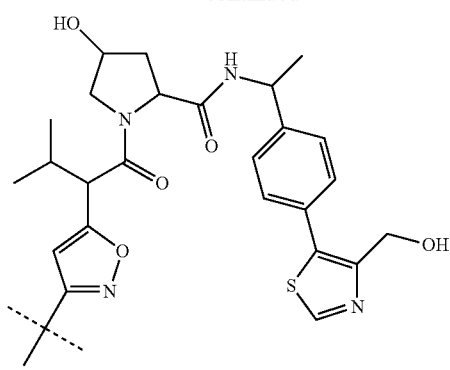
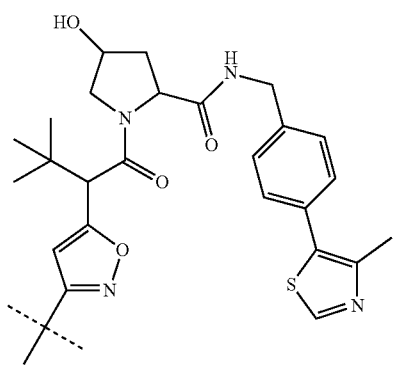
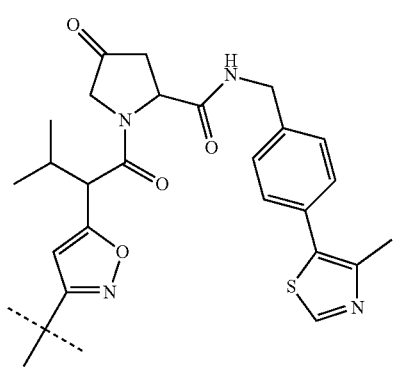
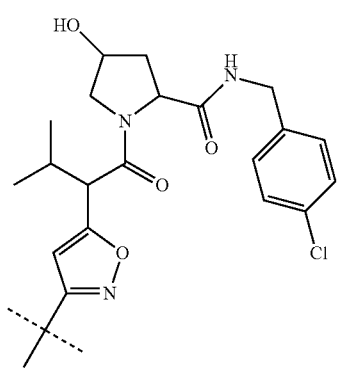
182
-continued
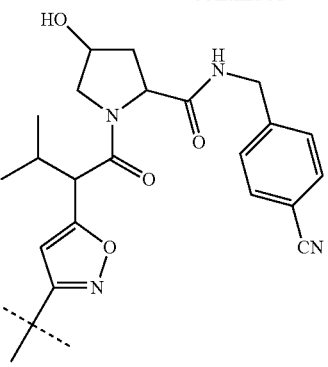
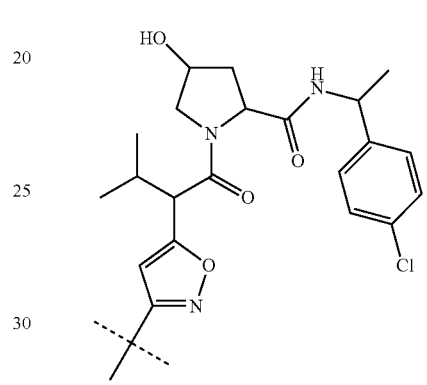
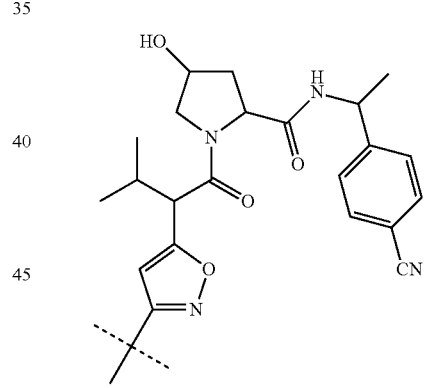
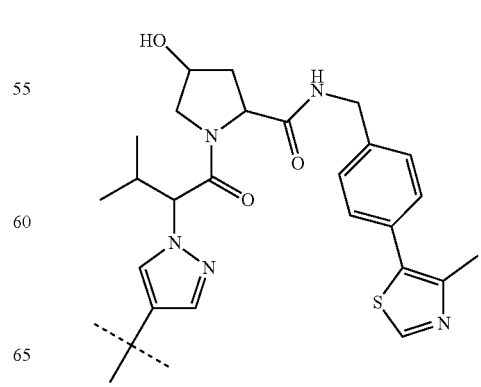

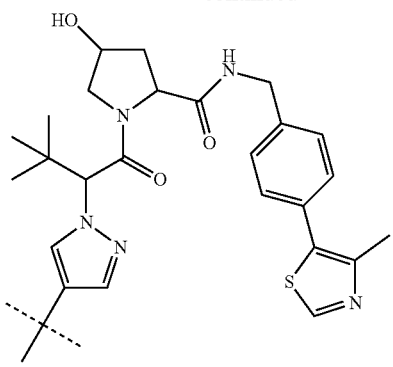

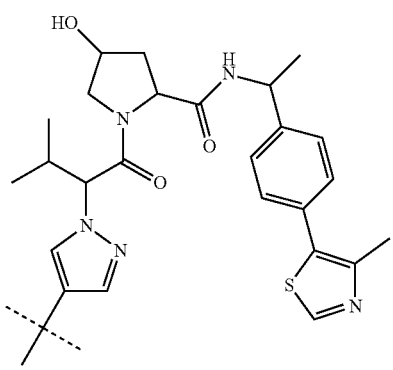

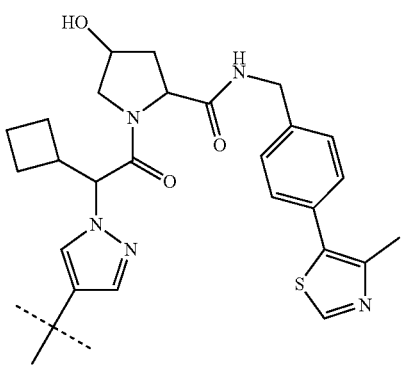

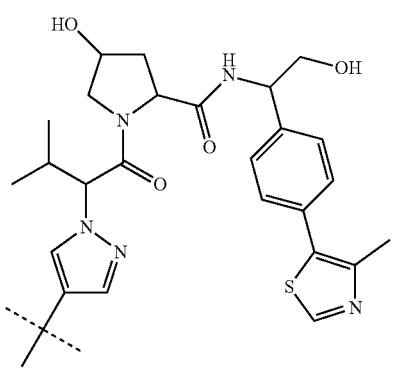

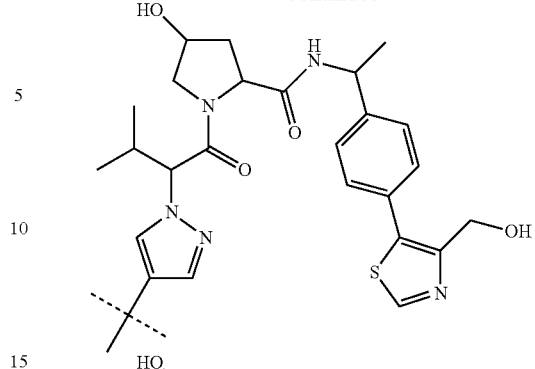

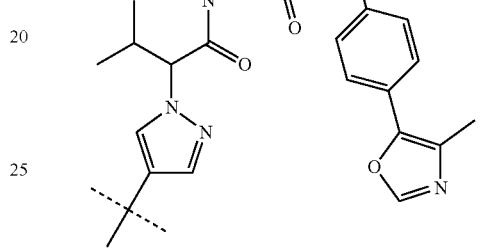

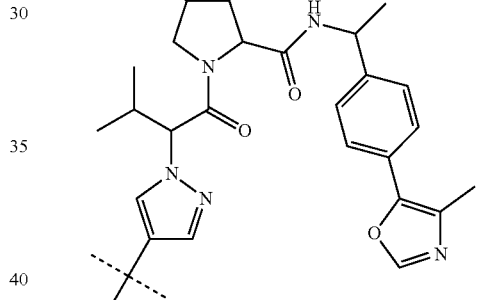

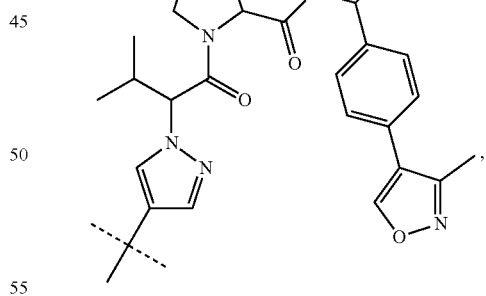

wherein, the phenyl ring in ULM-a1 through ULM-a15, ULM-b1 through ULM-b12, ULM-c1 through ULM-c15 and ULM-d1 through ULM-d9 is optionally substituted with fluorine, lower alkyl and alkoxy groups, and wherein the dashed line indicates the site of attachment of at least one PTM, another ULM (ULM') or a chemical linker moiety coupling at least one PTM or a ULM' or both to ULM-a.

In one embodiment, the phenyl ring in ULM-a1 through ULM-a15, ULM-b1 through ULM-b12, ULM-c1 through ULM-c15 and ULM-d1 through ULM-d9 can be functionalized as the ester to make it a part of the prodrug.

In certain embodiments, the hydroxyl group on the pyrrolidine ring of ULM-a1 through ULM-a15, ULM-b1 through ULM-b12, ULM-c1 through ULM-c15 and ULM-d1 through ULM-d9, respectively, comprises an ester-linked prodrug moiety.

In any of the aspects or embodiments described herein, the ULM and where present, ULM', are each independently a group according to the chemical structure:

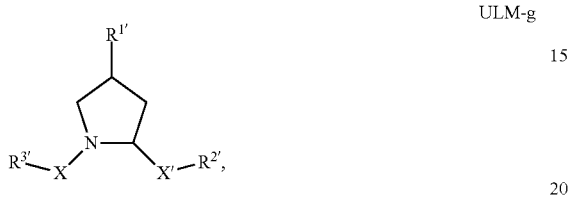

ULM-g wherein:
$R^{1'}$ of ULM-g is an optionally substituted $C_1$-$C_6$ alkyl group, an optionally substituted —($CH_2$) OH, an optionally substituted —($CH_2$)SH, an optionally substituted ($CH_2$)$_n$—O—($C_1$-$C_6$)alkyl group, an optionally substituted ($CH_2$)$_n$—WCOCW-($C_0$-$C_6$)alkyl group containing an epoxide moiety WCOCW where each W is independently H or a $C_1$-$C_3$ alkyl group, an optionally substituted —($CH_2$)$_n$COOH, an optionally substituted —($CH_2$)$_n$C(O)—($C_1$-$C_6$ alkyl), an optionally substituted —($CH_2$)$_n$NHC(O)—$R_1$, an optionally substituted —($CH_2$)$_n$C(O)—$NR_1R_2$, an optionally substituted —($CH_2$)$_n$OC(O)—$NR_1R_2$, —($CH_2O$)$_n$H, an optionally substituted —($CH_2$)$_n$OC(O)—($C_1$-$C_6$ alkyl), an optionally substituted —($CH_2$)$_n$C(O)—O—($C_1$-$C_6$ alkyl), an optionally substituted —($CH_2O$)$_n$COOH, an optionally substituted —($OCH_2$)$_n$O—($C_1$-$C_6$ alkyl), an optionally substituted —($CH_2O$)$_n$C(O)—($C_1$-$C_6$ alkyl), an optionally substituted —($OCH_2$)$_n$NHC(O)—$R_1$, an optionally substituted —($CH_2O$)$_n$C(O)—$NR_1R_2$, —($CH_2CH_2O$)$_n$H, an optionally substituted —($CH_2CH_2O$) COOH, an optionally substituted —($OCH_2CH_2$)$_n$O—($C_1$-$C_6$ alkyl), an optionally substituted —($CH_2CH_2O$)$_n$C(O)—($C_1$-$C_6$ alkyl), an optionally substituted —($OCH_2CH_2$)$_n$NHC(O)—$R_1$, an optionally substituted —($CH_2CH_2O$)$_n$C(O)—$NR_1R_2$, an optionally substituted —$SO_2R_S$, an optionally substituted $S(O)R_S$, $NO_2$, CN or halogen (F, Cl, Br, I, preferably F or Cl);

$R_1$ and $R_2$ of ULM-g are each independently H or a $C_1$-$C_6$ alkyl group which may be optionally substituted with one or two hydroxyl groups or up to three halogen groups (preferably fluorine);

$R_S$ of ULM-g is a $C_1$-$C_6$ alkyl group, an optionally substituted aryl, heteroaryl or heterocycle group or a —($CH_2$)$_m NR_1R_2$ group;

X and X' of ULM-g are each independently C=O, C=S, —S(O), $S(O)_2$, (preferably X and X' are both C=O);

$R^{2'}$ of ULM-g is an optionally substituted —($CH_2$)$_n$— (C=O)$_u$($NR_1$)$_v$($SO_2$)$_w$alkyl group, an optionally substituted —($CH_2$)$_n$—(C=O)$_u$($NR_1$)$_v$($SO_2$)$_w NR_{1N}R_{2N}$ group, an optionally substituted —($CH_2$)$_n$—(C=O)$_u$ ($NR_1$)$_v$($SO_2$)$_w$-Aryl, an optionally substituted —($CH_2$)$_n$—(C=O)$_u$($NR^1$)$_v$($SO_2$)$_w$-Heteroaryl, an optionally substituted —($CH_2$)$_n$—(C=O)$_v NR_1$($SO_2$)-Heterocycle, an optionally substituted —$NR^1$—($CH_2$) $_n$—C(O)$_u$($NR_1$)$_v$($SO_2$)$_n$-alkyl, an optionally substituted —$NR^1$—($CH_2$)$_n$—C(O)$_u$($NR_1$)$_v$($SO_2$)$_w$—$NR_{1N}R_{2N}$, an optionally substituted —$NR^1$—($CH_2$)$_n$—C(O)$_u$($NR_1$)$_v$($SO_2$)$_w$—$NR_1C(O)R_{1N}$, an optionally substituted —$NR^1$—($CH_2$)$_n$—(CO)$_u$($NR_1$)$_v$($SO_2$)-Aryl, an optionally substituted —$NR^1$—($CH_2$)$_n$—(C=O)$_u$($NR_1$)$_v$ ($SO_2$)$_w$-Heteroaryl or an optionally substituted —$NR^1$—($CH_2$)$_n$—(C=O)$_u$($NR_1$)$_v$($SO_2$)$_w$-Heterocycle, an optionally substituted —$X^{R2'}$-alkyl group; an optionally substituted —$X^{R2'}$-Aryl group; an optionally substituted —$X^{R2'}$-Heteroaryl group; an optionally substituted —$X^{2'}$-Heterocycle group; an optionally substituted;

$R^{3'}$ of ULM-g is an optionally substituted alkyl, an optionally substituted —($CH_2$)$_n$—(O)$_u$($NR_1$)$_v$($SO_2$)$_w$-alkyl, an optionally substituted —($CH_2$)$_n$—C(O)$_u$ ($NR_1$)$_v$($SO_2$)$_w$—$NR_{1N}R_{2N}$, an optionally substituted —($CH_2$)$_n$—C(O)$_u$($NR_1$)$_v$($SO_2$)$_w$—$NR_1C(O)R_{1N}$, an optionally substituted —($CH_2$)$_n$—C(O)$_u$($NR^1$)$^v$ ($SO_2$)$_w$—C(O)$NR_1R_2$, an optionally substituted —($CH_2$)$_n$—C(O)$_u$($NR_1$)$_v$($SO_2$)$_w$-Aryl, an optionally substituted —($CH_2$)$_n$—C(O)$_u$($NR_1$)$_v$($SO_2$)$_w$-Heteroaryl, an optionally substituted —($CH_2$)$_n$—C(O)$_u$ ($NR_1$)$_v$($SO_2$)$_w$-Heterocycle, an optionally substituted —$NR^1$—($CH_2$)—C(O)$_u$($NR_1$)$_v$($SO_2$)$_w$-alkyl, an optionally substituted —$NR^1$—($CH_2$)$_n$—C(O)$_u$($NR_1$)$_v$ ($SO_2$)$_w$— $NR_{1N}R_{2N}$, an optionally substituted —$NR^1$—($CH_2$)$_n$—C(O)$_u$($NR_1$)$_v$($SO_2$)$_w$—$NR_1C(O)$ $R_{1N}$, an optionally substituted —$NR^1$—($CH_2$)$_n$— C(O)$_u$($NR_1$)$_v$($SO_2$)$_w$-Aryl, an optionally substituted —$NR^1$—($CH_2$)$_n$—C(O)$_u$($NR_1$)$_v$($SO_2$)$_w$-Heteroaryl, an optionally substituted —$NR^1$—($CH_2$)$_n$—C(O)$_u$($NR_1$)$_v$ ($SO_2$)$_w$-Heterocycle, an optionally substituted —O— ($CH_2$)$_n$—(C=O)$_u$($NR_1$)$_v$($SO_2$)$_n$-alkyl, an optionally substituted —O—($CH_2$)$_n$—(C=O)$_u$($NR_1$)$_v$($SO_2$)$_w$— $NR^1NR_{2N}$, an optionally substituted —O—($CH_2$)n-(C=O)$_u$($NR^1$)$_v$($SO_2$)$_w$—$NR_1C(O)R_{1N}$, an optionally substituted —O—($CH_2$)$_n$—(C=O)$_u$($NR_1$)$_v$($SO_2$)$_w$-Aryl, an optionally substituted —O—($CH_2$)$_n$—(C=O)$_u$($NR_1$)$_v$($SO_2$)$_w$-Heteroaryl or an optionally substituted —O—($CH_2$)$_n$—(C=O)$_u$($NR_1$)$_v$($SO_2$)$_w$-Heterocycle; —($CH_2$)$_n$—(V)$_{n'}$—($CH_2$)$_n$—(V)$_{n'}$-alkyl group, an optionally substituted —($CH_2$)$_n$—(V)$_{n'}$— ($CH_2$)$_n$—(V)$_{n'}$-Aryl group, an optionally substituted —($CH_2$)$_n$—(V)$_{n'}$—($CH_2$)$_n$—(V)$_{n'}$-Heteroaryl group, an optionally substituted —($CH_2$)$_n$—(V)$_{n'}$—($CH_2$)$_n$— (V)$_{n'}$-Heterocycle group, an optionally substituted —($CH_2$)$_n$—N($R_1$,)(C=O)$_{m'}$—(V)$_{n'}$-alkyl group, an optionally substituted —($CH_2$)$_n$—N($R_1$,)(C=O)$_{m'}$— (V)$_{n'}$-Aryl group, an optionally substituted —($CH_2$)$_n$— N($R_1$,)(C=O)$_{m'}$—(V)$_{n'}$-Heteroaryl group, an optionally substituted —($CH_2$)$_n$—N($R_1$,)(C=O)$_{m'}$—(V)$_{n'}$-Heterocycle group, an optionally substituted —$X^{R3'}$-alkyl group; an optionally substituted —$X^{R3'}$-Aryl group; an optionally substituted —$X_{R3'}$-Heteroaryl group; an optionally substituted —$X^{R3'}$-Heterocycle group; an optionally substituted;

$R_{1N}$ and $R_{2N}$ of ULM-g are each independently H, $C_1$-$C_6$ alkyl which is optionally substituted with one or two hydroxyl groups and up to three halogen groups or an optionally substituted —($CH_2$)$_n$-Aryl, —($CH_2$)$_n$-Heteroaryl or —($CH_2$)$_n$-Heterocycle group;

V of ULM-g is O, S or $NR_1$;

$R_1$ of ULM-g is the same as above;

$R^1$ and $R_1$, of ULM-g are each independently H or a $C_1$-$C_3$ alkyl group;

$X^{R2'}$ and $X^{R3'}$ of ULM-g are each independently an optionally substituted $—(CH_2)_n—$, $—(CH_2)_n—CH(X_v)=CH(X_v)—$ (cis or trans), $—(CH_2)_n—CH=CH—$, $—(CH_2CH_2O)_n—$ or a $C_3$-$C_6$ cycloalkyl group, where $X_v$ is H, a halo or a $C_1$-$C_3$ alkyl group which is optionally substituted;

each m of ULM-g is independently 0, 1, 2, 3, 4, 5, 6;
each m' of ULM-g is independently 0 or 1;
each n of ULM-g is independently 0, 1, 2, 3, 4, 5, 6;
each n' of ULM-g is independently 0 or 1;
each u of ULM-g is independently 0 or 1;
each v of ULM-g is independently 0 or 1;
each w of ULM-g is independently 0 or 1; and
any one or more of $R^{1'}$, $R^{2'}$, $R^{3'}$, X and X' of ULM-g is optionally modified to be covalently bonded to the PTM group through a linker group when PTM is not ULM', or when PTM is ULM', any one or more of $R^{1'}$, $R^{2'}$, $R^{3'}$, X and X' of each of ULM and ULM' are optionally modified to be covalently bonded to each other directly or through a linker group, or a pharmaceutically acceptable salt, stereoisomer, solvate or polymorph thereof.

In any of the aspects or embodiments described herein, the ULM and when present, ULM', are each independently a group according to the chemical structure:

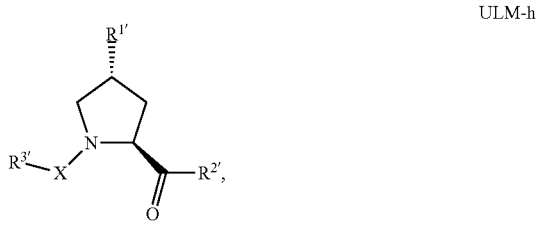

ULM-h wherein:
each of $R^{1'}$, $R^{2'}$ and $R^{3'}$ of ULM-h are the same as above and X is C=O, C=S, —S(O) group or a $S(O)_2$ group, more preferably a C=O group, and any one or more of $R^{1'}$, $R^{2'}$ and $R^{3'}$ of ULM-h are optionally modified to bind a linker group to which is further covalently bonded to the PTM group when PTM is not ULM', or when PTM is ULM', any one or more of $R^{1'}$, $R^{2'}$, $R^{3'}$ of each of ULM and ULM' are optionally modified to be covalently bonded to each other directly or through a linker group, or a pharmaceutically acceptable salt, enantiomer, diastereomer, solvate or polymorph thereof.

In any of the aspects or embodiments described herein, the ULM, and when present, ULM', are each independently according to the chemical structure:

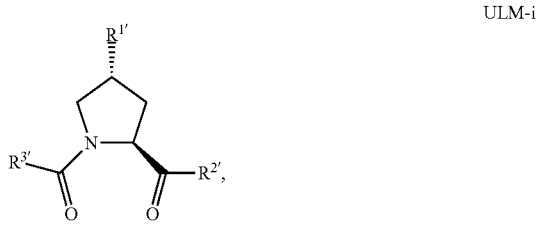

ULM-i wherein:
any one or more of $R^{1'}$, $R^{2'}$ and $R^{3'}$ of ULM-1 are optionally modified to bind a linker group to which is further covalently bonded to the PTM group when PTM is not ULM', or when PTM is ULM', any one or more of $R^{1'}$, $R^{2'}$, $R^{3'}$ of each of ULM and ULM' are optionally modified to be covalently bonded to each other directly or through a linker group, or
a pharmaceutically acceptable salt, enantiomer, diastereomer, solvate or polymorph thereof.

In further preferred aspects of the disclosure, $R^{1'}$ of ULM-g through ULM-i is preferably a hydroxyl group or a group which may be metabolized to a hydroxyl or carboxylic group, such that the compound represents a prodrug form of an active compound. Exemplary preferred $R^{1'}$ groups include, for example, $—(CH_2)_nOH$, $(CH_2)_n—O—(C_1-C_6)$alkyl group, $—(CH_2)_nCOOH$, $—(CH_2O)_nH$, an optionally substituted $—(CH_2)_nOC(O)—(C_1-C_6$ alkyl), or an optionally substituted $—(CH_2)_nC(O)—O—(C_1-C_6$ alkyl), wherein n is 0 or 1. Where $R^{1'}$ is or contains a carboxylic acid group, a hydroxyl group or an amine group, the hydroxyl group, carboxylic acid group or amine (each of which may be optionally substituted), may be further chemically modified to provide a covalent link to a linker group to which the PTM group (including a ULM' group) is bonded;

X and X', where present, of ULM-g and ULM-h are preferably a C=, C=S, —S(O) group or a $S(O)_2$ group, more preferably a C=O group;

$R^{2'}$ of ULM-g through ULM-i is preferably an optionally substituted $—NR^1$-T-Aryl, an optionally substituted $—NR^1$-T-Heteroaryl group or an optionally substituted $—NR^1$-T-Heterocycle, where $R^1$ is H or $CH_3$, preferably H and T is an optionally substituted $—(CH_2)_n—$ group, wherein each one of the methylene groups may be optionally substituted with one or two substituents, preferably selected from halogen, an amino acid sidechain as otherwise described herein or a $C_1$-$C_3$ alkyl group, preferably one or two methyl groups, which may be optionally substituted; and n is 0 to 6, often 0, 1, 2 or 3, preferably 0 or 1. Alternatively, T may also be a $—(CH_2O)_n—$ group, a $—(OCH_2)_n—$ group, a $—(CH_2CH_2O)_n—$ group, a $—(OCH_2CH_2)_n—$ group, all of which groups are optionally substituted.

Preferred Aryl groups for $R^{2'}$ of ULM-g through ULM-i include optionally substituted phenyl or naphthyl groups, preferably phenyl groups, wherein the phenyl or naphthyl group is optionally connected to a PTM (including a ULM' group) via a linker group and/or optionally substituted with a halogen (preferably F or Cl), an amine, monoalkyl- or dialkyl amine (preferably, dimethylamine), F, Cl, OH, COOH, $C_1$-$C_6$ alkyl, preferably $CH_3$, $CF_3$, OMe, $OCF_3$, $NO_2$, or CN group (each of which may be substituted in ortho-, meta- and/or para- positions of the phenyl ring, preferably para-), an optionally substituted phenyl group (the phenyl group itself is optionally connected to a PTM group, including a ULM' group, via a linker group), and/or optionally substituted with at least one of F, Cl, OH, COOH, $CH_3$, $CF_3$, OMe, $OCF_3$, $NO_2$, or CN group (in ortho-, meta- and/or para- positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methyl-substituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo-(preferably, F) or methylsubstituted pyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, an optionally substituted group according to the chemical structure:

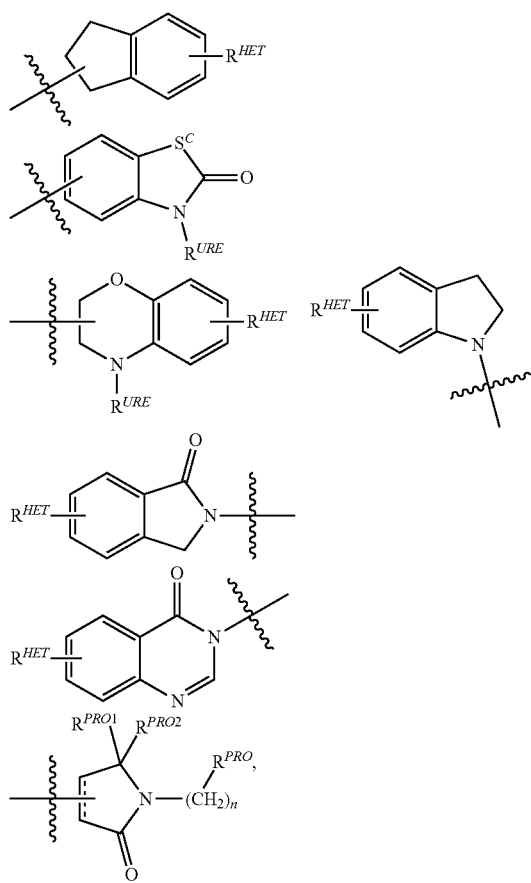

wherein:
$S^c$ of ULM-g through ULM-i is $CHR^{SS}$, $NR^{URE}$, or O;
$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);
$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);
$R^{URE}$ of ULM-g through ULM-i is H, a $C_1$-$C_6$ alkyl (preferably H or $C_1$-$C_3$ alkyl) or a —C(O)($C_1$-$C_6$ alkyl) each of which groups is optionally substituted with one or two hydroxyl groups or up to three halogen, preferably fluorine groups, or an optionally substituted phenyl group, an optionally substituted heteroaryl, or an optionally substituted heterocycle, preferably for example piperidine, morpholine, pyrrolidine, tetrahydrofuran);
$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrolidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;
$R^{PRO1}$ and $R^{PRO2}$ of ULM-g through ULM-i are each independently H, an optionally substituted $C_1$-$C_3$ alkyl group or together form a keto group; and
each n of ULM-g through ULM-i is independently 0, 1, 2, 3, 4, 5, or 6 (preferably 0 or 1), or an optionally substituted heterocycle, preferably tetrahydrofuran, tetrahydrothiene, piperidine, piperazine or morpholine (each of which groups when substituted, are preferably substituted with a methyl or halo (F, Br, Cl), each of which groups may be optionally attached a PTM group (including a ULM' group) via a linker group.

In certain preferred aspects,

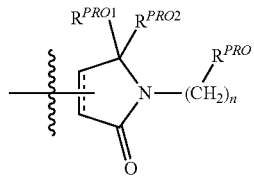

of ULM-g through ULM-i is a

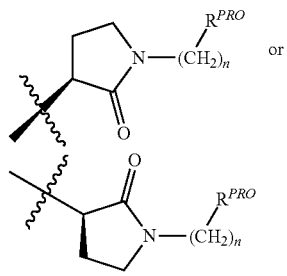

group,
where $R^{PRO}$ and n of ULM-g through ULM-i are the same as above.

Preferred heteroaryl groups for $R^{2'}$ of ULM-g through ULM-i include an optionally substituted quinoline (which may be attached to the pharmacophore or substituted on any carbon atom within the quinoline ring), an optionally substituted indole, an optionally substituted indolizine, an optionally substituted azaindolizine, an optionally substituted benzofuran, including an optionally substituted benzofuran, an optionally substituted isoxazole, an optionally substituted thiazole, an optionally substituted isothiazole, an optionally substituted thiophene, an optionally substituted pyridine (2-, 3-, or 4-pyridine), an optionally substituted imidazole, an optionally substituted pyrrole, an optionally substituted diazole, an optionally substituted triazole, a tetrazole, an optionally substituted oximidazole, or a group according to the chemical structure:

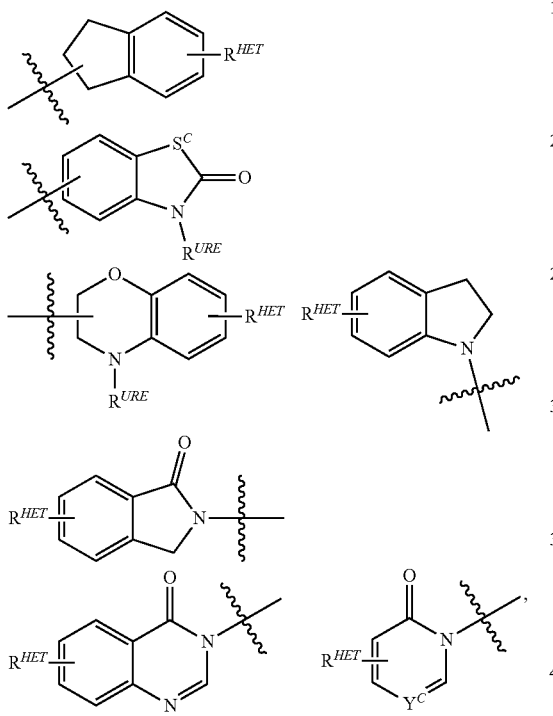

wherein:
$S^c$ of ULM-g through ULM-i is $CHR^{SS}$, $NR^{URE}$, or O;
$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ of ULM-g through ULM-i is H or a $C_1$-$C_6$ alkyl group (preferably $C_1$-$C_3$ alkyl);
$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);
$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and
$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl), each of which groups may be optionally connected to a PTM group (including a ULM' group) via a linker group.

Preferred heterocycle groups for $R^2$ of ULM-g through ULM-i include tetrahydrofuran, tetrahydrothiene, tetrahydroquinoline, piperidine, piperazine, pyrrolidine, morpholine, oxane or thiane, each of which groups may be optionally substituted, or a group according to the chemical structure:

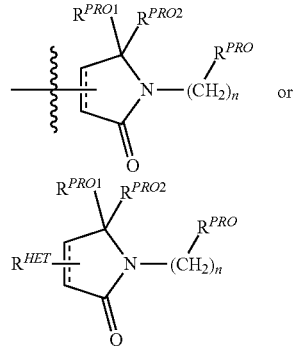

preferably, a

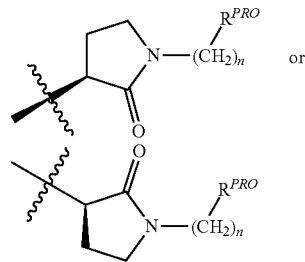

group,
wherein:
$R^{PRO}$ of ULM-g through ULM-i is H, optionally substituted $C_1$-$C_6$ alkyl or an optionally substituted aryl, heteroaryl or heterocyclic group;
$R^{PRO1}$ and $R^{PRO2}$ of ULM-g through ULM-i are each independently H, an optionally substituted $C_1$-$C_3$ alkyl group or together form a keto group and
each n of ULM-g through ULM-i is independently 0, 1, 2, 3, 4, 5, or 6 (often 0 or 1), each of which groups may be optionally connected to a PTM group (including a ULM' group) via a linker group.
Preferred $R^{2'}$ substituents of ULM-g through ULM-i also include specifically (and without limitation to the specific compound disclosed) the $R^{2'}$ substituents which are found in the identified compounds disclosed herein (which includes the specific compounds which are disclosed in the present specification, and the figures which are attached hereto). Each of these $R^{2'}$ substituents may be used in conjunction with any number of $R^{3'}$ substituents which are also disclosed herein.

$R^{3'}$ of ULM-g through ULM-i is preferably an optionally substituted -T-Aryl, an optionally substituted-T-Heteroaryl, an optionally substituted -T-Heterocycle, an optionally substituted-$NR^1$-T-Aryl, an optionally substituted —$NR^1$-T-Heteroaryl or an optionally substituted-$NR^1$-T-Heterocycle, where $R^1$ is H or a $C_1$-$C_3$ alkyl group, preferably H or $CH_3$, T is an optionally substituted —$(CH_2)_n$— group, wherein each one of the methylene groups may be optionally substituted with one or two substituents, preferably selected from halogen, a $C_1$-$C_3$ alkyl group or the sidechain of an amino acid as otherwise described herein, preferably methyl, which may be optionally substituted; and n is 0 to 6, often 0, 1, 2, or 3 preferably 0 or 1. Alternatively, T may also be a —$(CH_2O)_n$— group, a —$(OCH_2)_n$— group, a —$(CH_2CH_2O)_n$— group, a —$(OCH_2CH_2)_n$— group, each of which groups is optionally substituted.

Preferred aryl groups for $R^{3'}$ of ULM-g through ULM-i include optionally substituted phenyl or naphthyl groups, preferably phenyl groups, wherein the phenyl or naphthyl group is optionally connected to a PTM group (including a ULM' group) via a linker group and/or optionally substituted a halogen (preferably F or Cl), an amine, monoalkyl- or dialkyl amine (preferably, dimethylamine), an amido group (preferably a —$(CH_2)_m$—$NR_1C(O)R_2$ group where m, $R_1$ and R2 are the same as above), a halo (often F or Cl), OH, $CH_3$, CF3, OMe, $OCF_3$, $NO_2$, CN or a $S(O)_2R_S$ group ($R_S$ is a $C_1$-$C_6$ alkyl group, an optionally substituted aryl, heteroaryl or heterocycle group or a —$(CH_2)_mNR_1R_2$ group), each of which may be substituted in ortho-, meta- and/or para- positions of the phenyl ring, preferably para-), or an Aryl (preferably phenyl), Heteroaryl or Heterocycle. Preferably said substituent phenyl group is an optionally substituted phenyl group (i.e., the substituent phenyl group itself is preferably substituted with at least one of F, Cl, OH, SH, COOH, $CH_3$, $CF_3$, OMe, $OCF_3$, $NO_2$, CN or a linker group to which is attached a PTM group (including a ULM' group), wherein the substitution occurs in ortho-, meta- and/or para- positions of the phenyl ring, preferably para-), or a naphthyl group, which may be optionally substituted including as described above, an optionally substituted heteroaryl (preferably an optionally substituted isoxazole including a methylsubstituted isoxazole, an optionally substituted oxazole including a methylsubstituted oxazole, an optionally substituted thiazole including a methyl substituted thiazole, an optionally substituted pyrrole including a methylsubstituted pyrrole, an optionally substituted imidazole including a methylimidazole, a benzylimidazole or methoxybenzylimidazole, an oximidazole or methyloximidazole, an optionally substituted diazole group, including a methyldiazole group, an optionally substituted triazole group, including a methylsubstituted triazole group, a pyridine group, including a halo-(preferably, F) or methylsubstituted pyridine group or an oxapyridine group (where the pyridine group is linked to the phenyl group by an oxygen) or an optionally substituted heterocycle (tetrahydrofuran, tetrahydrothiophene, pyrrolidine, piperidine, morpholine, piperazine, tetrahydroquinoline, oxane or thiane. Each of the aryl, heteroaryl or heterocyclic groups may be optionally connected to a PTM group (including a ULM' group) with a linker group.

Preferred Heteroaryl groups for $R^3$ of ULM-g through ULM-i include an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —$(CH_2)_m$—O—$C_1$-$C_6$ alkyl group or an optionally substituted —$(CH_2)_m$—C(O)—O—$C_1$-$C_6$ alkyl group), an optionally substituted pyridine (2-, 3, or 4-pyridine) or a group according to the chemical structure:

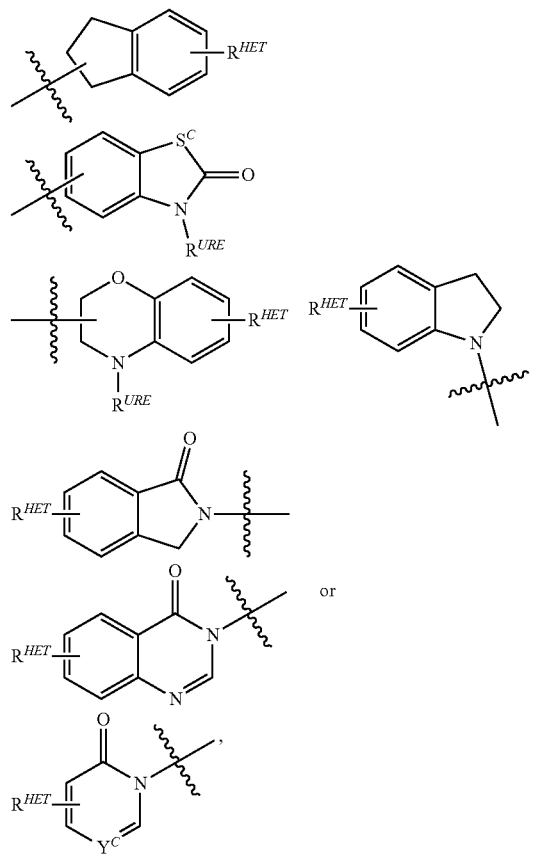

wherein:
$S^c$ of ULM-g through ULM-i is $CHR^{SS}$, $NR^{URE}$, or O;
$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a-C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl). Each of said heteroaryl groups may be optionally connected to a PTM group (including a ULM' group) via a linker group.

Preferred heterocycle groups for $R^{3'}$ of ULM-g through ULM-i include tetrahydroquinoline, piperidine, piperazine, pyrrolidine, morpholine, tetrahydrofuran, tetrahydrothiophene, oxane and thiane, each of which groups may be optionally substituted or a group according to the chemical structure:

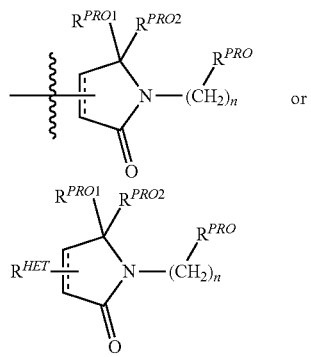

preferably, a

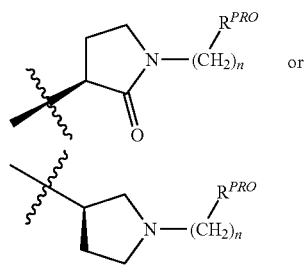

wherein:
$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrolidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group, and each n of ULM-g through ULM-i is 0, 1, 2, 3, 4, 5, or 6 (preferably 0 or 1), wherein each of said Heterocycle groups may be optionally connected to a PTM group (including a ULM' group) via a linker group.

Preferred $R^{3'}$ substituents of ULM-g through ULM-i also include specifically (and without limitation to the specific compound disclosed) the $R^{3'}$ substituents which are found in the identified compounds disclosed herein (which includes the specific compounds which are disclosed in the present specification, and the figures which are attached hereto). Each of these $R^{3'}$ substituents may be used in conjunction with any number of $R^{2'}$ substituents, which are also disclosed herein.

In certain alternative preferred embodiments, $R^{2'}$ of ULM-g through ULM-i is an optionally substituted —$NR_1$—$X^{R2'}$-alkyl group, —$NR_1$—$X^{R2'}$-Aryl group; an optionally substituted —$NR_1$—$X^{R2'}$-HET, an optionally substituted —$NR_1$—$X^{R2'}$-Aryl-HET or an optionally substituted —$NR_1$—$X^{R2'}$-HET-Aryl, wherein:

$R_1$ of ULM-g through ULM-i is H or a $C_1$-$C_3$ alkyl group (preferably H);

$X^{R2'}$ of ULM-g through ULM-i is an optionally substituted —$CH_2)_n$—, —$CH_2)_n$—CH($X_v$)=CH($X_v$)— (cis or trans), —$(CH_2)_n$—CH≡CH—, —($CH_2CH_2O$)— or a $C_3$-$C_6$ cycloalkyl group; and $X_v$ of ULM-g through ULM-i is H, a halo or a $C_1$-$C_3$ alkyl group which is optionally substituted with one or two hydroxyl groups or up to three halogen groups;

Alkyl of ULM-g through ULM-i is an optionally substituted C1-$C_{10}$ alkyl (preferably a $C_1$-$C_6$ alkyl) group (in certain preferred embodiments, the alkyl group is end-capped with a halo group, often a Cl or Br);

Aryl of ULM-g through ULM-i is an optionally substituted phenyl or naphthyl group (preferably, a phenyl group); and HET of ULM-g through ULM-i is an optionally substituted oxazole, isoxazole, thiazole, isothiazole, imidazole, diazole, oximidazole, pyrrole, pyrolidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl) or a group according to the chemical structure:

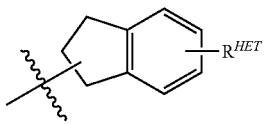

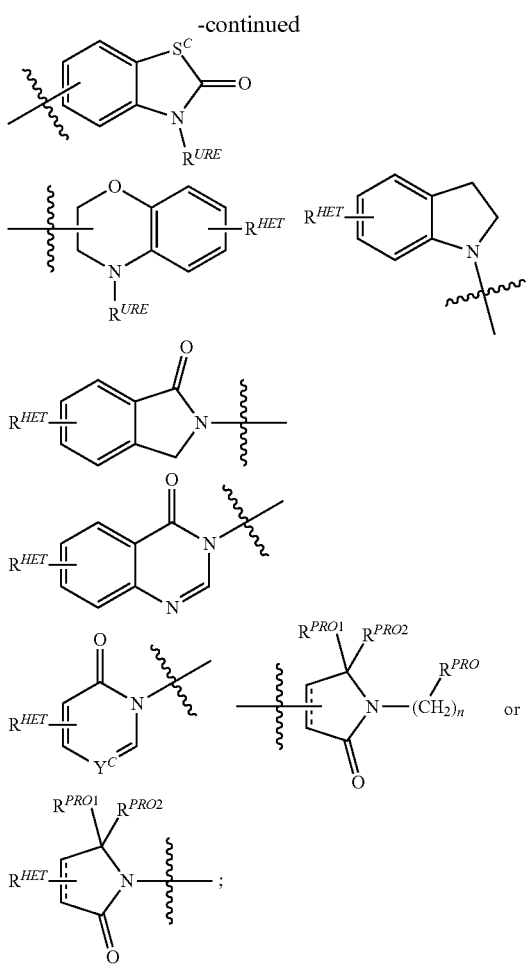

$S^C$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—R, where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrolidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group, and each n of ULM-g through ULM-i is independently 0, 1, 2, 3, 4, 5, or 6 (preferably 0 or 1).

Each of said groups may be optionally connected to a PTM group (including a ULM' group) via a linker group.

In certain alternative preferred embodiments of the present disclosure, $R^{3'}$ of ULM-g through ULM-i is an optionally substituted —$(CH_2)_n$—$(V)_{n'}$—$(CH_2)_n$—$(V)_{n'}$—$R^{S3'}$ group, an optionally substituted-$(CH_2)_n$—N($R_{1'}$)(C=O)$_m$—$(V)_{n'}$—$R^{S3'}$ group, an optionally substituted —$X^{R3'}$-alkyl group, an optionally substituted —$X^{R3'}$-Aryl group; an optionally substituted —$X^{R3'}$-HET group, an optionally substituted —$X^{R3'}$-Aryl-HET group or an optionally substituted —$X^{R3'}$-HET-Aryl group, wherein:

$R^{S3'}$ is an optionally substituted alkyl group ($C_1$-$C_{10}$, preferably $C_1$-$C_6$ alkyl), an optionally substituted Aryl group or a HET group;

$R_{1'}$ is H or a $C_1$-$C_3$ alkyl group (preferably H);

V is O, S or $NR_{1'}$;

$X^{R3'}$ is —$(CH_2)_n$—, —$(CH_2CH_2O)_n$—, —$(CH_2)_n$—CH$(X_v)$=CH$(X_v)$— (cis or trans), —$(CH_2)_n$—CH≡CH—, or a $C_3$-$C_6$ cycloalkyl group, all optionally substituted;

$X_v$ is H, a halo or a $C_1$-$C_3$ alkyl group which is optionally substituted with one or two hydroxyl groups or up to three halogen groups;

Alkyl is an optionally substituted $C_1$-$C_{10}$ alkyl (preferably a $C_1$-$C_6$ alkyl) group (in certain preferred embodiments, the alkyl group is end-capped with a halo group, often a Cl or Br);

Aryl is an optionally substituted phenyl or napthyl group (preferably, a phenyl group); and HET is an optionally substituted oxazole, isoxazole, thiazole, isothiazole, imidazole, diazole, oximidazole, pyrrole, pyrolidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl), or a group according to the chemical structure:

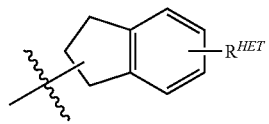

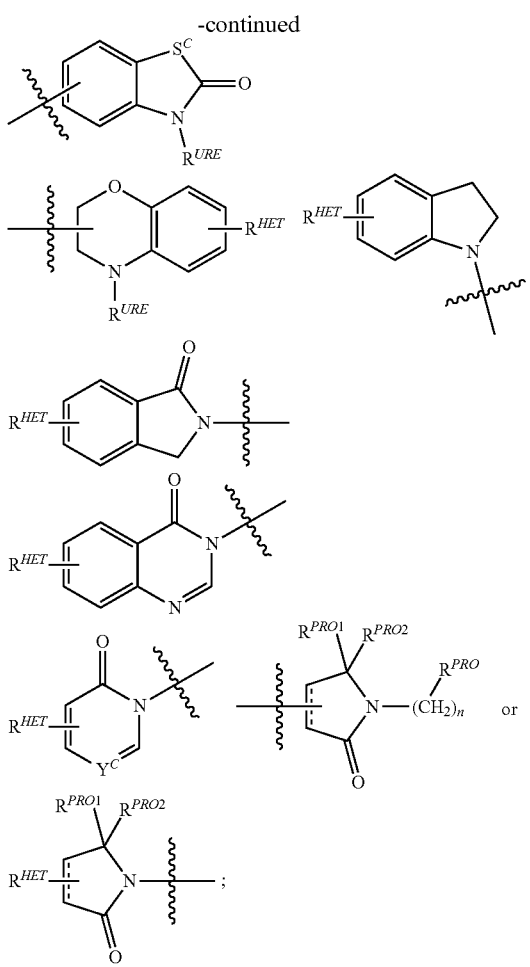

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—R, where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrolidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group;

each n of ULM-g through ULM-i is independently 0, 1, 2, 3, 4, 5, or 6 (preferably 0 or 1);

each m' of ULM-g through ULM-i is 0 or 1; and each n' of ULM-g through ULM-i is 0 or 1;

wherein each of said compounds, preferably on the alkyl, Aryl or Het groups, is optionally connected to a PTM group (including a ULM' group) via a linker group.

In alternative embodiments, $R^{3'}$ of ULM-g through ULM-i is —$(CH_2)_n$-Aryl, —$(CH_2CH_2O)_n$-Aryl, —$(CH_2)_n$-HET or —$(CH_2CH_2O)_n$-HET, wherein:

said Aryl of ULM-g through ULM-i is phenyl which is optionally substituted with one or two substitutents, wherein said substituent(s) is preferably selected from —$(CH_2)_n$OH, $C_1$-$C_6$ alkyl which itself is further optionally substituted with CN, halo (up to three halo groups), OH, —$(CH_2)_nO(C_1$-$C_6)$alkyl, amine, mono- or di-($C_1$-$C_6$ alkyl) amine wherein the alkyl group on the amine is optionally substituted with 1 or 2 hydroxyl groups or up to three halo (preferably F, Cl) groups, or said Aryl group of ULM-g through ULM-i is substituted with —$(CH_2)_n$OH, —$(CH_2)_n$—O—($C_1$-$C_6$)alkyl, —$(CH_2)_n$—O—$(CH_2)_n$—($C_1$-$C_6$)alkyl, —$(CH_2)_n$—C(O)($C_0$-$C_6$) alkyl, —$(CH_2)_n$—C(O)O($C_0$-$C_6$)alkyl, —$(CH_2)_n$—OC(O)($C_0$-$C_6$)alkyl, amine, mono- or di-($C_1$-$C_6$ alkyl) amine wherein the alkyl group on the amine is optionally substituted with 1 or 2 hydroxyl groups or up to three halo (preferably F, Cl) groups, CN, $NO_2$, an optionally substituted —$(CH_2)_n$—$(V)_{m'}$—$CH_2)_n$—$(V)_{m'}$—($C_1$-$C_6$)alkyl group, a —$(V)_{m'}$—$(CH_2CH_2O)_n$—$R^{PEG}$ group where V is O, S or $NR_{1'}$, $R_{1'}$ is H or a $C_1$-$C_3$ alkyl group (preferably H) and $R^{PEG}$ is H or a $C_1$-$C_6$ alkyl group which is optionally substituted (including being optionally substituted with a carboxyl group), or said Aryl group of ULM-g through ULM-i is optionally substituted with a heterocycle, including a heteroaryl, selected from the group consisting of oxazole, isoxazole, thiazole, isothiazole, imidazole, diazole, oximidazole, pyrrole, pyrolidine, furan, dihydrofuran, tetrahydrofuran, thiene, dihydrothiene, tetrahydrothiene, pyridine, piperidine, piperazine, morpholine, quinoline, benzofuran, indole, indolizine, azaindolizine, (when substituted each preferably substituted with a $C_1$-$C_3$ alkyl group, preferably methyl or a halo group, preferably F or Cl), or a group according to the chemical structure:

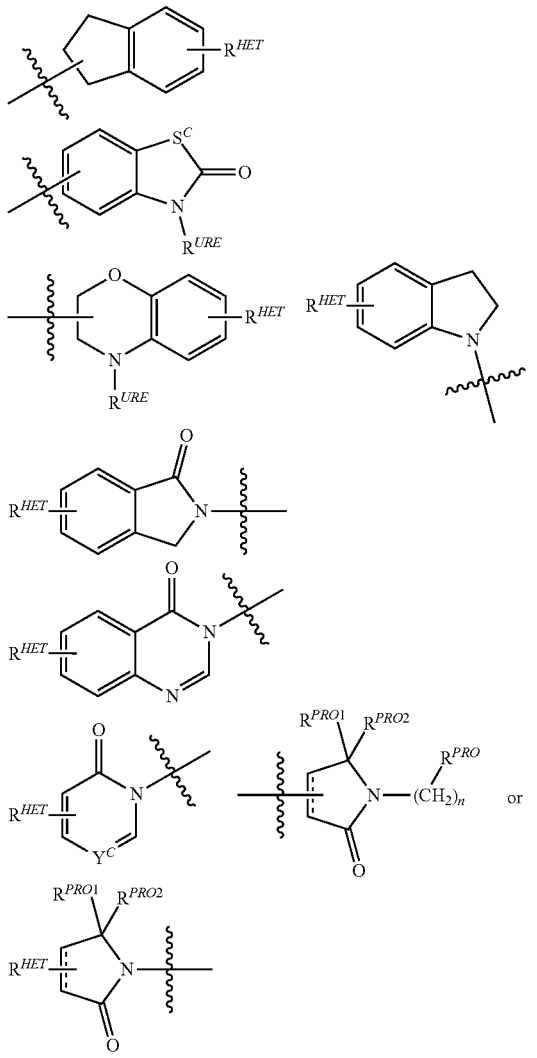

$S^c$ of ULM-g through ULM-i is $CHR^{SS}$, $NR^{URE}$, or O;
$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);
$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);
$R^{URE}$ of ULM-g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;
$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);
$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrolidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;
$R^{PRO1}$ and $R^{PRO2}$ of ULM-g through ULM-i are each independently H, an optionally substituted $C_1$-$C_3$ alkyl group or together form a keto group;
HET of ULM-g through ULM-i is preferably oxazole, isoxazole, thiazole, isothiazole, imidazole, diazole, oximidazole, pyrrole, pyrolidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine, or a group according to the chemical structure:

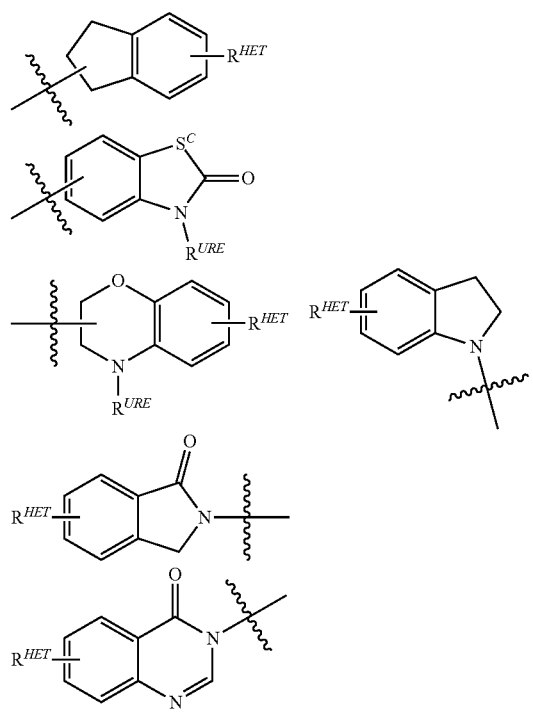

-continued

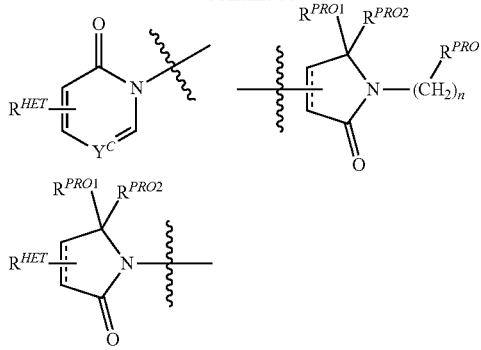

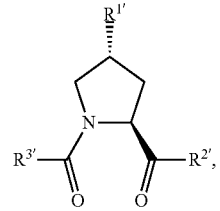 or $S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a-C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl, heteroaryl or heterocyclic group;

$R^{PRO1}$ and $R^{PRO2}$ of ULM-g through ULM-i are each independently H, an optionally substituted $C_1$-$C_3$ alkyl group or together form a keto group;

each m' of ULM-g through ULM-i is independently 0 or 1; and each n of ULM-g through ULM-i is independently 0, 1, 2, 3, 4, 5, or 6 (preferably 0 or 1), wherein each of said compounds, preferably on said Aryl or HET groups, is optionally connected to a PTM group (including a ULM' group) with a linker group.

In still additional embodiments, preferred compounds include those according to the chemical structure:

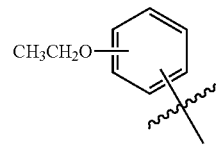

ULM-i wherein:

$R^{1'}$ of ULM-i is OH or a group which is metabolized in a patient or subject to OH;

$R^{2'}$ of ULM-i is a —NH—$CH_2$-Aryl-HET (preferably, a phenyl linked directly to a methyl substituted thiazole);

$R^{3'}$ of ULM-i is a —$CHR^{CR3'}$—NH—C(O)—$R^{3P1}$ group or a —$CHR^{CR3'}$—$R^{3P2}$ group;

$R^{CR3'}$ of ULM-i is a $C_1$-$C_4$ alkyl group, preferably methyl, isopropyl or tert-butyl;

$R^{3P1}$ of ULM-i is $C_1$-$C_3$ alkyl (preferably methyl), an optionally substituted oxetane group (preferably methyl substituted, a —($CH_2$) $OCH_3$ group where n is 1 or 2 (preferably 2), or a

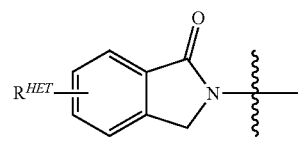

group (the ethyl ether group is preferably meta-substituted on the phenyl moiety), a morpholino group (linked to the carbonyl at the 2- or 3-position;

$R^{3P2}$ of ULM-i is a group;

Aryl of ULM-i is phenyl;

HET of ULM-i is an optionally substituted thiazole or isothiazole; and $R^{HET}$ of ULM-i is H or a halo group (preferably H);

or a pharmaceutically acceptable salt, stereoisomer, solvate or polymorph thereof, wherein each of said compounds is optionally connected to a PTM group (including a ULM' group) via a linker group.

In certain aspects, bifunctional compounds comprising a ubiquitin E3 ligase binding moiety (ULM), wherein ULM is a group according to the chemical structure:

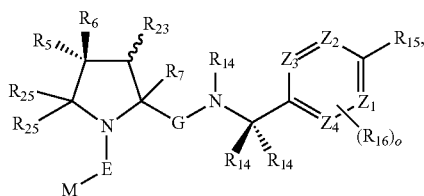
ULM-j wherein:
each $R_5$ and $R_6$ of ULM-j is independently OH, SH, or optionally substituted alkyl or $R_5$, $R_6$, and the carbon atom to which they are attached form a carbonyl;
$R_7$ of ULM-j is H or optionally substituted alkyl;
E of ULM-j is a bond, C=O, or C=S;
G of ULM-j is a bond, optionally substituted alkyl, —COOH or C=J;
J of ULM-j is O or N—$R_8$;
$R_8$ of ULM-j is H, CN, optionally substituted alkyl or optionally substituted alkoxy;
M of ULM-j is optionally substituted aryl, optionally substituted heteroaryl, optionally substituted heterocyclic or

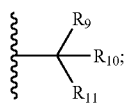

each $R_9$ and $R_{10}$ of ULM-j is independently H; optionally substituted alkyl, optionally substituted cycloalkyl, optionally substituted hydroxyalkyl, optionally substituted thioalkyl, a disulphide linked ULM, optionally substituted heteroaryl, or haloalkyl; or $R_9$, $R_{10}$, and the carbon atom to which they are attached form an optionally substituted cycloalkyl;
$R_{11}$ of ULM-j is optionally substituted heterocyclic, optionally substituted alkoxy, optionally substituted heteroaryl, optionally substituted aryl, or

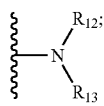

$R_{12}$ of ULM-j is H or optionally substituted alkyl;
$R_{13}$ of ULM-j is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl)carbamate,
each $R_{14}$ of ULM-j is independently H, haloalkyl, optionally substituted cycloalkyl, optionally substituted alkyl or optionally substituted heterocycloalkyl;
$R_{15}$ of ULM-j is H, optionally substituted heteroaryl, haloalkyl, optionally substituted aryl, optionally substituted alkoxy, or optionally substituted heterocyclyl;
each $R_{16}$ of ULM-j is independently halo, optionally substituted alkyl, optionally substituted haloalkyl, CN, or optionally substituted haloalkoxy;
each $R_{25}$ of ULM-j is independently H or optionally substituted alkyl; or both $R_{25}$ groups can be taken together to form an oxo or optionally substituted cycloalkyl group; $R_{23}$ of ULM-j is H or OH;
$Z_1$, $Z_2$, $Z_3$, and $Z_4$ of ULM-j are independently C or N; and o of ULM-j is 0, 1, 2, 3, or 4, or a pharmaceutically acceptable salt, stereoisomer, solvate or polymorph thereof.

In certain embodiments, wherein G of ULM-j is C=J, J is O, $R_7$ is H, each $R_{14}$ is H, and o is 0.

In certain embodiments, wherein G of ULM-j is C=J, J is O, $R_7$ is H, each $R_{14}$ is H, $R_{15}$ is optionally substituted heteroaryl, and o is 0. In other instances, E is C=O and M is

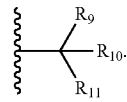

In certain embodiments, wherein E of ULM-j is C=O, $R_{11}$ is optionally substituted heterocyclic or

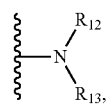

and M is

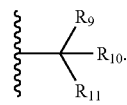

In certain embodiments, wherein E of ULM-j is C=O, M is

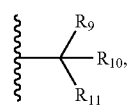

and $R_{11}$ is

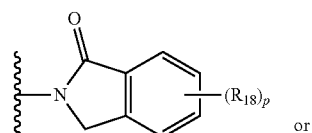 or

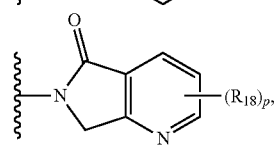

each $R_{18}$ is independently halo, optionally substituted alkoxy, cyano, optionally substituted alkyl, haloalkyl, or haloalkoxy; and p is 0, 1, 2, 3, or 4.

In certain embodiments, ULM and where present, ULM', are each independently a group according to the chemical structure:

ULM-k

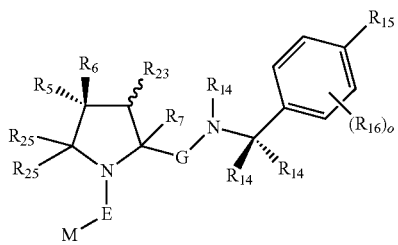

wherein:
G of ULM-k is C=J, J is O;
R$_7$ of ULM-k is H;
each R$_{14}$ of ULM-k is H;
o of ULM-k is 0;
R$_{15}$ of ULM-k is

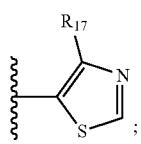

and
R$_{17}$ of ULM-k is H, halo, optionally substituted cycloalkyl, optionally substituted alkyl, optionally substituted alkenyl, and haloalkyl.

In other instances, R$_{17}$ of ULM-k is alkyl (e.g., methyl) or cycloalkyl (e.g., cyclopropyl).

In other embodiments, ULM and where present, ULM', are each independently a group according to the chemical structure:

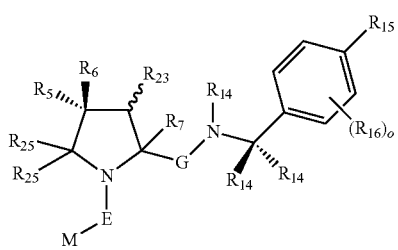

wherein:
G of ULM-k is C=J, J is O;
R$_7$ of ULM-k is H;
each R$_{14}$ of ULM-k is H;
o of ULM-k is 0; and
R$_{15}$ of ULM-k is selected from the group consisting of:

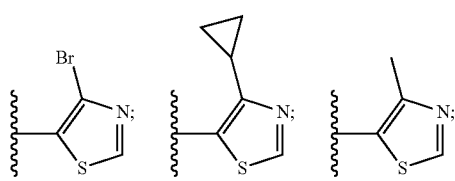

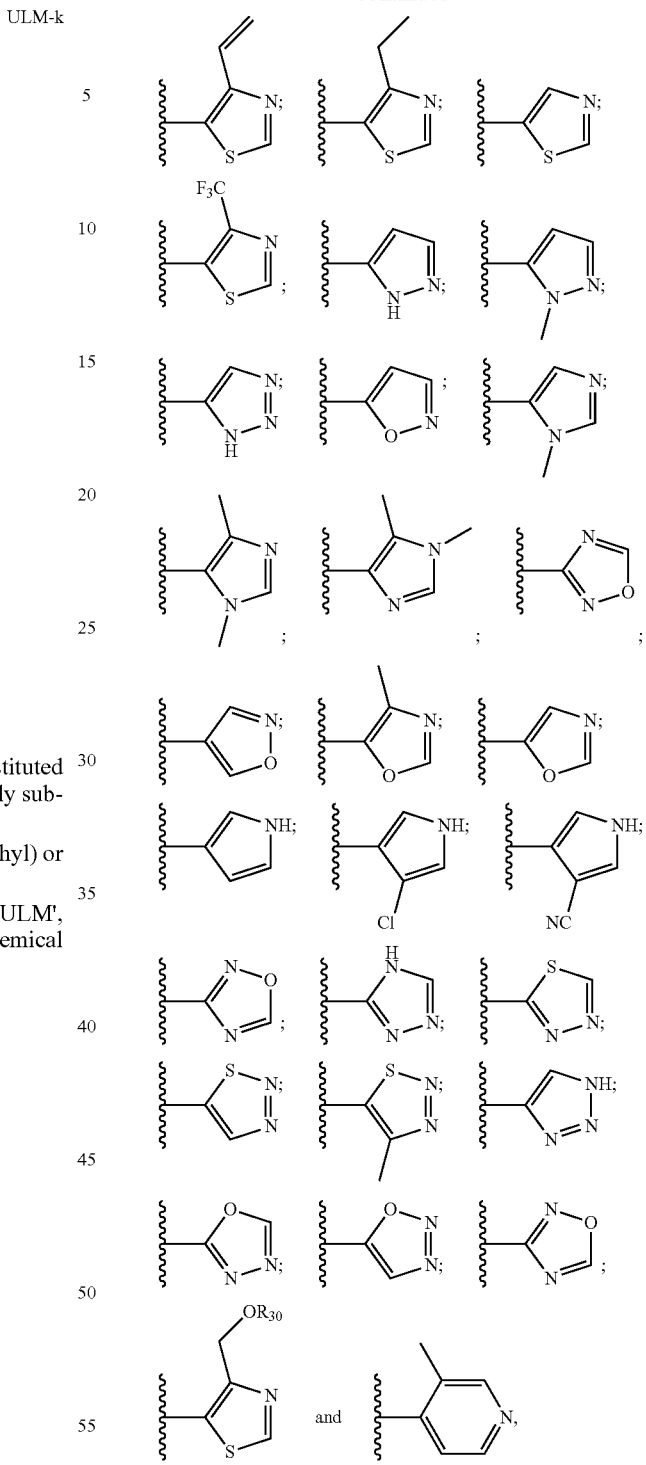

wherein R$_{30}$ of ULM-k is H or an optionally substituted alkyl.

In other embodiments, ULM and where present, ULM', are each independently a group according to the chemical structure:

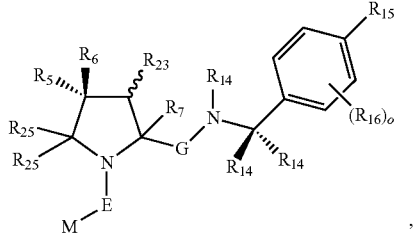
wherein:
E of ULM-k is C=O;
M of ULM-k is
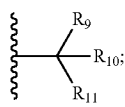
and
$R_{11}$ of ULM-k is selected from the group consisting of:
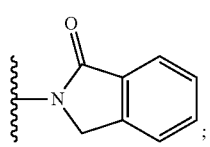 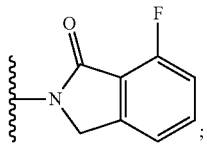
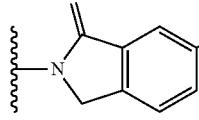 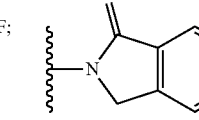
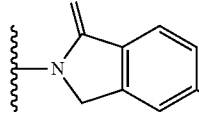 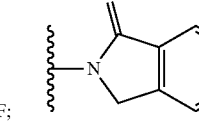
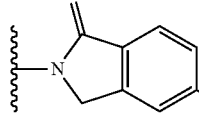 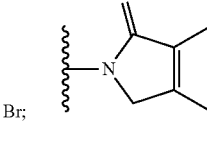
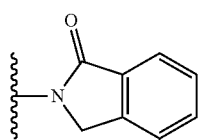 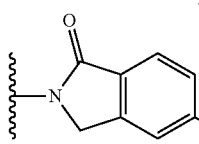
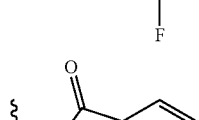 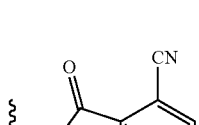
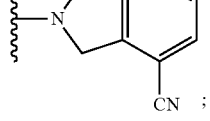 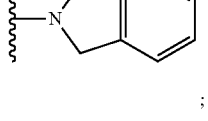
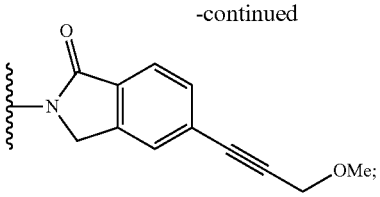
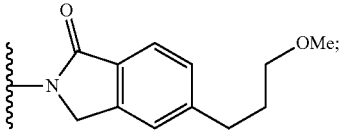
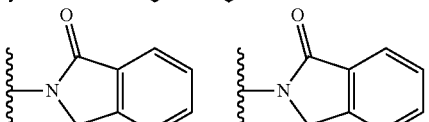
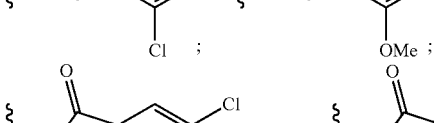
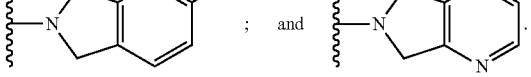
In still other embodiments, a compound of the chemical structure,
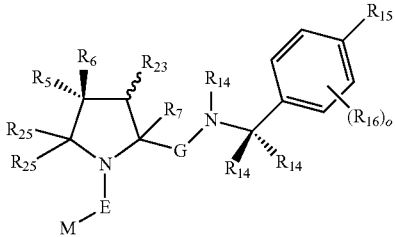
wherein E of ULM-k is C=O;
$R_{11}$ of ULM-k is
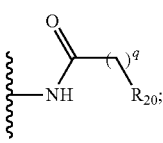
and
M of ULM-k is
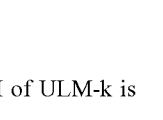
q of ULM-k is 1 or 2;
$R_{20}$ of ULM-k is H, optionally substituted alkyl, optionally substituted cycloalkyl, optionally substituted aryl, or

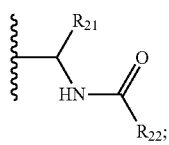
$R_{21}$ of ULM-k is H or optionally substituted alkyl; and
$R_{22}$ of ULM-k is H, optionally substituted alkyl, optionally substituted alkoxy, or haloalkyl.
In any embodiment described herein, $R_{11}$ of ULM-j or ULM-k is selected from the group consisting of:
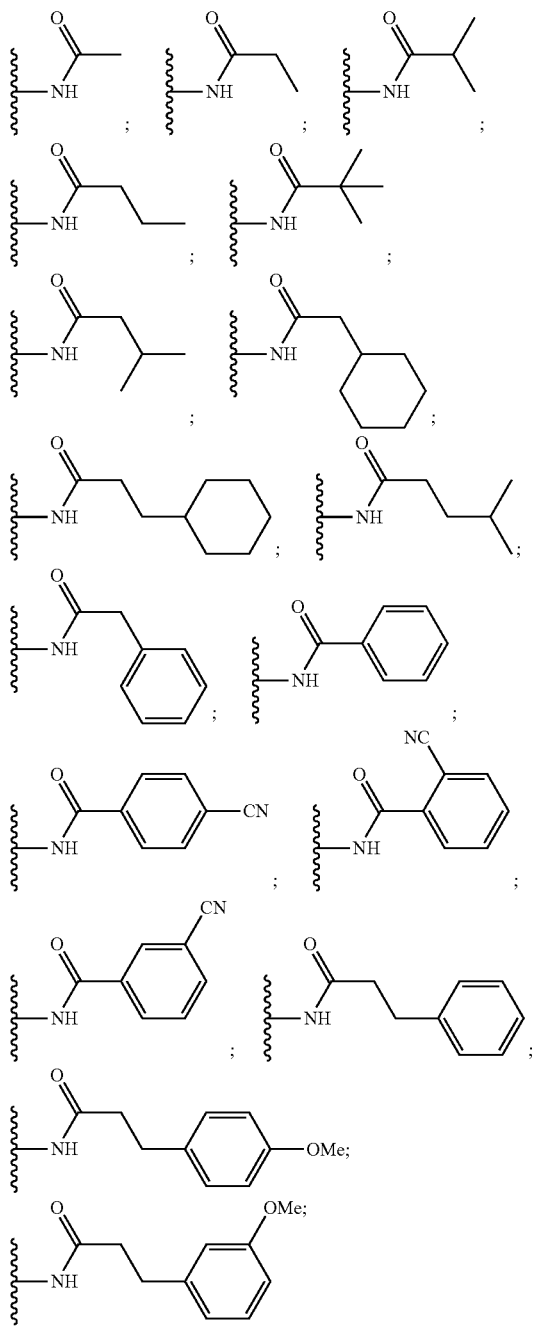
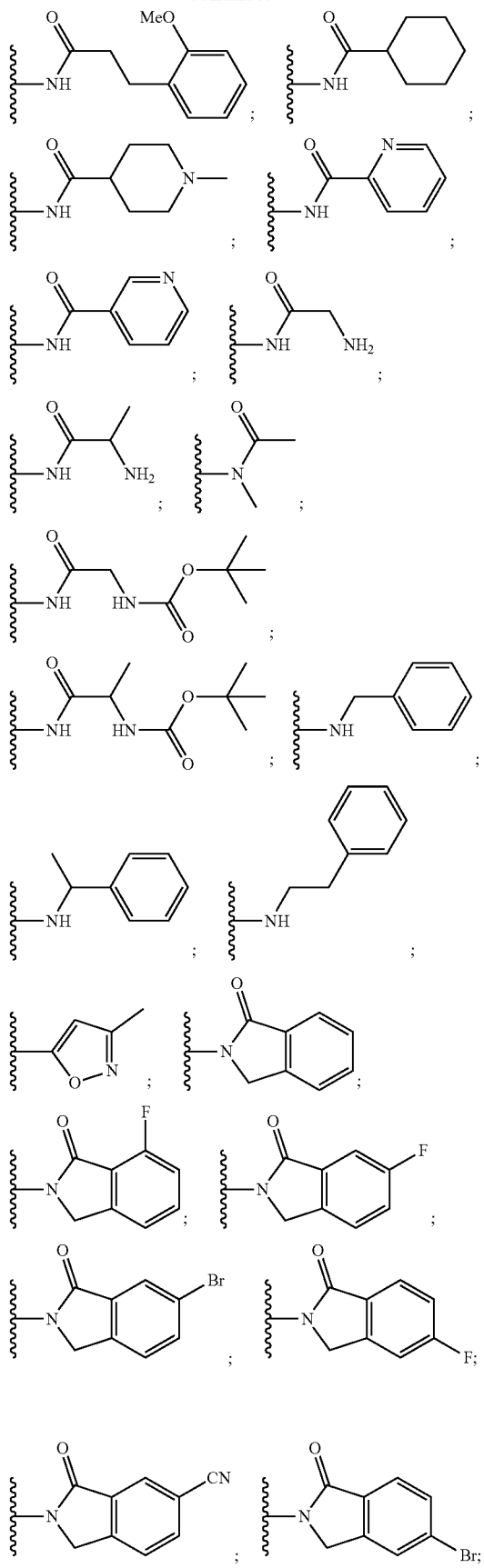

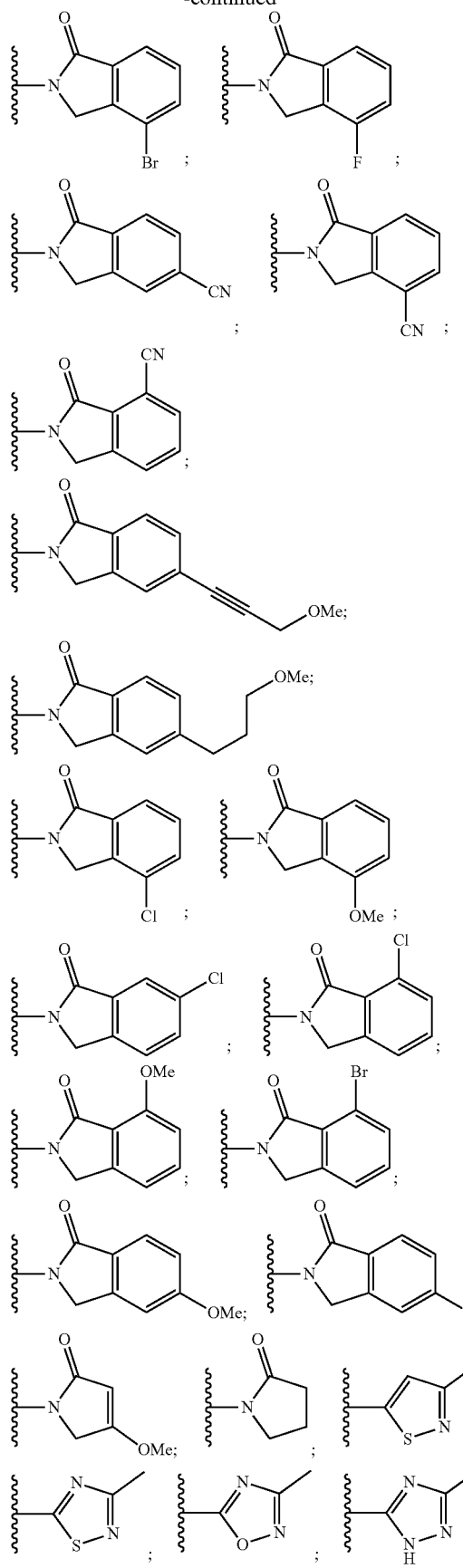
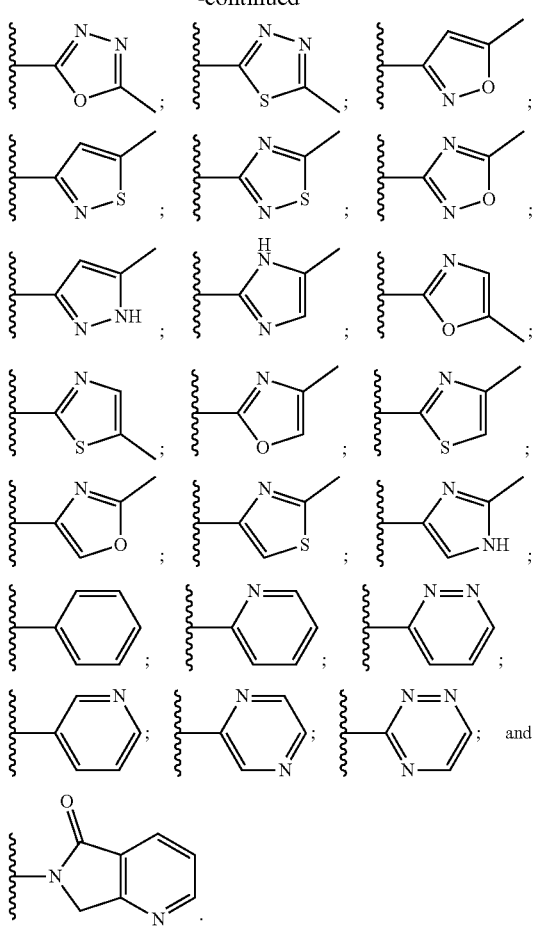
In certain embodiments, $R_{11}$ of ULM-j or ULM-k is selected from the group consisting of:
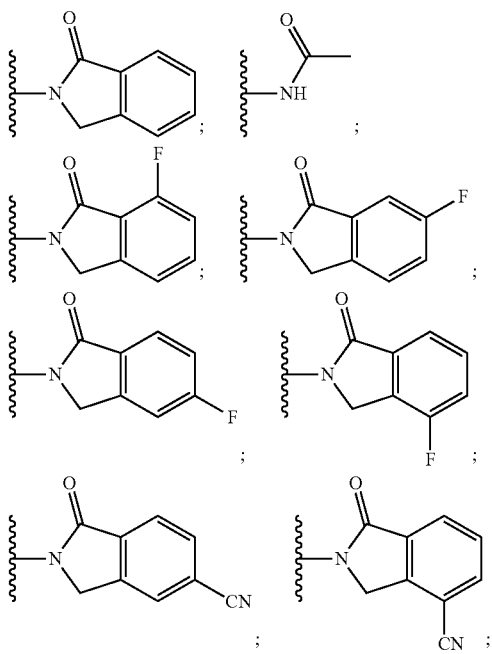

215
-continued
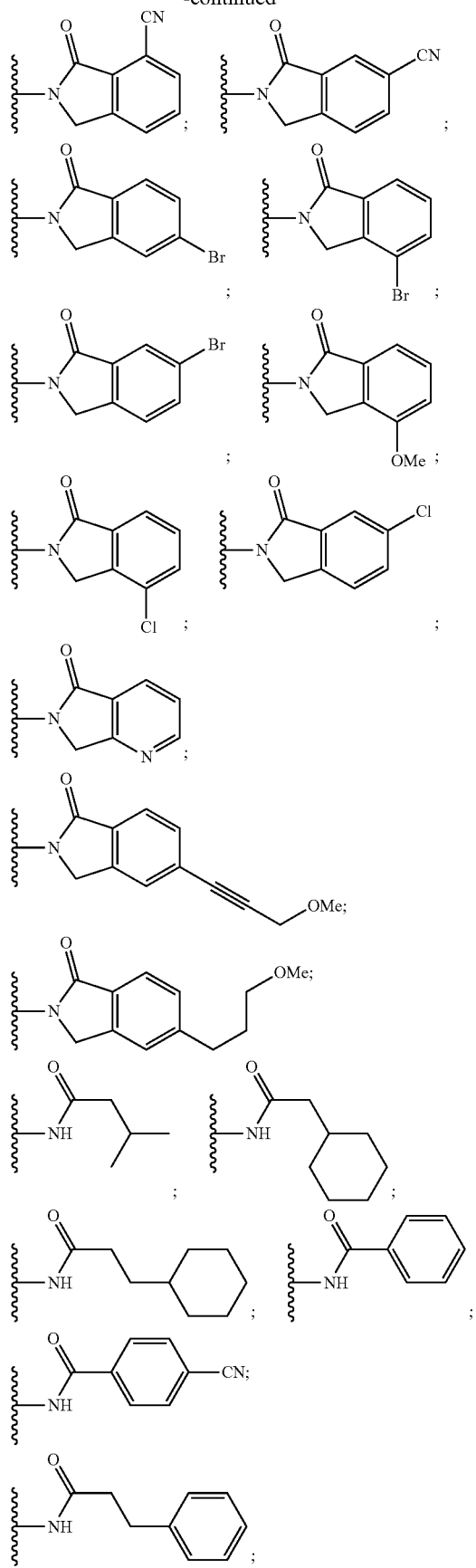
216
-continued
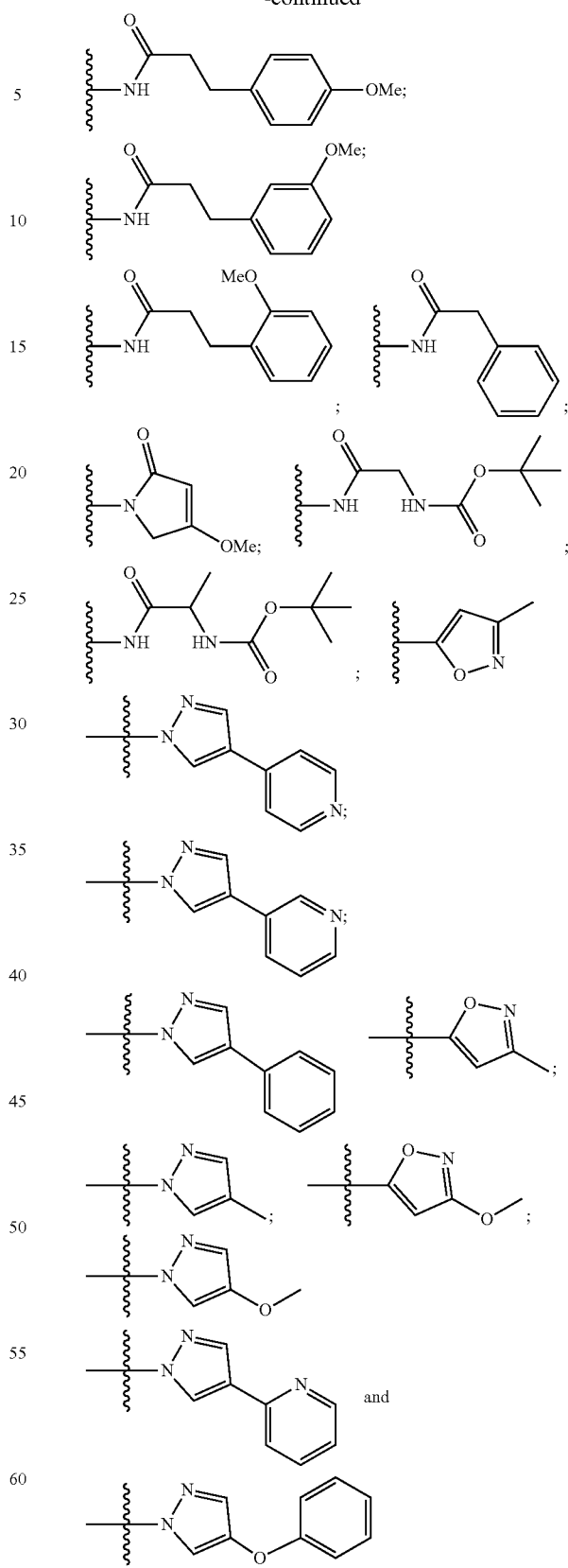
In certain embodiments, ULM (or when present ULM') is a group according to the chemical structure:

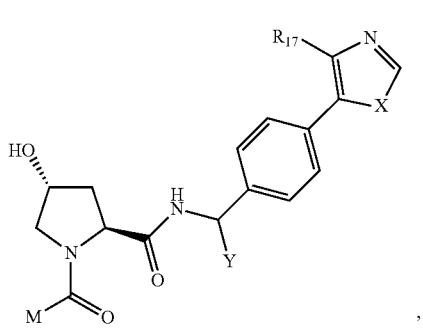

ULM-1 wherein:

X of ULM-1 is O or S;

Y of ULM-1 is H, methyl or ethyl;

$R_{17}$ of ULM-1 is H, methyl, ethyl, hydroxymethyl or cyclopropyl;

M of ULM-1 is optionally substituted aryl, optionally substituted heteroaryl, or

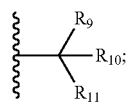

$R_9$ of ULM-1 is H;

$R_{10}$ of ULM-1 is H, optionally substituted alkyl, optionally substituted haloalkyl, optionally substituted heteroaryl, optionally substituted aryl, optionally substituted hydroxyalkyl, optionally substituted thioalkyl or cycloalkyl;

R11 of ULM-1 is optionally substituted heteroaromatic, optionally substituted heterocyclic, optionally substituted aryl or

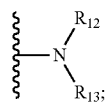

$R_{12}$ of ULM-1 is H or optionally substituted alkyl; and $R_{13}$ of ULM-1 is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl)carbamate.

In some embodiments, ULM and where present, ULM', are each independently a group according to the chemical structure:

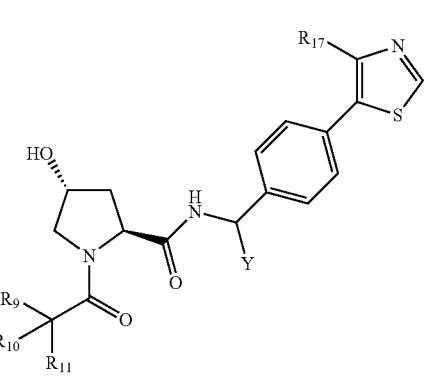

ULM-m wherein:

Y of ULM-m is H, methyol or ethyl $R_9$ of ULM-m is H;

$R_{10}$ is isopropyl, tert-butyl, sec-butyl, cyclopentyl, or cyclohexyl;

$R_{11}$ of ULM-m is optionally substituted amide, optionally substituted isoindolinone, optionally substituted isooxazole, optionally substituted heterocycles.

In other preferred embodiments of the disclosure, ULM and where present, ULM', are each independently a group according to the chemical structure:

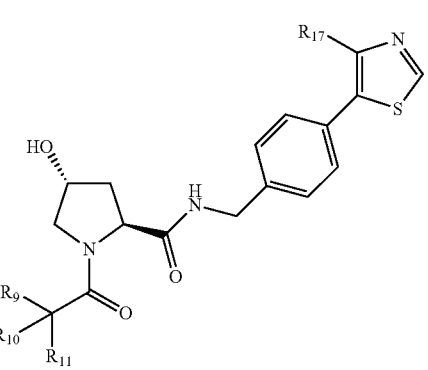

ULM-n wherein:

$R_{17}$ of ULM-n is methyl, ethyl, or cyclopropyl; and $R_9$, $R_{10}$, and $R_{11}$ of ULM-n are as defined above. In other instances, $R_9$ is H; and $R_{10}$ of ULM-n is H, alkyl, or cycloalkyl (preferably, isopropyl, tert-butyl, sec-butyl, cyclopentyl, or cyclohexyl).

In any of the aspects or embodiments described herein, the ULM (or when present, ULM') as described herein may be a pharmaceutically acceptable salt, enantiomer, diastereomer, solvate or polymorph thereof. In addition, in any of the aspects or embodiments described herein, the ULM (or when present, ULM') as described herein may be coupled to a PTM directly via a bond or by a chemical linker.

In certain aspects of the disclosure, the ULM moiety is selected from the group consisting of:

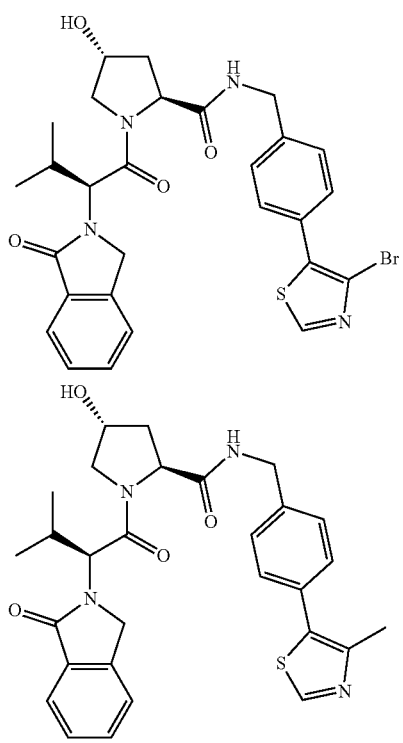
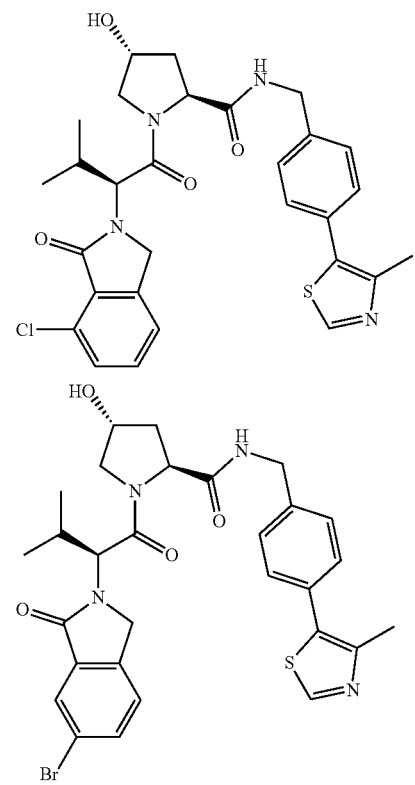
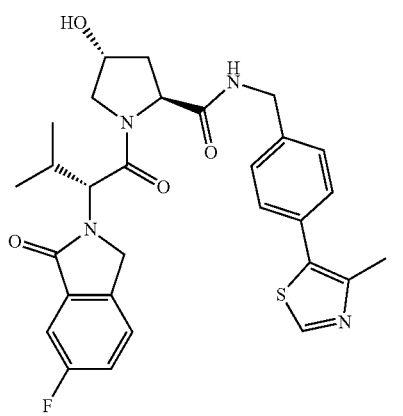
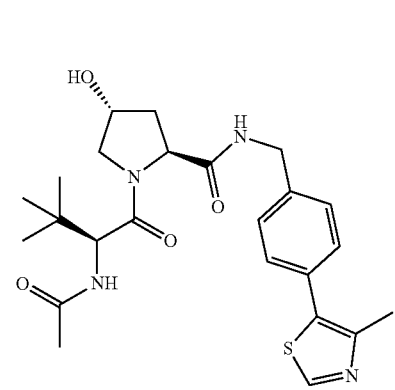
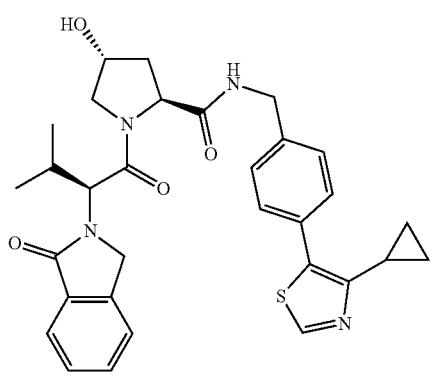
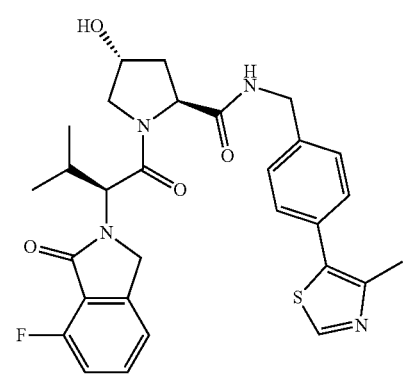

221
-continued
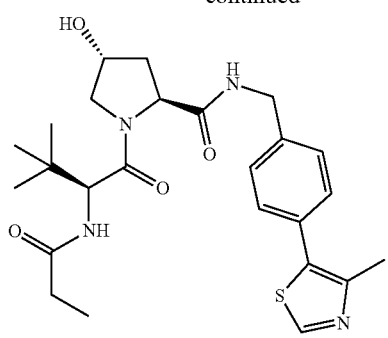
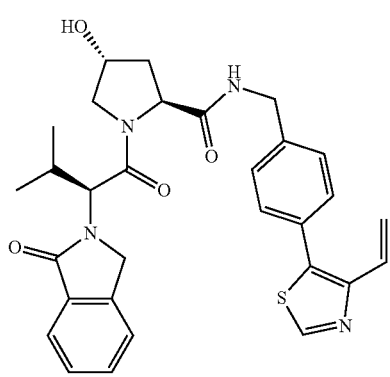
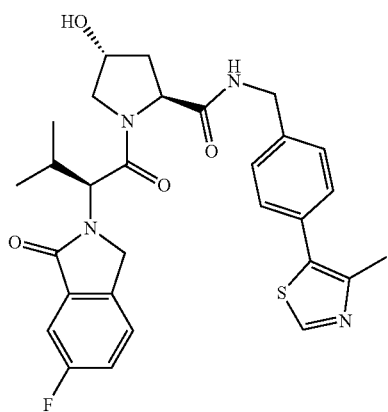
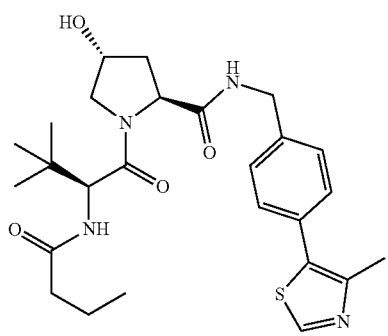
222
-continued
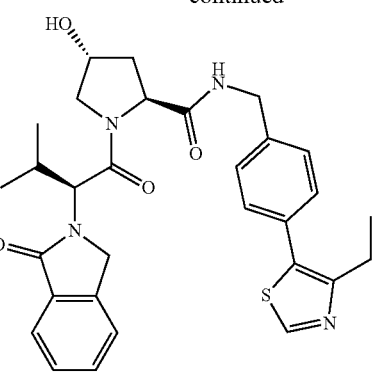
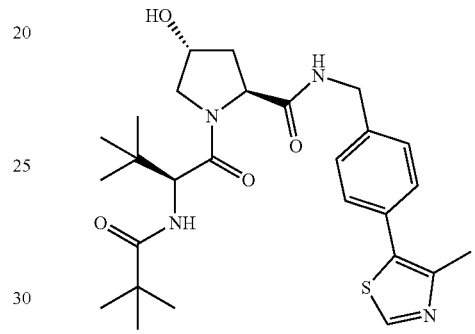
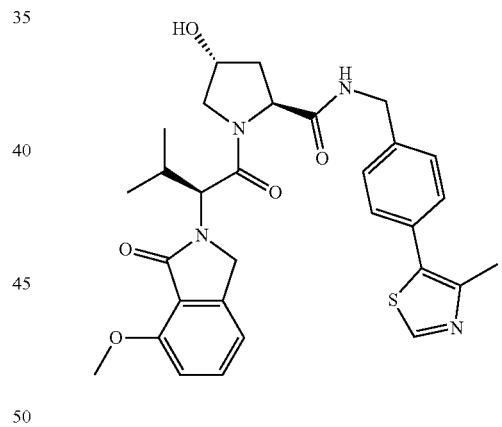
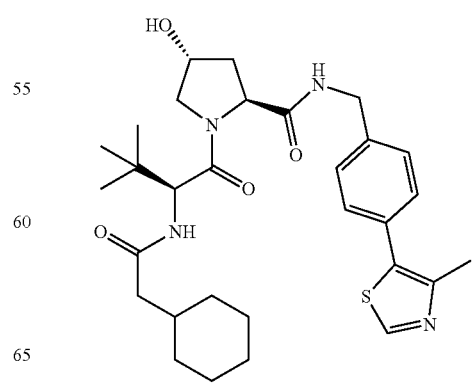

223
-continued
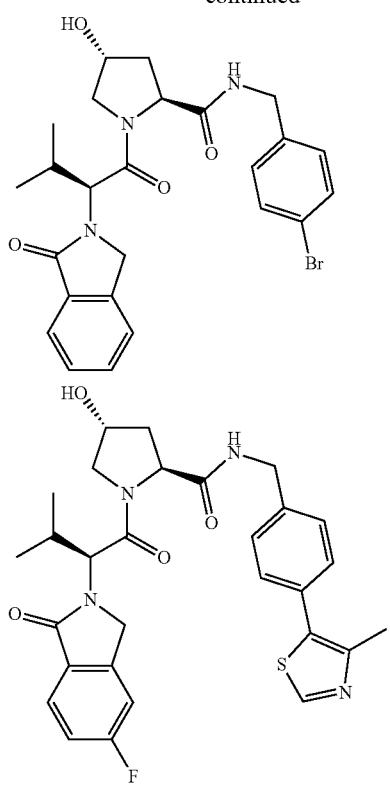
224
-continued
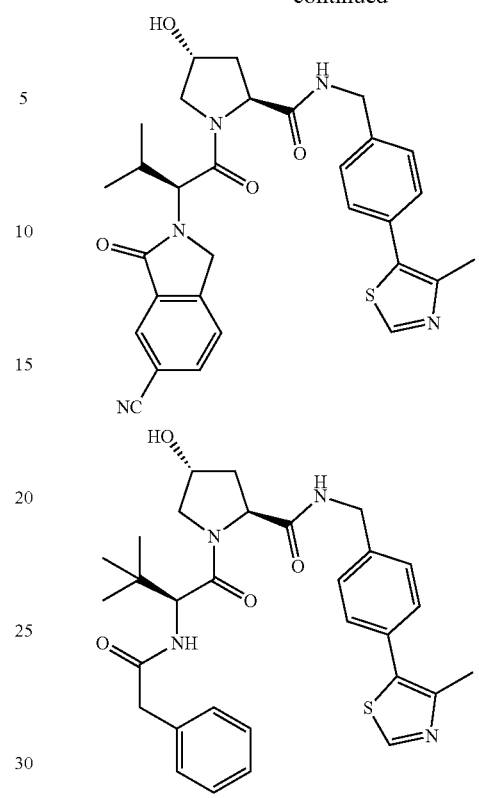
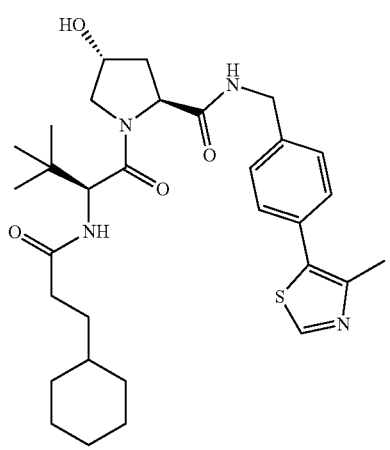
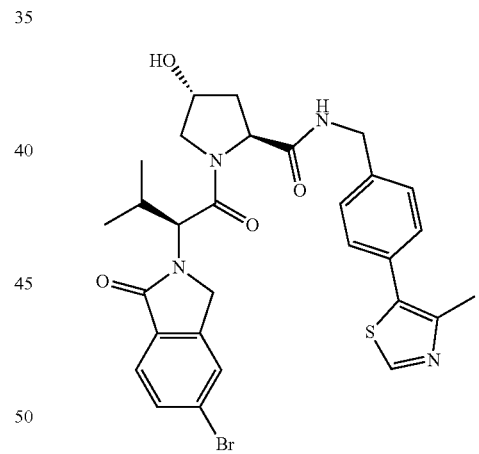
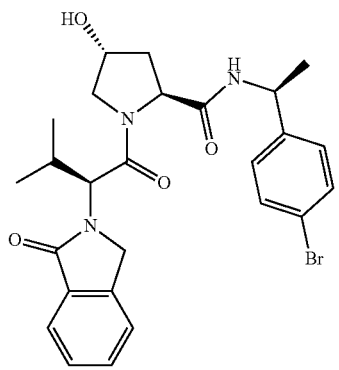
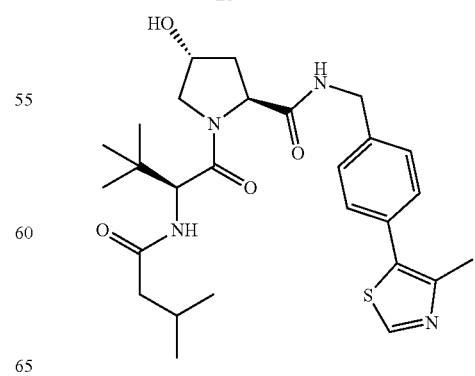

225
-continued
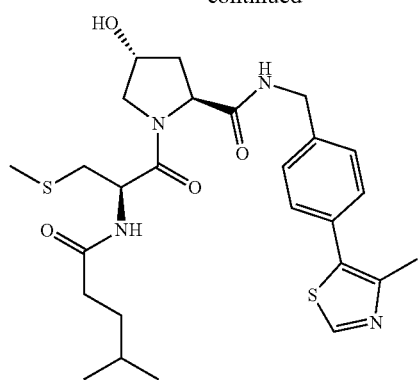
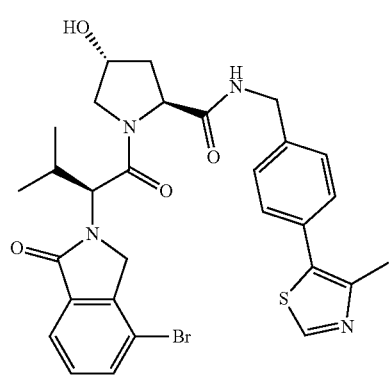
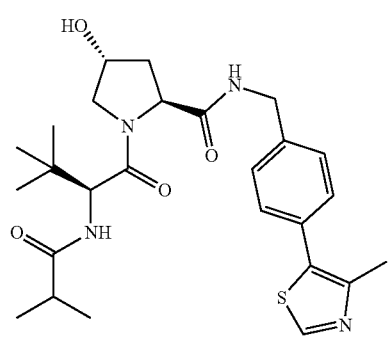
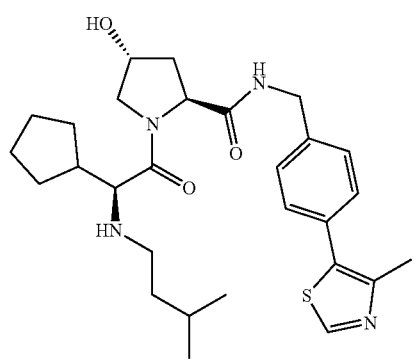
226
-continued
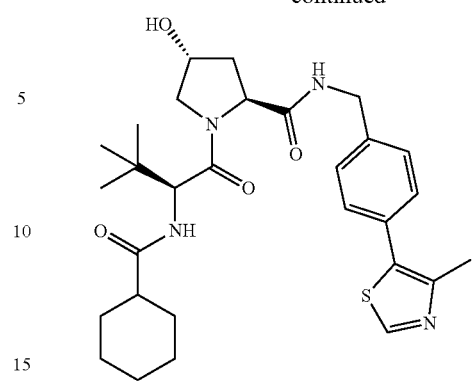
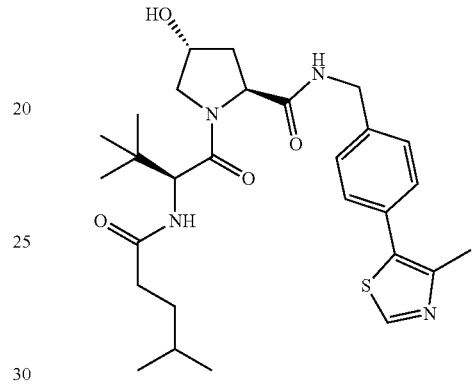
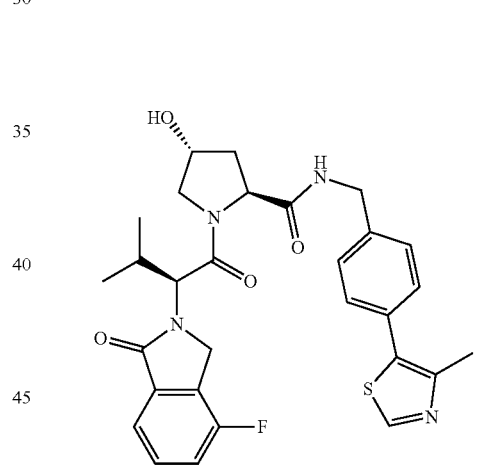
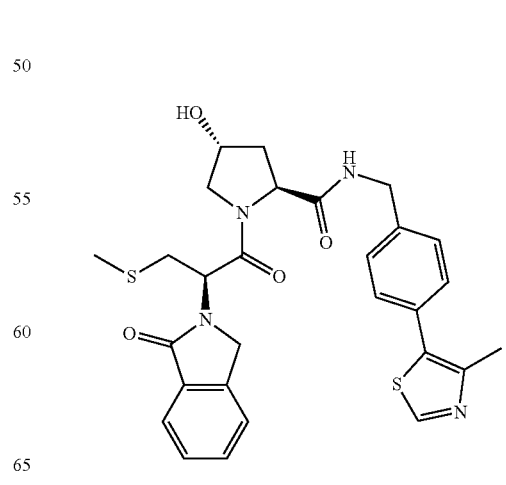

227
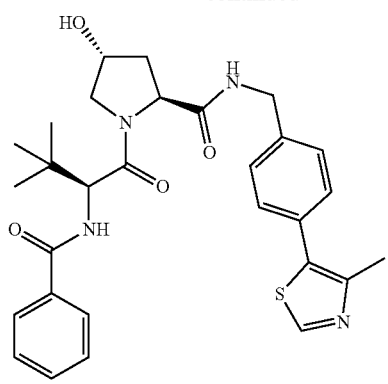
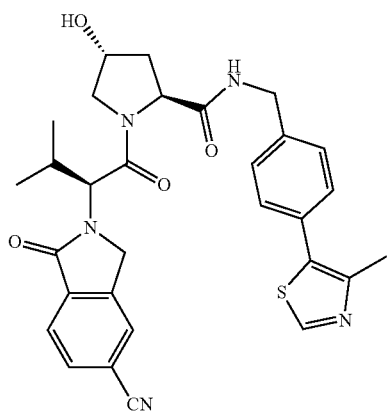
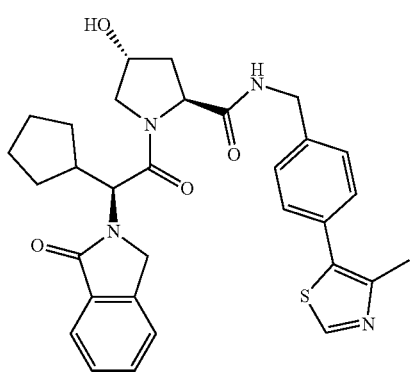
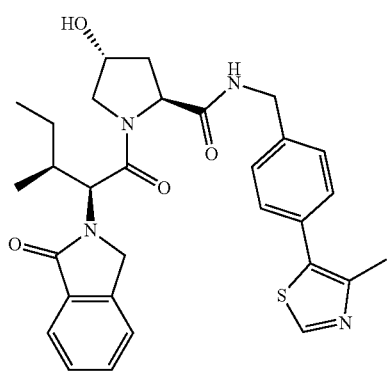
228
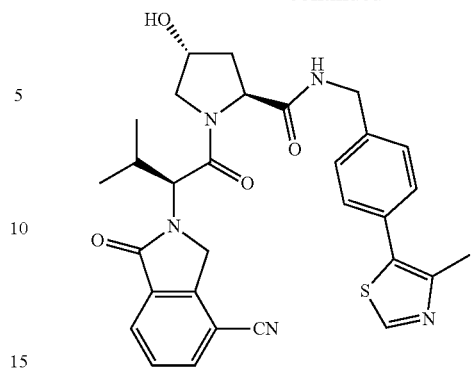
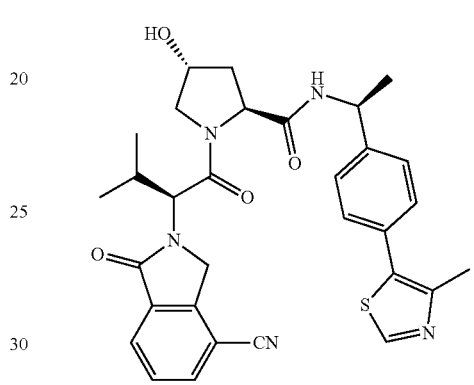
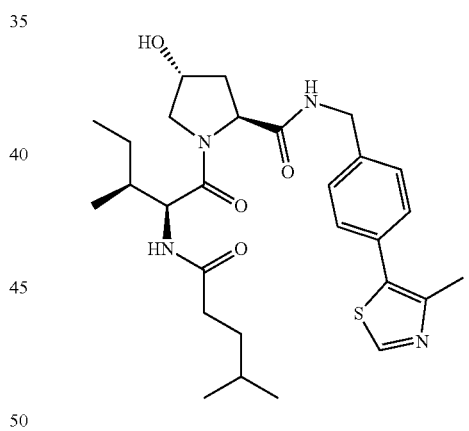
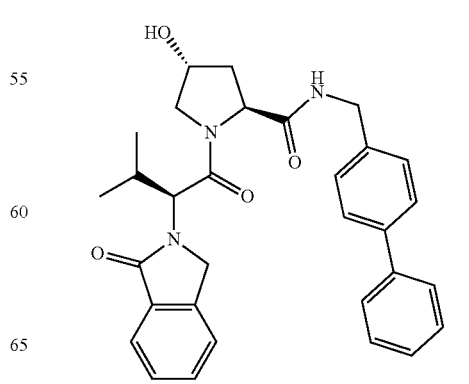

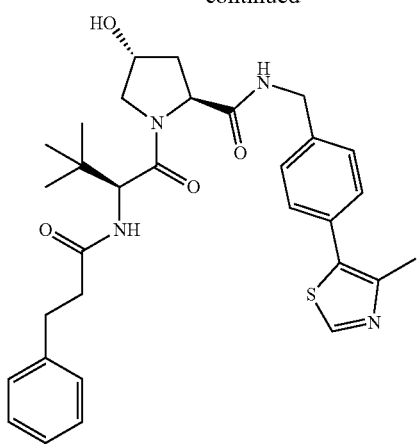
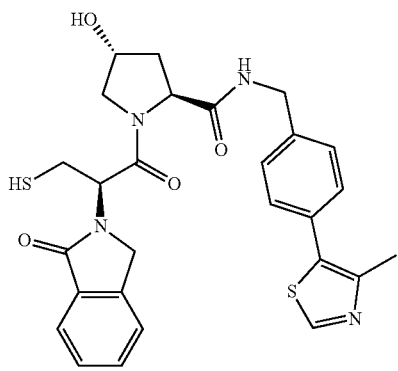
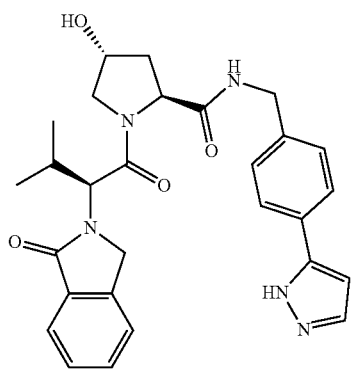
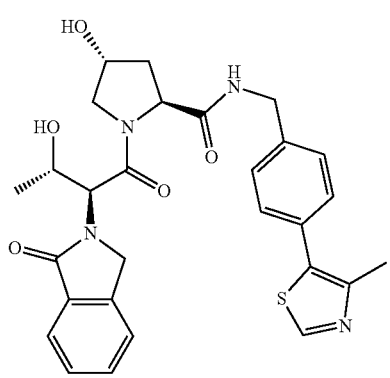
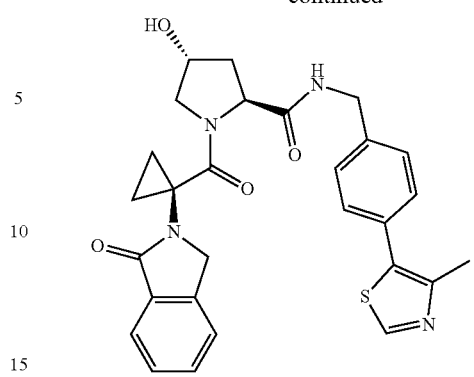
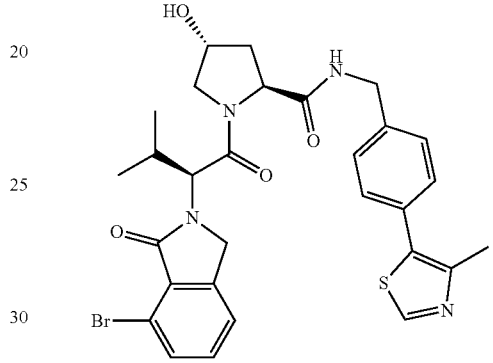
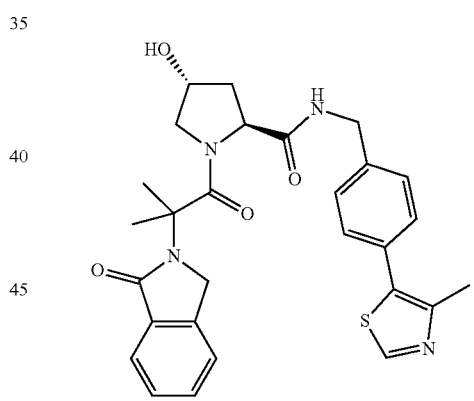
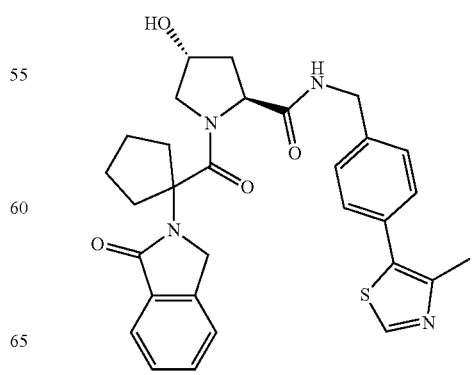

231
-continued
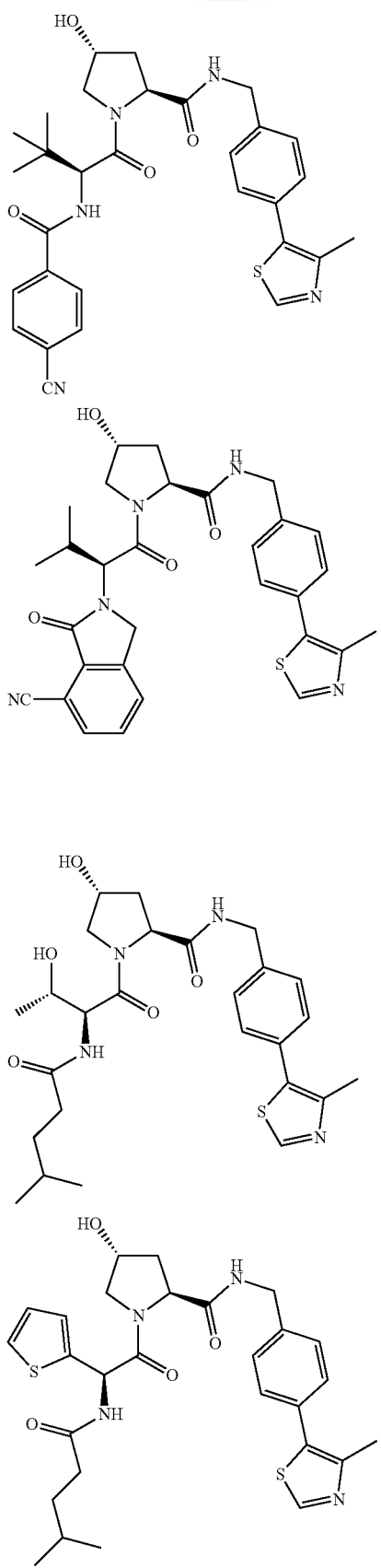
232
-continued
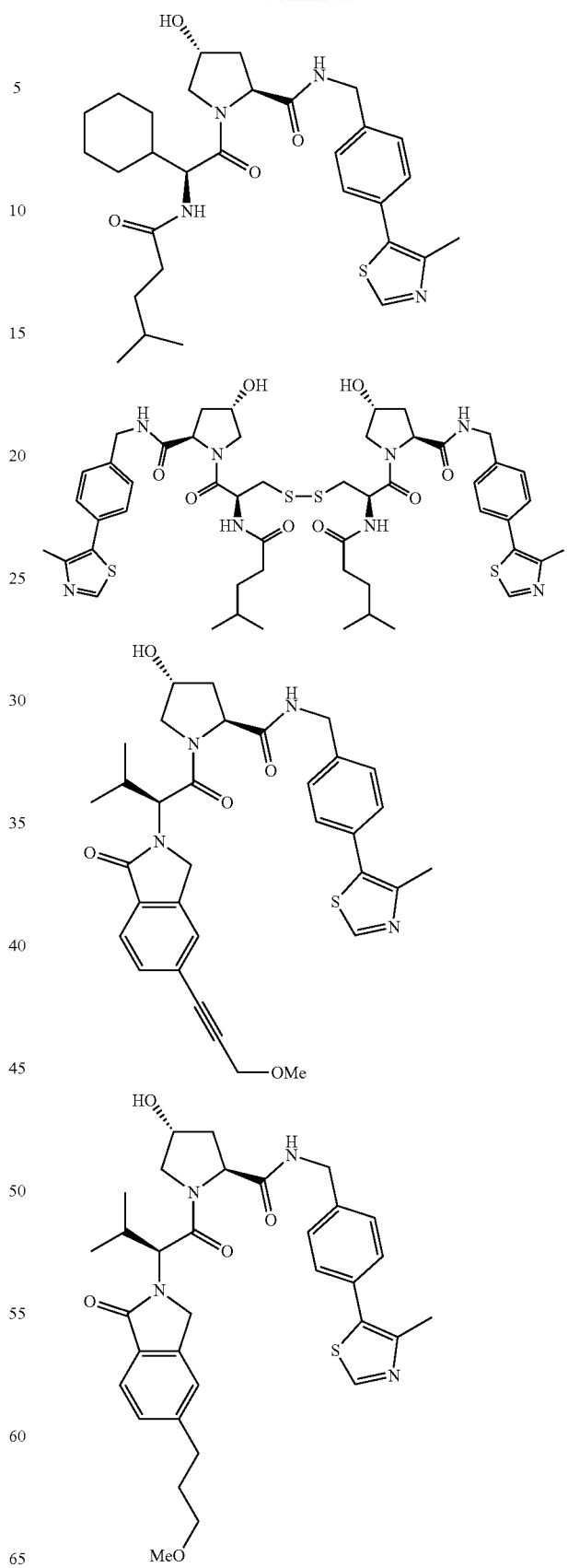

233
-continued
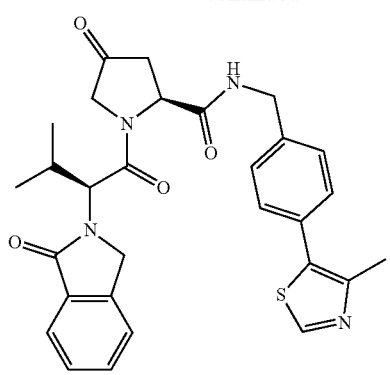
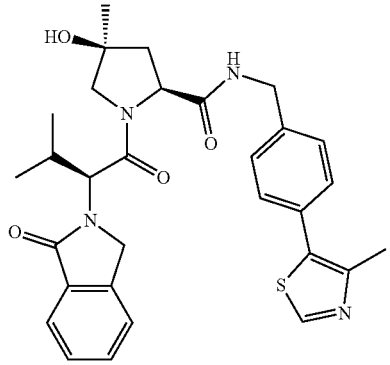
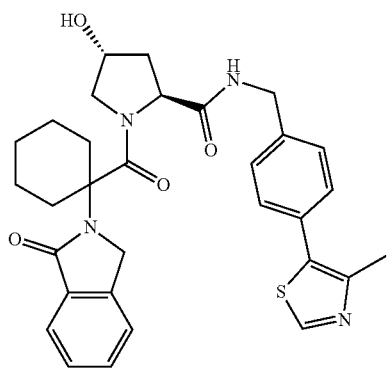
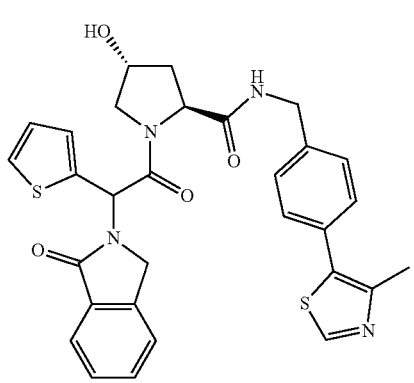
234
-continued
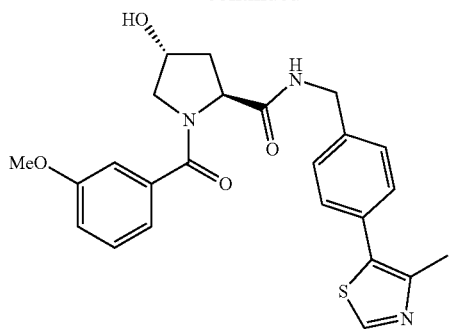
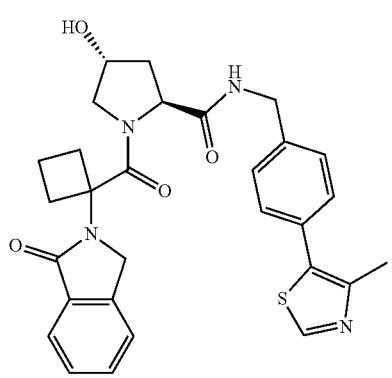
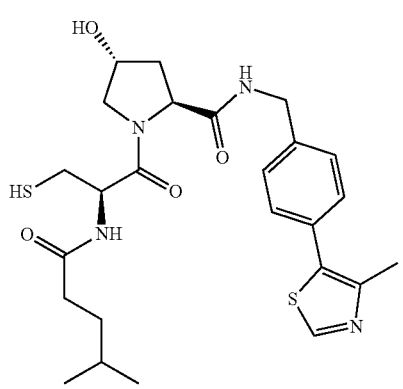
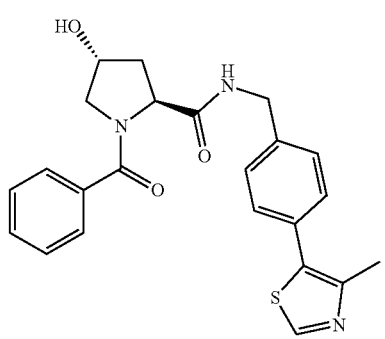

235
-continued
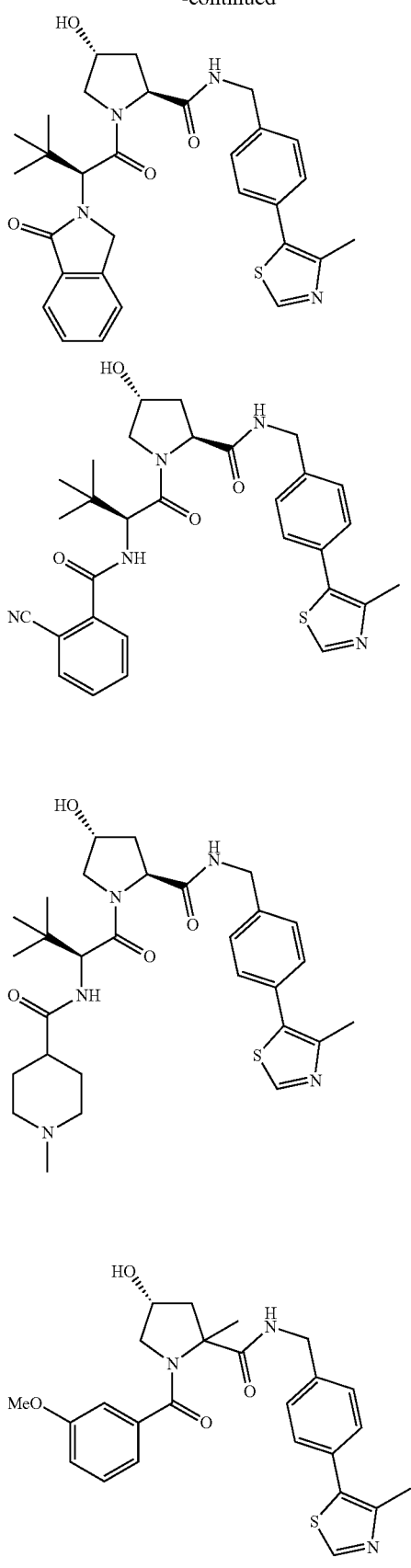
236
-continued
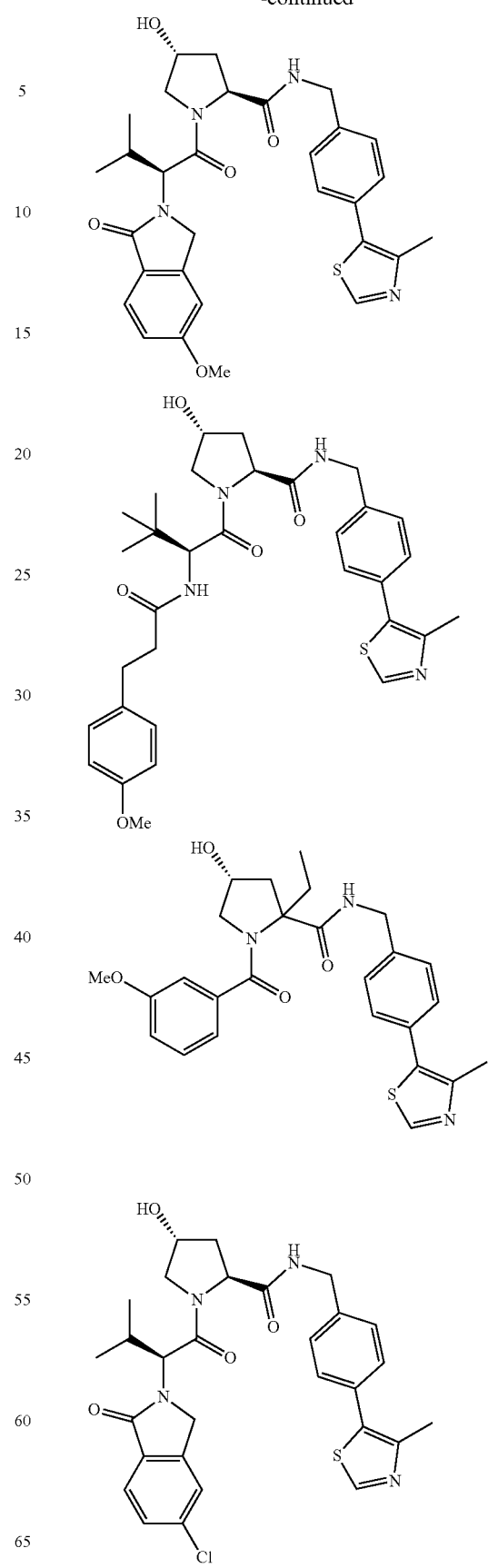

237
-continued
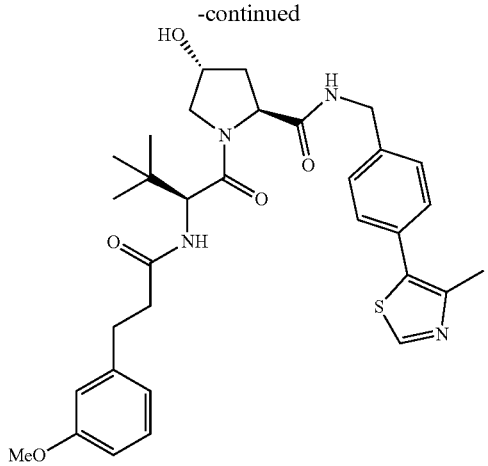
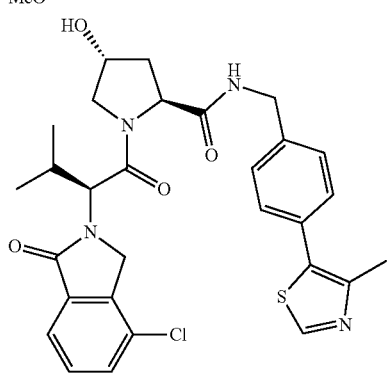
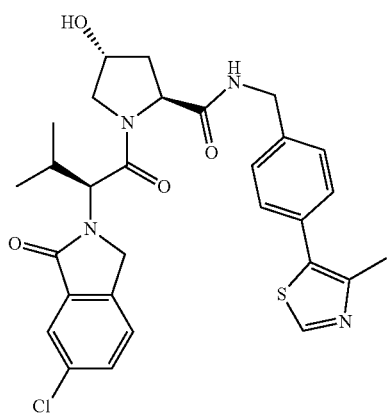
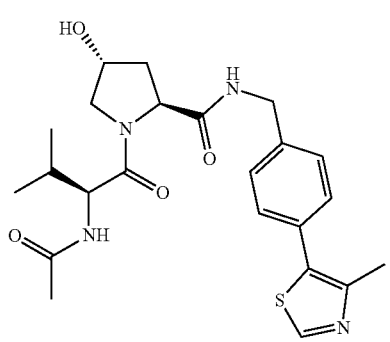
238
-continued
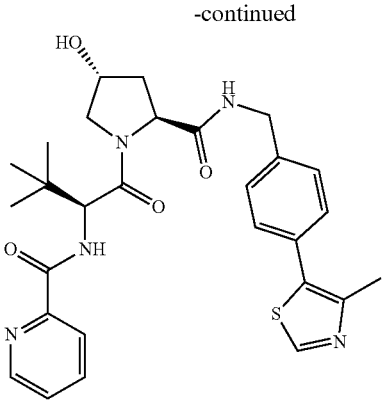
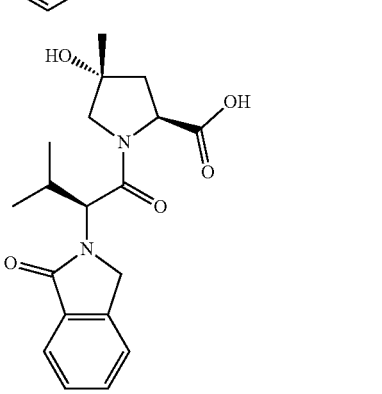
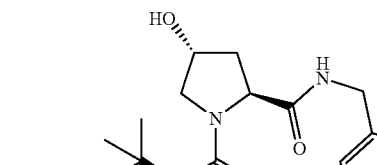
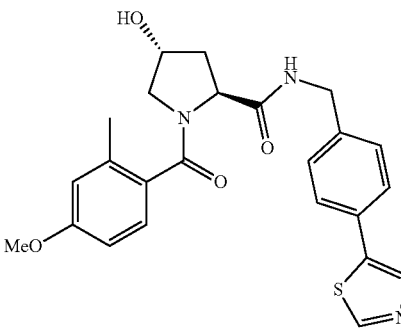

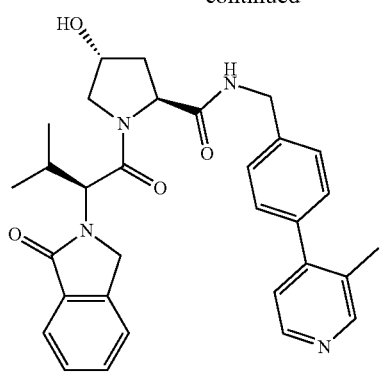
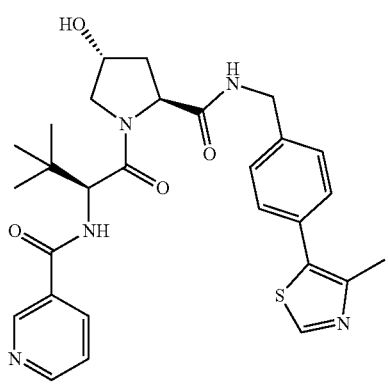
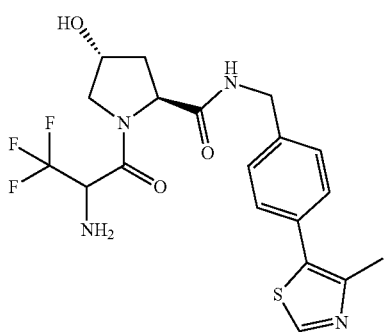
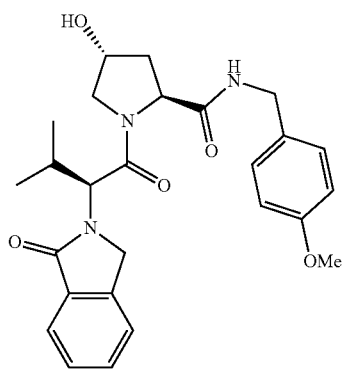
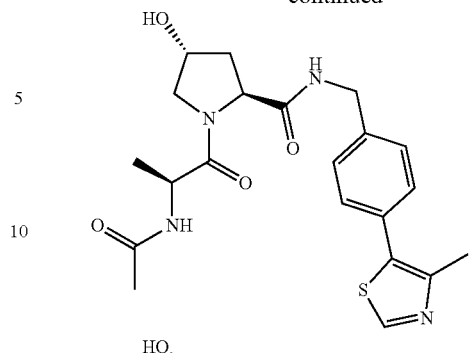
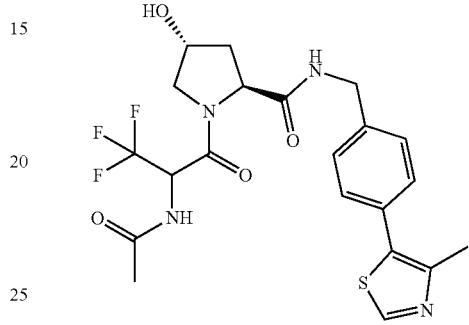
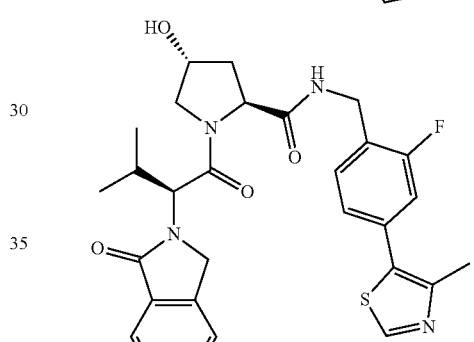
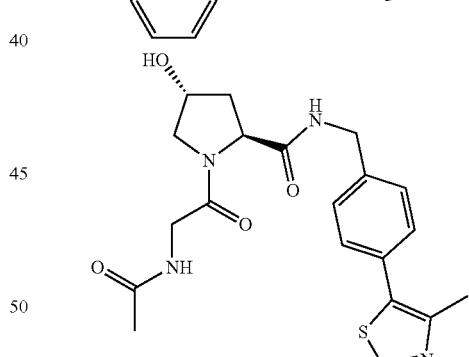
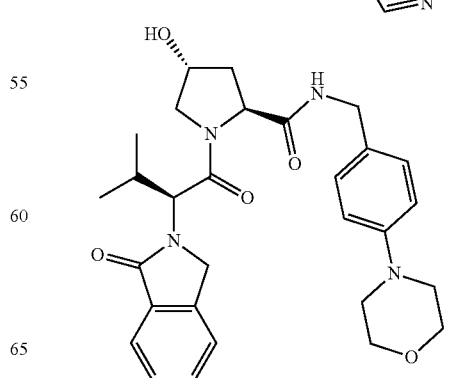

-continued
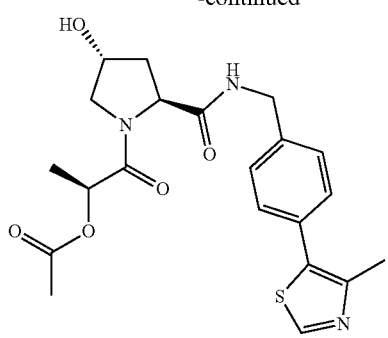
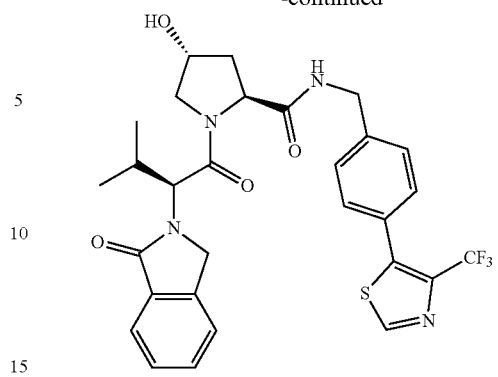
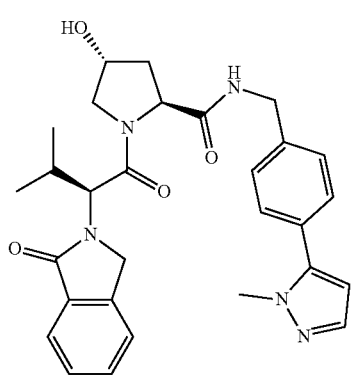
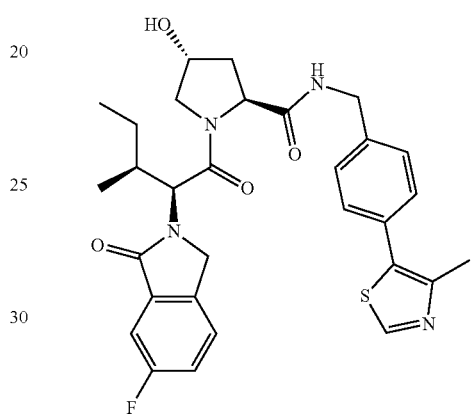
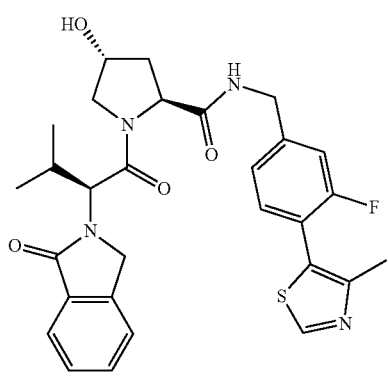
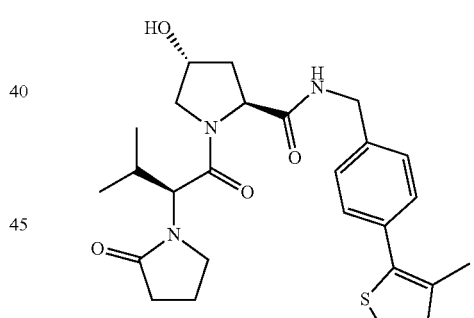
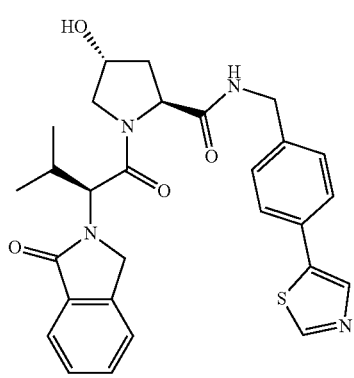
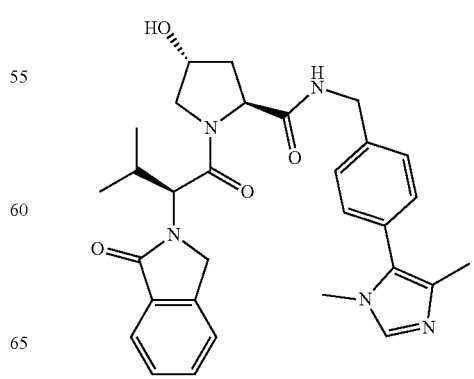

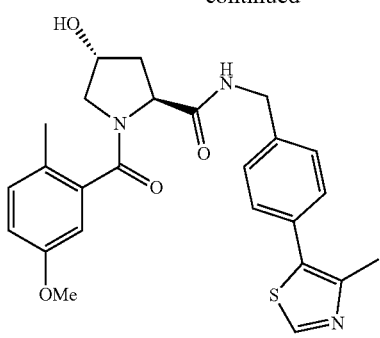
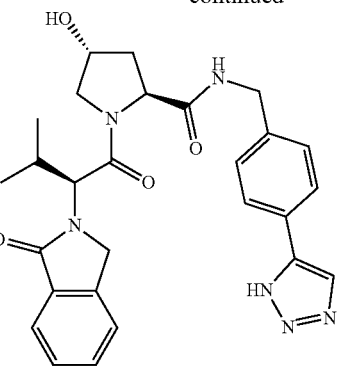
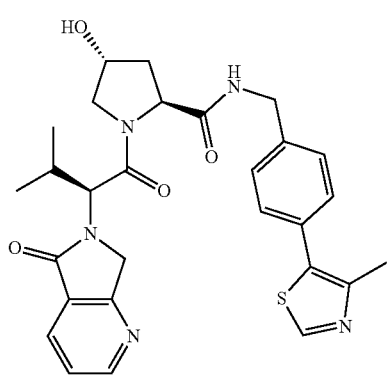
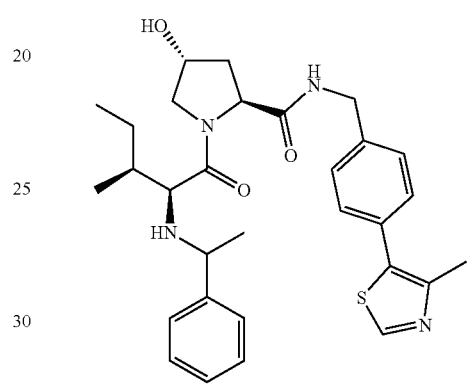
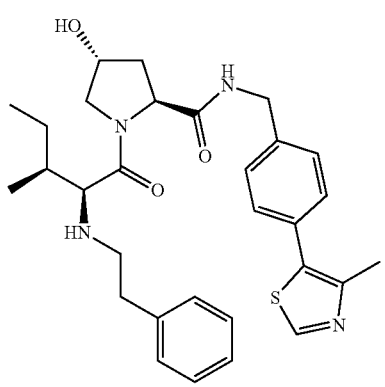
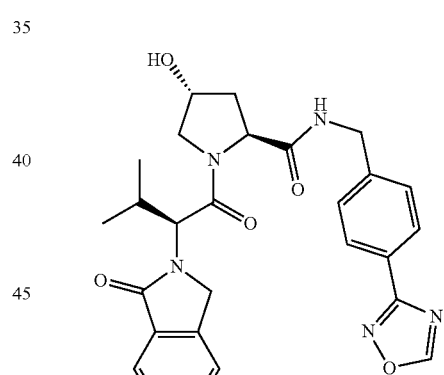
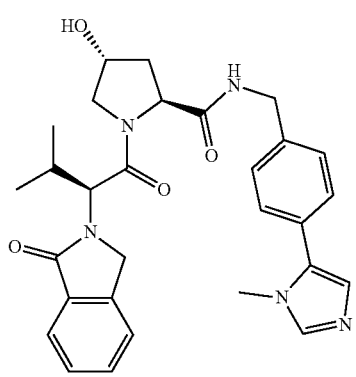
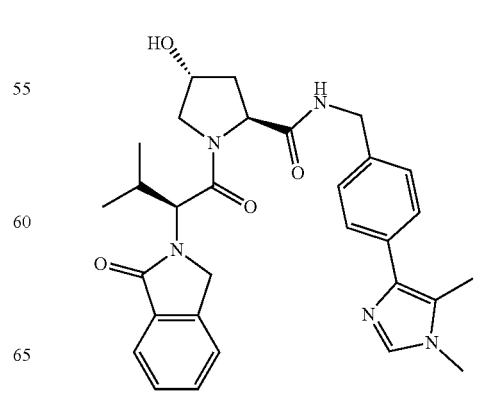

245
-continued
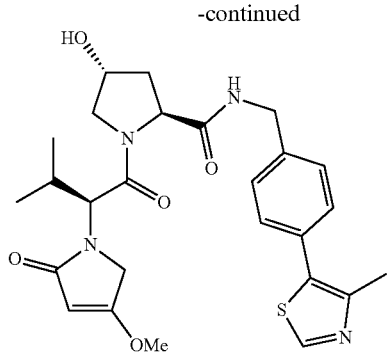
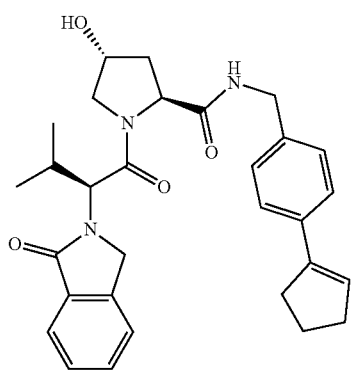
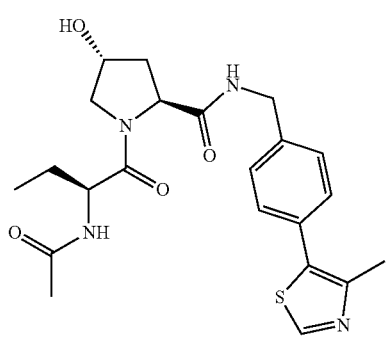
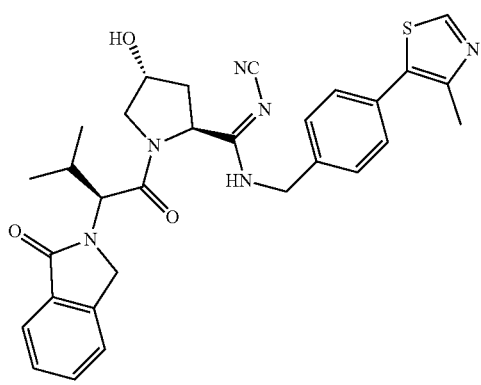
246
-continued
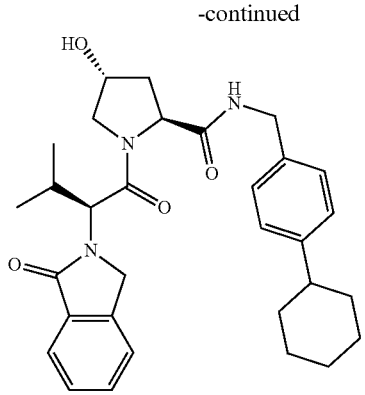
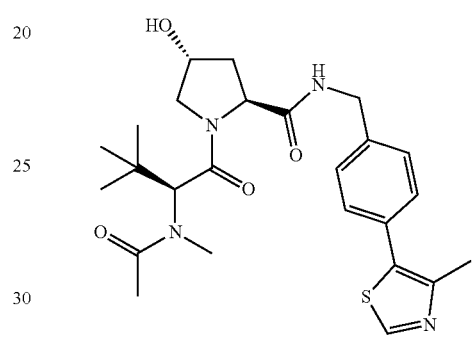
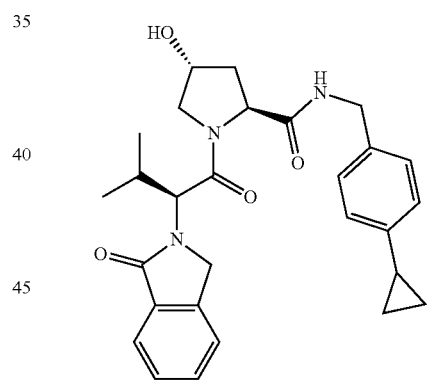
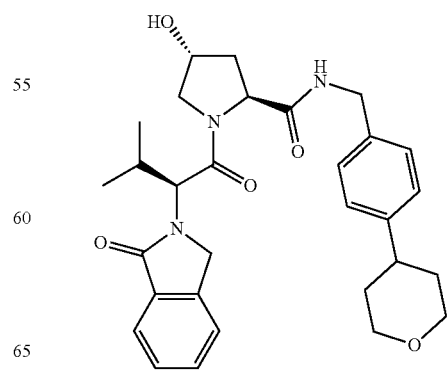

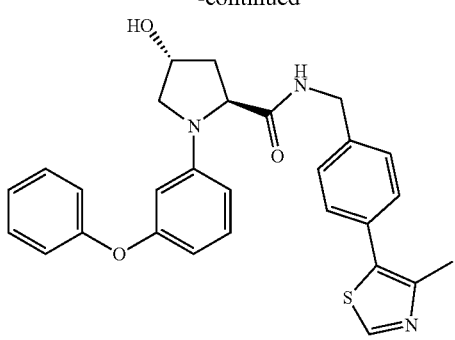
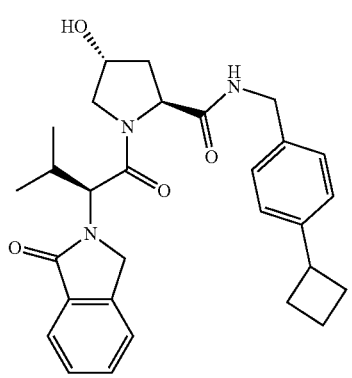
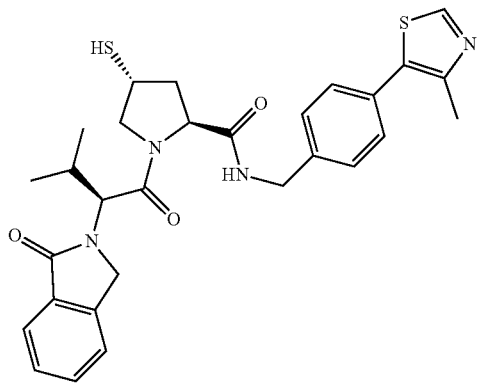
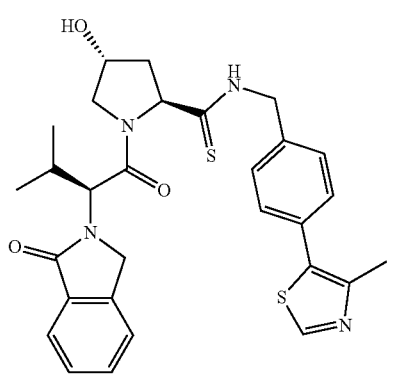
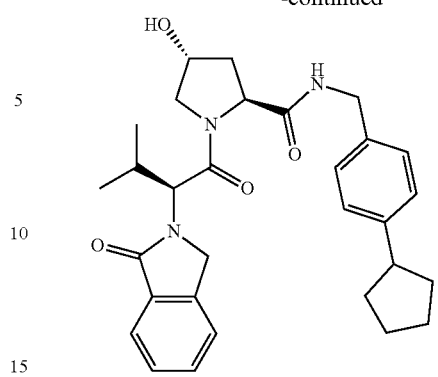
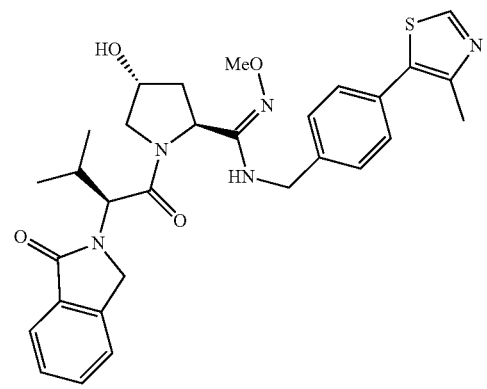
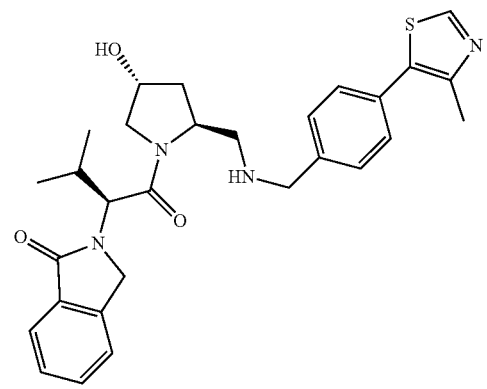
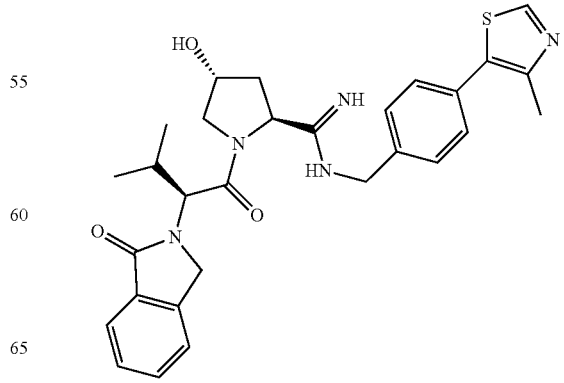

249
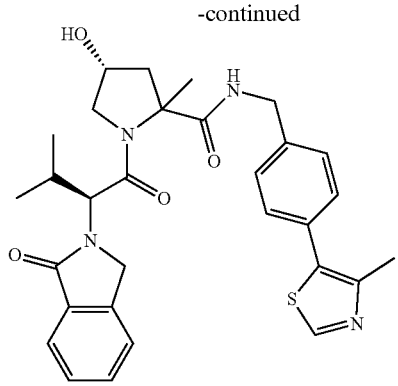
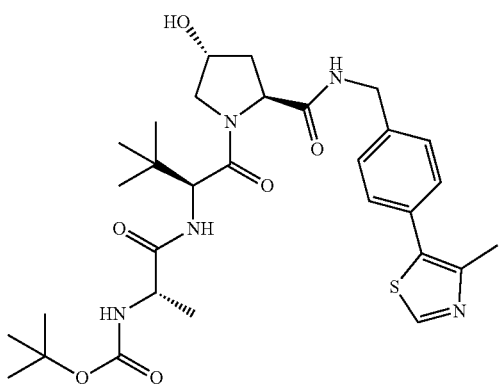
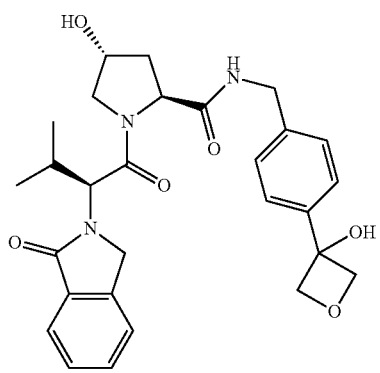
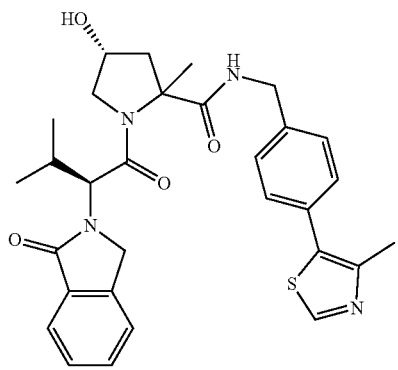
250
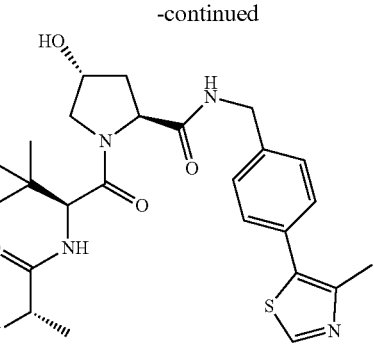
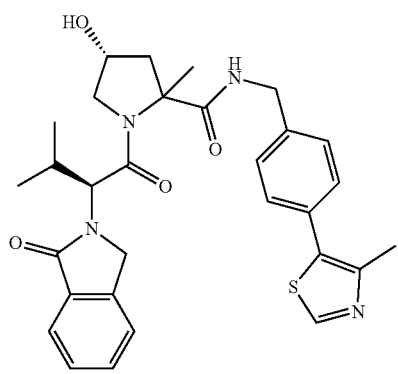
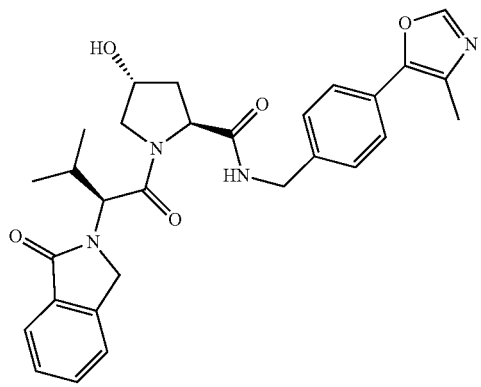
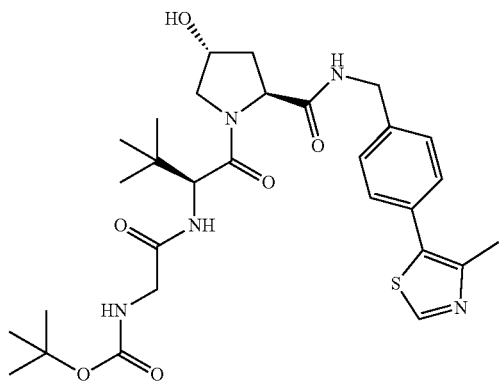

251
-continued
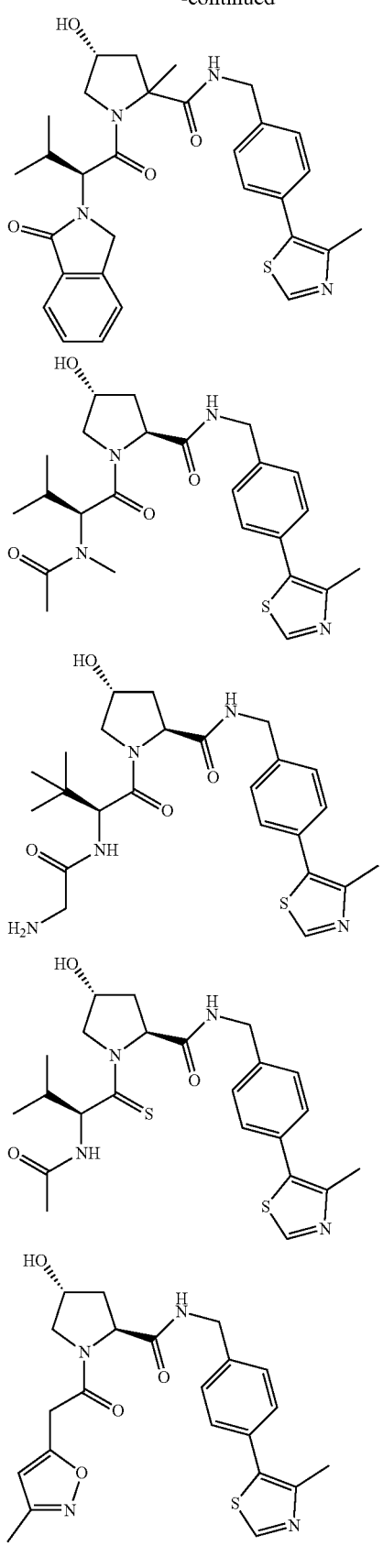
252
-continued
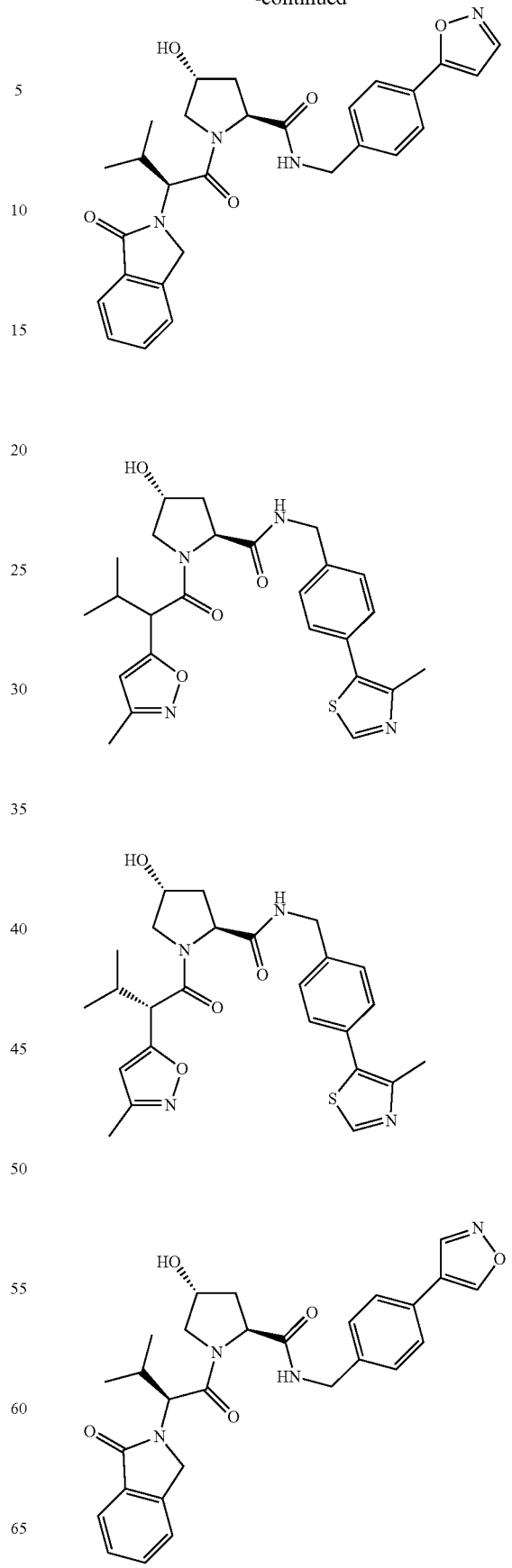

253
-continued
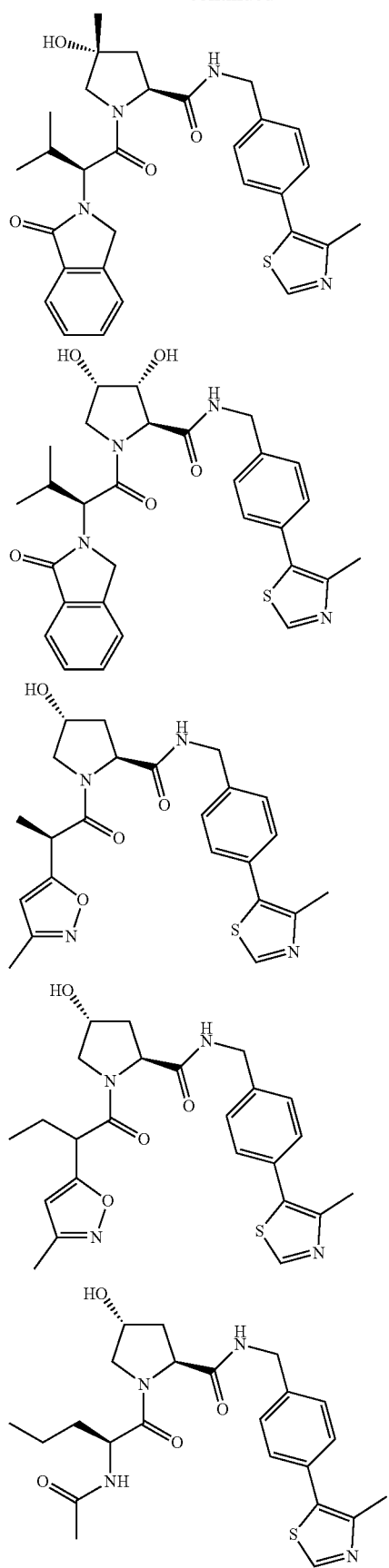
254
-continued
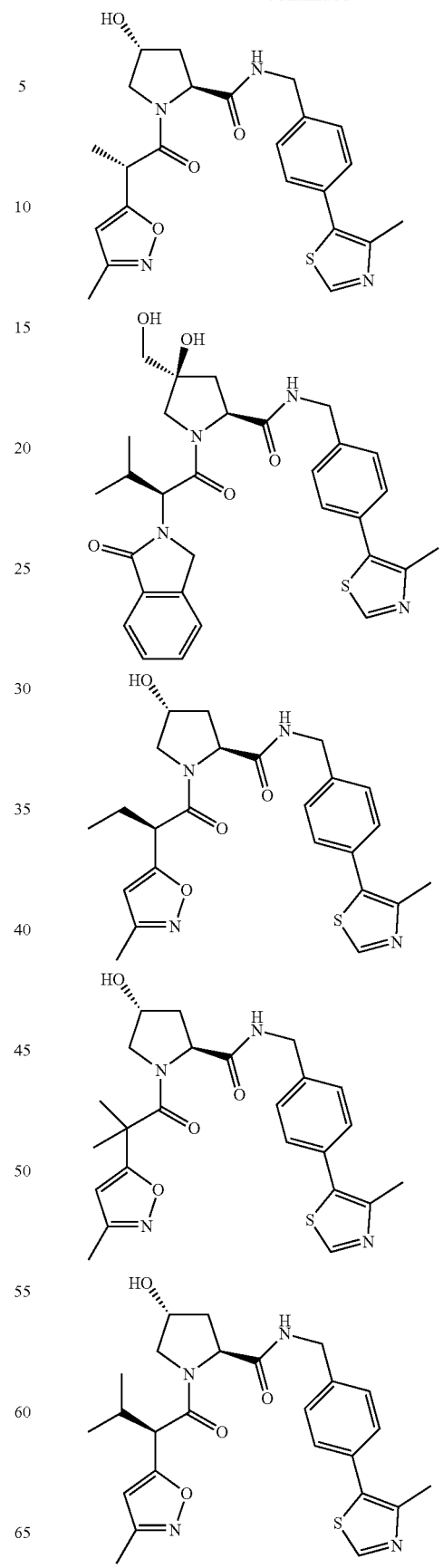

255
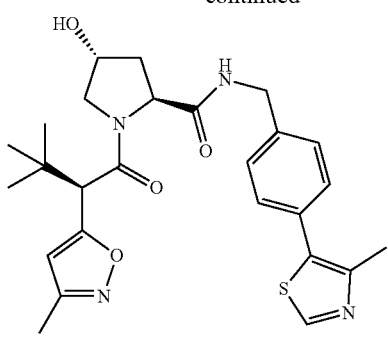
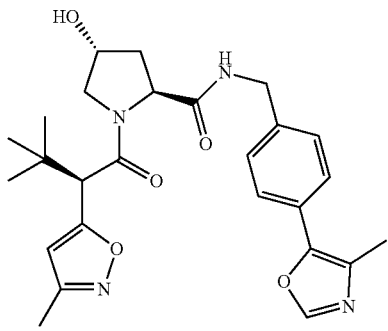
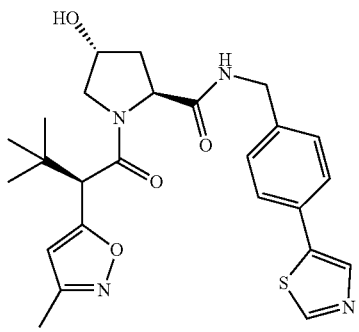
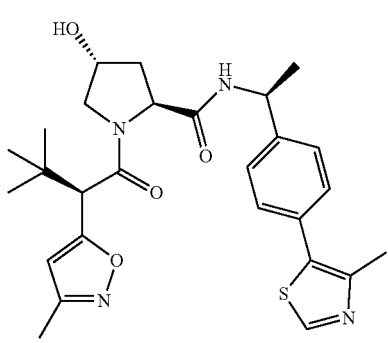
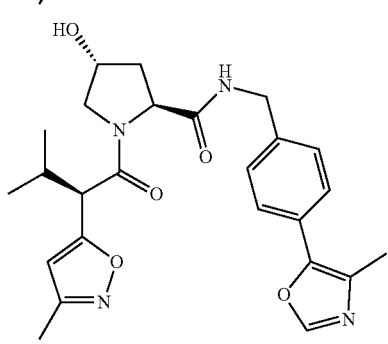
256
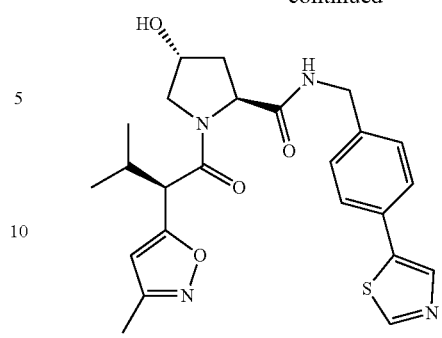
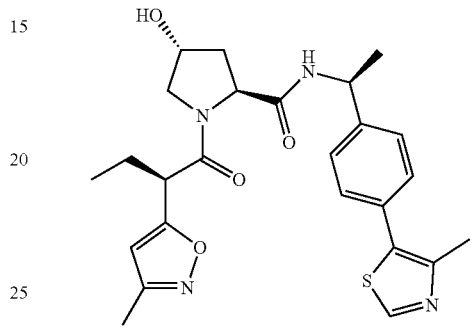
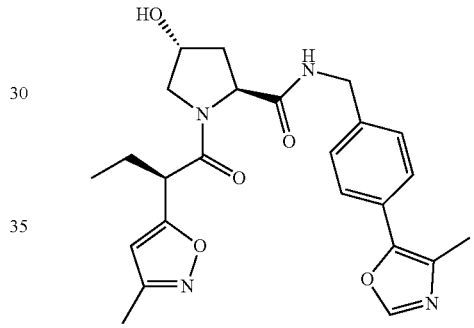
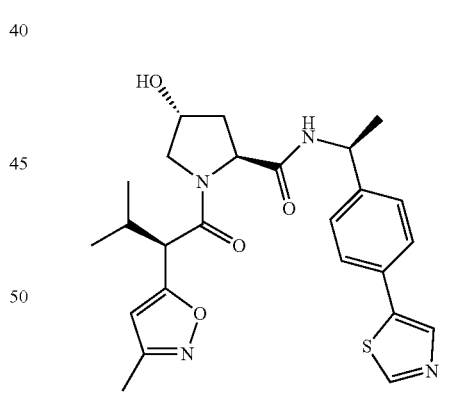
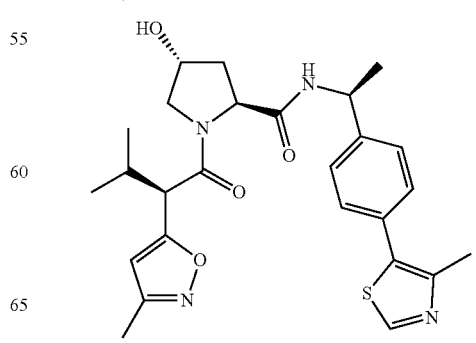

257
-continued
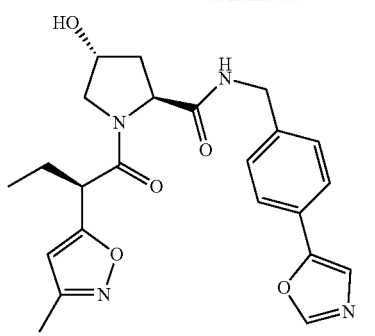
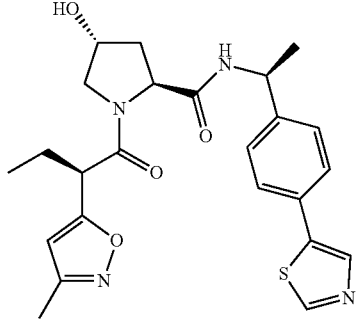
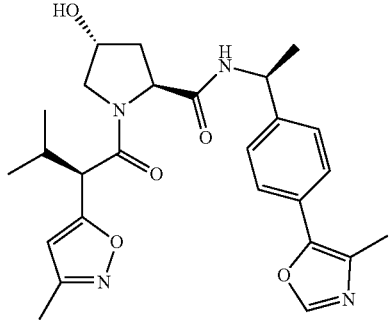
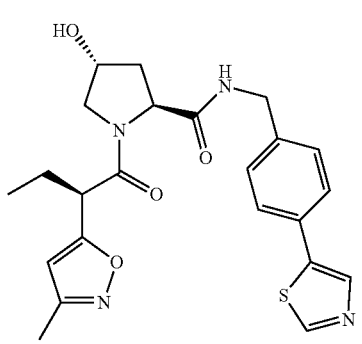
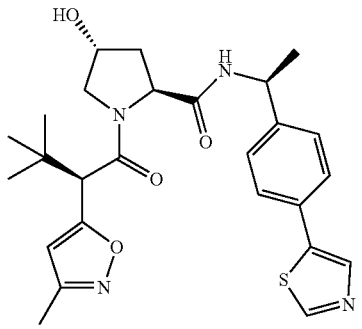
258
-continued
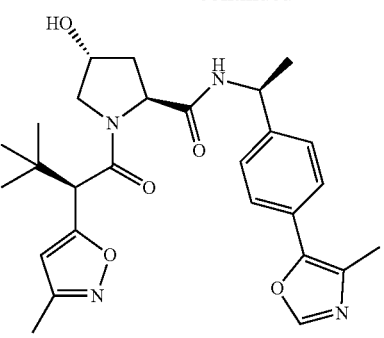
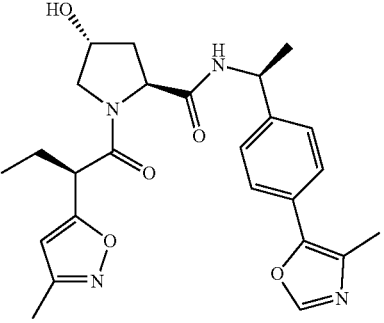
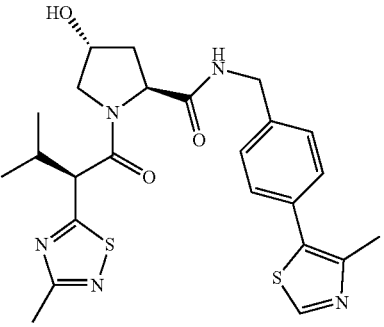
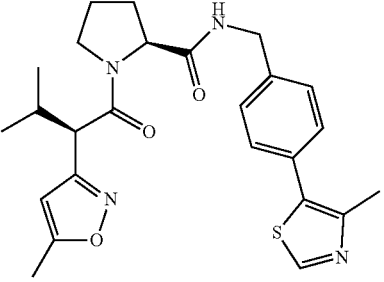
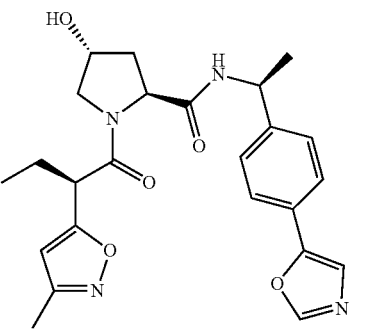

259
-continued
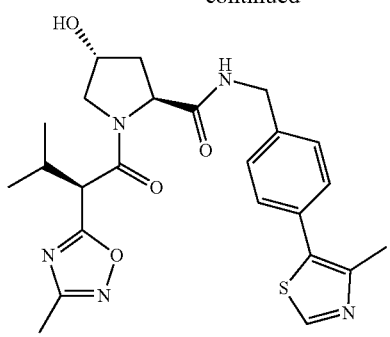
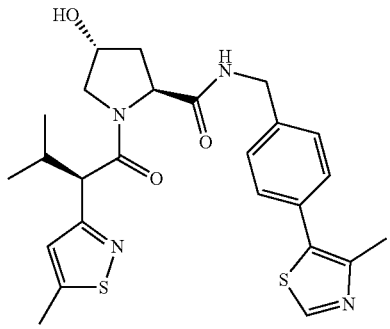
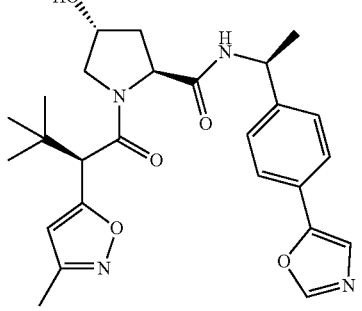
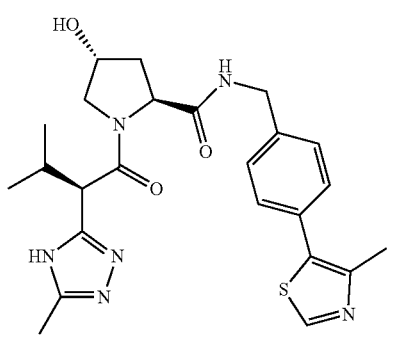
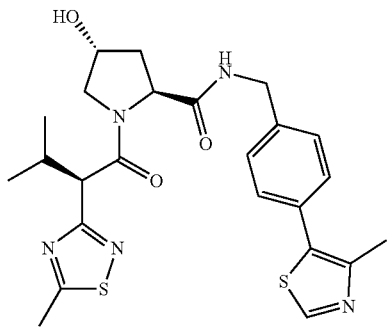
260
-continued
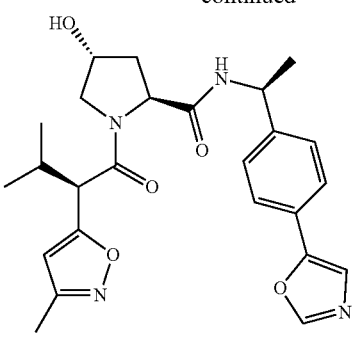
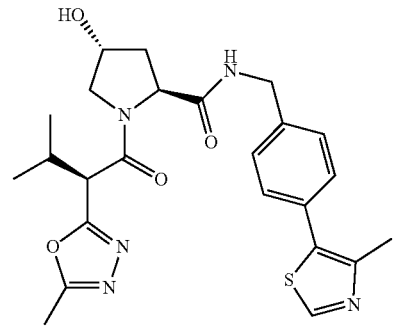
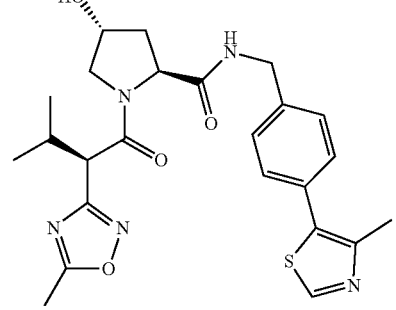
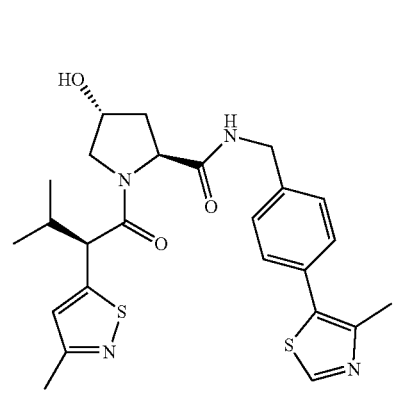
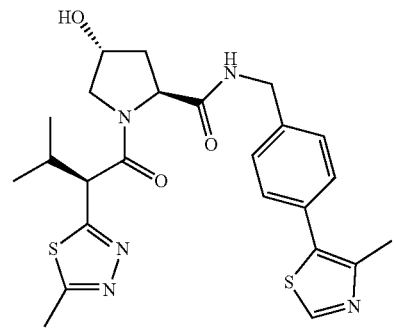

261
-continued
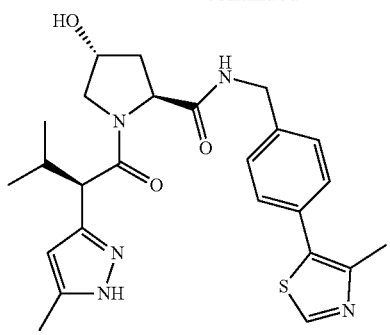
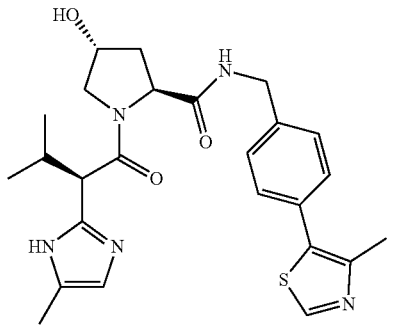
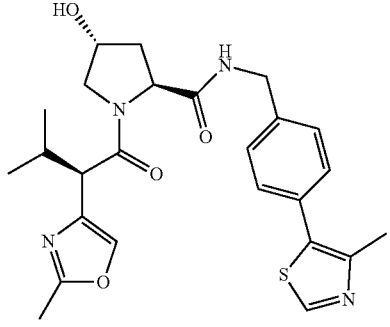
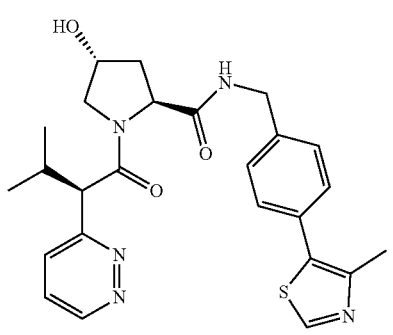
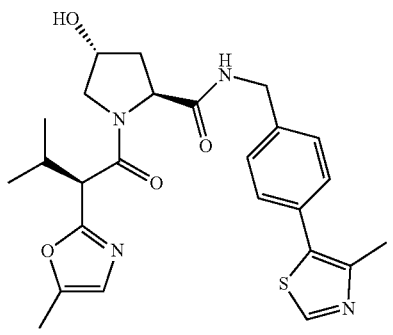
262
-continued
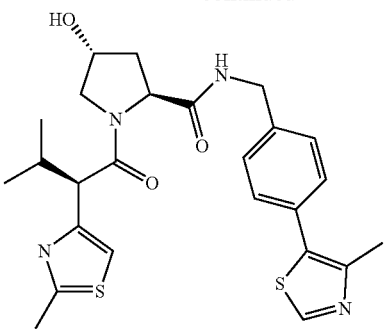
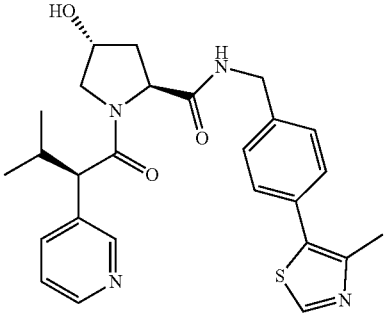
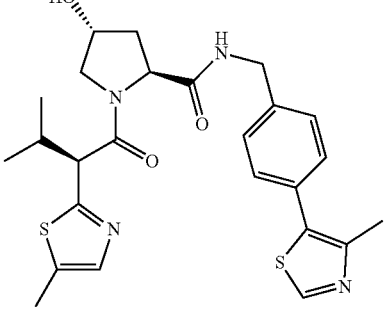
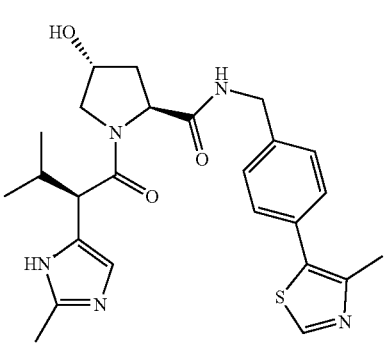
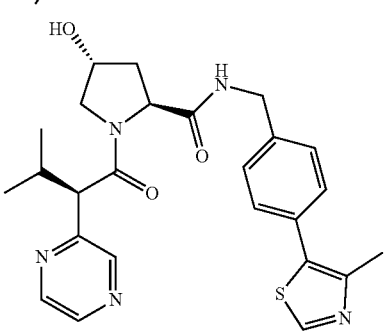

263
-continued
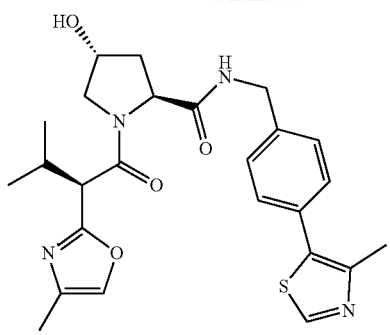
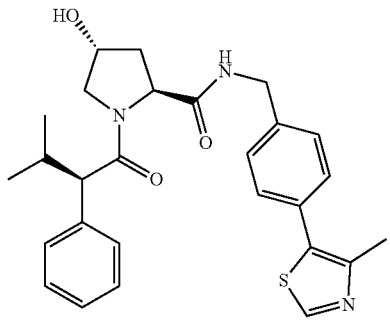
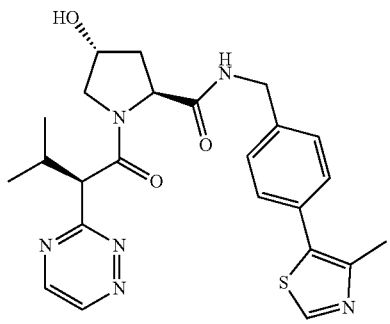
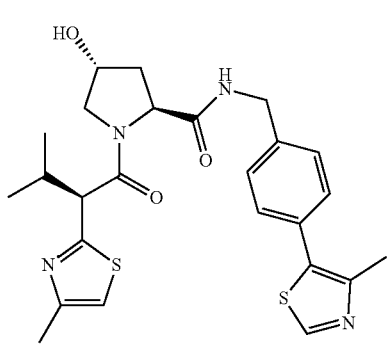
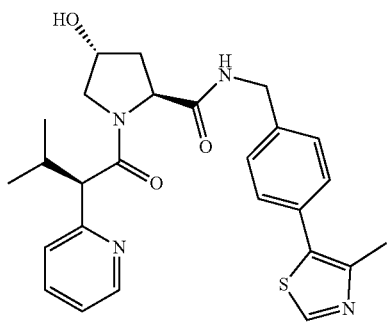
264
-continued
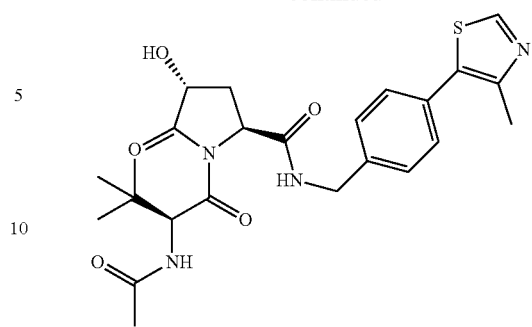
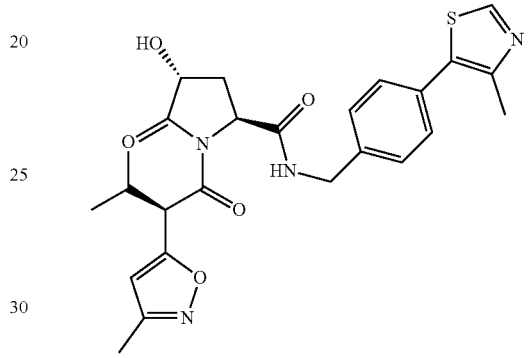
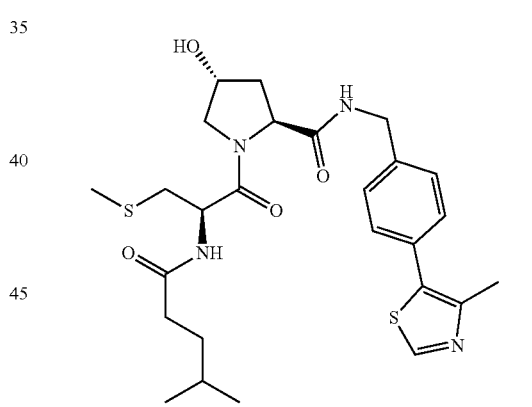
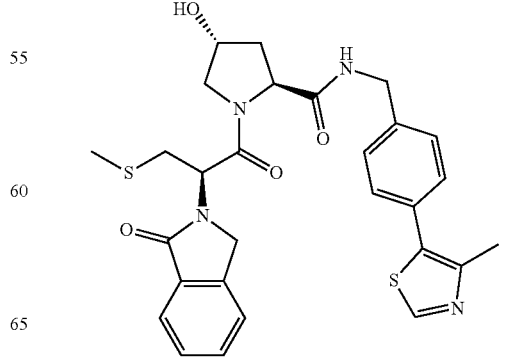

265
-continued
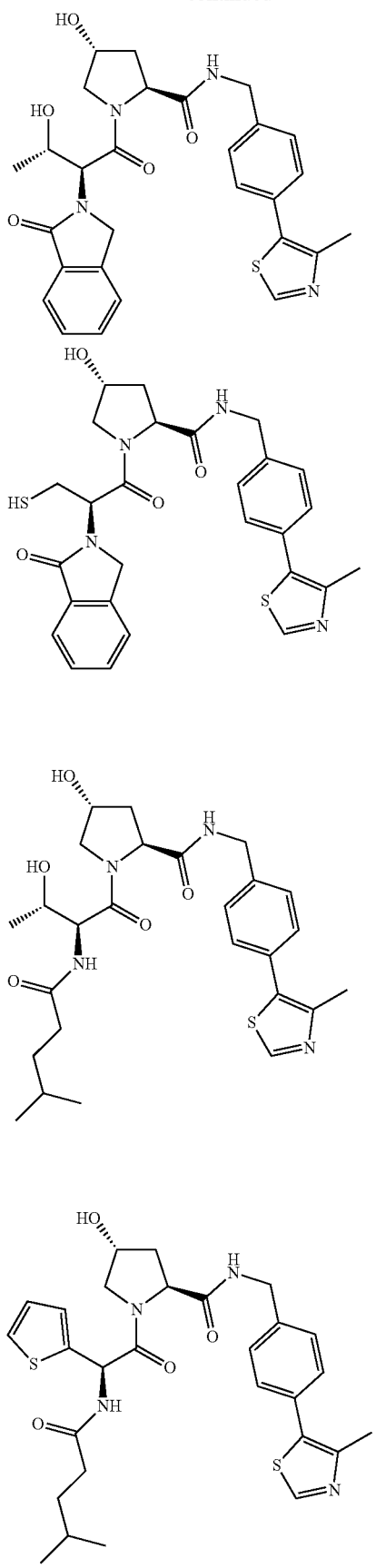
266
-continued
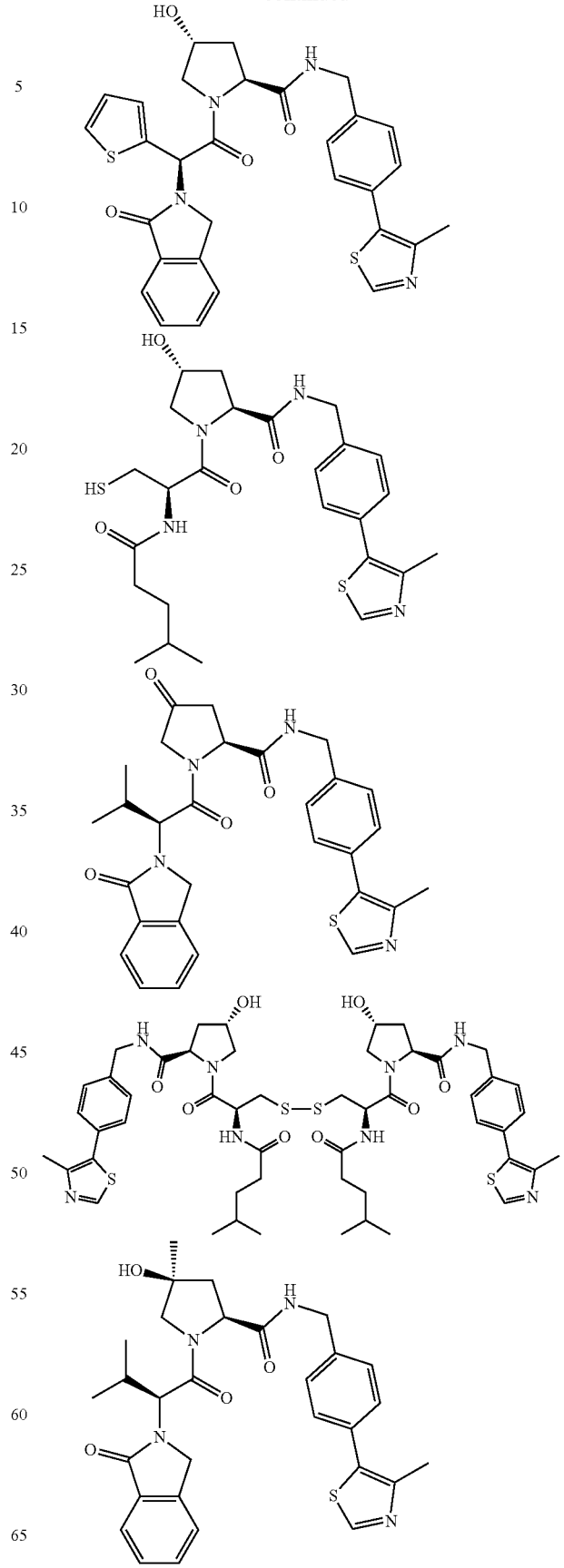

-continued
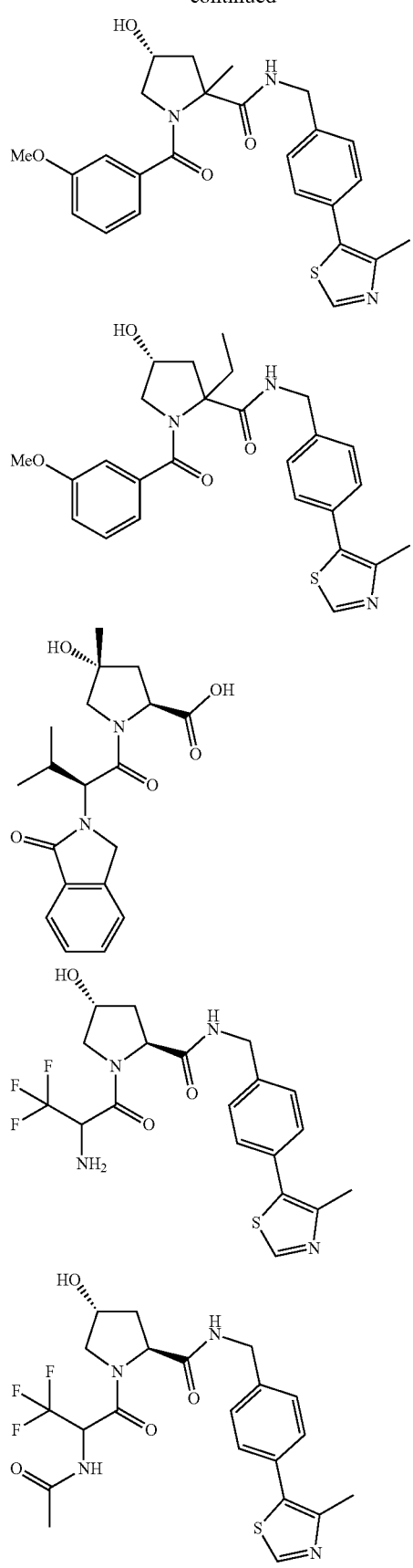
-continued
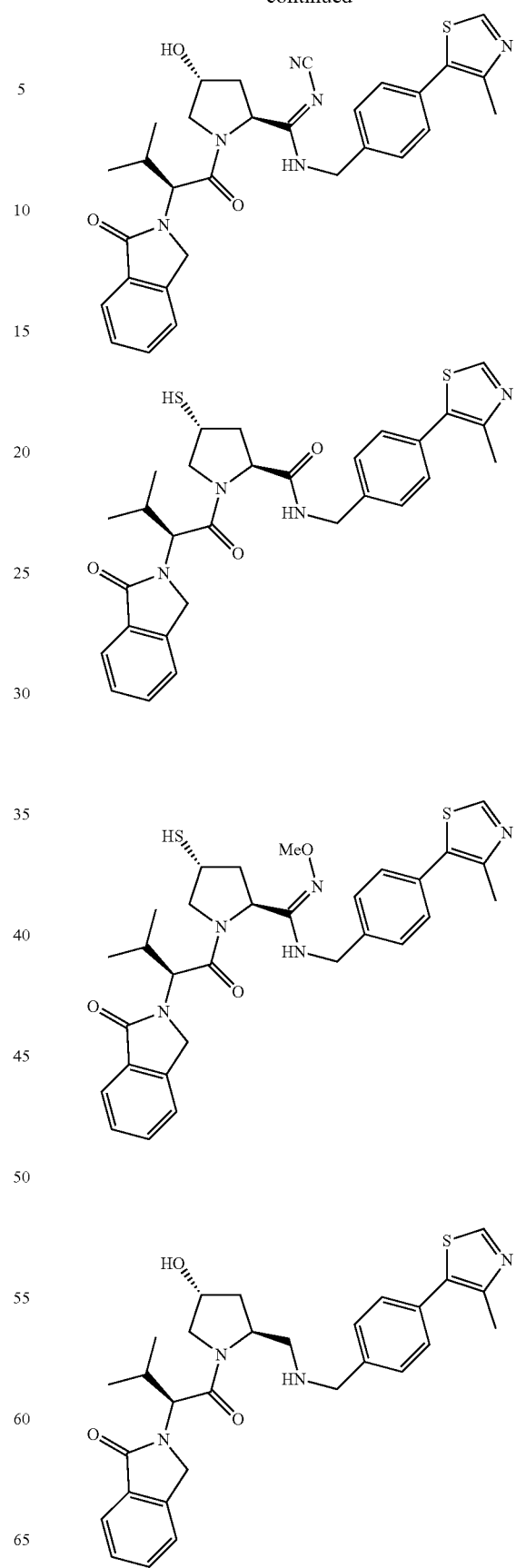

269
-continued
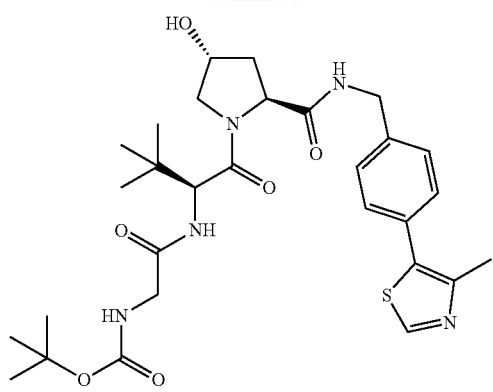
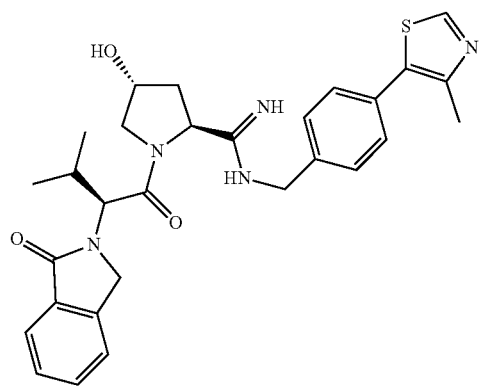
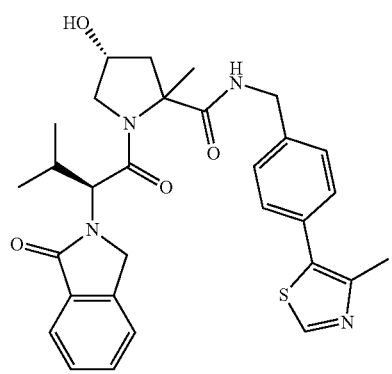
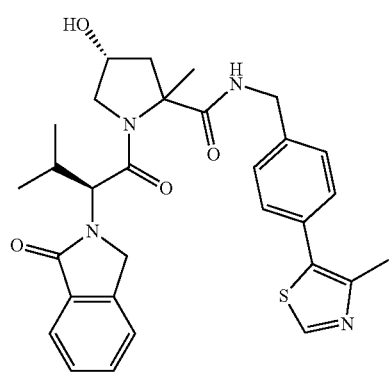
270
-continued
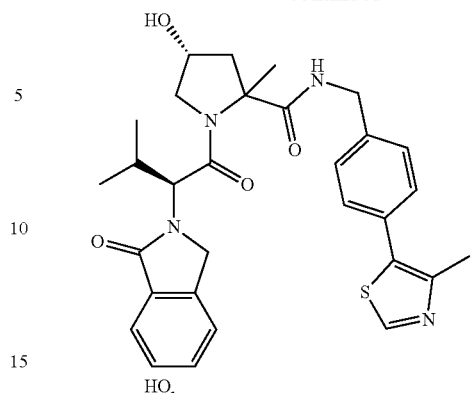
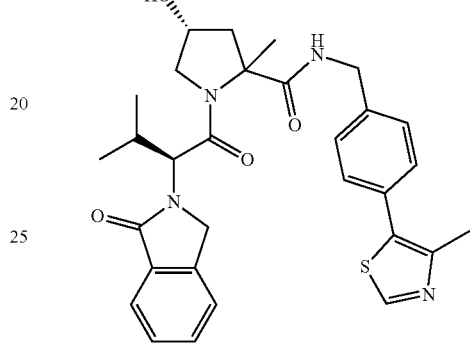
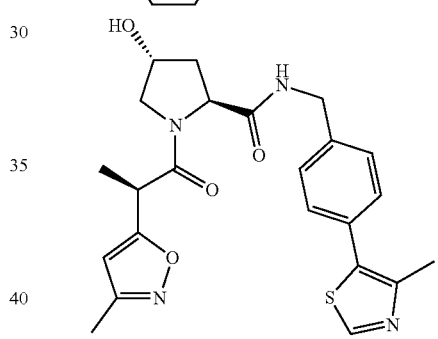
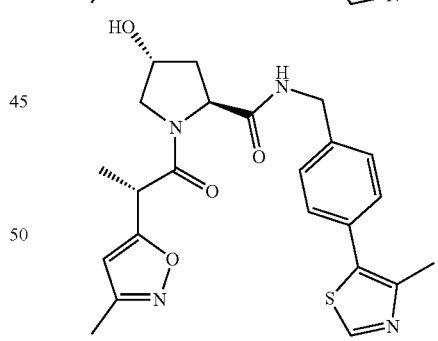
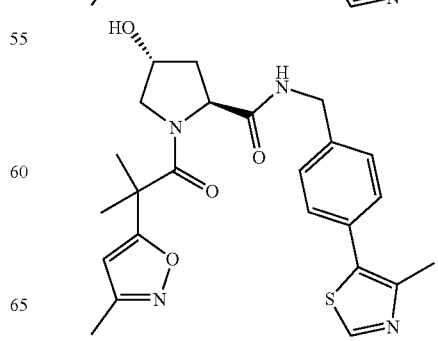

271
-continued
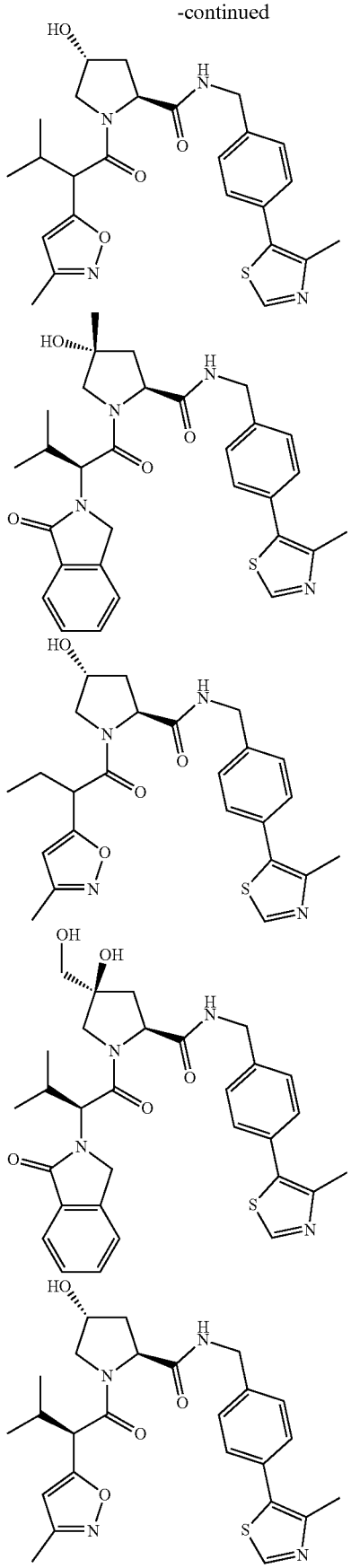
272
-continued
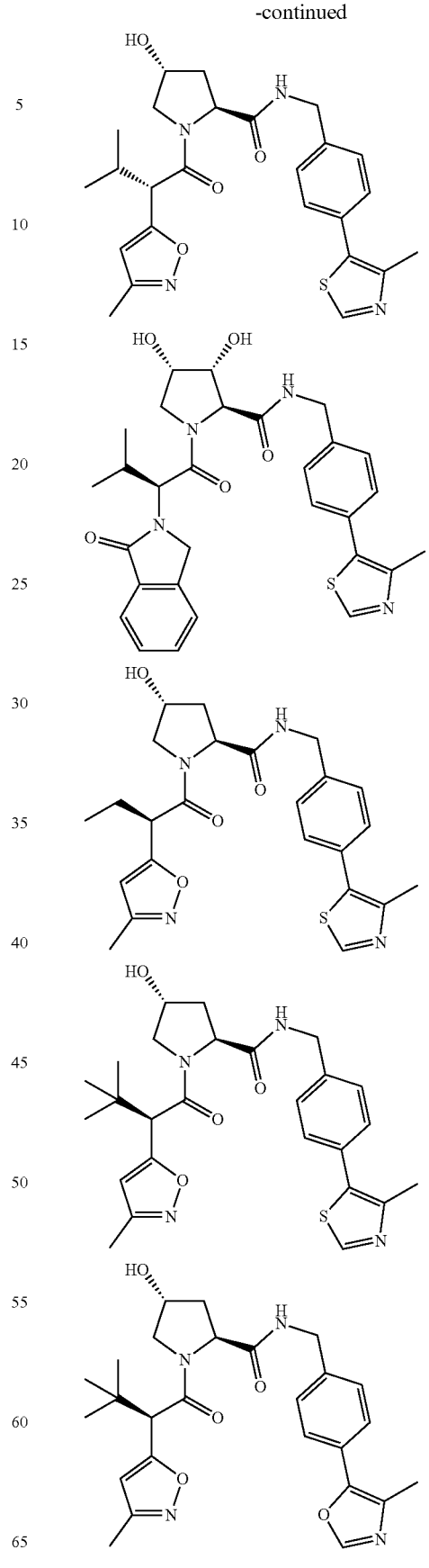

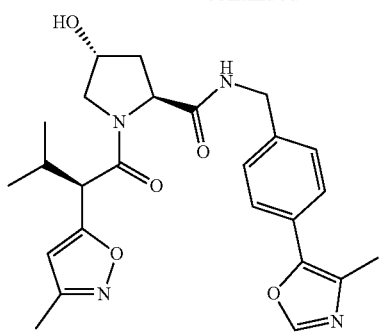
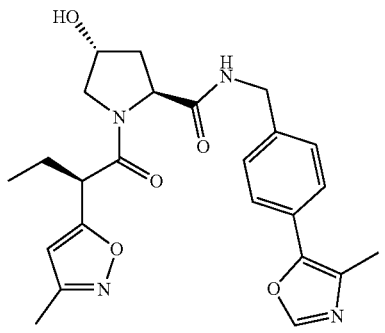
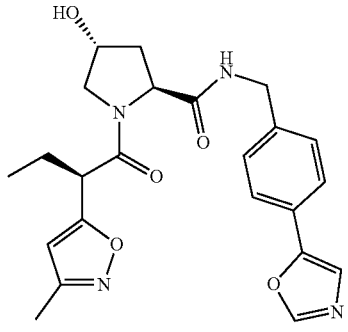
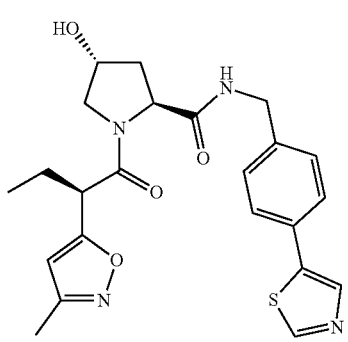
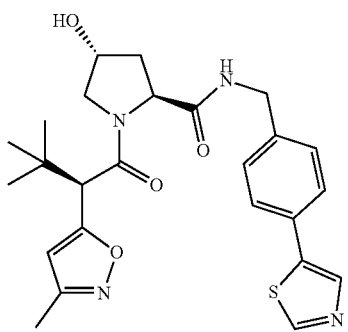

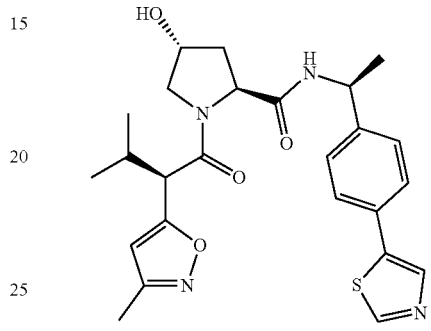
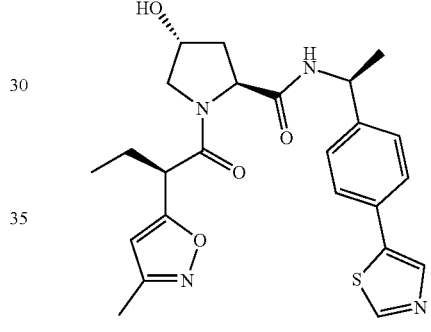
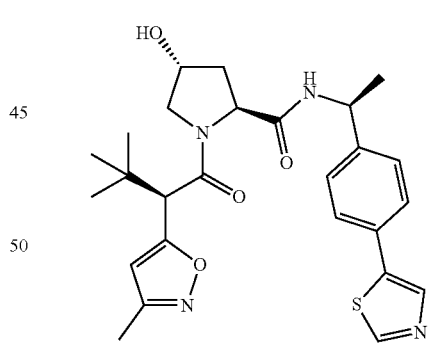

275
-continued
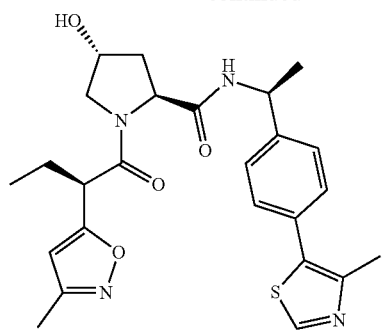
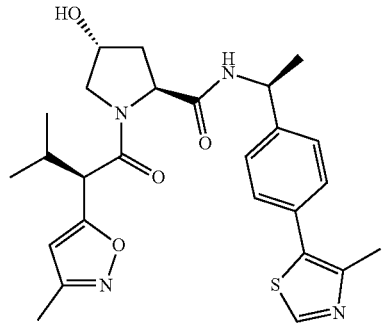
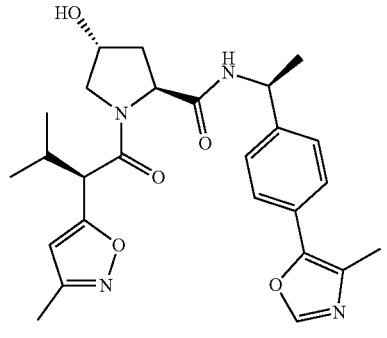
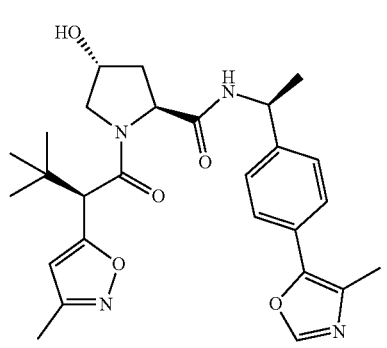
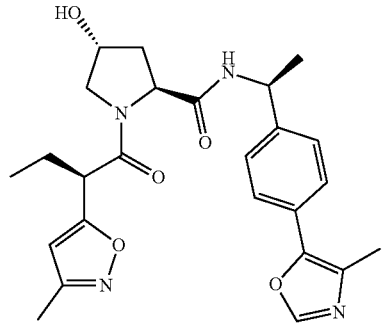
276
-continued

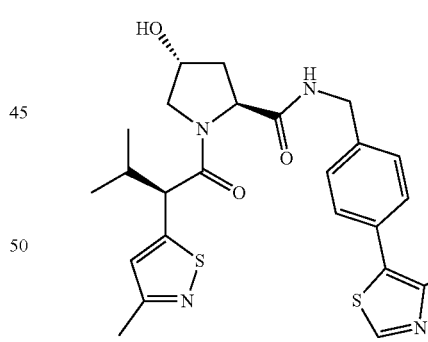


277
-continued
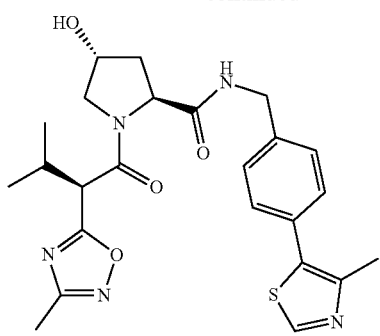
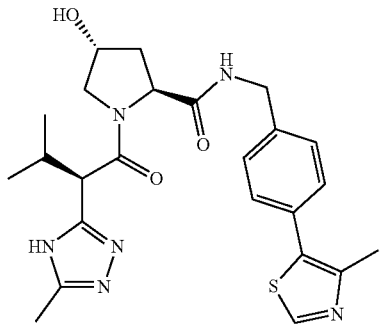
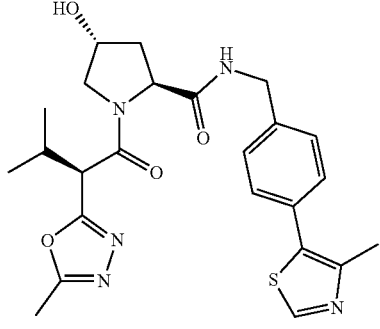
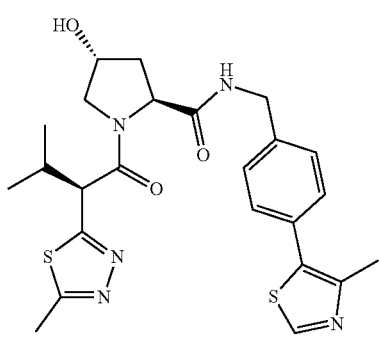
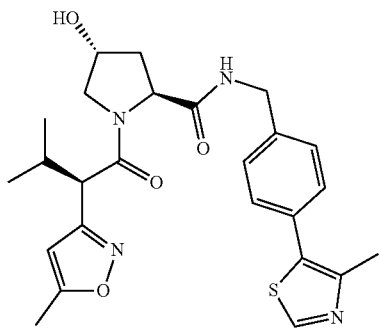
278
-continued
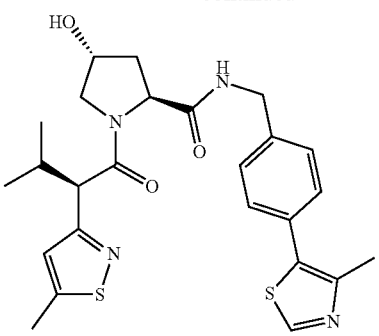
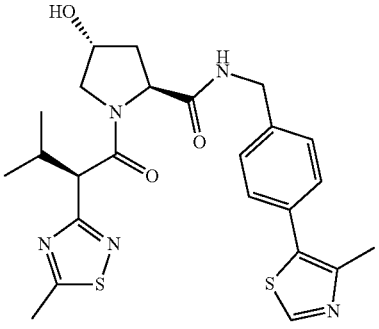
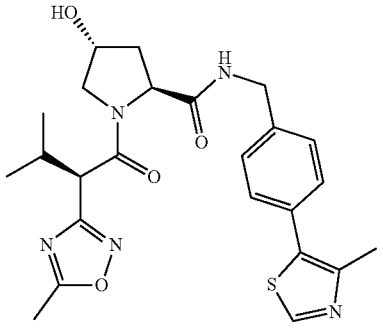
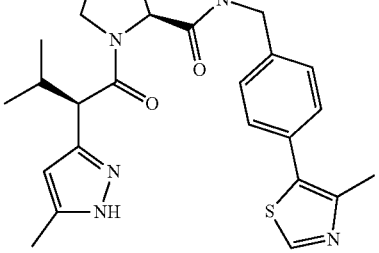
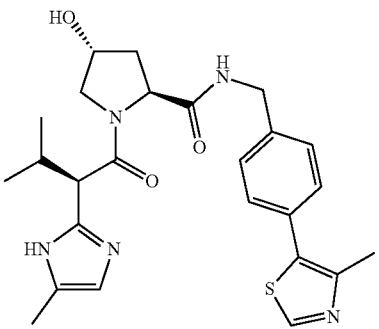

279
-continued
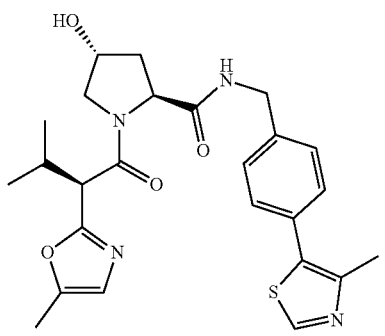
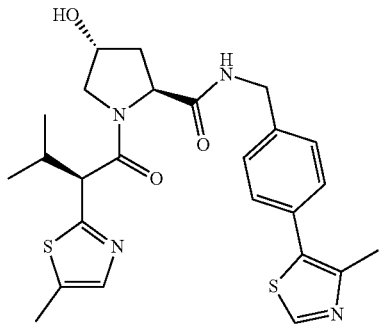
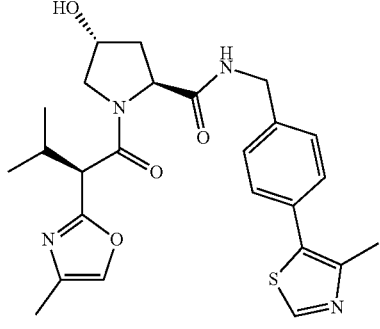
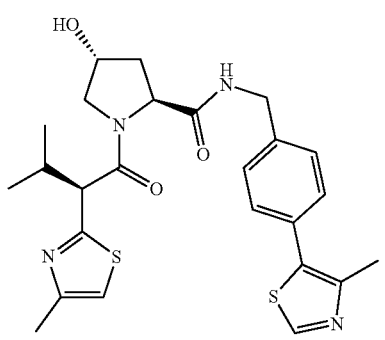
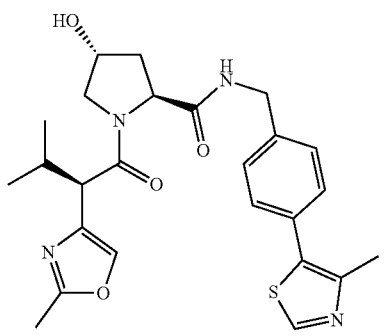
280
-continued

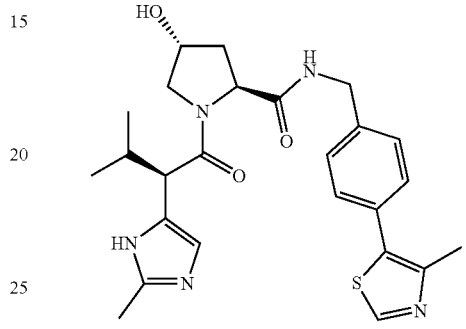
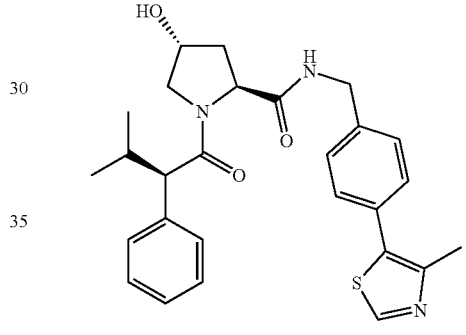
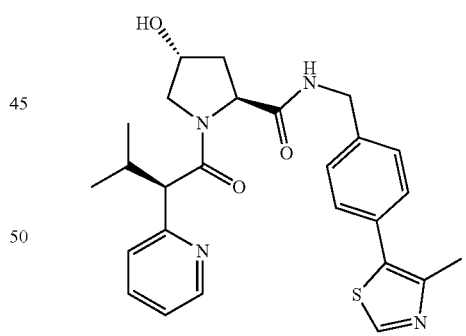
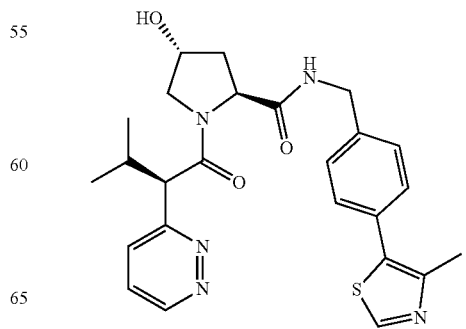

281
-continued
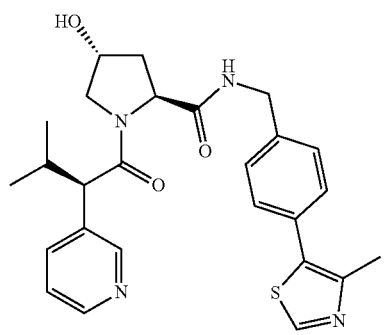
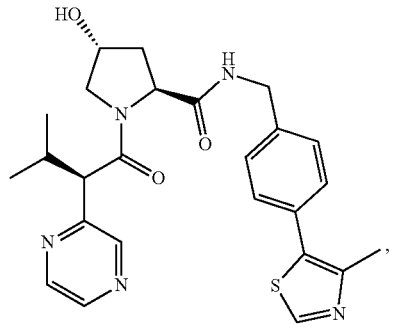
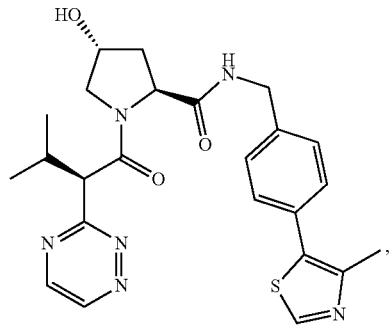
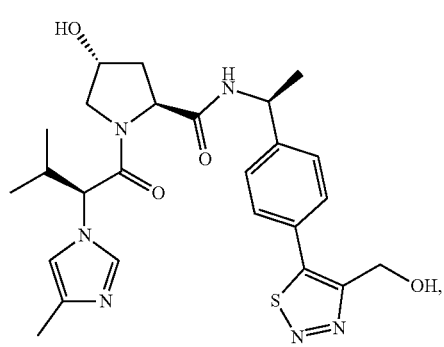
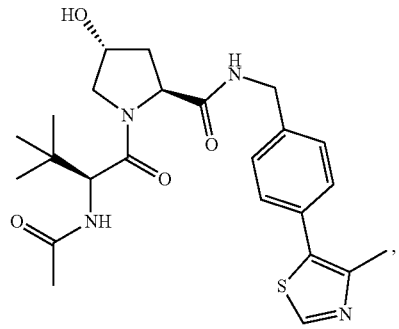
282
-continued
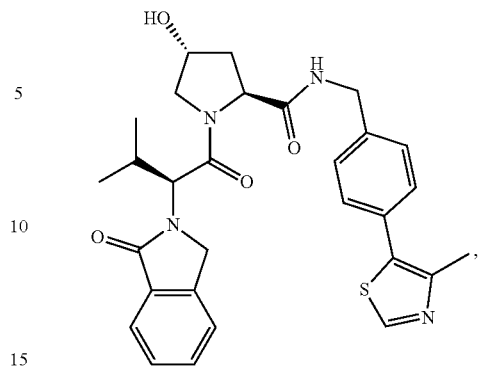
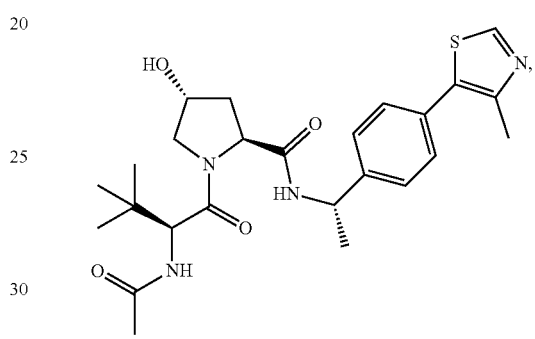
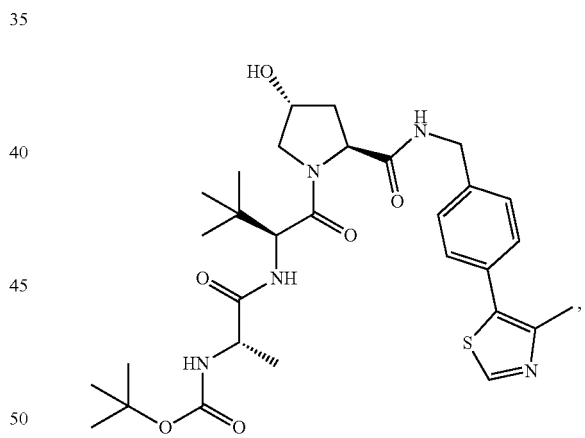
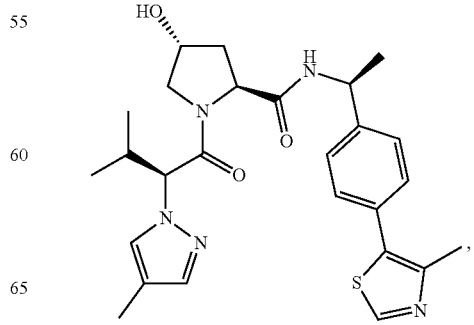

283
-continued
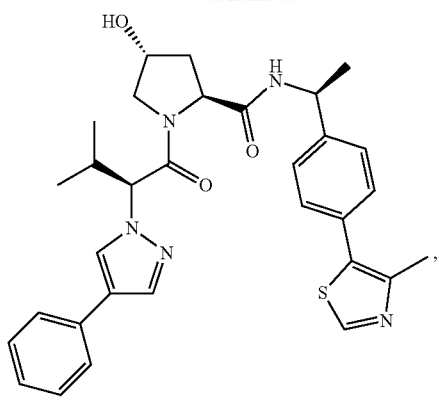
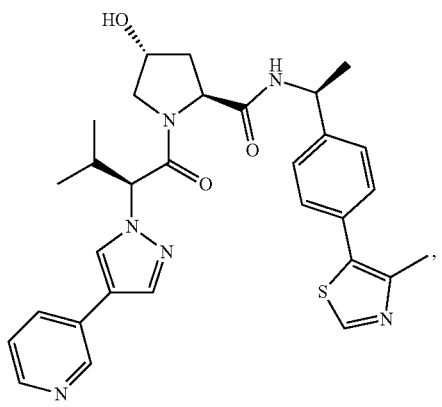
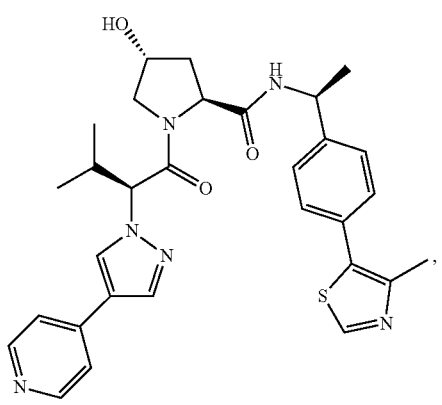
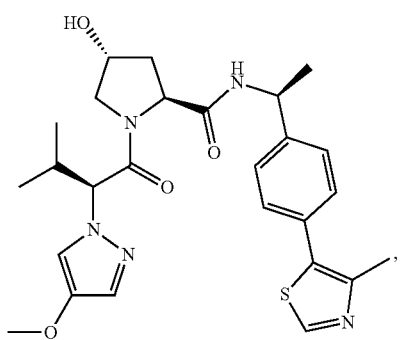
284
-continued
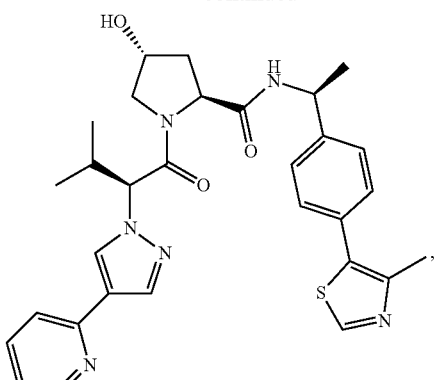
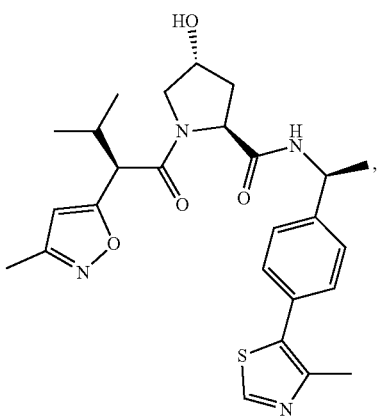
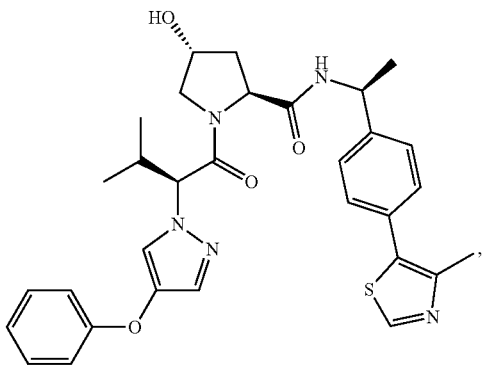
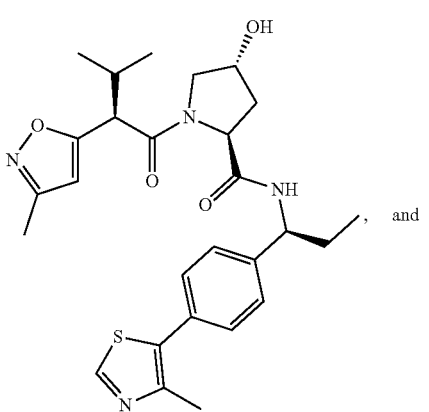, and -continued

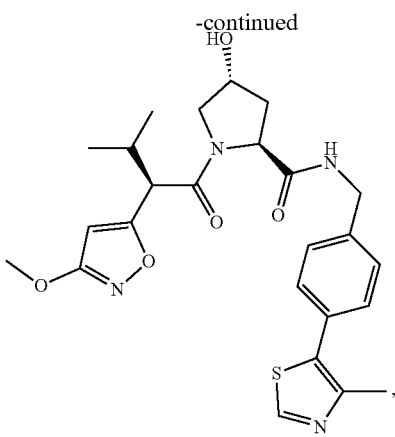

wherein the VLM may be connected to a PTM via a linker, as described herein, at any appropriate location, including, e.g., an aryl, heteroaryl, phenyl, or phenyl of an indole group, optionally via any appropriate functional group, such as an amine, ester, ether, alkyl, or alkoxy.

Exemplary Linkers

In certain embodiments, the compounds as described herein include one or more PTMs chemically linked or coupled to one or more ULMs (e.g., at least one of CLM, VLM, MLM, ILM, or a combination thereof) via a chemical linker (L). In certain embodiments, the linker group L is a group comprising one or more covalently connected structural units (e.g., $-A^L_1 \ldots (A^L)_q$- or $-(A^L)_q$-), wherein $A_1$ is a group coupled to PTM, and $A_q$ is a group coupled to ULM.

In certain embodiments, the linker group L is $-(A^L)_q$-:
$(A^L)_q$ is a group which is connected to at least one of a ULM (such as CLM, VLM, ILM, MLM, CLM', VLM', ILM', and/or MLM'), a PTM moiety, or a combination thereof; and
q of the linker is an integer greater than or equal to 1;
each $A^L$ is independently selected from the group consisting of, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}$=$CR^{L2}$, C≡C, $SiR^{L1}R^{L2}$, $P(O)R^{L1}$, $P(O)OR^{L1}$, $NR^{L3}C$(=NCN)$NR^{L4}$, $NR^{L3}C$(=NCN), $NR^{L3}C$(=$CNO_2$)$NR^{L4}$, $C_{3-11}$ cycloalkyl optionally substituted with 0-6 $R^{L1}$ and/or $R^{L2}$ groups, $C_{3-11}$ spirocycloalkyl optionally substituted with 0-9 $R^{L2}$ and/or RU groups, $C_{3-11}$ heterocyclyl optionally substituted with 0-6 $R^{L1}$ and/or $R^{L2}$ groups, $C_{5-13}$ spiroheterocycloalkyl optionally substituted with 0-8 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups; and
$R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$ alkyl, $N(C_{1-8}alkyl)_2$, $C_{3-11}$cycloalkyl, aryl, heteroaryl, $C_{3-11}$heterocyclyl, $OC_{1-8}$cycloalkyl, $SC_{1-8}$ cycloalkyl, $NHC_{1-8}$cycloalkyl, $N(C_{1-8}cycloalkyl)_2$, $N(C_{1-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, CC—$C_{1-8}$alkyl, CCH, CH=CH($C_{1-8}$ alkyl), C($C_{1-8}$alkyl)=CH($C_{1-8}$alkyl), C($C_{1-8}$alkyl)=C($C_{1-8}$ alkyl)2, Si(OH)3, Si($C_{1-8}$alkyl)$_3$, Si(OH)($C_{1-8}$alkyl)$_2$, $COC_{1-8}$alkyl, $CO_2H$, halogen, CN, $CF_3$, $CHF_2$, $CH_2F$, $NO_2$, $SF_5$, $SO_2NHC_{1-8}$ alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}$ alkyl)$_2$, $NHCONH_2$, $N(C_{1-8}alkyl)$ $SO_2NH(C_{1-8}alkyl)$, $N(C_{1-8}alkyl)$ $SO_2N(C_{1-8}alkyl)_2$, NH $SO_2NH(C_{1-8}alkyl)$, NH $SO_2N(C_{1-8}alkyl)_2$, NH $SO_2NH_2$.

In certain embodiments, q of the linker is an integer greater than or equal to 0. In certain embodiments, q is an integer greater than or equal to 1.

In certain embodiments, e.g., where q of the linker is greater than 2, $(A^L)_q$ is a group which is connected to ULM, and A, and $(A^L)_q$ are connected via structural units of the linker (L).

In certain embodiments, e.g., where q of the linker is 2, $(A^L)_q$ is a group which is connected to $A^L_1$ and to a ULM.

In certain embodiments, e.g., where q of the linker is 1, the structure of the linker group L is $-A^L_1$-, and $A^L_1$ is a group which is connected to a ULM moiety and a PTM moiety.

In certain embodiments, the linker (L) comprises a group represented by a general structure selected from the group consisting of:
—NR(CH$_2$)$_n$-(lower alkyl)-, —NR(CH$_2$)$_n$-(lower alkoxyl)-, —NR(CH$_2$)$_n$-(lower alkoxyl)-OCH$_2$—, —NR(CH$_2$)$_n$-(lower alkoxyl)-(lower alkyl)-OCH$_2$—, —NR(CH$_2$)$_n$-(cycloalkyl)-(lower alkyl)-OCH$_2$—, —NR(CH$_2$)$_n$-(hetero cyclyl)-, —NR(CH$_2$CH$_2$O)$_n$-(lower alkyl)-O—CH$_2$—, —NR(CH$_2$CH$_2$O)$_n$-(hetero cycloalkyl)-O—CH$_2$—, —NR(CH$_2$CH$_2$O)$_n$-Aryl-O—CH$_2$—, —NR(CH$_2$CH$_2$O)$_n$-(hetero aryl)-O—CH$_2$—, —NR(CH$_2$CH$_2$O)$_n$-(cyclo alkyl)-O-(hetero aryl)-O—CH$_2$, —NR(CH$_2$CH$_2$O)$_n$-(cyclo alkyl)-O-Aryl-O—CH$_2$—, —NR(CH$_2$CH$_2$O)$_n$-(lower alkyl)-NH-Aryl-O—CH$_2$—, —NR(CH$_2$CH$_2$O)$_n$-(lower alkyl)-O-Aryl-CH$_2$, —NR(CH$_2$CH$_2$O)$_n$-cycloalkyl-O-Aryl-, —NR(CH$_2$CH$_2$O)$_n$-cycloalkyl-O-(heteroaryl)l-, —NR(CH$_2$CH$_2$)$_n$-(cycloalkyl)-O-(heterocycle)-CH$_2$. —NR(CH$_2$CH$_2$)$_n$-(heterocycle)-(heterocycle)-CH$_2$, —N(R1R2)-(heterocycle)-CH$_2$; where
n of the linker can be 0 to 10;
R of the linker can be H, lower alkyl;
R1 and R2 of the linker can form a ring with the connecting N.

In certain embodiments, the linker (L) comprises a group represented by a general structure selected from the group consisting of:

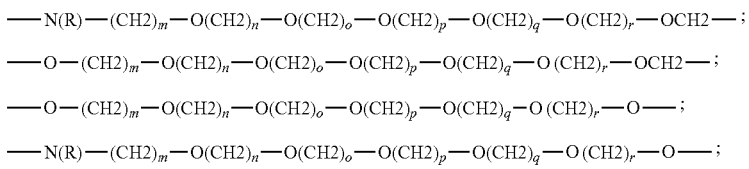

-continued
—(CH2)$_m$—O(CH2)$_n$—O(CH2)$_o$—O(CH2)$_p$—O(CH2)$_q$—O(CH2)$_r$—O—;
—(CH2)$_m$—O(CH2)$_n$—O(CH2)$_o$—O(CH2)$_p$—O(CH2)$_q$—O(CH2)$_r$—OCH2—;
—(CH$_2$)$_m$O(CH$_2$)$_r$—N⟨piperazine⟩N—(CH$_2$)$_o$O(CH$_2$)$_p$—;
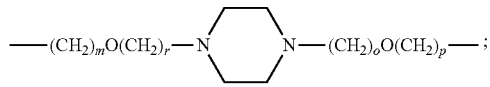
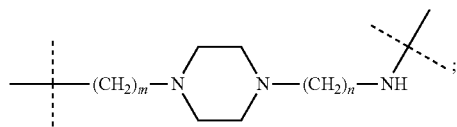
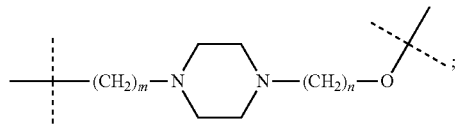
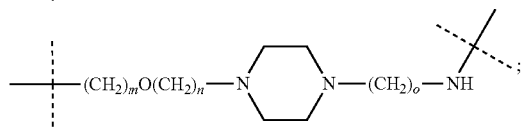
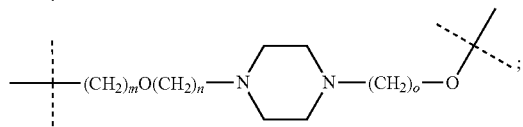
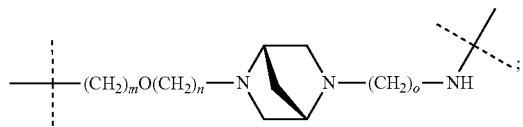
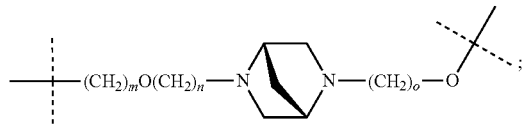
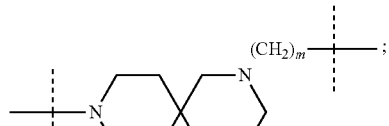
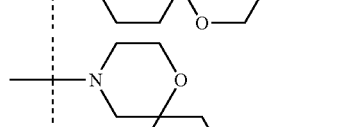
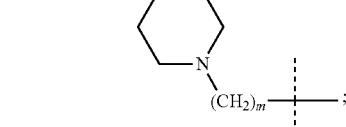
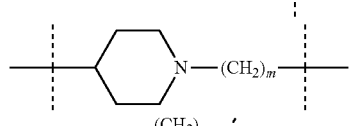
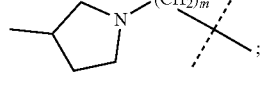
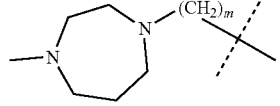

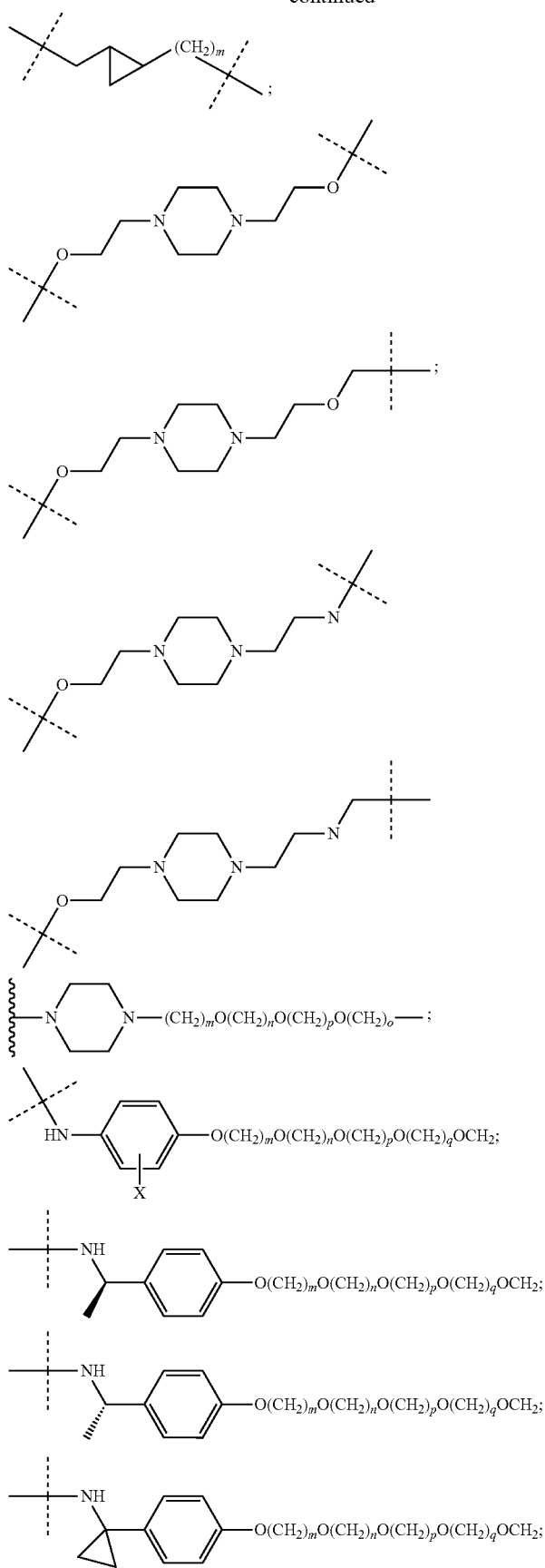

-continued
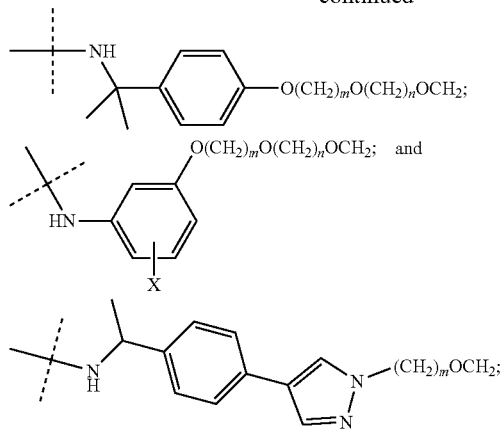
wherein
m, n, o, p, q, and r of the linker are independently 0, 1, 2, 3, 4, 5, 6;
when the number is zero, there is no N—O or O—O bond
R of the linker is H, methyl and ethyl;
X of the linker is H and F
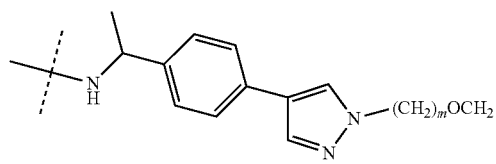
where m of the linker can be 2, 3, 4, 5
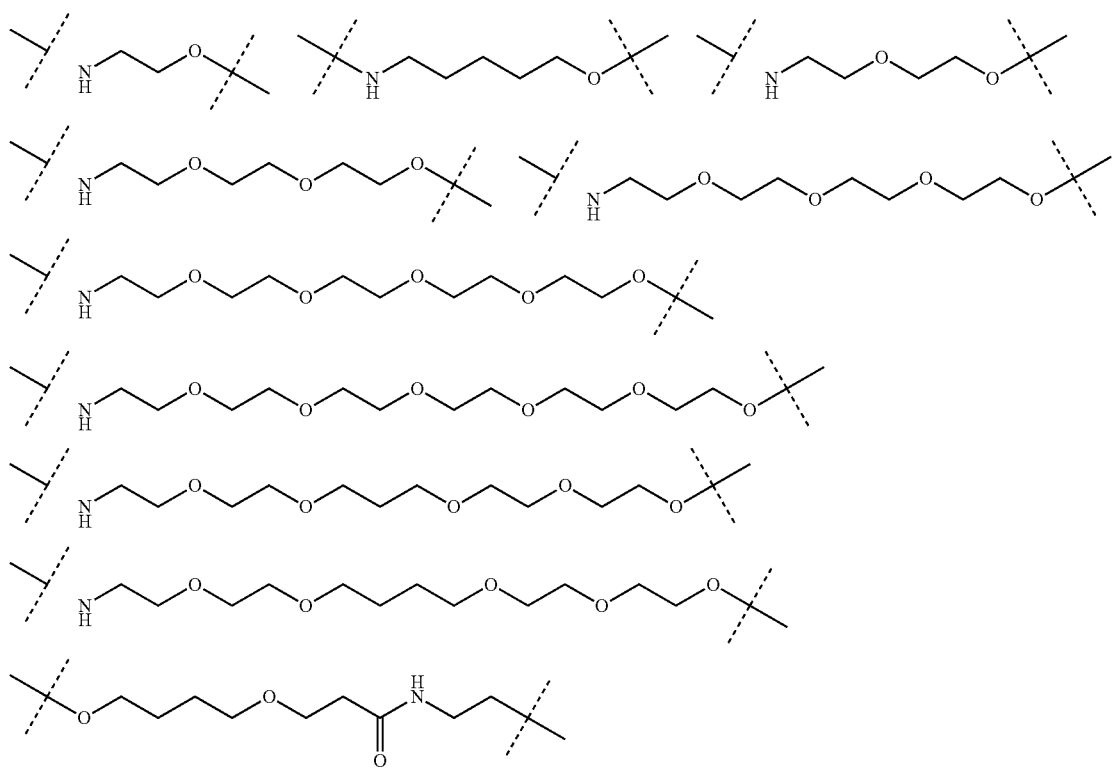

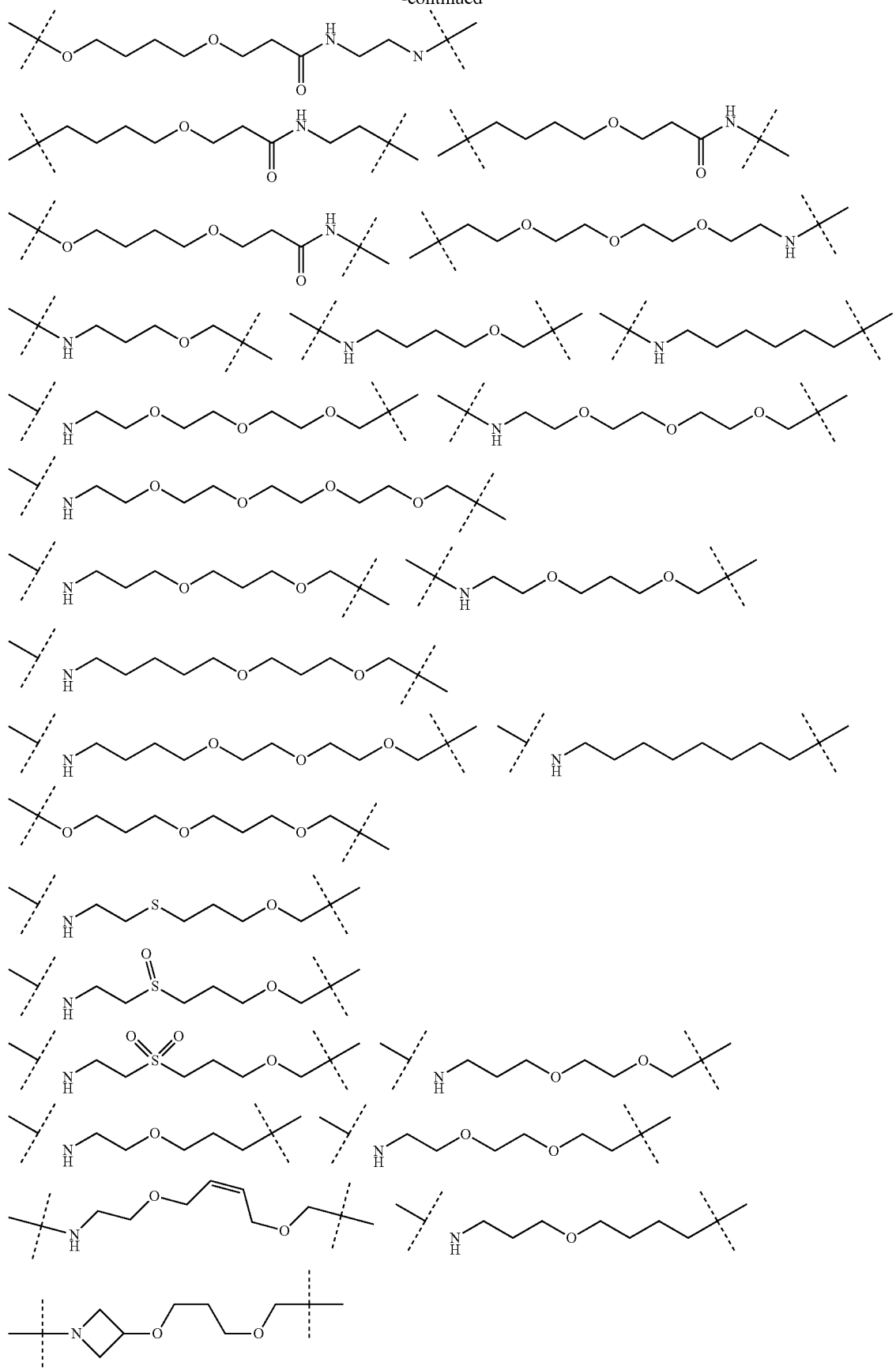

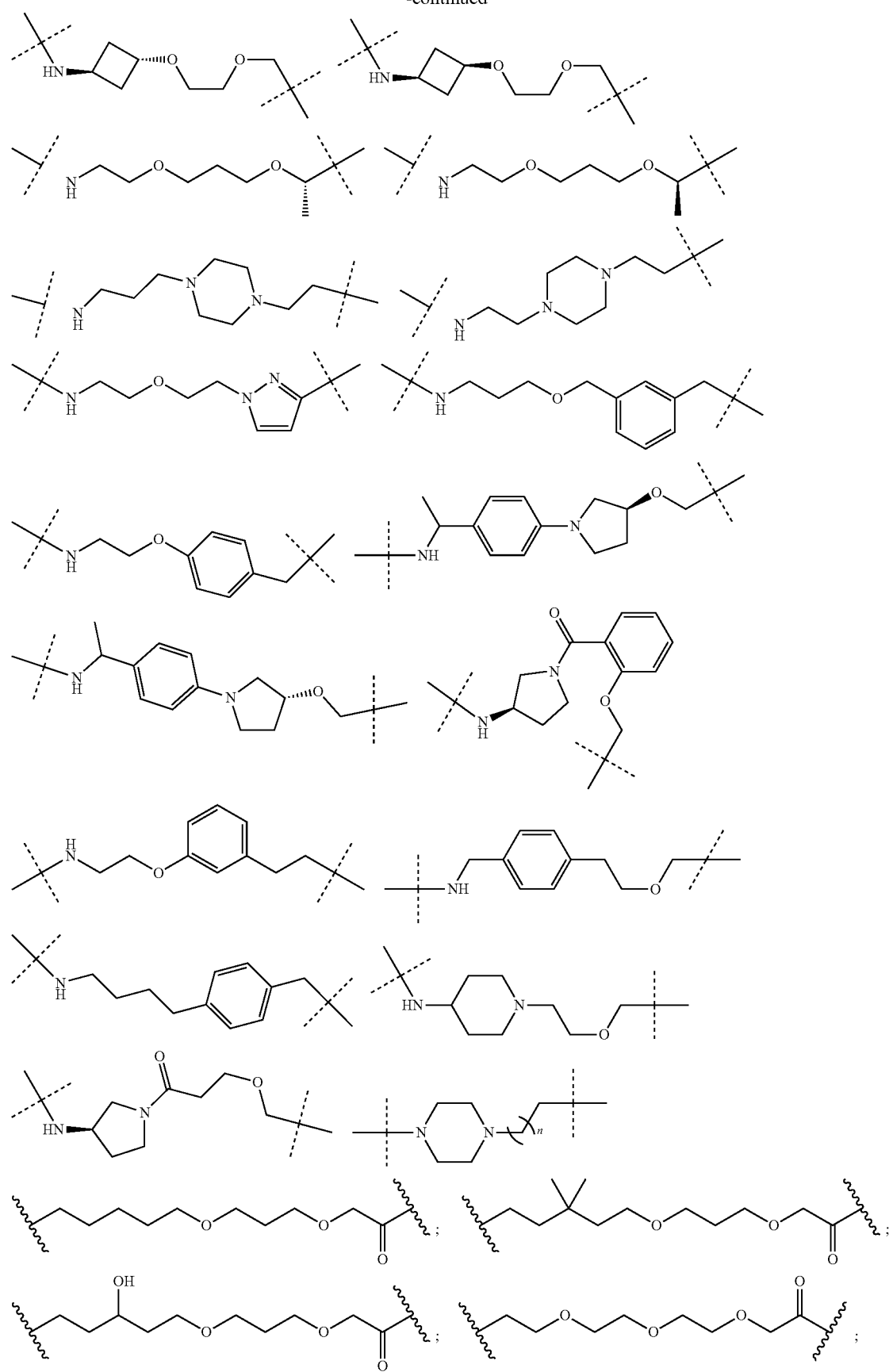

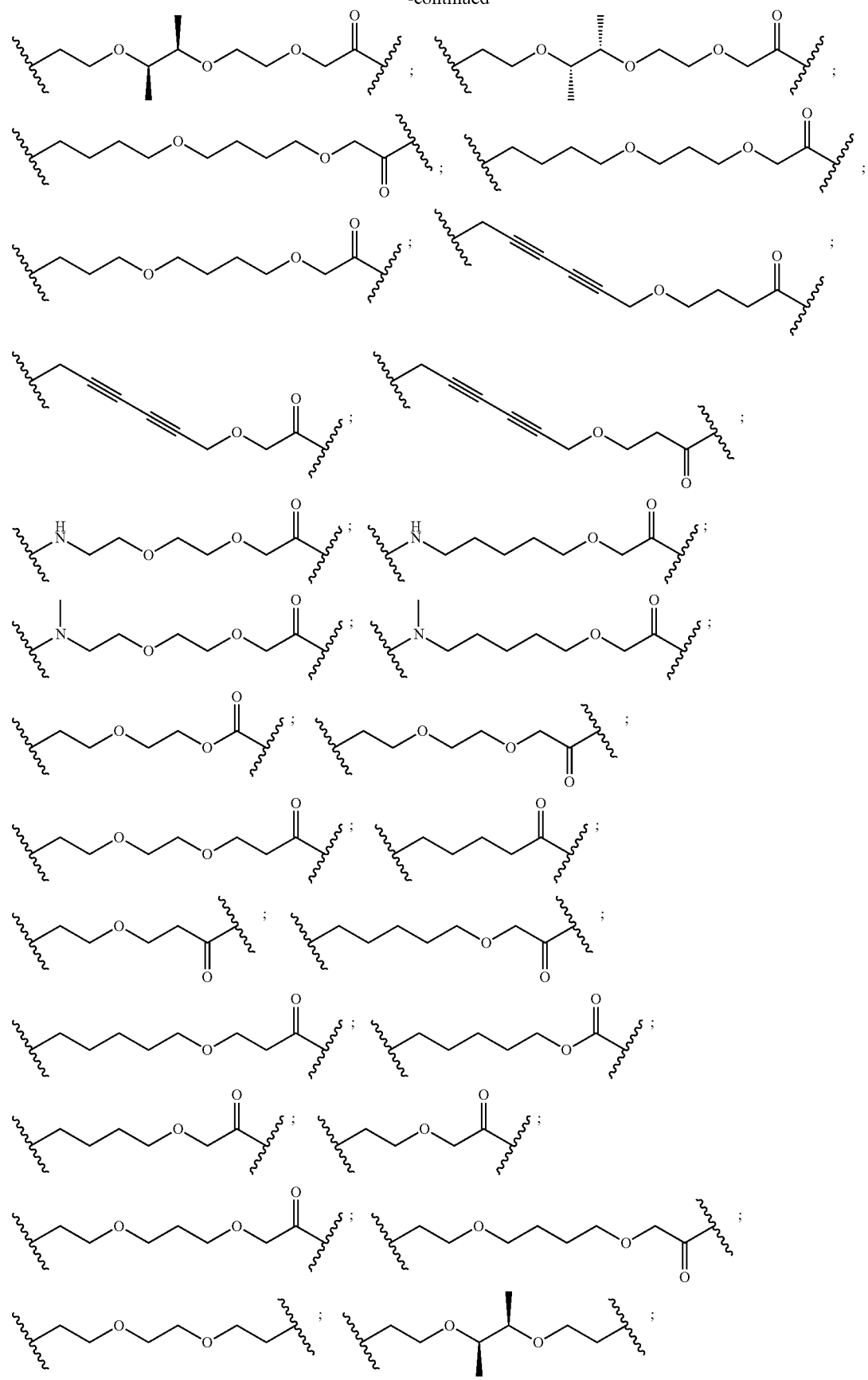

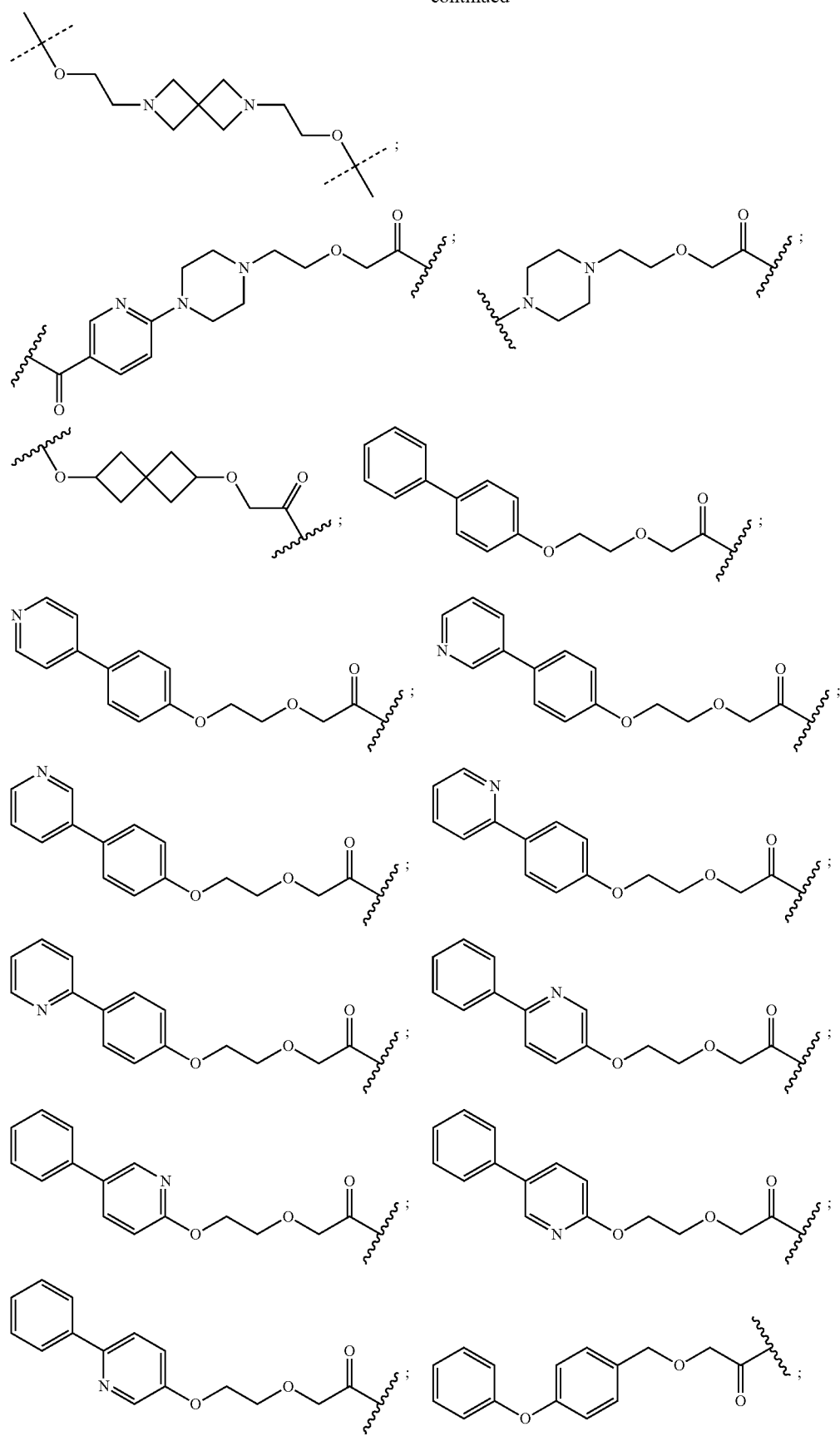

301 302
-continued
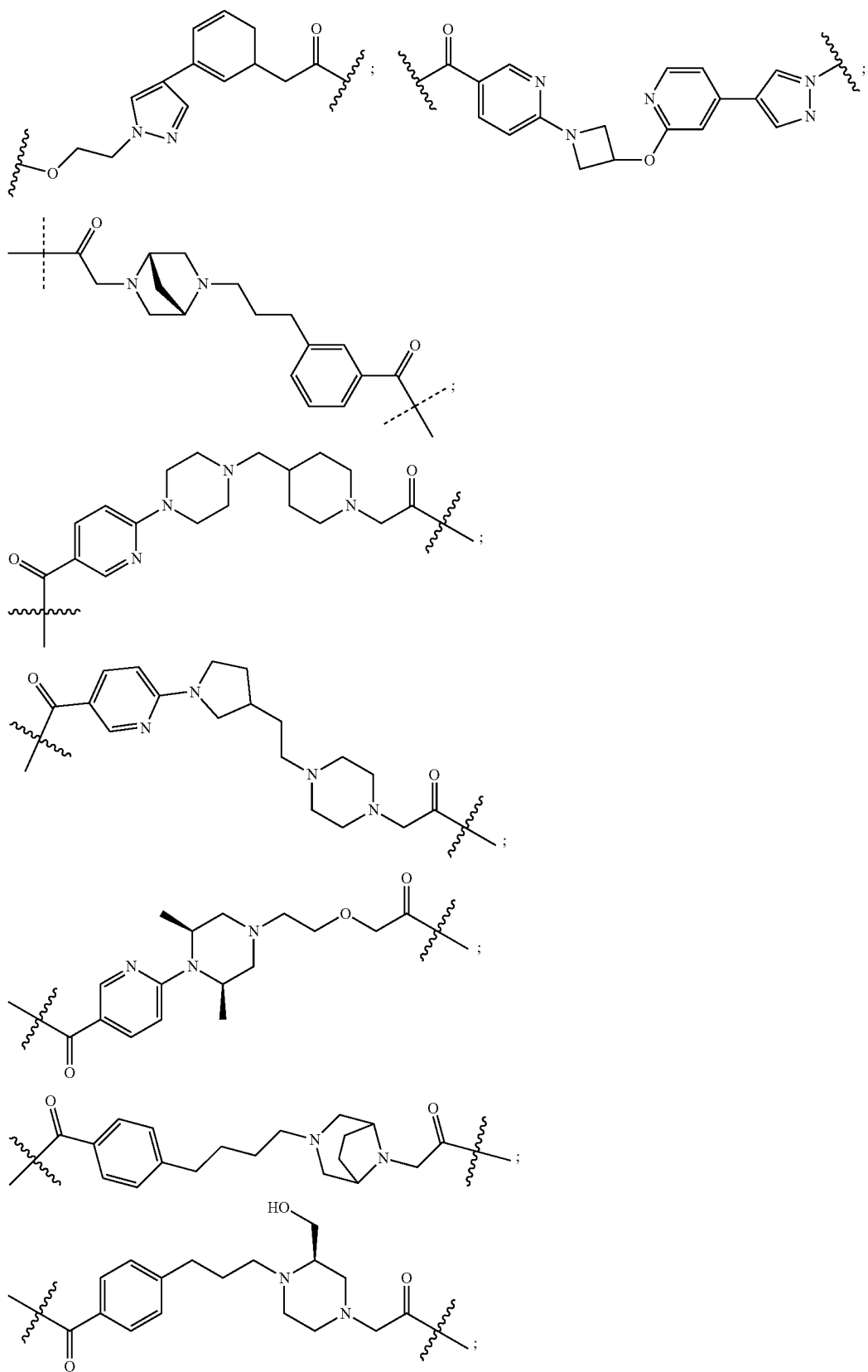

-continued
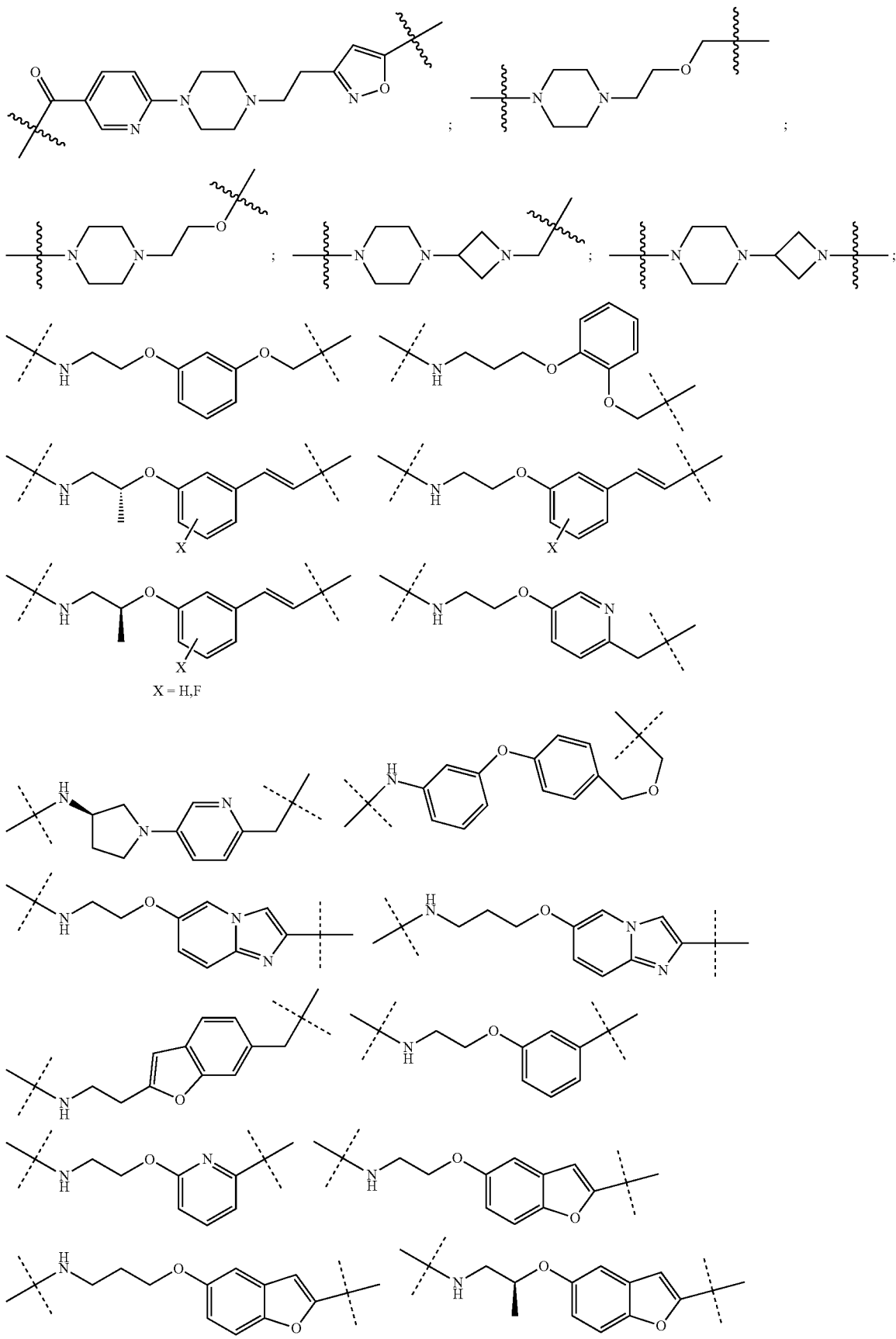

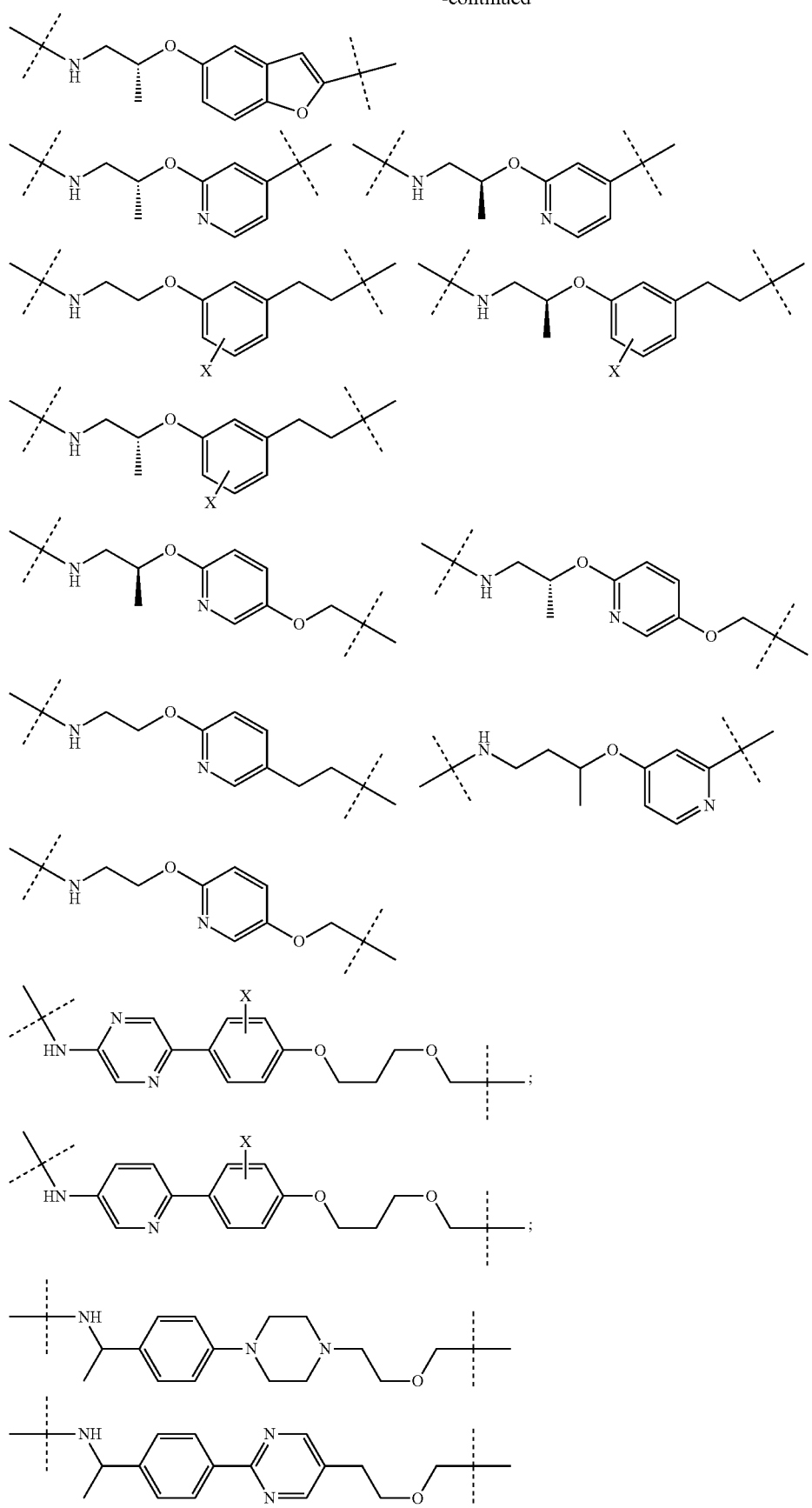

-continued
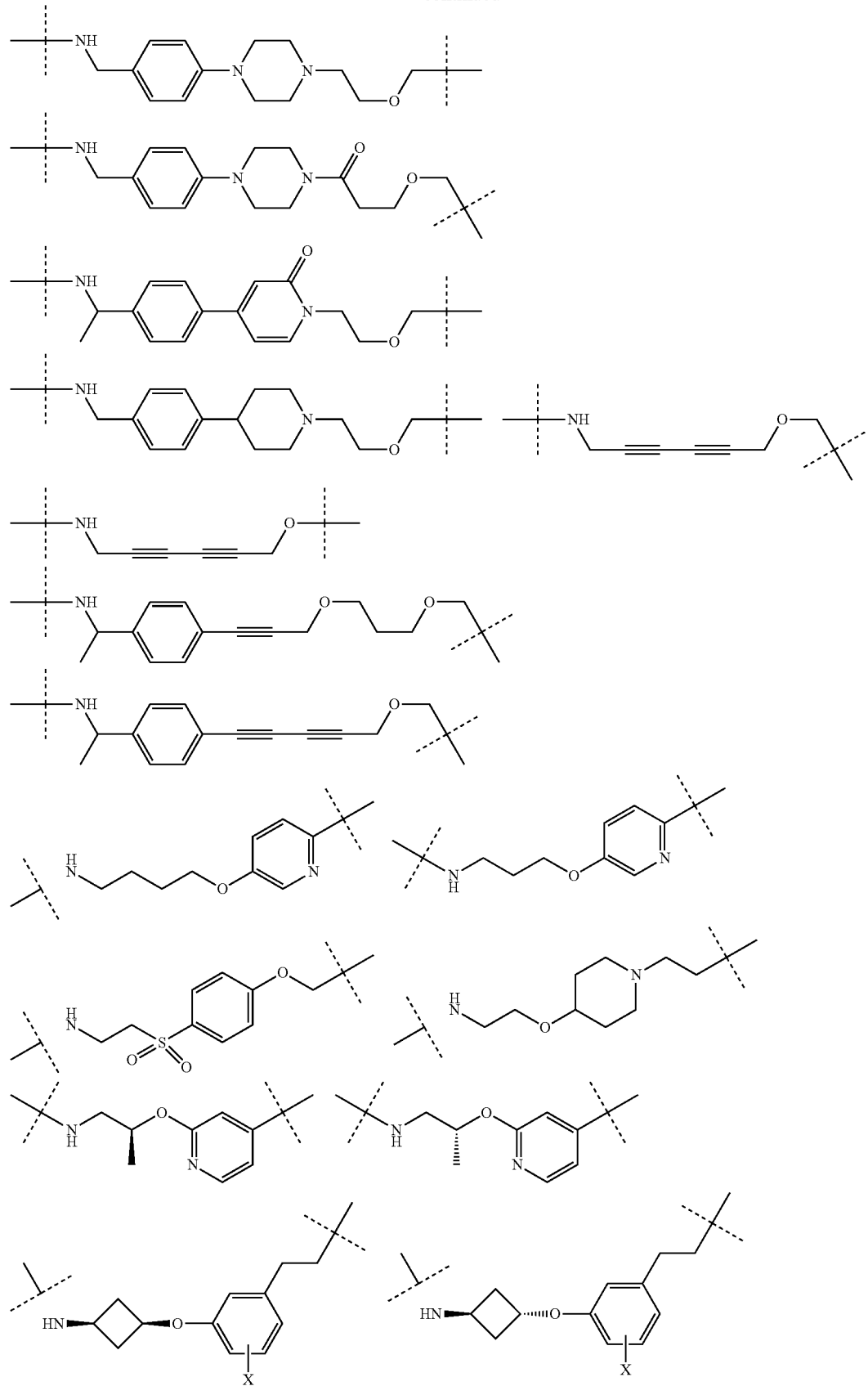

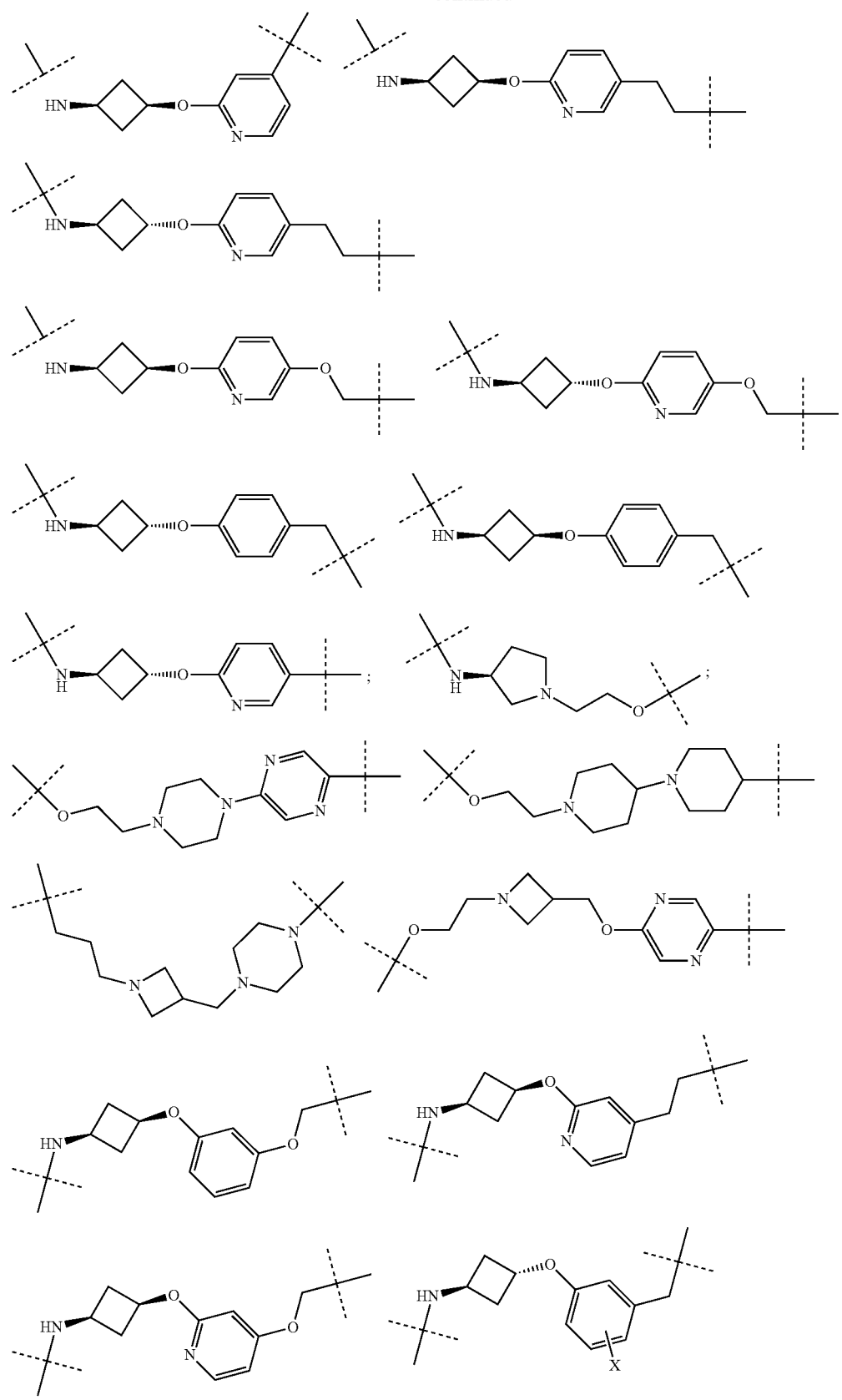

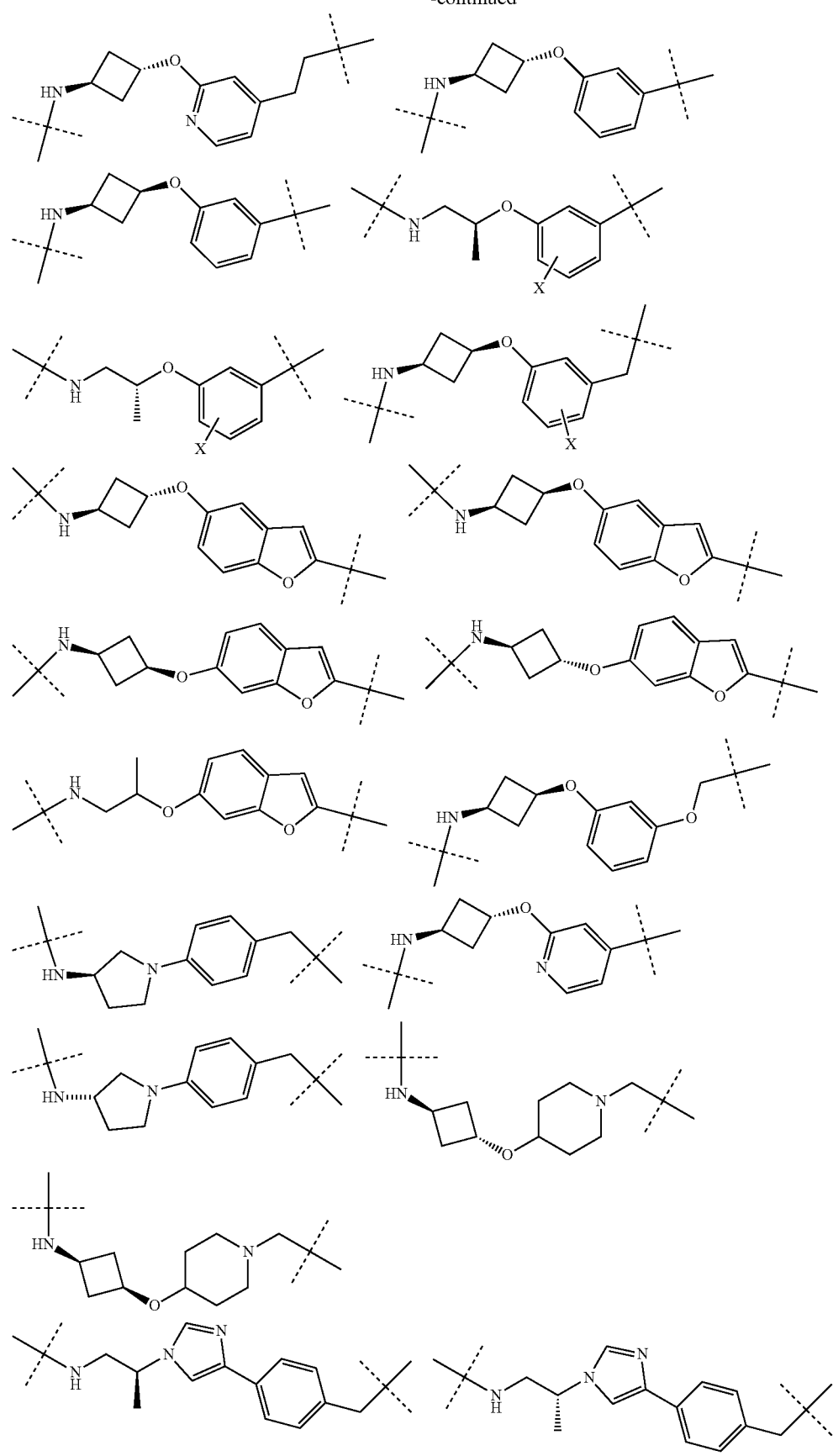

-continued
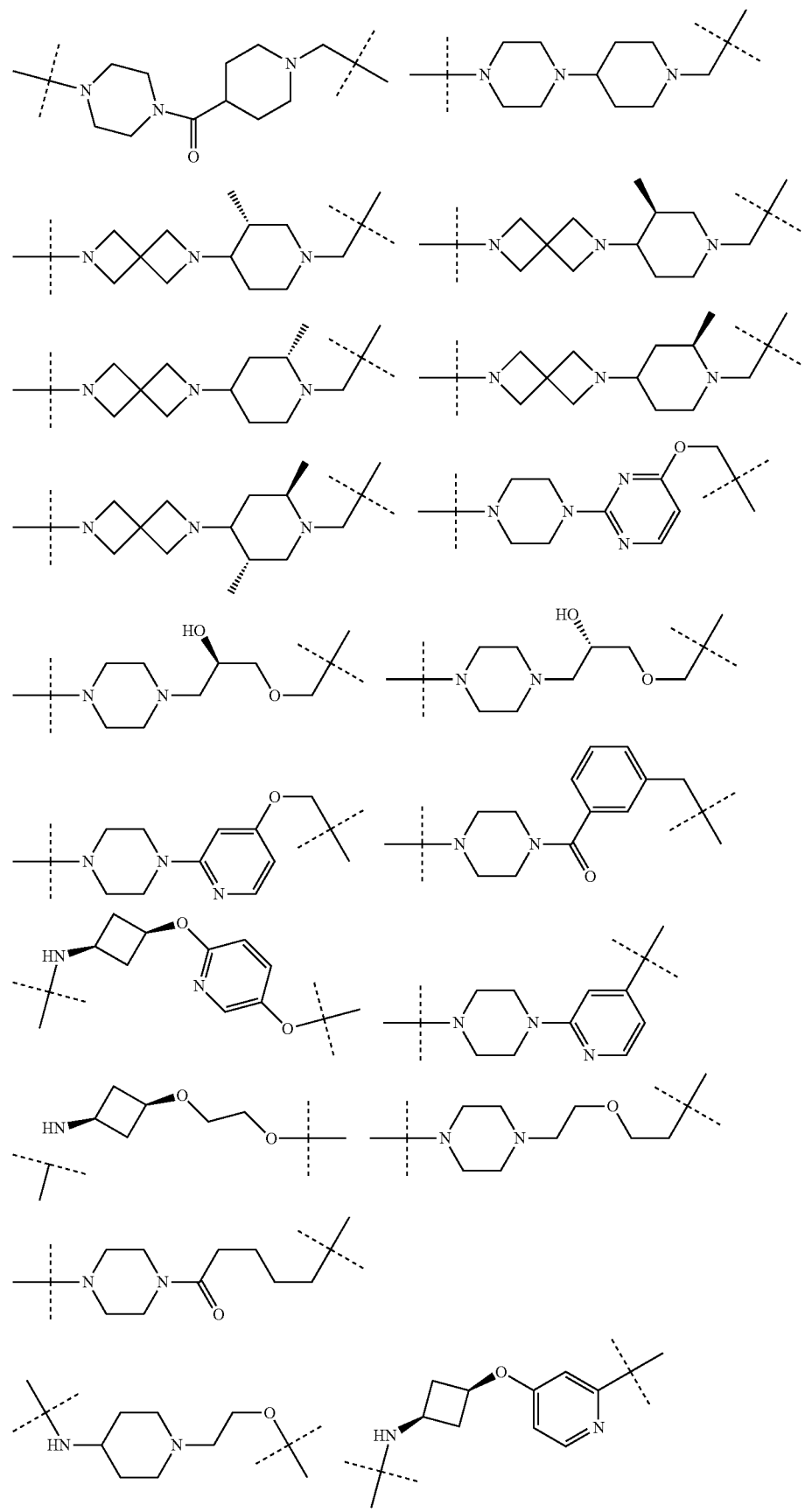

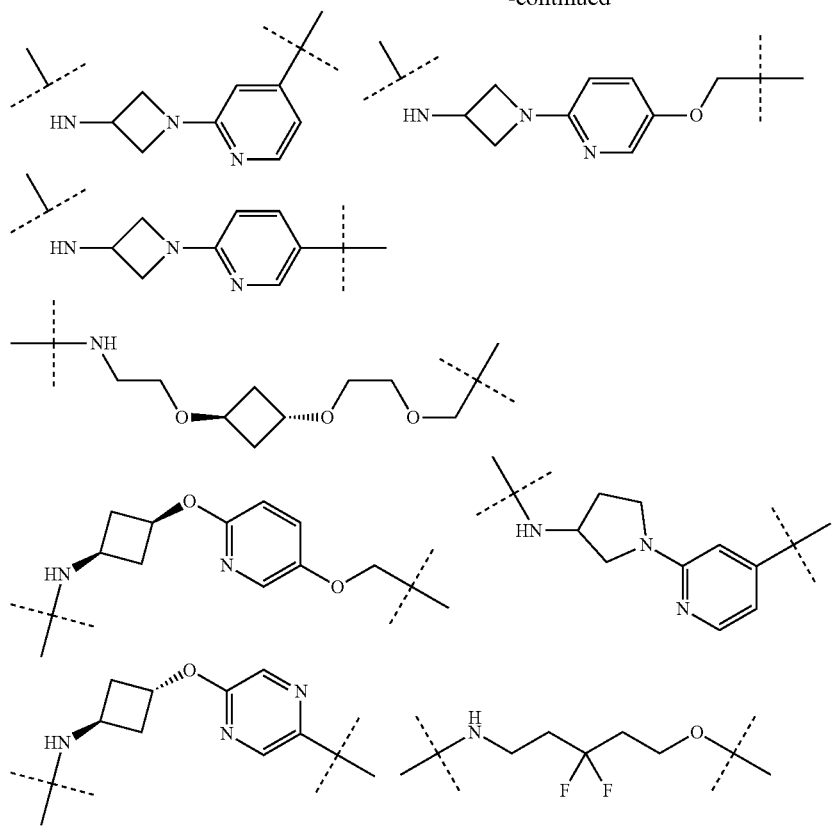
where each n and m of the linker can independently be 0, 1, 2, 3, 4, 5, 6.
In any aspect or embodiment described herein, the linker (L) is selected from the group consisting of:
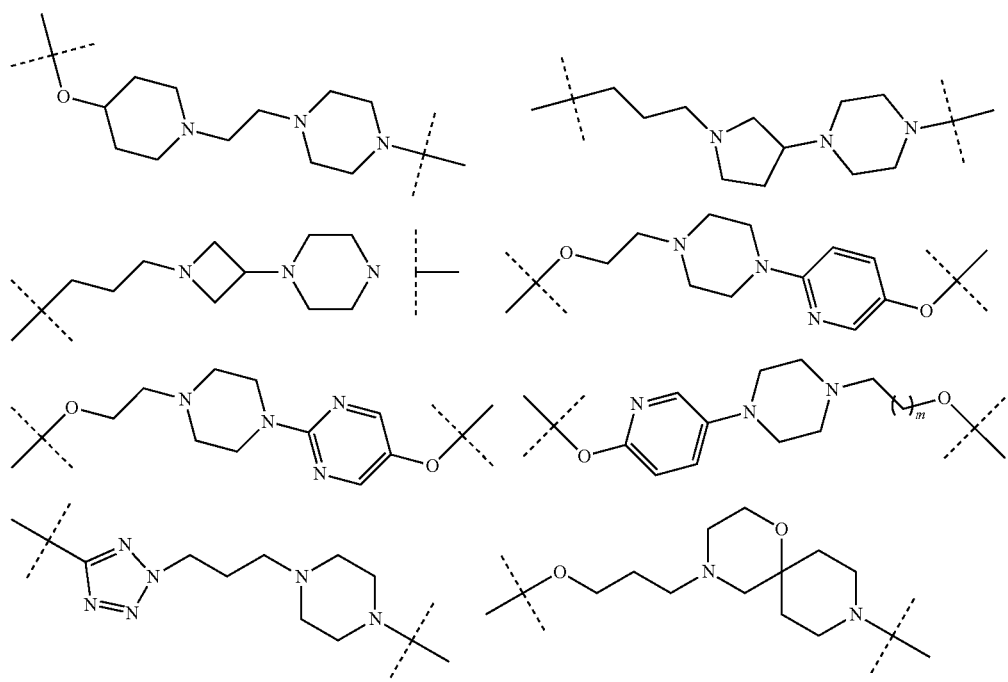

317 318
-continued
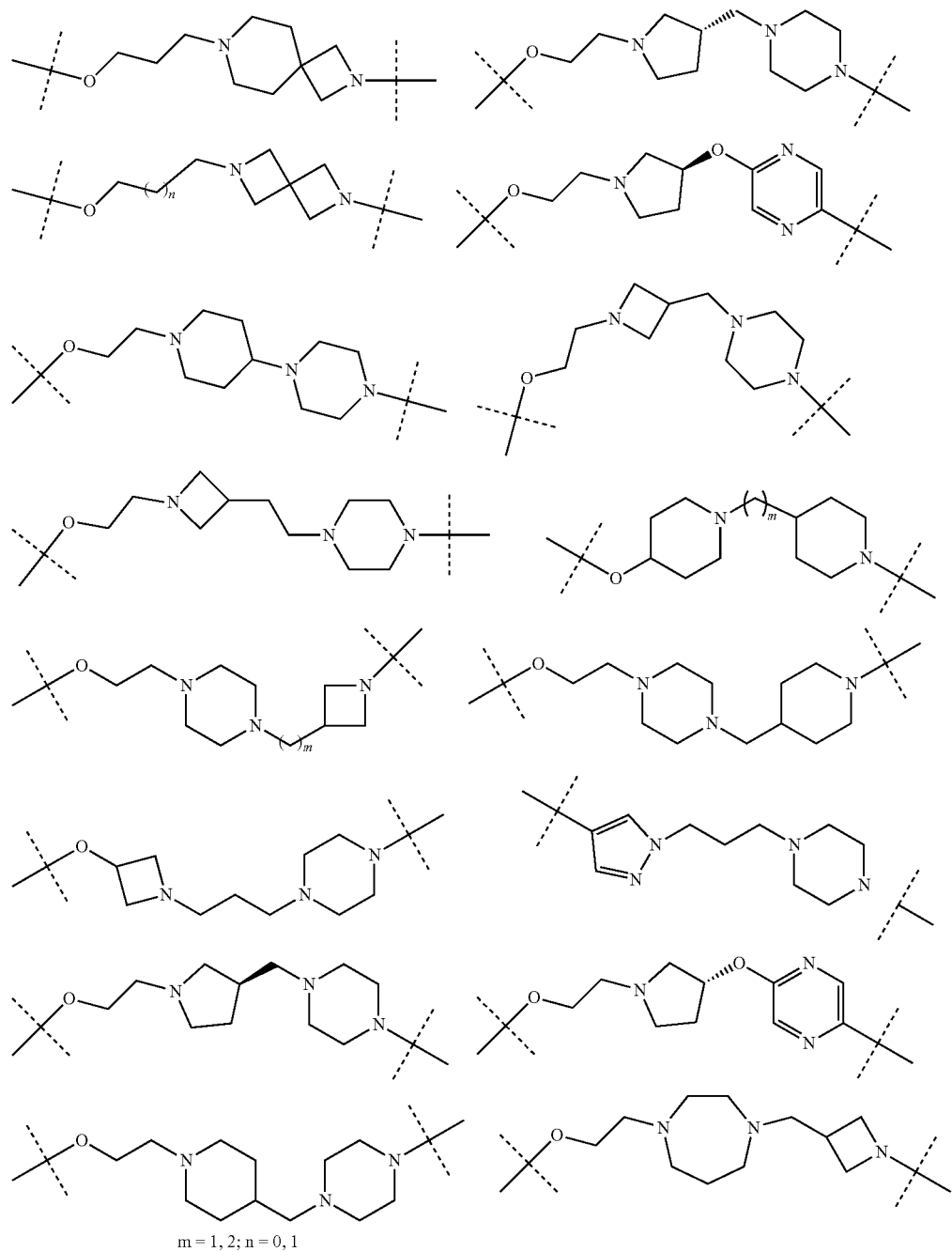
m = 1, 2; n = 0, 1
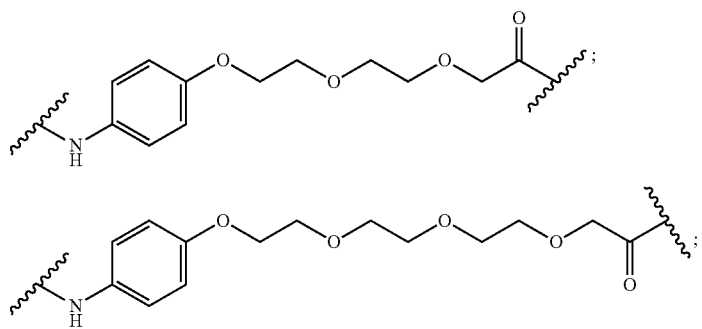

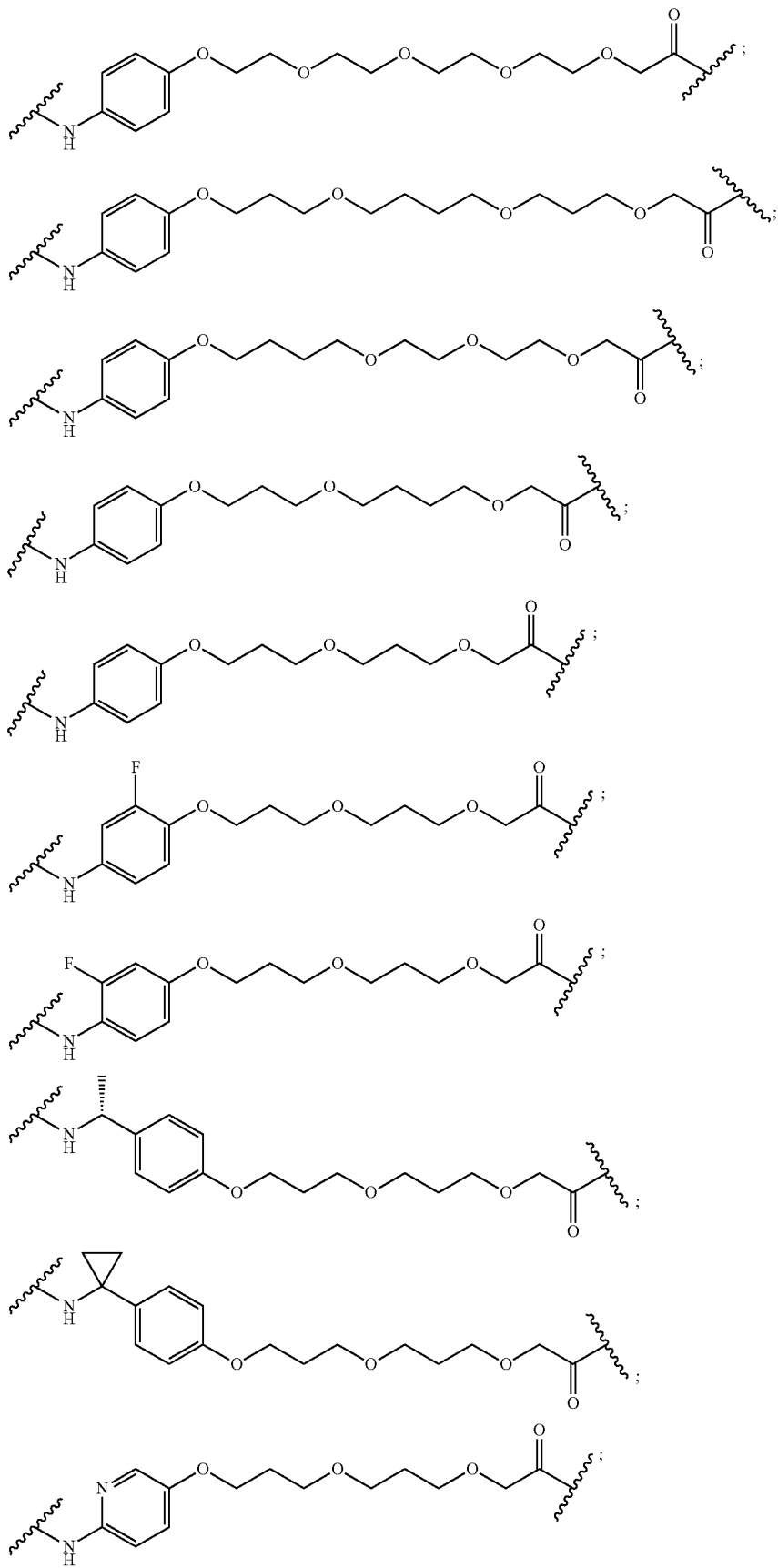

-continued
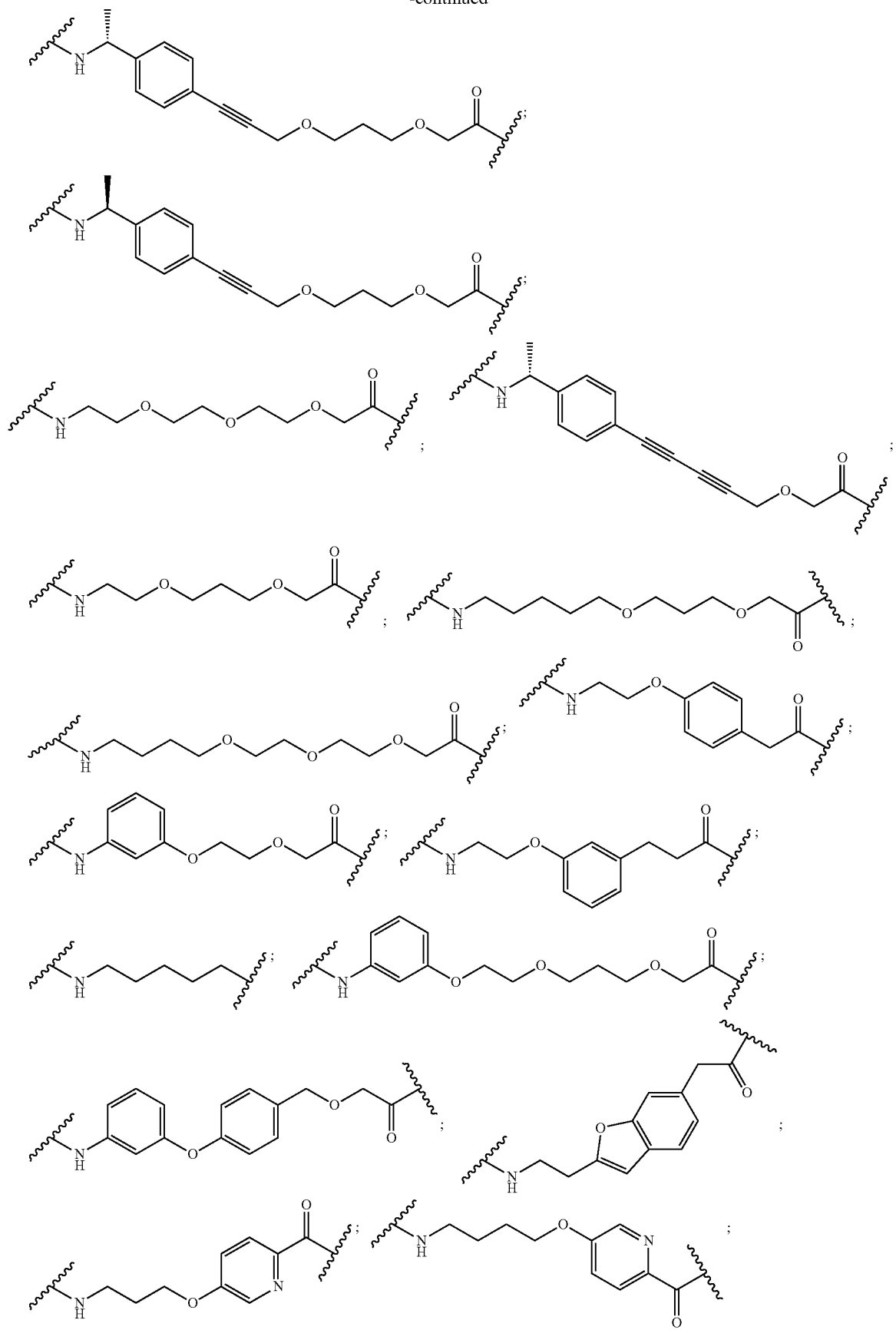

-continued
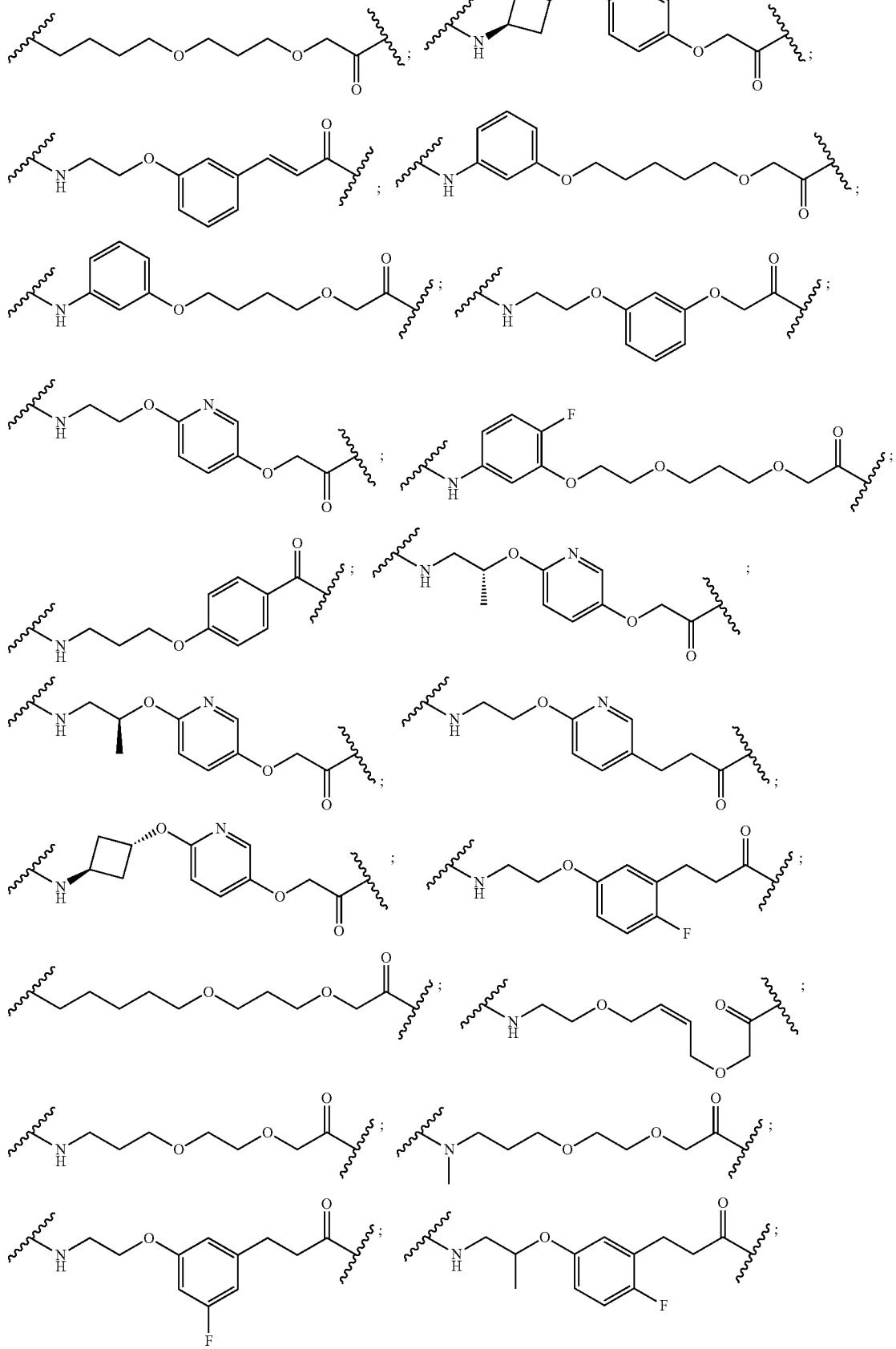

325 326
-continued
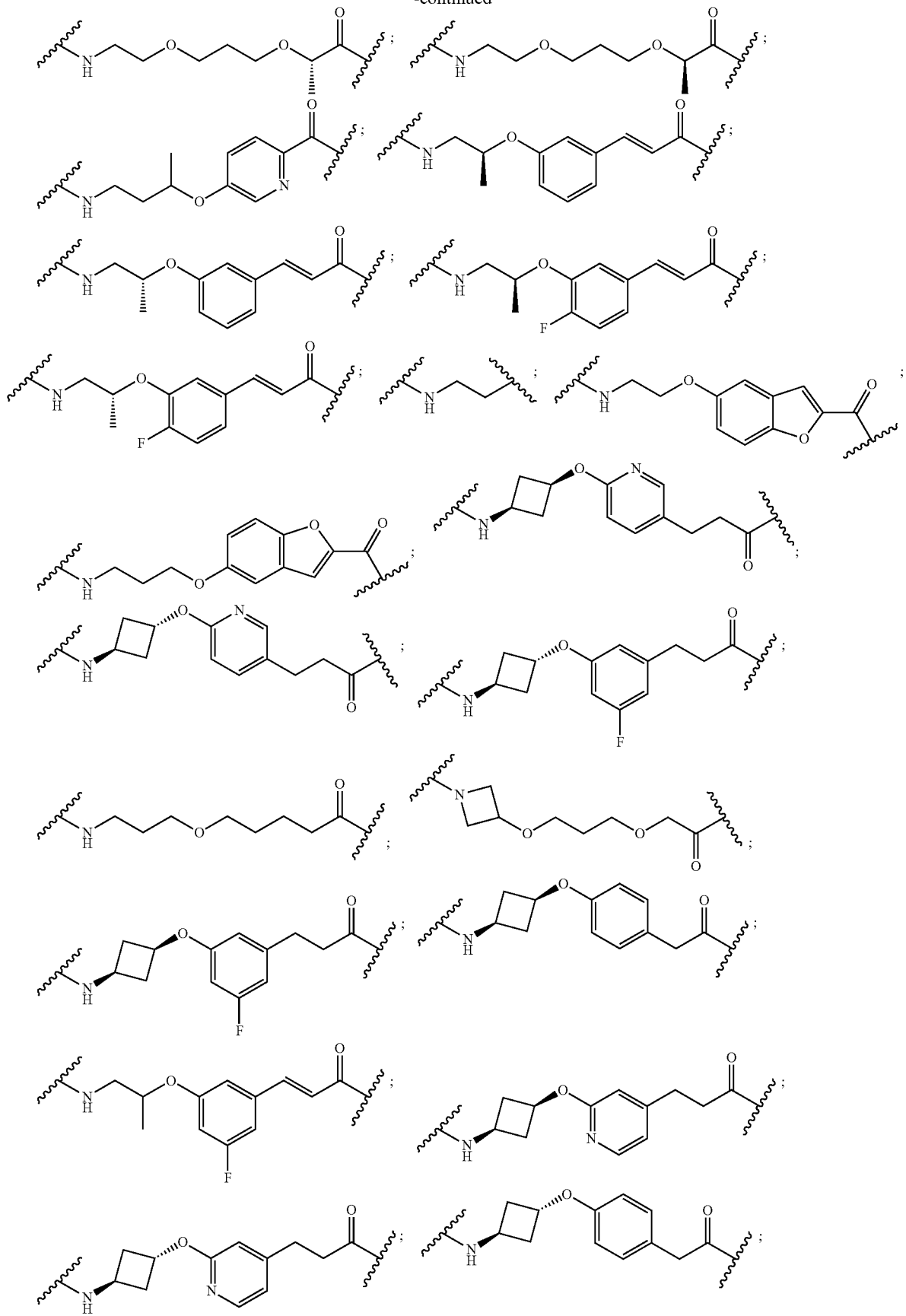

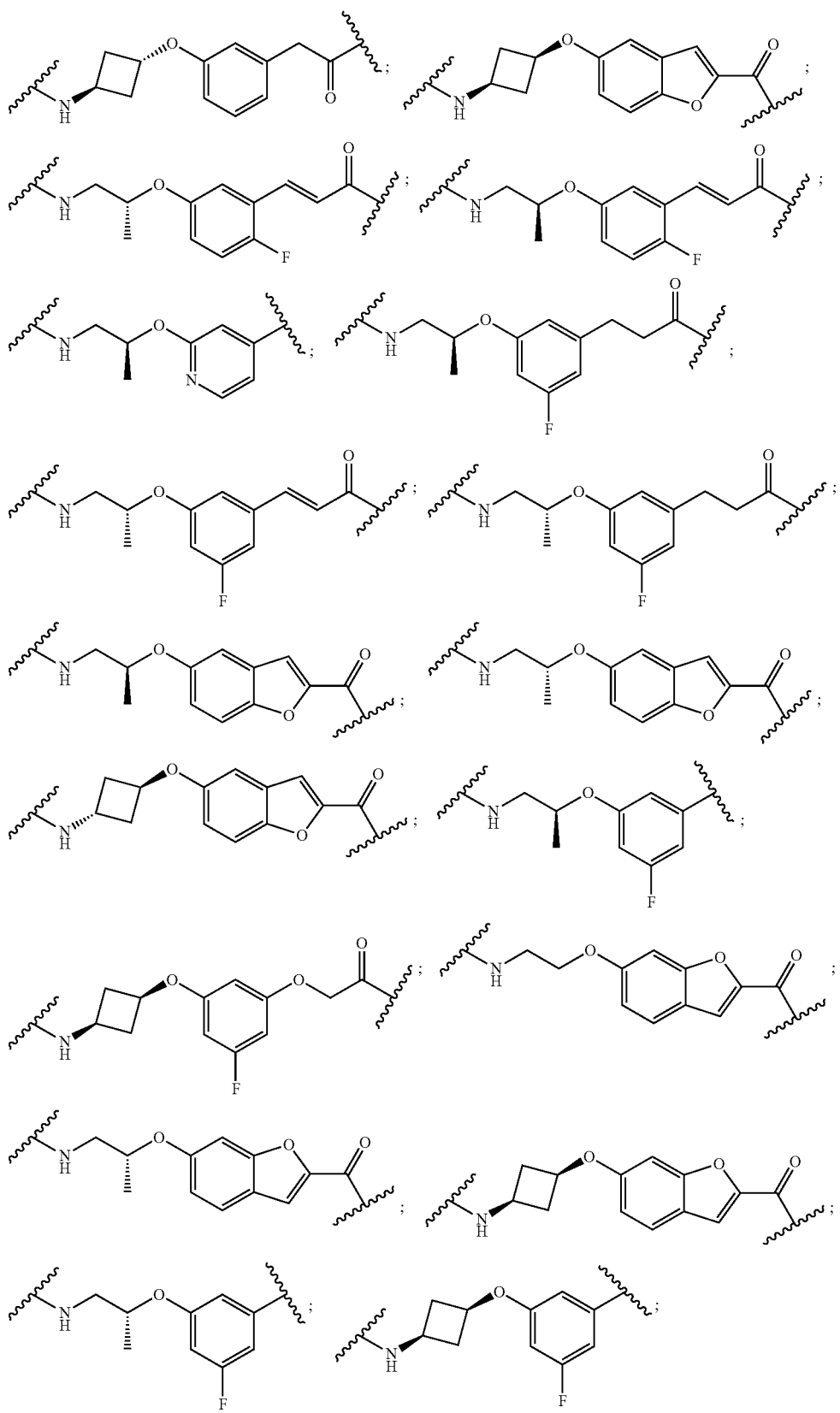

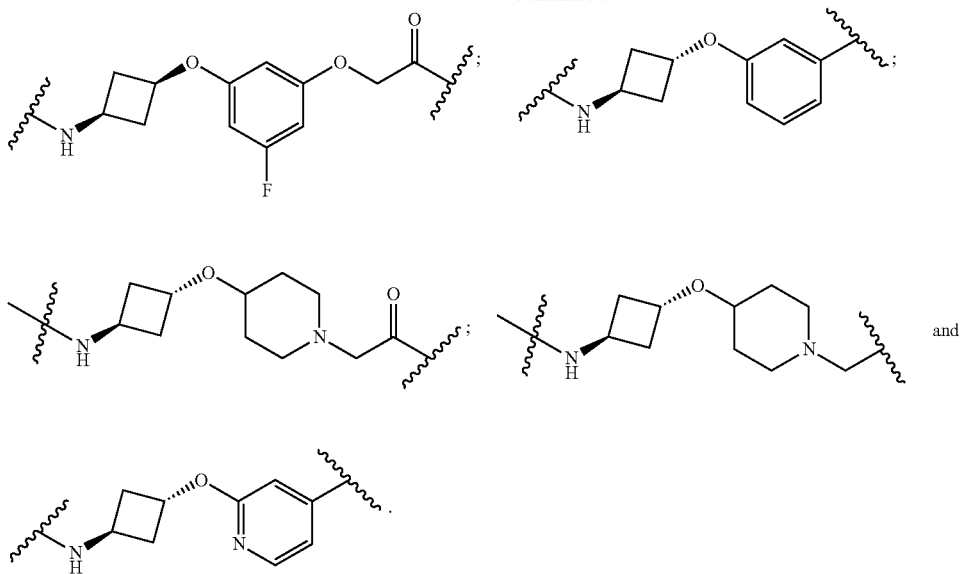
In any aspect or embodiment described herein, the linker (L) is selected from the group consisting of:
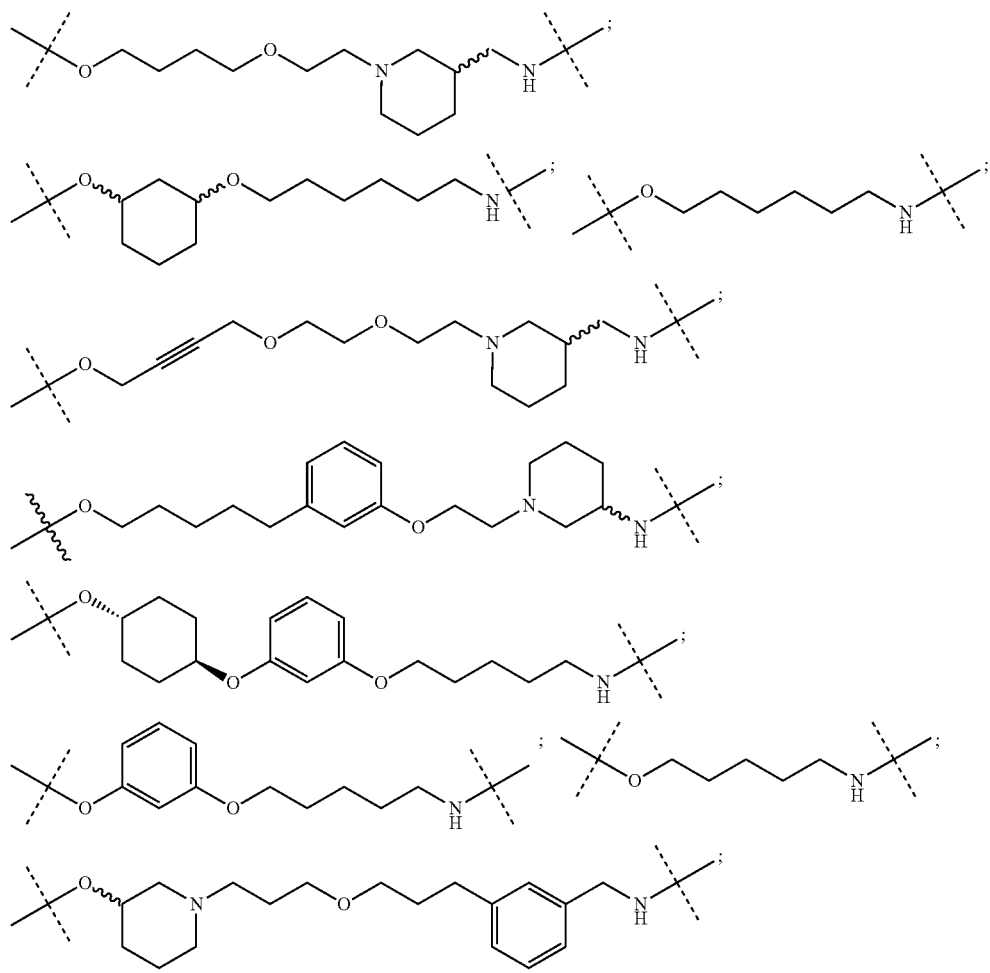

-continued
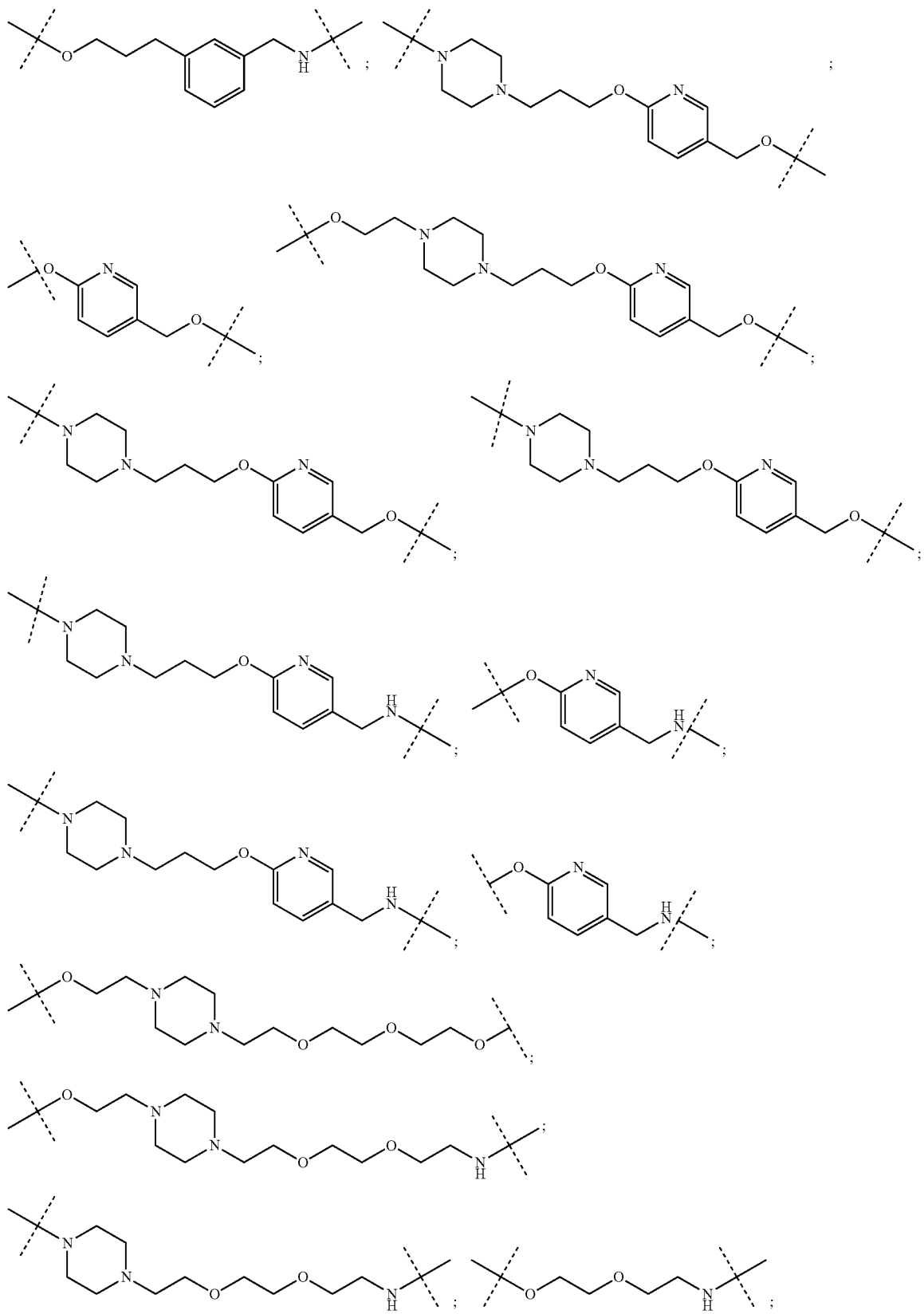

-continued
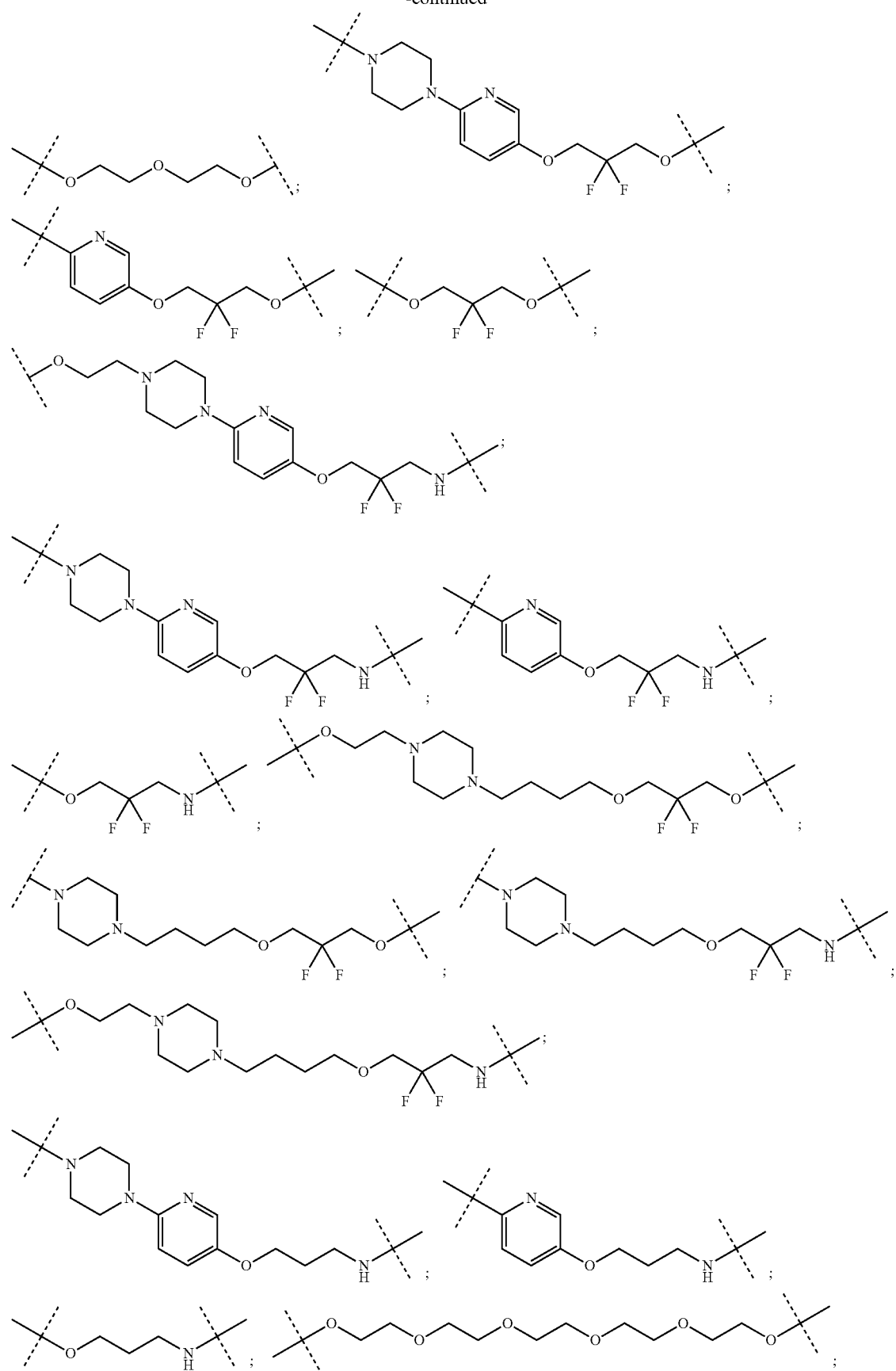

-continued
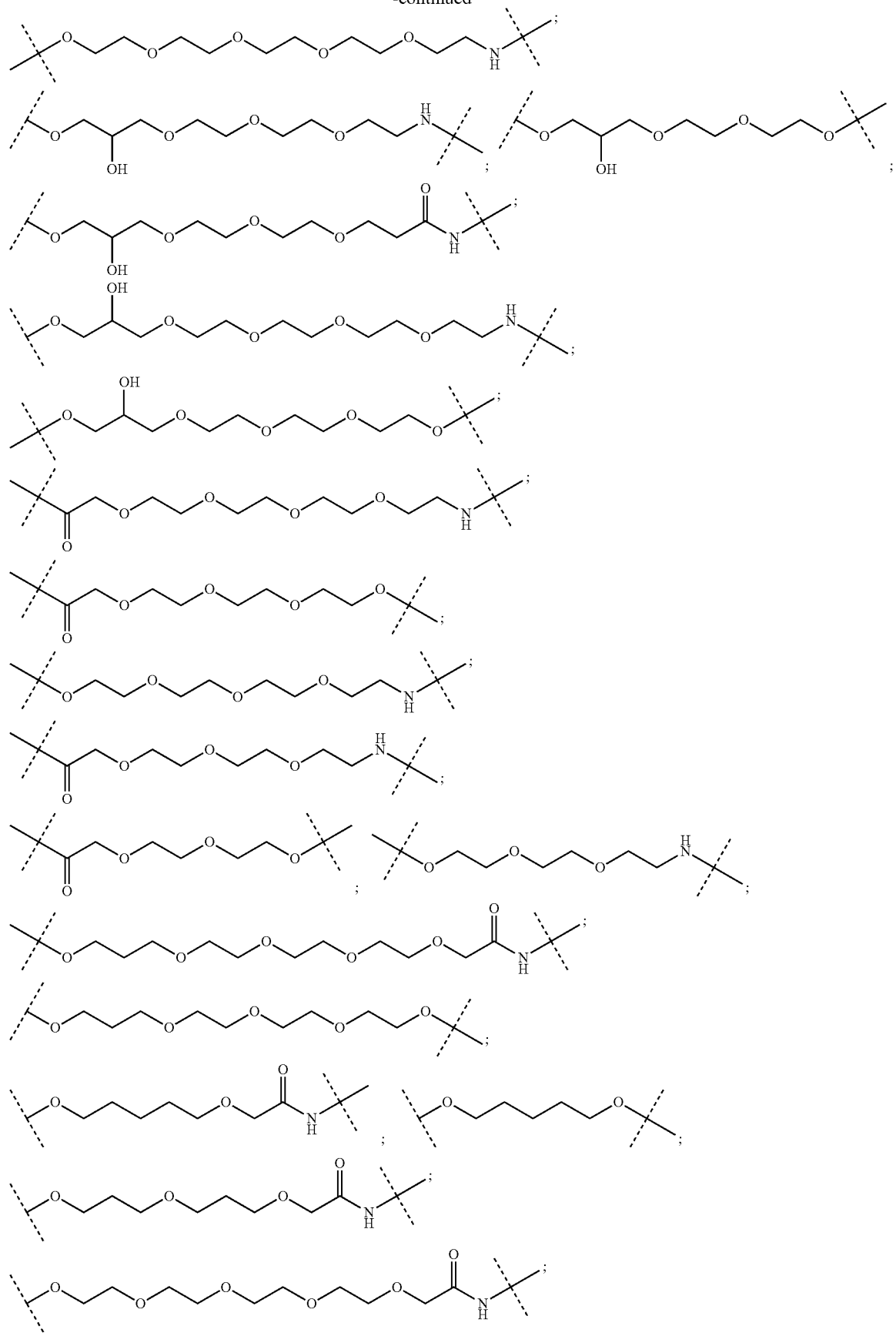

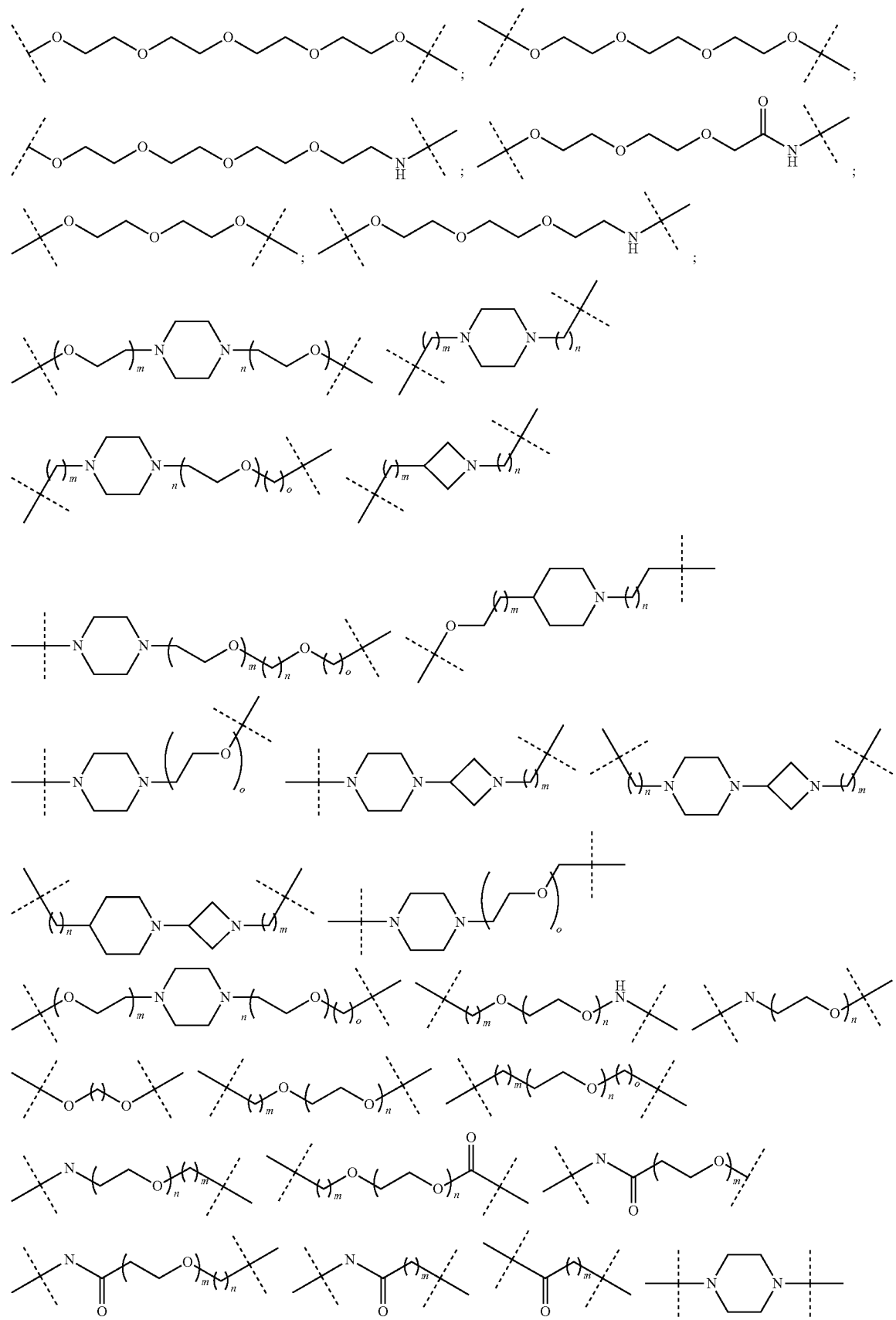

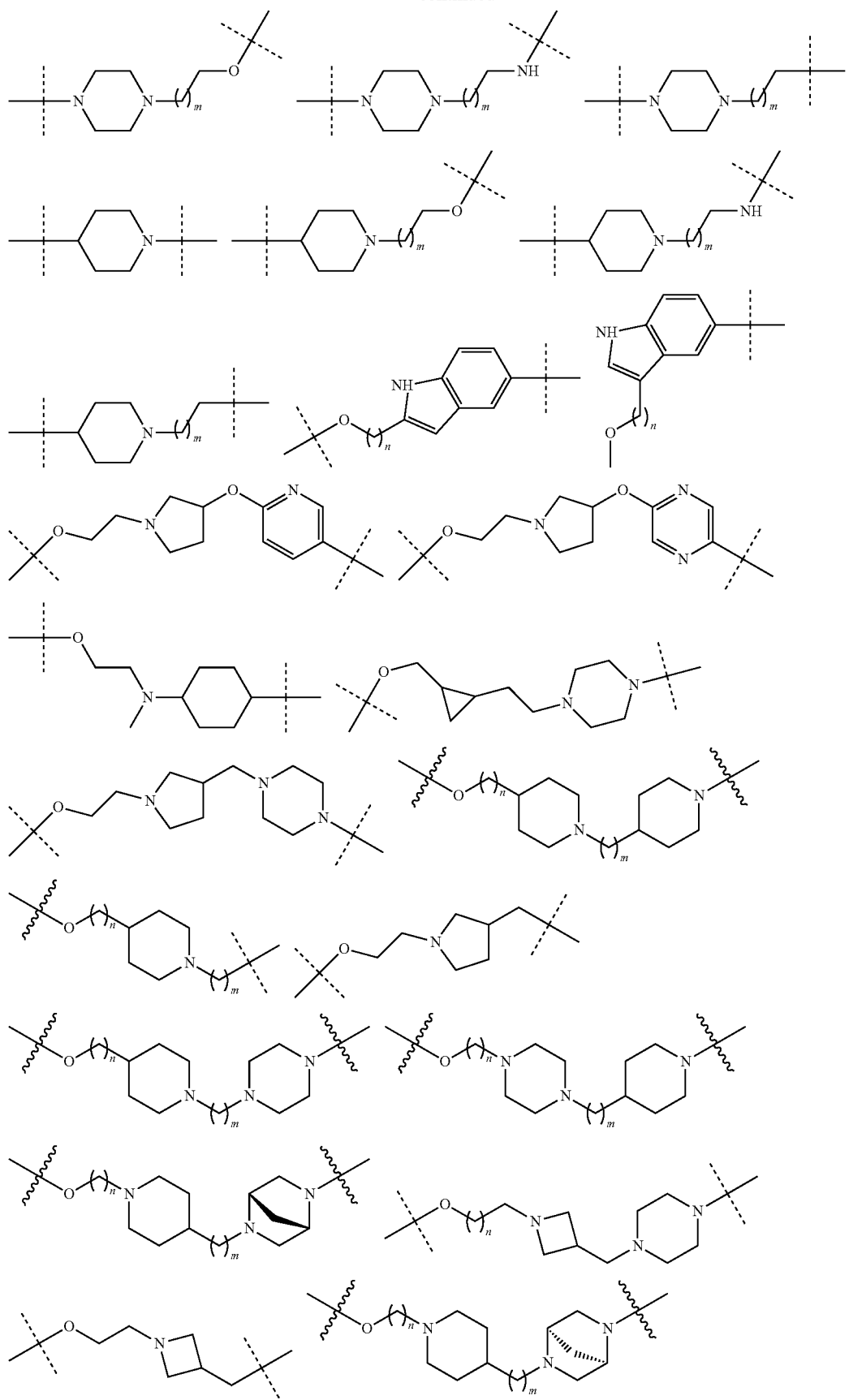

-continued
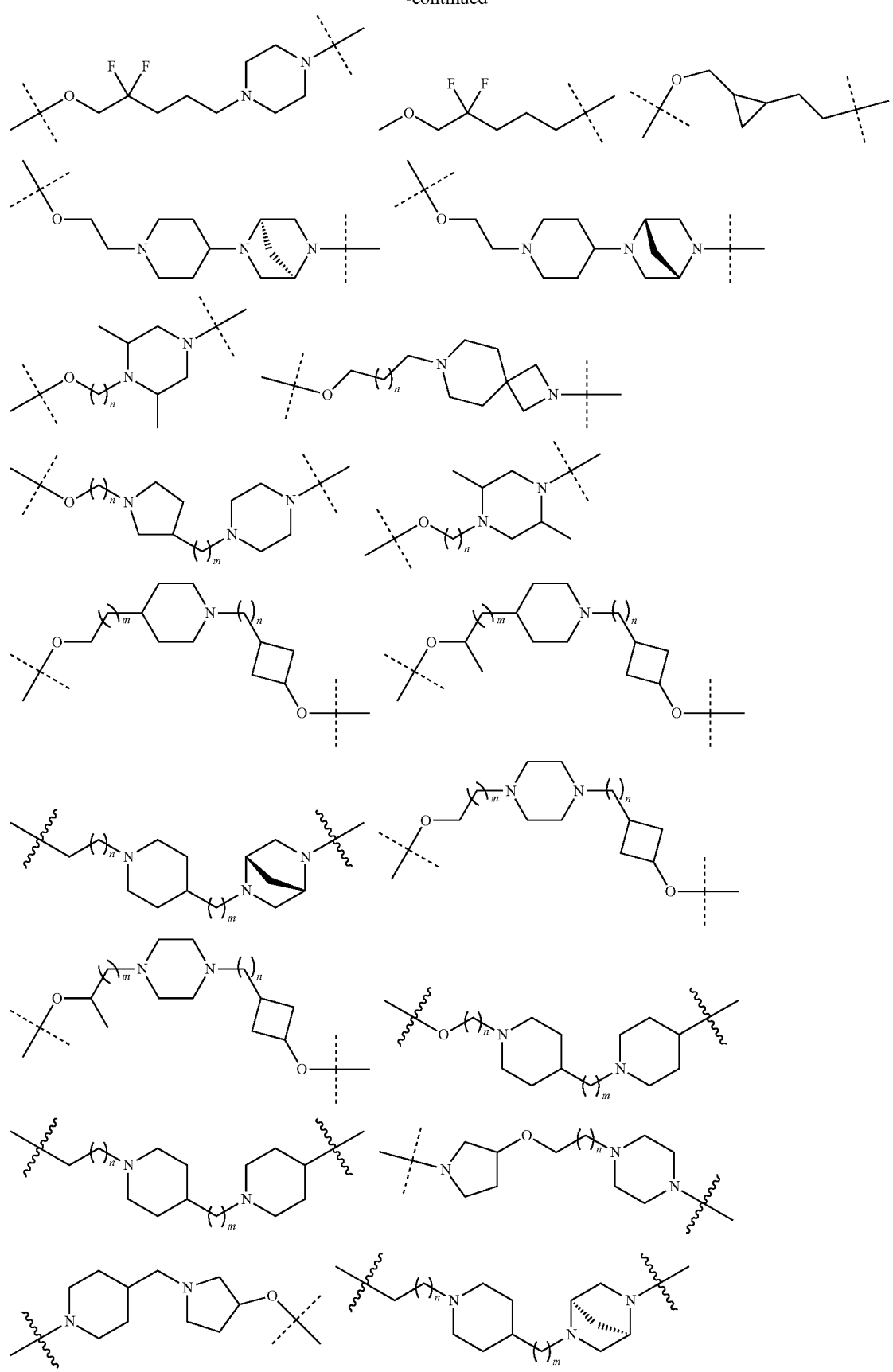

-continued
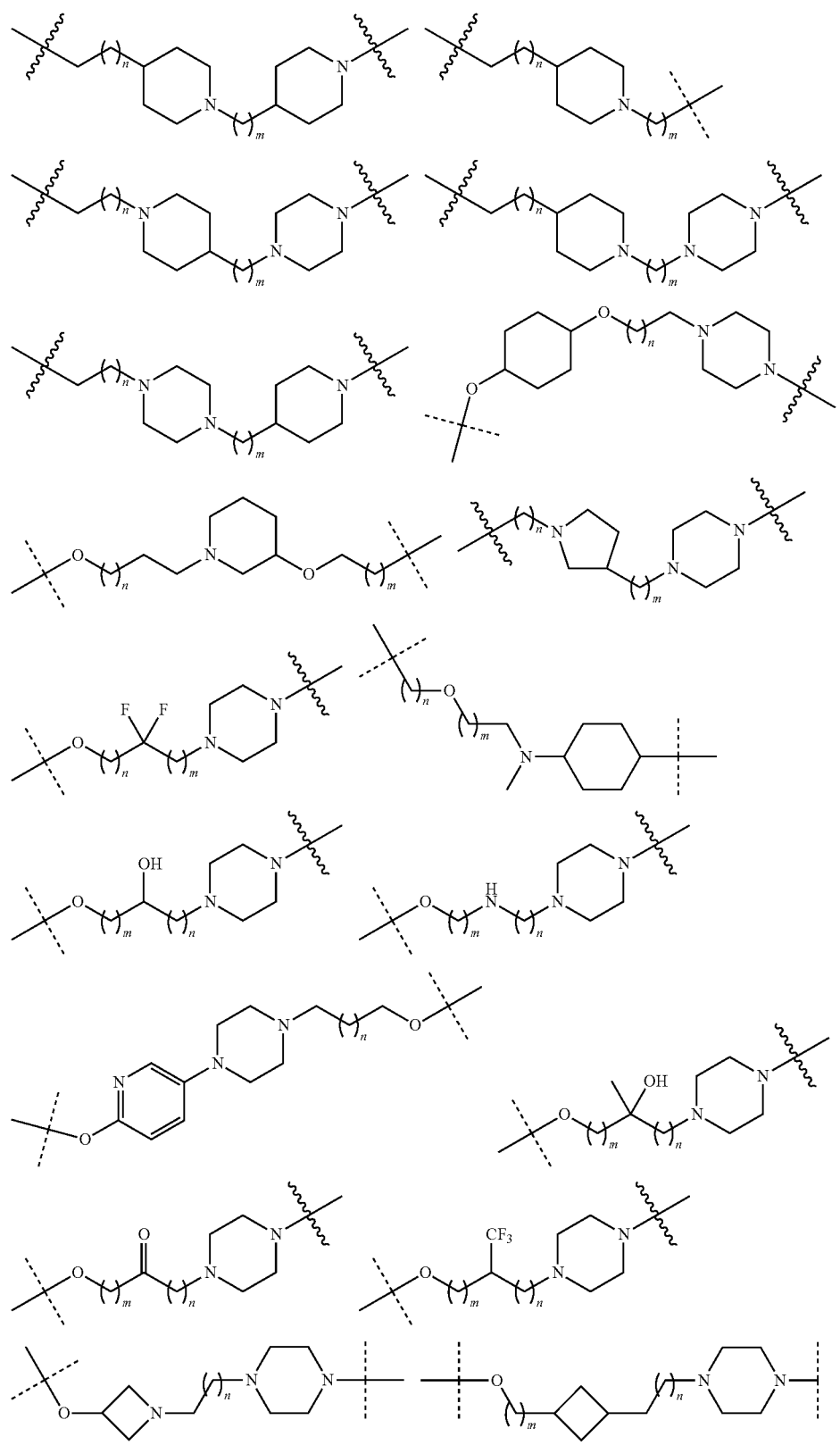

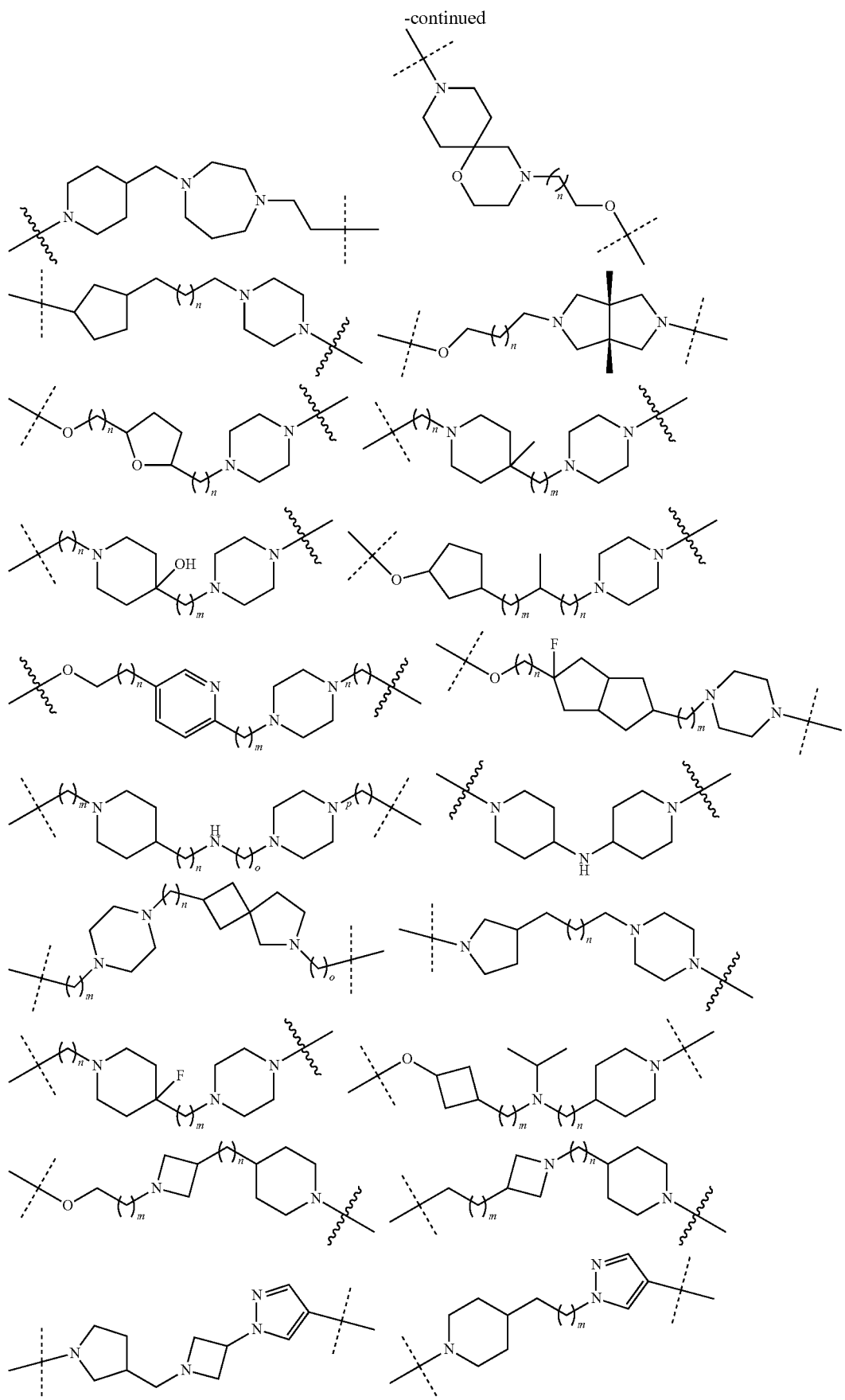

-continued
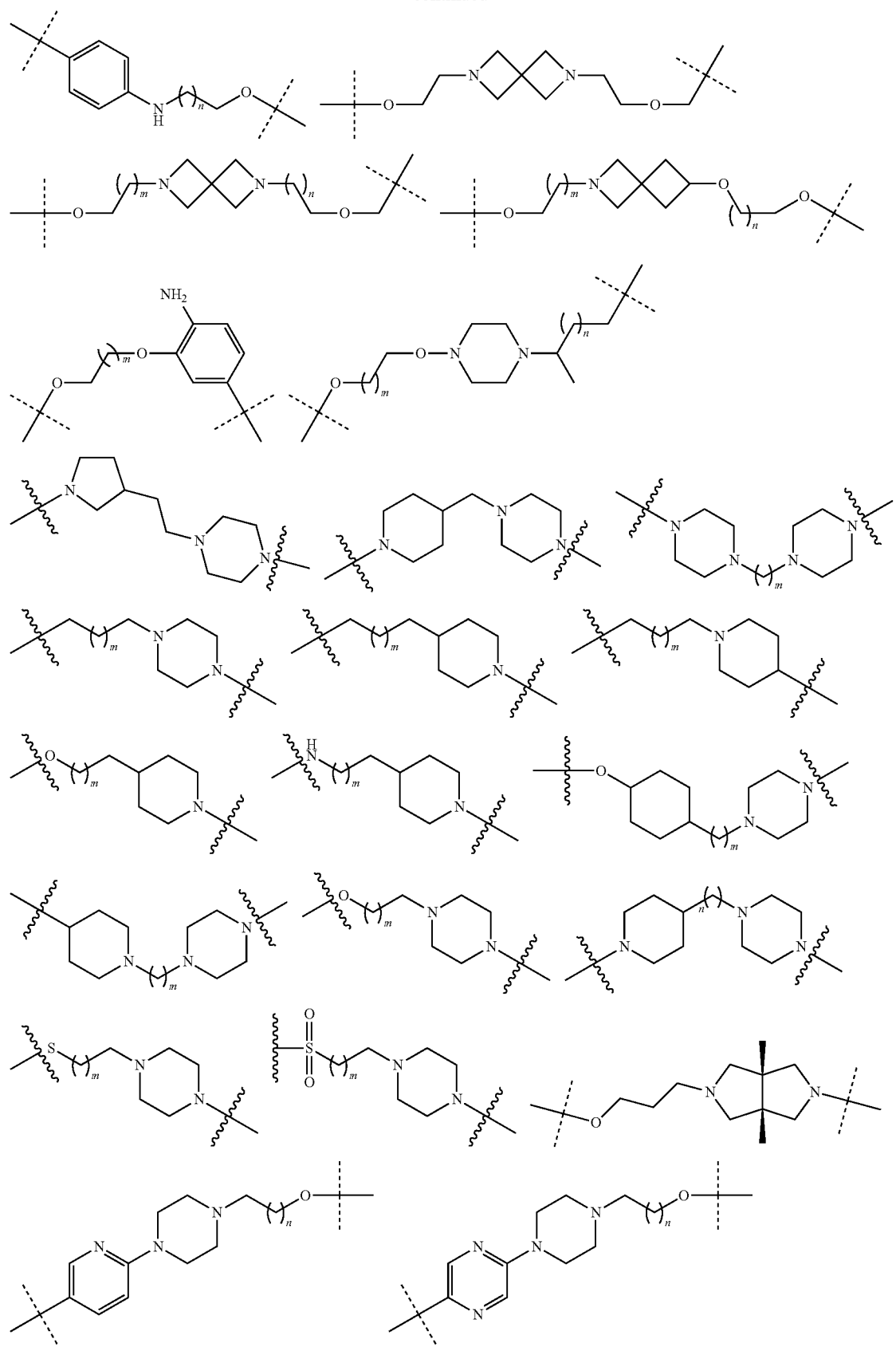

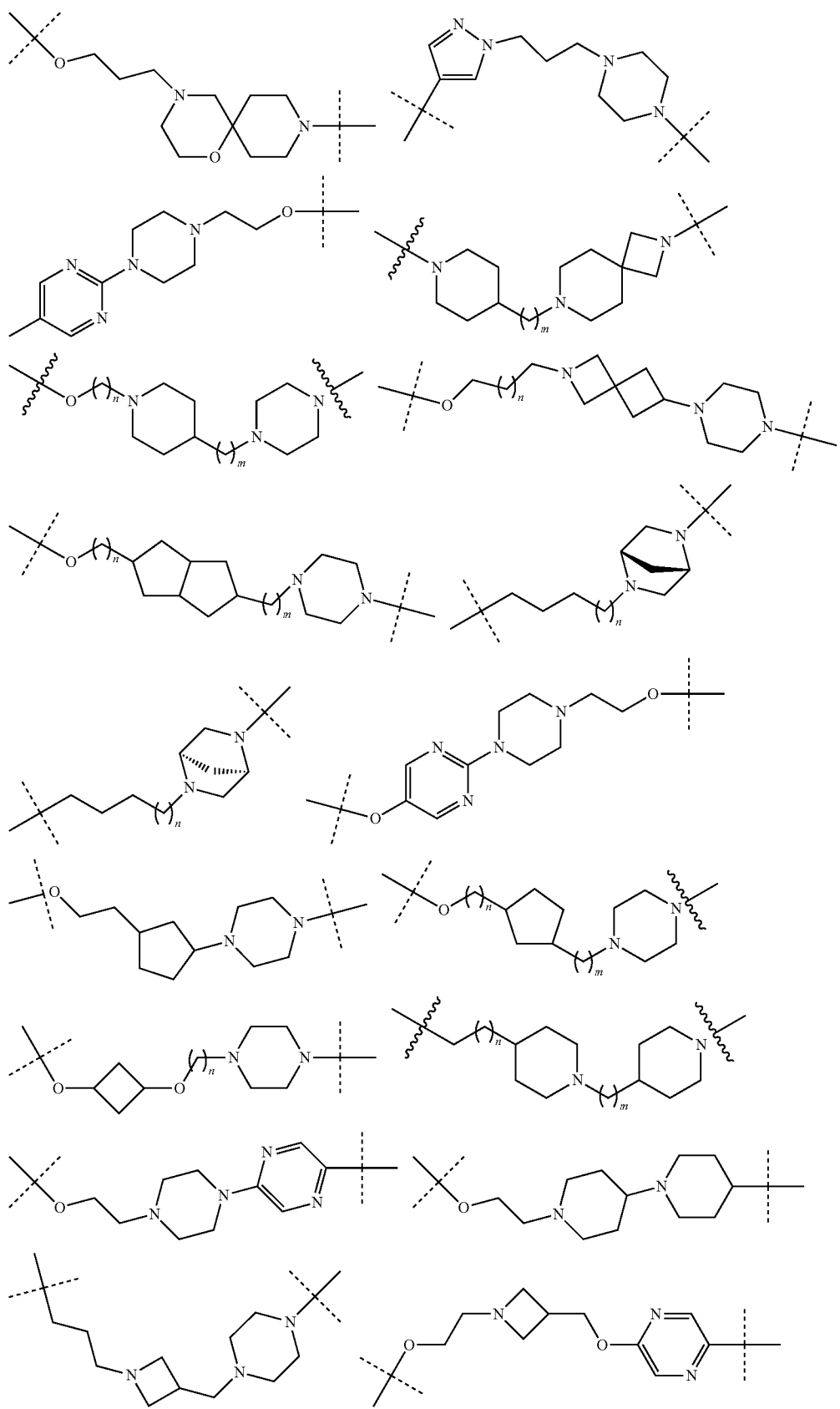

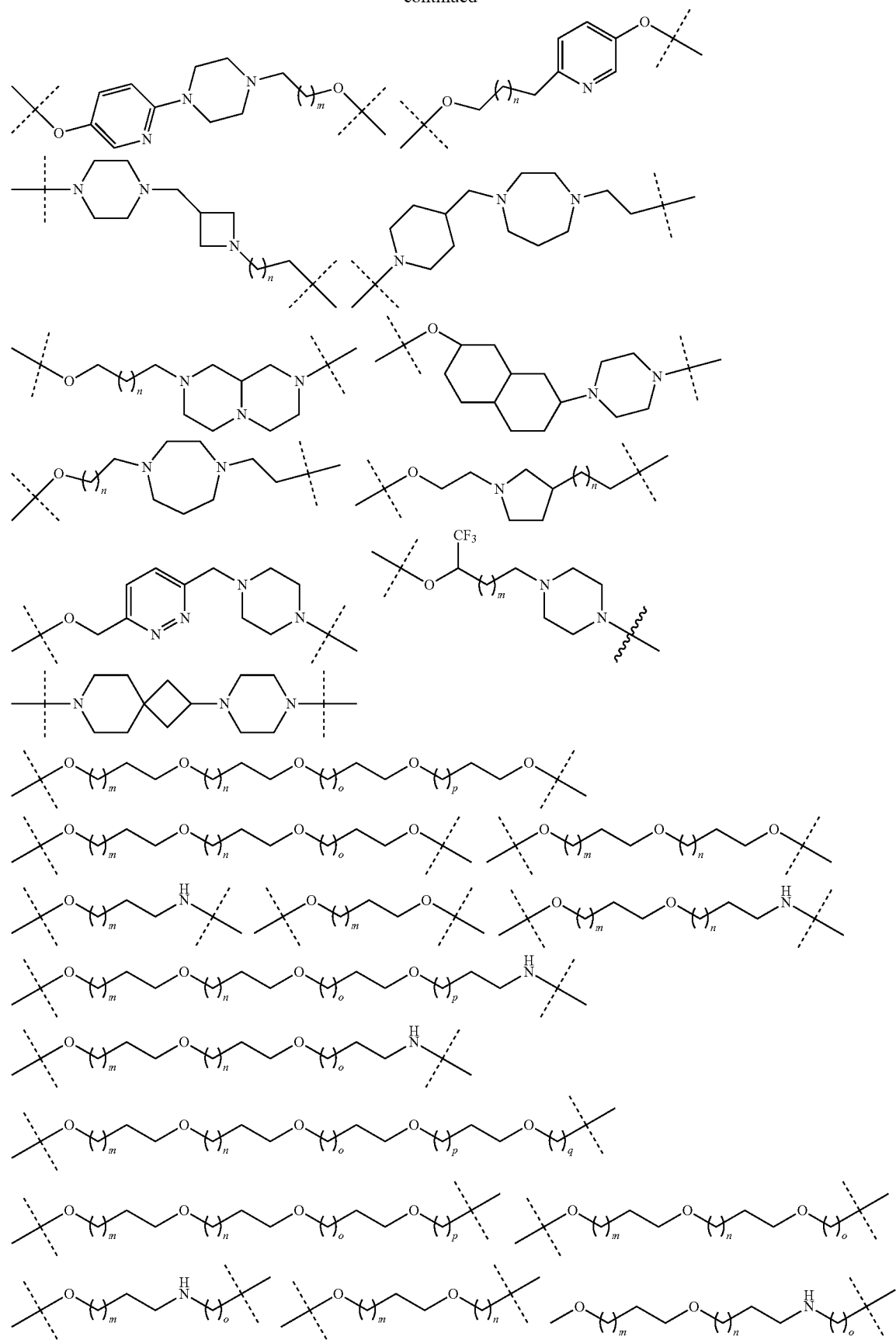

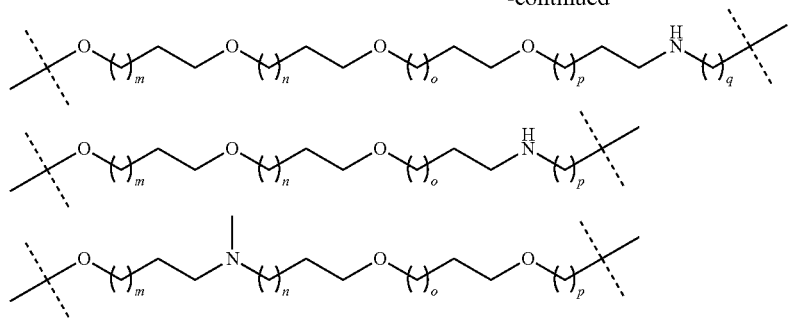
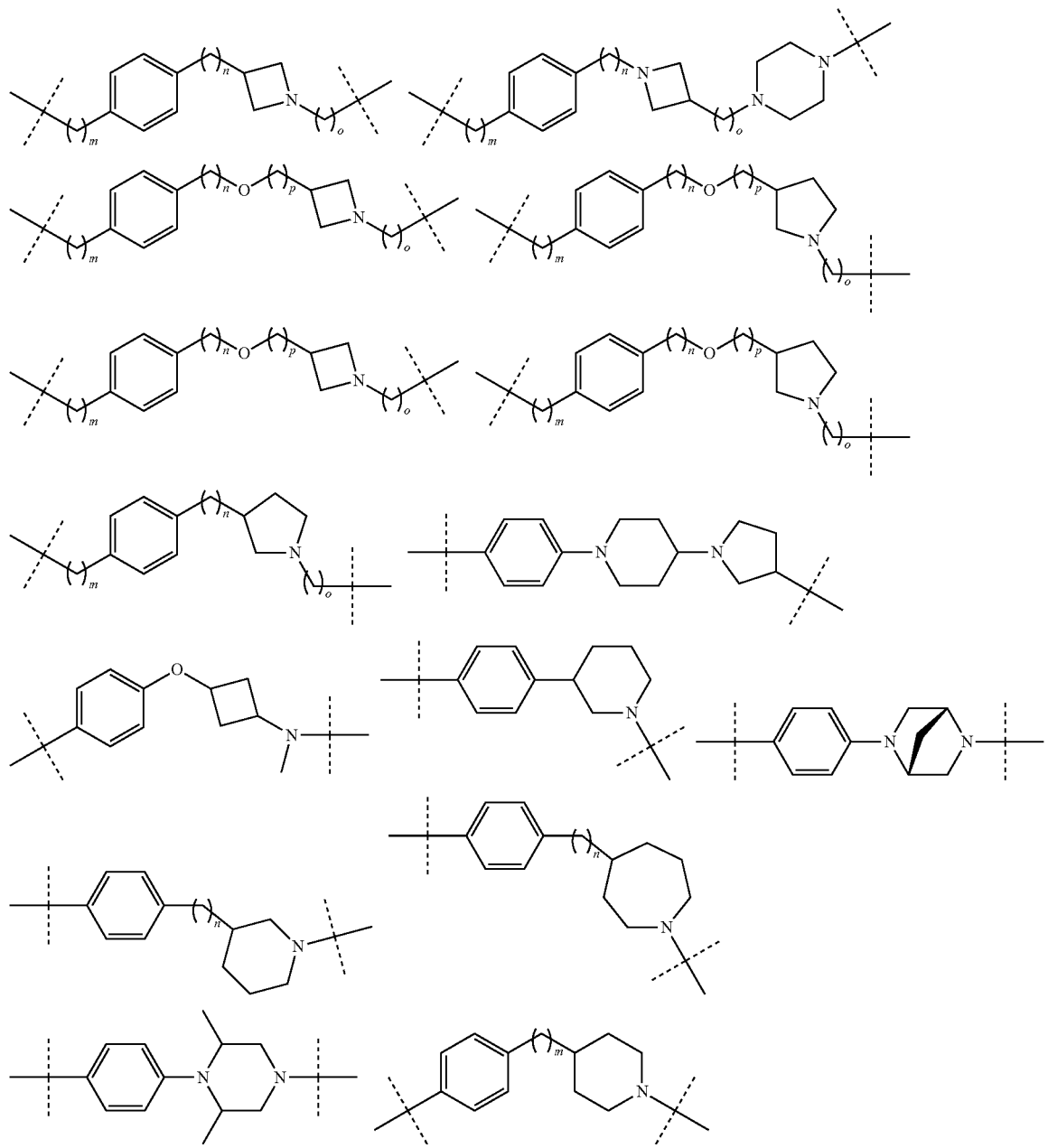

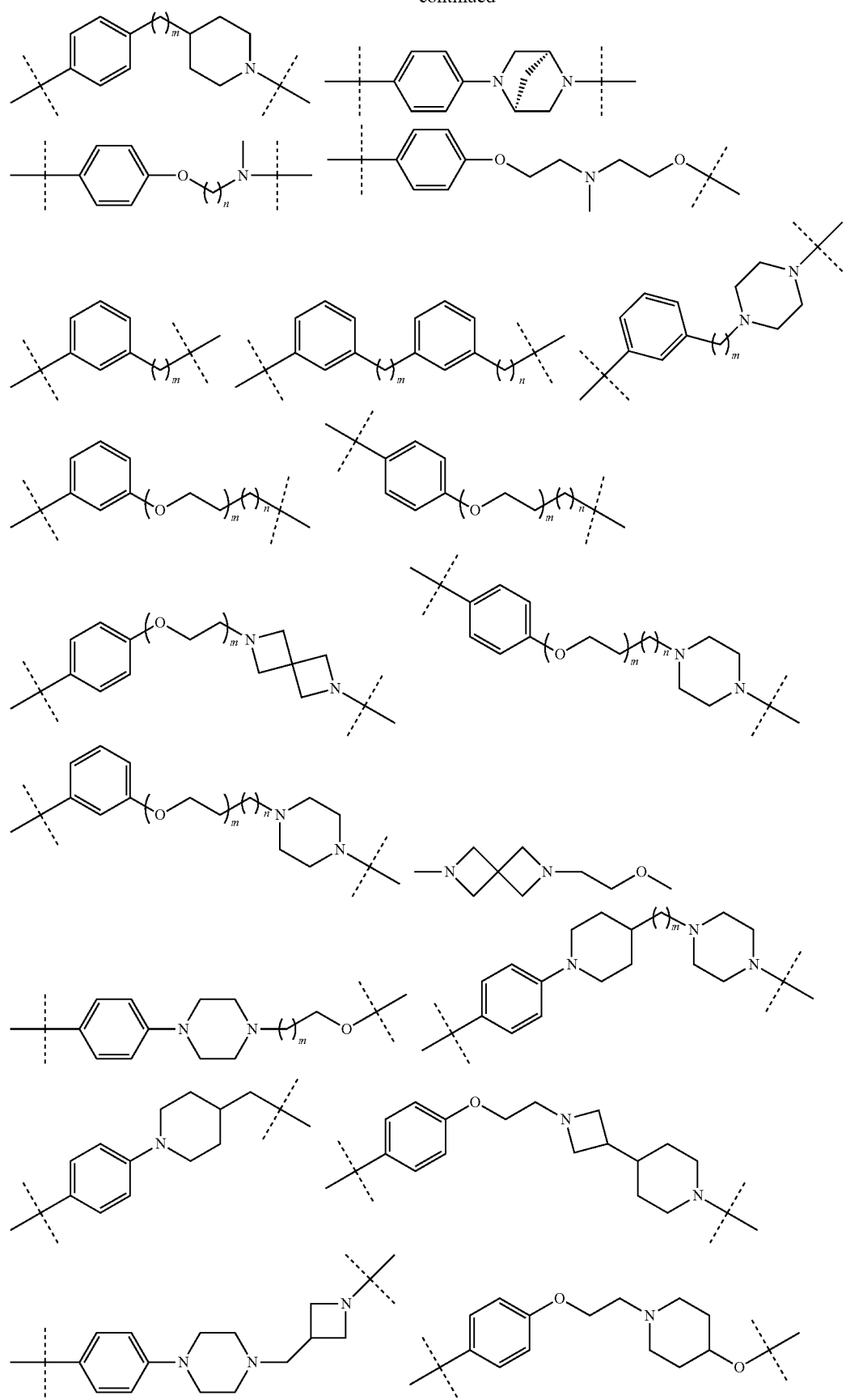

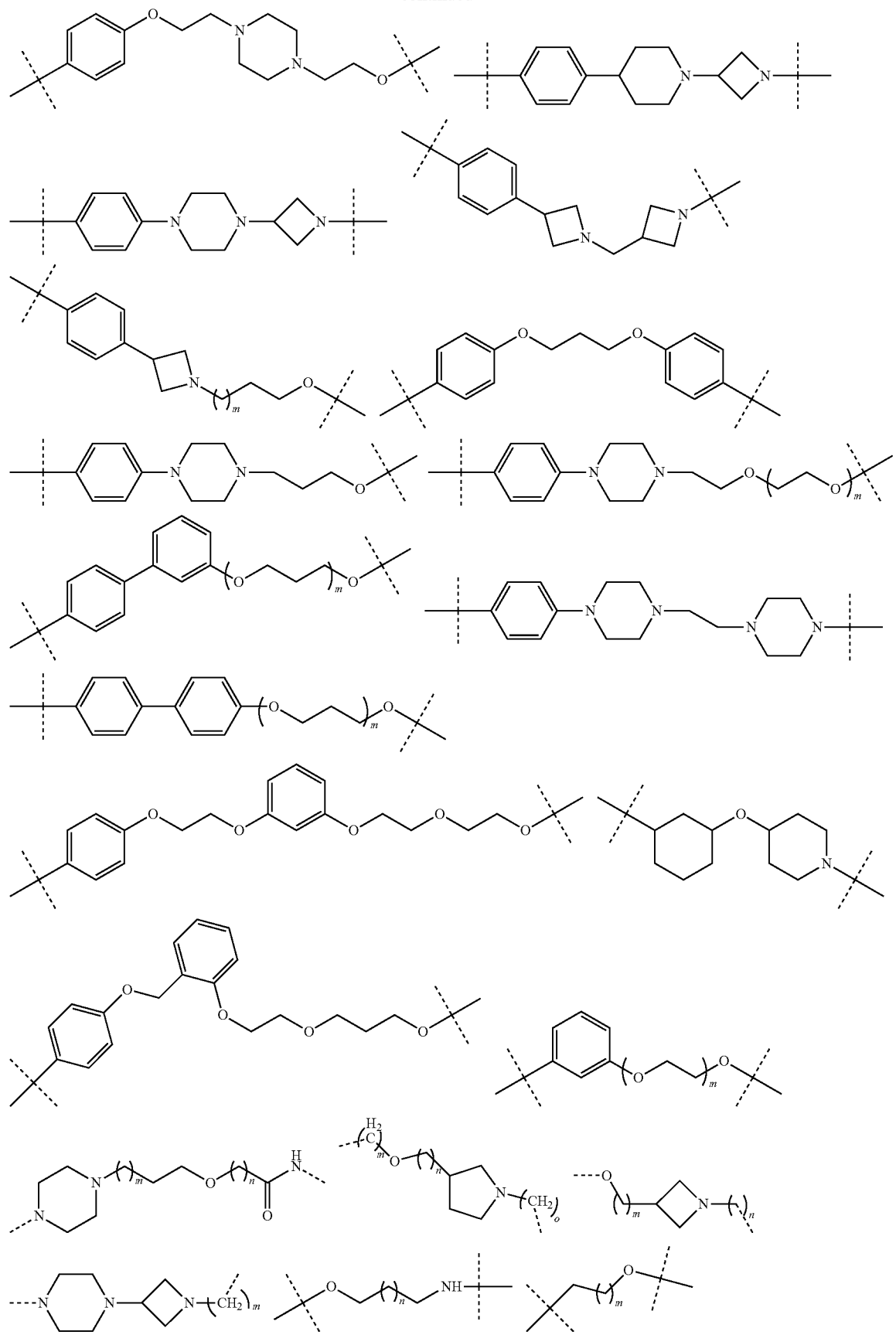

-continued
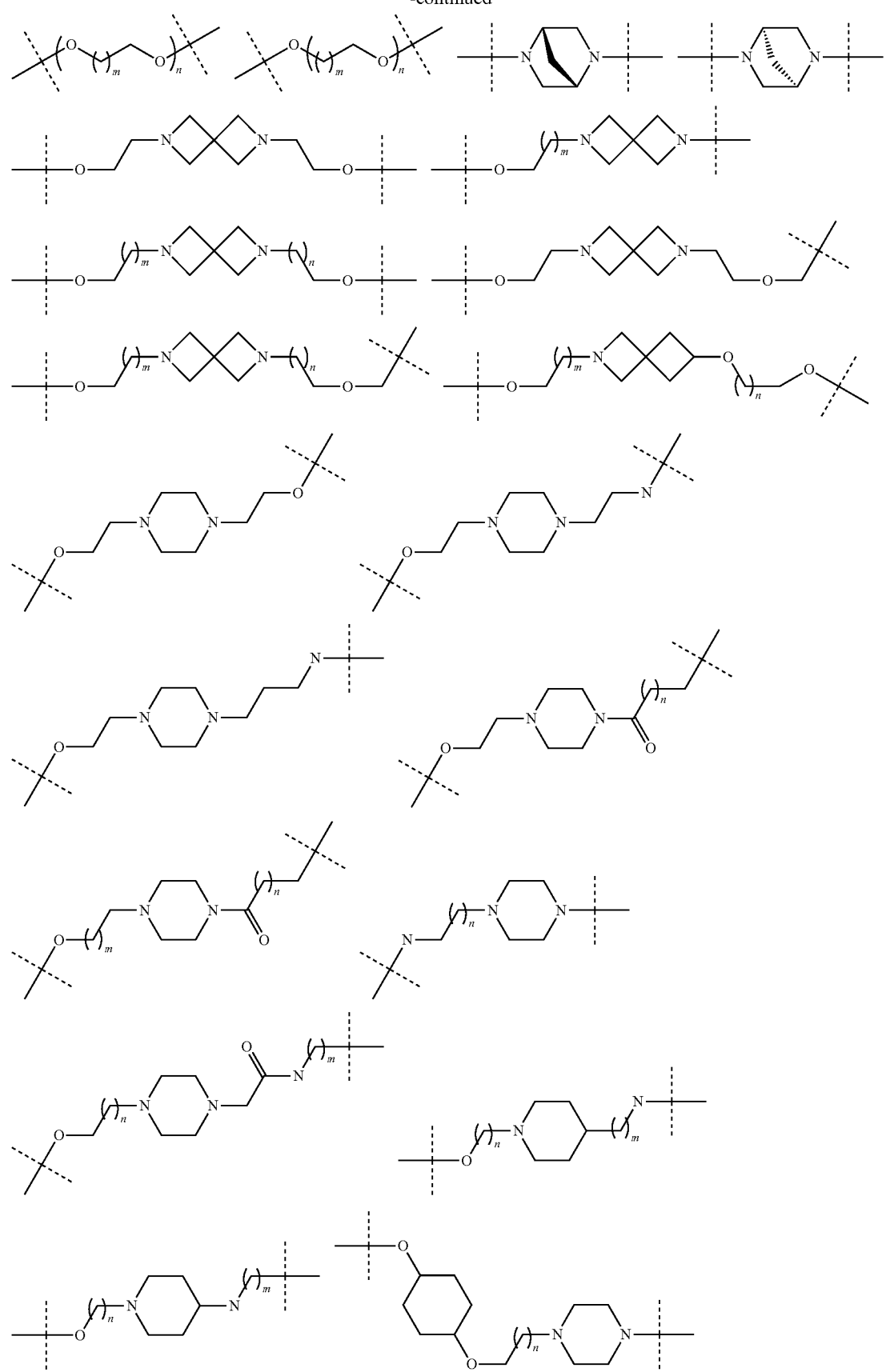

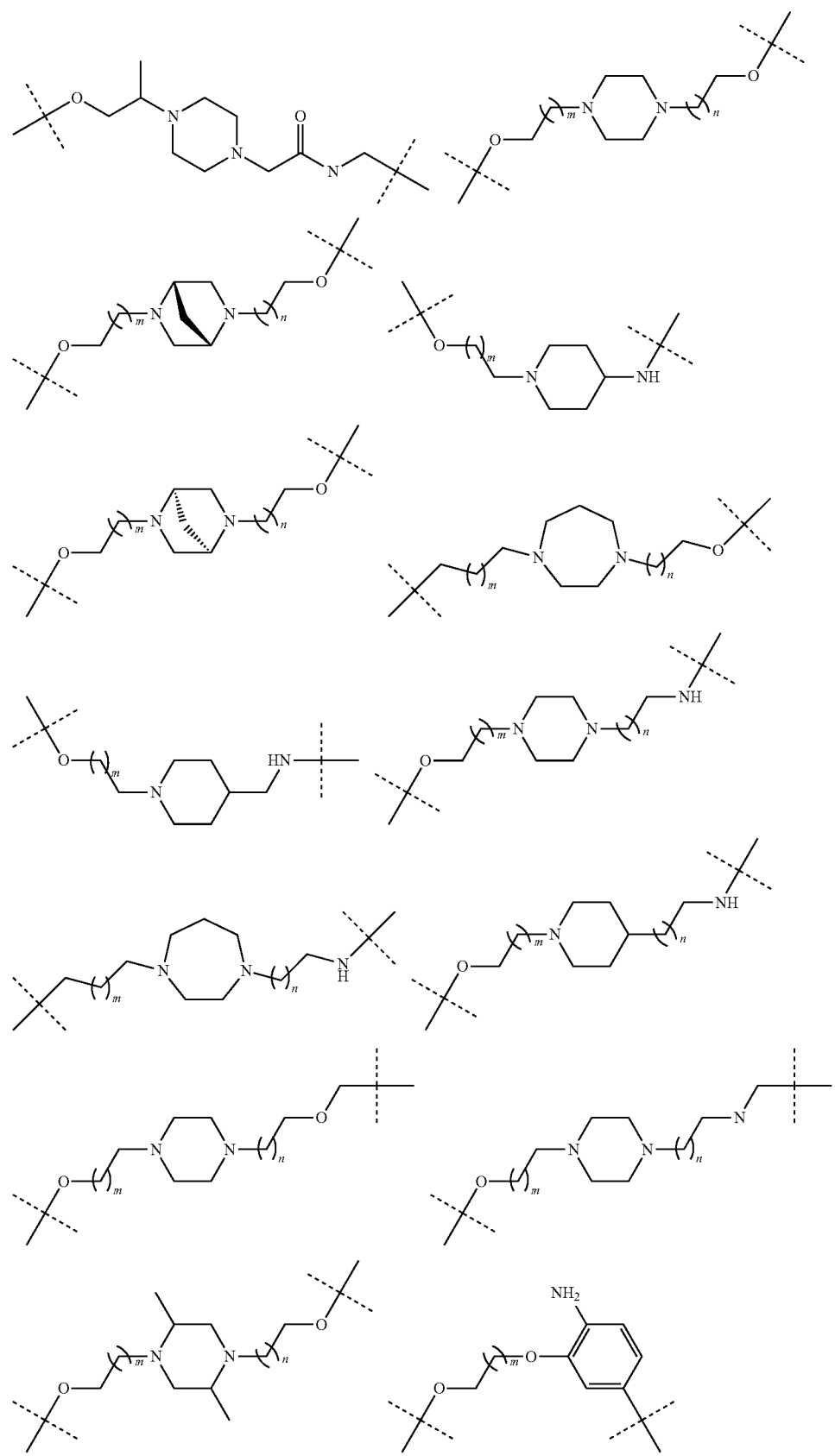

-continued
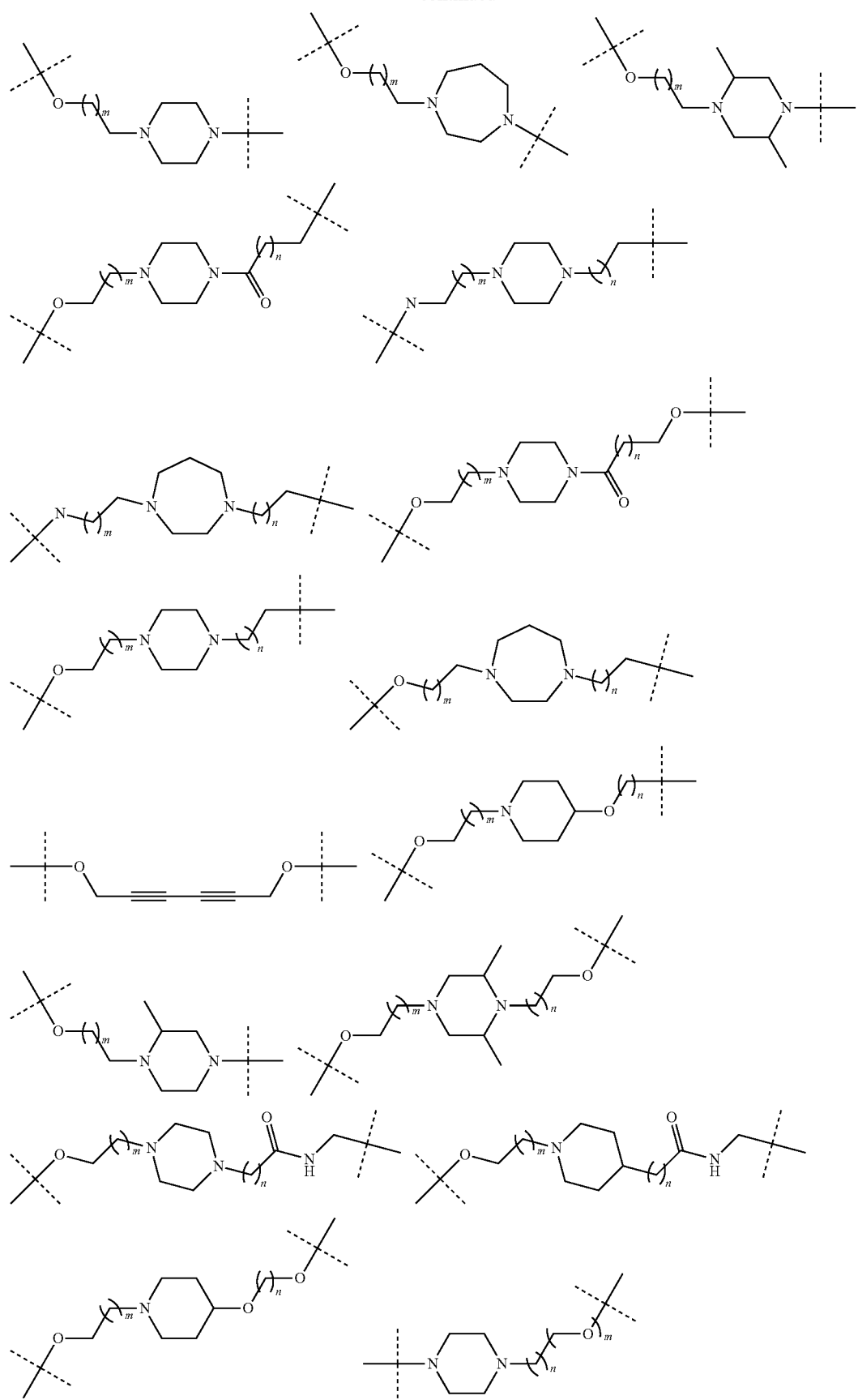

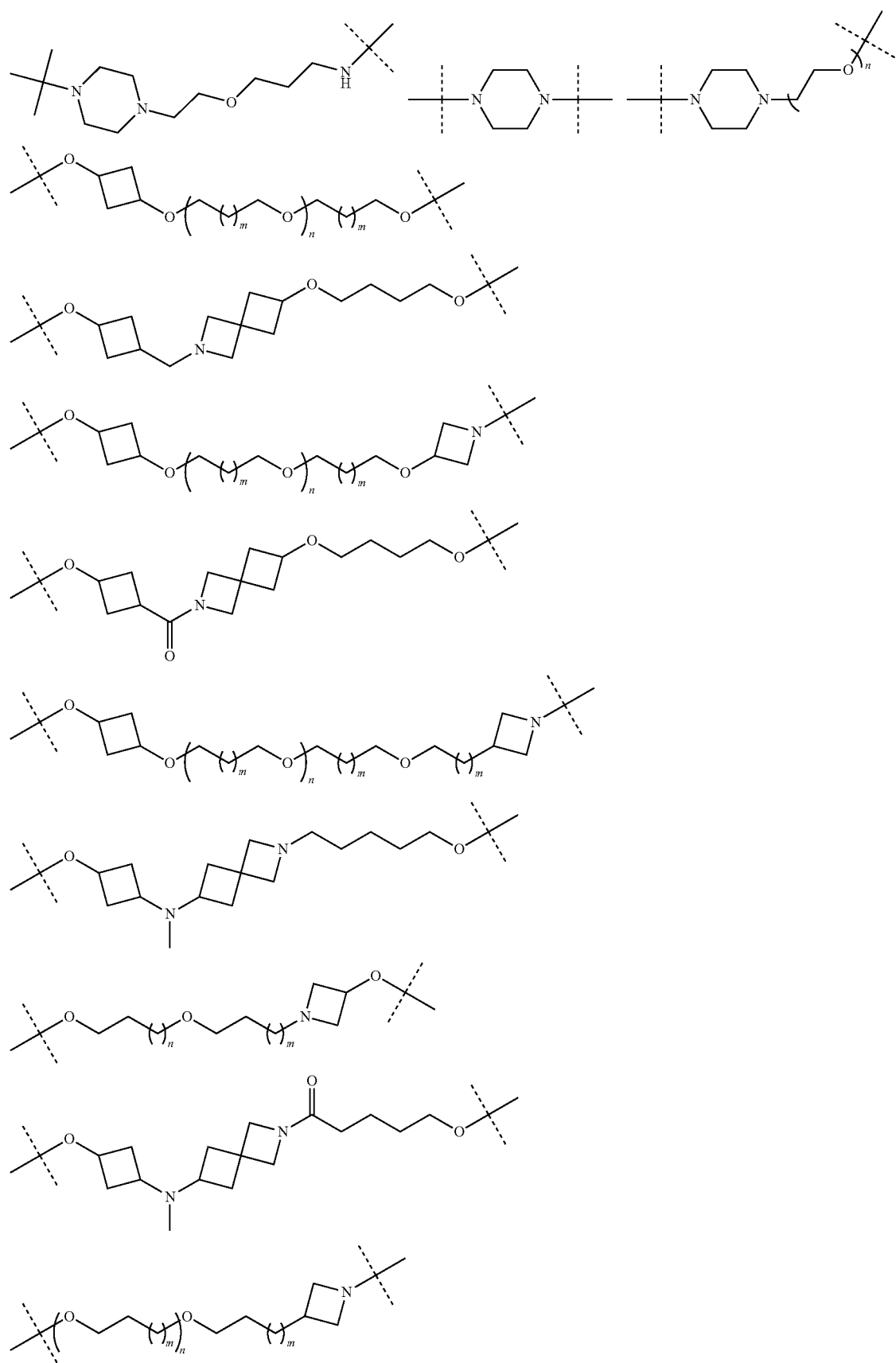

-continued
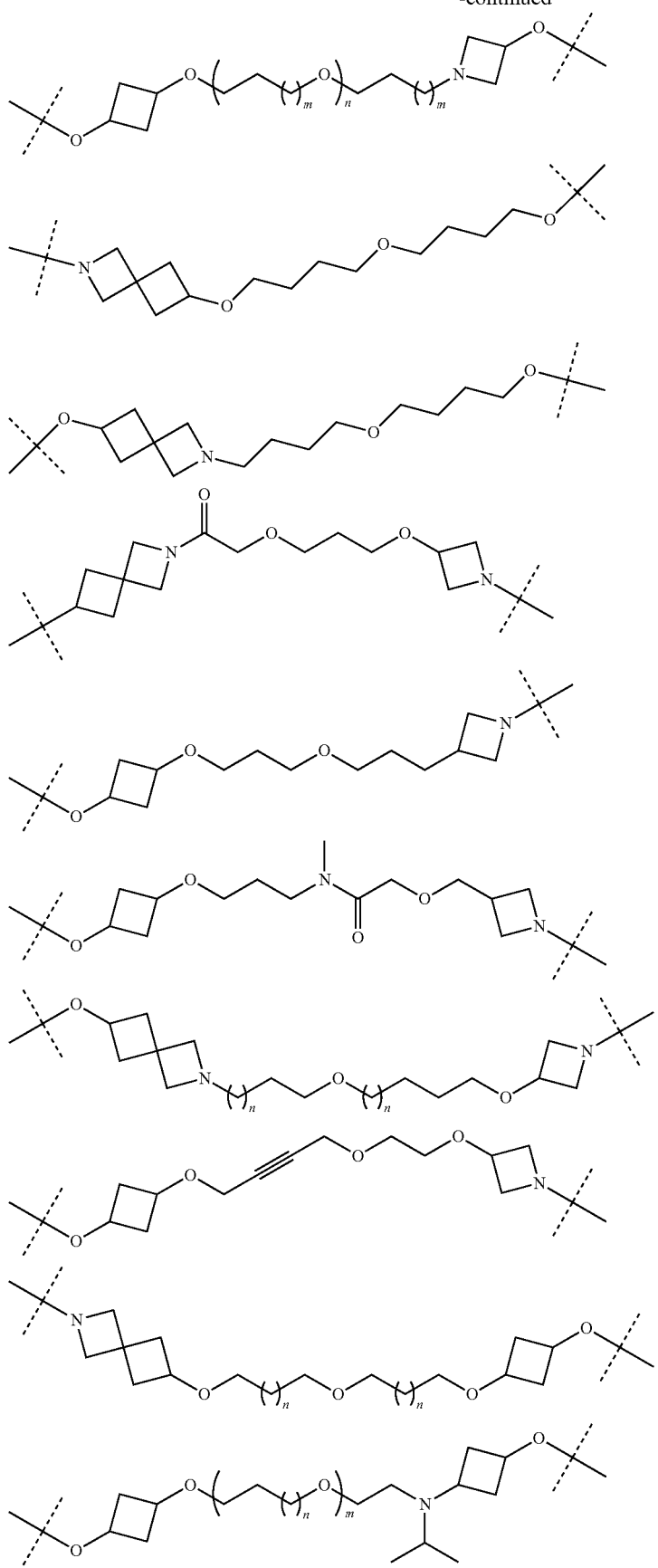

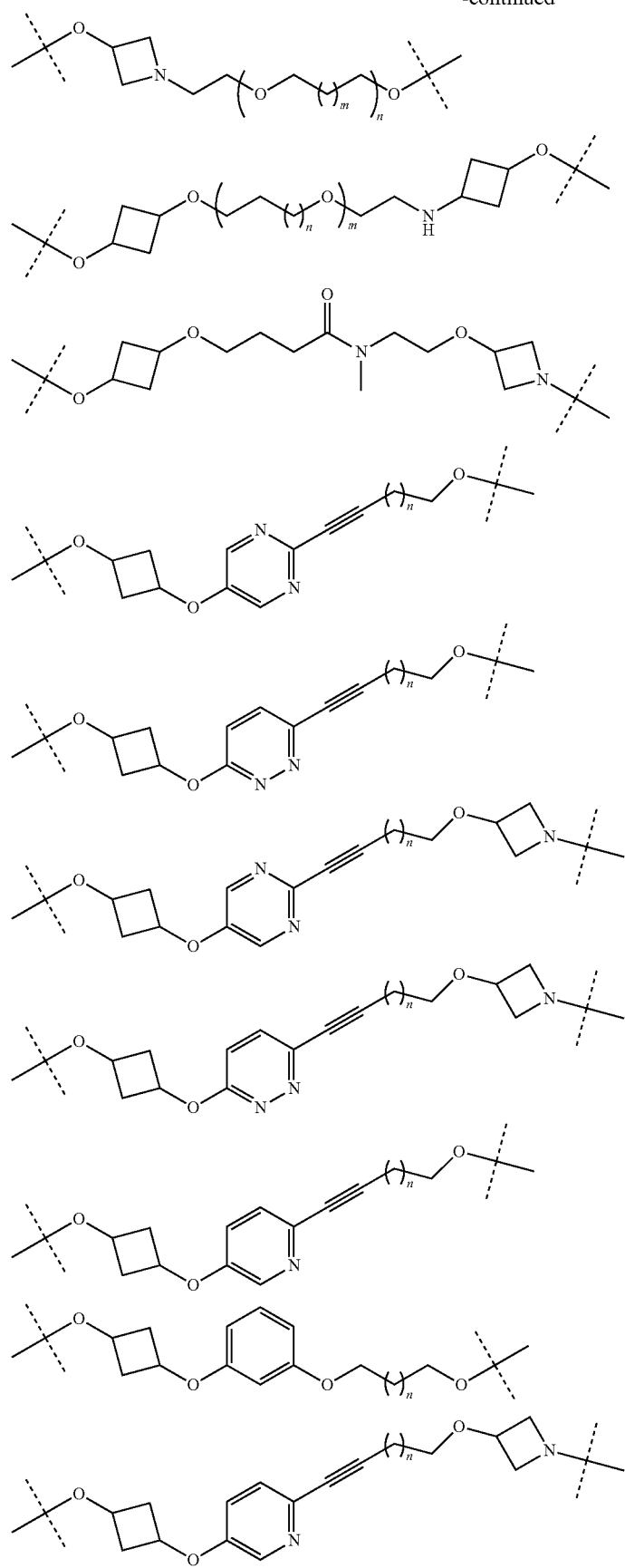

-continued
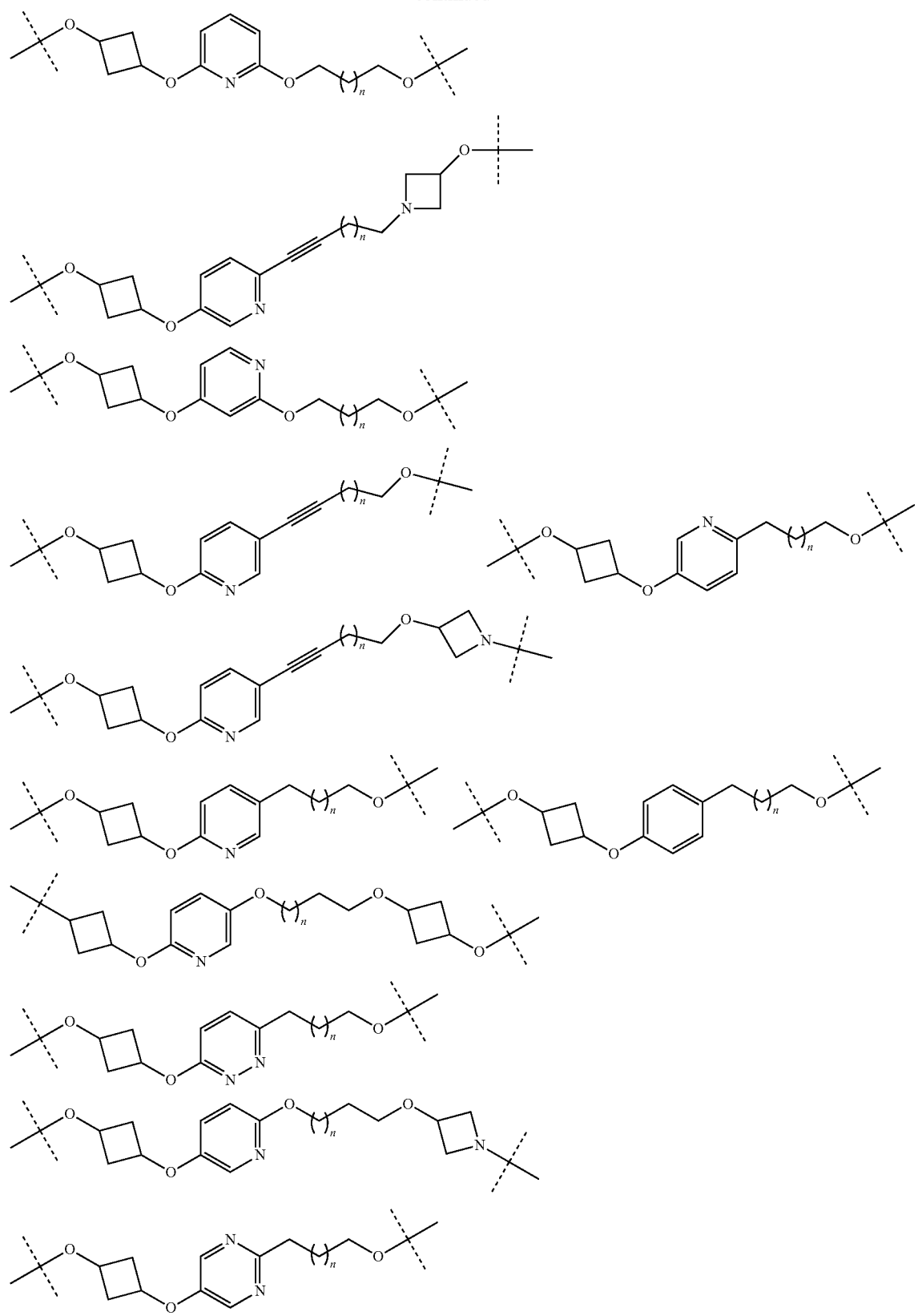

-continued
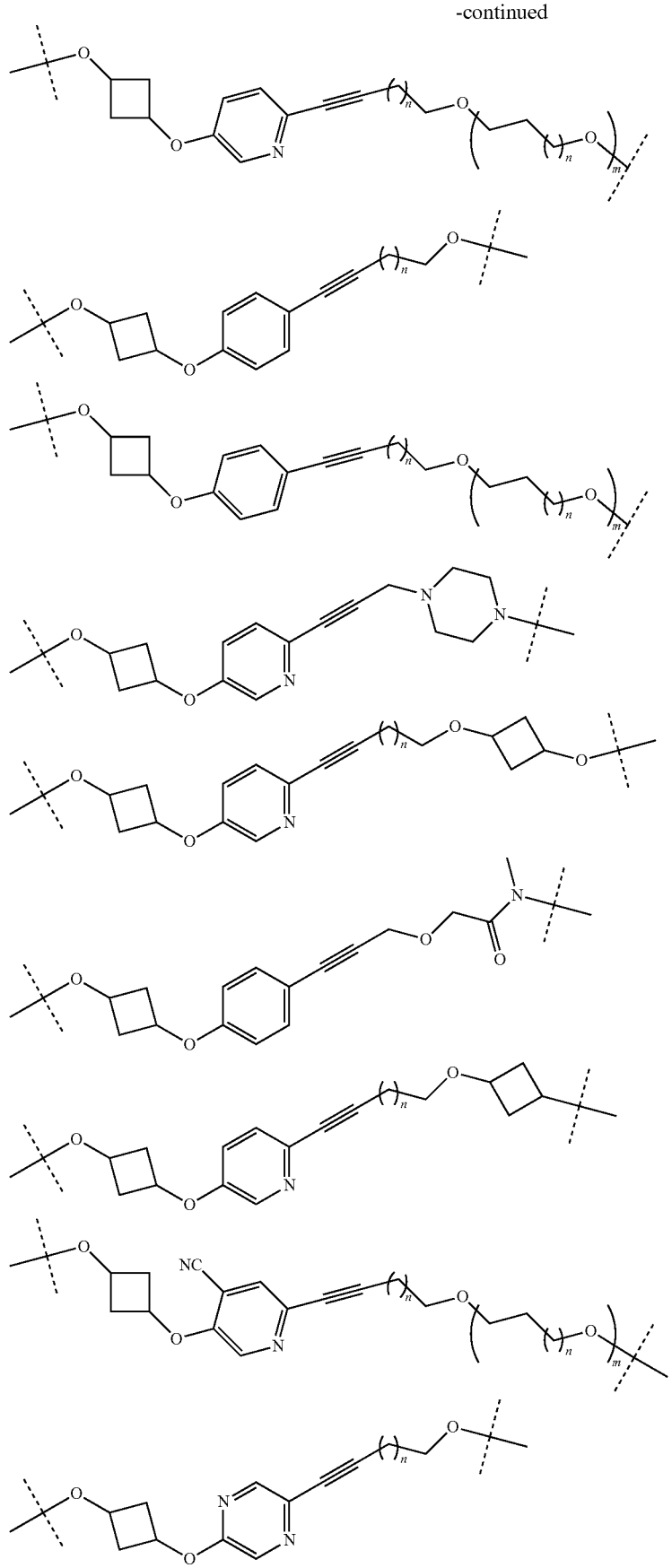

-continued
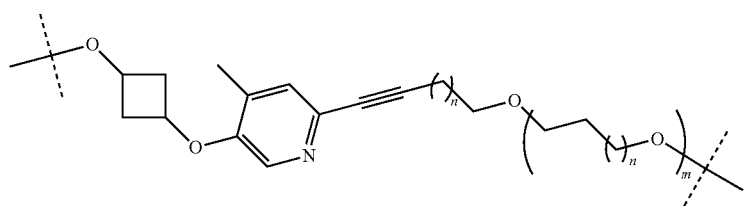
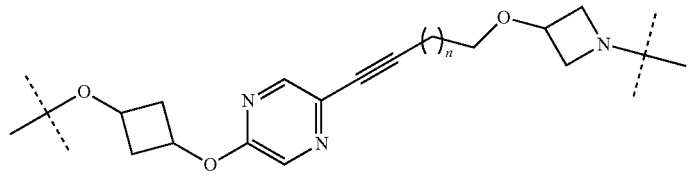
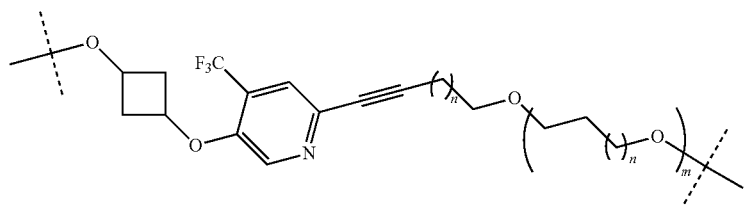
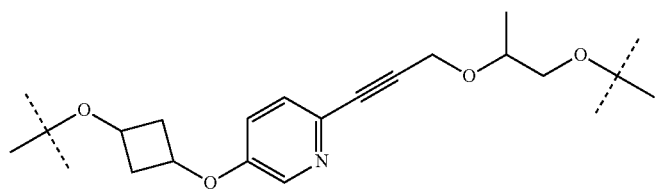
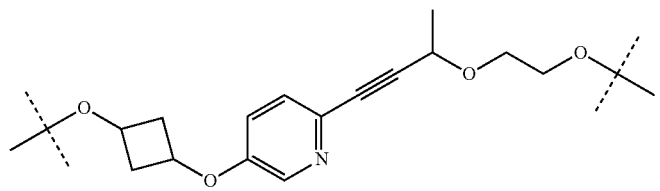
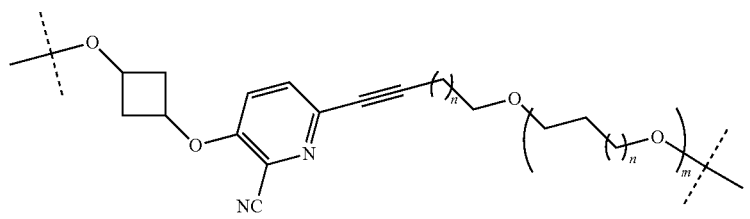
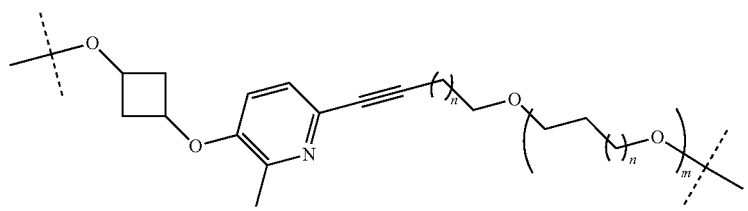
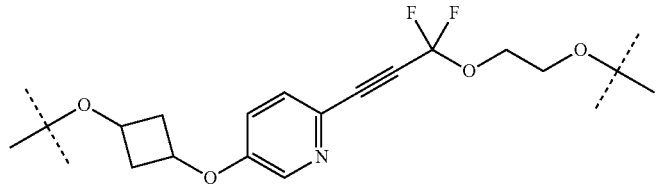

-continued
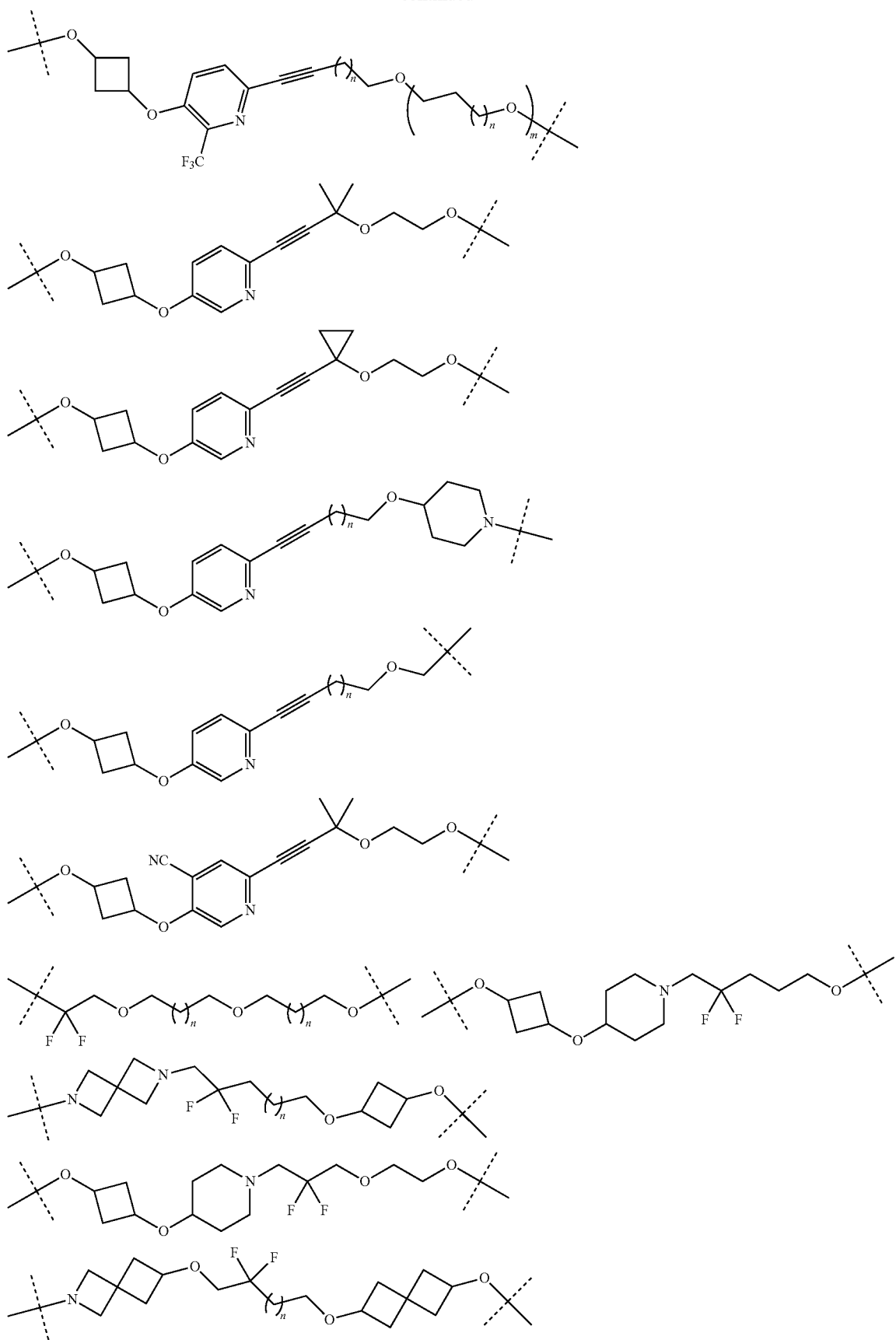

-continued
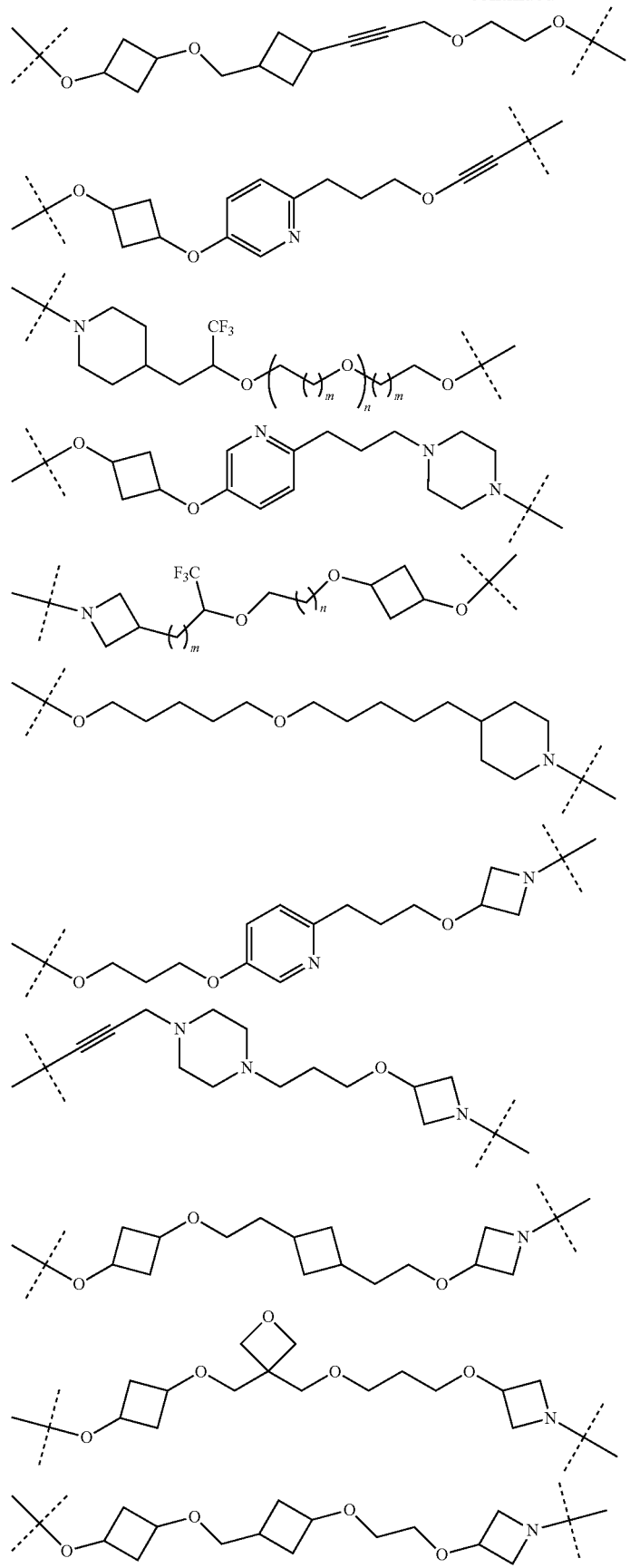

-continued
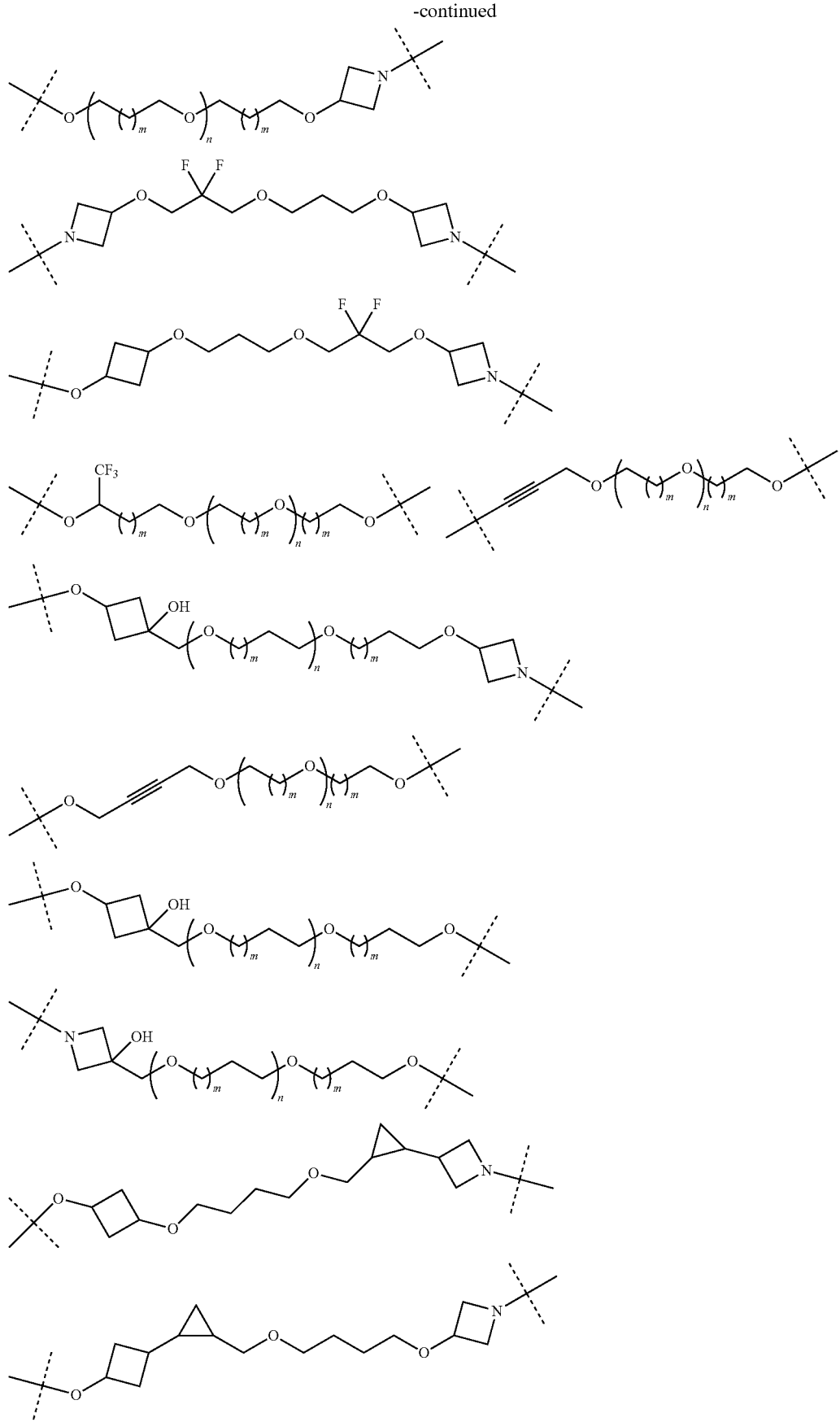

-continued
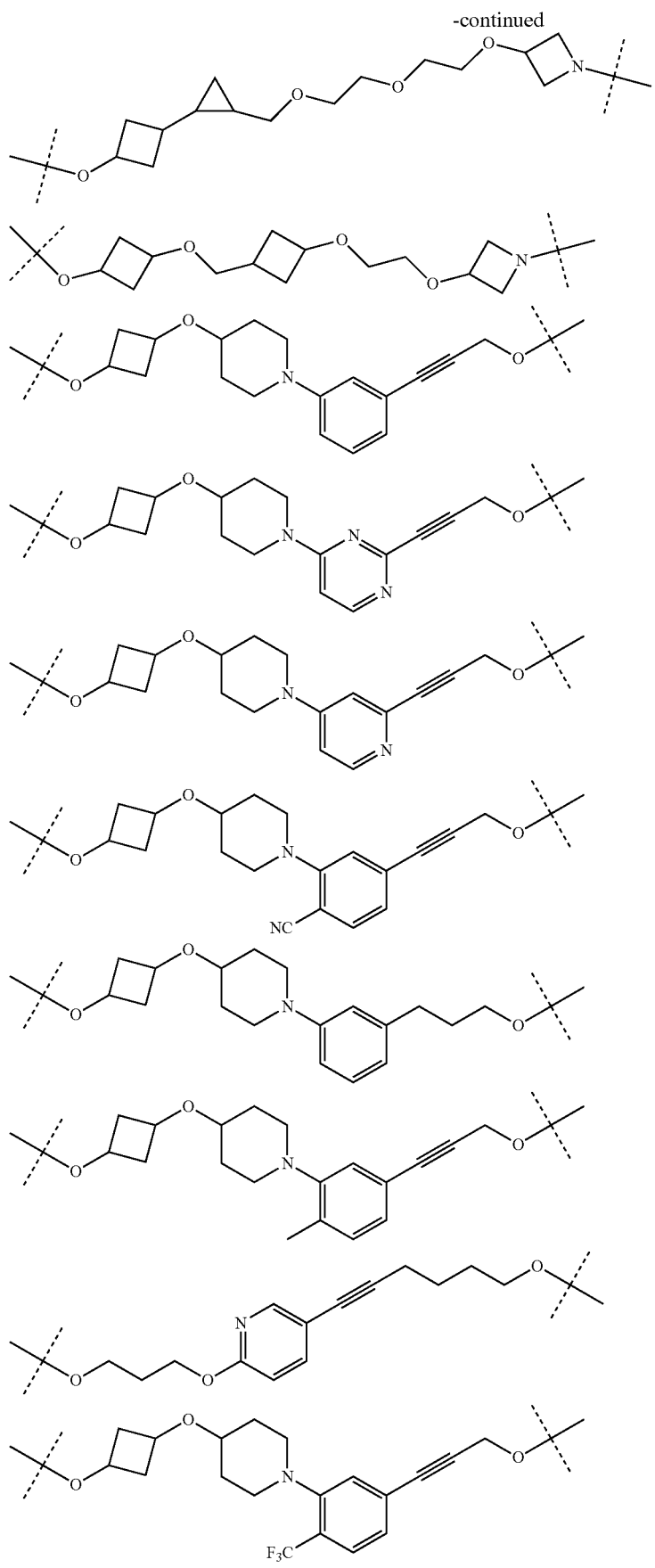

-continued
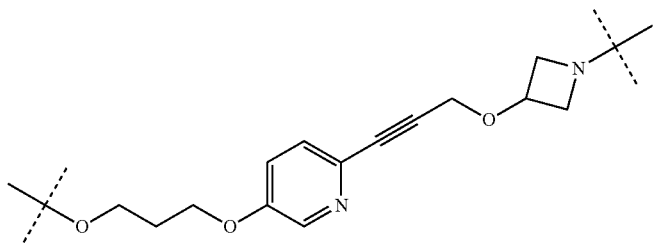
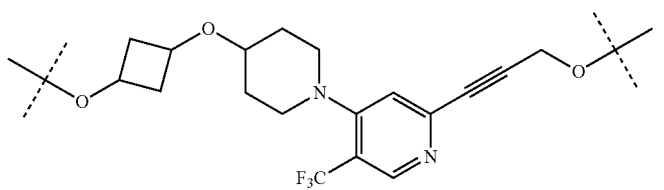
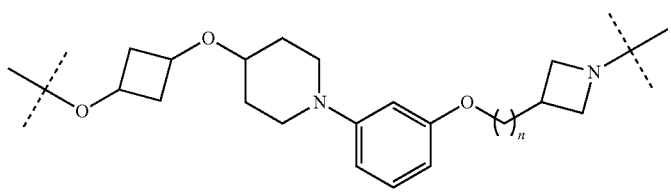
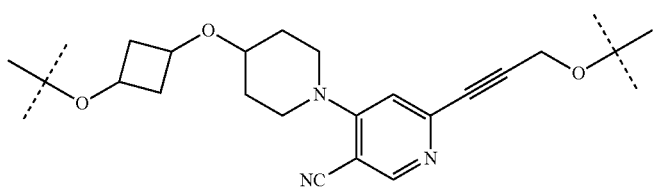
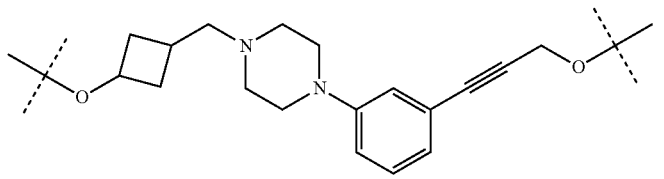
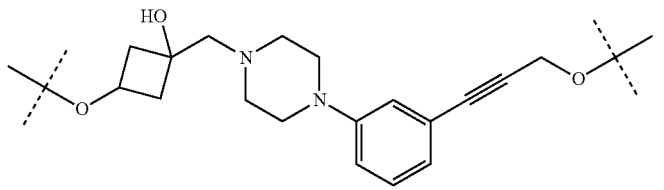
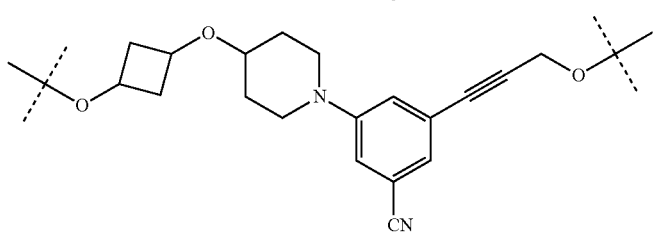
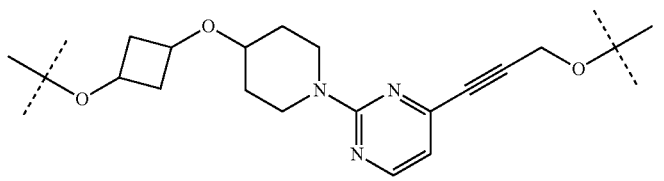

-continued
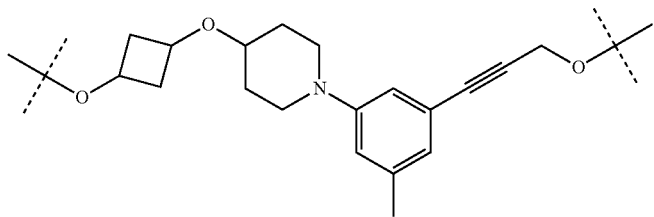
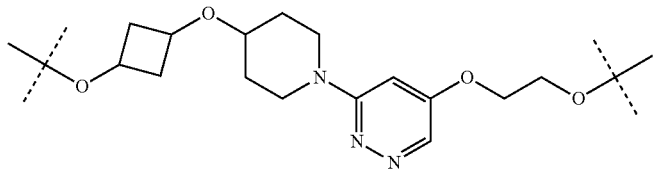
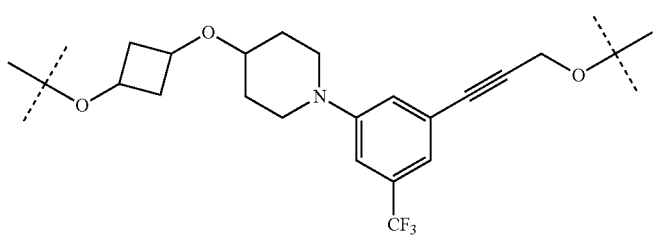
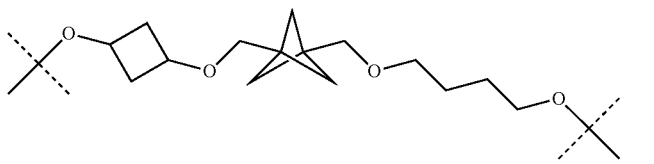
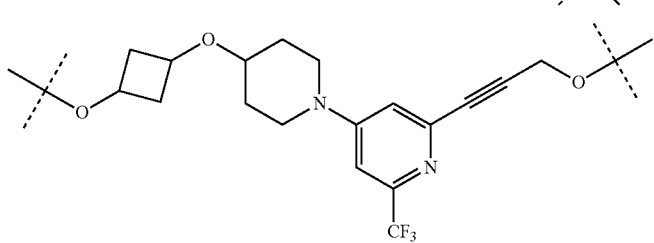
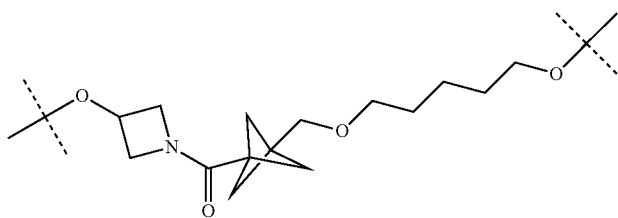
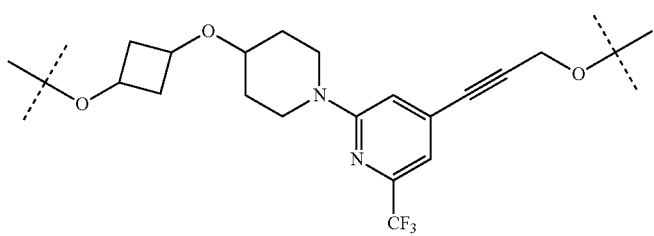
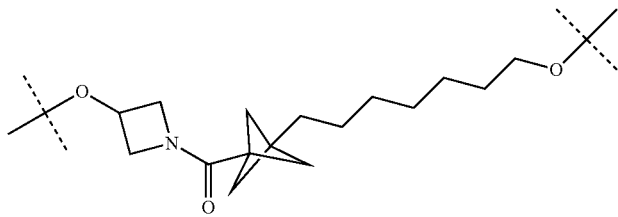

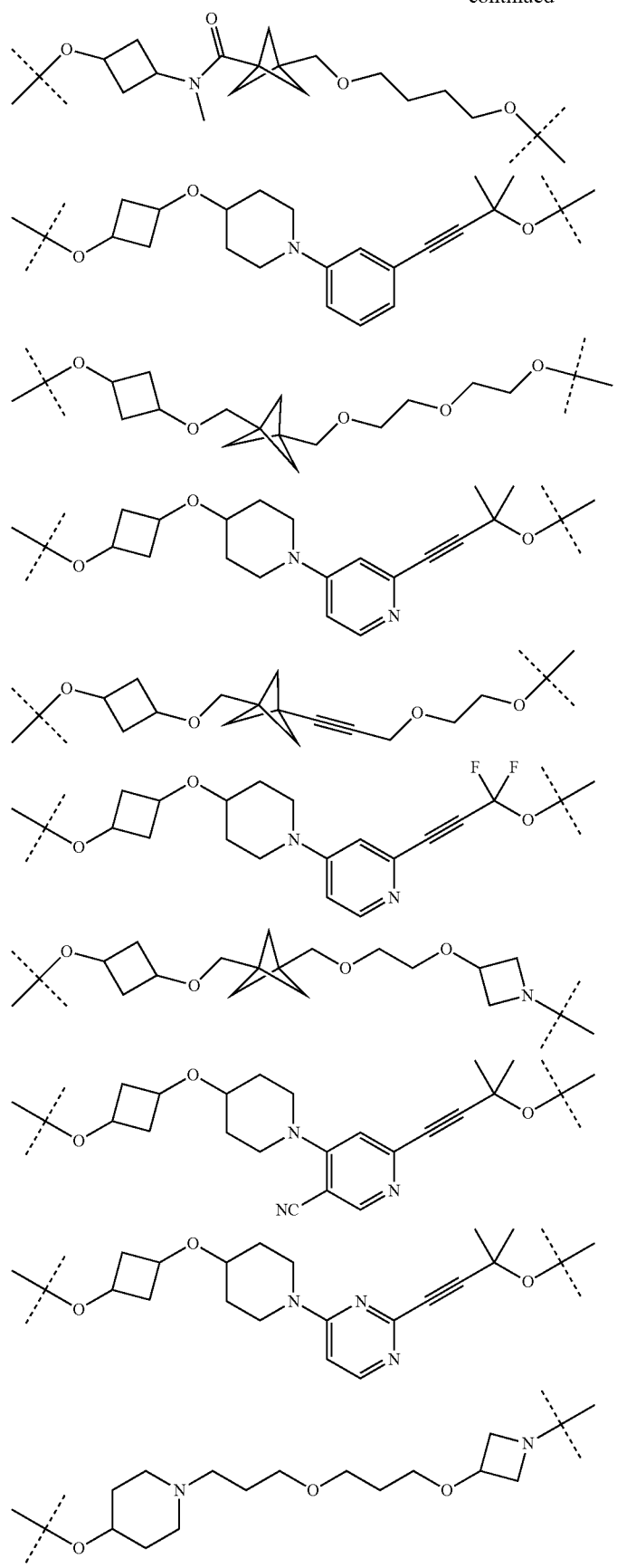

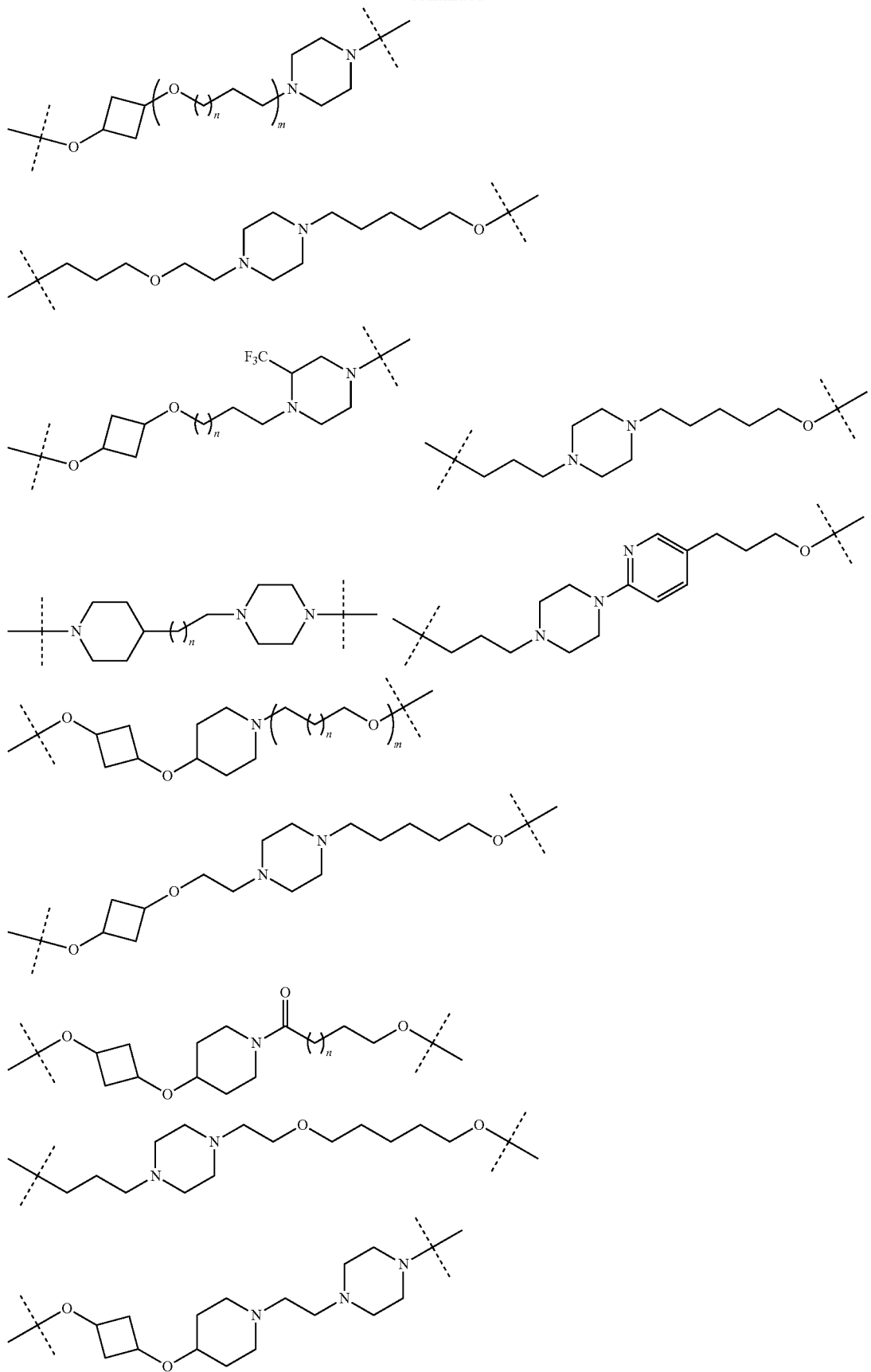

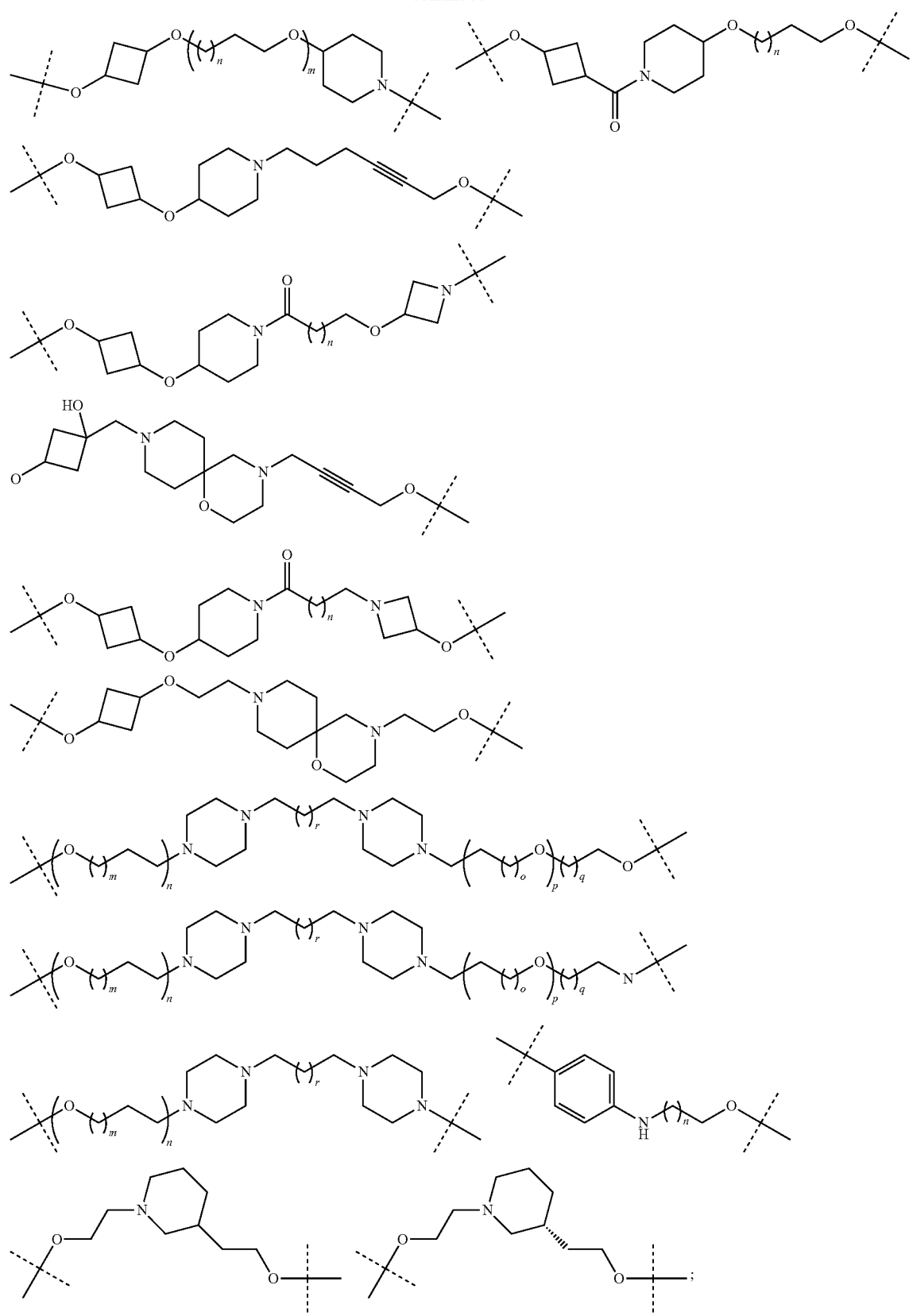

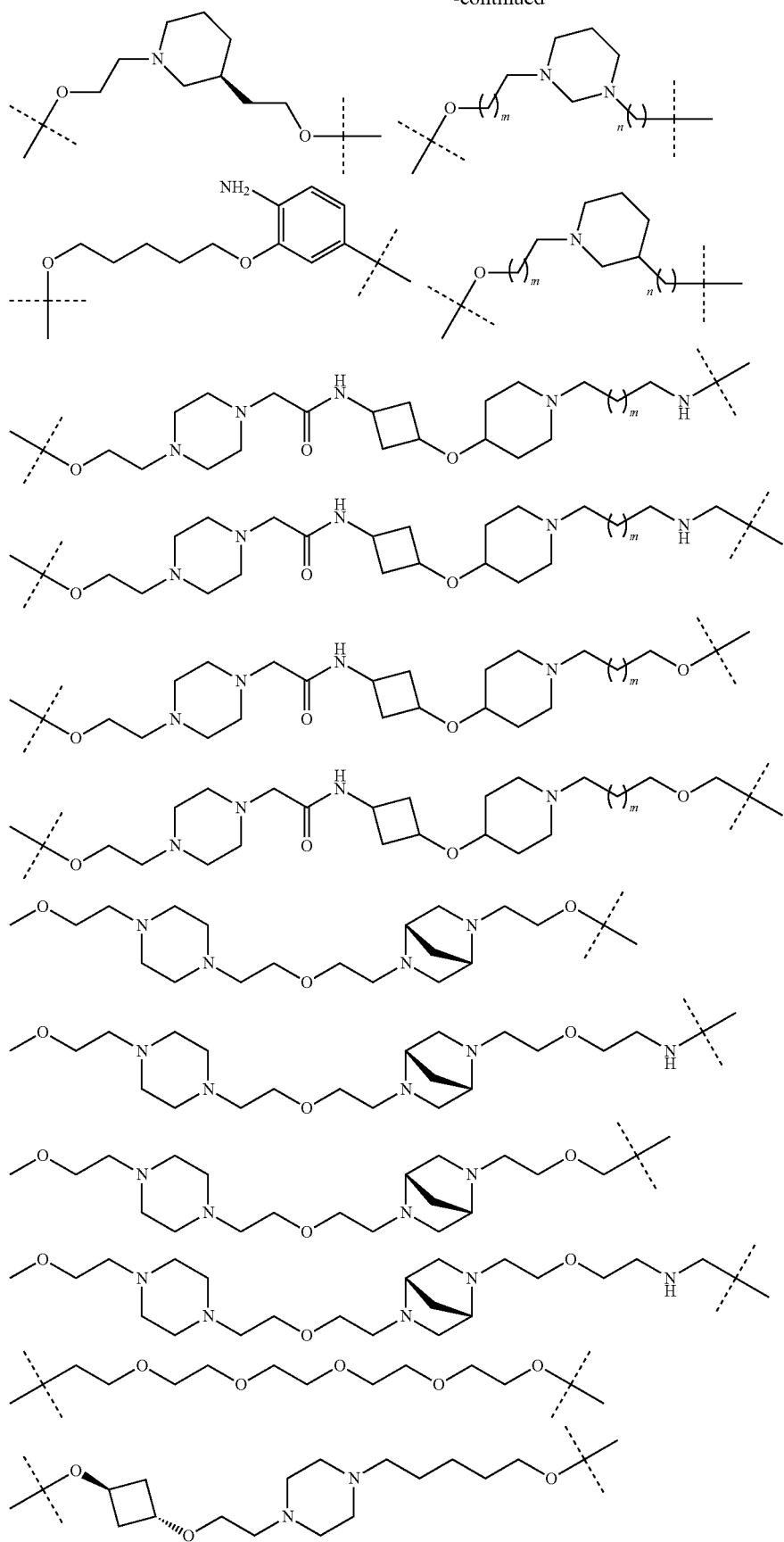

-continued
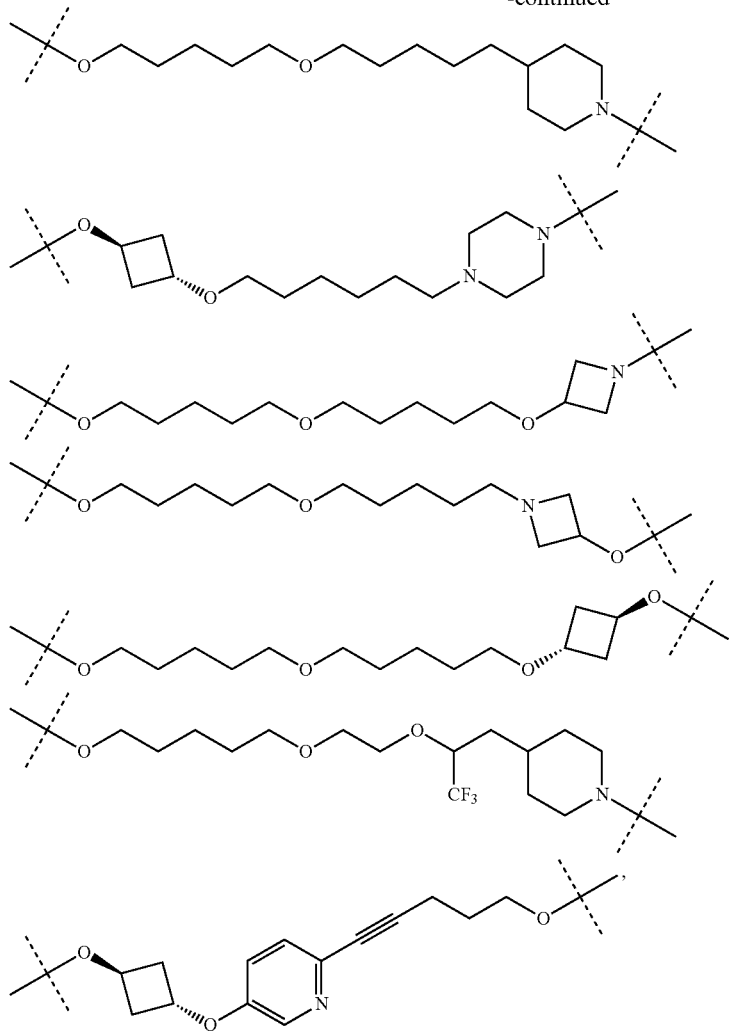
wherein each m, n, o and p is independently 0, 1, 2, 3, 4, 5, 6, or 7.
In any aspect or embodiment described herein, L is selected from the group consisting of:
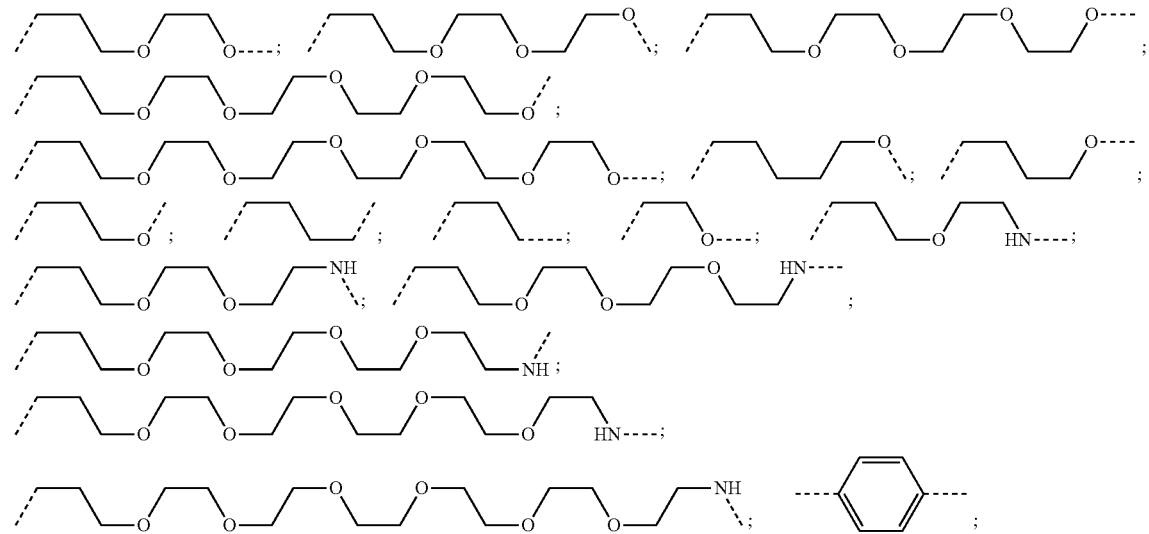

-continued
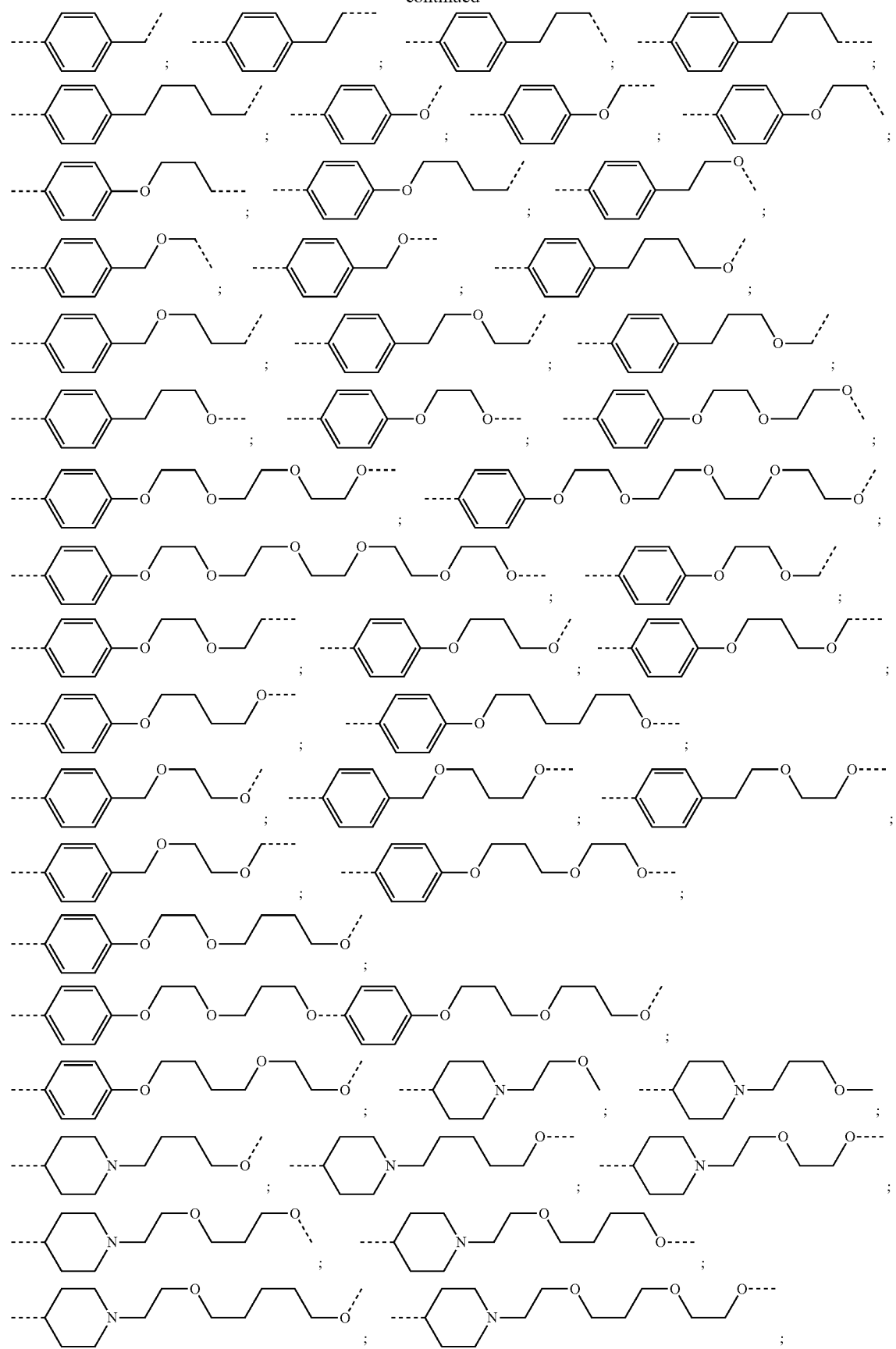

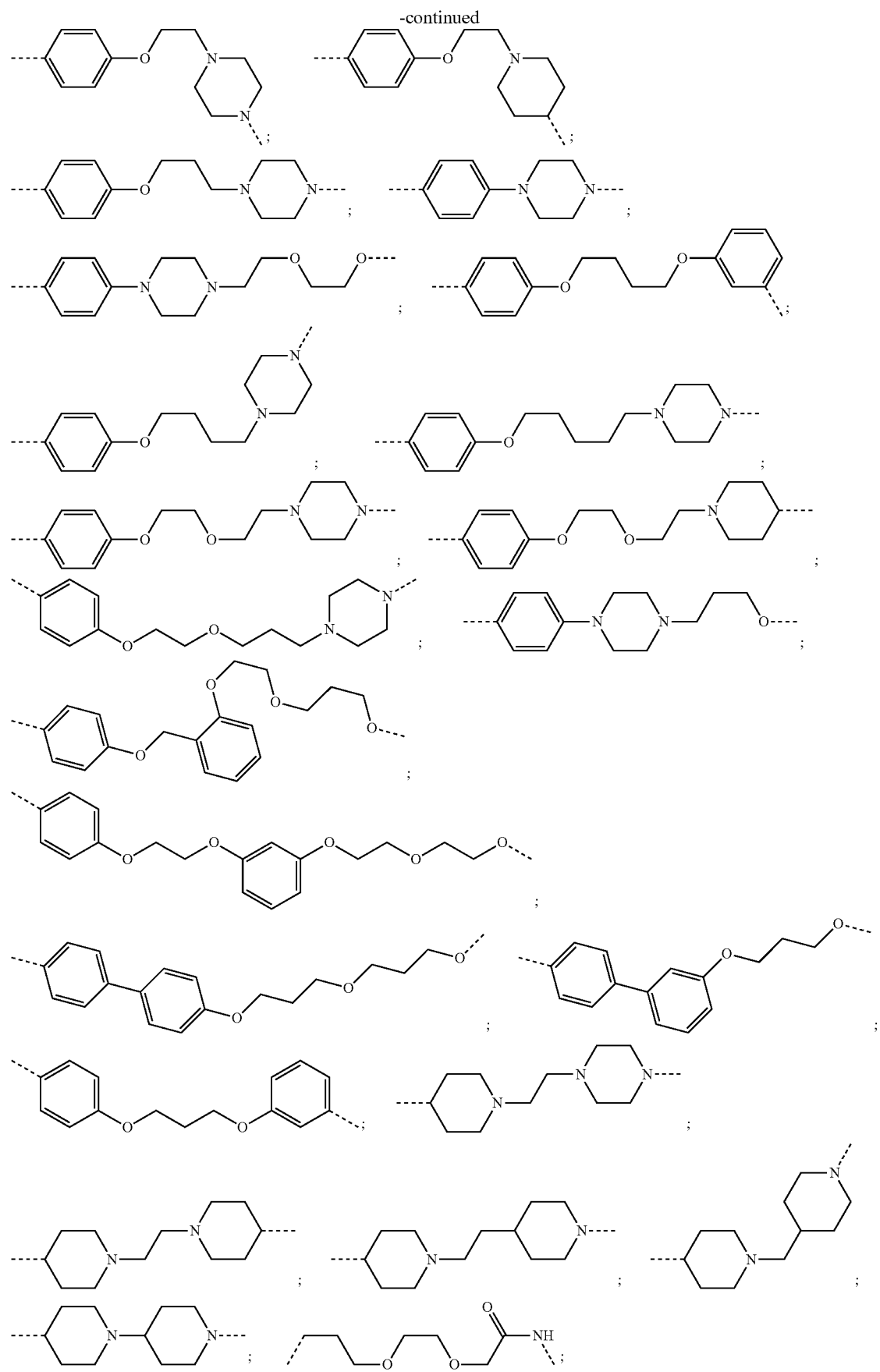

-continued
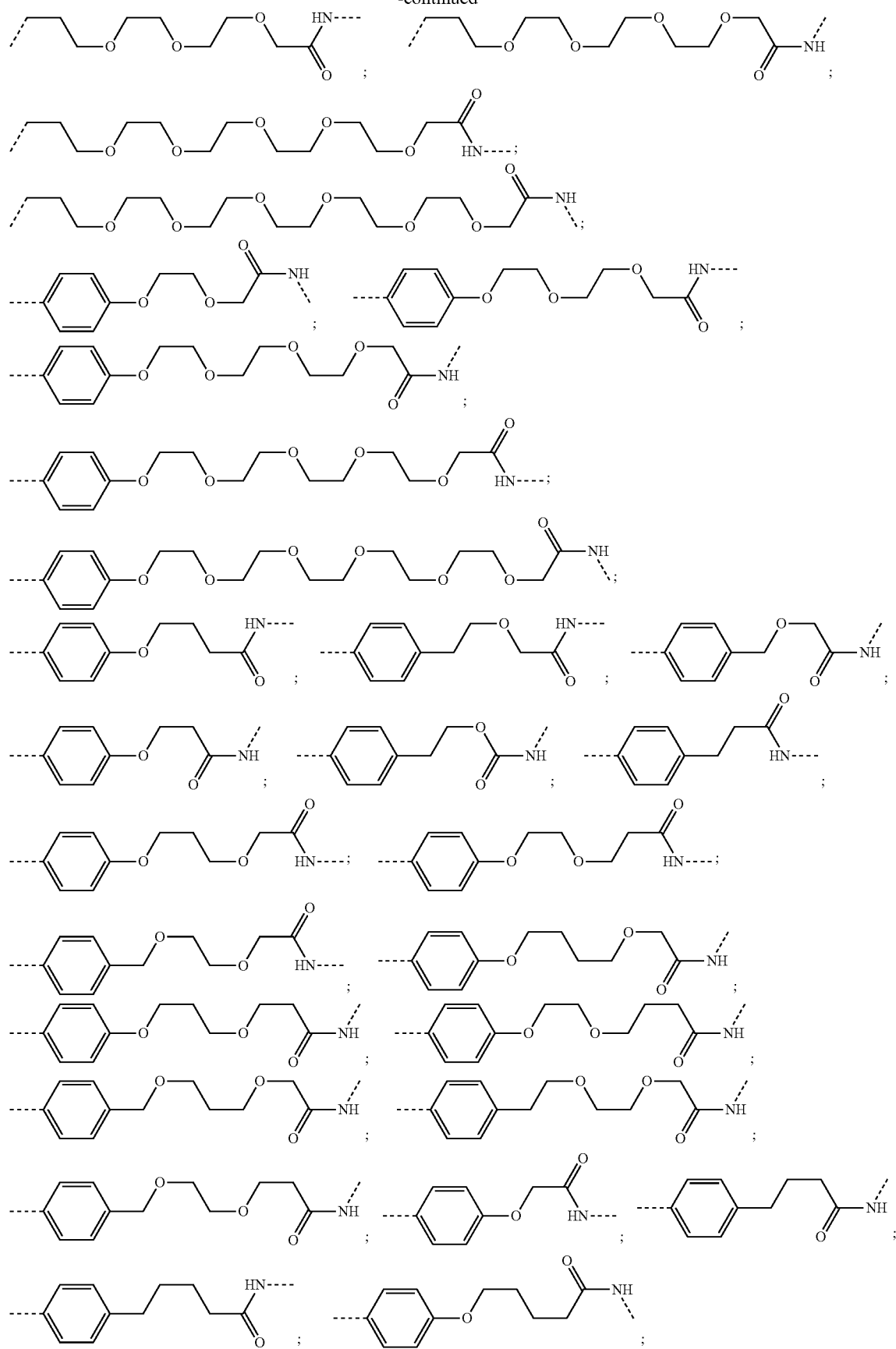

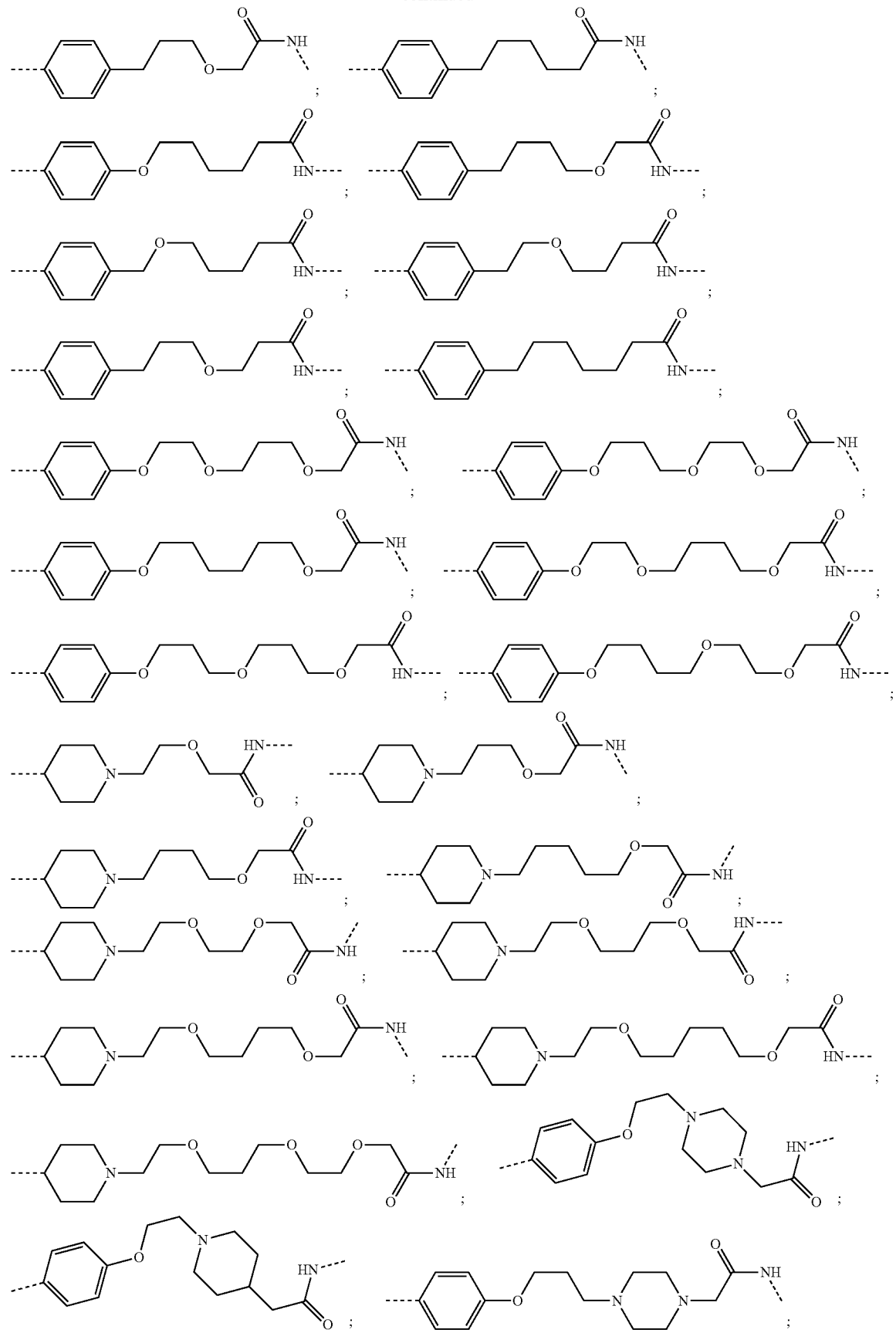

-continued
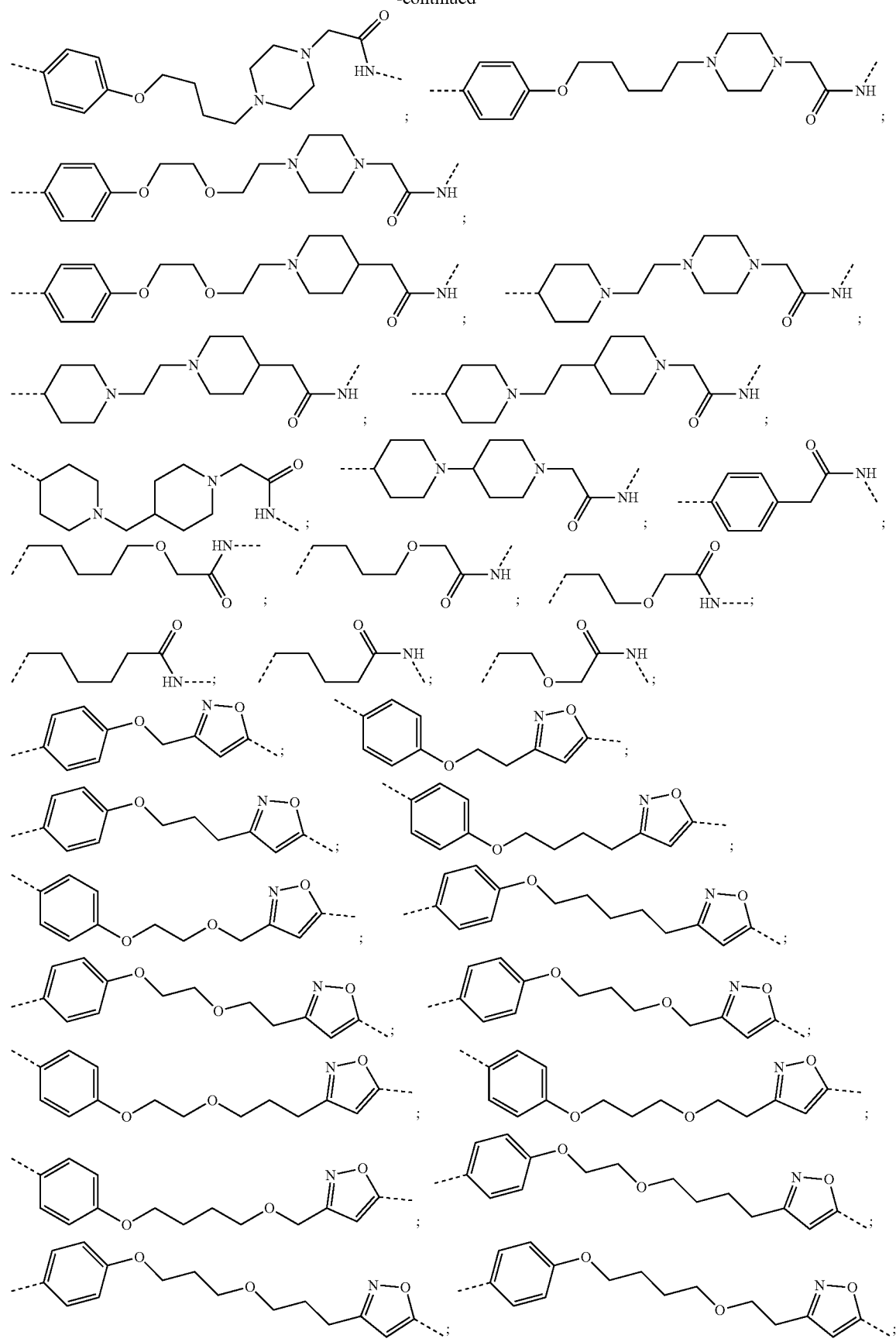

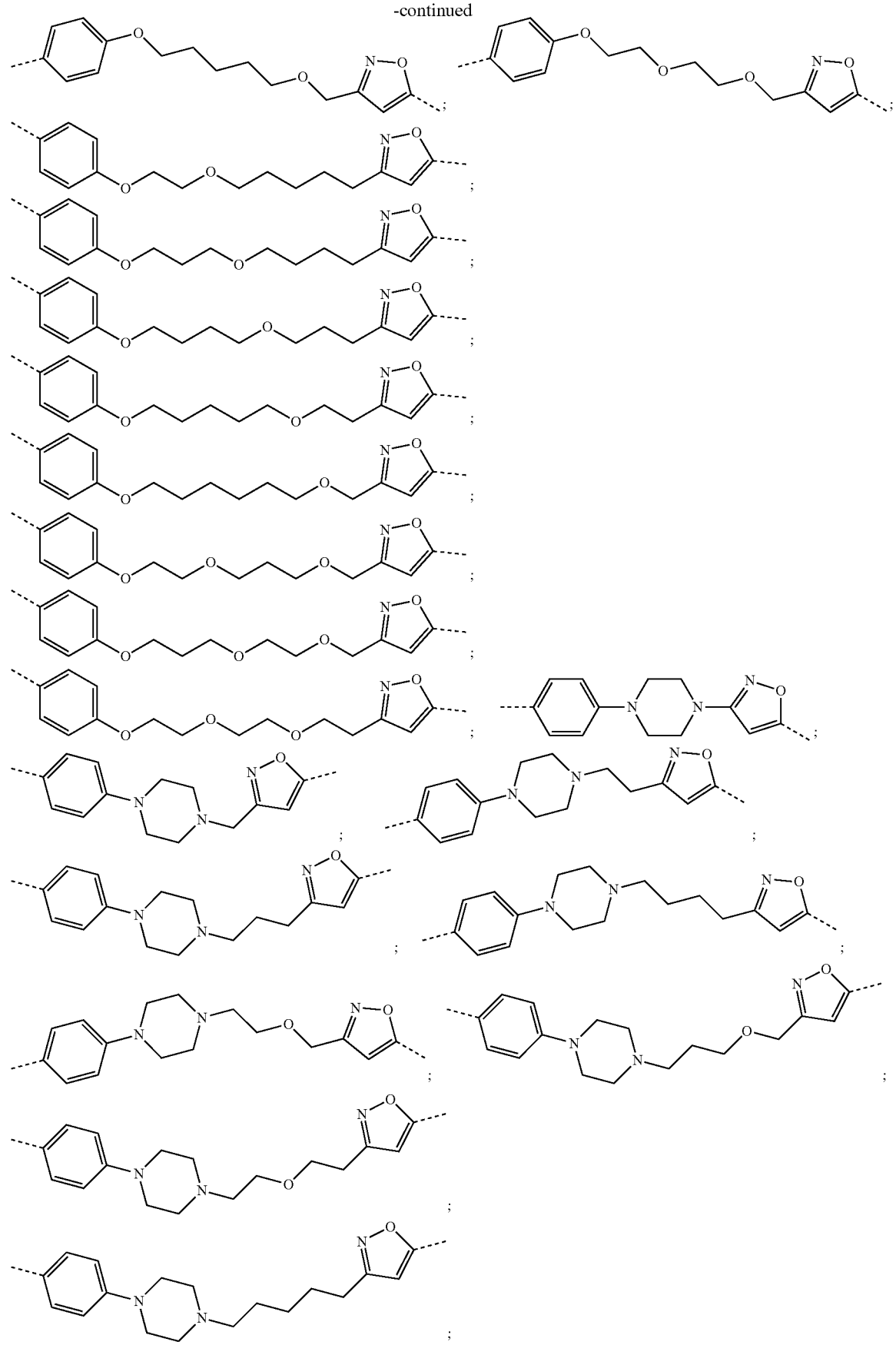

-continued
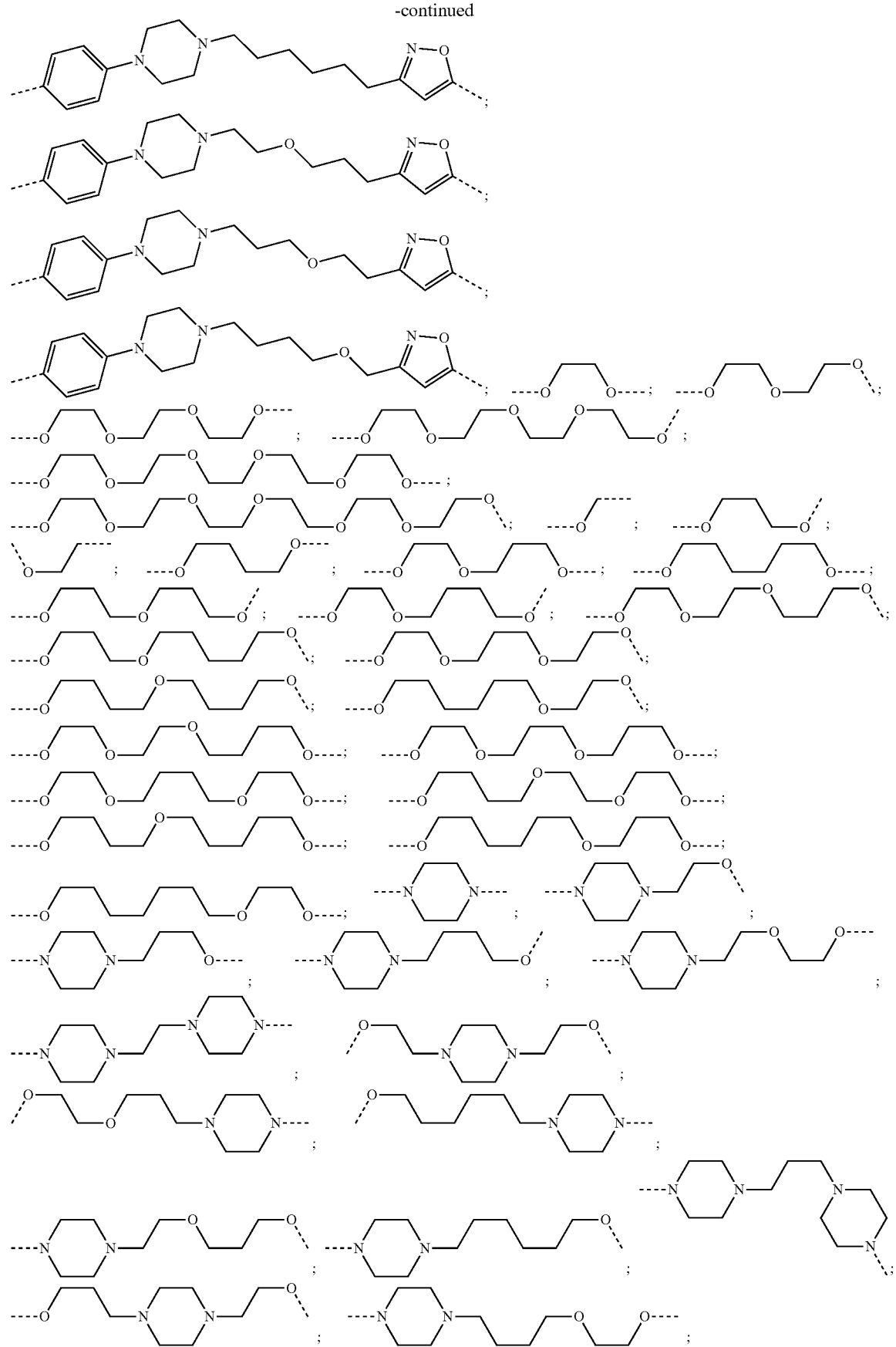

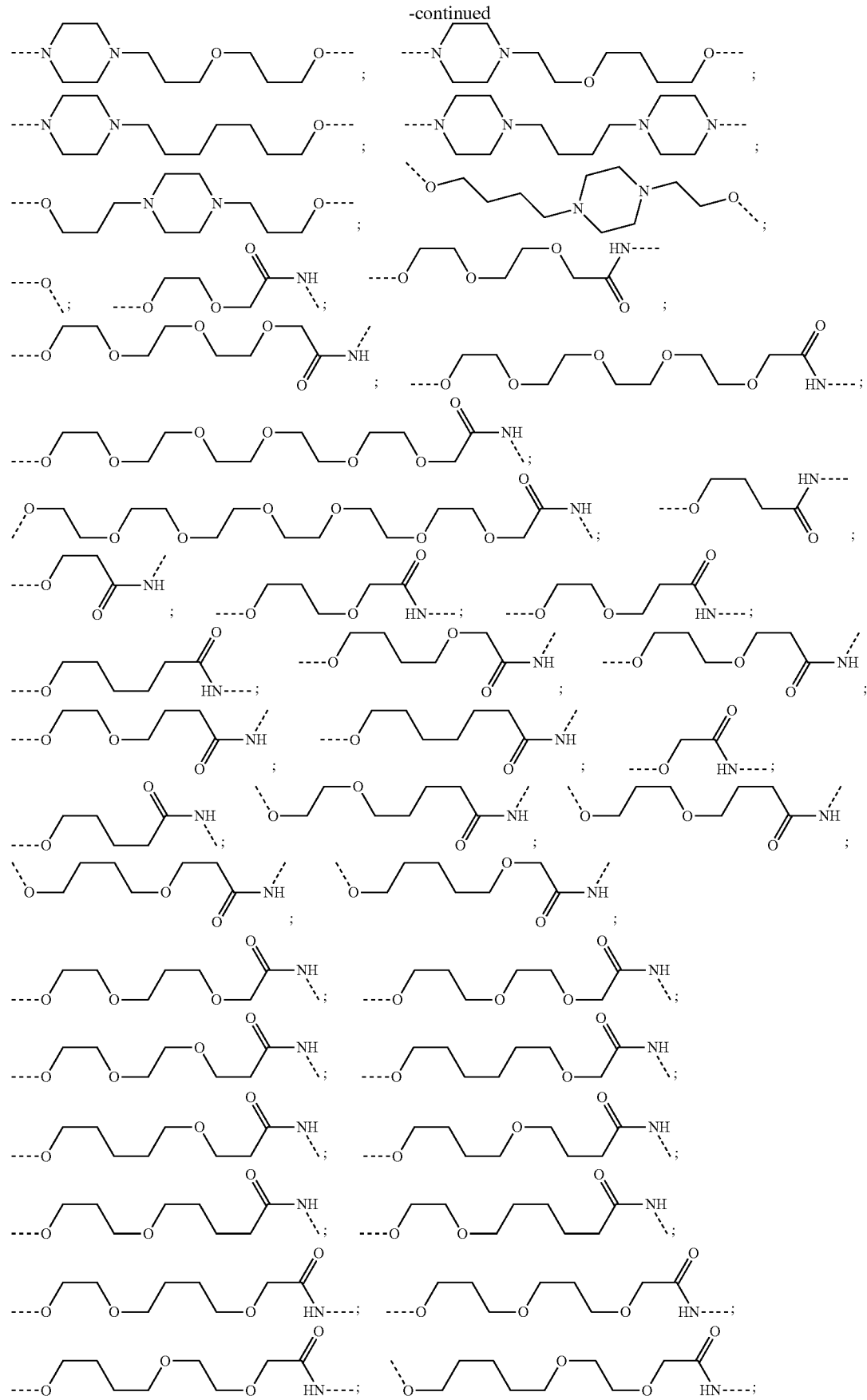

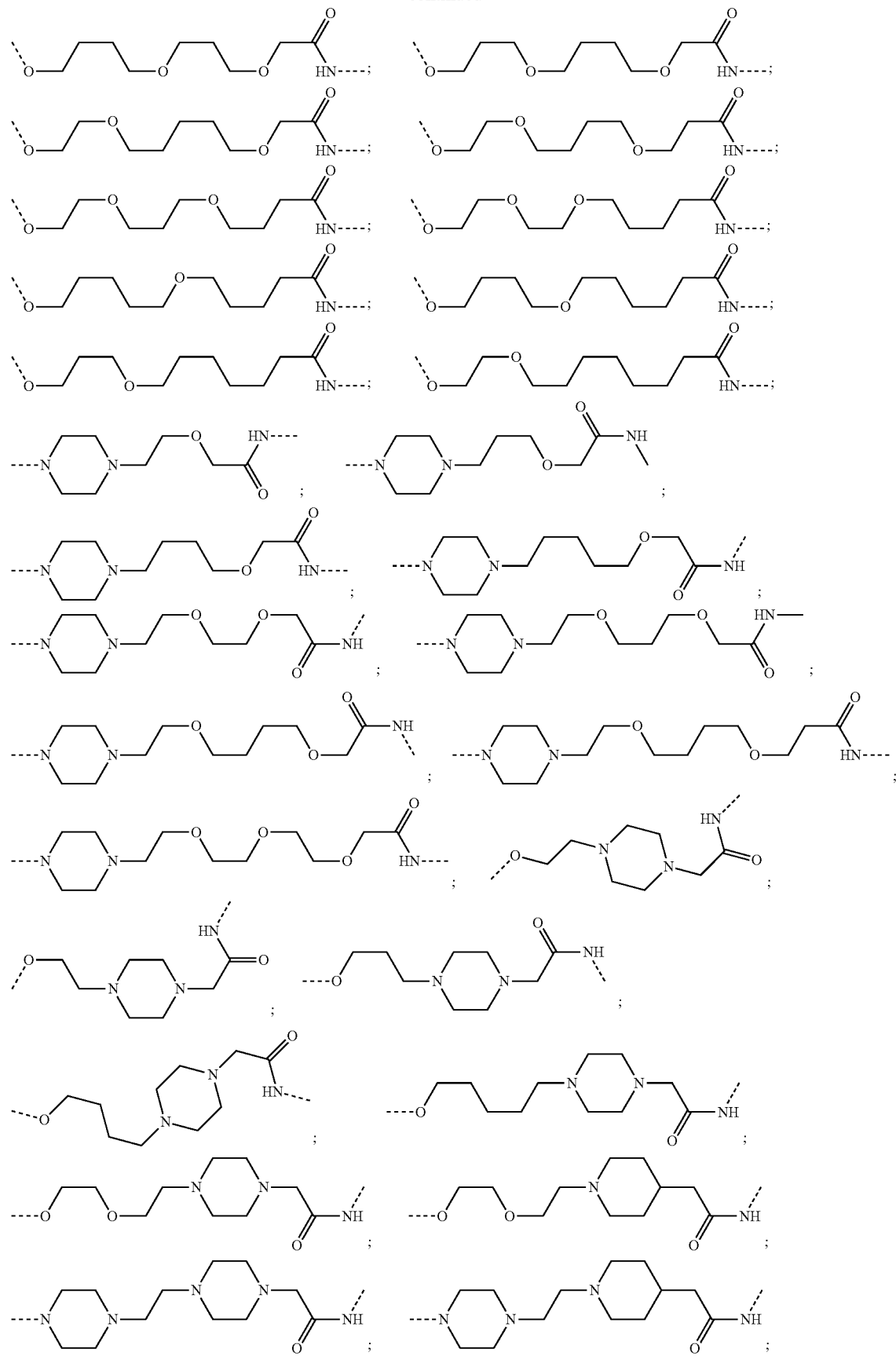

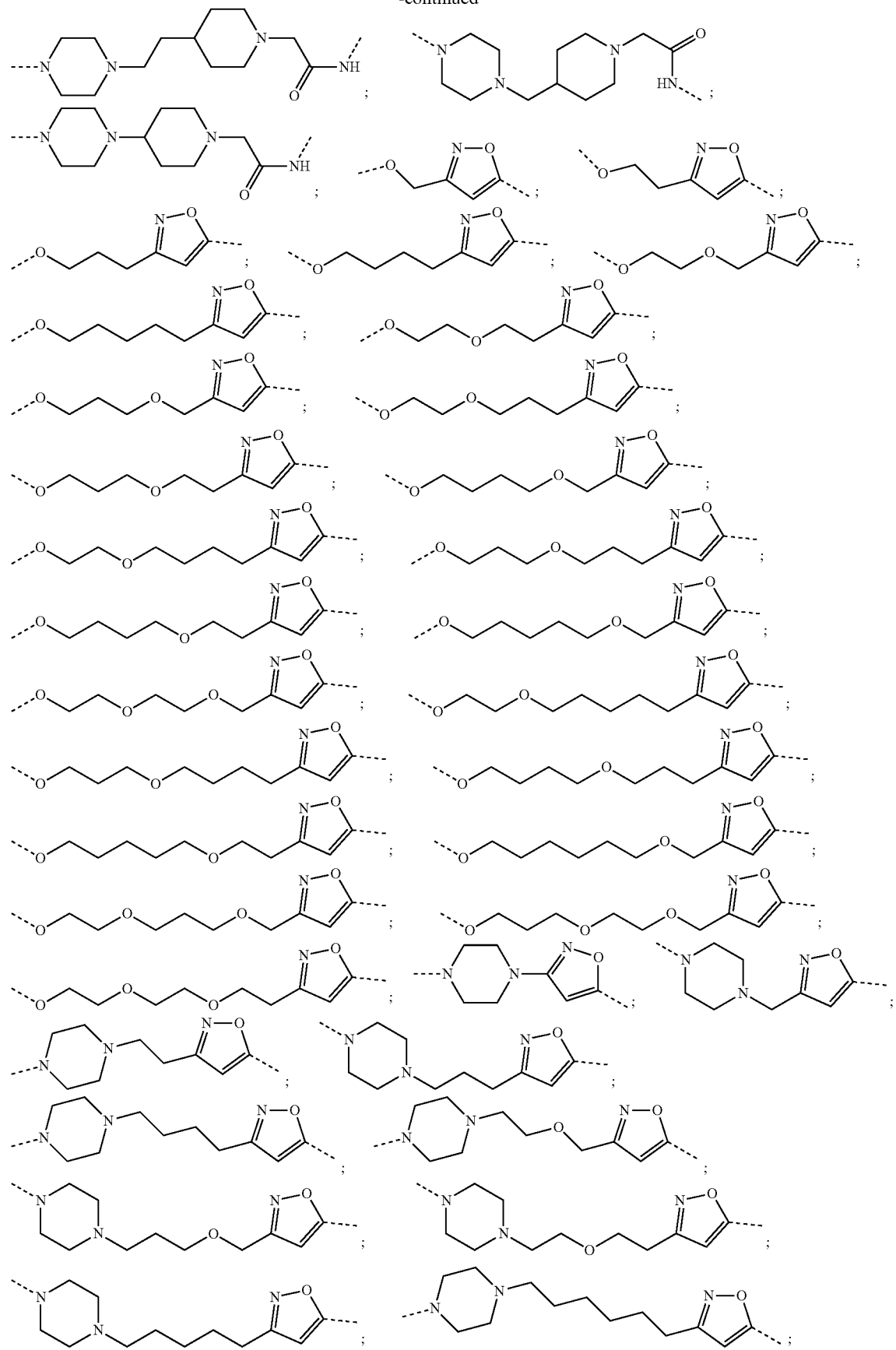

-continued

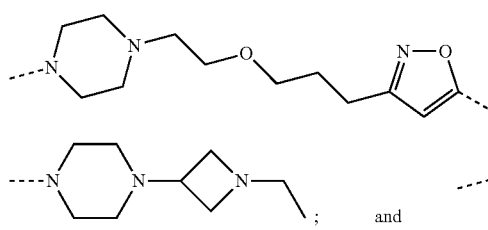

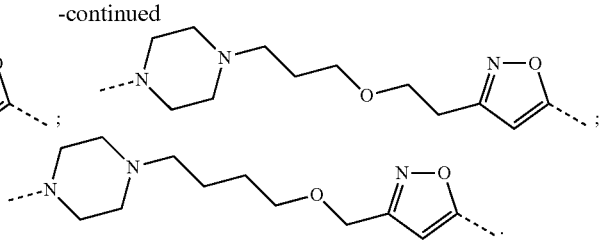

and

In additional embodiments, the linker (L) comprises a structure selected from, but not limited to the structure shown below, where a dashed line indicates the attachment point to the PTM or ULM moieties.

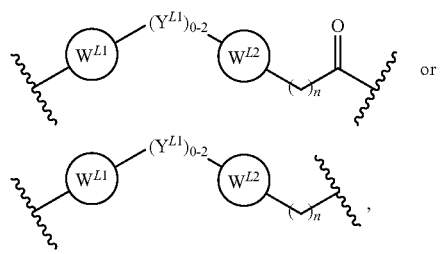

wherein:
- $W^{L1}$ and $W^{L2}$ are each independently a 4-8 membered ring with 0-4 heteroatoms, optionally substituted with $R^Q$, each $R^Q$ is independently a H, halo, OH, CN, CF$_3$, NH$_2$, carboxyl, C$_1$-C$_6$ alkyl (linear, branched, optionally substituted), C$_1$-C$_6$ alkoxy (linear, branched, optionally substituted), or 2 $R^Q$ groups taken together with the atom they are attached to, form a 4-8 membered ring system containing 0-4 heteroatoms;
- $Y^{L1}$ is each independently a bond, C$_1$-C$_6$ alkyl (linear, branched, optionally substituted) and optionally one or more C atoms are replaced with O; or C$_1$-C$_6$ alkoxy (linear, branched, optionally substituted);
- n is 0-10; and
- a dashed line indicates the attachment point to the PTM or ULM moieties.

In additional embodiments, the linker (L) comprises a structure selected from, but not limited to the structure shown below, where a dashed line indicates the attachment point to the PTM or ULM moieties.

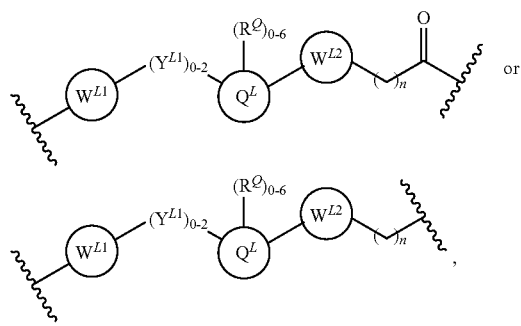

wherein:
- $W^{L1}$ and $W^{L2}$ are each independently aryl, heteroaryl, cyclic, heterocyclic, C$_{1-6}$ alkyl (linear, branched, optionally substituted), C1-C6 alkoxy (linear, branched, optionally substituted), bicyclic, biaryl, biheteroaryl, or biheterocyclic, each optionally substituted with $R^Q$, each $R^Q$ is independently a H, halo, OH, CN, CF$_3$, NH$_2$, carboxyl, hydroxyl, nitro, C≡CH, C$_{2-6}$ alkenyl, C$_{2-6}$ alkynyl, C$_1$-C$_6$ alkyl (linear, branched, optionally substituted), C$_1$-C$_6$ alkoxy (linear, branched, optionally substituted), OC$_{1-3}$alkyl (optionally substituted by 1 or more —F), OH, NH$_2$, NR$^{Y1}$R$^{Y2}$, CN, or 2 $R^Q$ groups taken together with the atom they are attached to, form a 4-8 membered ring system containing 0-4 heteroatoms;
- $Y^{L1}$ is each independently a bond, NR$^{YL1}$, O, S, NR$^{YL2}$, CR$^{YL1}$R$^{YL2}$, C═O, C═S, SO, SO$_2$, C$_1$-C$_6$ alkyl (linear, branched, optionally substituted) and optionally one or more C atoms are replaced with O; C$_1$-C$_6$ alkoxy (linear, branched, optionally substituted);
- $Q^L$ is a 3-6 membered alicyclic or aromatic ring with 0-4 heteroatoms, biheterocyclic, or bicyclic, optionally bridged, optionally substituted with 0-6 $R^Q$, each $R^Q$ is independently H, C$_{1-4}$ alkyl (linear, branched, optionally substituted by 1 or more halo, C$_{1-6}$ alkoxyl), or 2 $R^Q$ groups taken together with the atom they are attached to, form a 3-8 membered ring system containing 0-2 heteroatoms);
- R$^{YL1}$, R$^{YL2}$ are each independently H, OH, C$_{1-6}$ alkyl (linear, branched, optionally substituted by 1 or more halo, C$_{1-6}$ alkoxyl), or R$^1$, R$^2$ together with the atom they are attached to, form a 3-8 membered ring system containing 0-2 heteroatoms);
- n is 0-10; and
- a dashed line indicates the attachment point to the PTM or ULM moieties.

In additional embodiments, the linker group is optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any of the embodiments of the compounds described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

In another embodiment, the present disclosure is directed to a compound which comprises a PTM group as described above, which binds to a target protein (e.g., ER) or polypeptide, which is ubiquitinated by an ubiquitin ligase and is chemically linked directly to the ULM group or through a linker moiety L, or PTM is alternatively a ULM' group which is also an E3 ubiquitin ligase binding moiety, which may be the same or different than the ULM group as described above and is linked directly to the ULM group directly or through the linker moiety; and L is a linker moiety as described above which may be present or absent and which chemically (covalently) links ULM to PTM, or a pharmaceutically acceptable salt, enantiomer, stereoisomer, solvate or polymorph thereof.

In certain embodiments, the linker group L is a group comprising one or more covalently connected structural units independently selected from the group consisting of:

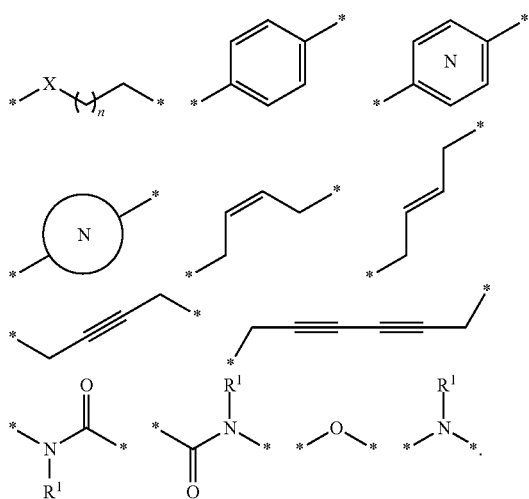

The X is selected from the group consisting of O, N, S, S(O) and $SO_2$; n is integer from 1 to 5; $R^{Z1}$ is hydrogen or alkyl,

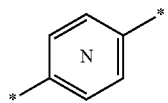

is a mono- or bicyclic aryl or heteroaryl optionally substituted with 1-3 substituents selected from alkyl, halogen, haloalkyl, hydroxy, alkoxy or cyano

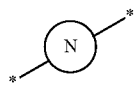

is a mono- or bicyclic cycloalkyl or a heterocycloalkyl optionally substituted with 1-3 substituents selected from alkyl, halogen, haloalkyl, hydroxy, alkoxy or cyano; and the phenyl ring fragment can be optionally substituted with 1, 2 or 3 substituents selected from the group consisting of alkyl, halogen, haloalkyl, hydroxy, alkoxy and cyano. In an embodiment, the linker group L comprises up to 10 covalently connected structural units, as described above.

Although the ULM group and PTM group may be covalently linked to the linker group through any group which is appropriate and stable to the chemistry of the linker, in preferred aspects of the present disclosure, the linker is independently covalently bonded to the ULM group and the PTM group preferably through an amide, ester, thioester, keto group, carbamate (urethane), carbon or ether, each of which groups may be inserted anywhere on the ULM group and PTM group to provide maximum binding of the ULM group on the ubiquitin ligase and the PTM group on the target protein to be degraded. (It is noted that in certain aspects where the PTM group is a ULM group, the target protein for degradation may be the ubiquitin ligase itself). In certain preferred aspects, the linker may be linked to an optionally substituted alkyl, alkylene, alkene or alkyne group, an aryl group or a heterocyclic group on the ULM and/or PTM groups.

Exemplary PTMs

In preferred aspects of the disclosure, the PTM group is a group, which binds to target proteins. Targets of the PTM group are numerous in kind and are selected from proteins that are expressed in a cell such that at least a portion of the sequences is found in the cell and may bind to a PTM group. The term "protein" includes oligopeptides and polypeptide sequences of sufficient length that they can bind to a PTM group according to the present disclosure. Any protein in a eukaryotic system or a microbial system, including a virus, bacteria or fungus, as otherwise described herein, are targets for ubiquitination mediated by the compounds according to the present disclosure. Preferably, the target protein is a eukaryotic protein.

PTM groups according to the present disclosure include, for example, any moiety which binds to a protein specifically (binds to a target protein) and includes the following non-limiting examples of small molecule target protein moieties: Hsp90 inhibitors, kinase inhibitors, HDM2 & MDM2 inhibitors, compounds targeting Human BET Bromodomain-containing proteins, HDAC inhibitors, human lysine methyltransferase inhibitors, angiogenesis inhibitors, nuclear hormone receptor compounds, immunosuppressive compounds, and compounds targeting the aryl hydrocarbon receptor (AHR), among numerous others. The compositions described below exemplify some of the members of small molecule target protein binding moieties. Such small molecule target protein binding moieties also include pharmaceutically acceptable salts, enantiomers, solvates and polymorphs of these compositions, as well as other small molecules that may target a protein of interest. These binding moieties are linked to the ubiquitin ligase binding moiety preferably through a linker in order to present a target protein (to which the protein target moiety is bound) in proximity to the ubiquitin ligase for ubiquitination and degradation.

Any protein, which can bind to a protein target moiety or PTM group and acted on or degraded by an ubiquitin ligase is a target protein according to the present disclosure. In general, target proteins may include, for example, structural proteins, receptors, enzymes, cell surface proteins, proteins pertinent to the integrated function of a cell, including proteins involved in catalytic activity, aromatase activity, motor activity, helicase activity, metabolic processes (anabolism and catabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eukaryotes and prokaryotes including humans as targets for drug therapy, other animals, including domesticated animals, microbials for the determination of targets for antibiotics and other antimicrobials and plants, and even viruses, among numerous others.

The present disclosure may be used to treat a number of disease states and/or conditions, including any disease state and/or condition in which proteins are dysregulated and where a patient would benefit from the degradation and/or inhibition of proteins.

In an additional aspect, the description provides therapeutic compositions comprising an effective amount of a compound as described herein or salt form thereof, and a pharmaceutically acceptable carrier, additive or excipient, and optionally an additional bioactive agent. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer. In certain additional embodiments, the disease is breast cancer. In certain additional embodiments, the disease is at least one of breast cancer, uterine cancer, ovarian cancer, prostate cancer, endometrial cancer, endometriosis, or a combination thereof.

In alternative aspects, the present disclosure relates to a method for treating a disease state or ameliorating the symptoms of a disease or condition in a subject in need thereof by degrading a protein or polypeptide through which a disease state or condition is modulated comprising administering to said patient or subject an effective amount, e.g., a therapeutically effective amount, of at least one compound as described hereinabove, optionally in combination with a pharmaceutically acceptable carrier, additive or excipient, and optionally an additional bioactive agent, wherein the composition is effective for treating or ameliorating the disease or disorder or symptom thereof in the subject. The method according to the present disclosure may be used to treat a large number of disease states or conditions including cancer, by virtue of the administration of effective amounts of at least one compound described herein. The disease state or condition may be a disease caused by a microbial agent or other exogenous agent such as a virus, bacteria, fungus, protozoa or other microbe or may be a disease state, which is caused by overexpression of a protein, which leads to a disease state and/or condition.

In another aspect, the description provides methods for identifying the effects of the degradation of proteins of interest in a biological system using compounds according to the present disclosure.

The term "target protein" is used to describe a protein or polypeptide, which is a target for binding to a compound according to the present disclosure and degradation by ubiquitin ligase hereunder. Such small molecule target protein binding moieties also include pharmaceutically acceptable salts, enantiomers, solvates and polymorphs of these compositions, as well as other small molecules that may target a protein of interest. These binding moieties are linked to at least one ULM group (e.g. VLM, CLM, ILM, and/or MLM) through at least one linker group L.

Target proteins, which may be bound to the protein target moiety and degraded by the ligase to which the ubiquitin ligase binding moiety is bound, include any protein or peptide, including fragments thereof, analogues thereof, and/or homologues thereof. Target proteins include proteins and peptides having any biological function or activity including structural, regulatory, hormonal, enzymatic, genetic, immunological, contractile, storage, transportation, and signal transduction. More specifically, a number of drug targets for human therapeutics represent protein targets to which protein target moiety may be bound and incorporated into compounds according to the present disclosure. These include proteins which may be used to restore function in numerous polygenic diseases, including for example B7.1 and B7, TINFR1m, TNFR2, NADPH oxidase, BcIIBax and other partners in the apotosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuramimidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-alphaR, ICAMI, Cat+ channels, VCAM, VLA-4 integrin, selectins, CD40/CD40L, newokinins and receptors, inosine monophosphate dehydrogenase, p38 MAP Kinase, RaslRaflMEWERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors, adenosine receptors, adenosine kinase and AMP deaminase, purinergic receptors (P2Y1, P2Y2, P2Y4, P2Y6, P2XI-7), famesyl-transferases, geranylgeranyl transferase, TrkA a receptor for NGF, beta-amyloid, tyrosine kinase Flk-IIKDR, vitronectin receptor, integrin receptor, Her-21 neu, telomerase inhibition, cytosolic phospholipaseA2 and EGF receptor tyrosine kinase. Additional protein targets include, for example, ecdysone 20-monooxygenase, ion channel of the GABA gated chloride channel, acetylcholinesterase, voltage-sensitive sodium channel protein, calcium release channel, and chloride channels. Still further target proteins include Acetyl-CoA carboxylase, adenylosuccinate synthetase, protoporphyrinogen oxidase, and enolpyruvylshikimate-phosphate synthase.

These various protein targets may be used in screens that identify compound moieties which bind to the protein and by incorporation of the moiety into compounds according to the present disclosure, the level of activity of the protein may be altered for therapeutic end result.

The term "protein target moiety" or PTM is used to describe a small molecule which binds to a target protein or other protein or polypeptide of interest and places/presents that protein or polypeptide in proximity to an ubiquitin ligase such that degradation of the protein or polypeptide by ubiquitin ligase may occur. Non-limiting examples of small molecule target protein binding moieties include Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR), among numerous others. The compositions described below exemplify some of the members of the small molecule target proteins.

Exemplary protein target moieties according to the present disclosure include, haloalkane halogenase inhibitors, Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR).

The compositions described herein exemplify some of the members of these types of small molecule target protein binding moieties. Such small molecule target protein binding moieties also include pharmaceutically acceptable salts, enantiomers, solvates and polymorphs of these compositions, as well as other small molecules that may target a protein of interest. References which are cited herein below are incorporated by reference herein in their entirety.

In another aspect, the present disclosure provides a compound or PTM of Formula ($I_{PTM}$):

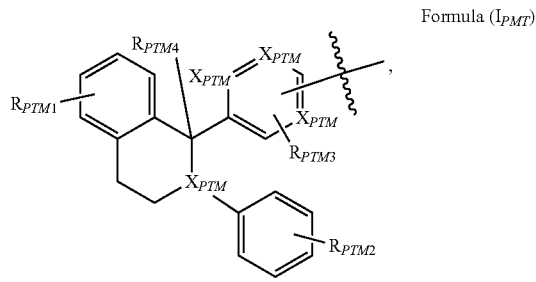

Formula ($I_{PMT}$)

wherein:
each $X_{PTM}$ is independently CH, N;

⸺ indicates the site of attachment of at least one linker, VLM, VLM', CLM, CLM', ILM, ILM', VLM, PTM, PTM', or a combination thereof;
each $R_{PTM1}$ is independently OH, halogen, O(CO)$R_{PTM}$, where $R_{PTM}$ is alkyl or cycloalkyl group with 1 to 6 carbons or aryl groups, substitution can be mono-, di- or tri-substituted; each $R_{PTM2}$ is independently H, halogen, CN, CF$_3$, alkoxy, substitution can be mono- or di-substitution; and
each $R_{PTM3}$ is independently H, halogen, substitution can be mono- or di-substitution.

In any aspect or embodiment described herein, the PTM is represented by the Formula ($II_{PTM}$):

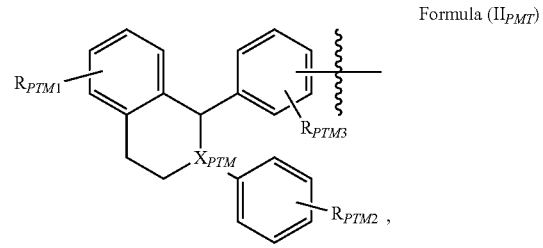

Formula ($II_{PMT}$)

wherein:
$X_{PTM}$ is CH, N;

⸺ indicates the site of attachment of at least one linker, VLM, VLM', CLM, CLM', ILM, ILM', VLM, PTM, PTM', or a combination thereof;
each $R_{PTM1}$ is independently OH, halogen (e.g., F);
each $R_{PTM2}$ is independently H, halogen (e.g., F), CF$_3$. substitution can be mono- or di-substitution; and
each $R_{PTM3}$ is independently halogen (e.g. F), substitution can be mono- or di-substitution.

In certain embodiments, at least one of L
$X_{PTM}$ of Formula ($II_{PTM}$) is CH;
$R_{PTM1}$ of Formula ($II_{PTM}$) is OH;
$R_{PTM2}$ of Formula ($II_{PTM}$) is H;
each $R_{PTM3}$ of Formula ($II_{PTM}$) is independently H or F; or
a combination thereof.

Exemplary ER PROTACs

The present disclosure identifies compounds that are capable of inhibiting estrogen receptor function, including compounds which degrade the estrogen receptor.

As described above, in any aspect or embodiment described herein, the present disclosure provides bifunctional PROTAC compounds comprising: at least one of a tetrahydronaphthalene group, a tetrahydroisoquinoline group, or a combination thereof; a linker, and at least one of a VHL binding ligand, cereblon binding ligand, or a combination thereof.

In any aspect or embodiment described herein, the compound is selected from the group consisting of compounds 1-547 (as shown in Tables 1 and 2), and salts and polymorphs thereof.

Therapeutic Compositions

Pharmaceutical compositions comprising combinations of an effective amount of at least one bifunctional compound as described herein, and one or more of the compounds otherwise described herein, all in effective amounts, in combination with a pharmaceutically effective amount of a carrier, additive or excipient, represents a further aspect of the present disclosure.

The present disclosure includes, where applicable, the compositions comprising the pharmaceutically acceptable salts, in particular, acid or base addition salts of compounds as described herein. The acids which are used to prepare the pharmaceutically acceptable acid addition salts of the aforementioned base compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

The compounds as described herein may, in accordance with the disclosure, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein, optionally in combination with a pharmaceutically acceptable carrier, additive or excipient. Compounds according to the present disclosure may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions as described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. In certain preferred aspects of the disclosure, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition as described herein that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present disclosure.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present disclosure including pharmaceutically acceptable salts, solvates or polymorphs, thereof optionally in a pharmaceutically acceptable carrier or diluent, either alone, or in combination with other known therapeutic agents as otherwise identified herein.

These compounds can be administered by any appropriate route, for example, orally, parenterally, intravenously, intradermally, subcutaneously, or topically, including transdermally, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 µM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its pro-drug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as anti-cancer agents, among others. In certain preferred aspects of the disclosure, one or more compounds according to the present disclosure are coadministered with another bioactive agent, such as an anti-cancer agent or a would healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Therapeutic Methods

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer and/or endometriosis, which may be treated using compounds according to the present disclosure are set forth hereinabove.

The description provides therapeutic compositions as described herein for effectuating the degradation of proteins of interest for the treatment or amelioration of a disease, e.g., cancer. In certain additional embodiments, the disease is breast cancer, uterine cancer, ovarian cancer, endometrial cancer, endometriosis, neurodegenerative disease, inflammatory disease (e.g., lupus erythematosus), an autoimmune disease (e.g., lupus erythematosus), or a combination thereof. As such, in another aspect, the description provides a method of ubiquitinating/degrading a target protein in a cell. In certain embodiments, the method comprises administering a bifunctional compound as described herein comprising, e.g., a ULM and a PTM, preferably linked through a linker moiety, as otherwise described herein, wherein the ULM is coupled to the PTM and wherein the ULM recognizes a ubiquitin pathway protein (e.g., an ubiquitin ligase, such as an E3 ubiquitin ligase including cereblon, VHL, IAP, and/or MDM2) and the PTM recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cell, e.g., cell of a patient. In certain embodiments, the method comprises administering an effective amount of a compound as described herein, optionally including a pharmaceutically acceptable excipient, carrier, adjuvant, another bioactive agent or combination thereof.

In additional embodiments, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

In another aspect, the description provides methods for identifying the effects of the degradation of proteins of interest in a biological system using compounds according to the present disclosure.

In another embodiment, the present disclosure is directed to a method of treating a human patient in need for a disease state or condition modulated through a protein where the degradation of that protein will produce a therapeutic effect in the patient, the method comprising administering to a patient in need an effective amount of a compound according to the present disclosure, optionally in combination with another bioactive agent. The disease state or condition may be a disease caused by a microbial agent or other exogenous agent such as a virus, bacteria, fungus, protozoa or other microbe or may be a disease state, which is caused by overexpression of a protein (e.g., ER), which leads to a disease state and/or condition The term "disease state or condition" is used to describe any disease state or condition wherein protein dysregulation (i.e., the amount of ER expressed in a patient is elevated) occurs and where degradation of one or more proteins in a patient may provide beneficial therapy or relief of symptoms to a patient in need thereof. In certain instances, the disease state or condition may be cured.

Disease states or conditions which may be treated using compounds according to the present disclosure include, for example, asthma, autoimmune diseases such as multiple sclerosis, various cancers, diabetes, heart disease, hypertension, inflammatory bowel disease, endometreosis, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, endometrial, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, glioblastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present disclosure include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

The term "bioactive agent" is used to describe an agent, other than a compound according to the present disclosure, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

The term "additional anti-cancer agent" is used to describe an anti-cancer agent, which may be combined with compounds according to the present disclosure to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a P13 kinase inhibitor, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-1-TM-601, ALT-110, BIO 140, CC 8490, cilengitide, gimatecan, IL13-PE38QQR, INO 1001, IPdR$_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-IC11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS- 247550, BMS-310705, droloxifene, 4-hydroxytamoxifen, pipendoxifene, ERA-923, arzoxifene, fulvestrant, acolbifene, lasofoxifene, idoxifene, TSE-424, HMR- 3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "anti-HIV agent" or "additional anti-HIV agent" includes, for example, nucleoside reverse transcriptase inhibitors (NRTI), other non-nucloeoside reverse transcriptase inhibitors (i.e., those which are not representative of the present disclosure), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used in coadministration with compounds according to the present disclosure include, for example, other NNRTI's (i.e., other than the NNRTI's according to the present disclosure) may be selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furancarbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis (methoxycarbonyl)-6,6-diphenylhexenoate), Methyl 3-Bromo-5-(1-5-bromo-4-methoxy-3-(methoxycarbonyl) phenyl)hept-1-enyl)-2-methoxybenzoate (Alkenyldiarylmethane analog, Adam analog), (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-cyano-2-indolyl)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl] piperazine, 1-[3-(Ethylamino)-2-[pyridinyl]-4-[(5-hydroxy-2-indolyl)carbonyl]piperazine, 1-[(6-Formyl-2-indolyl) carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S (1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl)]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4,7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+XR)-9b-(3,5-Dimethylphenyl-2,3-dihydrothiazolo[2,3-a]isoindol-5(9bH)-one, Tivirapine (R86183), UC-38 and UC-84, among others.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

General Synthetic Approach

The synthetic realization and optimization of the bifunctional molecules as described herein may be approached in a step-wise or modular fashion. For example, identification of compounds that bind to the target molecules can involve high or medium throughput screening campaigns if no suitable ligands are immediately available. It is not unusual for initial ligands to require iterative design and optimization cycles to improve suboptimal aspects as identified by data from suitable in vitro and pharmacological and/or ADMET assays. Part of the optimization/SAR campaign would be to probe positions of the ligand that are tolerant of substitution and that might be suitable places on which to attach the linker chemistry previously referred to herein. Where crystallographic or NMR structural data are available, these can be used to focus such a synthetic effort.

In a very analogous way one can identify and optimize ligands for an E3 Ligase, i.e. ULMs/ILMs/VLMs/CLMs/ILMs.

With PTMs and ULMs (e.g. ILMs, VLMs, CLMs, and/or ILMs) in hand, one skilled in the art can use known synthetic methods for their combination with or without a linker moiety. Linker moieties can be synthesized with a range of compositions, lengths and flexibility and functionalized such that the PTM and ULM groups can be attached sequentially to distal ends of the linker. Thus a library of bifunctional molecules can be realized and profiled in in vitro and in vivo pharmacological and ADMET/PK studies. As with the PTM and ULM groups, the final bifunctional molecules can be subject to iterative design and optimization cycles in order to identify molecules with desirable properties.

In some instances, protecting group strategies and/or functional group interconversions (FGIs) may be required to facilitate the preparation of the desired materials. Such chemical processes are well known to the synthetic organic chemist and many of these may be found in texts such as "Greene's Protective Groups in Organic Synthesis" Peter G. M. Wuts and Theodora W. Greene (Wiley), and "Organic Synthesis: The Disconnection Approach" Stuart Warren and Paul Wyatt (Wiley).

Protein Level Control

This description also provides methods for the control of protein levels with a cell. This is based on the use of compounds as described herein, which are known to interact with a specific target protein such that degradation of a target protein in vivo will result in the control of the amount of protein in a biological system, preferably to a particular therapeutic benefit.

The following examples are used to assist in describing the present disclosure, but should not be seen as limiting the present disclosure in any way.

Specific Embodiments of the Present Disclosure

The present disclosure encompasses the following specific embodiments. These following embodiments may include all of the features recited in a proceeding embodiment, as specified. Where applicable, the following embodiments may also include the features recited in any proceeding embodiment inclusively or in the alternative (e.g., an eighth embodiment may include the features recited in a first embodiment, as recited, and/or the features of any of the second through seventh embodiments).

In certain embodiments, the description provides the following exemplary ER PROTAC molecules (such as the compounds in Tables 1 and 2, e.g., Compounds 1-547), including salts, prodrugs, polymorphs, analogs, derivatives, and deuterated forms thereof.

An aspect of the present disclosure provides a bifunctional compound having the chemical structure:

ULM-L-PTM, or a pharmaceutically acceptable salt, enantiomer, stereoisomer, solvate, polymorph or prodrug thereof, wherein:
the ULM is a small molecule E3 ubiquitin ligase binding moiety that binds an E3 ubiquitin ligase; the L is a bond or a chemical linking moiety connecting the ULM and the PTM; and the PTM is an estrogen receptor protein targeting moiety represented by the chemical structure:

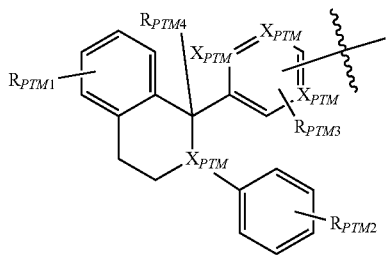

Formula (I$_{PTM}$)

or

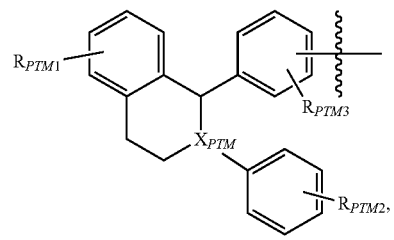

Formula (II$_{PTM}$)

wherein:
each $X_{PTM}$ is independently CH, N;

$\xi$ indicates the site of attachment of at least one of the linker, the ULM, a ULM', a PTM', or a combination thereof;

each $R_{PTM1}$ is independently OH, halogen, alkoxy, methoxy, ethoxy, O(CO)R$_{PTM}$, wherein the substitution can be a mono-, di- or tri-substitution and R$_{PTM}$ is alkyl or cycloalkyl group with 1 to 6 carbons or aryl groups;

each $R_{PTM2}$ is independently H, halogen, CN, CF$_3$, linear or branched alkyl (e.g., linear or branched C1-C4 alkyl), alkoxy, methoxy, ethoxy, wherein the substitution can be mono- or di-substitution;

each $R_{PTM3}$ is independently H, halogen, wherein the substitution can be mono- or di-substitution; and $R_{PTM4}$ is a H, alkyl, methyl, ethyl.

In any aspect or embodiment described herein, the E3 ubiquitin ligase binding moiety that targets an E3 ubiquitin ligase selected from the group consisting of Von Hippel-Lindau (VLM), cereblon (CLM), mouse double-minute homolog2 (MLM), and IAP (ILM).

In any aspect or embodiment described herein, the ULM is a Von Hippel-Lindau (VHL) ligase-binding moiety (VLM) with a chemical structure represented by:

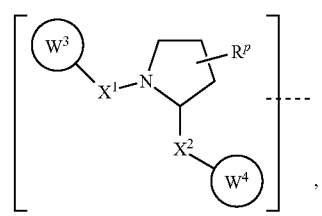

wherein:
$X^1$, $X^2$ are each independently selected from the group of a bond, O, NR$^{Y3}$, CR$^{Y3}$R$^{Y4}$, C=O, C=S, SO, and SO$_2$;

$R^{Y3}$, $R^{Y4}$ are each independently selected from the group of H, linear or branched C$_{1-6}$ alkyl, optionally substituted by 1 or more halo, optionally substituted C$_{1-6}$ alkoxyl (e.g., optionally substituted by 0-3 R$^P$ groups);

$R^P$ is 0, 1, 2, or 3 groups each independently selected from the group H, halo, —OH, C$_{1-3}$ alkyl, C=O;

W$^3$ is selected from the group of an optionally substituted -T-N(R$^{1a}$R$^{1b}$)X$^3$, -T-N(R$^{1a}$R$^{1b}$), -T-Aryl, an optionally substituted -T-Heteroaryl, an optionally substituted -T-Heterocycle, an optionally substituted —NR$^1$-T-Aryl, an optionally substituted —NR$^1$-T-Heteroaryl or an optionally substituted —NR$^1$-T-Heterocycle;

X$^3$ is C=O, R$^1$, R$^{1a}$, R$^{1b}$;

each of $R^1$, $R^{1a}$, $R^{1b}$ us independently selected from the group consisting of H, linear or branched $C_1$-$C_6$ alkyl group optionally substituted by 1 or more halo or —OH groups, $R^{Y3}C=O$, $R^{Y3}C=S$, $R^{Y3}SO$, $R^{Y3}SO_2$, $N(R^{Y3}R^{Y4})C=O$, $N(R^{Y3}R^{Y4})C=S$, $N(R^{Y3}R^{Y4})SO$, and $N(R^{Y3}R^{Y4})SO_2$;

T is selected from the group of an optionally substituted alkyl, —(CH$_2$)$_n$— group, wherein each one of the methylene groups is optionally substituted with one or two substituents selected from the group of halogen, methyl, a linear or branched $C_1$-$C_6$ alkyl group optionally substituted by 1 or more halogen or —OH groups or an amino acid side chain optionally substituted; and n is 0 to 6, $W^4$ is

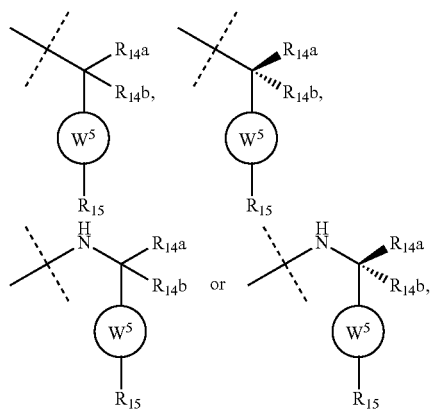

$R_{14a}$, $R_{14b}$, are each independently selected from the group of H, haloalkyl, or optionally substituted alkyl;

$W^5$ is selected from the group of a phenyl or a 5-10 membered heteroaryl, $R_{15}$ is selected from the group of H, halogen, CN, OH, NO$_2$, N $R_{14a}R_{14b}$, $OR_{14a}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy; aryl, heteroaryl, cycloalkyl, or cycloheteroalkyl;

and wherein the dashed line indicates the site of attachment of at least one PTM, another ULM (ULM') or a chemical linker moiety coupling at least one PTM or a ULM' or both to ULM.

In any aspect or embodiment described herein, the ULM is a Von Hippel-Lindau (VHL) ligase-binding moiety (VLM) with a chemical structure represented by:

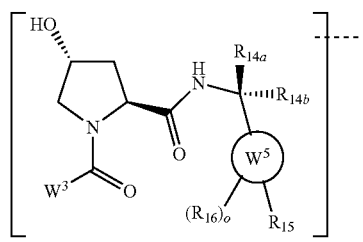

wherein:

$W^3$ is selected from the group of an optionally substituted aryl, optionally substituted heteroaryl, or

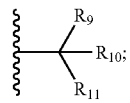

$R_9$ and $R_{10}$ are independently hydrogen, optionally substituted alkyl, optionally substituted cycloalkyl, optionally substituted hydroxyalkyl, optionally substituted heteroaryl, or haloalkyl, or $R_9$, $R_{10}$, and the carbon atom to which they are attached form an optionally substituted cycloalkyl;

$R_{11}$ is selected from the group of an optionally substituted heterocyclic, optionally substituted alkoxy, optionally substituted heteroaryl, optionally substituted aryl,

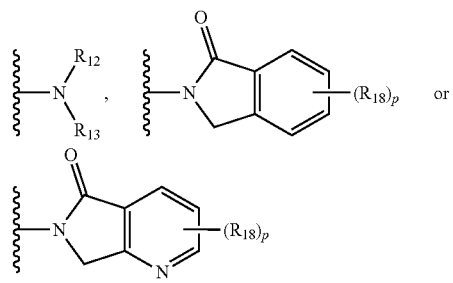

$R_{12}$ is selected from the group of H or optionally substituted alkyl;

$R_{13}$ is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

$R_{14a}$, $R_{14b}$. are each independently selected from the group of H, haloalkyl, or optionally substituted alkyl;

$W^5$ is selected from the group of a phenyl or a 5-10 membered heteroaryl, $R_{15}$ is selected from the group of H, halogen, CN, OH, NO$_2$, N $R_{14a}R_{14b}$, $OR_{14a}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy; aryl, heteroaryl, cycloalkyl, or cycloheteroalkyl, each optionally substituted;

$R_{16}$ is independently selected from the group of H, halo, optionally substituted alkyl, optionally substituted haloalkyl, hydroxy, or optionally substituted haloalkoxy;

o is 0, 1, 2, 3, or 4;

$R_{18}$ is independently selected from the group of halo, optionally substituted alkoxy, cyano, optionally substituted alkyl, haloalkyl, haloalkoxy or a linker, and p is 0, 1, 2, 3, or 4, and wherein the dashed line indicates the site of attachment of at least one PTM, another ULM (ULM') or a chemical linker moiety coupling at least one PTM or a ULM' or both to ULM.

In any aspect or embodiment described herein, the ULM has a chemical structure selected from the group of:

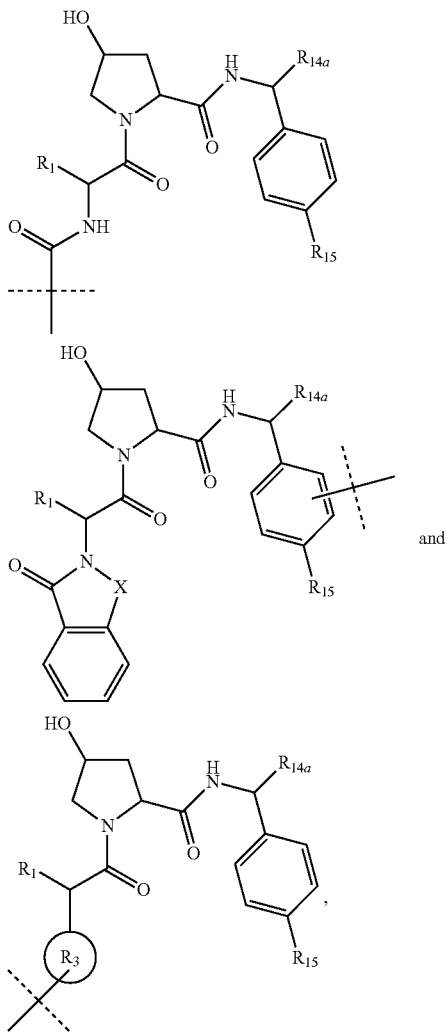

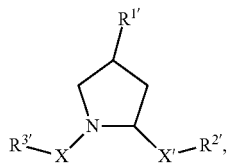

ULM-g wherein:

R¹' of ULM-g is an optionally substituted $C_1$-$C_6$ alkyl group, an optionally substituted —$(CH_2)_n$OH, an optionally substituted —$(CH_2)_n$SH, an optionally substituted $(CH_2)_n$—O—($C_1$-$C_6$)alkyl group, an optionally substituted $(CH_2)_n$—WCOCW-($C_0$-$C_6$)alkyl group containing an epoxide moiety WCOCW where each W is independently H or a $C_1$-$C_3$ alkyl group, an optionally substituted —$(CH_2)_n$COOH, an optionally substituted —$(CH_2)_n$C(O)—($C_1$-$C_6$ alkyl), an optionally substituted —$(CH_2)_n$NHC(O)—$R_1$, an optionally substituted —$(CH_2)_n$C(O)—$NR_1R_2$, an optionally substituted —$(CH_2)_n$OC(O)—$NR_1R_2$, —$(CH_2O)_n$H, an optionally substituted —$(CH_2)_n$OC(O)—($C_1$-$C_6$ alkyl), an optionally substituted —$(CH_2)_n$C(O)—O—($C_1$-$C_6$ alkyl), an optionally substituted —$(CH_2O)_n$COOH, an optionally substituted —$(OCH_2)_n$O—($C_1$-$C_6$ alkyl), an optionally substituted —$(CH_2O)_n$C(O)—($C_1$-$C_6$ alkyl), an optionally substituted —$(OCH_2)_n$NHC(O)—$R_1$, an optionally substituted —$(CH_2O)_n$C(O)—$NR_1R_2$, —$(CH_2CH_2O)_n$H, an optionally substituted —$(CH_2CH_2O)_n$COOH, an optionally substituted —$(OCH_2CH_2)_n$O—($C_1$-$C_6$ alkyl), an optionally substituted —$(CH_2CH_2O)_n$C(O)—($C_1$-$C_6$ alkyl), an optionally substituted —$(OCH_2CH_2)_n$NHC(O)—$R_1$, an optionally substituted —$(CH_2CH_2O)_n$C(O)—$NR_1R_2$, an optionally substituted —$SO_2R_S$, an optionally substituted $S(O)R_S$, $NO_2$, CN or halogen (F, Cl, Br, I, preferably F or Cl);

$R_1$ and $R_2$ of ULM-g are each independently H or a $C_1$-$C_6$ alkyl group which may be optionally substituted with one or two hydroxyl groups or up to three halogen groups (preferably fluorine);

$R_S$ of ULM-g is a $C_1$-$C_6$ alkyl group, an optionally substituted aryl, heteroaryl or heterocycle group or a —$(CH_2)_nNR_1R_2$ group;

X and X' of ULM-g are each independently C=O, C=S, —S(O), $S(O)_2$, (preferably X and X' are both C=O);

R²' of ULM-g is an optionally substituted —$(CH_2)_n$—$(C=O)_u(NR_1)_v(SO_2)_w$alkyl group, an optionally substituted —$(CH_2)_n$—$(C=O)_u(NR_1)_v(SO_2)_wNR_{1N}R_{2N}$ group, an optionally substituted $(CH_2)_n$—$(C=O)_u(NR_1)_v(SO_2)_w$-Aryl, an optionally substituted —$(CH_2)_n$—$(C=O)_u(NR_1)_v(SO_2)_w$-Heteroaryl, an optionally substituted —$(CH_2)_n$—$(C=O)_vNR_1(SO_2)_w$-Heterocycle, an optionally substituted —$NR^1$—$(CH_2)_n$—$C(O)_u(NR_1)_v(SO_2)_w$-alkyl, an optionally substituted —$NR^1$—$(CH_2)_n$—$C(O)_u(NR_1)_v(SO_2)_w$—$NR_{1N}R_{2N}$, an optionally substituted —$NR^1$—$(CH_2)_n$—$C(O)_u(NR_1)_v(SO_2)_w$—$NR_1C(O)R_{1N}$, an optionally substituted —$NR^1$—$(CH_2)$—$(C=O)_u(NR_1)_v(SO_2)_w$-Aryl, an optionally substituted —$NR^1$—$(CH_2)_n$—$(C=O)_u(NR_1)_v(SO_2)_w$-Heteroaryl or an optionally substituted —$NR^1$—$(CH_2)_n$—$(C=O)_vNR_1(SO_2)_w$-Heterocycle, an optionally substituted —$X^{R2'}$-alkyl group; an optionally substituted —$X^{R2'}$-Aryl group; an wherein:

$R_1$ is H, ethyl, isopropyl, tert-butyl, sec-butyl, cyclopropyl, cyclobutyl, cyclopentyl, or cyclohexyl; optionally substituted alkyl, optionally substituted hydroxyalkyl, optionally substituted heteroaryl, or haloalkyl;

$R_{14a}$ is H, haloalkyl, optionally substituted alkyl, methyl, fluoromethyl, hydroxymethyl, ethyl, isopropyl, or cyclopropyl;

$R_{15}$ is selected from the group consisting of H, halogen, CN, OH, $NO_2$. optionally substituted heteroaryl, optionally substituted aryl; optionally substituted alkyl, optionally substituted haloalkyl, optionally substituted haloalkoxy, cycloalkyl, or cycloheteroalkyl;

X is C, $CH_2$, or C=O $R_3$ is absent or an optionally substituted 5 or 6 membered heteroaryl; and wherein the dashed line indicates the site of attachment of at least one PTM, another ULM (ULM') or a chemical linker moiety coupling at least one PTM or a ULM' or both to the ULM.

In any aspect or embodiment described herein, the ULM comprises a group according to the chemical structure:

optionally substituted —X$^{R2'}$-Heteroaryl group; an optionally substituted —X$^{R2'}$ Heterocycle group; an optionally substituted;

R$^{3'}$ of ULM-g is an optionally substituted alkyl, an optionally substituted —(CH$_2$)$_n$—(O)$_u$(NR$_1$)$_v$(SO$_2$)$_w$-alkyl, an optionally substituted —(CH$_2$)$_n$—C(O)$_u$(NR$_1$)$_v$(SO$_2$)$_w$—NR$_{1N}$R$_{2N}$, an optionally substituted —(CH$_2$)$_n$—C(O)$_u$(NR$_1$)$_v$(SO$_2$)$_w$—NR$_1$C(O)R$_{1N}$, an optionally substituted —(CH$_2$)$_n$—C(O)$_u$(NR$_1$)$_v$(SO)$_w$—C(O)NR$_1$R$_2$, an optionally substituted —(CH$_2$)$_n$—C(O)$_u$(NR$_1$)$_v$(SO$_2$)$_w$-Aryl, an optionally substituted —(CH$_2$)$_n$—C(O)$_u$(NR$_1$)$_v$(SO$_2$)$_w$-Heteroaryl, an optionally substituted —(CH$_2$)$_n$—C(O)$_u$(NR$_1$)$_v$(SO$_2$)$_w$-Heterocycle, an optionally substituted —NR$^1$—(CH$_2$)$_n$—C(O)$_u$(NR$_1$)$_v$(SO$_2$)$_w$-alkyl, an optionally substituted —NR$^1$—(CH$_2$)$_n$—C(O)$_u$(NR$_1$)$_v$(SO$_2$)$_w$—NR$_{1N}$R$_{2N}$, an optionally substituted —NR$^1$—(CH$_2$)$_n$—C(O)$_u$(NR$_1$)$_v$(SO$_2$)$_w$—NR$_1$C(O)R$_{1N}$, an optionally substituted —NR$^1$—(CH$_2$)$_n$—C(O)$_u$(NR$_1$)SO$_2$)$_w$-Aryl, an optionally substituted —NR$^1$—(CH$_2$)$_n$—C(O)$_u$(NR$_1$)$_v$(SO$_2$)$_w$-Heteroaryl, an optionally substituted —NR$^1$—(CH$_2$)$_n$—C(O)$_u$(NR$_1$)$_v$(SO$_2$)$_w$-Heterocycle, an optionally substituted —O—(CH$_2$)$_n$—(C=O)$_u$(NR$_1$)$_v$(SO$_2$)$_w$-alkyl, an optionally substituted —O—(CH$_2$)n-(C=O)$_u$(NR$_1$)$_v$(SO$_2$)$_w$—NR$_{1N}$R$_{2N}$, an optionally substituted —O—(CH$_2$)n-(C=O)$_u$(NR$_1$)$_v$(SO$_2$)$_w$—NR$_1$C(O)R$_{1N}$, an optionally substituted —O—(CH$_2$)n-(C=O)$_u$(NR$_1$)$_v$(SO$_2$)$_w$-Aryl, an optionally substituted —O—(CH$_2$)$_n$—(C=O)$_u$(NR$_1$)$_v$(SO$_2$)$_w$-Heteroaryl or an optionally substituted —O—(CH$_2$)$_n$—(C=O)$_u$(NR$_1$)$_v$(SO$_2$)$_w$-Heterocycle; —(CH$_2$)$_n$—(V)$_{n'}$—(CH$_2$)$_n$—(V)$_{n'}$-alkyl group, an optionally substituted —(CH$_2$)$_n$—(V)$_{n'}$—(CH$_2$)$_n$—(V)$_{n'}$-Aryl group, an optionally substituted —(CH$_2$)$_n$—(V)$_{n'}$—(CH$_2$)$_n$—(V)$_{n'}$-Heteroaryl group, an optionally substituted —(CH$_2$)$_n$—(V)$_{n'}$—(CH$_2$)$_n$—(V)$_{n'}$-Heterocycle group, an optionally substituted —(CH$_2$)$_n$—N(R$_{1'}$)(C=O)$_{m'}$—(V)$_{n'}$-alkyl group, an optionally substituted —(CH$_2$)$_n$—N(R$_{1'}$)(C=O)$_{n'}$—(V)$_{n'}$-Aryl group, an optionally substituted —(CH$_2$)$_n$—N(R$_{1'}$)(C=O)$_{m'}$—(V)$_{n'}$-Heteroaryl group, an optionally substituted —(CH$_2$)$_n$—N(R$_{1'}$)(C=O)$_{m'}$—(V)$_{n'}$-Heterocycle group, an optionally substituted —X$^{R3'}$-alkyl group; an optionally substituted —X$^{R3'}$-Aryl group; an optionally substituted —X$^{R3'}$-Heteroaryl group; an optionally substituted —X$^{R3'}$-Heterocycle group; an optionally substituted;

R$_{1N}$ and R$_{2N}$ of ULM-g are each independently H, C$_1$-C$_6$ alkyl which is optionally substituted with one or two hydroxyl groups and up to three halogen groups or an optionally substituted —(CH$_2$)$_n$-Aryl, —(CH$_2$)$_n$-Heteroaryl or —(CH$_2$)$_n$-Heterocycle group;

V of ULM-g is O, S or NR$_1$;

R$_1$ of ULM-g is the same as above;

R$^1$ and R$_{1'}$ of ULM-g are each independently H or a C$_1$-C$_3$ alkyl group;

X$^{R2'}$ and X$^{R3'}$ of ULM-g are each independently an optionally substituted —CH$_2$)$_n$—, —CH$_2$)$_n$—CH(X$_v$)=CH(X$_v$)— (cis or trans), —CH$_2$)$_n$—CH=CH—, —(CH$_2$CH$_2$O)$_n$— or a C$_3$-C$_6$ cycloalkyl group, where X$_v$ is H, a halo or a C$_1$-C$_3$ alkyl group which is optionally substituted;

each m of ULM-g is independently 0, 1, 2, 3, 4, 5, 6;
each m' of ULM-g is independently 0 or 1;
each n of ULM-g is independently 0, 1, 2, 3, 4, 5, 6;
each n' of ULM-g is independently 0 or 1;
each u of ULM-g is independently 0 or 1;
each v of ULM-g is independently 0 or 1;
each w of ULM-g is independently 0 or 1; and any one or more of R$^{1'}$, R$^{2'}$, R$^{3'}$, X and X' of ULM-g is optionally modified to be covalently bonded to the PTM group through a linker group when PTM is not ULM', or when PTM is ULM', any one or more of R$^{1'}$, R$^{2'}$, R$^{3'}$, X and X' of each of ULM and ULM' are optionally modified to be covalently bonded to each other directly or through a linker group, or a pharmaceutically acceptable salt, stereoisomer, solvate or polymorph thereof.

In any aspect or embodiment described herein, the ULM is a cereblon E3 ligase-binding moiety (CLM) selected from the group consisting of a thalidomide, lenalidomide, pomalidomide, analogs thereof, isosteres thereof, or derivatives thereof.

In any aspect or embodiment described herein, the CLM has a chemical structure represented by:

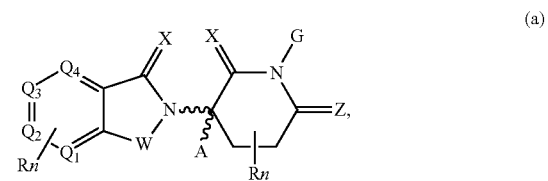

(a)

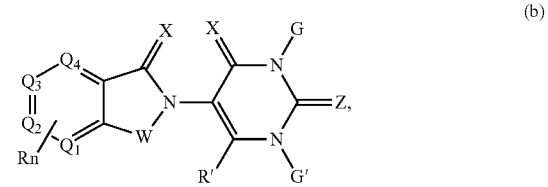

(b)

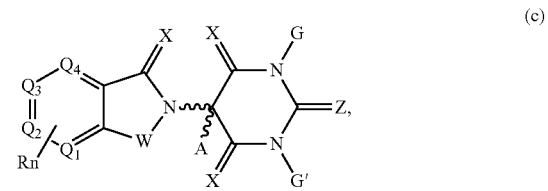

(c)

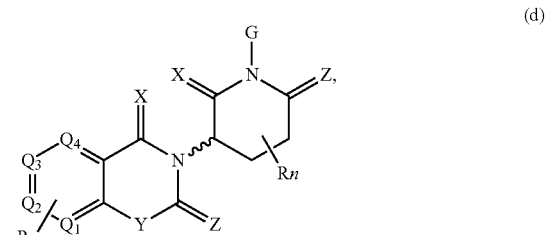

(d)

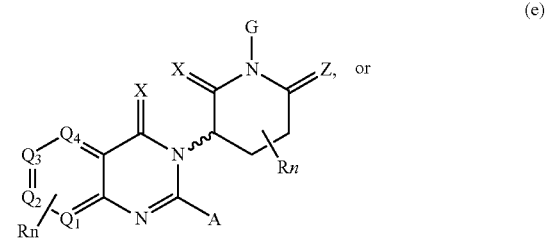

(e)

-continued (f)
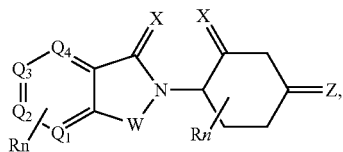

wherein:
W is selected from the group consisting of $CH_2$, CHR, C=O, $SO_2$, NH, and N-alkyl;
each X is independently selected from the group consisting of O, S, and $H_2$.
Y is selected from the group consisting of $CH_2$, —C=CR', NH, N-alkyl, N-aryl, N-hetaryl, N-cycloalkyl, N-heterocyclyl, O, and S;
Z is selected from the group consisting of O, S, and $H_2$;
G and G' are independently selected from the group consisting of H, alkyl (linear, branched, optionally substituted), OH, R'OCOOR, R'OCONRR", $CH_2$-heterocyclyl optionally substituted with R', and benzyl optionally substituted with R';
$Q_1$, $Q_2$, $Q_3$, and $Q_4$ represent a carbon C substituted with a group independently selected from R', N or N-oxide;
A is independently selected from the group H, alkyl (linear, branched, optionally substituted), cycloalkyl, Cl and F;
R comprises —CONR'R", —OR', —NR'R", —SR', —$SO_2$R', —$SO_2$NR'R", —CR'R"—, —CR'NR'R"—, (—CR'O)$_n$R", -aryl, -hetaryl, -alkyl (linear, branched, optionally substituted), -cycloalkyl, -heterocyclyl, —P(O)(OR')R", —P(O)R'R", —OP(O)(OR')R", —OP(O)R'R", —Cl, —F, —Br, —I, —$CF_3$, —CN, —NR'$SO_2$NR'R", —NR'CONR'R", —CONR'COR", —NR'C(=N—CN)NR'R", —C(=N—CN)NR'R", —NR'C(=N—CN)R", —NR'C(=C—$NO_2$)NR'R", —$SO_2$NR'COR", —$NO_2$, —$CO_2$R', —C(C=N—OR')R", —CR'=CR'R", —CCR', —S(C=O)(C=N—R')R", —$SF_5$ and —$OCF_3$;
R' and R" are independently selected from the group consisting of a bond, H, alkyl, cycloalkyl, aryl, heteroaryl, heterocyclic, —C(=O)R, heterocyclyl, each of which is optionally substituted;
∿ represents a bond that may be stereospecific ((R) or (S)) or non-stereospecific; and
$R_n$ comprises a functional group or an atom,
wherein n is an integer from 1-10, and wherein
when n is 1, $R_n$ is modified to be covalently joined to the linker group (L), and
when n is 2, 3, or 4, then one $R_a$ is modified to be covalently joined to the linker group (L), and any other $R_n$ is optionally modified to be covalently joined to a PTM, a CLM, a second CLM having the same chemical structure as the CLM, a CLM', a second linker, or any multiple or combination thereof.

In any aspect or embodiment described herein, the CLM has a chemical structure represented by:

(h)
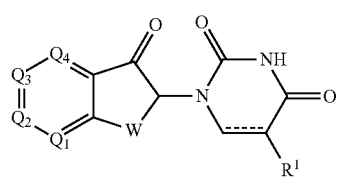

(i)
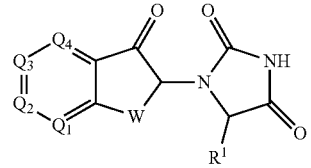

(j)
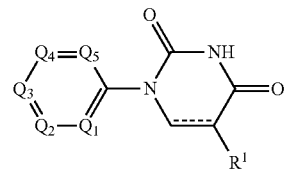

(k)
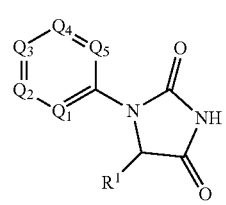

(l)
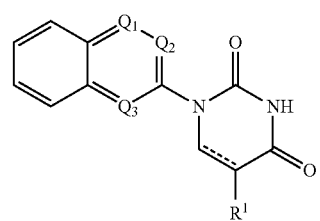

(m)
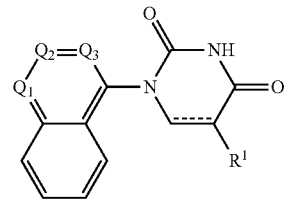

(n)
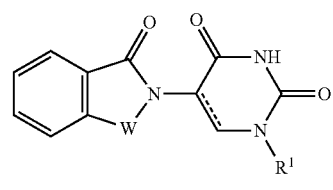

(o)
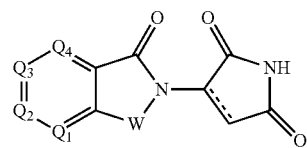

(p)
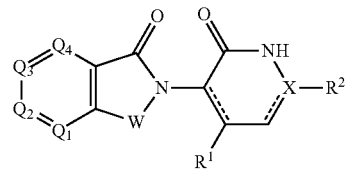

447
-continued

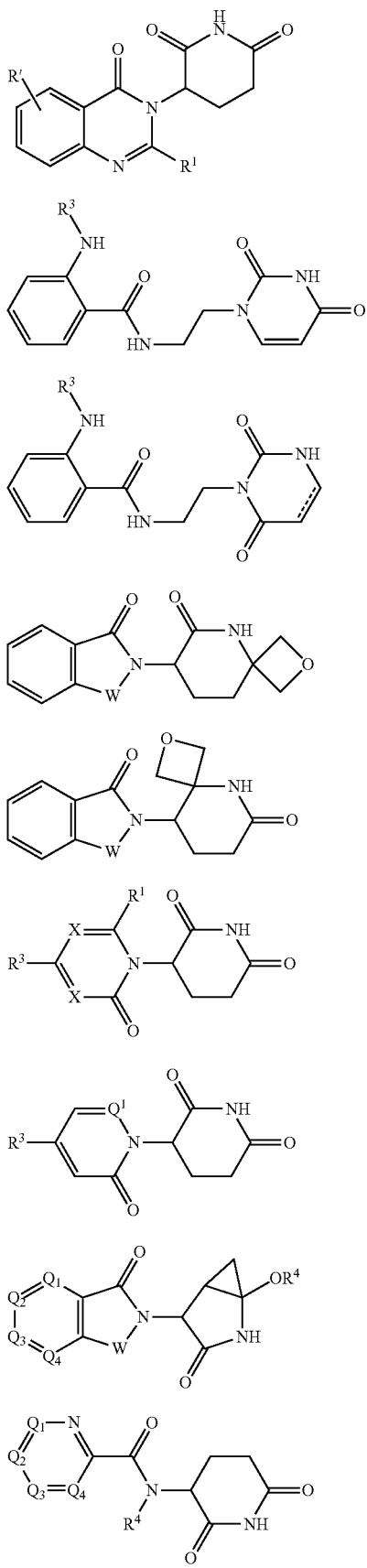

448
-continued

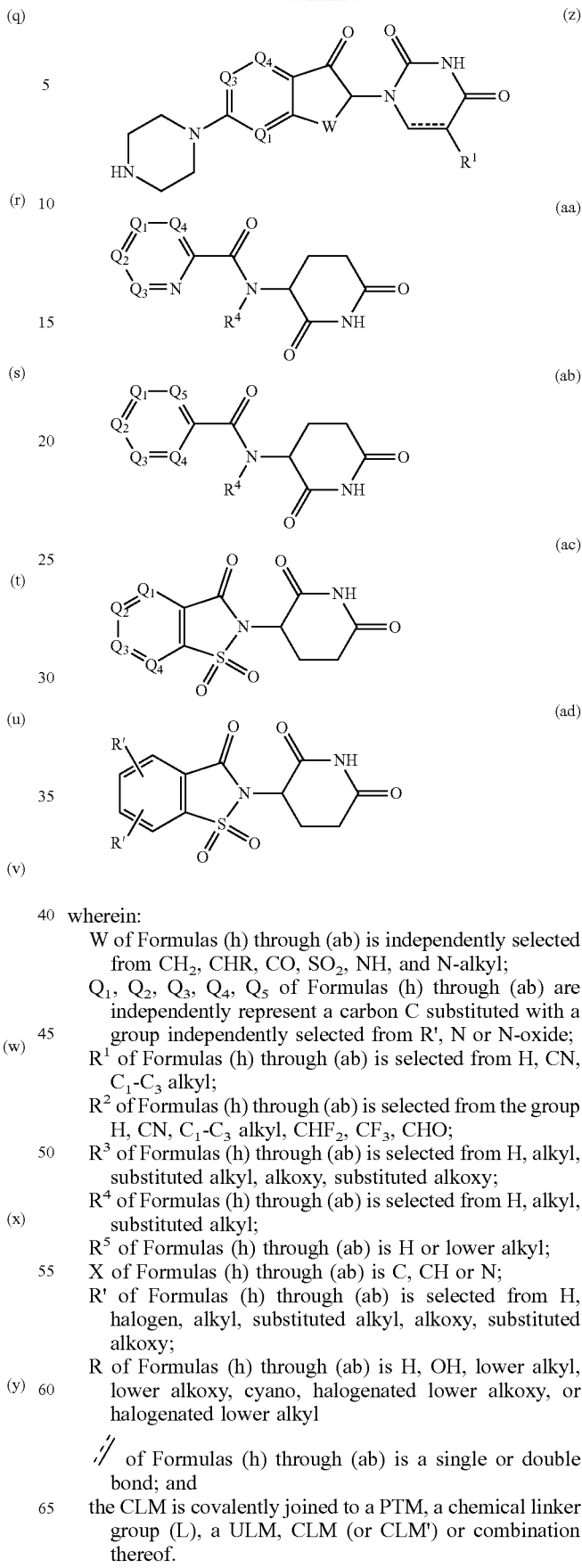

wherein:
W of Formulas (h) through (ab) is independently selected from $CH_2$, CHR, CO, $SO_2$, NH, and N-alkyl;
$Q_1$, $Q_2$, $Q_3$, $Q_4$, $Q_5$ of Formulas (h) through (ab) are independently represent a carbon C substituted with a group independently selected from R', N or N-oxide;
$R^1$ of Formulas (h) through (ab) is selected from H, CN, $C_1$-$C_3$ alkyl;
$R^2$ of Formulas (h) through (ab) is selected from the group H, CN, $C_1$-$C_3$ alkyl, $CHF_2$, $CF_3$, CHO;
$R^3$ of Formulas (h) through (ab) is selected from H, alkyl, substituted alkyl, alkoxy, substituted alkoxy;
$R^4$ of Formulas (h) through (ab) is selected from H, alkyl, substituted alkyl;
$R^5$ of Formulas (h) through (ab) is H or lower alkyl;
X of Formulas (h) through (ab) is C, CH or N;
R' of Formulas (h) through (ab) is selected from H, halogen, alkyl, substituted alkyl, alkoxy, substituted alkoxy;
R of Formulas (h) through (ab) is H, OH, lower alkyl, lower alkoxy, cyano, halogenated lower alkoxy, or halogenated lower alkyl ⫶ of Formulas (h) through (ab) is a single or double bond; and
the CLM is covalently joined to a PTM, a chemical linker group (L), a ULM, CLM (or CLM') or combination thereof.

In any aspect or embodiment described herein, the ULM is a (MDM2) binding moiety (MLM) with a chemical moiety selected from the group consisting of a substituted imidazolines, a substituted spiro-indolinones, a substituted pyrrolidines, a substituted piperidinones, a substituted morpholinones, a substituted pyrrolopyrimidines, a substituted imidazolopyridines, a substituted thiazoloimidazoline, a substituted pyrrolopyrrolidinones, and a substituted isoquinolinones.

In any aspect or embodiment described herein, the ULM is a IAP E3 ubiquitin ligase binding moiety (ILM) comprising the amino acids alanine (A), valine (V), proline (P), and isoleucine (I) or their unnatural mimetics.

In any aspect or embodiment described herein, the ULM is a IAP E3 ubiquitin ligase binding moiety (ILM) comprising a AVPI tetrapeptide fragment or derivative thereof.

In any aspect or embodiment described herein, the linker (L) comprises a chemical structural unit represented by the formula:

$$-(A^L)_q-,$$

wherein:
$(A^L)_q$ is a group which is connected to at least one of ULM, PTM, or both; and
q is an integer greater than or equal to 1,
each $A^L$ is independently selected from the group consisting of, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR$, CO, $CR^{L1}=CR^{L2}$, C≡C, $SiR^{L1}R^{L2}$, P(O)$R^{L1}$, P(O)O$R^{L1}$, $NR^{L3}C(=NCN)NR^{L4}$, $NR^{L3}C(=NCN)$, $NR^{L3}C(=CNO_2)NR^{L4}$, $C_{3-11}$cycloalkyl optionally substituted with 0-6 $R^{L1}$ and/or $R^{L2}$ groups, $C_{3-11}$heterocyclyl optionally substituted with 0-6 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups;

$R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}$alkyl$)_2$, $C_{3-11}$cycloalkyl, aryl, heteroaryl, $C_{3-11}$heterocyclyl, $OCl_{1-8}$cycloalkyl, $SC_{1-8}$cycloalkyl, $NHC_{1-8}$cycloalkyl, $N(C_{1-8}$cycloalkyl$)_2$, $N(C_{1-8}$cycloalkyl)($C_{1-8}$alkyl), OH, $NH_2$, SH, $SO_2C_{1-8}$ alkyl, P(O)(O$C_{1-8}$alkyl)($C_{1-8}$alkyl), P(O)(O$C_{1-8}$alkyl$)_2$, CC—$C_{1-8}$alkyl, CCH, CH=CH($C_{1-8}$alkyl), C($C_{1-8}$alkyl)=CH($C_{1-8}$alkyl), C($C_{1-8}$alkyl)=C($C_{1-8}$ alkyl$)_2$, Si(OH)$_3$, Si($C_{1-8}$alkyl)$_3$, Si(OH)($C_{1-8}$alkyl)$_2$, COC$_{1-8}$alkyl, CO$_2$H, halogen, CN, CF$_3$, CHF$_2$, CH$_2$F, NO$_2$, SF$_5$, SO$_2$NHC$_{1-8}$alkyl, SO$_2$N(C$_{1-8}$alkyl)$_2$, SONHC$_{1-8}$ alkyl, SON(C$_{1-8}$alkyl)$_2$, CONHC$_{1-8}$alkyl, CON(C$_{1-8}$alkyl)$_2$, N(C$_{1-8}$alkyl)CONH(C$_{1-8}$alkyl), N(C$_{1-8}$alkyl)CON(C$_{1-8}$alkyl)$_2$, NHCONH(C$_{1-8}$alkyl), NHCON(C$_{1-8}$alkyl)$_2$, NHCONH$_2$, N(C$_{1-8}$alkyl) SO$_2$NH(C$_{1-8}$ alkyl), N(C$_{1-8}$alkyl) SO$_2$N(C$_{1-8}$alkyl)$_2$, NH SO$_2$NH(C$_{1-8}$alkyl), NH SO$_2$N(C$_{1-8}$alkyl)$_2$, NH SO$_2$NH$_2$.

In any aspect or embodiment described herein, the linker (L) comprises a group represented by a general structure selected from the group consisting of:

—N(R)—(CH2)$_m$—O(CH2)$_n$—O(CH2)$_o$—O(CH2)$_p$—O(CH2)$_q$—O(CH2)$_r$—OCH2—;

—O—(CH2)$_m$—O(CH2)$_n$—O(CH2)$_o$—O(CH2)$_p$—O(CH2)$_q$—O(CH2)$_r$—OCH2—;

—O—(CH2)$_m$—O(CH2)$_n$—O(CH2)$_o$—O(CH2)$_p$—O(CH2)$_q$—O(CH2)$_r$—O—;

—N(R)—(CH2)$_m$—O(CH2)$_n$—O(CH2)$_o$—O(CH2)$_p$—O(CH2)$_q$—O(CH2)$_r$—O—;

—(CH2)$_m$—O(CH2)$_n$—O(CH2)$_o$—O(CH2)$_p$—O(CH2)$_q$—O(CH2)$_r$—O—;

—(CH2)$_m$—O(CH2)$_n$—O(CH2)$_o$—O(CH2)$_p$—O(CH2)$_q$—O(CH2)$_r$—OCH2—;

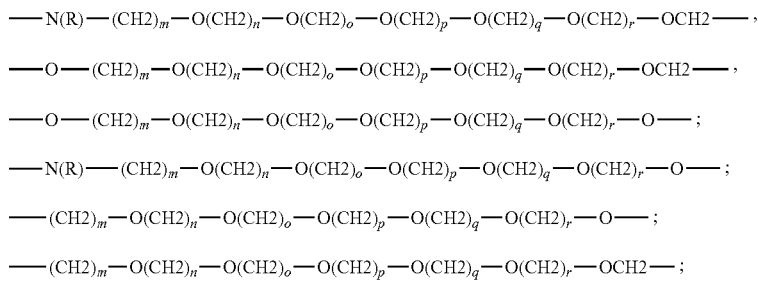

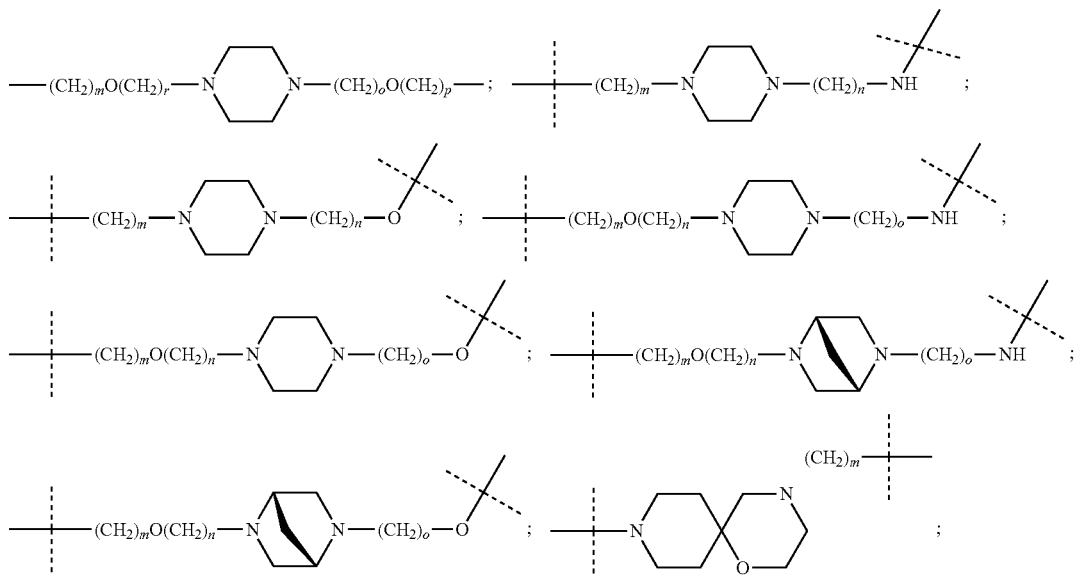

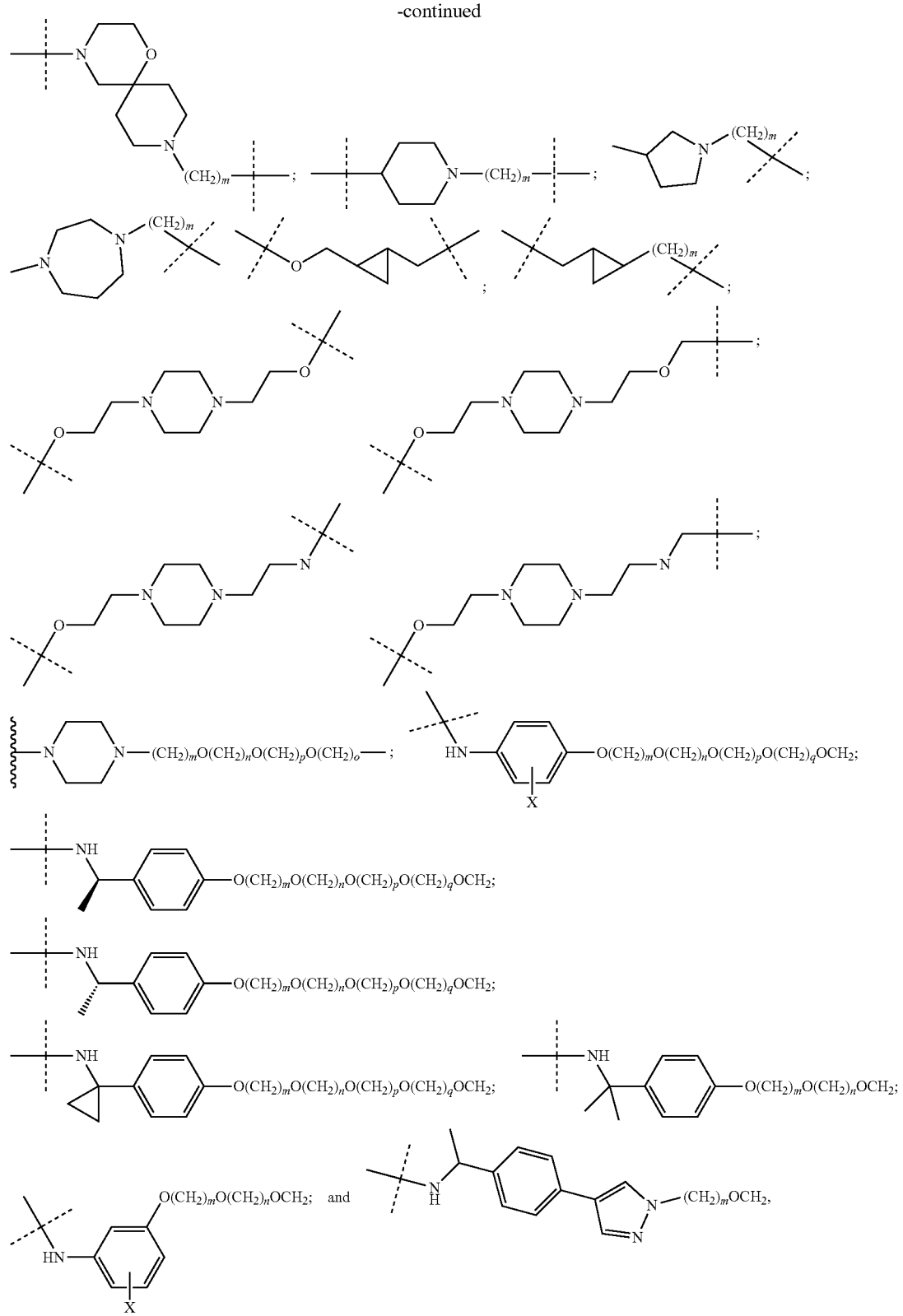
wherein m, n, o, p, q, and r, are independently 0, 1, 2, 3, 4, 5, 6, with the proviso that when the number is zero, there is no N—O or O—O bond, R is selected from the group H, methyl and ethyl, and X is selected from the group H and F;

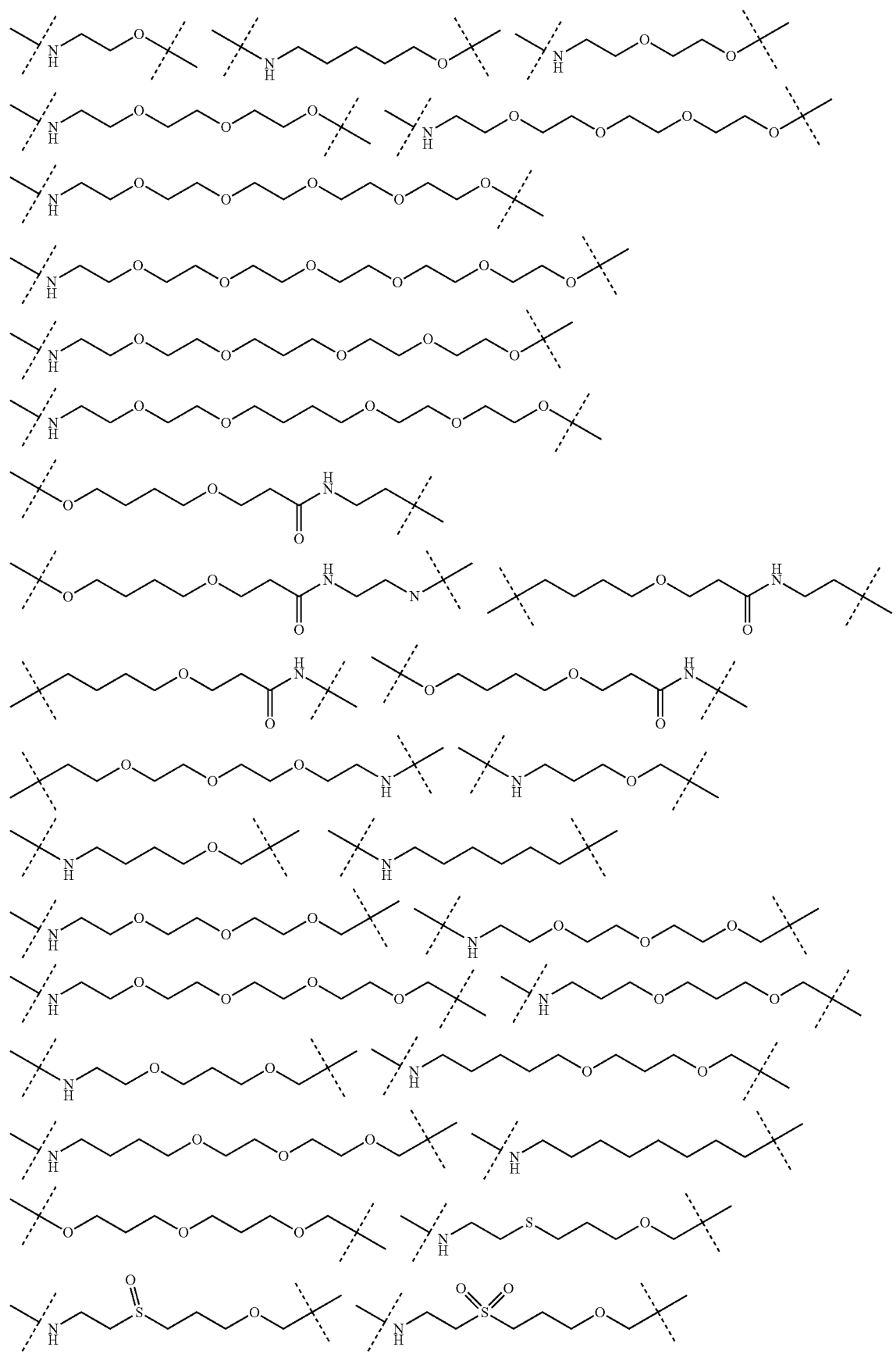

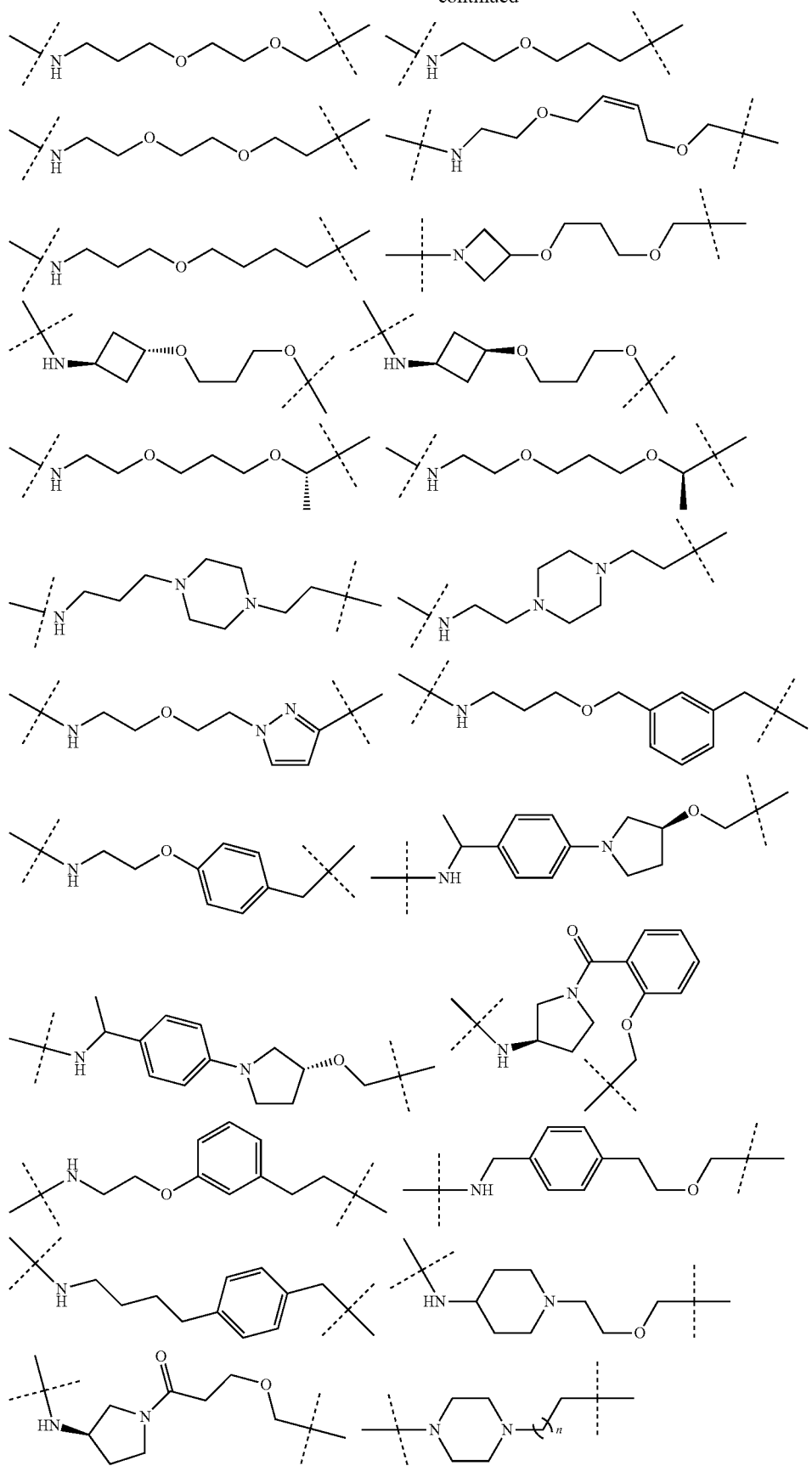

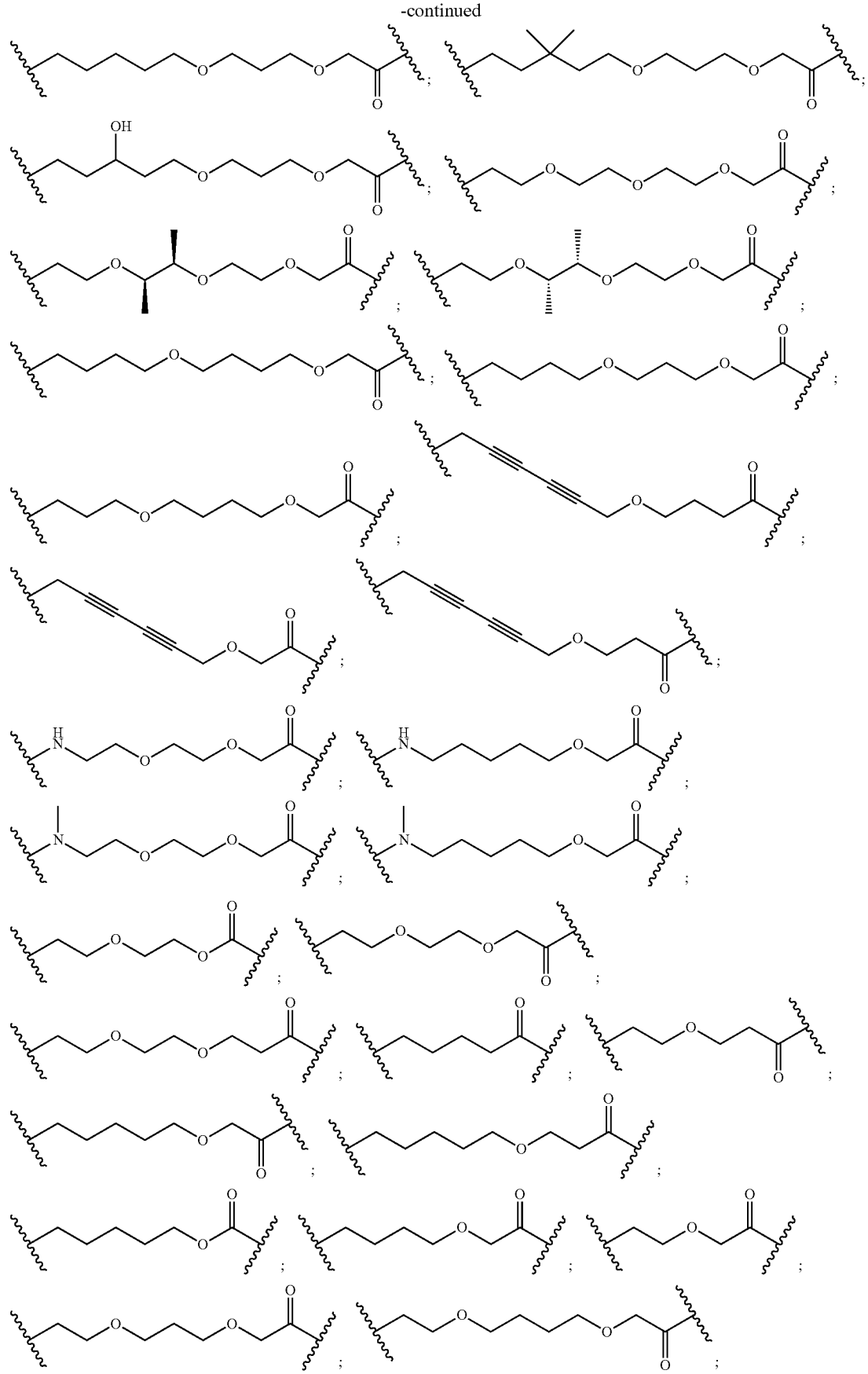

-continued
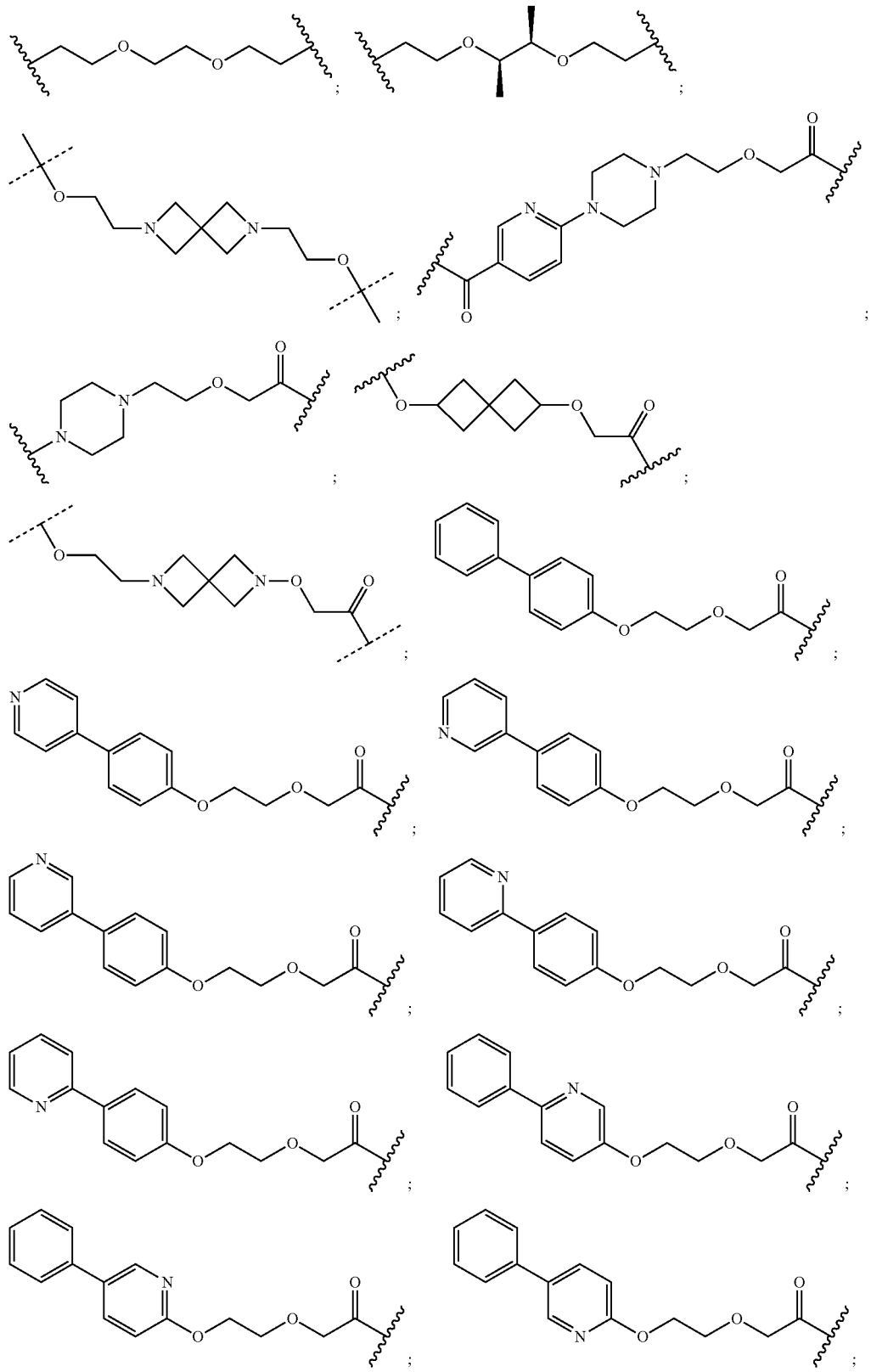

-continued
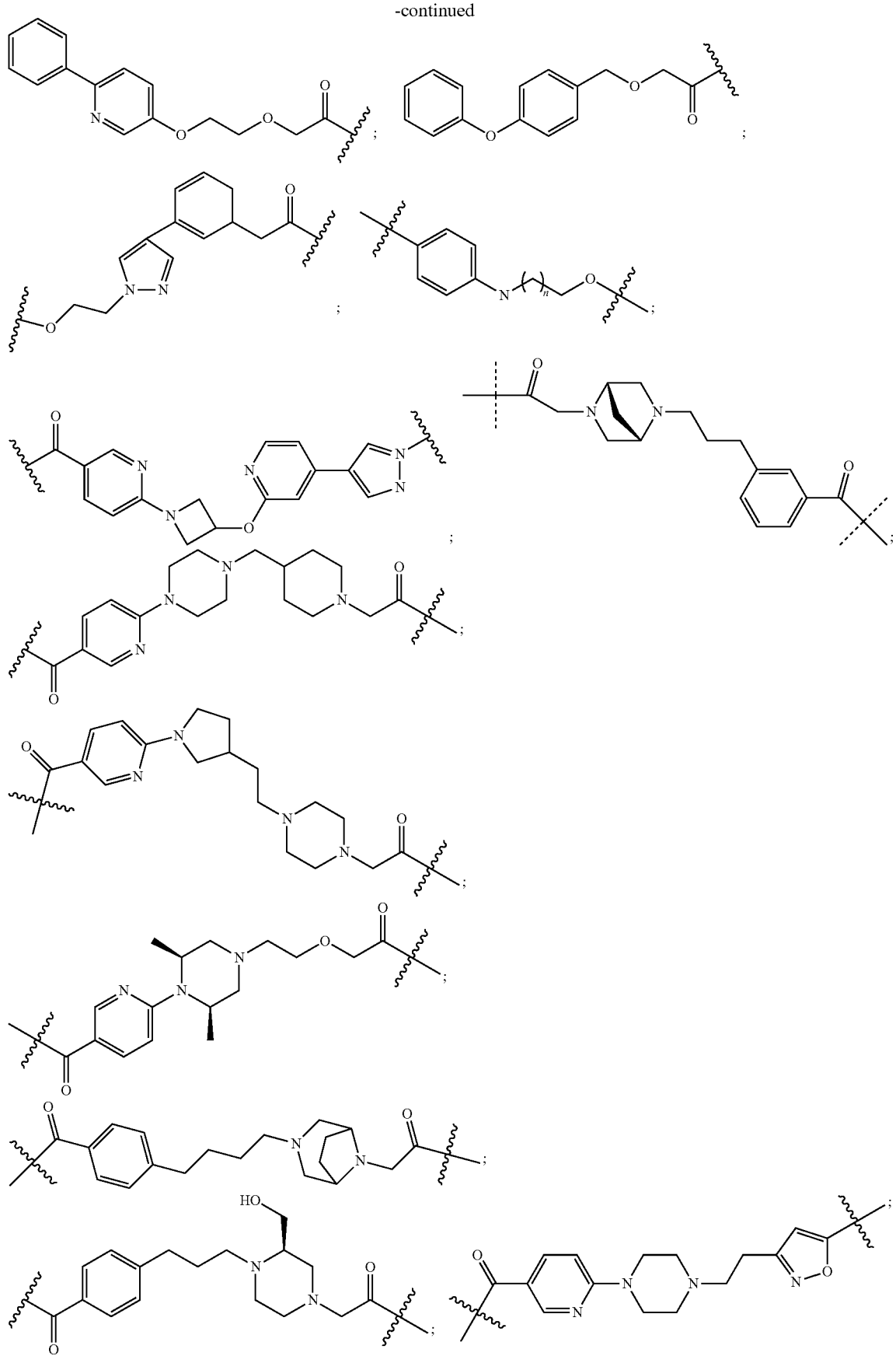

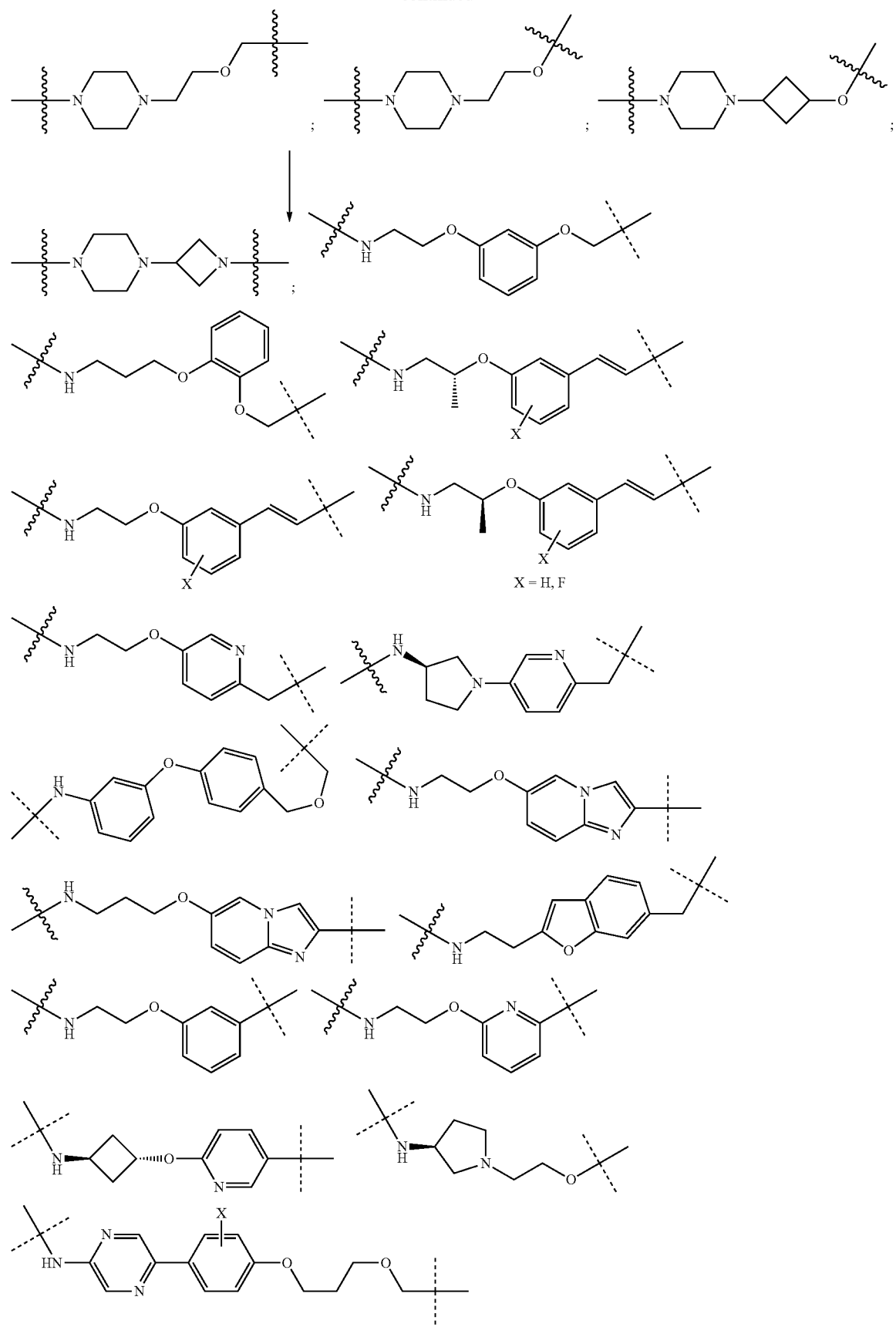

-continued
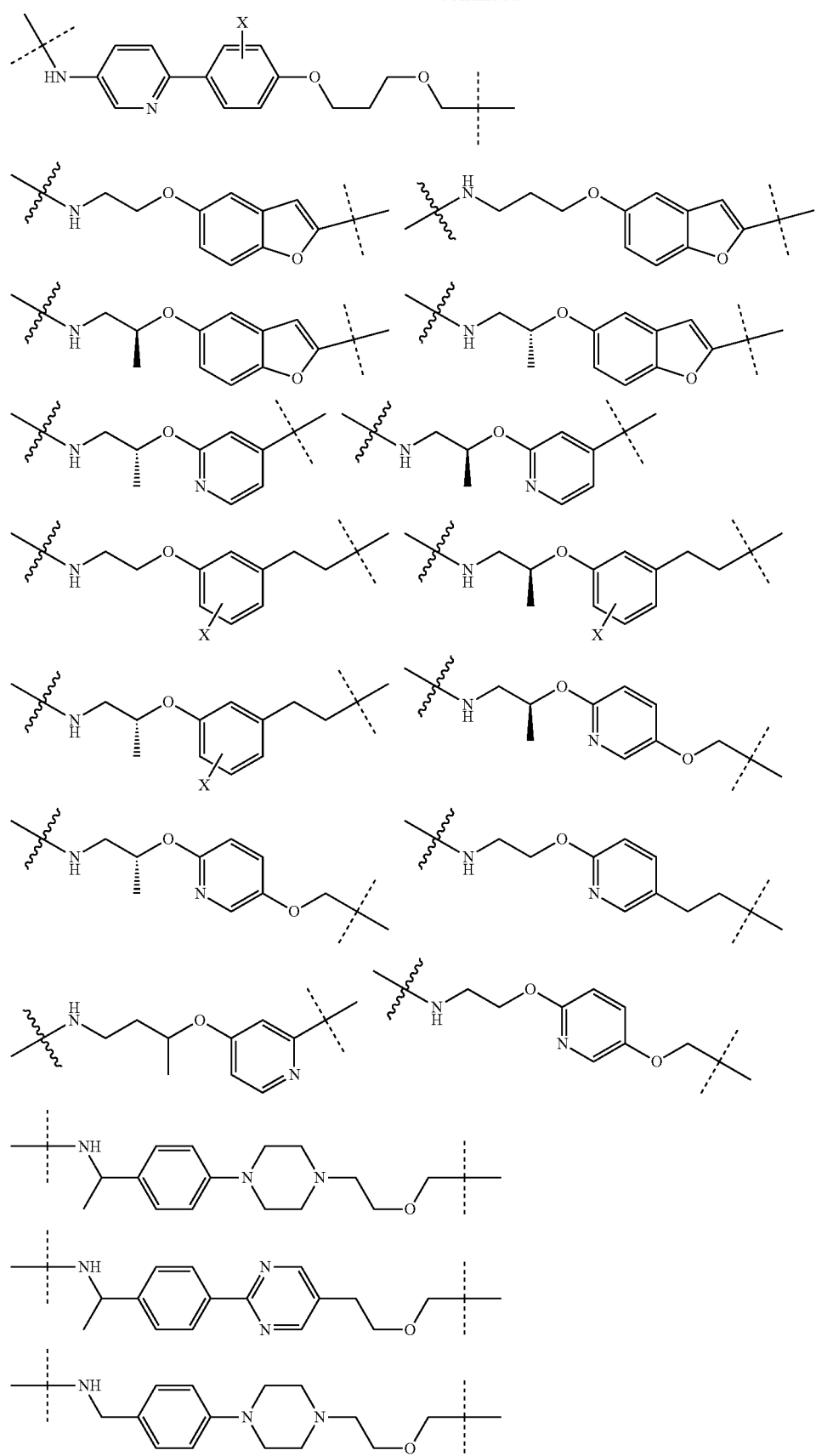

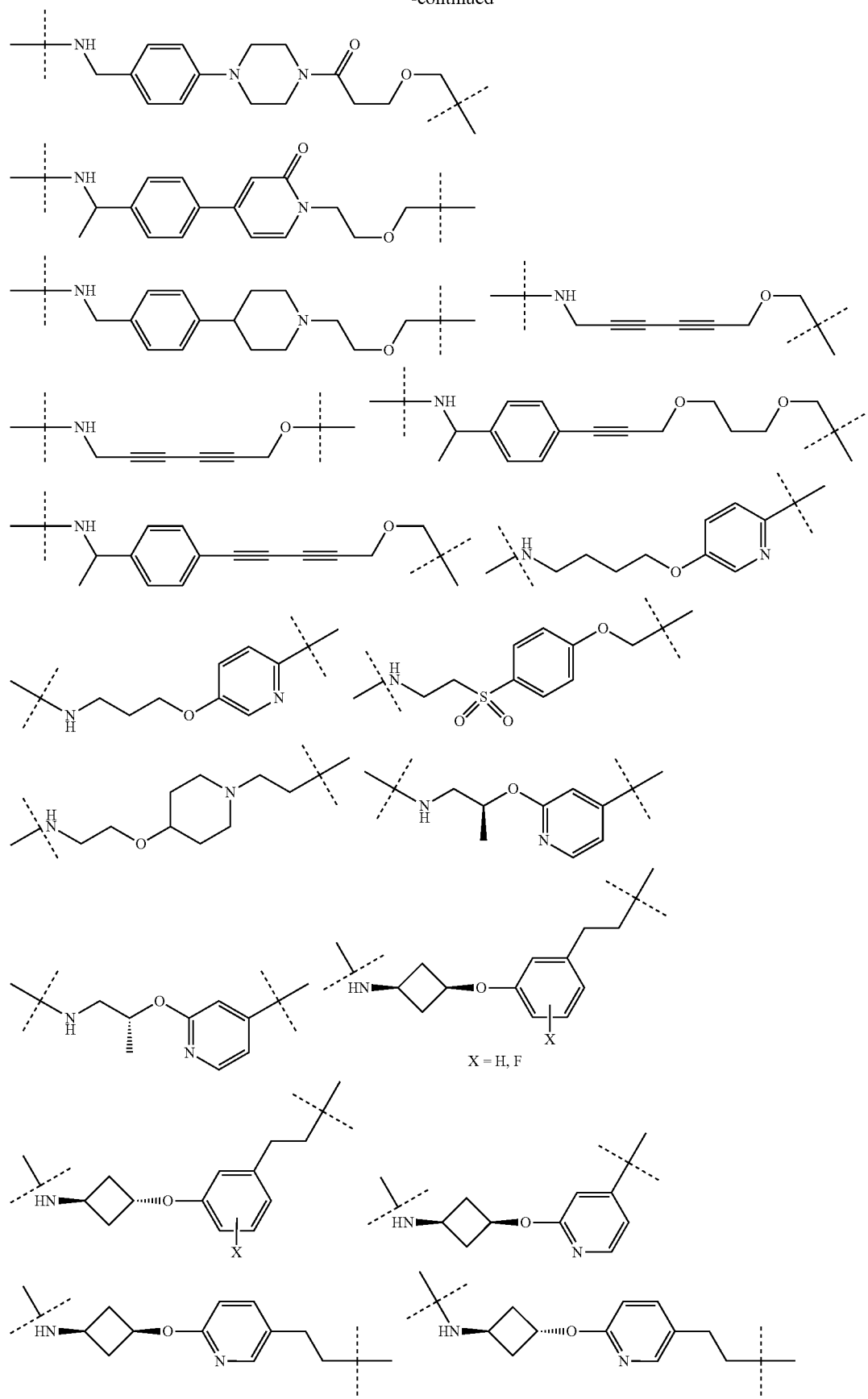

-continued
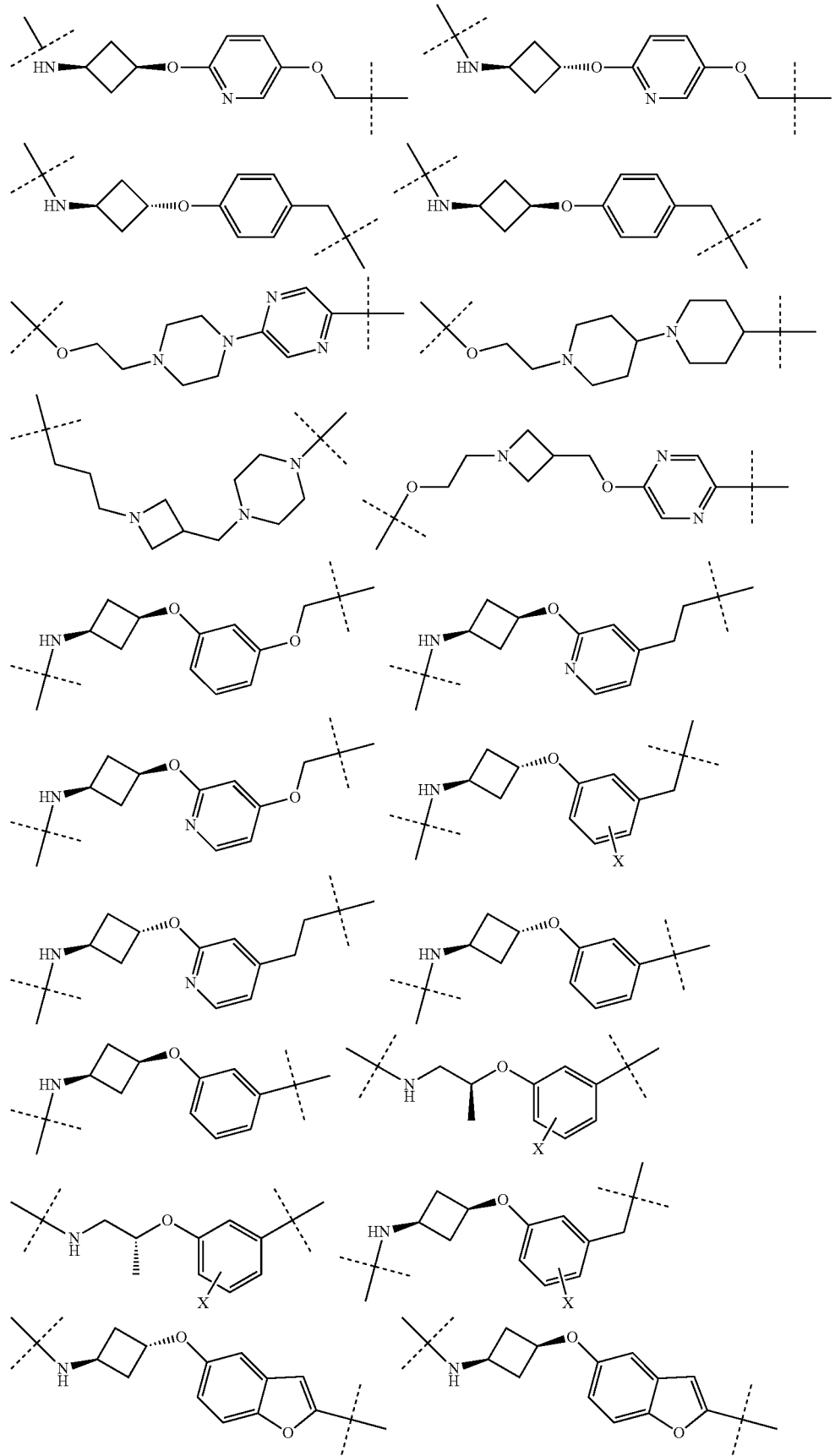

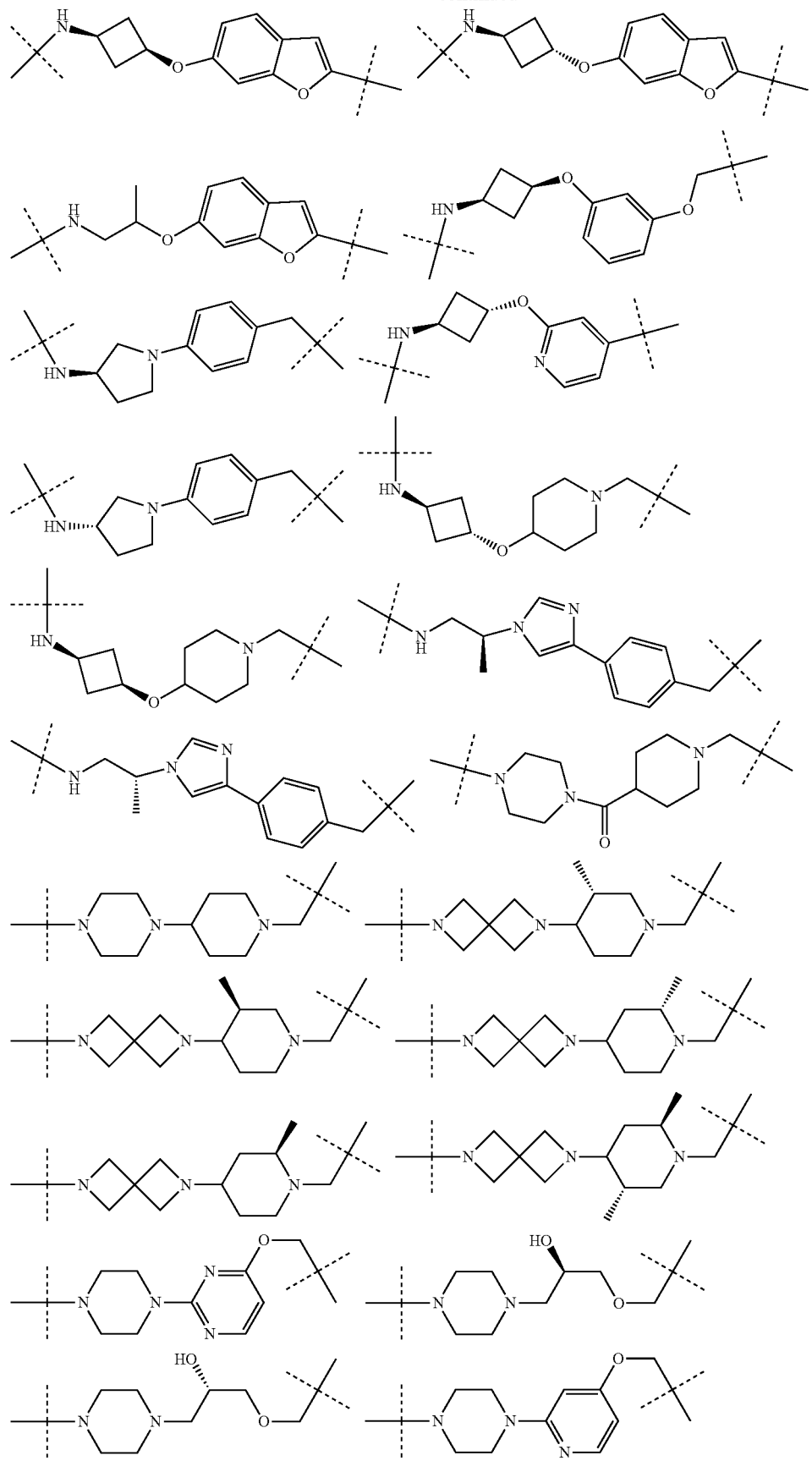

-continued
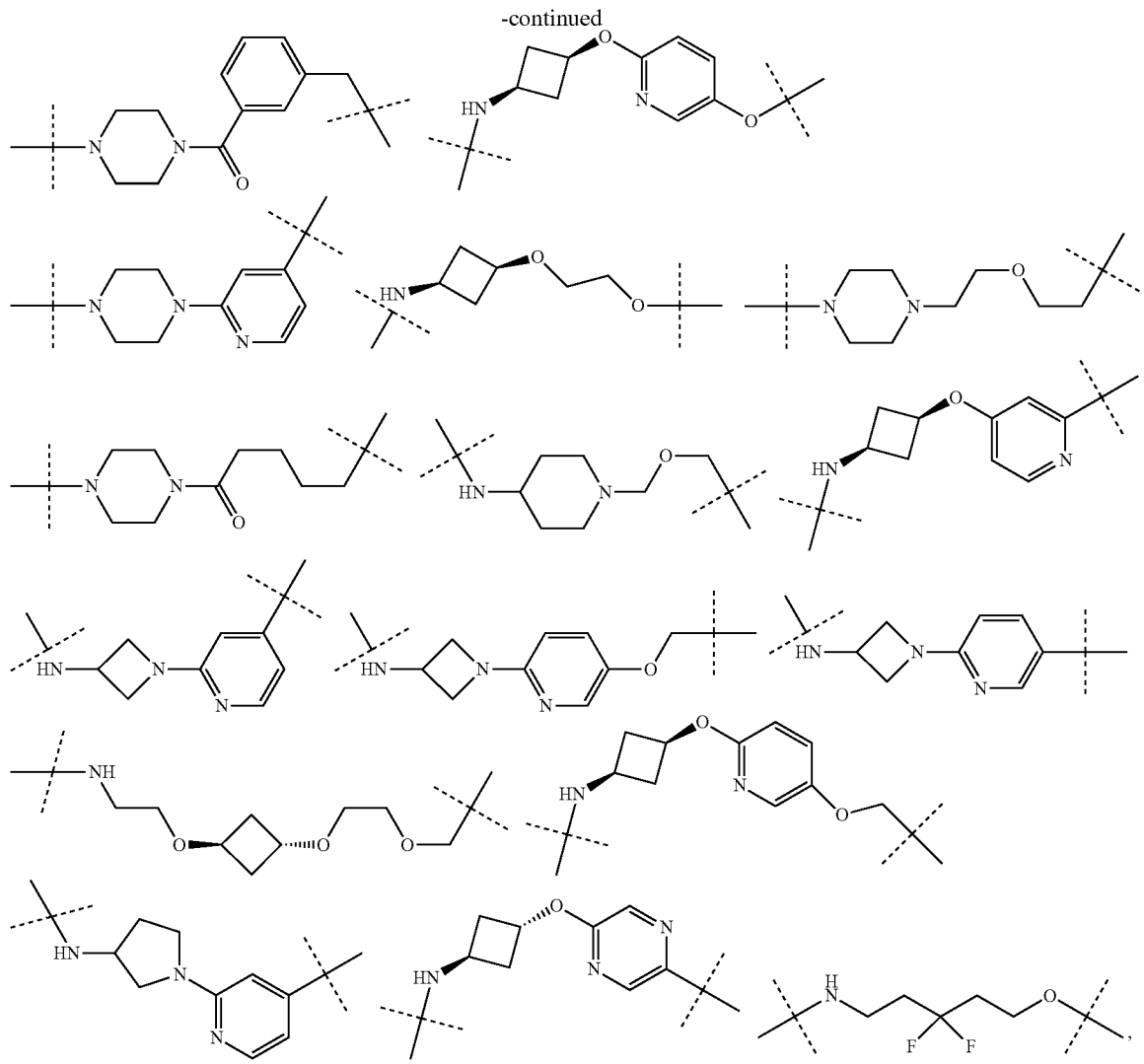
wherein each n and m of the linker can independently be 0, 1, 2, 3, 4, 5, 6.
In any aspect or embodiment described herein, the linker (L) is selected from the group consisting of:
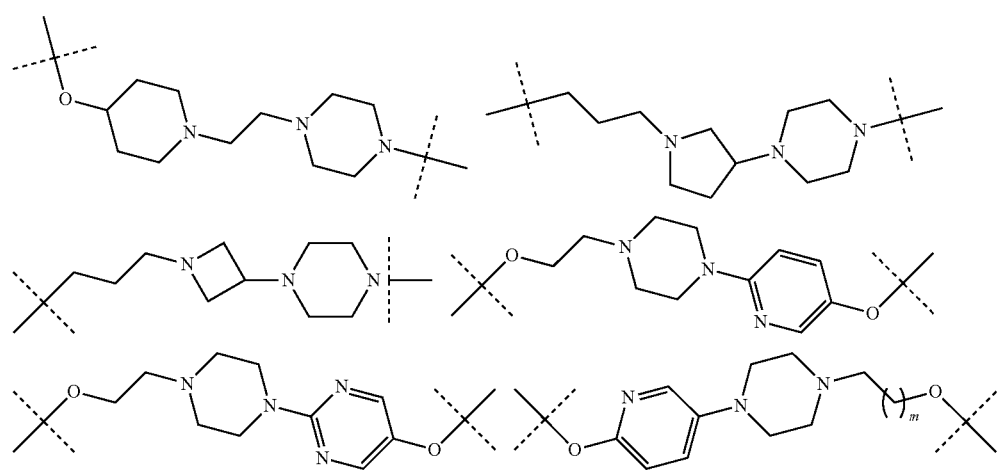

-continued
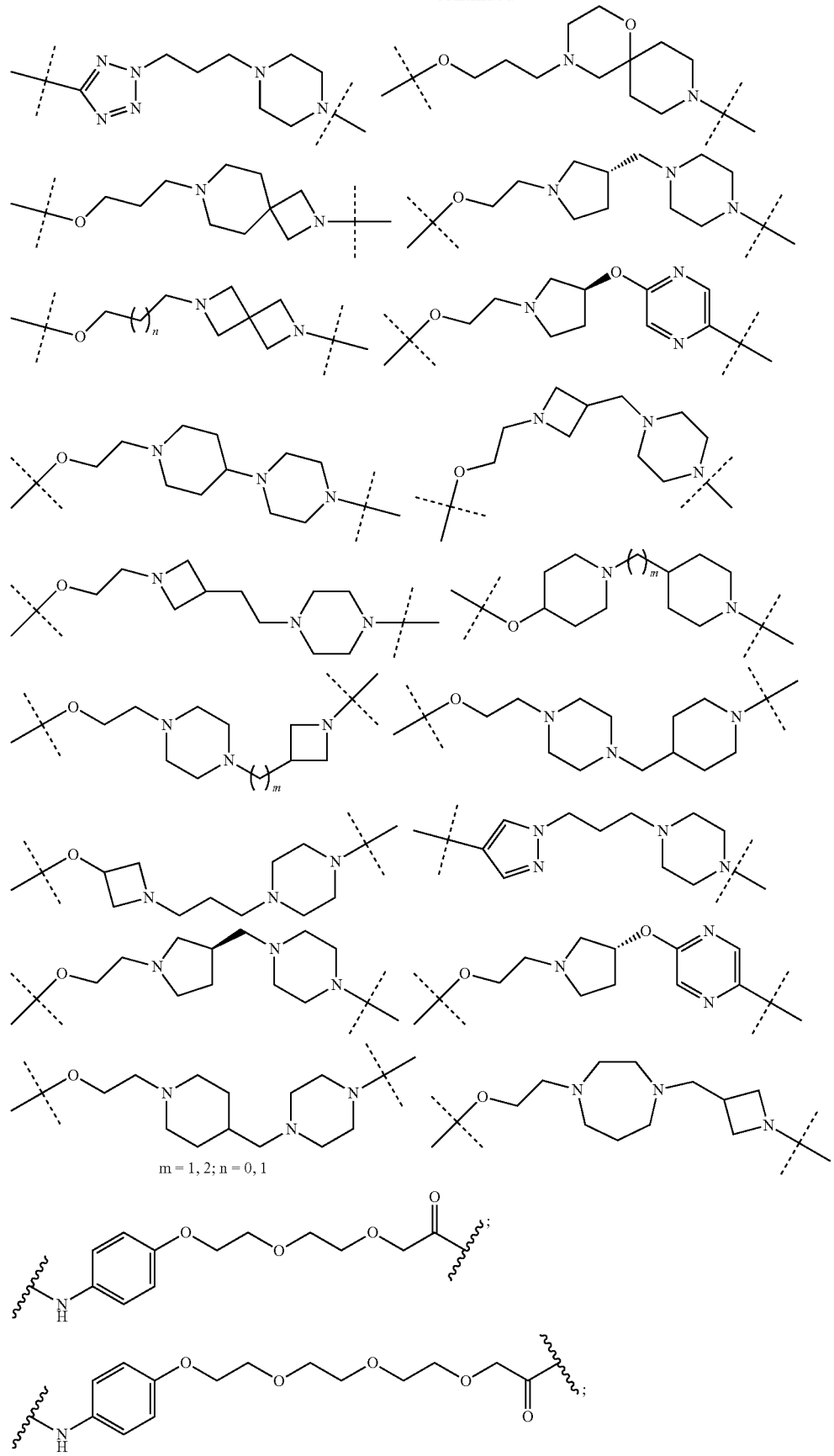
m = 1, 2; n = 0, 1

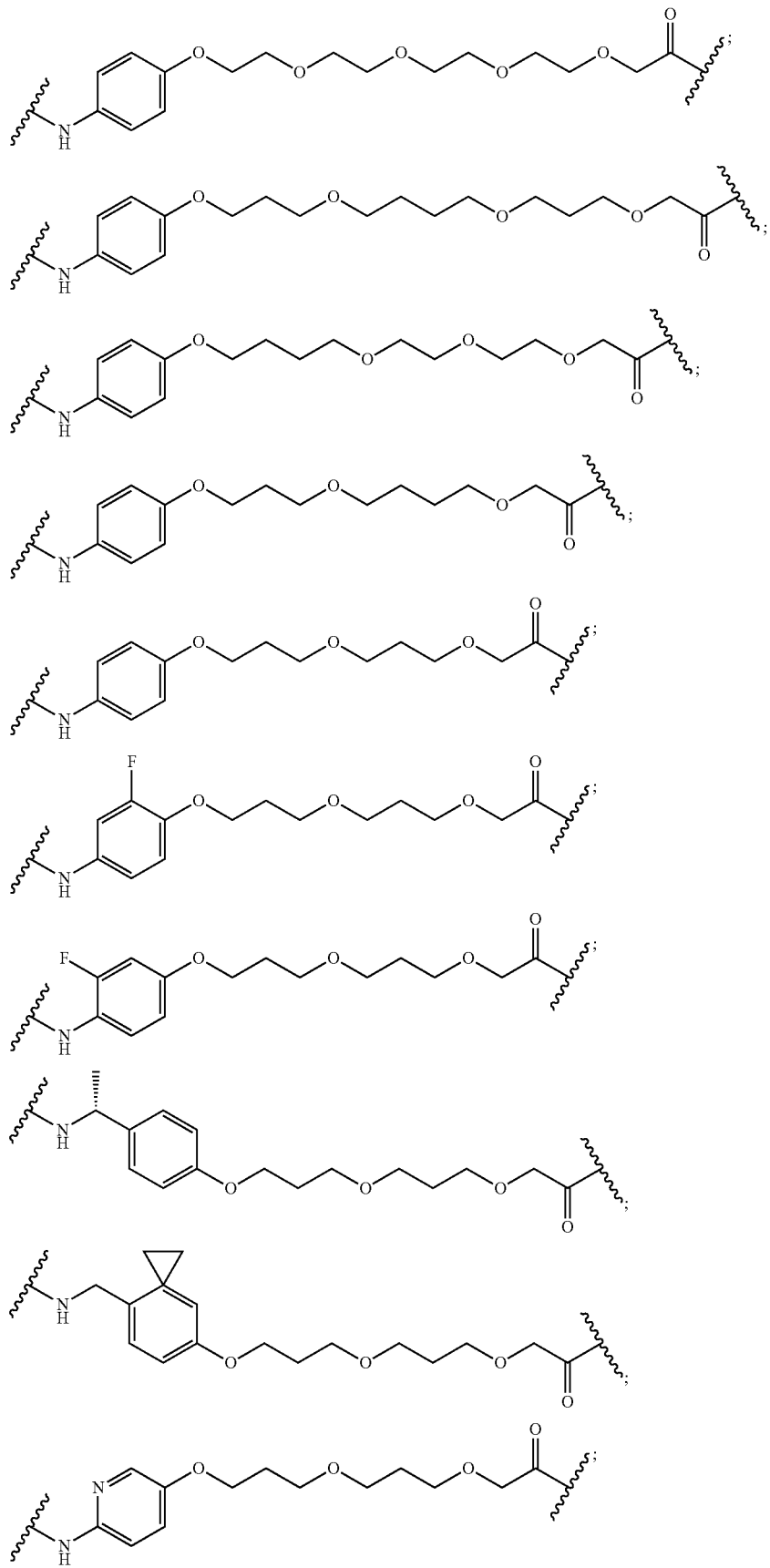

-continued
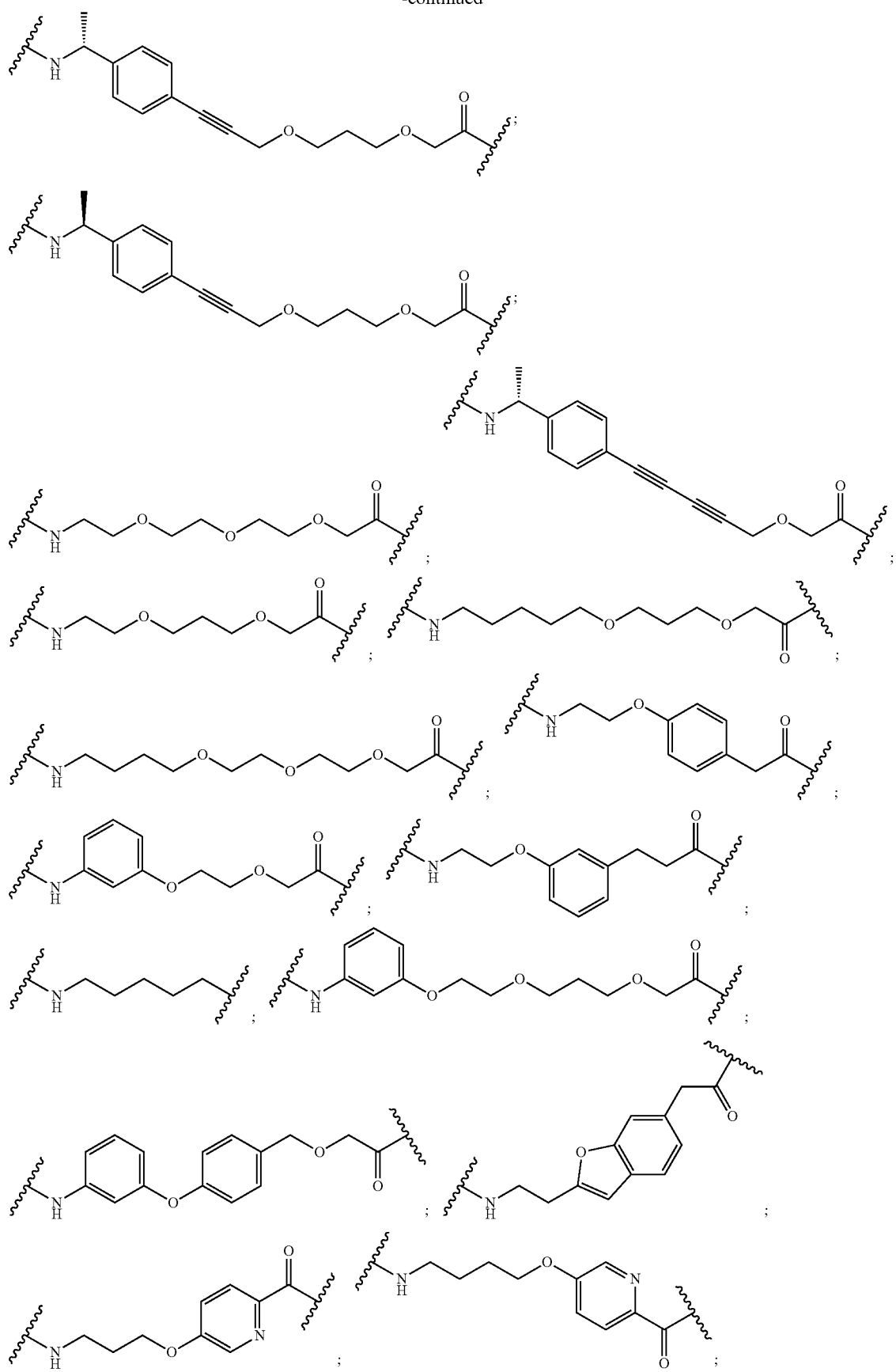

-continued
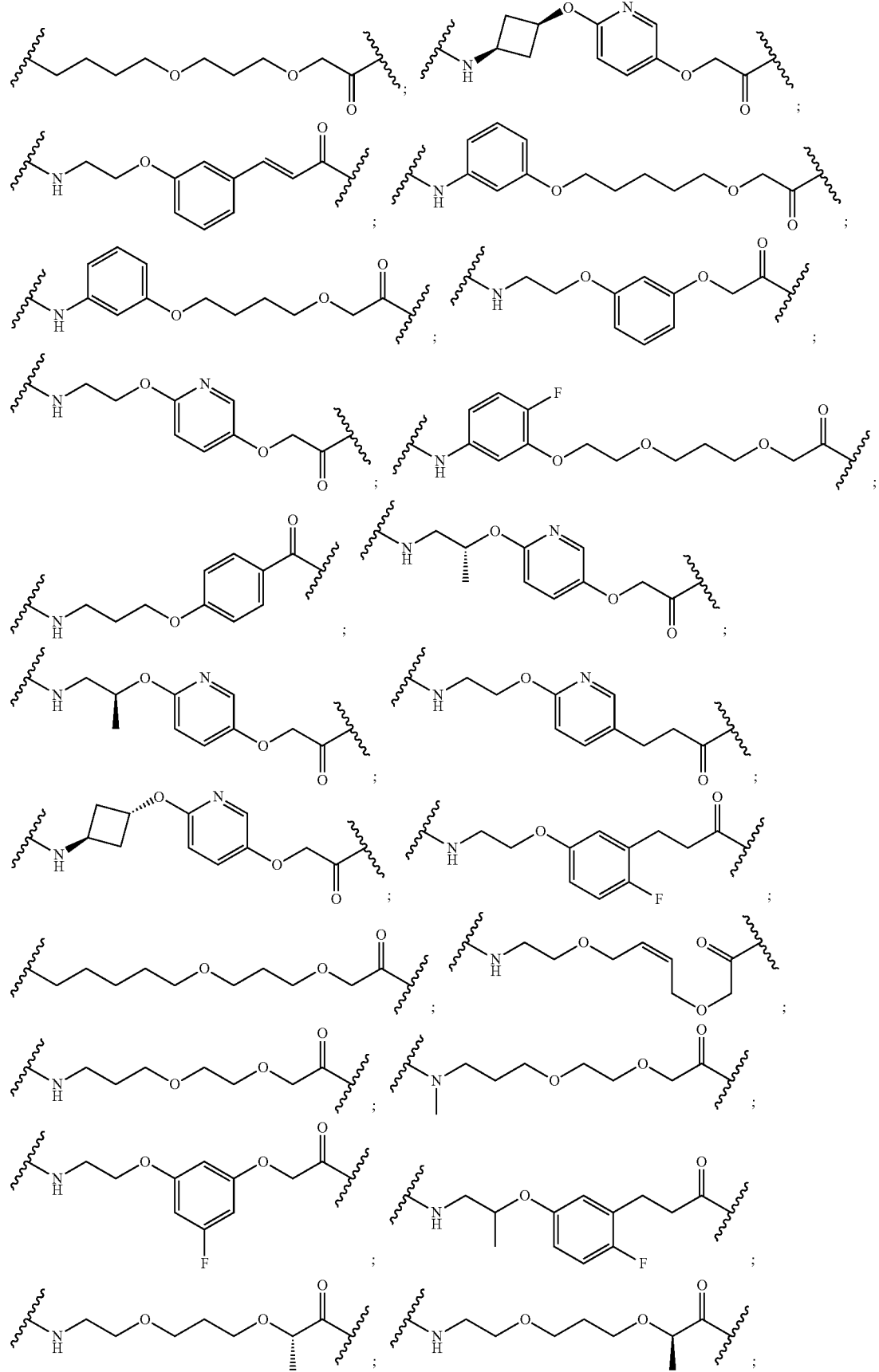

-continued
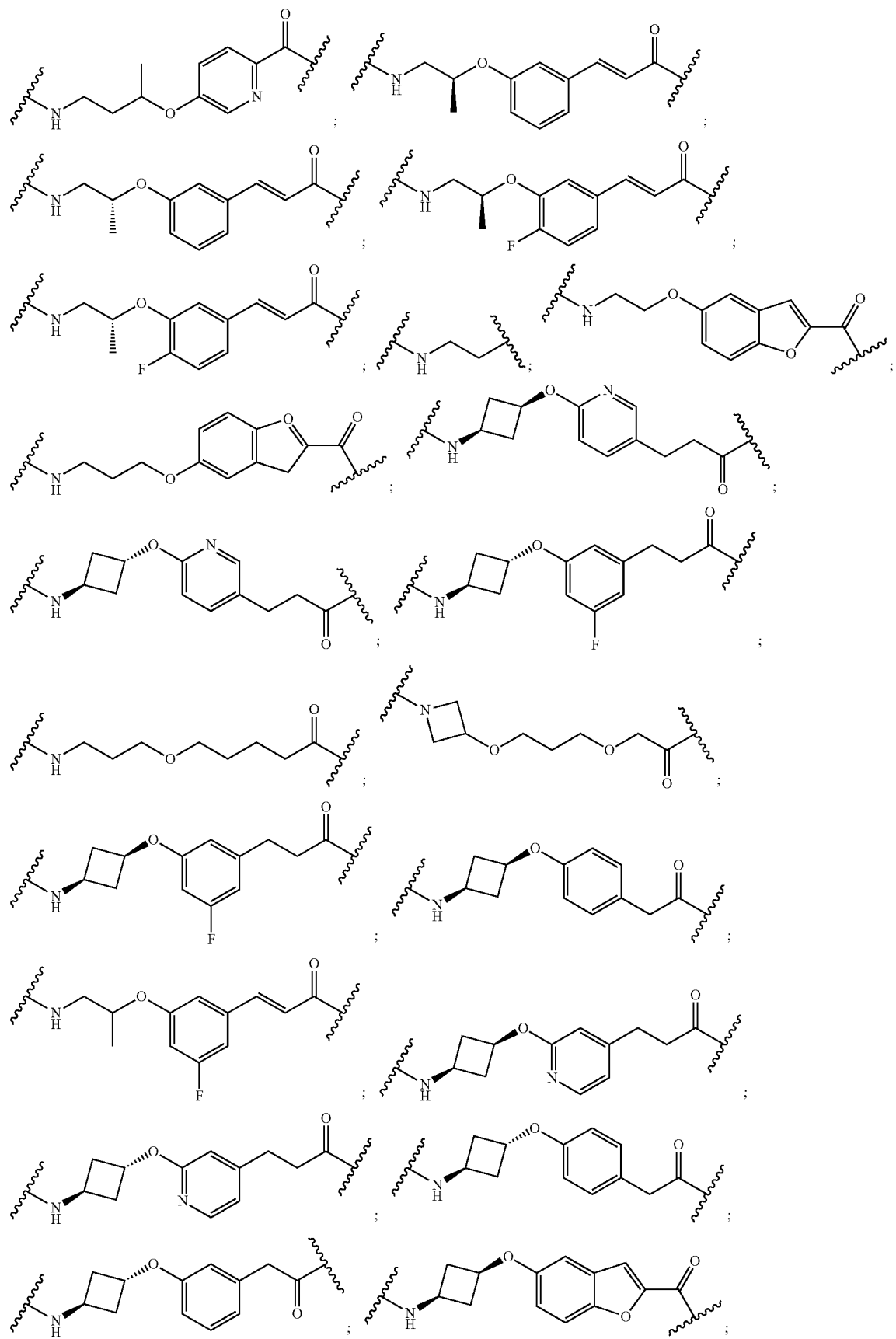

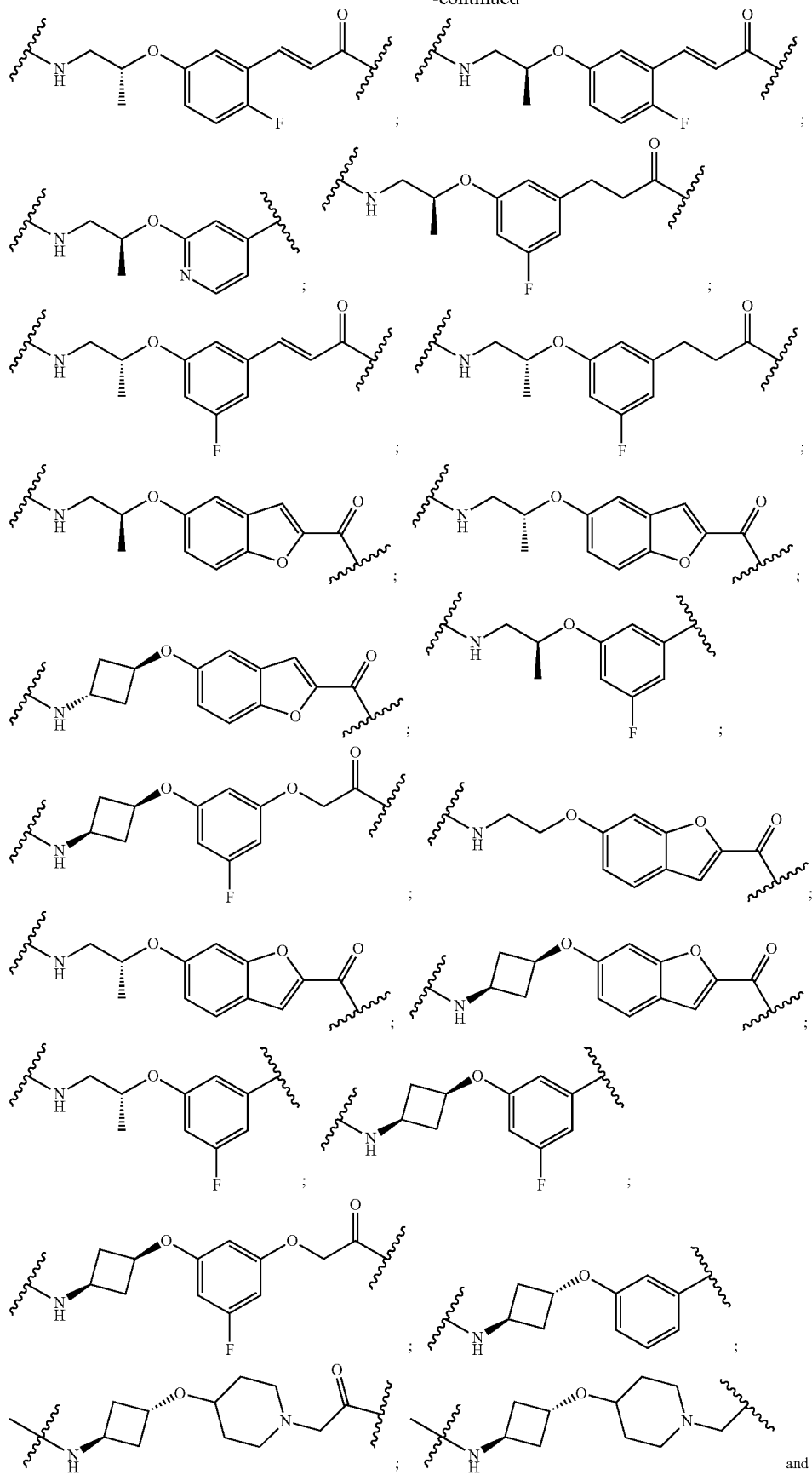

-continued
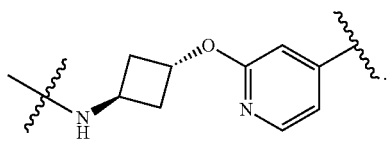
In any aspect or embodiment described herein, the linker (L) is selected from the group consisting of:
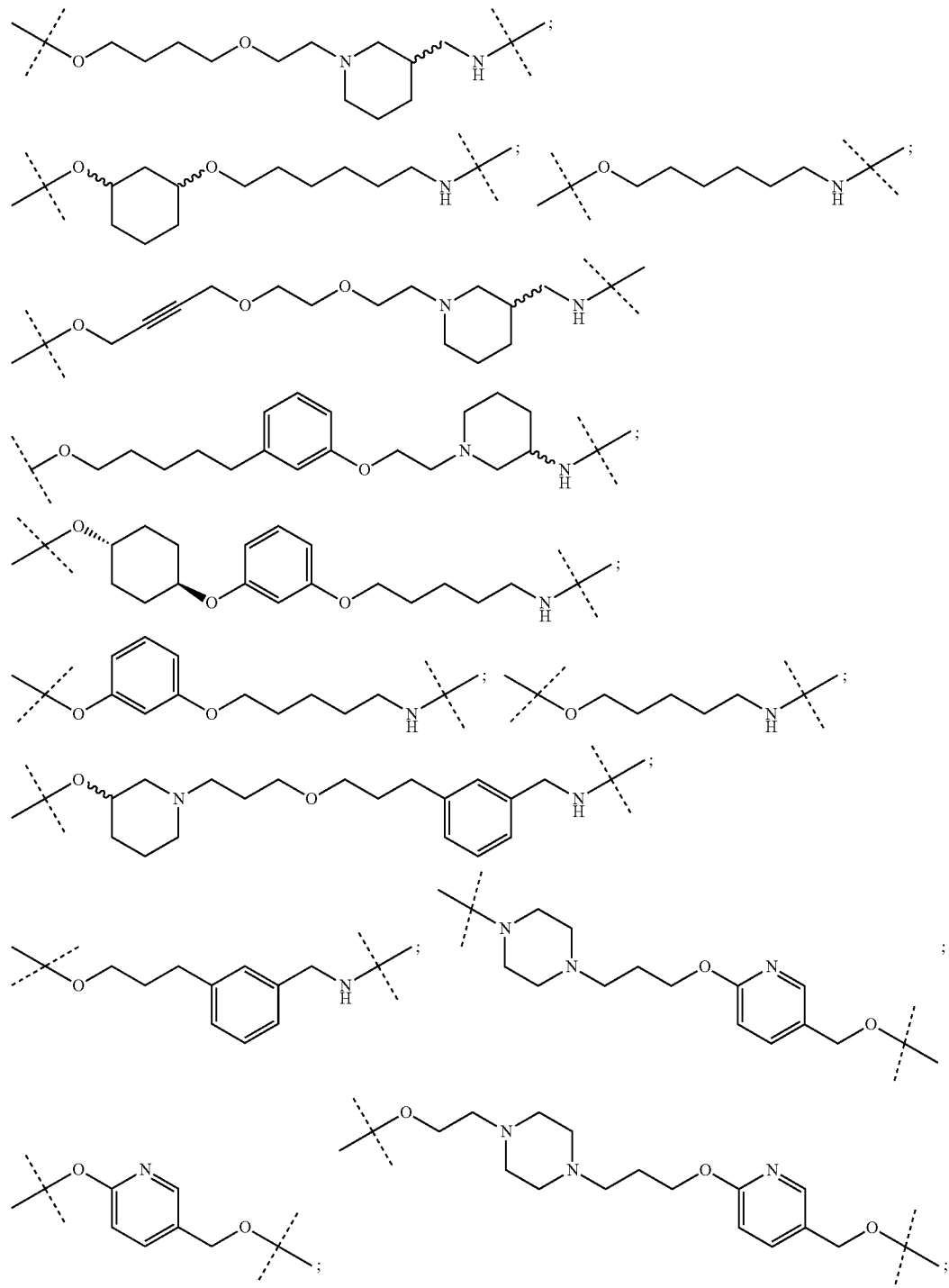

489 490
-continued
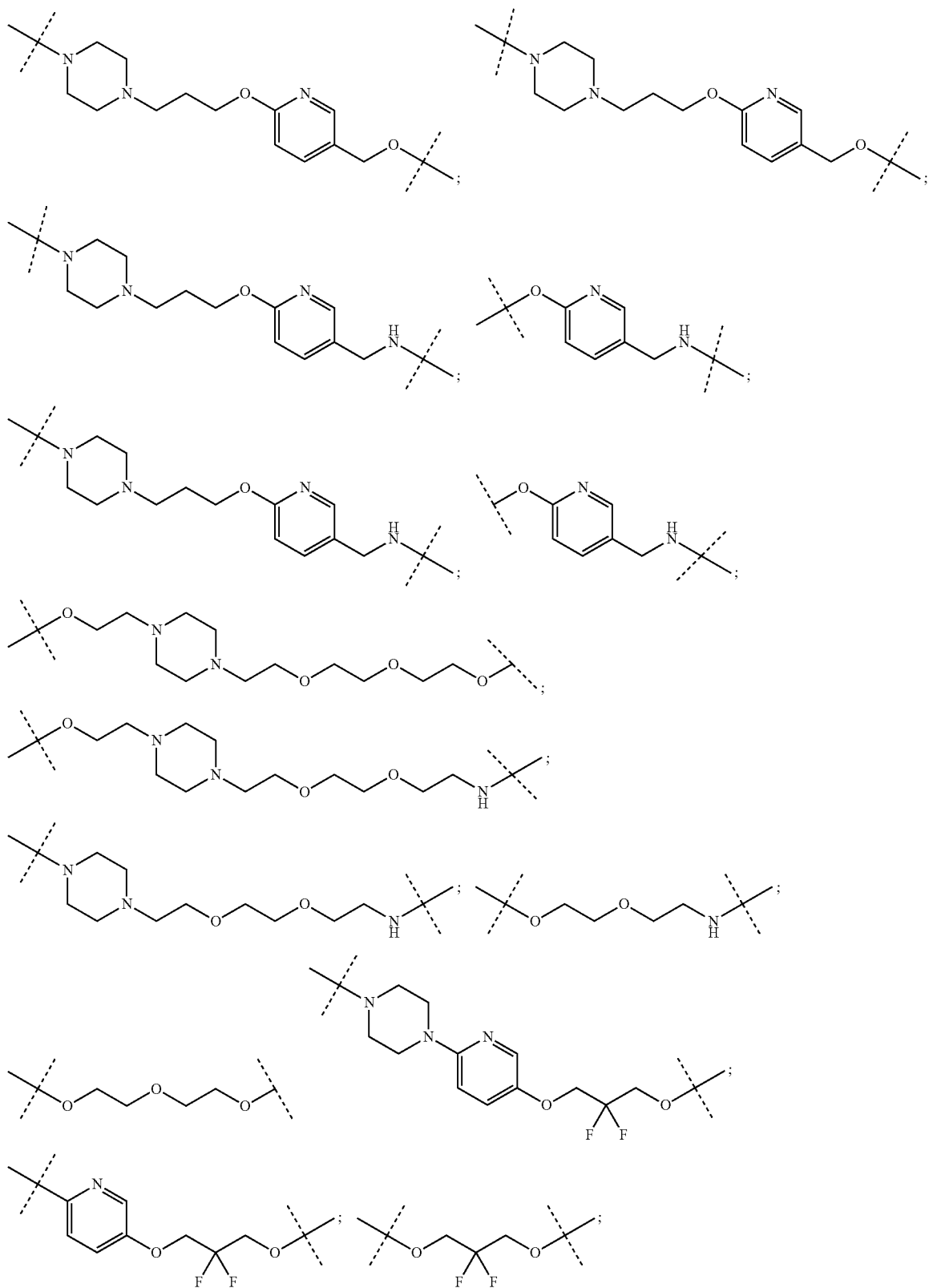

-continued
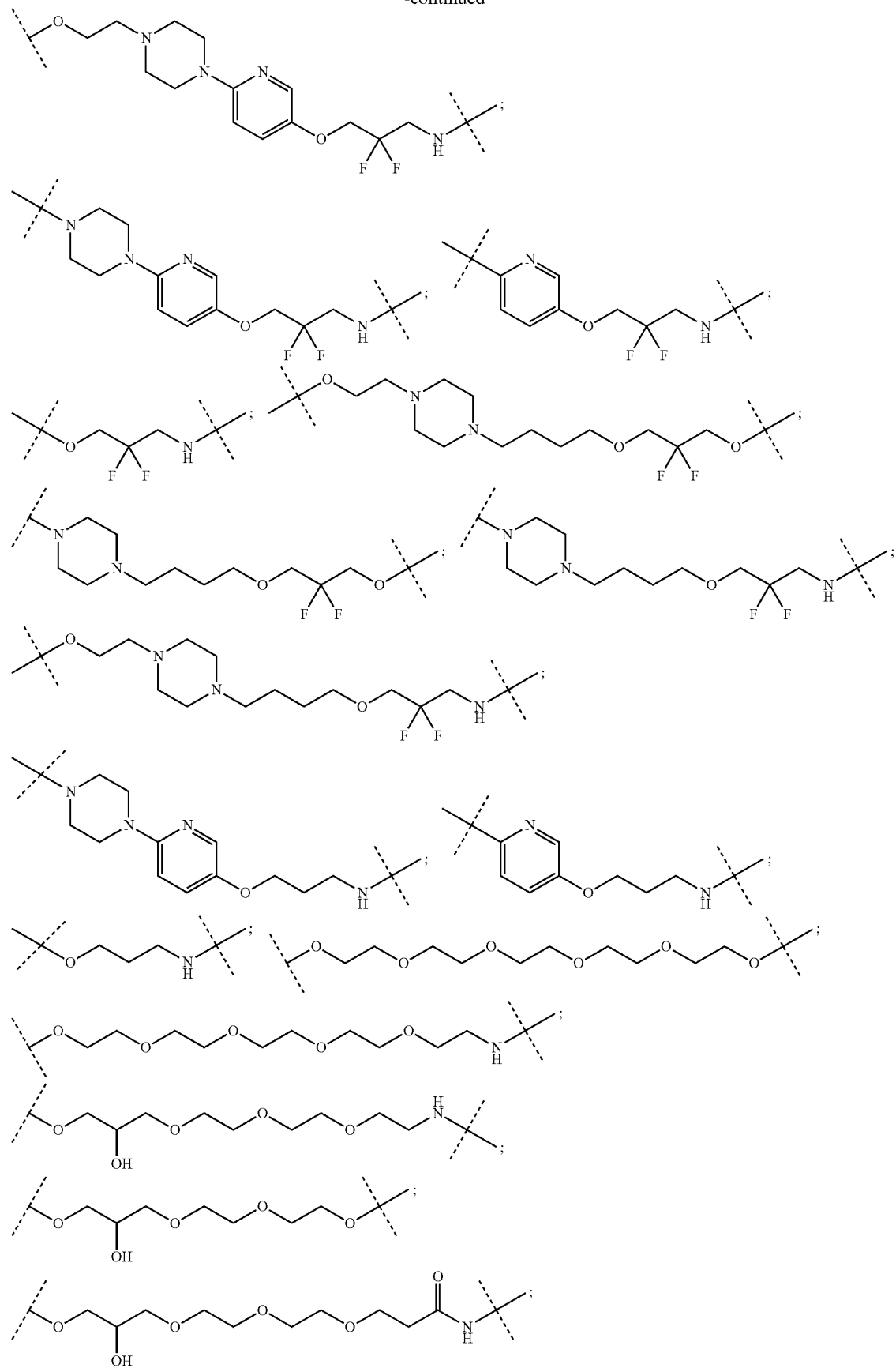

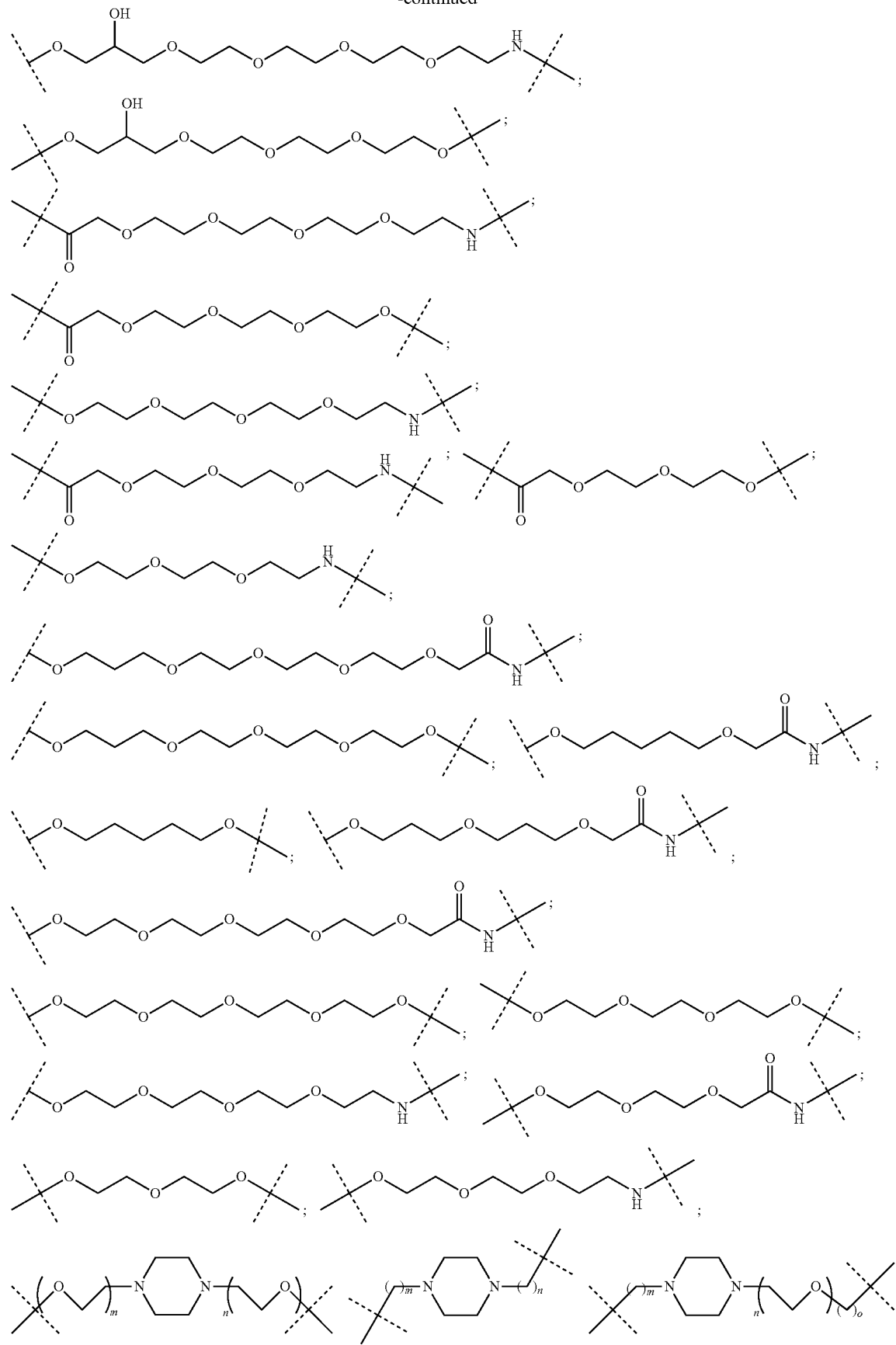

-continued
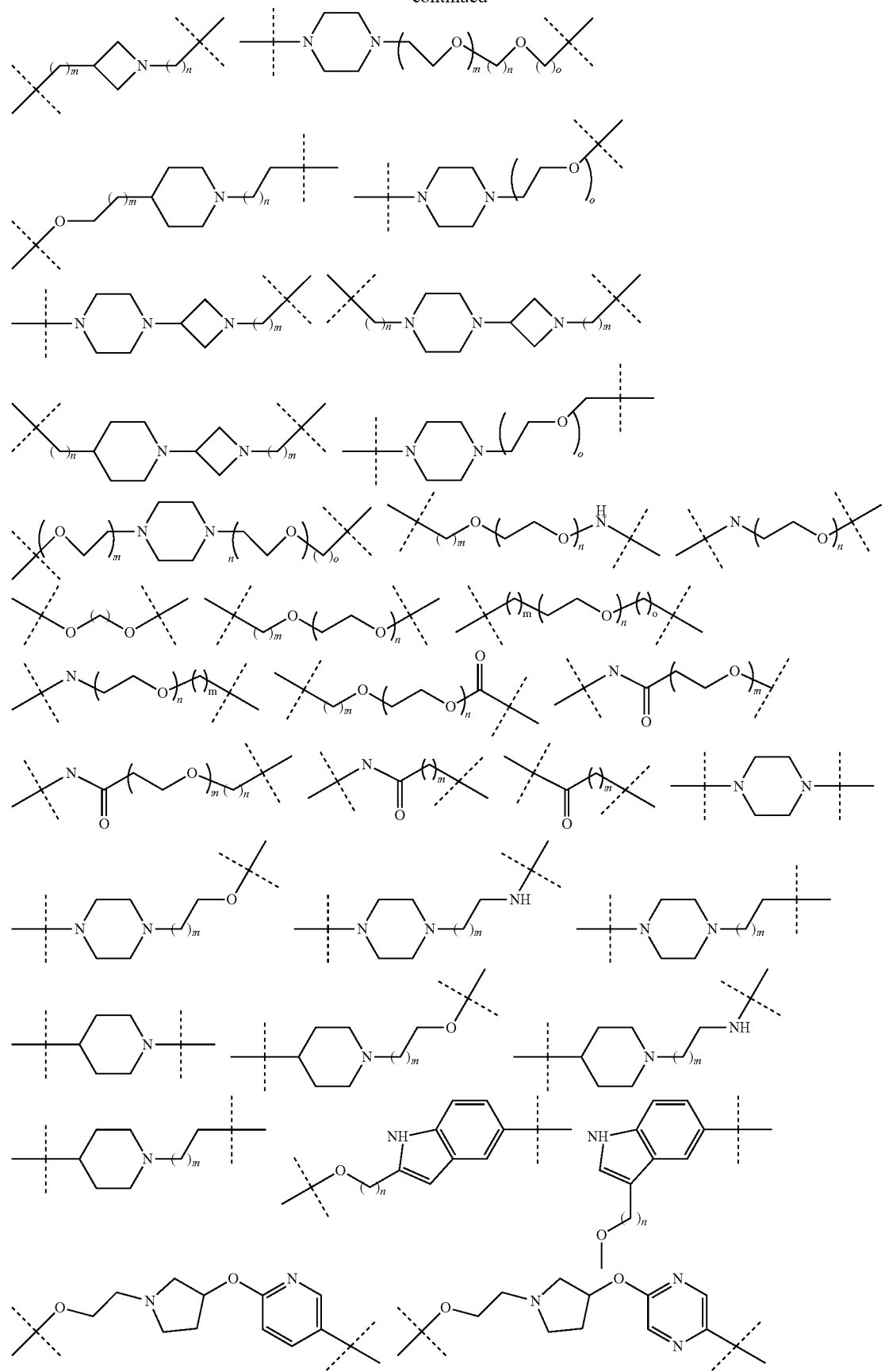

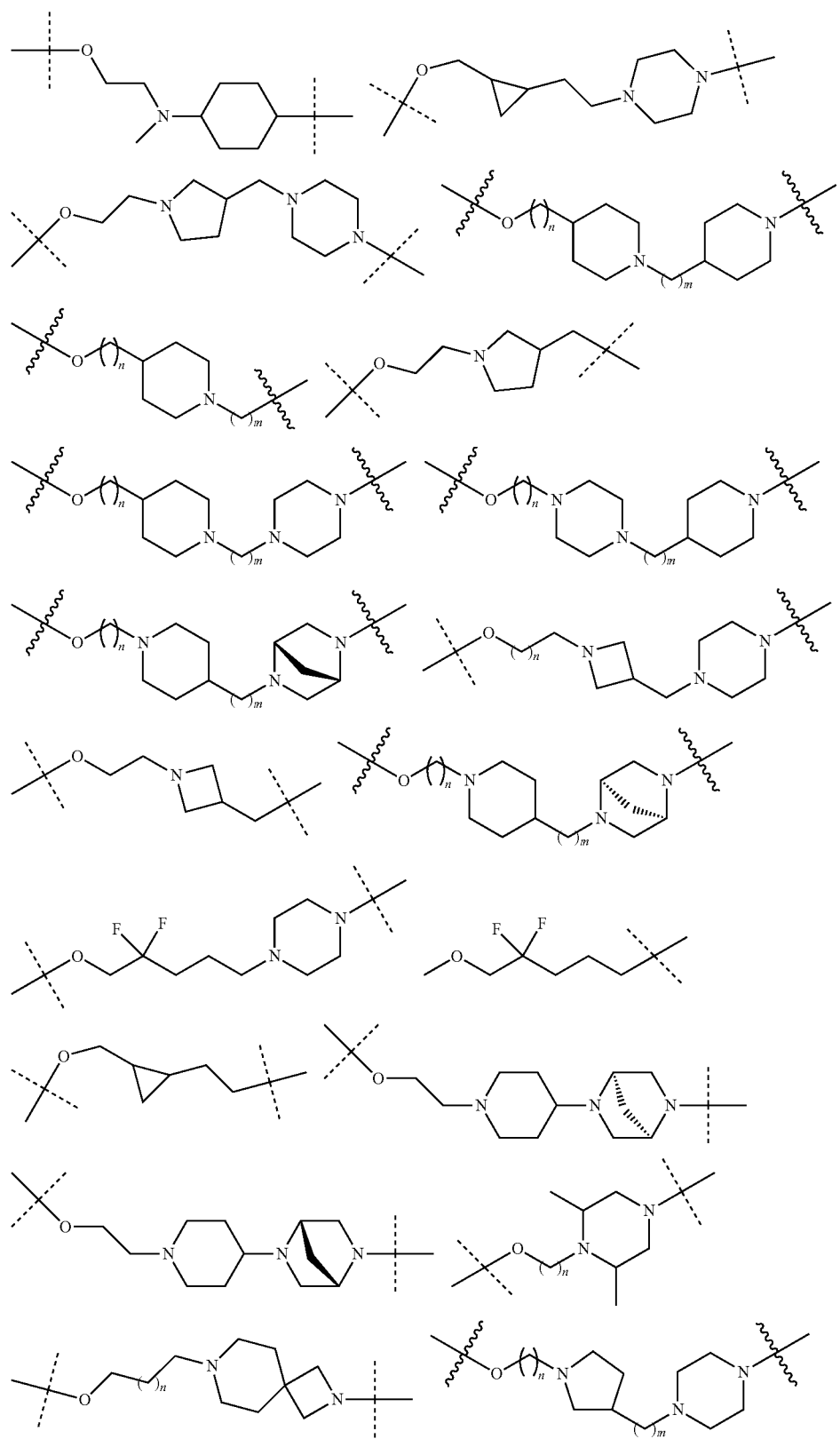

-continued
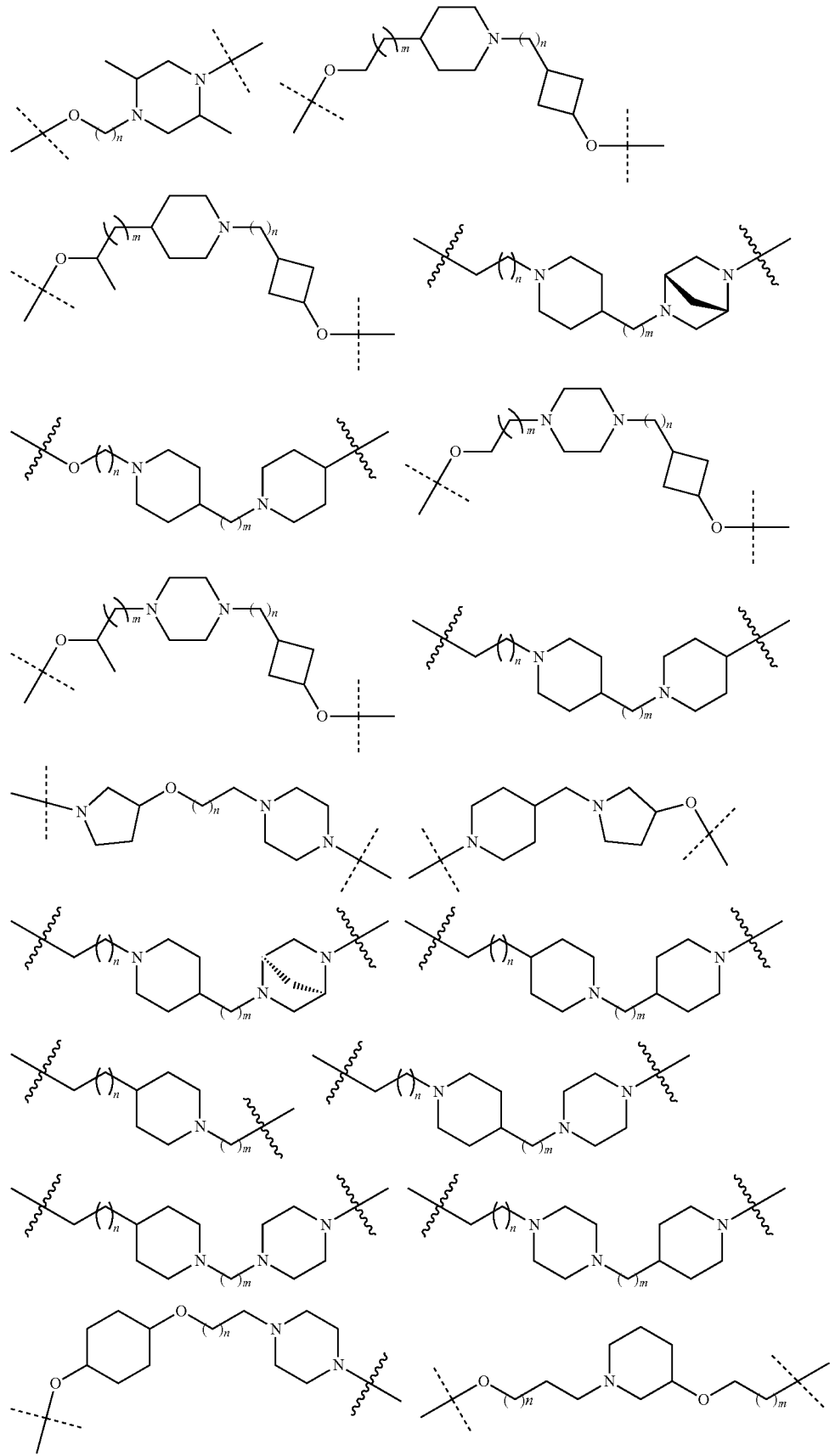

-continued
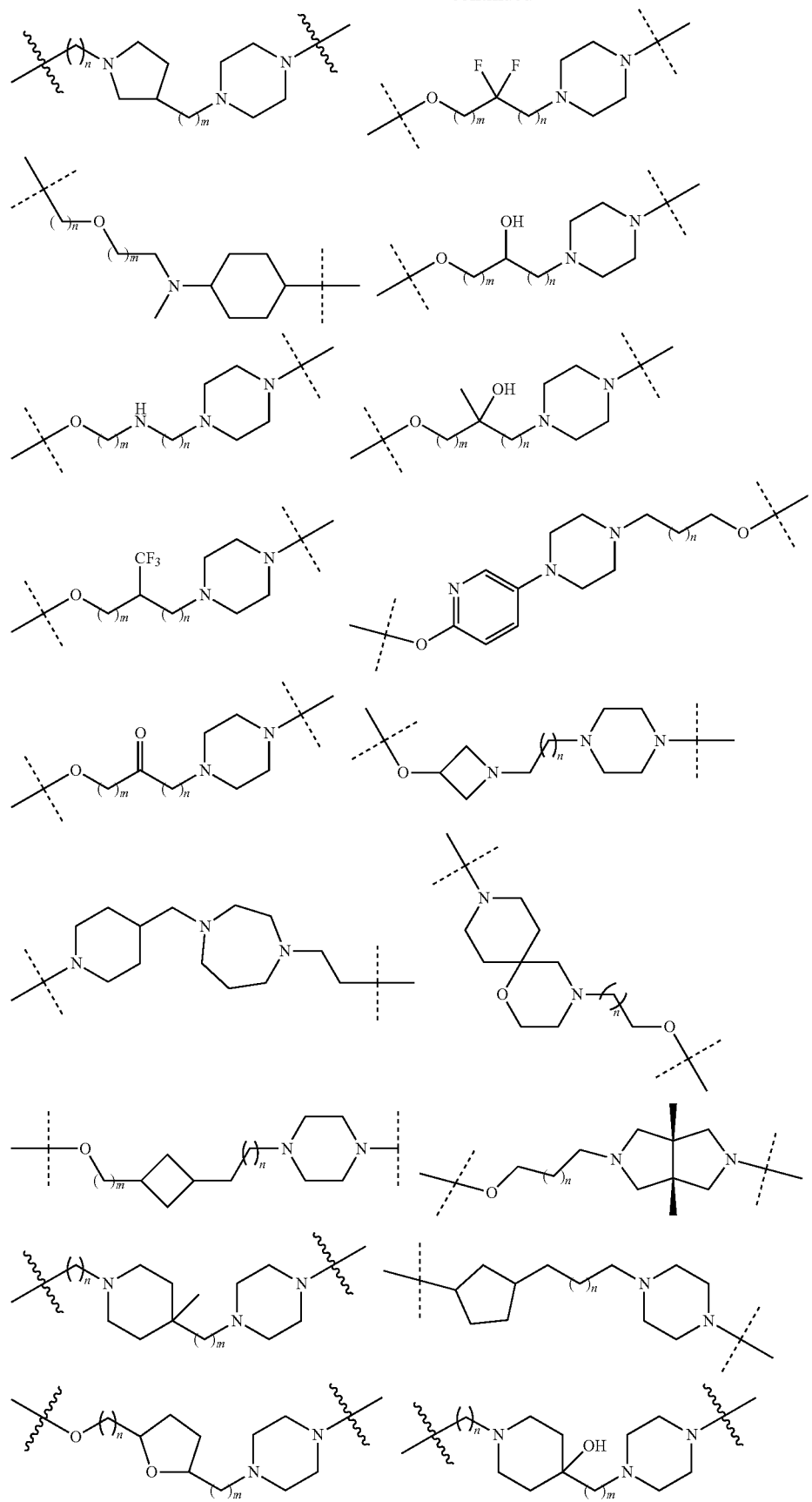

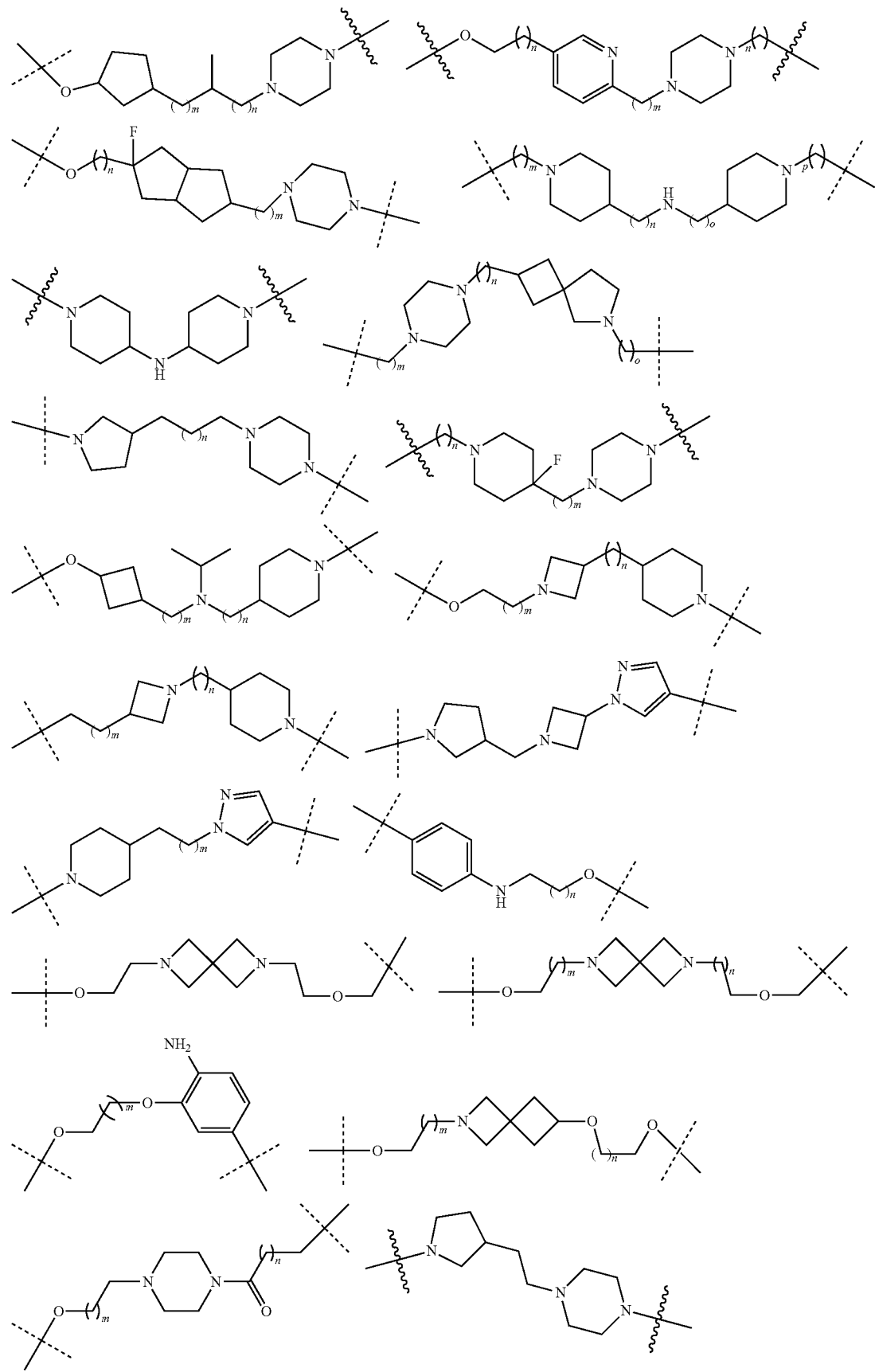

505 -continued 506
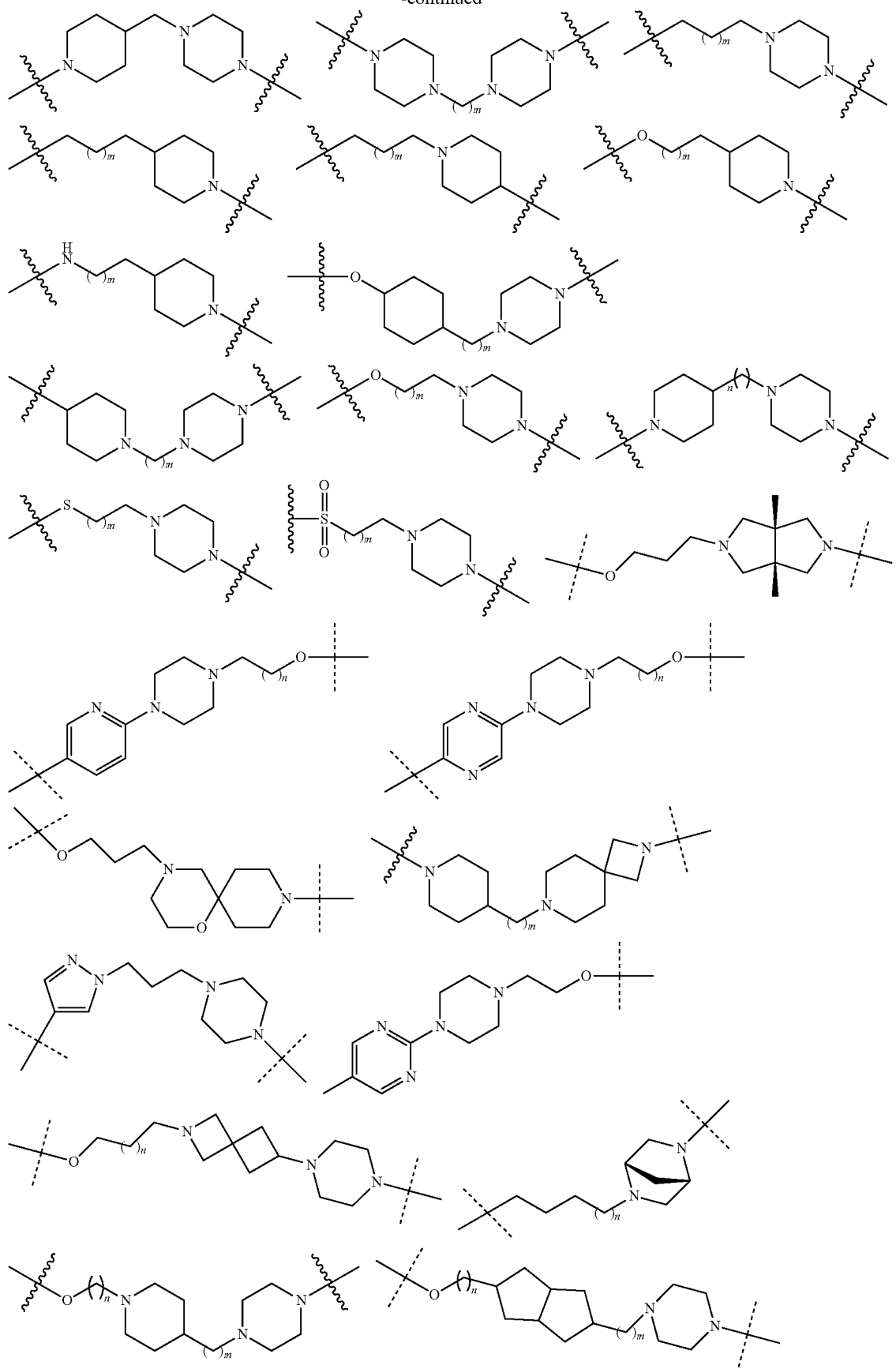

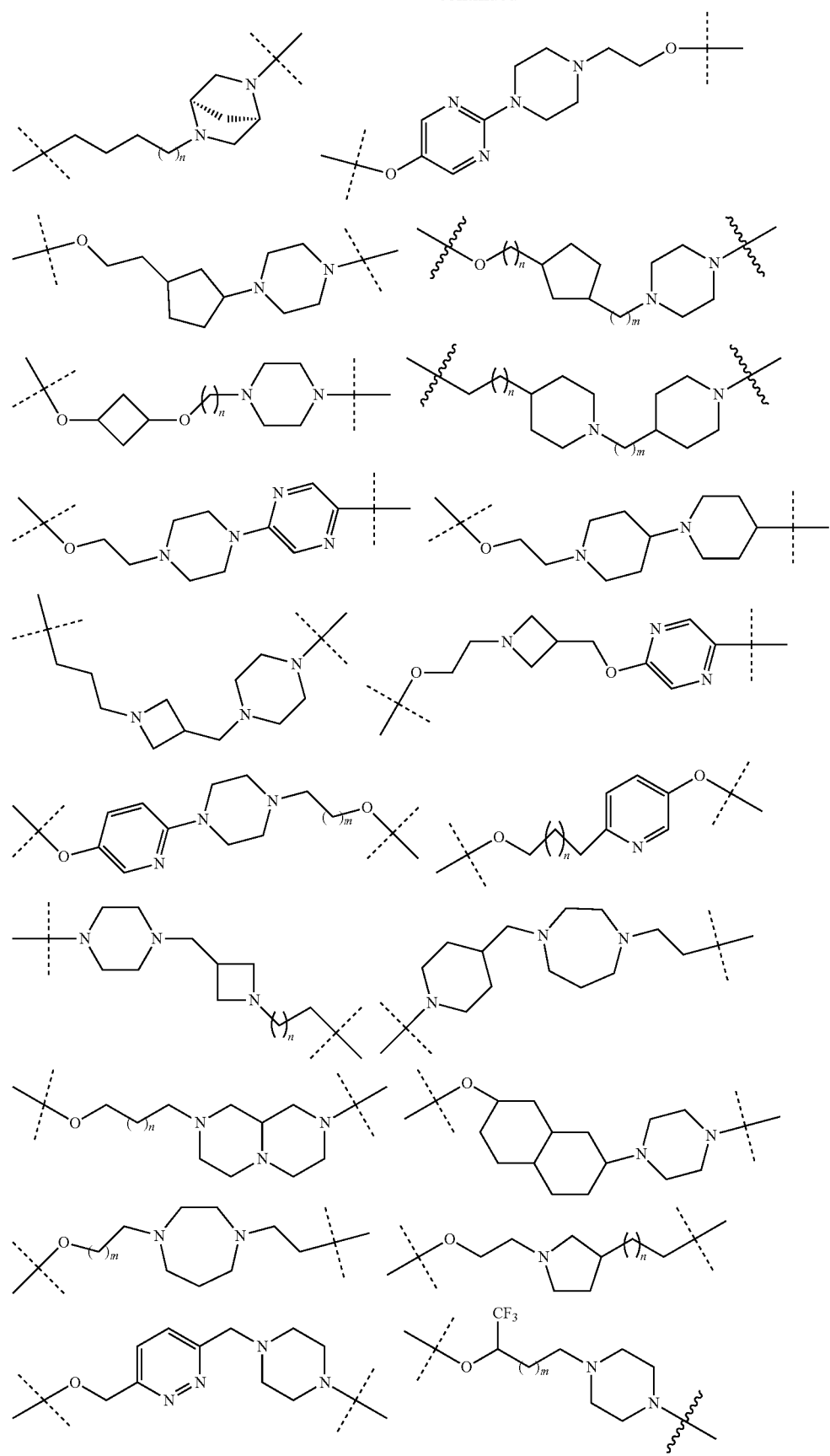

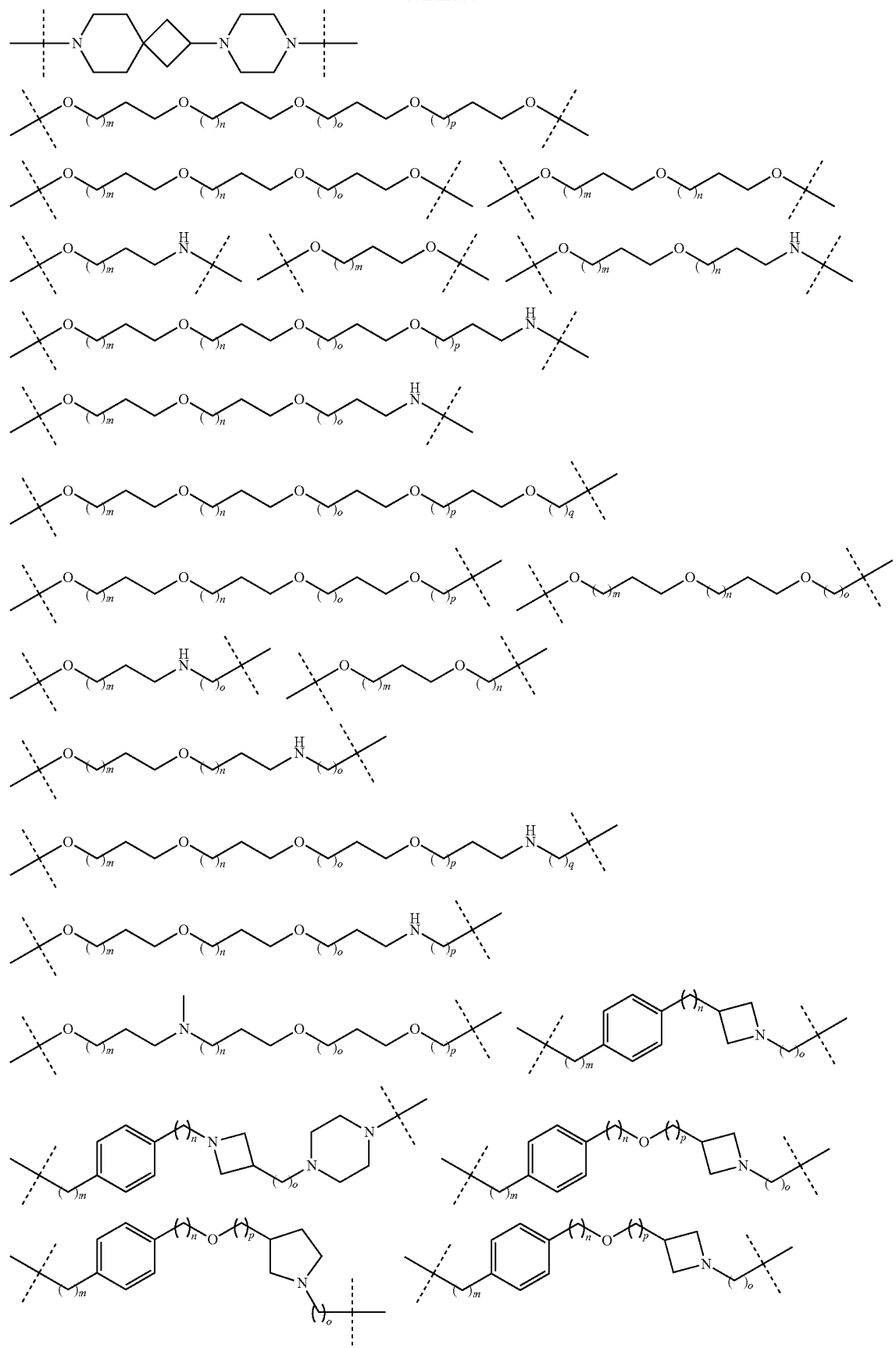

-continued
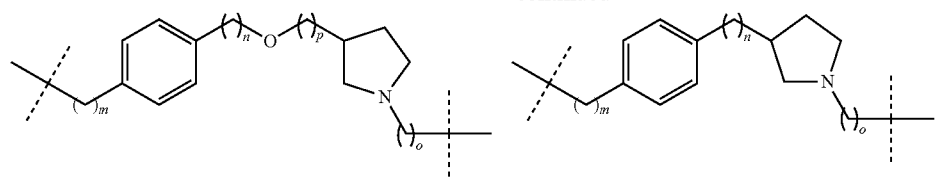
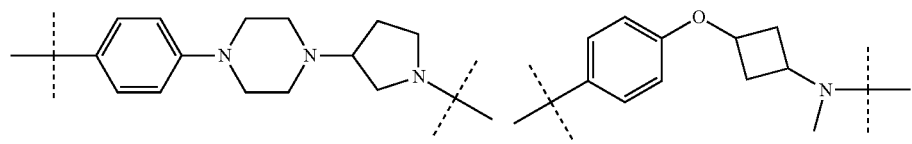
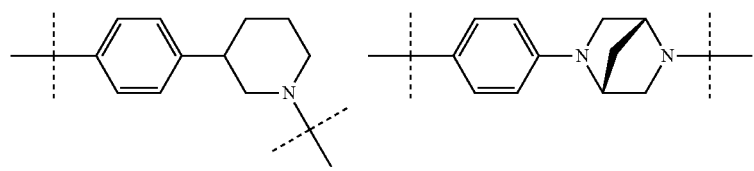
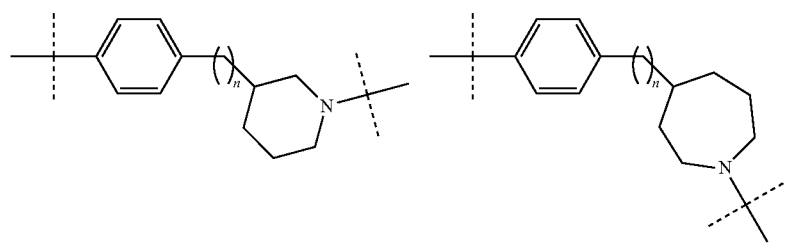
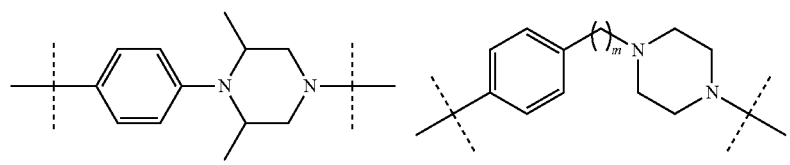
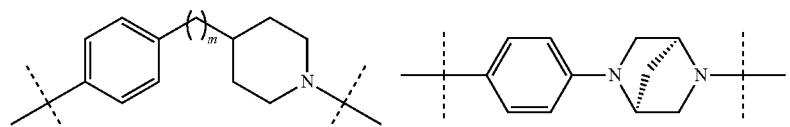
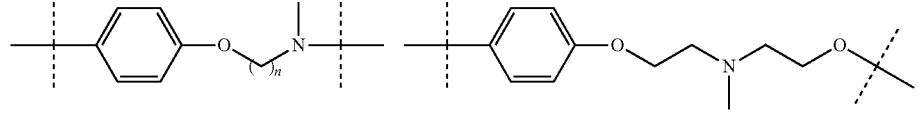
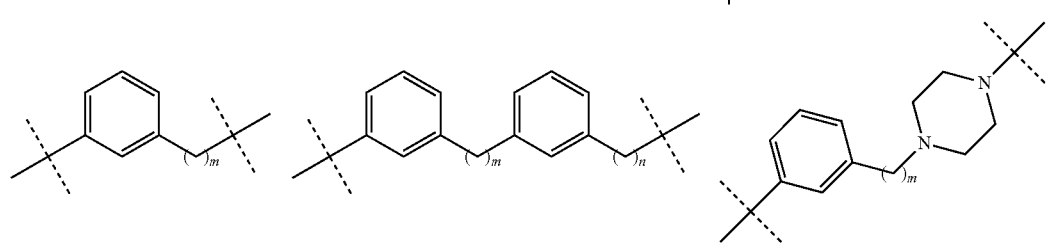
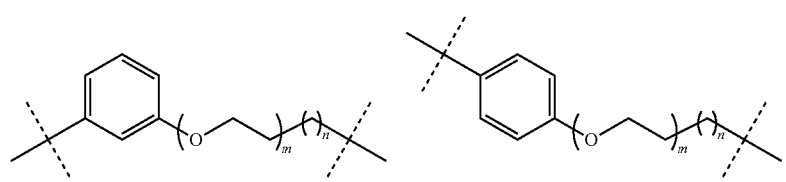

-continued
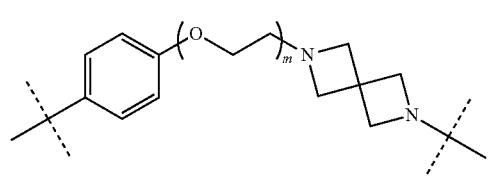
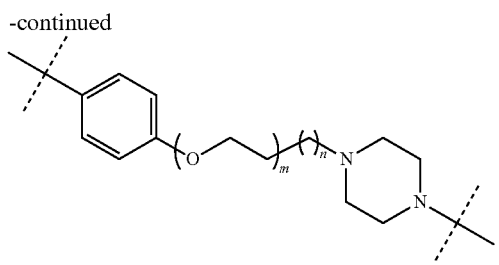
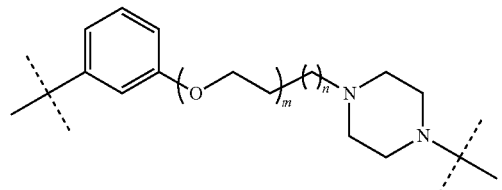
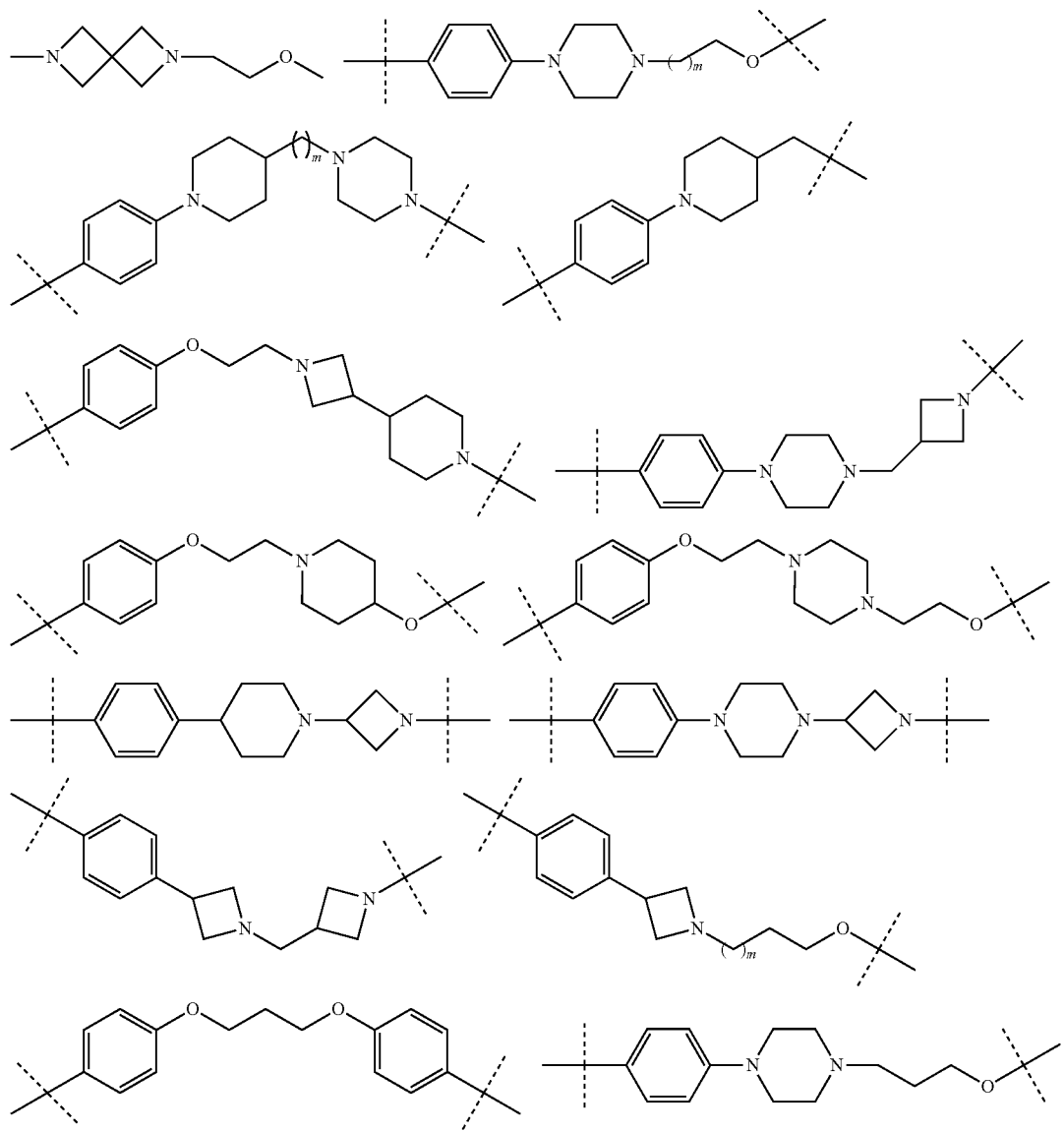

515 516
-continued
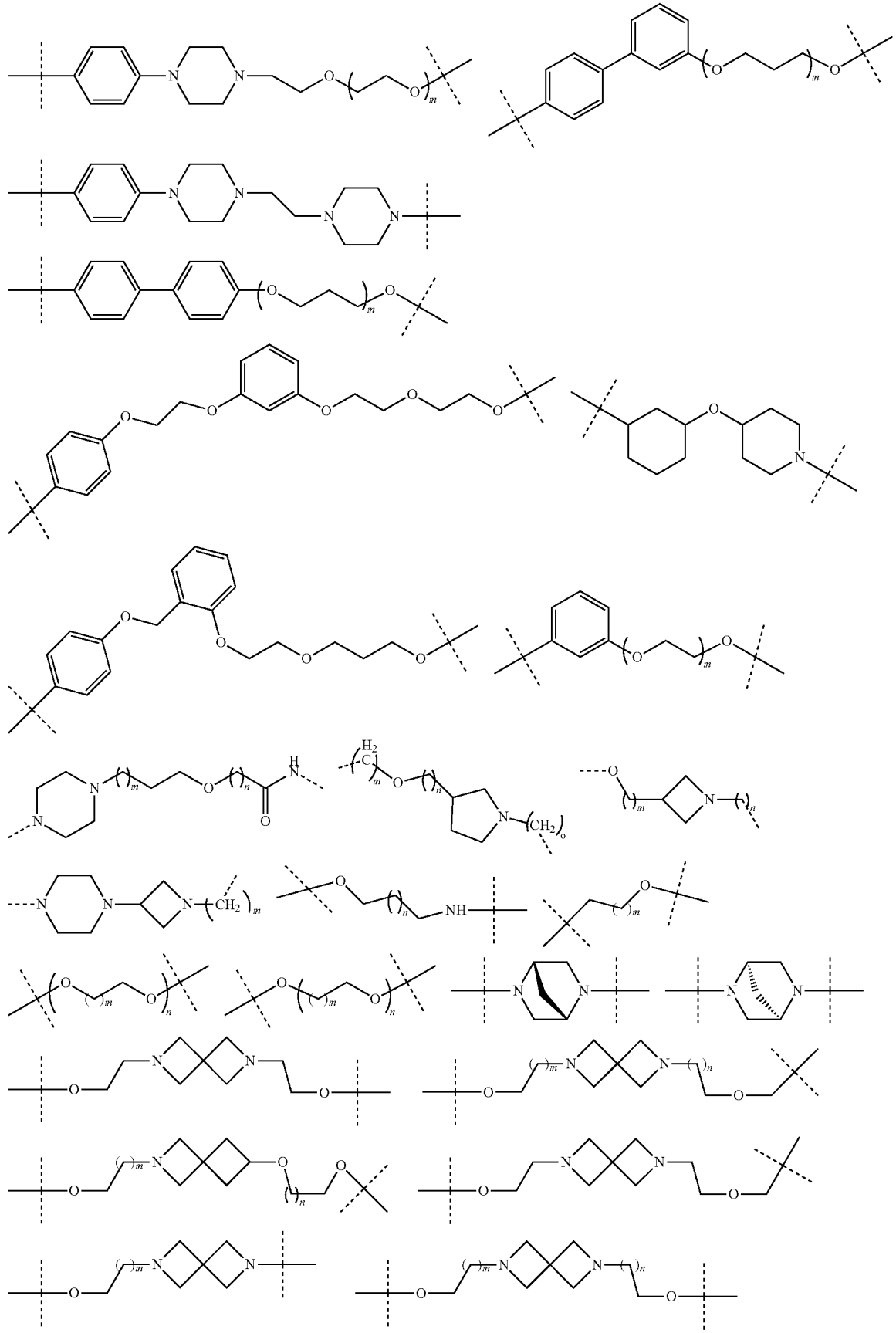

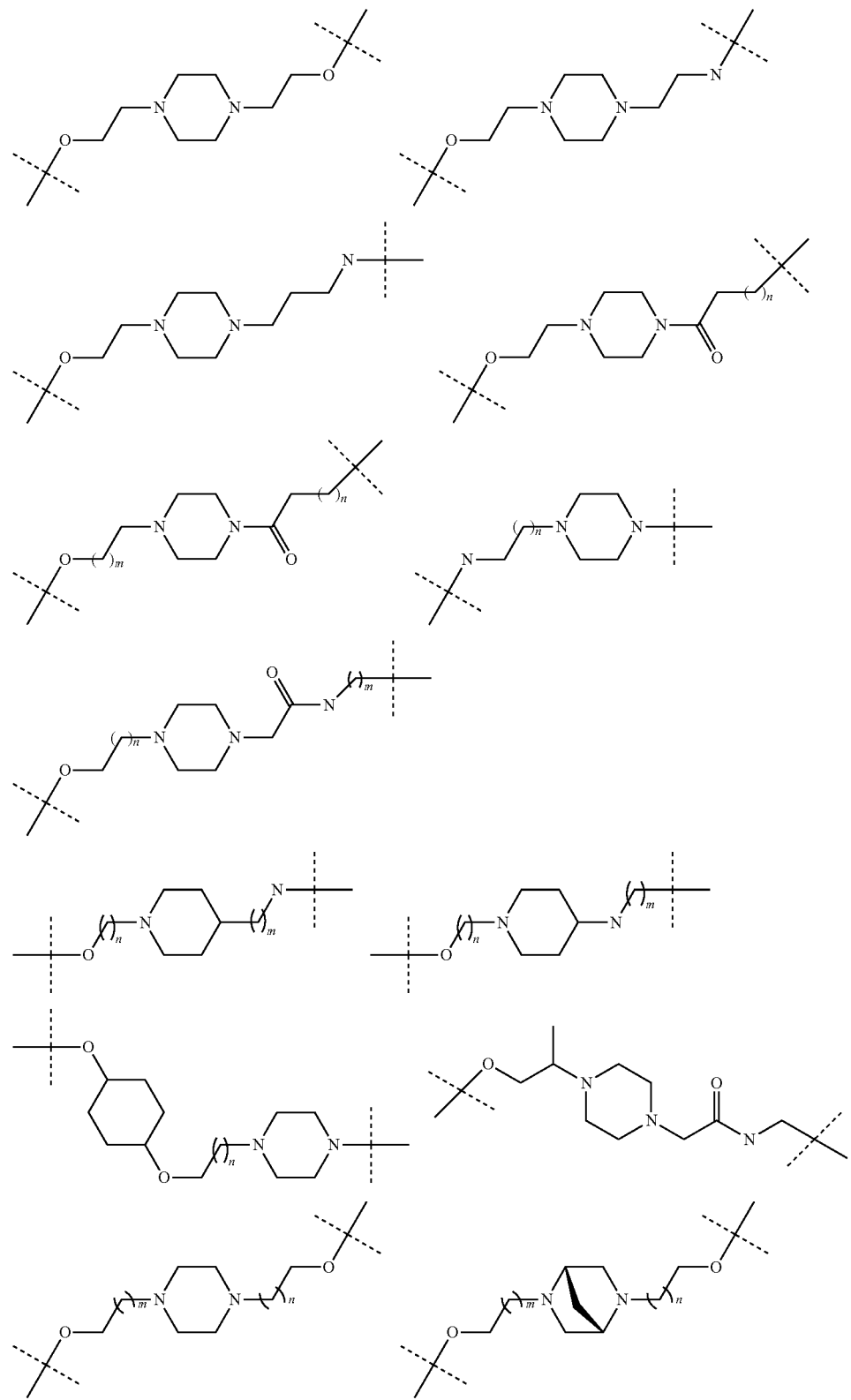

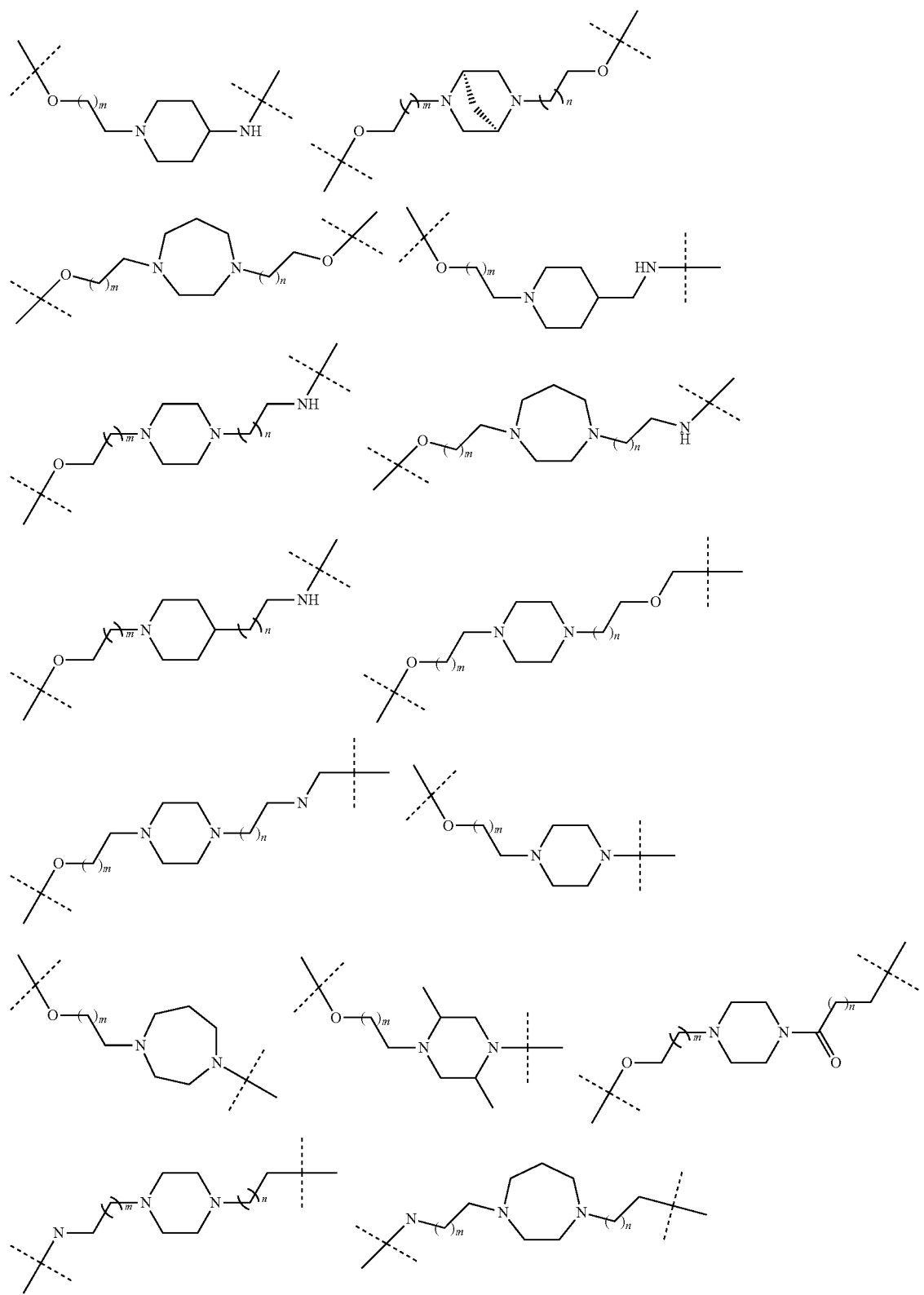

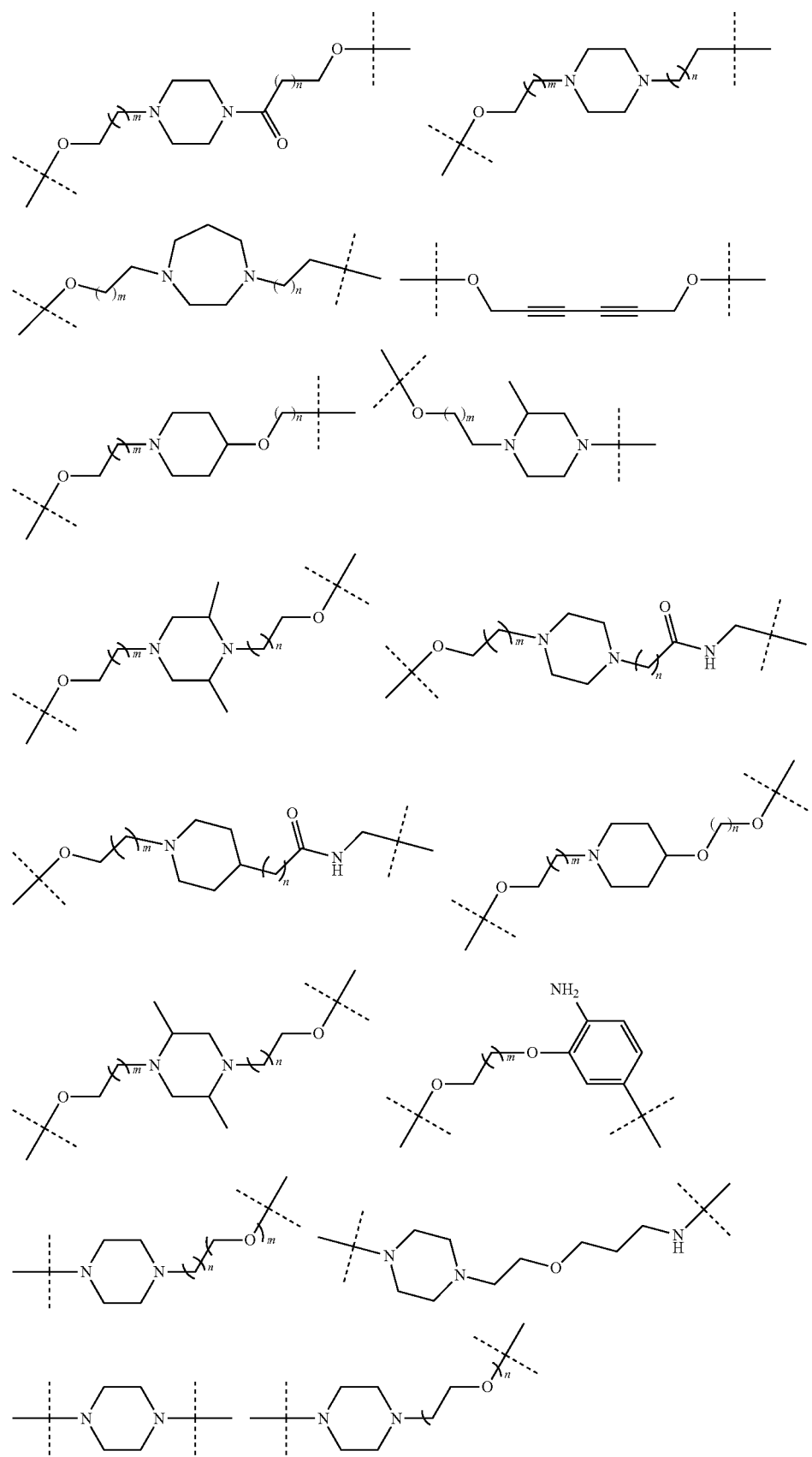

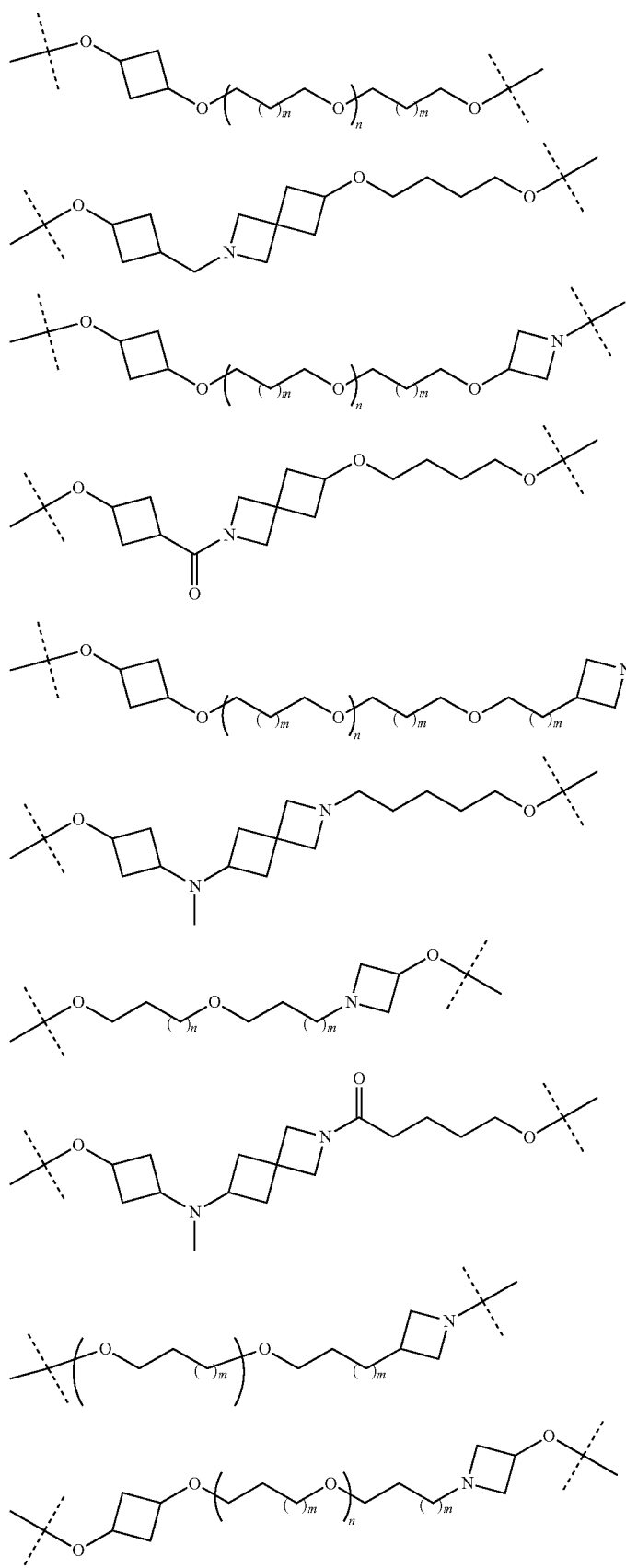

-continued
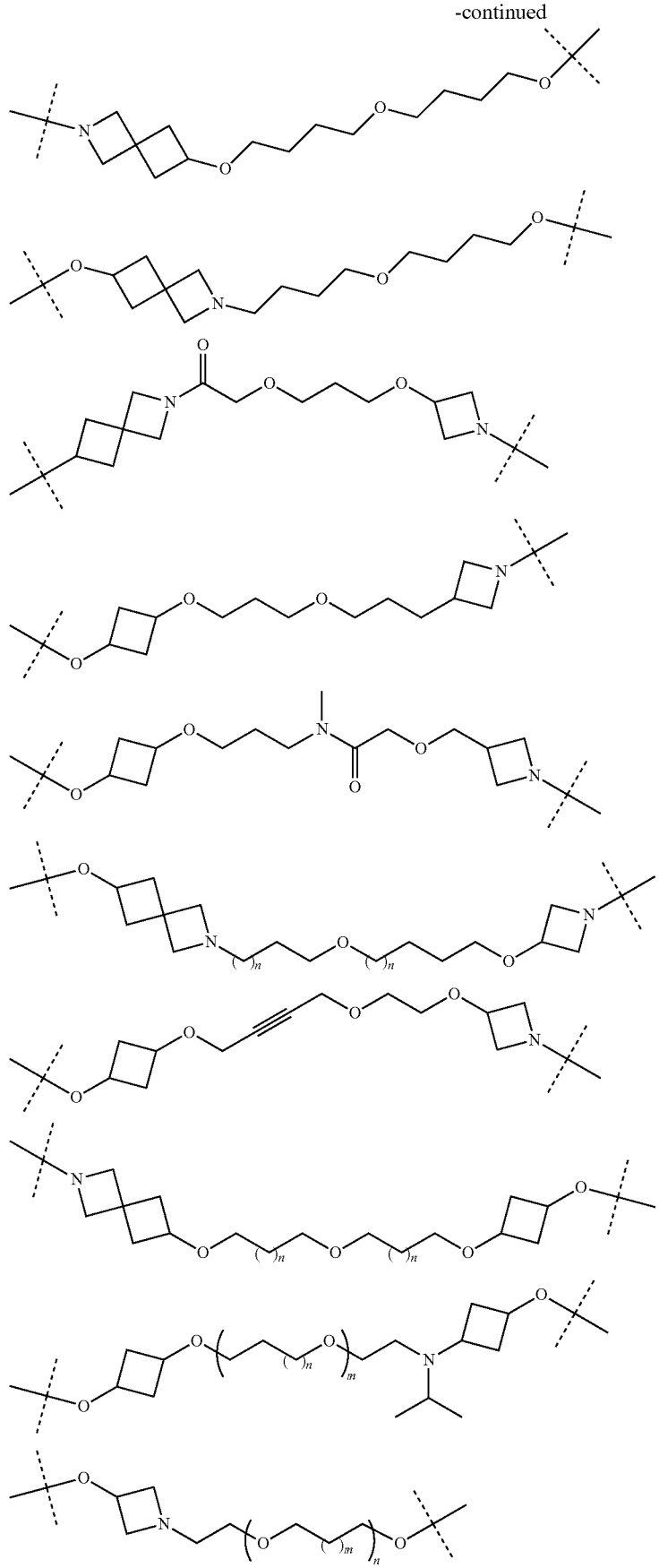

-continued
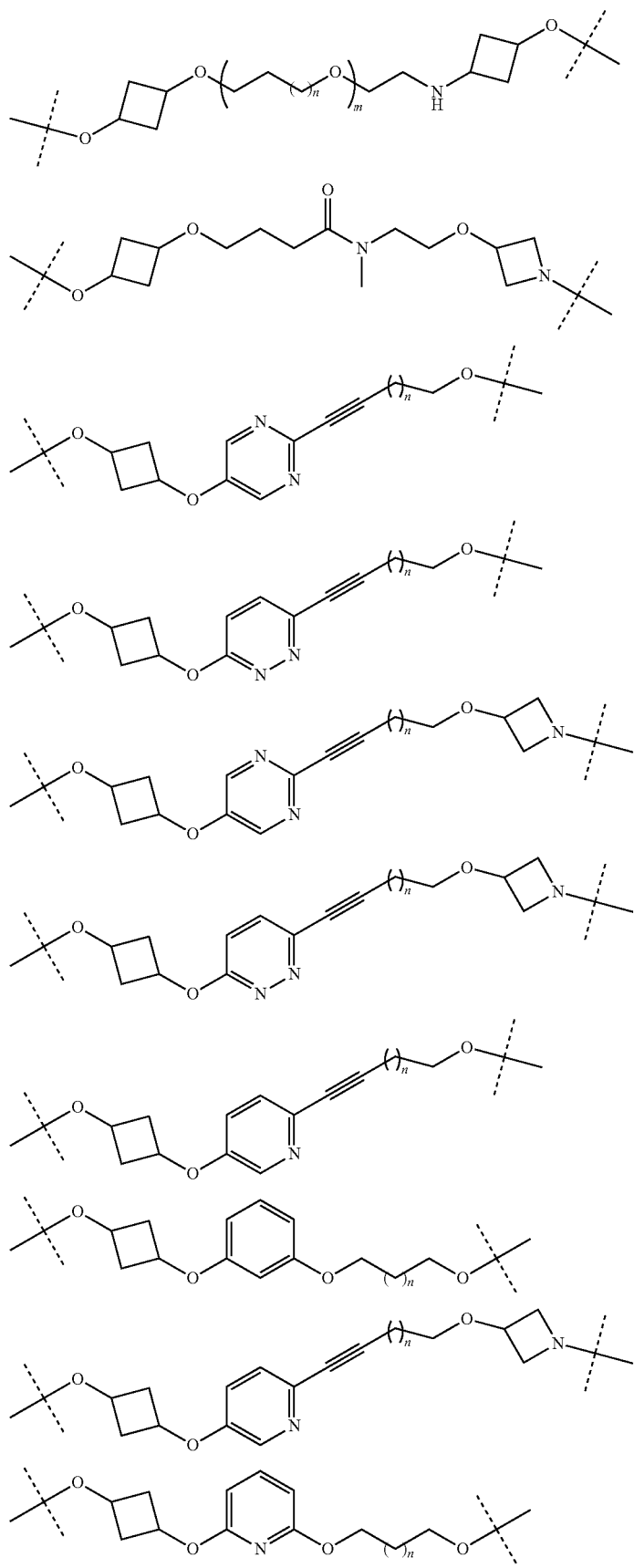

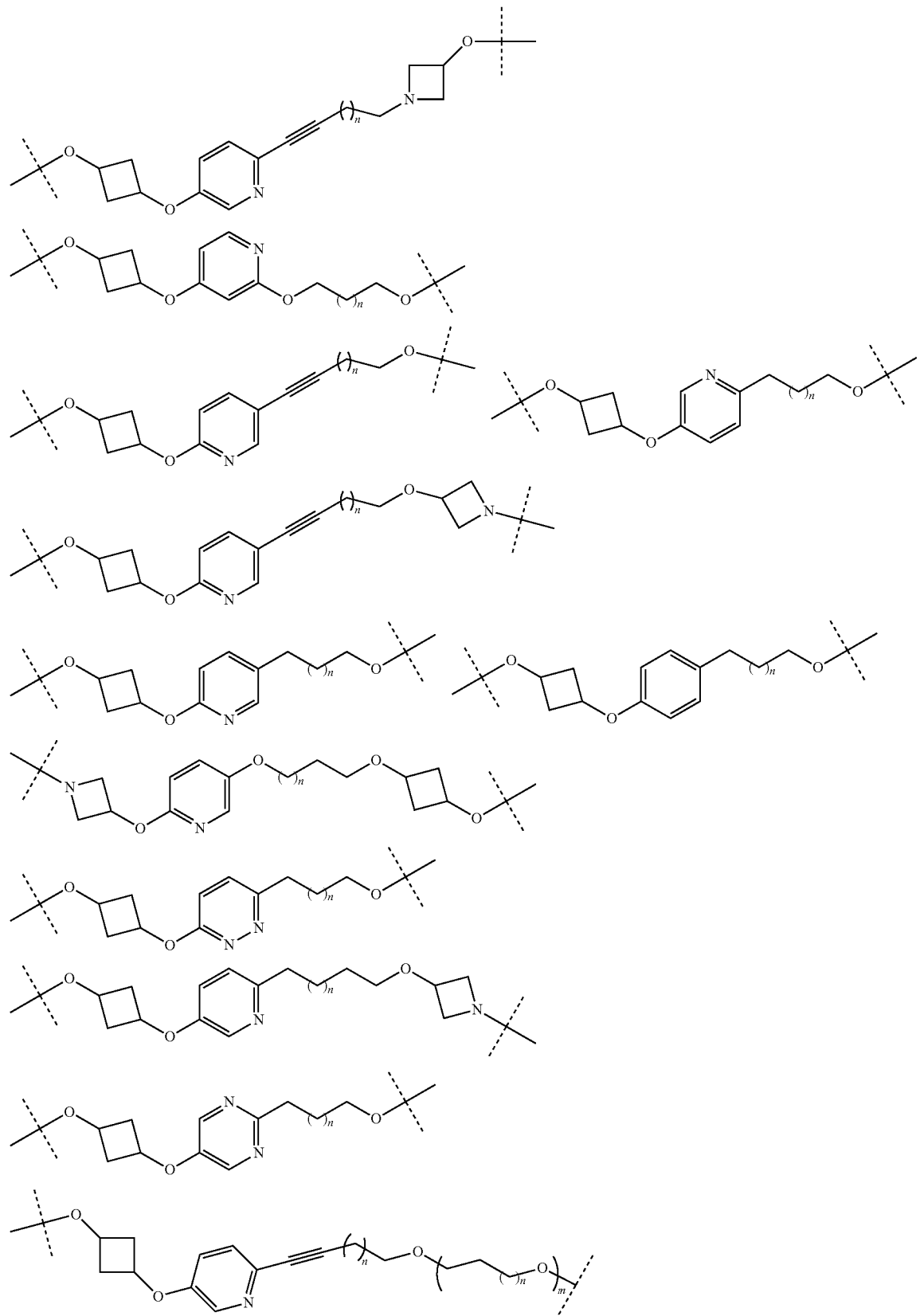

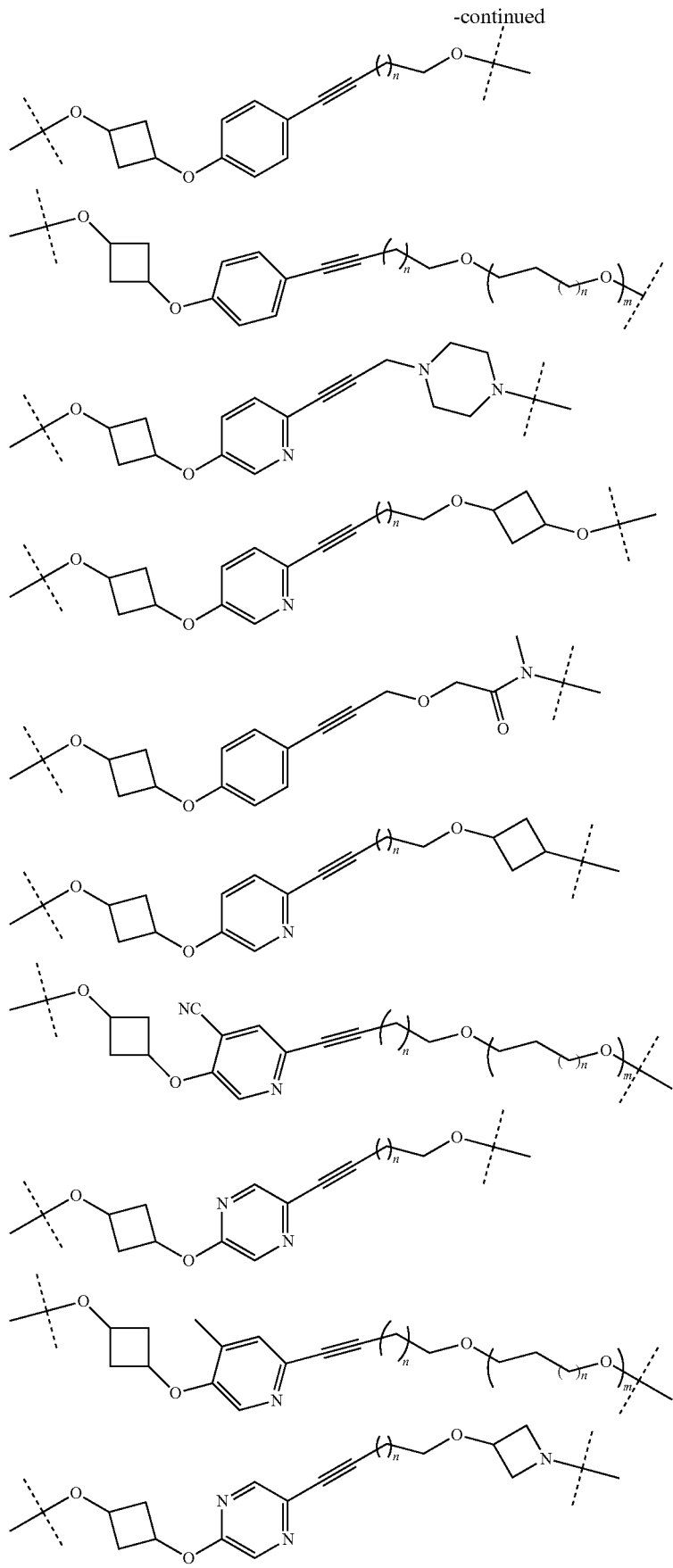

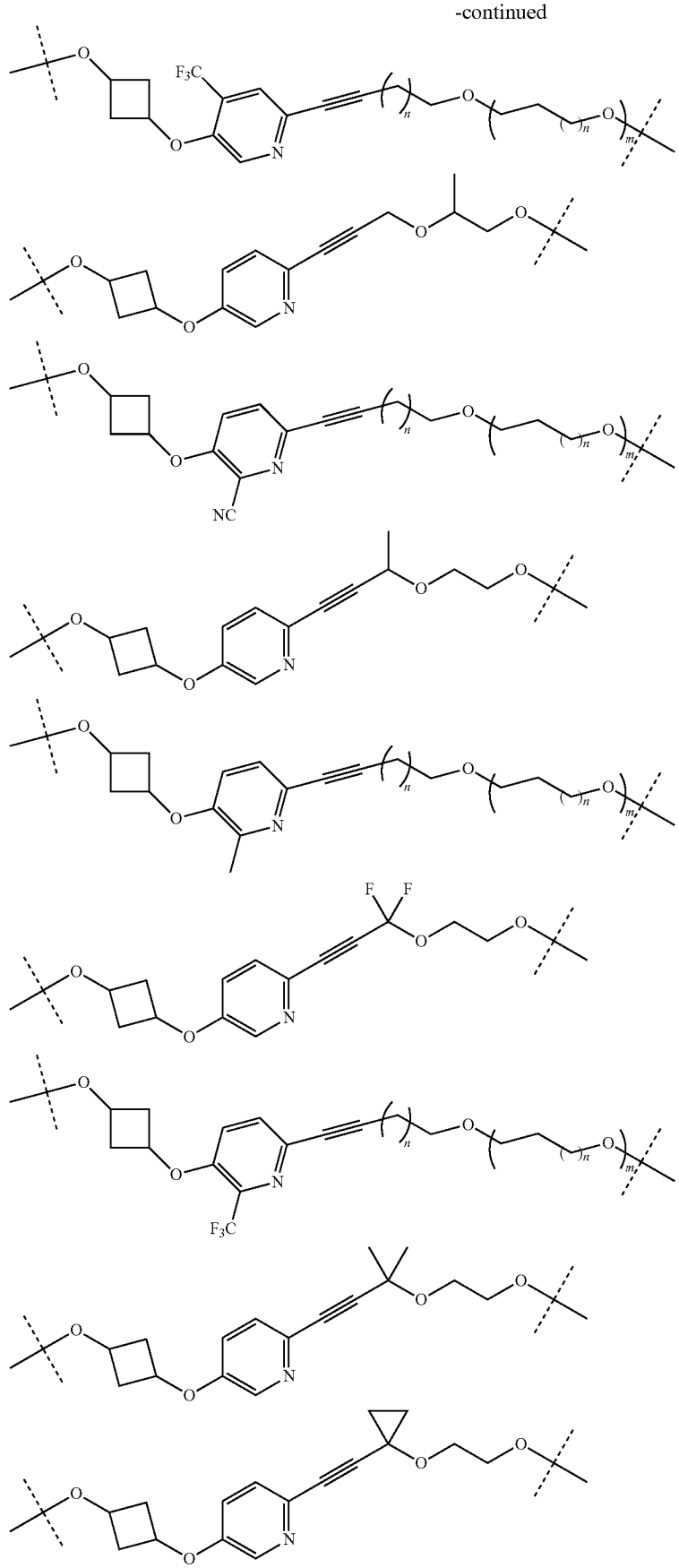

-continued
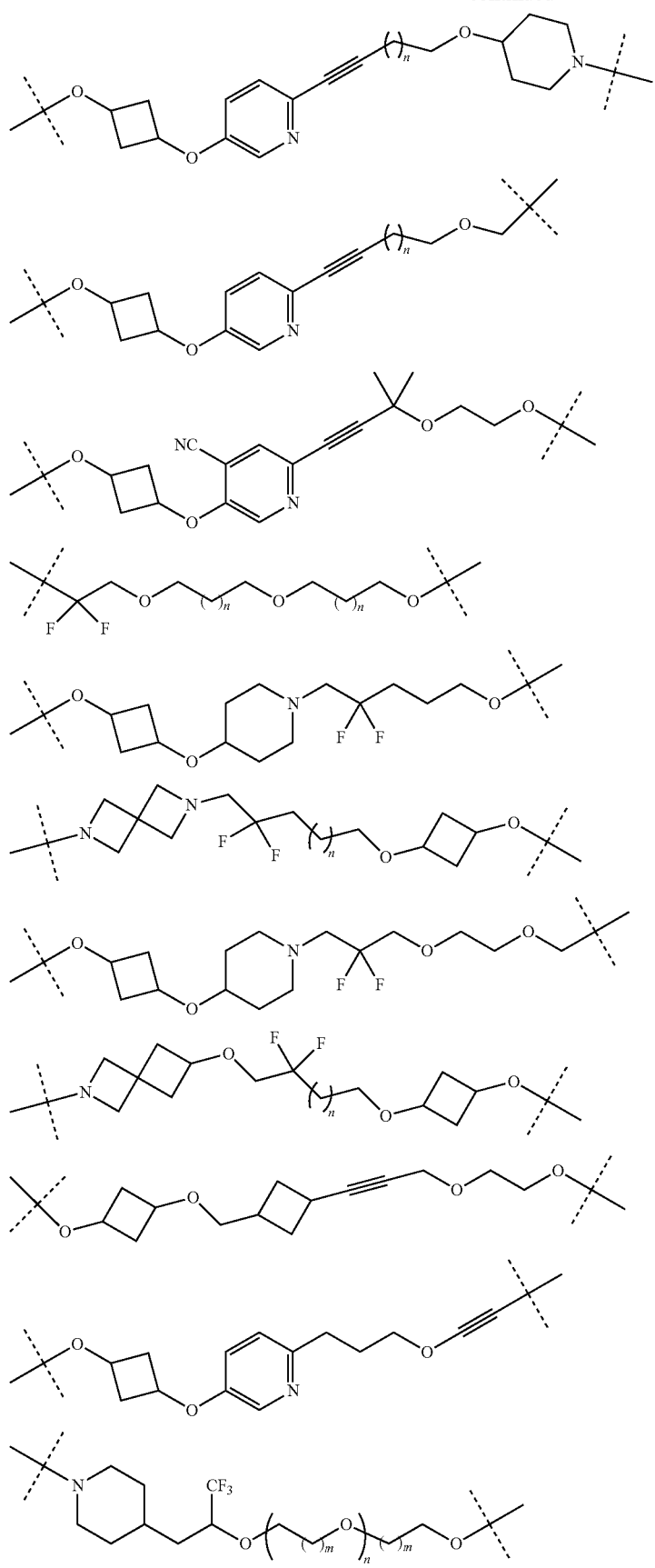

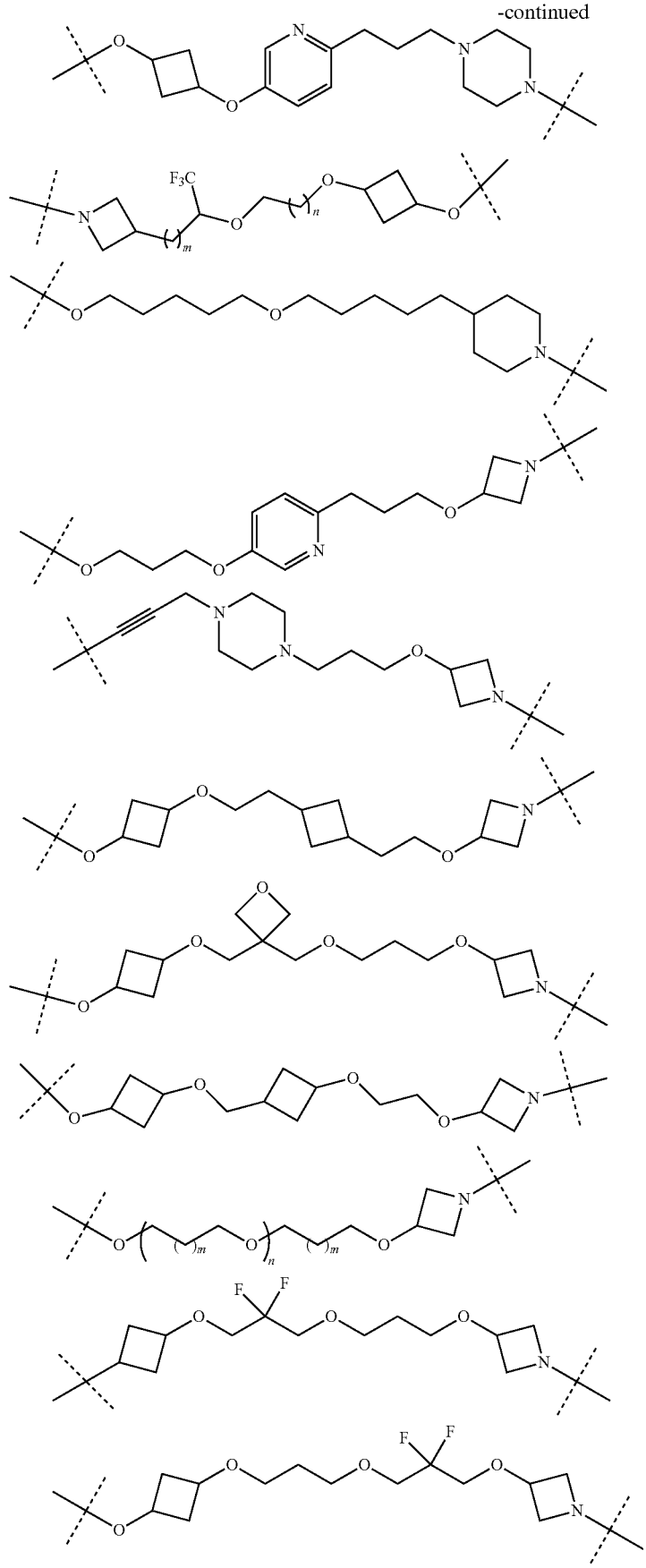

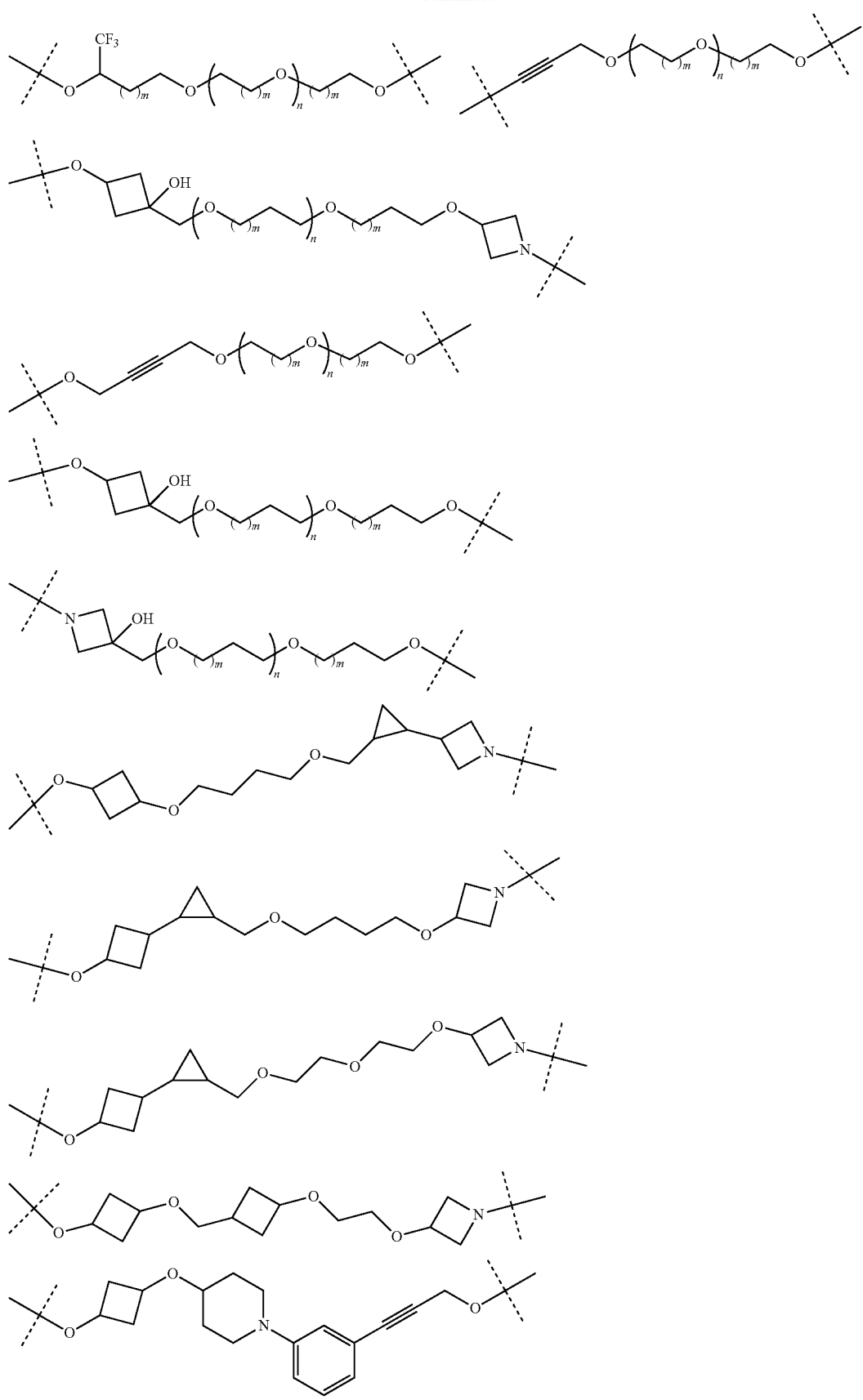

-continued
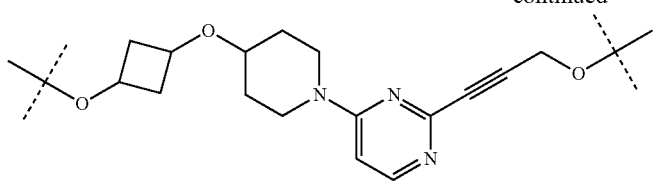
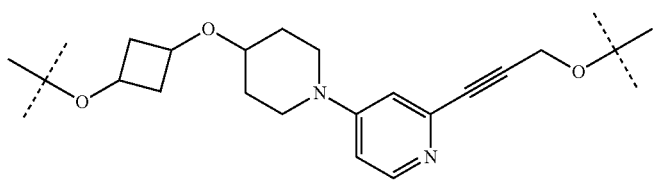
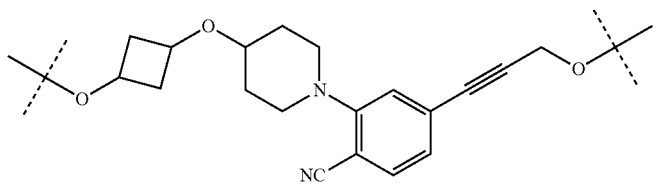
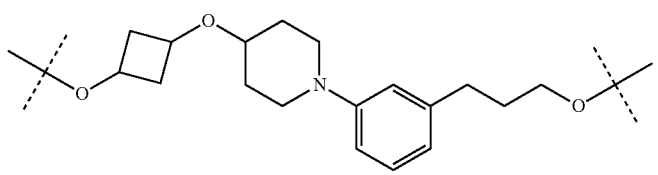
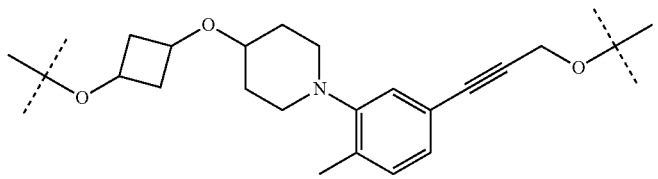
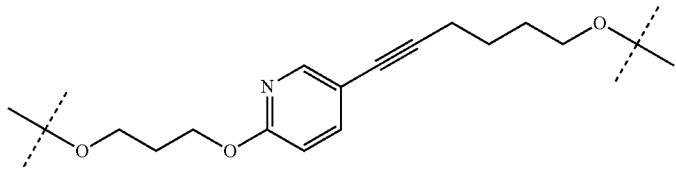
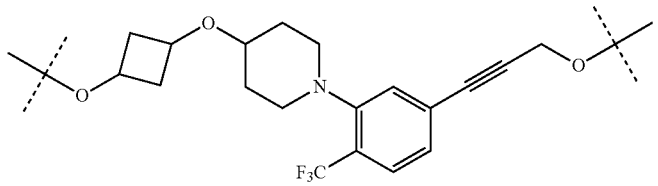
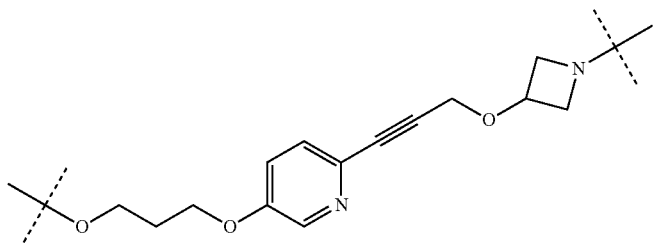
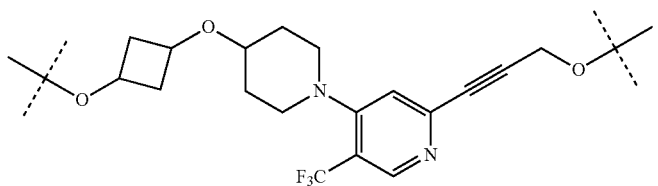

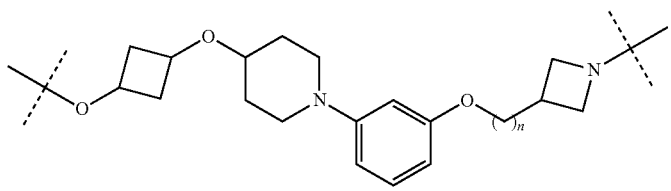
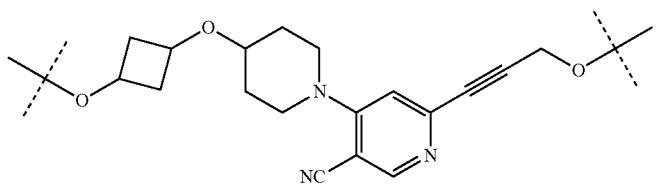
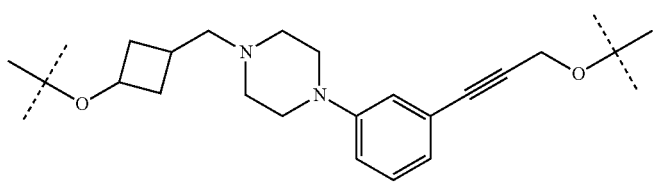
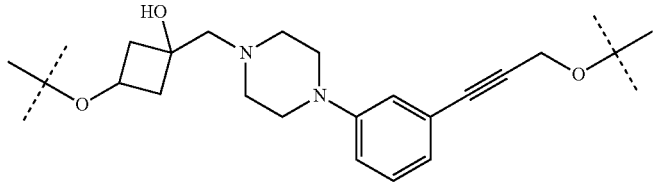
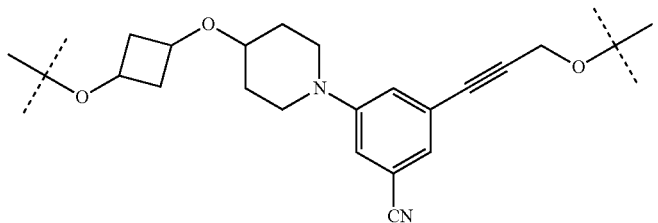
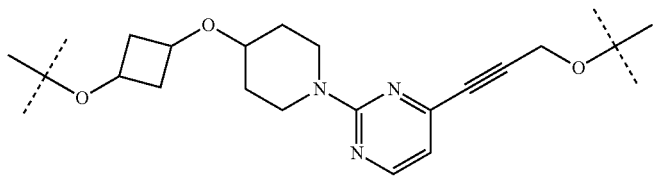
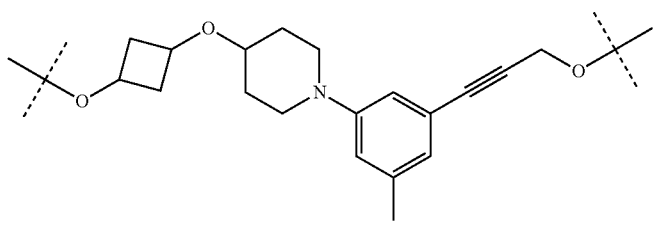
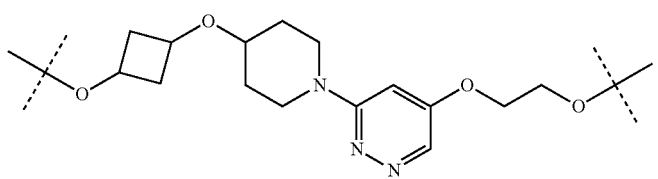

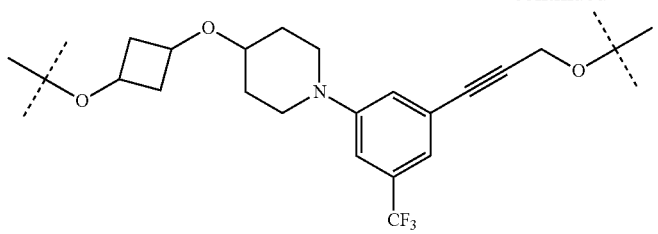
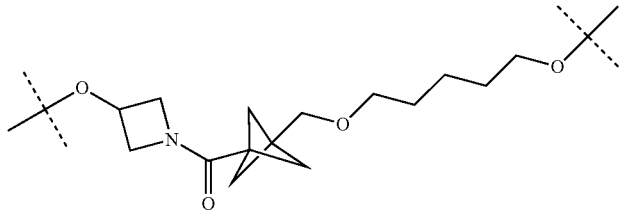
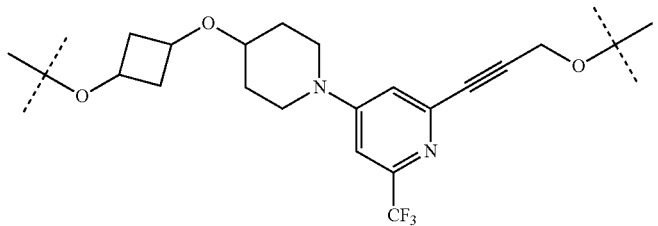
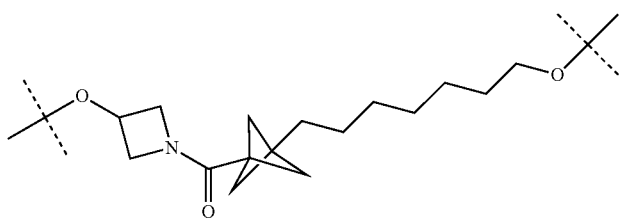
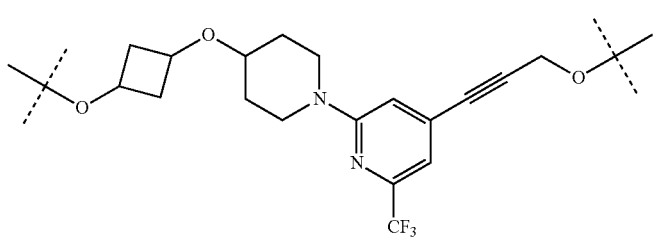
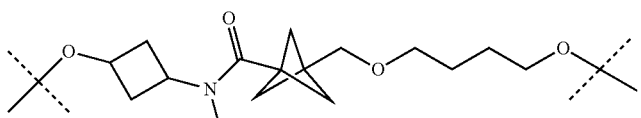
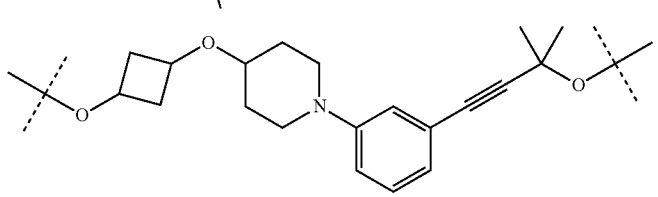
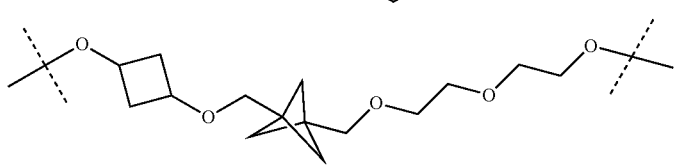

-continued
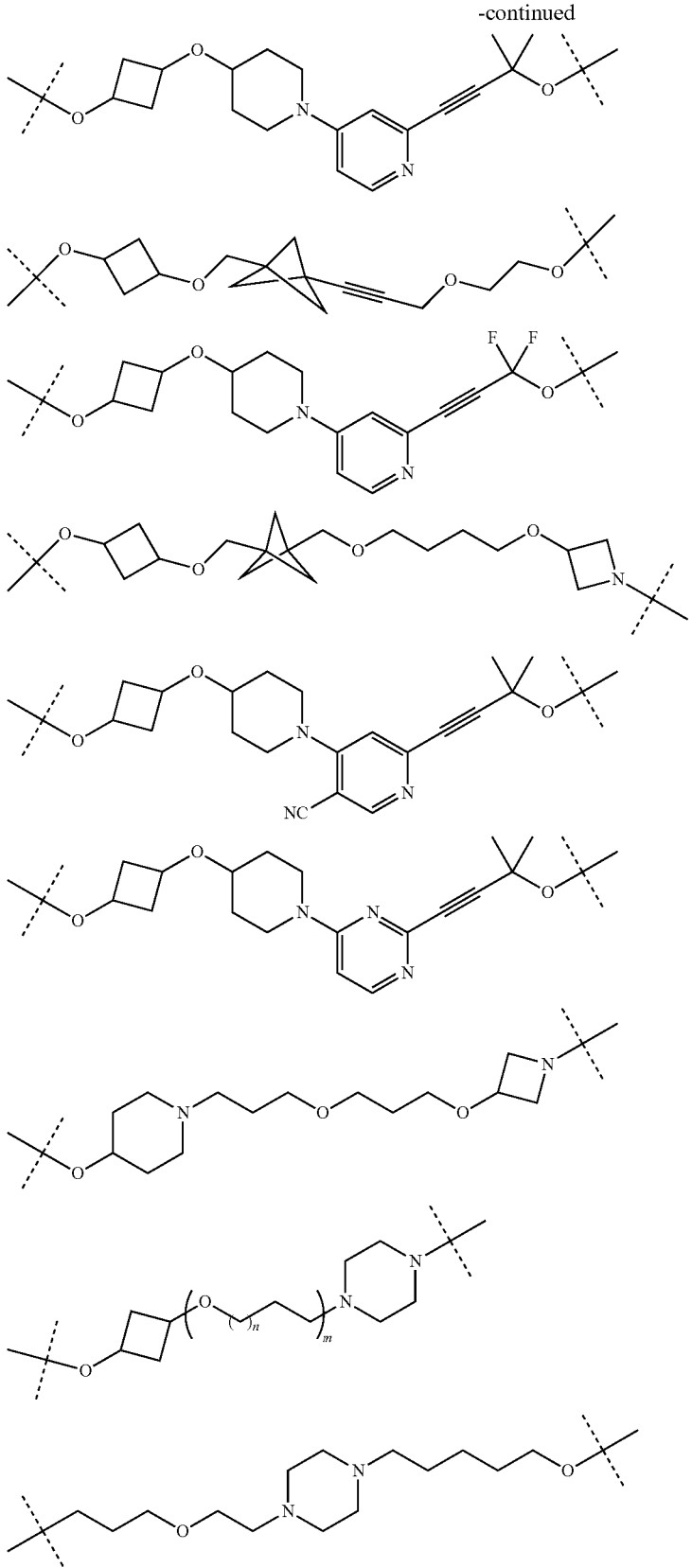

-continued
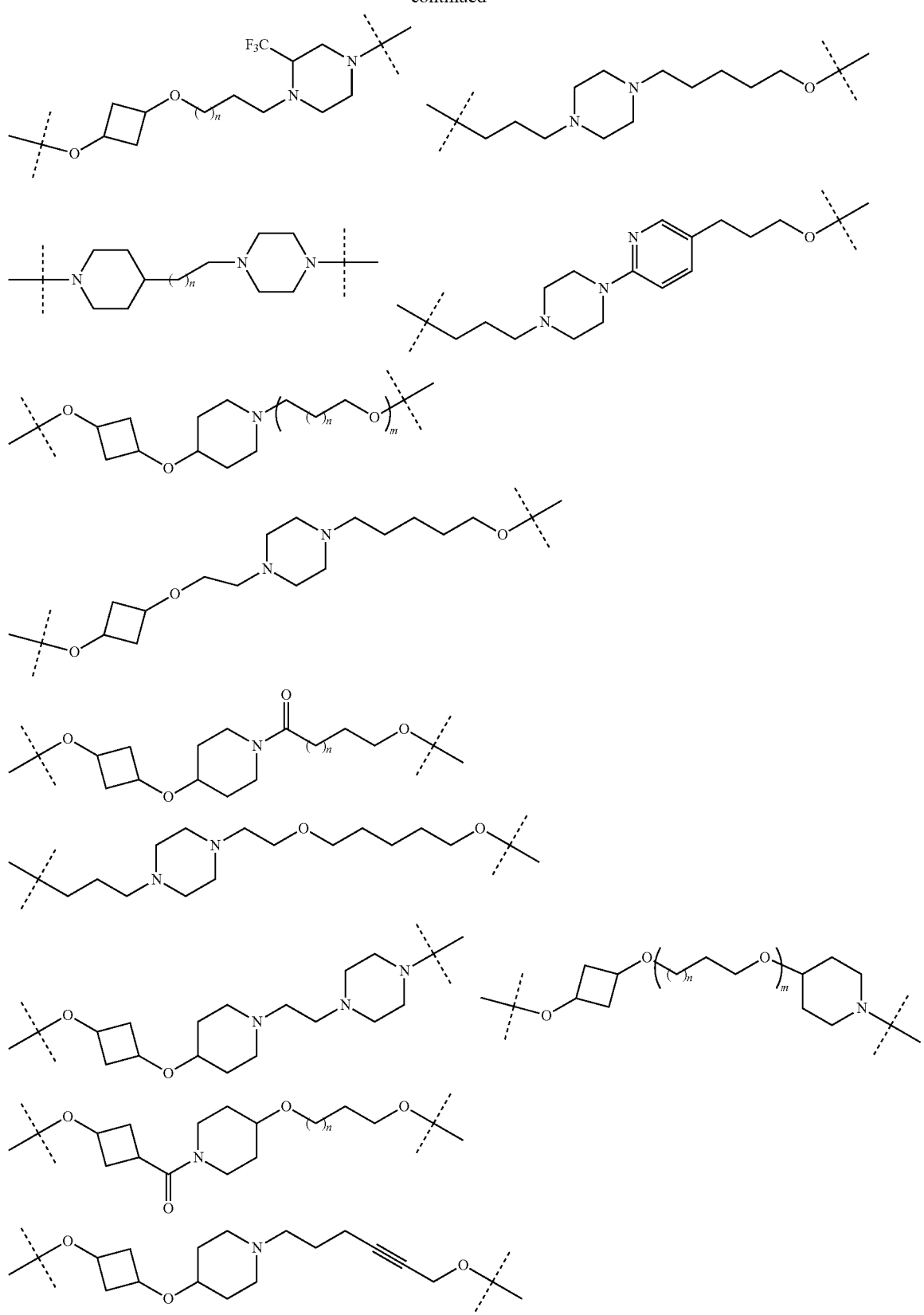

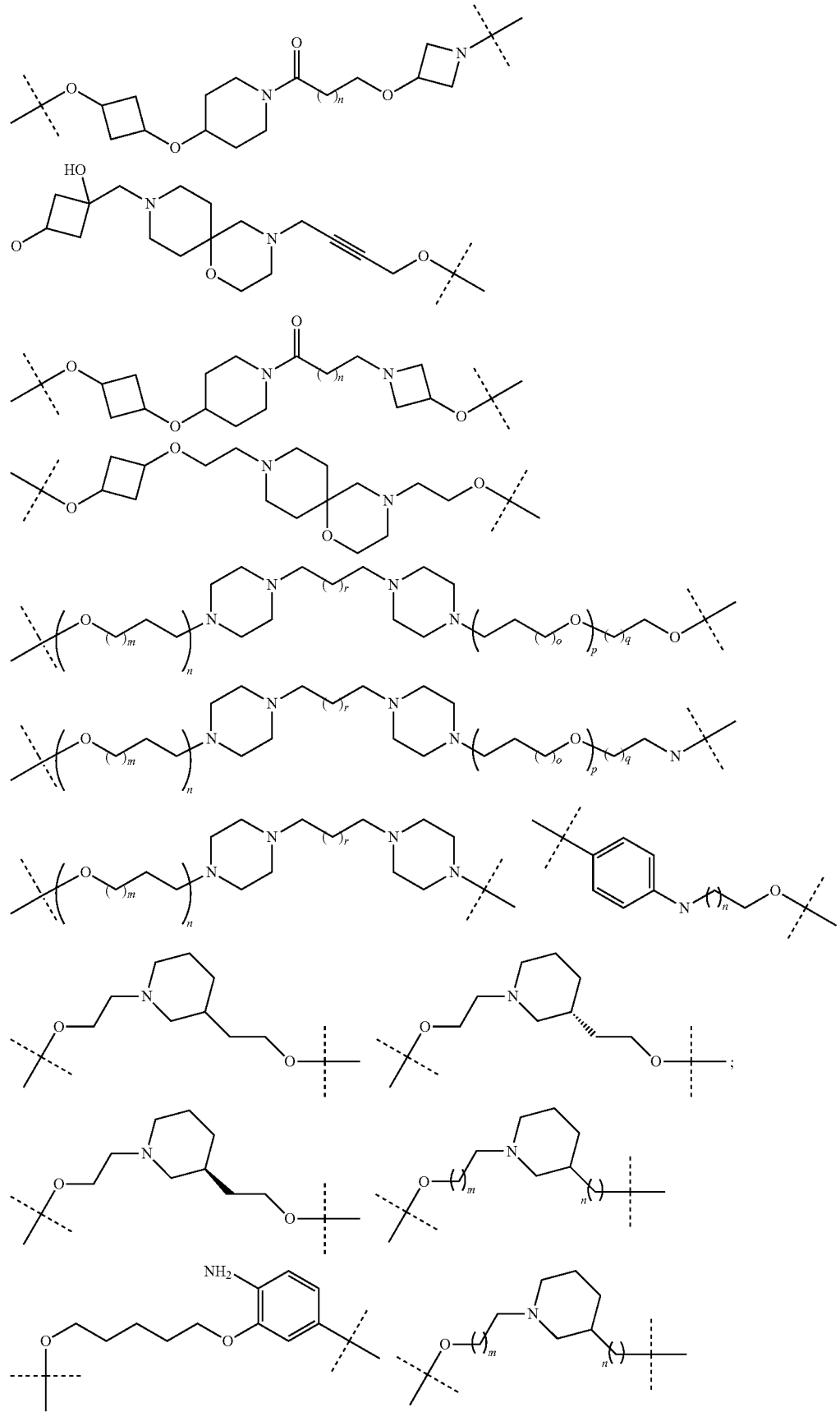

-continued
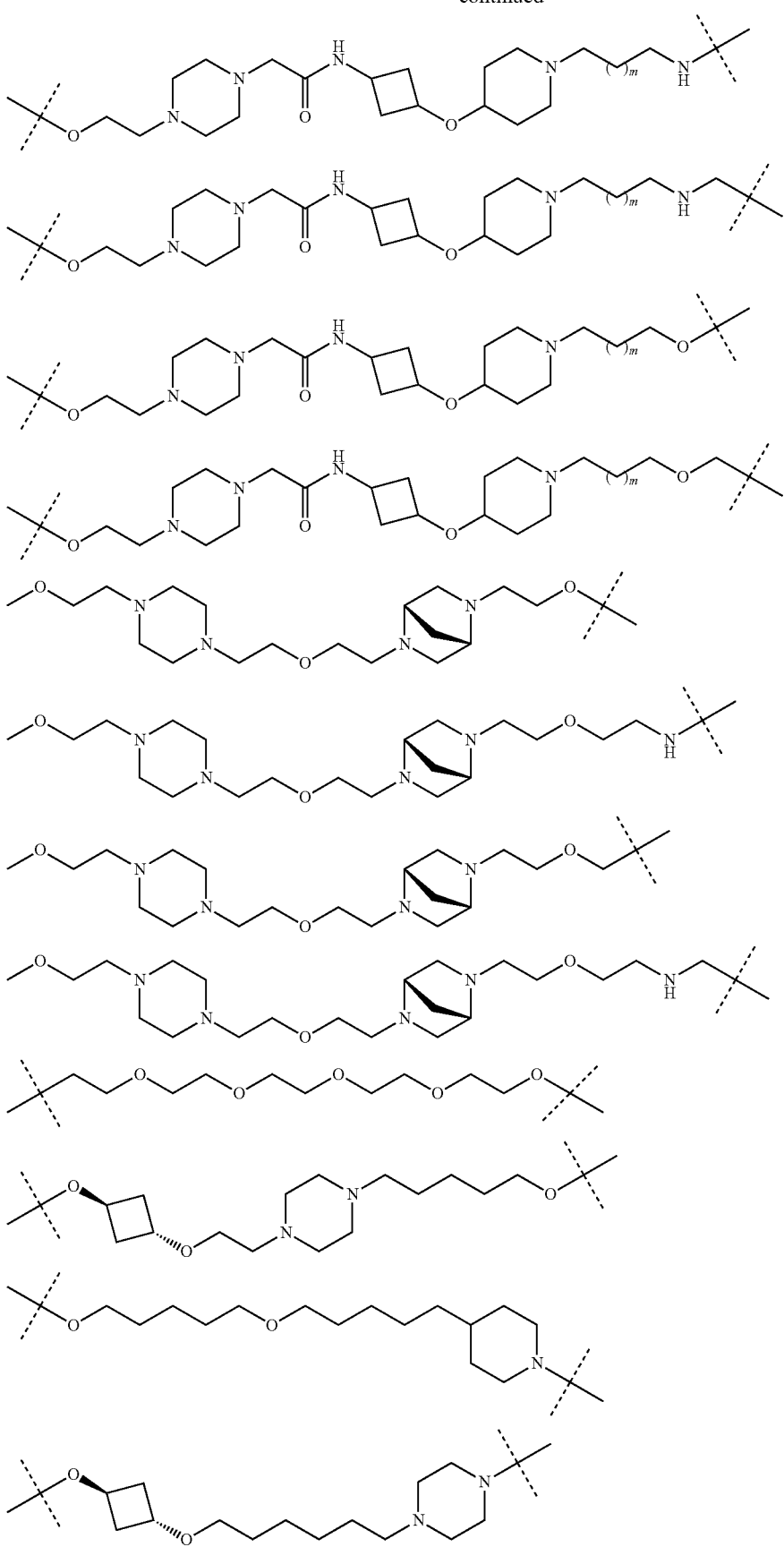

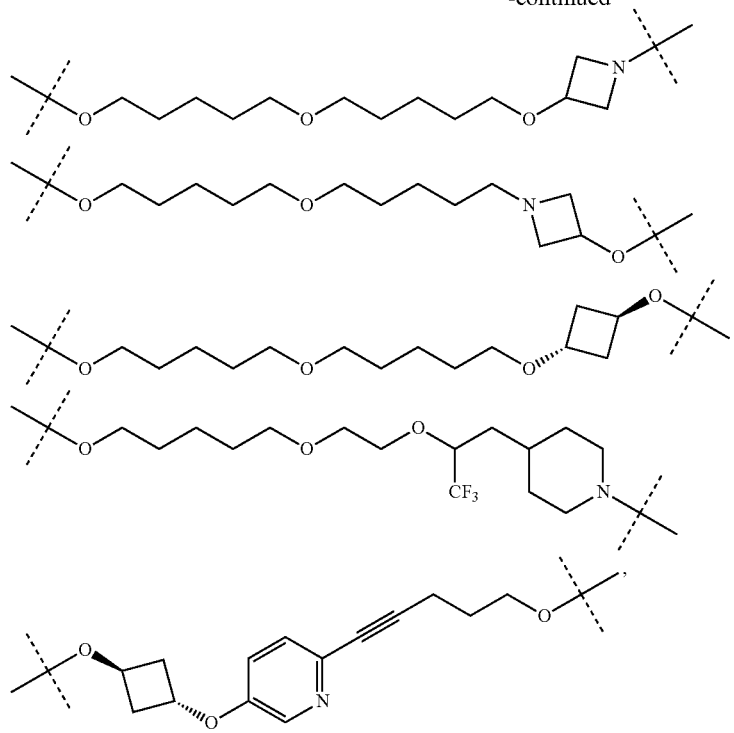
wherein each m, n, o and p is independently 0, 1, 2, 3, 4, 5, 6, or 7.
In any aspect or embodiment described herein, L is selected from the group consisting of:
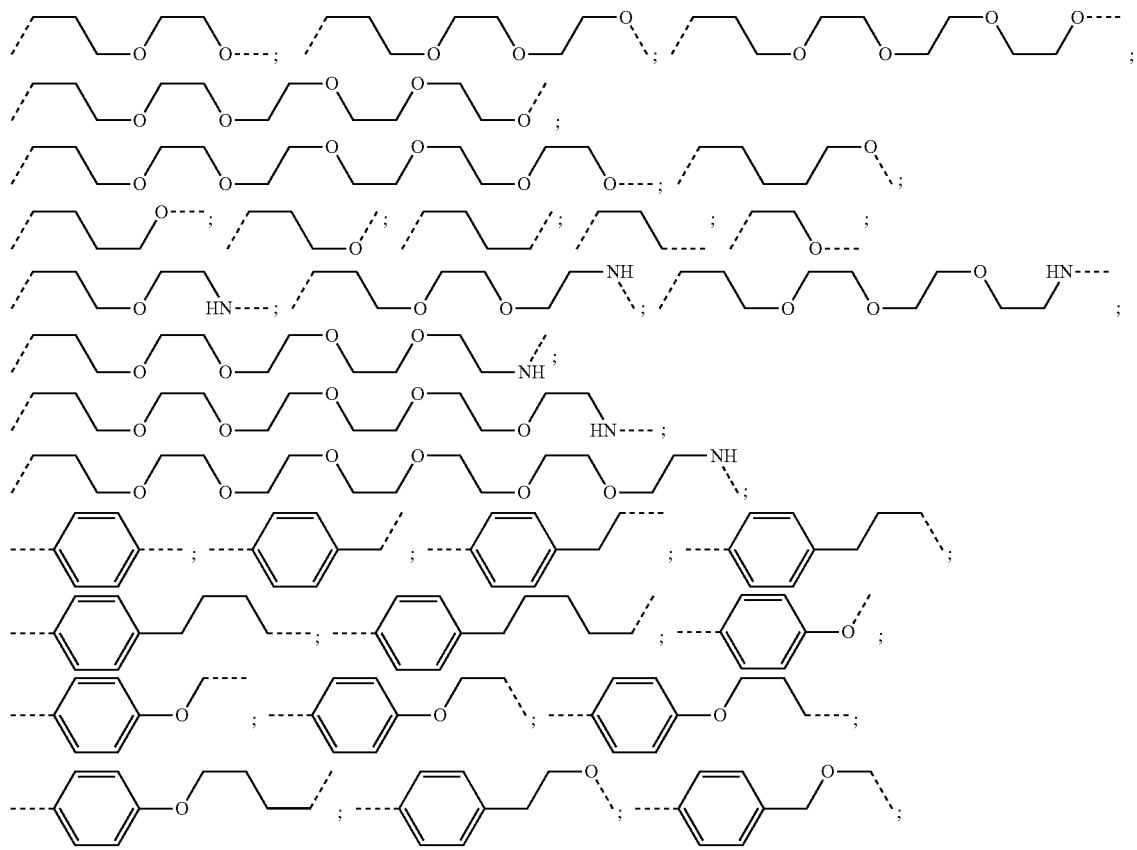

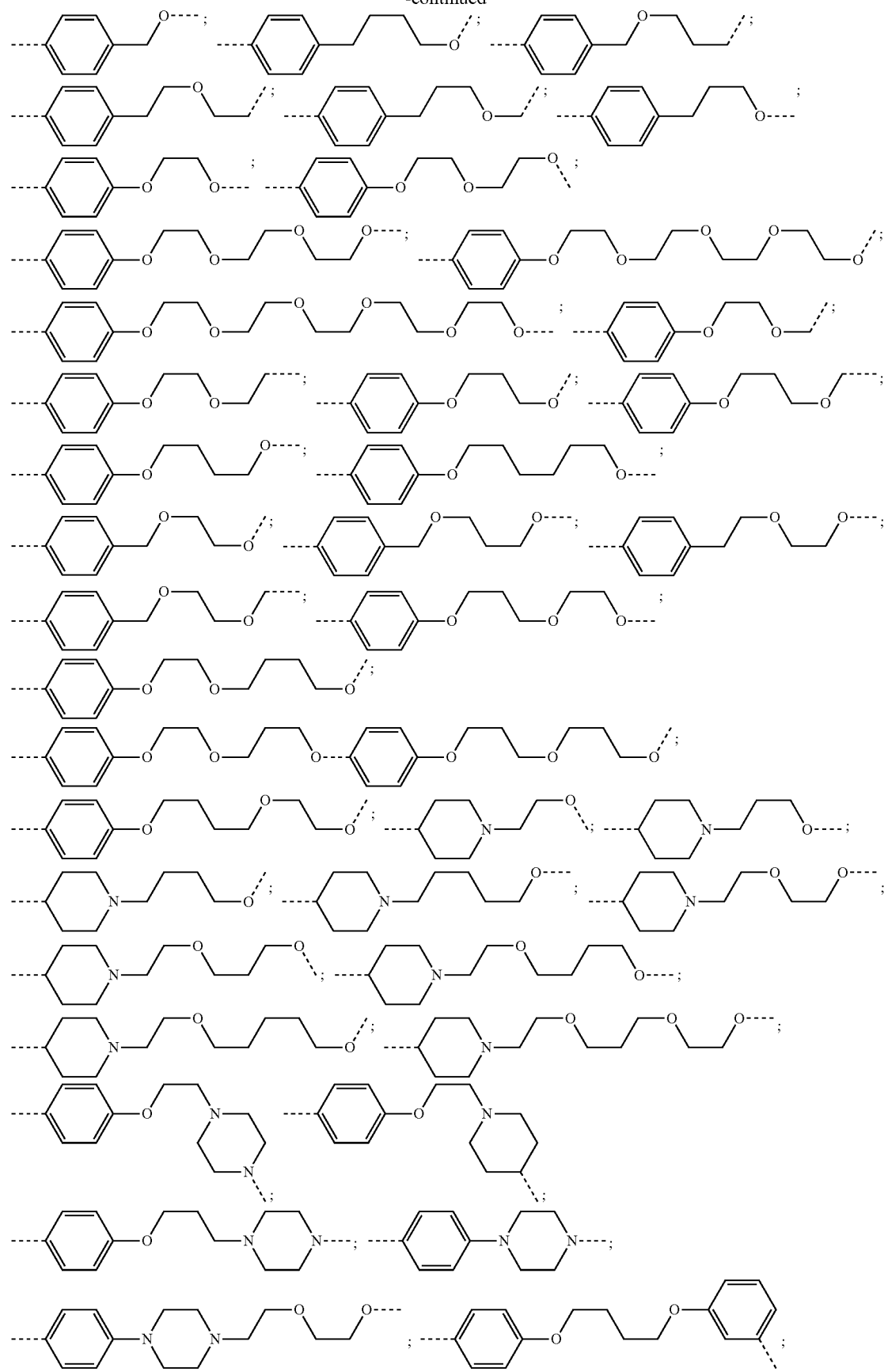

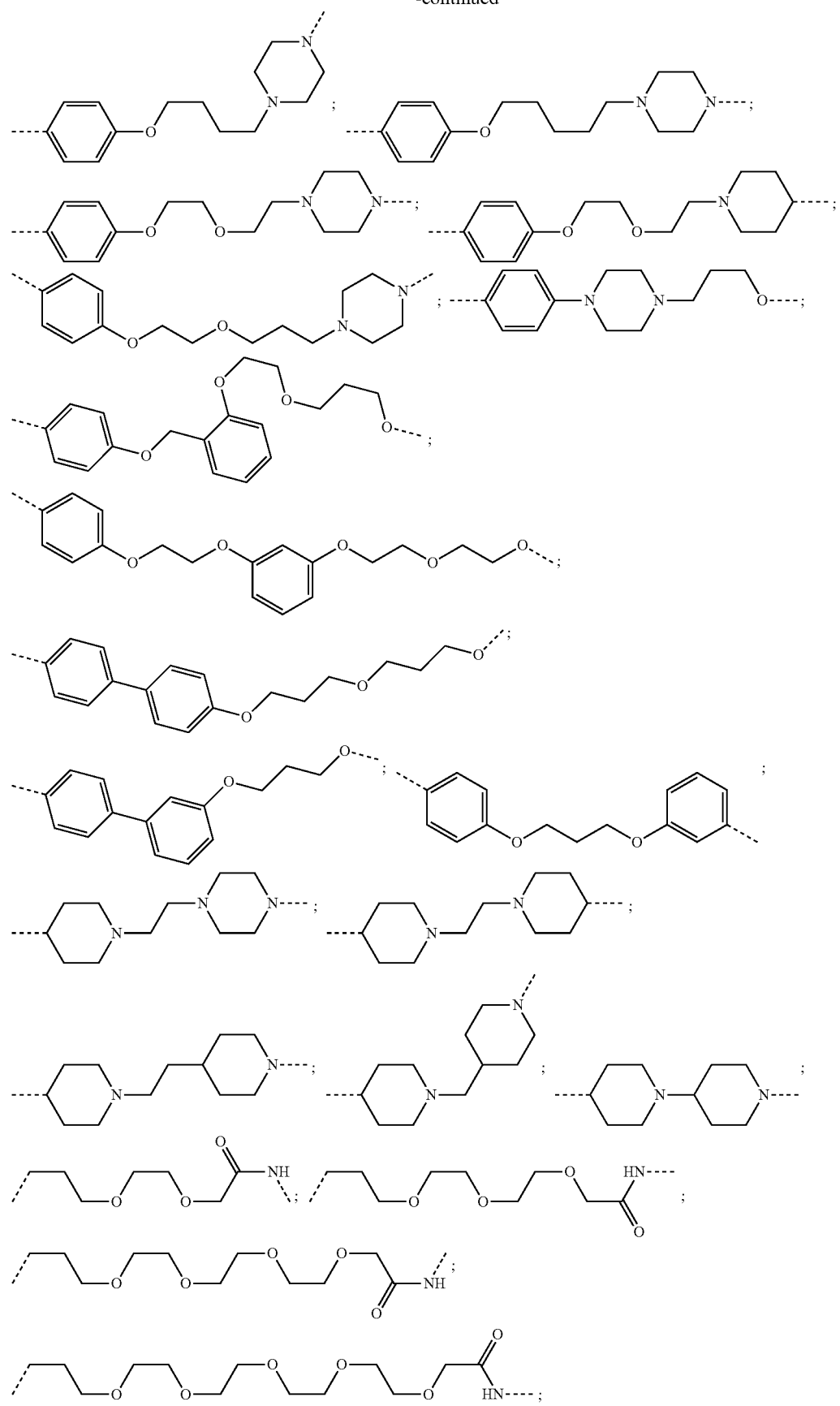

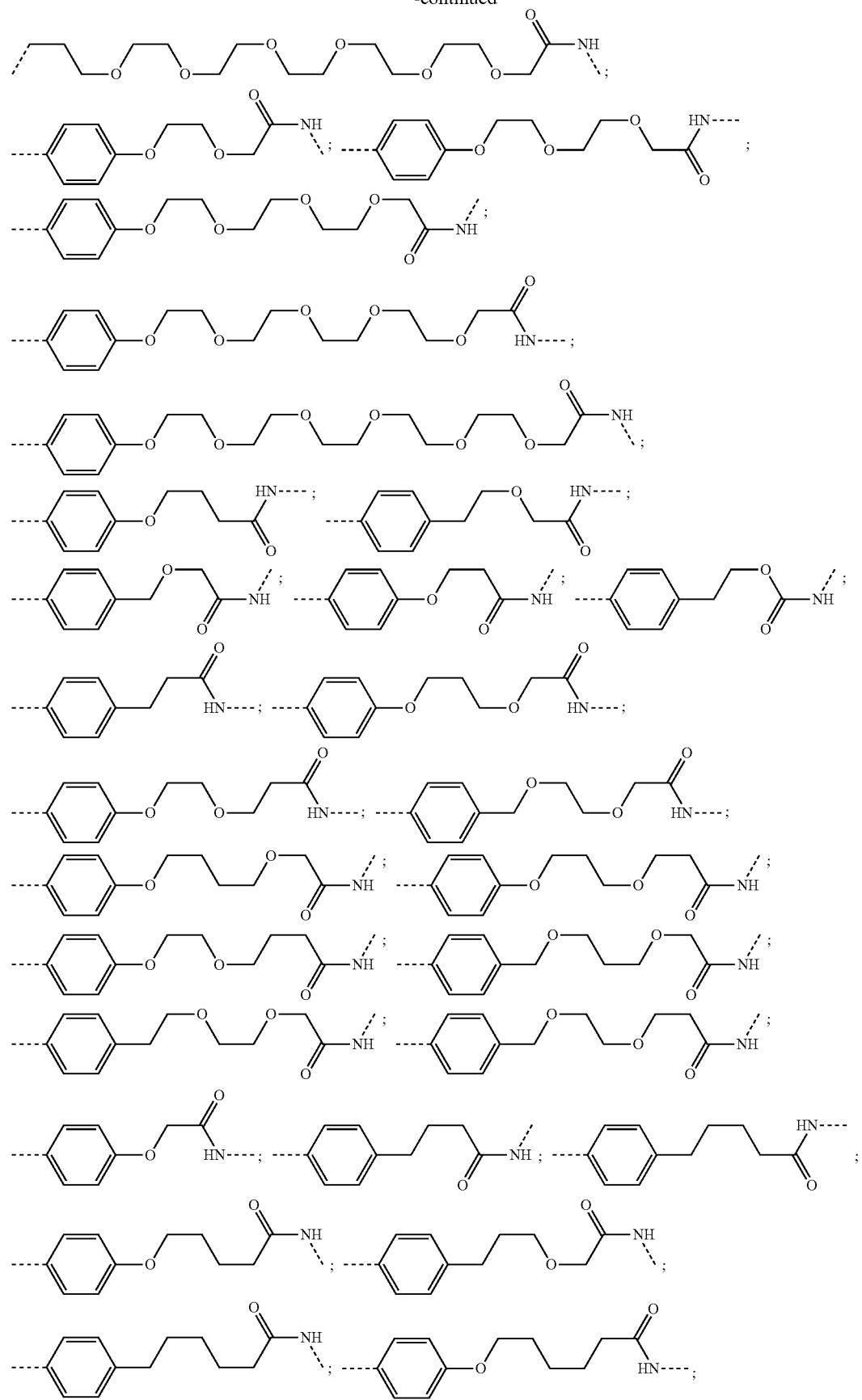

-continued
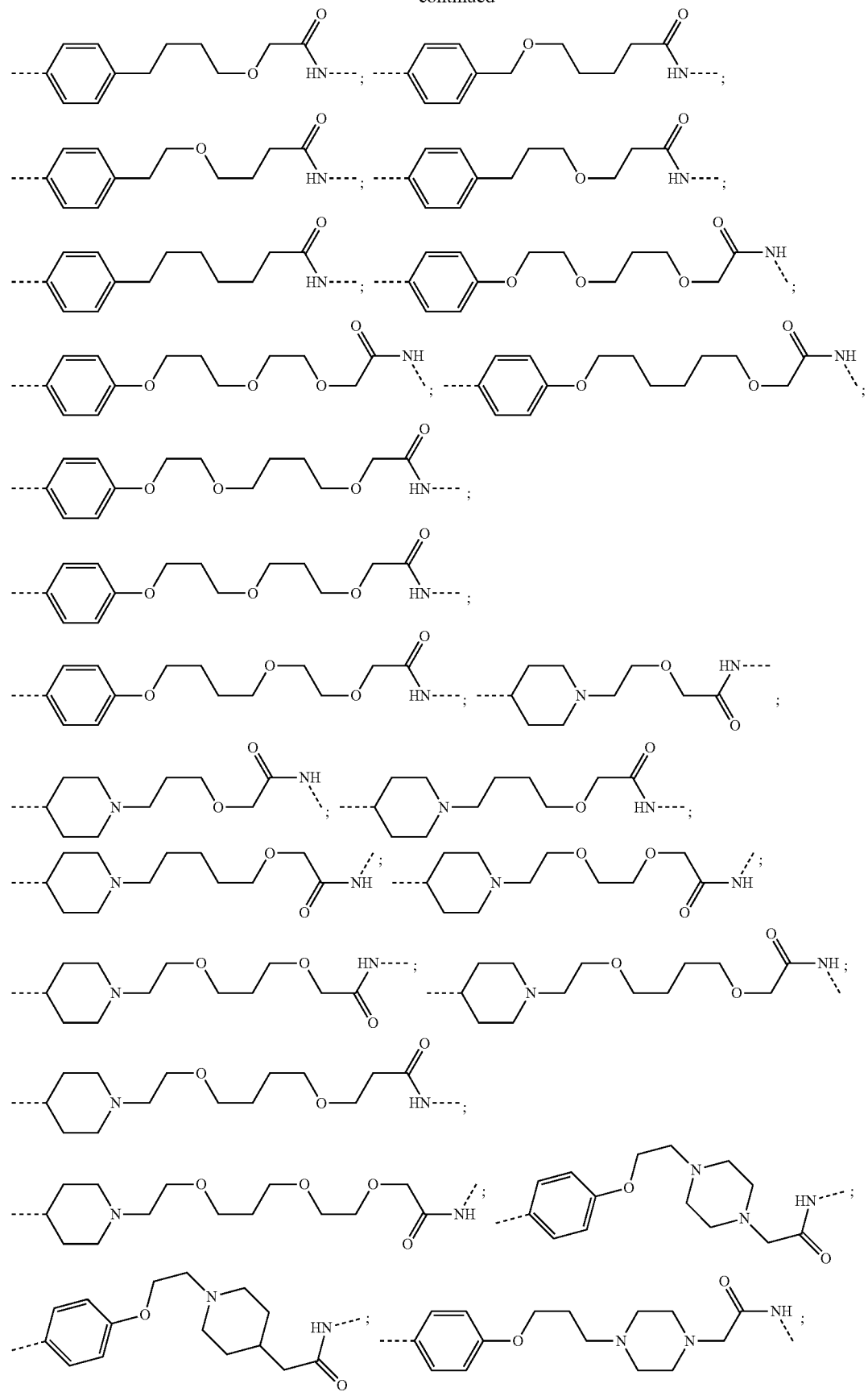

565 566
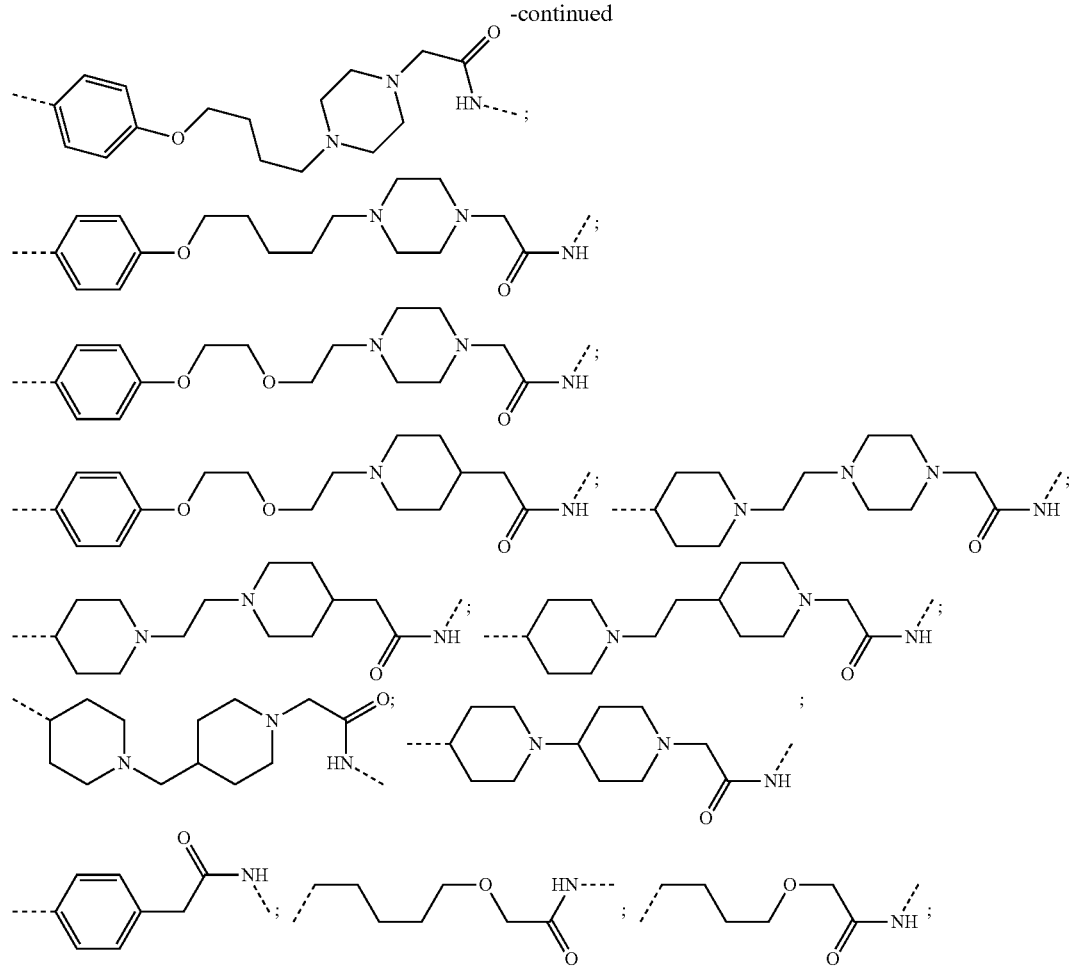
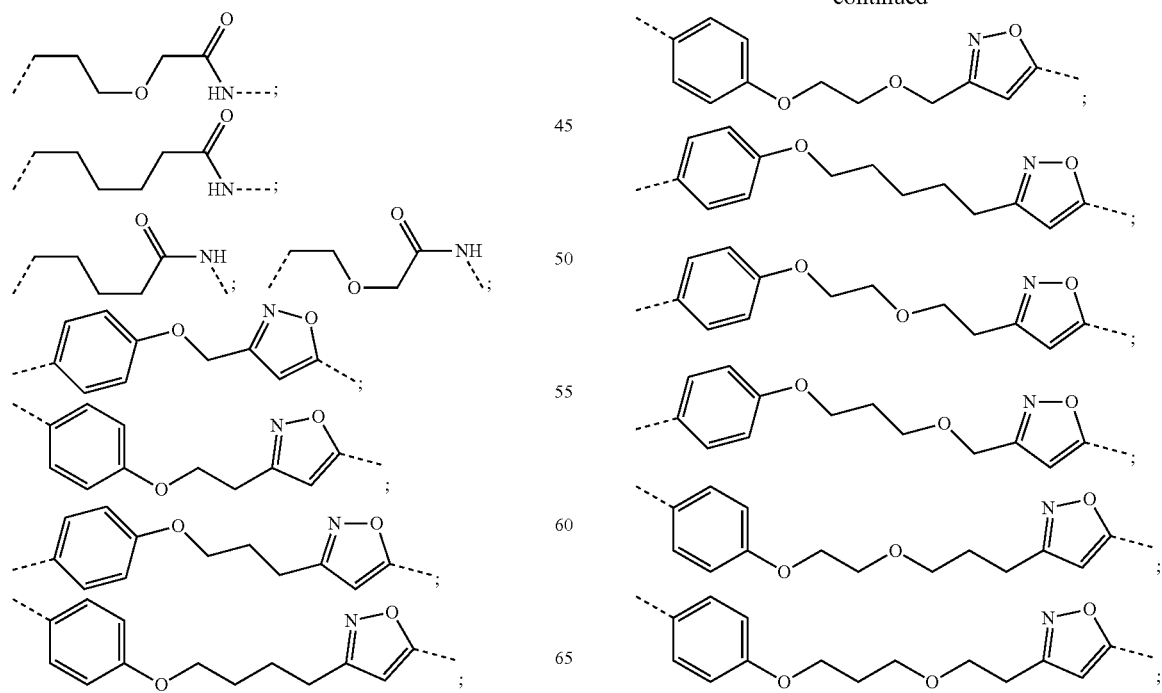

567
-continued
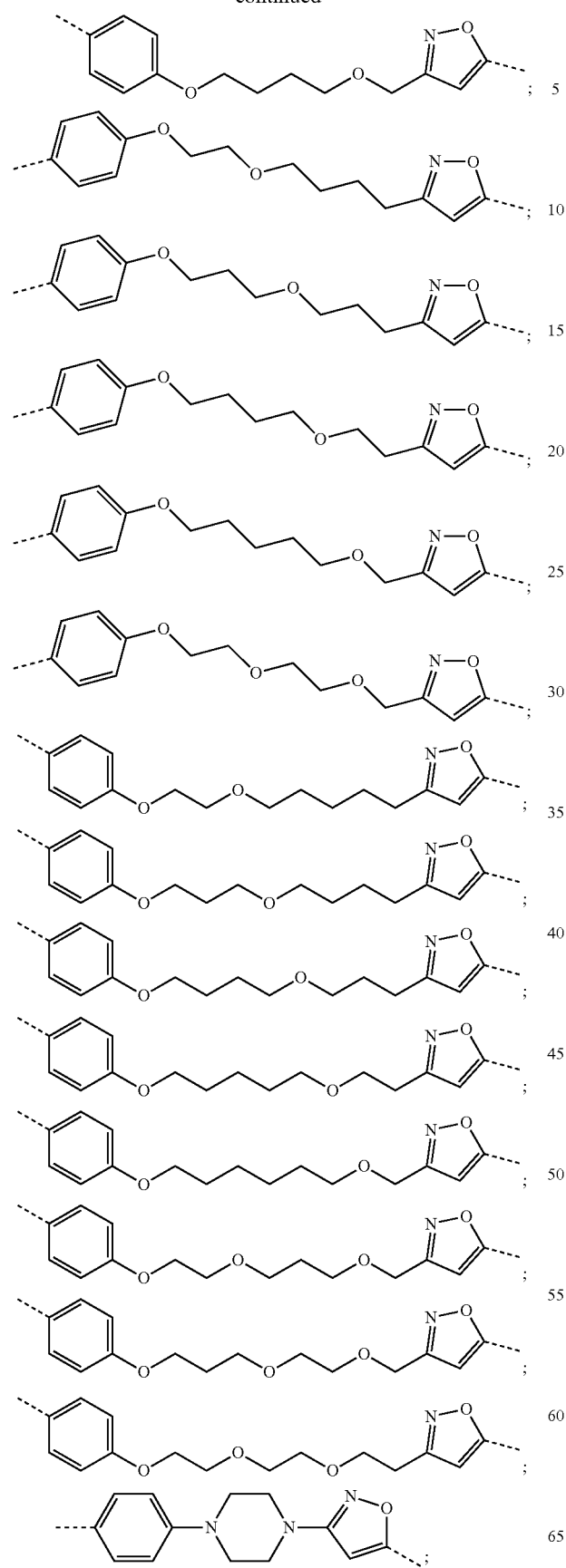
568
-continued
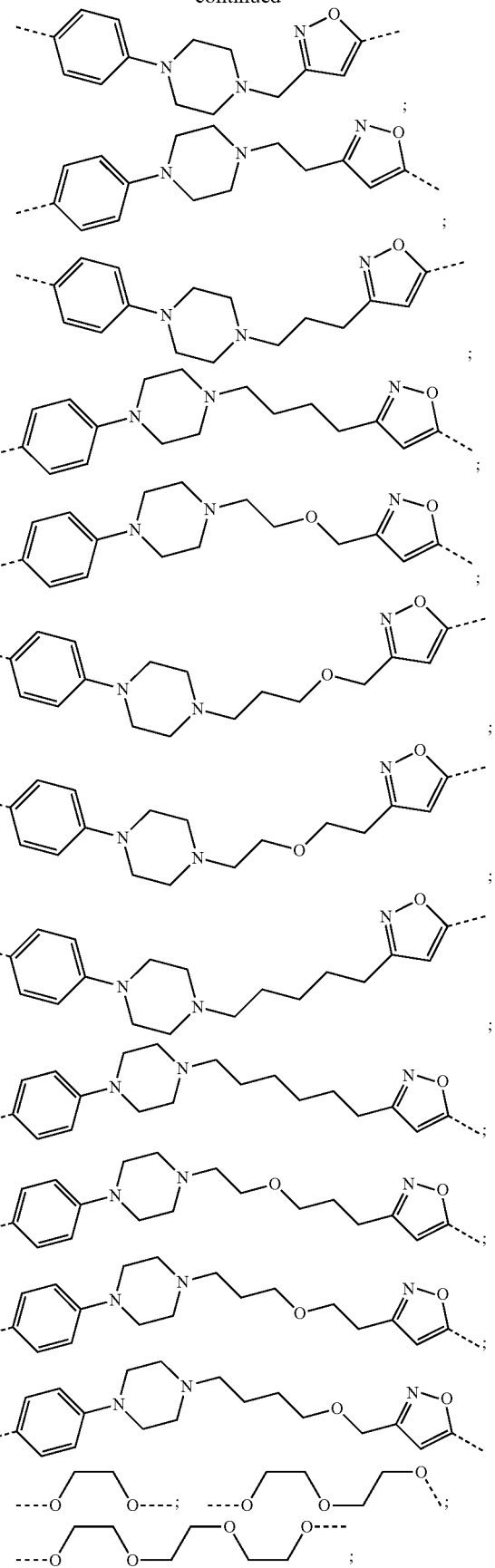

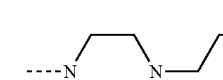

571
-continued
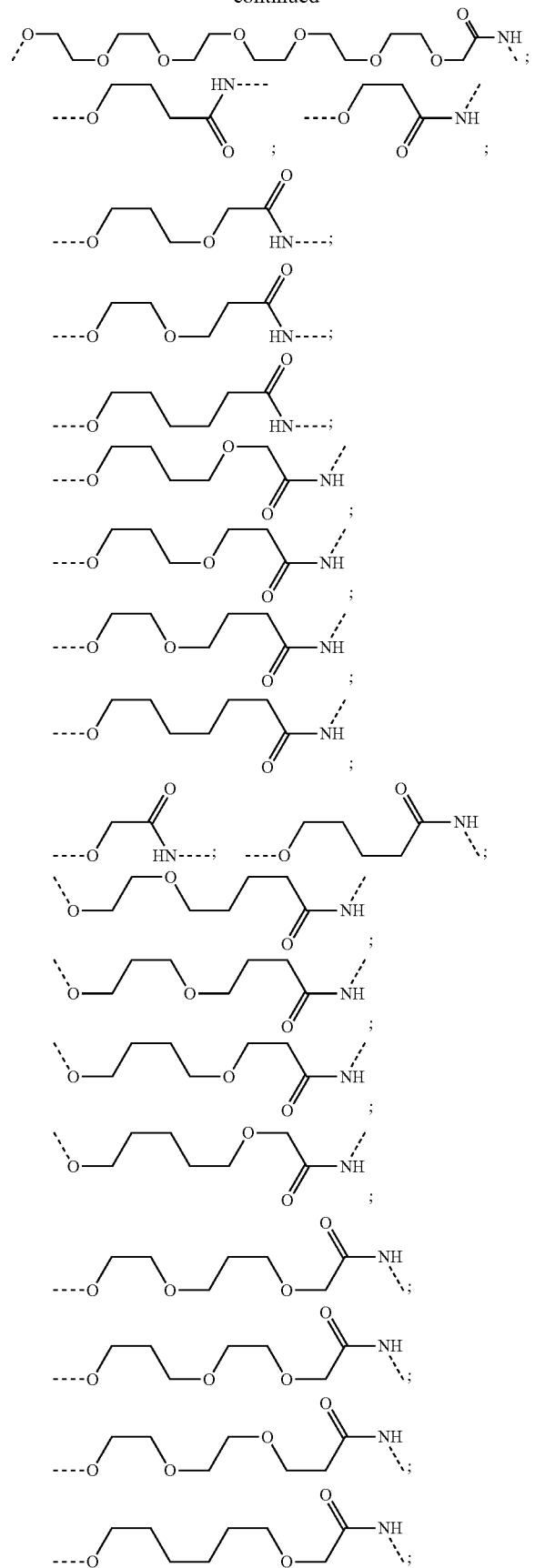
572
-continued
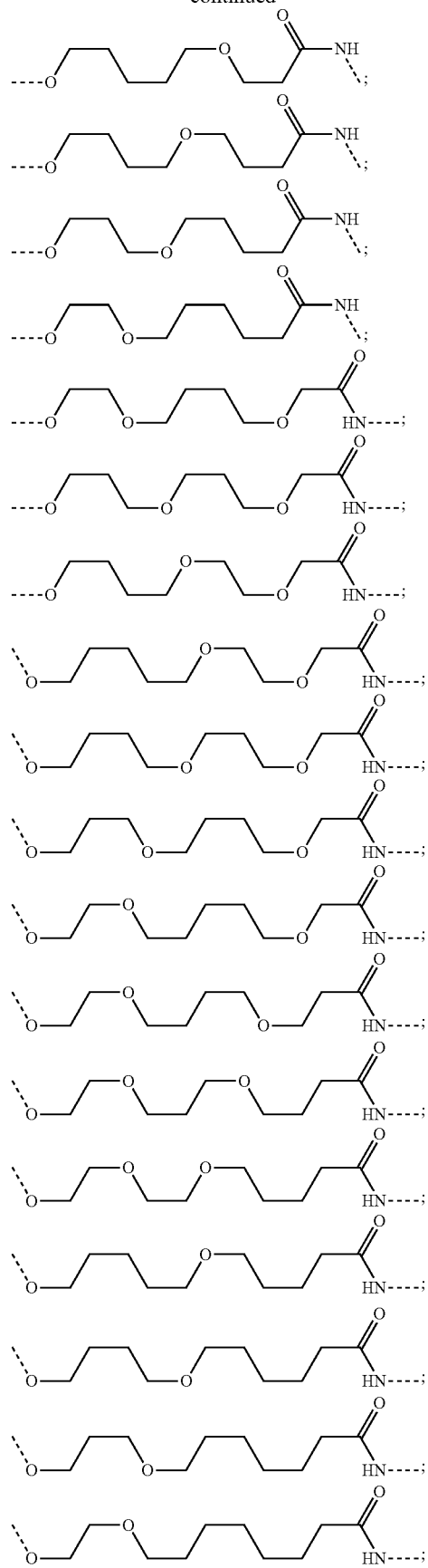

573
-continued
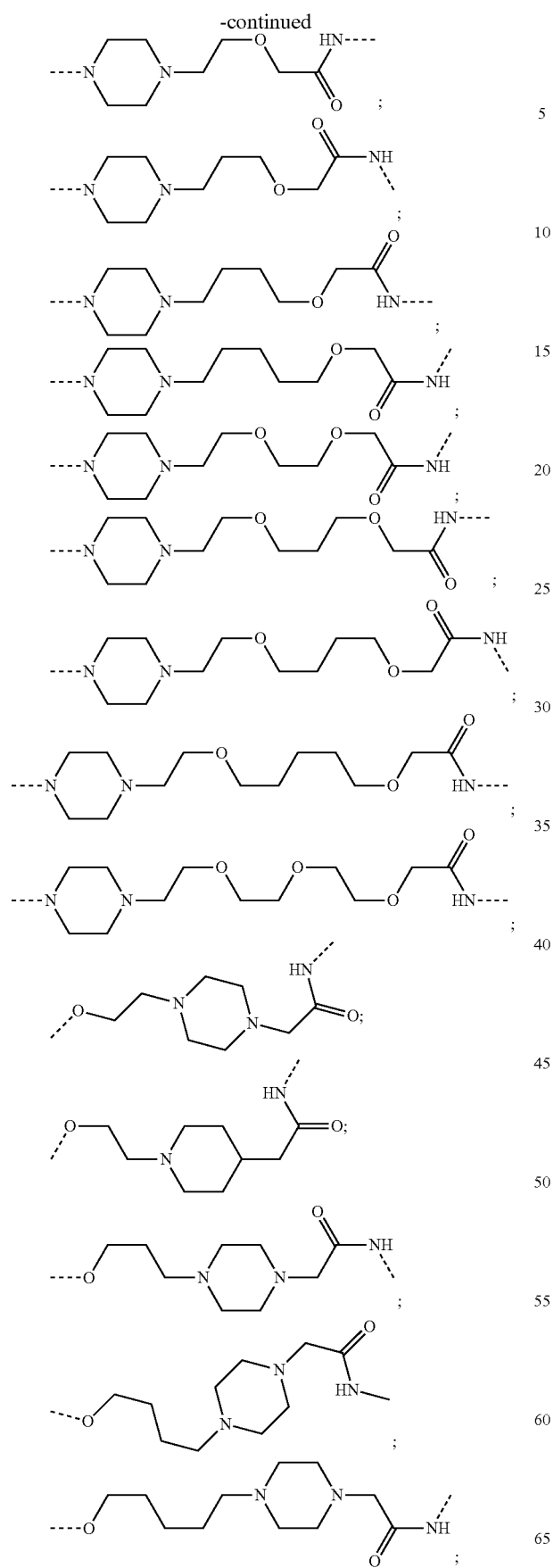
574
-continued
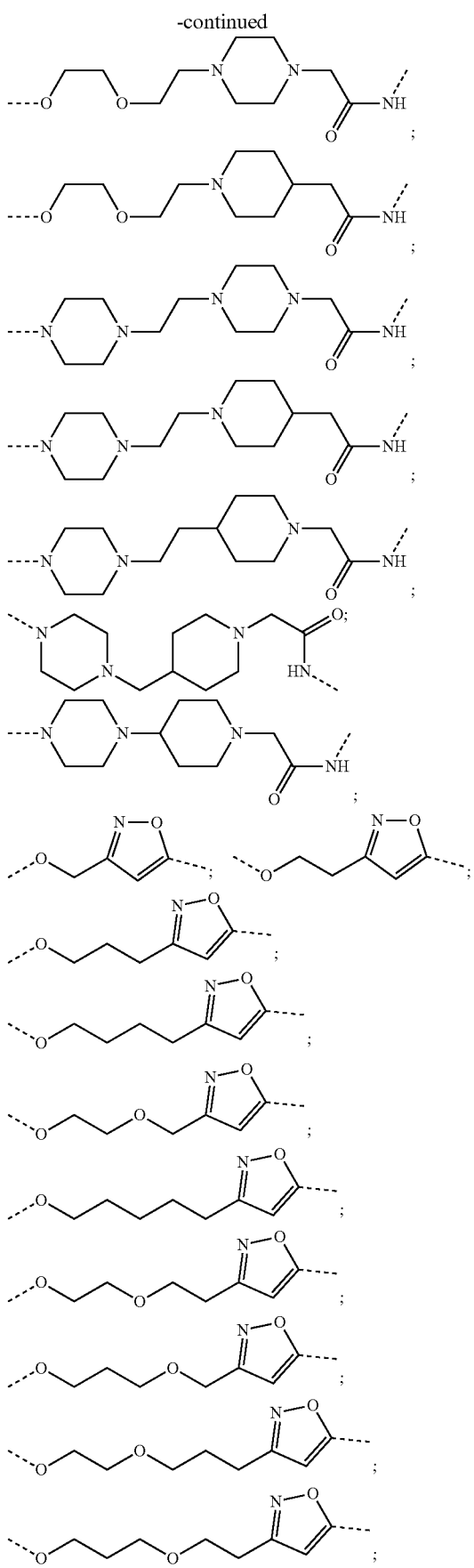

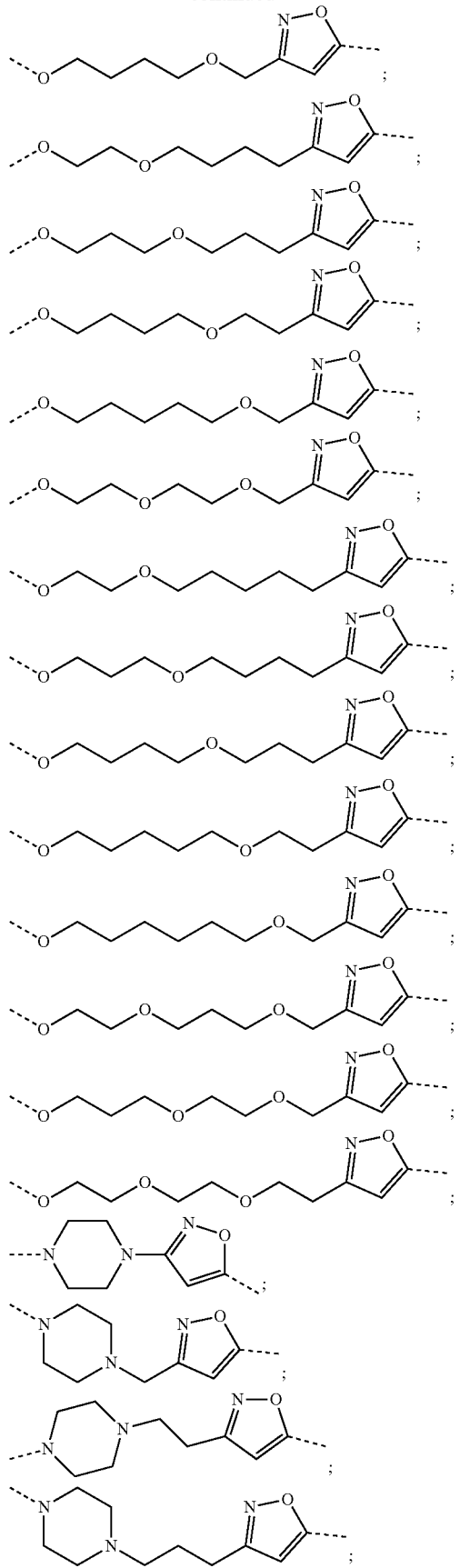

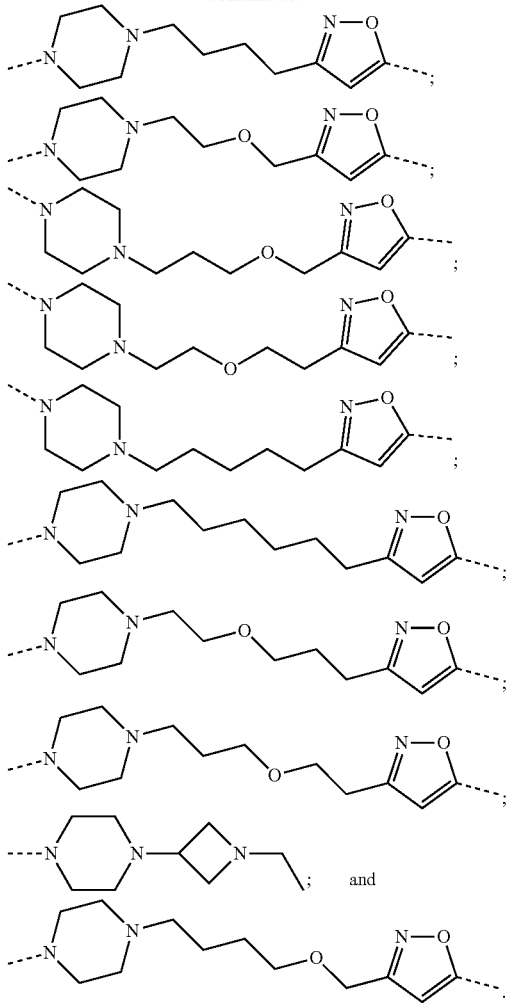

In any aspect or embodiment described herein, the linker (L) is a polyethylenoxy group optionally substituted with aryl or phenyl comprising from 1 to 10 ethylene glycol units.

In any aspect or embodiment described herein, the linker (L) comprises the following chemical structure:

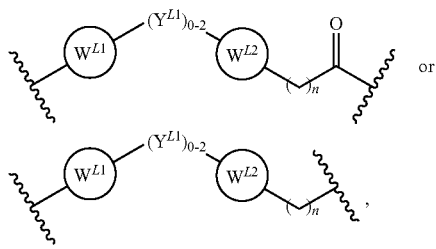

wherein:
$W^{L1}$ and $W^{L2}$ are each independently a 4-8 membered ring with 0-4 heteroatoms, optionally substituted with RQ, each RQ is independently a H, halo, OH, CN, CF3, $NH_2$, carboxyl, $C_1$-$C_6$ alkyl (linear, branched, optionally substituted), C1-C6 alkoxy (linear, branched, optionally substituted), or 2 RQ groups taken together with the atom they are attached to, form a 4-8 membered ring system containing 0-4 heteroatoms;

$Y^{L1}$ is each independently a bond, C1-C6 alkyl (linear, branched, optionally substituted) and optionally one or more C atoms are replaced with O; or C1-C6 alkoxy (linear, branched, optionally substituted);

n is an integer from 0-10; and a ⌇ indicates the attachment point to the PTM or ULM moieties.

In any aspect or embodiment described herein, the linker (L) comprises the following chemical structure:

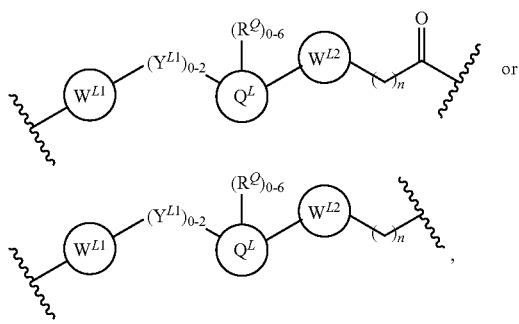

wherein:
$W^{L1}$ and $W^{L2}$ are each independently aryl, heteroaryl, cyclic, heterocyclic, $C_{1-6}$ alkyl (linear, branched, optionally substituted), C1-C6 alkoxy (linear, branched, optionally substituted), bicyclic, biaryl, biheteroaryl, or biheterocyclic, each optionally substituted with $R^Q$, each $R^Q$ is independently a H, halo, OH, CN, $CF_3$, $NH_2$, carboxyl, hydroxyl, nitro, C≡CH, $C_{2-6}$ alkenyl, $C_{2-6}$ alkynyl, $C_1$-$C_6$ alkyl (linear, branched, optionally substituted), $C_1$-$C_6$ alkoxy (linear, branched, optionally substituted), $OC_{1-3}$alkyl (optionally substituted by 1 or more —F), OH, $NH_2$, $NR^{Y1}R^{Y2}$, CN, or 2 $R^Q$ groups taken together with the atom they are attached to, form a 4-8 membered ring system containing 0-4 heteroatoms;

$Y^{L1}$ is each independently a bond, $NR^{YL1}$, O, S, $NR^{YL2}$, $CR^{YL1}R^{YL2}$, C=O, C=S, SO, $SO_2$, $C_1$-$C_6$ alkyl (linear, branched, optionally substituted) and optionally one or more C atoms are replaced with O; $C_1$-$C_6$ alkoxy (linear, branched, optionally substituted);

$Q^L$ is a 3-6 membered alicyclic or aromatic ring with 0-4 heteroatoms, biheterocyclic, or bicyclic, optionally bridged, optionally substituted with 0-6 RQ, each RQ is independently H, $C_{1-6}$ alkyl (linear, branched, optionally substituted by 1 or more halo, $C_{1-6}$ alkoxyl), or 2 $R^Q$ groups taken together with the atom they are attached to, form a 3-8 membered ring system containing 0-2 heteroatoms);

$R^{YL1}$, $R^{YL2}$ are each independently H, OH, $C_{1-6}$ alkyl (linear, branched, optionally substituted by 1 or more halo, $C_{1-6}$ alkoxyl), or $R^1$, $R^2$ together with the atom they are attached to, form a 3-8 membered ring system containing 0-2 heteroatoms);

n is an integer from 0-10; and a ⌇ indicates the attachment point to the PTM or ULM moieties.

In any aspect or embodiment described herein, the compound comprises multiple ULMs, multiple PTMs, multiple linkers or any combinations thereof.

In any aspect or embodiment described herein, the compound is selected from the group consisting of: Compounds 1-547 (i.e., a compound selected from Table 1 or Table 2).

Another aspect of the present disclosure provides a composition comprising an effective amount of a bifunctional compound of the present disclosure, and a pharmaceutically acceptable carrier.

In any aspect or embodiment described herein, the composition further comprises at least one of additional bioactive agent or another bifunctional compound of any of claims 1-23.

In any aspect or embodiment described herein, the additional bioactive agent is anti-cancer agent.

A further aspect of the present disclosure provides a composition comprising a pharmaceutically acceptable carrier and an effective amount of at least one compound of the present disclosure for treating a disease or disorder in a subject, the method comprising administering the composition to a subject in need thereof, wherein the compound is effective in treating or ameliorating at least one symptom of the disease or disorder.

In any aspect or embodiment described herein, the disease or disorder is associated with estrogen receptor accumulation and aggregation.

In any aspect or embodiment described herein, the disease or disorder is cancer or a neoplasia associated with estrogen receptor accumulation and aggregation.

In any aspect or embodiment described herein, the disease or disorder is breast cancer or uterine cancer.

In any aspect or embodiment described herein, the disease or disorder is endometriosis.

General Synthetic Approach

The synthetic realization and optimization of the bifunctional molecules as described herein may be approached in a step-wise or modular fashion. For example, identification of compounds that bind to the target molecules can involve high or medium throughput screening campaigns if no suitable ligands are immediately available. It is not unusual for initial ligands to require iterative design and optimization cycles to improve suboptimal aspects as identified by data from suitable in vitro and pharmacological and/or ADMET assays. Part of the optimization/SAR campaign would be to probe positions of the ligand that are tolerant of substitution and that might be suitable places on which to attach the linker chemistry previously referred to herein. Where crystallographic or NMR structural data are available, these can be used to focus such a synthetic effort.

In a very analogous way one can identify and optimize ligands for an E3 Ligase, i.e. ULMs/VLMs/CLMs.

With PTMs and ULMs (e.g. VLMs and/or CLMs) in hand, one skilled in the art can use known synthetic methods for their combination with or without a linker moiety. Linker moieties can be synthesized with a range of compositions, lengths and flexibility and functionalized such that the PTM and ULM groups can be attached sequentially to distal ends of the linker. Thus, a library of bifunctional molecules can be realized and profiled in vitro and in vivo pharmacological and ADMET/PK studies. As with the PTM and ULM groups, the final bifunctional molecules can be subject to iterative design and optimization cycles in order to identify molecules with desirable properties.

Compounds of the present disclosure [e.g., the general Formulas (I), ($I_{PTM}$) and ($II_{PTM}$) and bifunctional compounds comprising the same] may be prepared by methods known in the art of organic synthesis as set forth in the specific exemplary compounds or compounds described in this application. In all of the methods, it is well understood that protecting groups for sensitive or reactive groups may be employed where necessary in accordance with general principles of chemistry. Protecting groups are manipulated according to standard methods of organic synthesis (T. W. Green and P. G. M. Wuts (1999) Protective Groups in Organic Synthesis, 3$^{rd}$ edition, John Wiley & Sons). These groups are removed at a convenient stage of the compound synthesis using methods that are readily apparent to those skilled in the art. The selection of processes as well as the reaction conditions and order of their execution shall be consistent with the preparation of compounds of the present disclosure, including compounds of Formulas (I), (I$_{PTM}$) and (II$_{PTM}$) and bifunctional compounds comprising the same. Schemes described below illustrate the general methods of preparing compounds with the structure featured as Formulas (I), (I$_{PTM}$) and (II$_{PTM}$).

Compounds of the present disclosure may be synthesized by connecting the ER binding fragment prepared according to Scheme 1-1 through Scheme 1-40 with the cereblon binding fragment prepared according to Scheme 2-1 through Scheme 2-47. The detailed synthesis of representative compounds of the present disclosure, are further described in Scheme 3-1 through Scheme 3-88.

Abbreviations:
ACN: acetonitrile
ADDP: 1,1'-(azodicarbonyl)dipiperidine
BAST: N,N-bis(2-methoxyethyl)aminosulfur trifluoride
BPO: benzoyl peroxide
Cbz: Carbonylbezyloxy
DAST: diethylaminosulfur trifluoride
DBE: 1,2-dibromoethane
DCE: 1,2-dichloroethane
DCM: dichloromethane
DEAD: diethyl azodicarboxylate
DIAD: diisopropyl azodicarboxylate
DIBAL: disiobutylaluminium hydride
DIEA or DIPEA: diisopropylethylamine
DMA: N,N-dimethylacetamide
DMF: N,N-dimethylformamide
DMP: Dess-Martin periodinane
EA: ethyl acetate
EDCI: 1-ethyl-3-(3-dimethylaminopropyl)carbodiimide
HBTU: N,N,N'N'-tetramethyl-O-(1H-benzotriazol-1-yl) uronium hexafluorophosphate
HMDS: bis(trimethylsilyl)amine
HMPA: hexamethylphosphoramide
LDA: lithium diisopropylamide
MCPBA: meta-chloroperoxybenzoic acid
MsCl: methanesulfonyl chloride
M.W: microwave
NBS: N-bromosuccinimide
NMP: N-methylpyrrolidone
PCC: pyridinium chlorochromate
Pd-118 or Pd(dtpf)Cl$_2$: 1,1'-bis(di-tert-butylphosphino)ferrocene dichloropalladium
Pd(dppf)Cl$_2$: 1,1'-bis(diphenylphosphino)ferrocene dichloropalladium
Pd(dba)$_2$: bis(dibenzylideneacetone)palladium
Pd$_2$(dba)$_3$: Tris(dibenzylideneacetone)dipalladium
PPTS: pyridium p-tolunesulfonate
PTSA: p-toluenesulfonic acid
RuPhos-Pd-G3: [(2-dicyclohexylphosphino-2',6'-diisopropoxy-1,1'-biphenyl)-2-(2'-amino-1,1'-biphenyl)] palladium(II) methanesulfonate
RuPhos-Pd-G2: Chloro[(2-dicyclohexylphosphino-2',6'-diisopropoxy-1,1'-biphenyl)-2-(2'-amino-1,1'-biphenyl)] palladium(II)
SFC: supercritical fluid chromatography
t-BuXPhos-Pd-G3: [(2-di-tert-butylphosphino-2',4',6'-triisopropyl-1,1'-biphenyl)-2-(2'-amino-1,1'-biphenyl)] palladium(II) methanesulfonate
TEA: trimethylamine
TFA: trifluoroacetic acid
TLC: thin layer chromatography
TMP: 2,2,6,6-tetramethylpiperidine
TEMPO: 2,2,6,6-tetramethylpiperidine-N-oxide
TosCl or TsCl: p-toluenesulfonyl chloride
TsOH: p-toluenesulfonic acid
XantPhos: 4,5-bis(diphenylphosphino)-9,9-dimethylxanthene
XPhos: 2-dicyclohexylphosphino-2'4'6'-triisopropylbiphenyl
XPhos-Pd-G3: [(2-dicyclohexylphosphino-2',4',6'-triisopropyl-1,1'-biphenyl)-2-(2'-amino-1,1'-biphenyl)] palladium(II) methanesulfonate
12354-85-7: bis(pentamethylcyclopentadienylrhodium dichloride)

General synthetic schemes 1-1 through 1-40 described the routes used to prepare exemplary ER ligands and exemplary ER ligands with partial linker moieties connected thereto.

General synthetic scheme 1-1 to prepare intermediate.

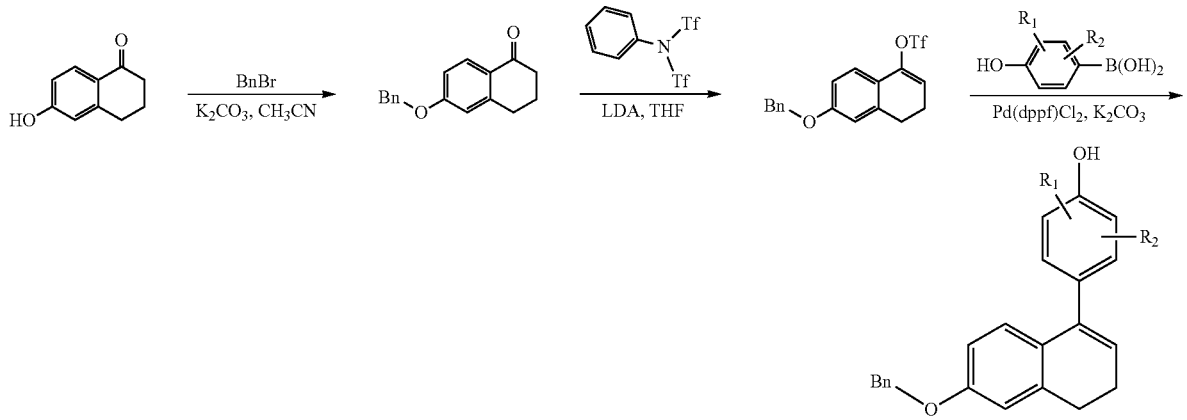

-continued
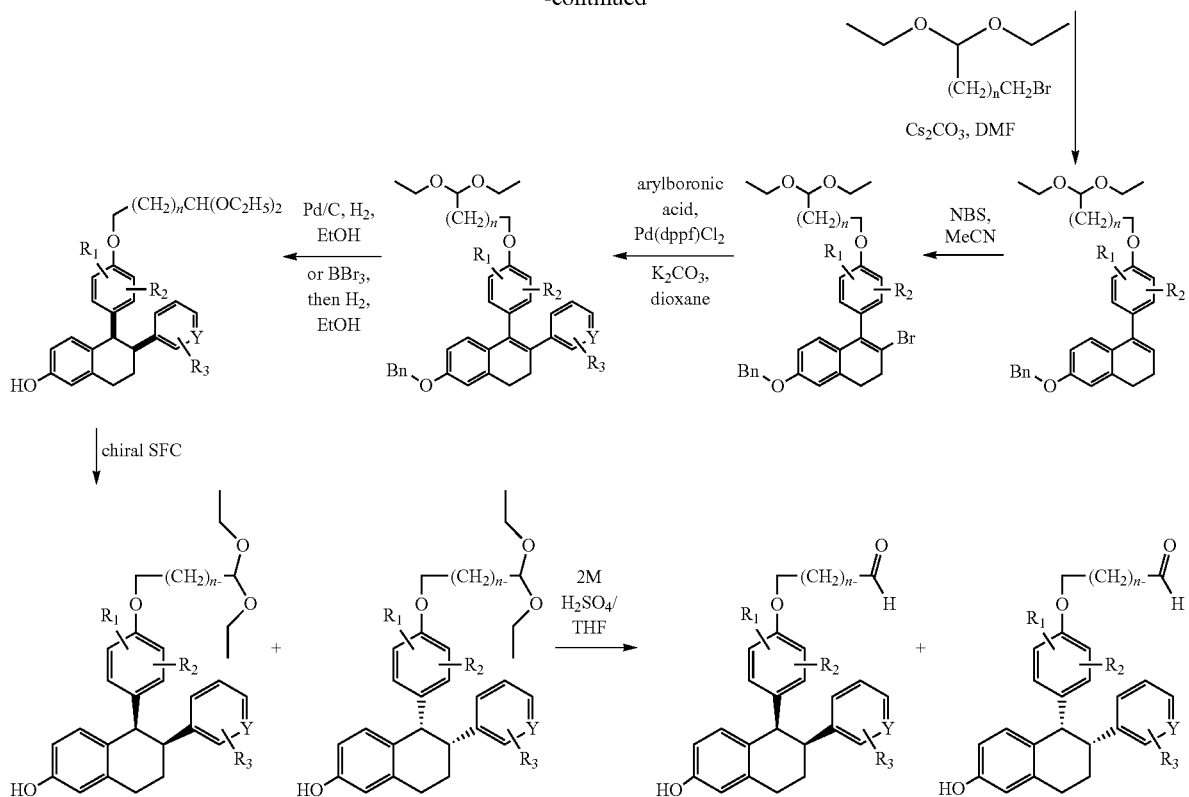
Wherein the number n can be 0 to 4; Y can be CH, N; $R_1$, $R_2$ and $R_3$ can be H, F, $C_F$. In the case of benzyl group deprotection using $BBr_3$, the acetal functional group will also be deprotected to lead to the desired aldehyde intermediate.
General synthetic scheme 1-2 to prepare intermediate.
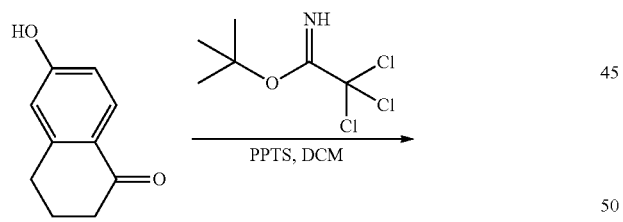
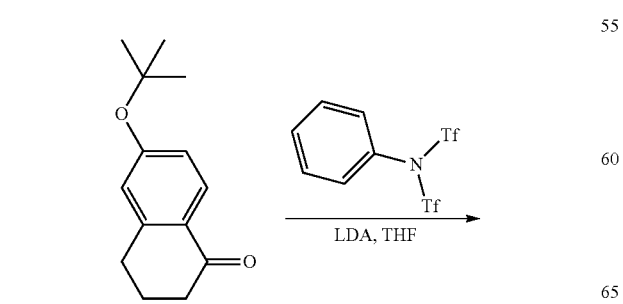
-continued
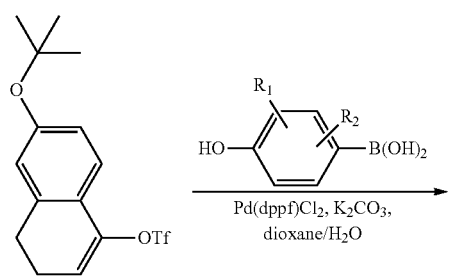

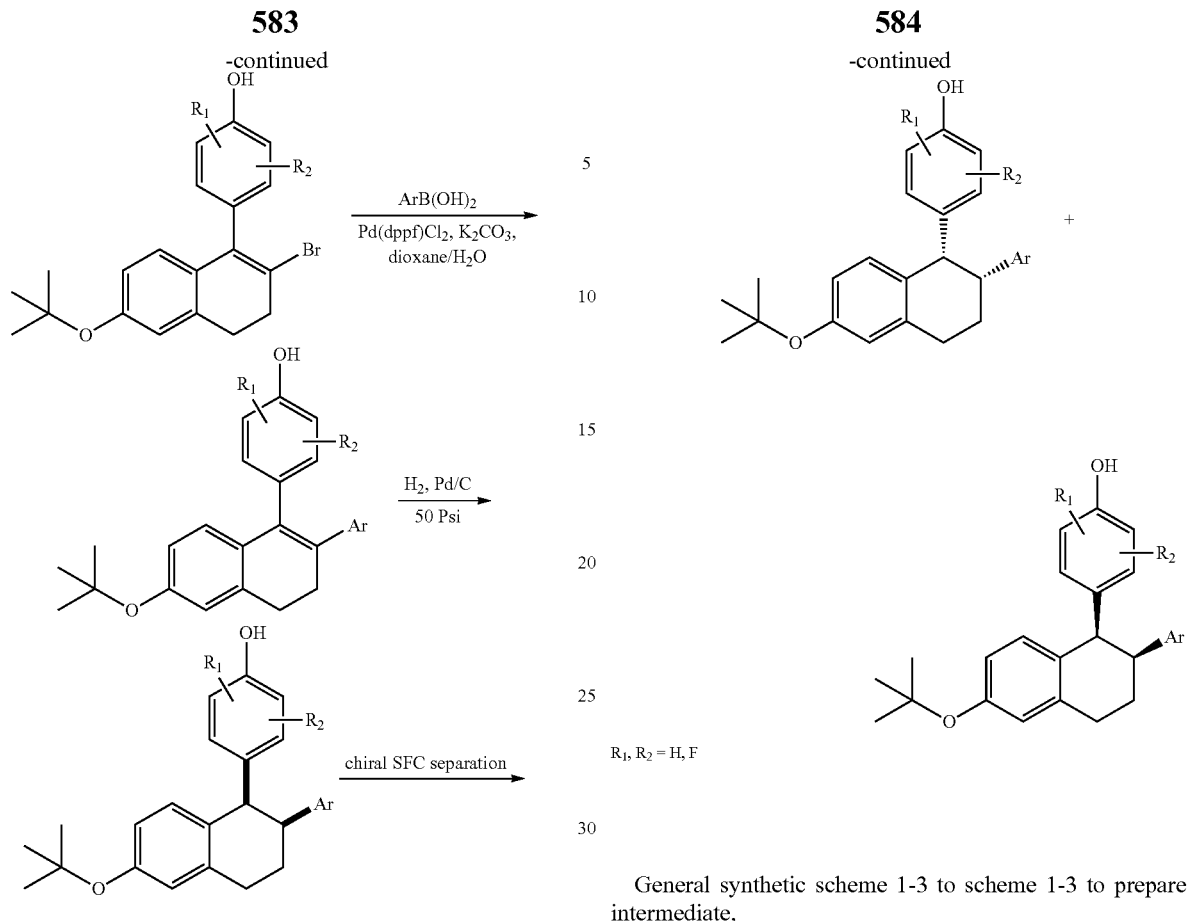
$R_1, R_2 = H, F$
General synthetic scheme 1-3 to scheme 1-3 to prepare intermediate,
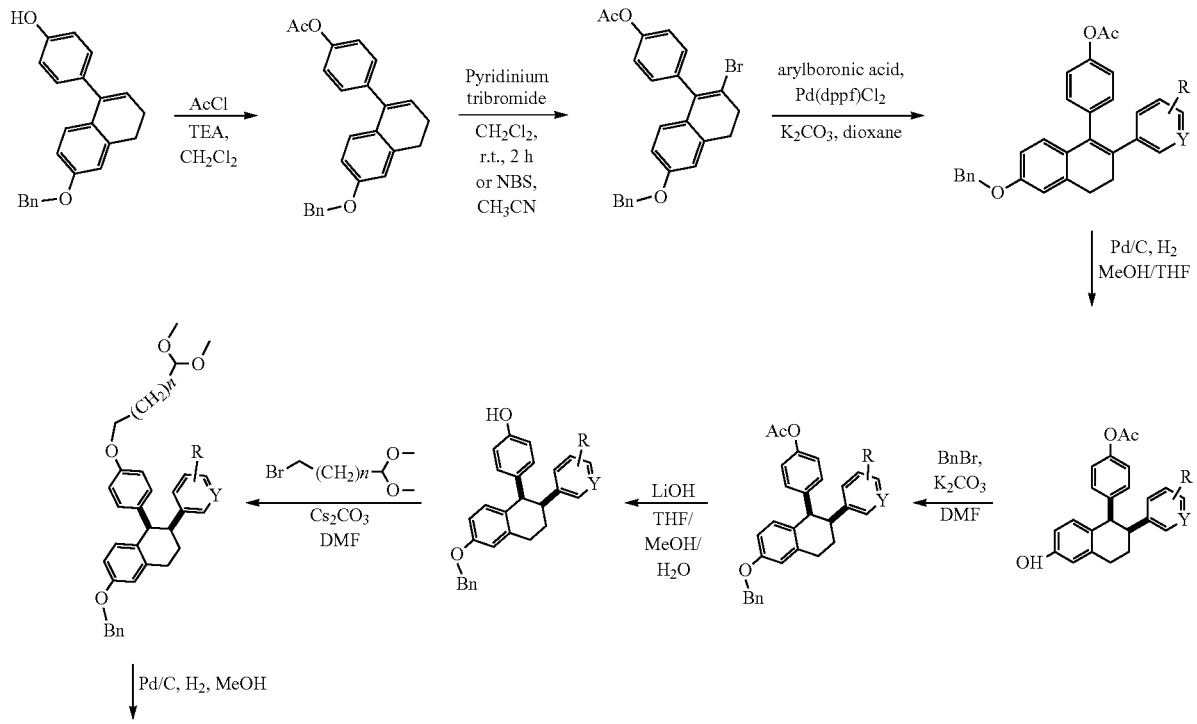

-continued
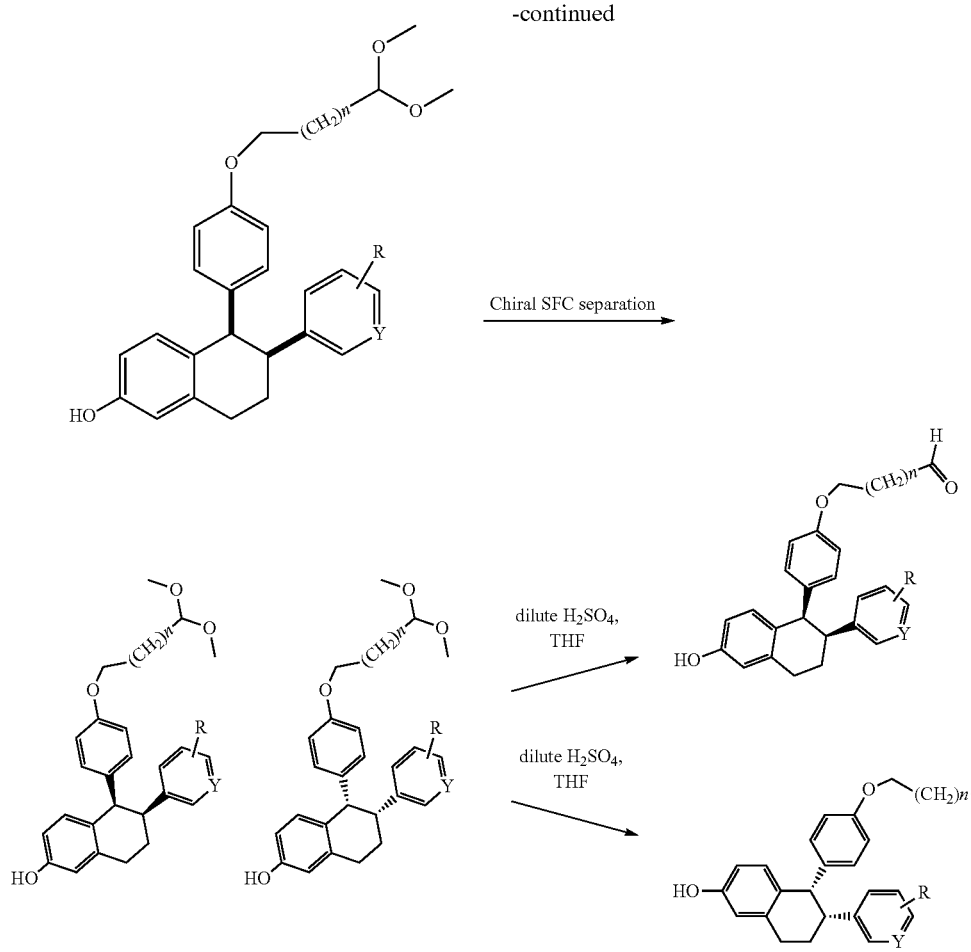
where n=0, 1, 2, 3, 4; Y=CH, N; R=H, F, CF$_3$
General synthetic scheme 1-4 to prepare intermediate.
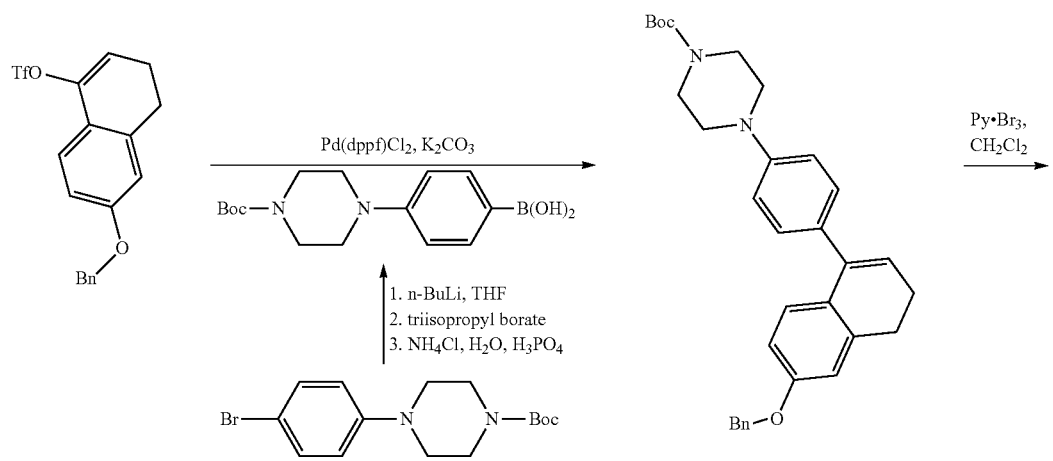

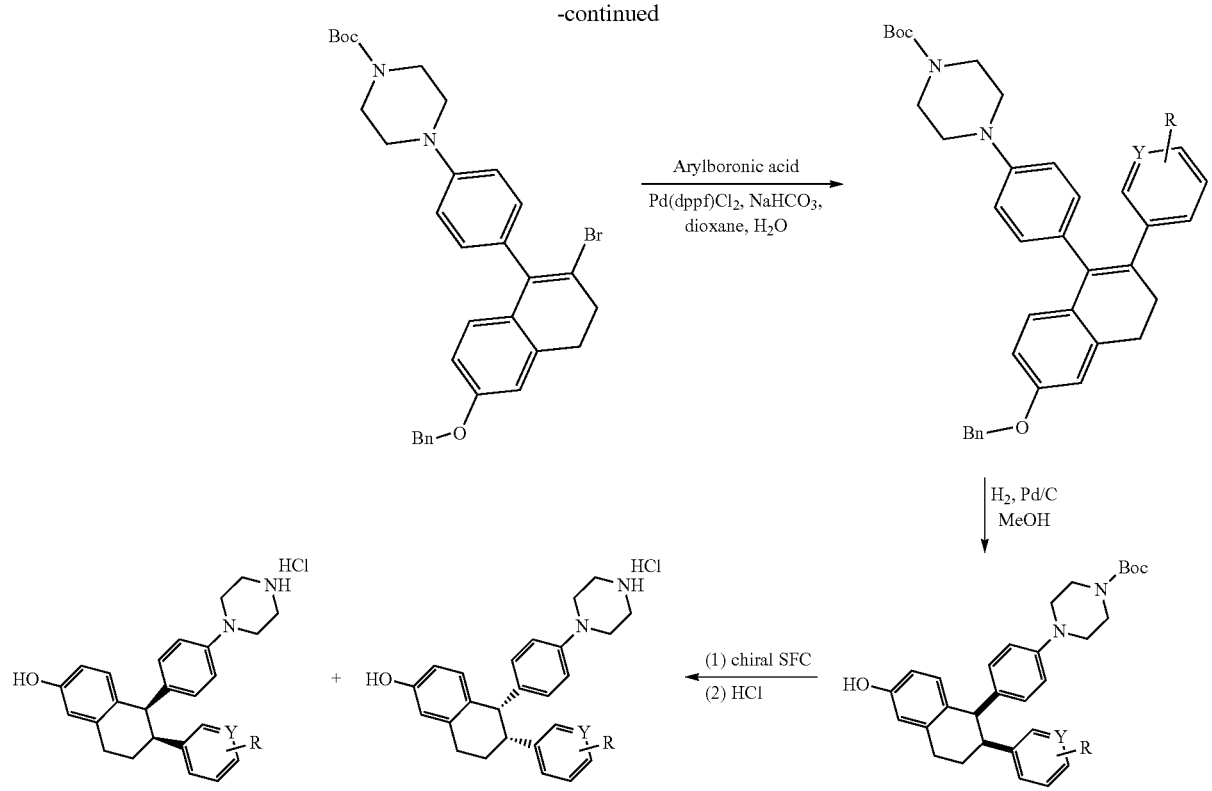
where Y=CH, N; R=H, F, CF₃
General synthetic scheme 1-5 to prepare intermediate.
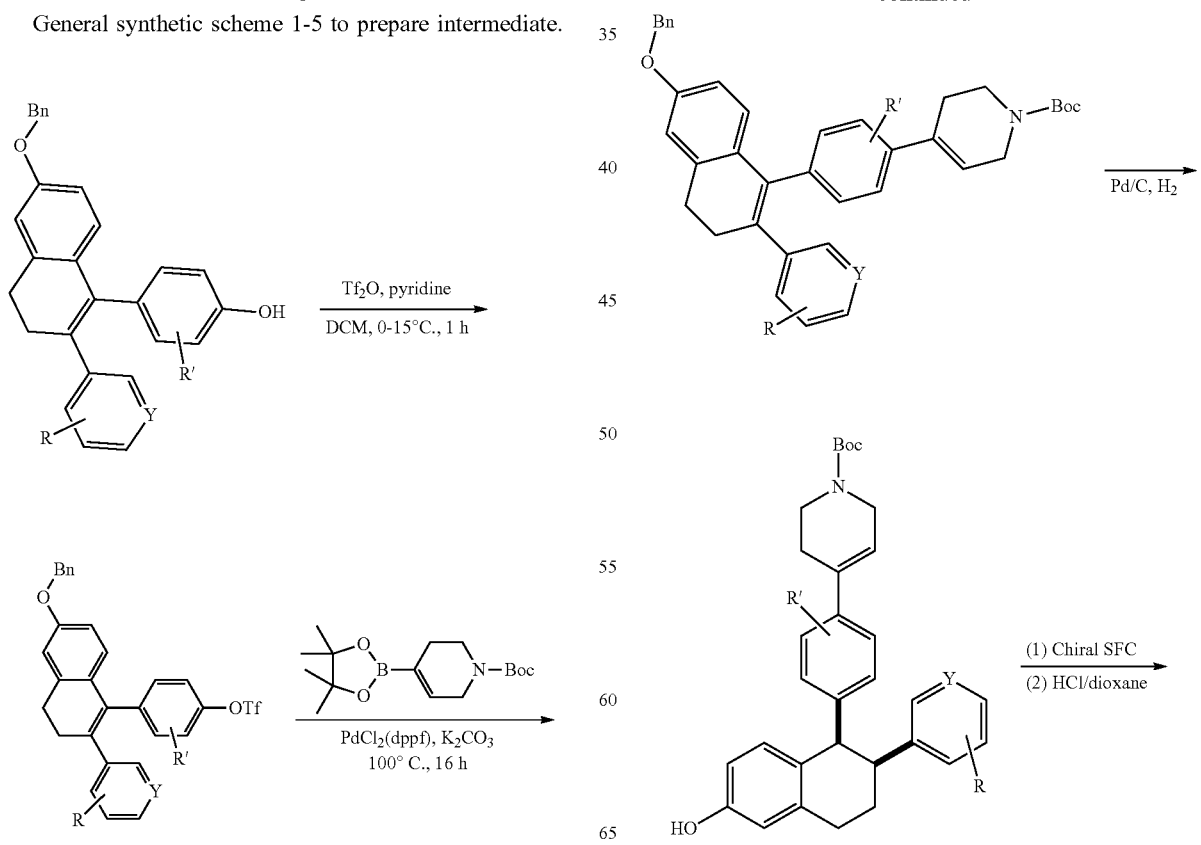

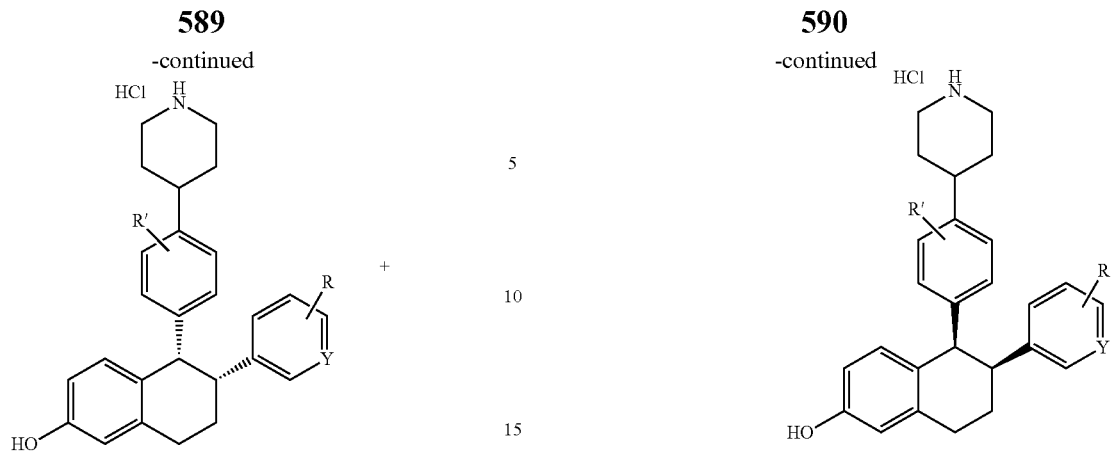
where Y=CH, N; R=H, F, CF$_3$
General synthetic scheme 1-6 to prepare intermediate.
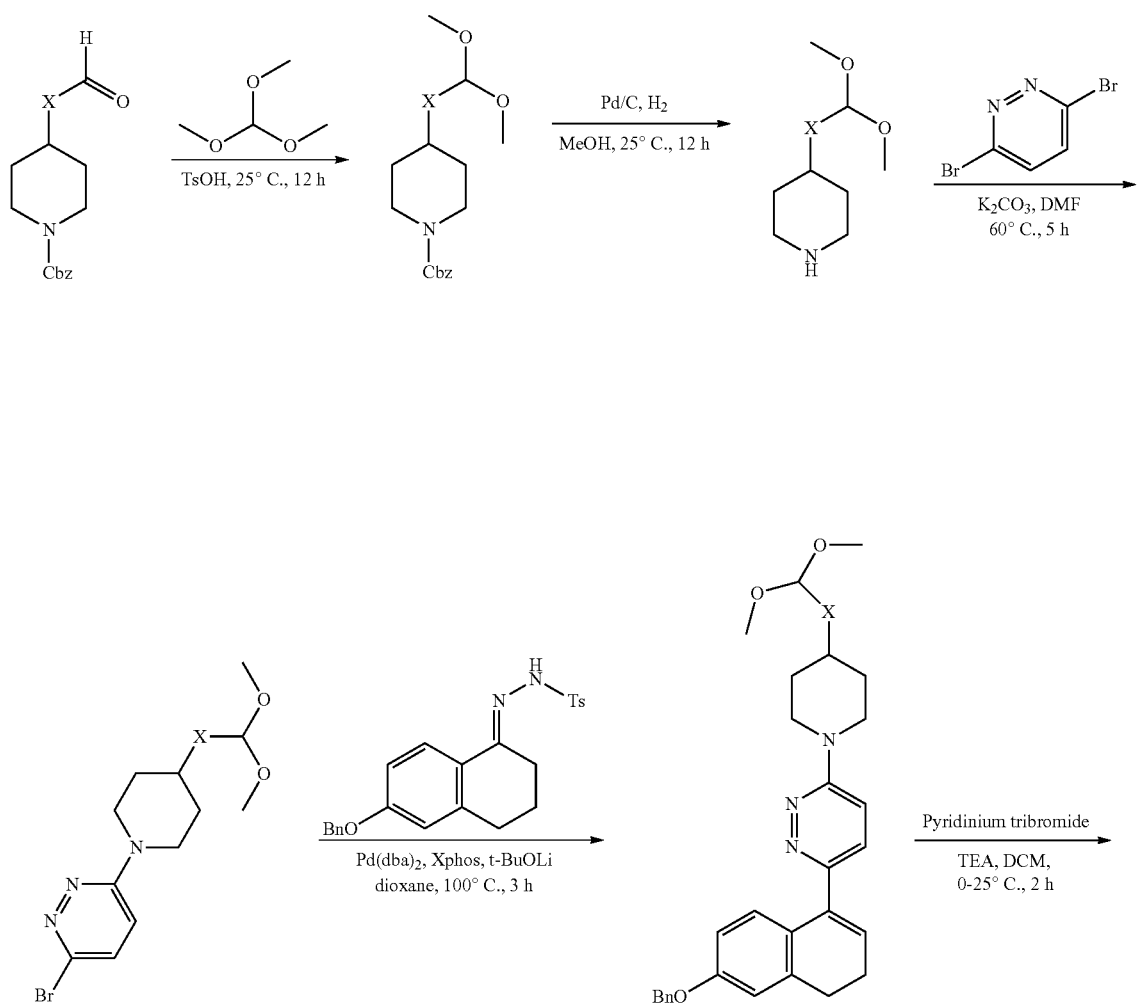

591
592
-continued
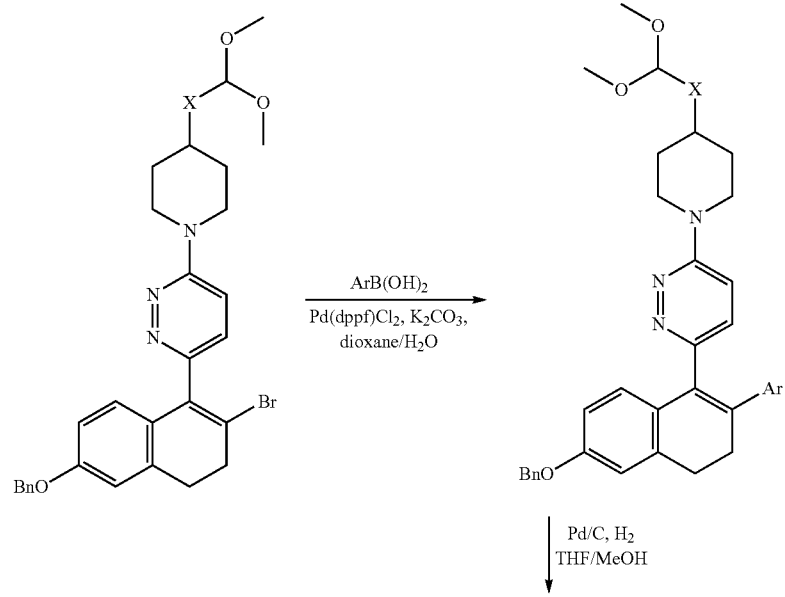
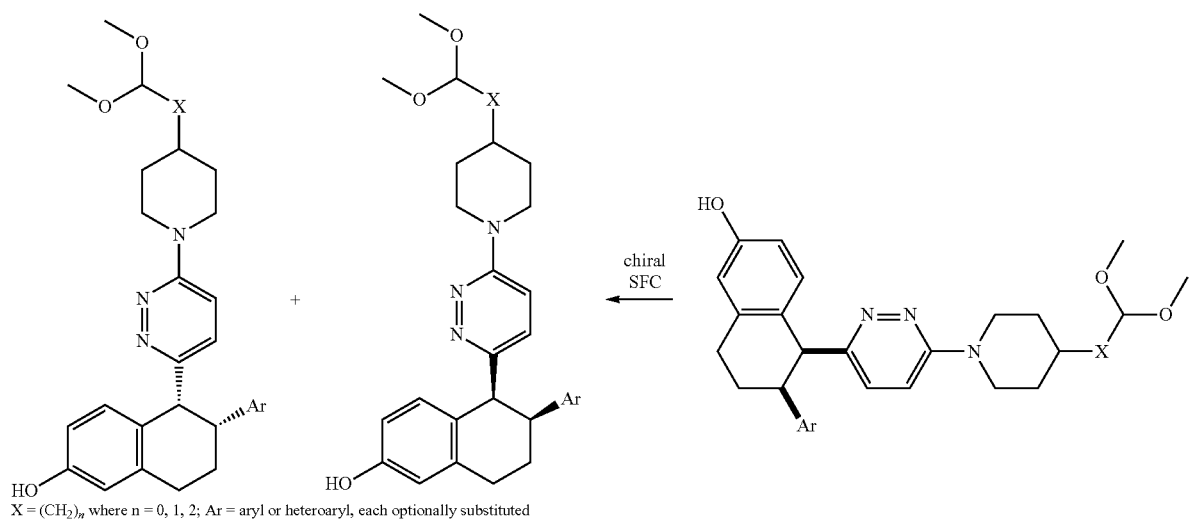
X = (CH$_2$)$_n$ where n = 0, 1, 2; Ar = aryl or heteroaryl, each optionally substituted
General synthetic scheme 1-7 to prepare intermediate.
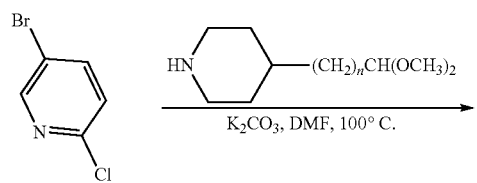

593
-continued
594
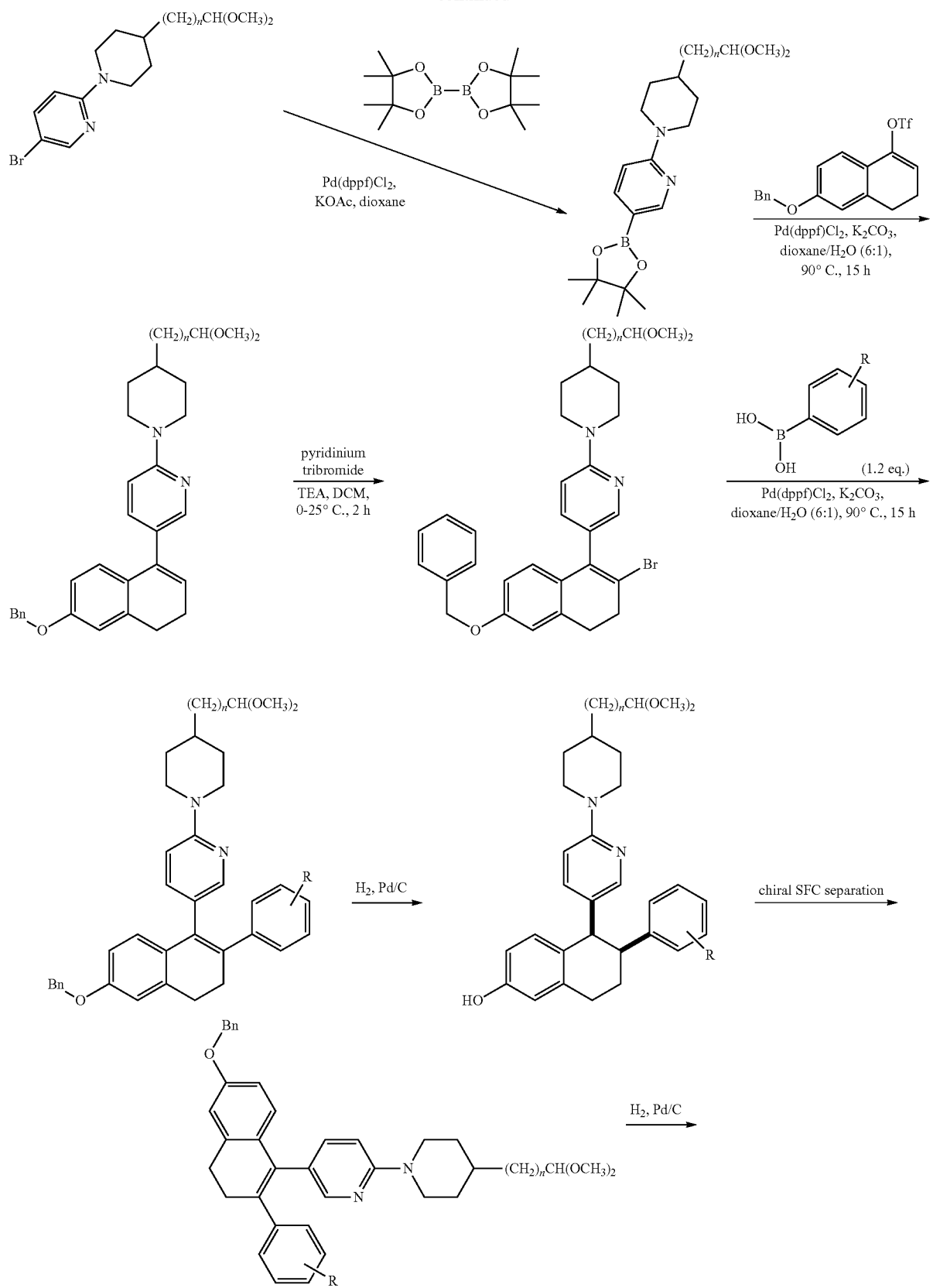

595
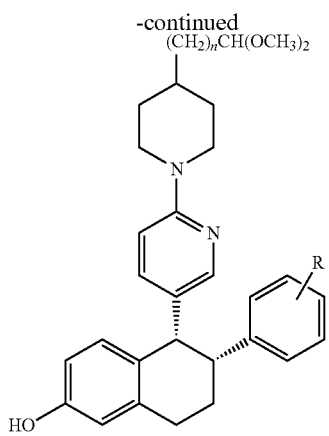
n = 0, 1, 2; R = H, F, alkoxy, CF$_3$
General synthetic scheme 1-8 to prepare intermediate.
596
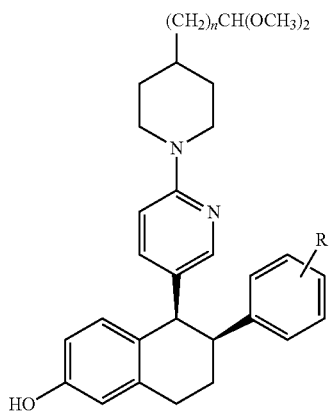
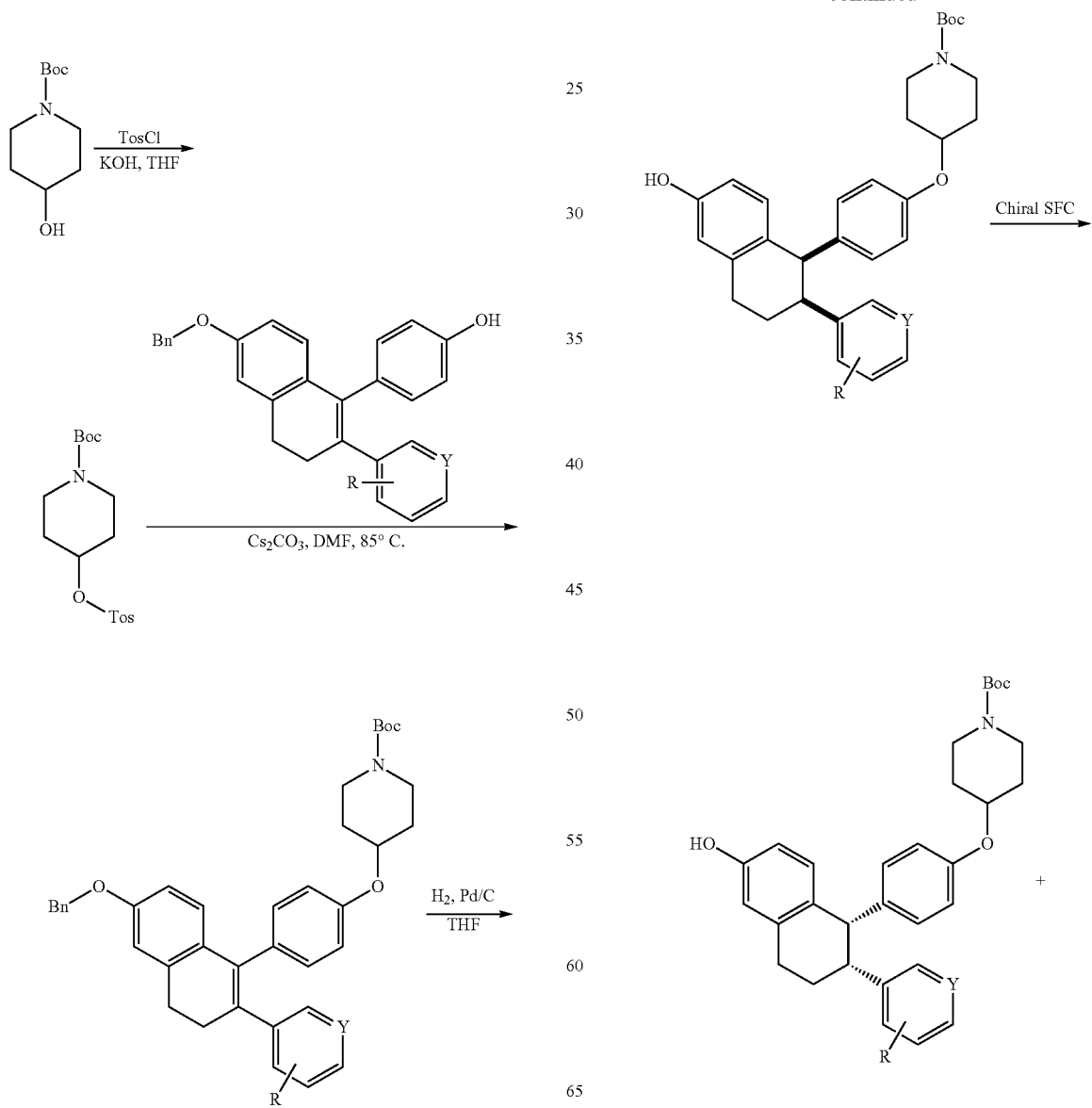

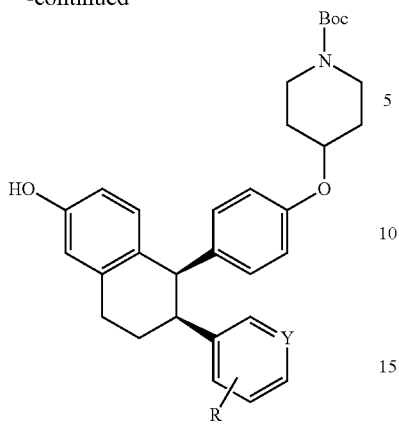
where Y=CH, N; R=H, F, CF₃
General synthetic scheme 1-9 to prepare intermediate.
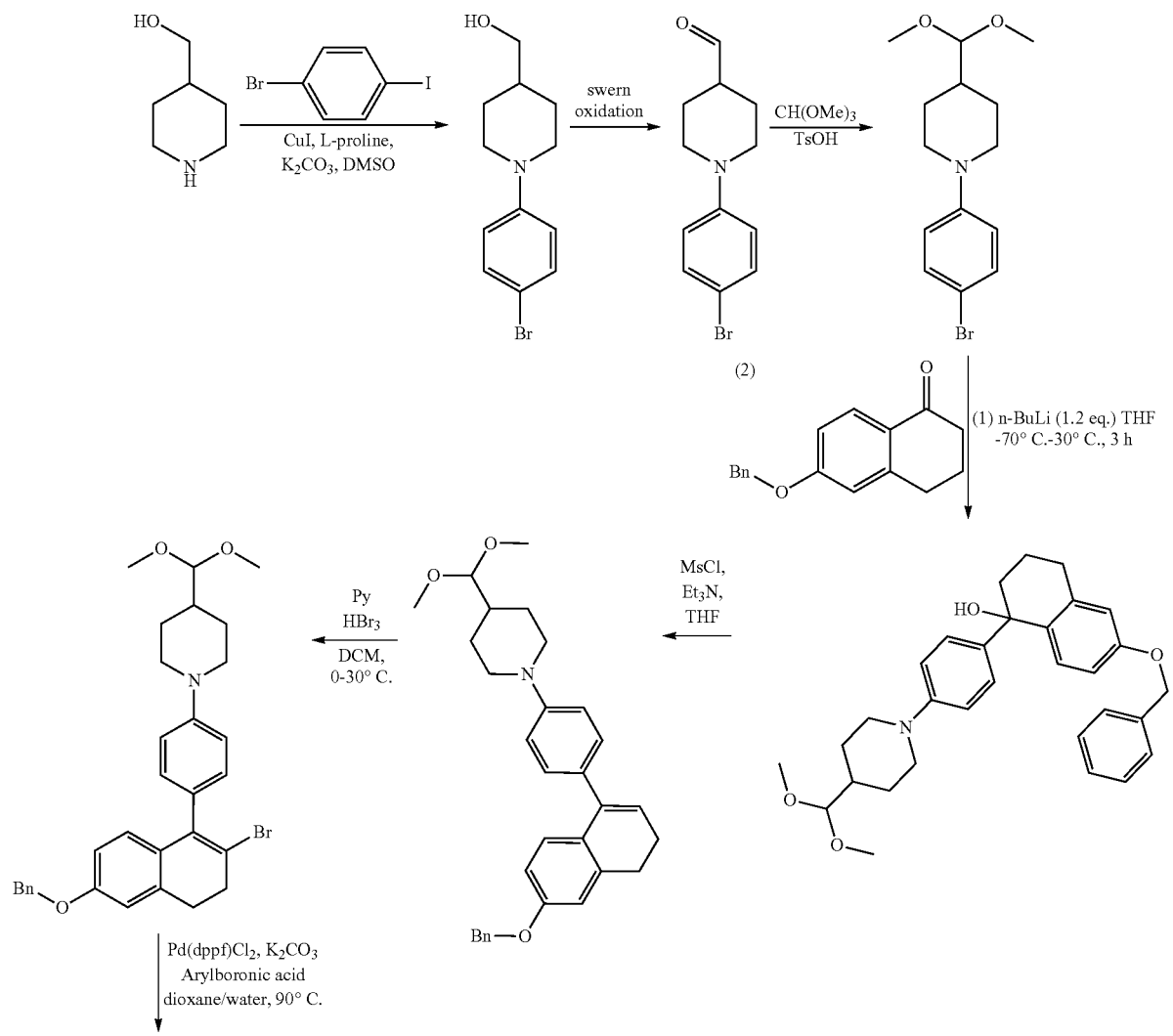

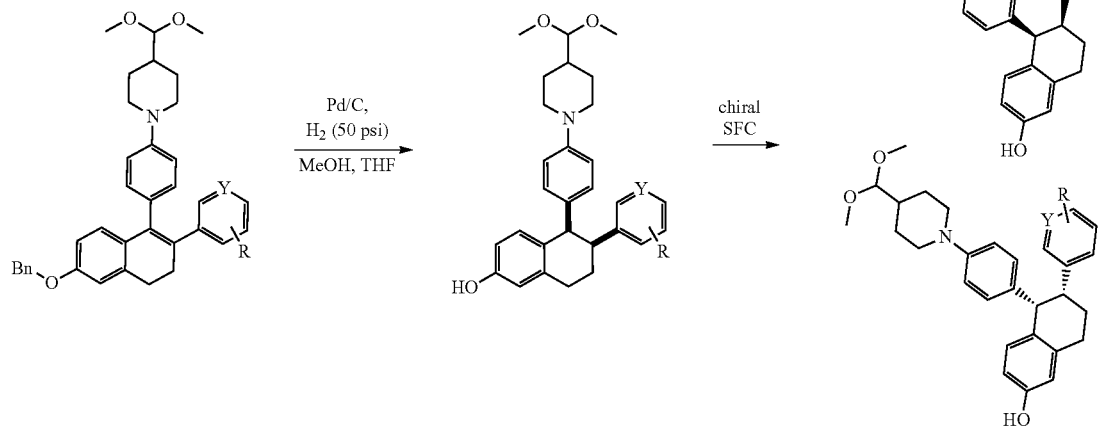
where Y=CH, N; R=H, F, $CF_3$
General synthetic scheme 1-10 to prepare intermediate.
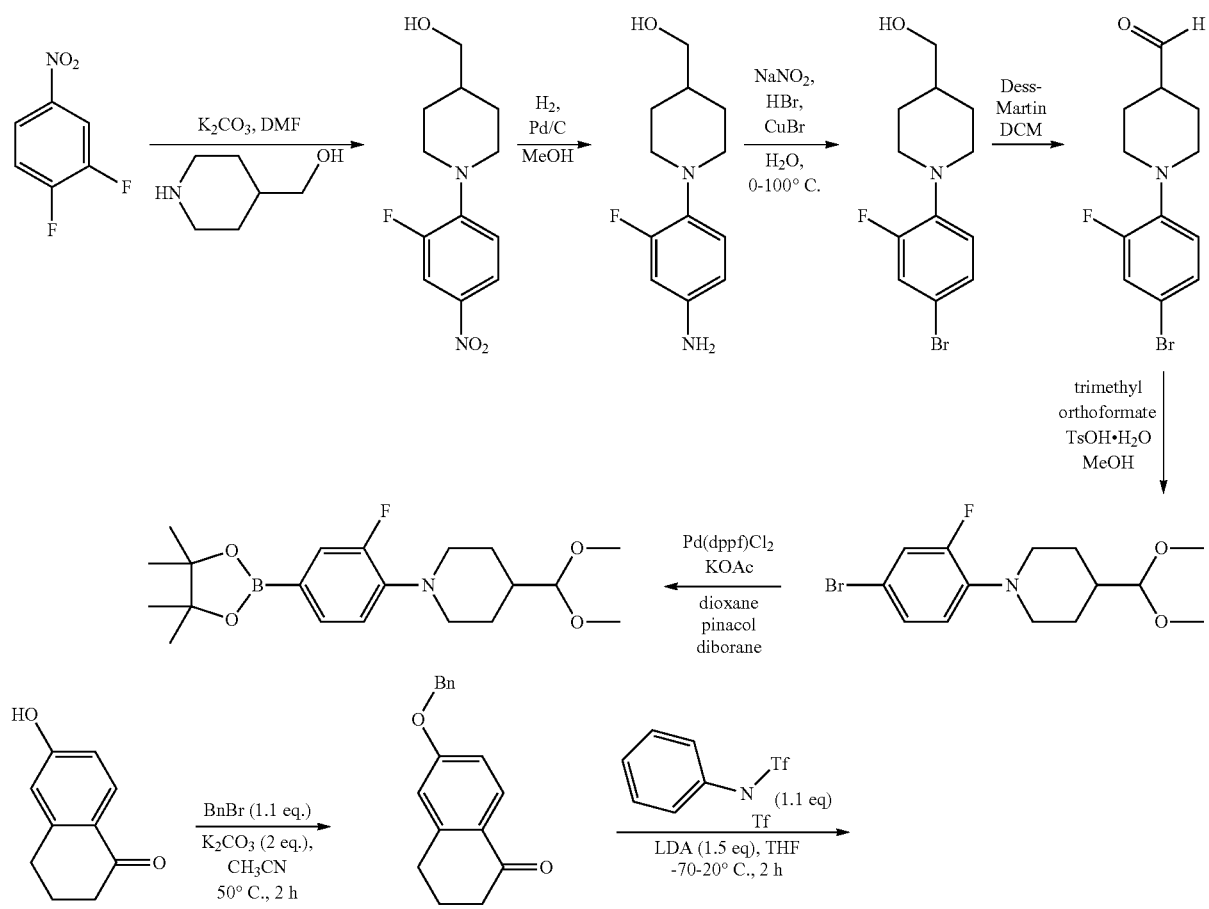

601
602
-continued
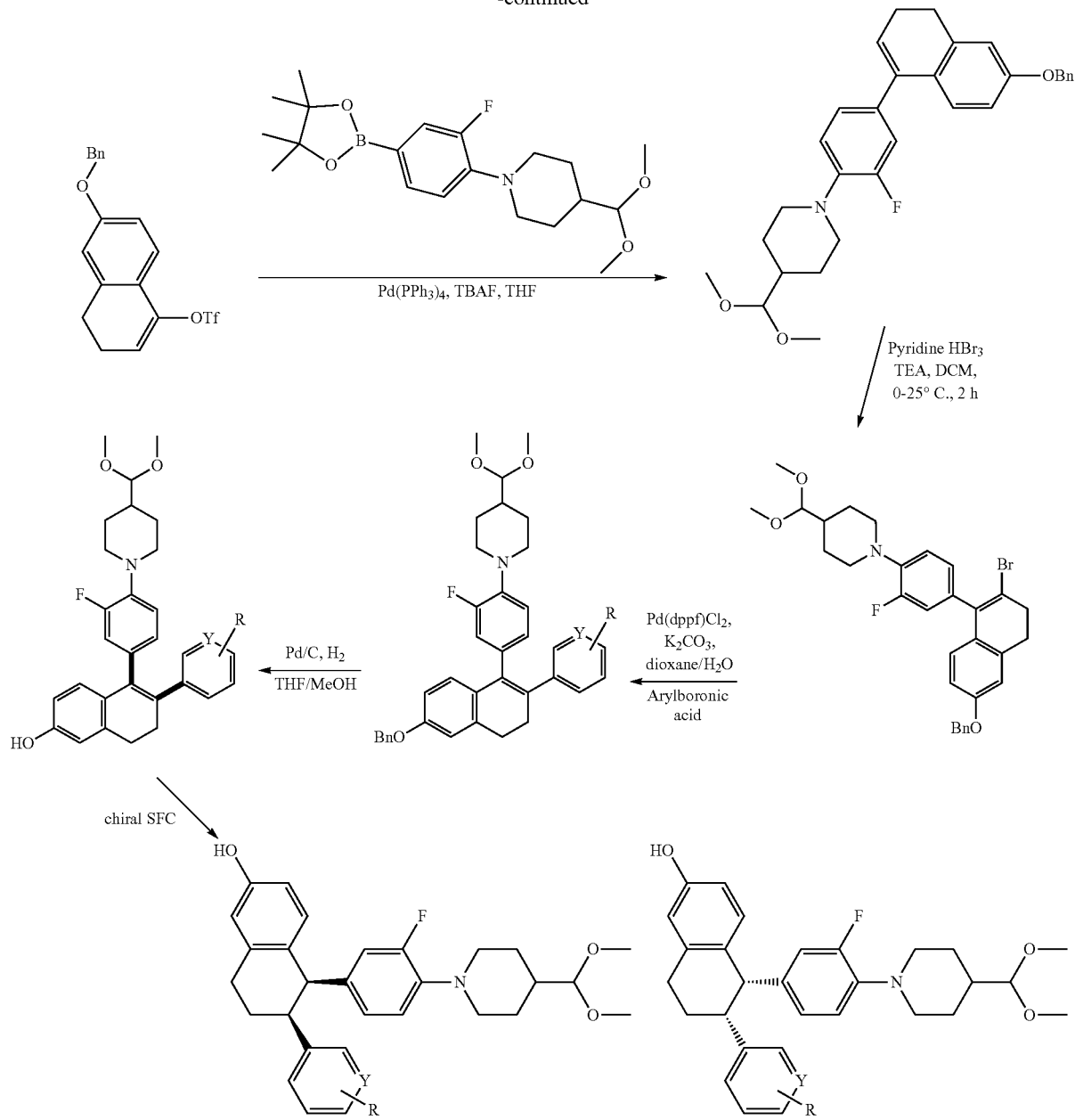
where Y=CH, N; R=H, F, CF₃
General synthetic scheme 1-11 to prepare intermediate.
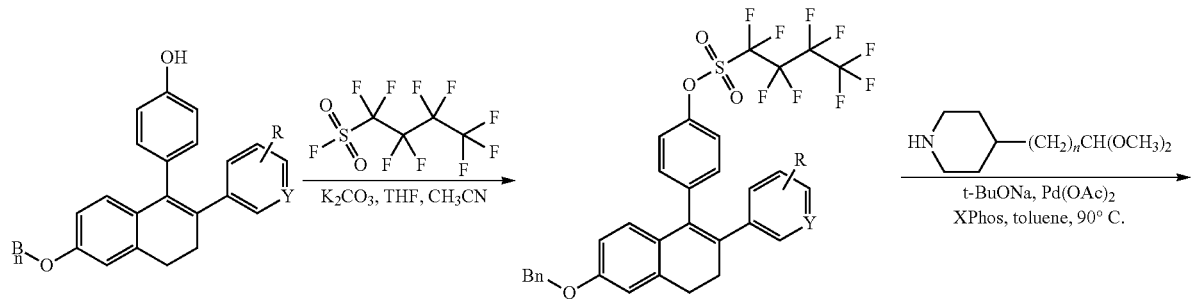

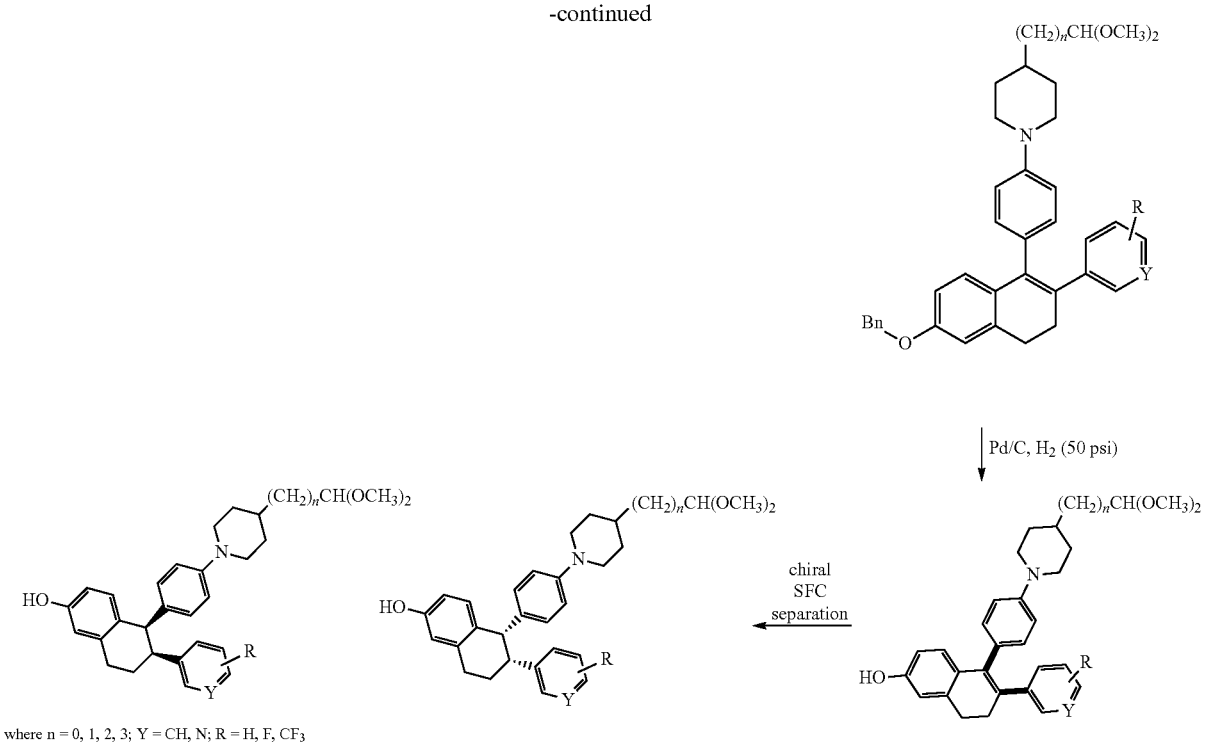
where n = 0, 1, 2, 3; Y = CH, N; R = H, F, CF$_3$
General synthetic scheme 1-12 to prepare intermediate.
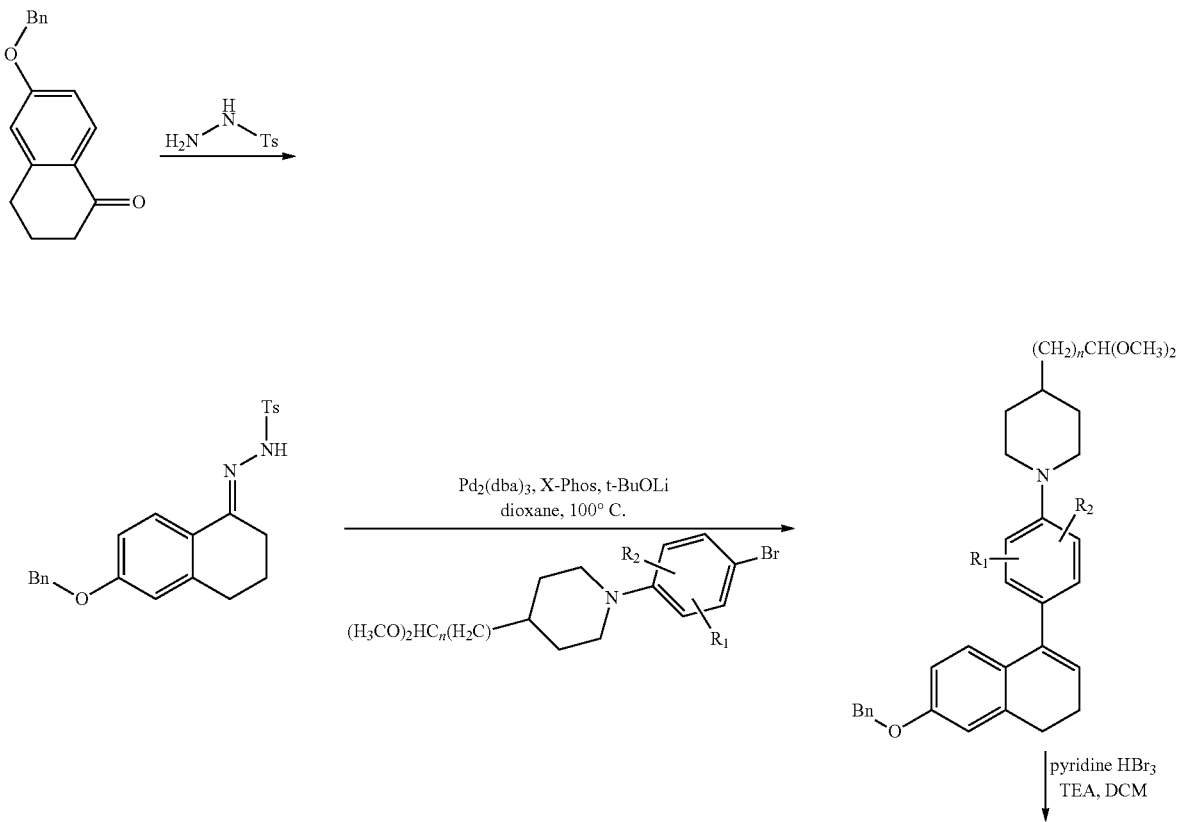

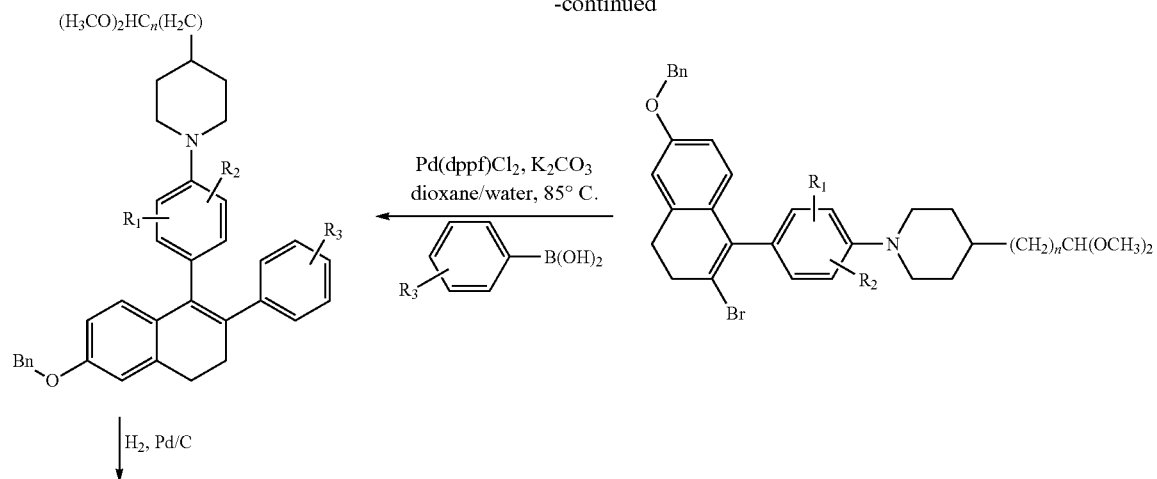
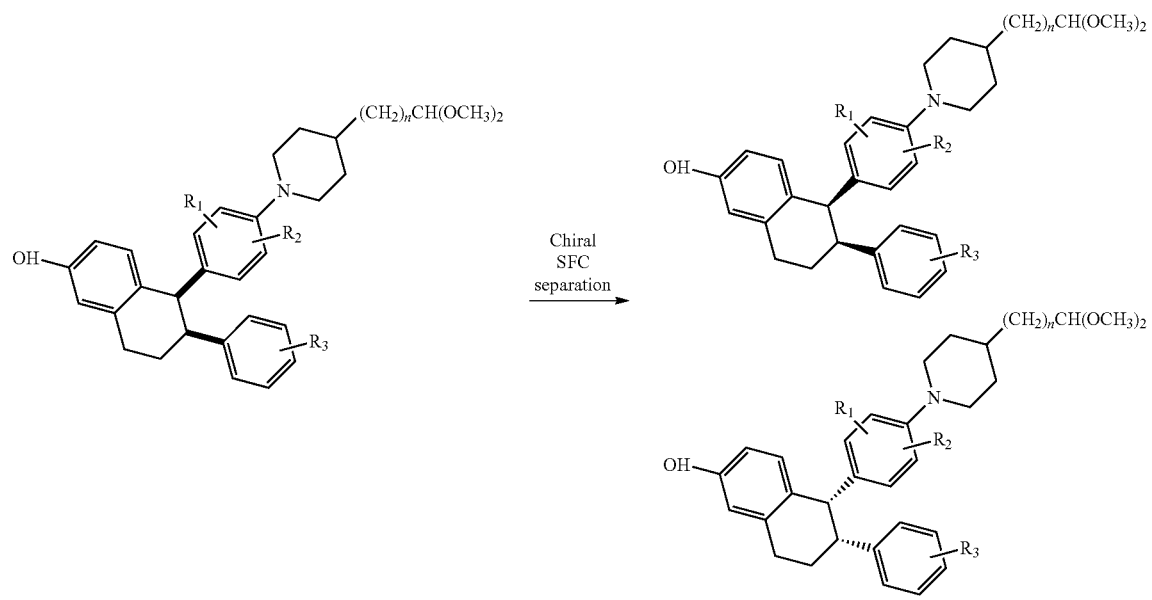
where n=0, 1, 2, 3; $R_1$, $R_2$ and $R_3$ — H, F, $CF_3$
General synthetic scheme 1-13 to prepare intermediate.
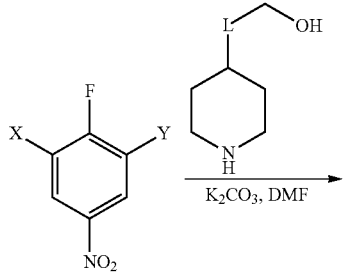
-continued
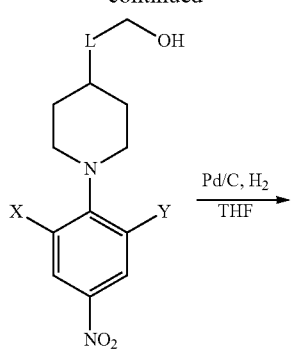

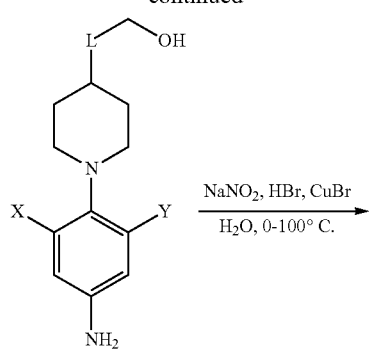
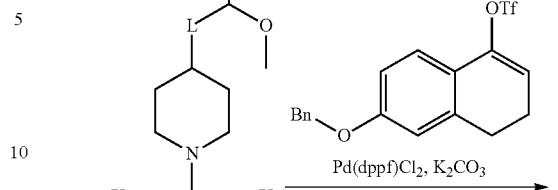
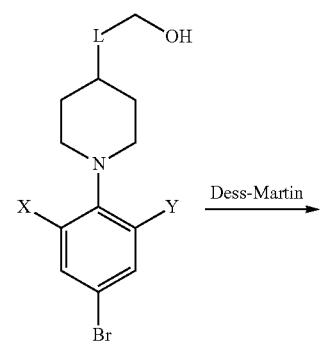
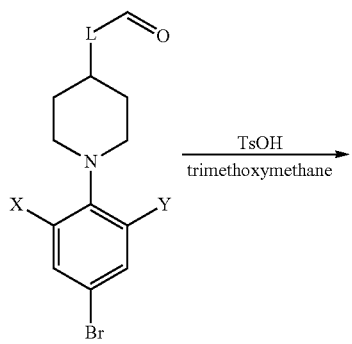
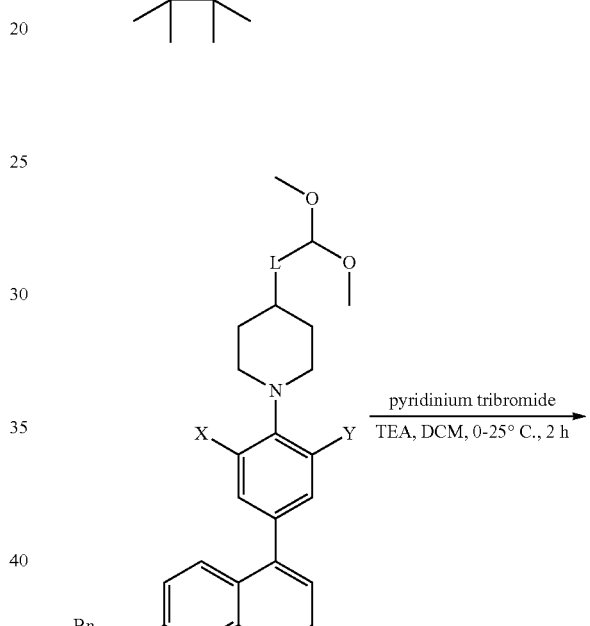
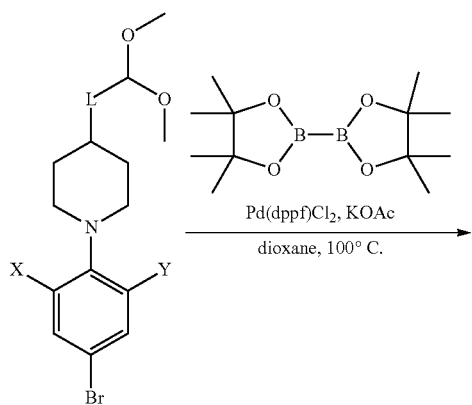
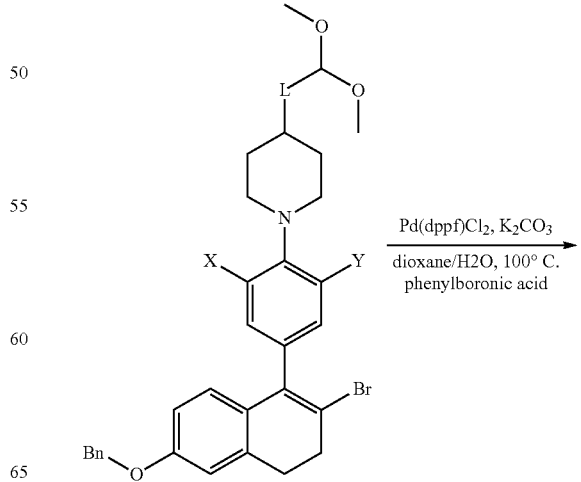

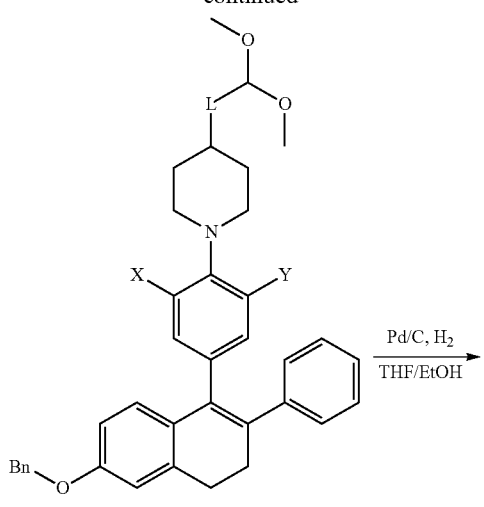
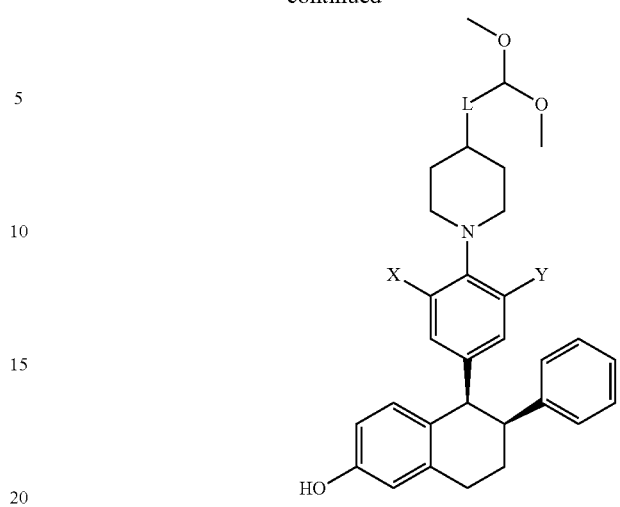
X and Y = H, F; L = $(CH_2)_n$ where n = 0, 1, 2
General synthetic scheme 1-14 to prepare intermediate.
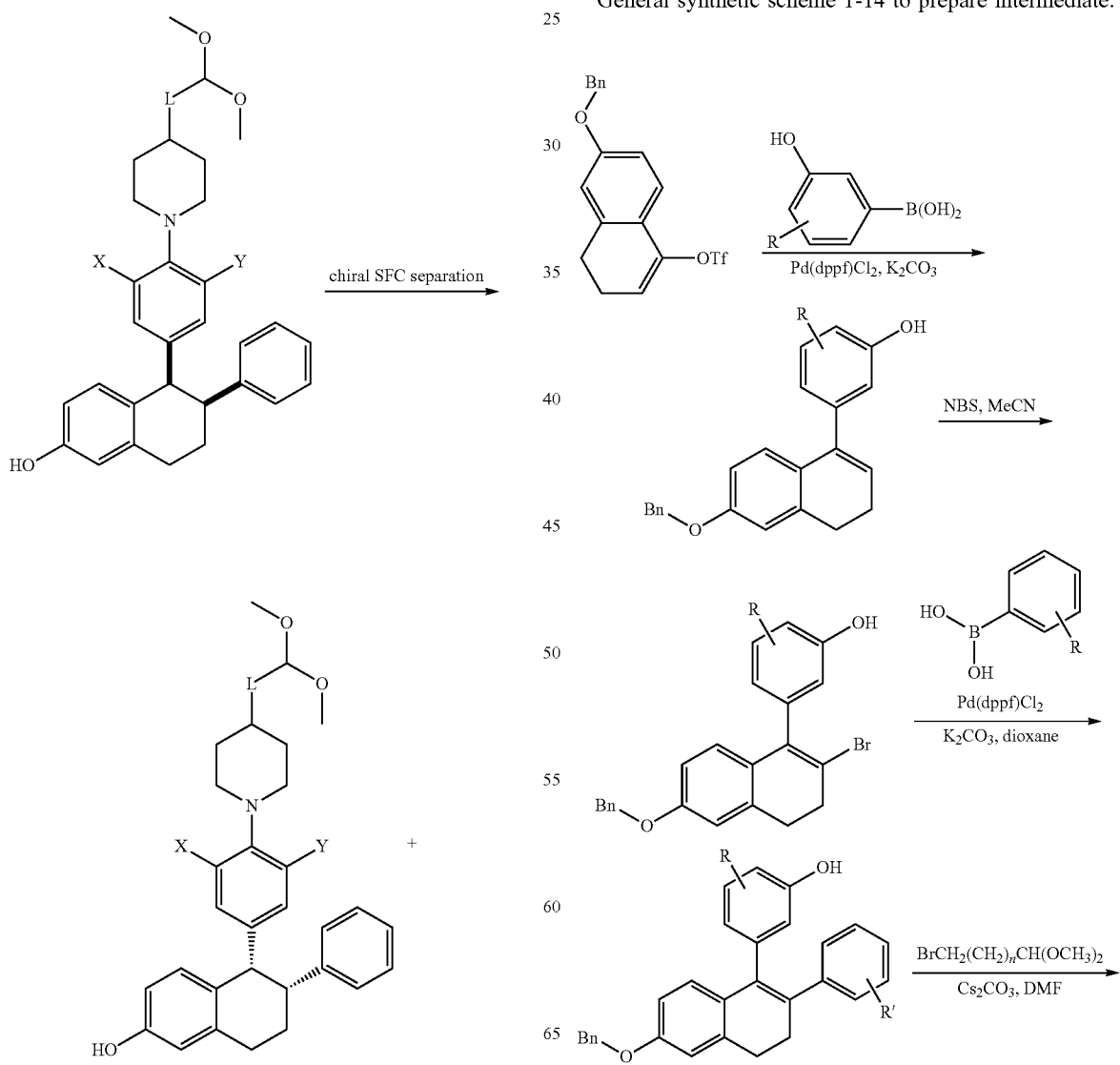

611
-continued
612
-continued
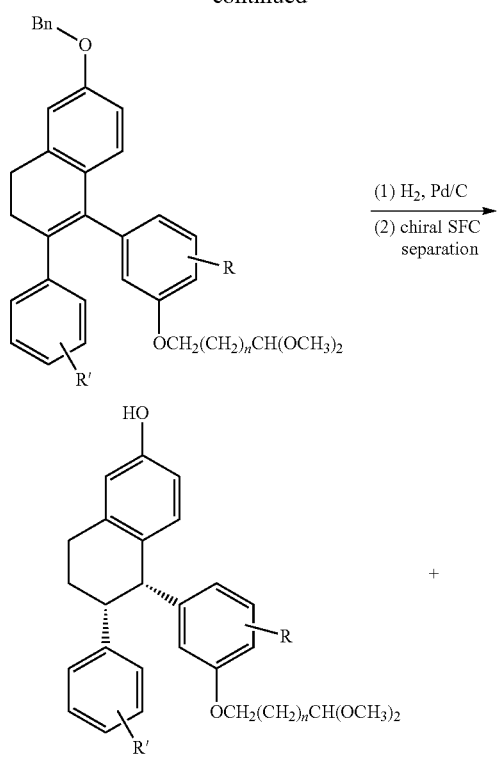
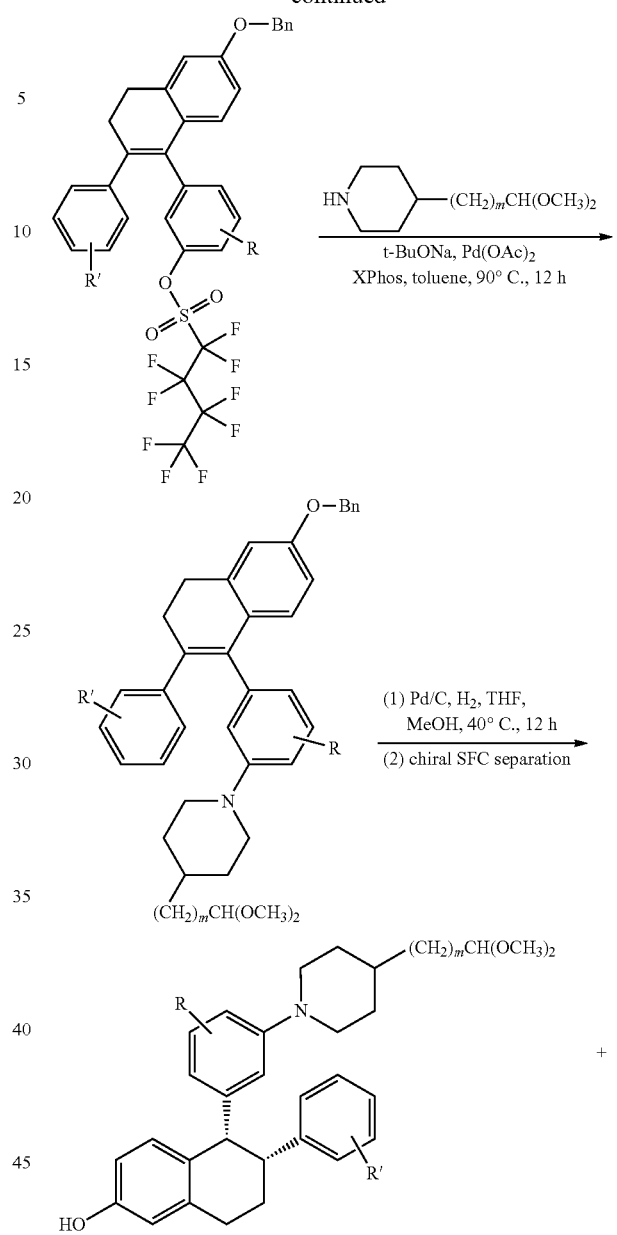
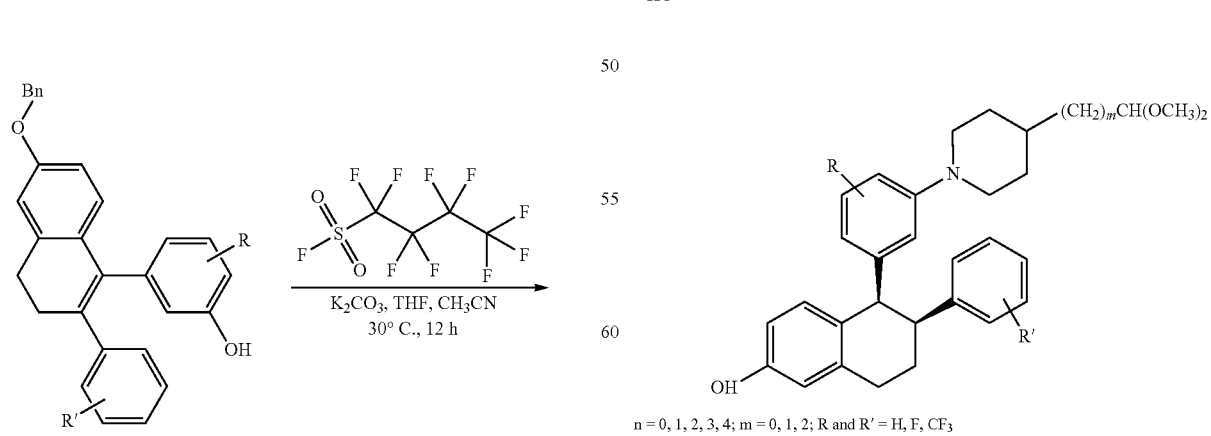
n = 0, 1, 2, 3, 4; m = 0, 1, 2; R and R' = H, F, CF₃

613
General synthetic scheme 1-15 to prepare intermediate.
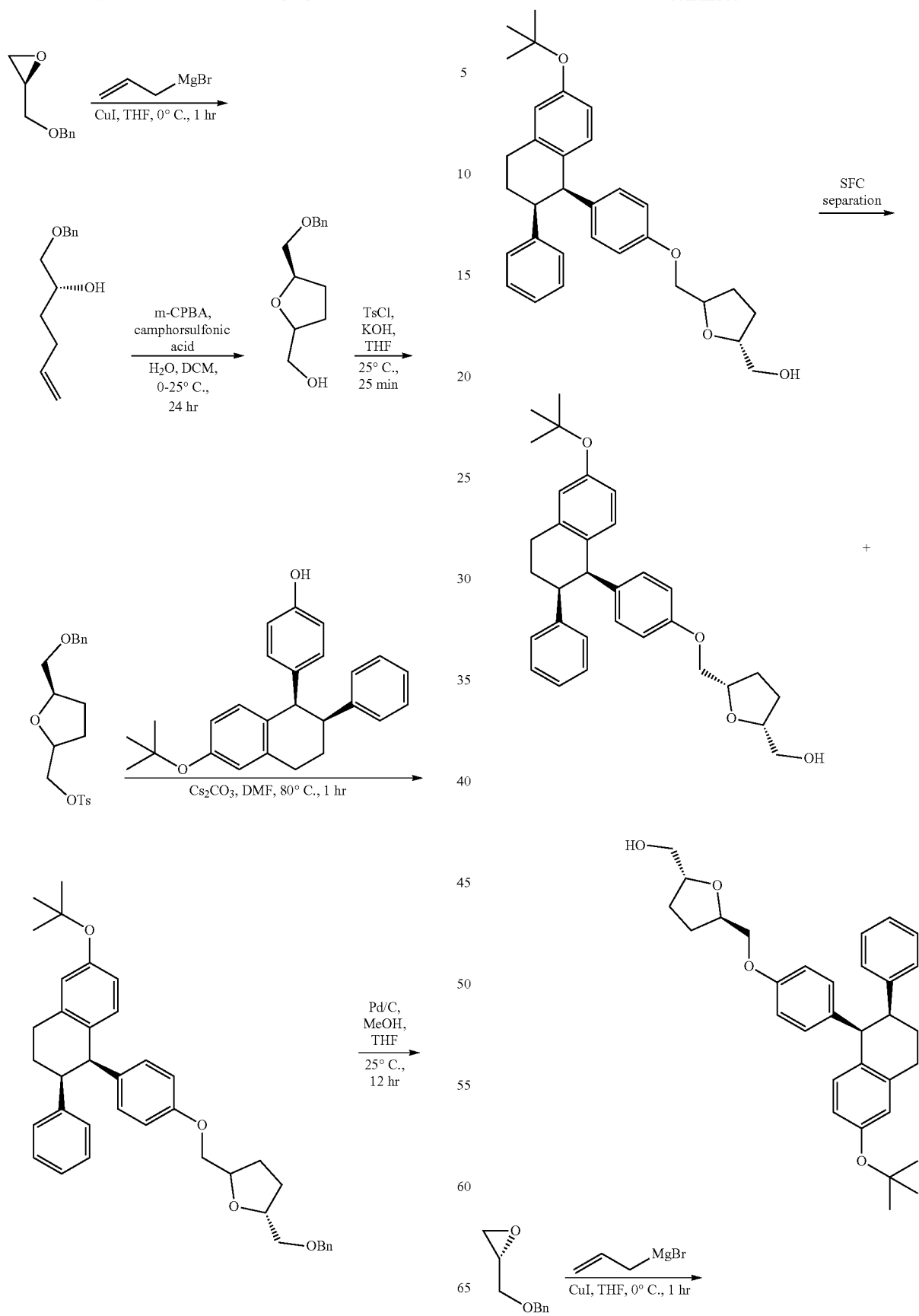

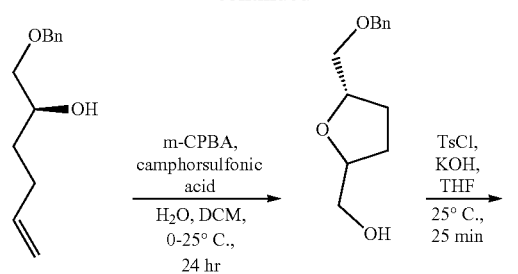
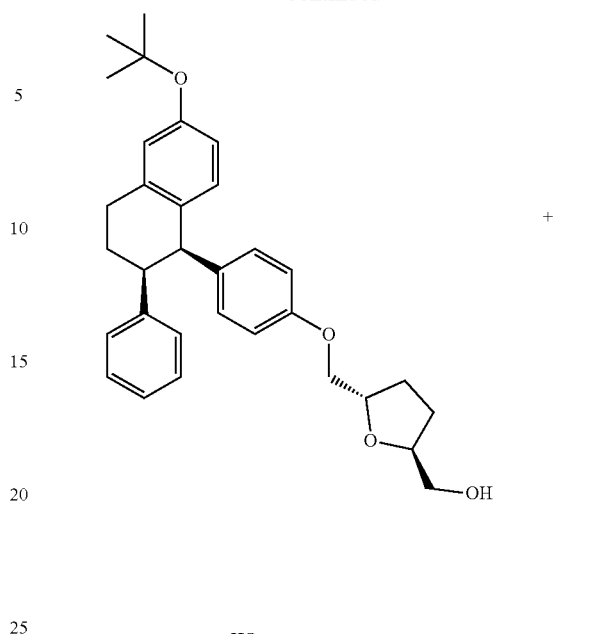
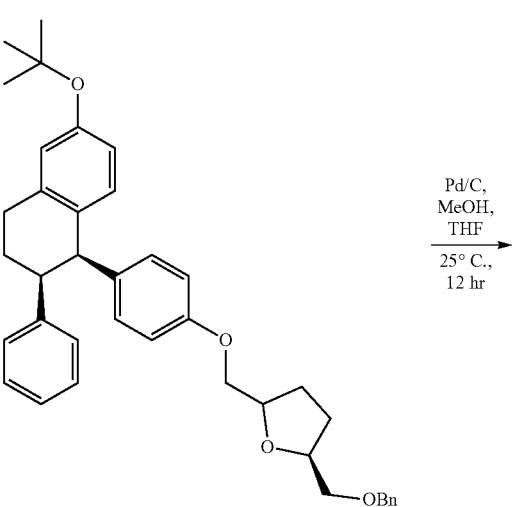
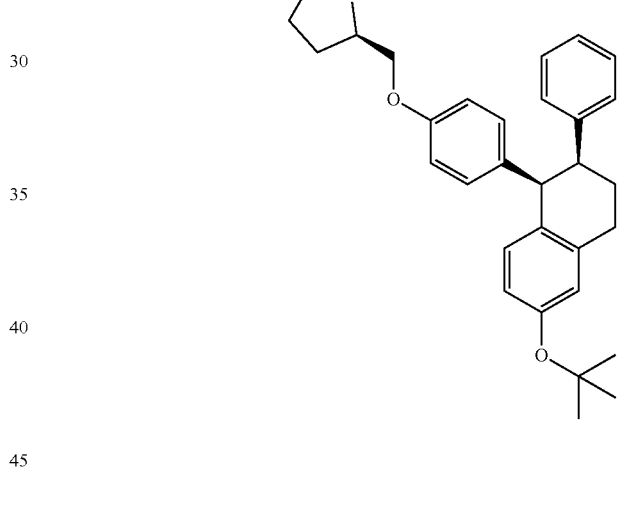
General synthetic scheme 1-16 to prepare intermediate.
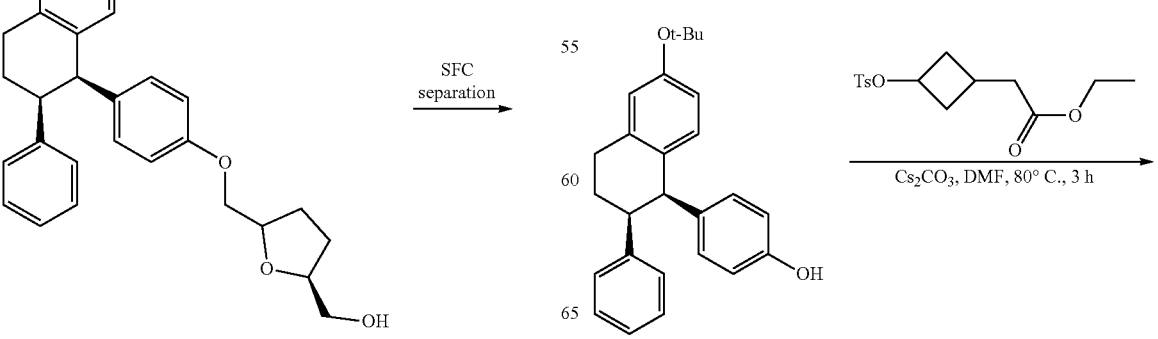

617
-continued
618
-continued
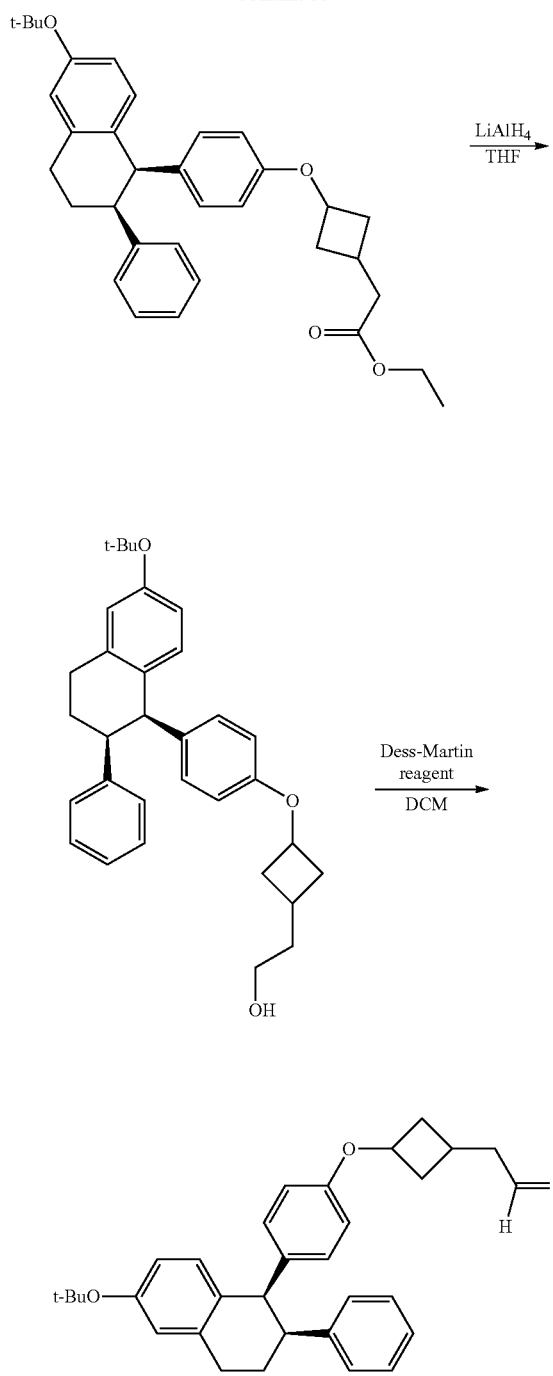
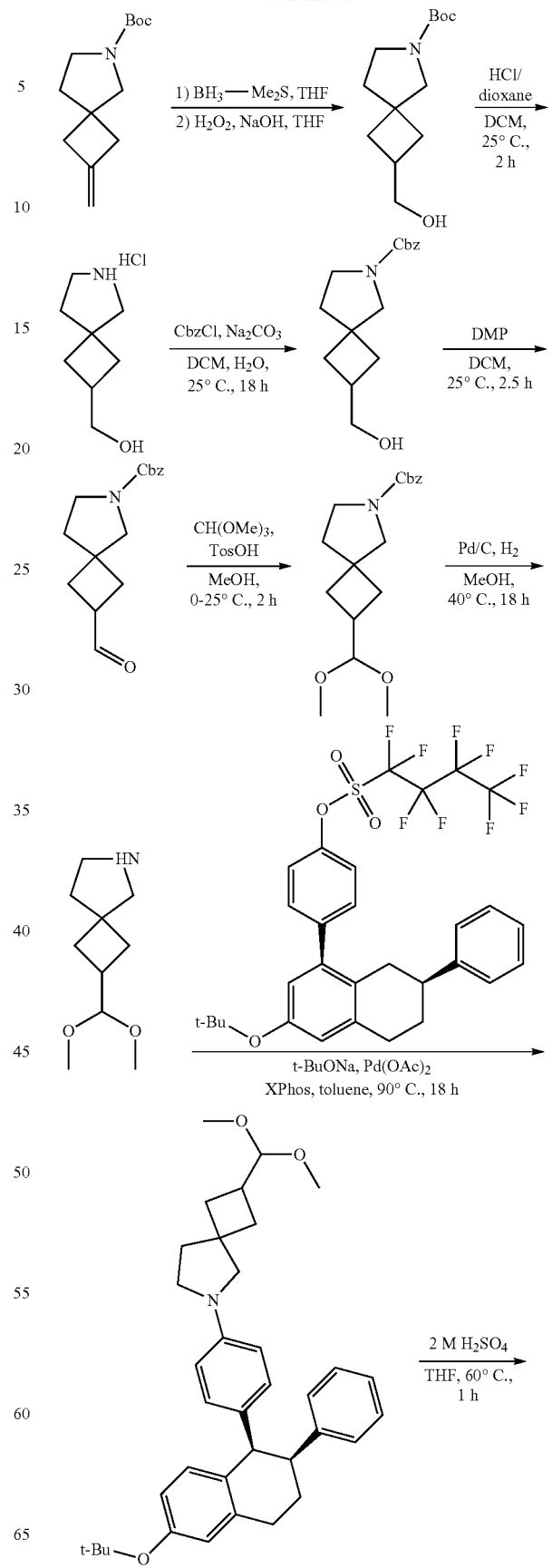
General synthetic scheme 1-17 to prepare intermediate.
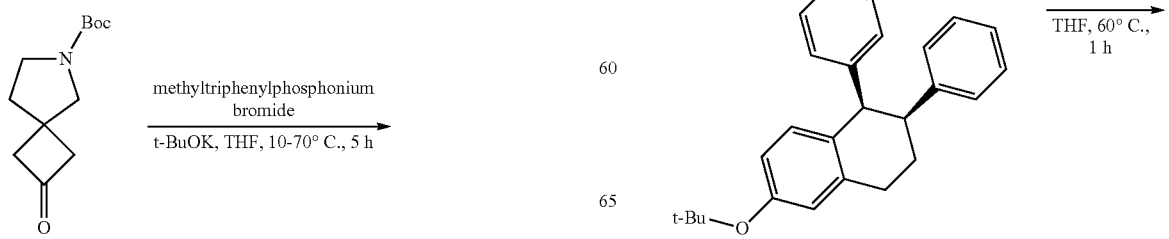

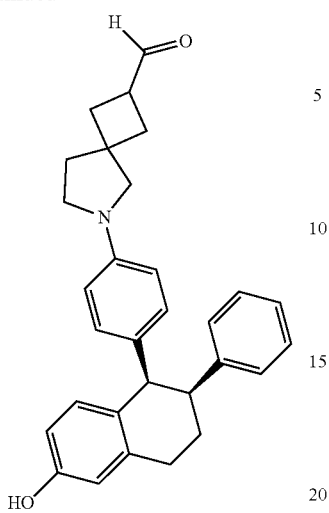
General synthetic scheme 1-18 to prepare intermediate.
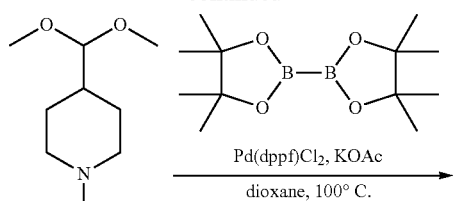
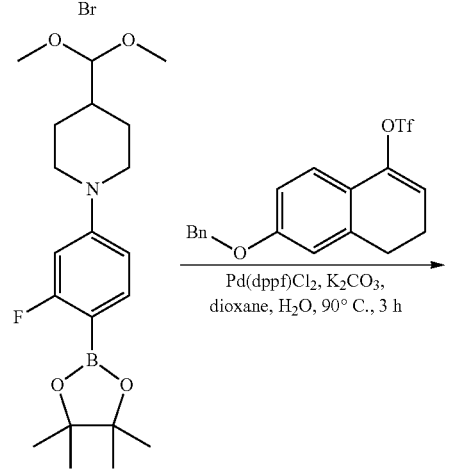
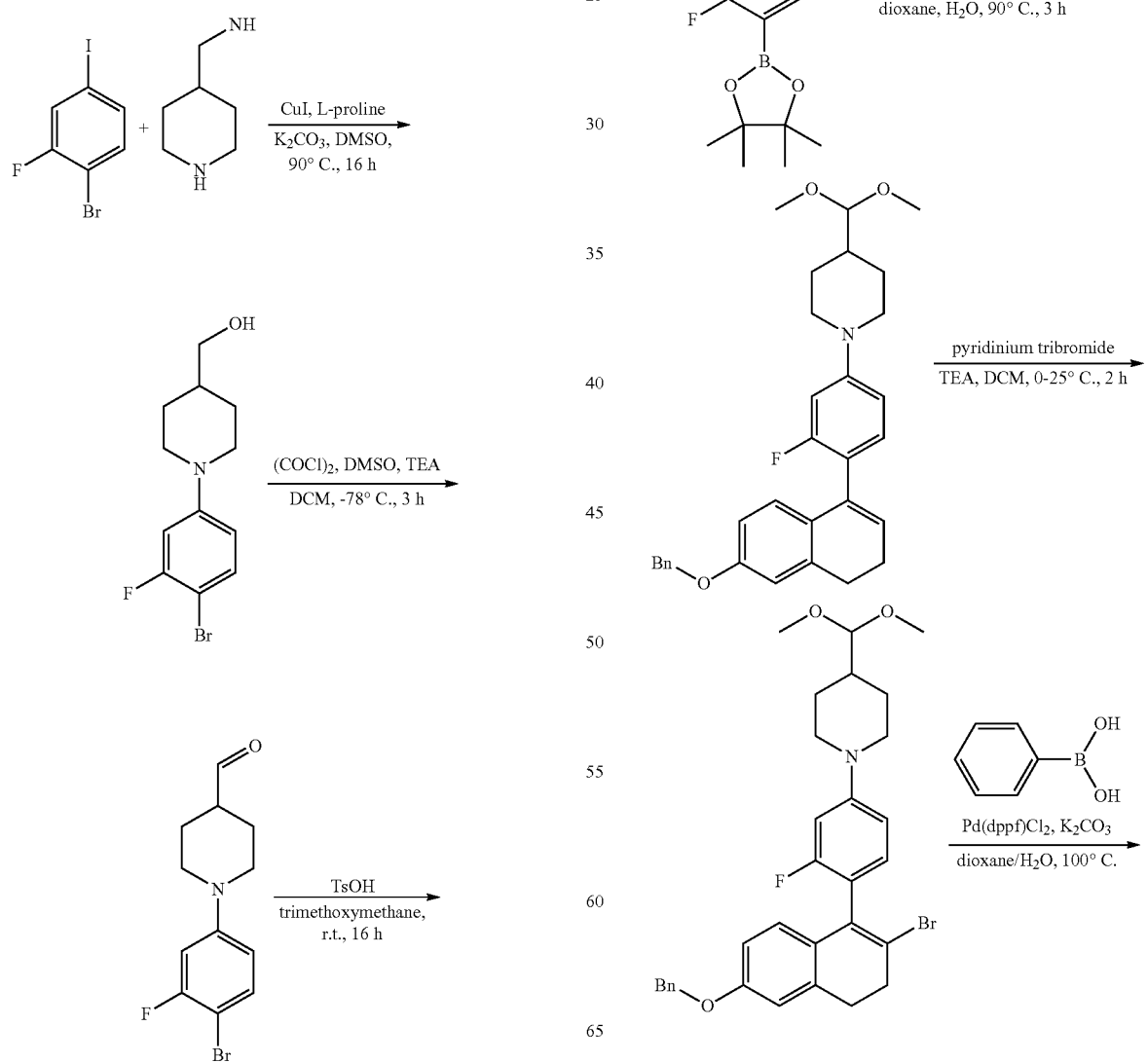

622
General synthetic scheme 1-19 to prepare intermediate.
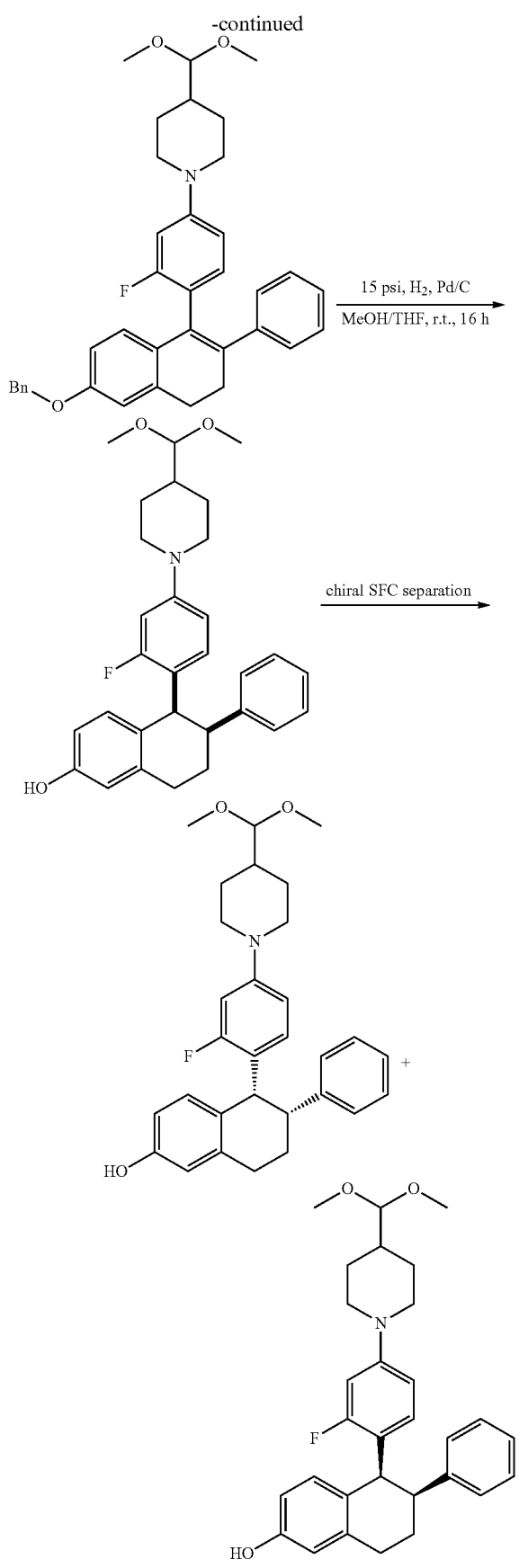

623
-continued
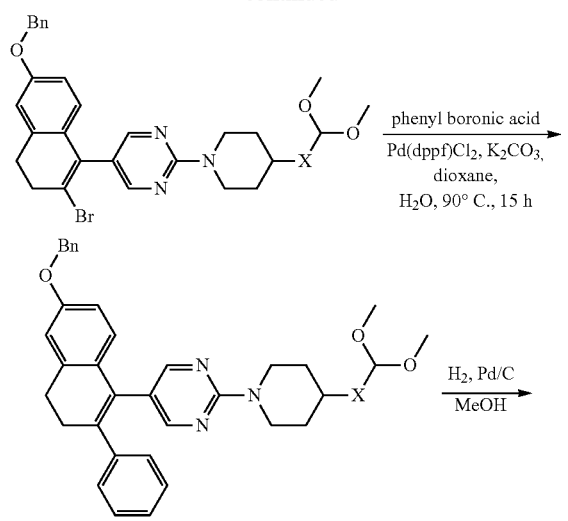
X = (CH₂)ₘ where n = 0, 1, 2
624
General synthetic scheme 1-20 to prepare intermediate.
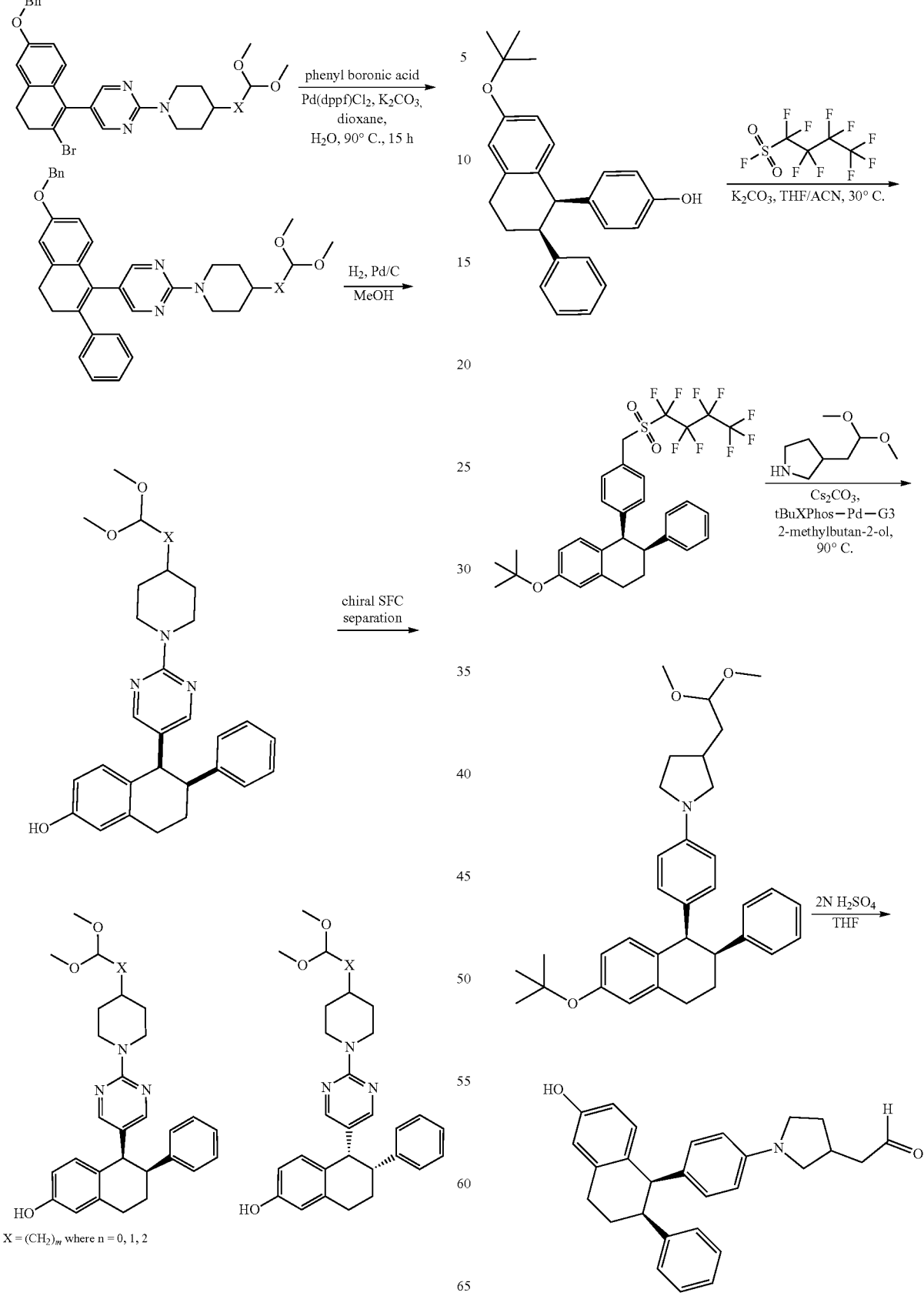

General synthetic scheme 1-21 to prepare intermediate.
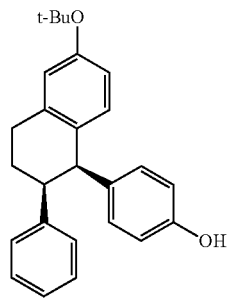
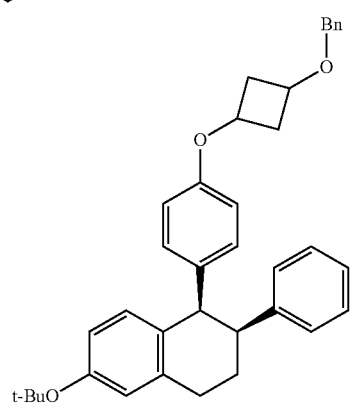
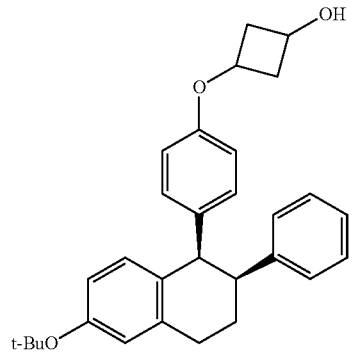
-continued
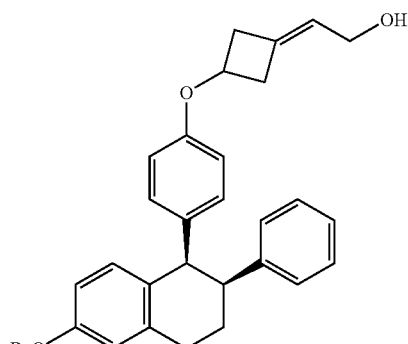
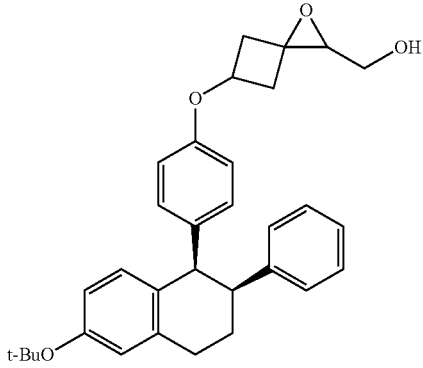
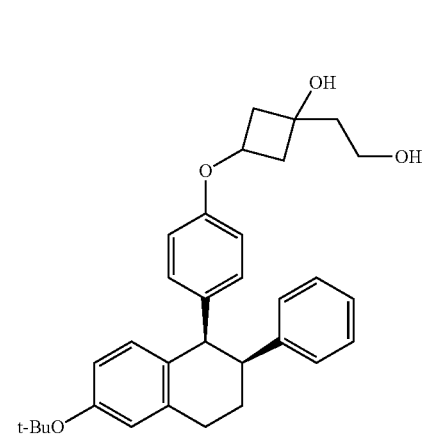
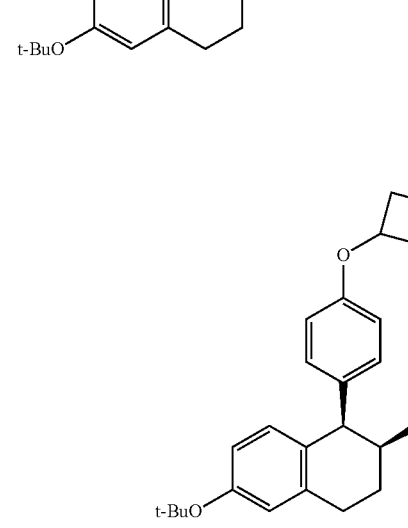

627
General synthetic scheme 1-22 to prepare intermediate.
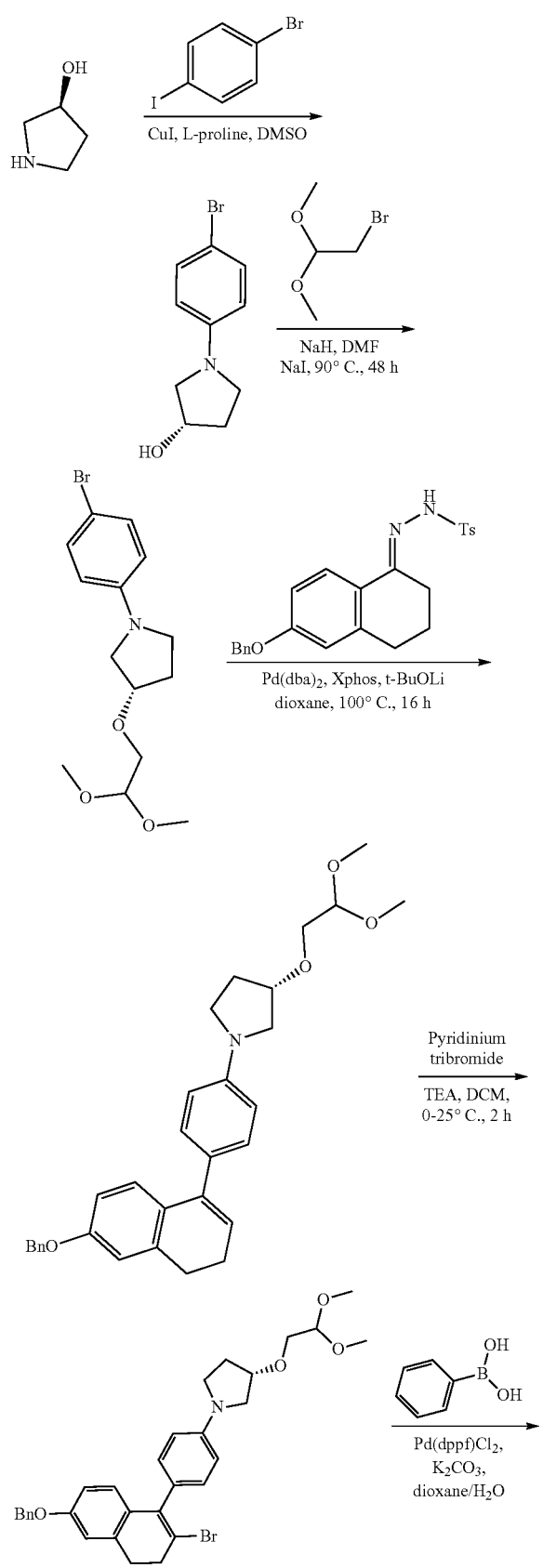
628
-continued
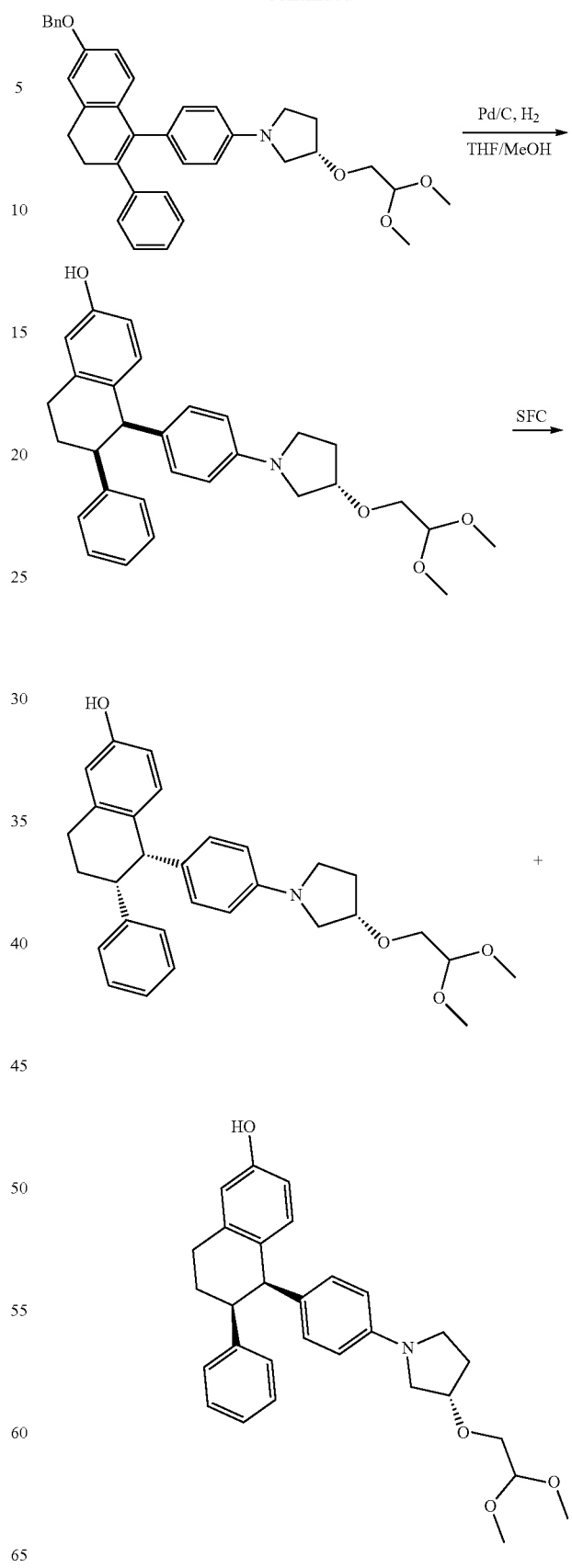

General synthetic scheme 1-23 to prepare intermediate.
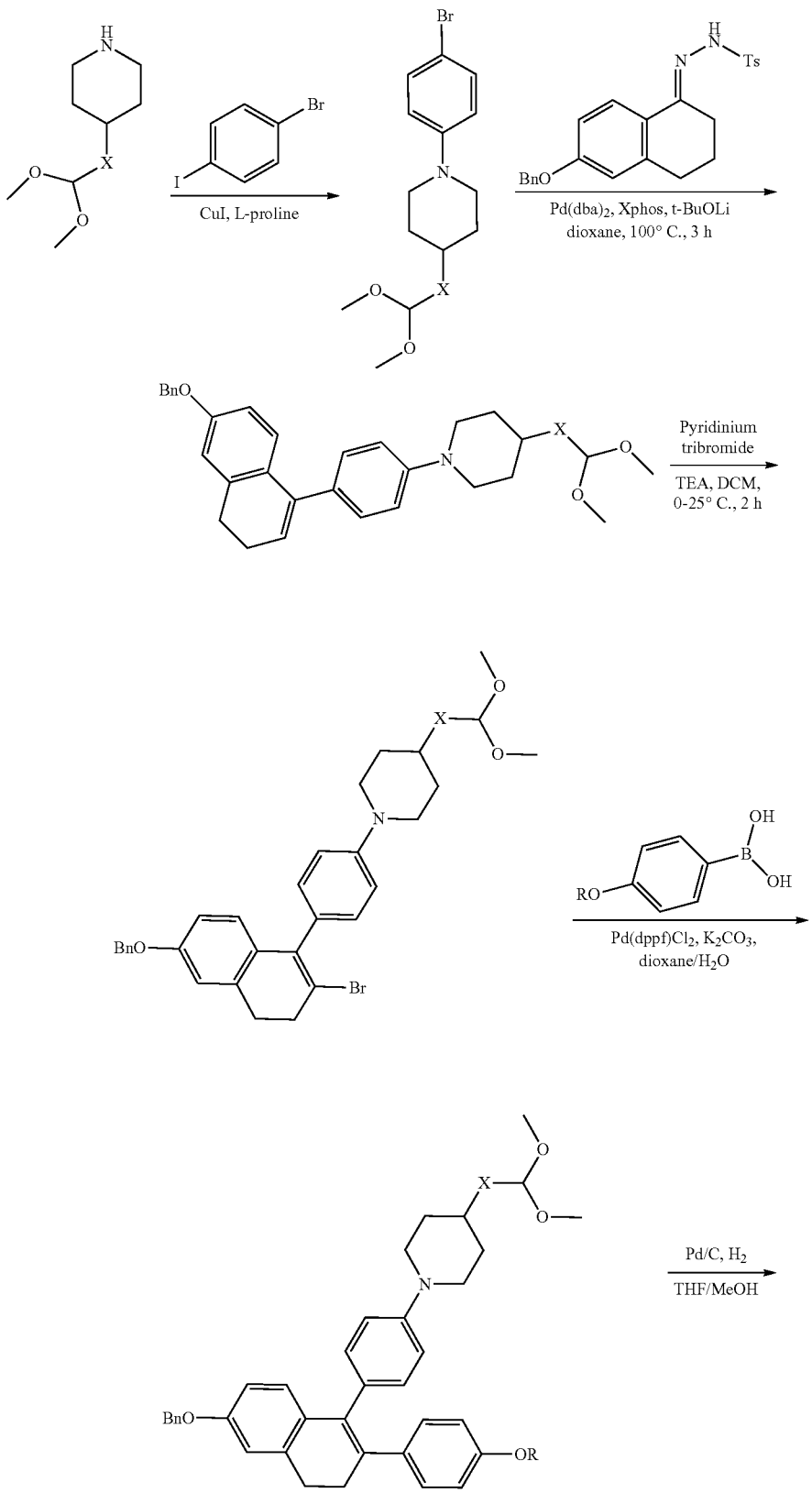

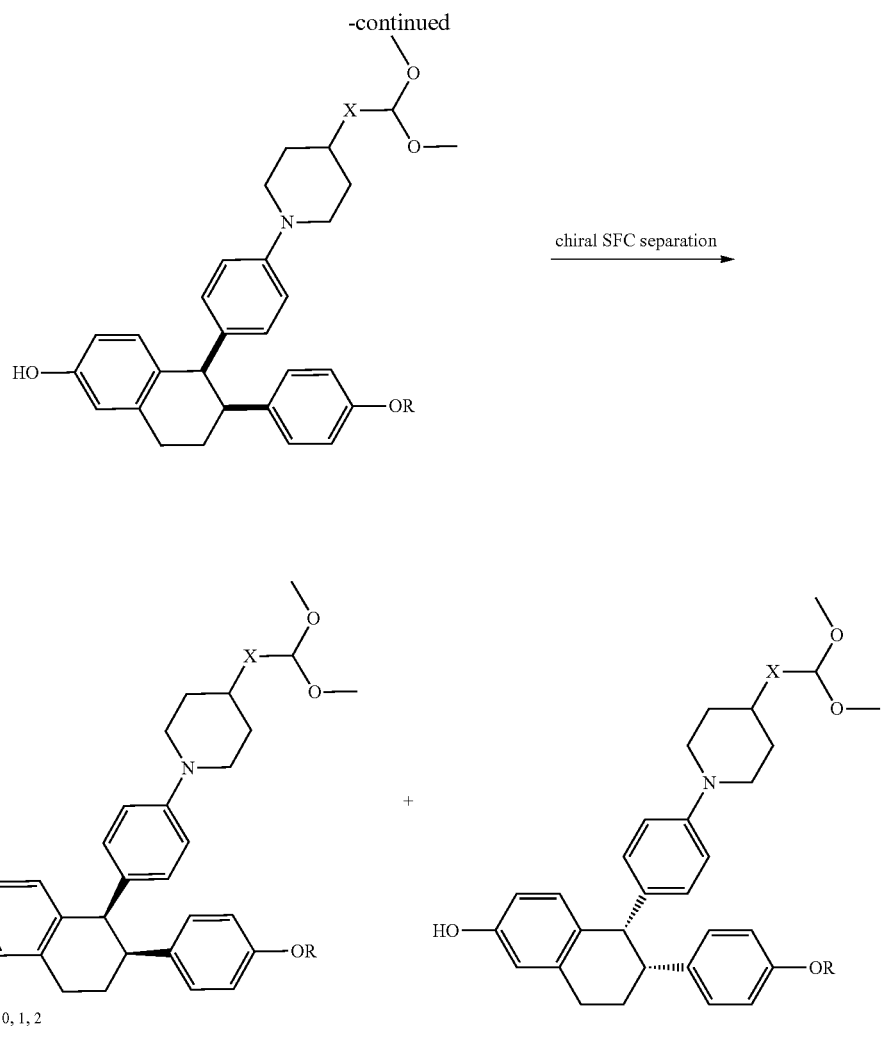
General synthetic scheme 1-24 to prepare intermediate.
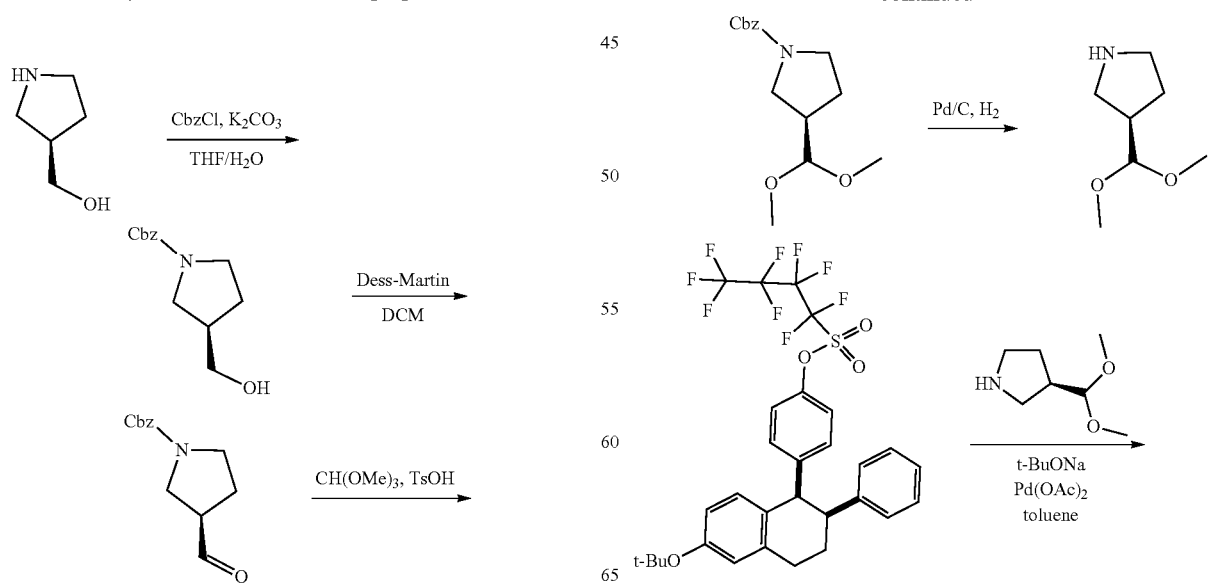

633
-continued
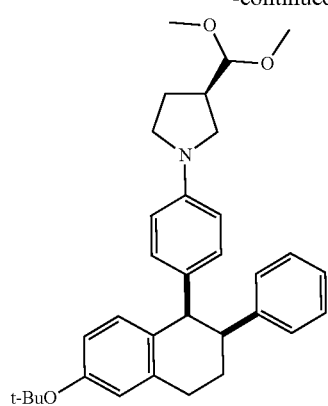
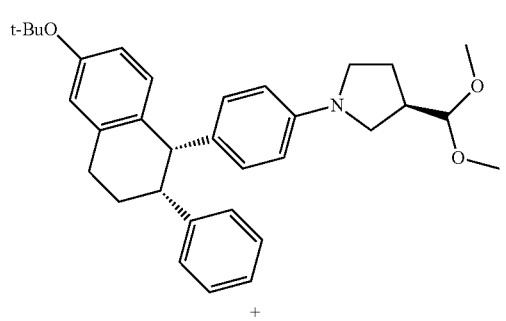
+
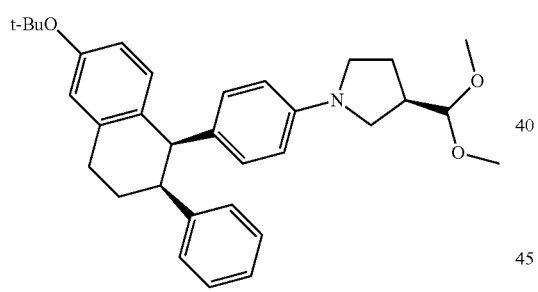
General synthetic scheme 1-25 to prepare intermediate.
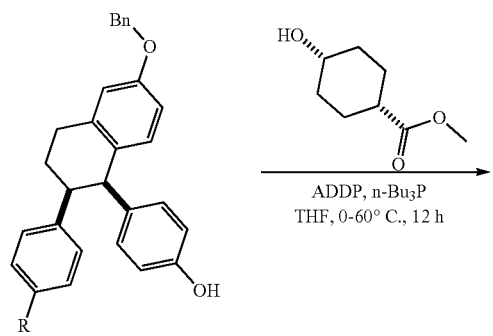
634
-continued
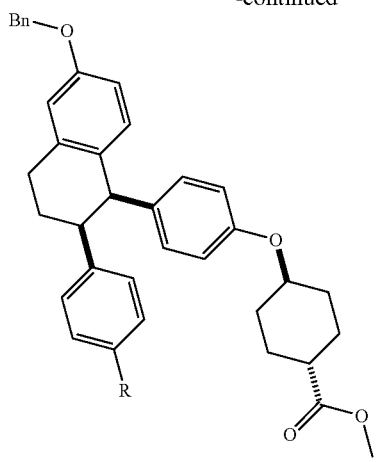
1) LiAlH$_4$, THF, 0-15 °C., 10 min
2) Separated by chiral SFC
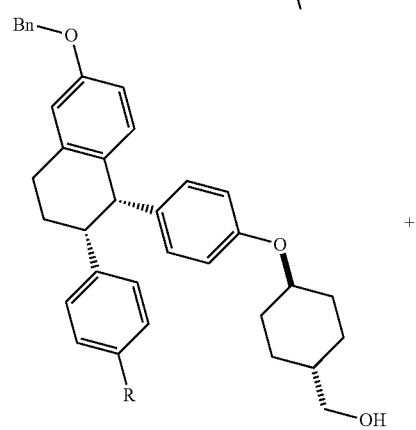
+
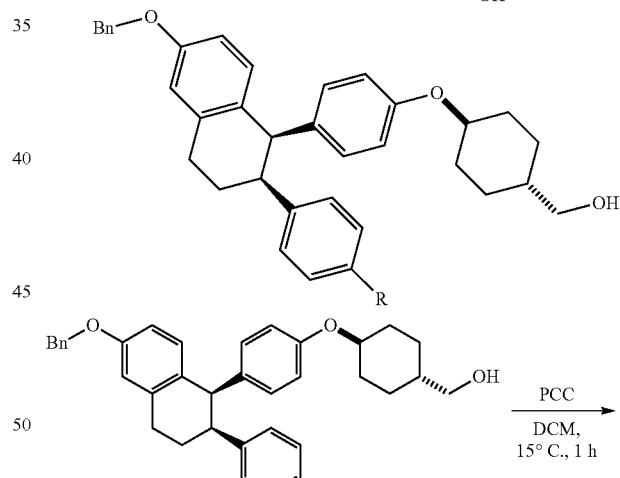
R = H, F, CF$_3$
General synthetic scheme 1-26a and 1-26b to prepare intermediates.

635
Scheme 1-26a
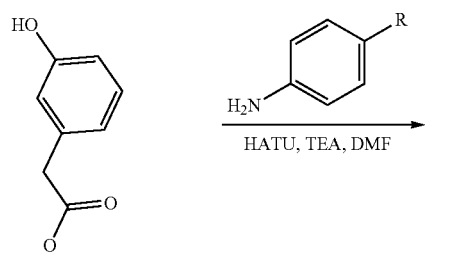
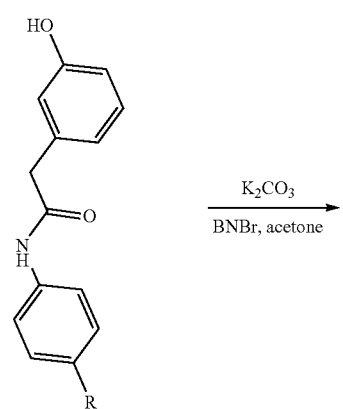
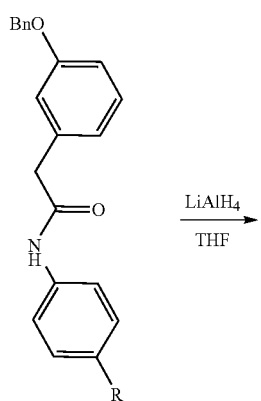
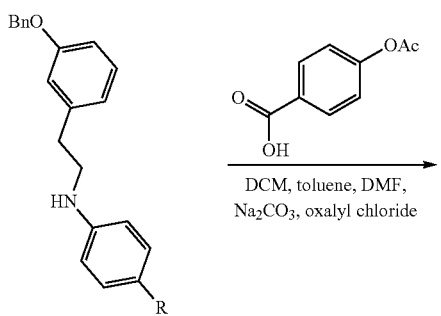
636
-continued
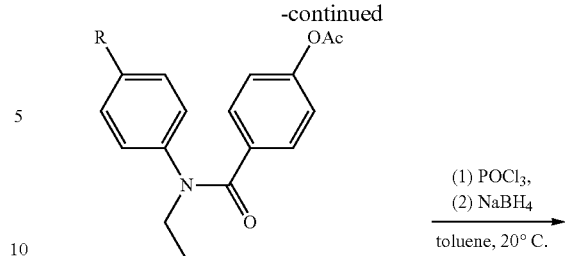
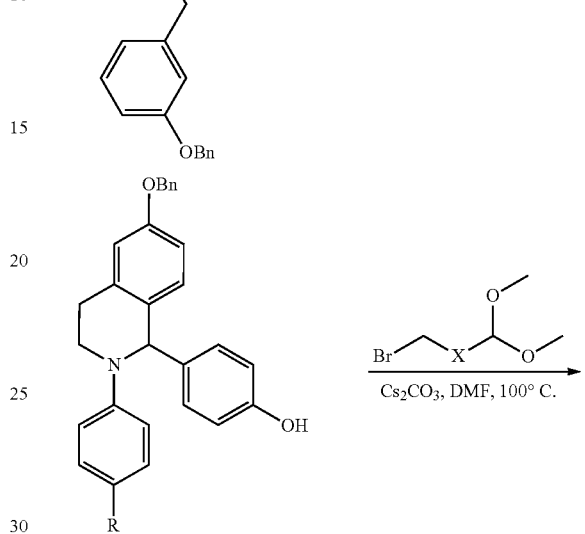
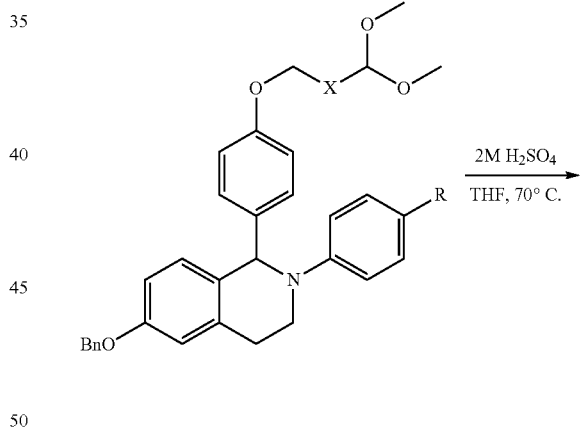
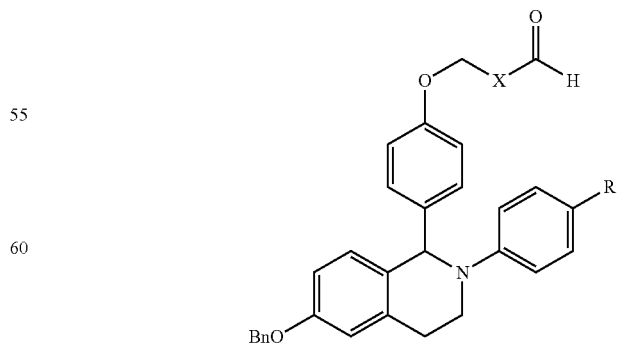
R = H, F, isopropyl, CF$_3$; X = (CH$_2$)$_n$ where n = 0, 1, 2, 3

Scheme 1-26b
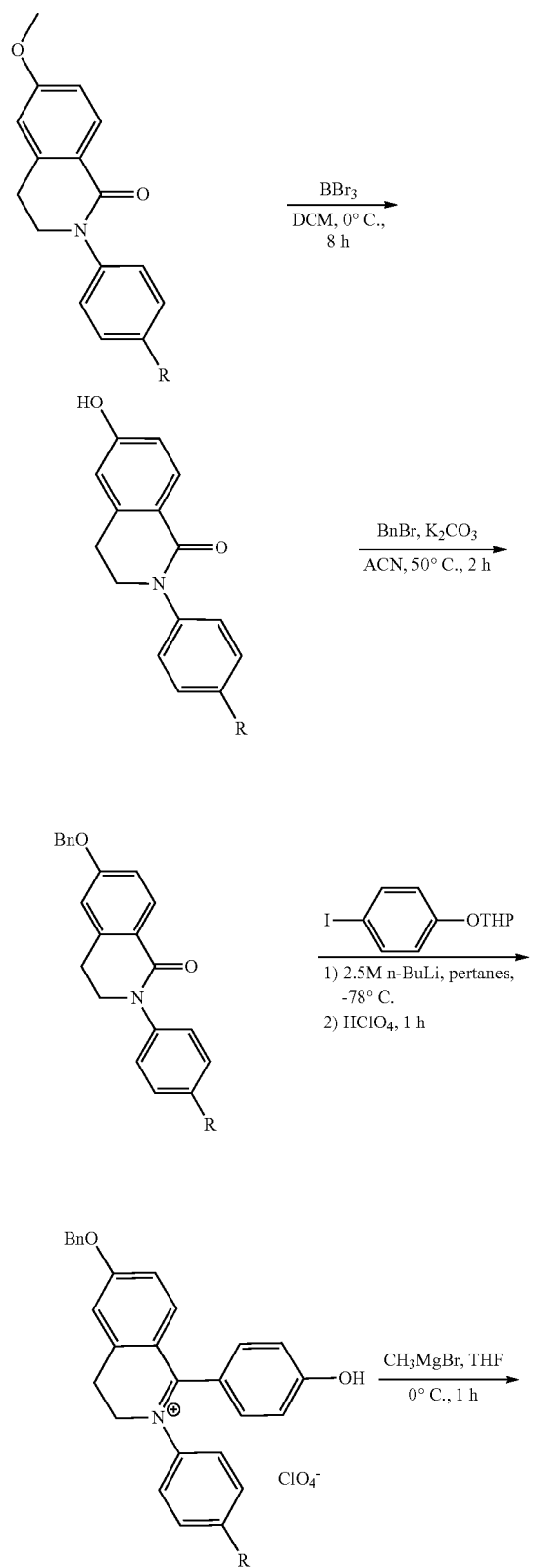
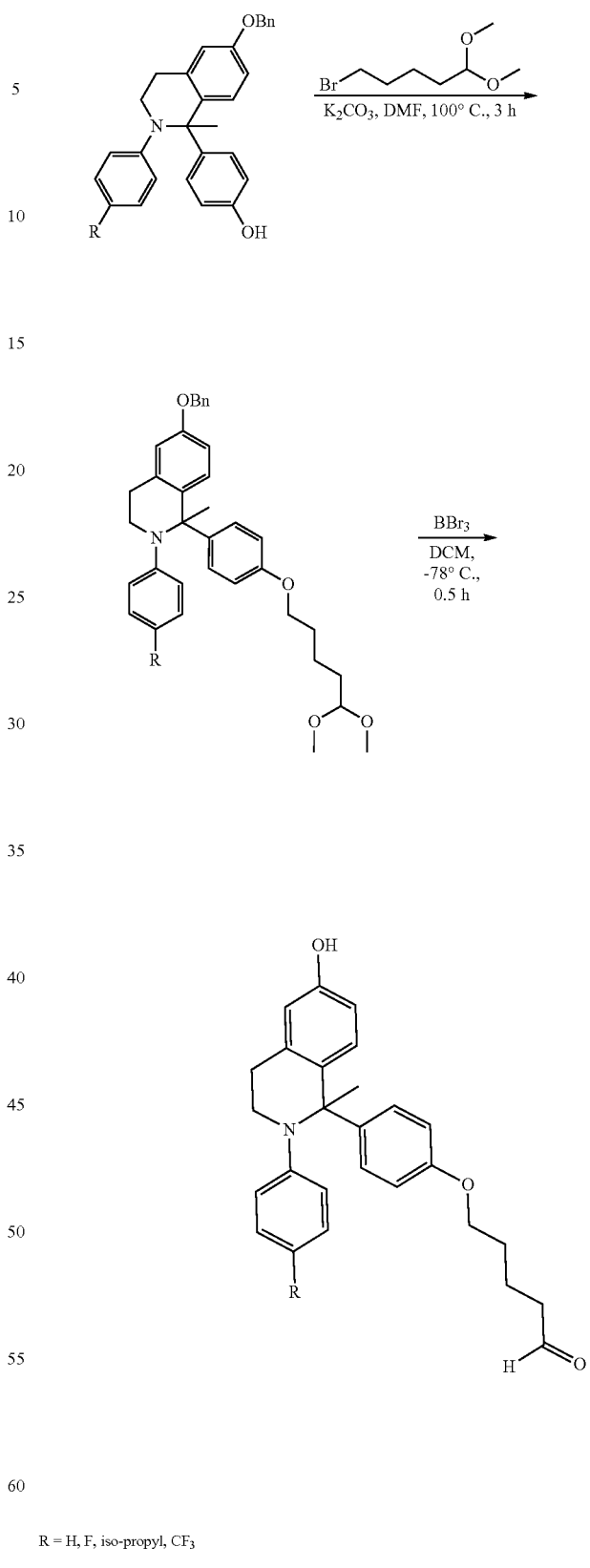
R = H, F, iso-propyl, CF₃

General synthetic scheme 1-27 to prepare intermediate.
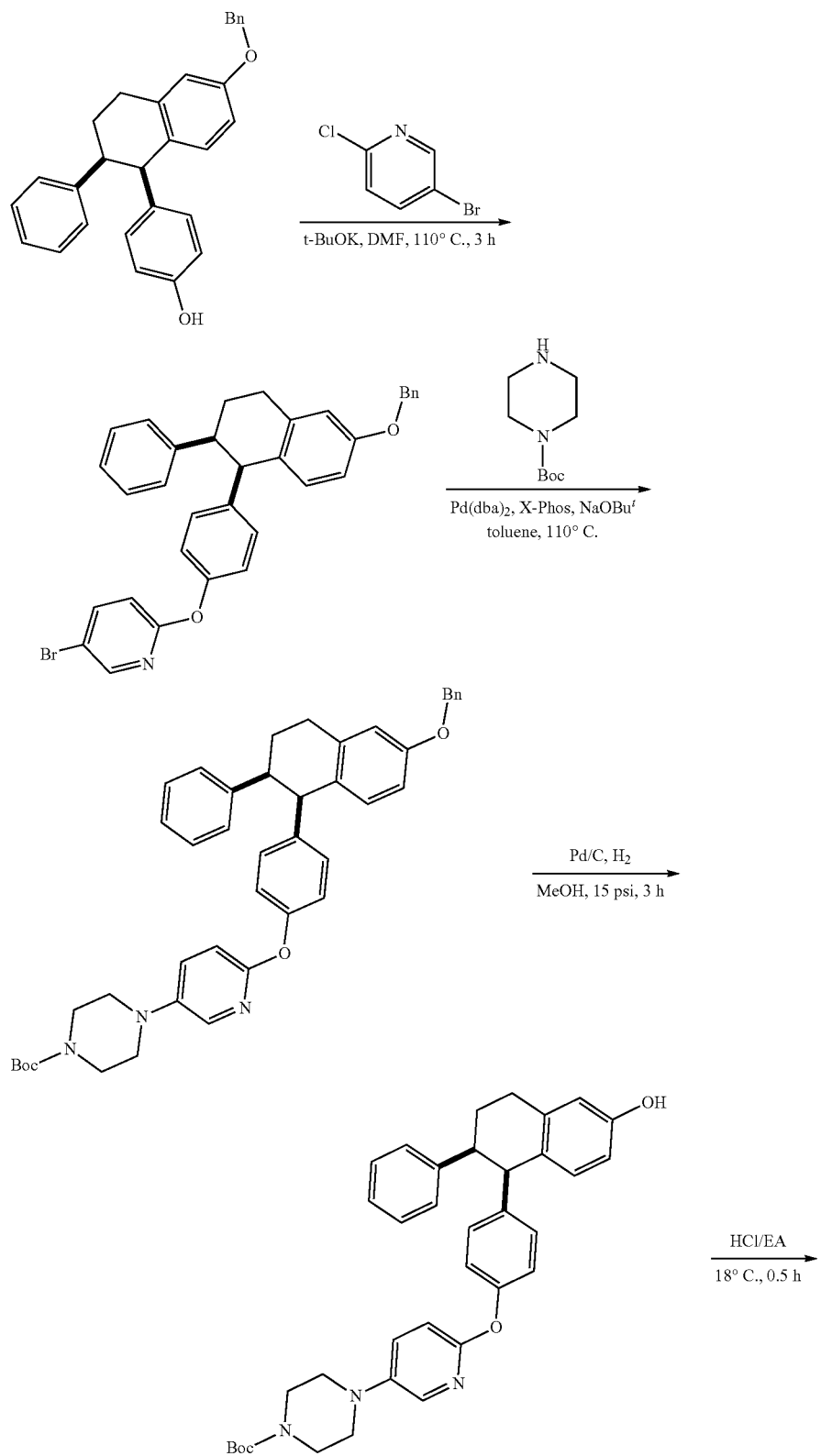

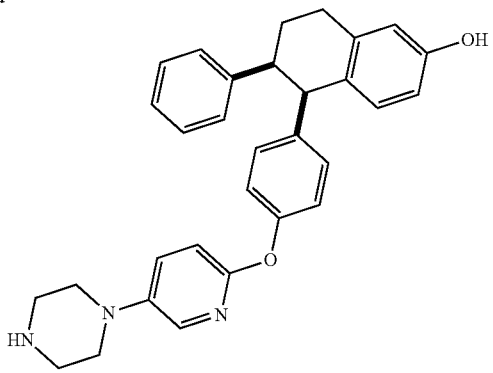
General synthetic scheme 1-28 to prepare intermediate.
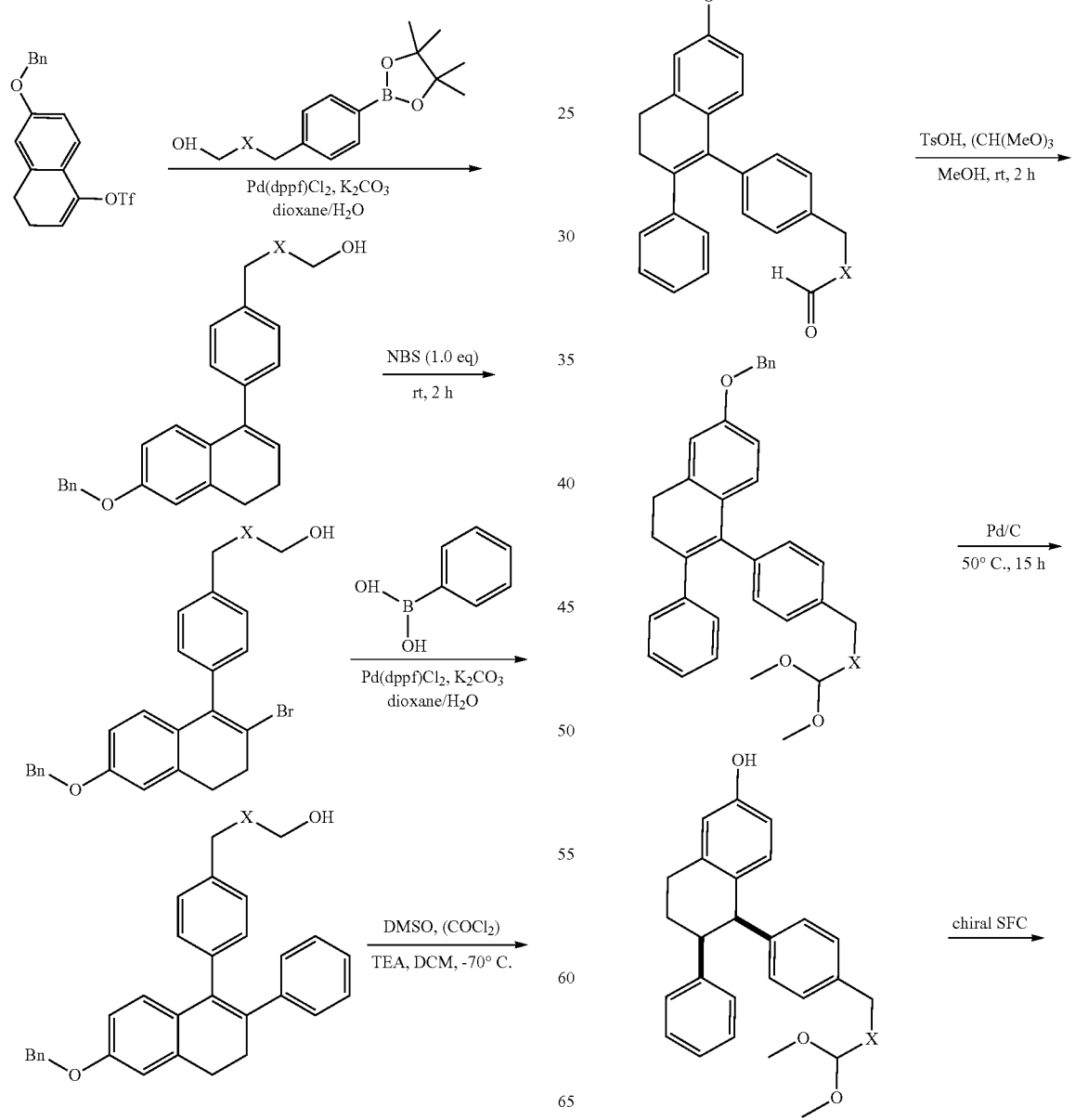

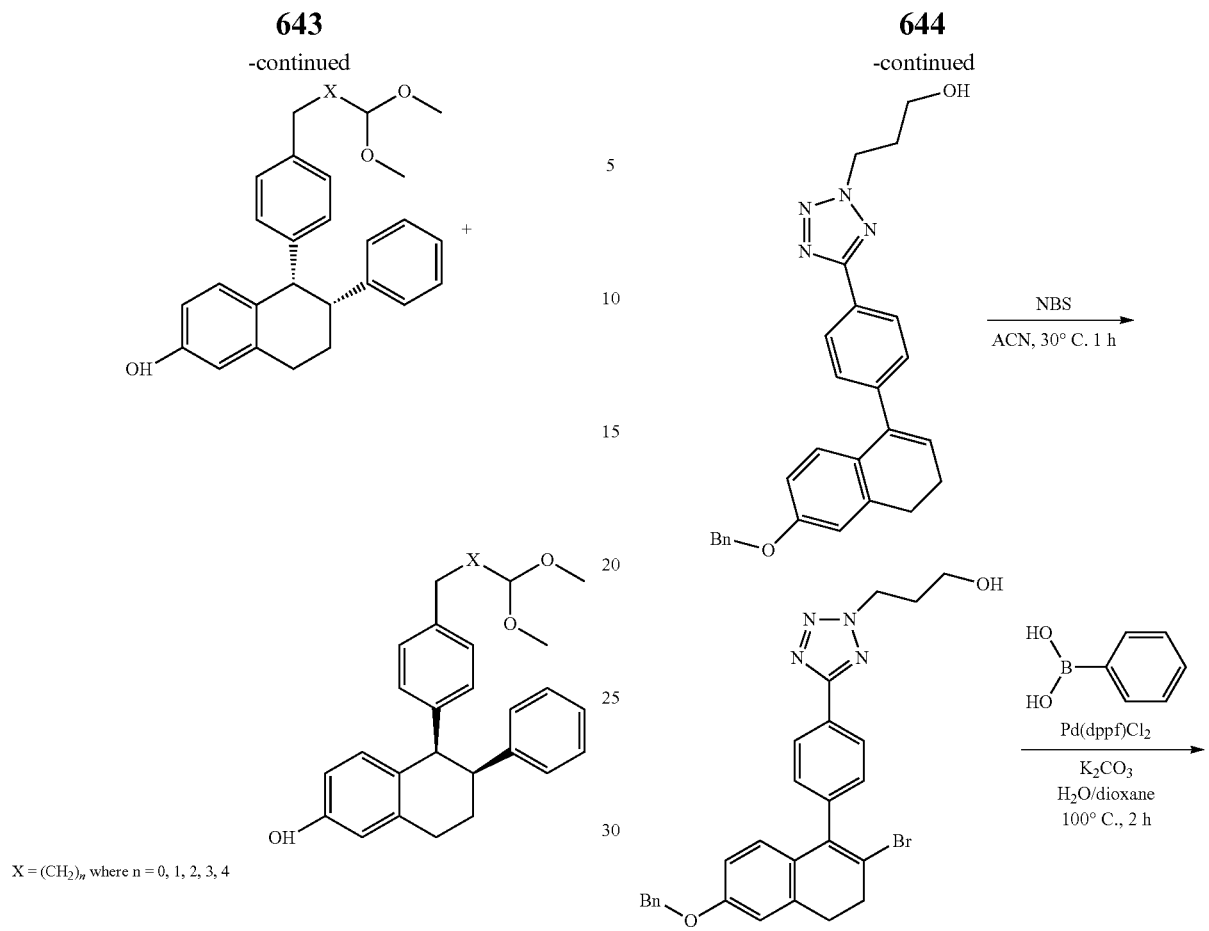
X = (CH₂)ₙ where n = 0, 1, 2, 3, 4
General synthetic scheme 1-29 to prepare intermediate.
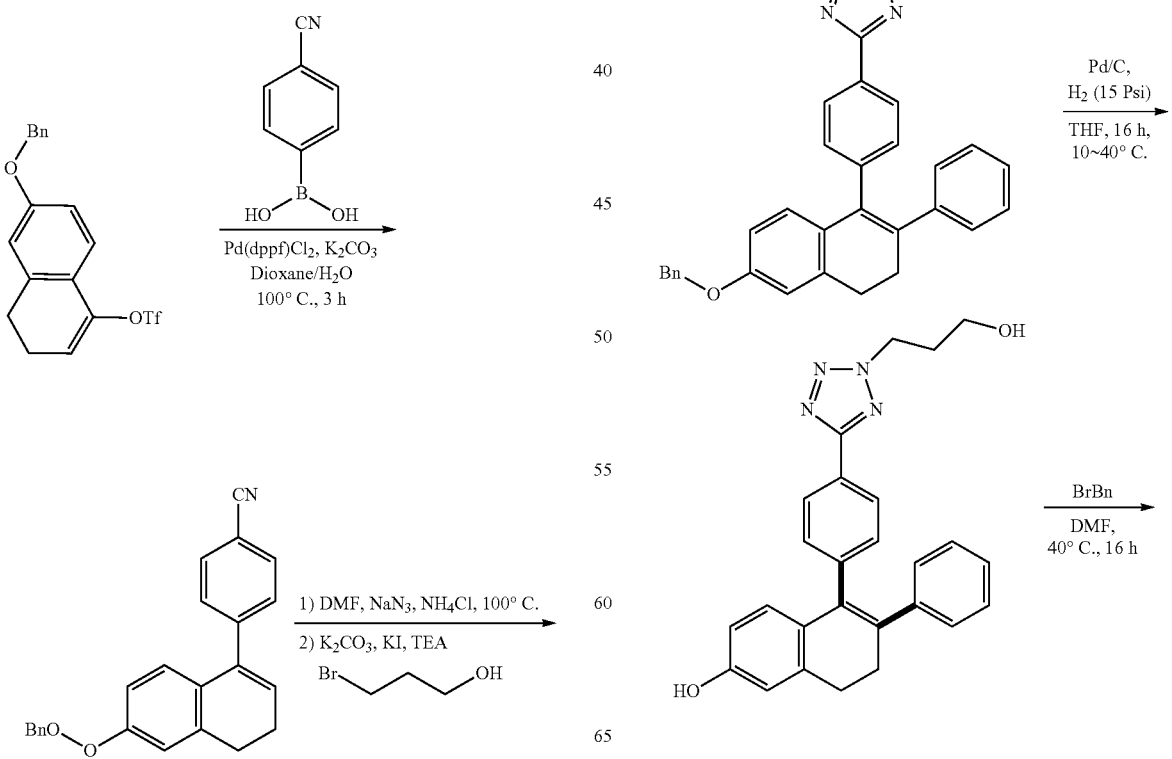

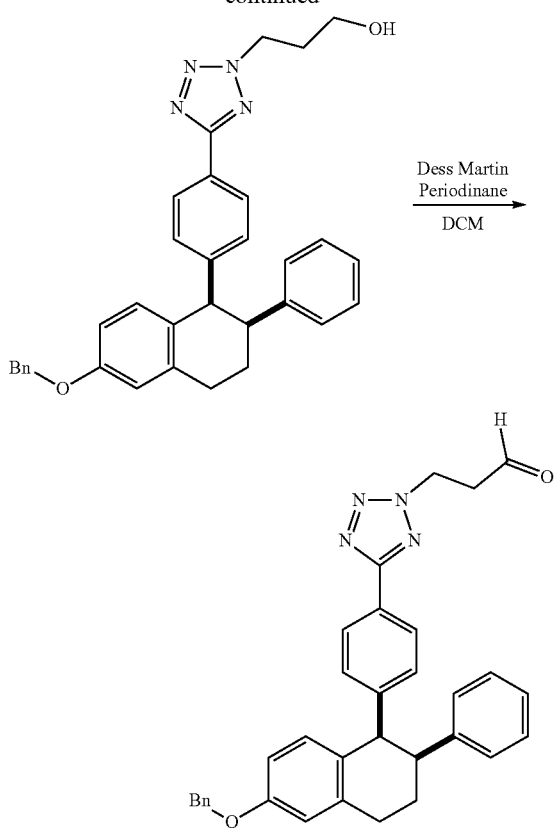
General synthetic scheme 1-30 to prepare intermediate.
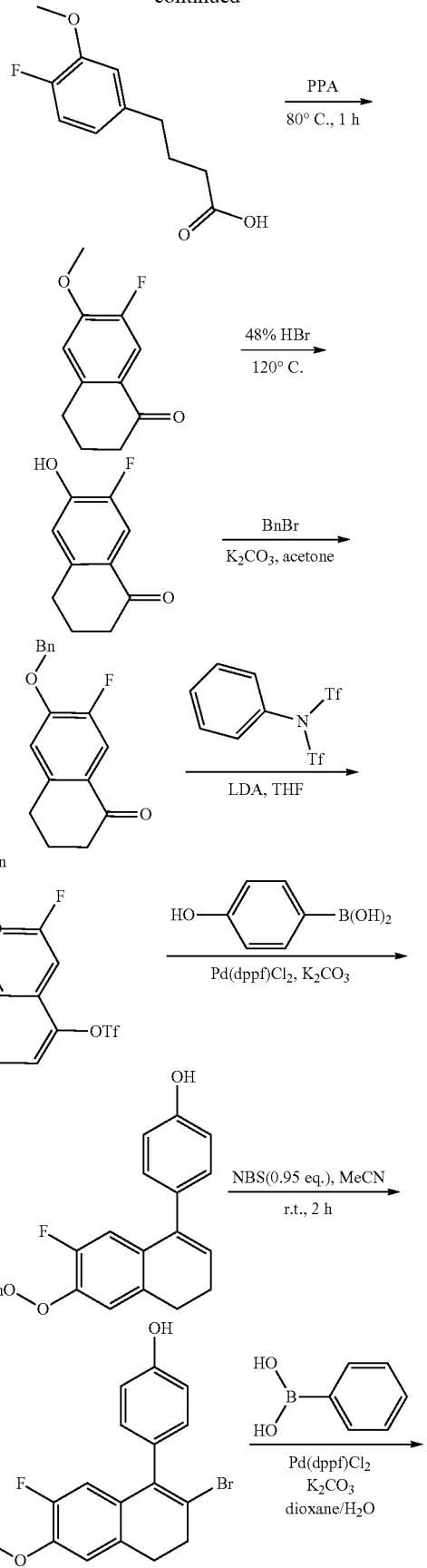

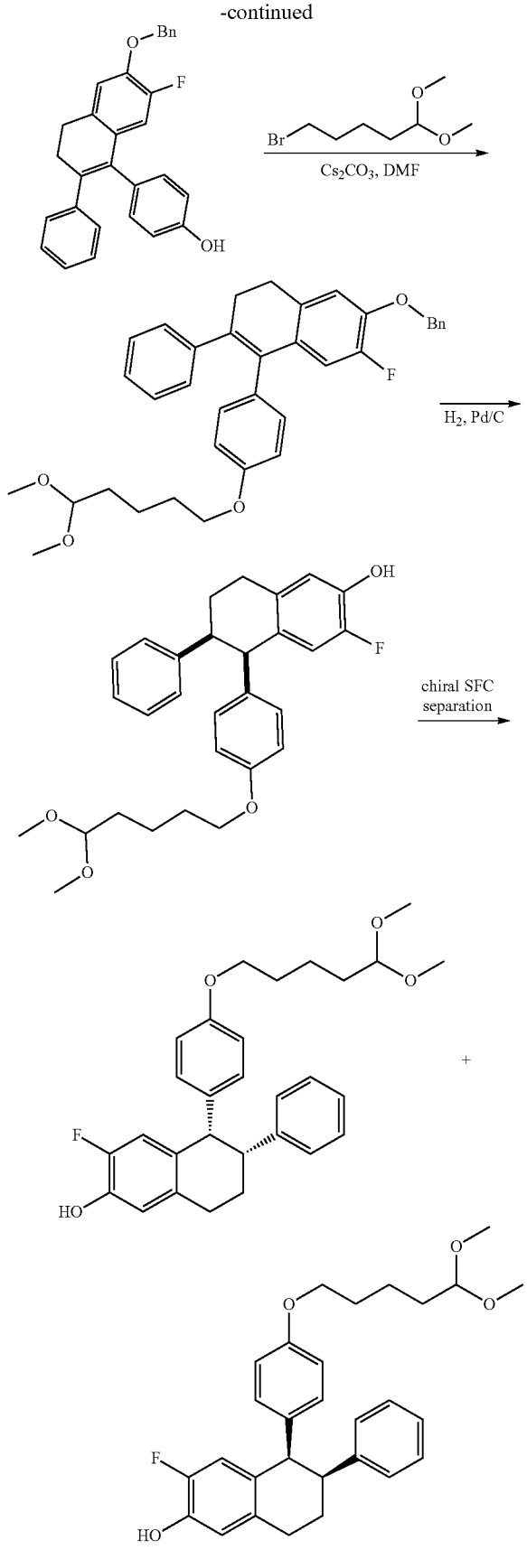
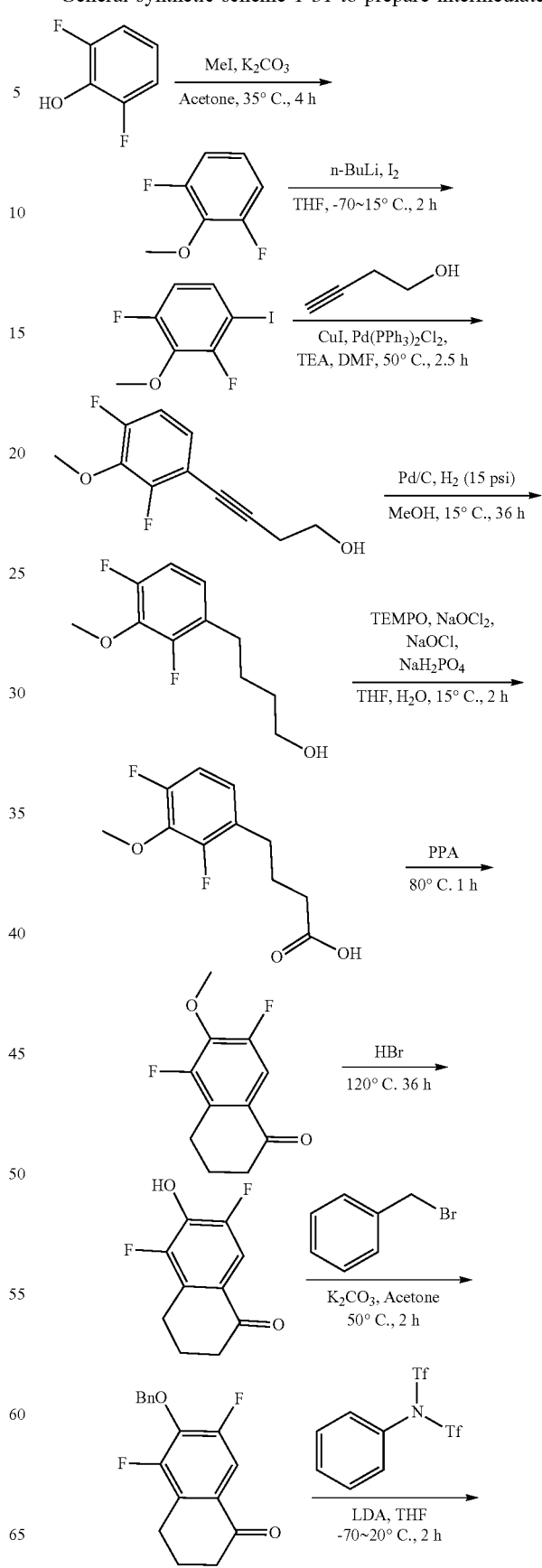
General synthetic scheme 1-31 to prepare intermediate.

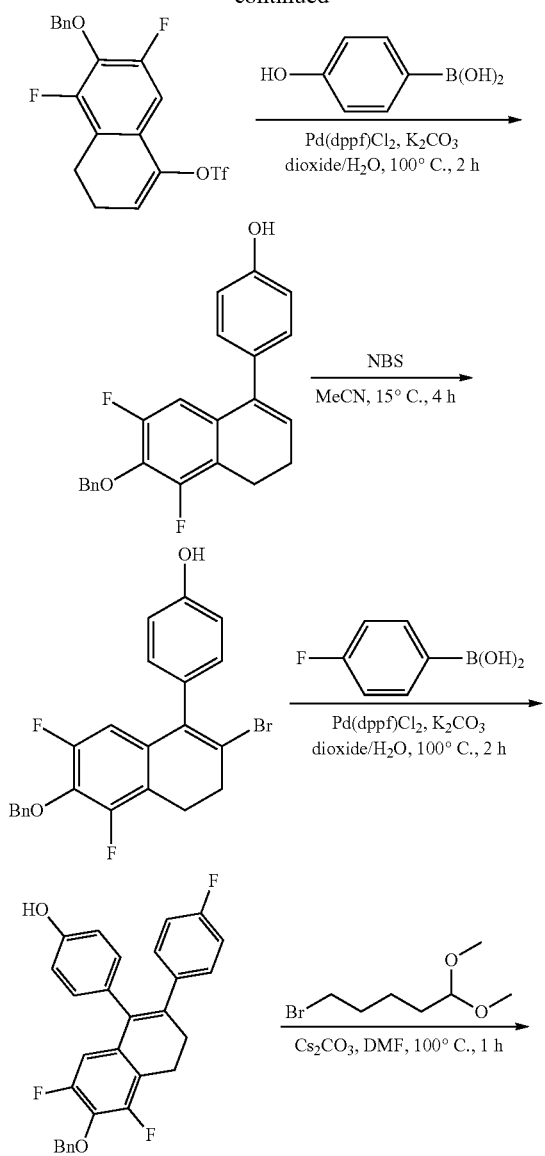
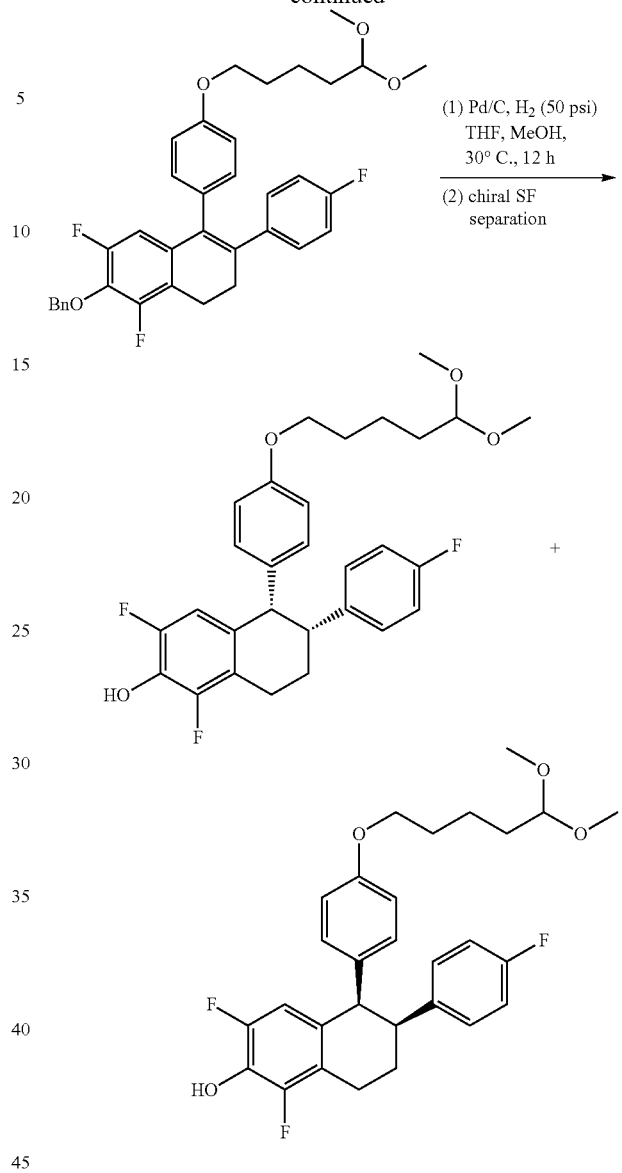
General synthetic scheme 1-32 to prepare intermediate.
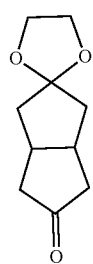
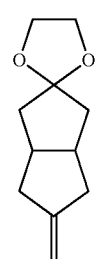

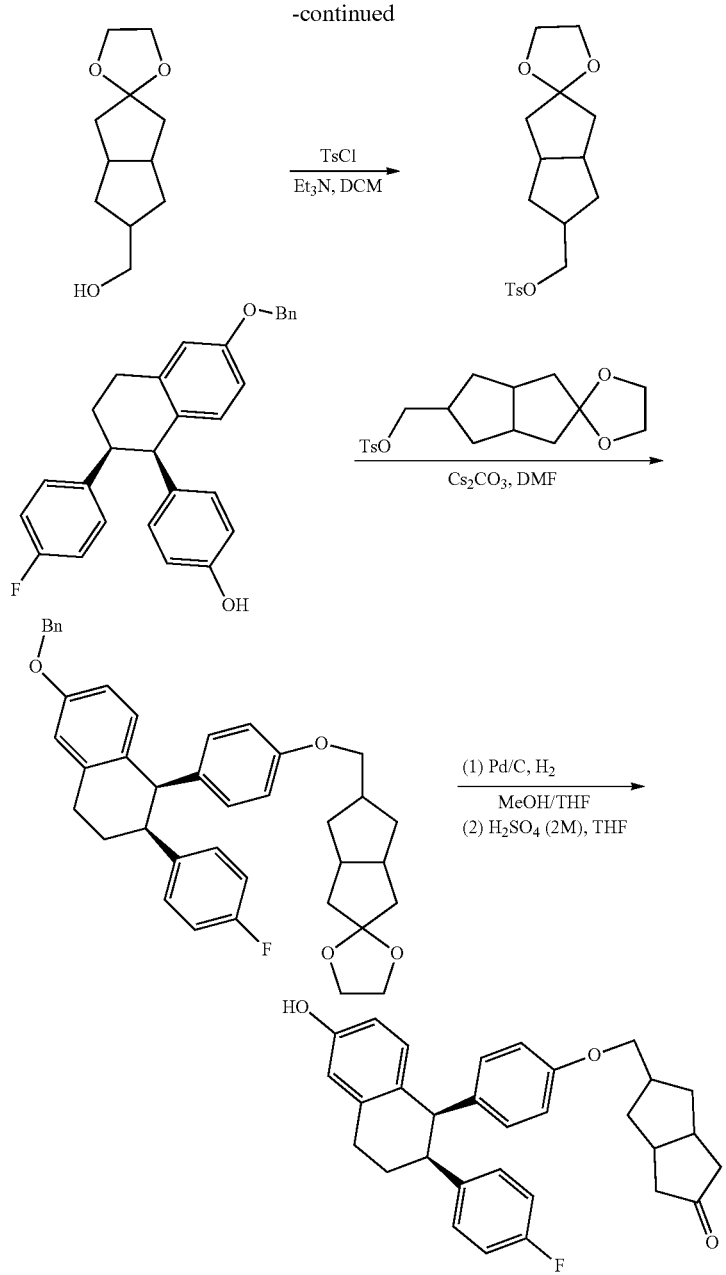
General synthetic scheme 1-33 to prepare intermediate.
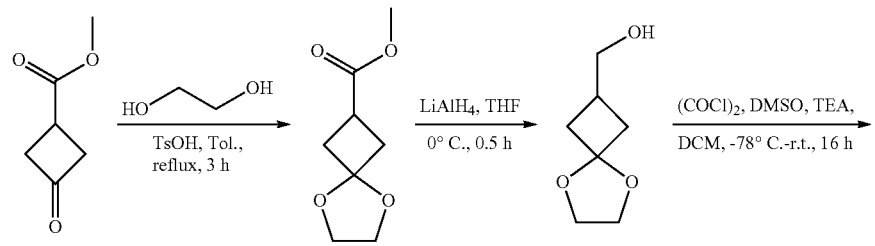

-continued
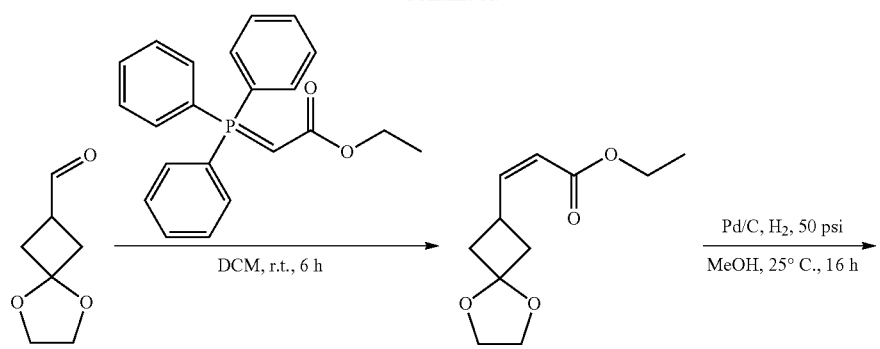
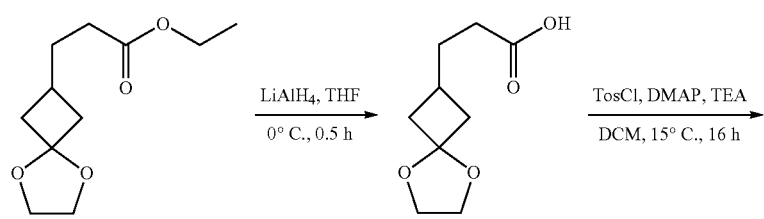
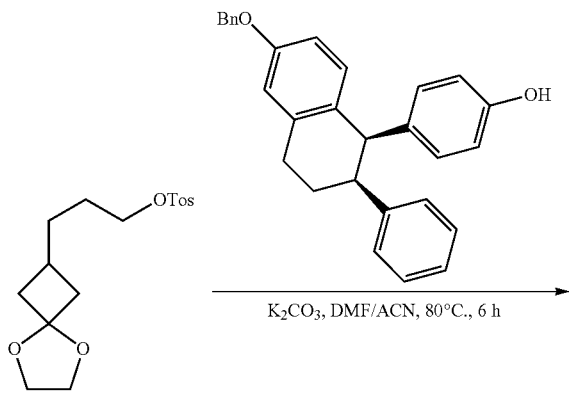
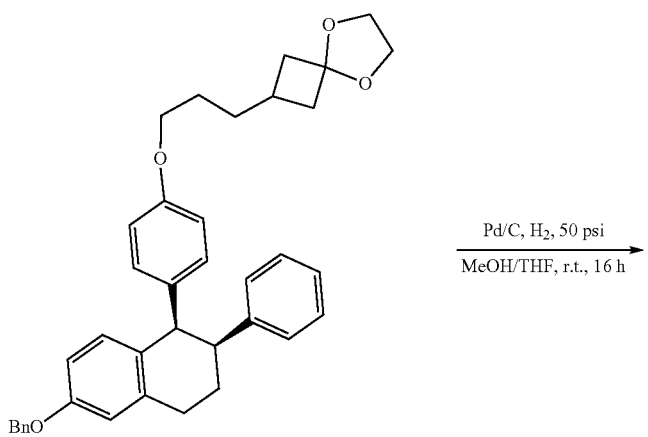

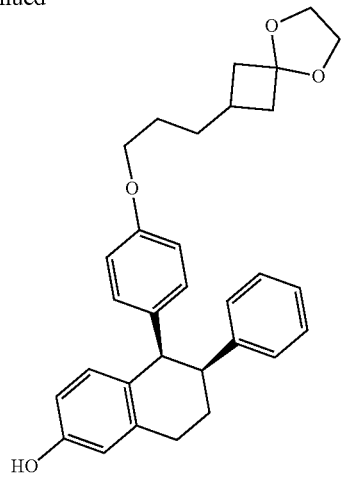
General synthetic scheme 1-34 to prepare intermediate.
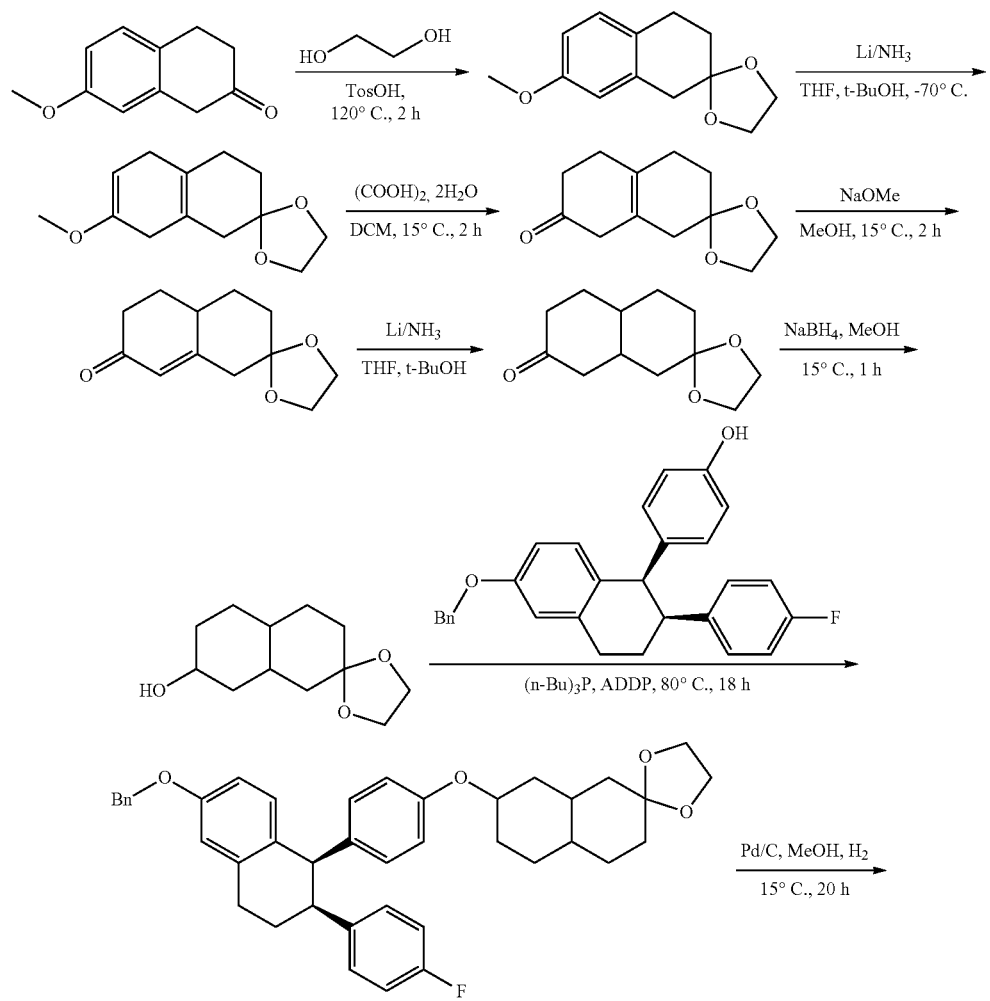

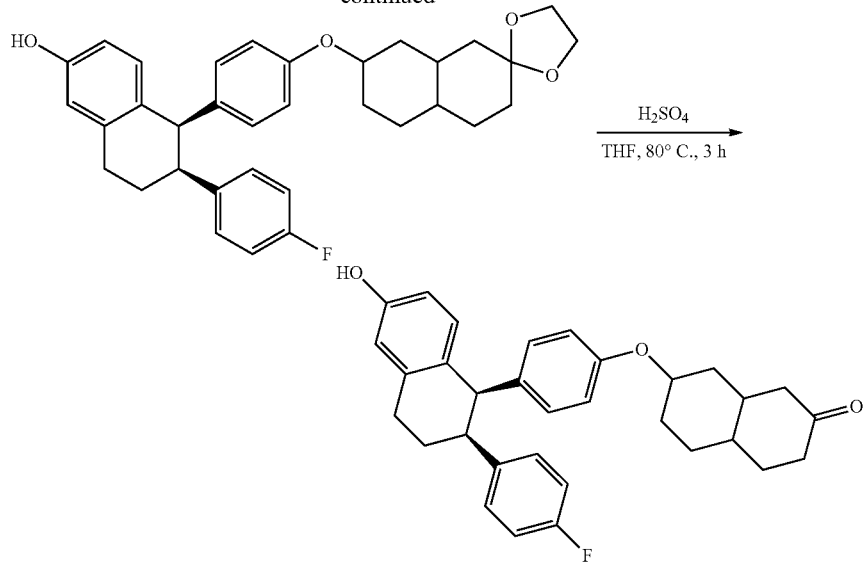
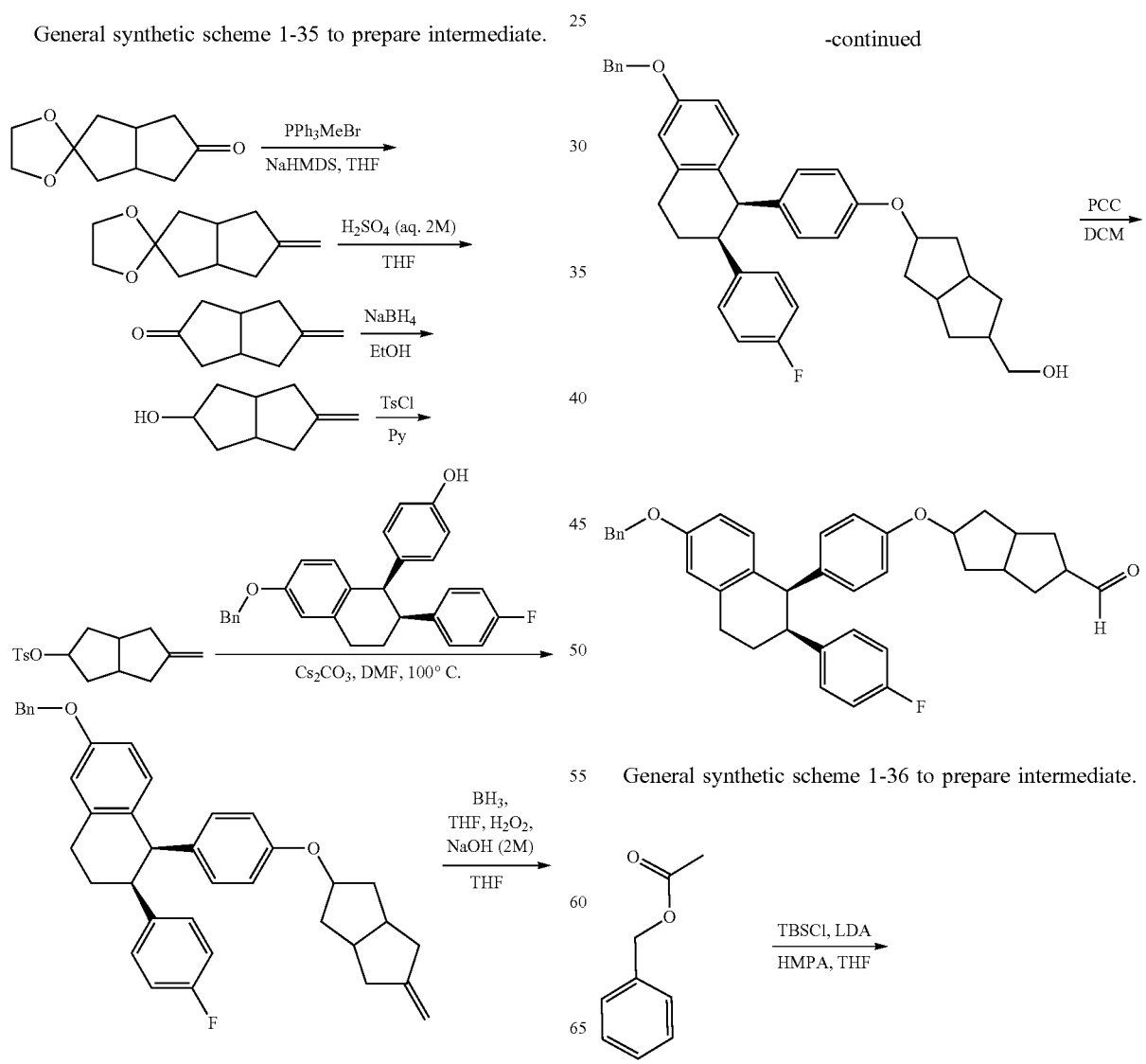
General synthetic scheme 1-35 to prepare intermediate.
General synthetic scheme 1-36 to prepare intermediate.

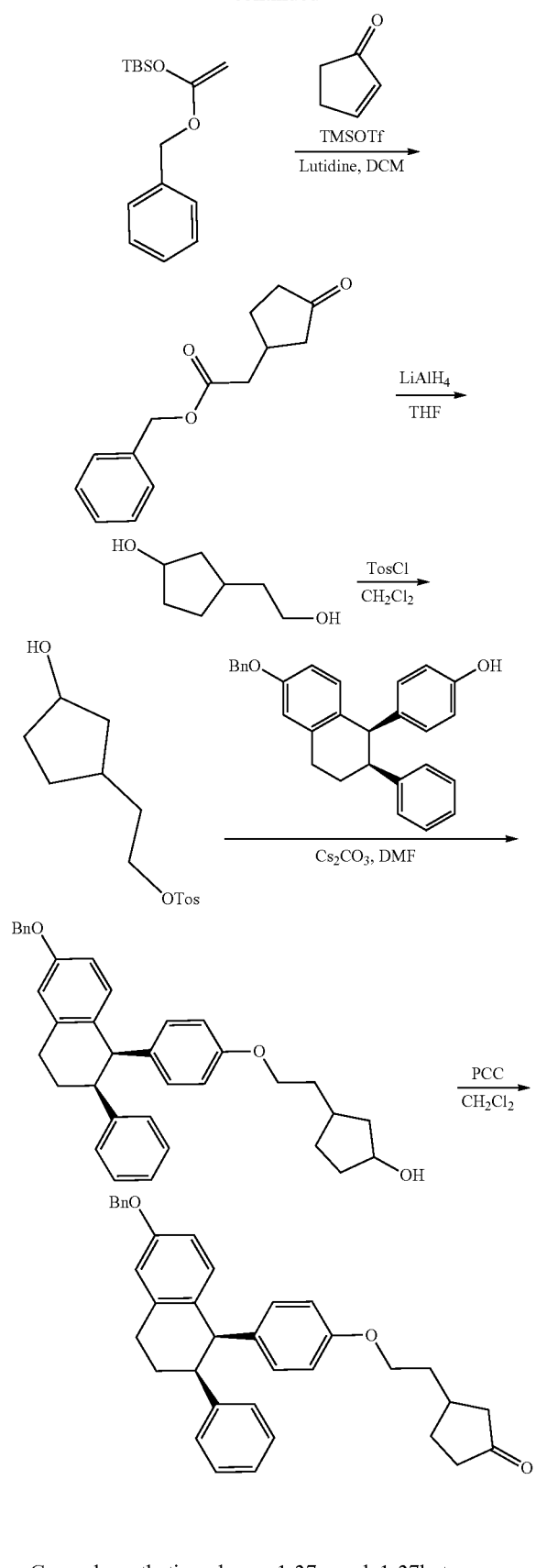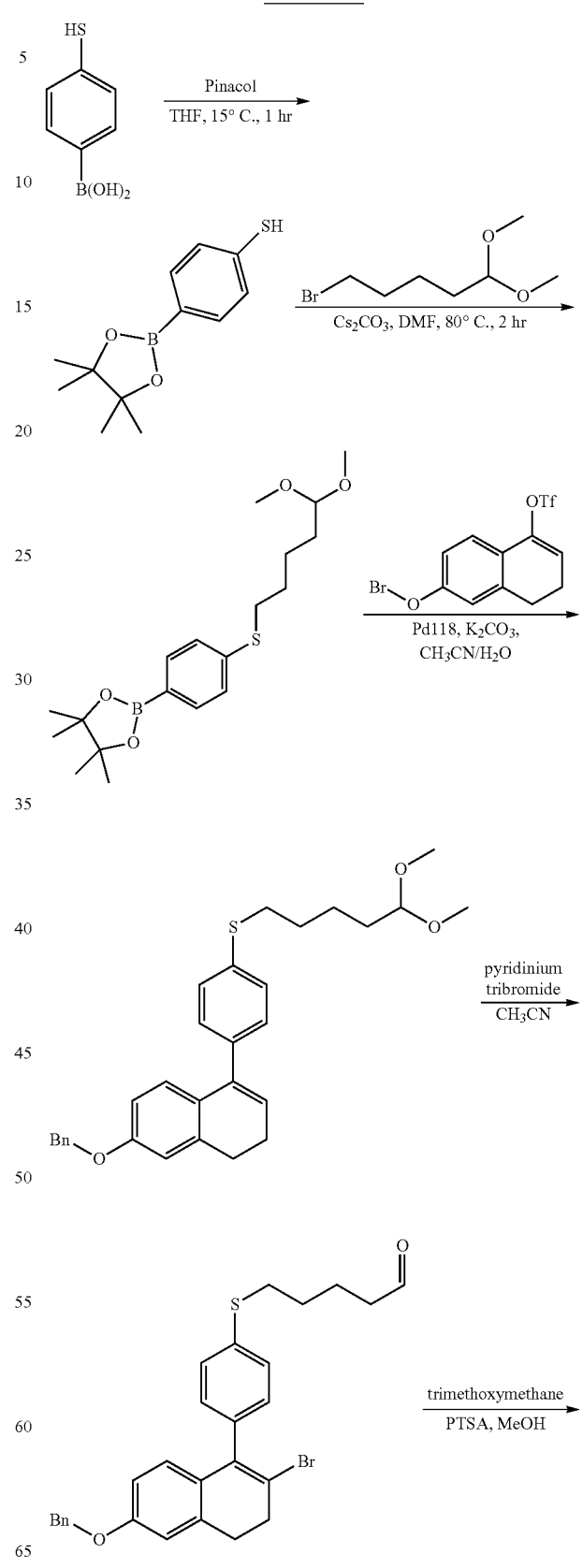
Scheme 1-37a
General synthetic scheme 1-37a and 1-37b to prepare intermediates.

661
-continued
662
-continued
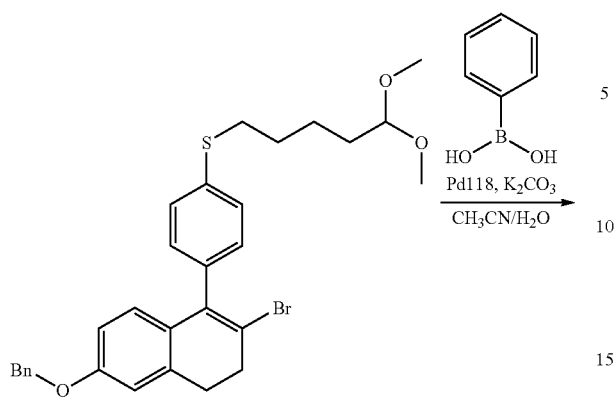
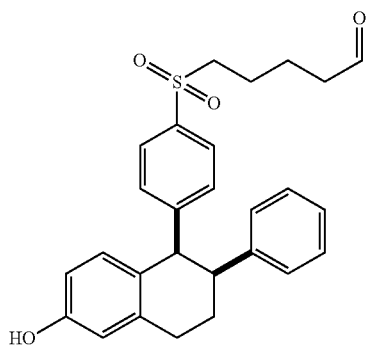
Scheme 1-37b
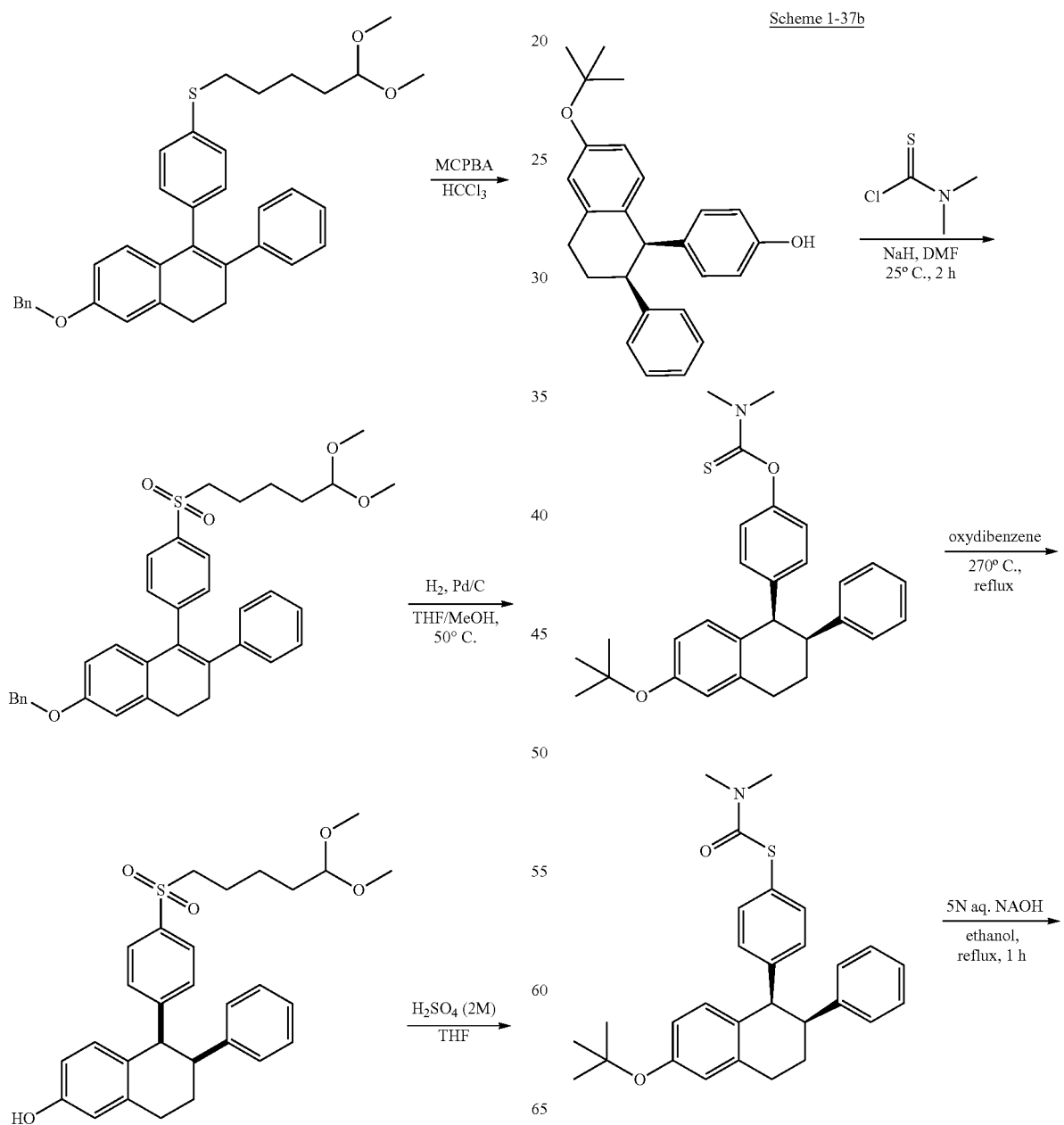

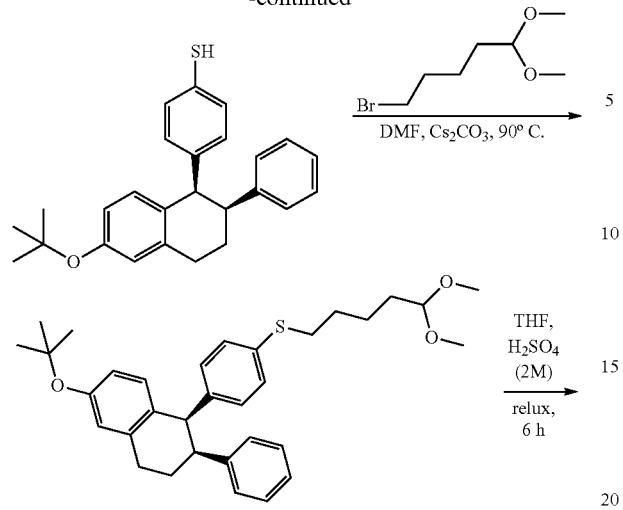
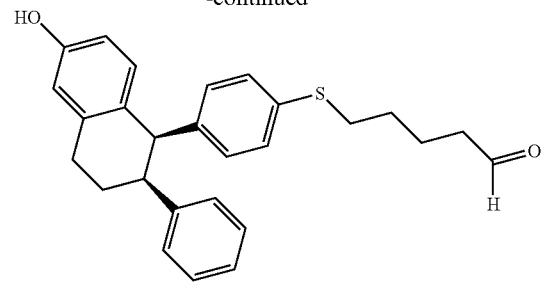
General synthetic scheme 1-38 to prepare intermediate.
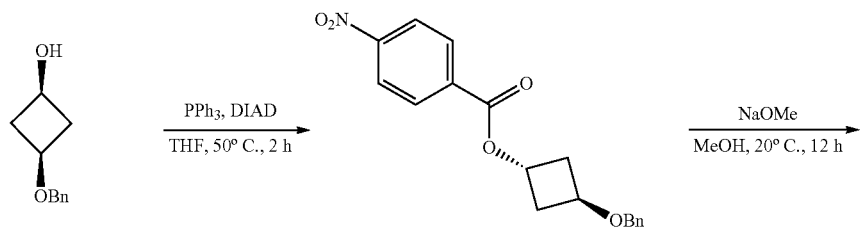
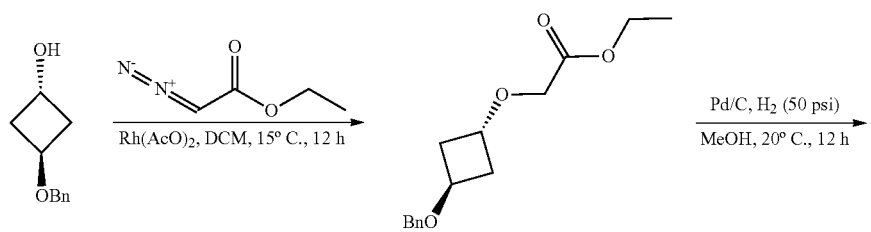
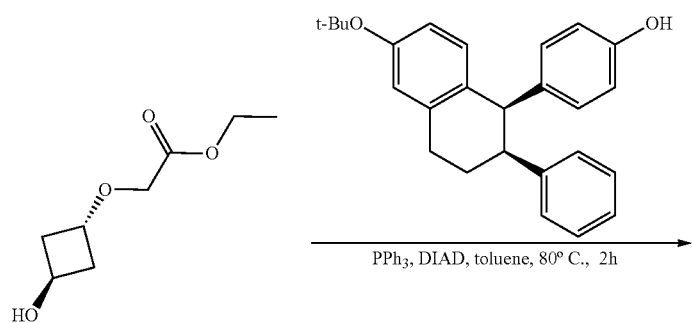

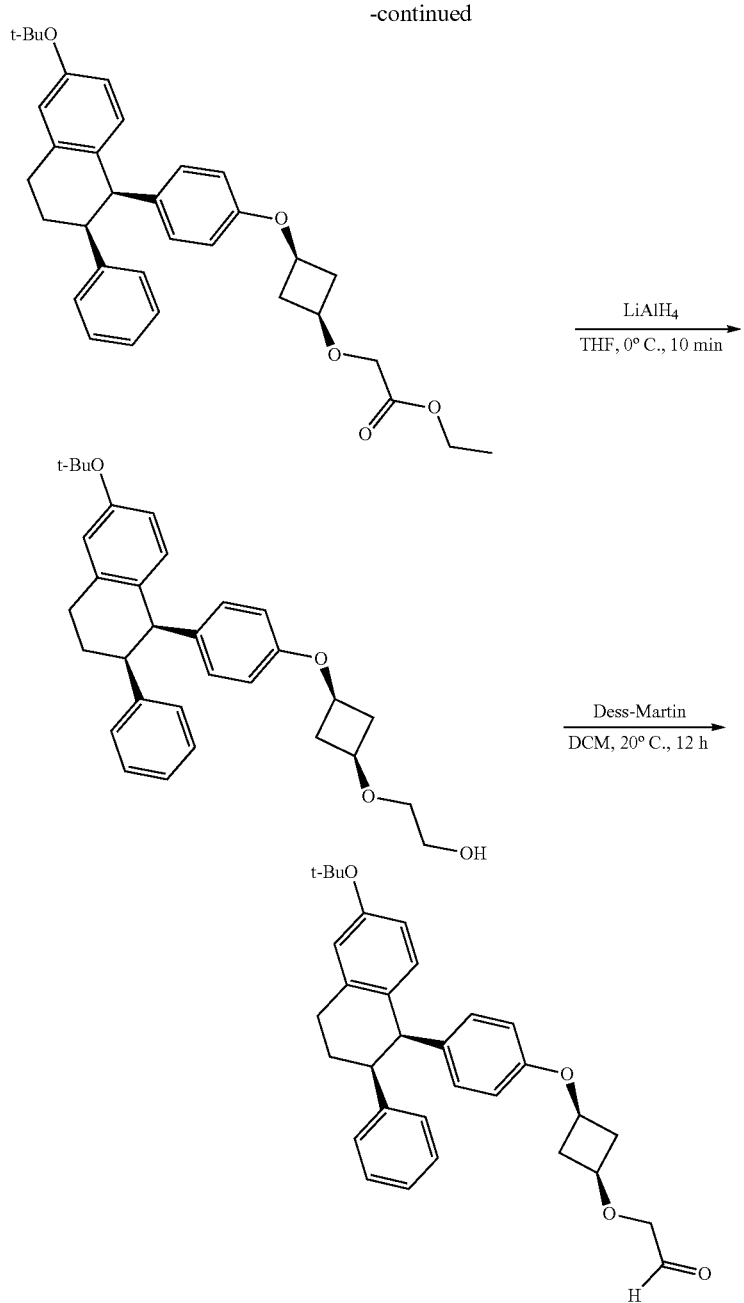
General synthetic scheme 1-39 to prepare intermediate.
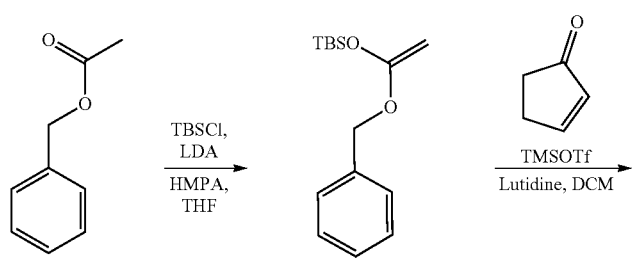

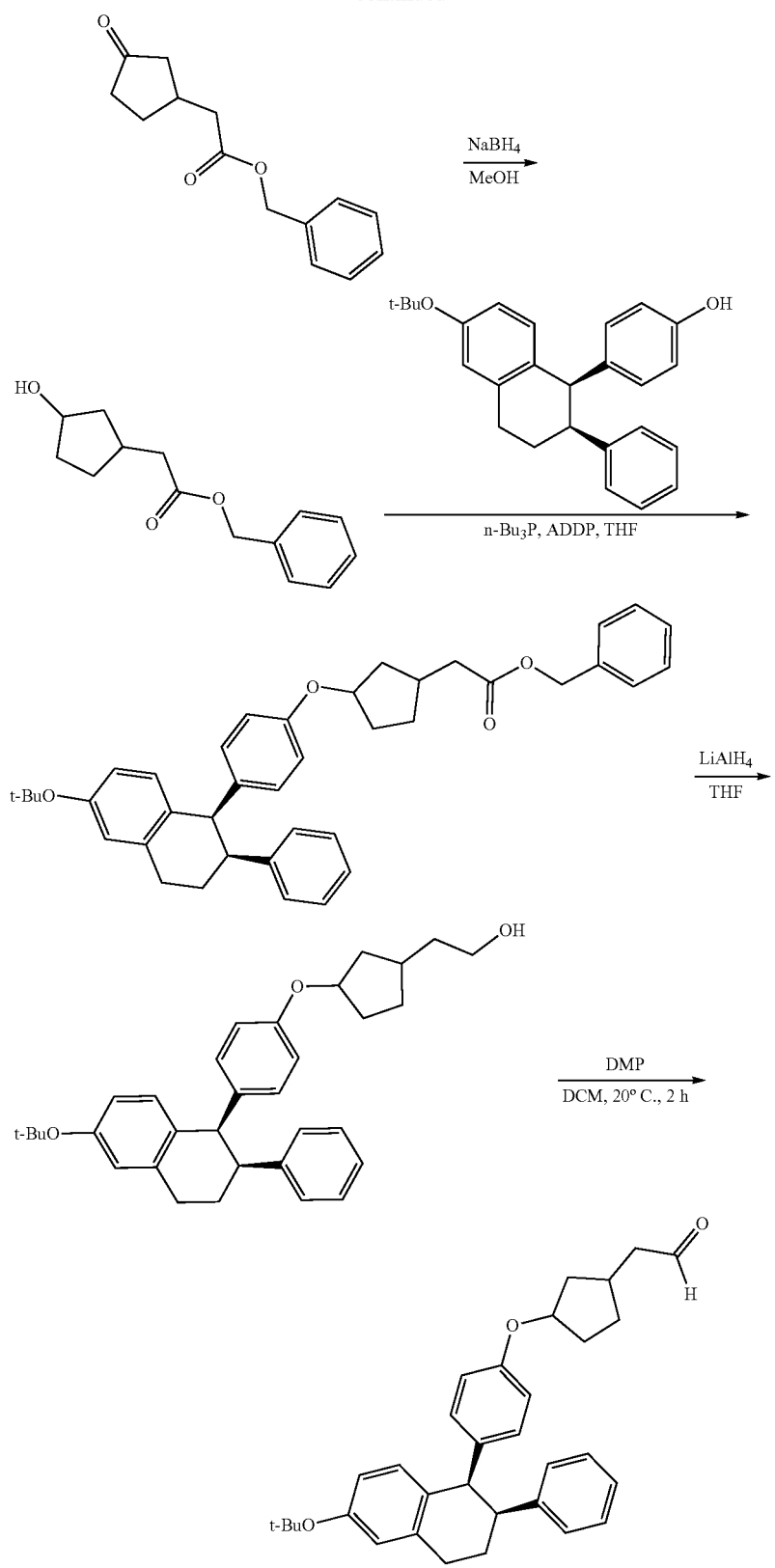

669
General synthetic scheme 1-40 to prepare intermediate.
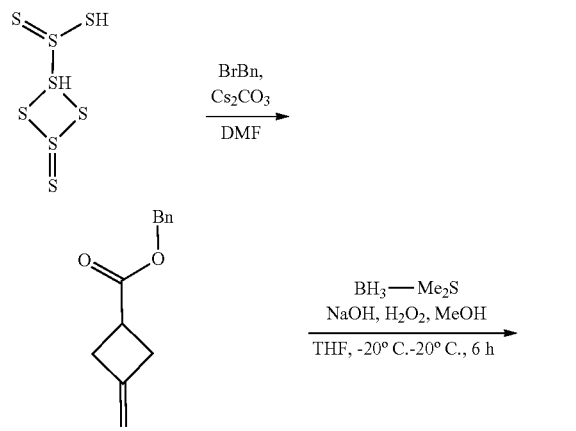
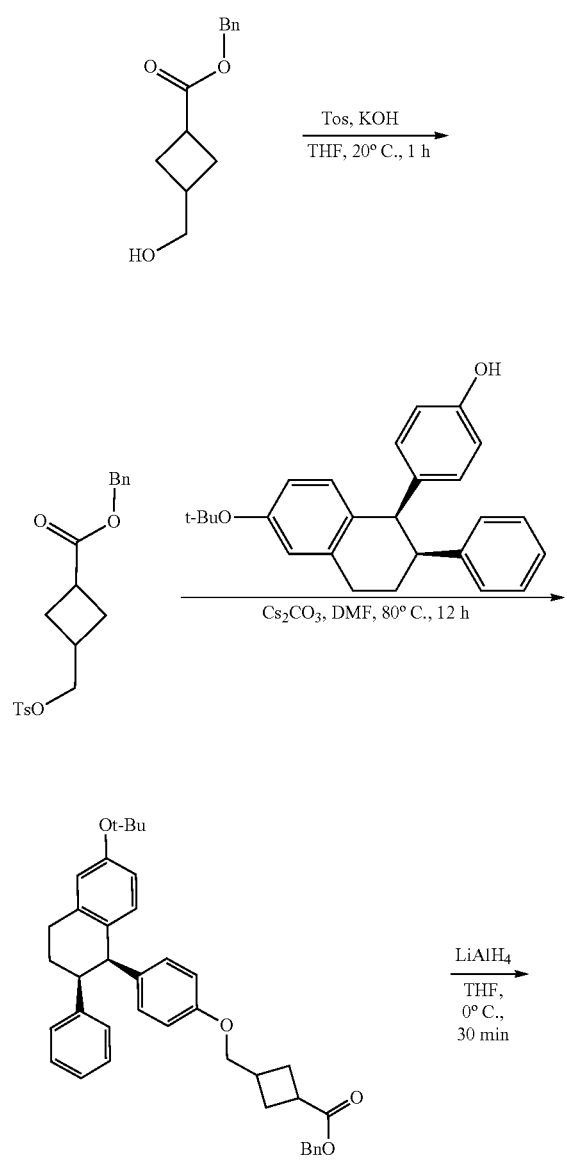
670
-continued
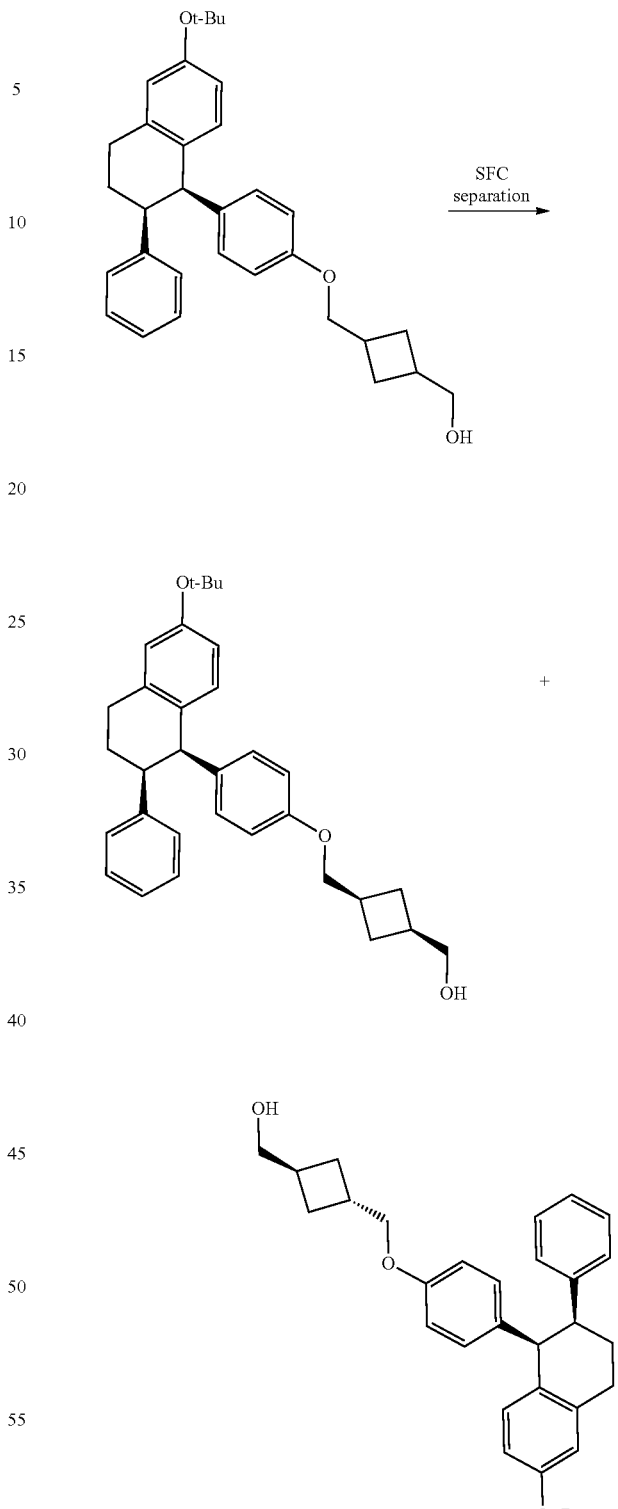
General synthetic schemes 2-1 through 2-47 describe the routes used to prepare representative cereblon binding moieties and cereblon binding moieties with partial linker moieties connected thereto.
General synthetic schemes 2-1a through 2-id to prepare intermediates.

Scheme 2-1a
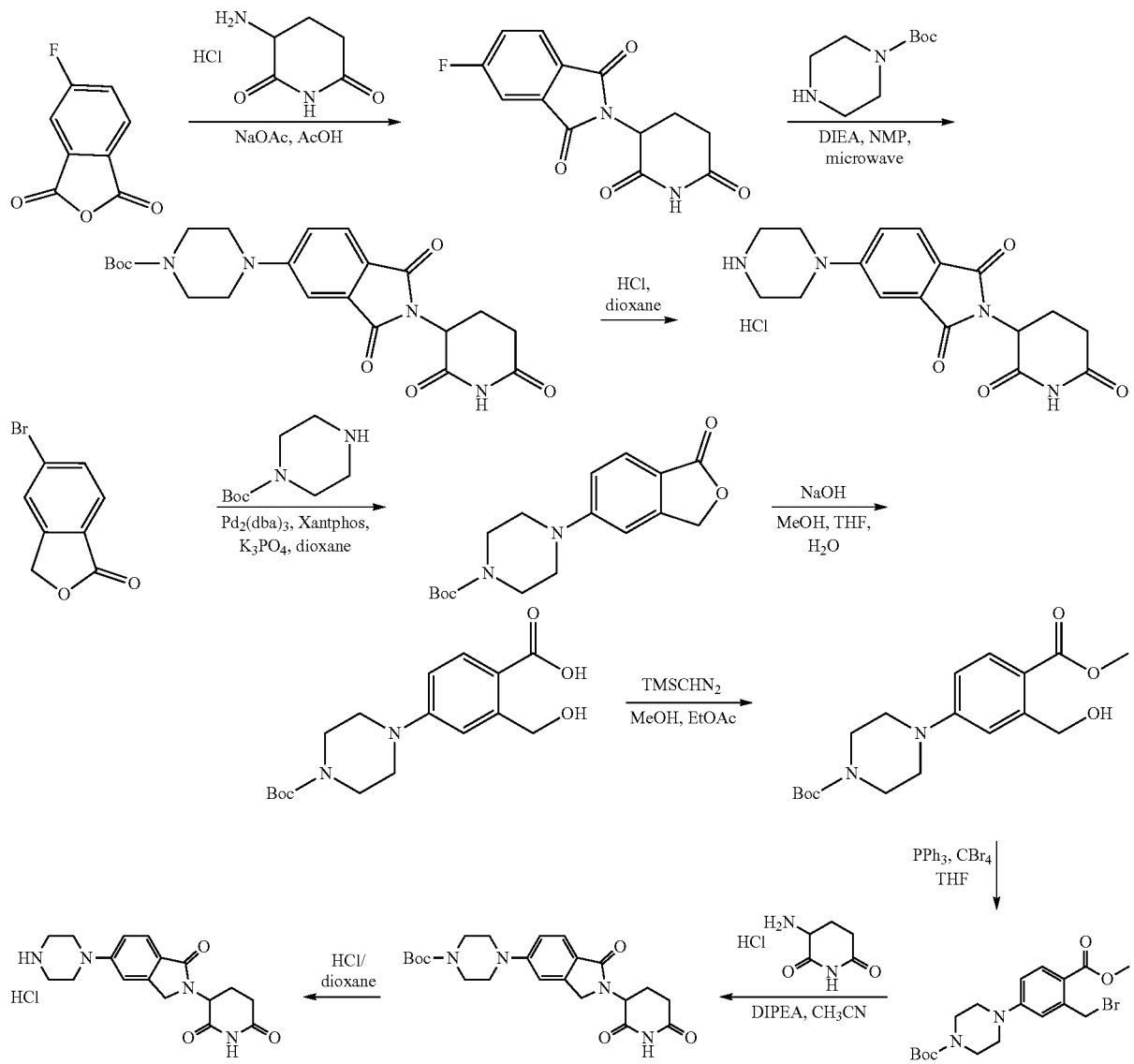
Scheme 2-1b
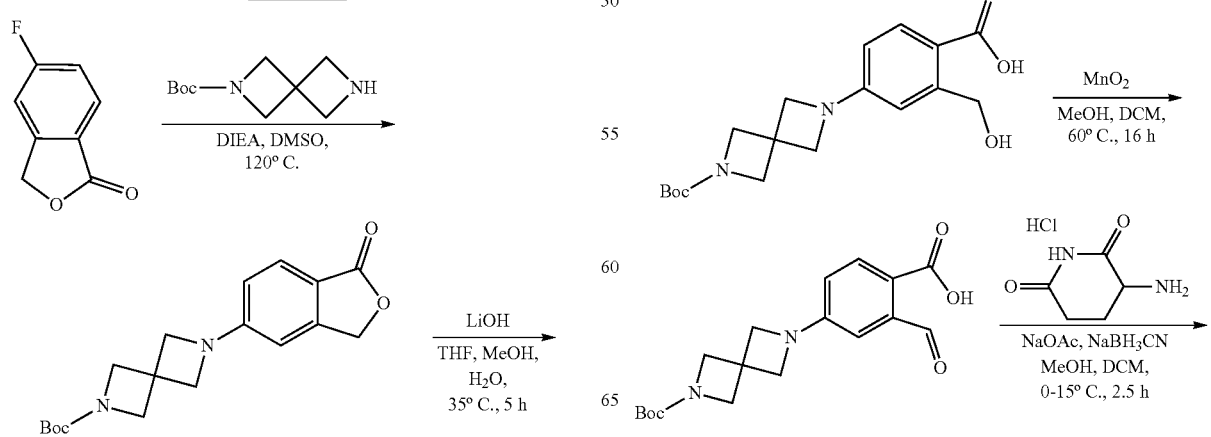

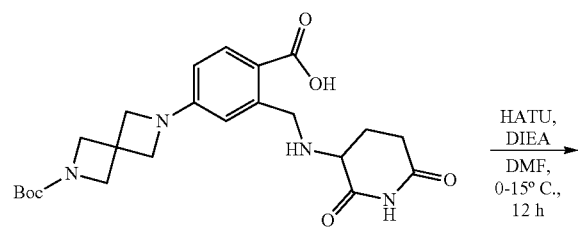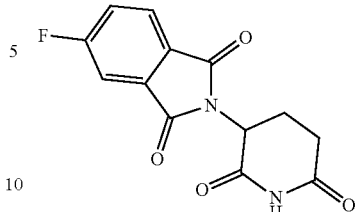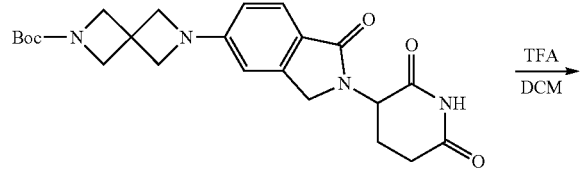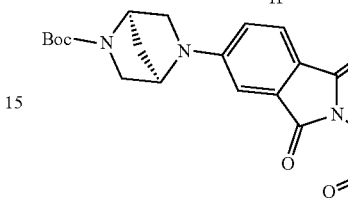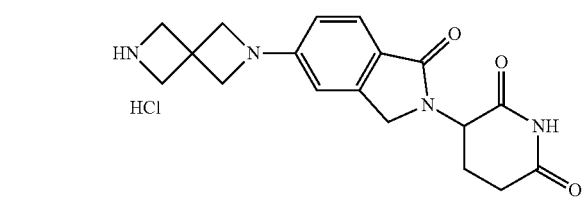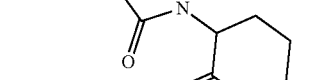
Scheme 2-1c
Scheme 2-1d
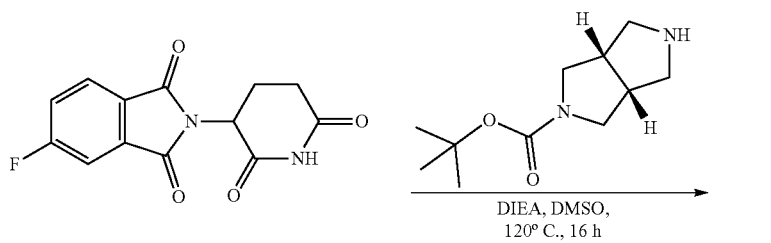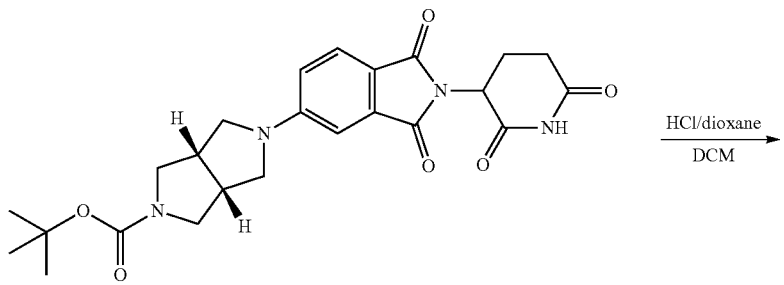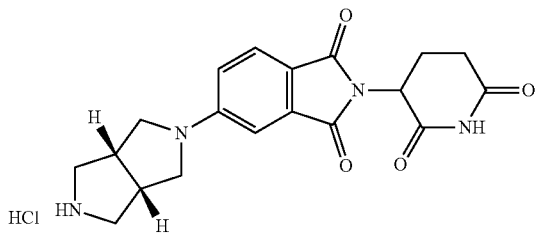

General synthetic scheme 2-2 to prepare intermediate.
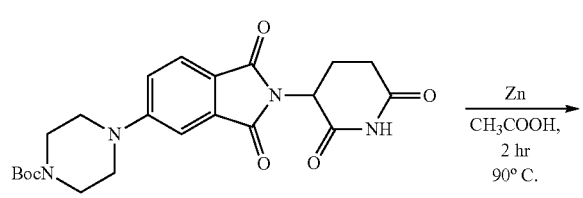
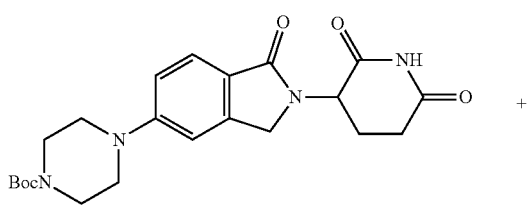
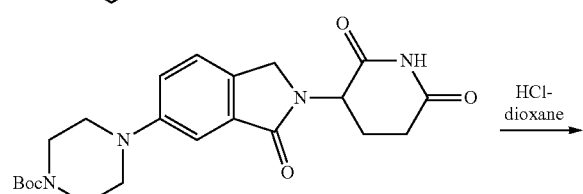
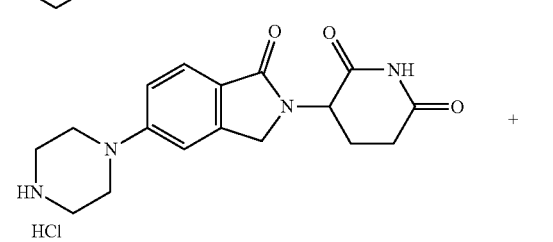
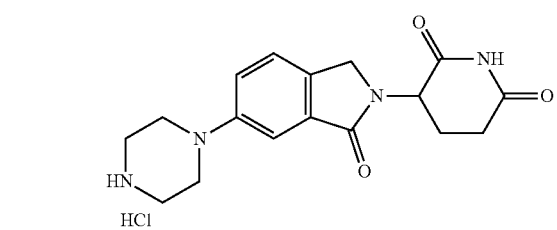
General synthetic scheme 2-3 to prepare intermediate.
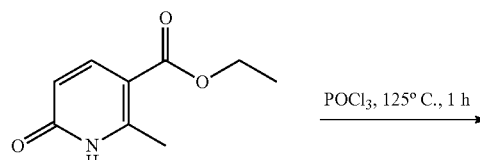
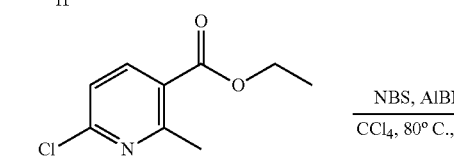
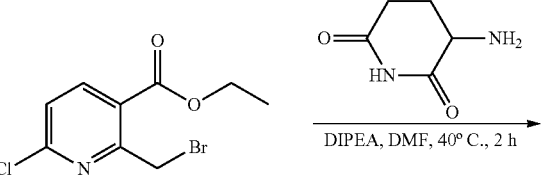
-continued
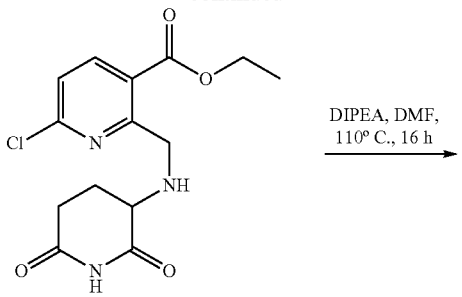
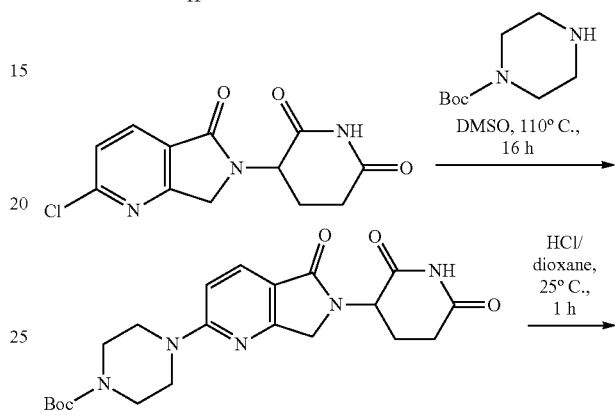
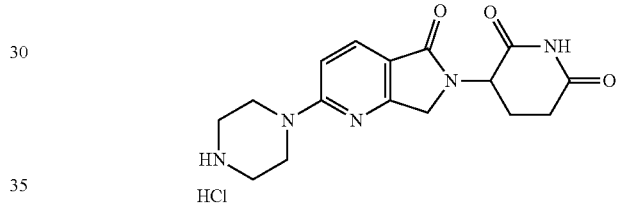
General synthetic scheme 2-4 to prepare intermediate.
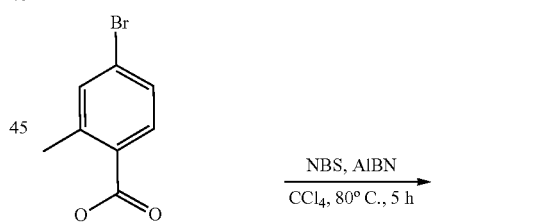
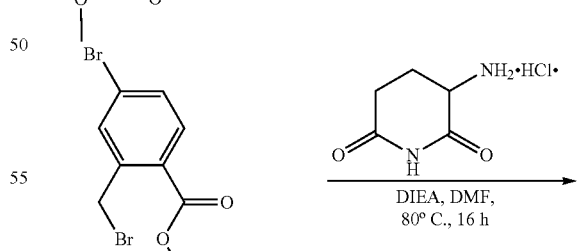
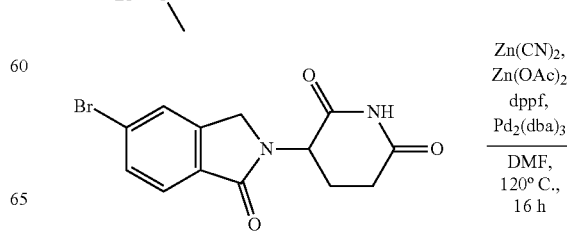

677
-continued
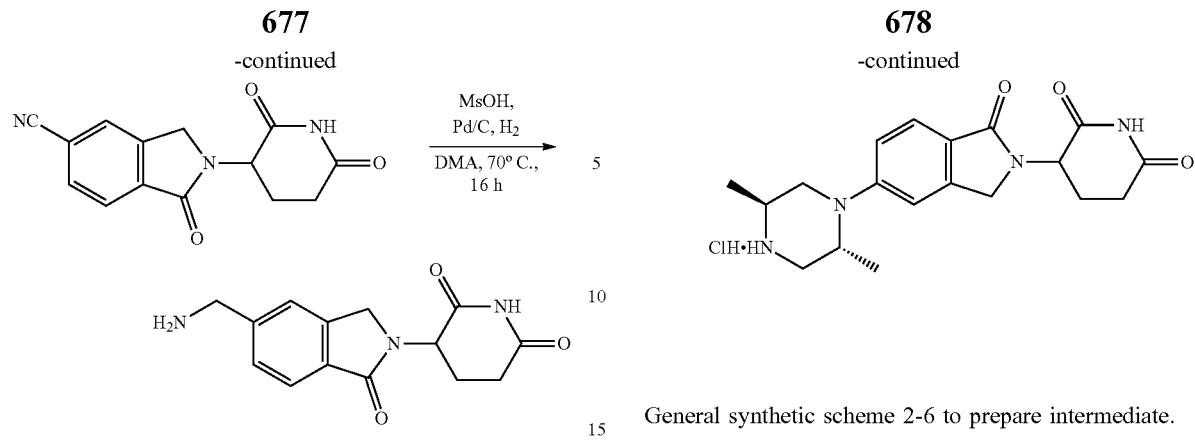
General synthetic scheme 2-5 to prepare intermediate.
678
-continued
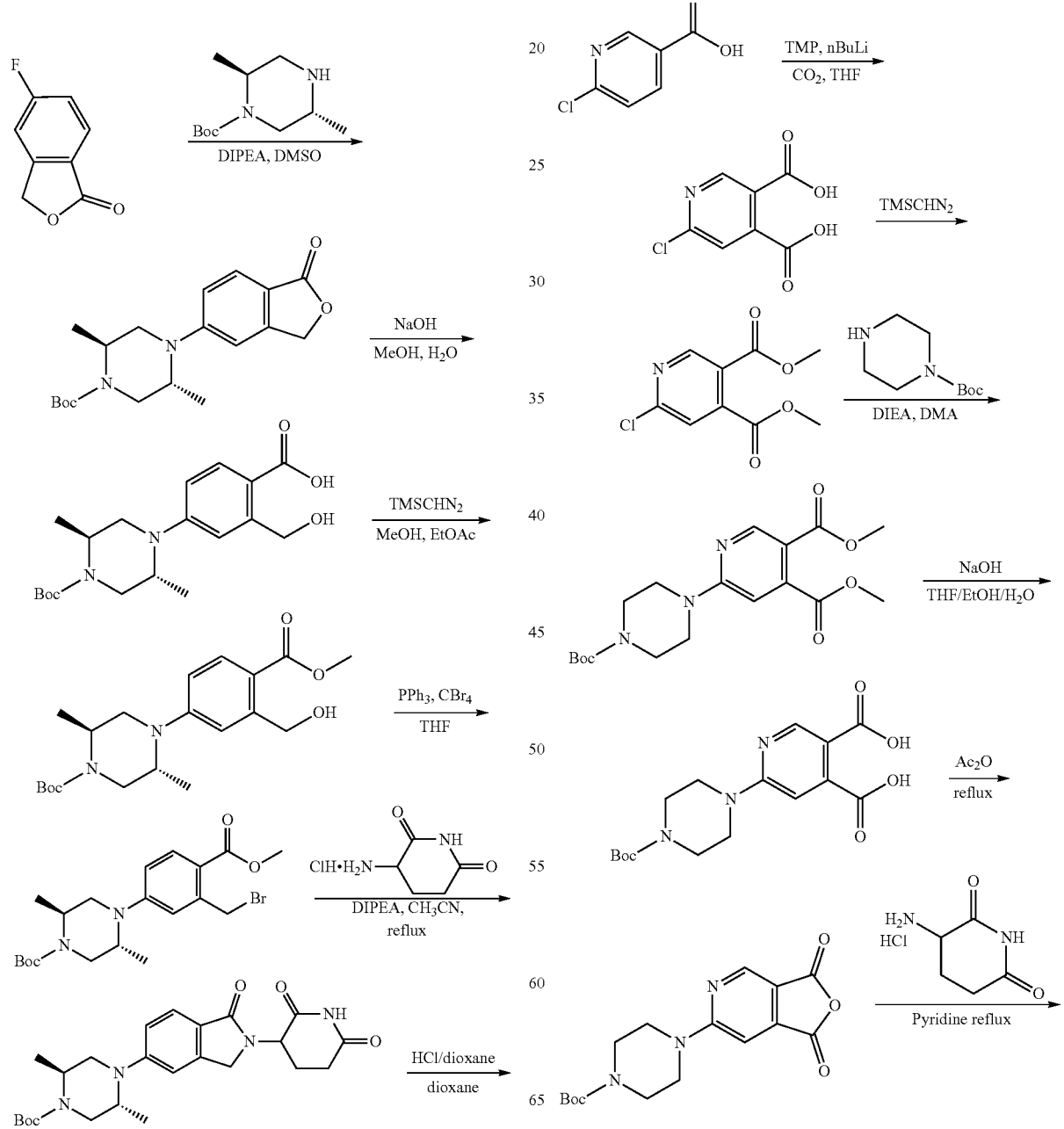
General synthetic scheme 2-6 to prepare intermediate.

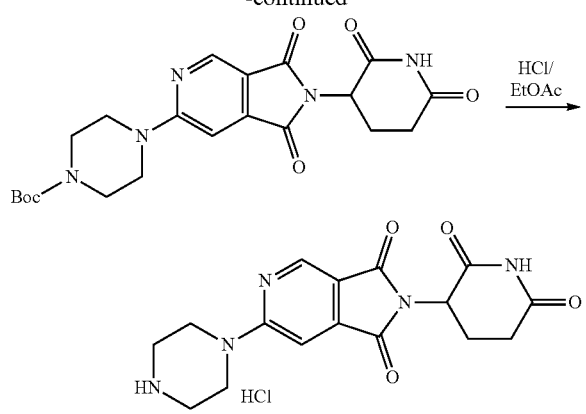
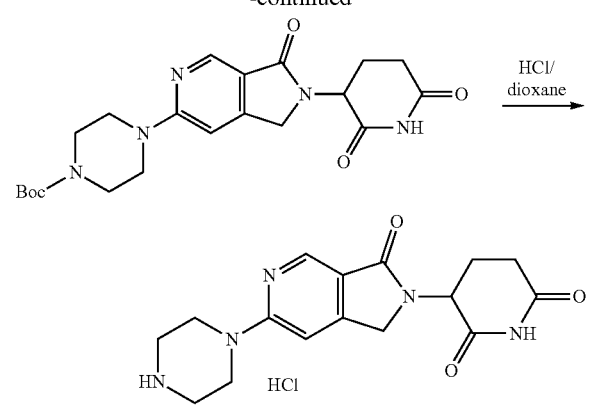
General synthetic scheme 2-7 to prepare intermediate.
General synthetic schemes 2-8a and 2-8b to prepare intermediate.
Scheme 2-8a
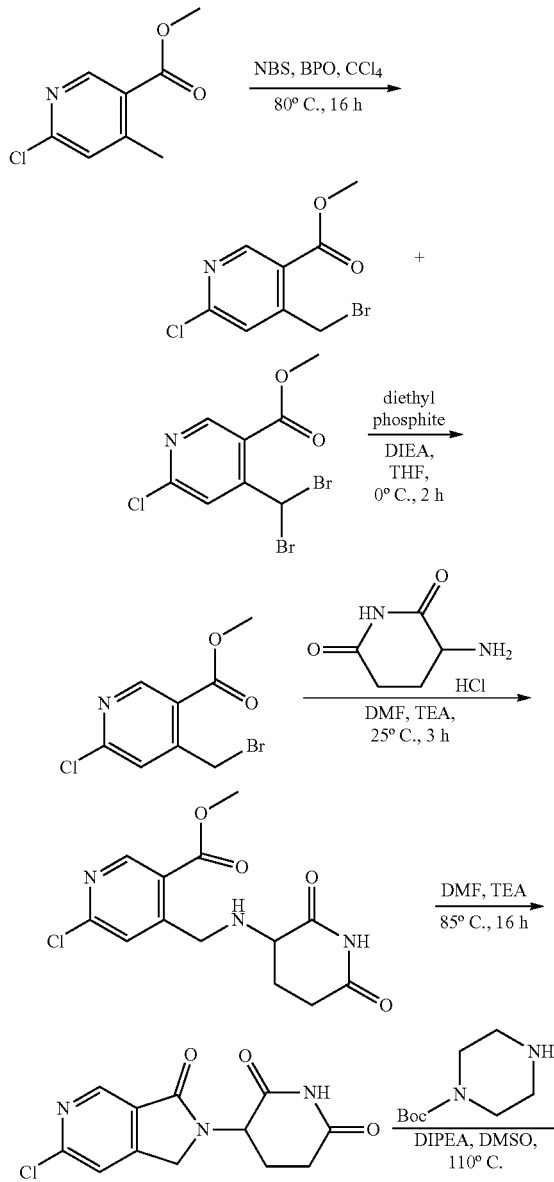
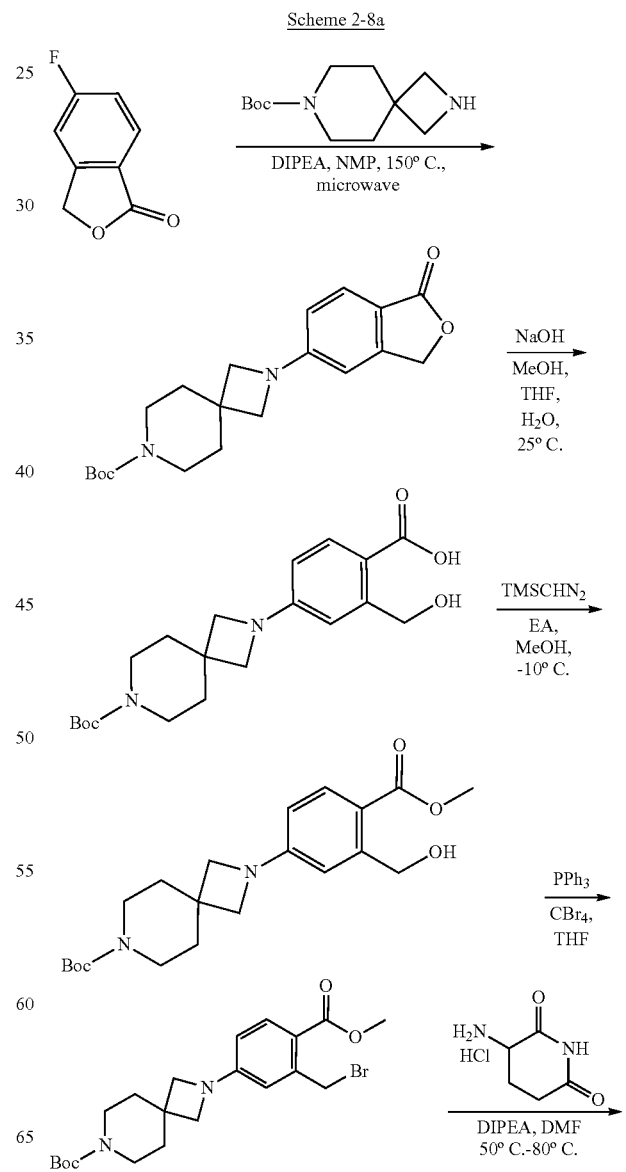

681
-continued
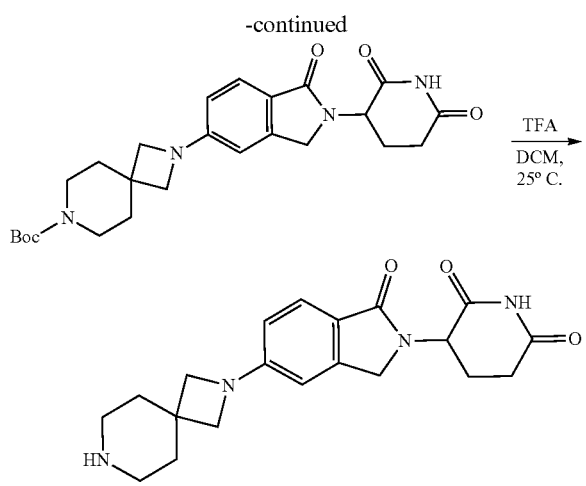
Scheme 2-8b
682
-continued
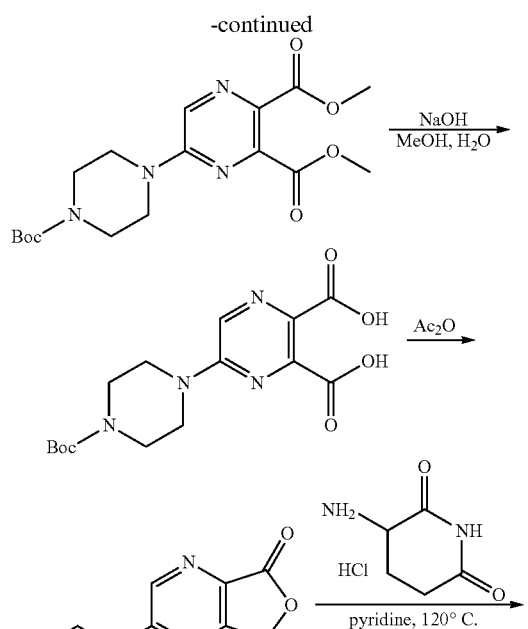
General synthetic scheme 2-10 to prepare intermediate.
General synthetic scheme 2-9 to prepare intermediate.
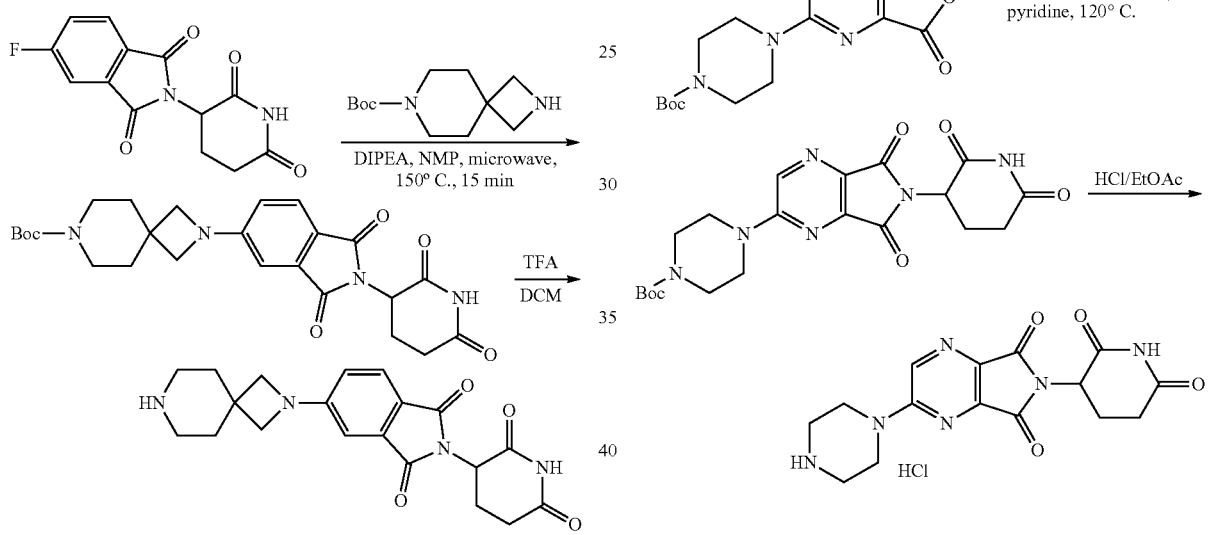
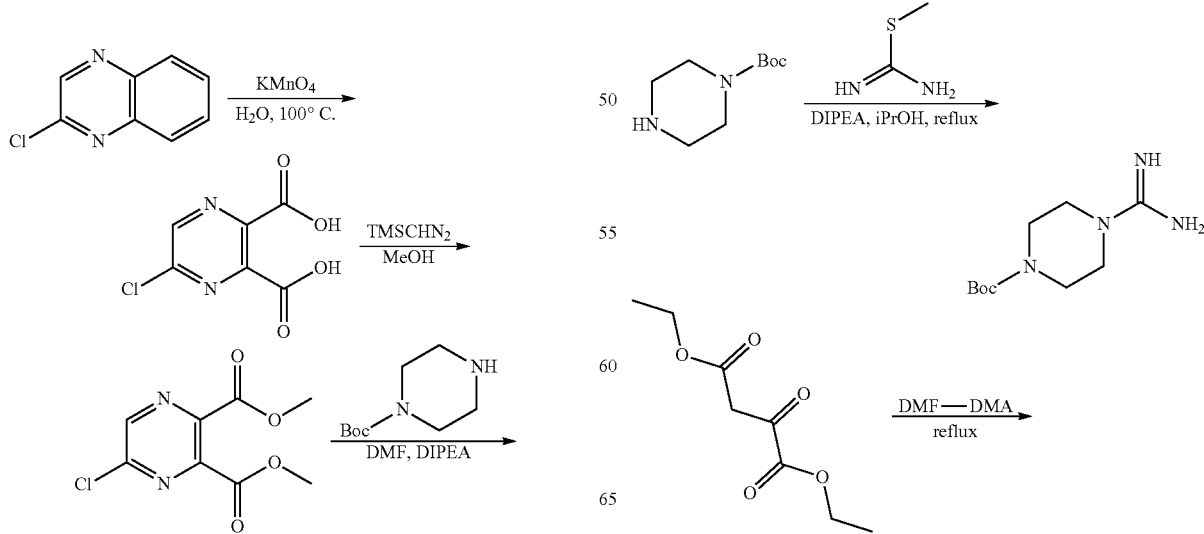

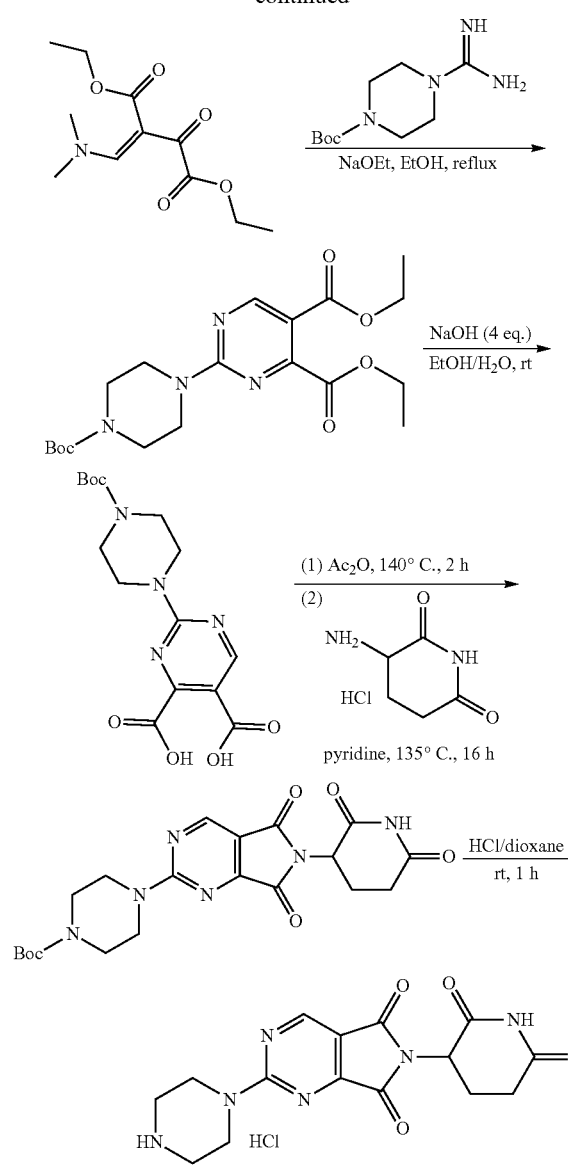
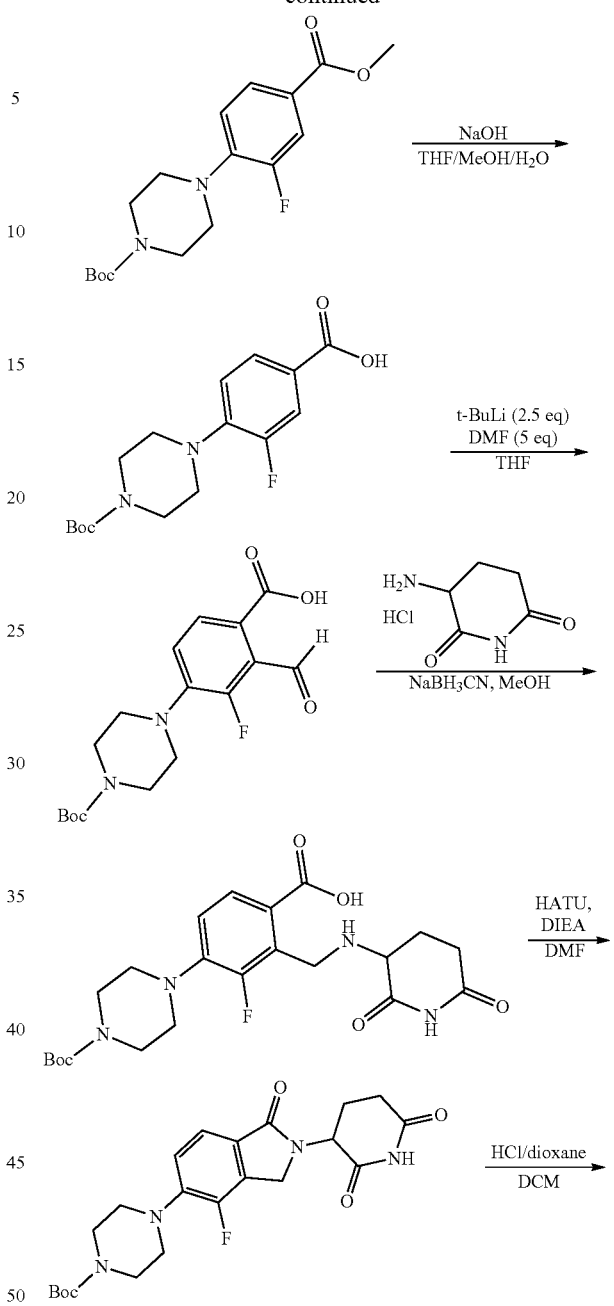
General synthetic schemes 2-11a through 2-11b to prepare intermediates.
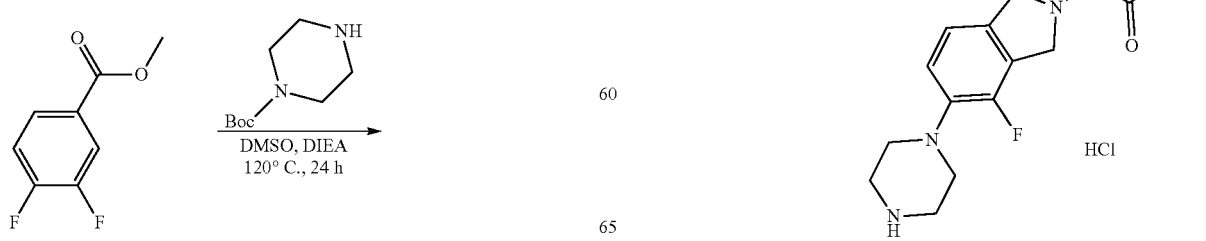
Scheme 2-11a Scheme 2-11b
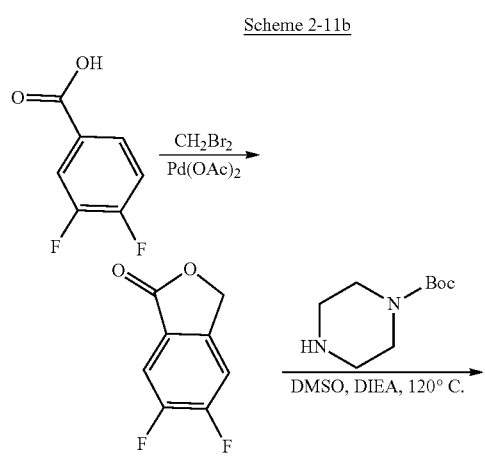
-continued
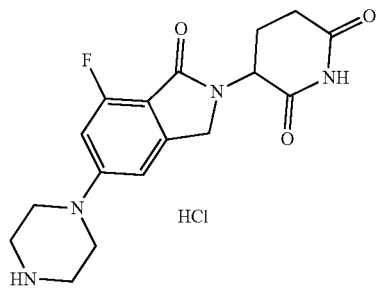
Scheme 2-11c
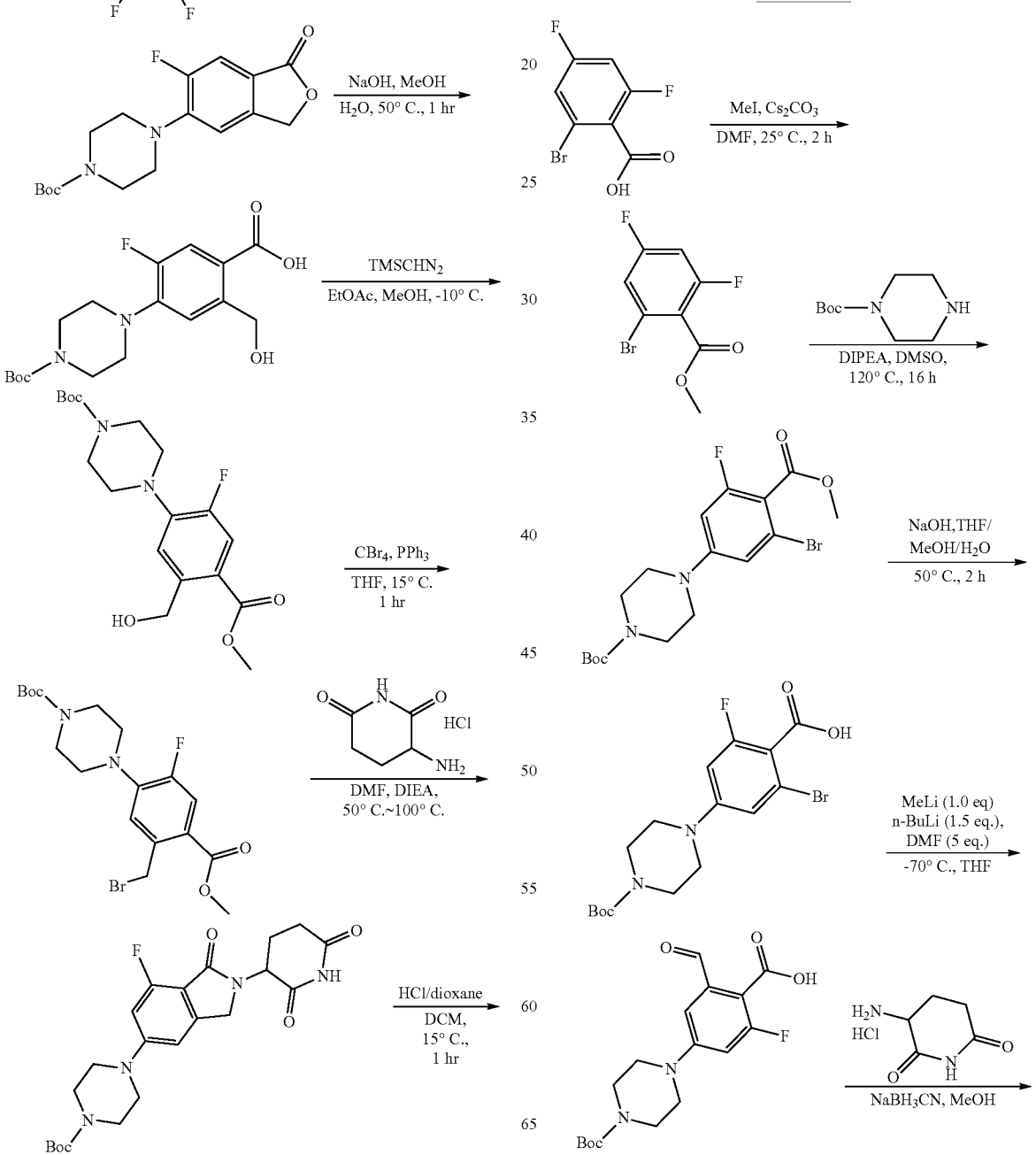

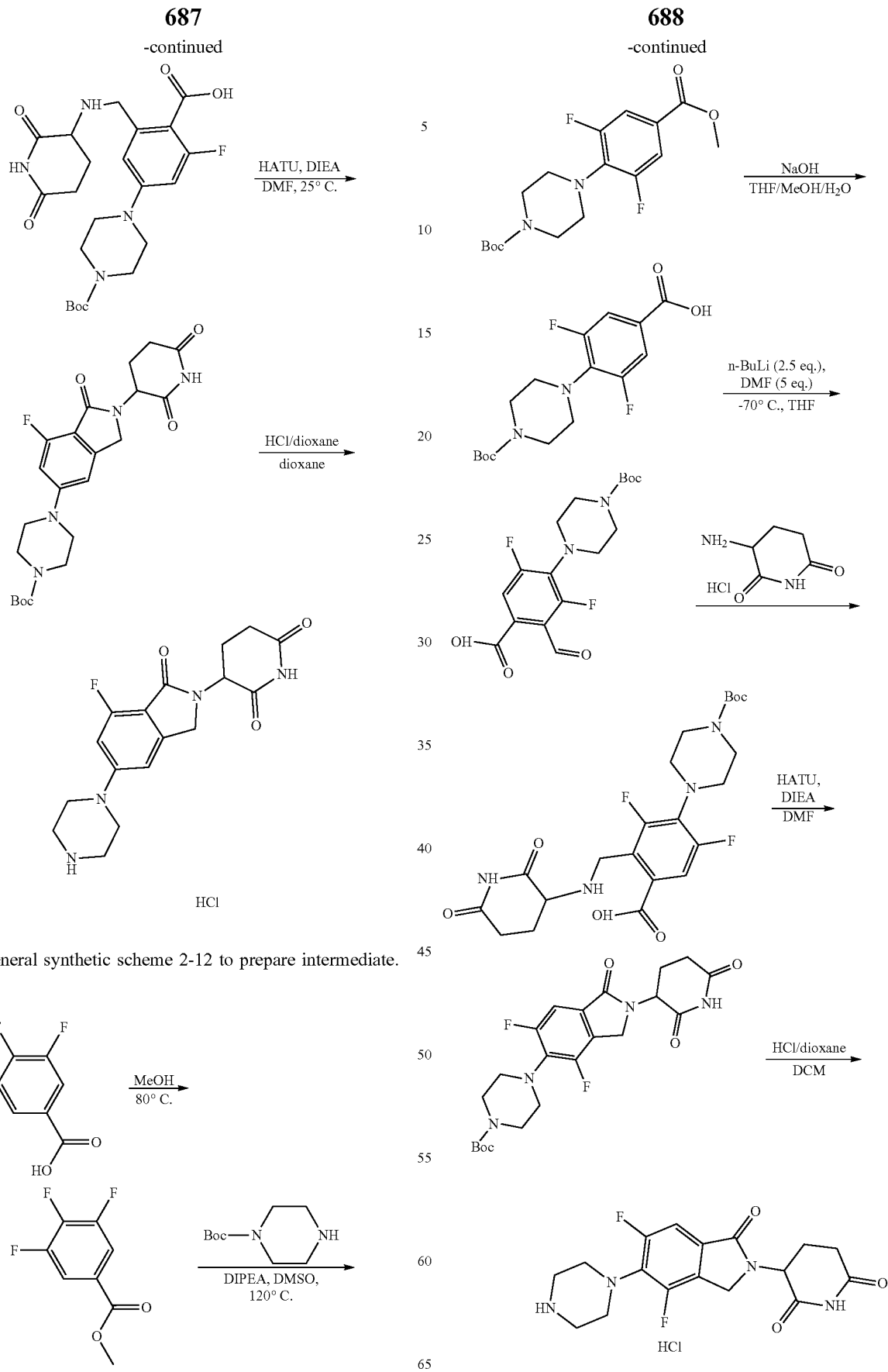
General synthetic scheme 2-12 to prepare intermediate.

General synthetic scheme 2-13 to prepare intermediate.
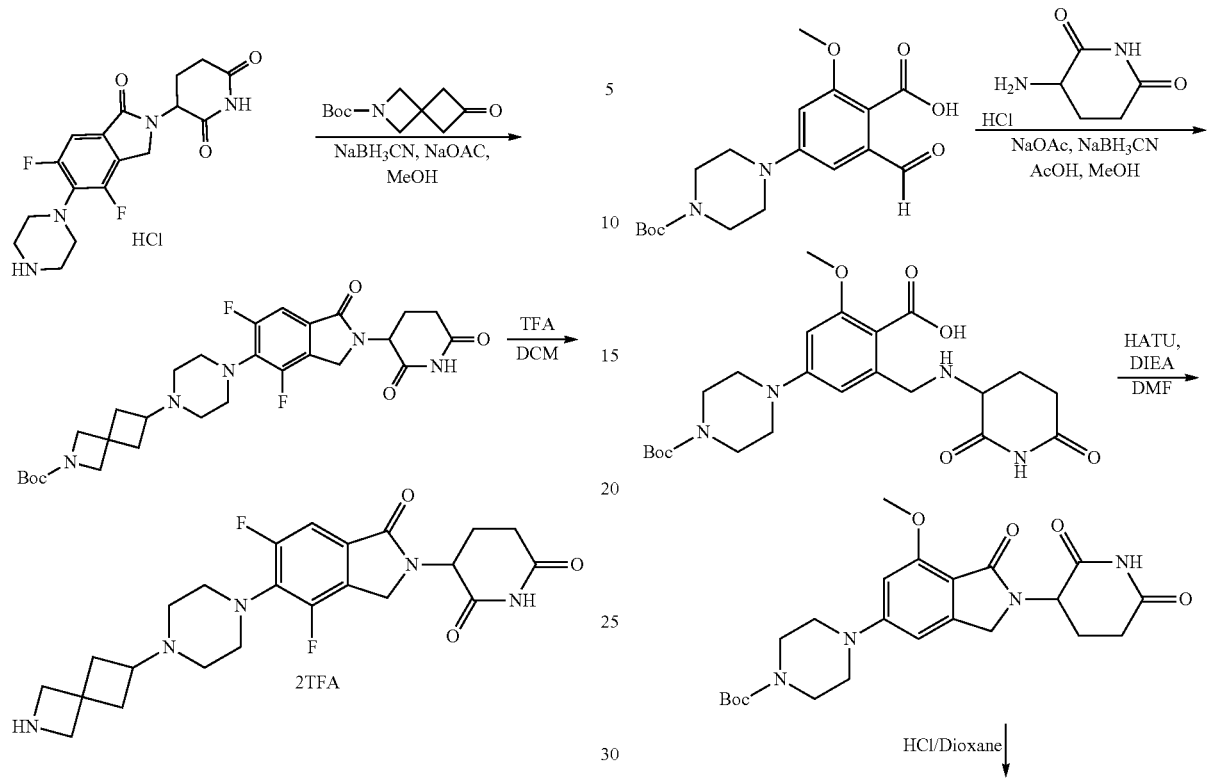
General synthetic scheme 2-14 to prepare intermediate.
-continued
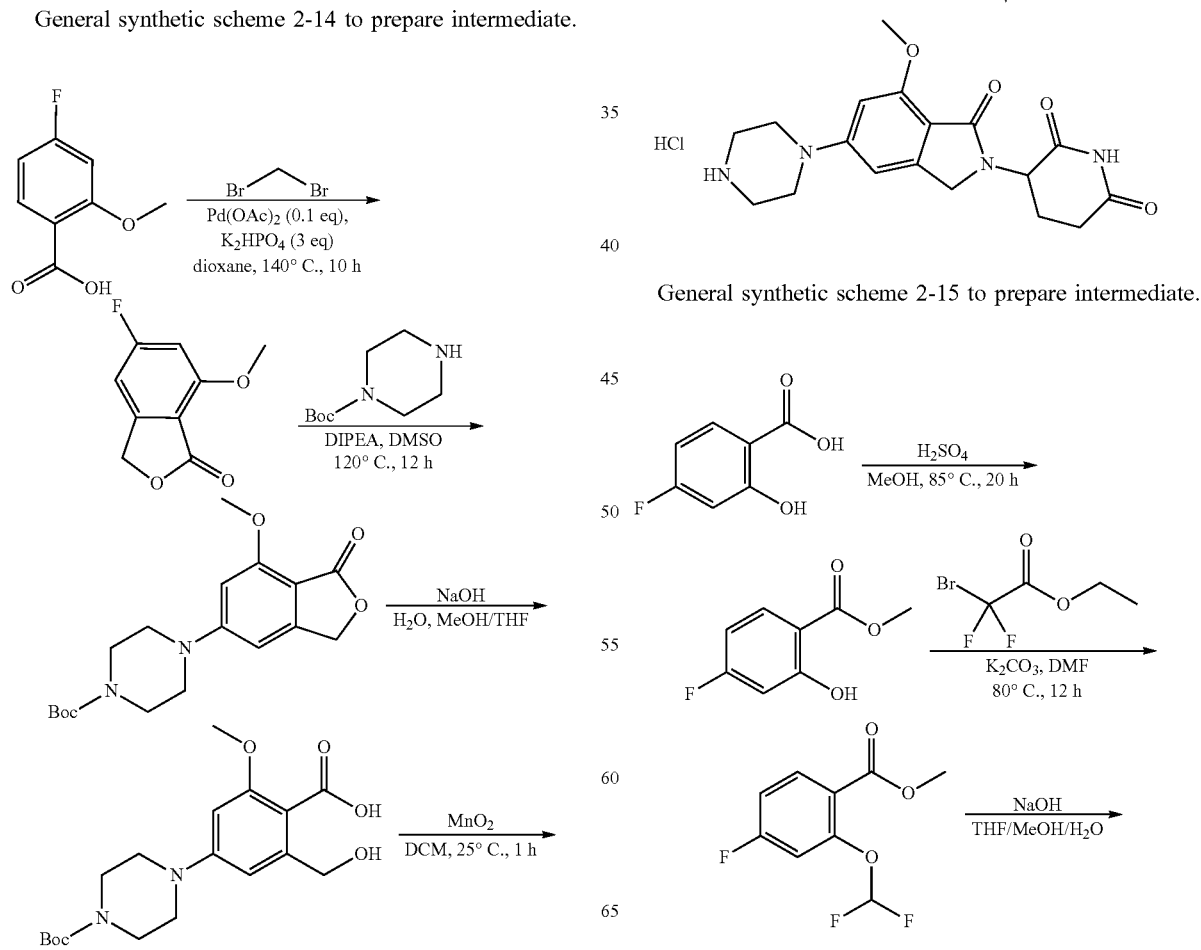
General synthetic scheme 2-15 to prepare intermediate.

691
-continued
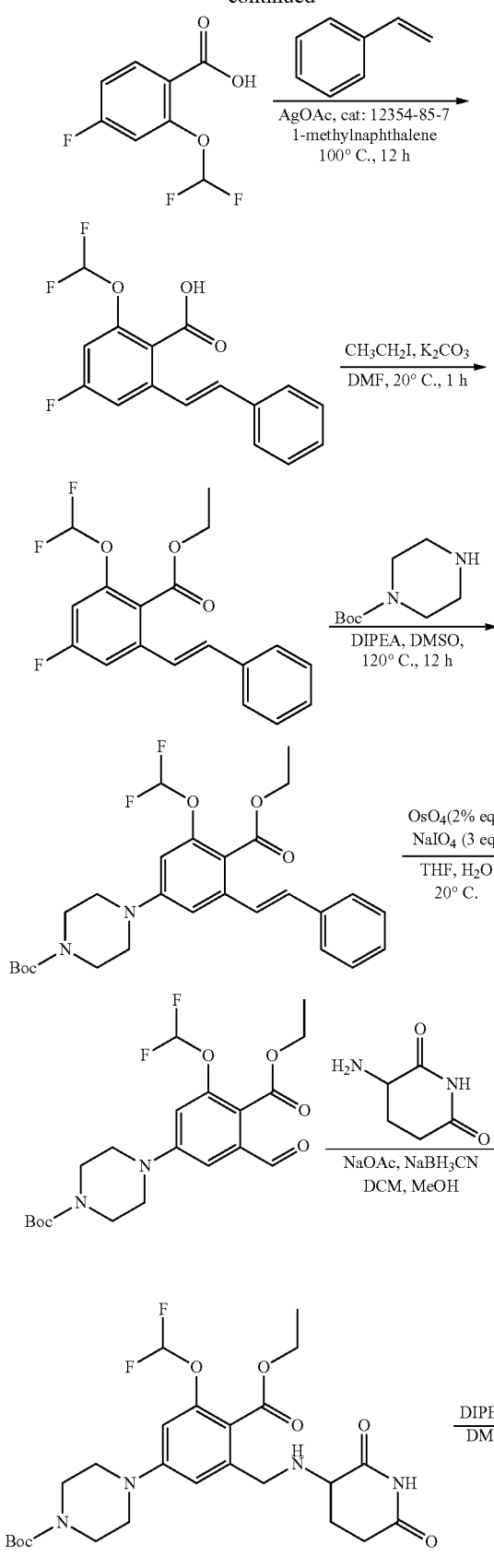
692
-continued
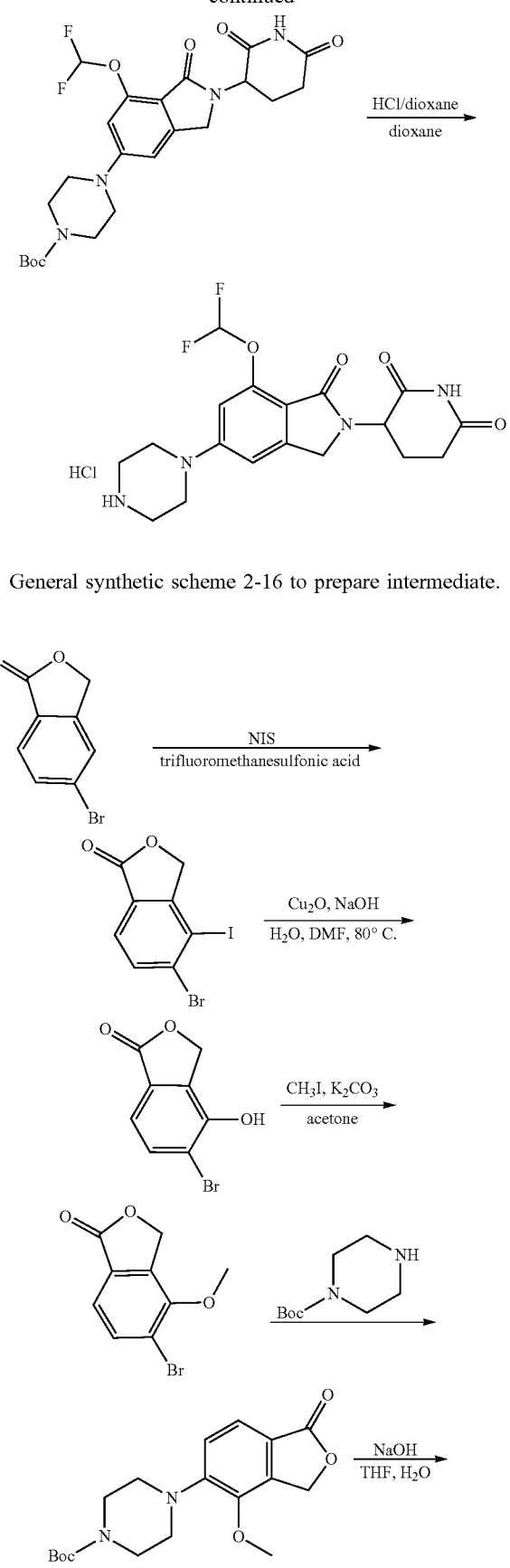
General synthetic scheme 2-16 to prepare intermediate.

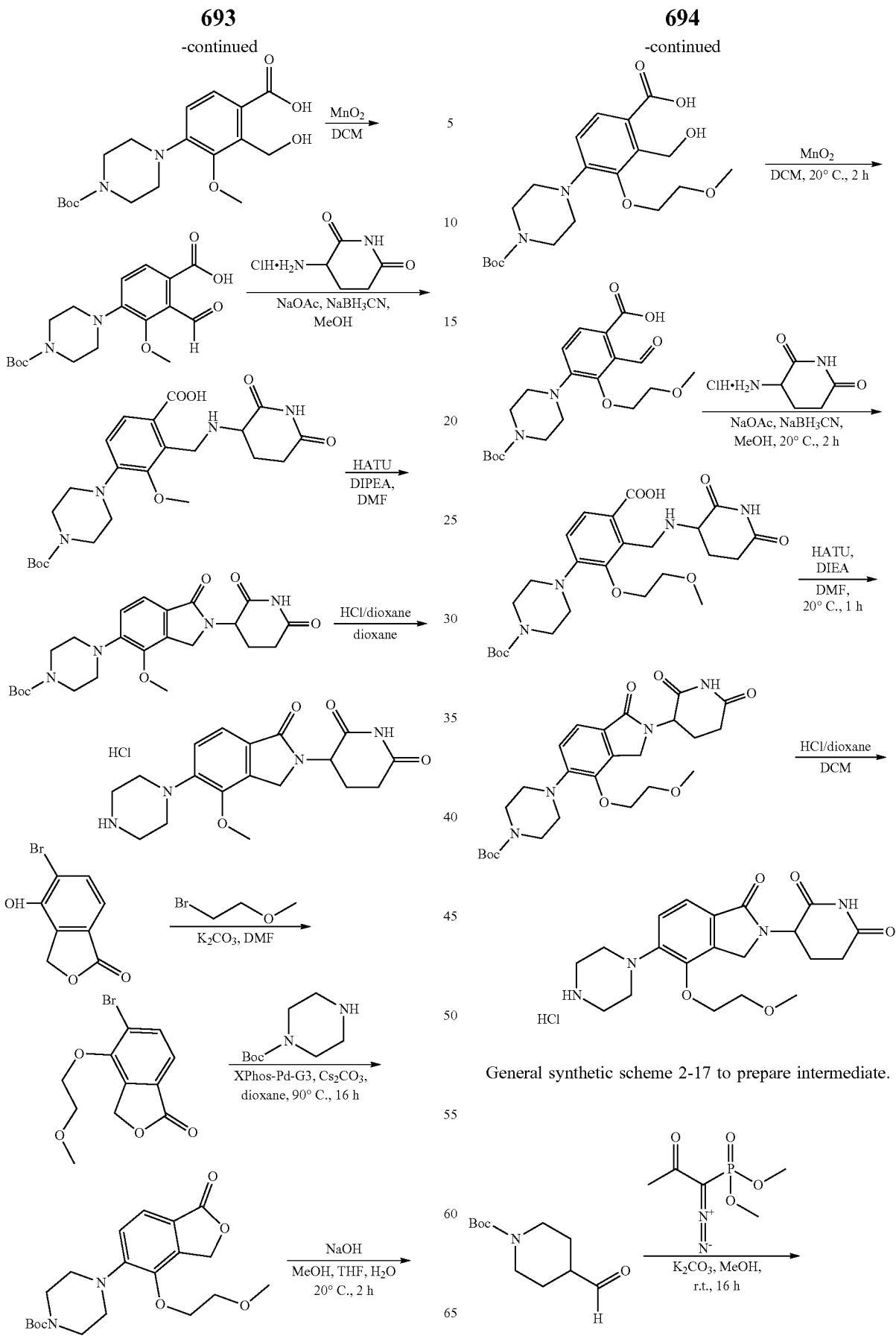
General synthetic scheme 2-17 to prepare intermediate.

695
-continued
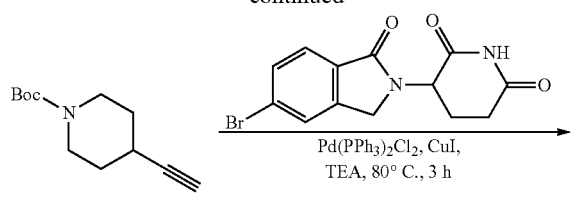
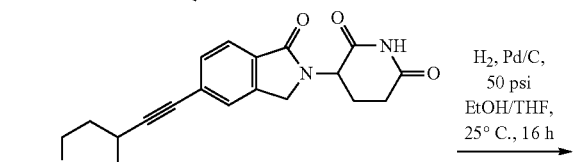
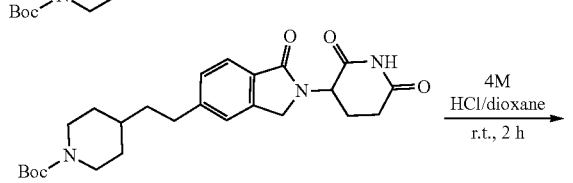
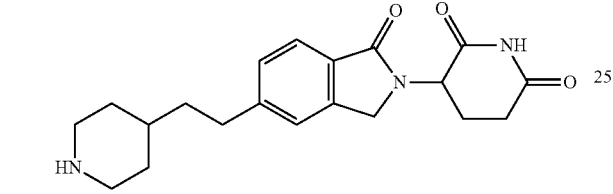
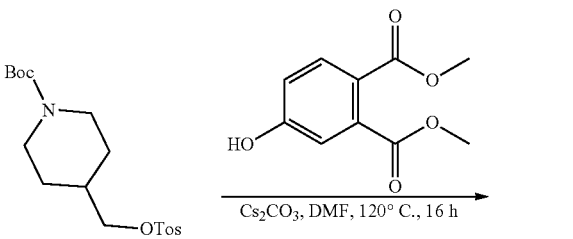
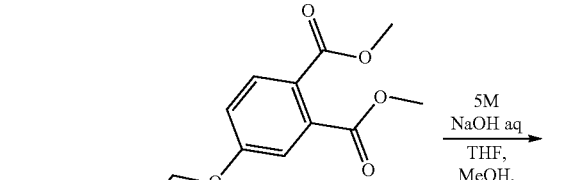
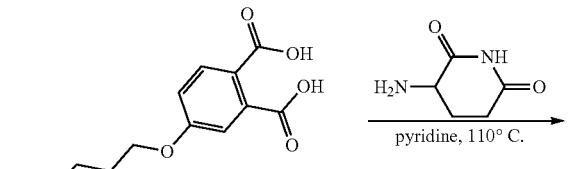
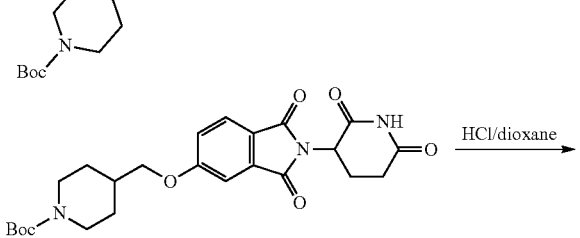
696
-continued
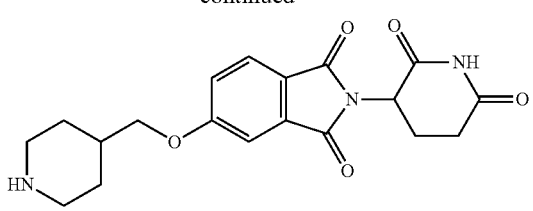
General synthetic scheme 2-18a through 2-18b to prepare intermediate.
Scheme 2-18a
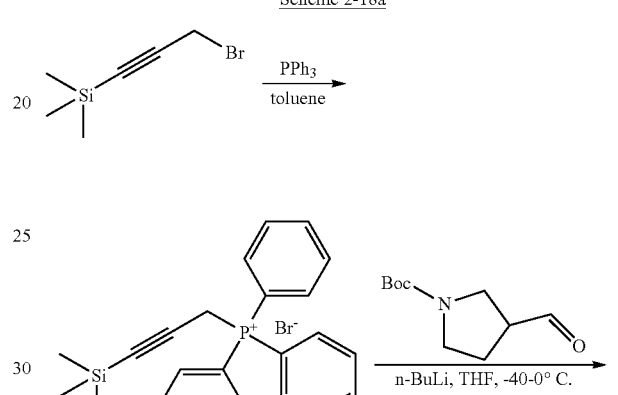
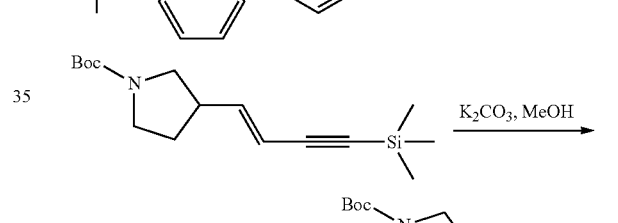
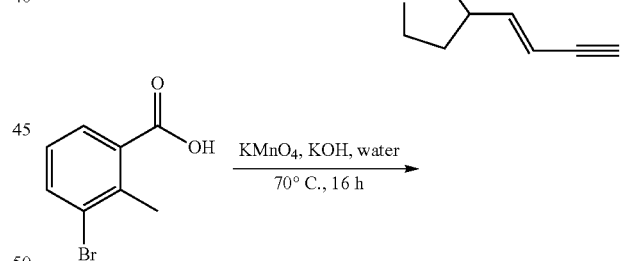
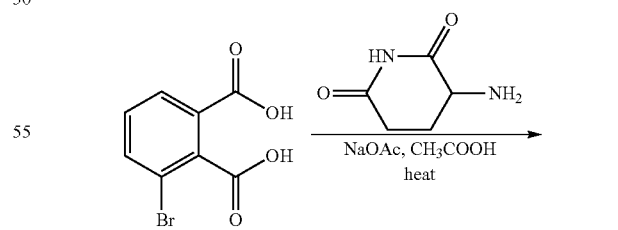
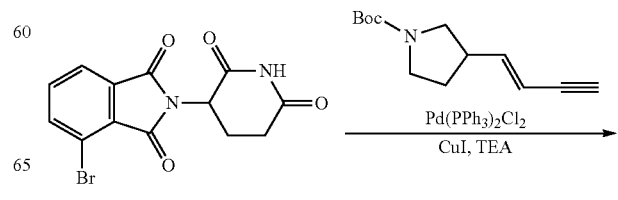

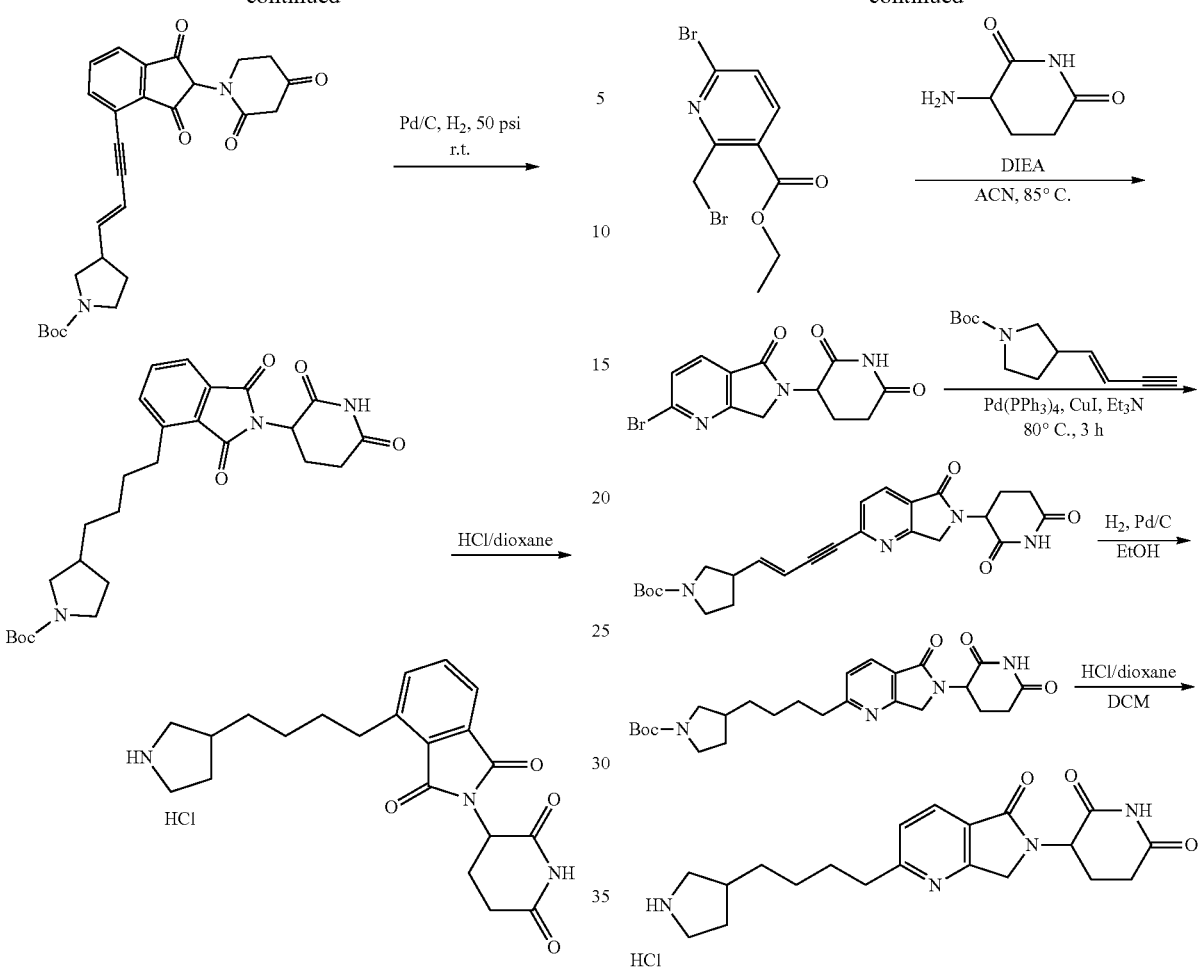
General synthetic scheme 2-19 to prepare intermediate.

699
-continued

General synthetic scheme 2-20a through 2-20b to prepare intermediate.

Scheme 2-20a

700
-continued

Scheme 2-20b

General synthetic scheme 2-21 to prepare intermediate.
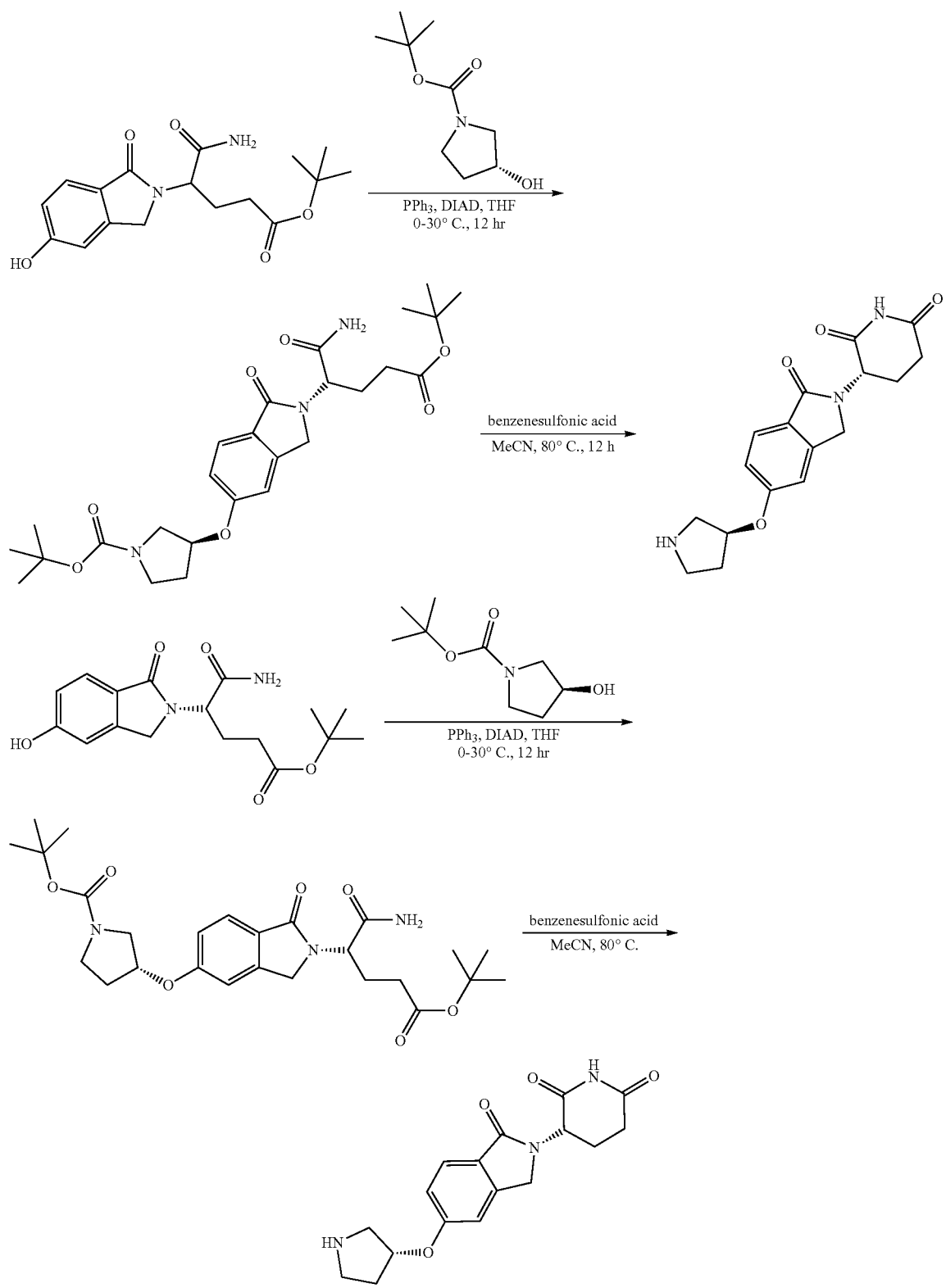

703
General synthetic scheme 2-22 to prepare intermediate.
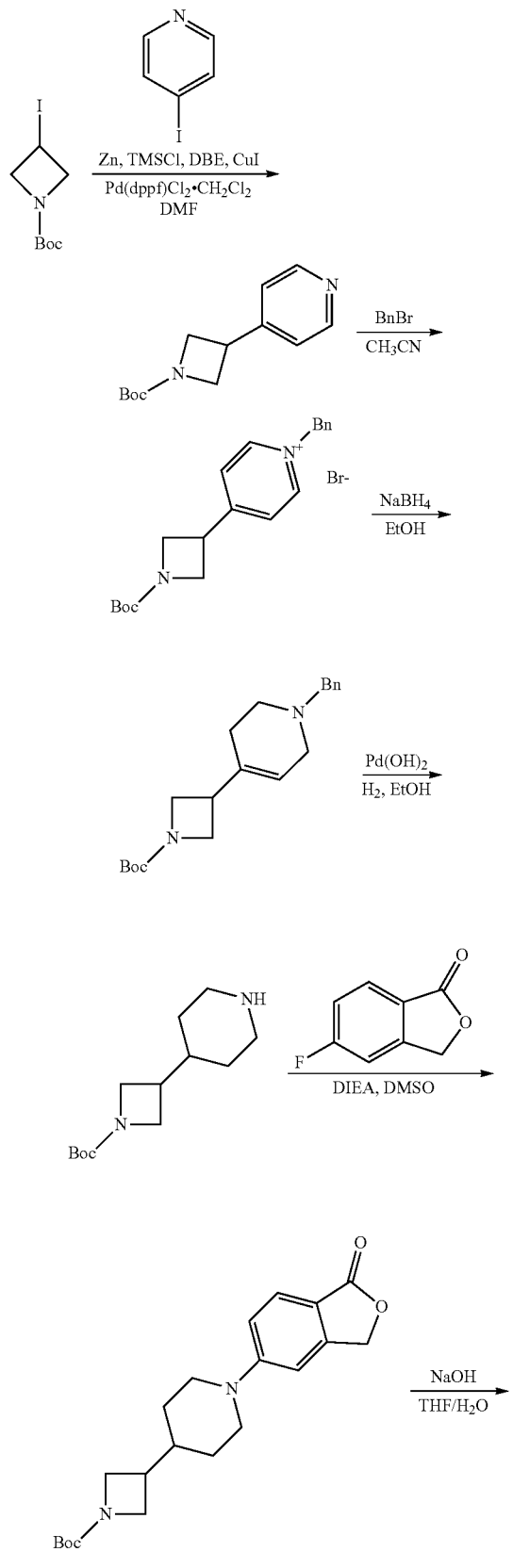
704
-continued
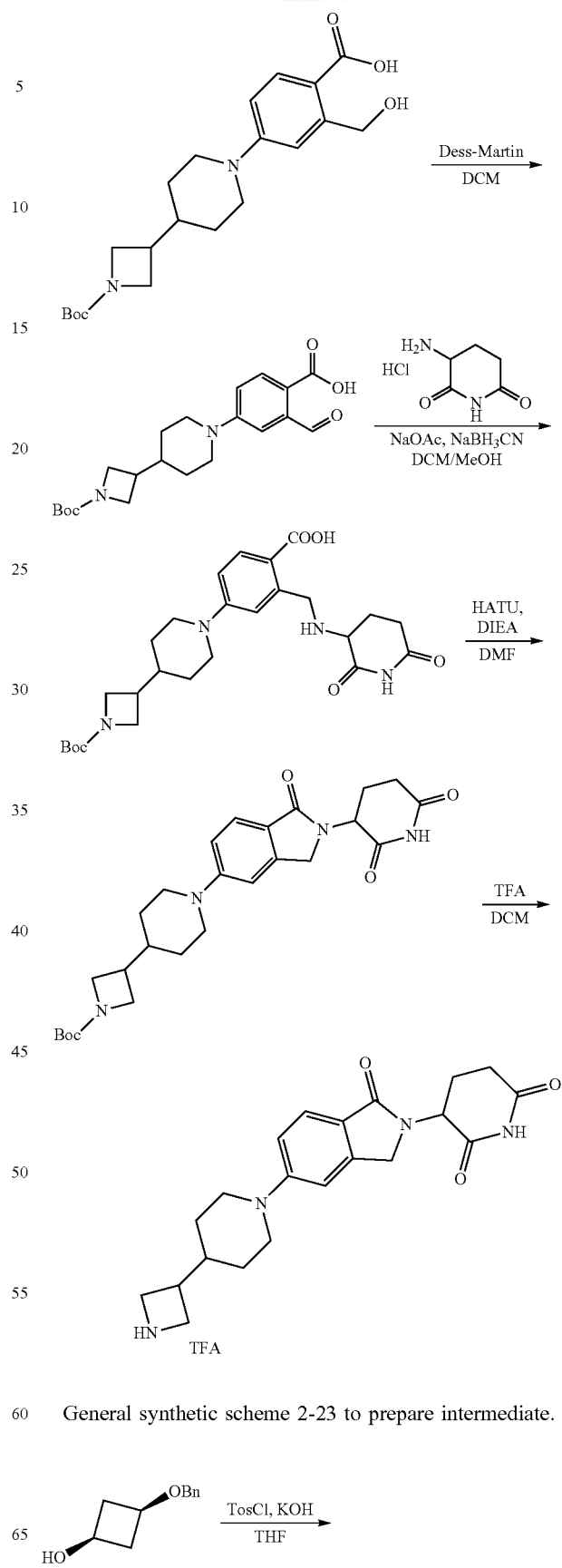
General synthetic scheme 2-23 to prepare intermediate.

705
-continued
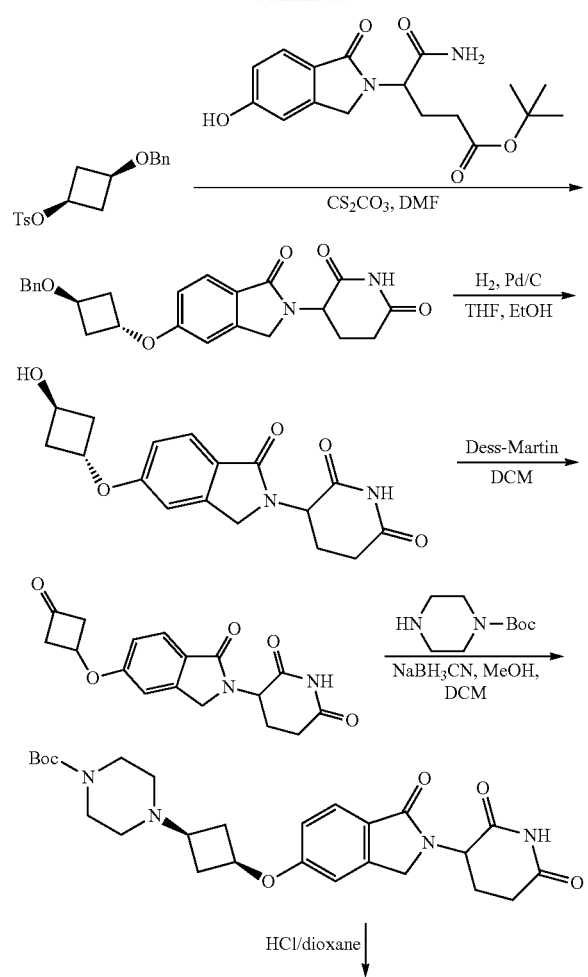
General synthetic scheme 2-24 to prepare intermediate.
706
-continued
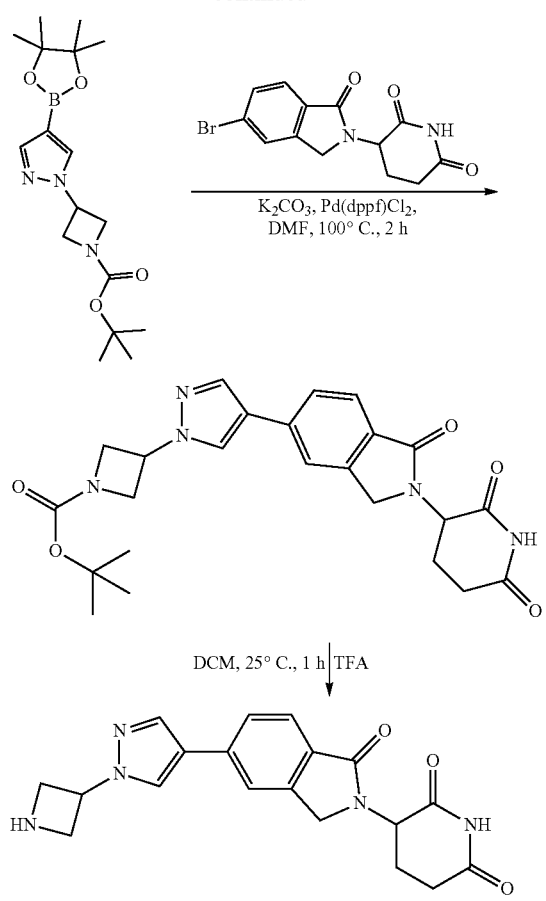
General synthetic scheme 2-25 to prepare intermediate.
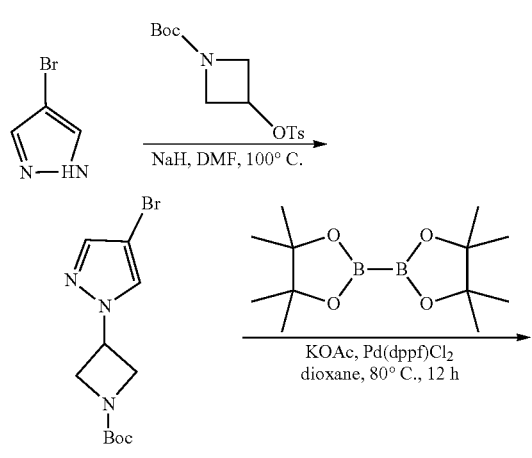
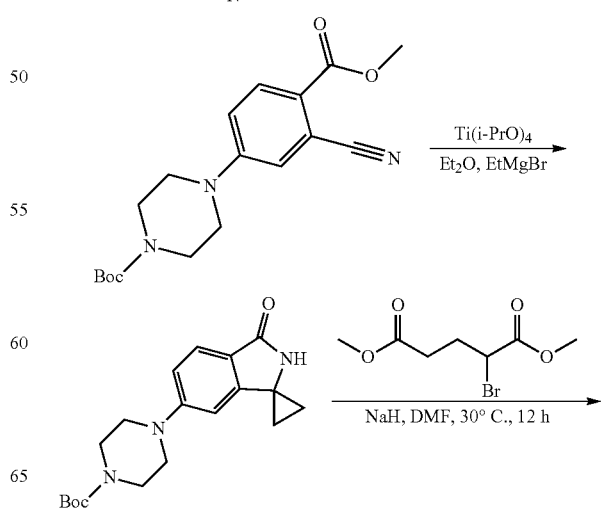

707
-continued
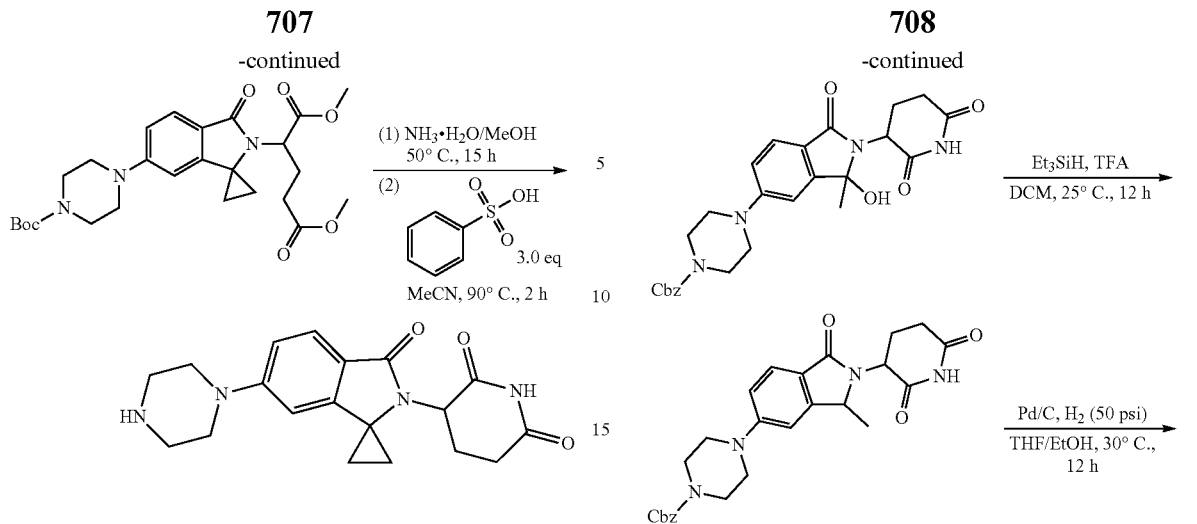
General synthetic scheme 2-26 to prepare intermediate.
708
-continued
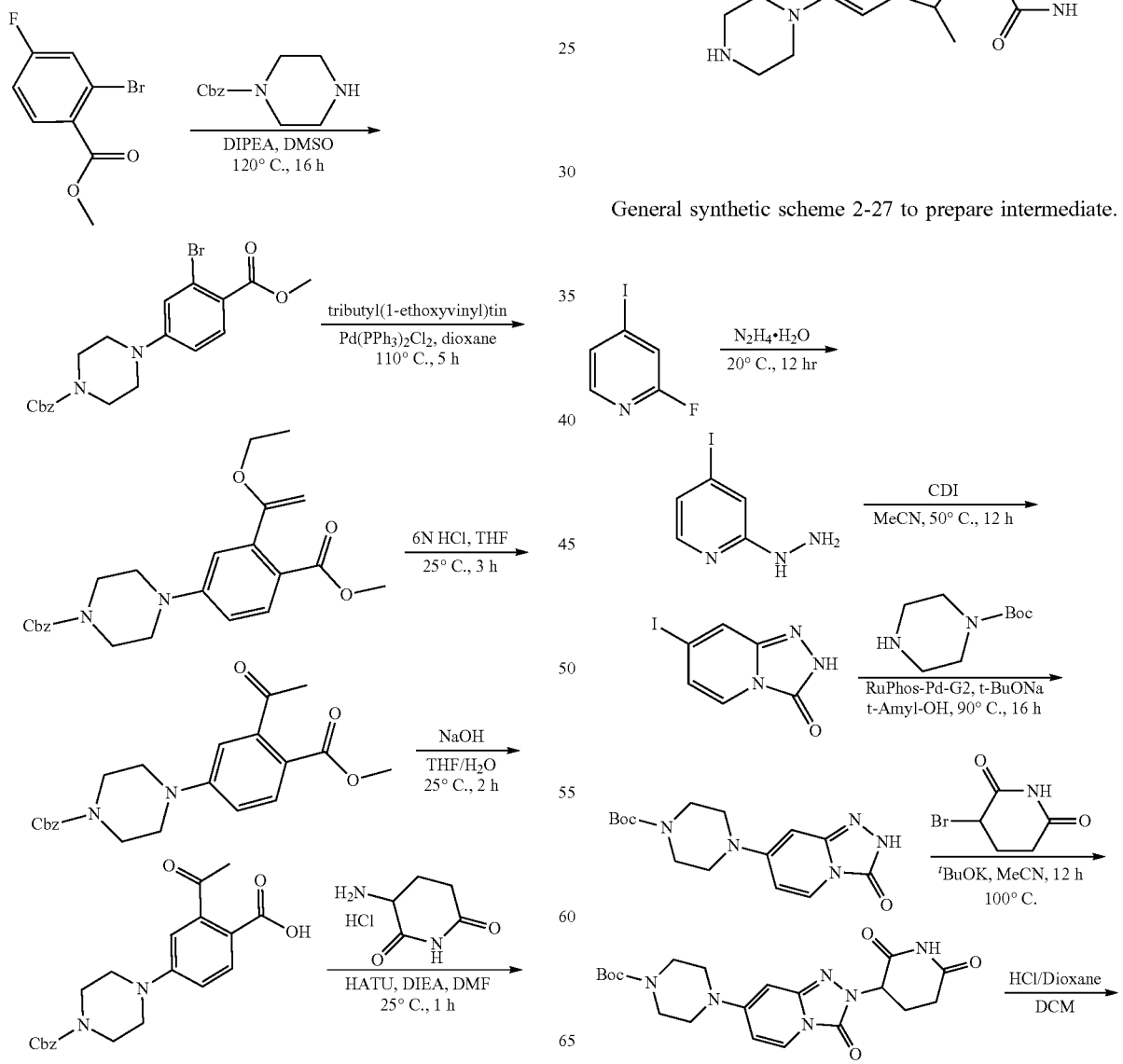
General synthetic scheme 2-27 to prepare intermediate.

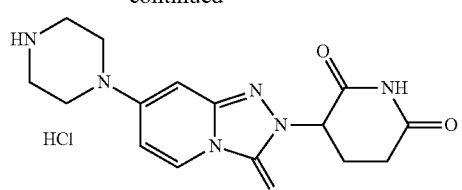
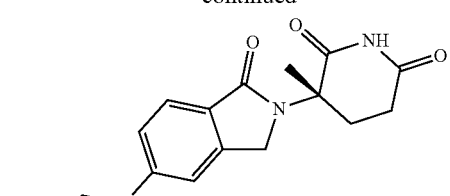
General synthetic scheme 2-28 to prepare intermediate.
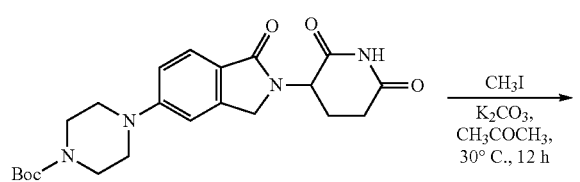
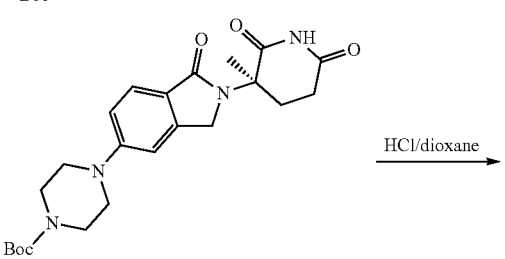
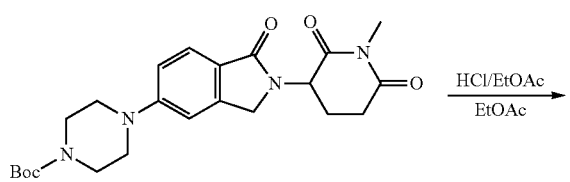
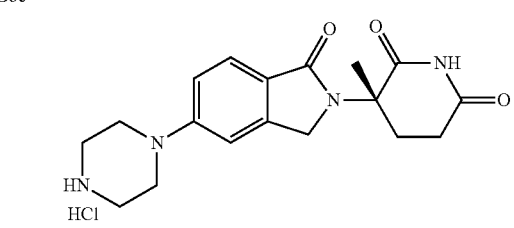
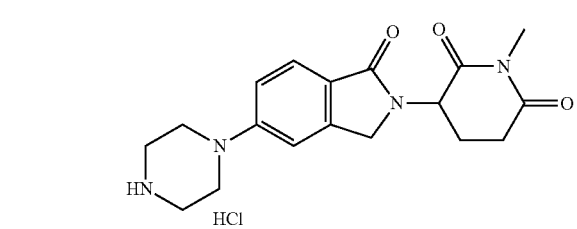
General synthetic scheme 2-29 to prepare intermediate.
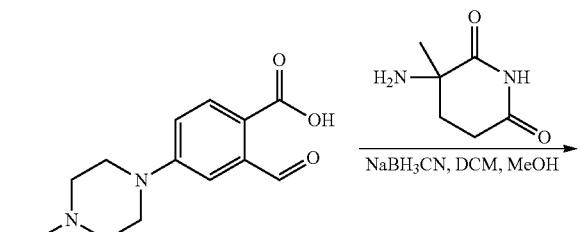
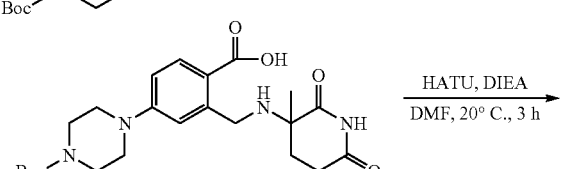
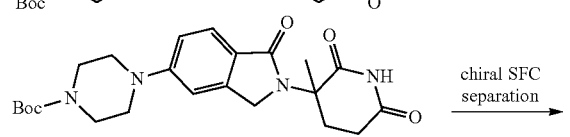
General synthetic scheme 2-30 to prepare intermediate.
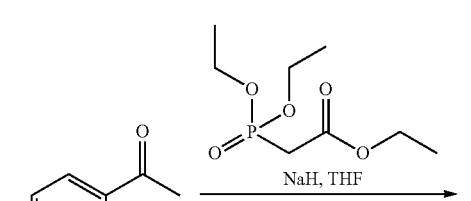
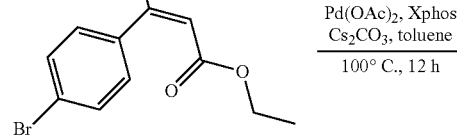

711
-continued
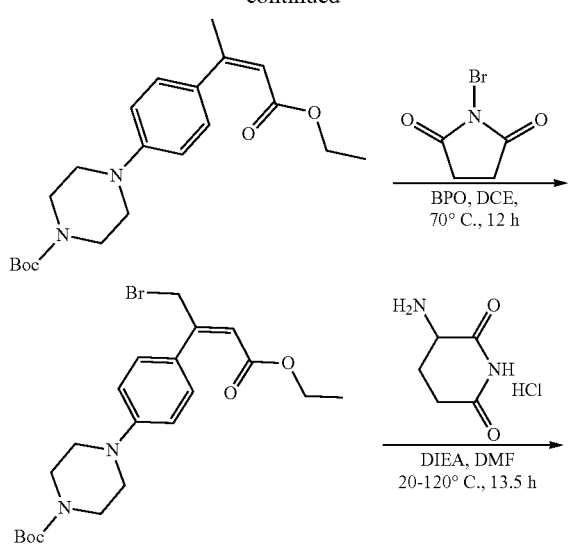
712
-continued
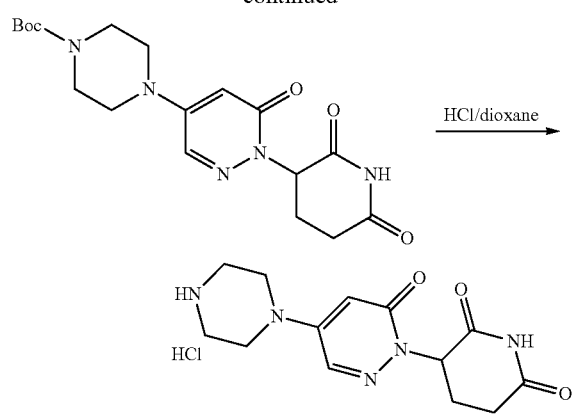
General synthetic scheme 2-32 to prepare intermediate.
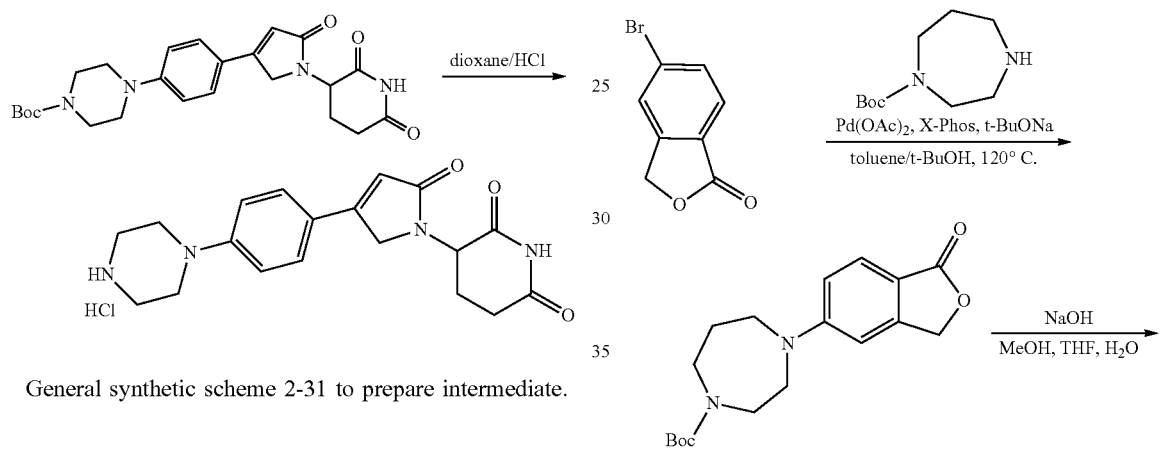
General synthetic scheme 2-31 to prepare intermediate.
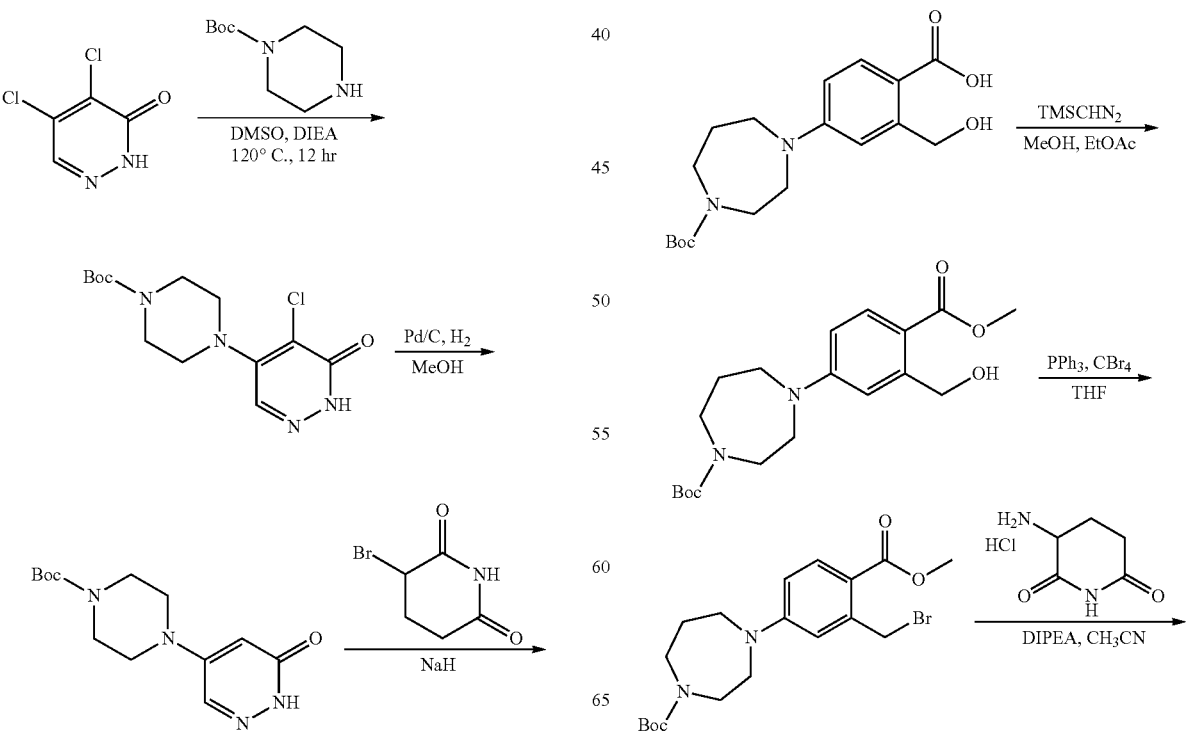

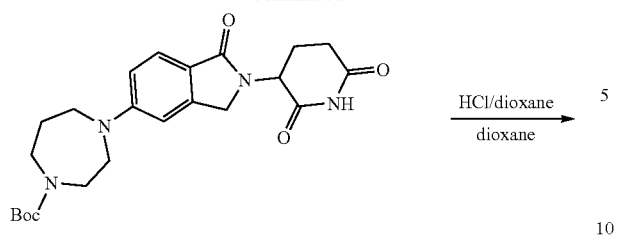
713
-continued
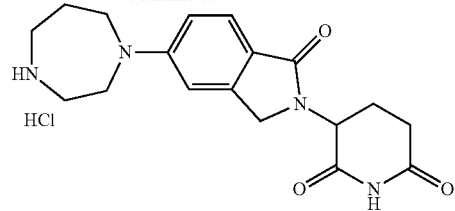
714
-continued
General synthetic scheme 2-33 to prepare intermediate.
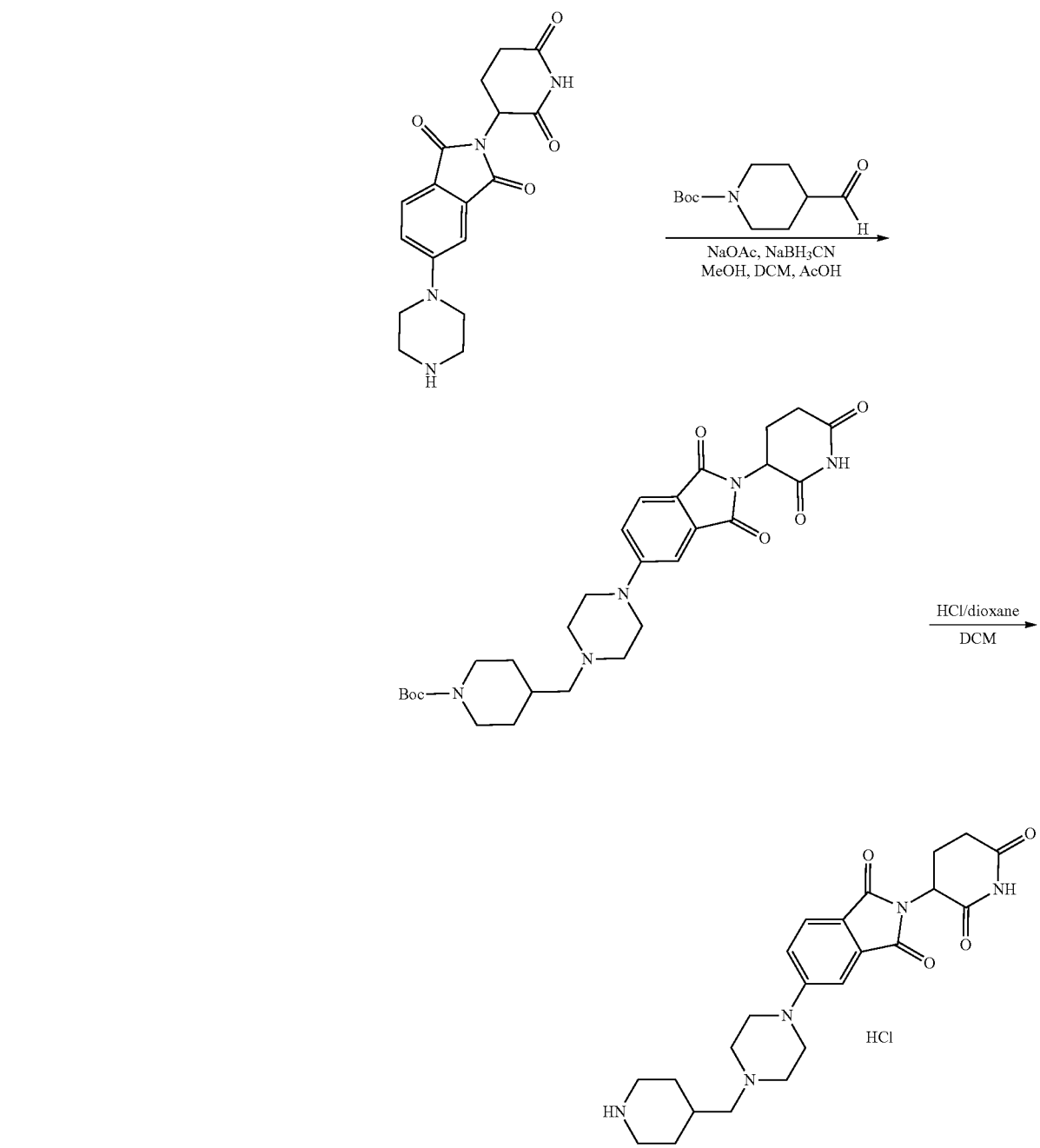

-continued
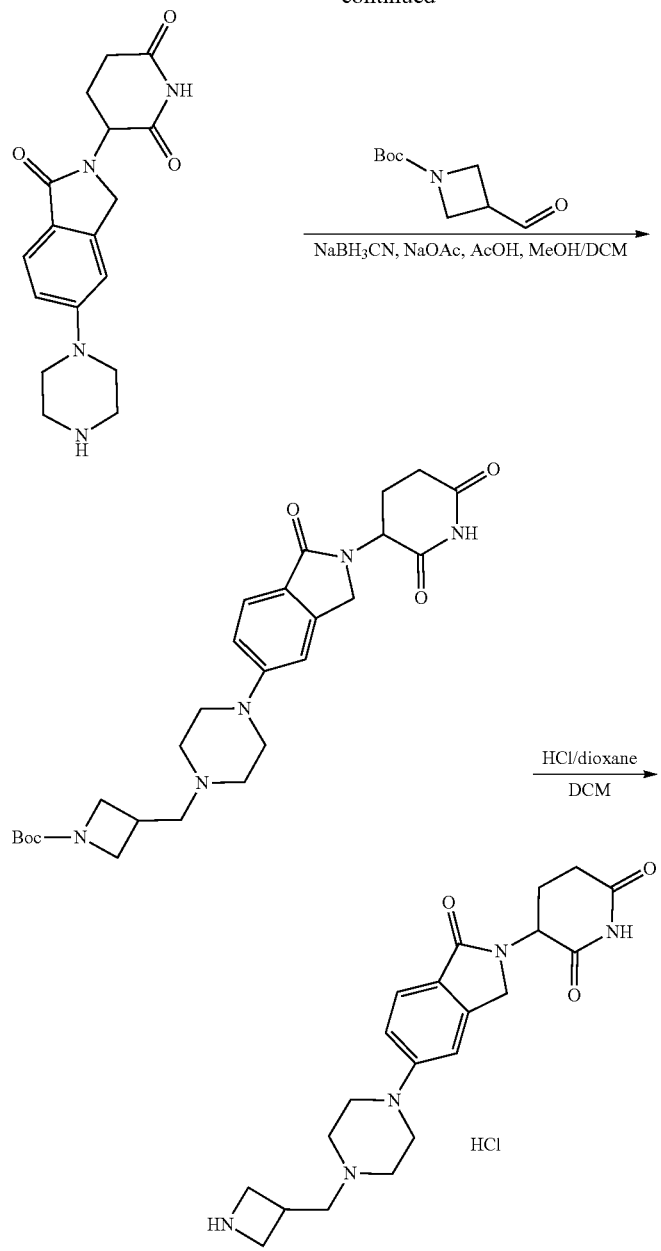
General synthetic scheme 2-34 to prepare intermediate.
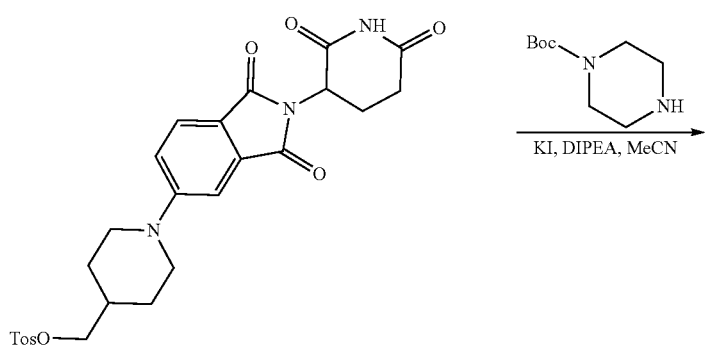

717
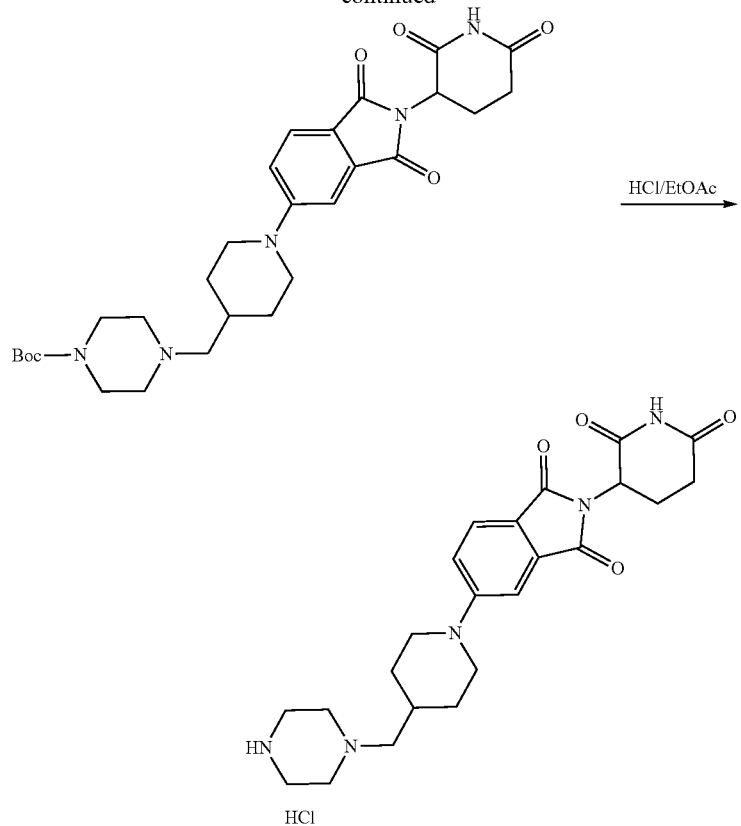
General synthetic scheme 2-35 to prepare intermediate.
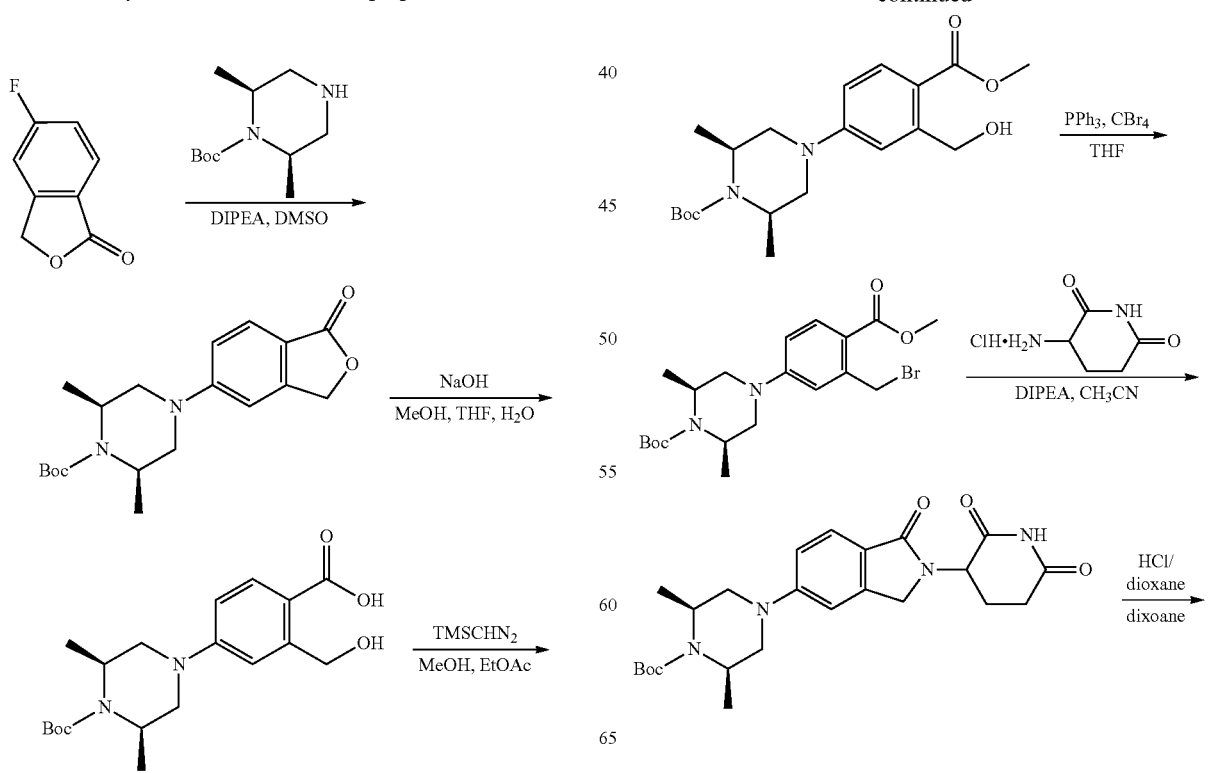

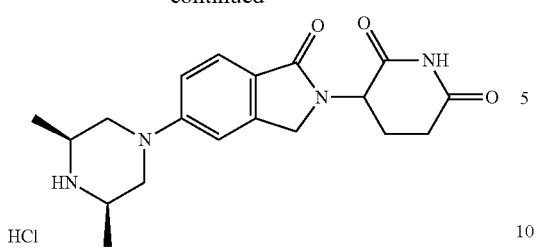
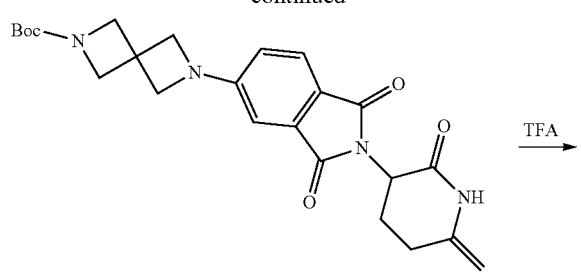
General synthetic scheme 2-36 to prepare intermediate.
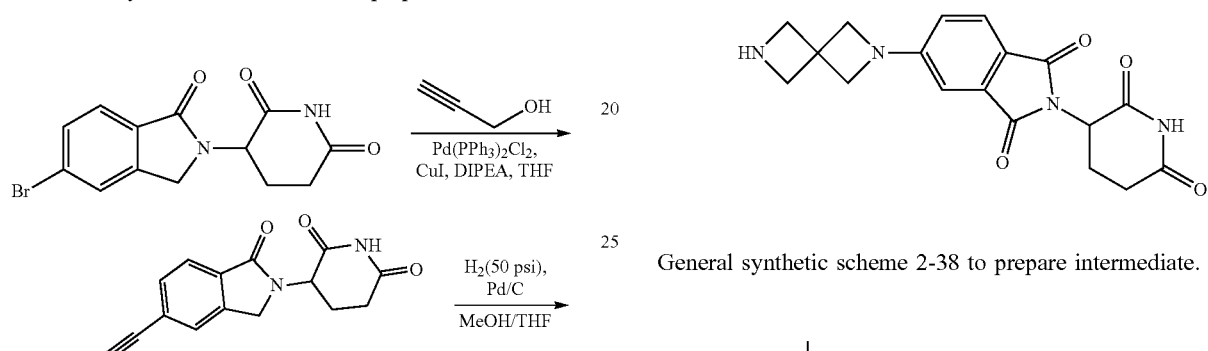
General synthetic scheme 2-38 to prepare intermediate.
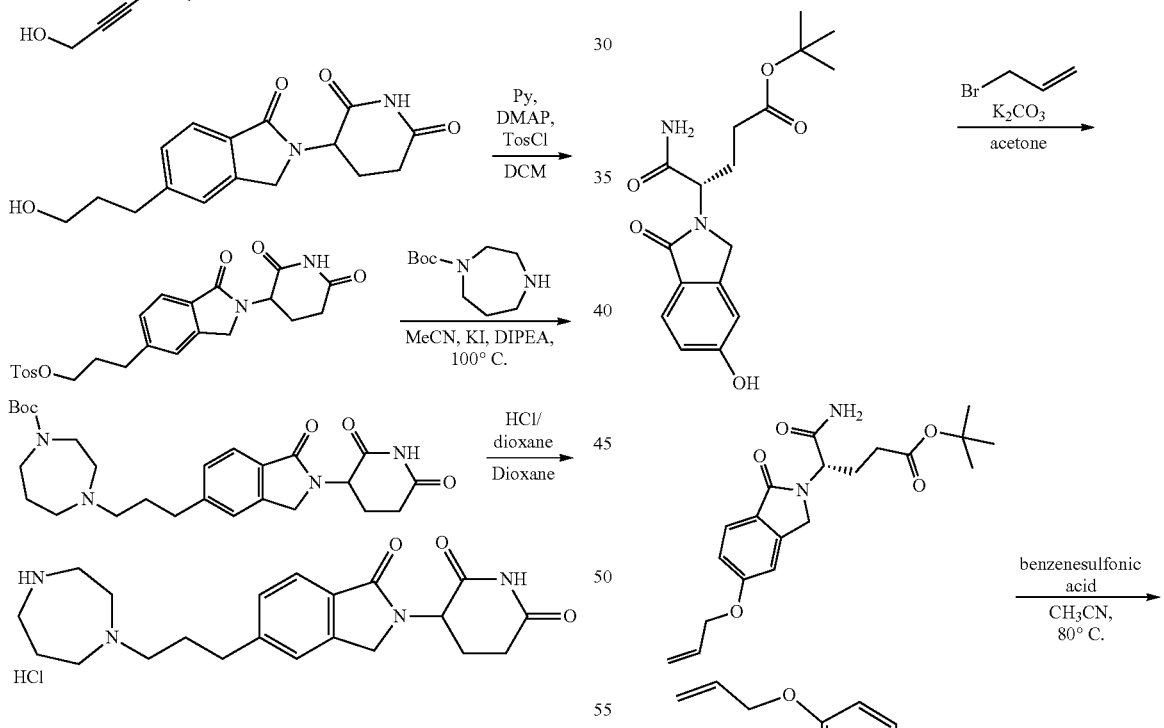
General synthetic scheme 2-37 to prepare intermediate.
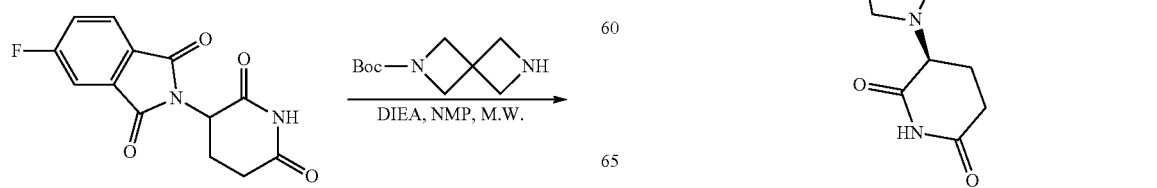

721
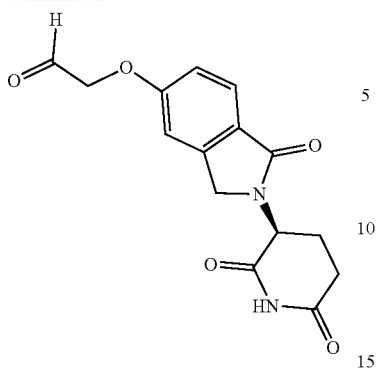
722
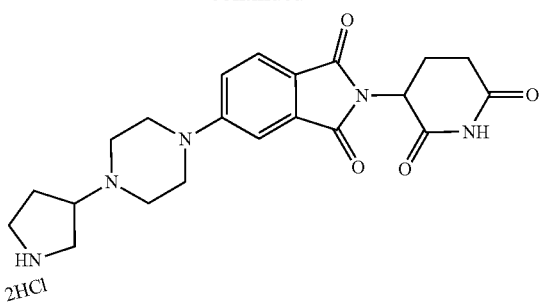
General synthetic scheme 2-39 to prepare intermediate.
General synthetic scheme 2-40 to prepare intermediate.
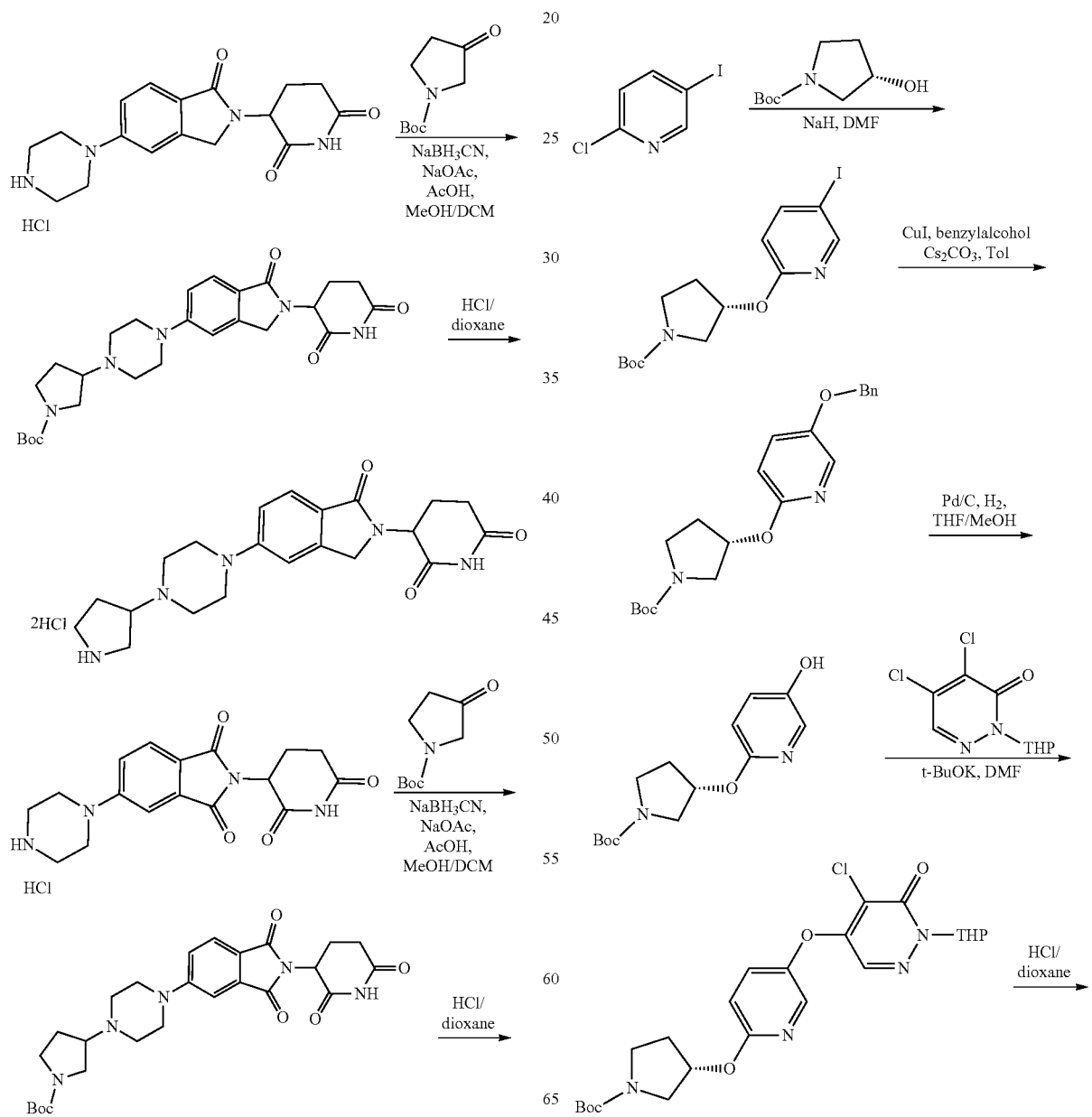

723
-continued
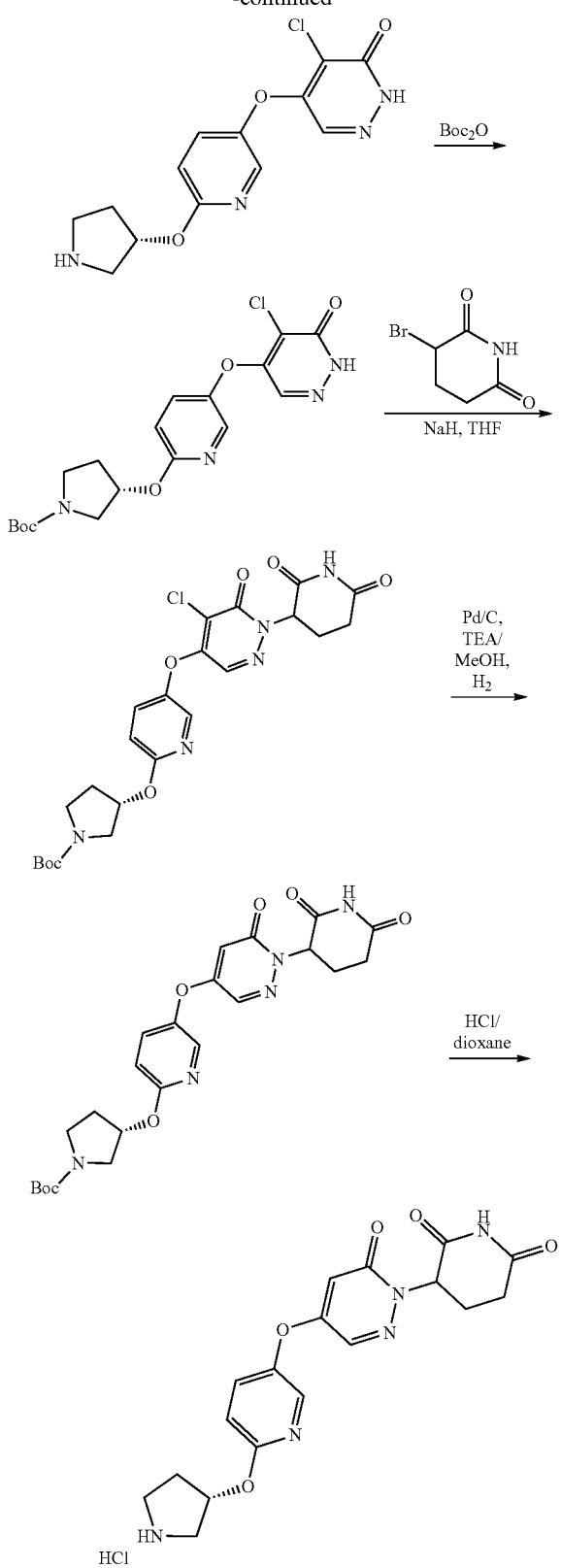
724
Scheme 2-41a
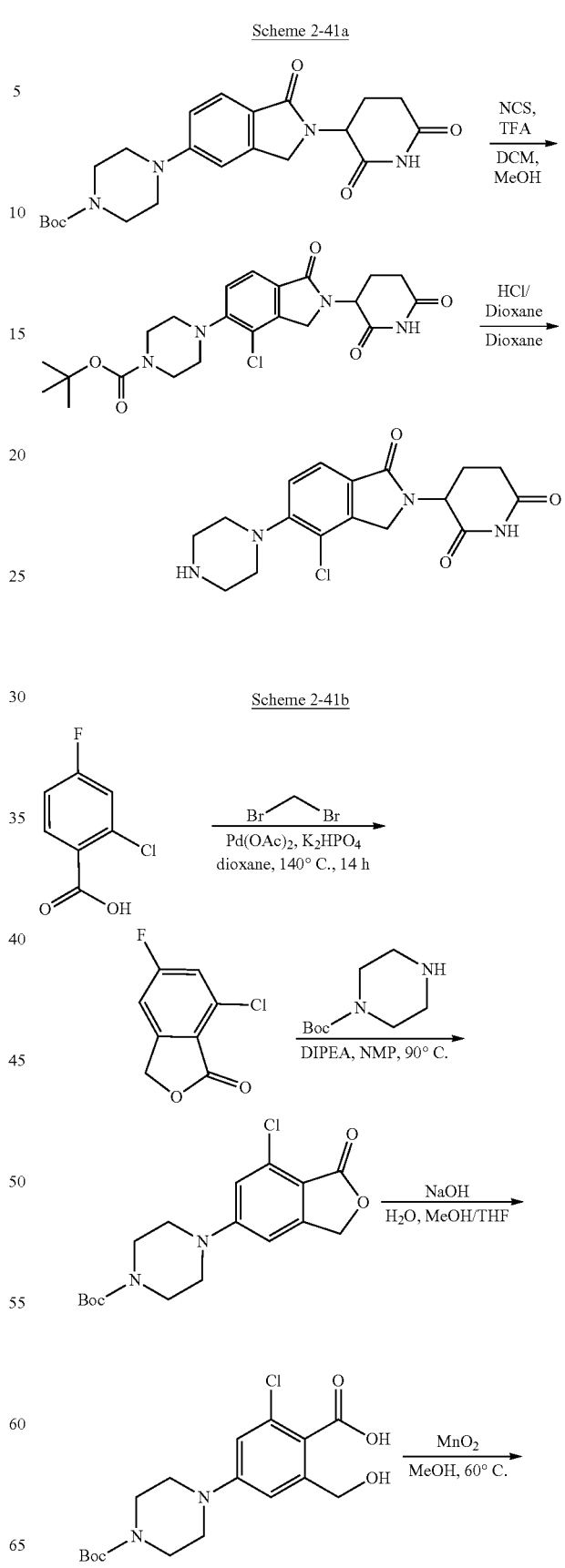
General synthetic scheme 2-41a and 2-41b to prepare intermediates.

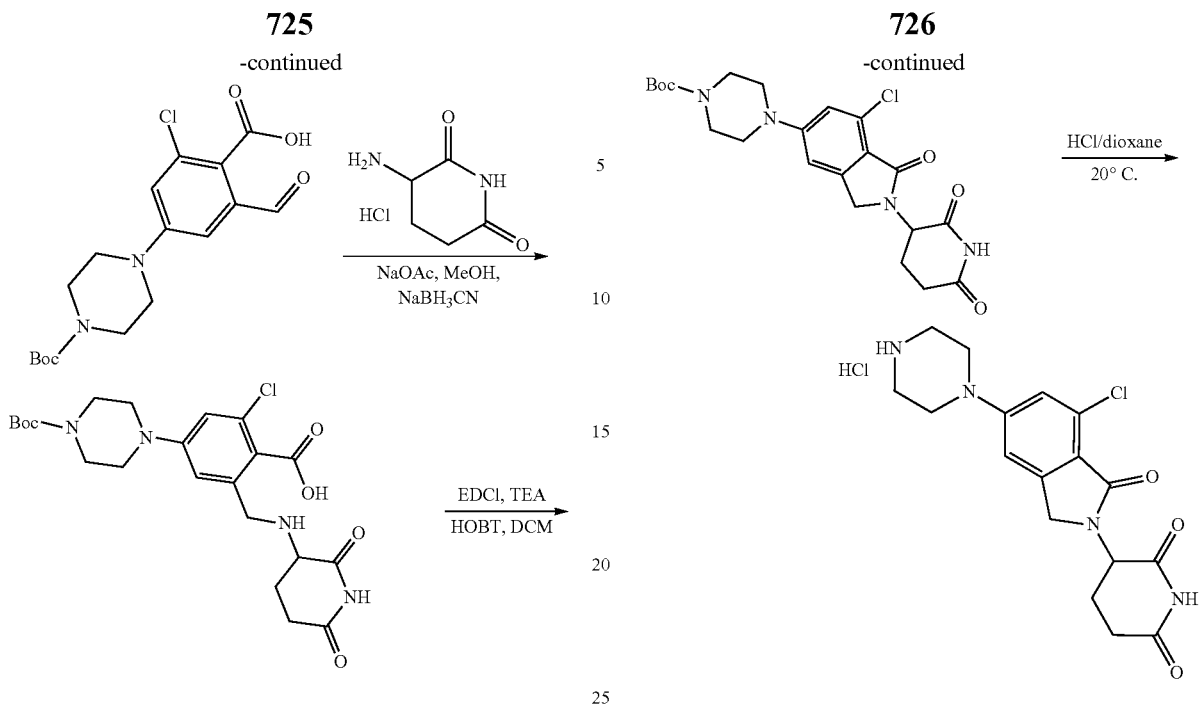
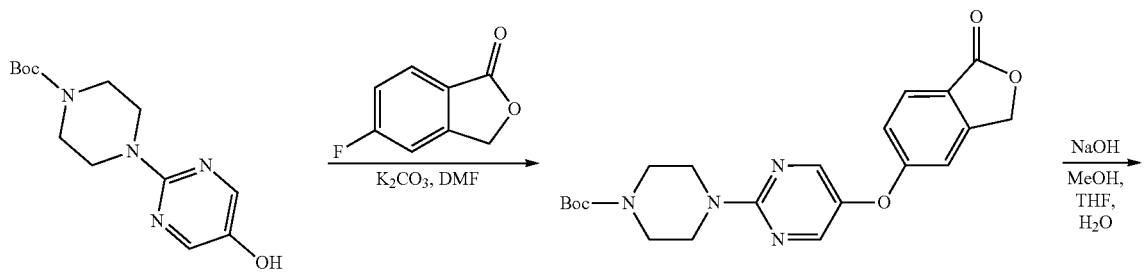
General synthetic scheme 2-42 to prepare intermediate.
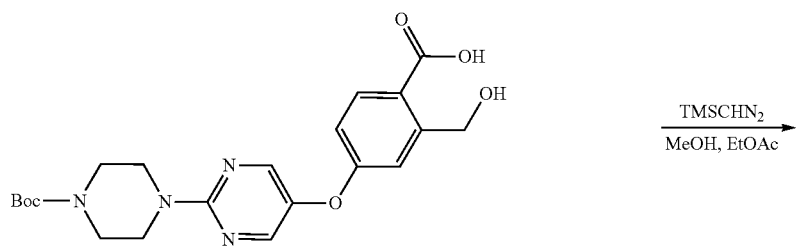
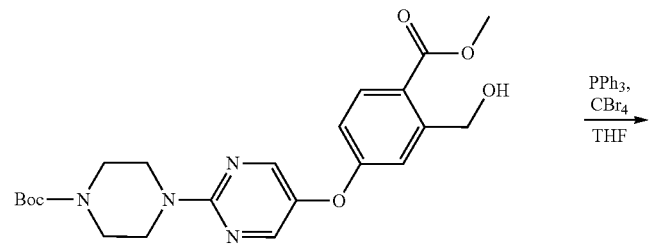

727 728
-continued
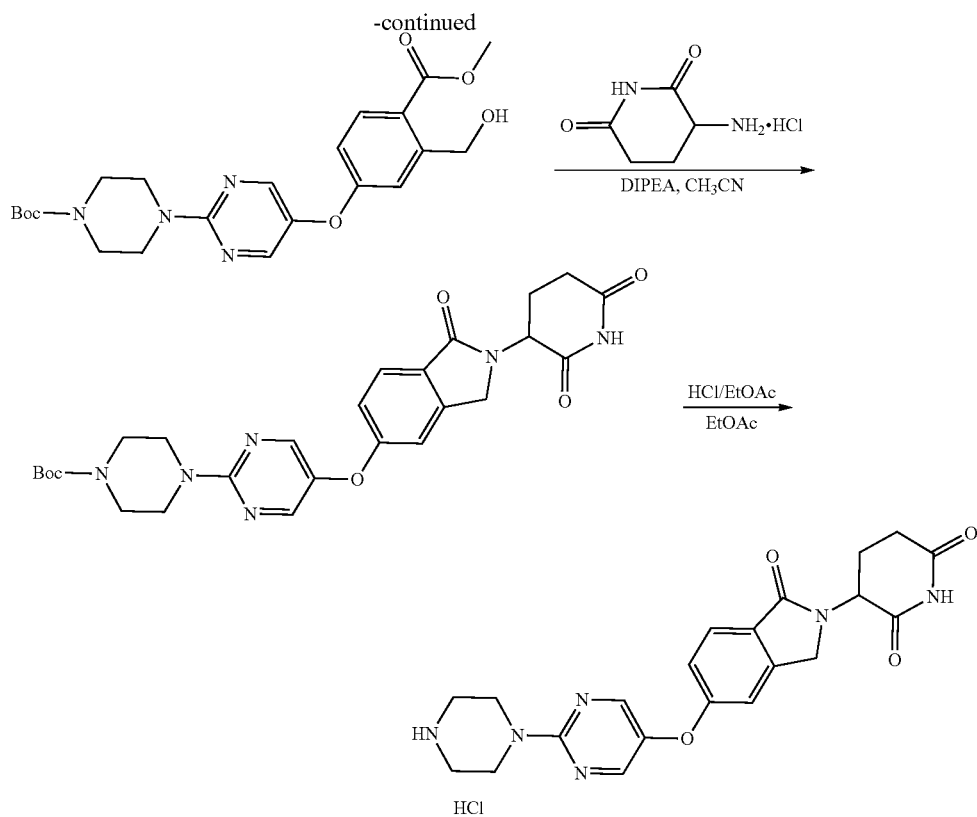
General synthetic scheme 2-43 to prepare intermediate.
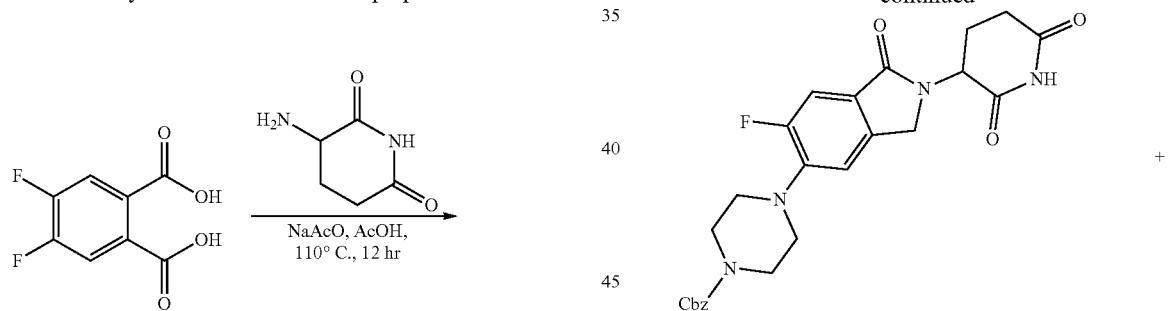
General synthetic scheme 2-22 to prepare intermediate.
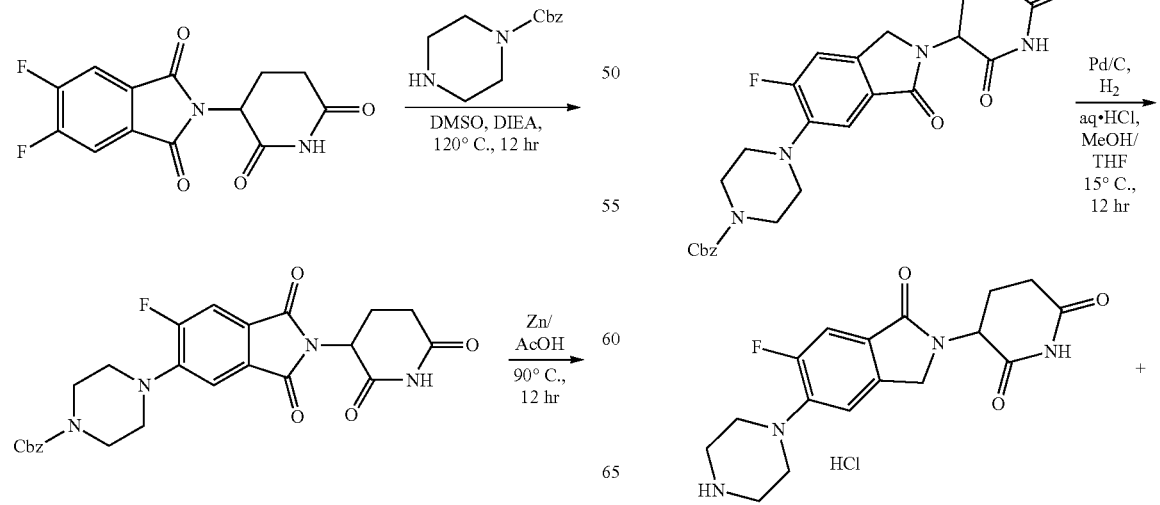

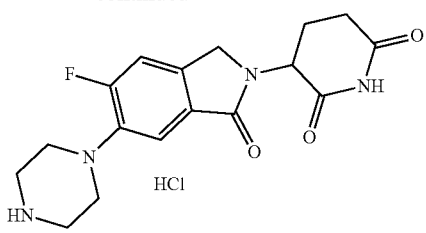
General synthetic scheme 2-44 to prepare intermediate.
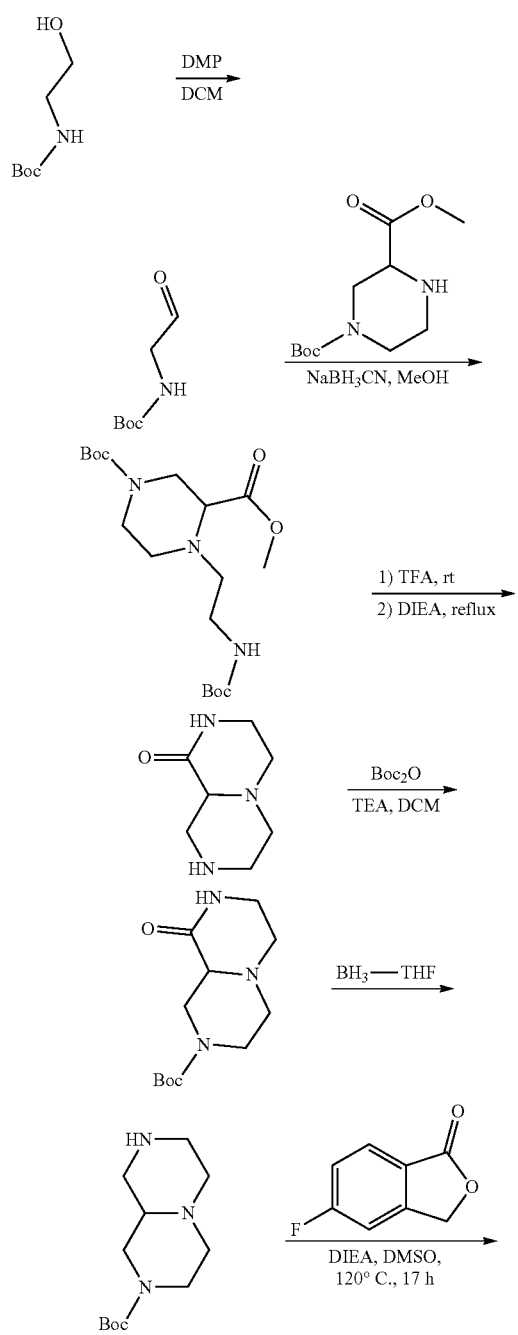
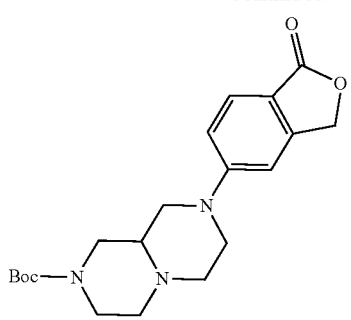

General synthetic scheme 2-25a through 2-45c to prepare intermediates. Scheme 2-45a
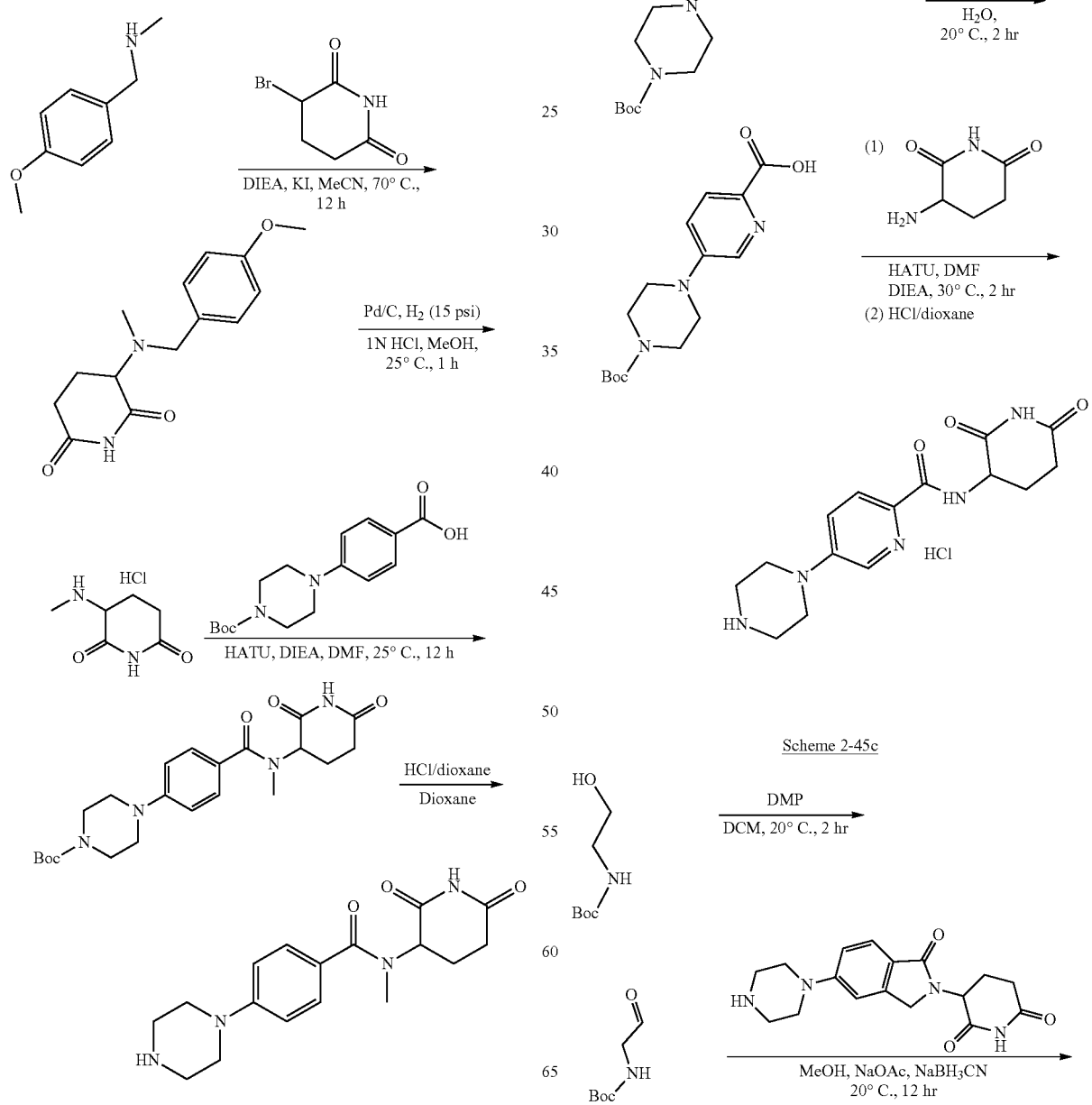

733
-continued
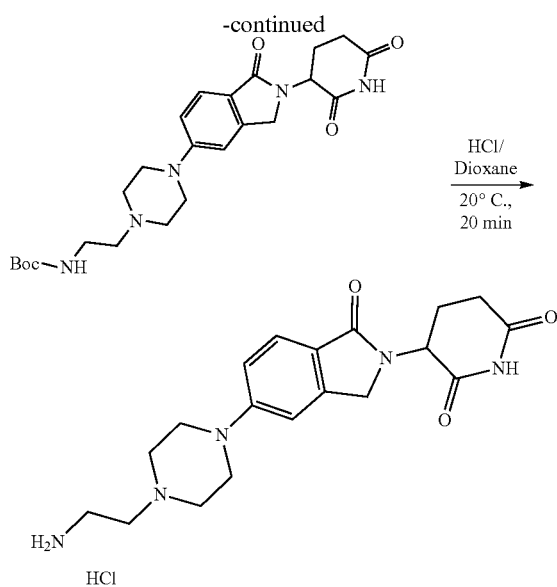
General synthetic scheme 2-46 to prepare intermediate.
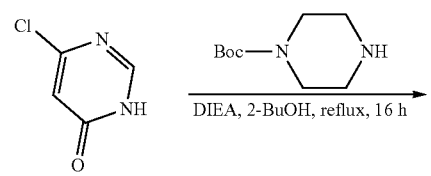
734
-continued
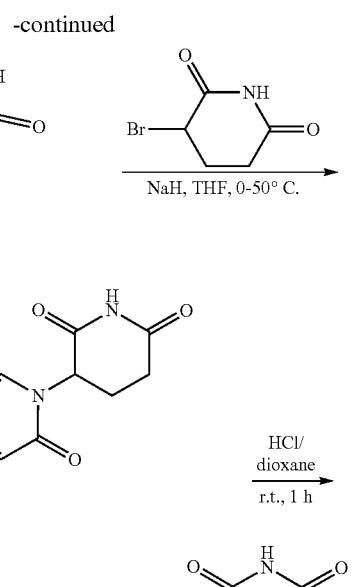
General synthetic scheme 2-47 to prepare intermediate.
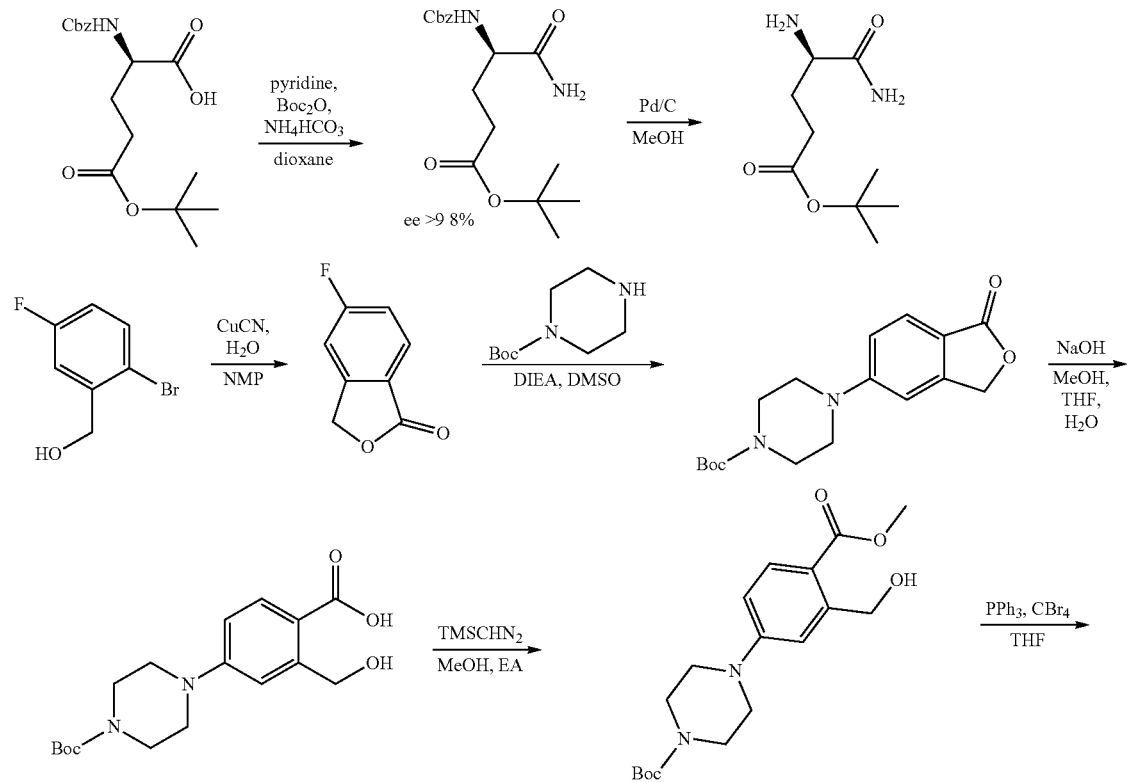

735
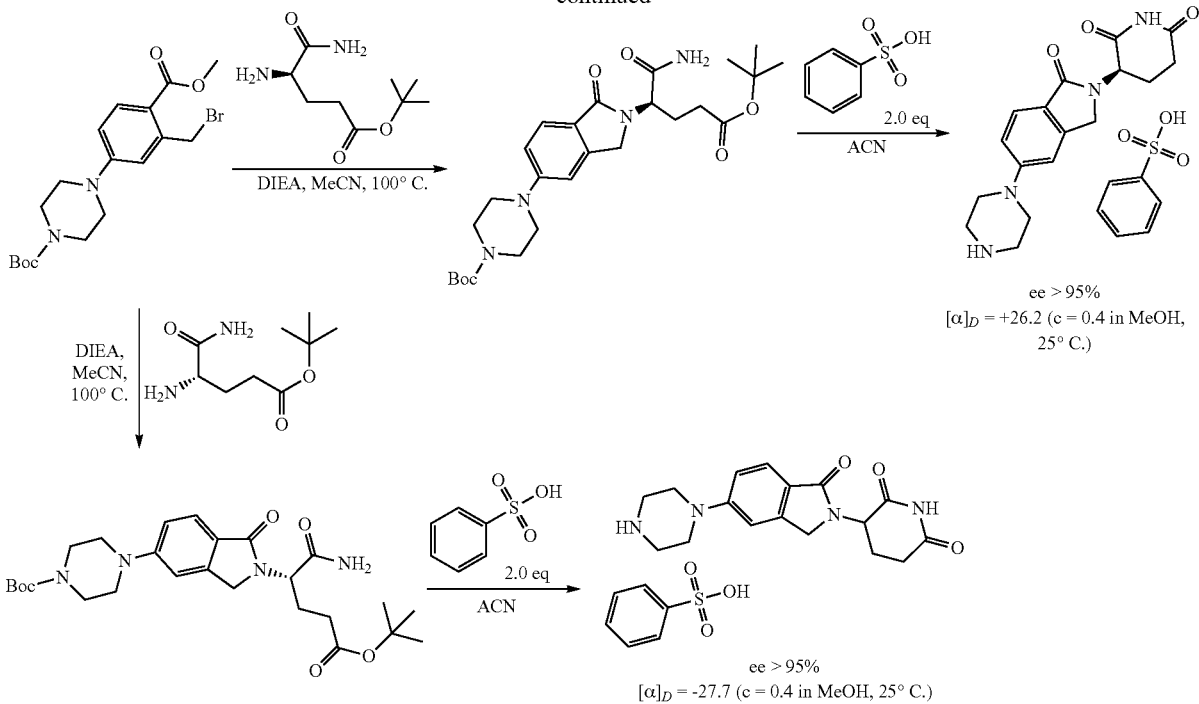
736
-continued
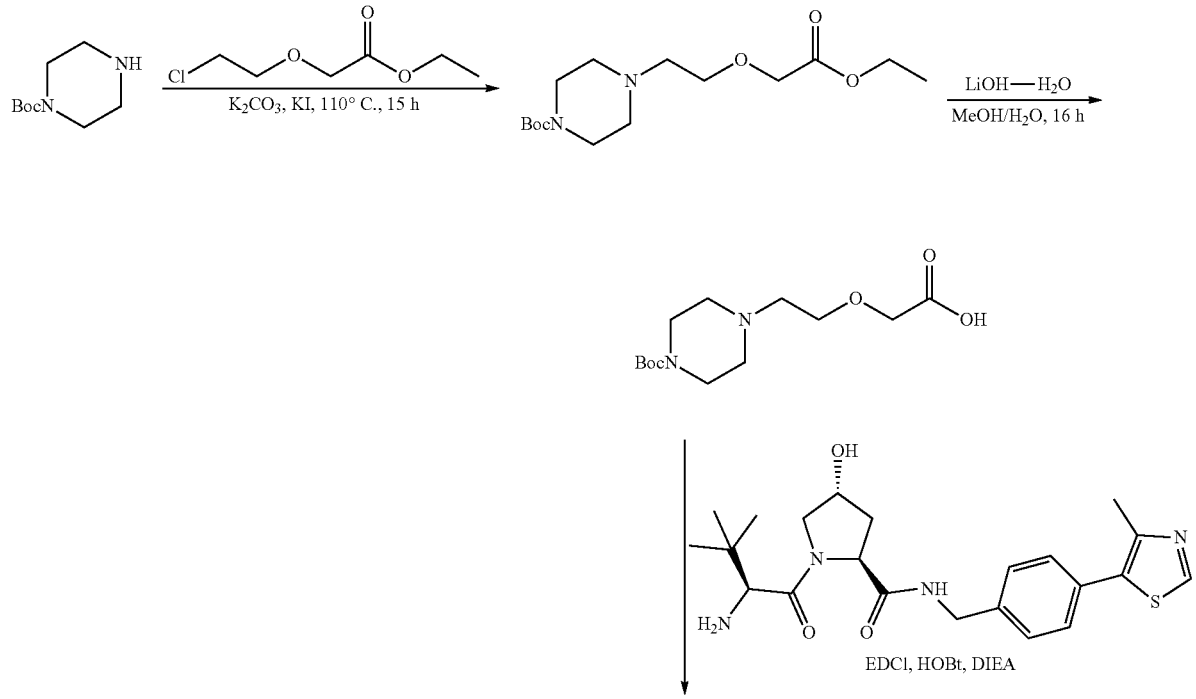
General synthetic schemes 3-1 through 3-88 described the routes used to prepare representative chimeric compounds of the present disclosure.
General synthetic scheme 3-1.

737                                                                                         738
-continued
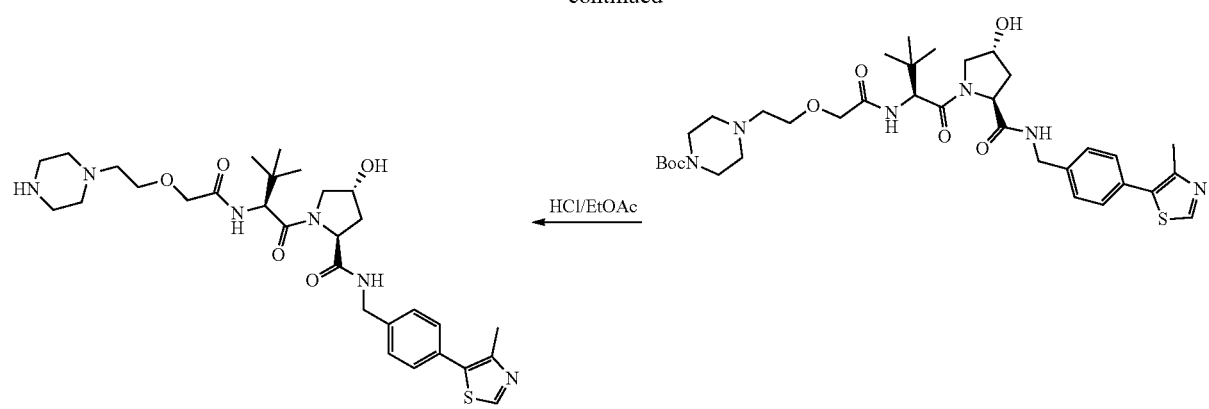
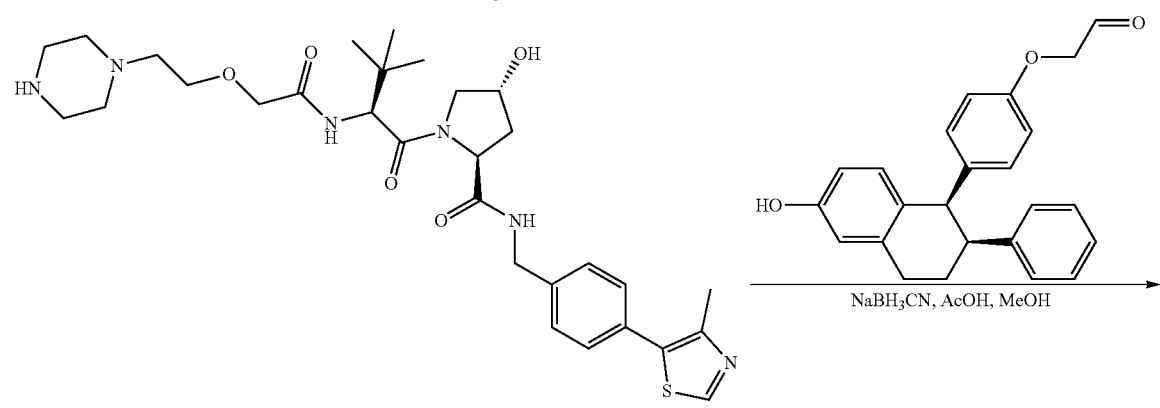
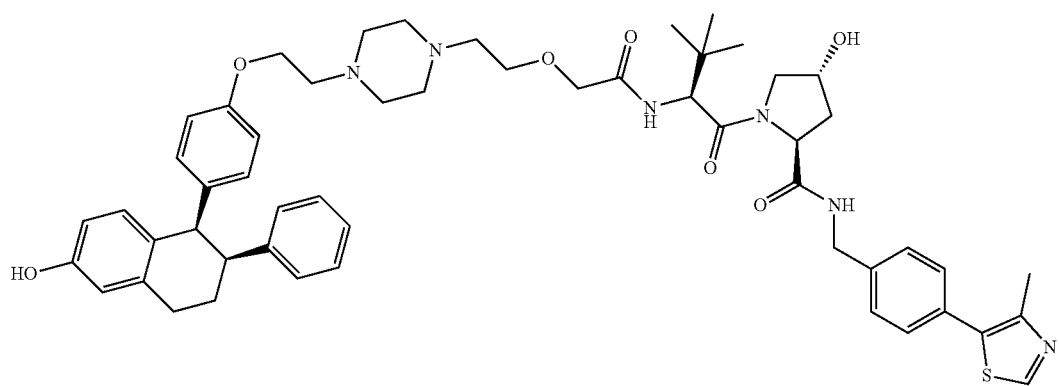
Compound 1
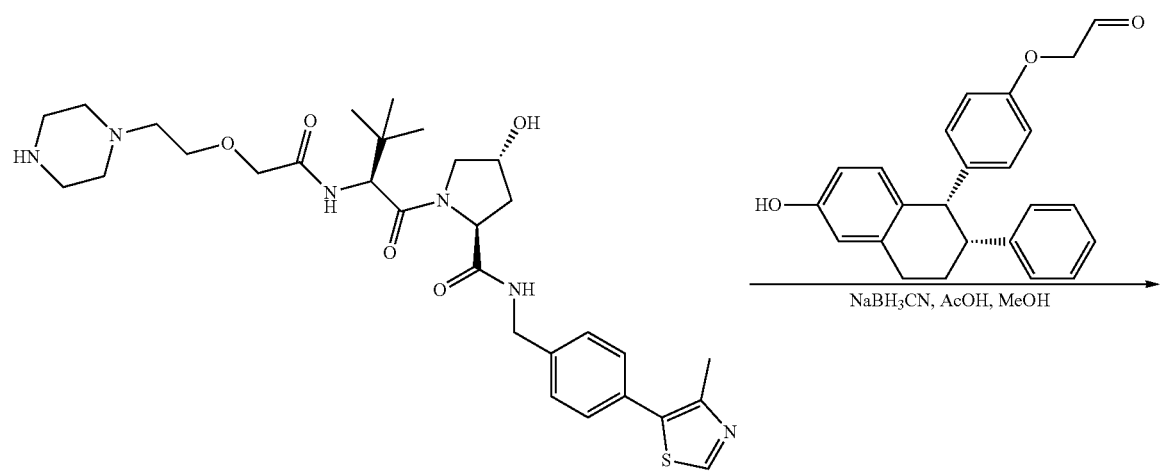

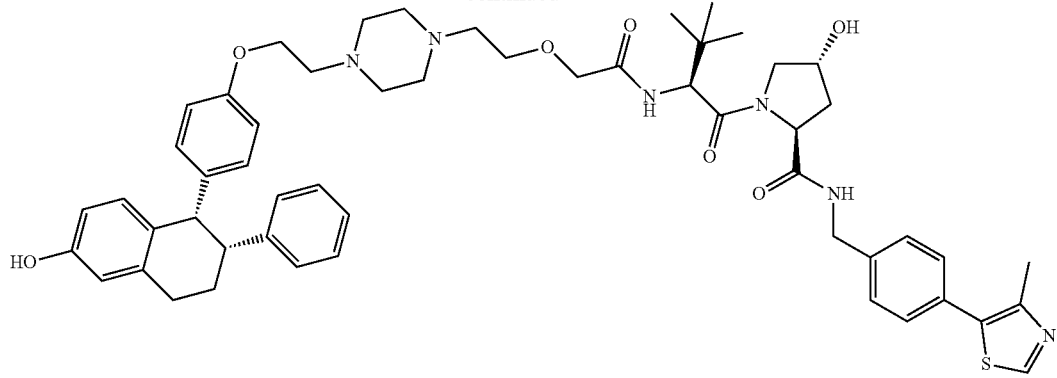
Compound 2
Alternatively, compound 1 and compound 2 can also be prepared using synthetic scheme 3-2.
General synthetic scheme 3-2.
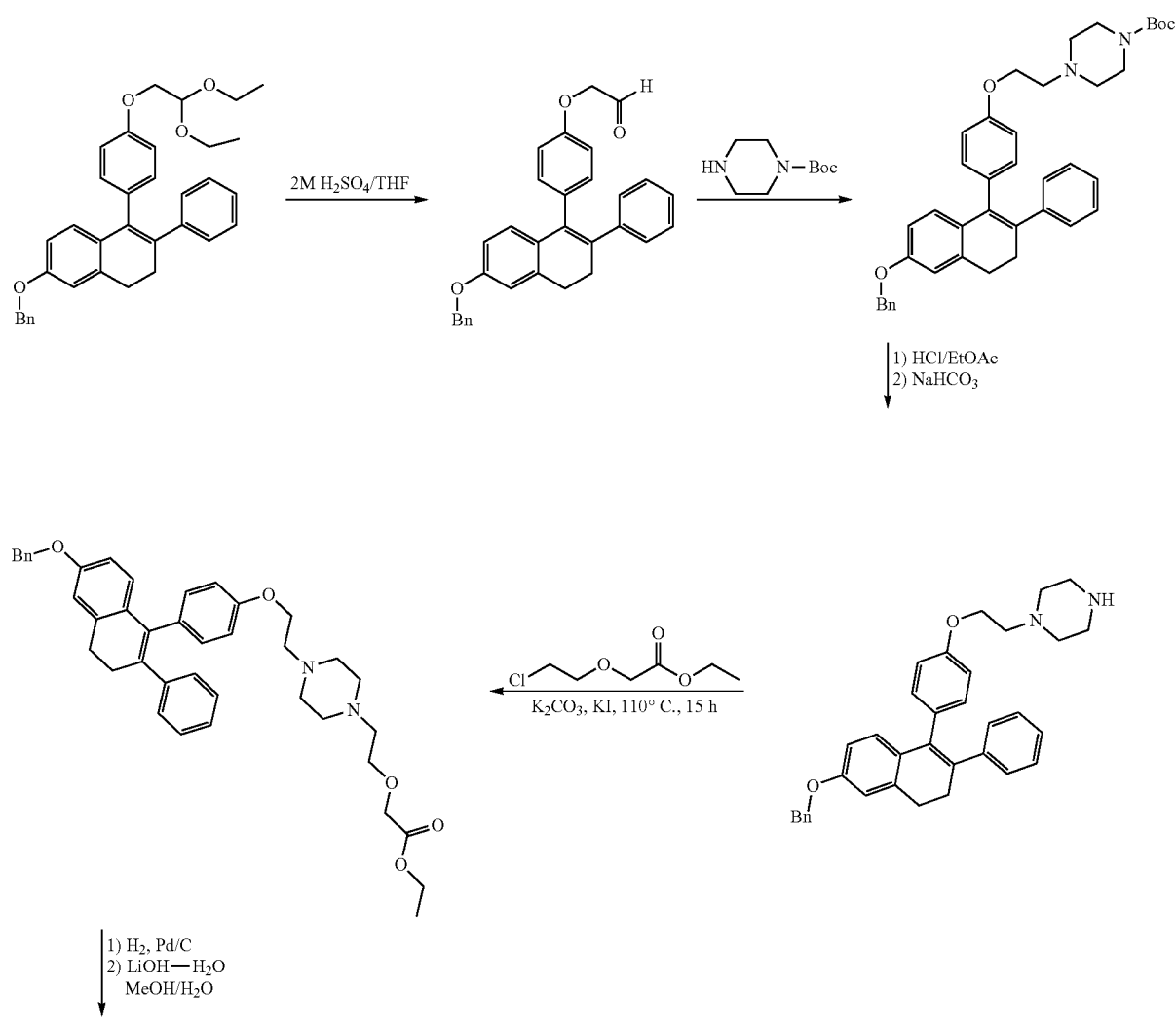

-continued
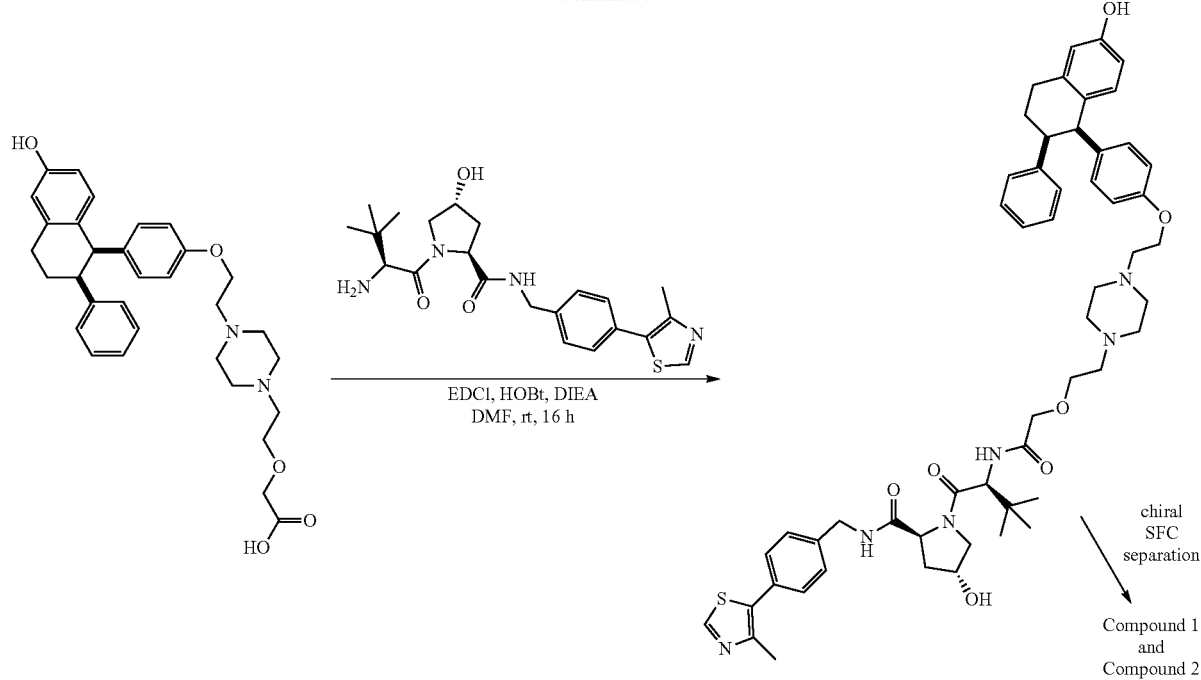
General synthetic scheme 3-3.
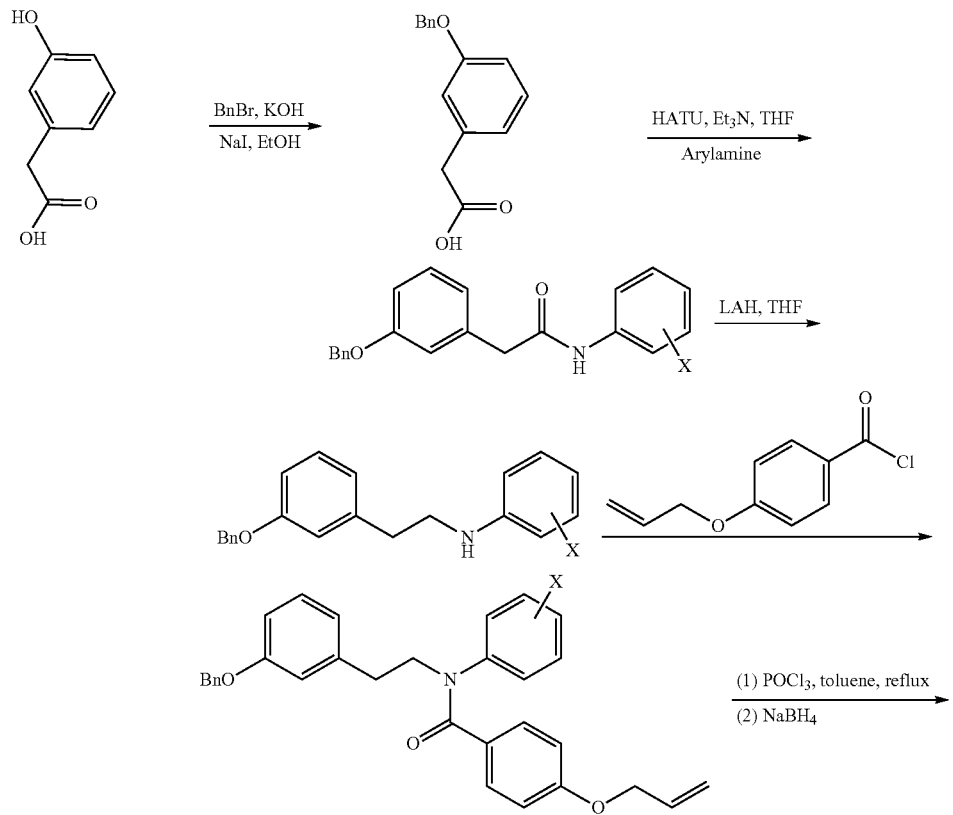

743
744
-continued
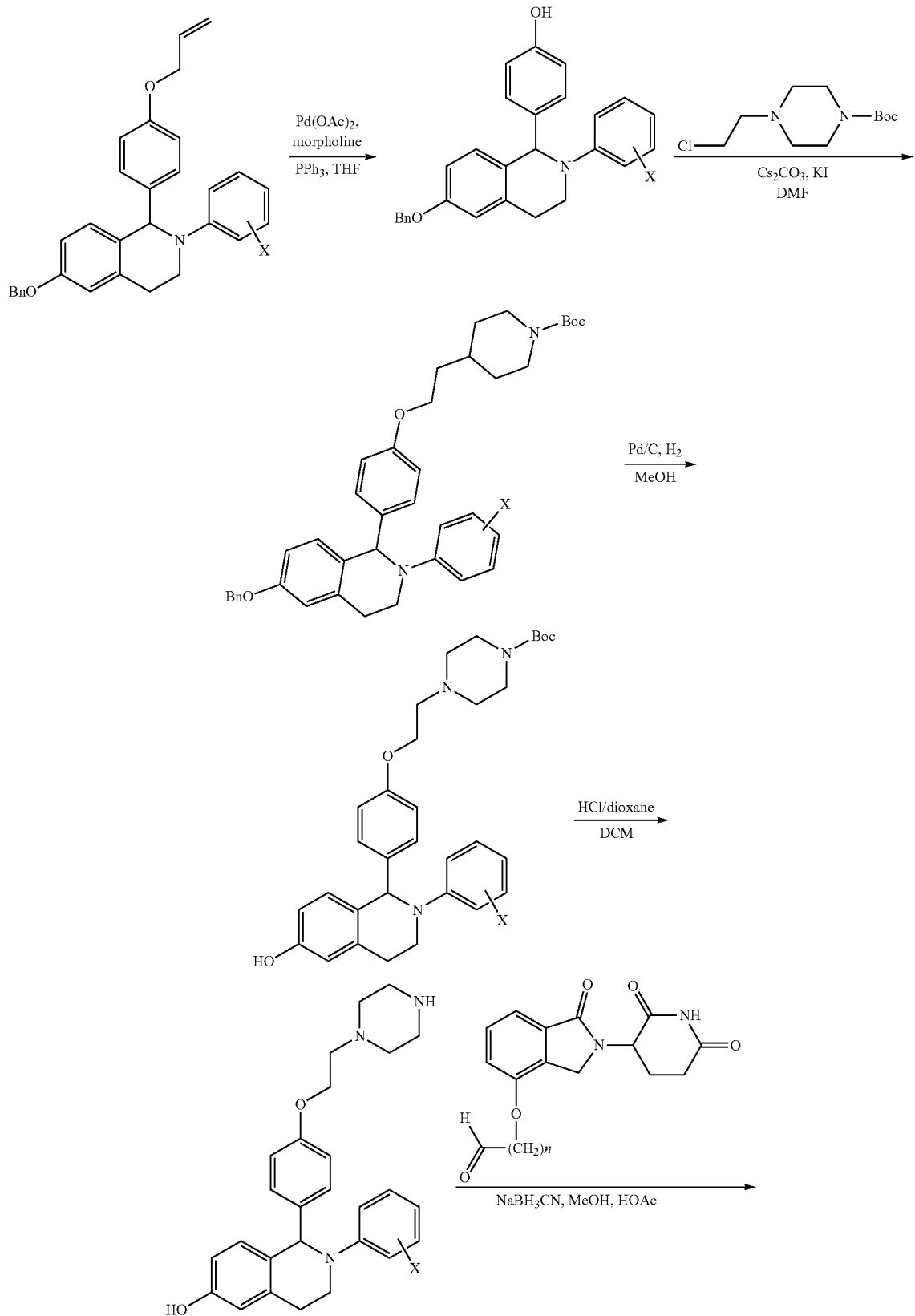

-continued
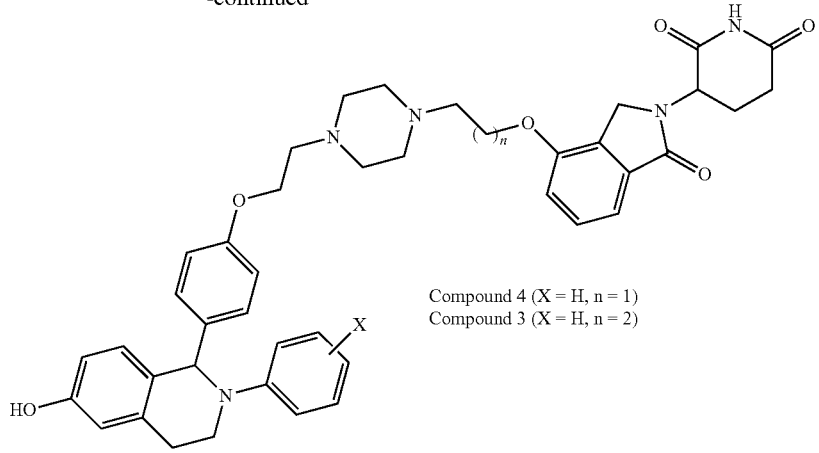
Compound 4 (X = H, n = 1)
Compound 3 (X = H, n = 2)
20
Where X in Scheme 3-3 can be H, F, $C_1$-$C_6$ alkyl (linear, branched, optionally substituted), $OCH_3$, $CF_3$; and the aryl ring can be mono- or di-substituted with X.
General synthetic scheme 3-4.
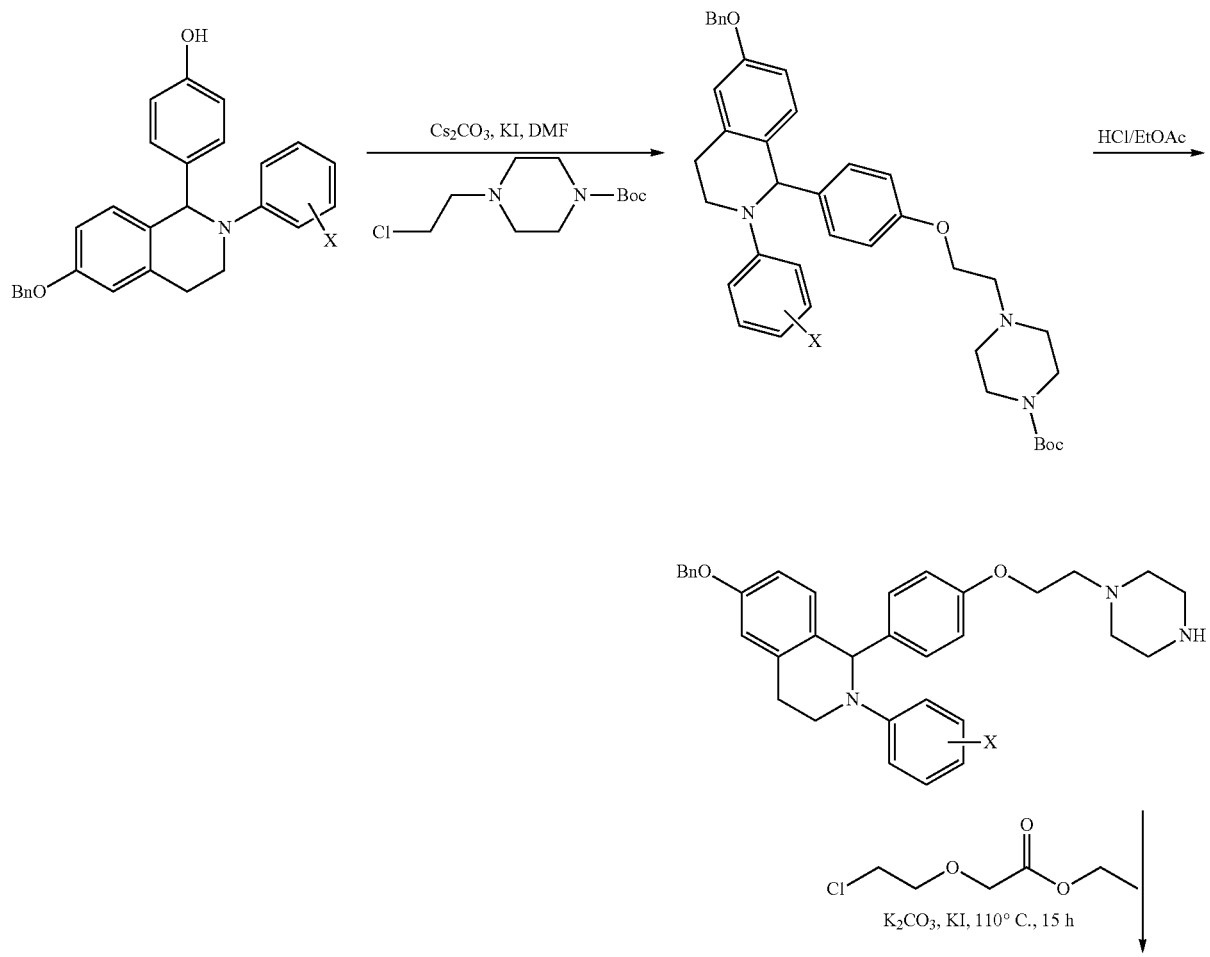

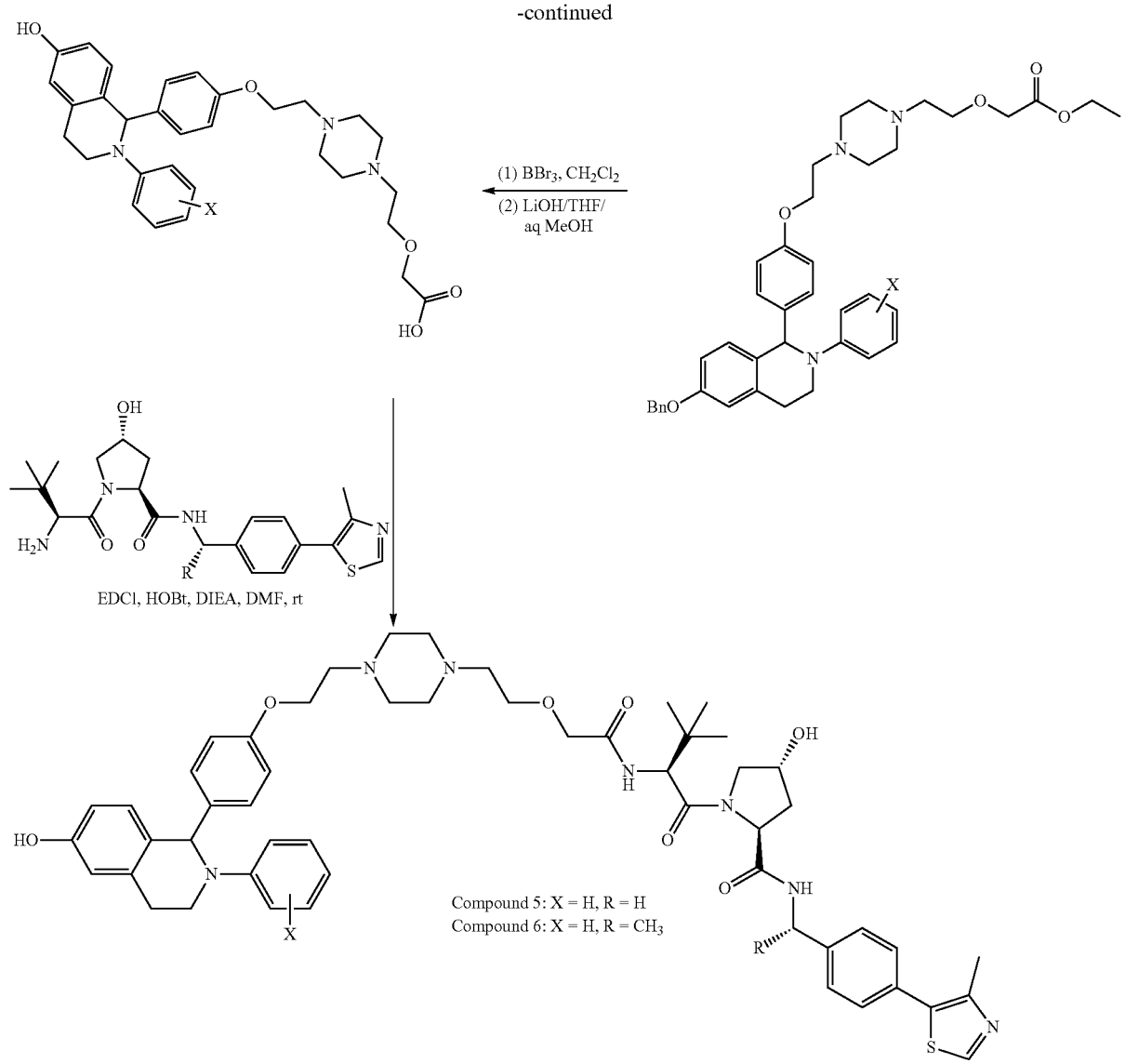
General synthetic scheme 3-5.
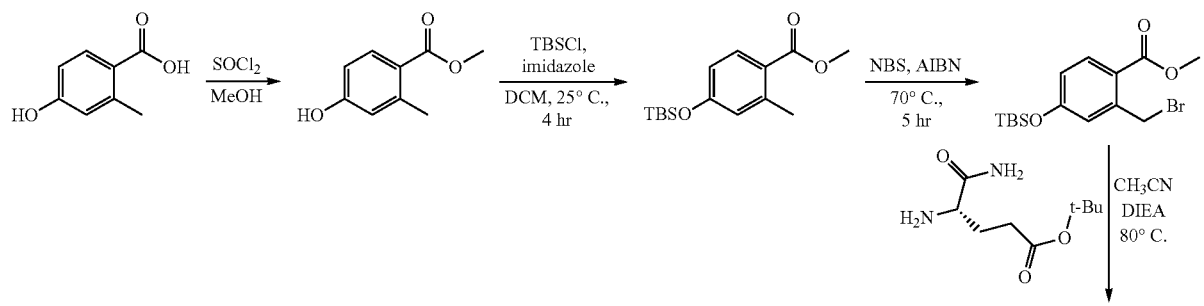

749 750
-continued
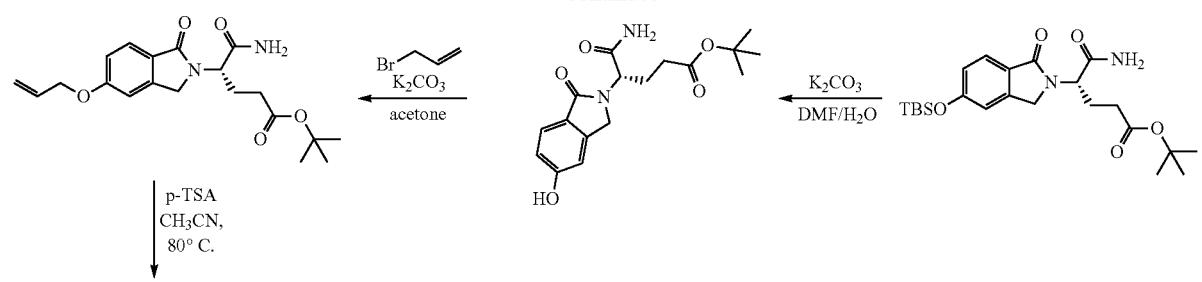
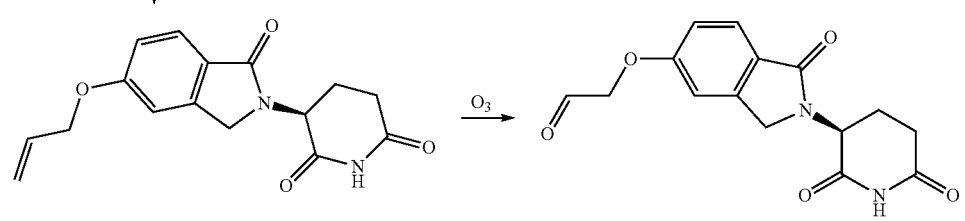
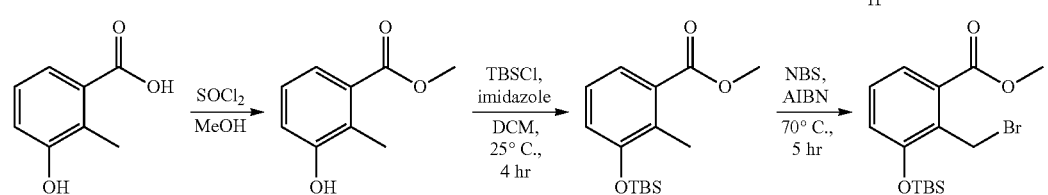
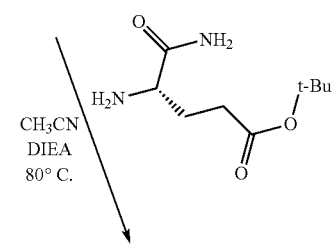
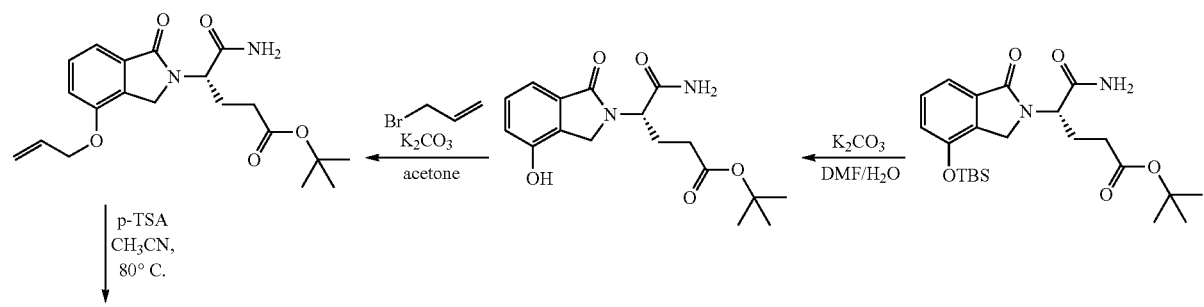
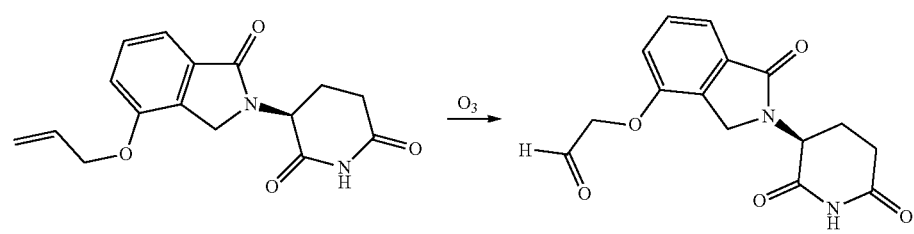

751 752
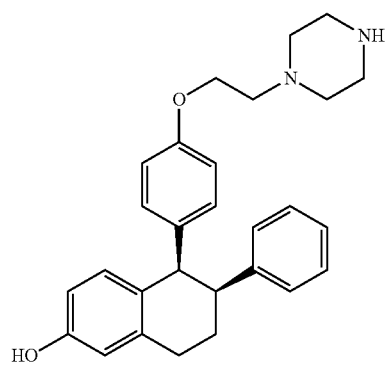
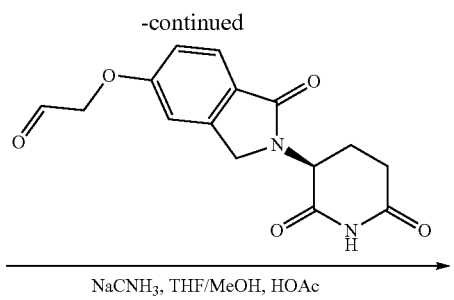
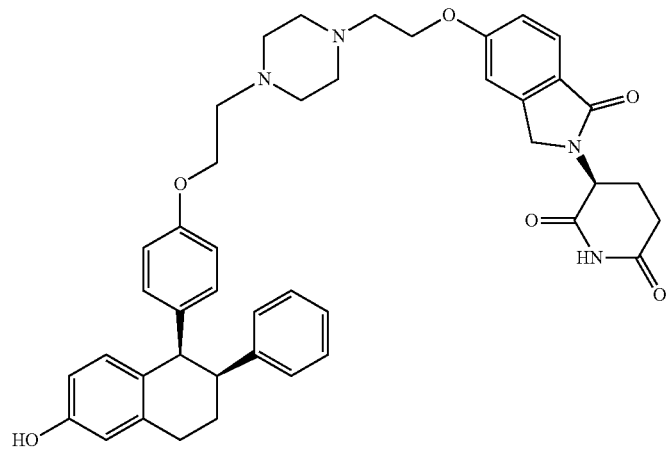
Compound 8
General synthetic scheme 3-6.
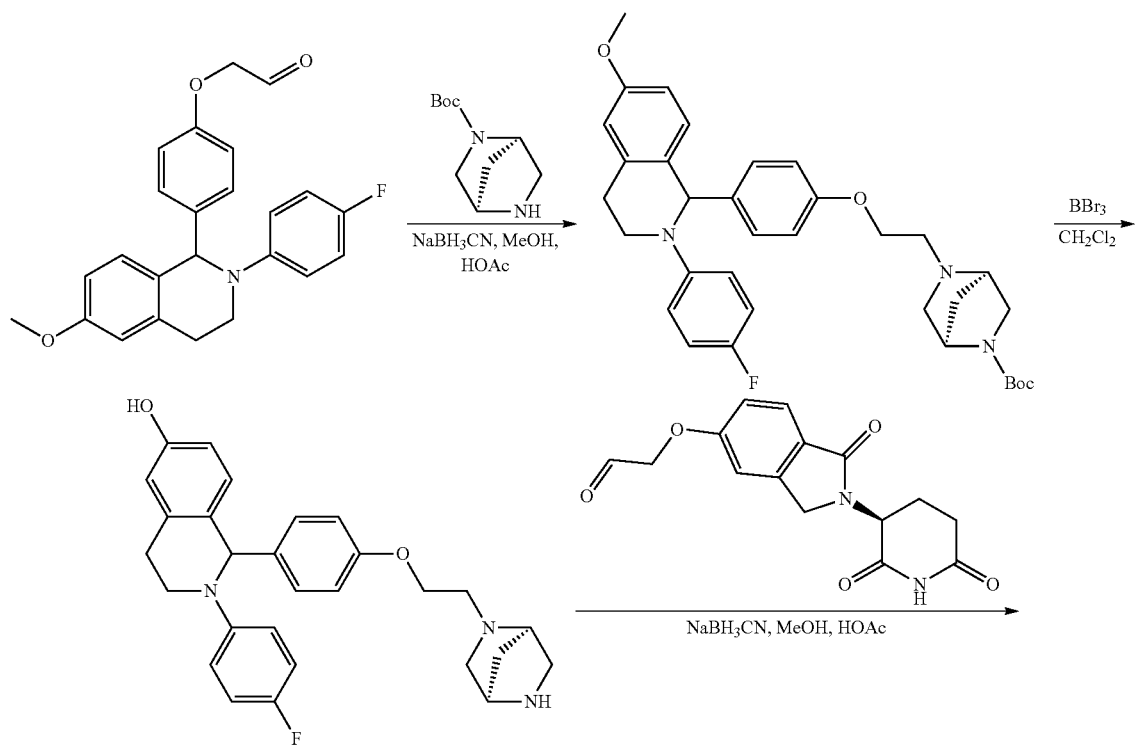

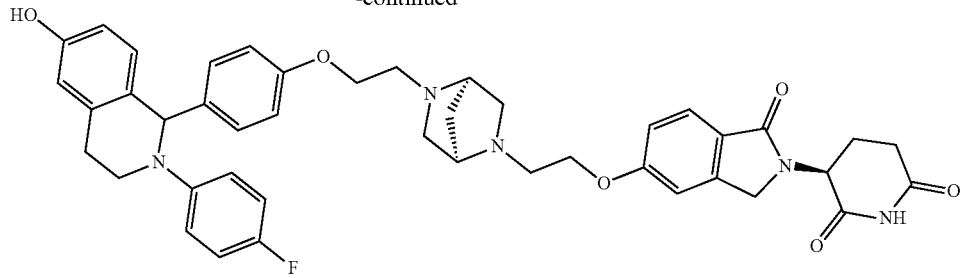
Compound 9
General synthetic scheme 3-7.
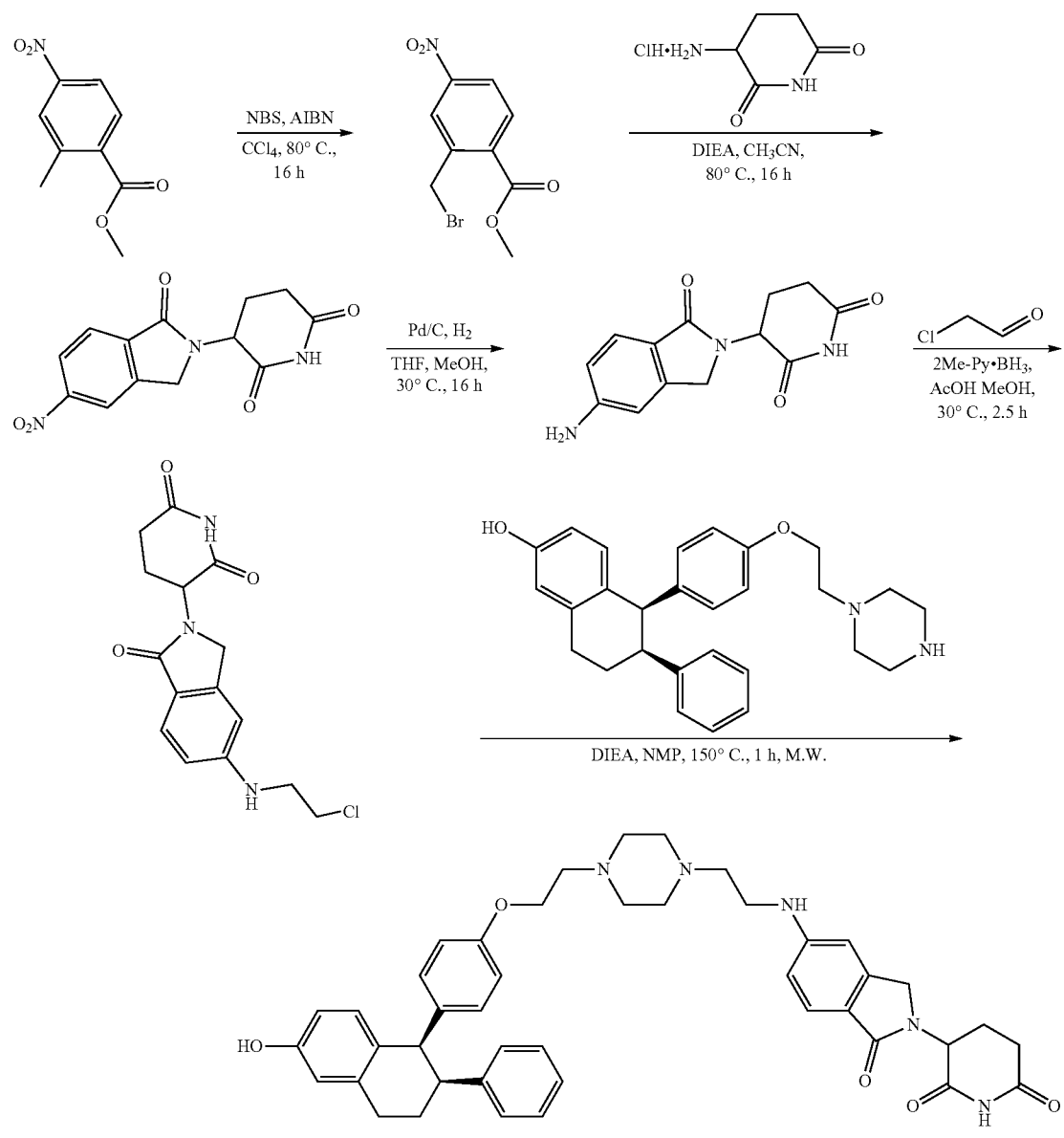
Compound 11

General synthetic scheme 3-8.
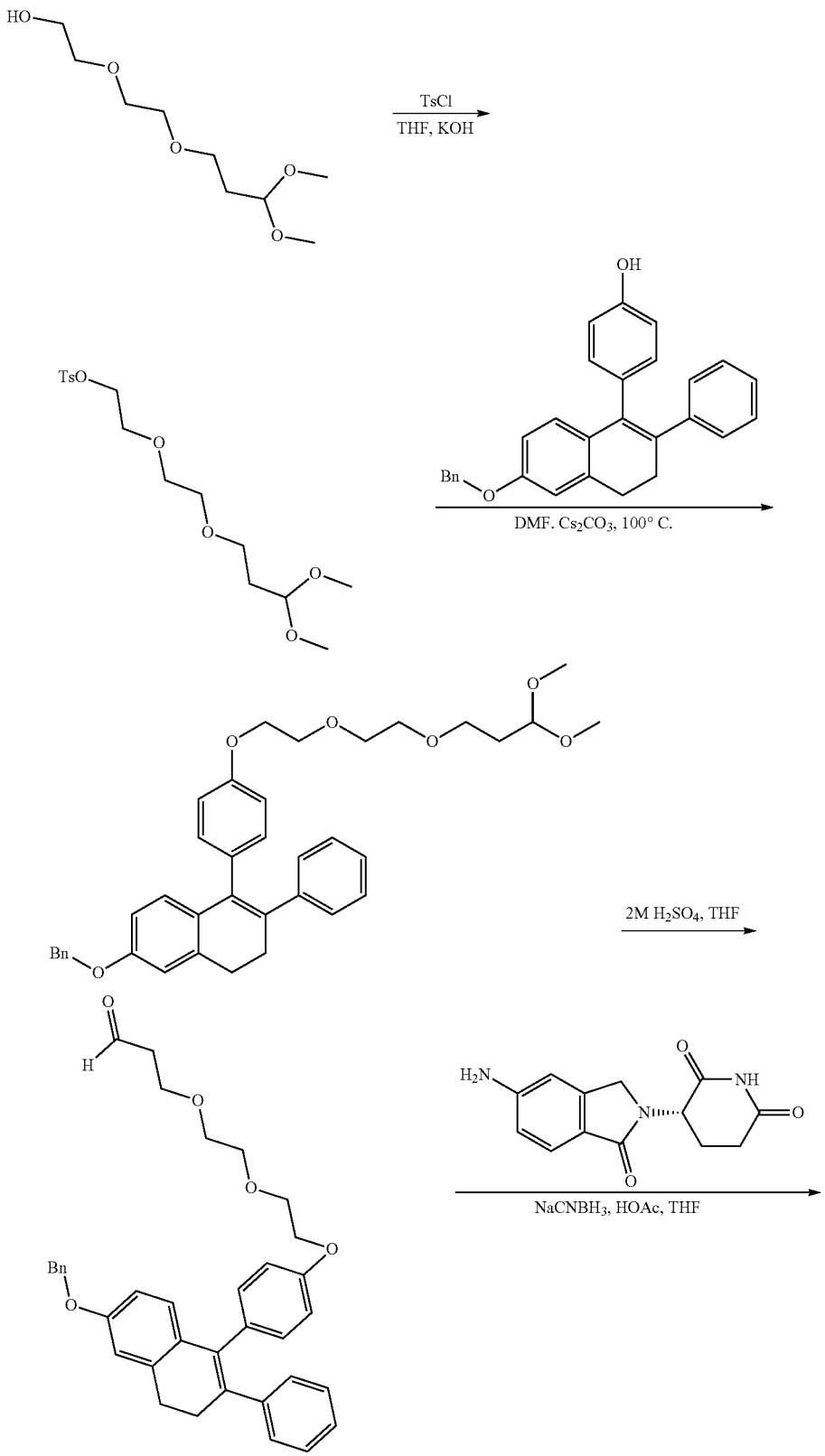

757 758
-continued
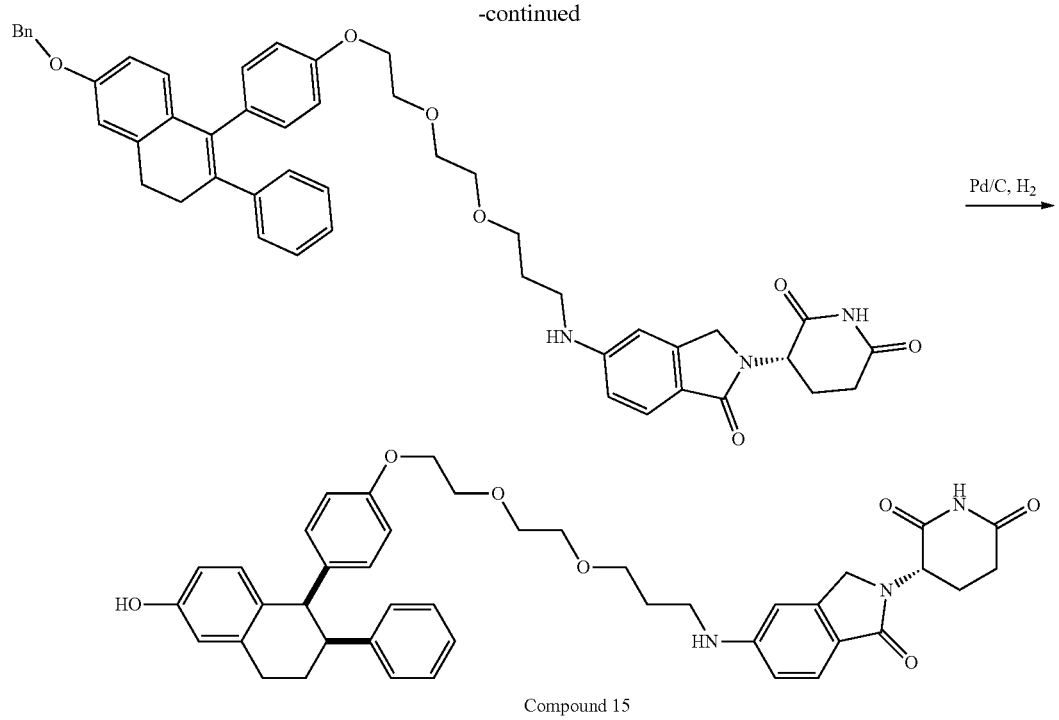
General synthetic scheme 3-9.
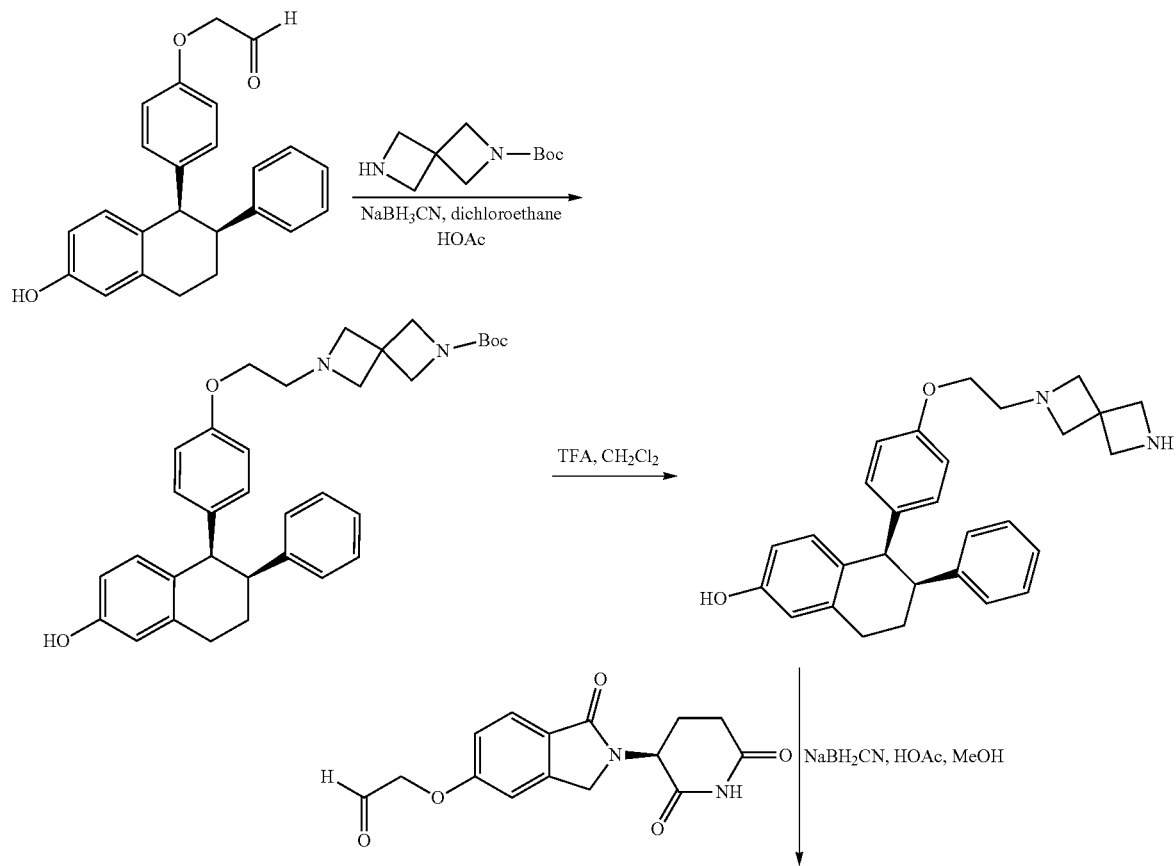

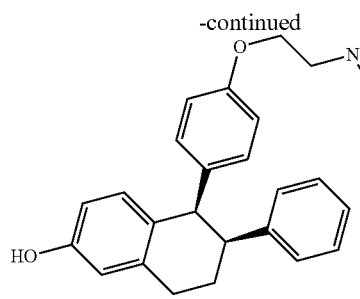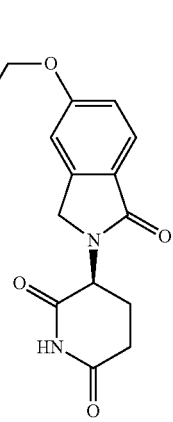
Compound 19
General synthetic scheme 3-10.
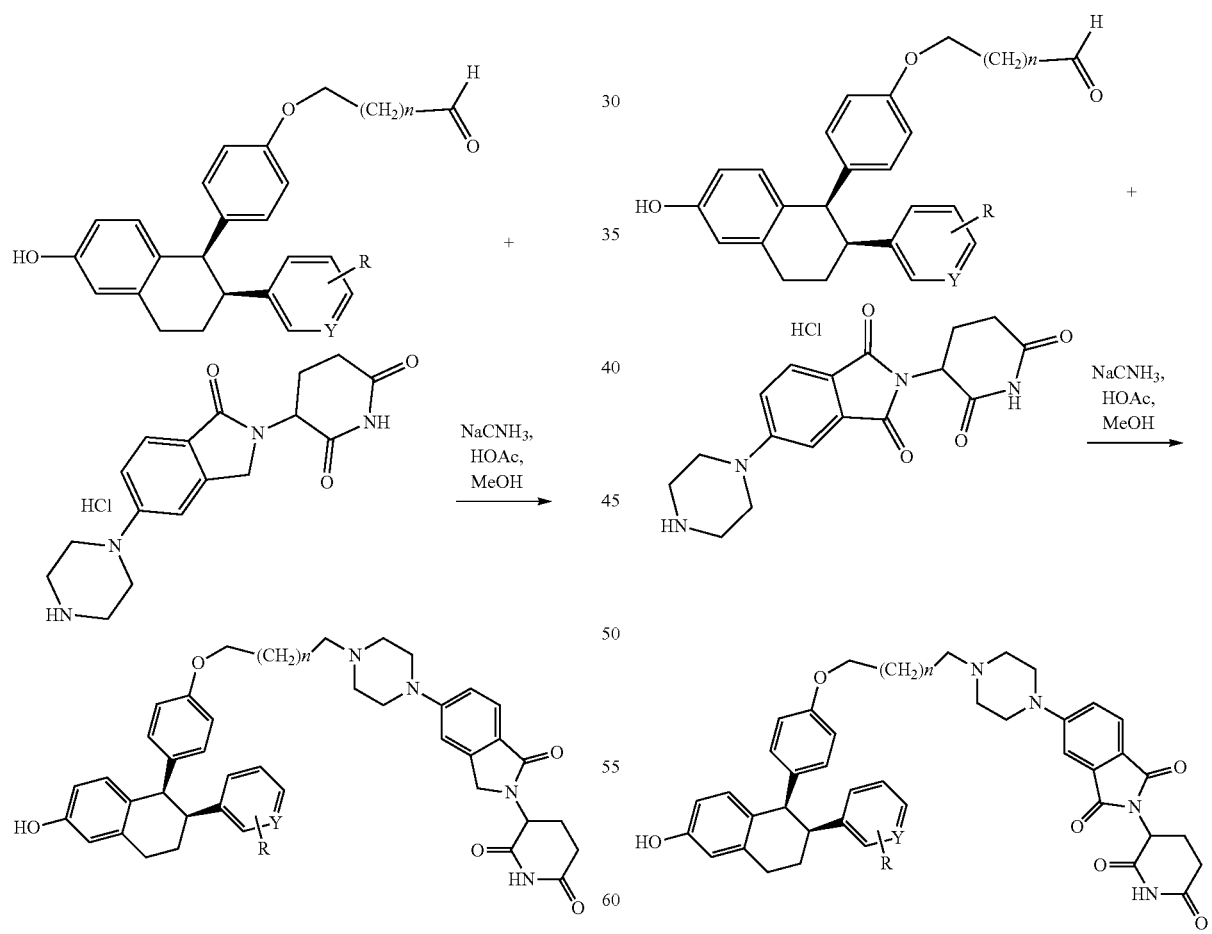

General synthetic scheme 3-11.
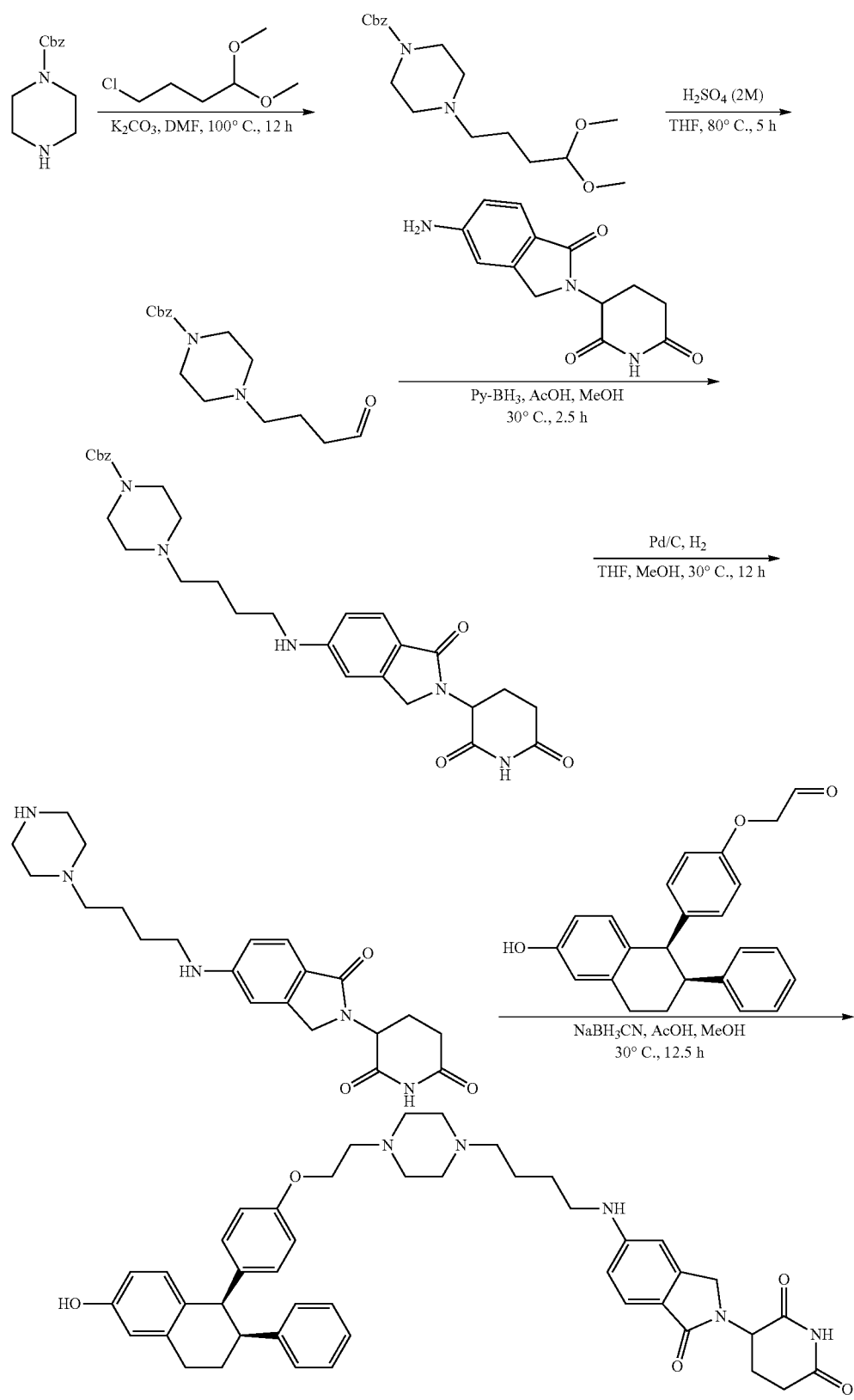
Compound 26

General synthetic scheme 3-12.

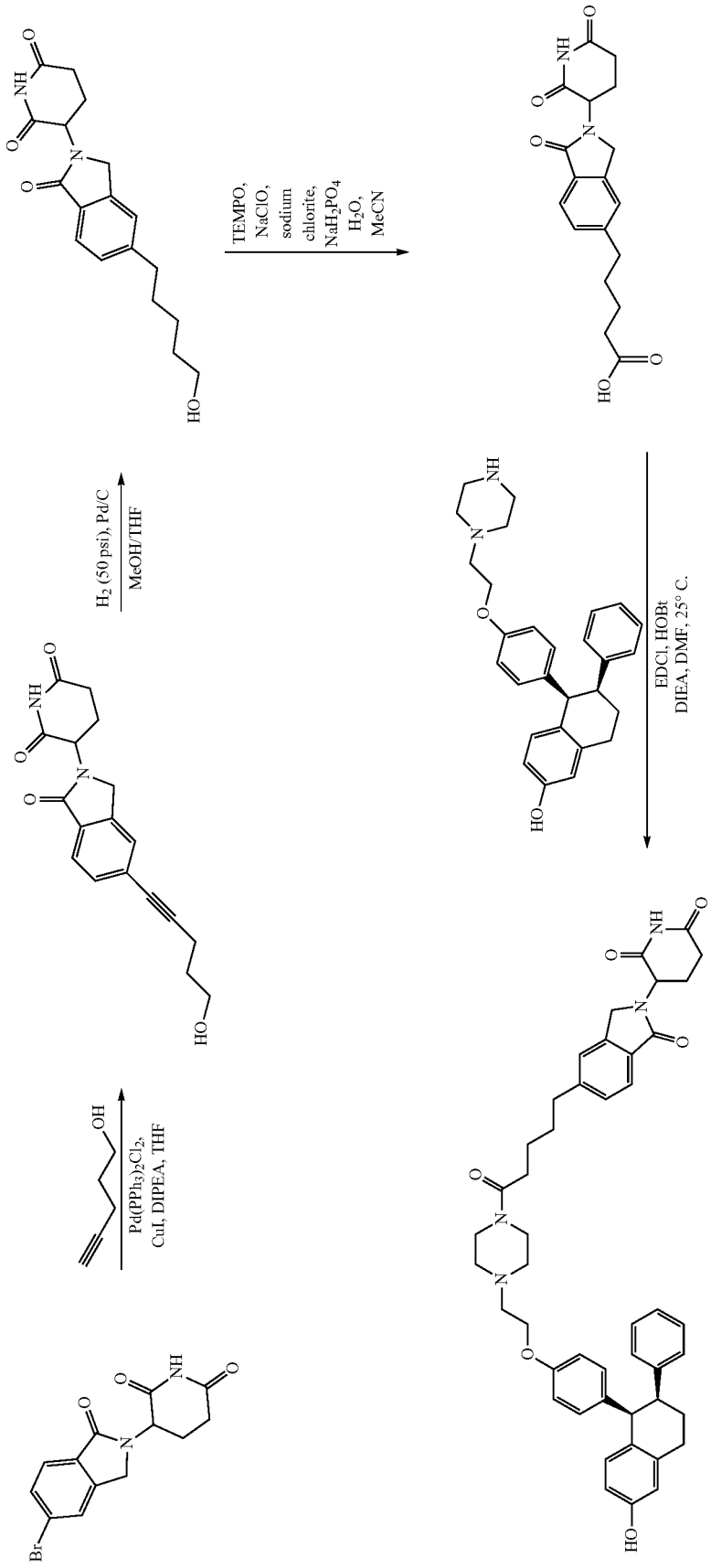

General synthetic scheme 3-13.
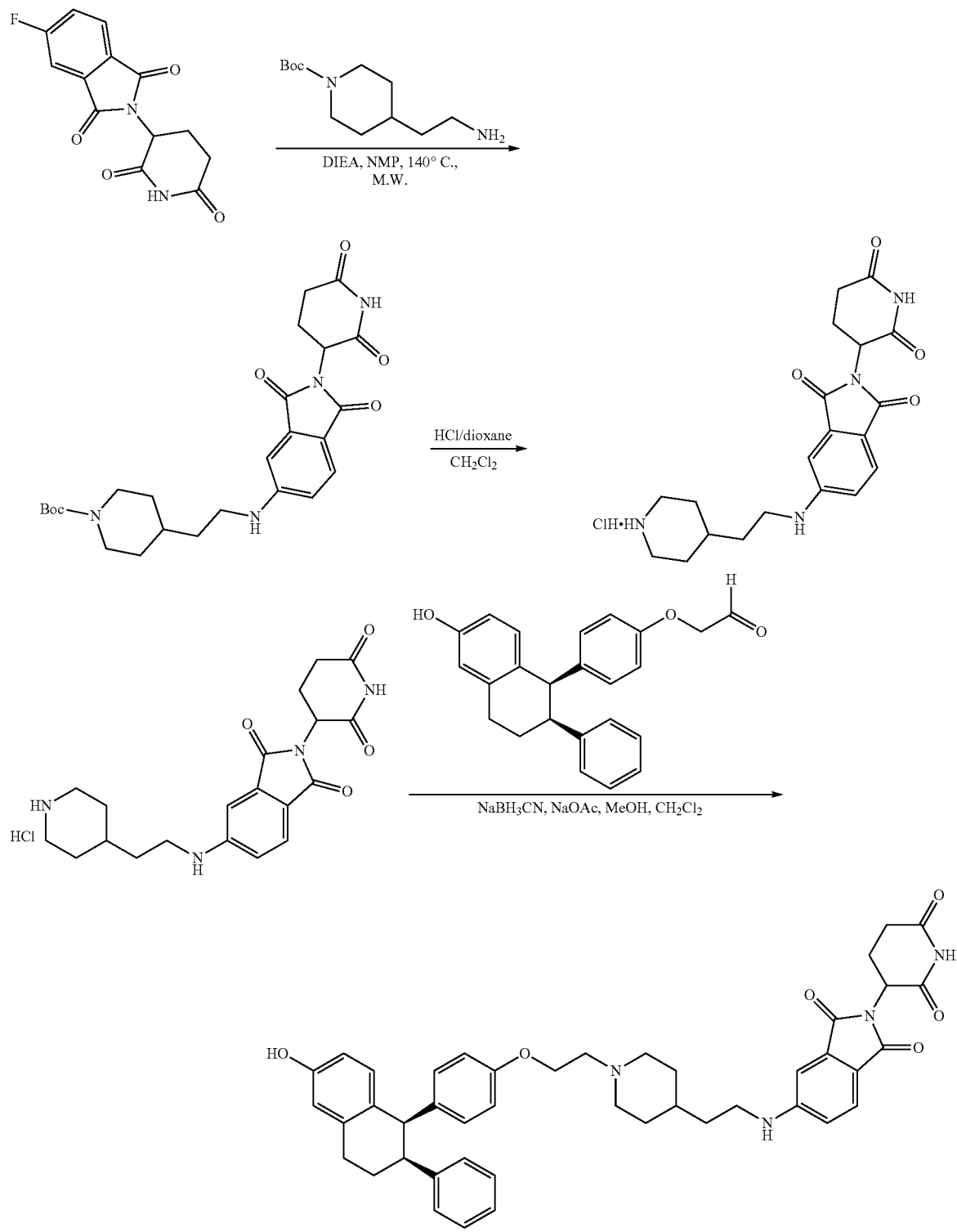
Compound 39

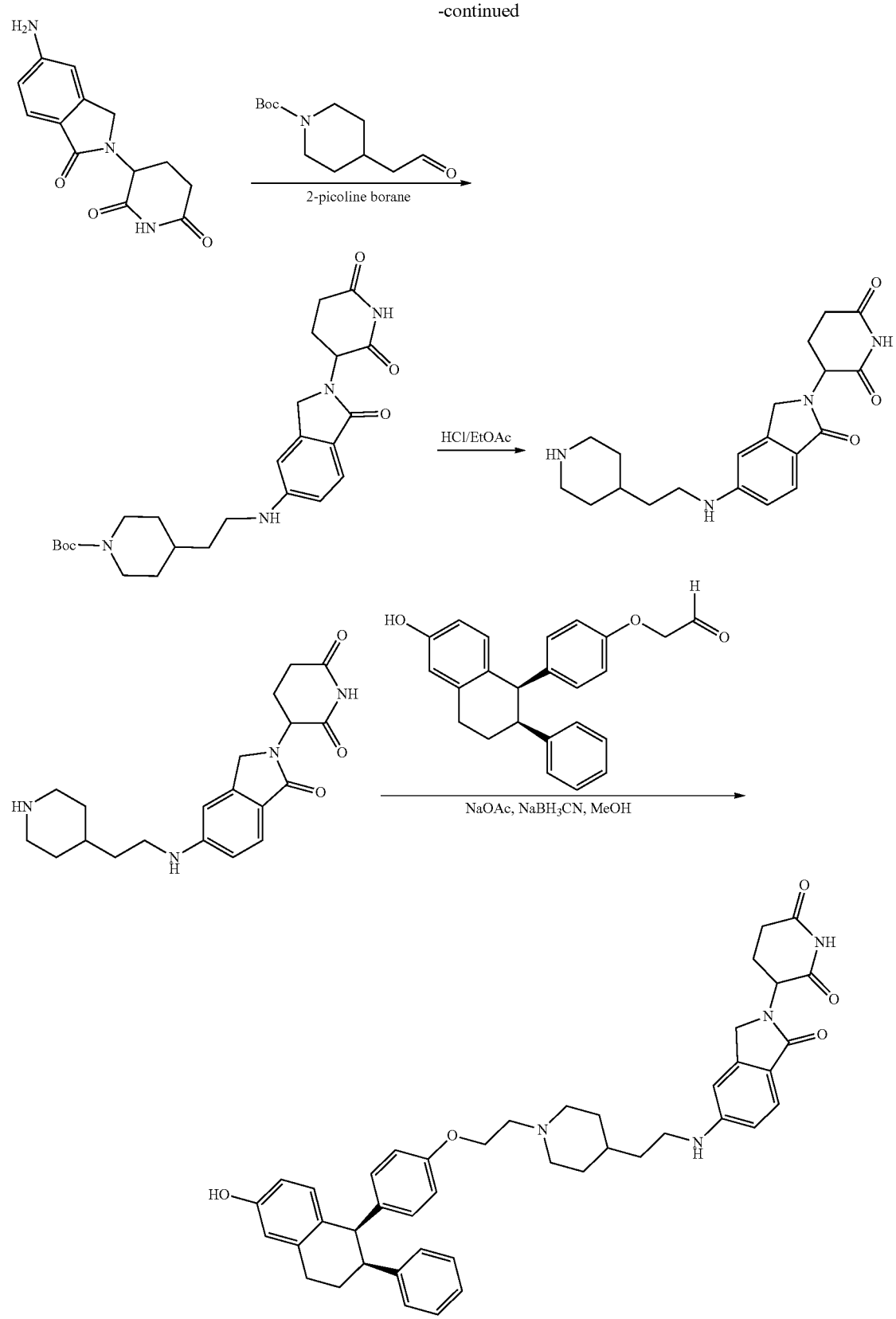
Compound 41

General synthetic scheme 3-14.
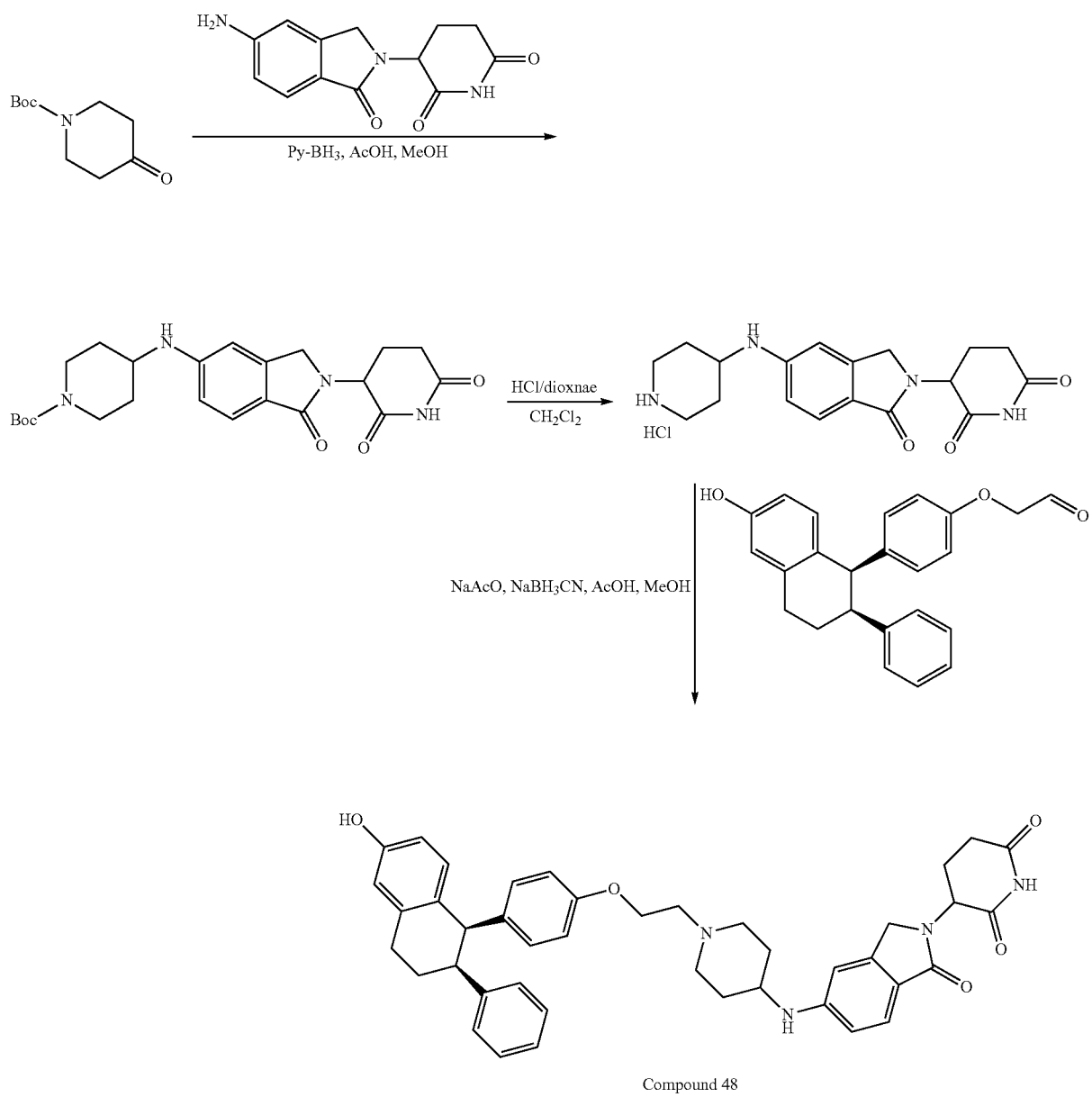
Compound 48
General synthetic scheme 3-15.
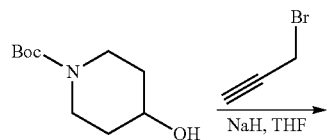

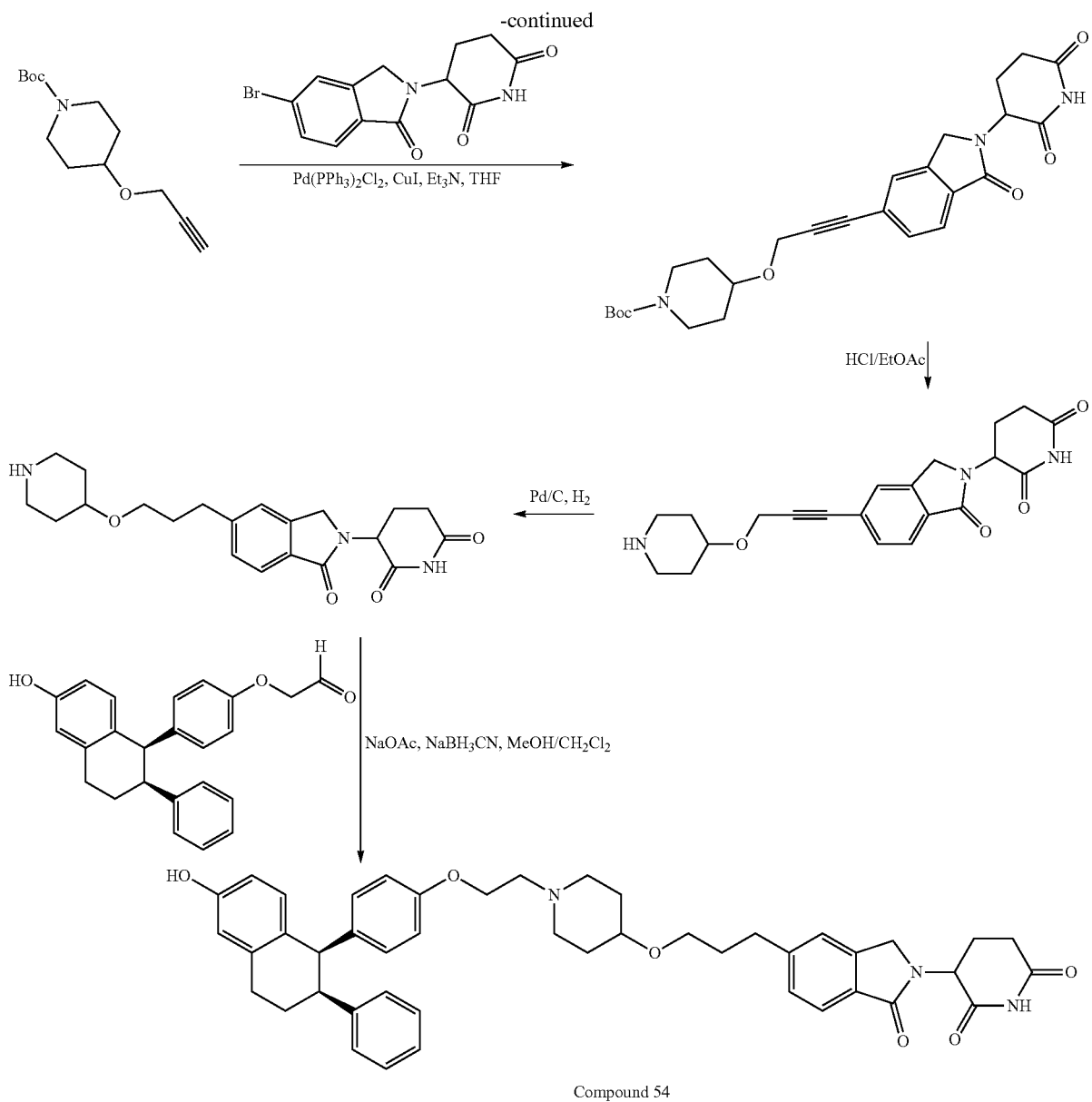
Compound 54
General synthetic scheme 3-16.
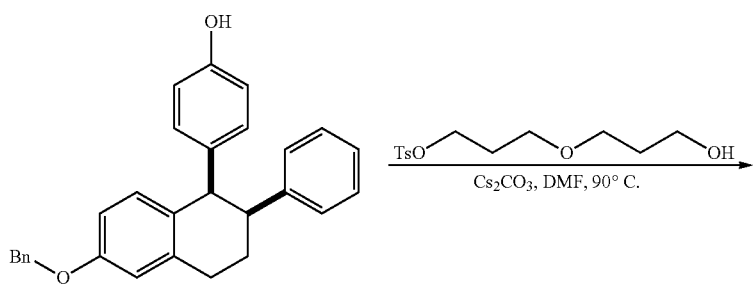

-continued
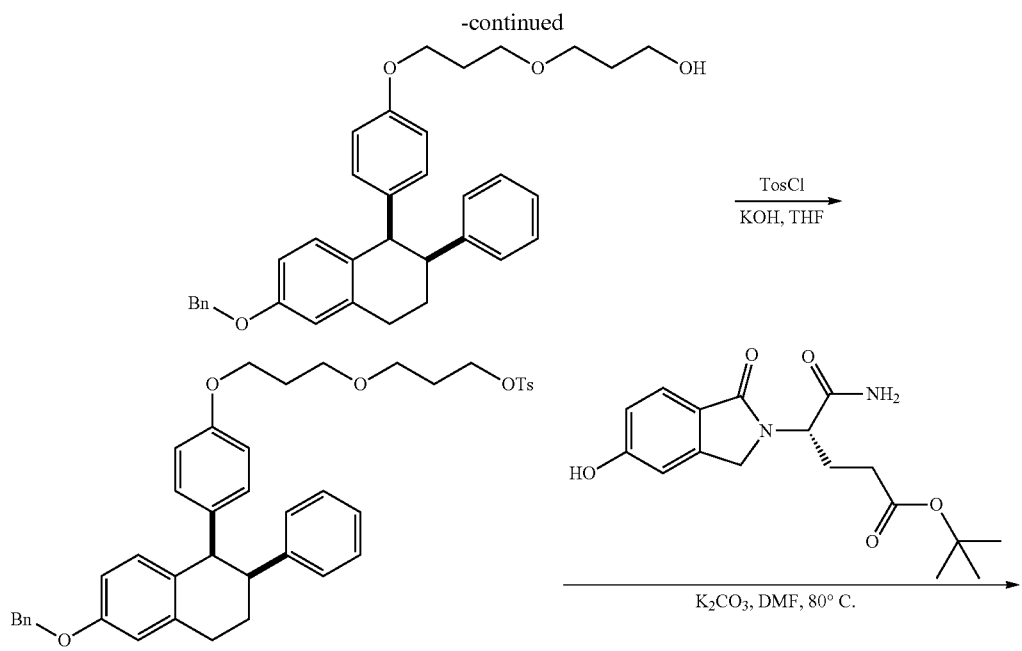
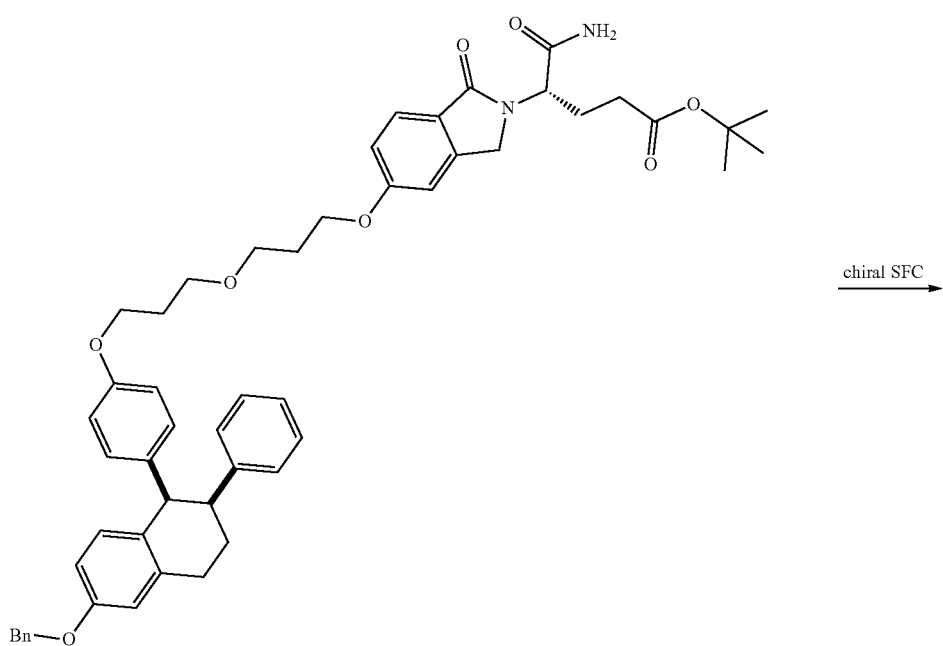

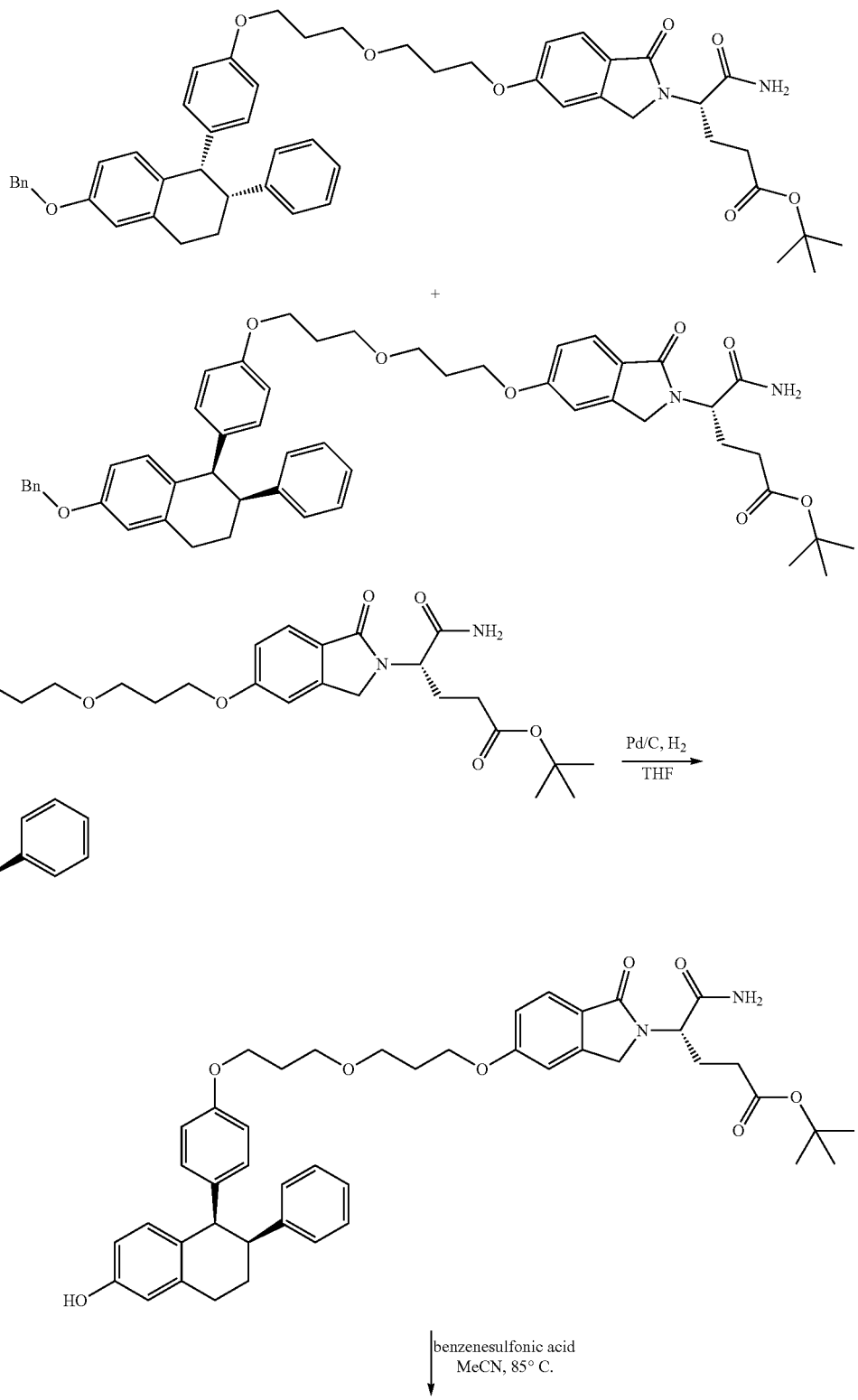

-continued
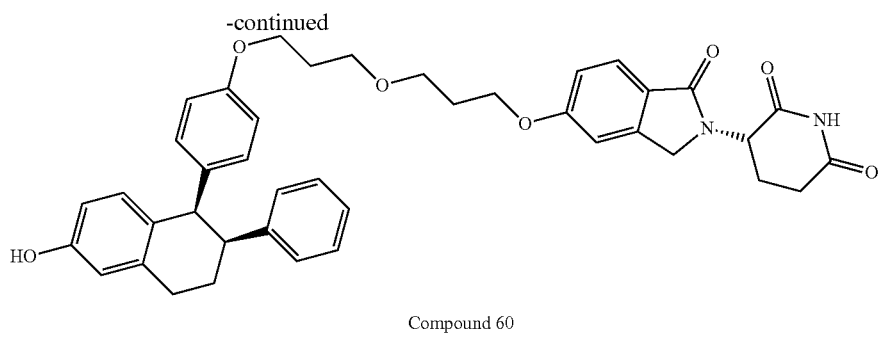
Compound 60
General synthetic scheme 3-17.
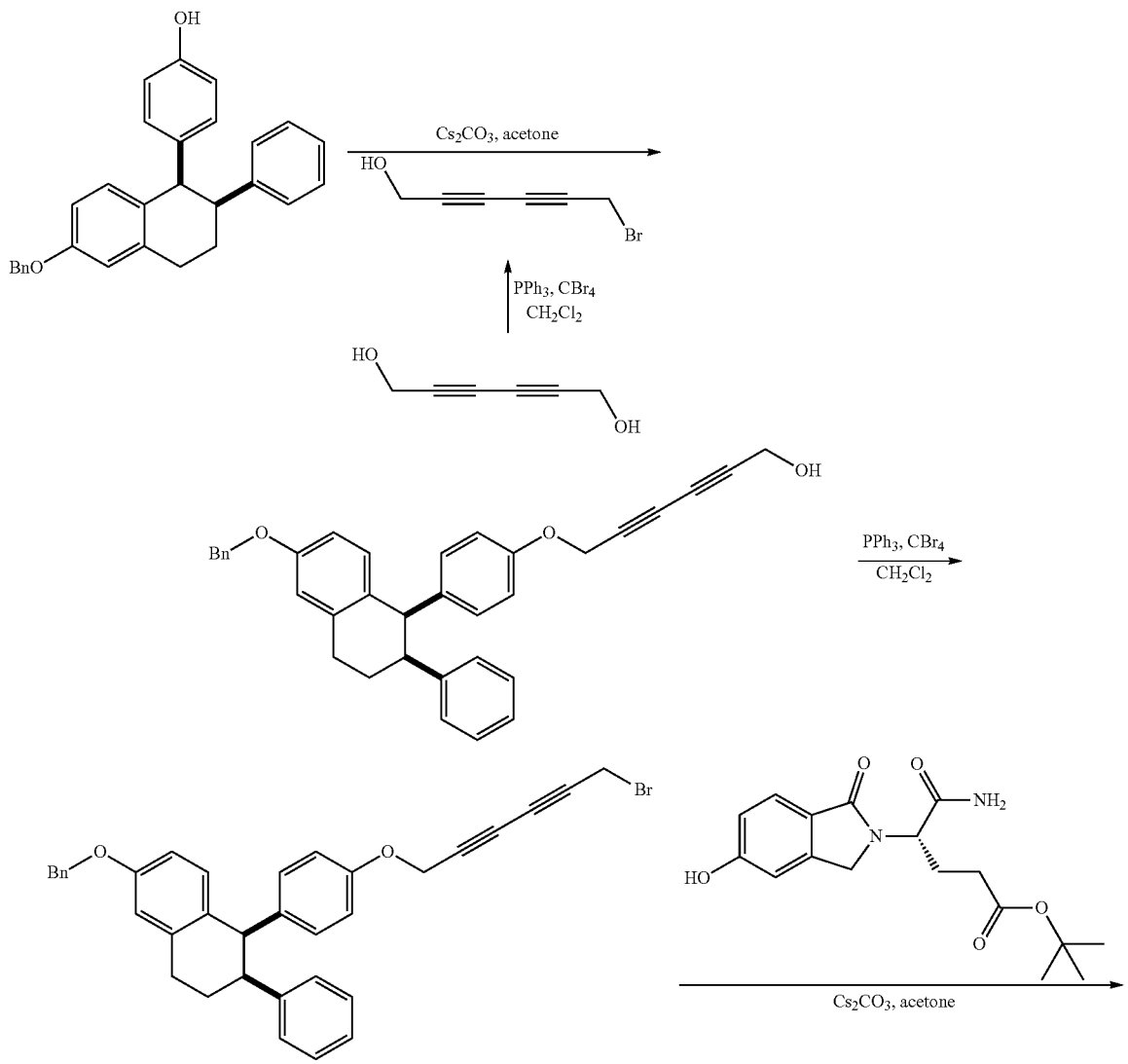

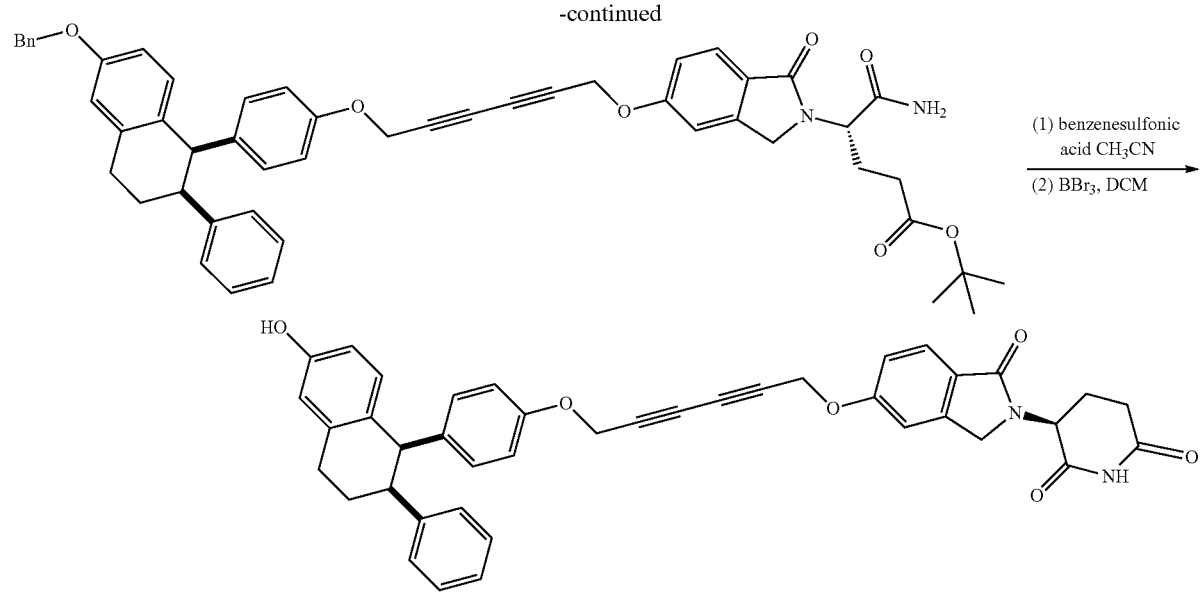
Compound 72
General synthetic scheme 3-18.
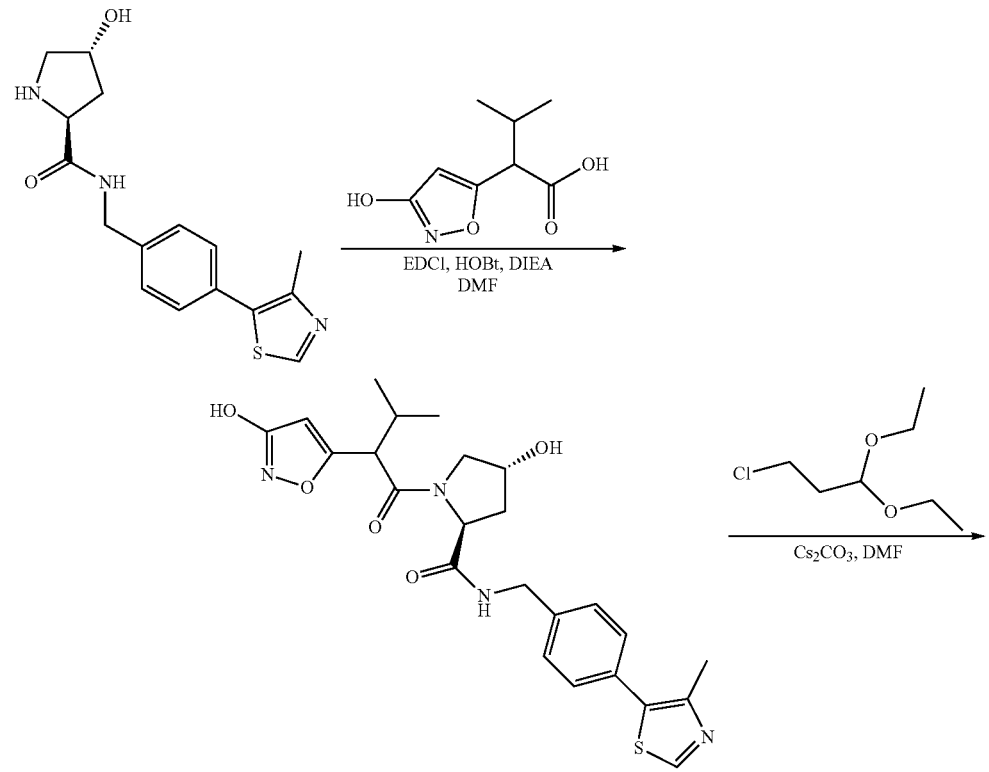

-continued
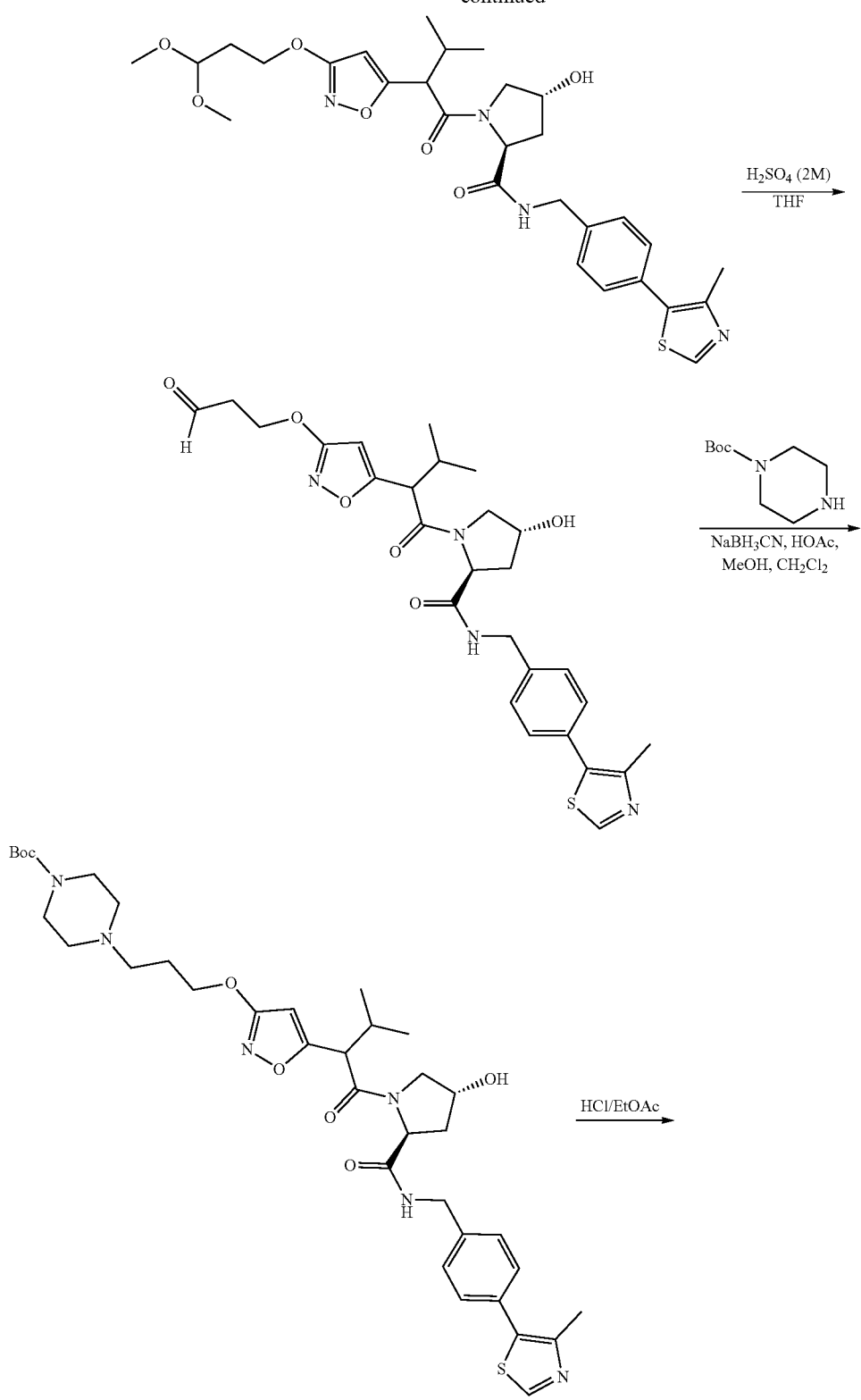

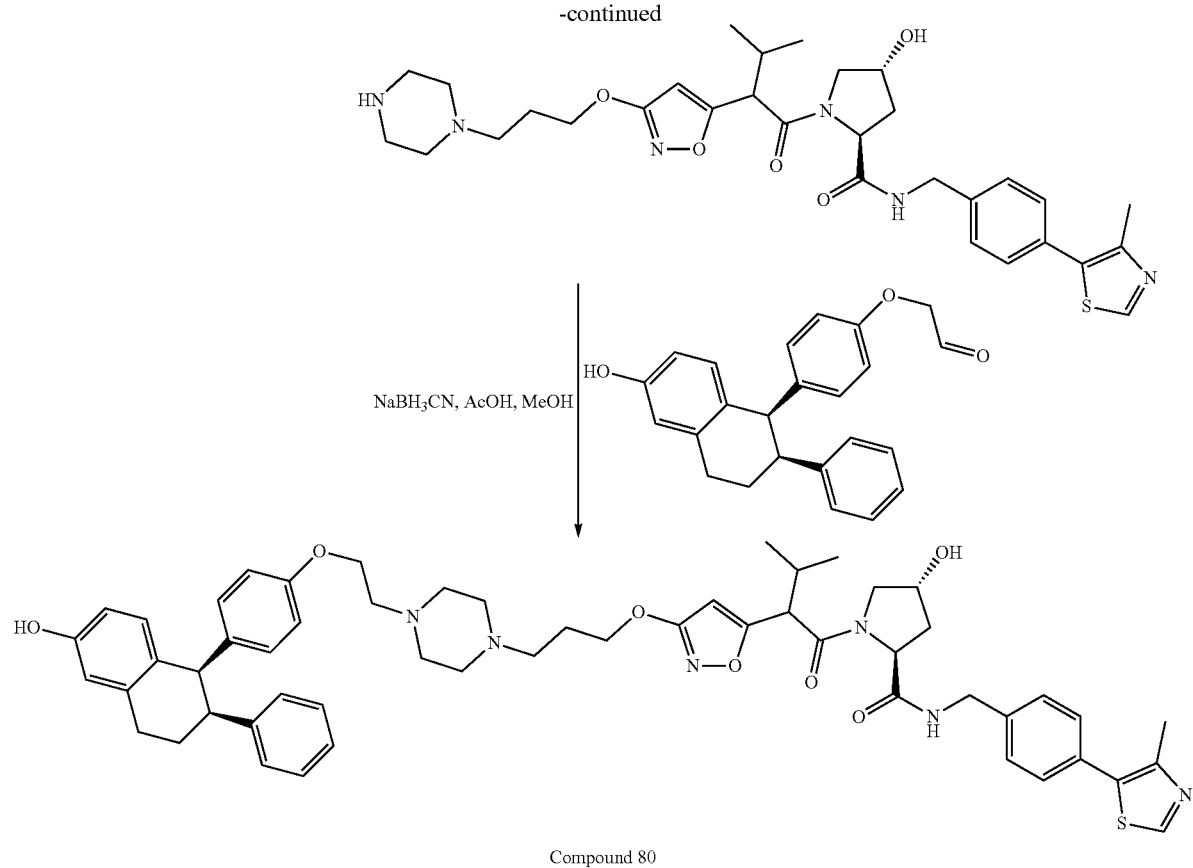
Compound 80
General synthetic scheme 3-19.
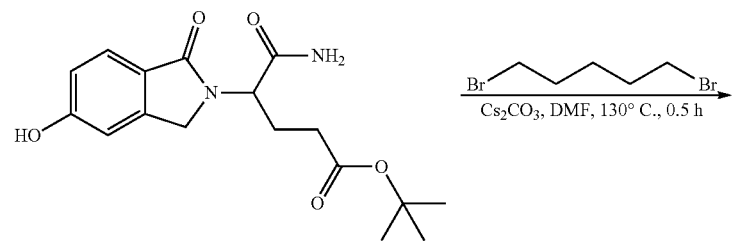
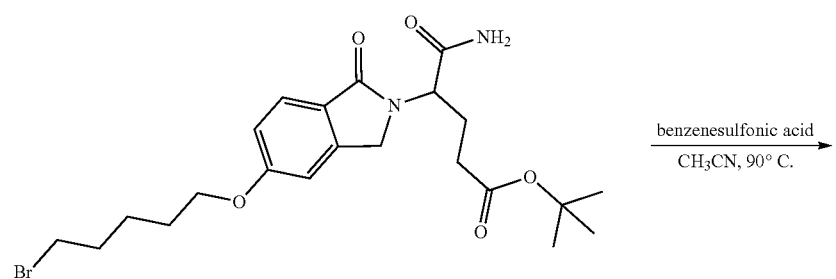

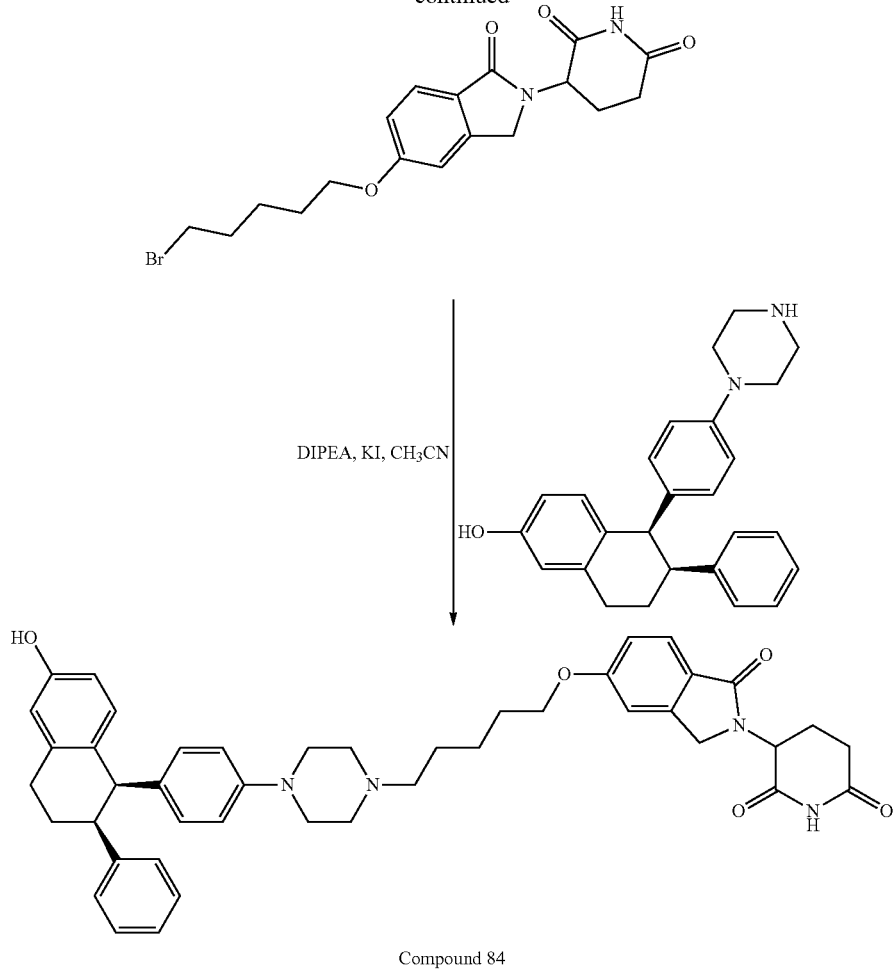
Compound 84
General synthetic scheme 3-20.
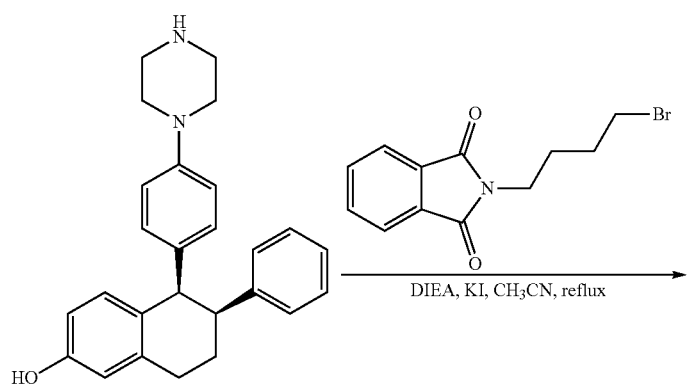

-continued
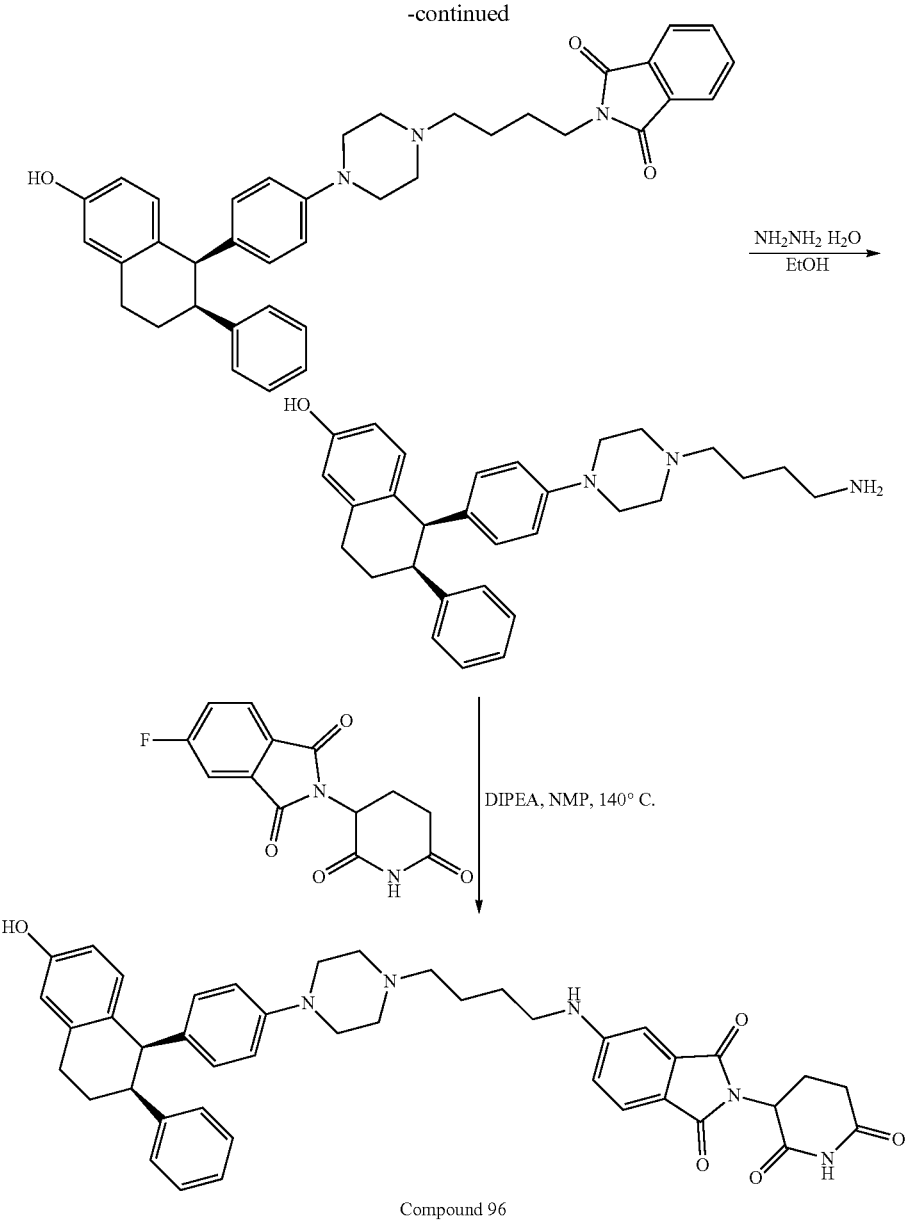
Compound 96
General synthetic scheme 3-21.
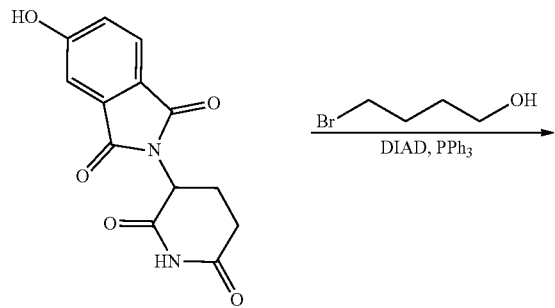

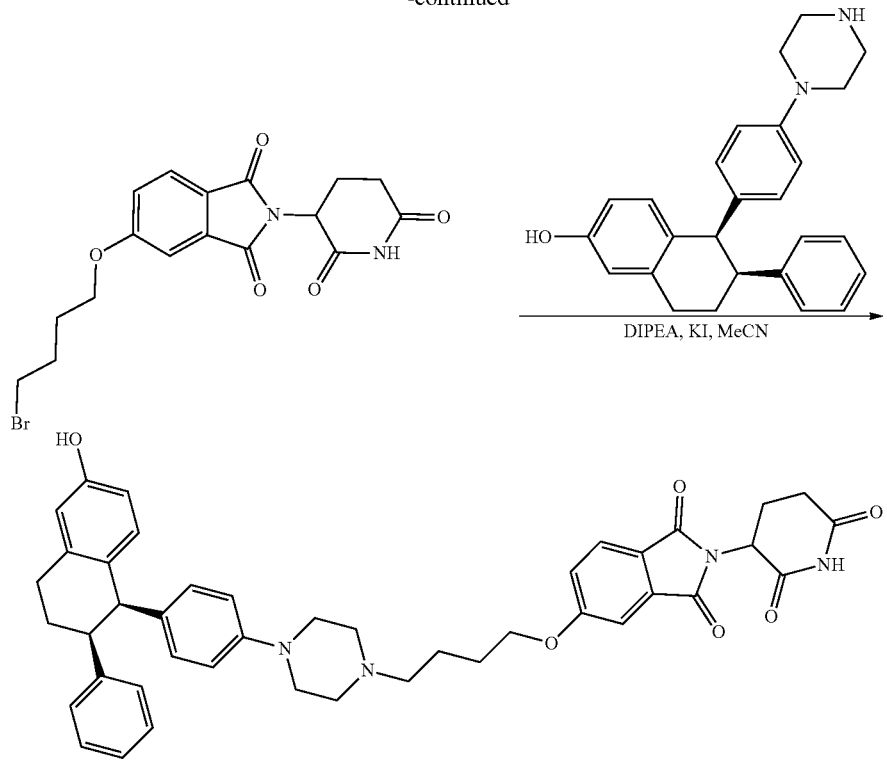
Compound 86
General synthetic scheme 3-22.
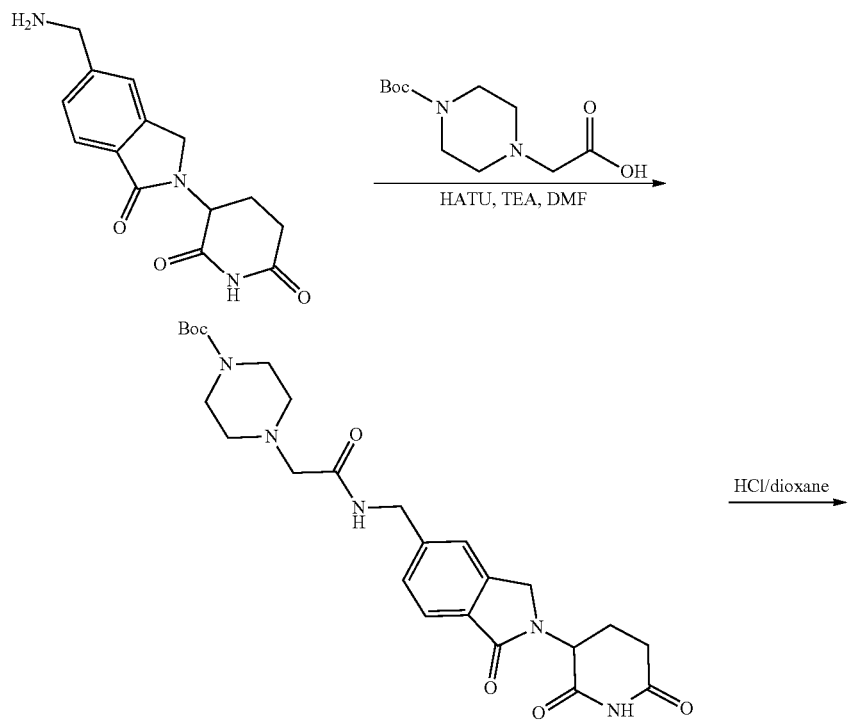

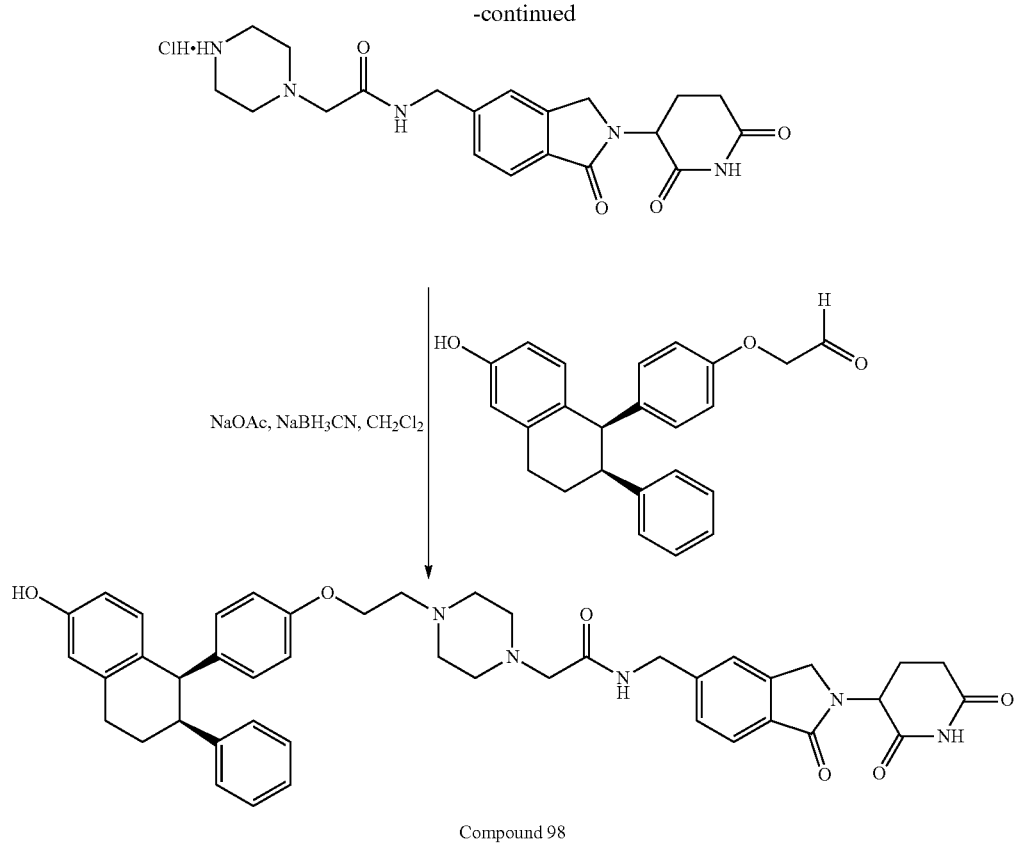
Compound 98
General synthetic scheme 3-23.
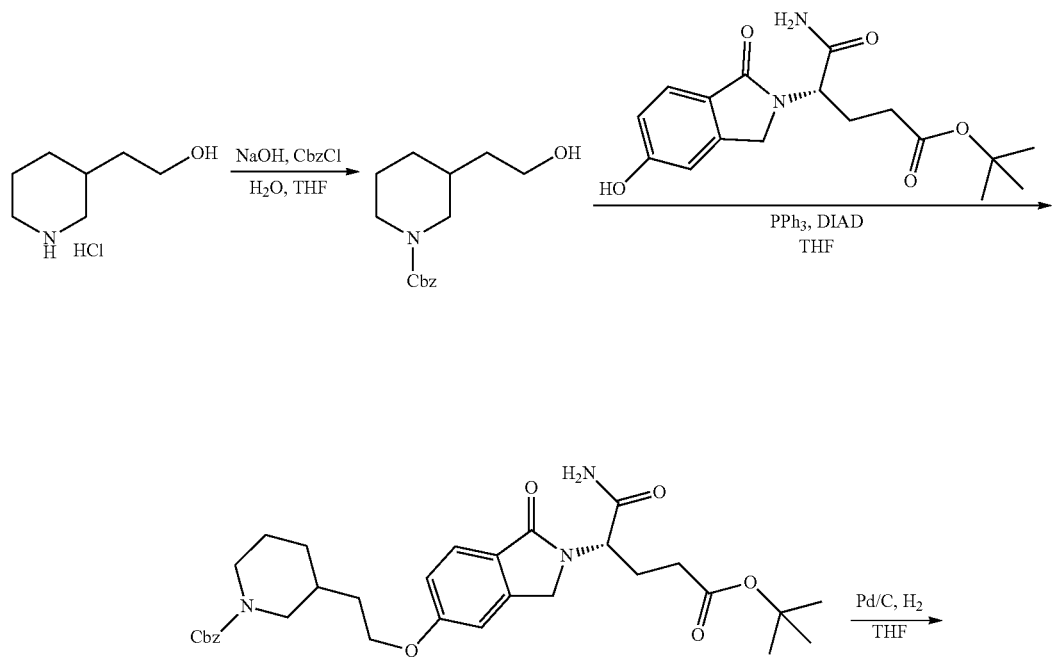

795 796
-continued
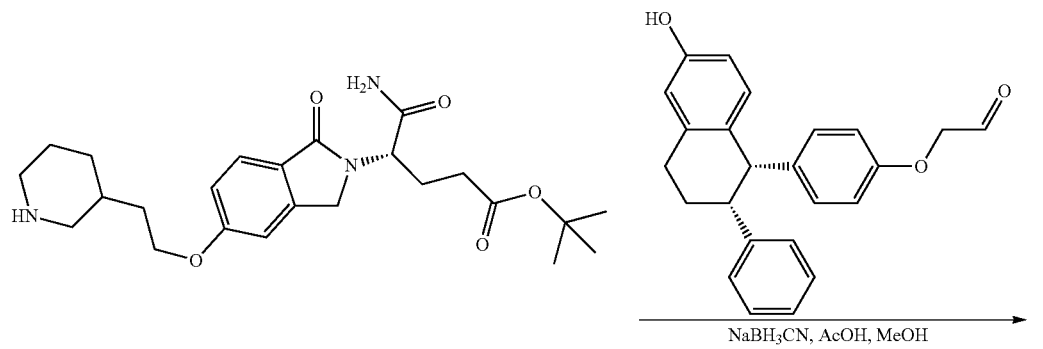
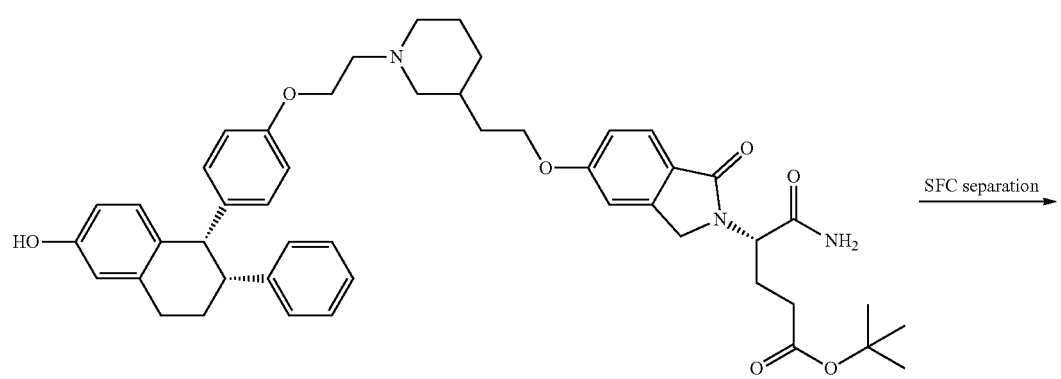
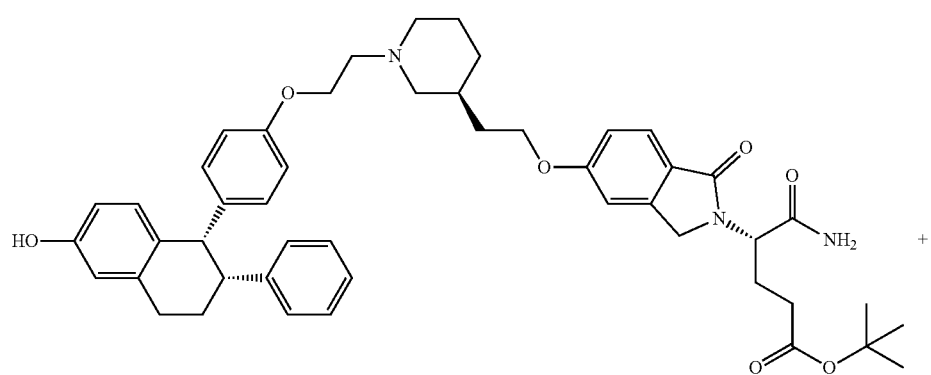
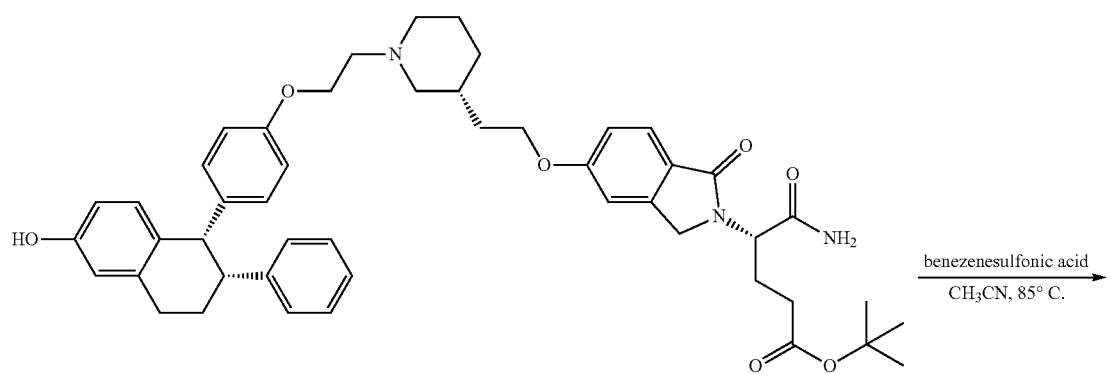

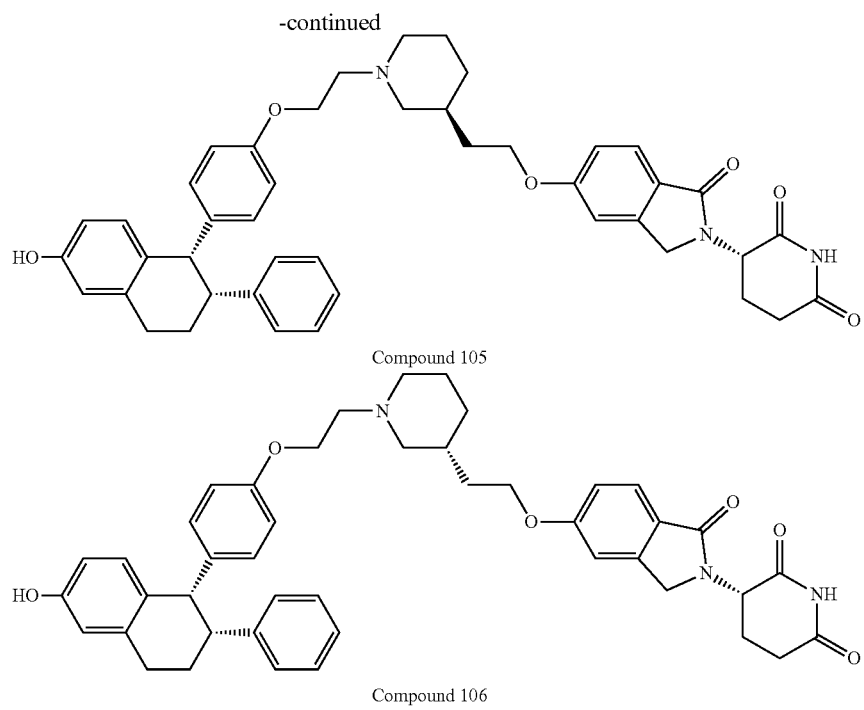
Compound 105
Compound 106
General synthetic scheme 3-24 to prepare are claimed compounds
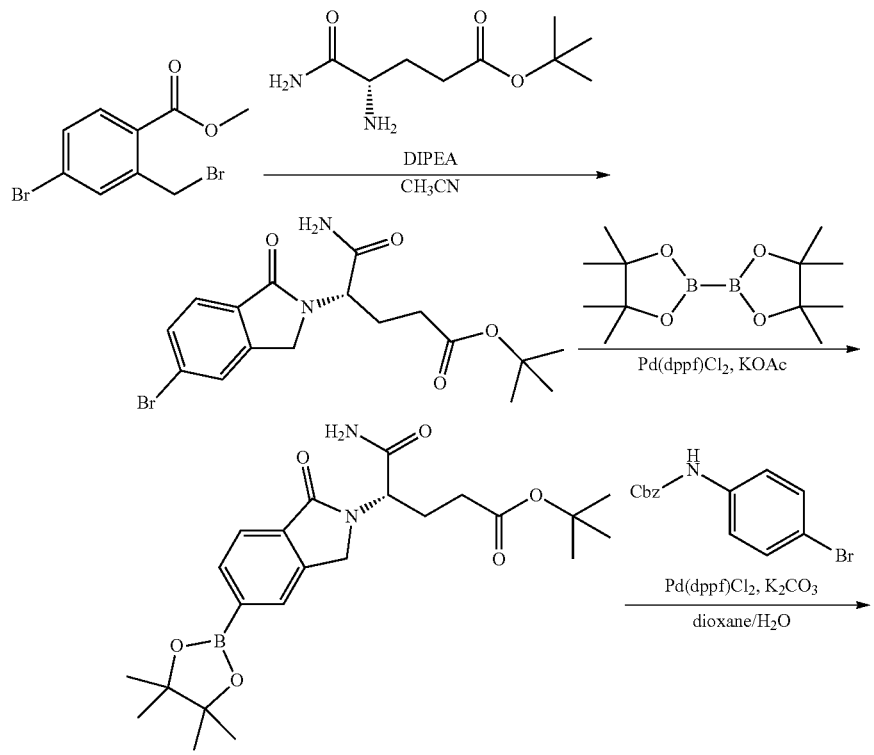

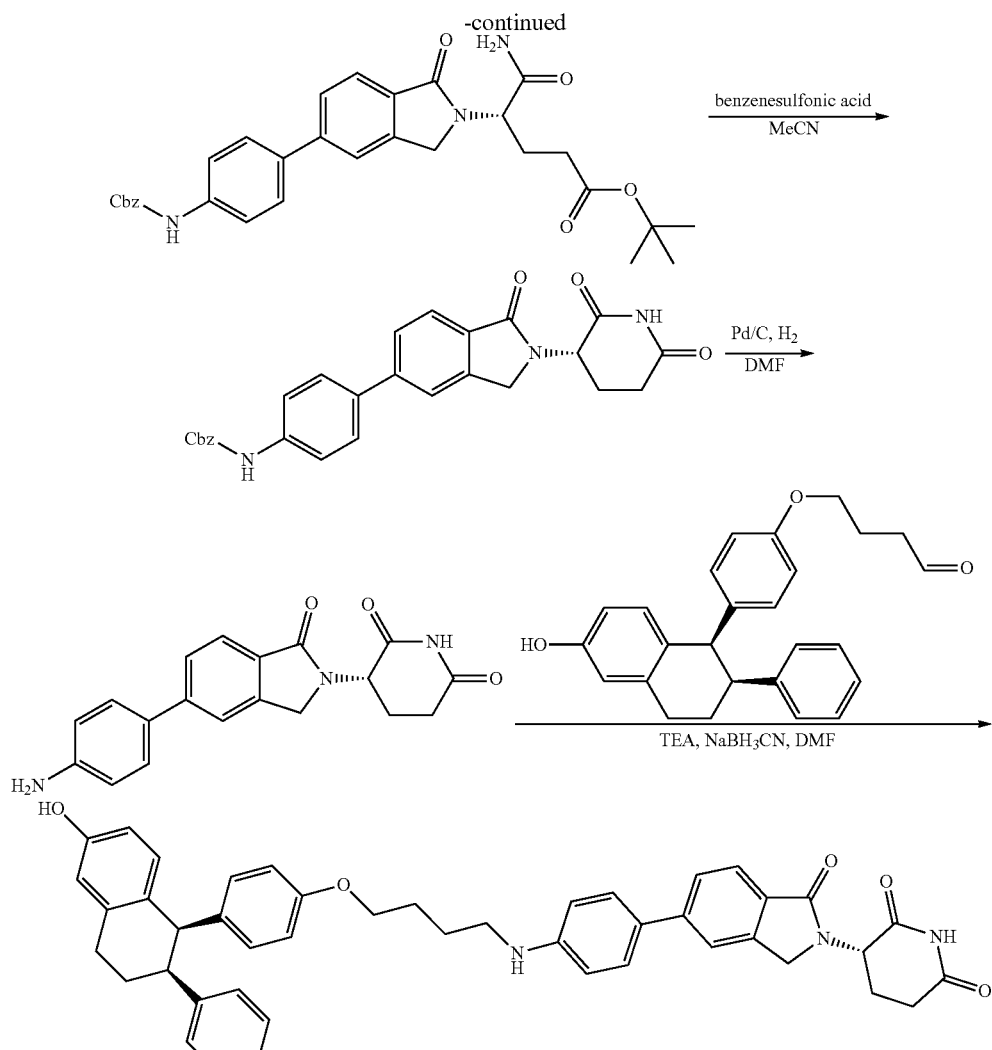
Compound 108
General synthetic scheme 3-25.
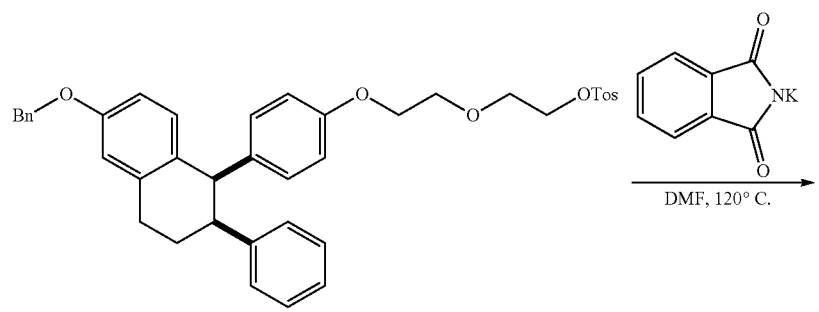

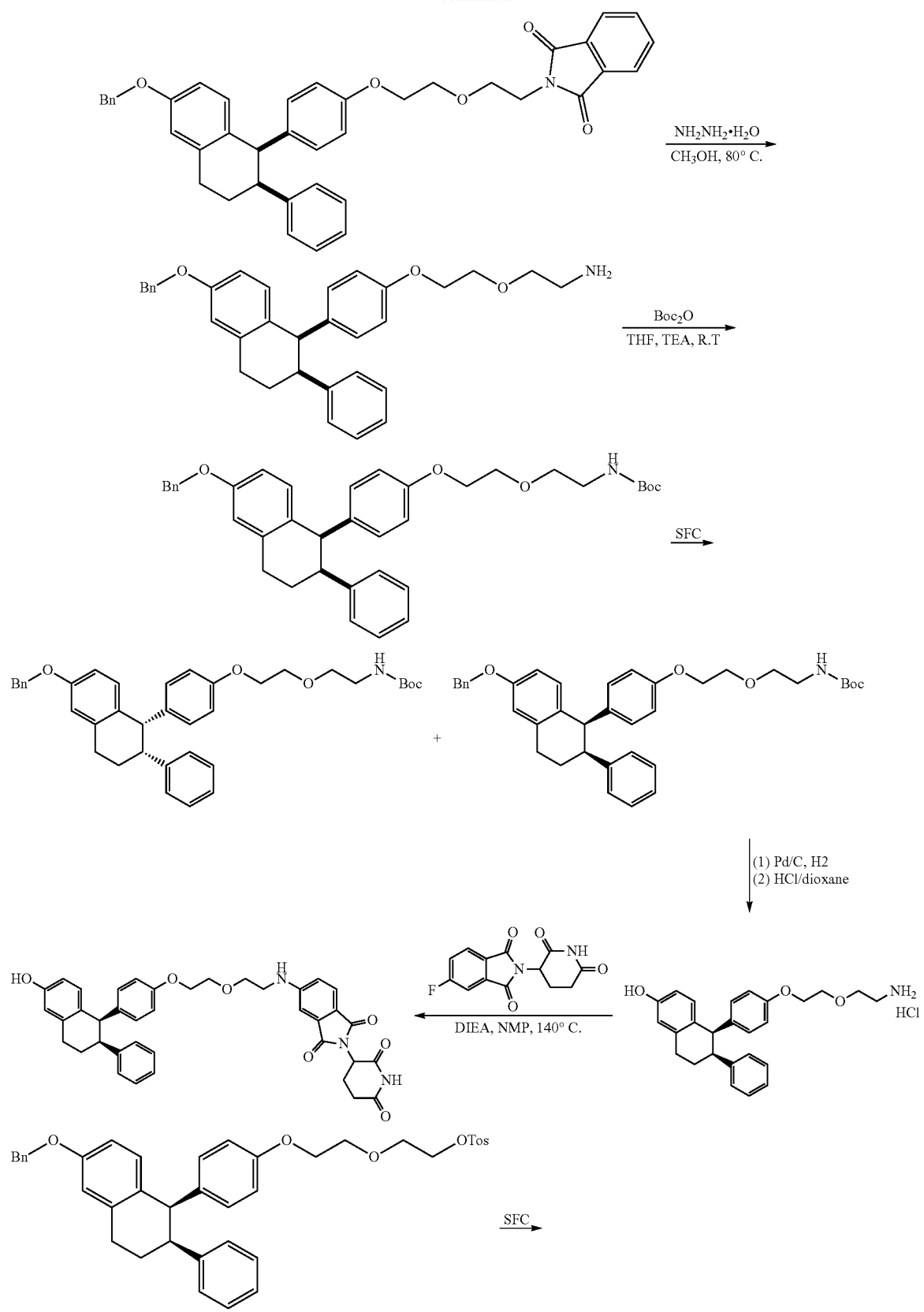

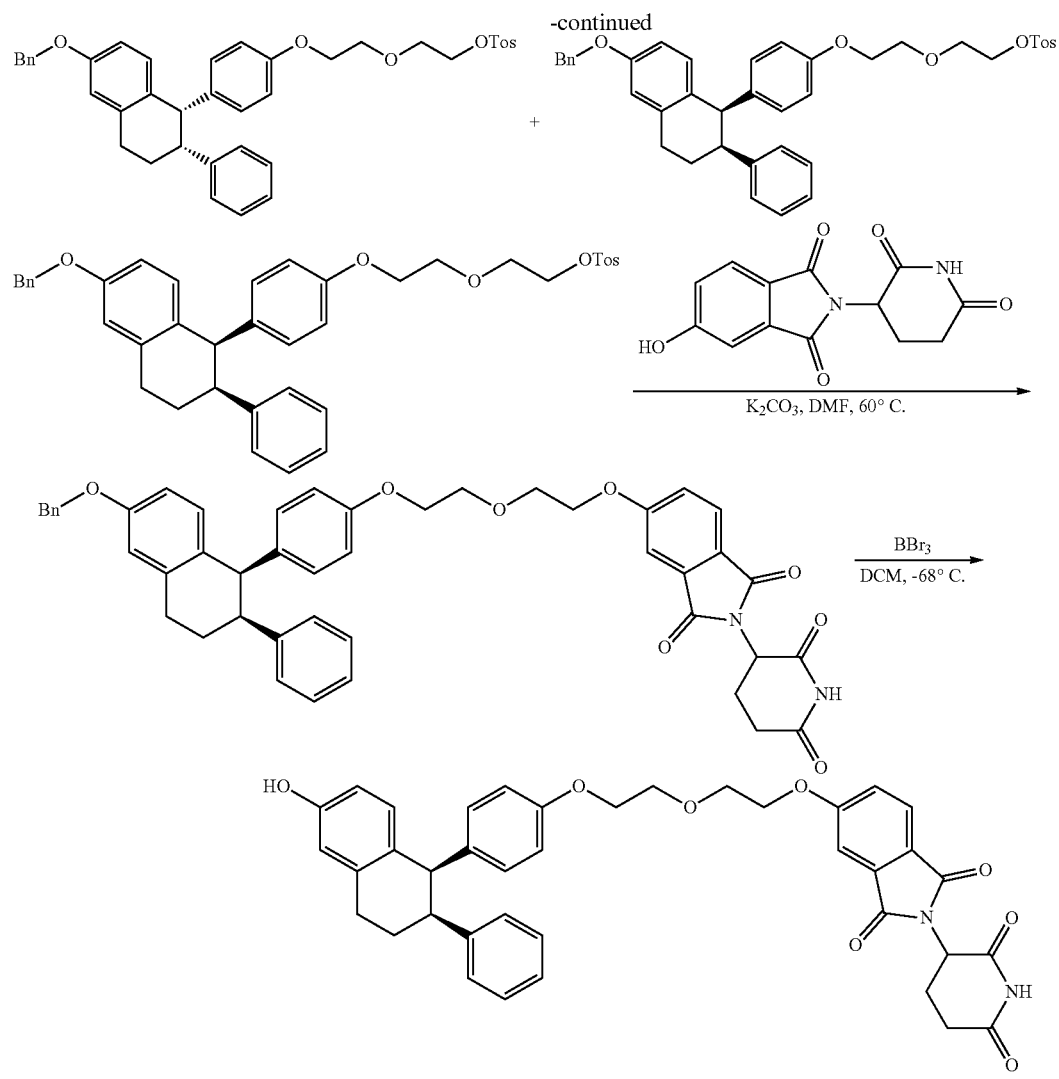
Compound 112
General synthetic scheme 3-26.
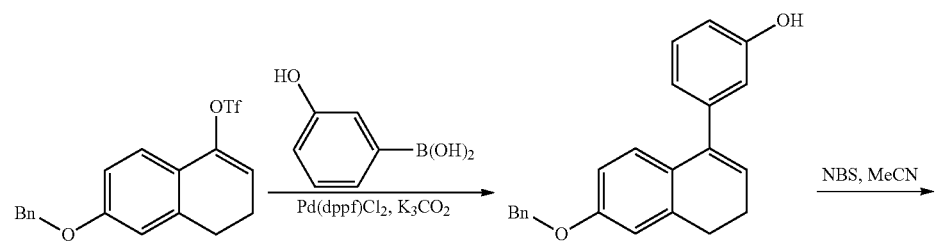

-continued
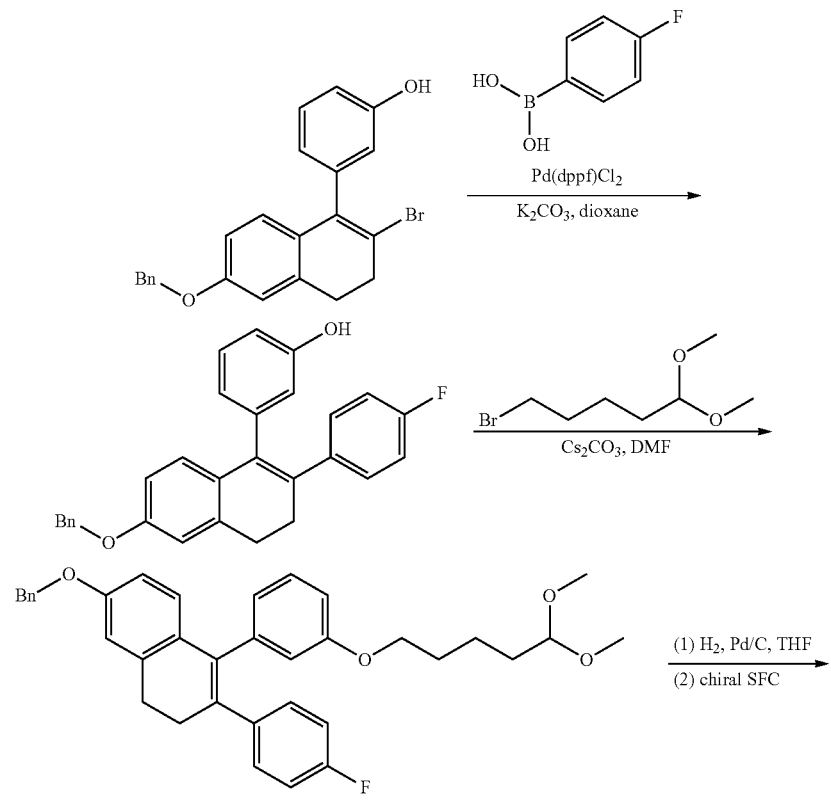
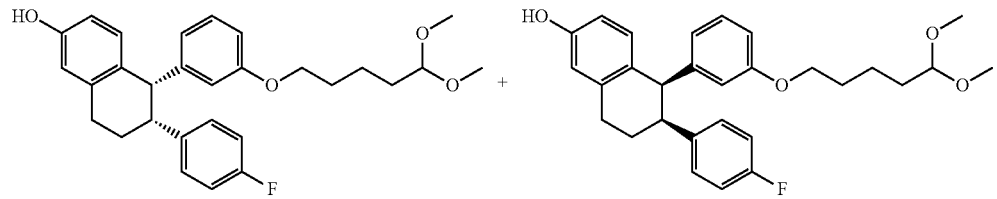
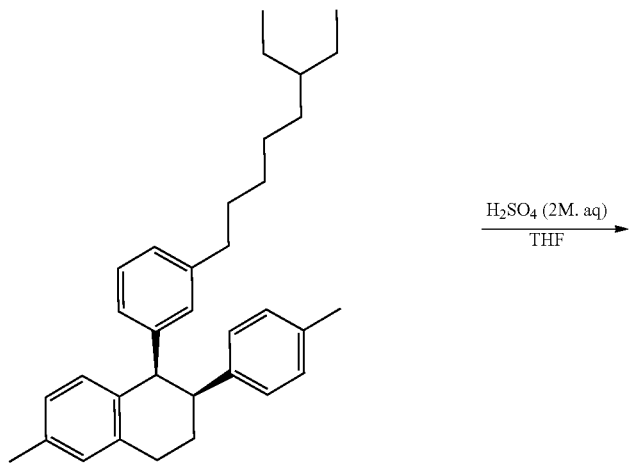

807
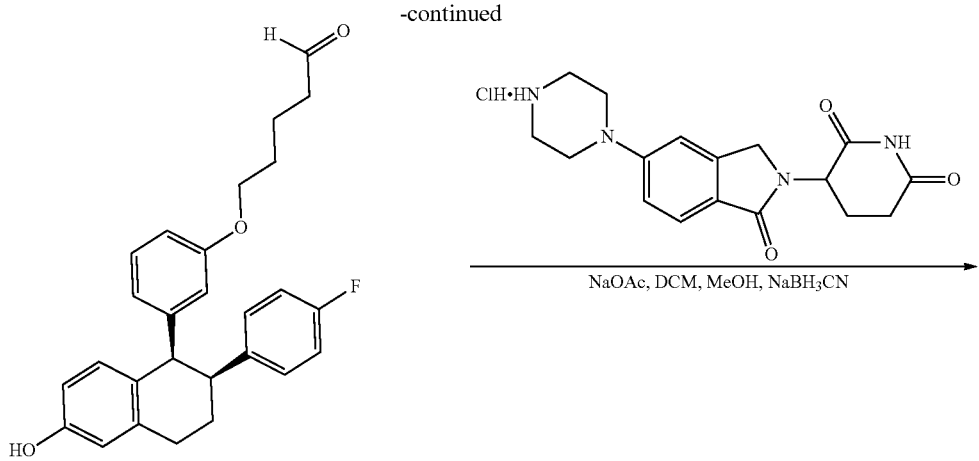
Compound 128
General synthetic scheme 3-27.
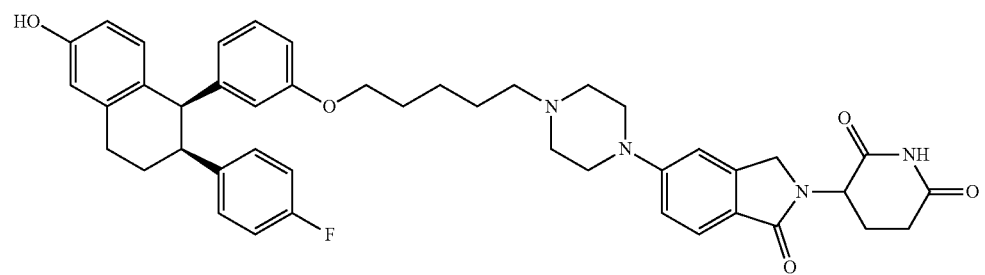
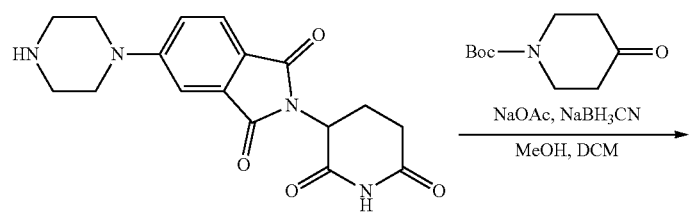
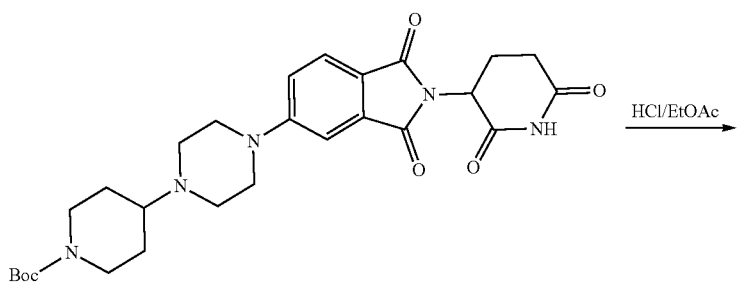

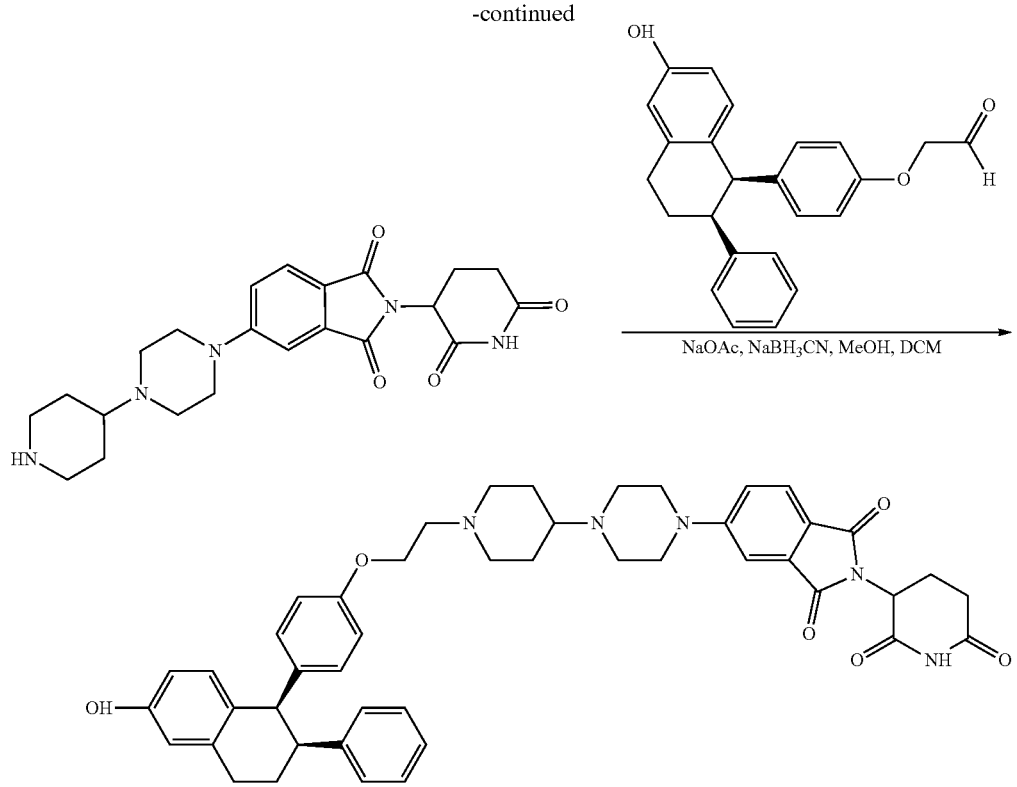
General synthetic scheme 3-28.

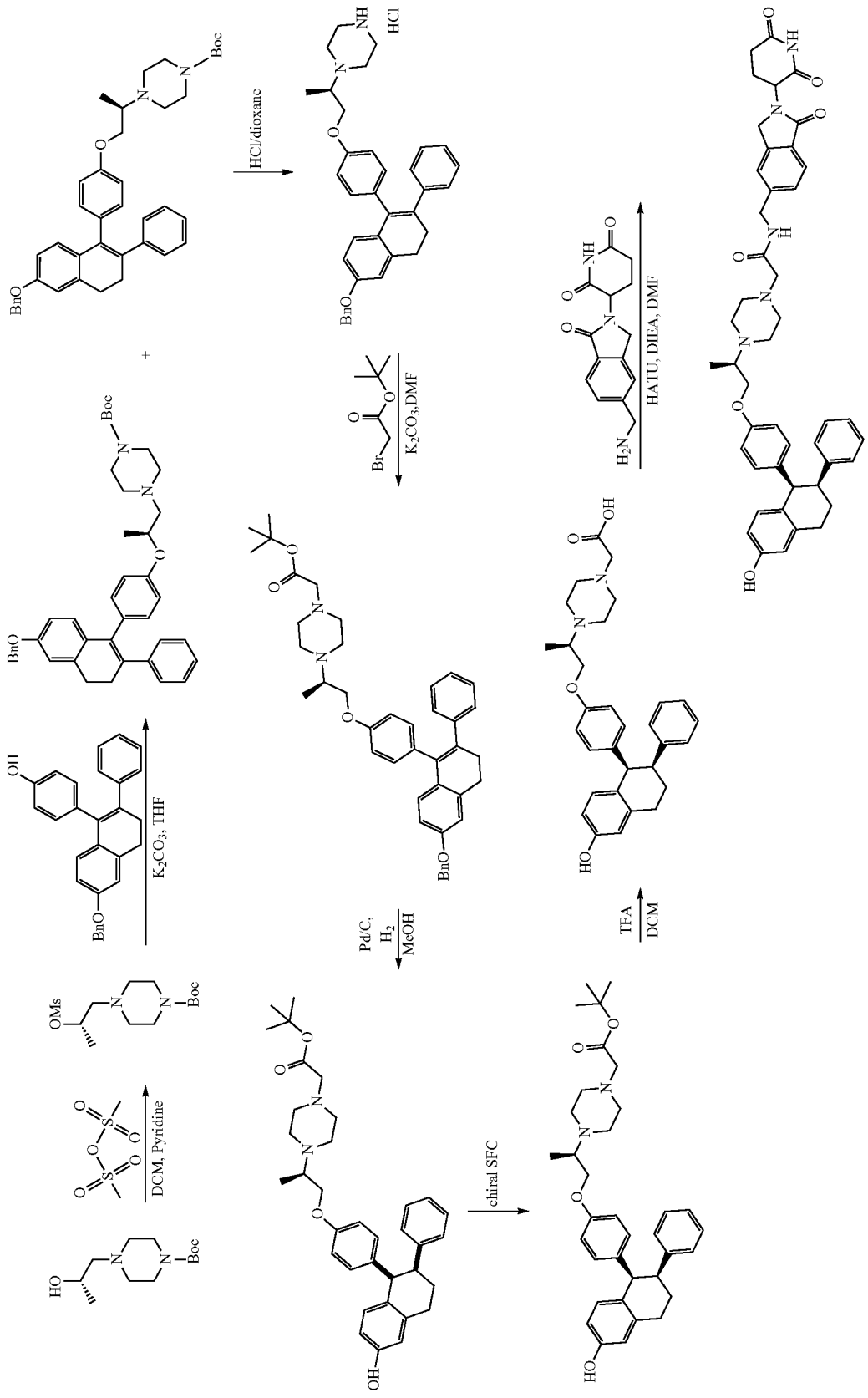

General synthetic scheme 3-29.

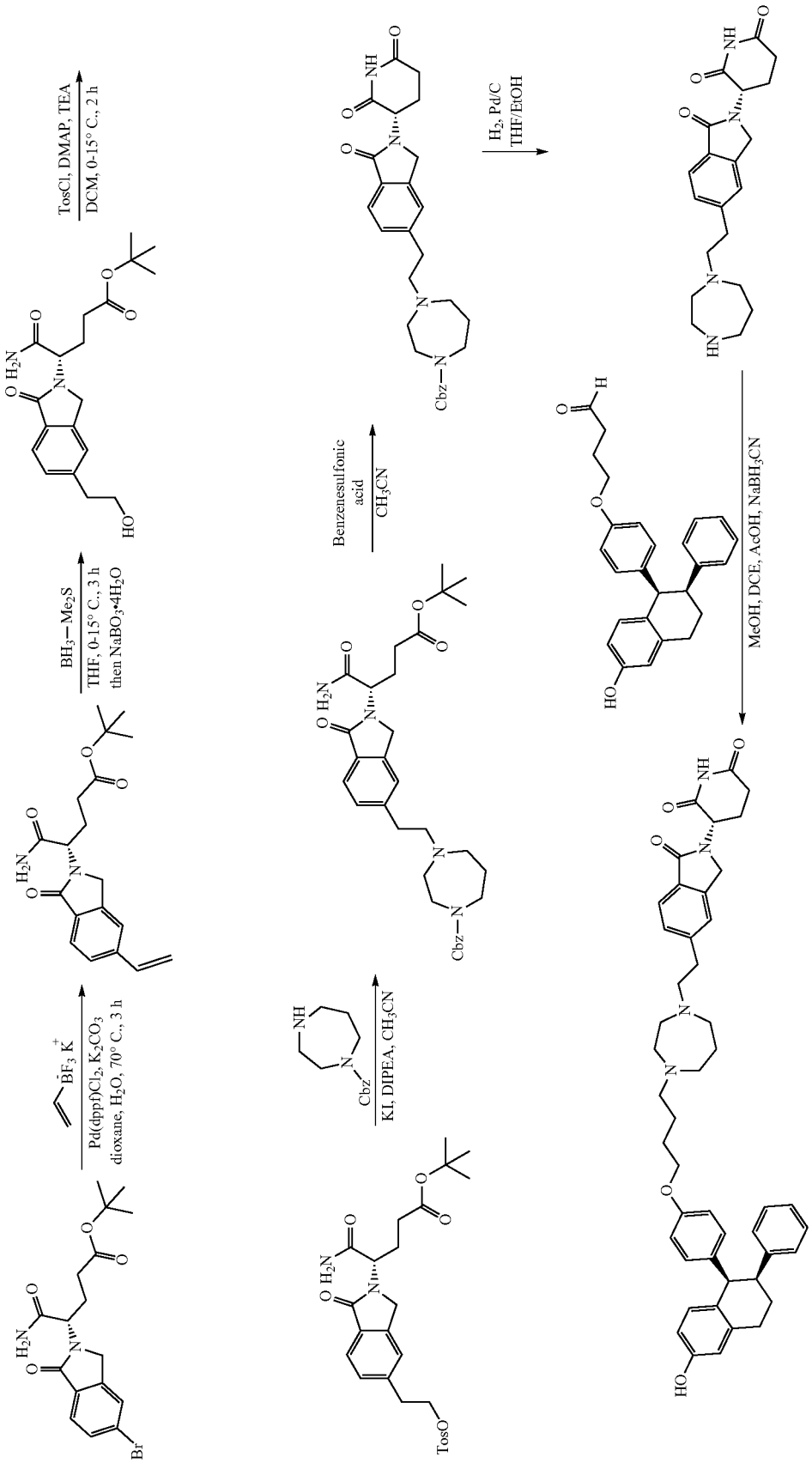

General synthetic scheme 3-30.
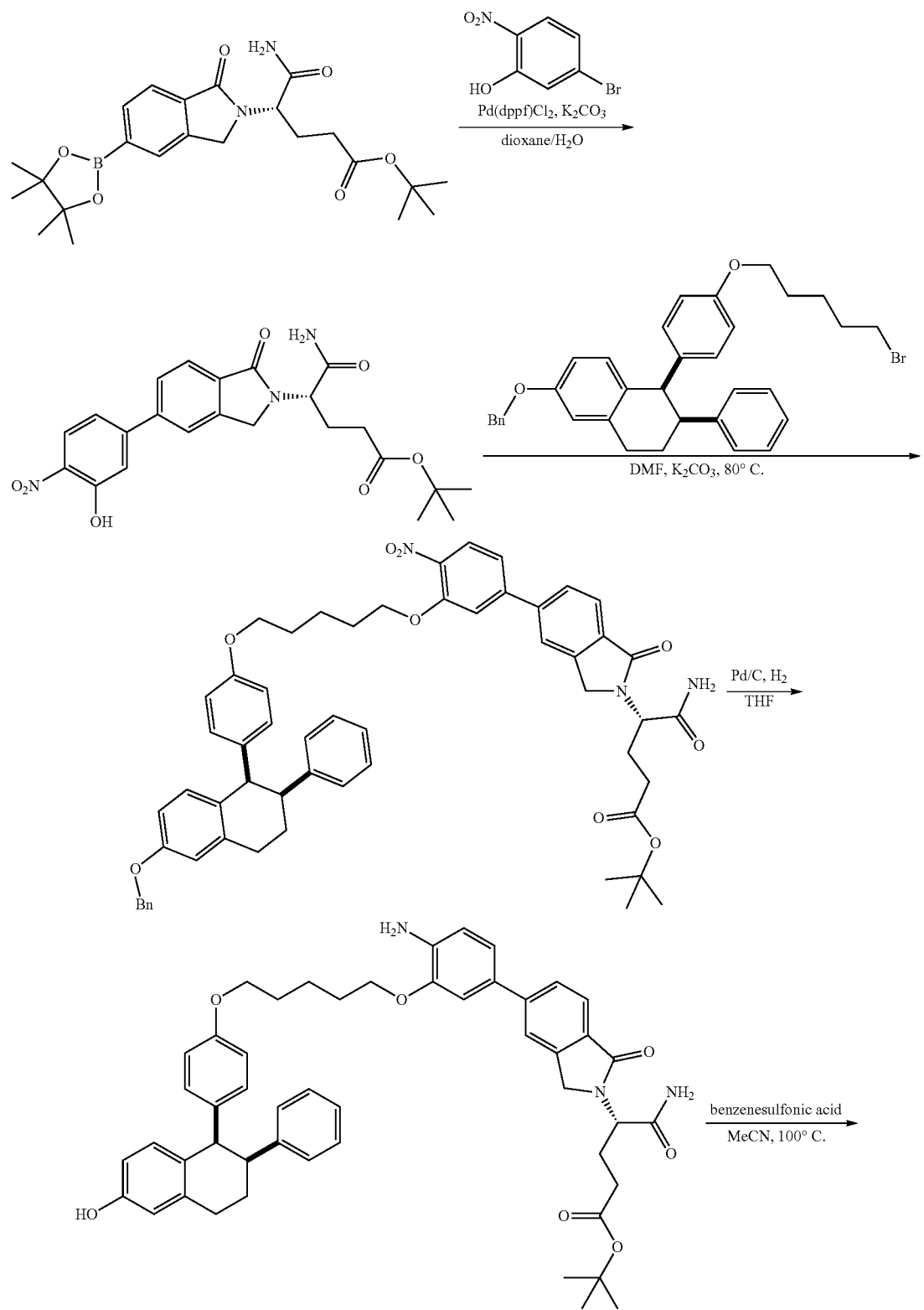

-continued
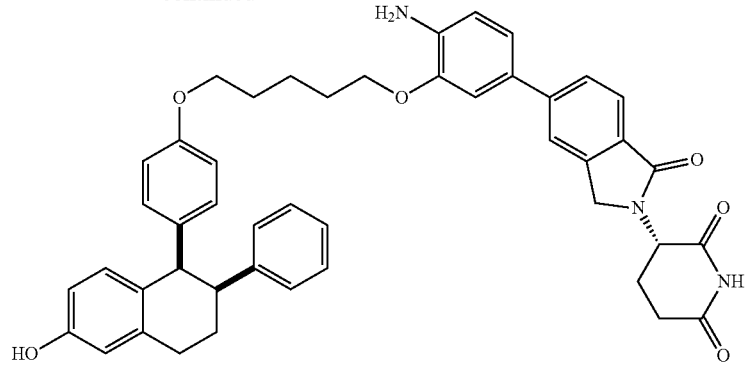
Compound 165
General synthetic scheme 3-31.

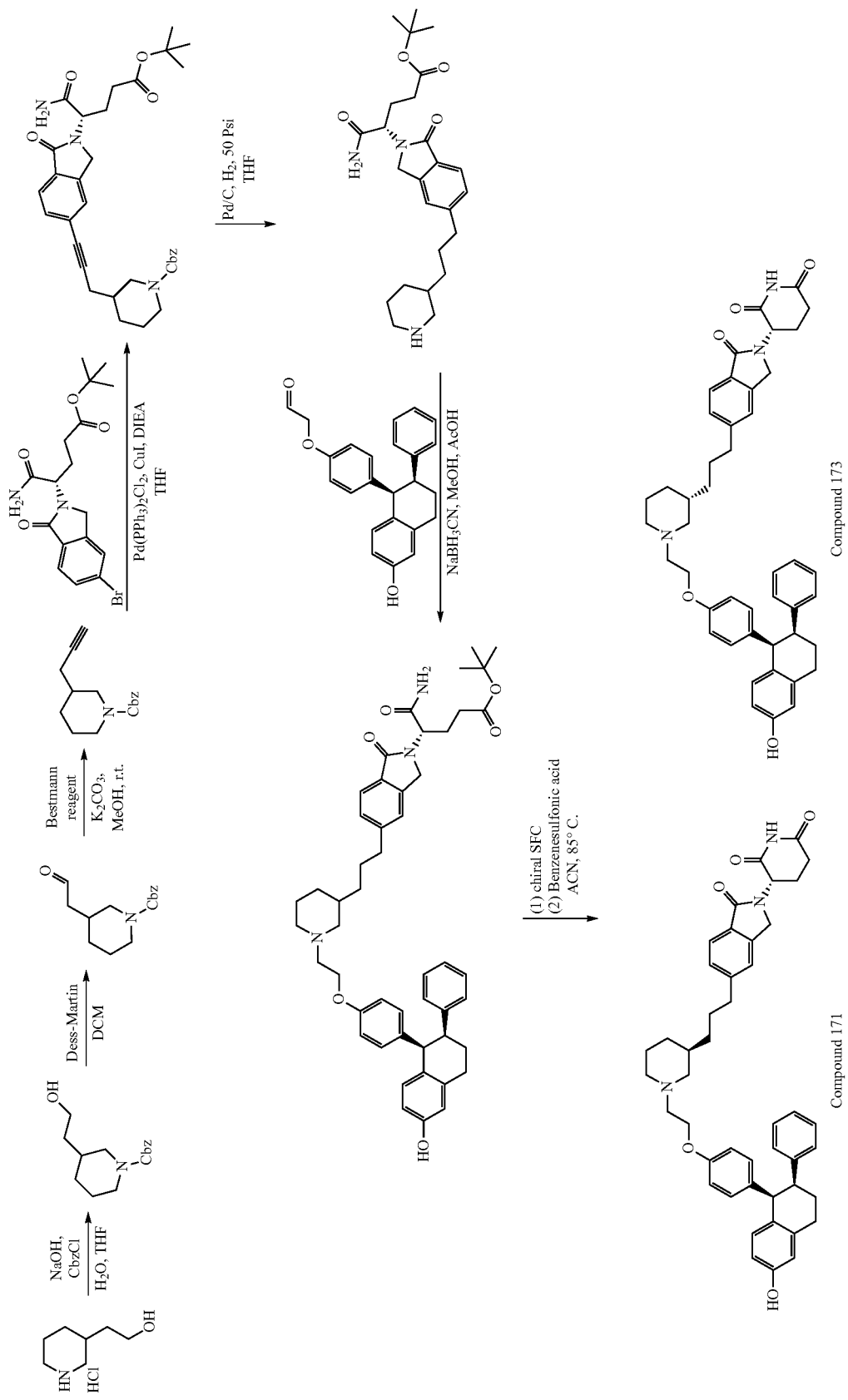

General synthetic scheme 3-32.
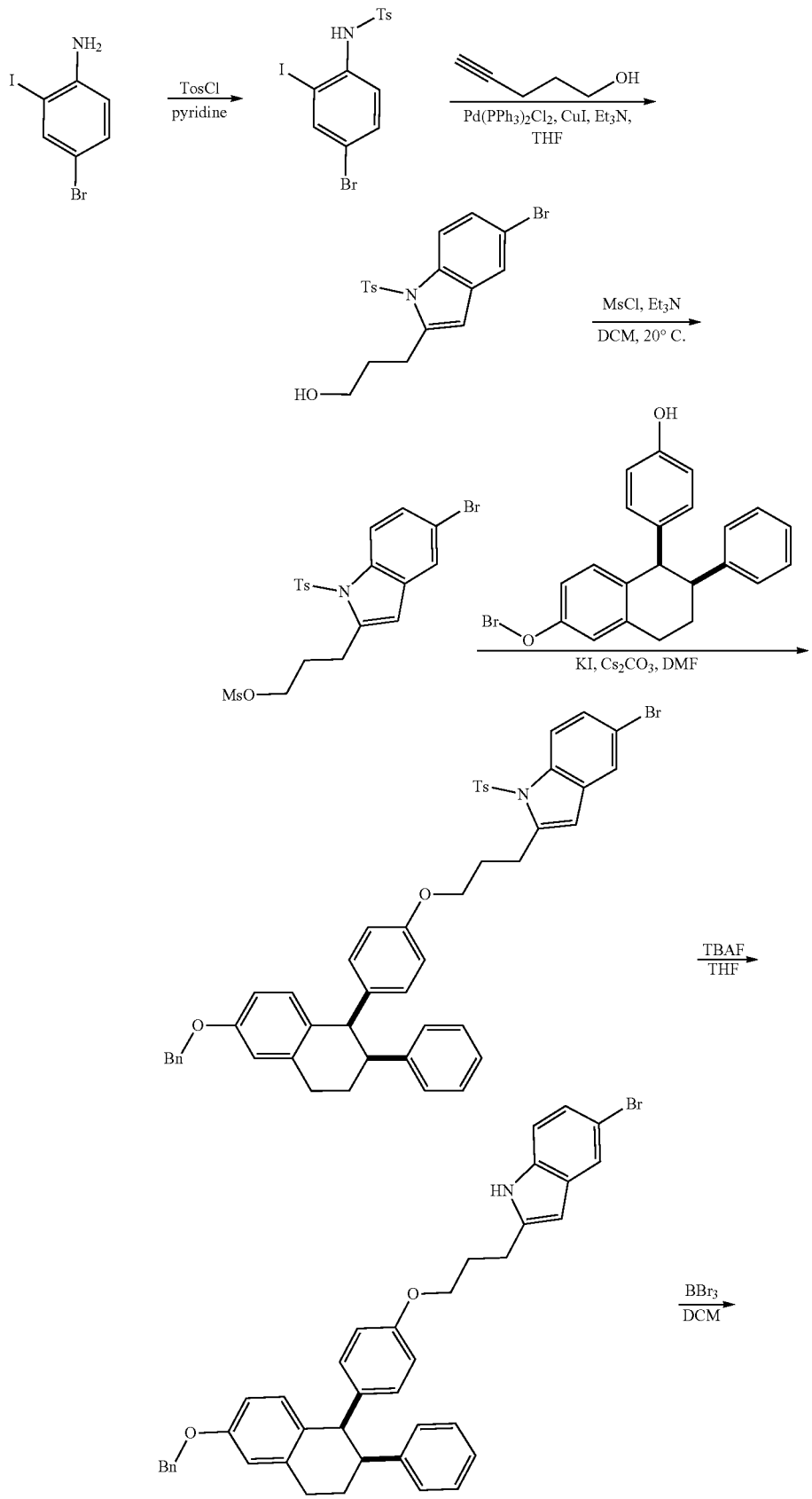

-continued
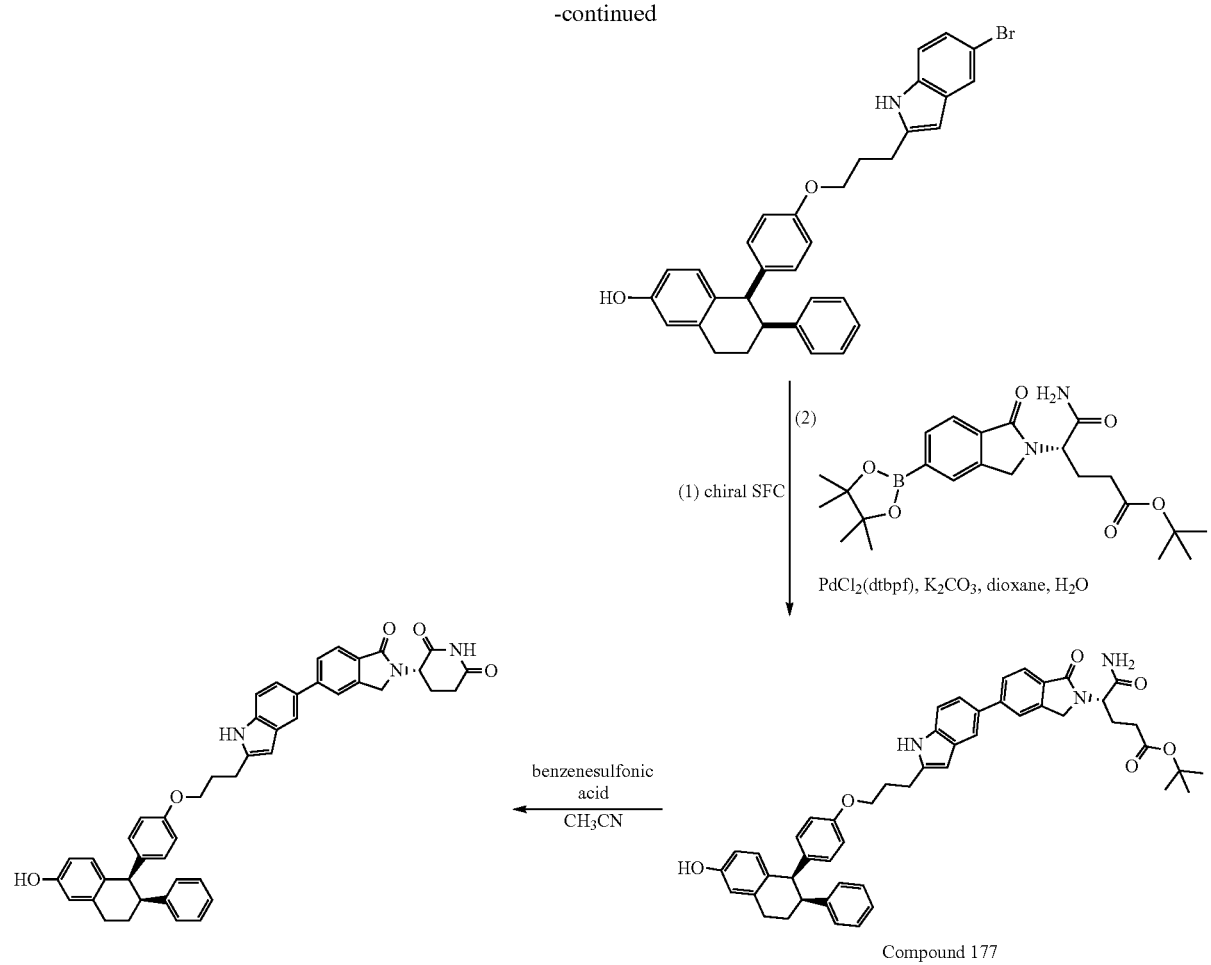
Compound 177
General synthetic scheme 3-33.
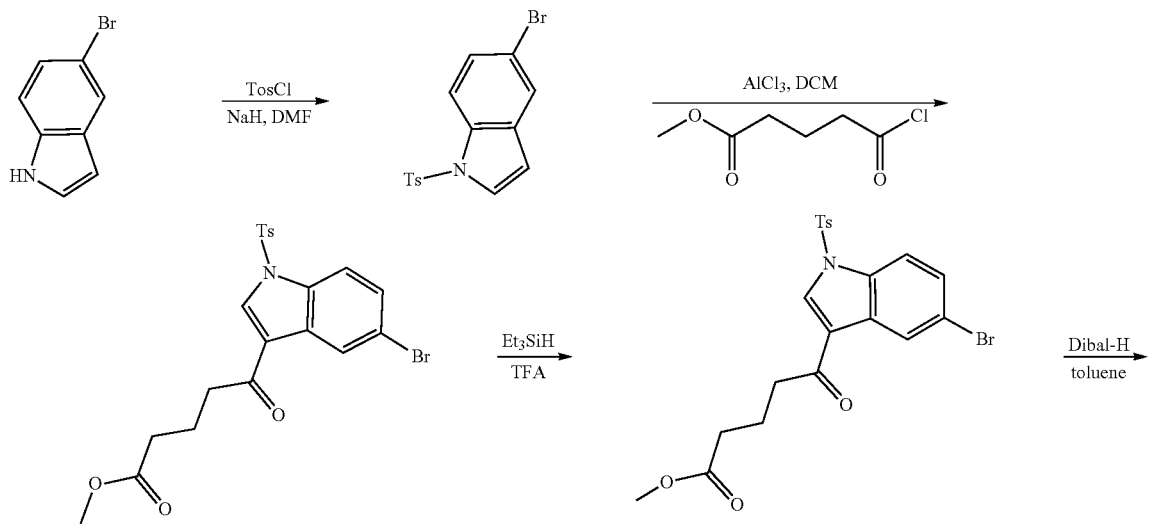

-continued
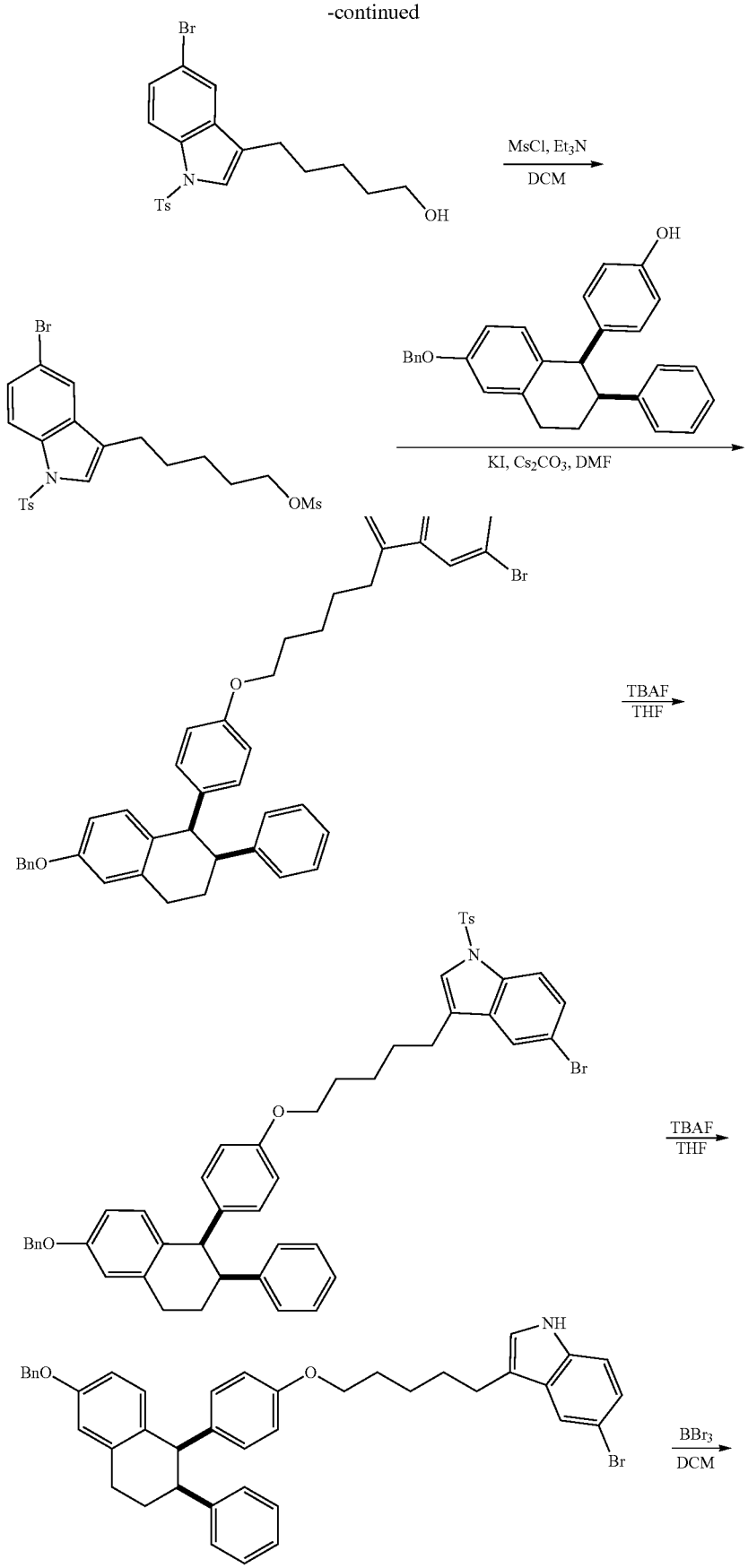

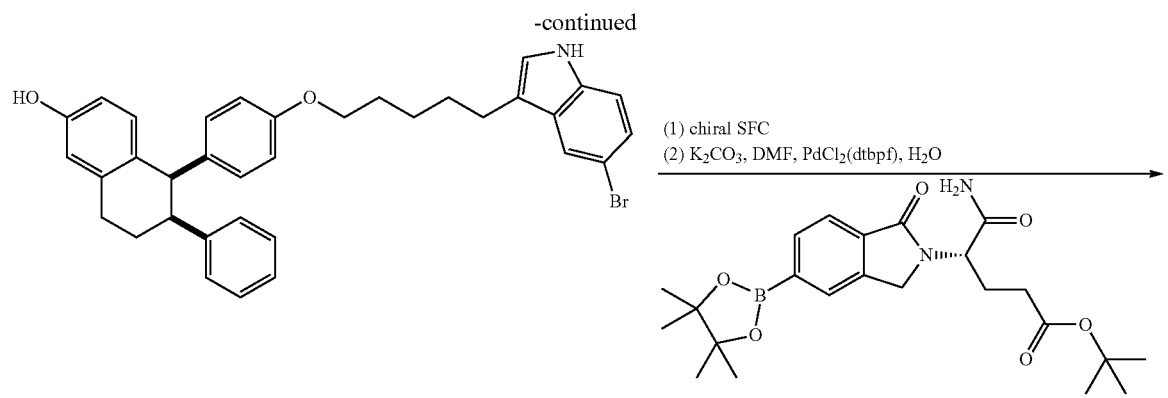
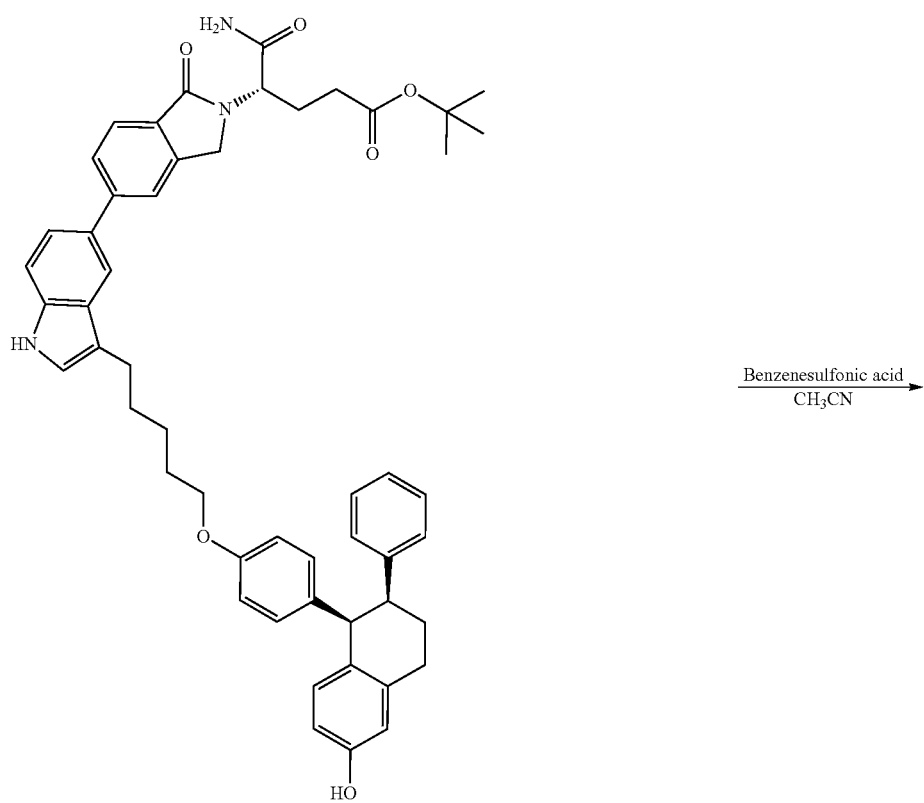

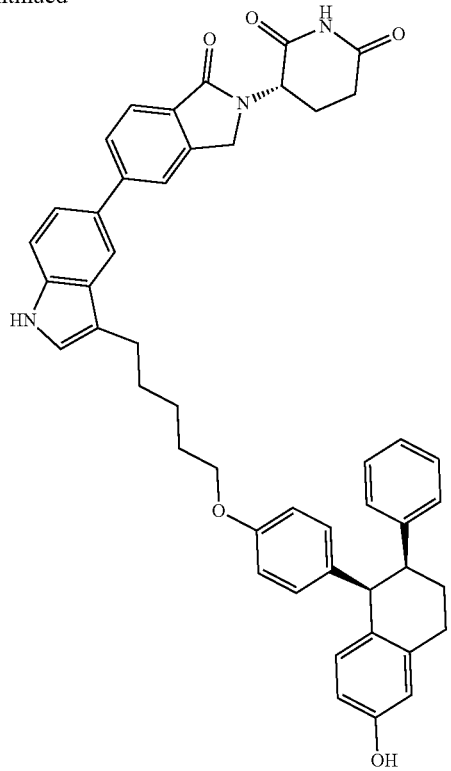
Compound 181
General synthetic scheme 3-34.
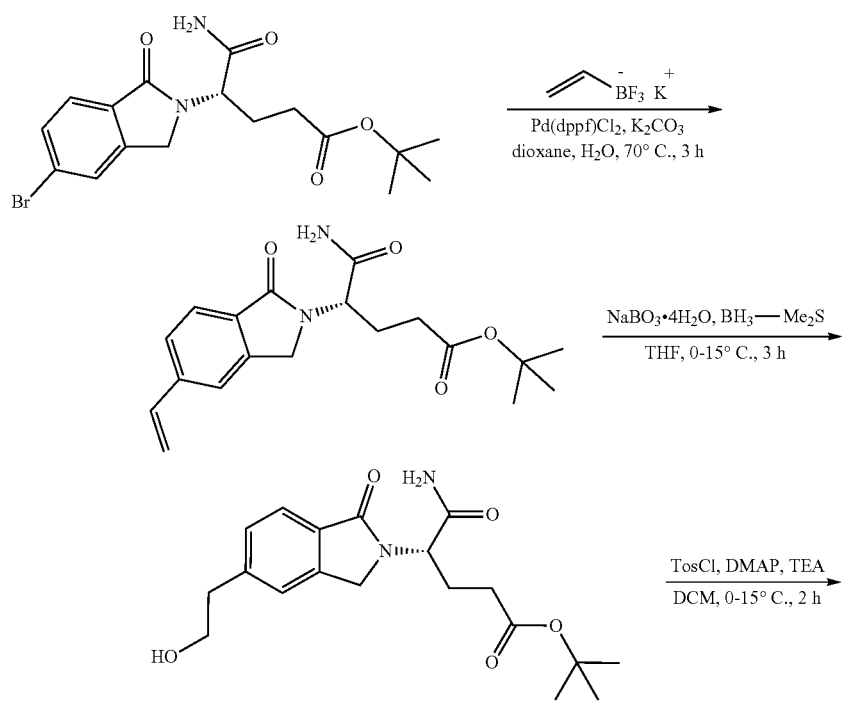

-continued
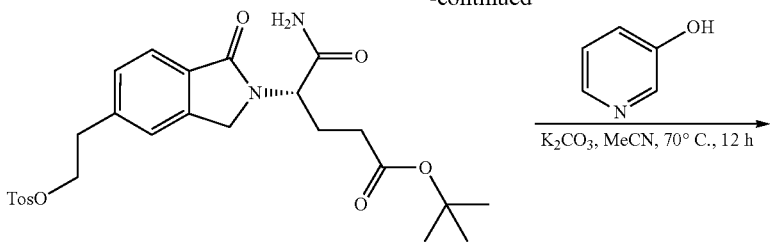
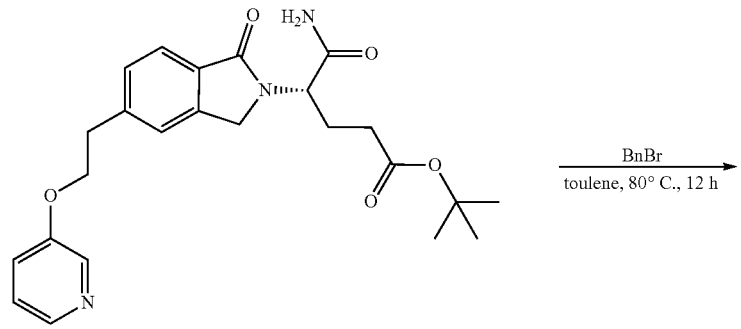
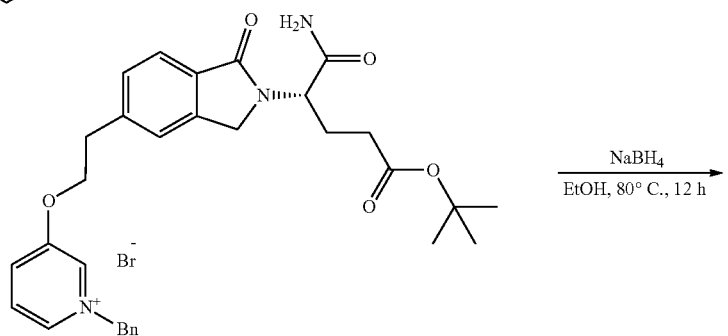
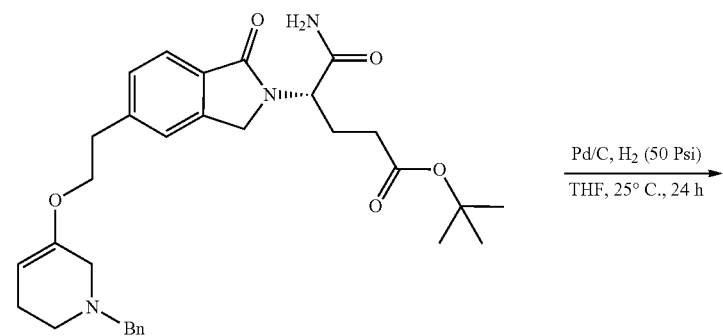
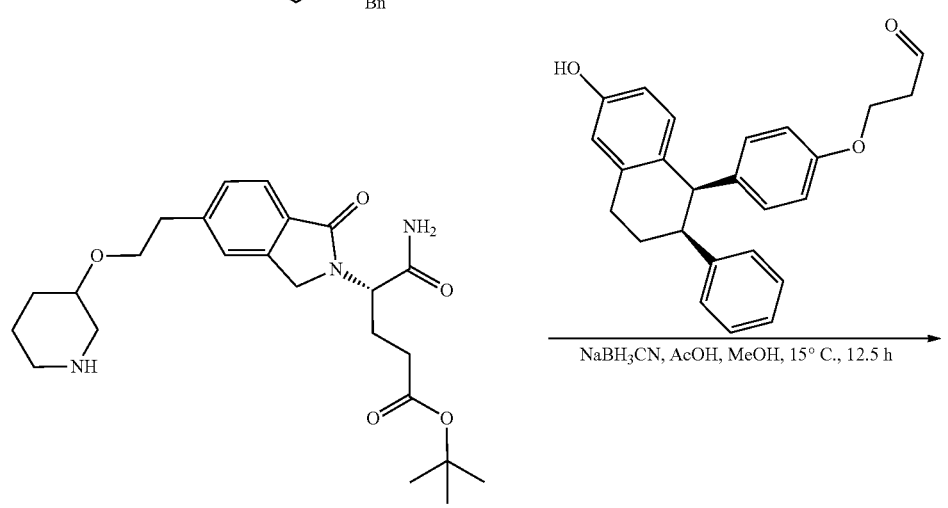

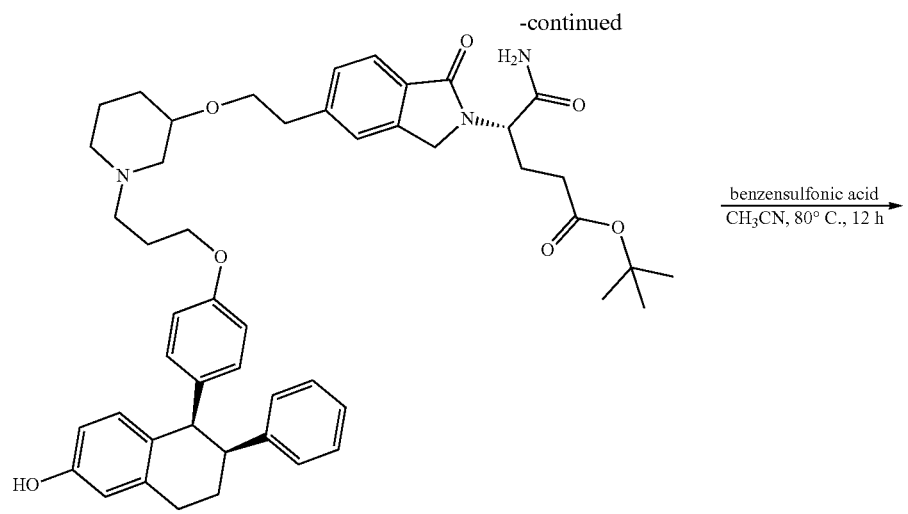
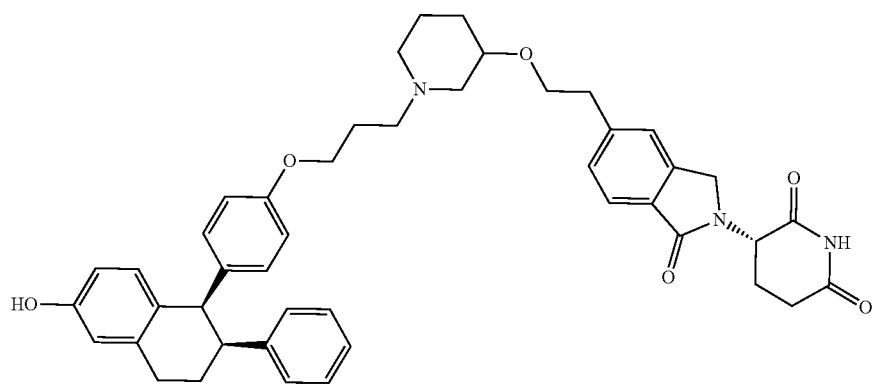
Compound 187
General synthetic scheme 3-35.
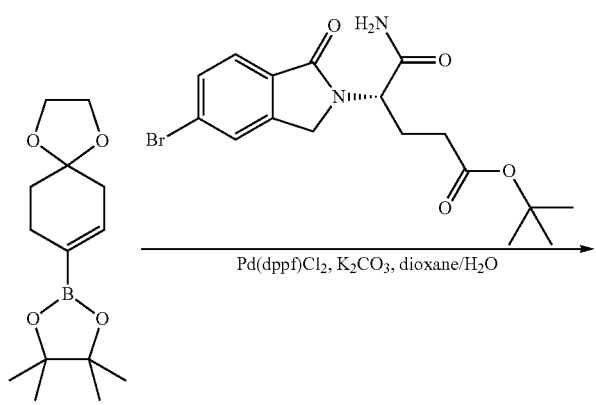

-continued
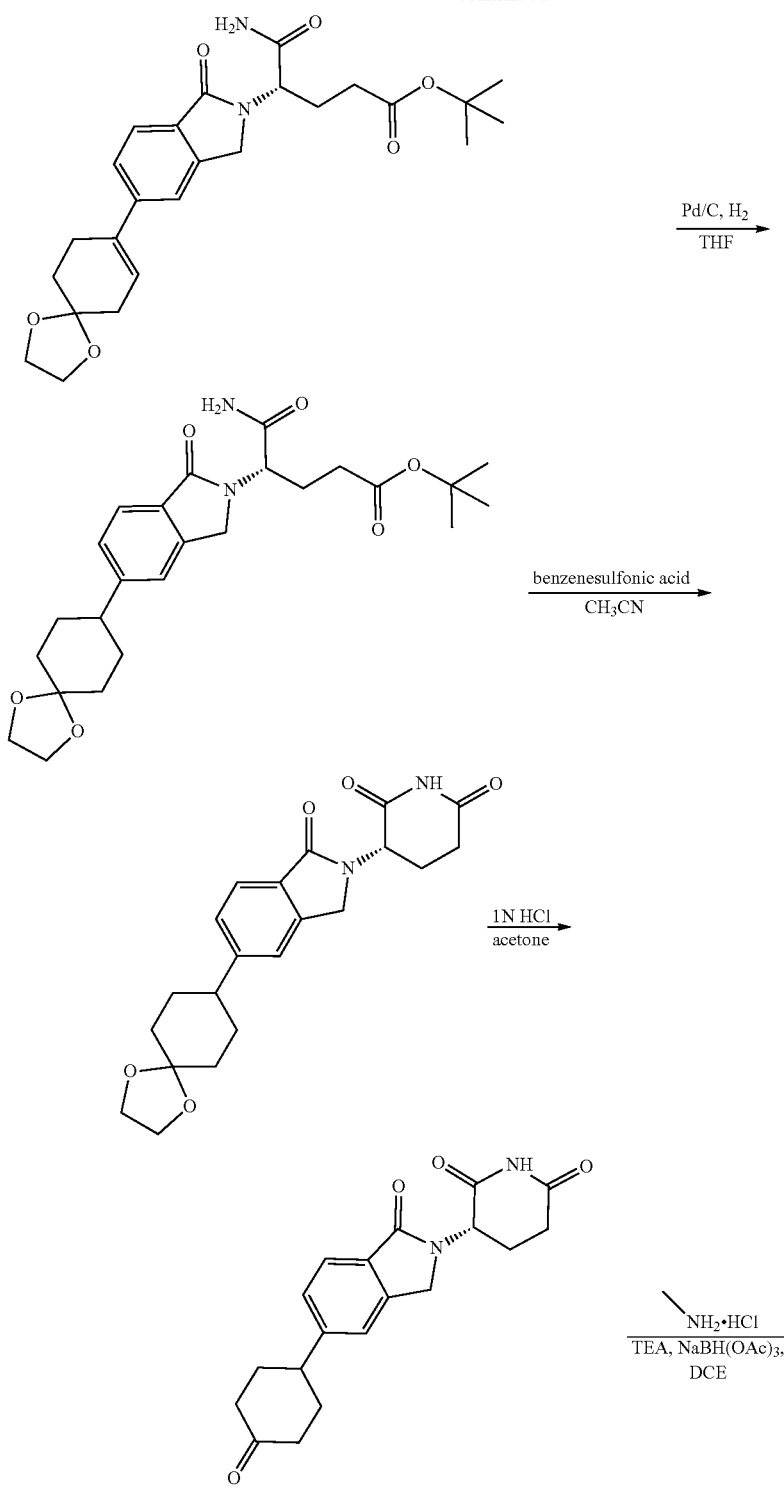

839
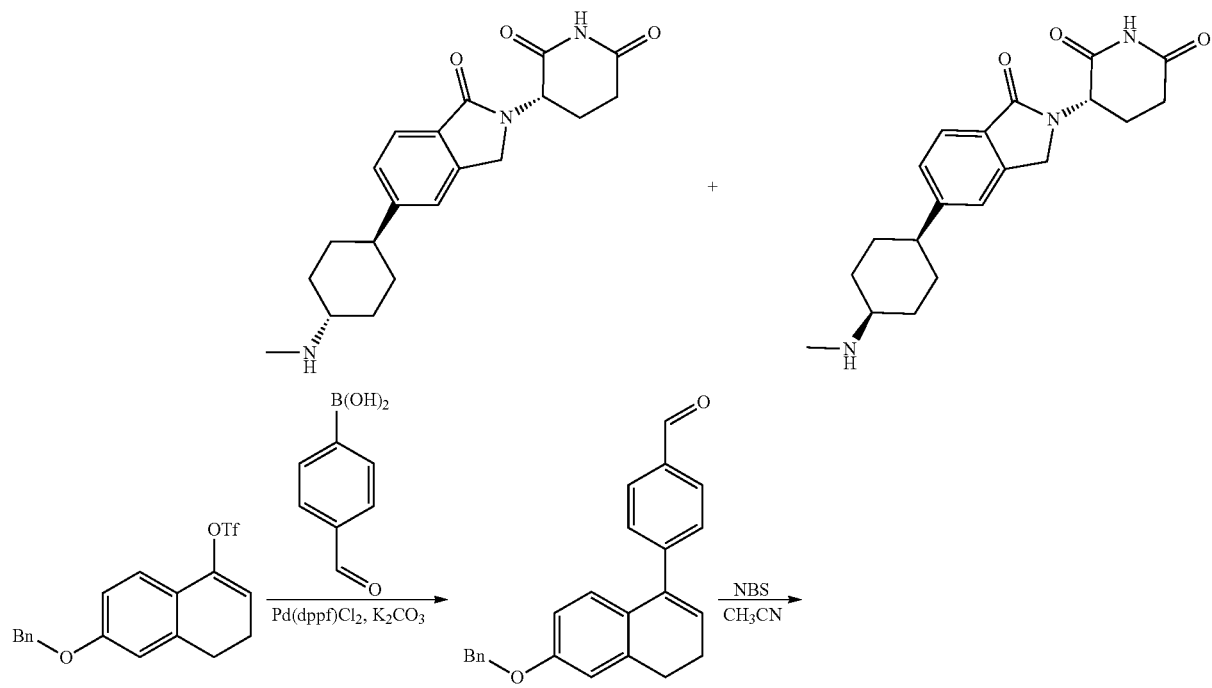
840
+
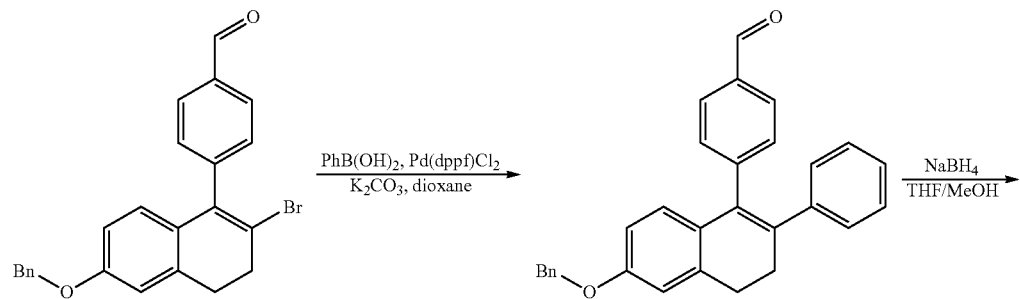
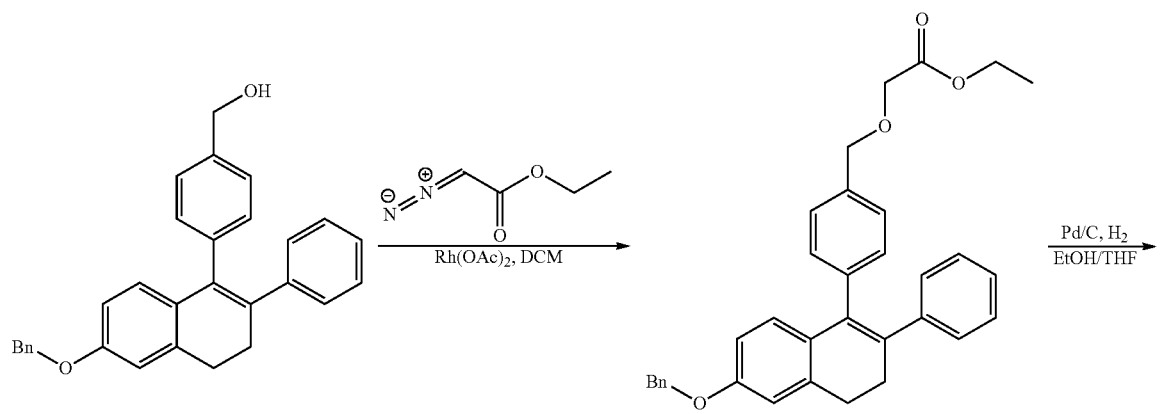

841 842
-continued
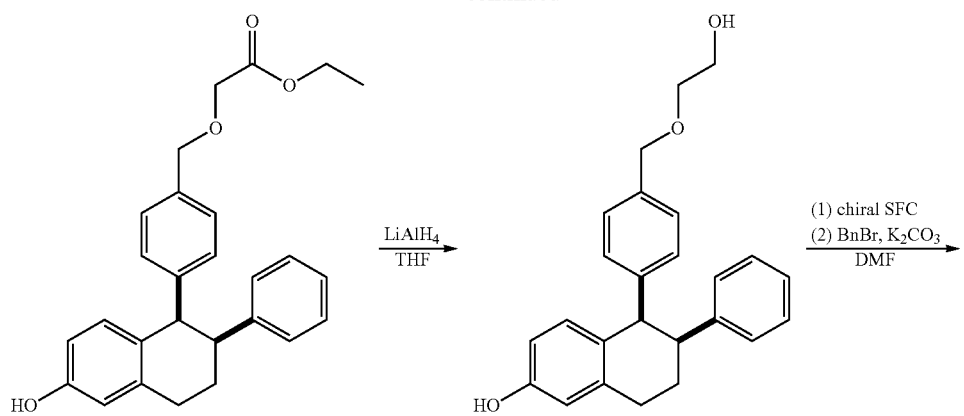
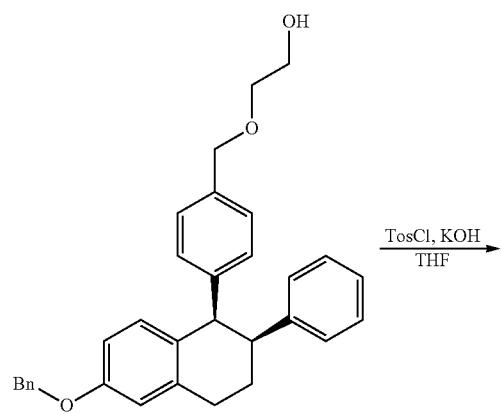
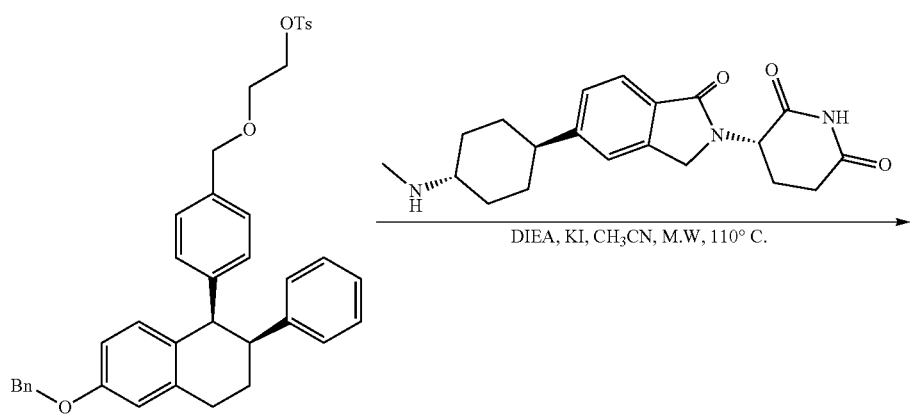

-continued
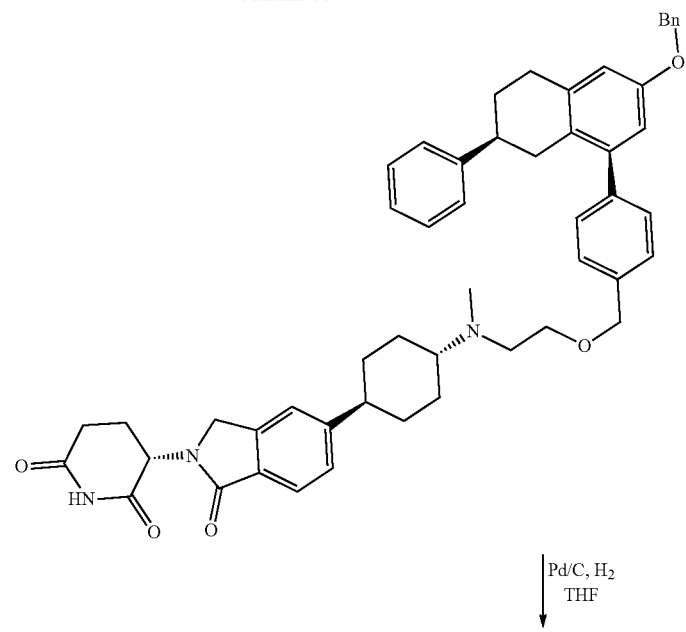
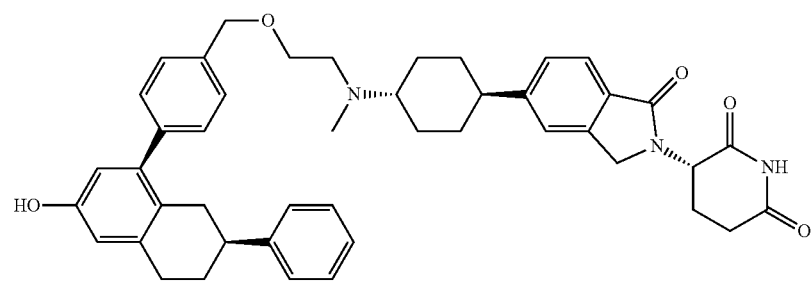
Compound 191
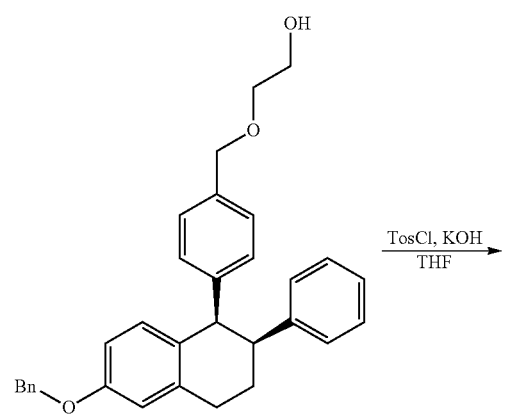

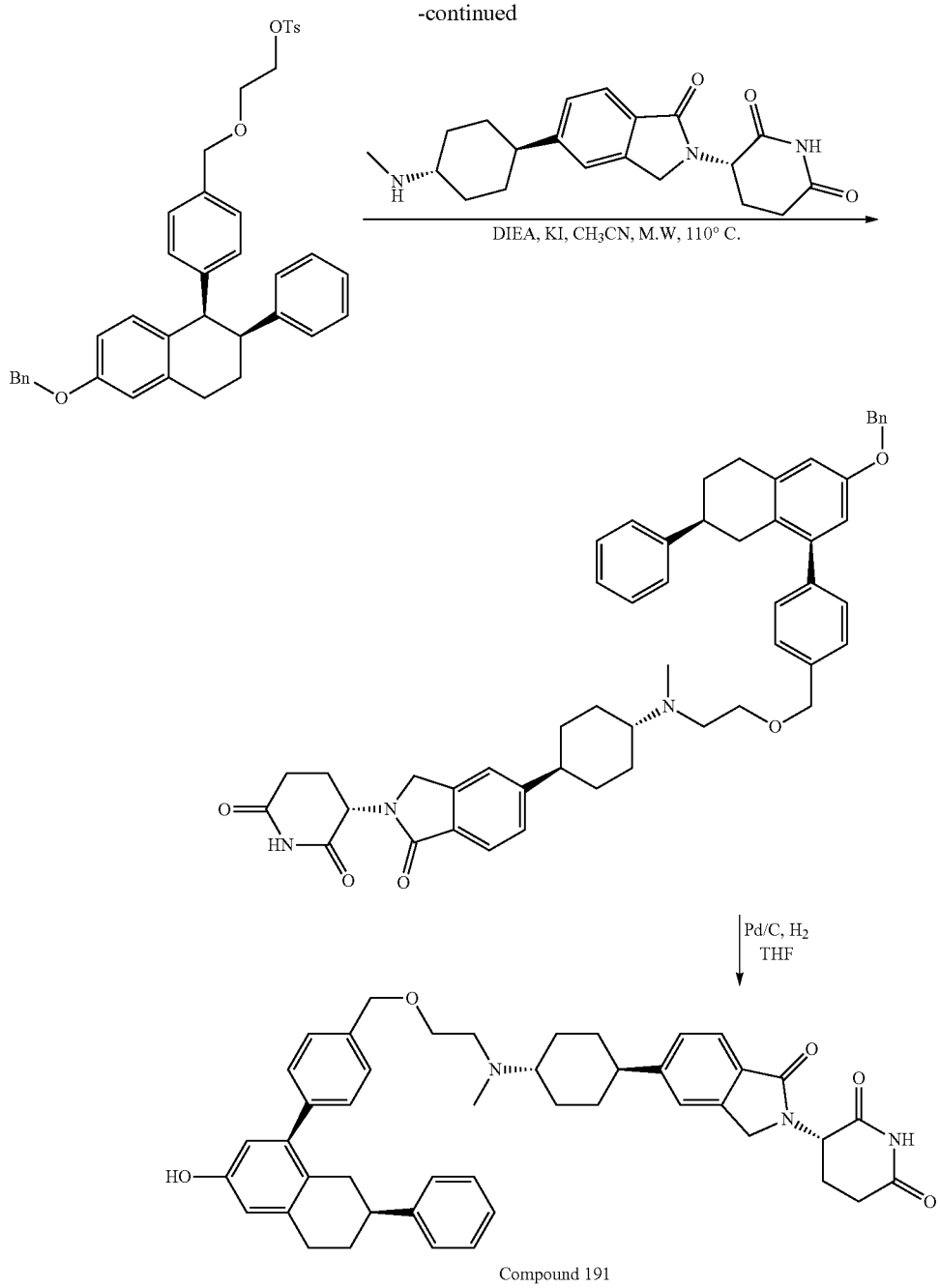
Compound 191
General synthetic scheme 3-36.
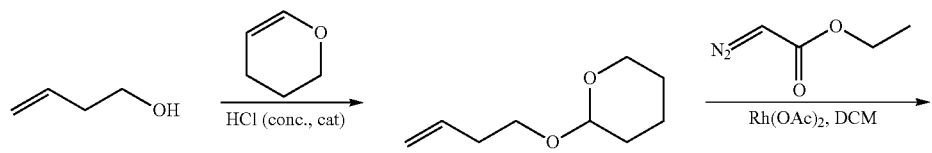

847 848
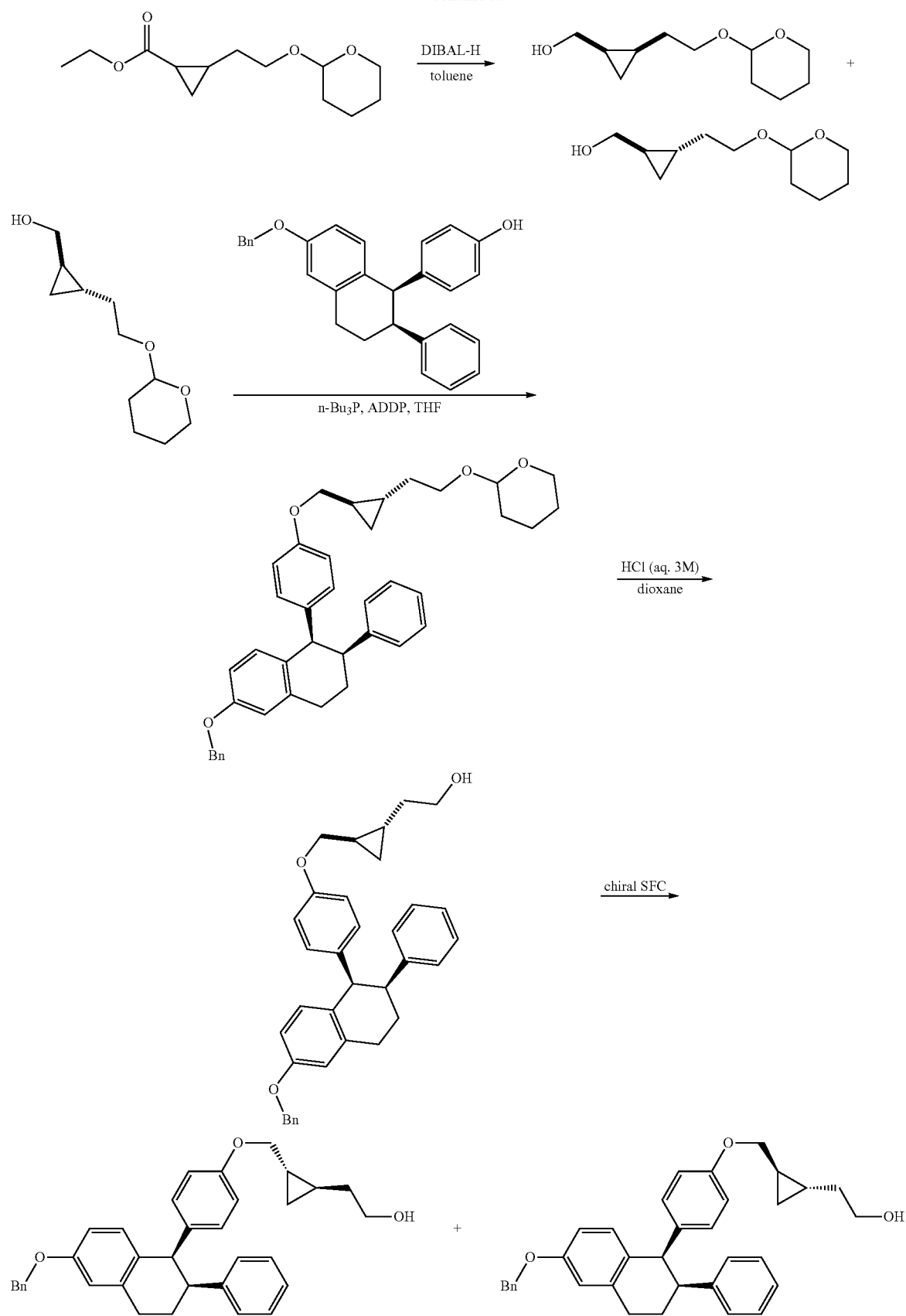

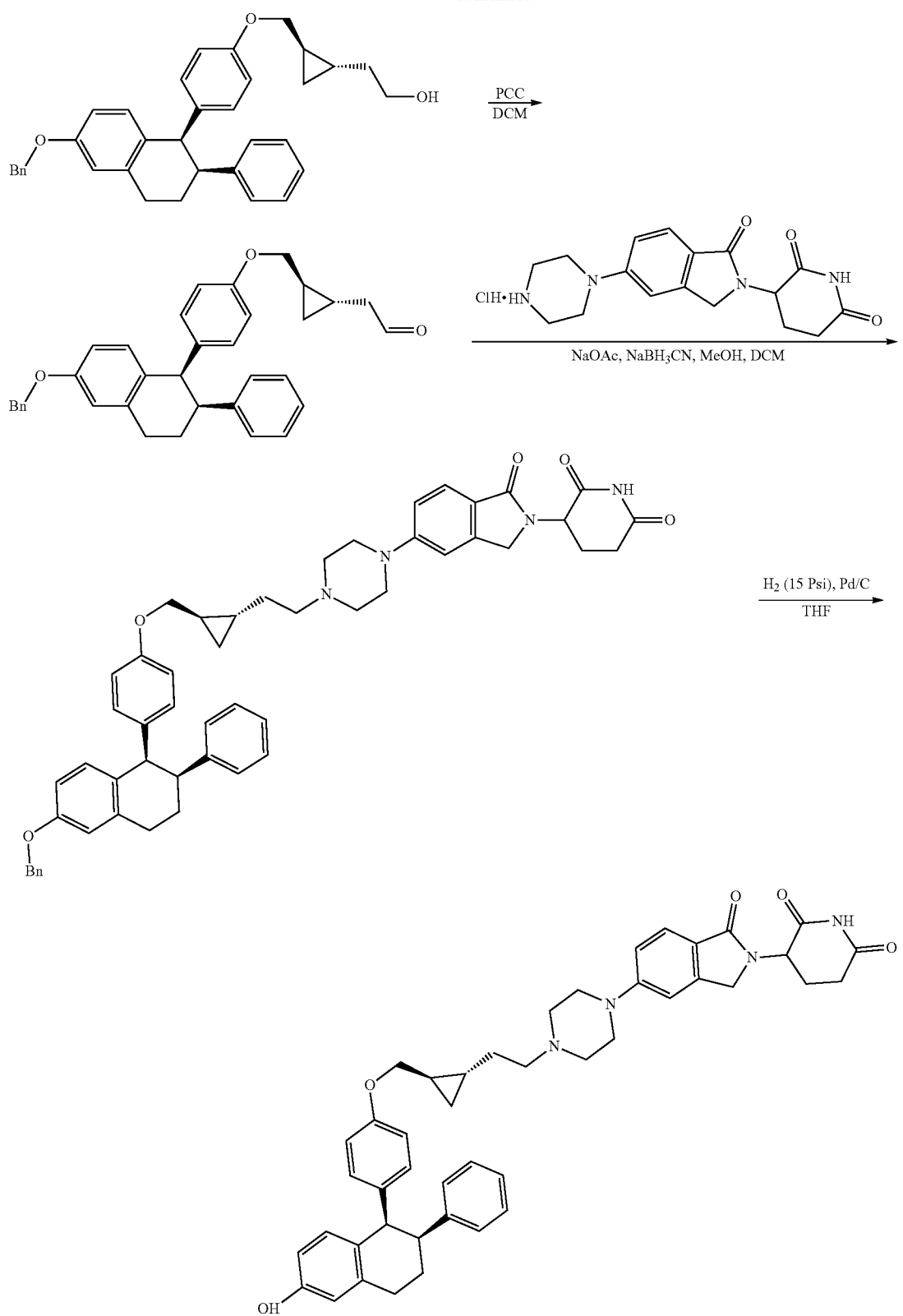
Compound 200

General synthetic scheme 3-37.
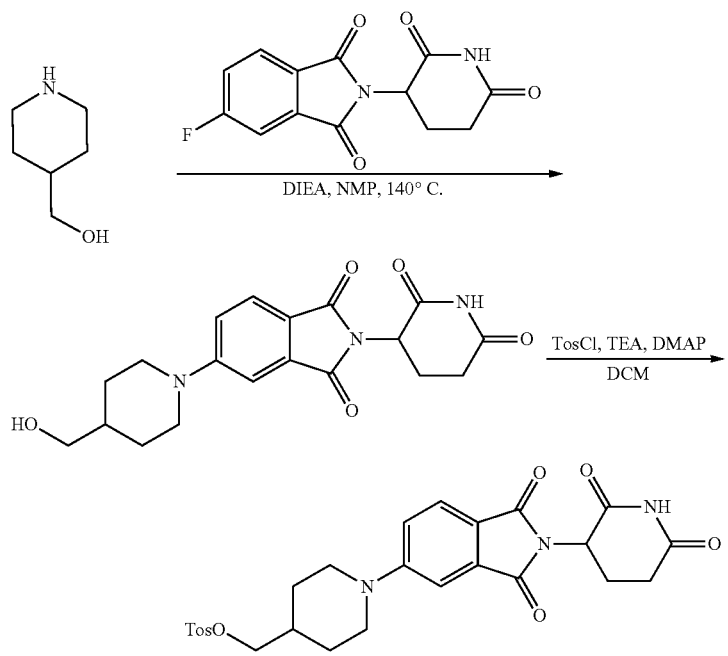
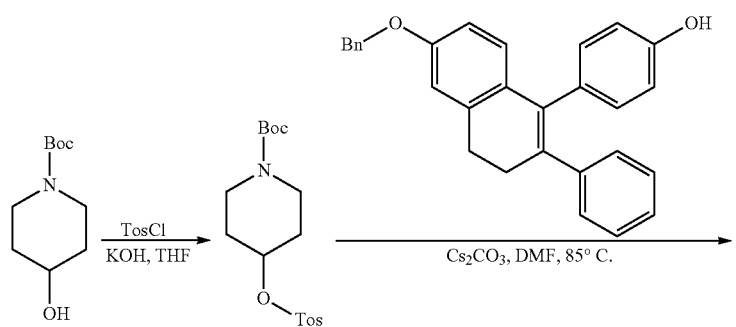
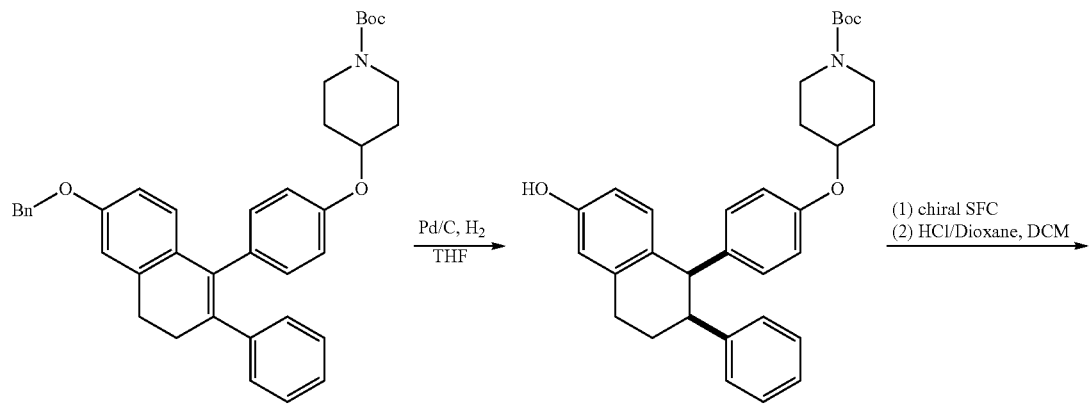

853 854
-continued
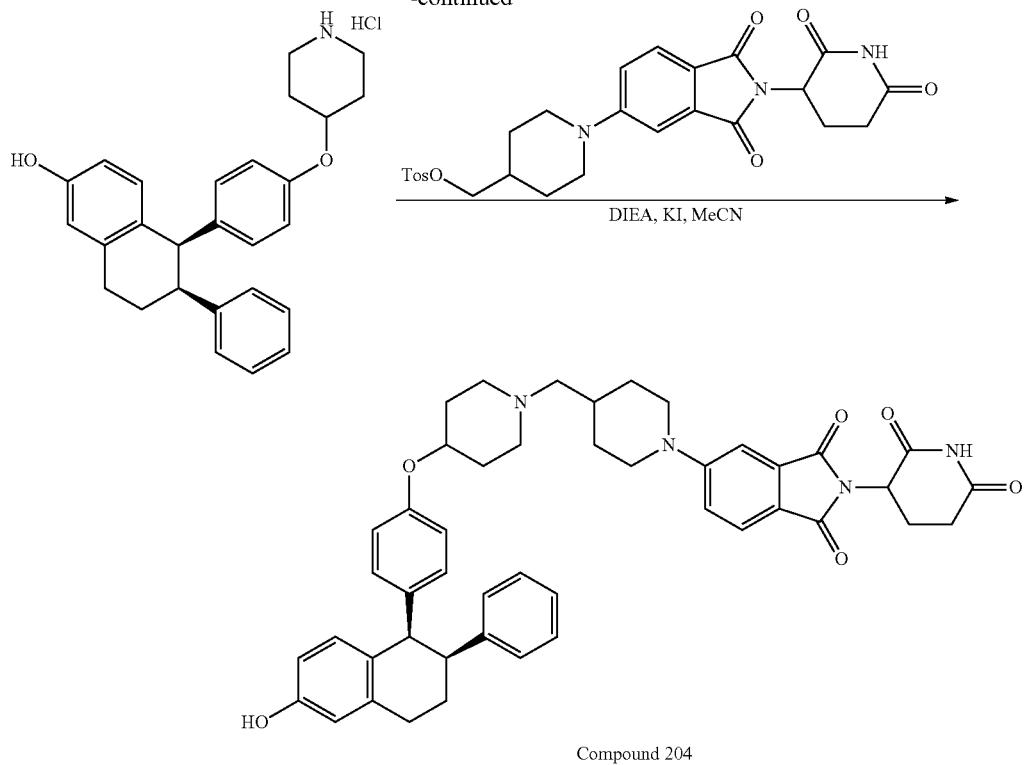
Compound 204
General synthetic scheme 3-38.
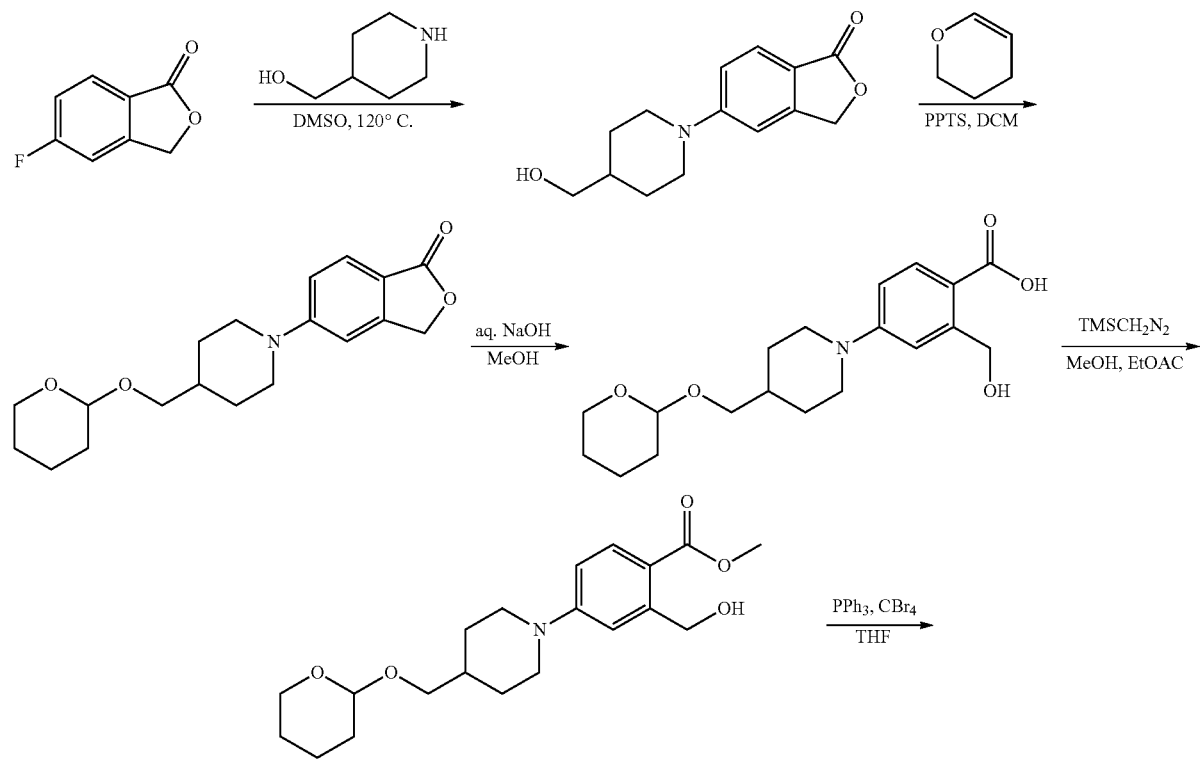

-continued
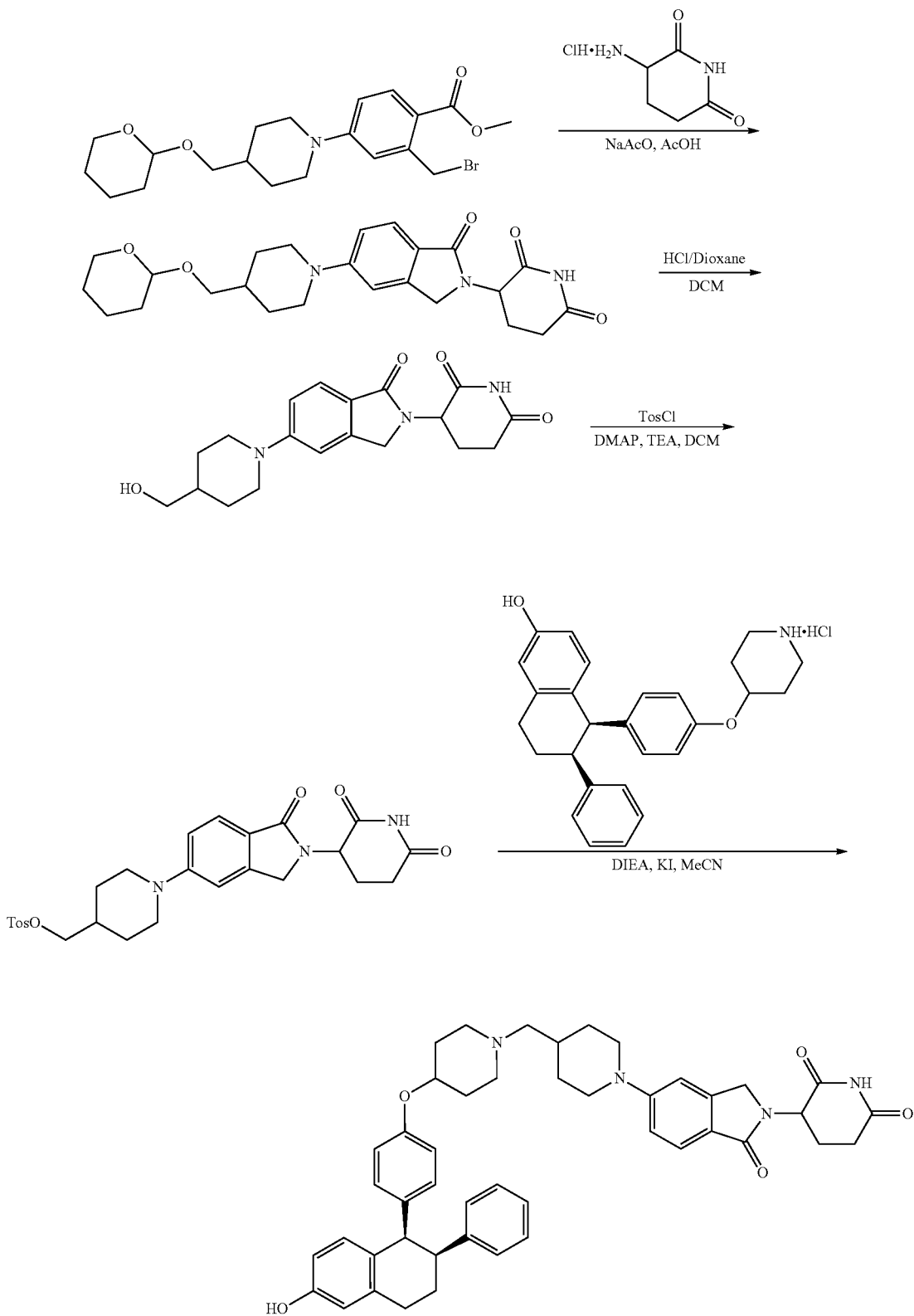
Compound 241

General synthetic scheme 3-39.
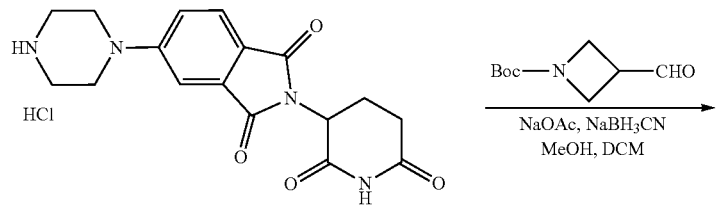
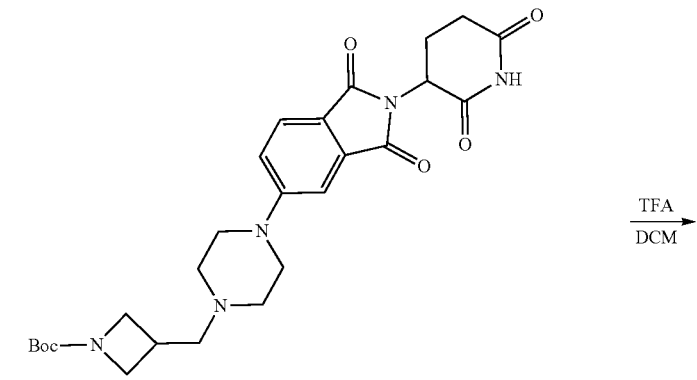
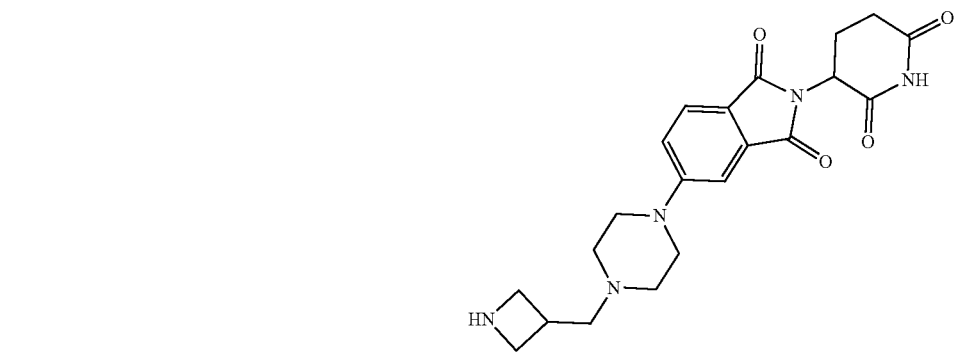
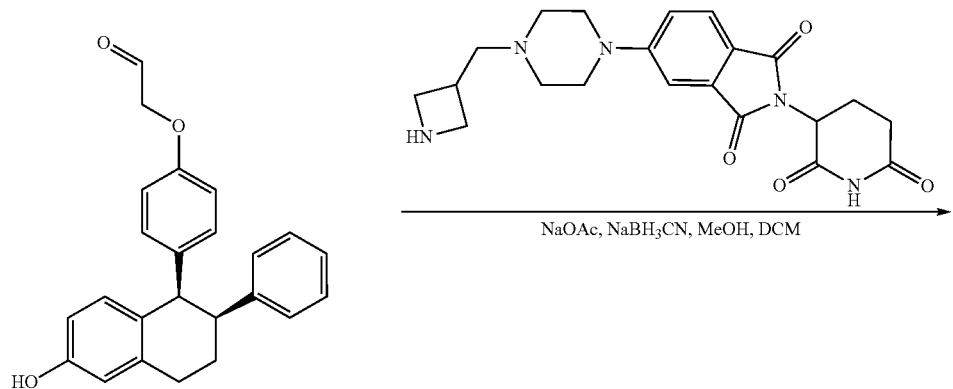

-continued
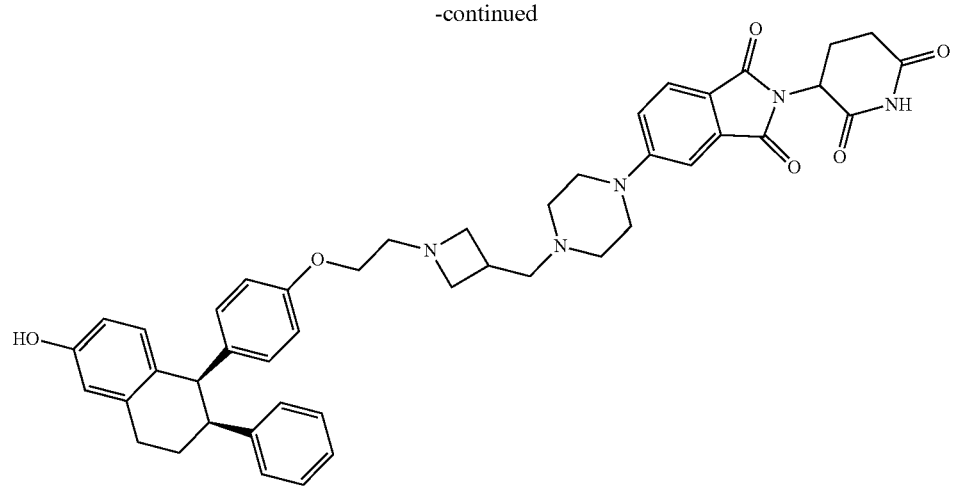
Compound 210
General synthetic scheme 3-40.

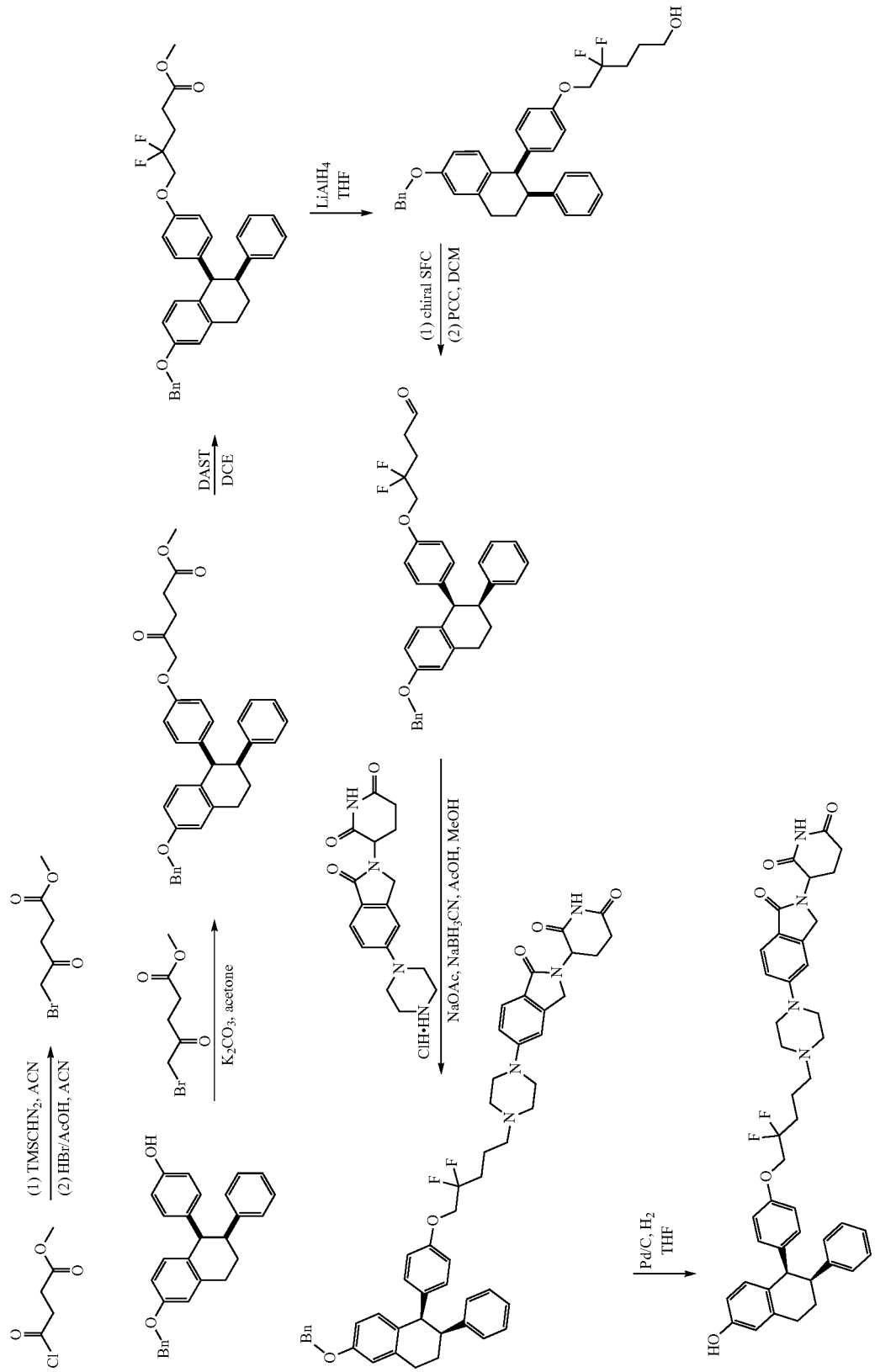

General synthetic scheme 3-41.
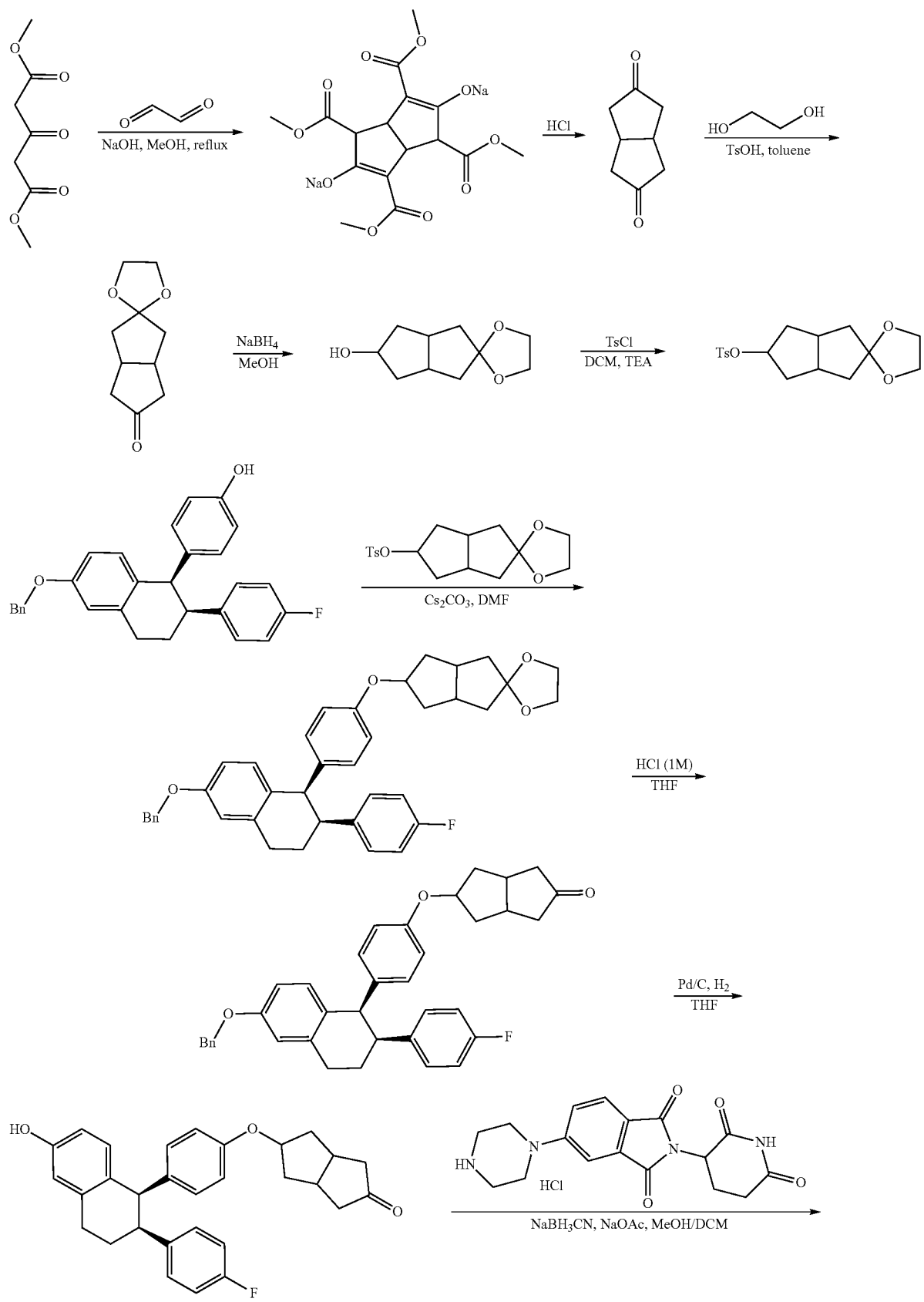

-continued
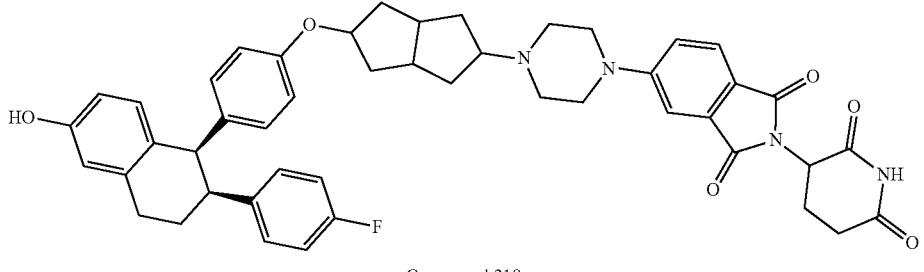
Compound 218
General synthetic scheme 3-42.
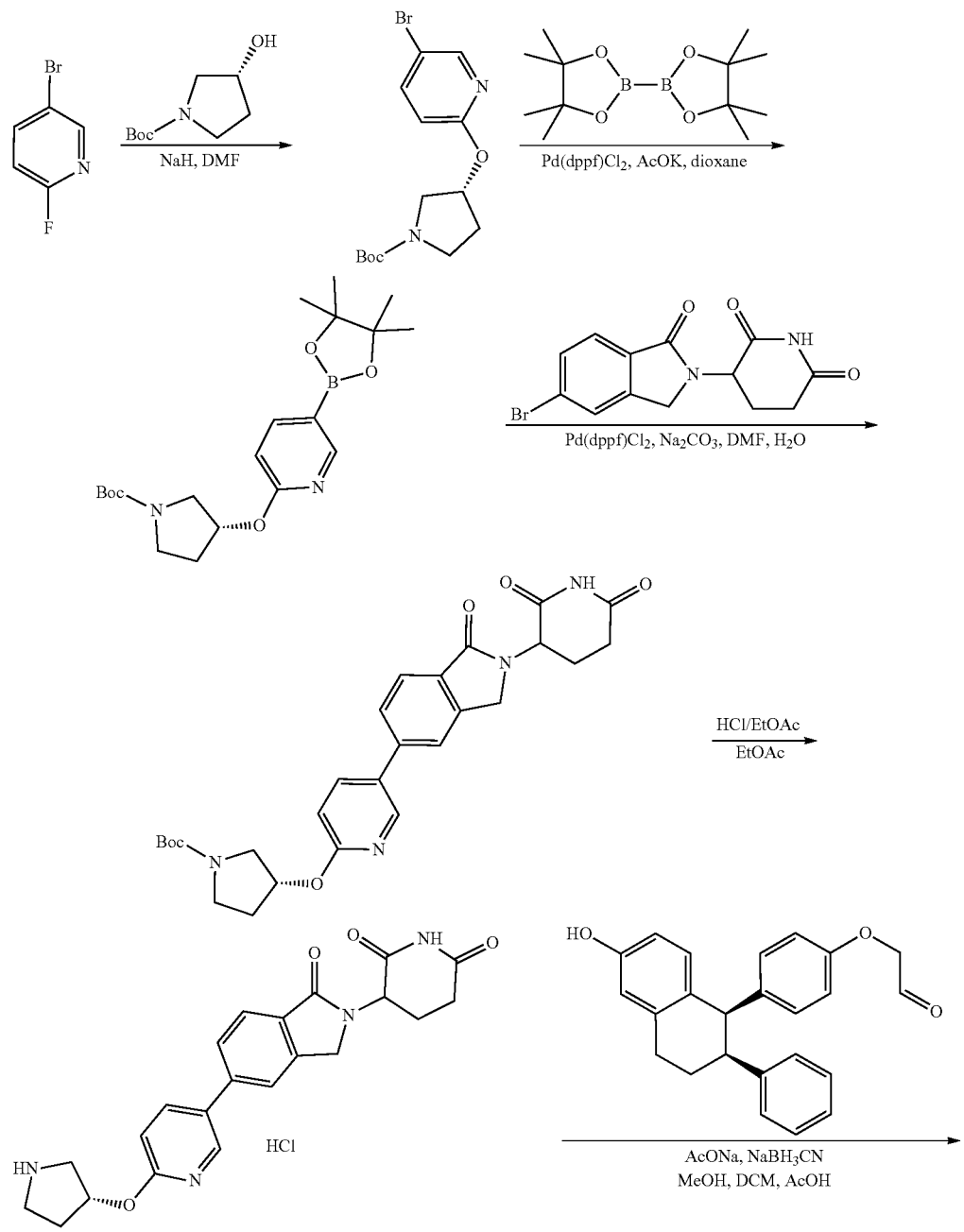

-continued
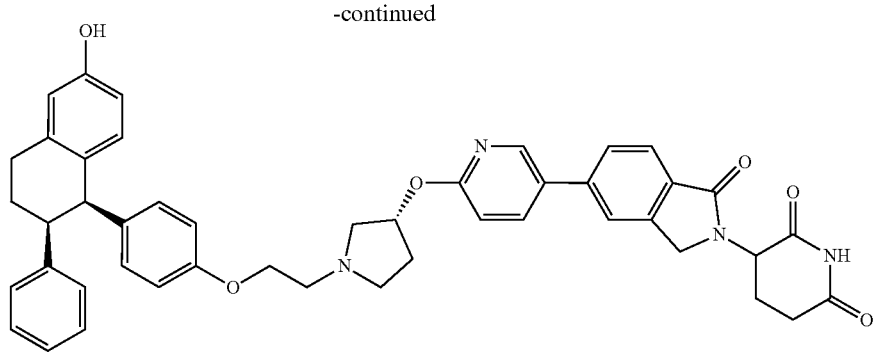
Compound 223
General synthetic scheme 3-43.
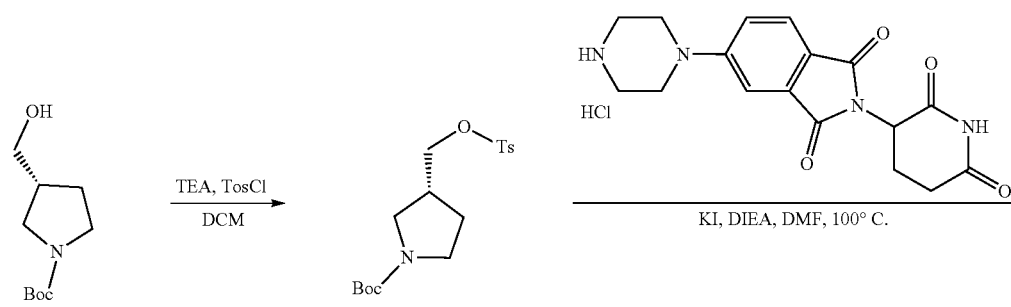
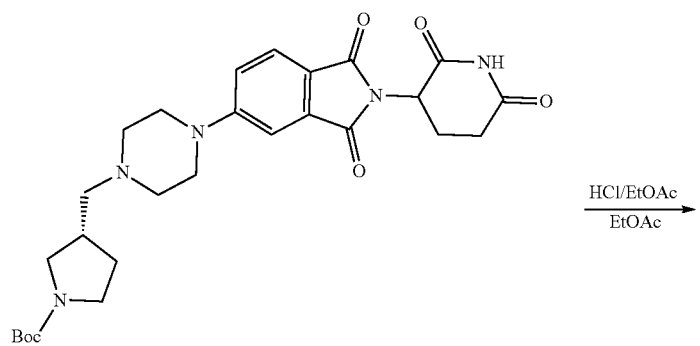
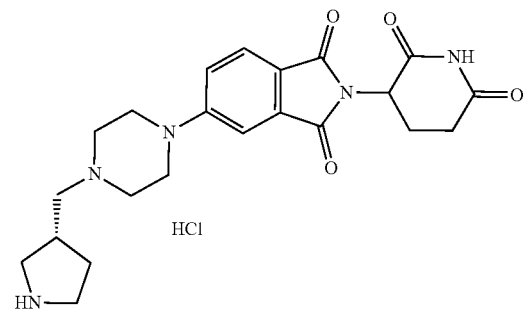

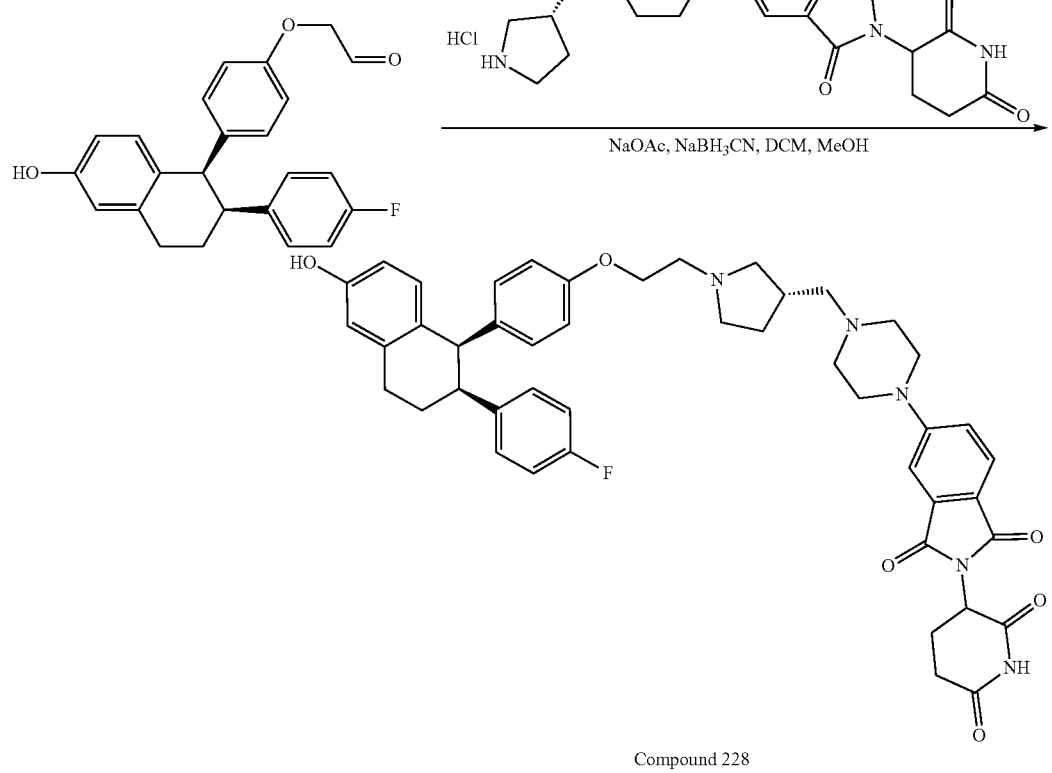
Compound 228
General synthetic scheme 3-44 to prepare claimed compounds.
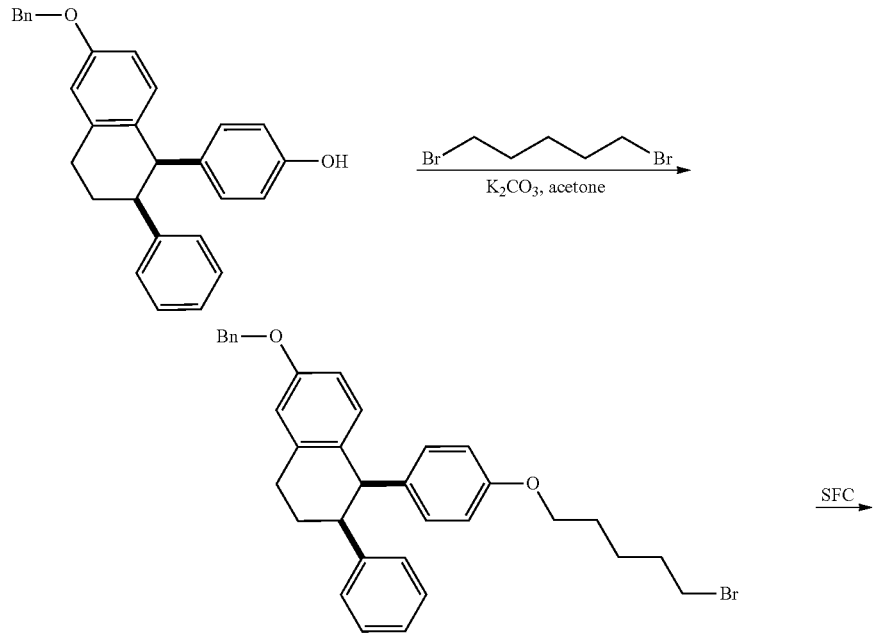

871 872
-continued
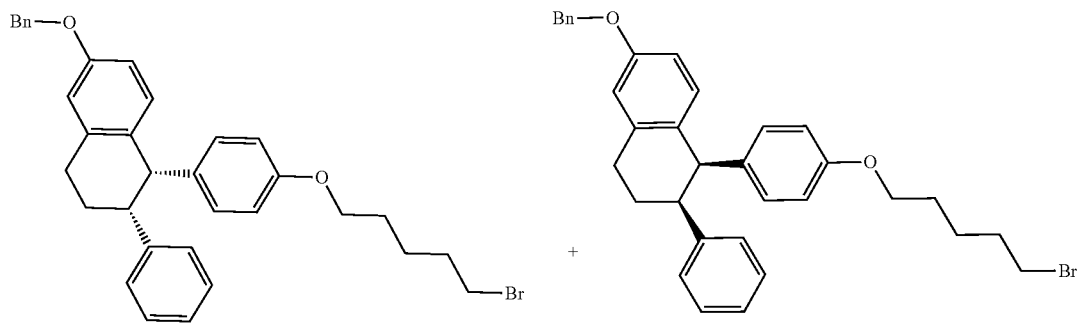
+
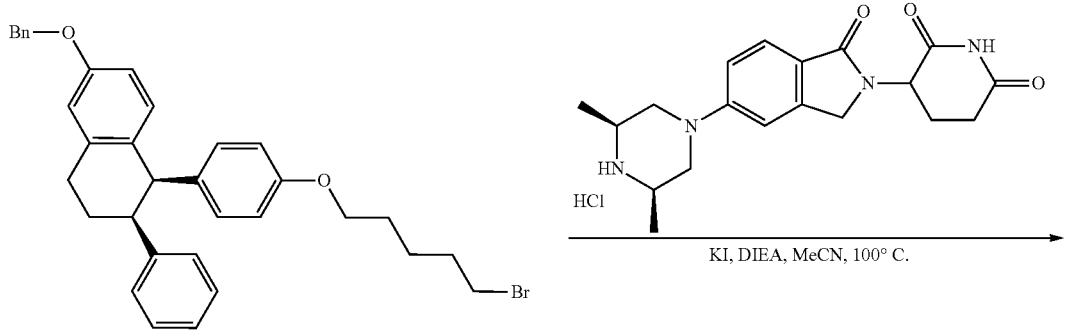
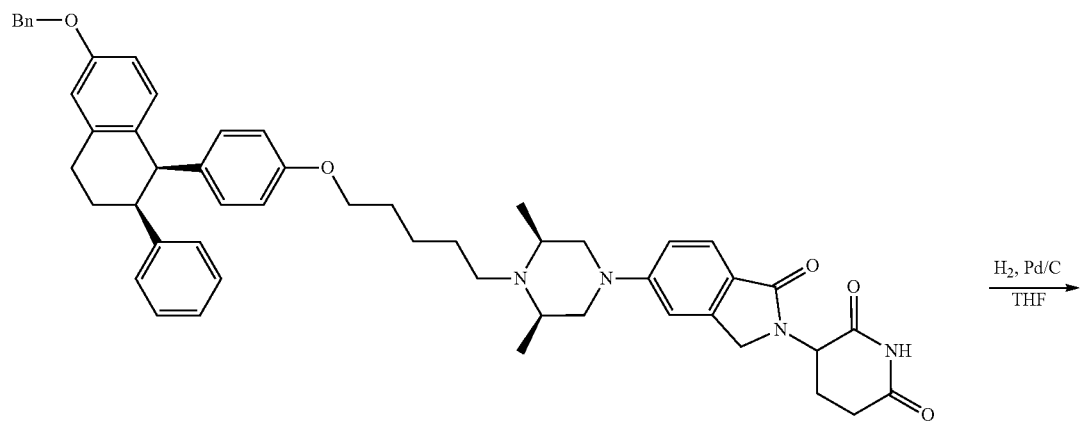
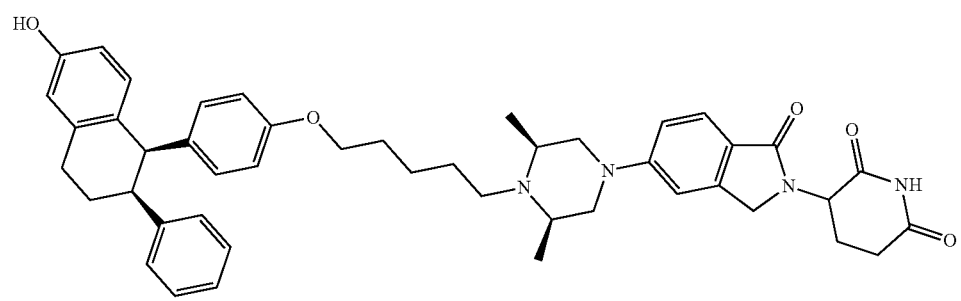
Compound 239

General synthetic scheme 3-45 to prepare claimed compounds.
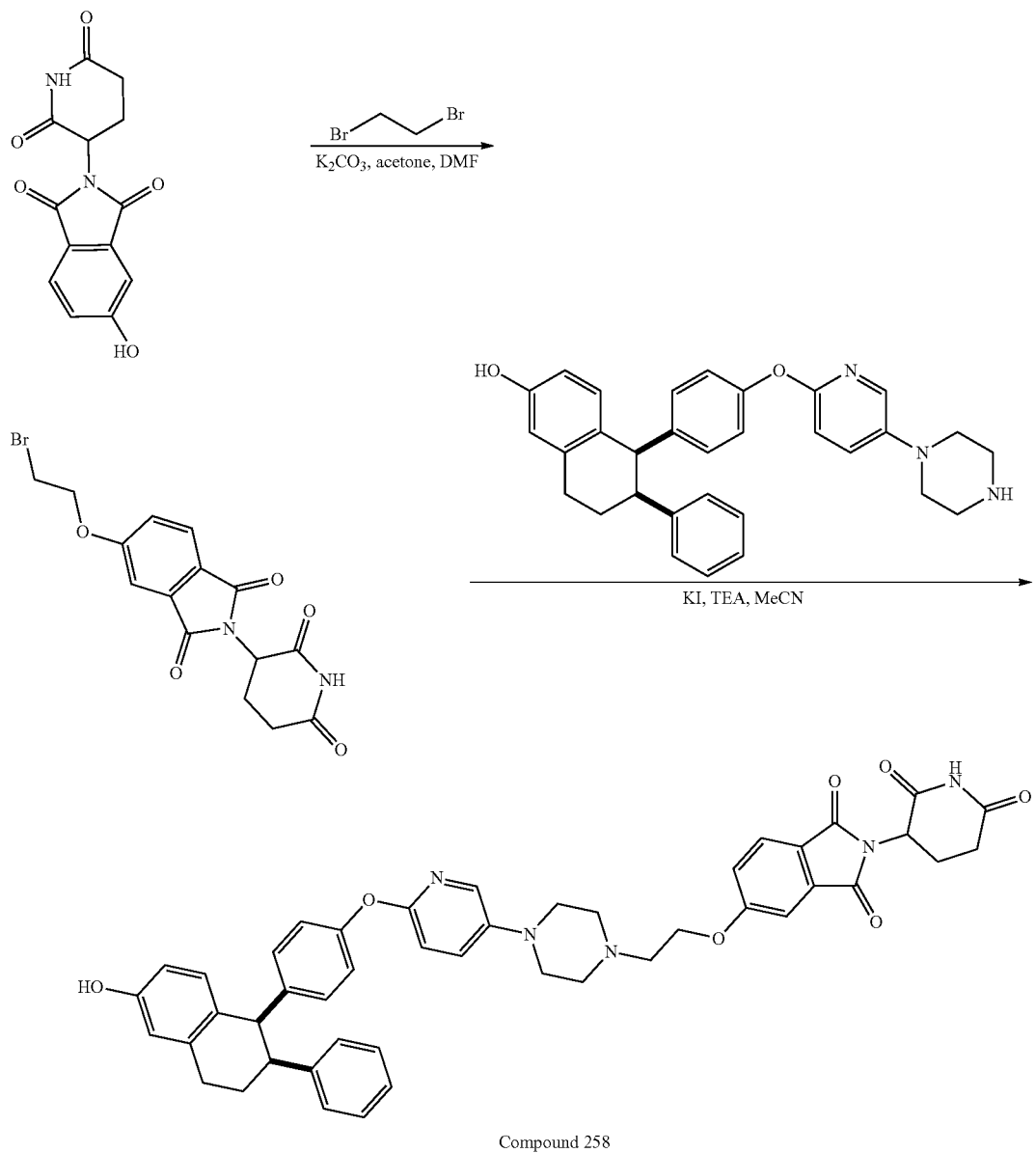
Compound 258
General synthetic scheme 3-46 to prepare claimed compounds.
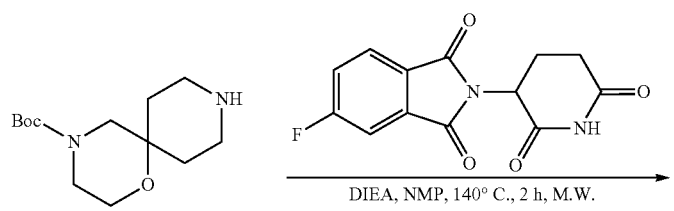

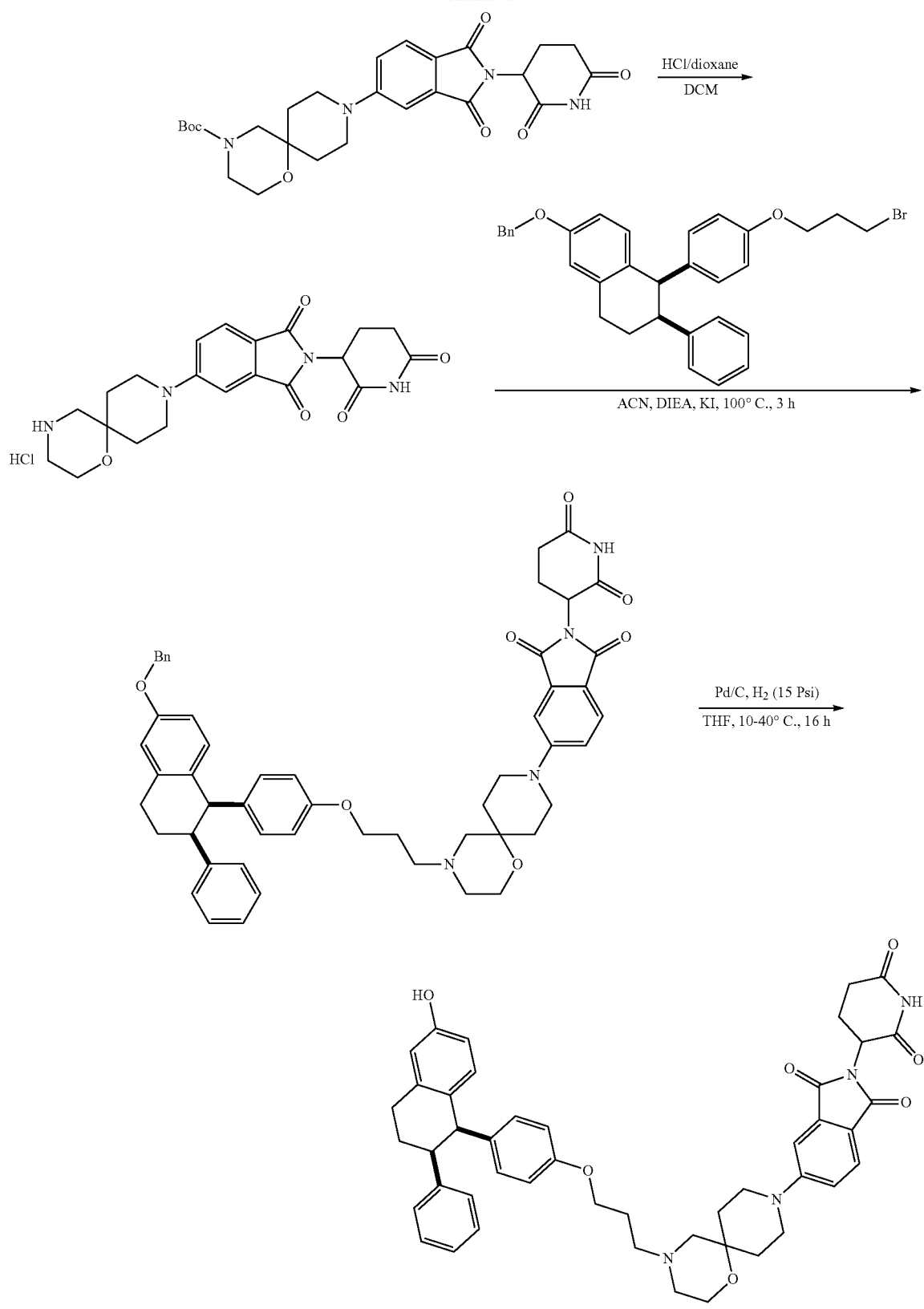

General synthetic scheme 3-47.
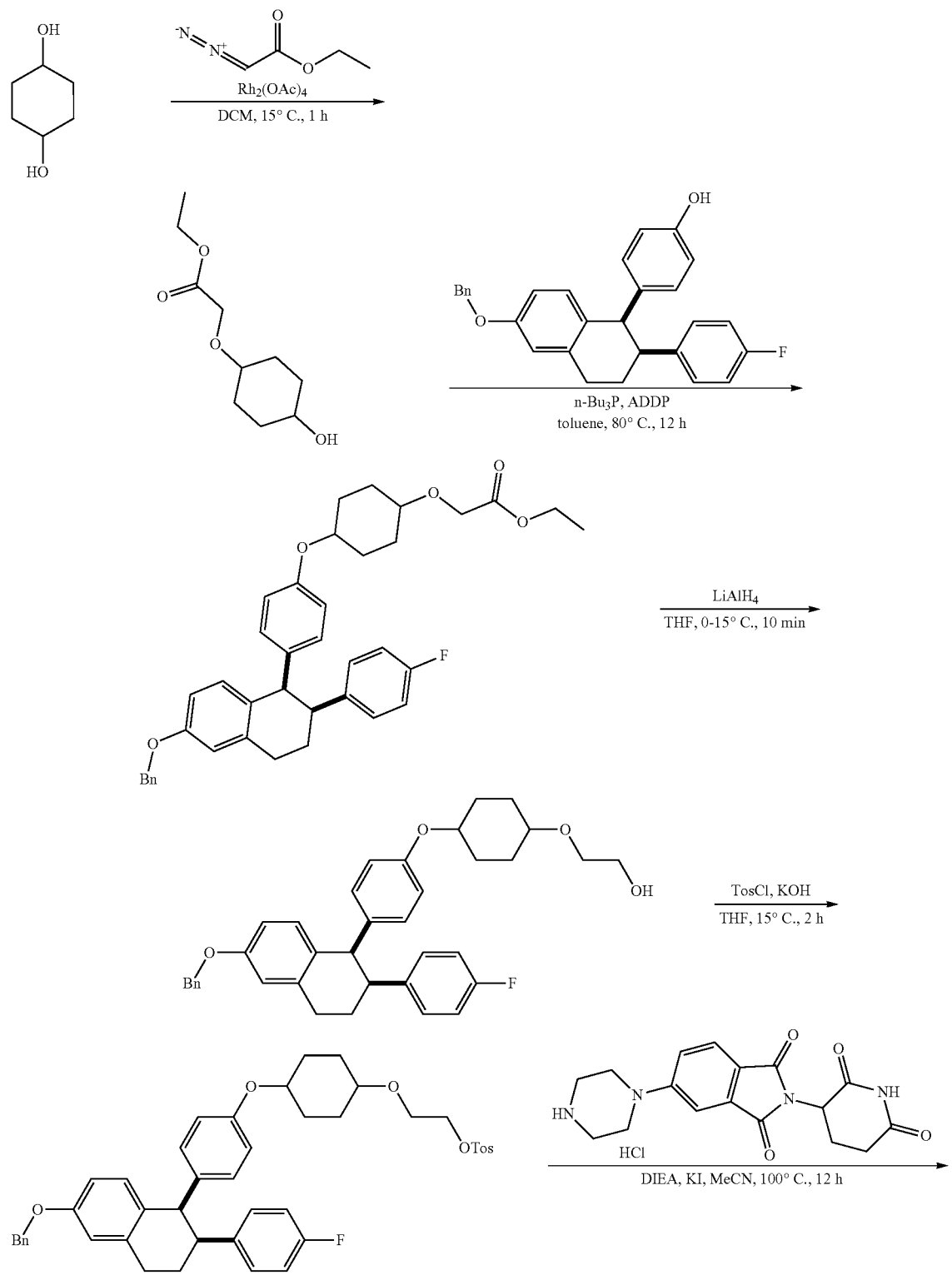

-continued
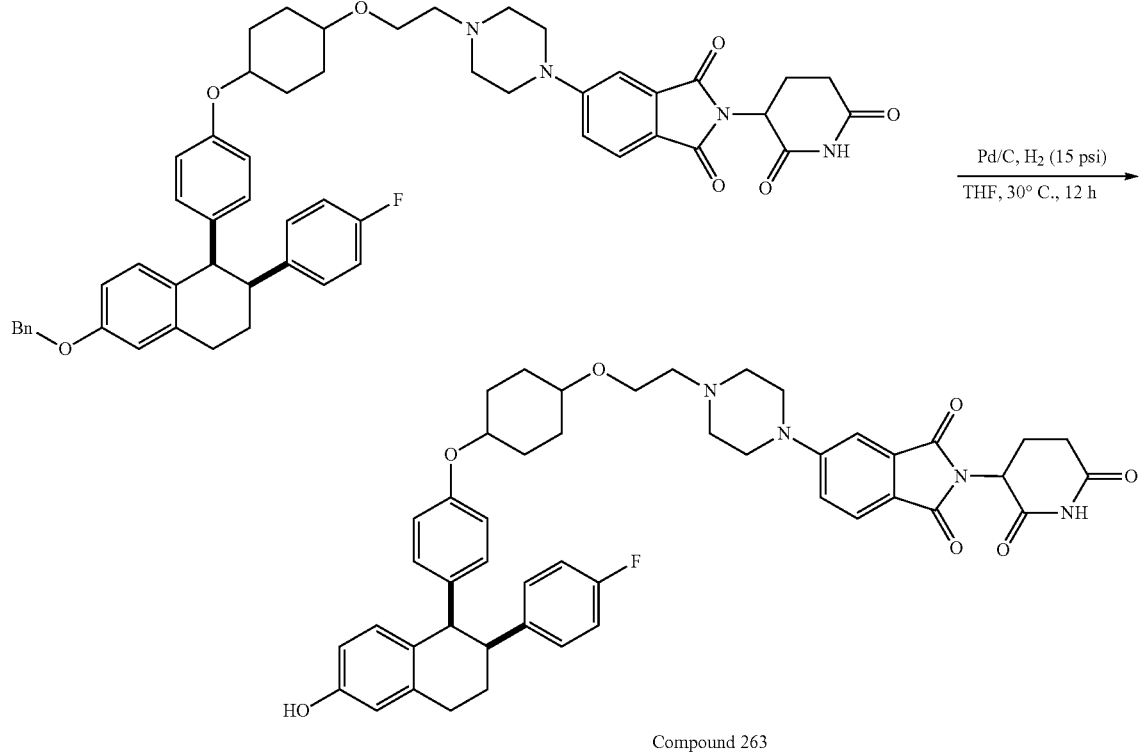
Compound 263
General synthetic scheme 3-48.
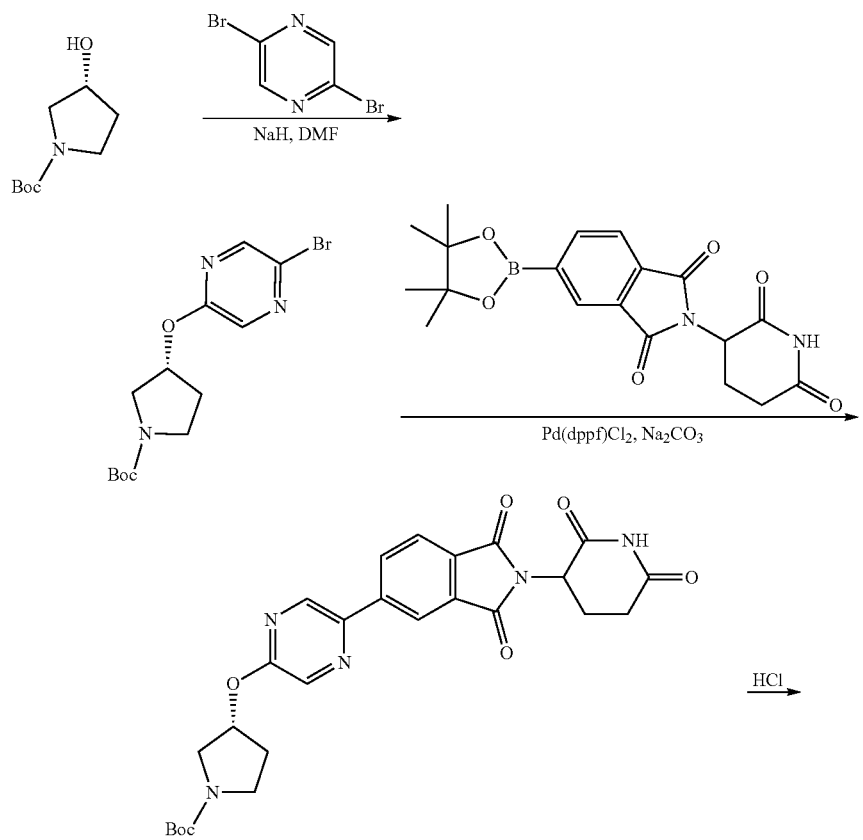

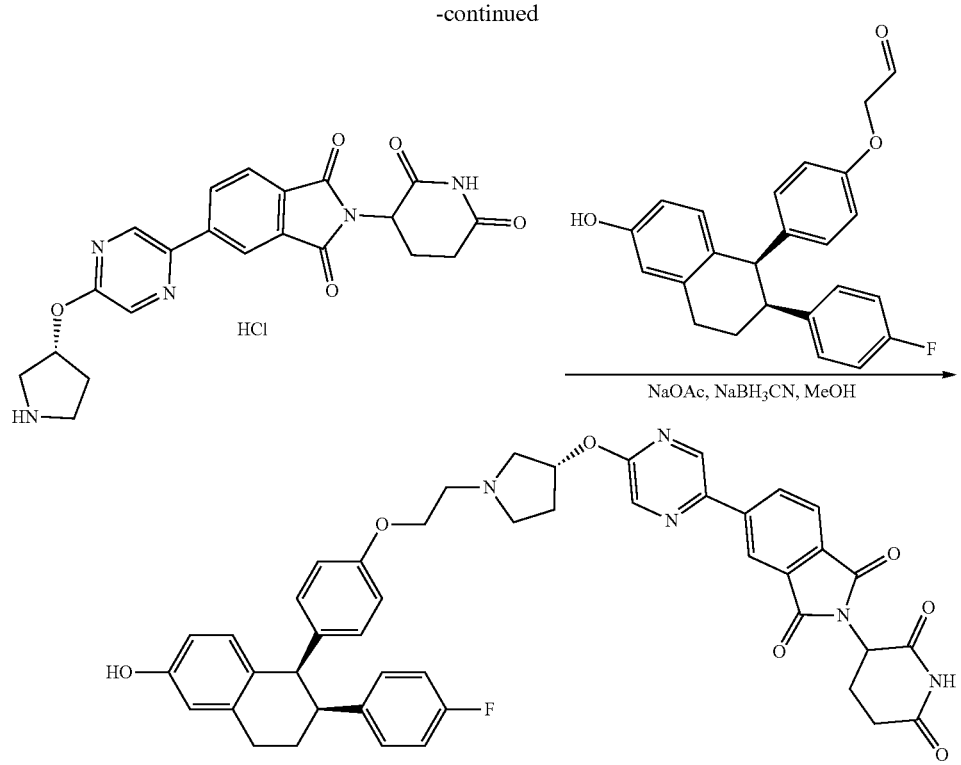
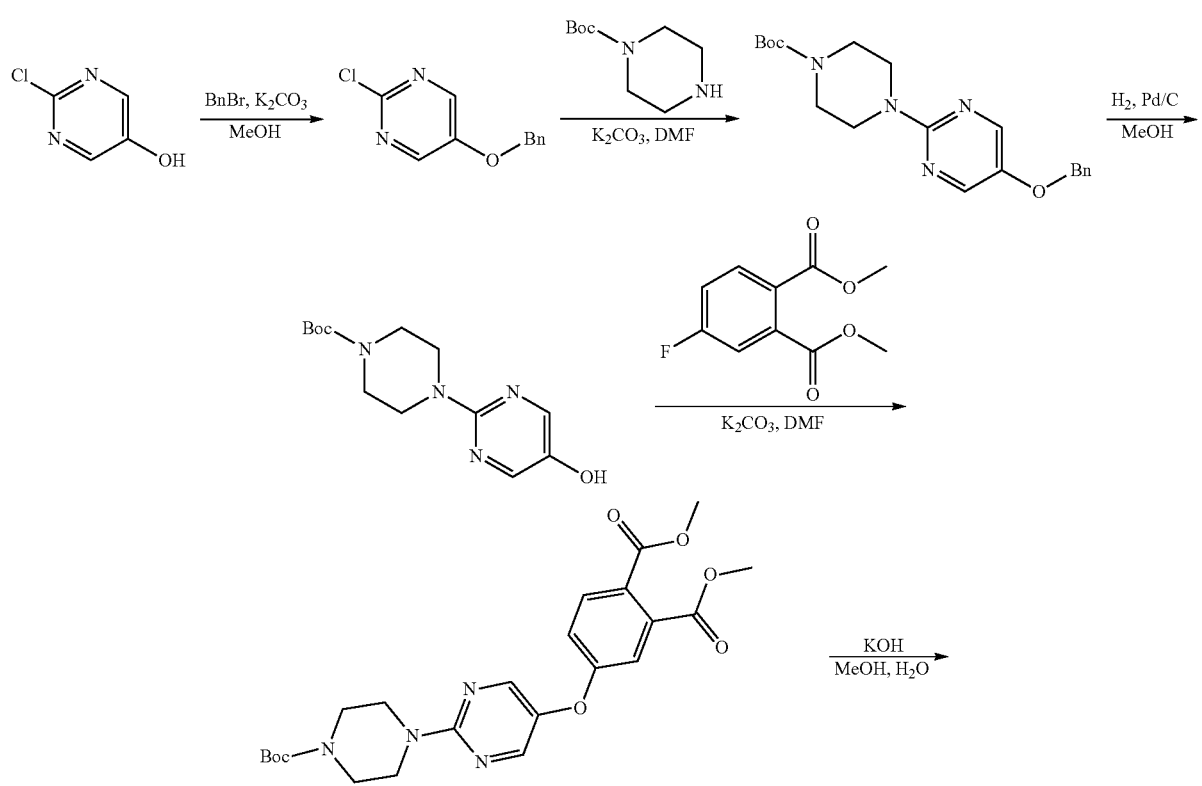
General synthetic scheme 3-49 to prepare claimed compounds.

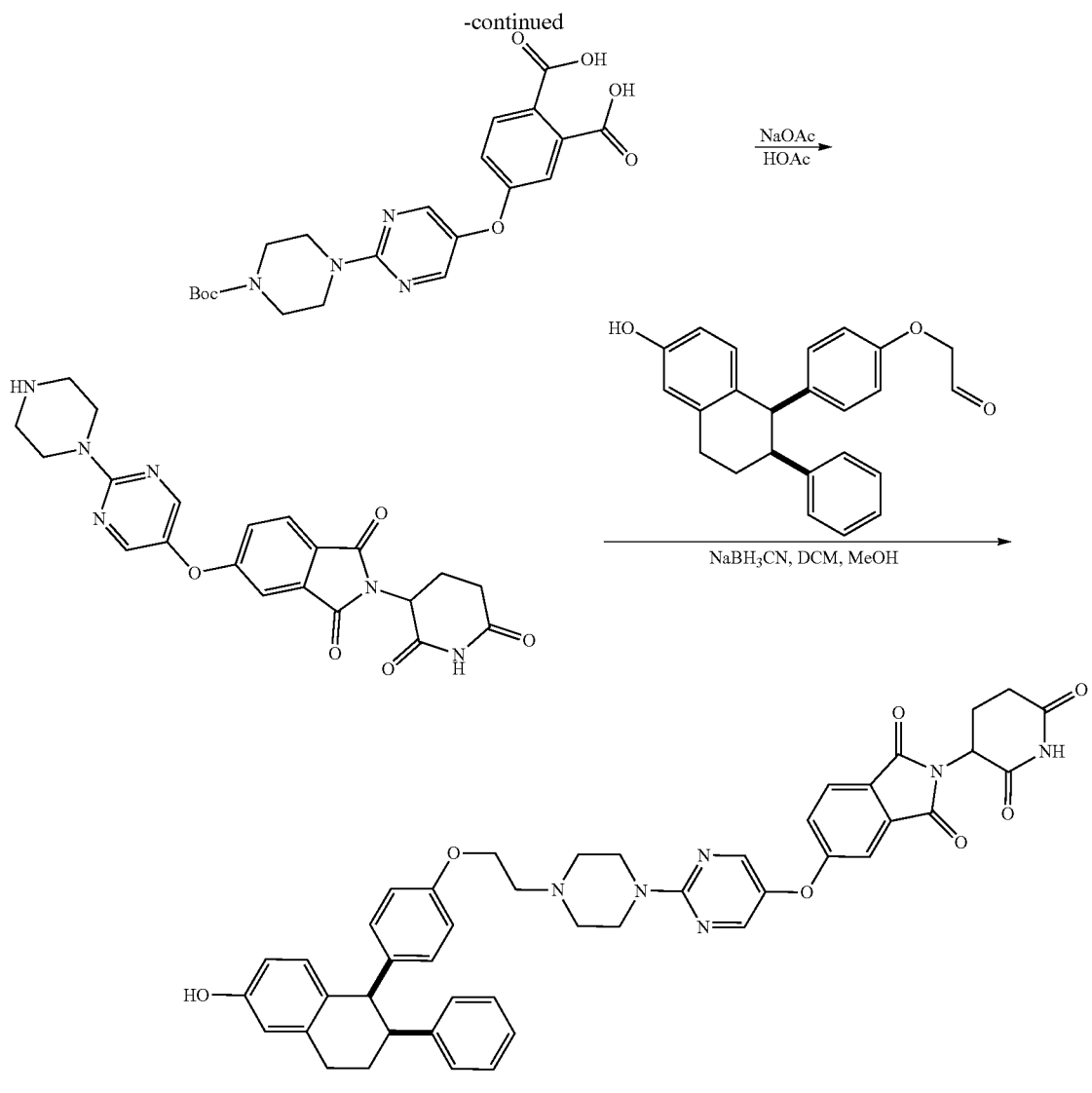
Compound 275
General synthetic scheme 3-50.
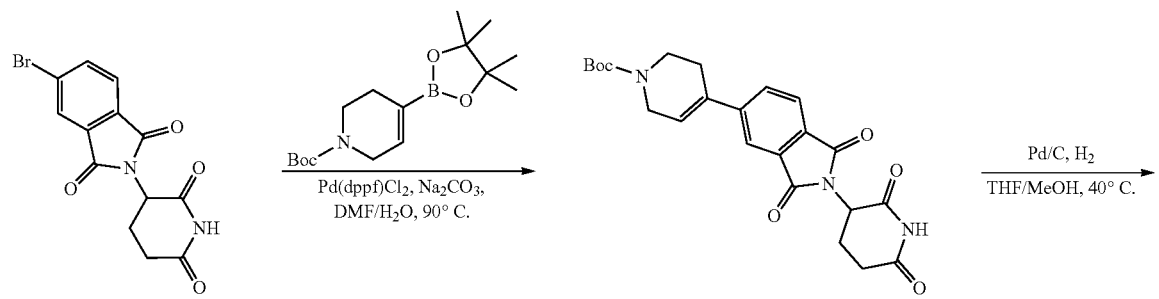

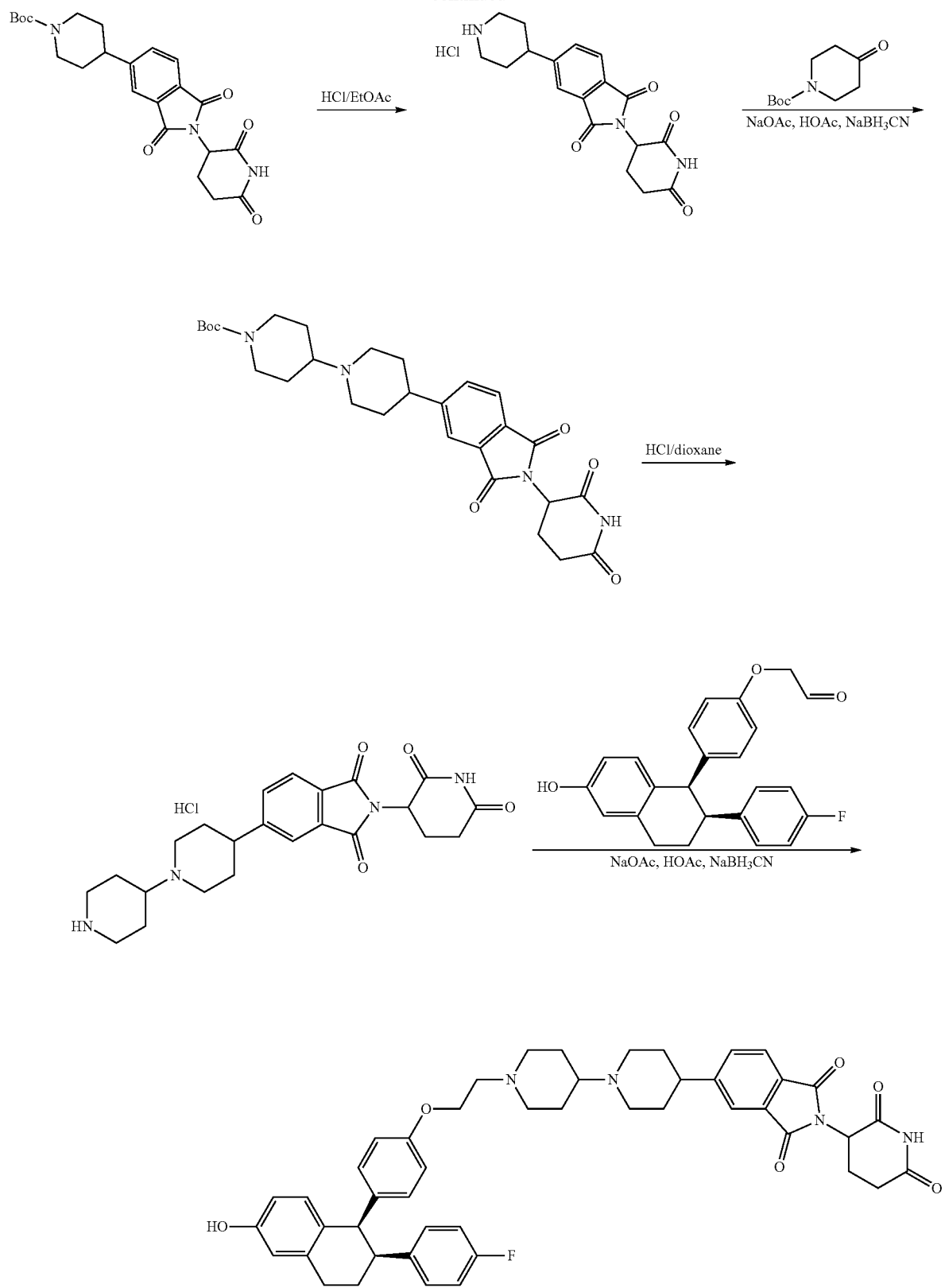

General synthetic scheme 3-51.
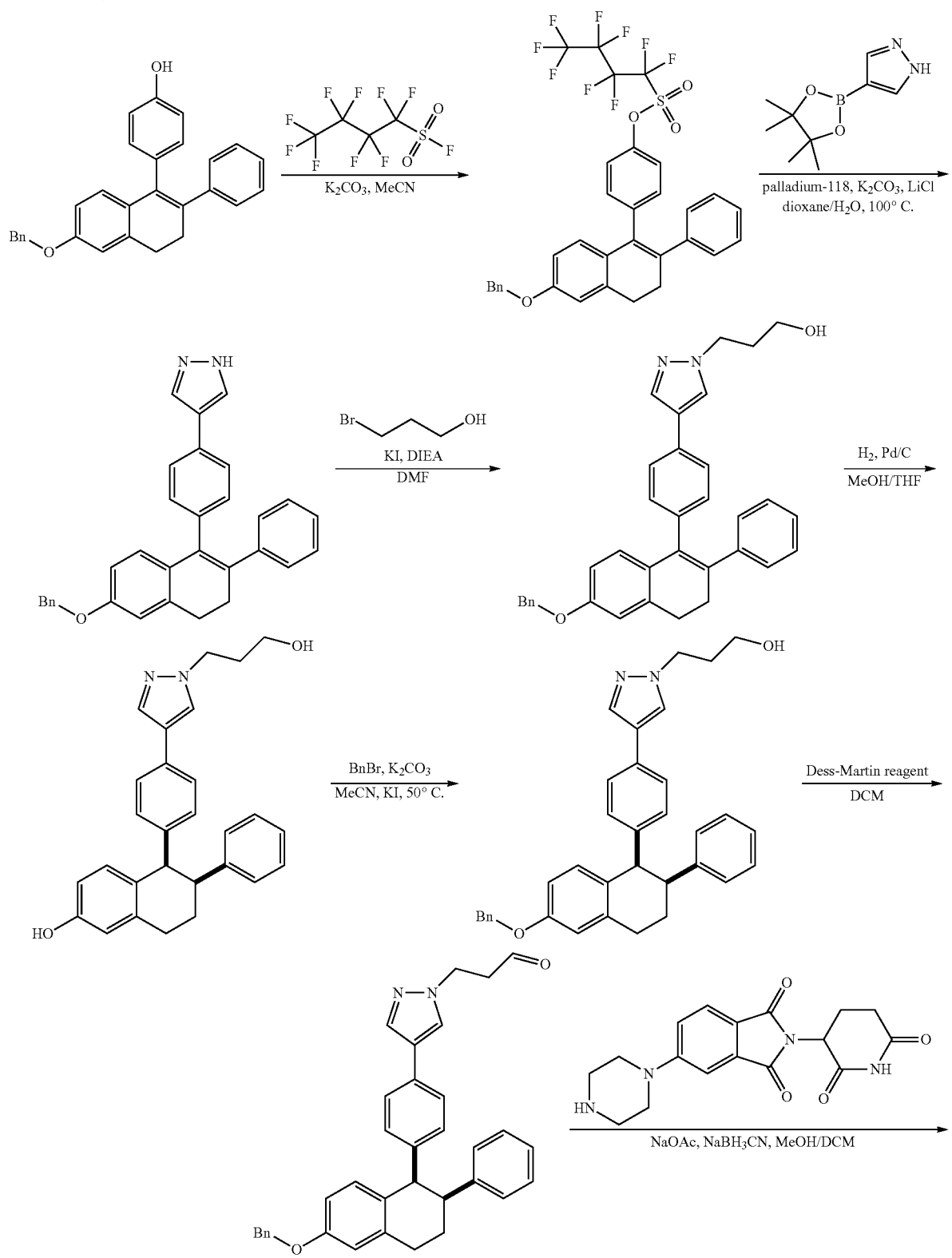

889    890
-continued
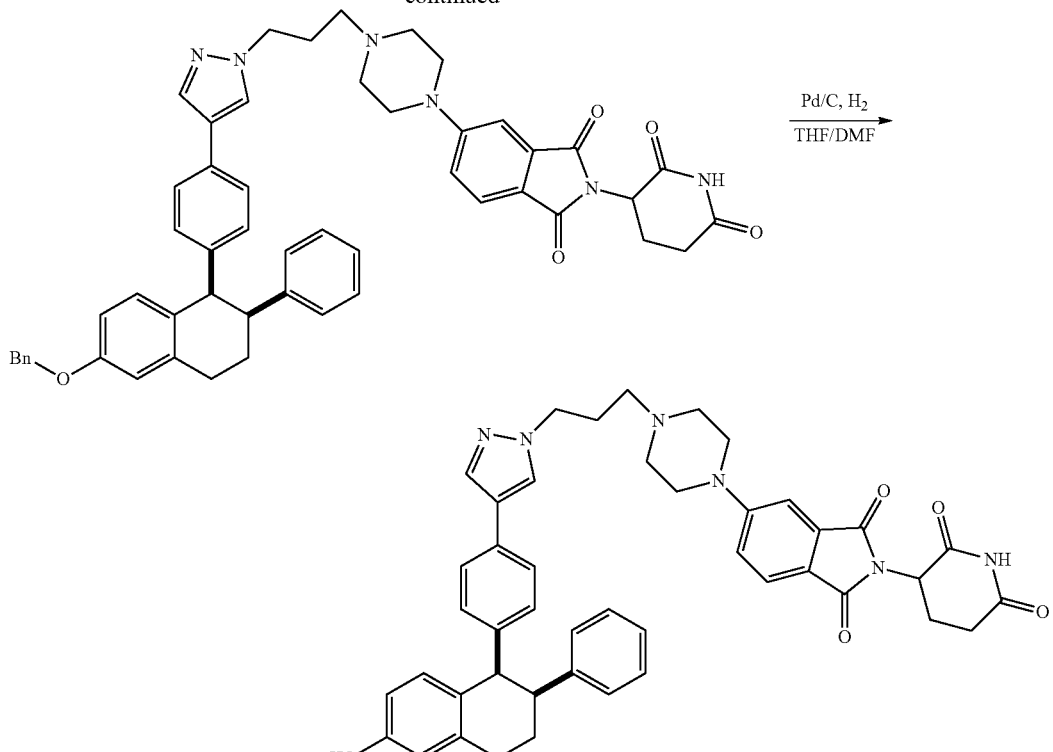
Compound 306
General synthetic scheme 3-52.
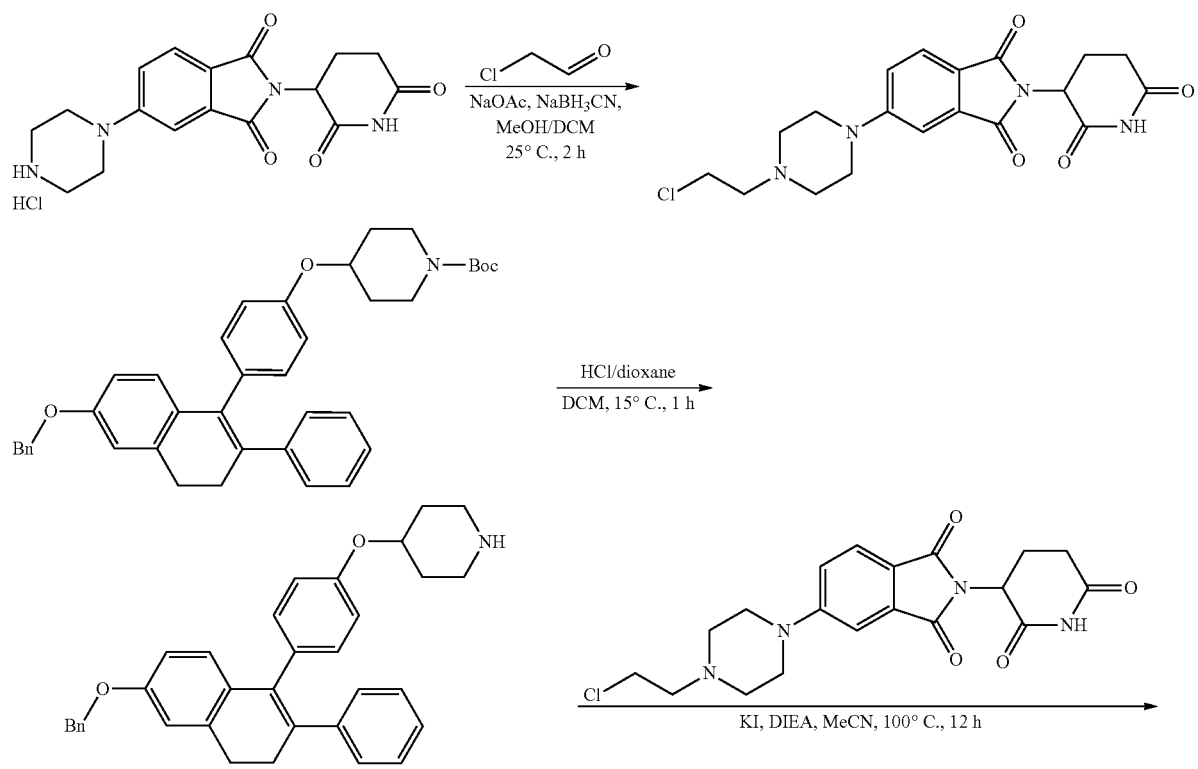

-continued
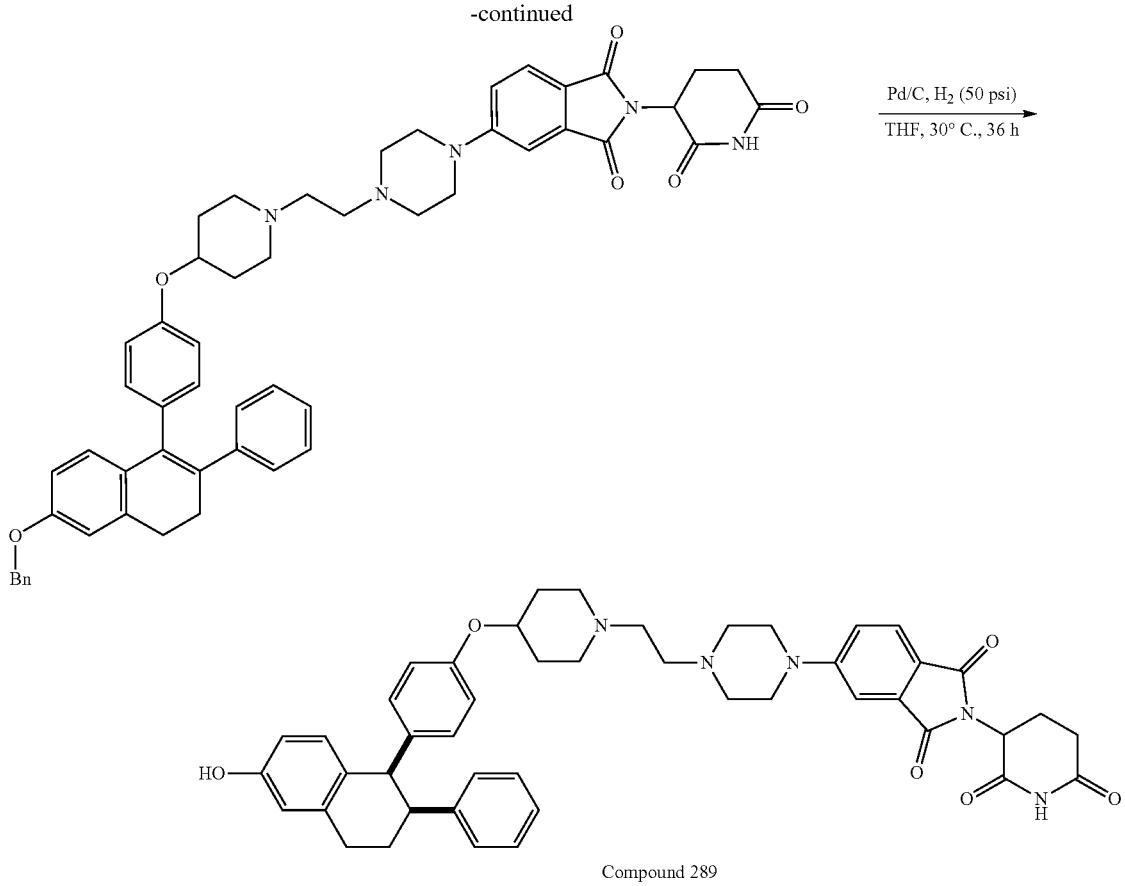
Compound 289
General synthetic scheme 3-53.
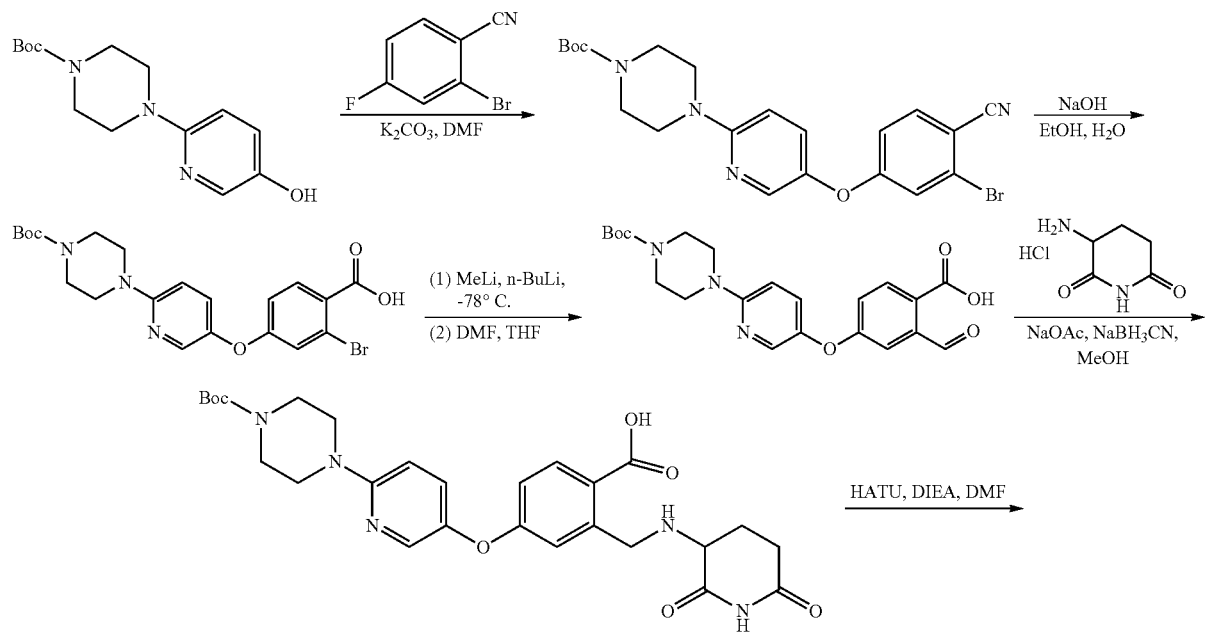

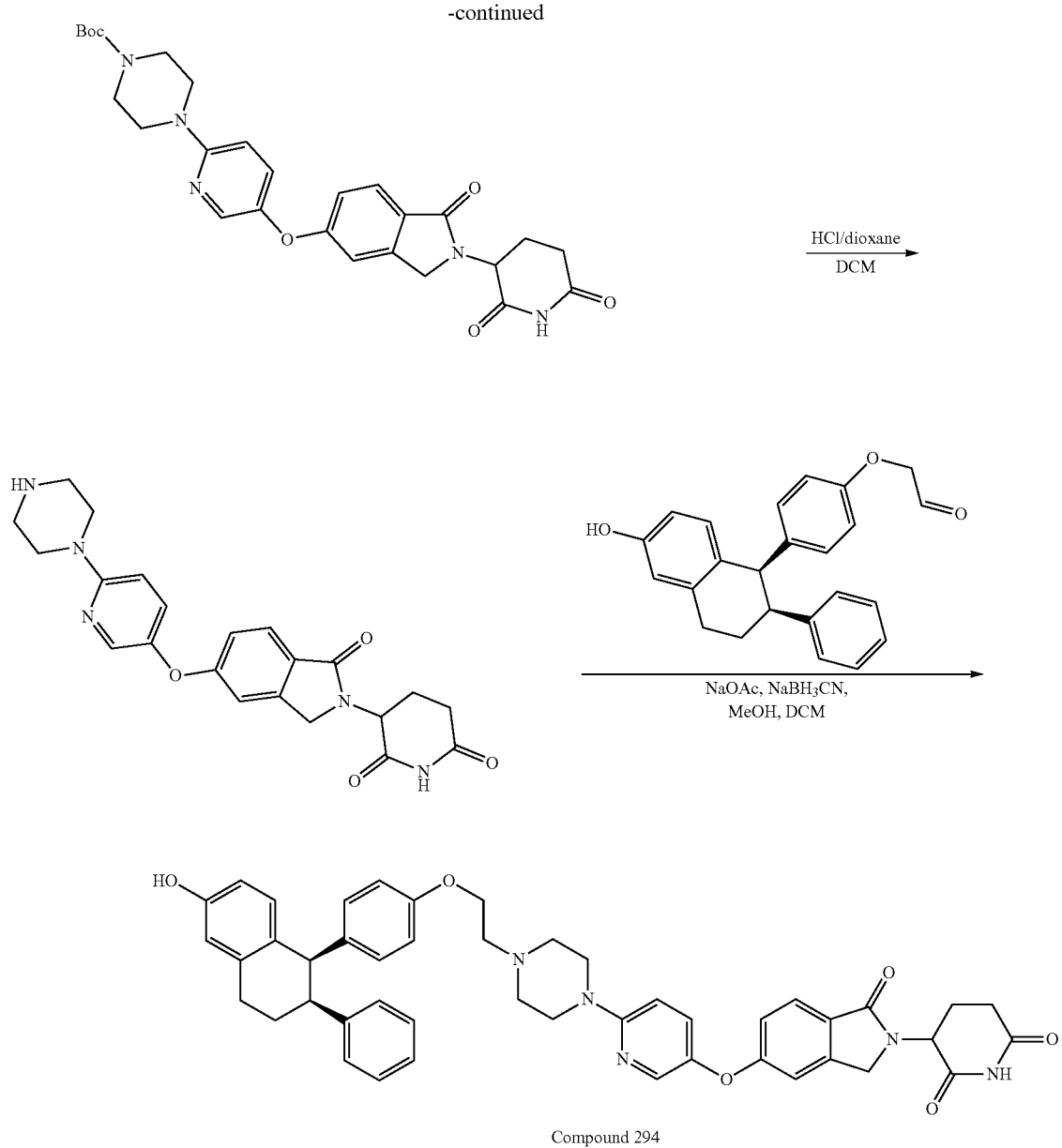
Compound 294
General synthetic scheme 3-54.
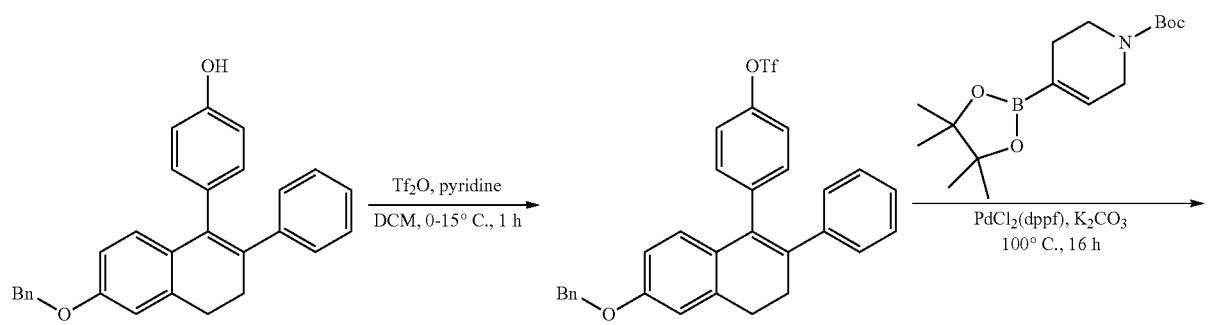

895 896
-continued
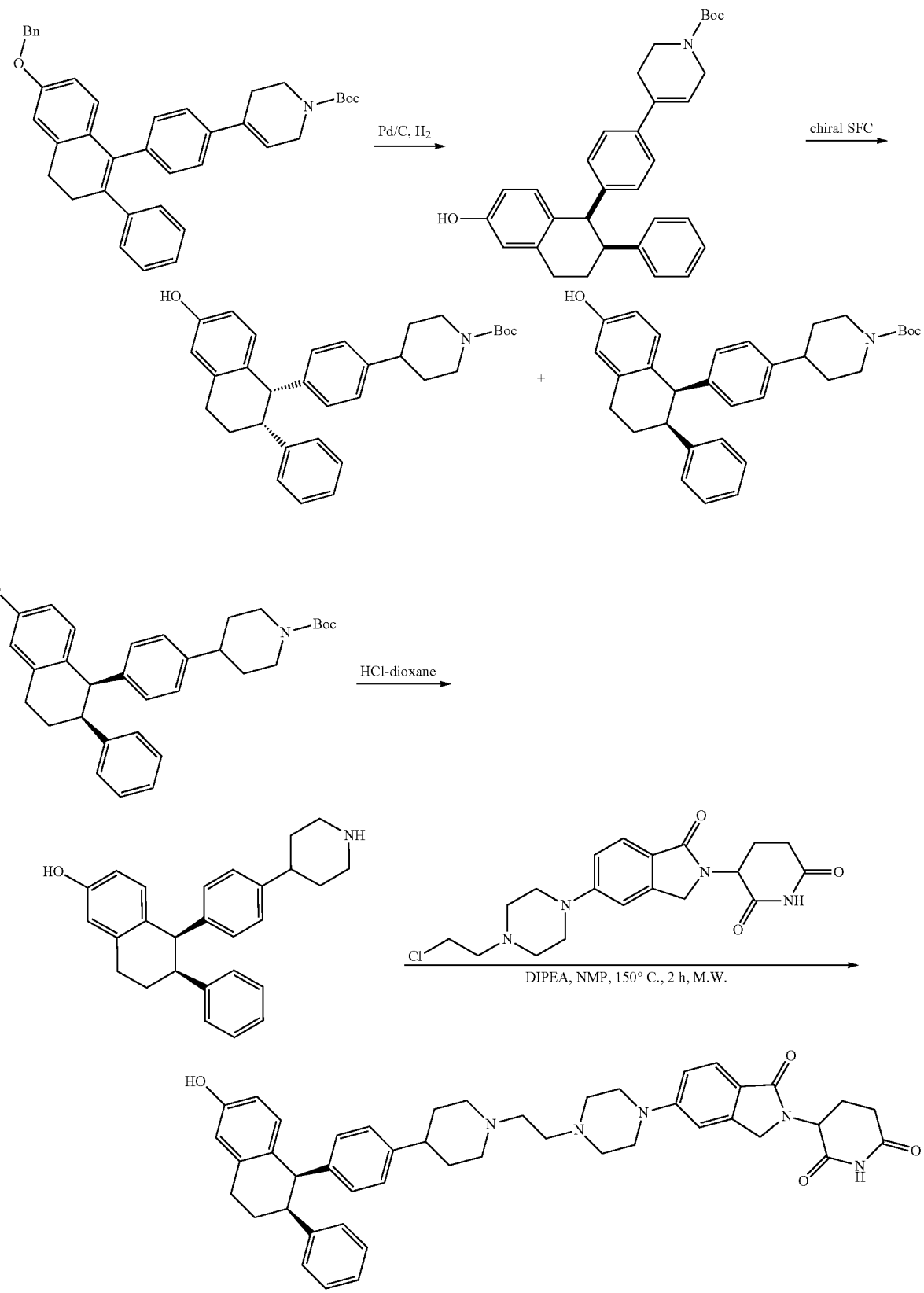
Compound 298

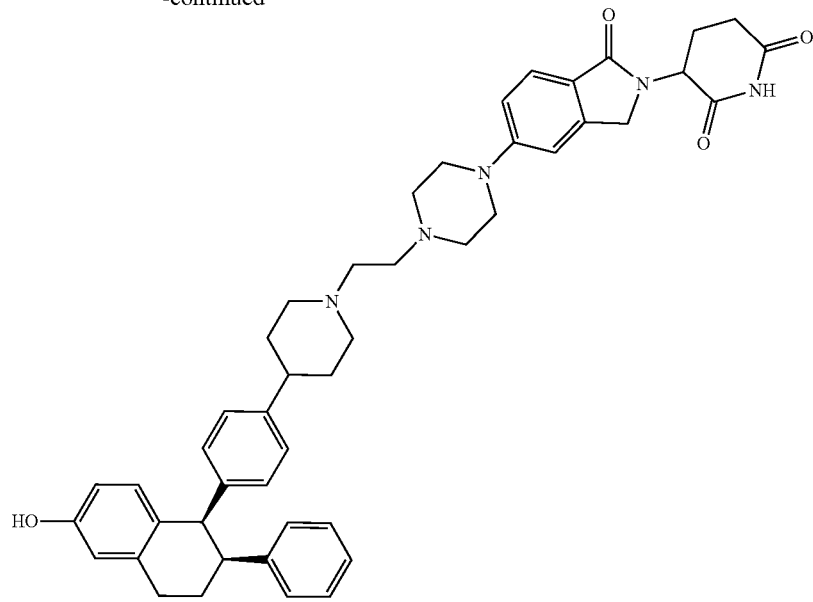
Compound 298
General synthetic scheme 3-55.
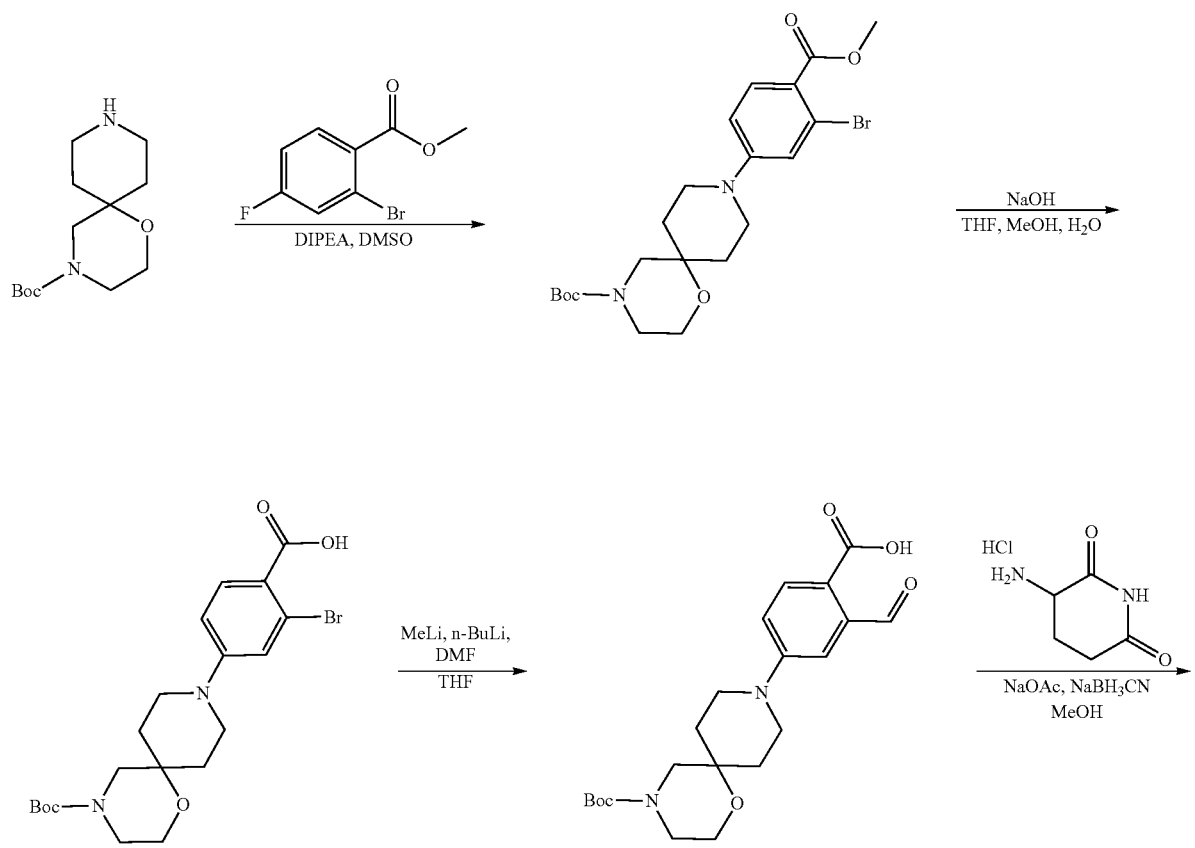

899
900
-continued
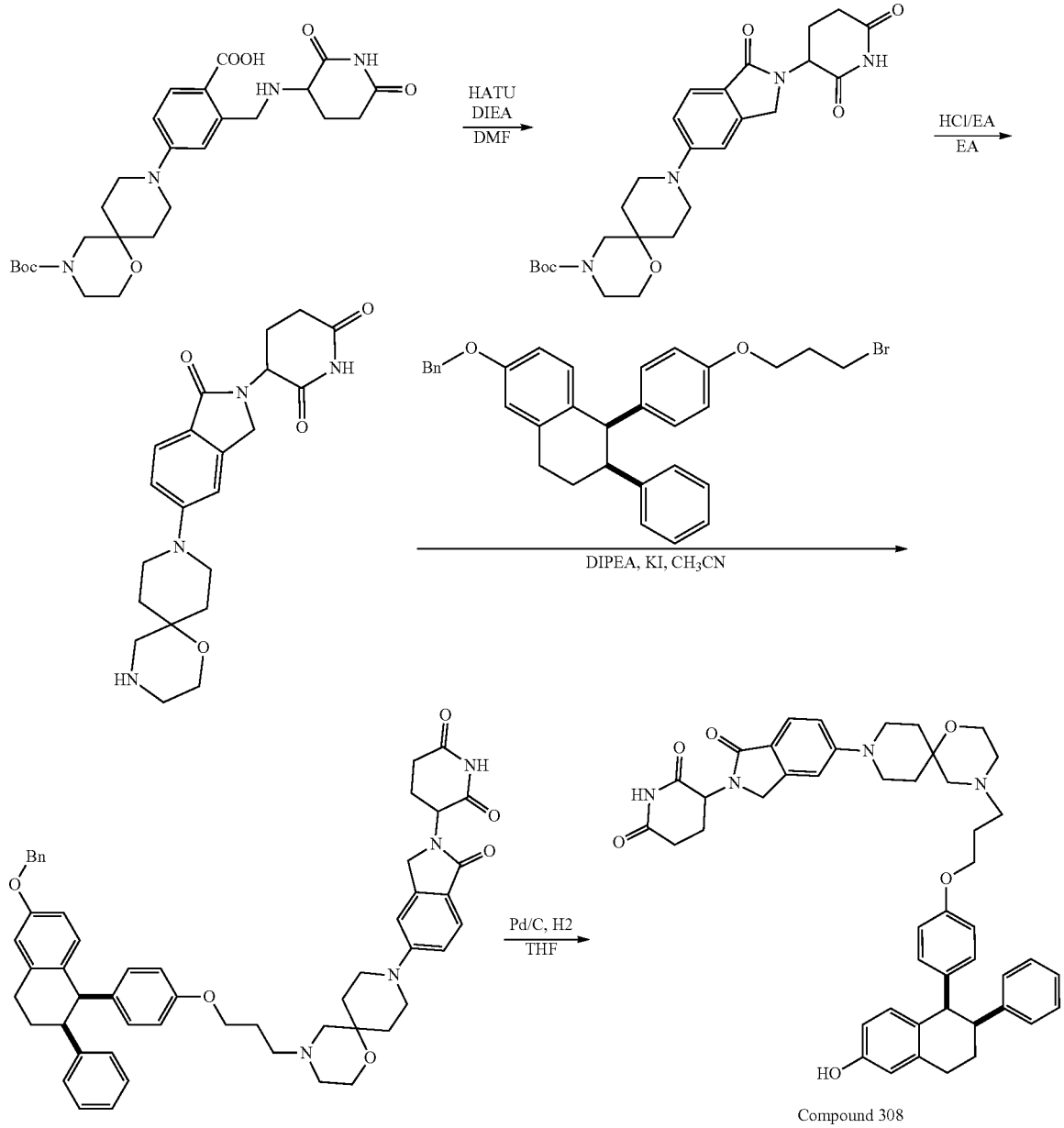
General synthetic scheme 3-57.
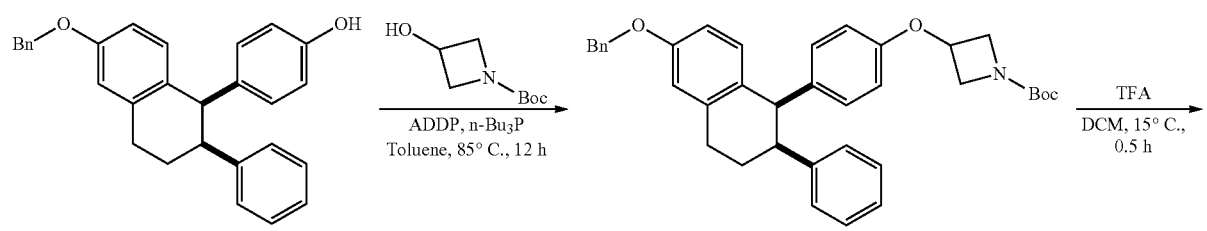

901                                         902
-continued
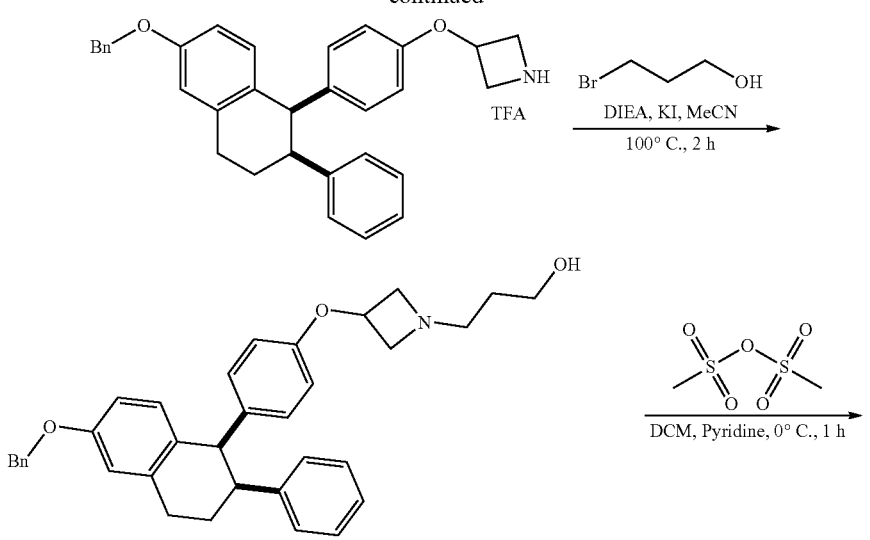
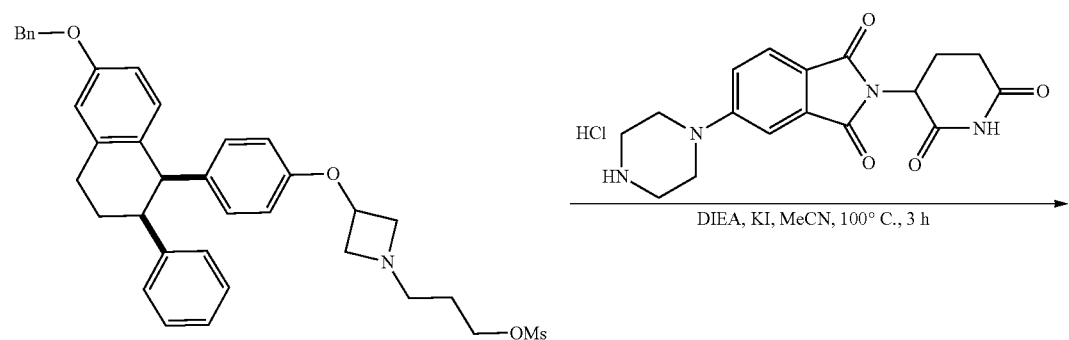
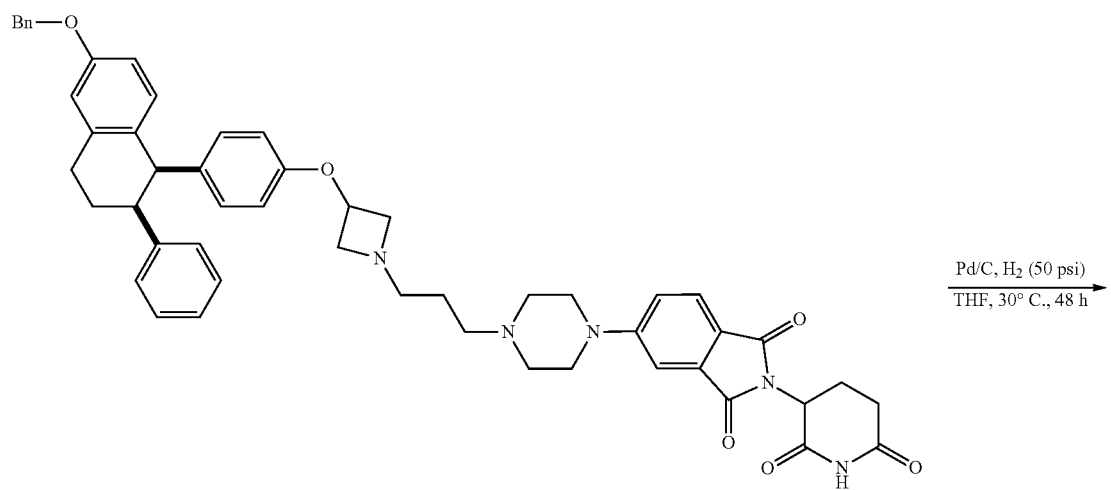

-continued
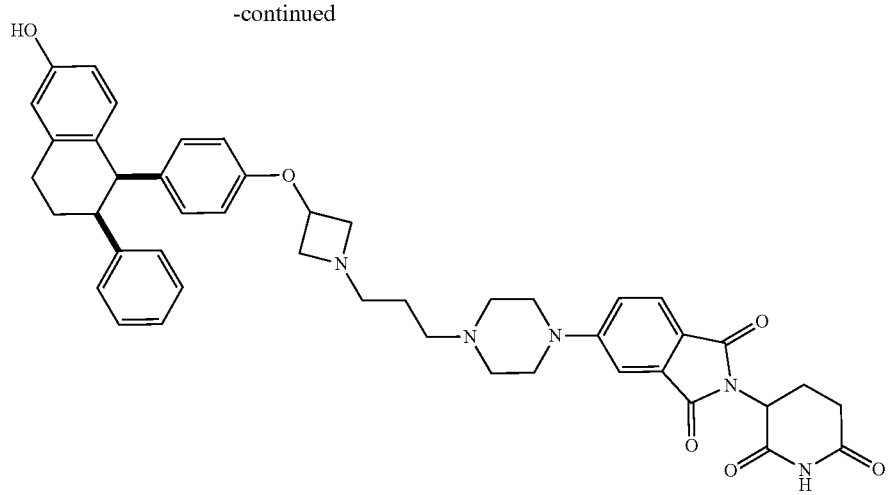
Compound 336
General synthetic scheme 3-58.
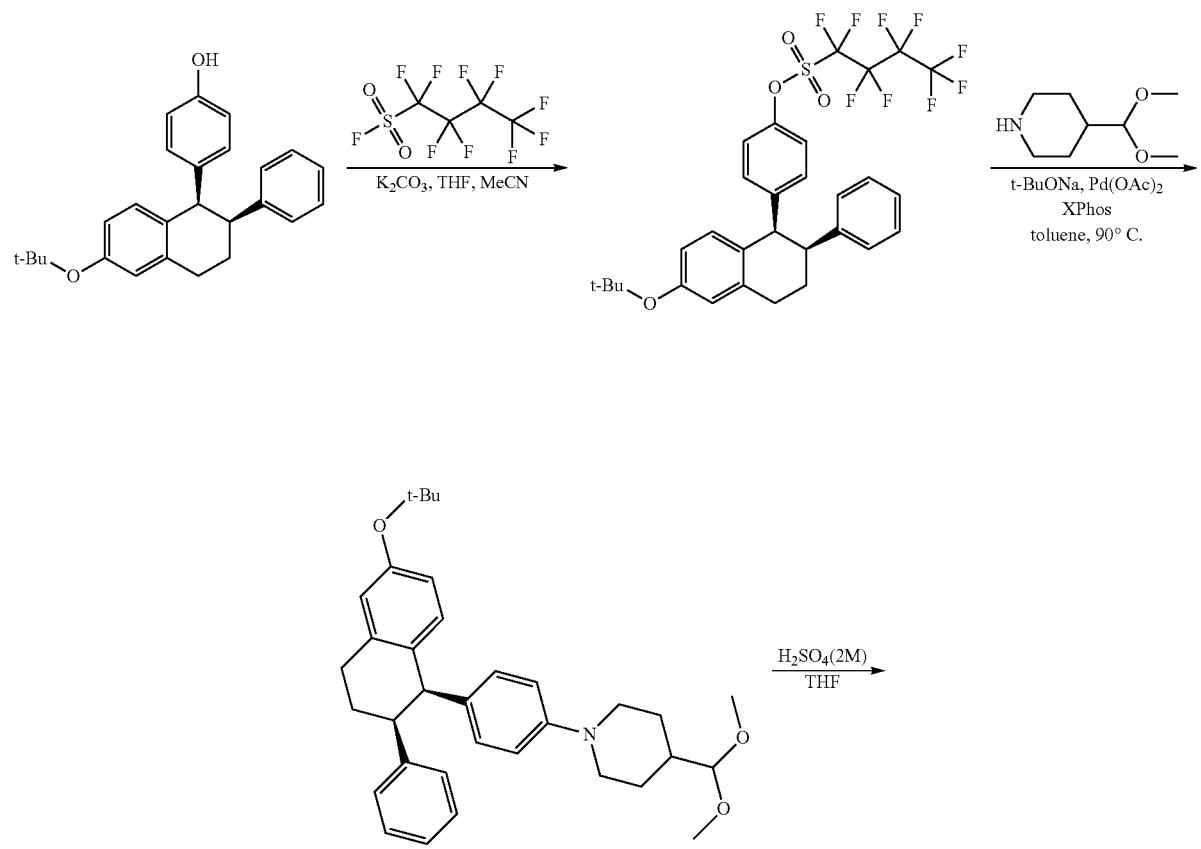

905 906
-continued
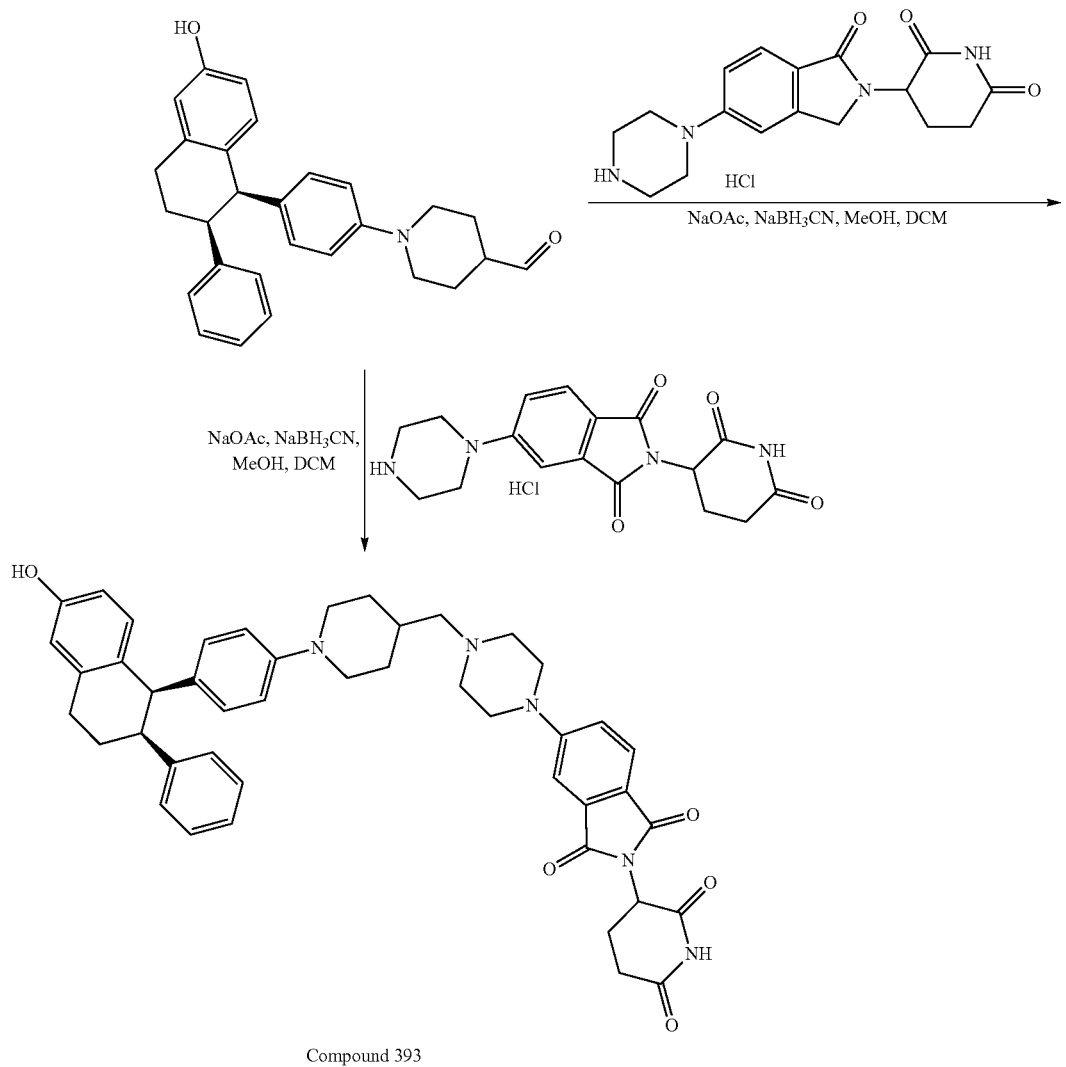
Compound 393
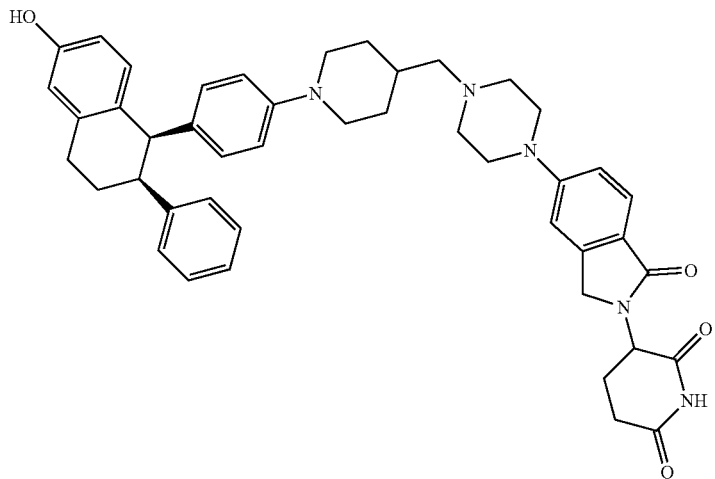
Compound 341

907 908
General synthetic scheme 3-59.
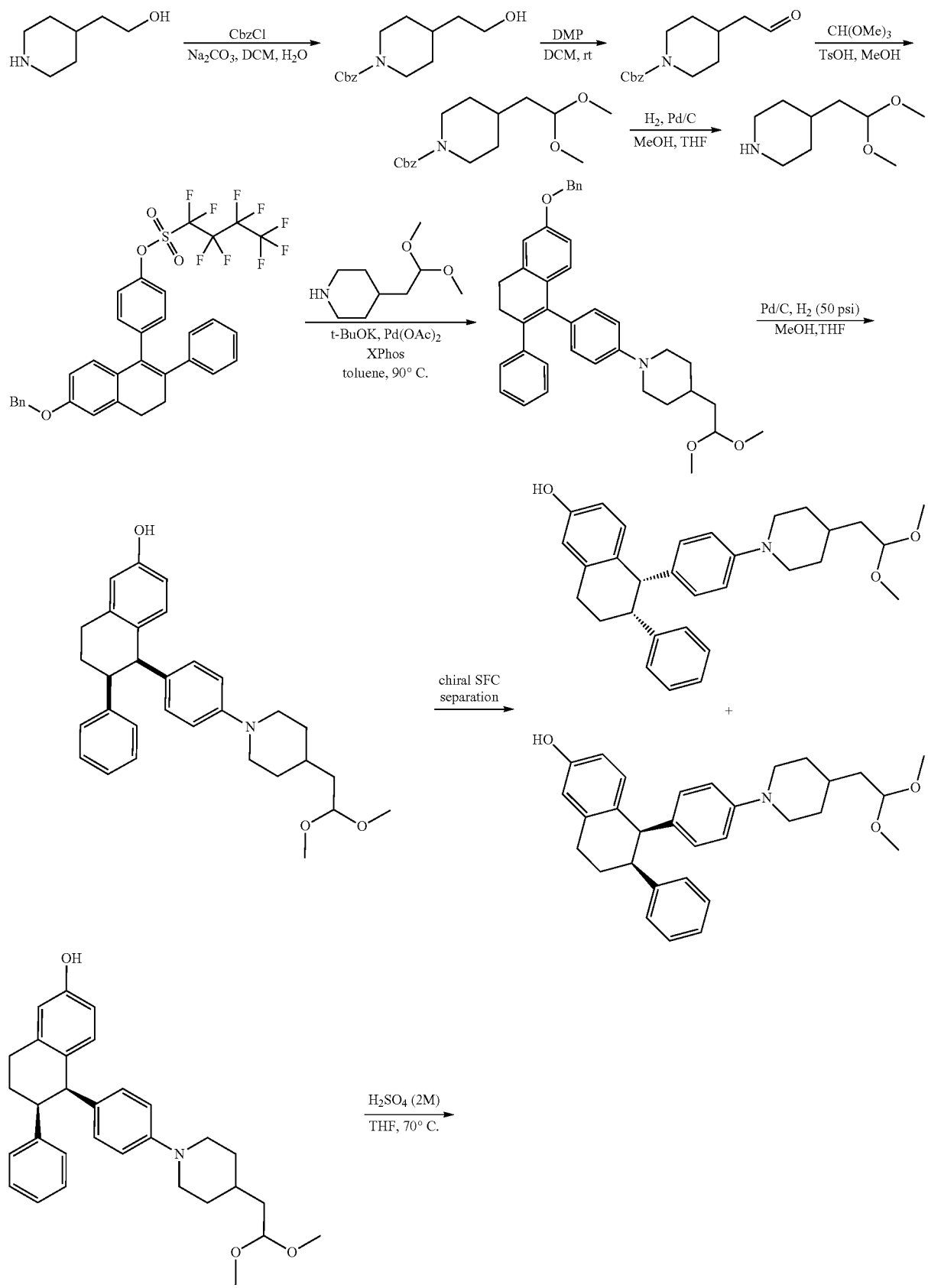

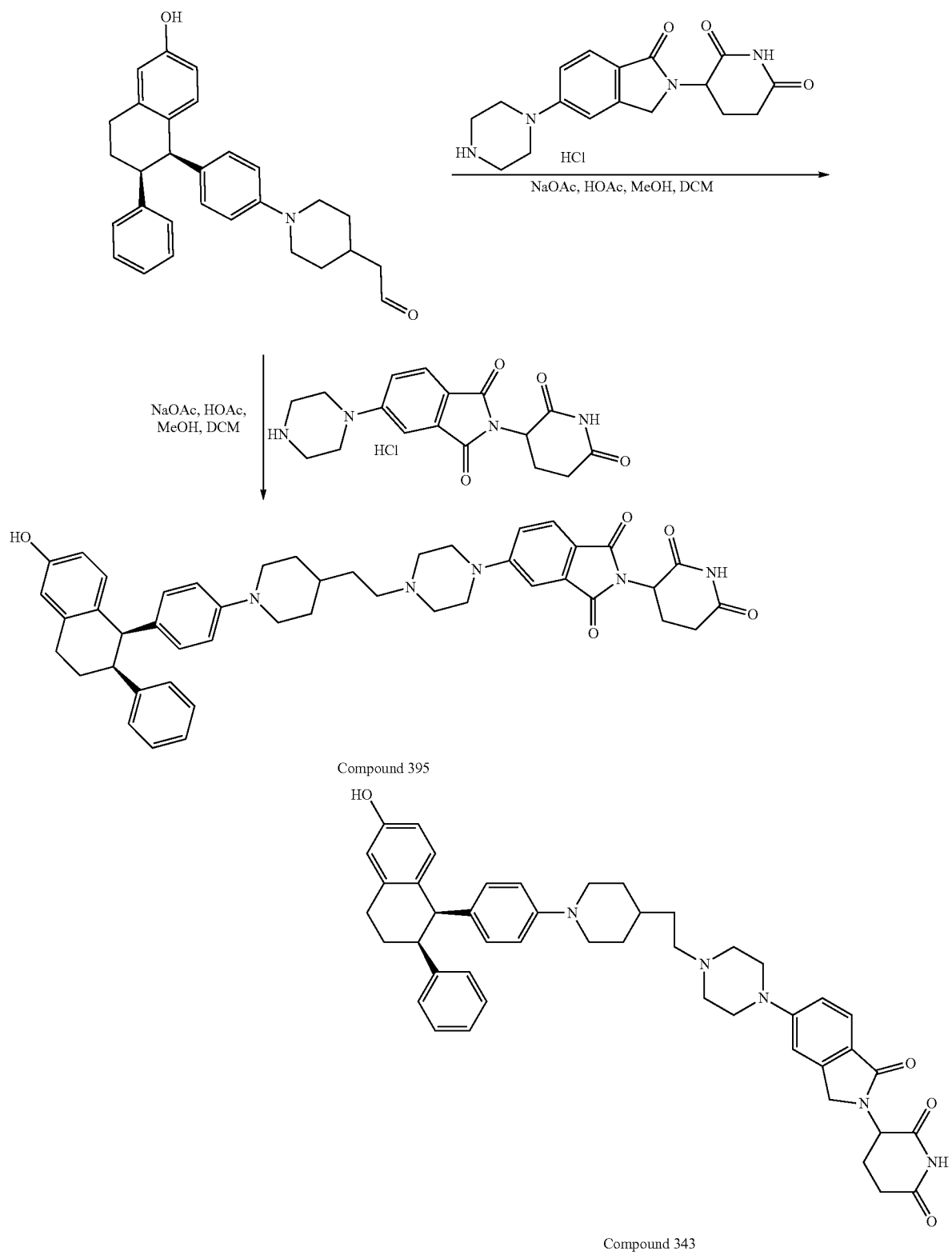

General synthetic scheme 3-60.
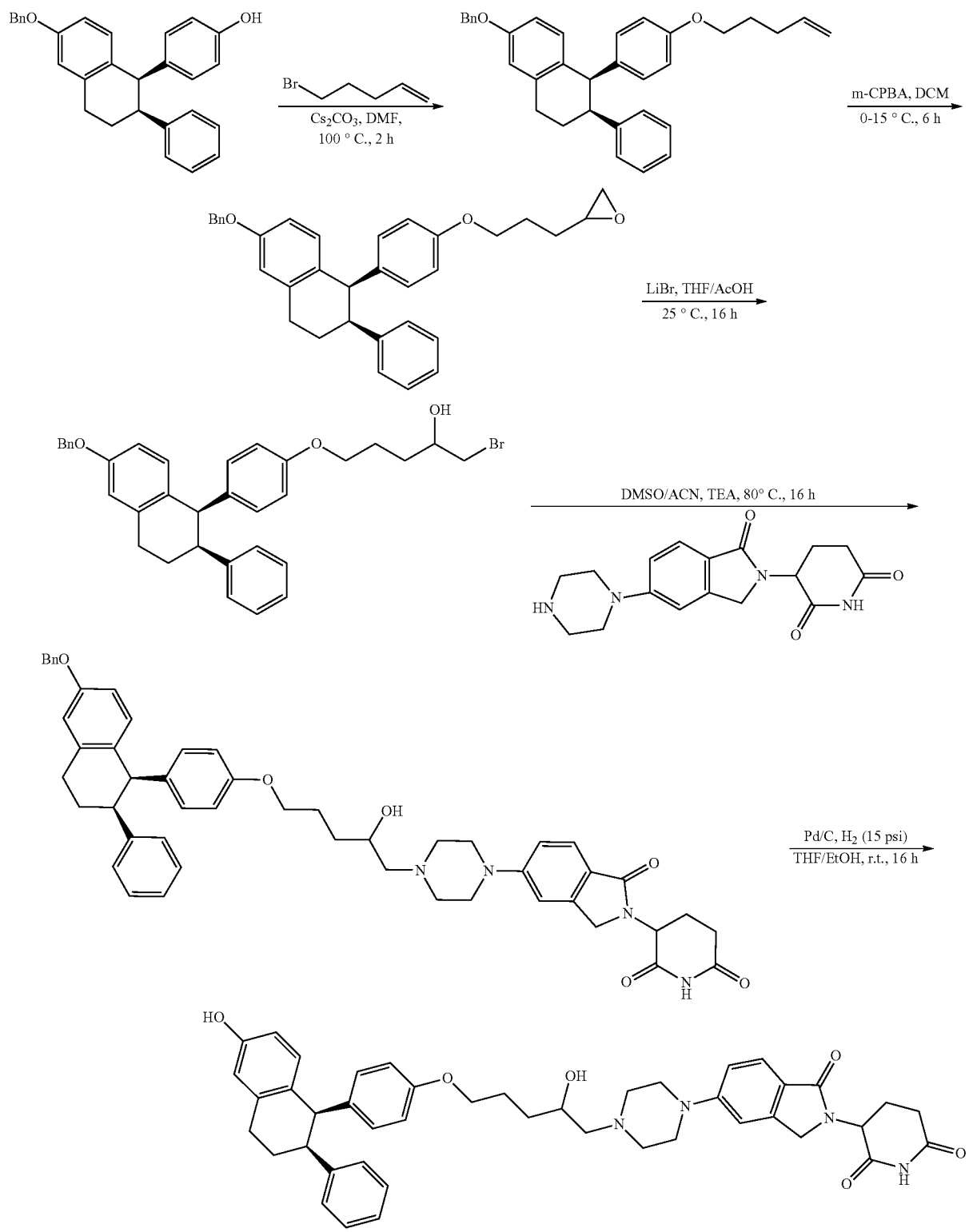
Compound 360

913 914
General synthetic scheme 3-61.
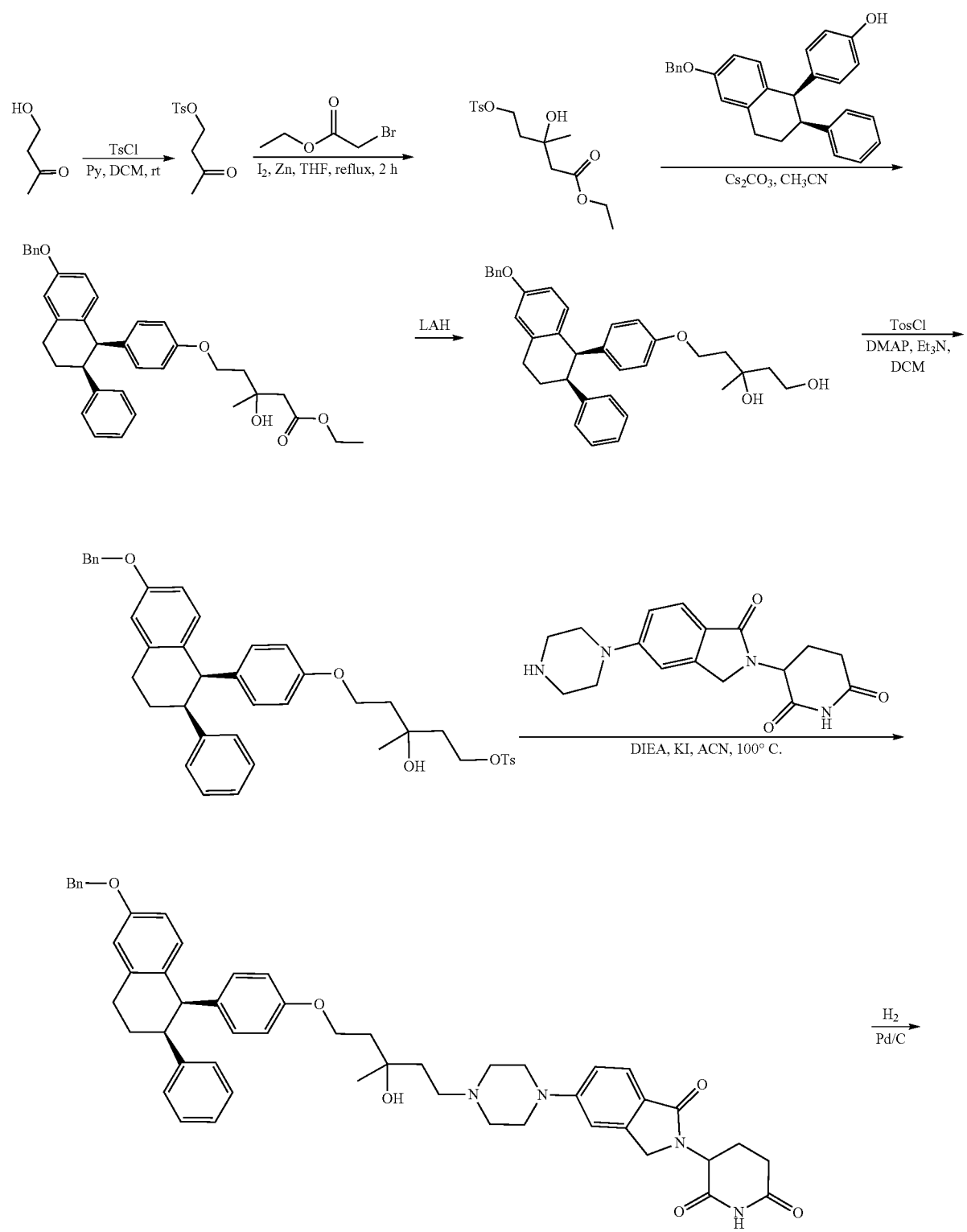

-continued
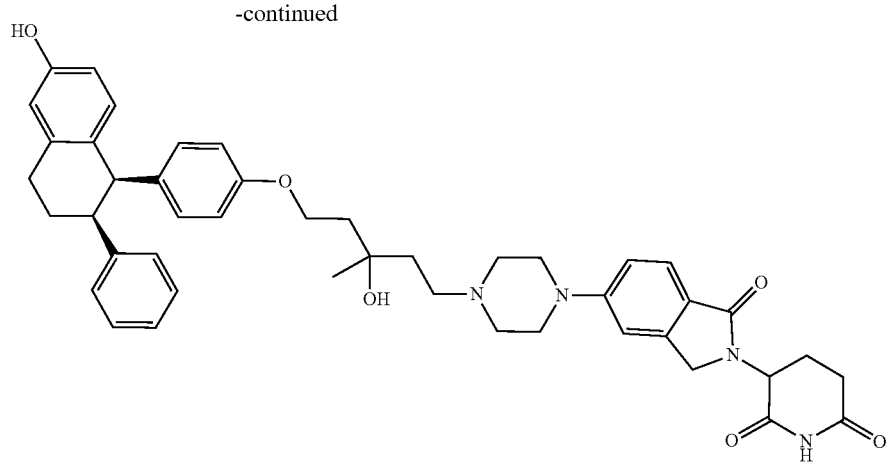
Compound 363
General synthetic scheme 3-62.
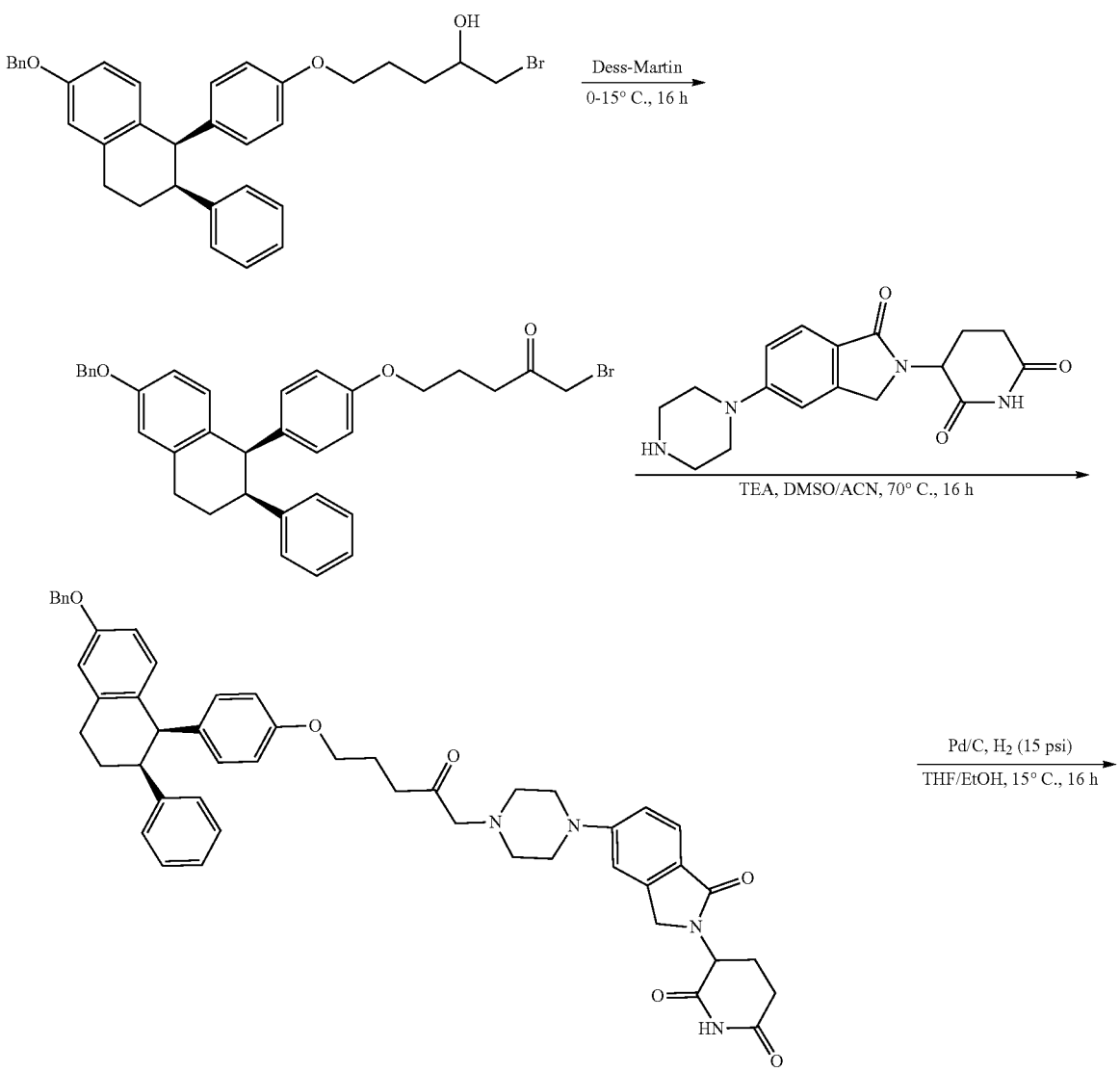

-continued
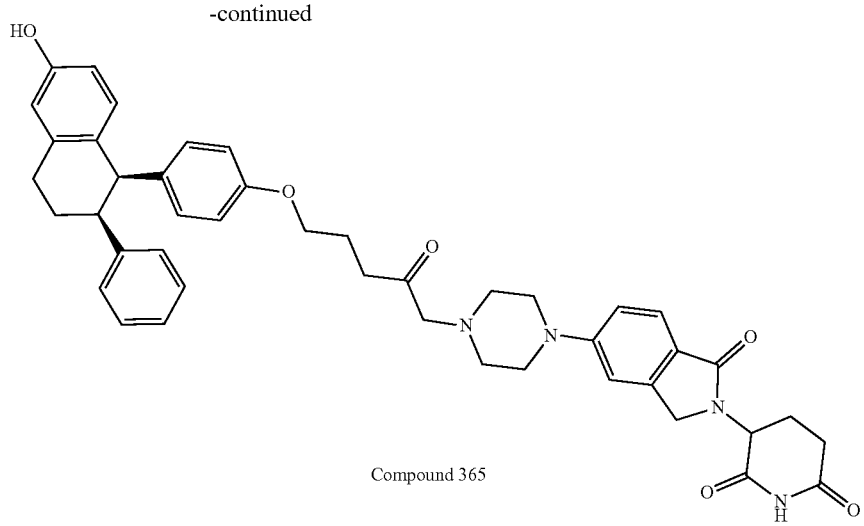
Compound 365
General synthetic scheme 3-63.
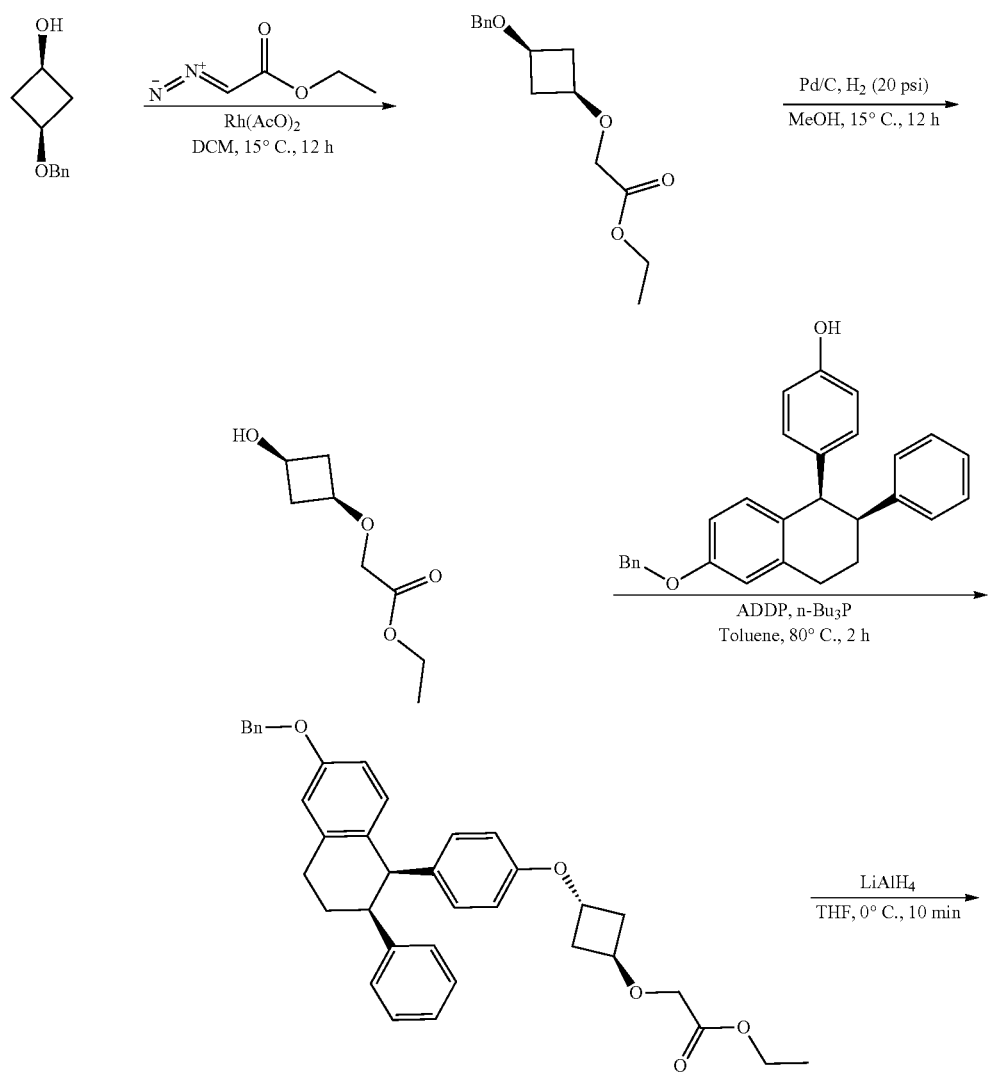

-continued
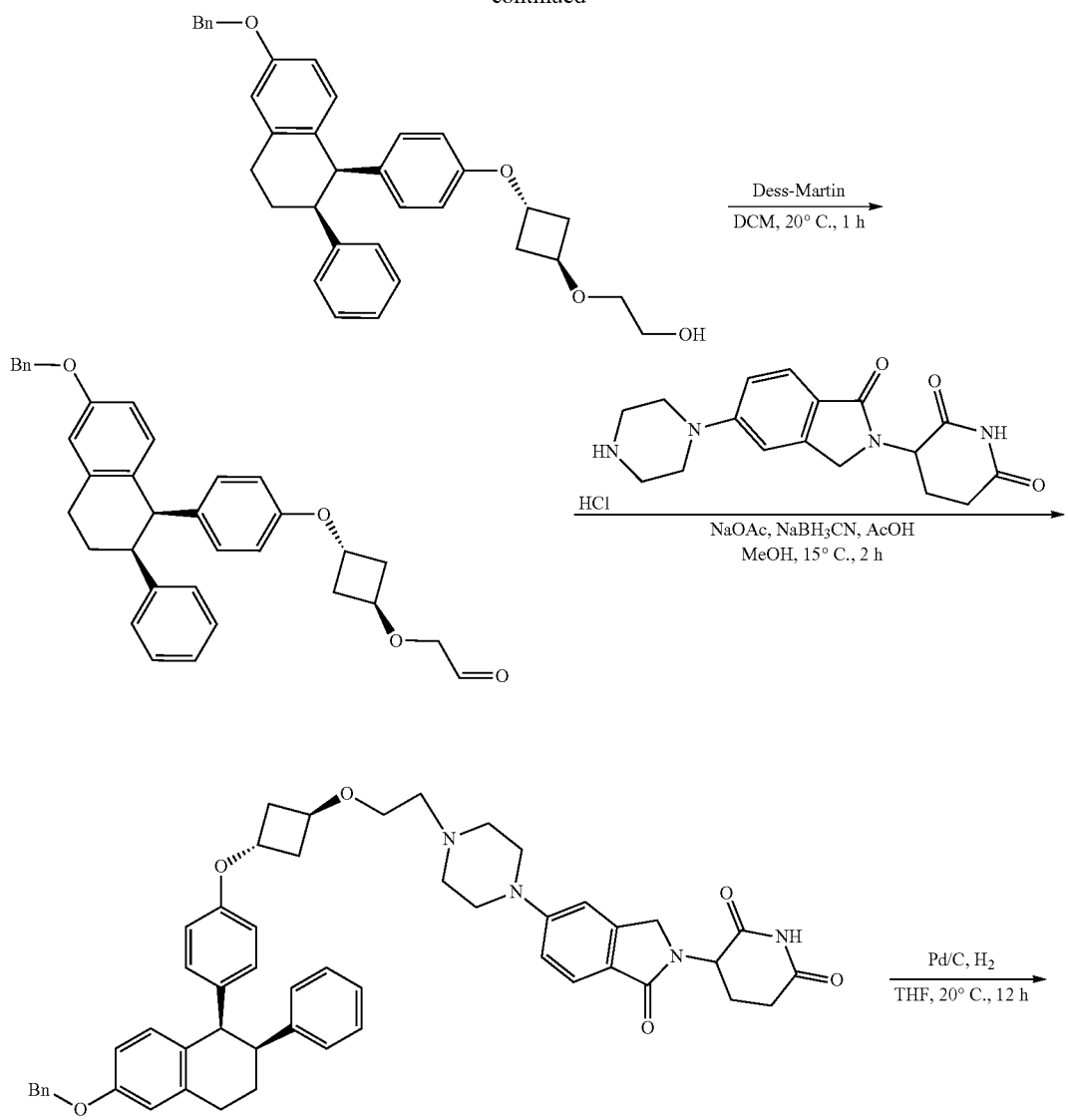
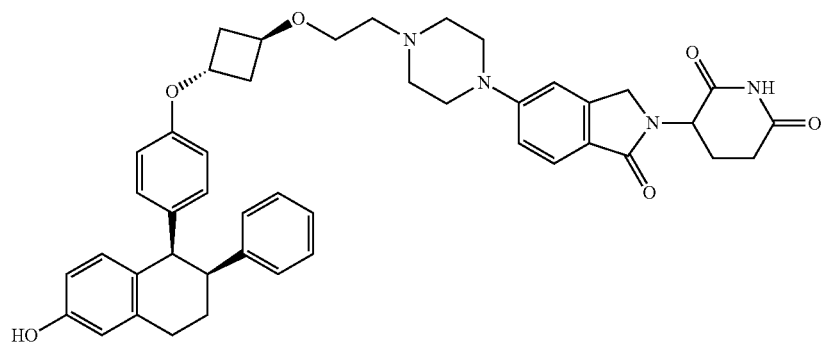
Compound 374

921 922
General synthetic scheme 3-64.
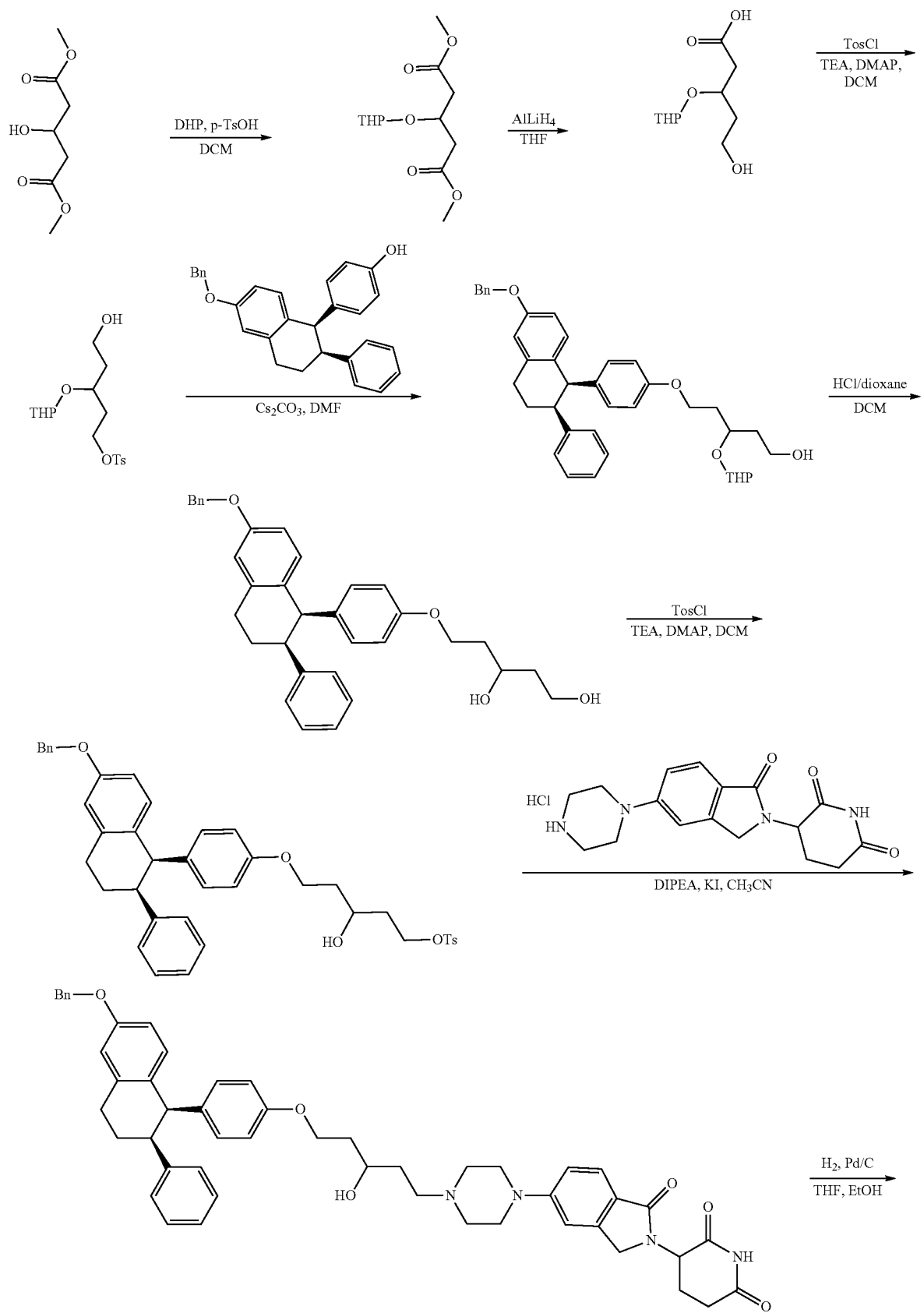

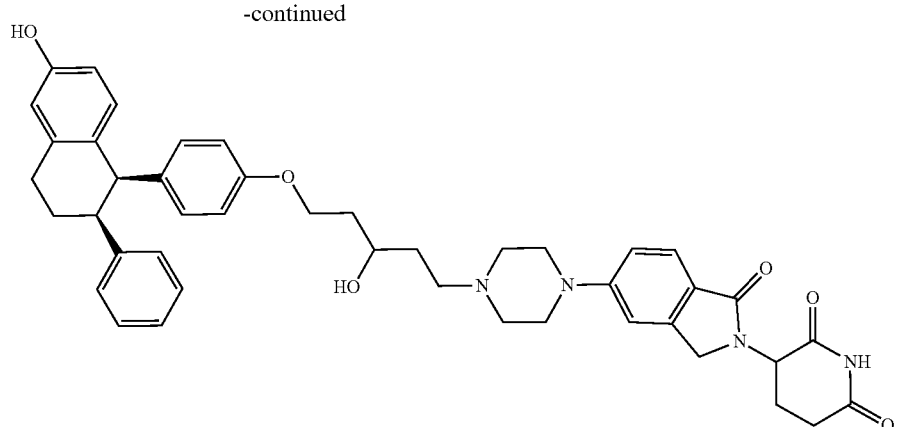
Compound 377
General synthetic scheme 3-65.
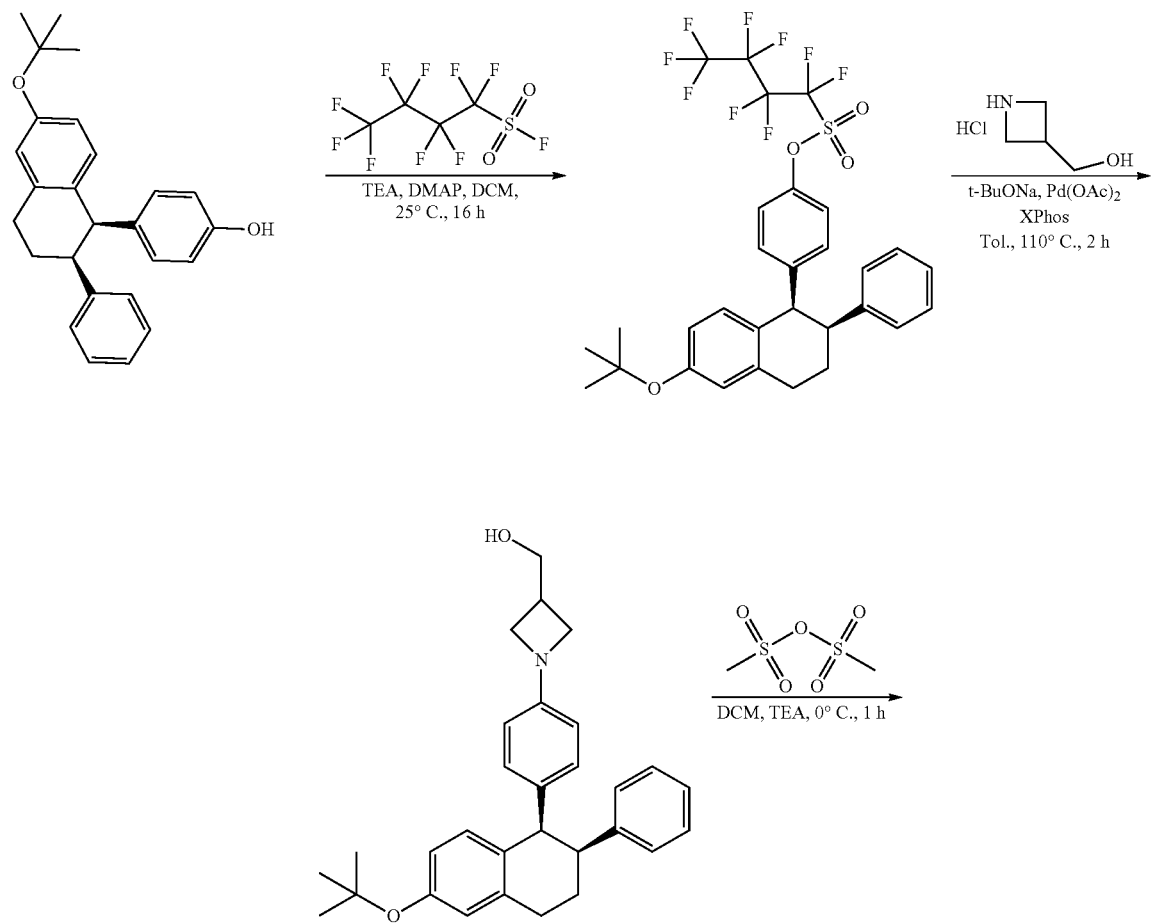

-continued
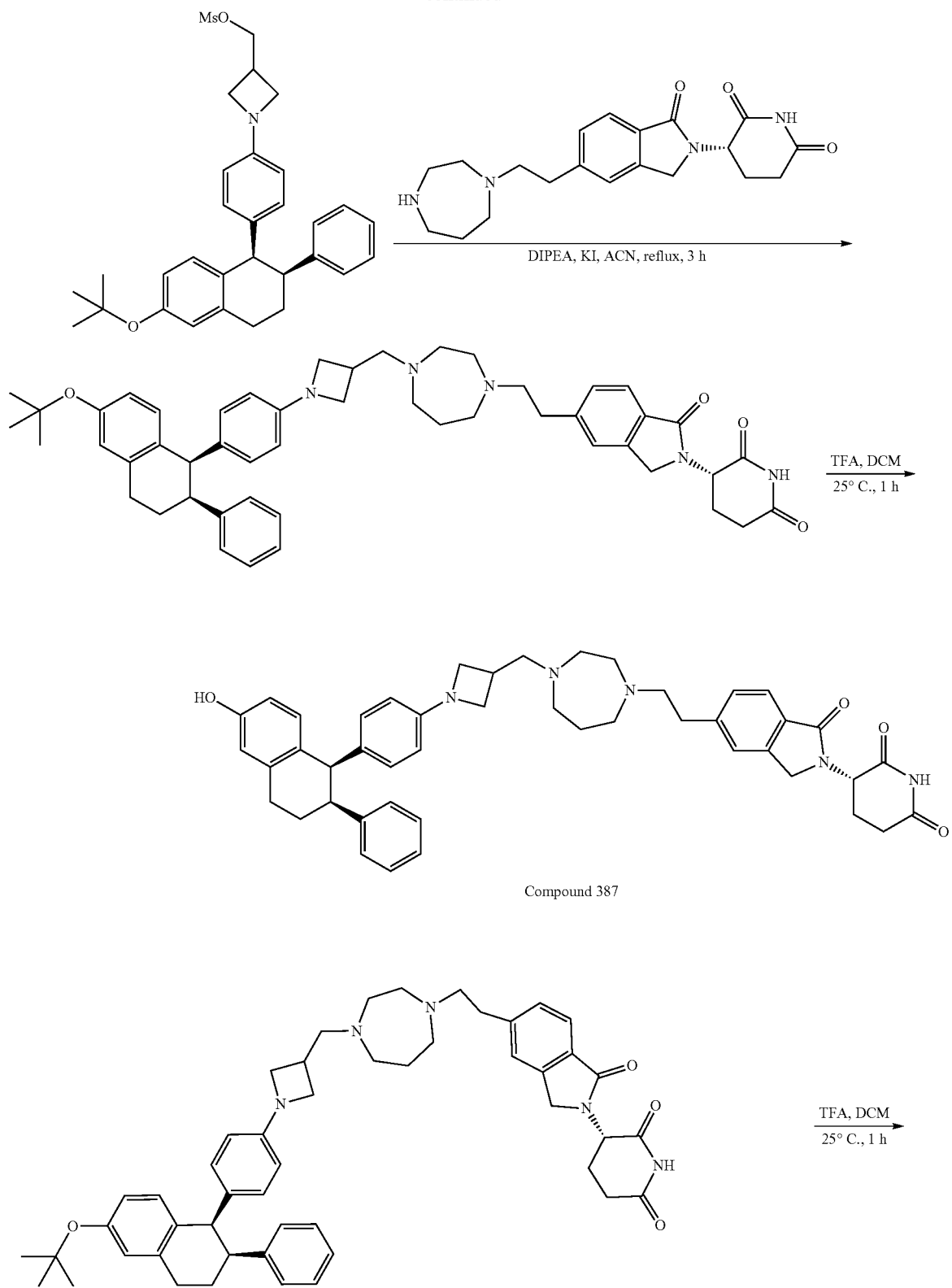
Compound 387

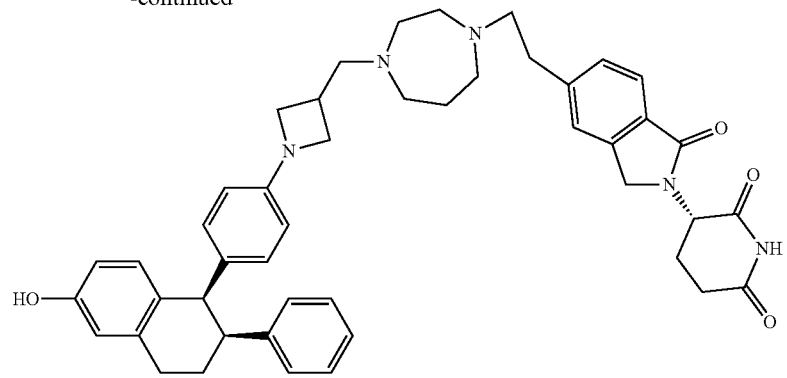
Compound 387
General synthetic scheme 3-66.
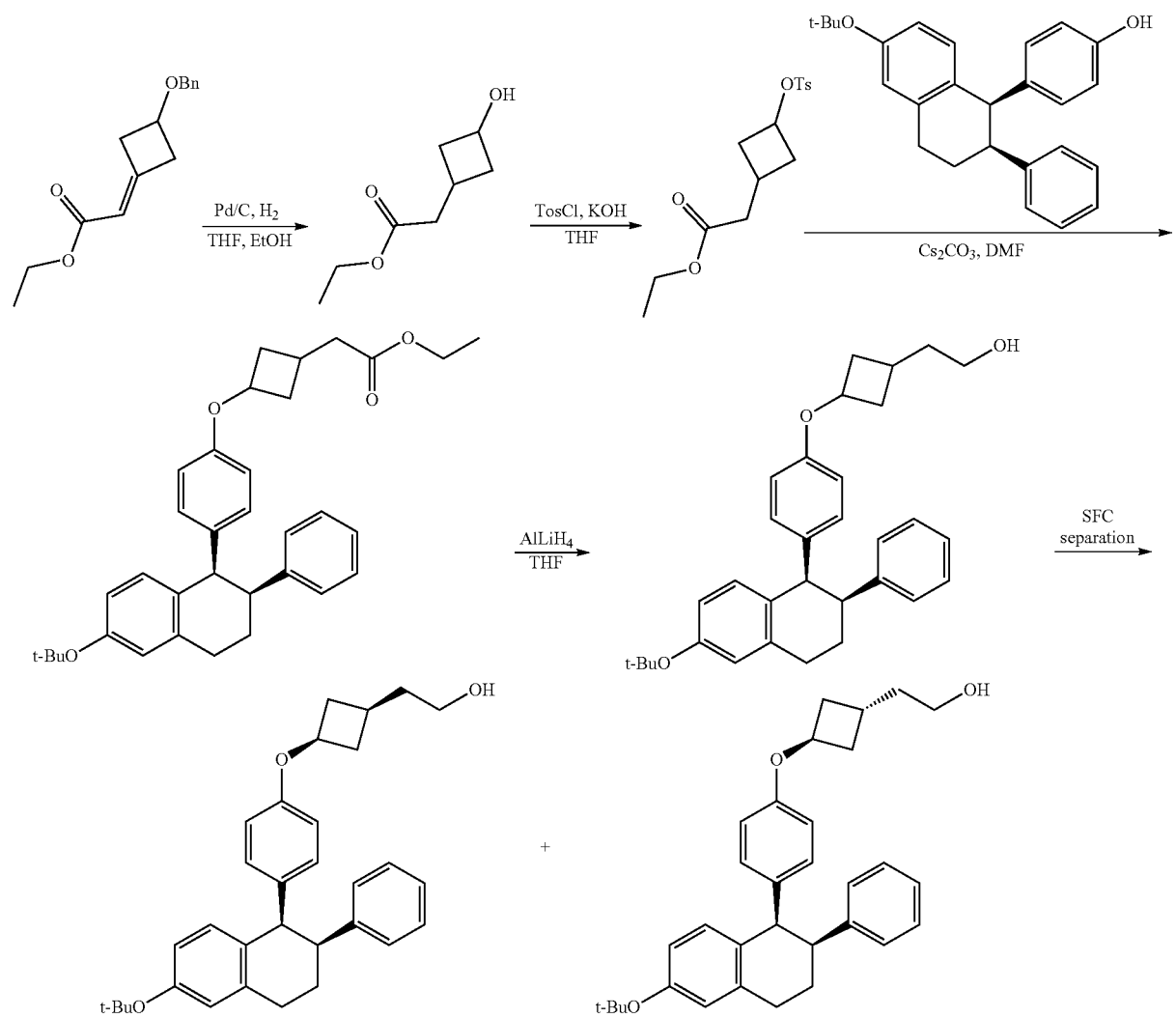

-continued
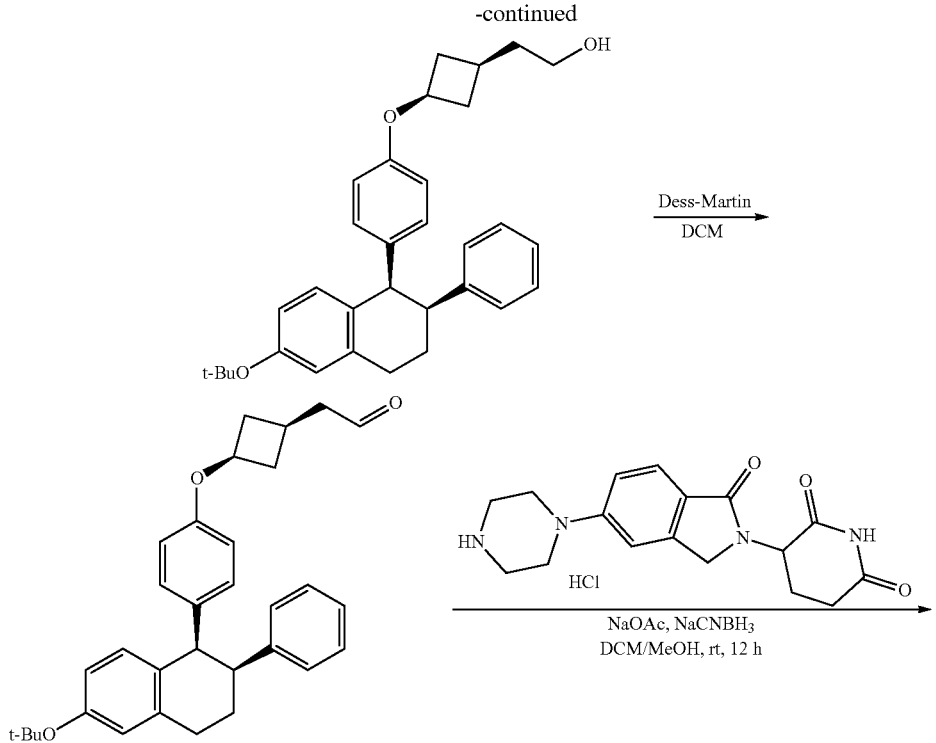
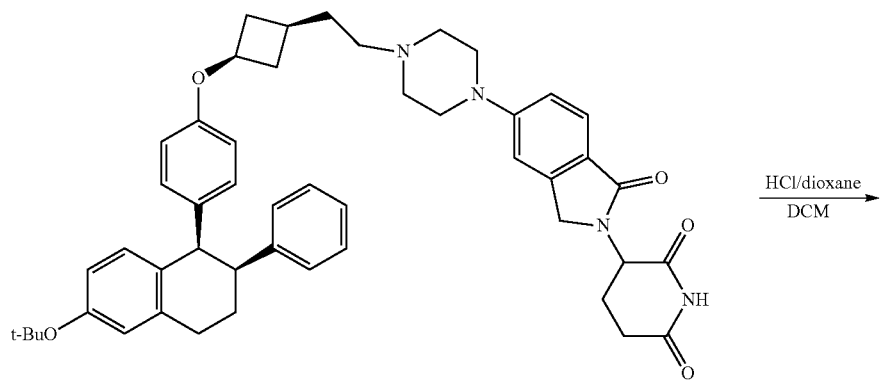
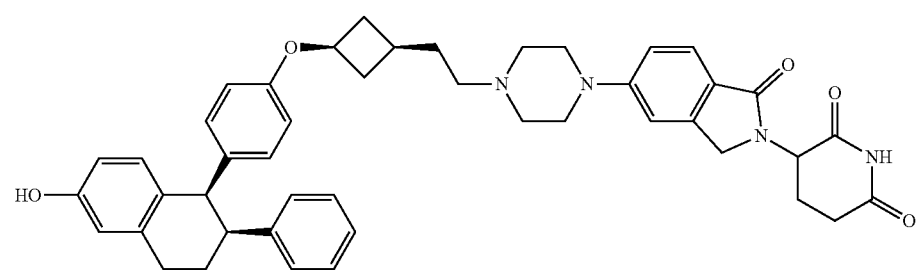
Compound 398

931 932
General synthetic scheme 3-67.
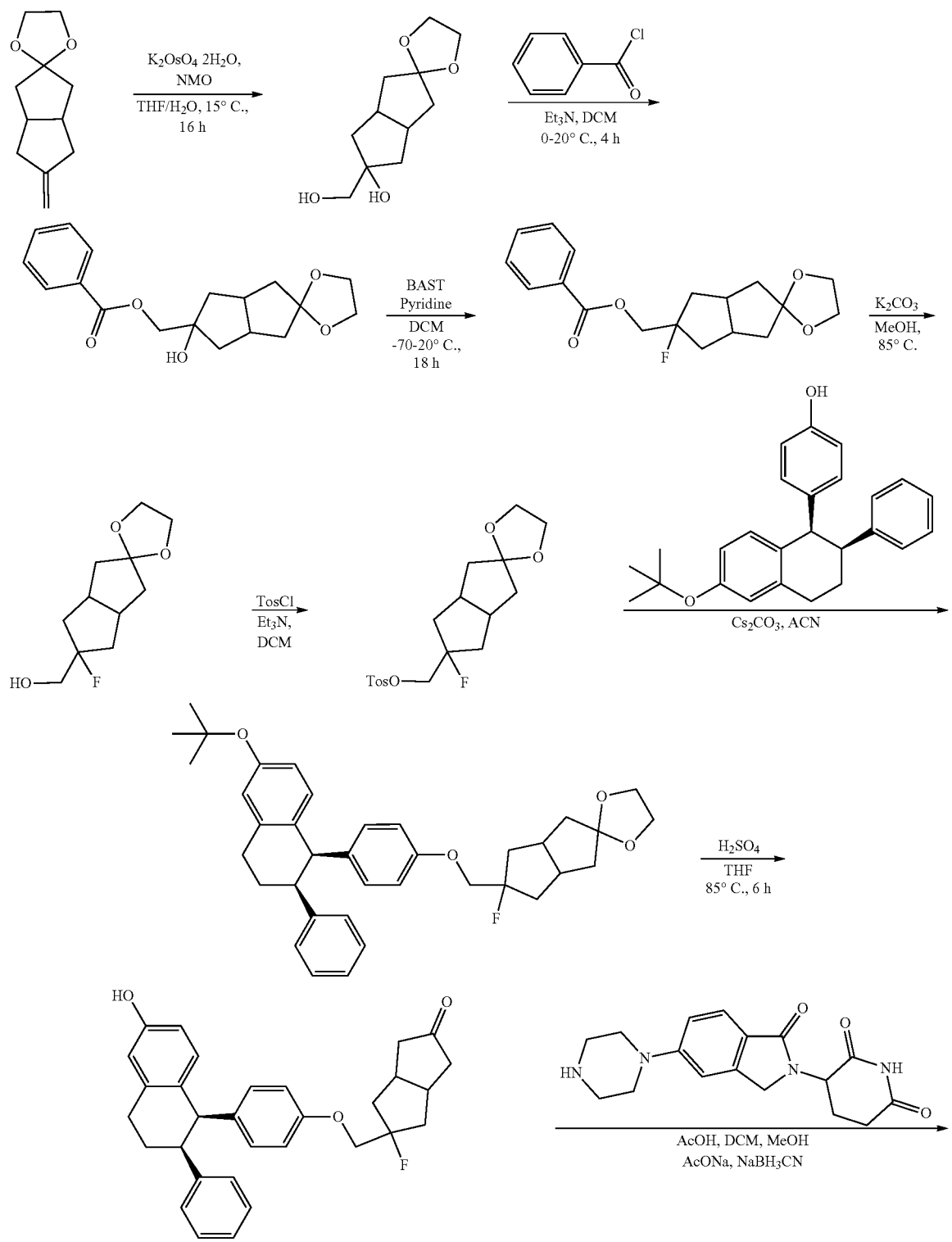

-continued
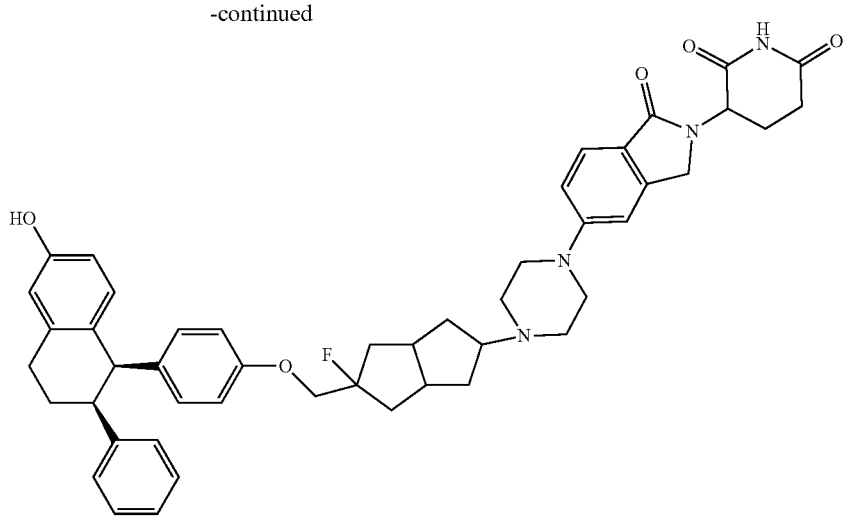
Compound 404
General synthetic scheme 3-68.
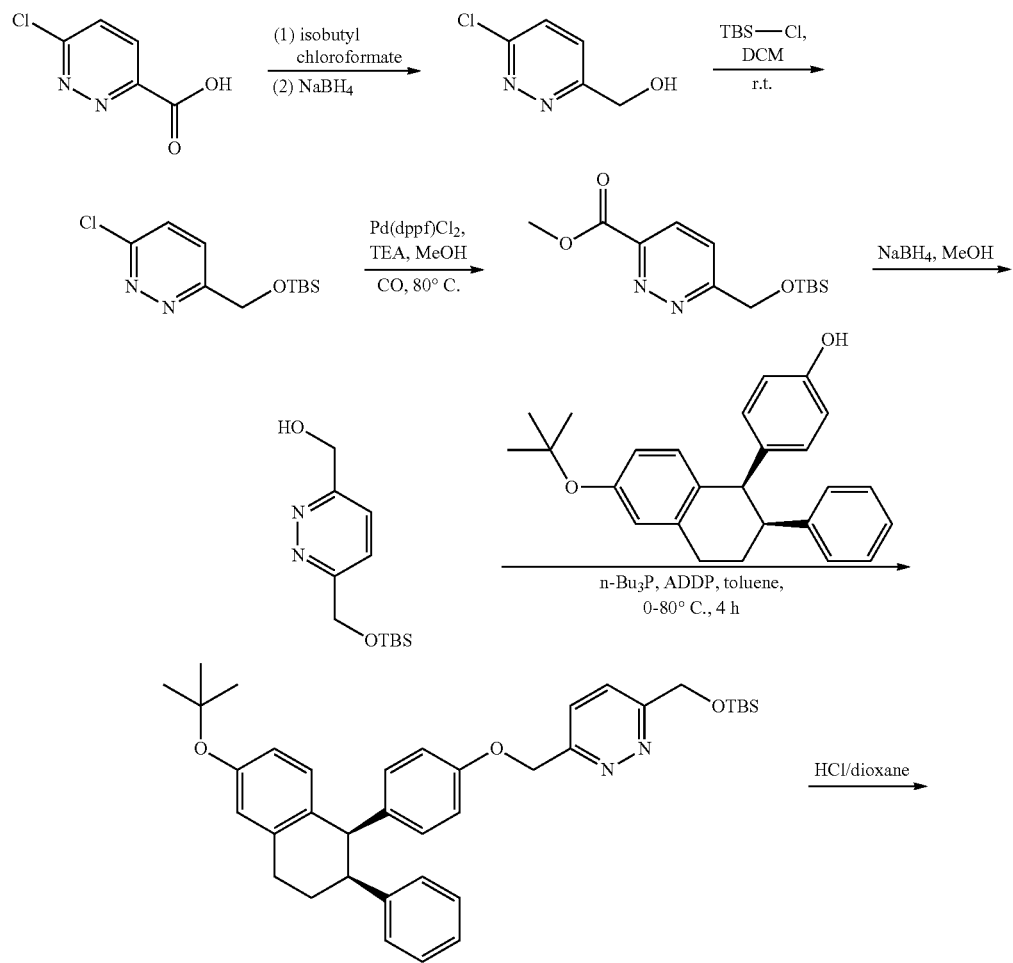

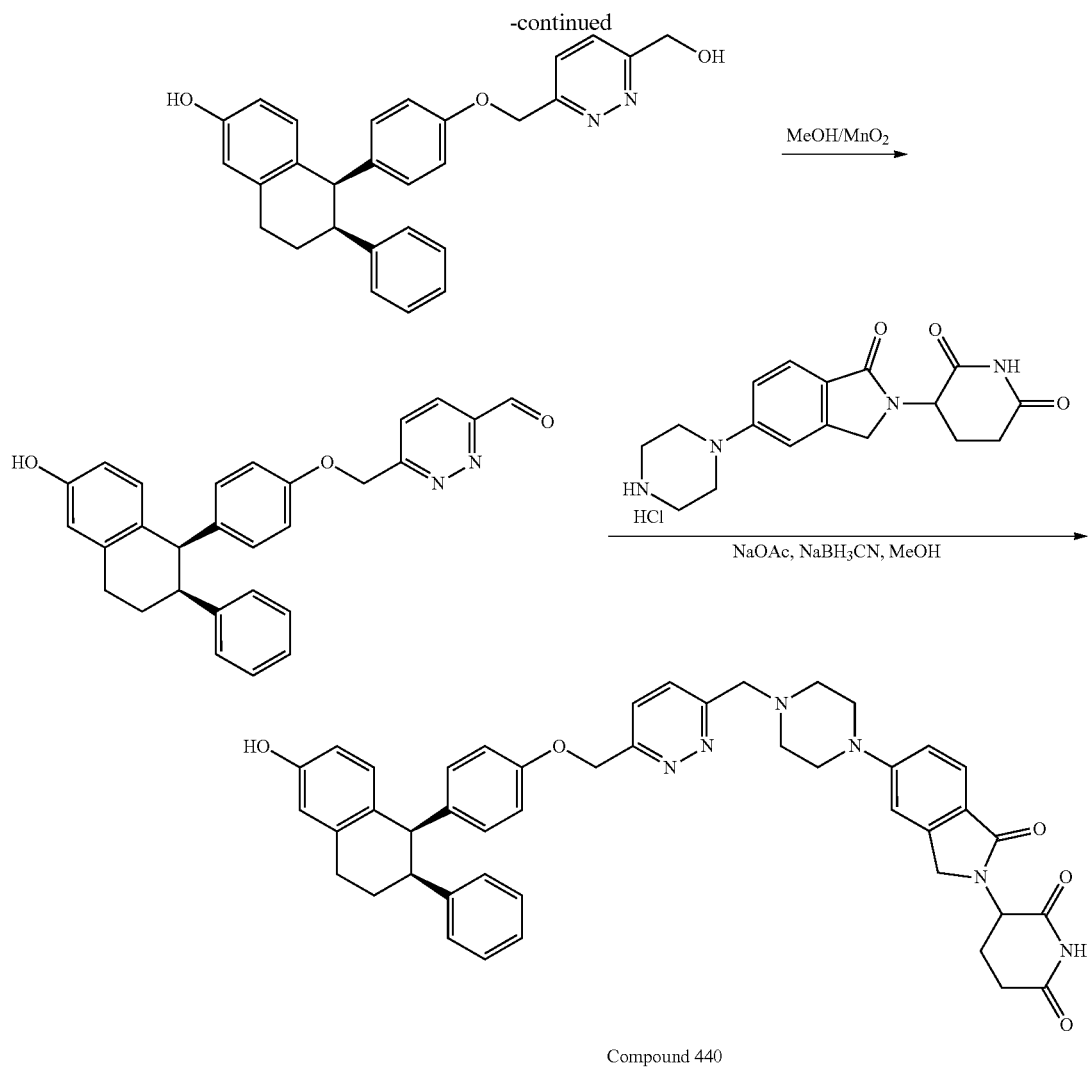
General synthetic scheme 3-69.
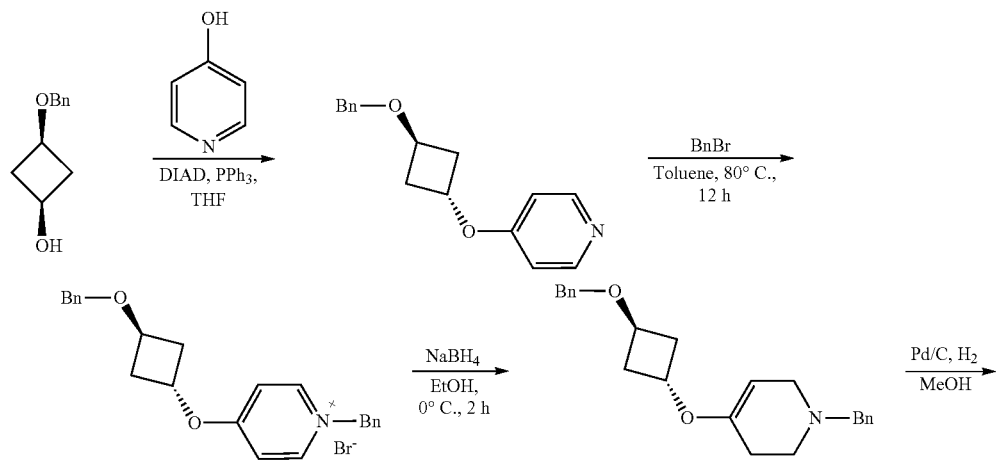

937                    938
-continued
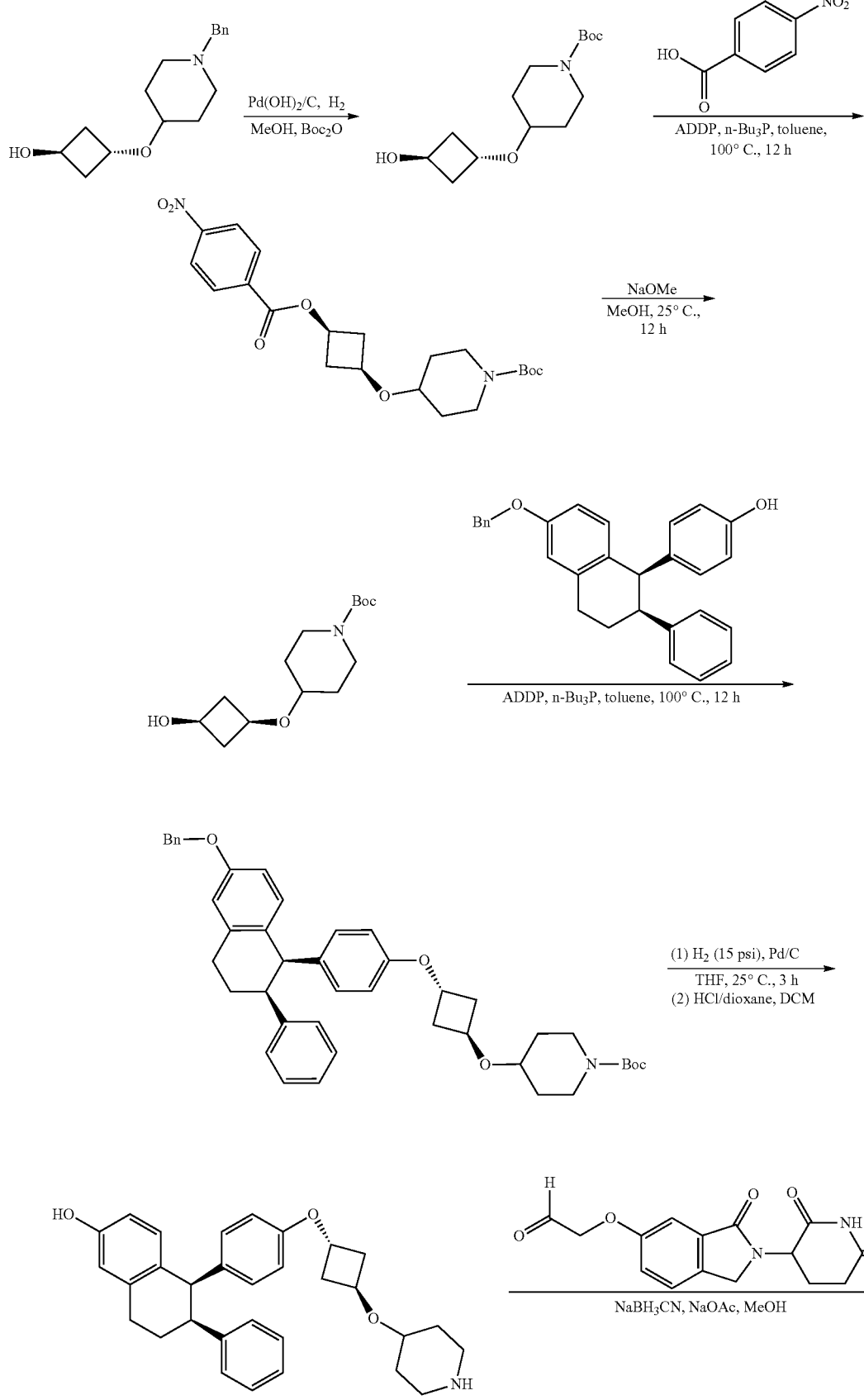

-continued
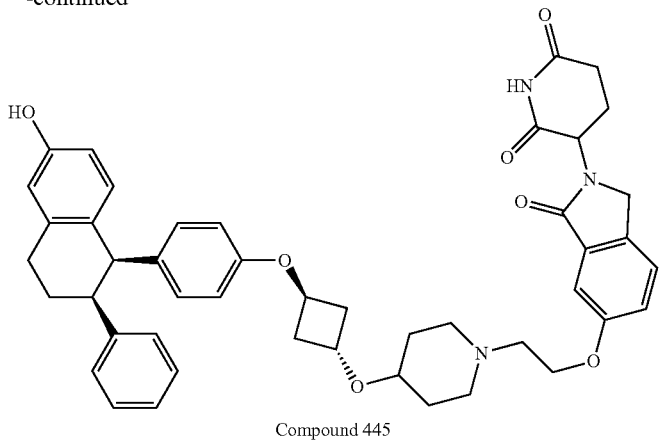
Compound 445
General synthetic scheme 3-70.
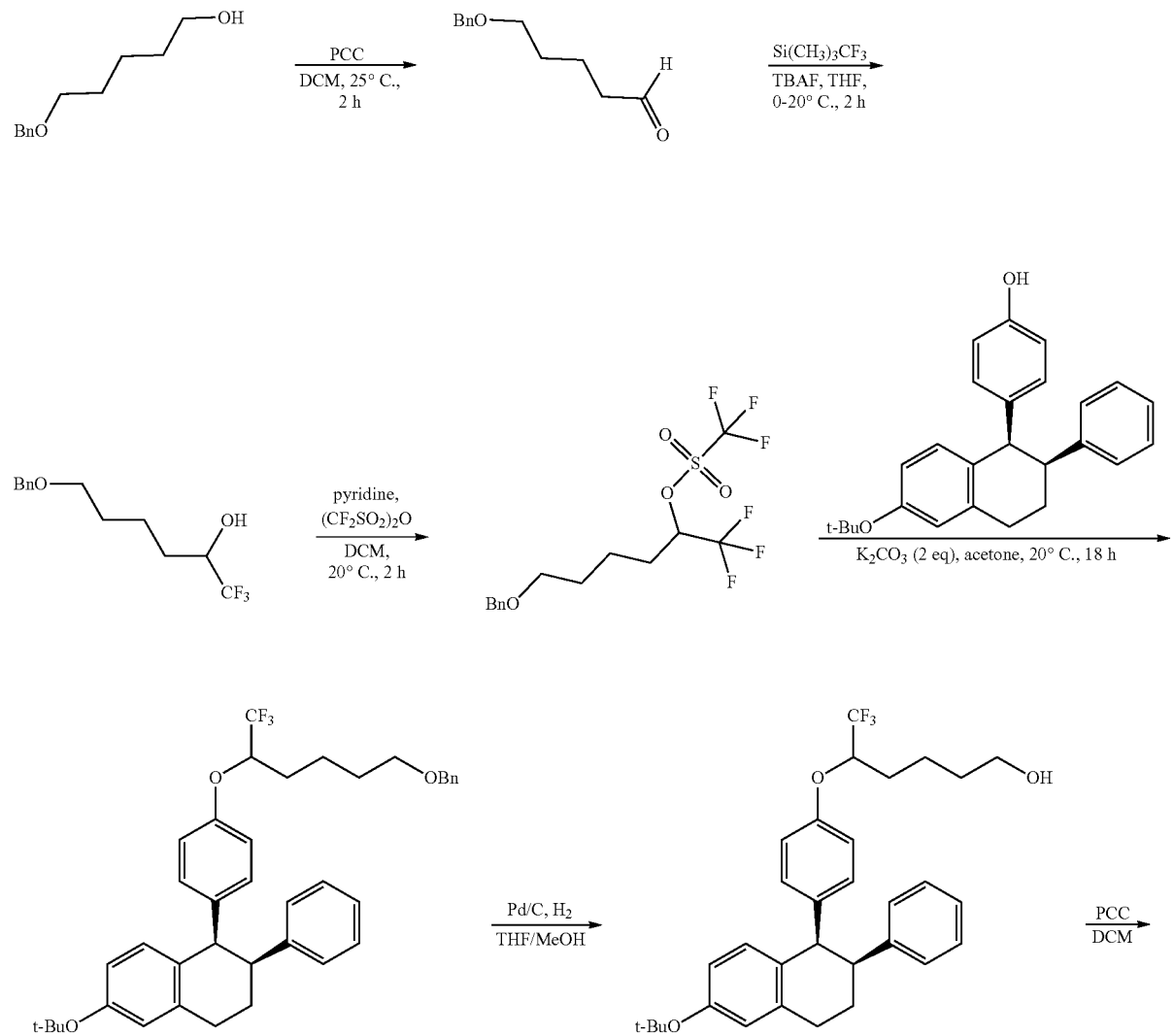

941 942
-continued
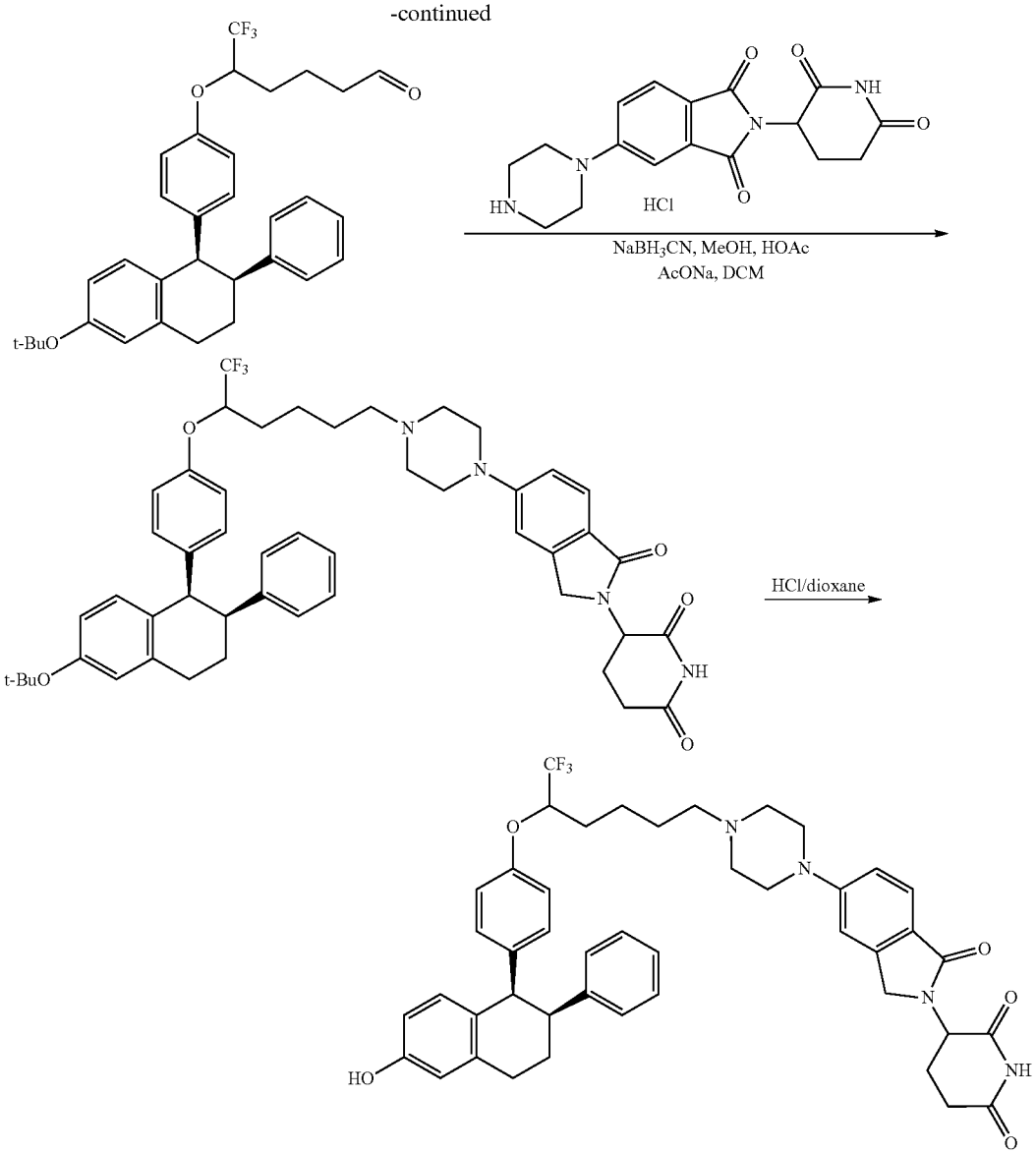
Compound 447
General synthetic scheme 3-71.
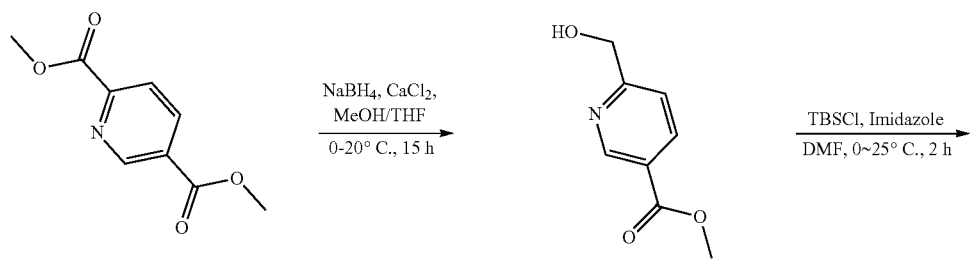

943 944
-continued
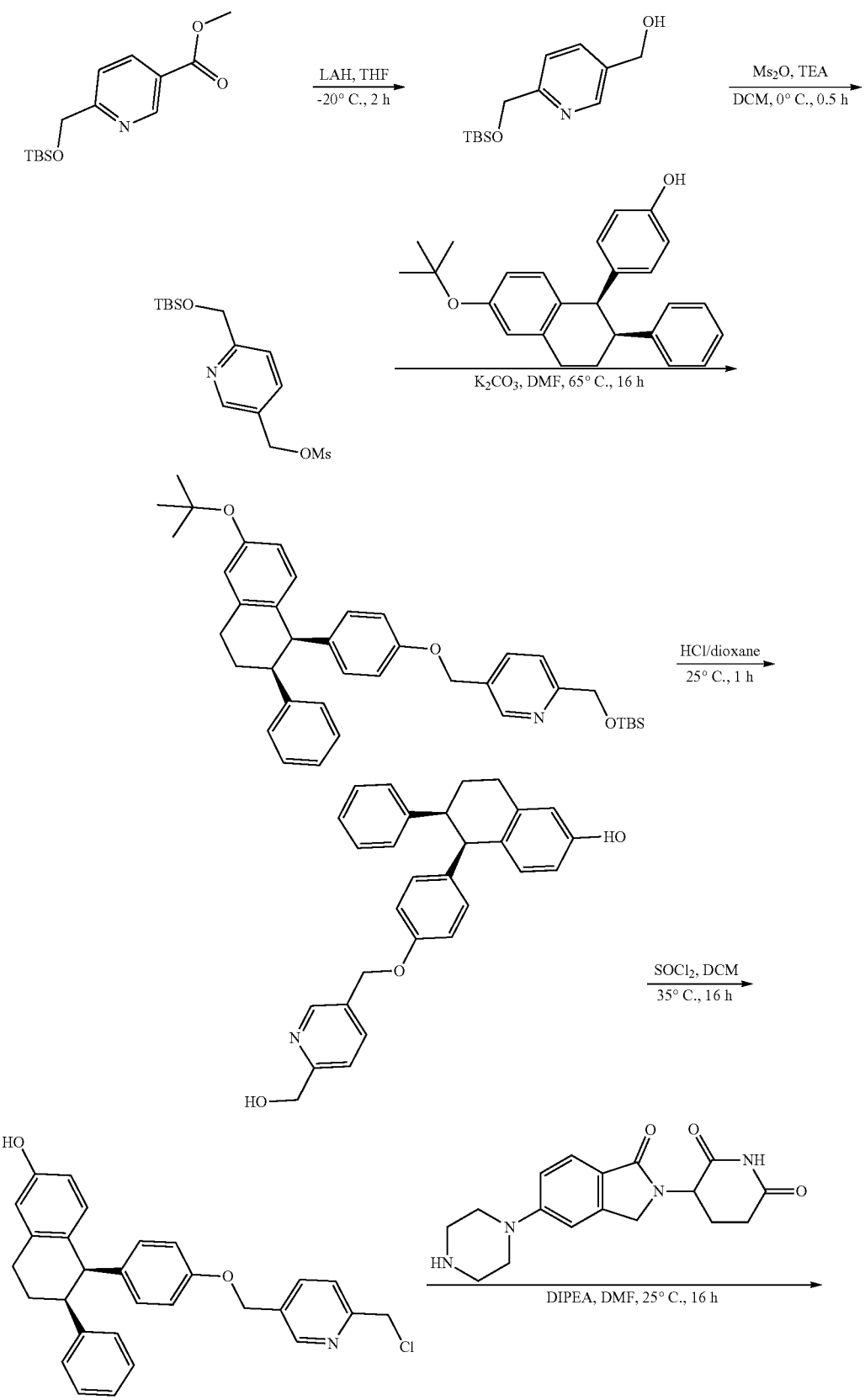

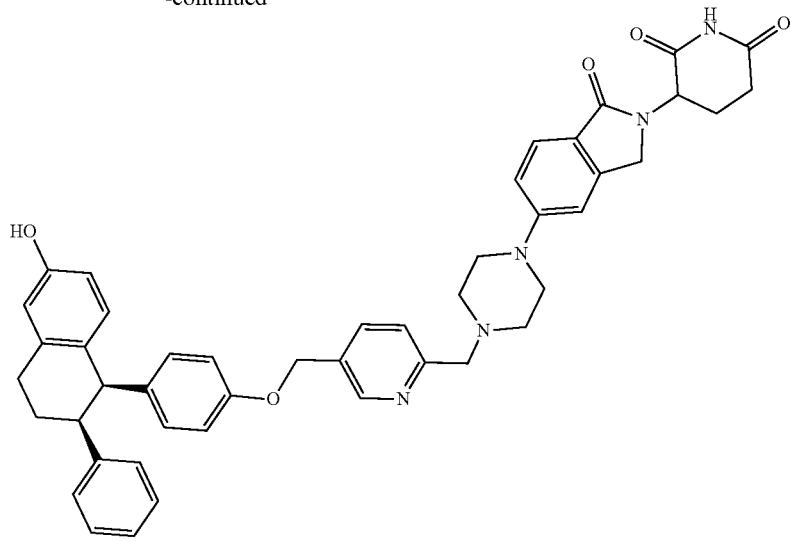
Compound 448
General synthetic scheme 3-73.
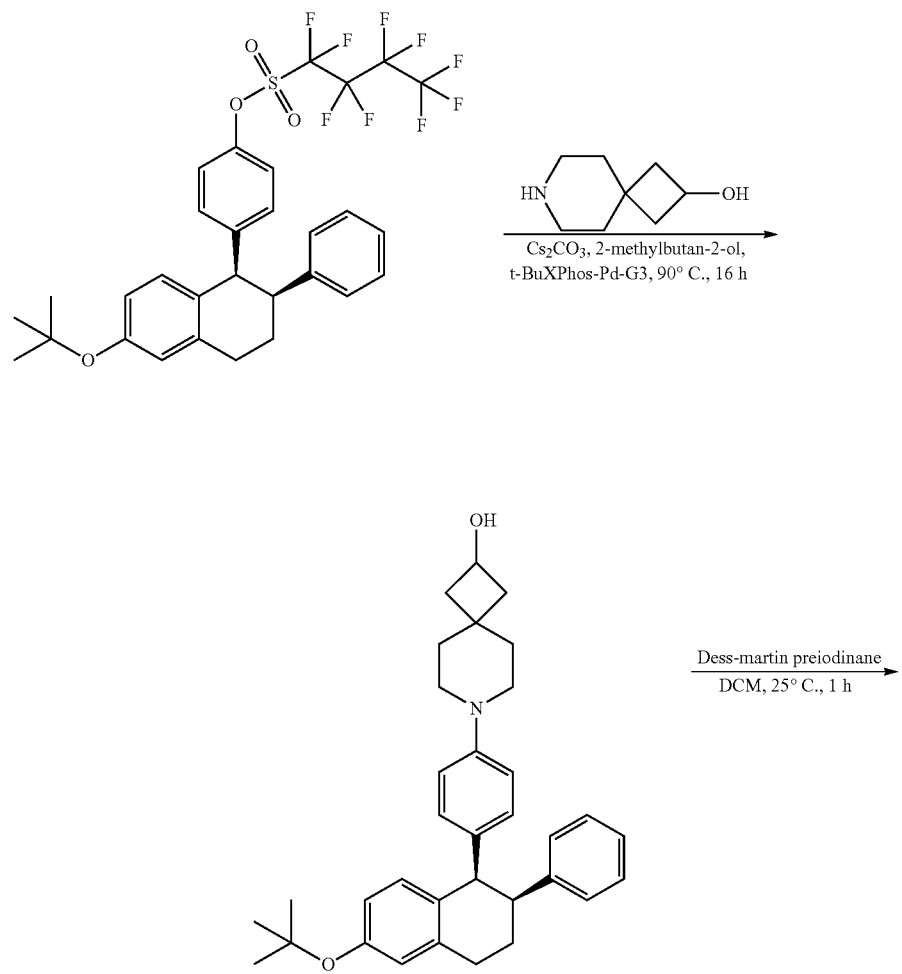

947
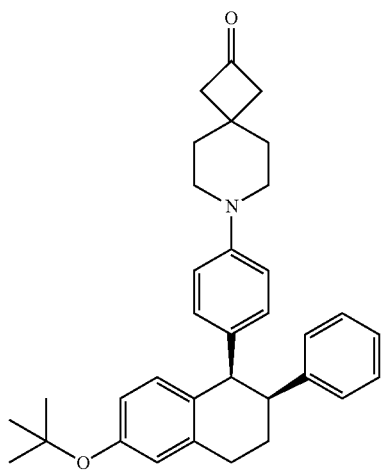
948
-continued
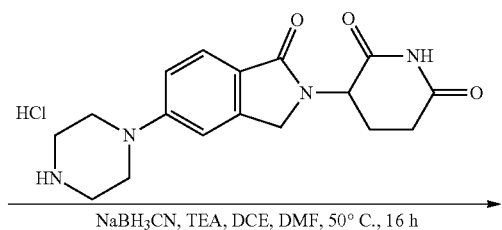
NaBH₃CN, TEA, DCE, DMF, 50° C., 16 h
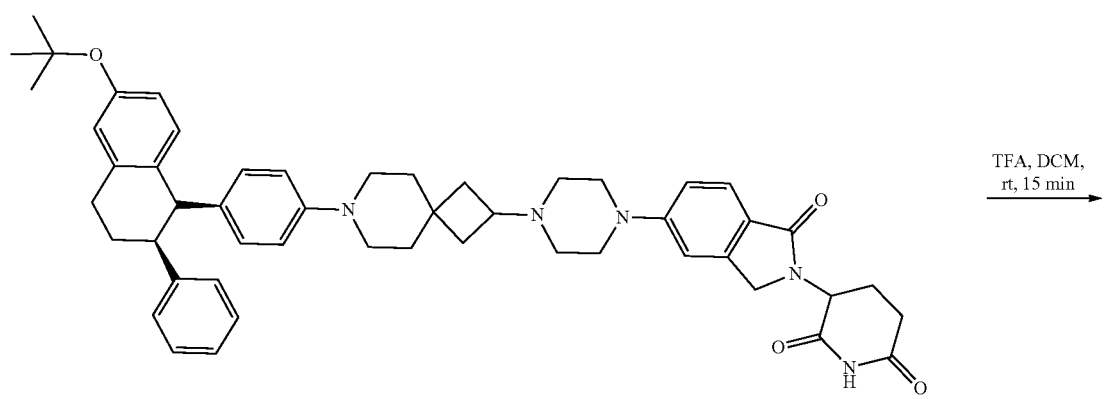
TFA, DCM, rt, 15 min
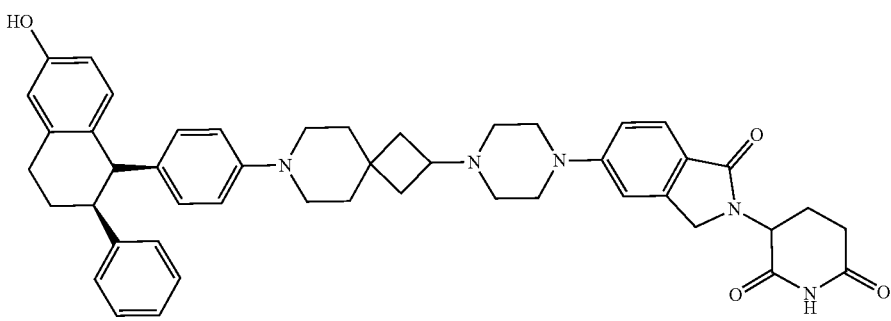
Compound 465

General synthetic scheme 3-74.
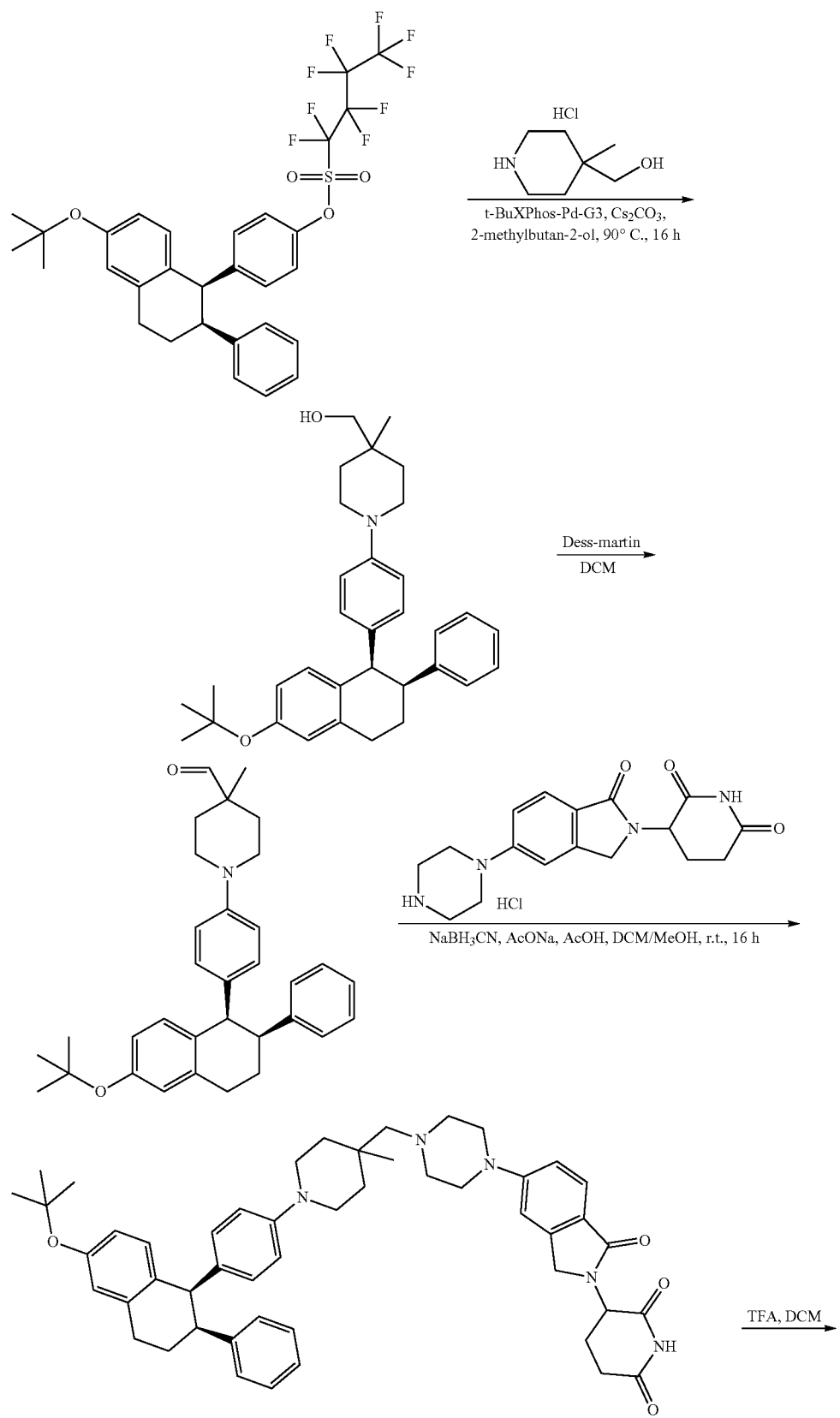

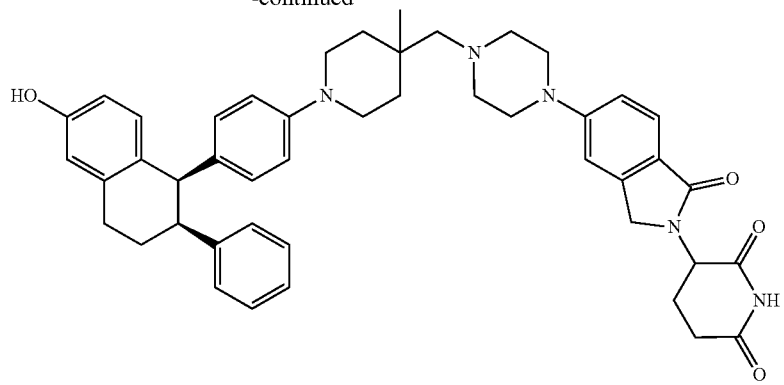
Compound 491
General synthetic scheme 3-75.
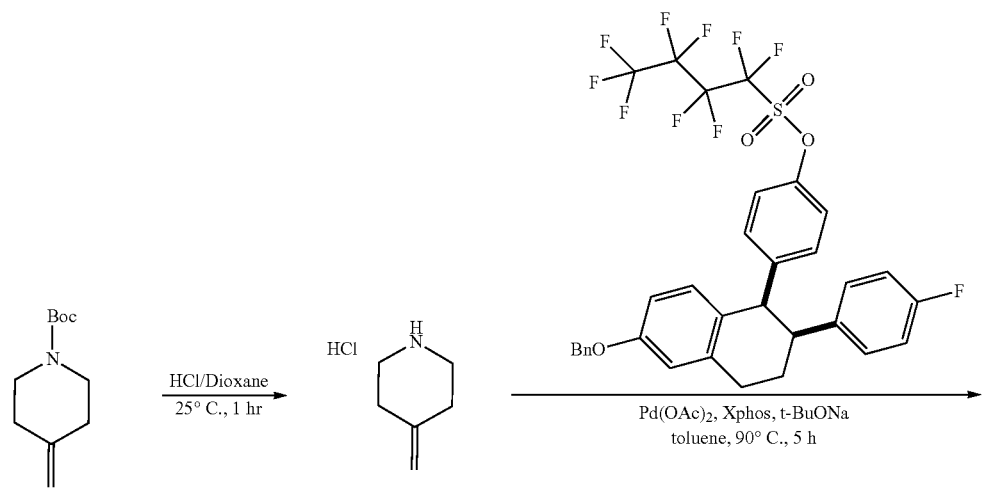
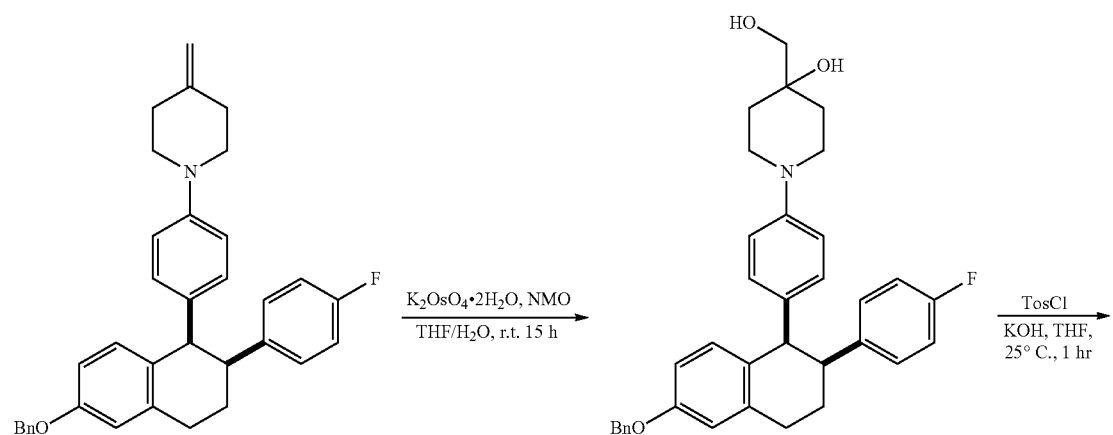

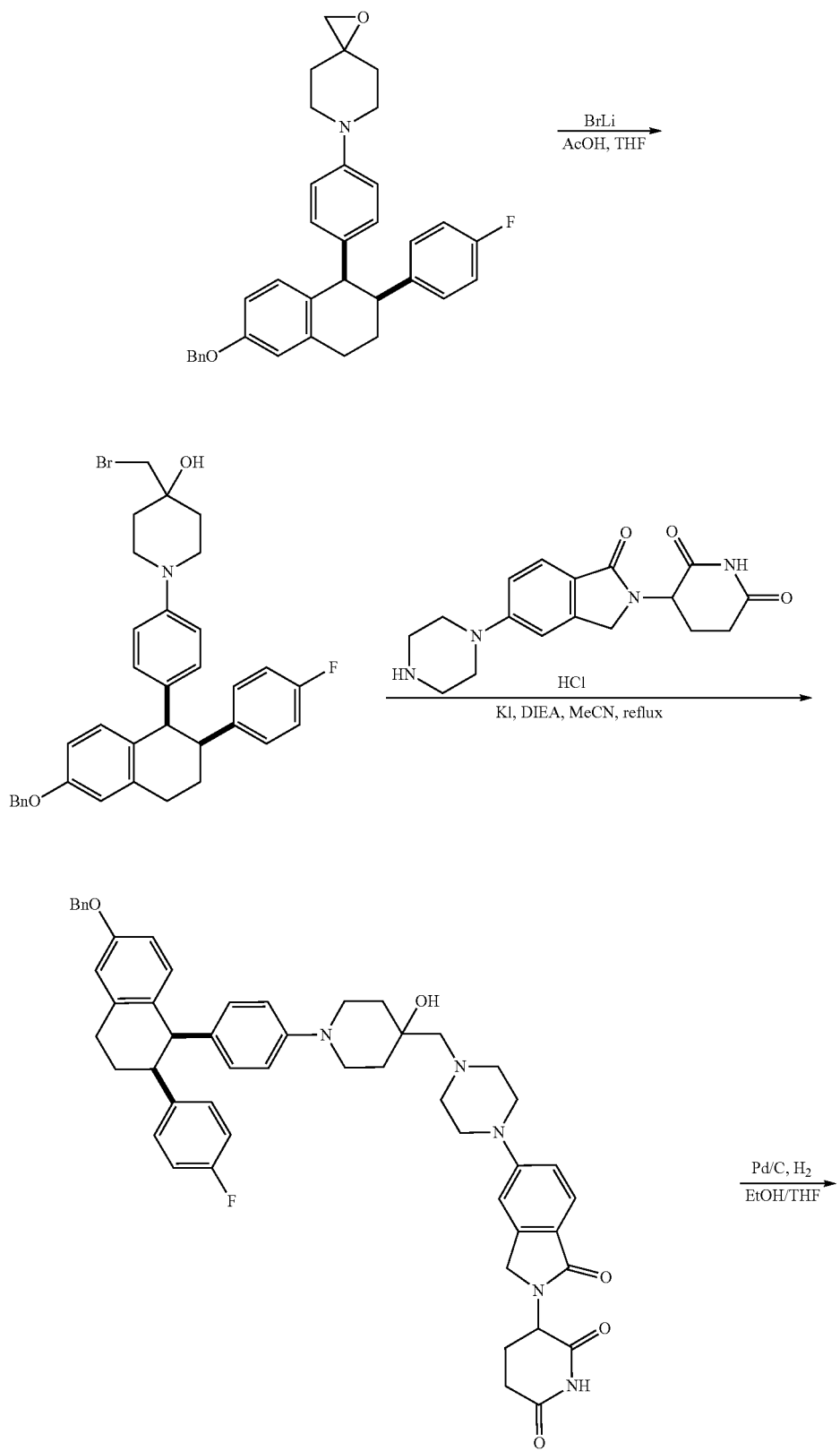

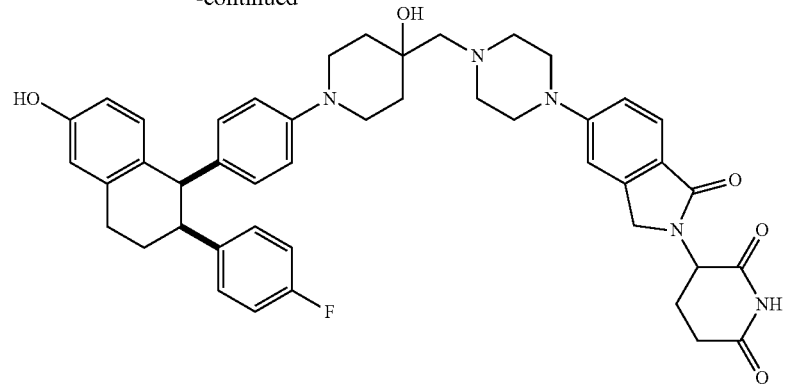
Compound 494
General synthetic scheme 3-76.
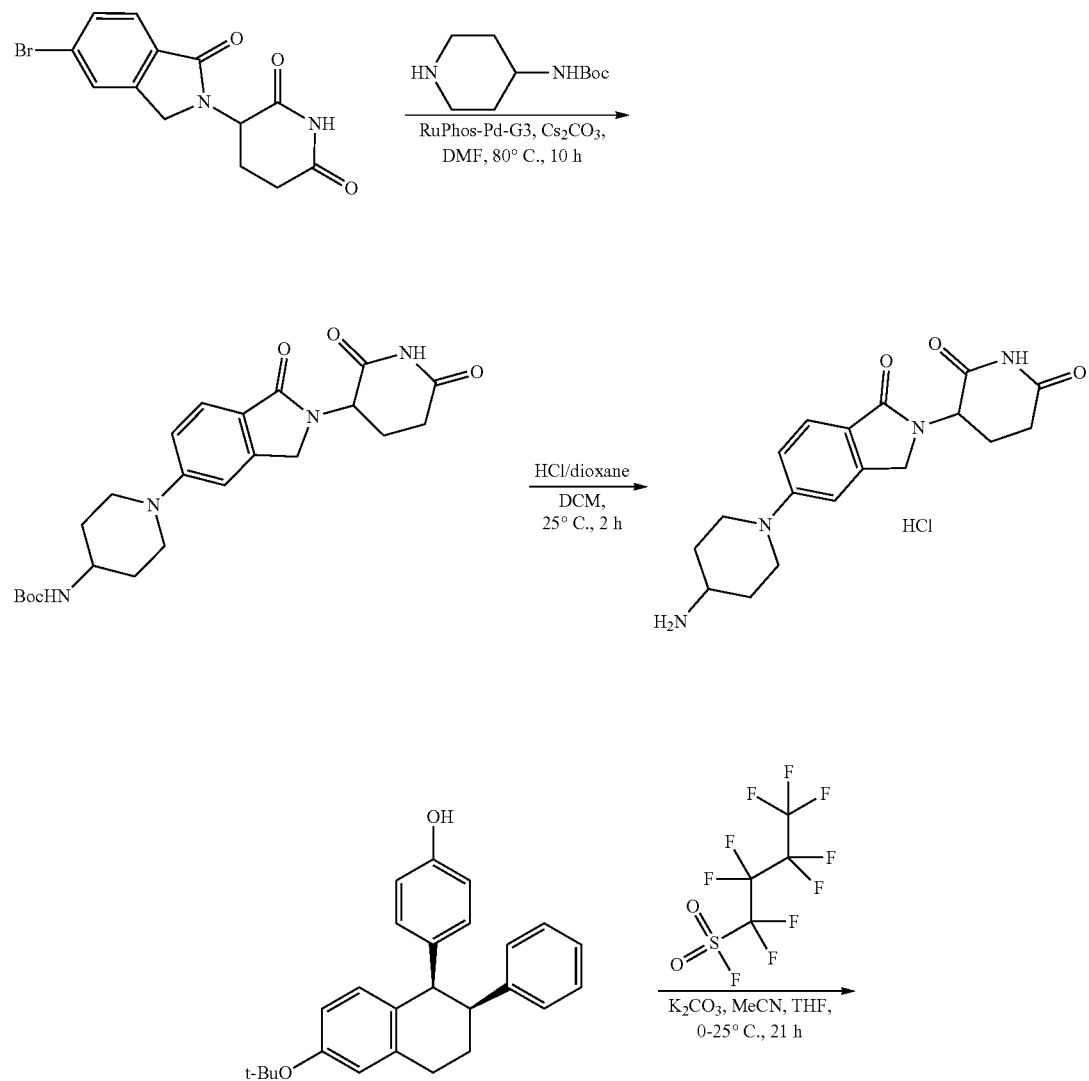

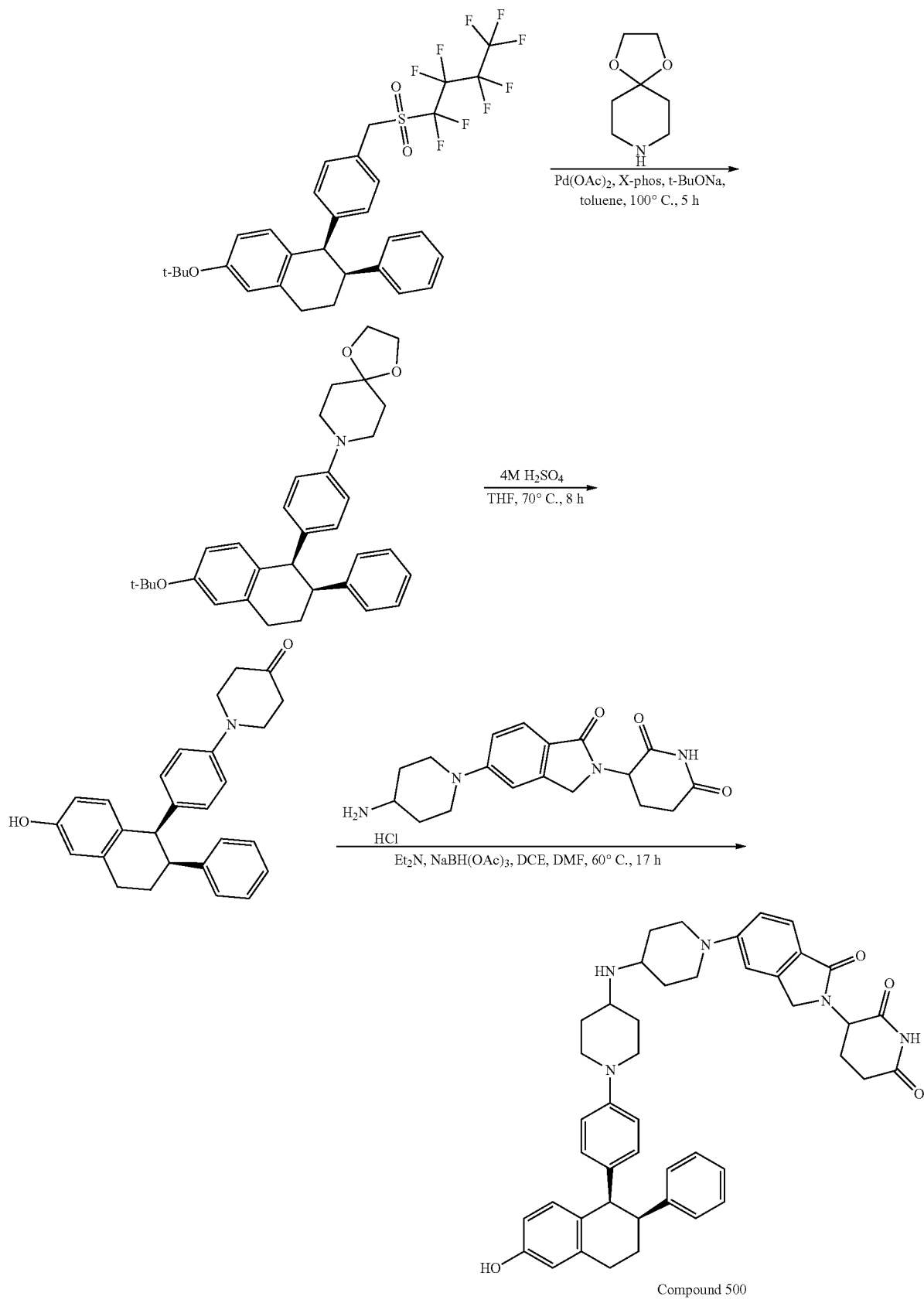

General synthetic scheme 3-77.
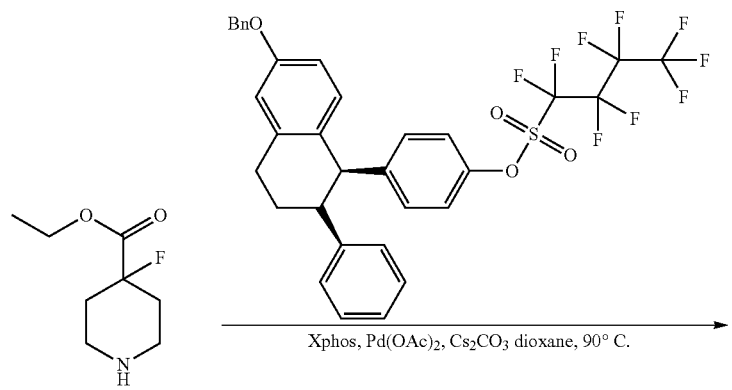
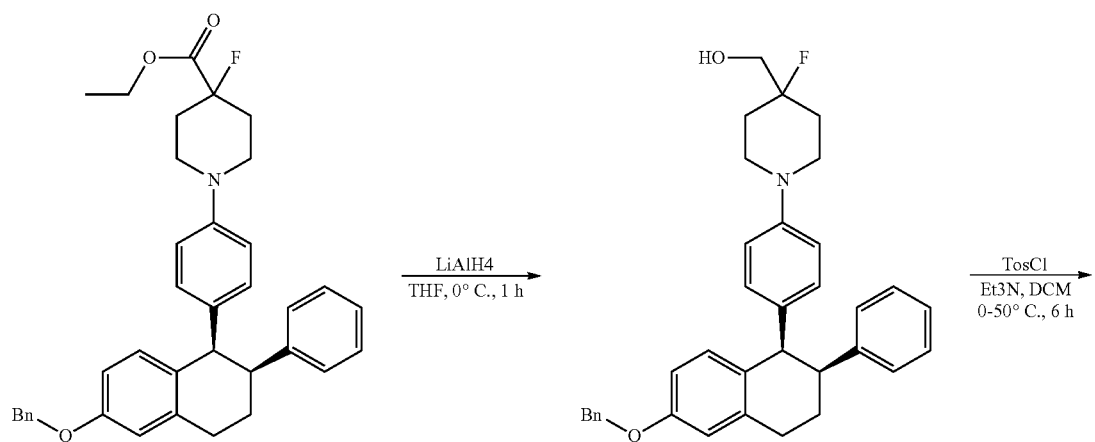
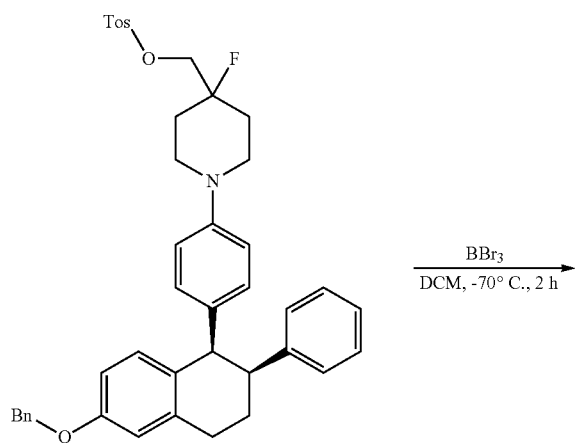

-continued
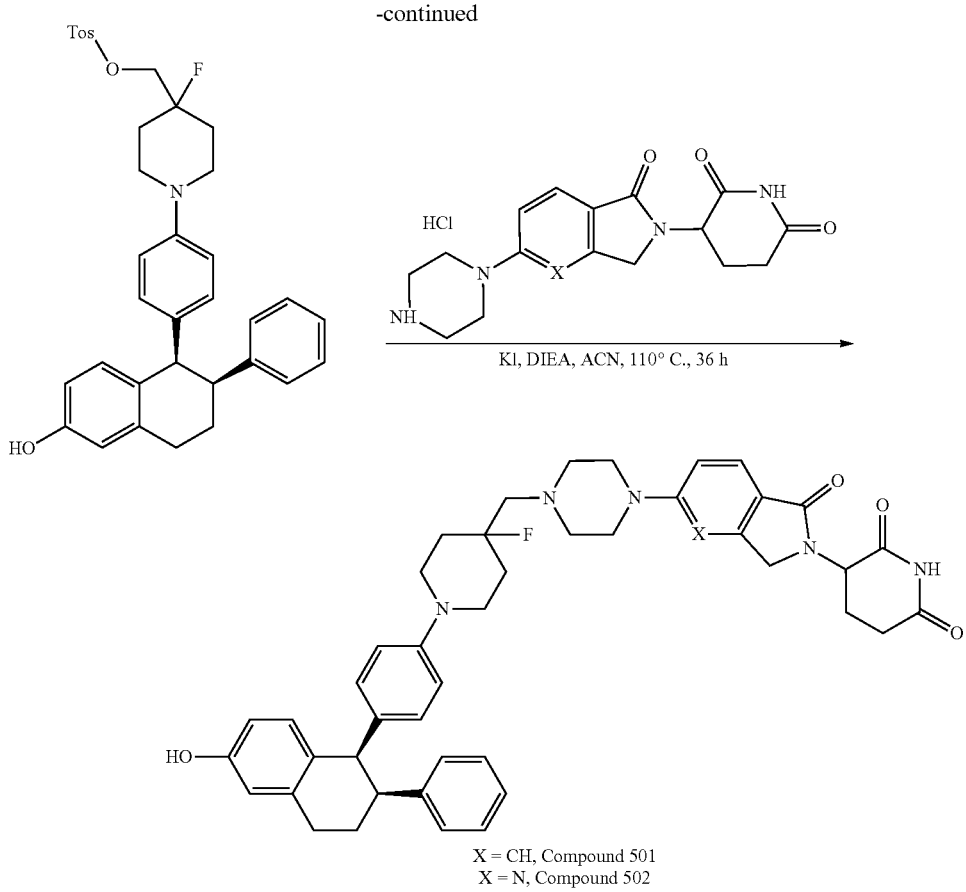
X = CH, Compound 501
X = N, Compound 502
General synthetic scheme 3-78.
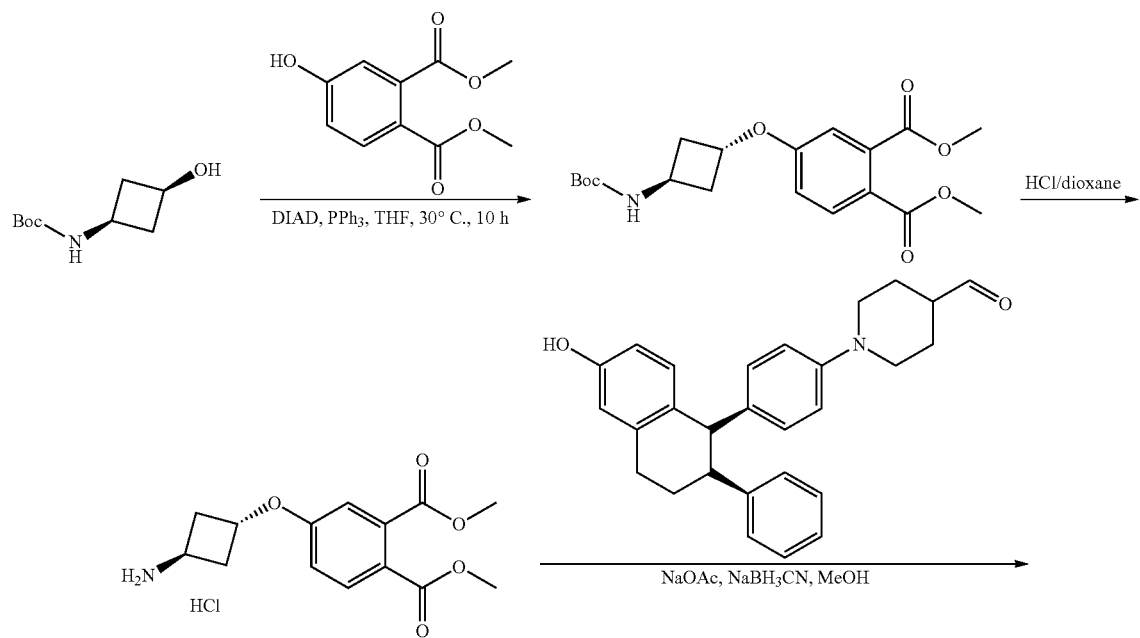

-continued
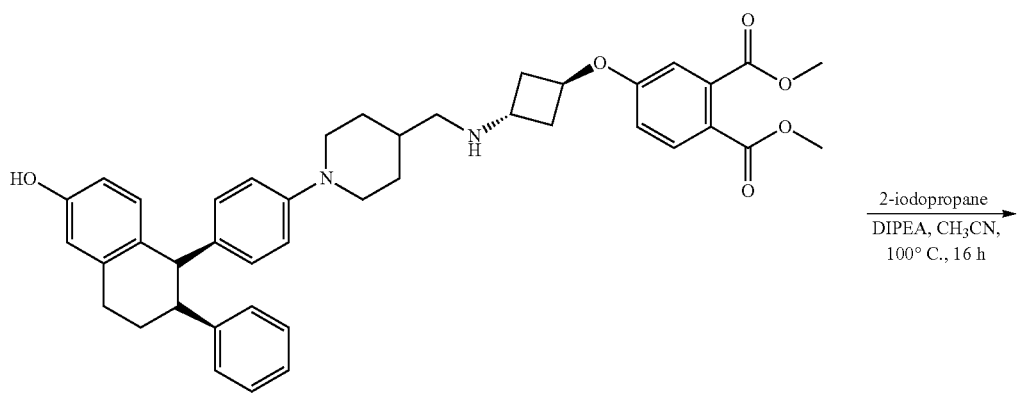
2-iodopropane
DIPEA, CH₃CN,
100° C., 16 h
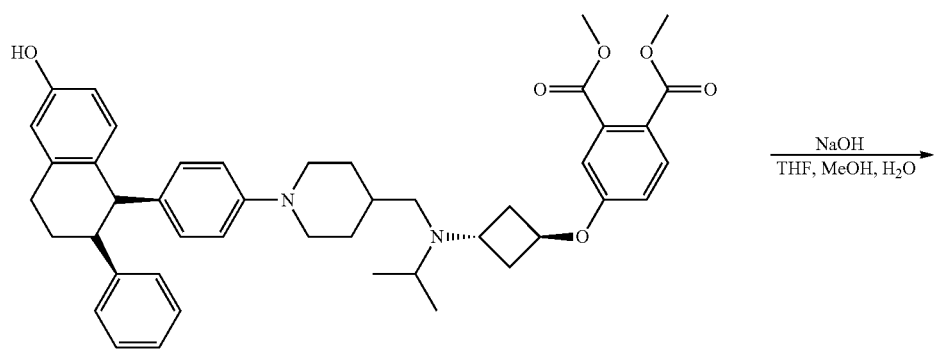
NaOH
THF, MeOH, H₂O
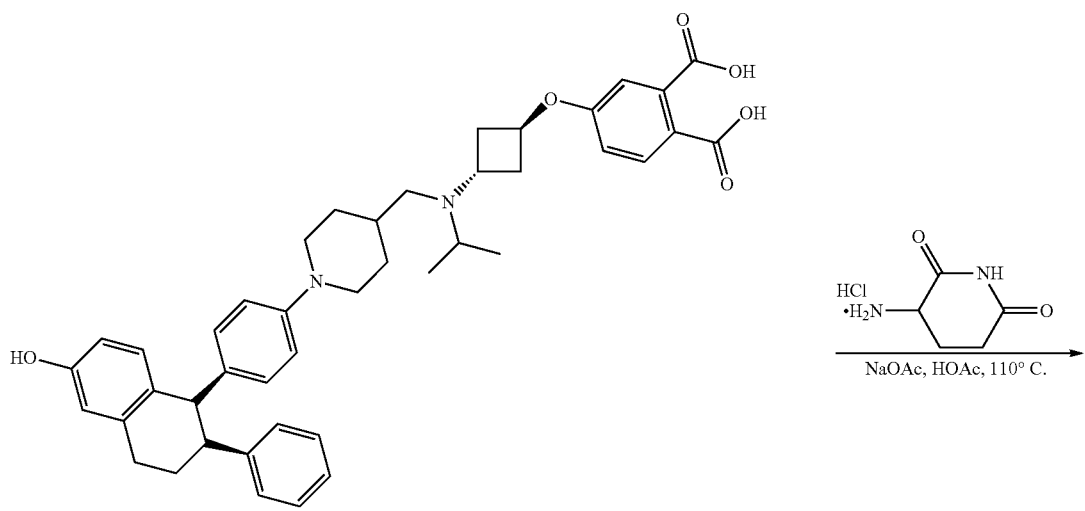
HCl·H₂N— [glutarimide]
NaOAc, HOAc, 110° C.

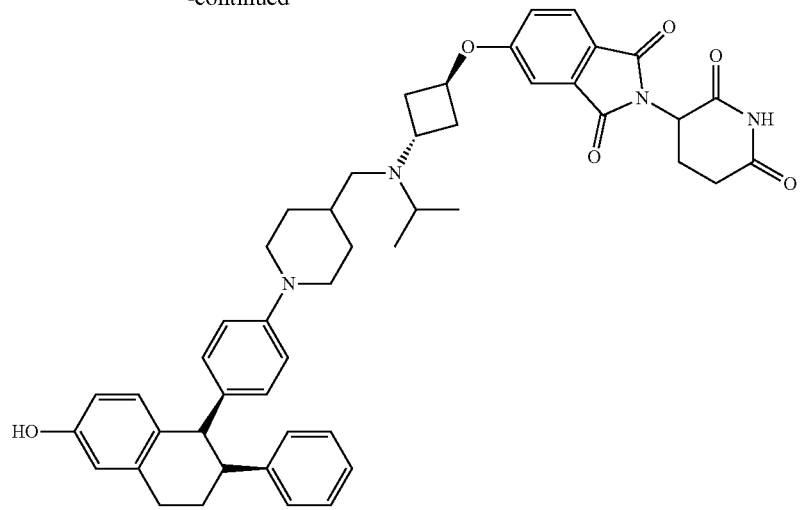
Compound 513
General synthetic scheme 3-80.
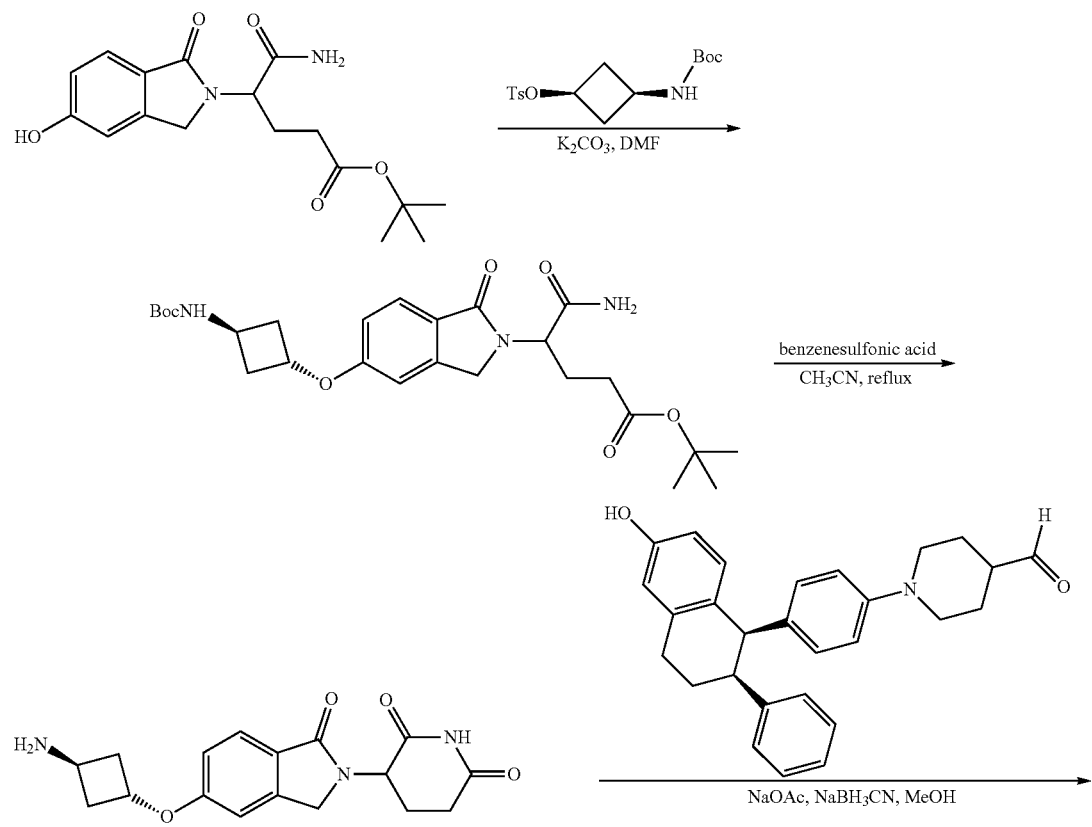

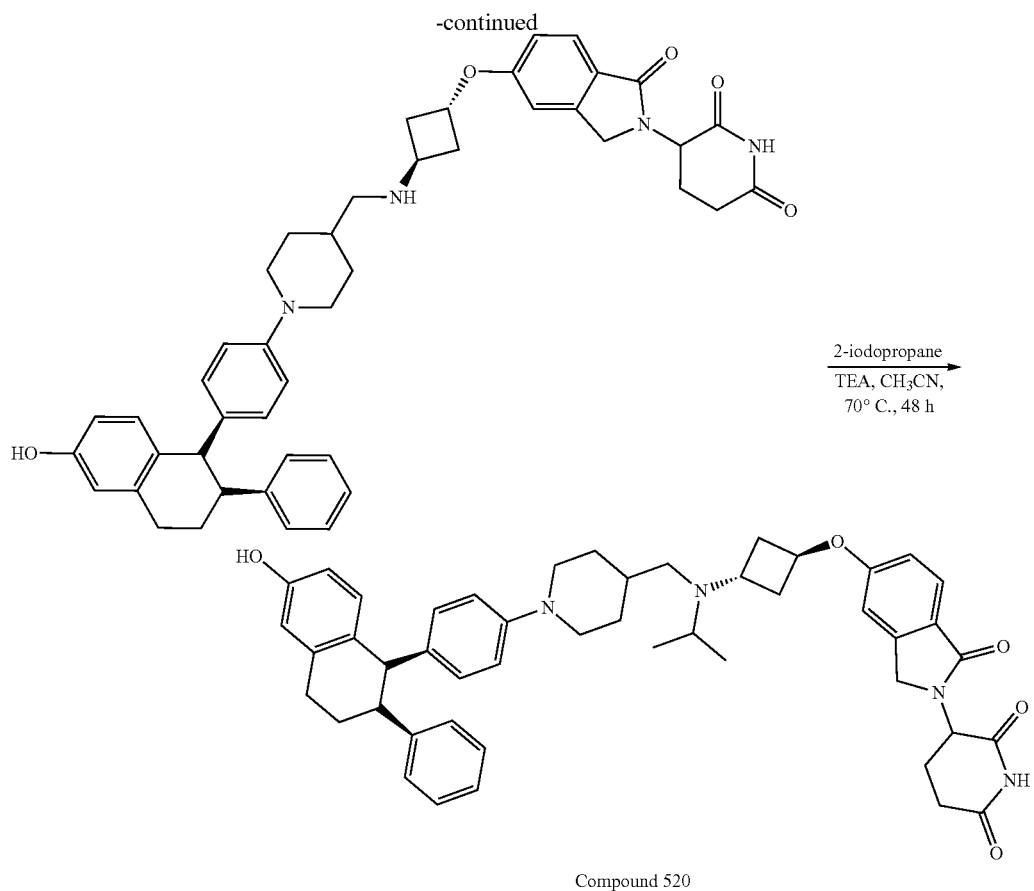
Compound 520
General synthetic scheme 3-81.
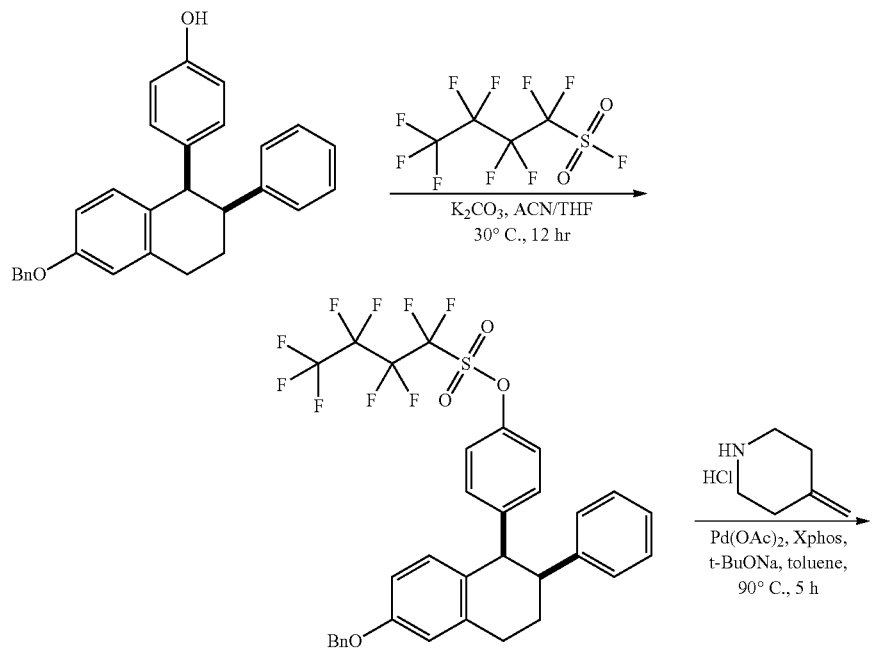

-continued
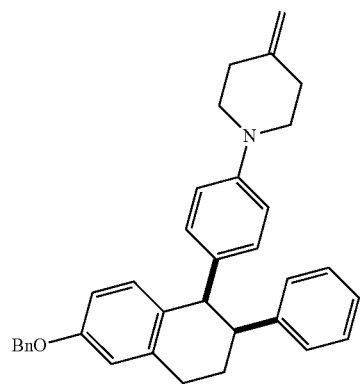
K$_2$OsO$_4$·2H$_2$O, NMO
───────────────────
THF/H$_2$O, 25° C., 16 h
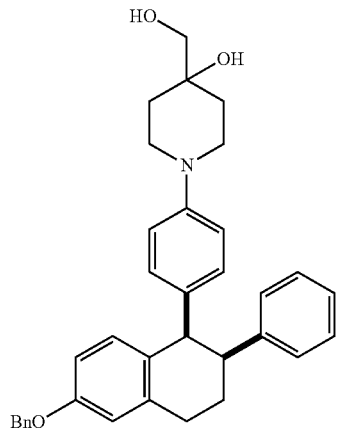
TosCl, THF
──────────
KOH, 30° C., 1 hr
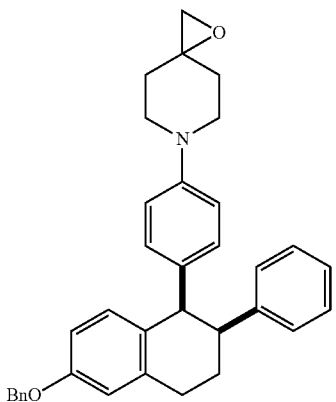
HN(piperazine)N—Cbz
───────────────────
DMF, DIEA, 120° C., 12 hr
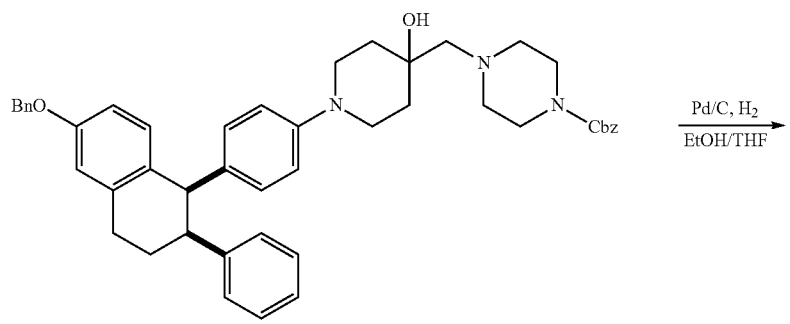
Pd/C, H$_2$
──────────
EtOH/THF
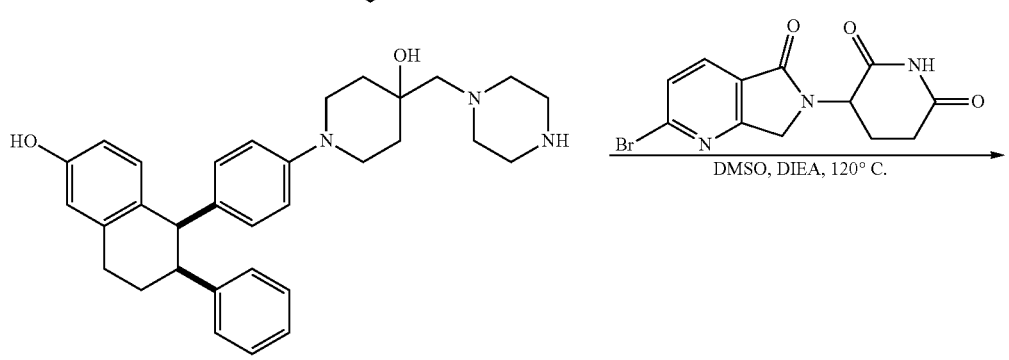
DMSO, DIEA, 120° C.

-continued
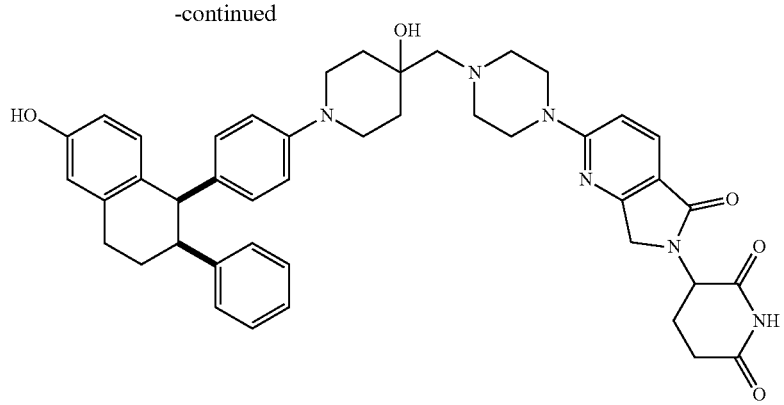
Compound 521
General synthetic scheme 3-82.
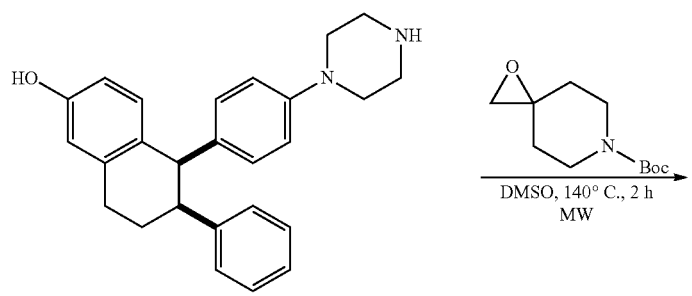
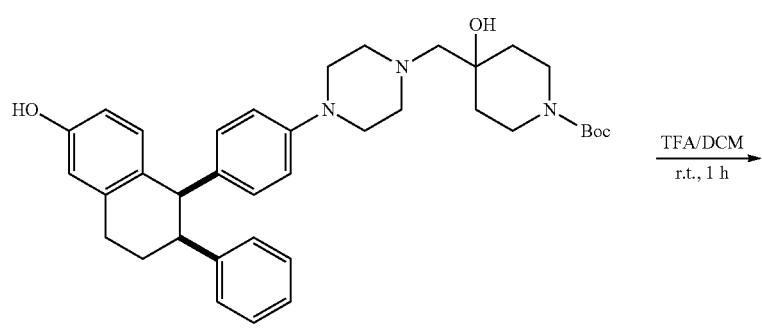
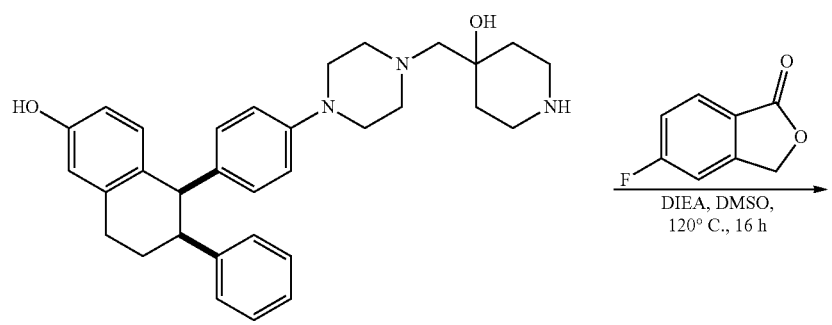

973 974
-continued
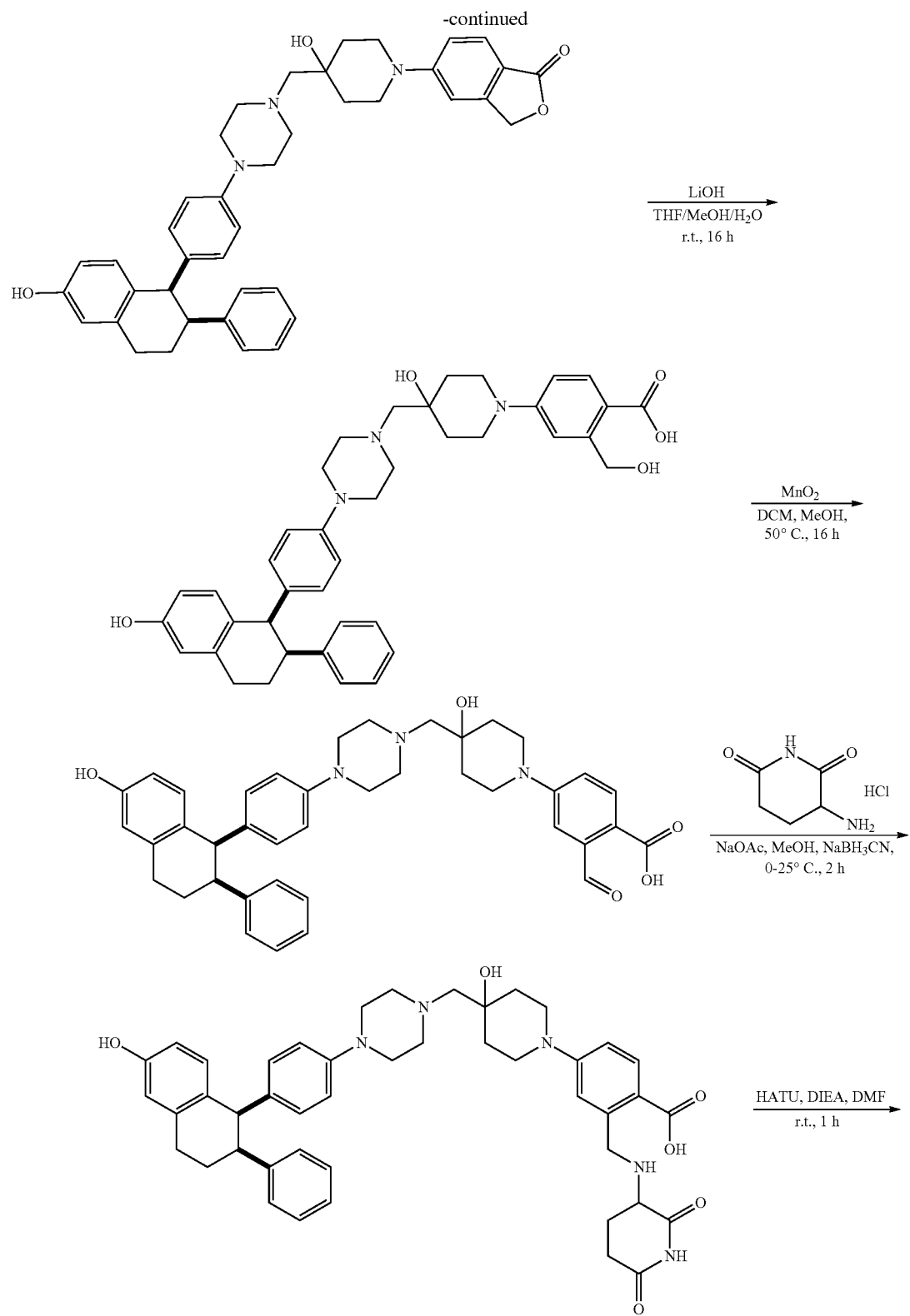

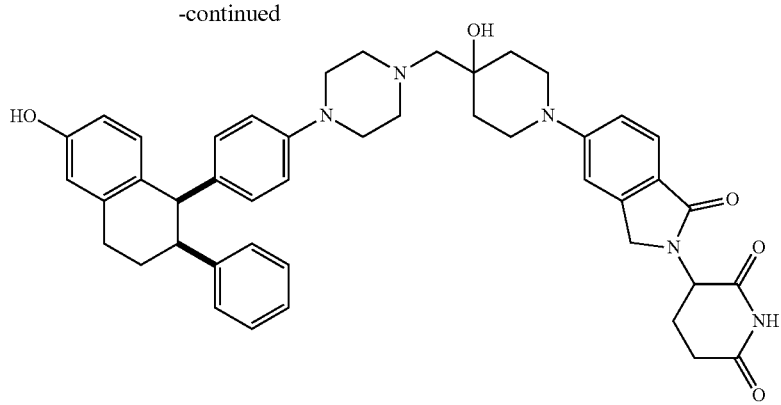
Compound 522
General synthetic scheme 3-83.
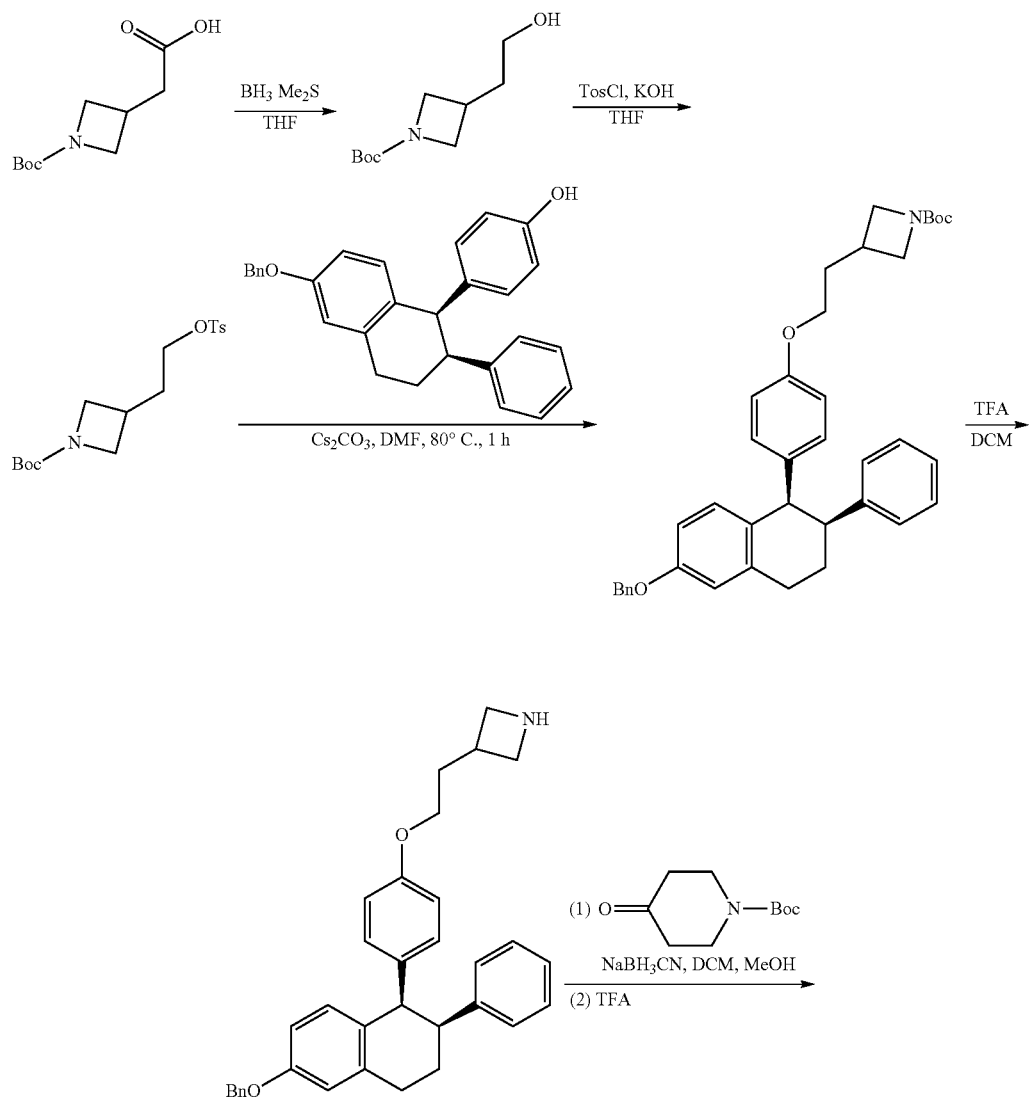

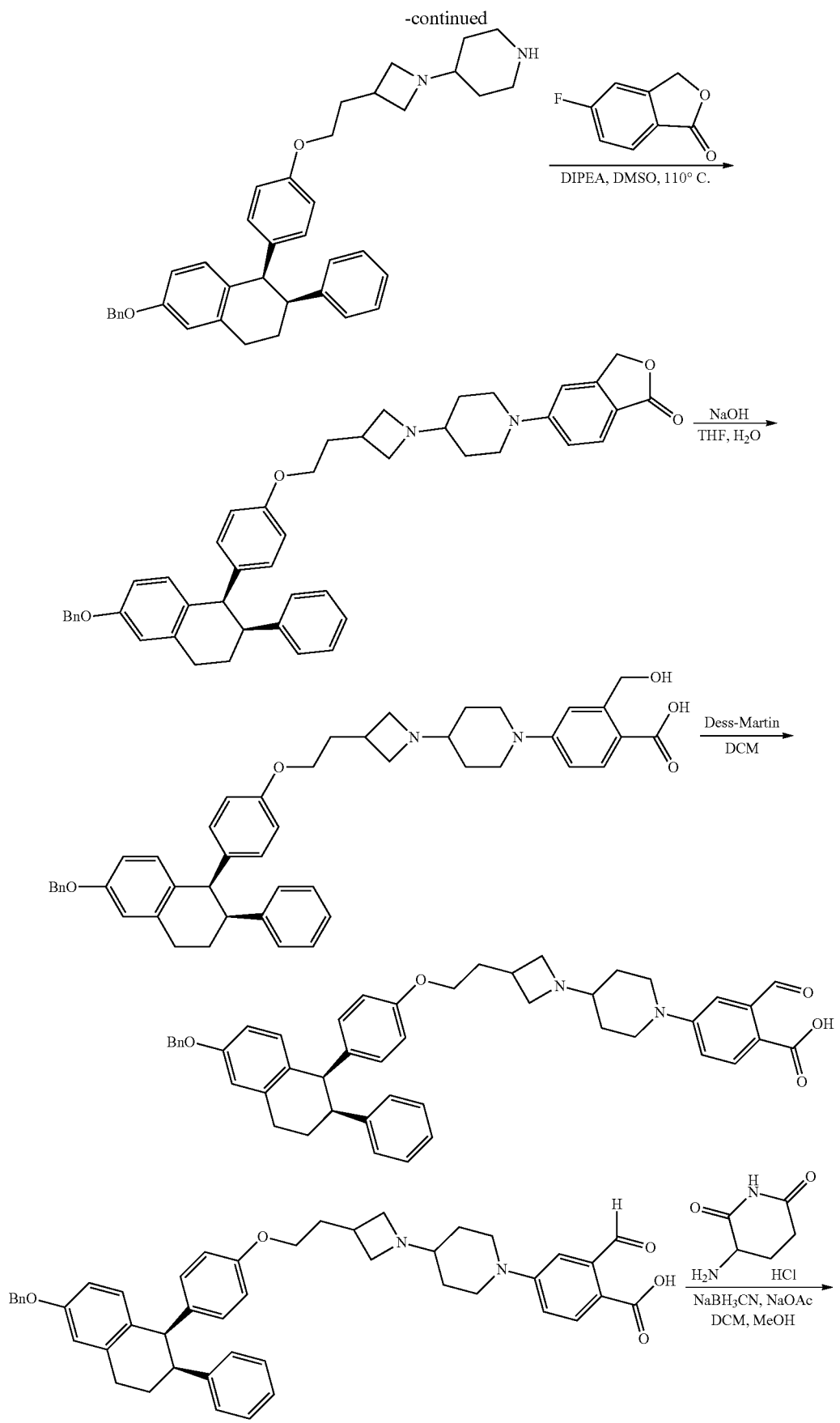

979 980
-continued
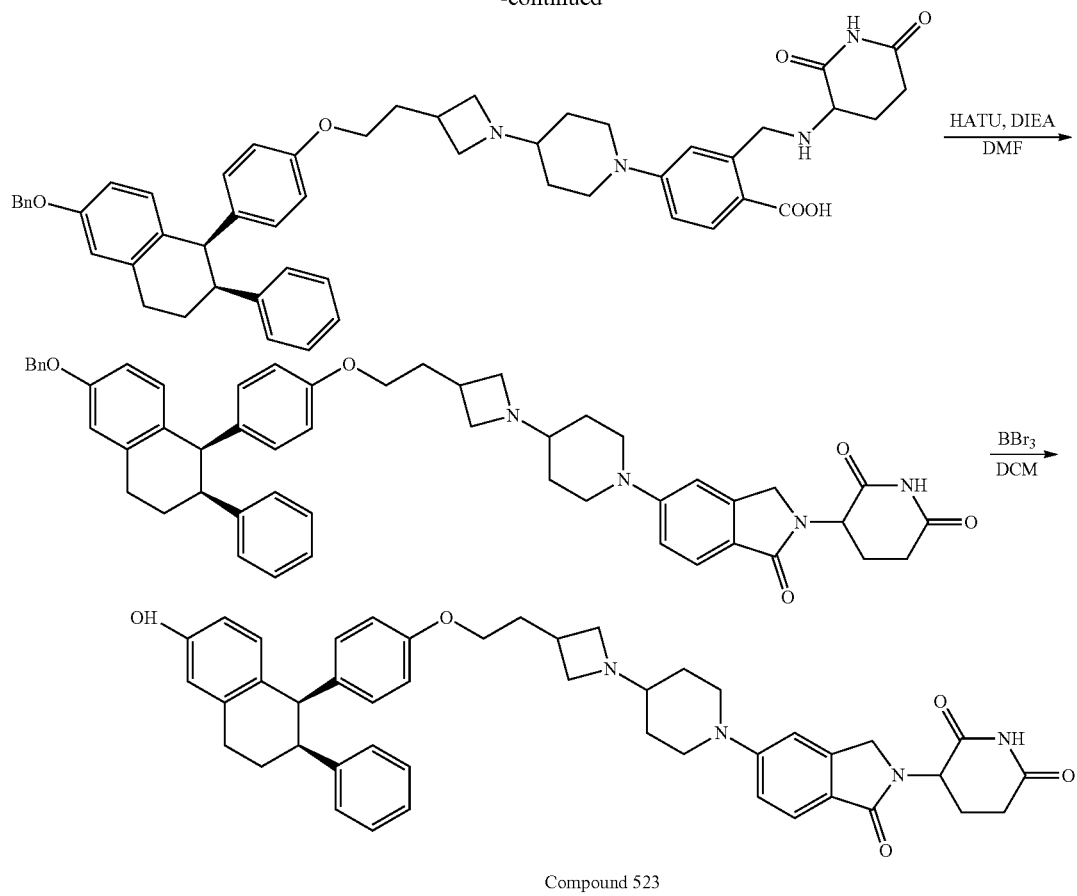
Compound 523
General synthetic scheme 3-84.
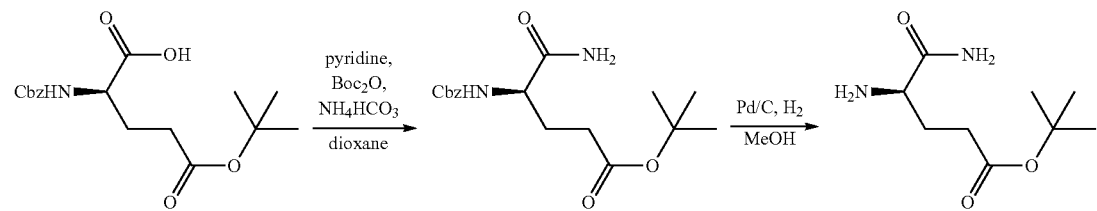
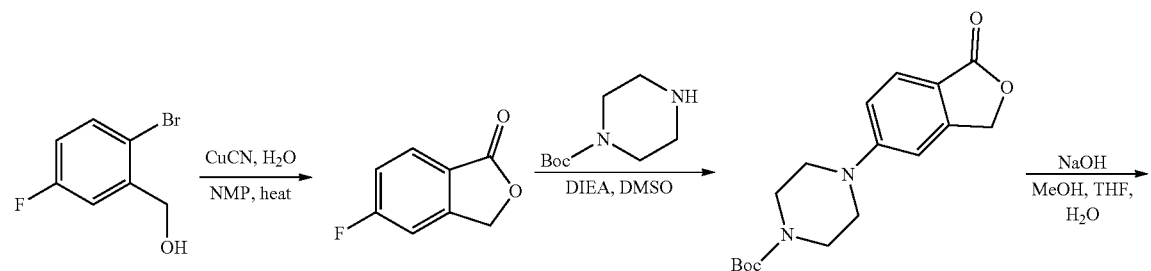

981            982
-continued
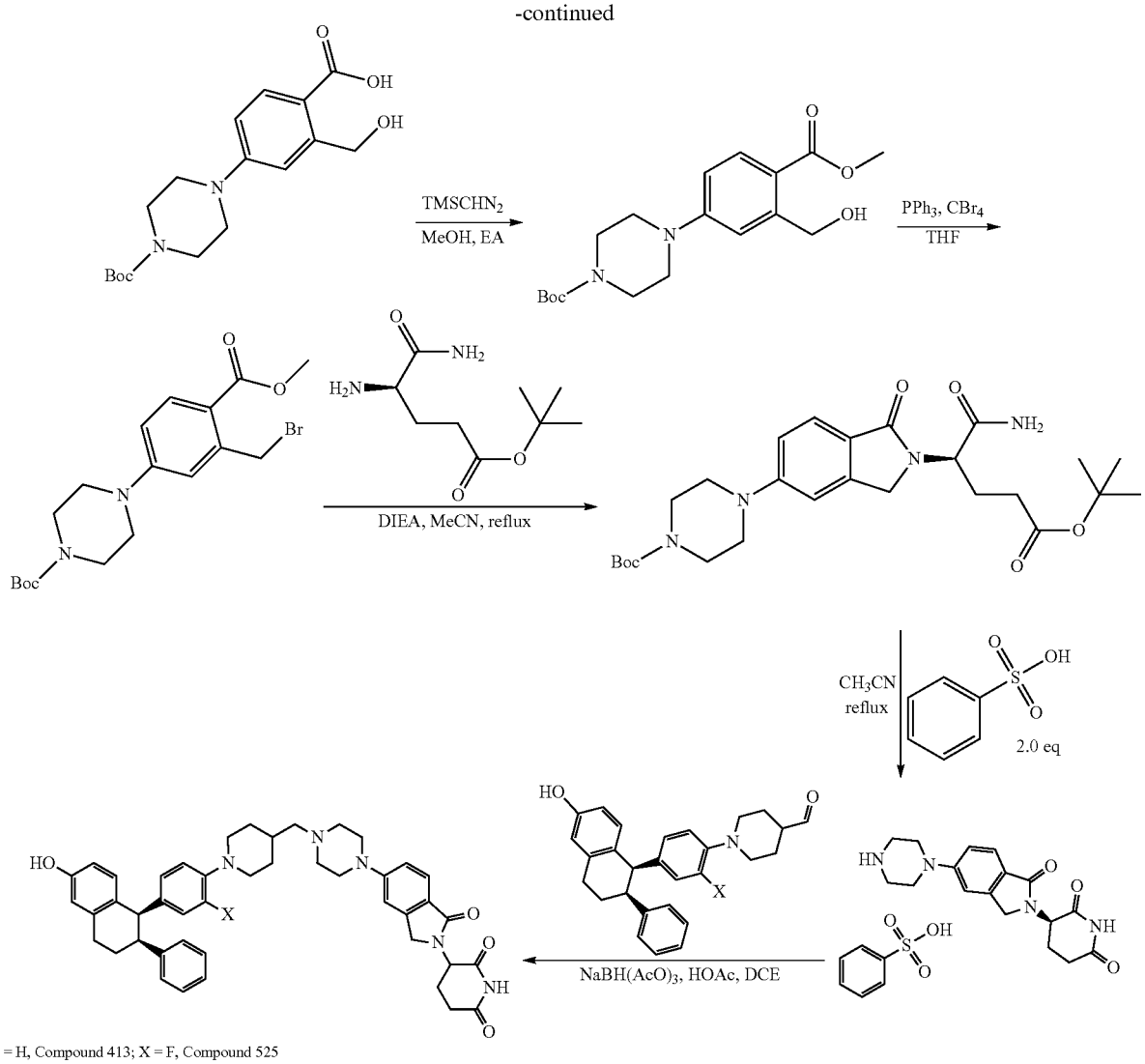
X = H, Compound 413; X = F, Compound 525
General synthetic scheme 3-85.
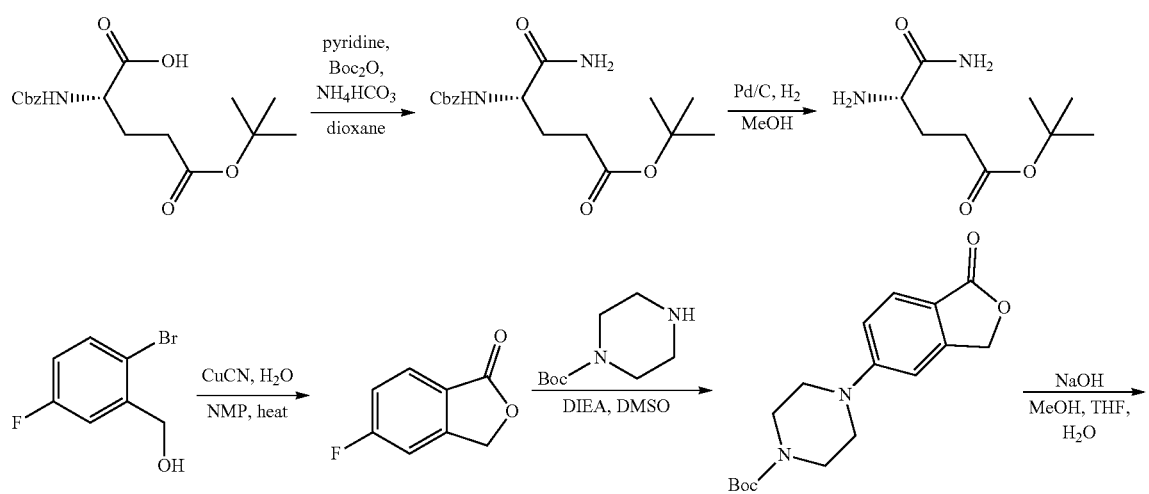

983 984
-continued
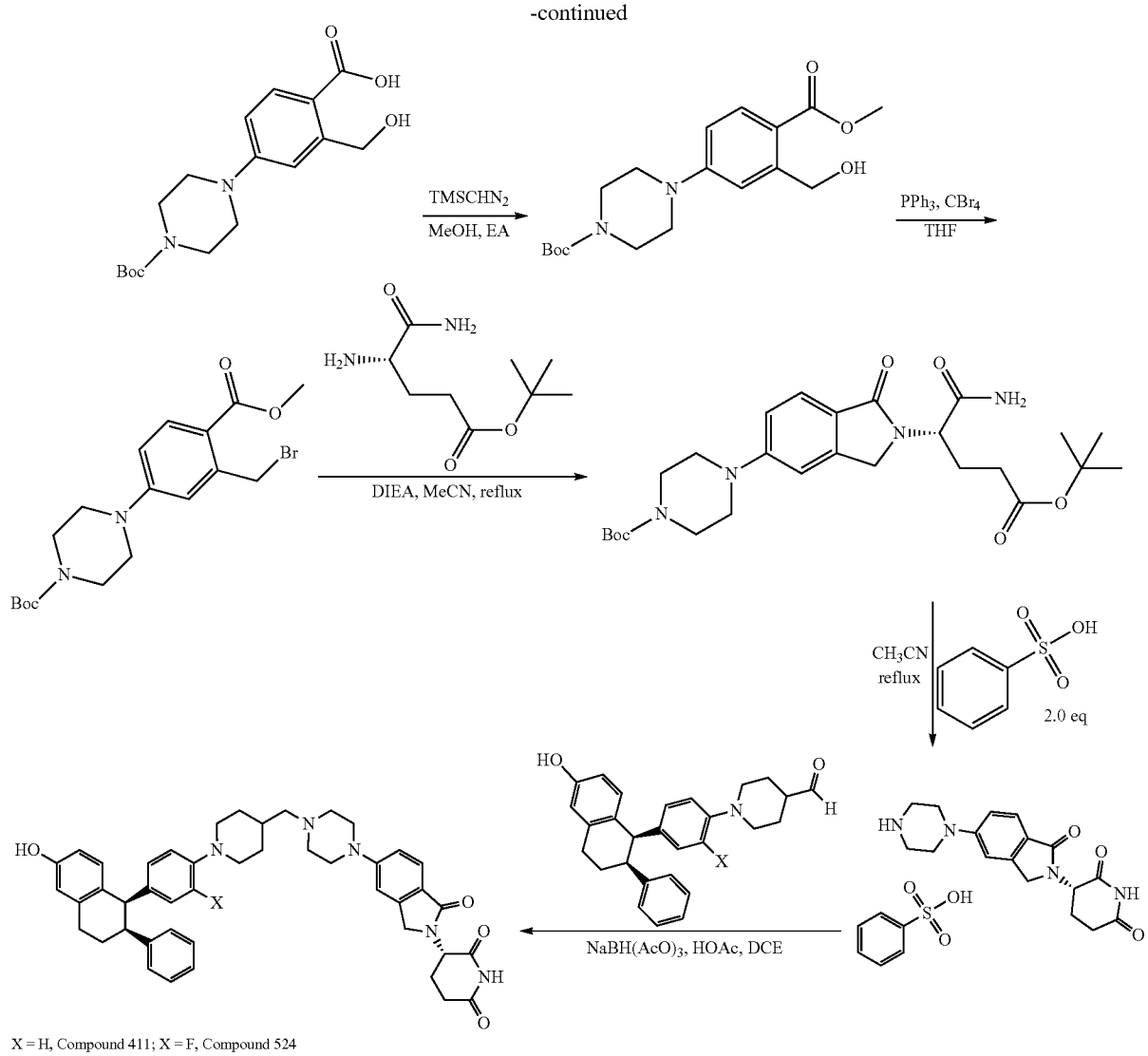
X = H, Compound 411; X = F, Compound 524
General synthetic scheme 3-86.
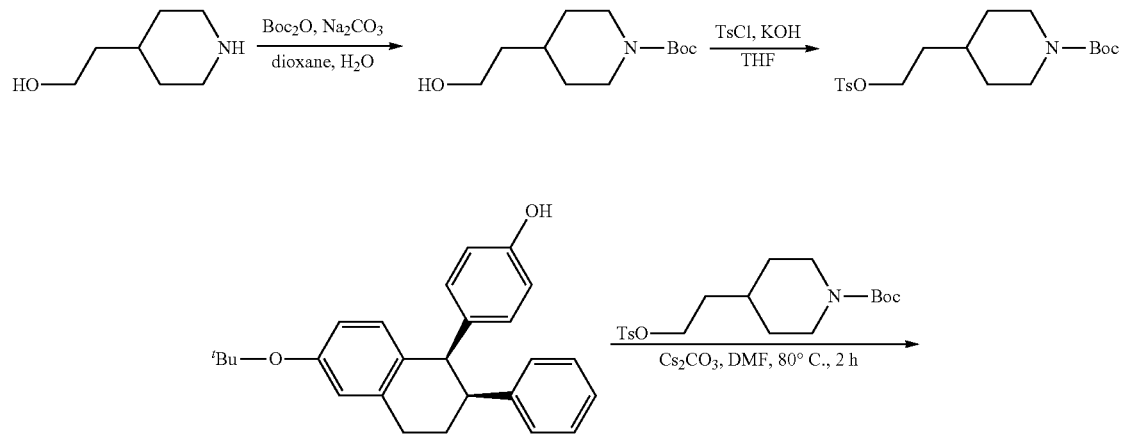

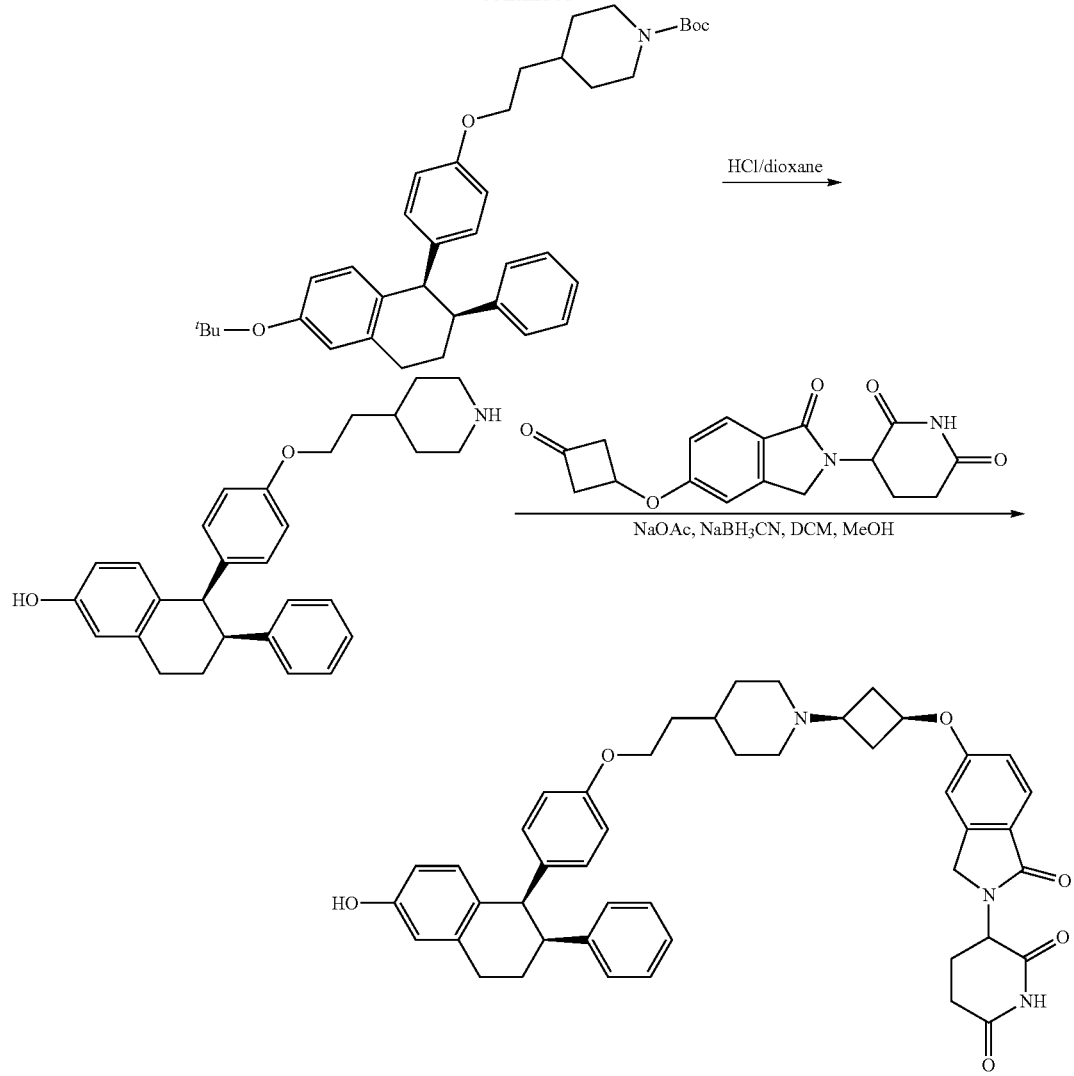
Compound 526
General synthetic scheme 3-87.
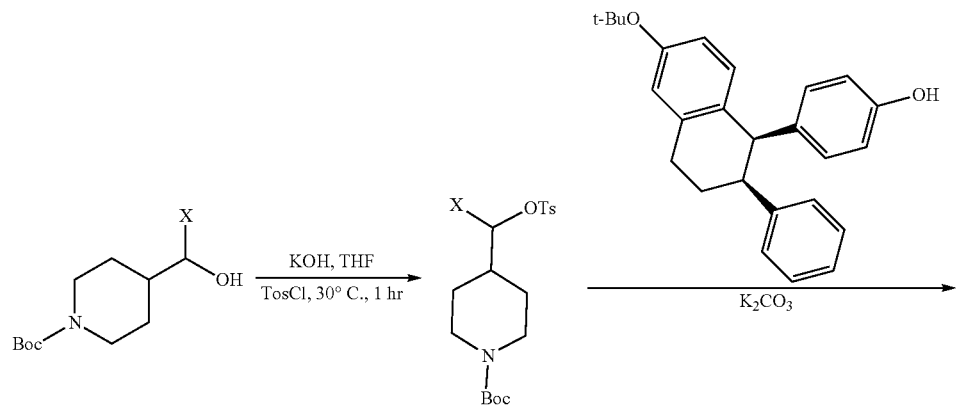

987 988
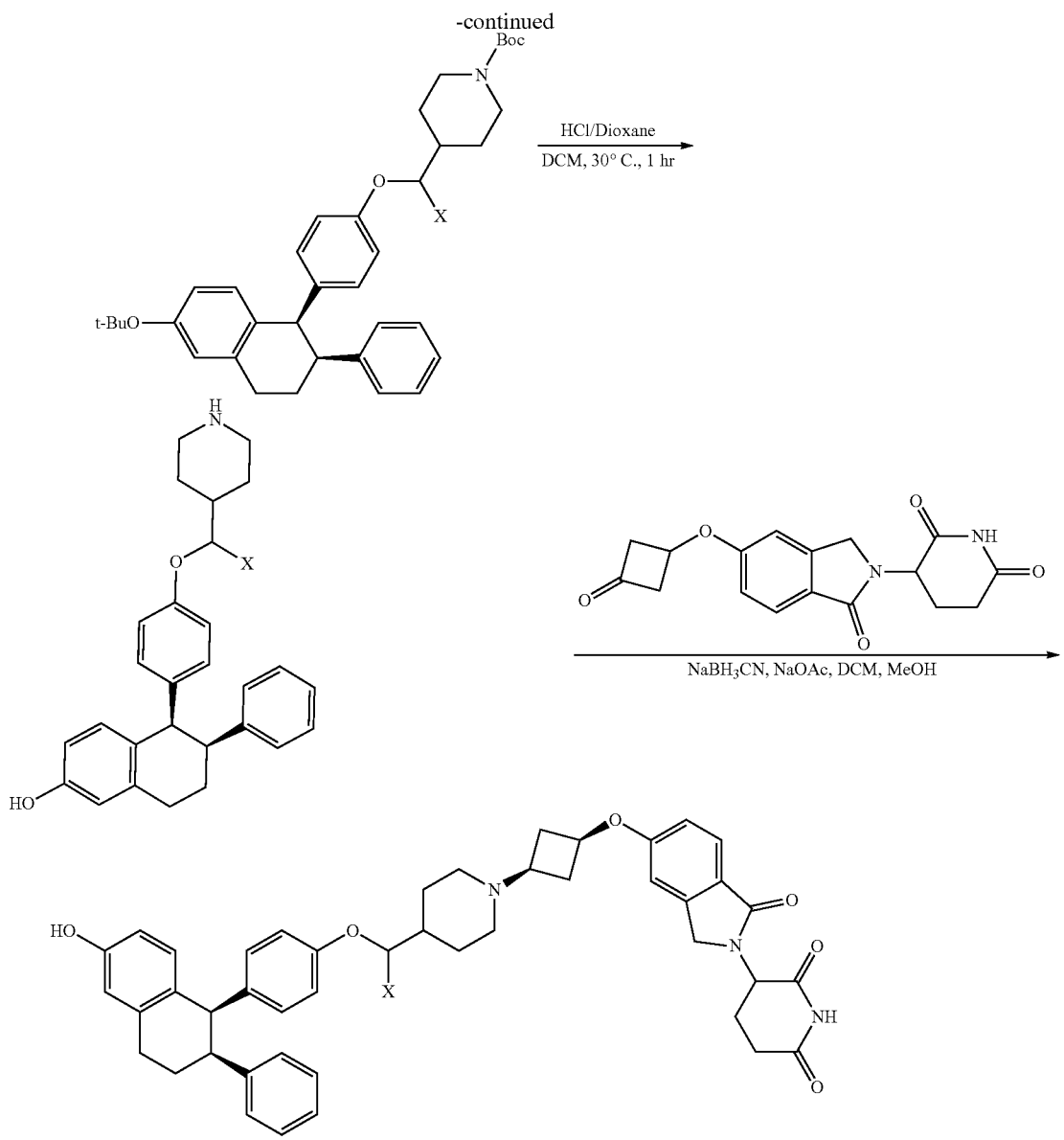
X = H, Compound 531
X = CH₃, Compound 532
General synthetic scheme 3-88.
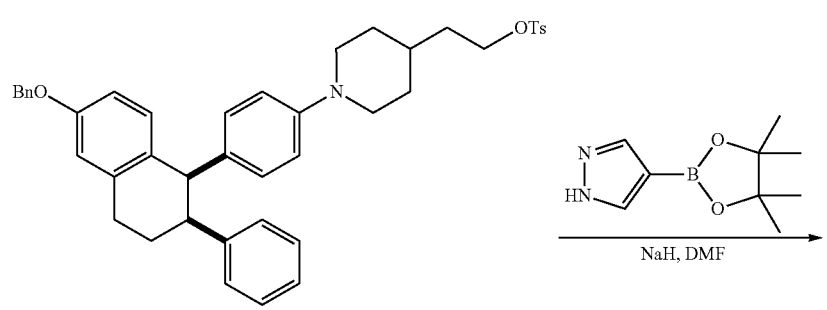

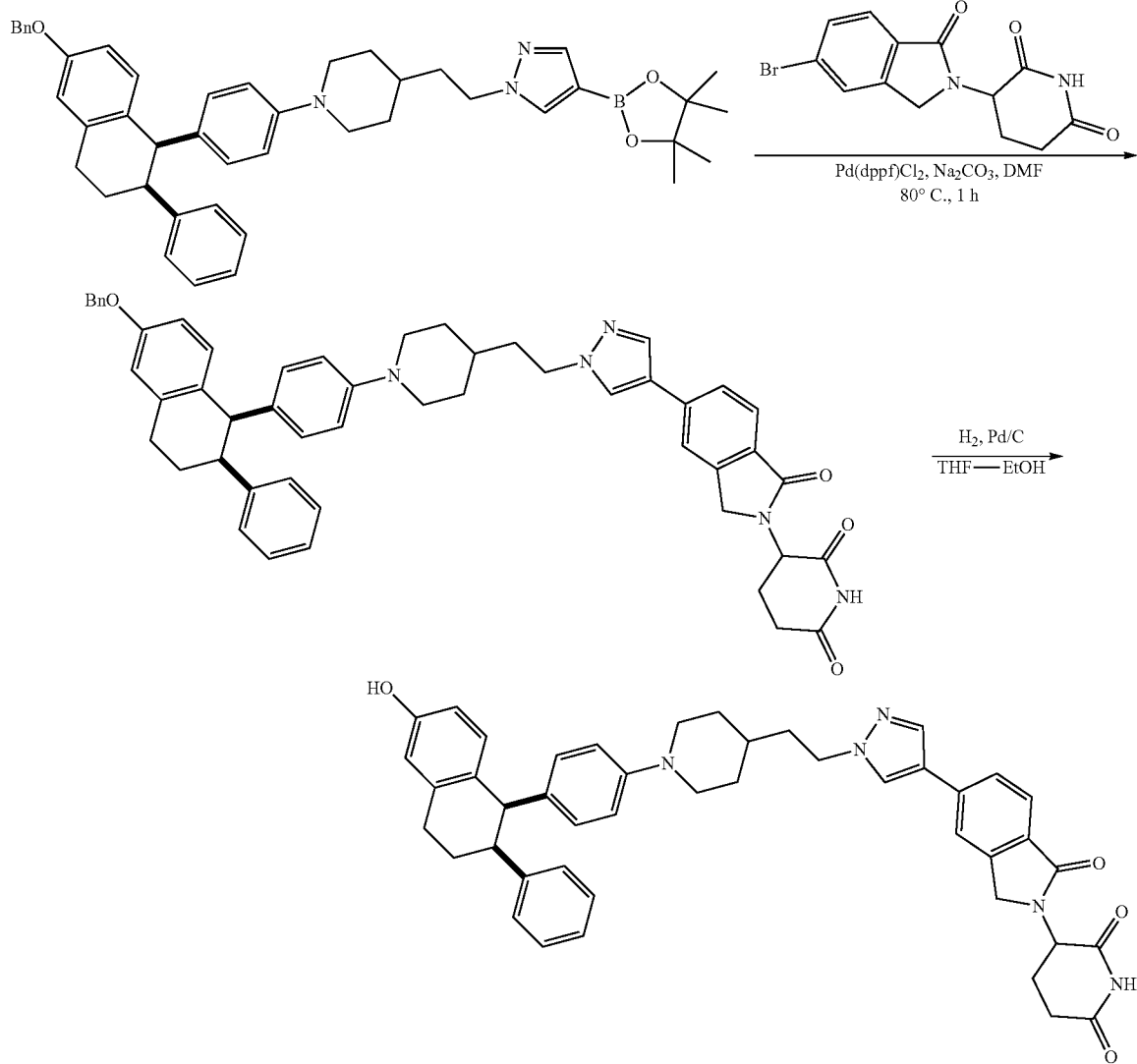

Compound 541

EXAMPLES

All synthesized compounds were characterized by $^1$H-NMR and purity was analyzed by LC/MS under the wave length of 214 and 254 nM with UV detection. Purity of each compound in Table 1 and Table 2 was over 90%. The observed molecular weight from LC/MS was listed in Table 1 (see FIG. 5) and Table 2 (see FIG. 6) as [M+H]$^+$. The synthetic methods used for preparing individual compound are listed in Table 1 and Table 2. Some molecules in Table 1 and Table 2 were obtained as salt forms, such as hydrochloride, acetate, formate, or triflate. Only structures of the neutral form of each compound were listed. $^1$H-NMR of representative compounds are listed in Table 3 (see FIG. 7). Although the chemical names listed in Table 3 are for the neutral forms of the exemplary compounds, the corresponding $^1$H-NMR data includes both neutral forms and salt forms.

All synthesized chimeric molecules were assessed for target engagement in T47D cells using the commercial kit of ERE luciferase reporter gene assay. In the assay, 10% FBS was included and estrogen level was measured to be 10 pM. Target engagement was expressed as IC$_{50}$ in the suppression of estrogen induced signing and the result was listed in Table 1 and Table 2.

Exemplary compounds of the present disclosure were tested for ER$_\alpha$ degradation in MCF7 cells using an In-Cell Western™ Assay (LI-COR®; Lincoln, Nebr.). Degradation activity is listed in Table 3 as DC$_{50}$ and D$_{max}$, where DC$_{50}$ was calculated based on curve fit using ACAS dose response module (McNeil & Co Inc.). D$_{max}$ was calculated based on the equation [(ERα highest level—ER$_\alpha$ lowest level)/(ER$_\alpha$ highest level)].

Figure 2:
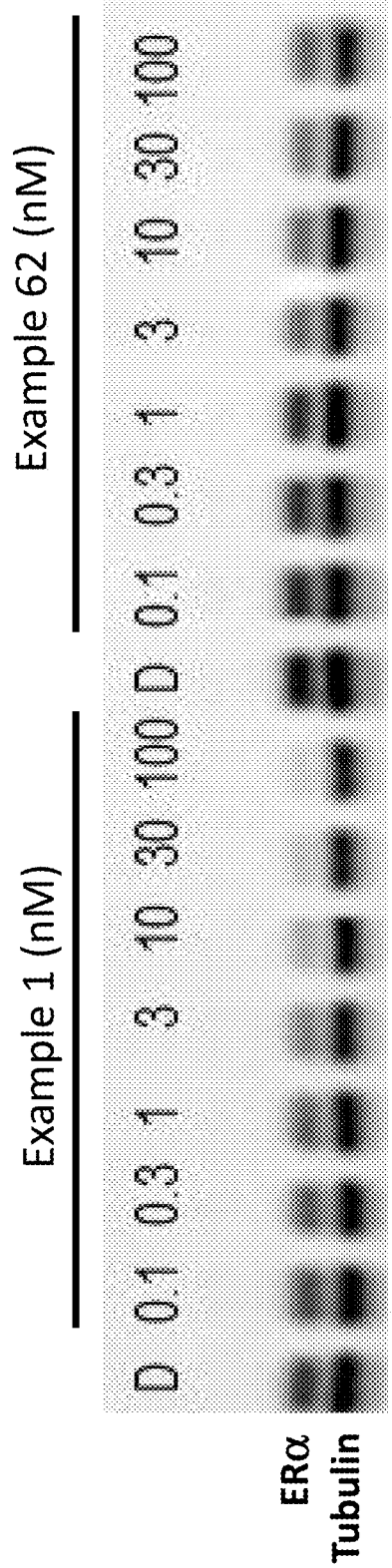
FIG. 2. Degradation of ERα in MCF7 cells by exemplary compounds of the present disclosure: Example 1 and Example 62. MCF7 Cells were treated with compounds at 7 concentrations (100 nM, 30 nM, 10 nM, 3 nM, 1 nM, 0.3 nM and 0.1 nM) in the presence of 10% FBS. Cells were incubated for 48 hours before lysis. The lysate was analyzed by immunoblotting. D: DMSO.
Figure 3:
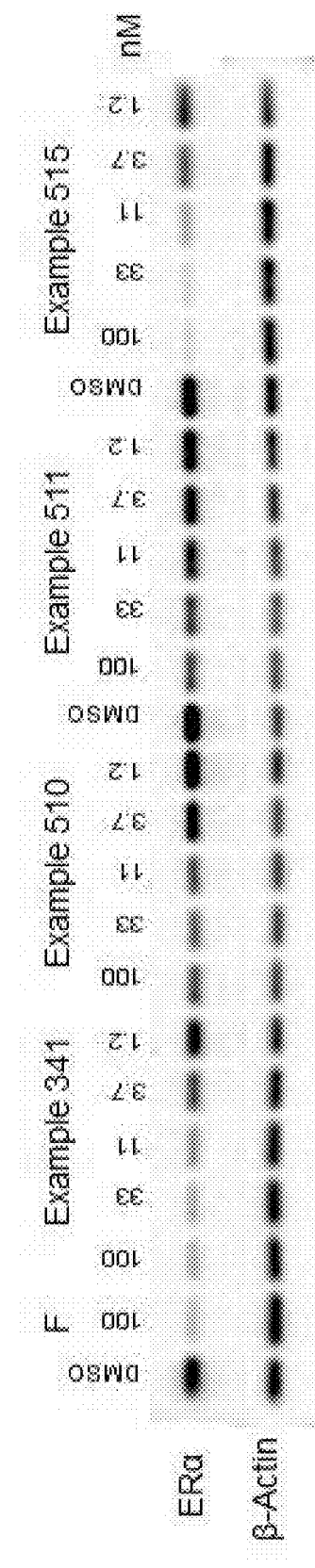
FIG. 3. Degradation of ERα in MCF7 cells by exemplary compounds of the present disclosure: Example 341, Example 510, Example 511 and Example 515. MCF7 Cells were treated with compounds at 5 concentrations (100 nM, 33 nM, 11 nM, 3.7 nM, and 1.2 nM) or with Fulvestrant at 100 nM in the presence of 10% FBS. Cells were incubated for 72 hours before lysis. The lysate was analyzed by immunoblotting. F: Fulvestrant.

The exemplary compounds that demonstrated degradation activity, as shown in Table 3, were further tested for ERα degradation in MCF7 cells using standard western blot methodology. FIG. 2 and FIG. 3 illustrate represent exemplary compounds from the western blot assay.

Figure 4:
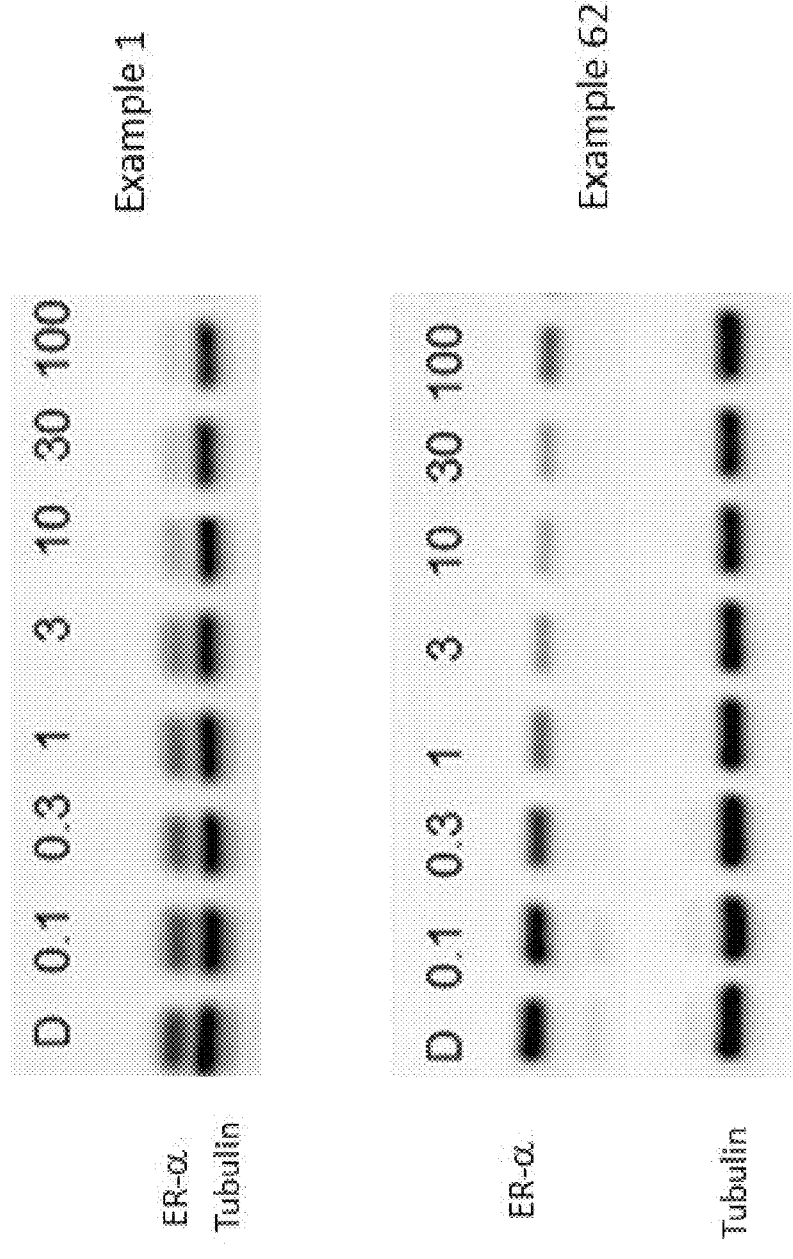
FIG. 4. Degradation of ERα in T47D cells by exemplary compounds of the present disclosure: Example 1 and 62. T47D Cells were treated with compounds at 7 concentrations (100 nM, 30 nM, 10 nM, 3 nM, 1 nM, 0.3 nM, and 0.1 nM) or with DMSO in the presence of 10% FBS. Cells were incubated for 72 hours before lysis. The lysate was analyzed by immunoblotting. D: DMSO.
Figure 8A:
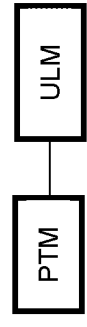
FIG. 8a is an illustration of a bifunctional or PROTAC compound, which comprises an E3 ubiquitin ligase binding moiety (i.e., a ligand for an E3 ubquitin ligase or "ULM" group), and a moiety that binds a target protein (i.e., a protein/polypeptide targeting ligand or "PTM" group) such that the target protein/polypeptide is placed in proximity to the ubiquitin ligase to effect degradation (and inhibition) of that protein.
Figure 8B:
FIG. 8b is an illustration of a bifunctional or PROTAC compound where the bifunctional compound further comprises a chemical linker ("L").
Figure 8C:
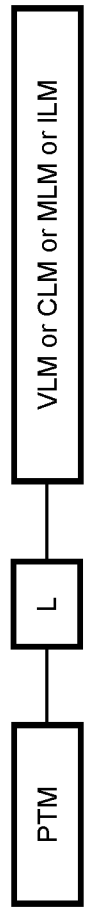
FIG. 8c is an illustration of a bifunctional or PROTAC compound where the PTM is a protein/polypeptide targeting moiety; "L" is a linker (e.g. a bond or a chemical linker group) coupling the PTM and at least one of VLM, CLM, MLM, ILM, or a combination thereof; VLM is Von Hippel-Lindau E3 ubiquitin ligase binding moiety that binds to VHL E3 ligase; CLM is cereblon E3 ubiquitin ligase binding moiety that binds to cereblon; MLM is an MDM2 E3 ubiquitin ligase binding moiety; and ILM is a IAP binding moiety which binds to IAP.

Compounds prepared in this application were also analyzed for their ability to degrade ERα in MCF7 and T47D cells. FIG. 4 shows the degradation result of selected exemplary compounds.

ERE Luciferase Assay to Assess Target Engagement for Exemplary Compounds.

T47D-KBluc cells (ATCC # CRL_2865, T47D human breast cancer cells stably transfected with estrogen responsive element/promoter/luciferase reporter gene) were seeded into 96-well white opaque plates in RPMI growth medium supplemented with 10% fetal bovine serum and allowed to adhere overnight in a 37° C. humidified incubator. The following day, cells were treated with PROTACs in a 12-point concentration curve (top final concentration of 300 nM with subsequent concentrations being 3-fold less with 2 pM being the lowest concentration in the assay). Each PROTAC was tested independently in two experiments on 96-well plates. After 24 hours, media was removed and lysis buffer was added to the wells. Following lysis, Bright-Glo™ Luciferase Assay Substrate (Promega, Madison Wis.) was added and the luciferase activity was measured using a Cytation 3 plate reader (BioTek™, Winooski, Vt.). Each compound was assayed in duplicates and the activity was calculated as $IC_{50}$ using GraphPad Prism software (San Diego, Calif.).

Estrogen Receptor-Alpha (ERα) Degradation Assay in MCF-7 Cells Using Western Blot Method.

The exemplary novel ERα degraders were assessed for their activity in degrading ERα in MCF-7 cells via western blot. The assay was carried out in the presence of 10% female bovine serum (FBS) or high percentage of human or mouse serum.

The western blot assay performed on the exemplary compounds of the present disclosure was performed by one of the following two assays, which provides comparable results.

MCF7 cells were grown in DMEM/F12 with 10% fetal bovine serum and seeded at 24,000 cells per well in 100 µl into 96-well clear tissue culture plates. The following day, the cells were treated with PROTACs in a 7-point concentration curve with 100 nM being the top concentration and serial dilutions to make the other concentrations (30 nM, 10 nM, 3 nM, 1 nM, and 0.3 nM). At all concentrations, 0.01% DMSO is the final concentration in the well. The following day, the plates are aspirated, washed with 50 µl of cold PBS. The cells are lysed with 50 µl/well 4° C. Cell Lysis Buffer (Catalog #9803; Cell Signaling Technology, Danvers, Mass.) (20 mM Tris-HCL (pH 7.5), 150 mM NaCl, 1 mM $Na_2EDTA$, 1 mM EGTA, 1% Triton, 2.5 mM sodium pyrophosphate, 1 mM B-glycerophosphate, 1 mM sodium vanadate, 1 ug/ml leupeptin). Lysates were clarified at 16,000×g for 10 minutes, and 2 µg of protein was subjected to SDS-PAGE analysis and followed by immunoblotting according to standard protocols. The antibodies used were ERα (Cell Signaling Technologies Catalog #8644), and Tubulin (Sigma Catalog # T9026; St. Louis, Mo.). Detection reagents were Clarity Western ECL substrate (Bio-Rad Catalog #170-5060; Hercules, Calif.).

Alternatively, MCF7 cells were grown in DMEM/F12 with 10% fetal bovine serum and seeded at 24,000 cells per well in 500 µl in 24-well clear tissue culture plates. The following day, the cells were treated with PROTACs in a 5-point concentration curve (100 nM, 33 nM, 11 nM, 3.7 nM, and 1.2 nM) in the presence of 0.01% DMSO. After 72 hours, the wells are aspirated and washed with 500 µl of PBS. The cells are lysed with 100 µl/well 4° C. Cell Lysis Buffer (Catalog #9803; Cell Signaling Technology, Danvers, Mass.) (20 mM Tris-HCL (pH 7.5), 150 mM NaCl, 1 mM $Na_2EDTA$, 1 mM EGTA, 1% Triton, 2.5 mM sodium pyrophosphate, 1 mM B-glycerophosphate, 1 mM sodium vanadate, 1 ug/ml leupeptin). Lysates were clarified at 16,000×g for 10 minutes, and 2 µg of protein was subjected to SDS-PAGE analysis and followed by immunoblotting according to standard protocols. The antibodies used were ERα (Cell Signaling Technologies Catalog #8644), and Tubulin (Sigma Catalog # T9026; St. Louis, Mo.). Detection reagents were Clarity Western ECL substrate (Bio-Rad Catalog #170-5060; Hercules, Calif.).

Estrogen Receptor-Alpha (ERα) Degradation Assay in T47D Cells Using Western Blot Method.

The same protocol that was described above with MCF7 cells was utilized, except that T47D cells were utilized instead of the MCF7 cells.

Estrogen Receptor-Alpha (ERα) Degradation Assay Using in-Cell Western™ Assay.

Degradation of ERα by claimed compounds were determined in MCF7 cells using an In-Cell Western™ assay. Briefly, MCF7 cells were plated in 96-well plates (2000 cells per well in 100 µl media) and incubated at 37° C. under an atmosphere of 5% $CO_2$ in a humidified incubator overnight. One-hundred (100) µl of media containing test compound (at 2× concentration) was added to the appropriate wells to provide 11 serially decreasing concentrations (top final concentration, 1 pM then 3-fold less for the next 10 concentrations); a vehicle control (DMSO) was also added for each compound. For each experiment, all compounds were assayed on duplicate plates. Cells were then incubated for 5 days in the above-mentioned environment. The assay was terminated by removal of media, a single wash with ice-cold PBS and the addition of 50 µl paraformaldehyde (PFA: 4% in PBS). After 15 minutes in PFA at room temperature, the cells were permeabilized in Tris-phosphate-buffered saline with Tween (0.1%) (TBST) supplemented with Triton X-100 (0.5%) for 15 minutes. Cells were then blocked in BSA (TBST with BSA, 3%) for one hour. Primary antibodies for the detection of ERα (rabbit monoclonal, 1:1000, Cell Signaling Technology Catalog #8644) and tubulin (mouse monoclonal, 1:5000, Sigma Catalog # T6074) in TBST with BSA (3%) were added. The cells were incubated overnight at 4° C. The cells were then washed thrice with TBST at room temperature and then incubated with anti-rabbit and anti-mouse fluorescently-labelled secondary antibodies (IRDye®; LI-COR; Lincoln, Nebr.) in LI-COR blocking buffer (Catalog #927-50000) for one hour at room temperature. Following 3 washes with TBST, the buffer was removed and the plates were read on an Odyssey® infrared imaging system (LI-COR®; Lincoln, Nebr.) at 700 nm and 800 nm. Using commercial software (ImageStudio™; LI-COR, Lincoln, Nebr.), the staining intensity for ERα and tubulin in each well was quantified and exported for analysis. For each data point, ERα intensity was normalized to tubulin intensity and for each compound all normalized intensity values were normalized to the vehicle control. $DC_{50}$ and $D_{max}$ values were determined following a 4-parameter $IC_{50}$ curve fit using ACAS dose response module (McNeil & Co Inc.).

The degradation data was categorized as follows: Degradation $DC_{50}$ ranges: $DC_{50}$<5 nM (A); 5 nM<$DC_{50}$<50 nM (B); $DC_{50}$>50 nM (C); and Degradation Dmax ranges: $D_{max}$>75% (A); 50%<$D_{max}$<75 (B); $D_{max}$<50% (C). The degradation activity of the exemplary compounds is listed in Table 3.

Experiment Procedures of Synthesizing ER PROTACs

Synthesis of (2S,4R)-4-hydroxy-1-[(2S)-2-(2-{2-[4-(2-{4-[(1R,2S)-6-hydroxy-2-phenyl-1,2,3,4-tetrahydronaphthalen-1-yl]phenoxy)ethyl)piperazin-1-yl]ethoxy}acetamido)-3,3-dimethylbutanoyl]-N-{[4-(4-methyl-1,3-thiazol-5-yl)phenyl]methyl}pyrrolidine-2-carboxamide (Exemplary Compound 1)

Step 1: Preparation of tert-butyl 4-(2-(2-ethoxy-2-oxoethoxy)ethyl) piperazine-1-carboxylate

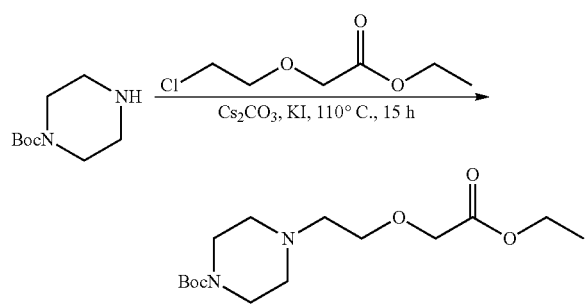

To a solution of tert-butyl piperazine-1-carboxylate (1.50 g, 8.05 mmol, 1.00 eq) in N,N-dimethylformamide (30 mL) was added cesium carbonate (2.89 g, 8.86 mmol, 1.10 eq), potassium iodide (134 mg, 0.8 mmol, 0.10 eq) and ethyl 2-(2-chloroethoxy)acetate (1.68 g, 10.06 mmol, 1.25 eq) at 25° C. The resulting mixture was stirred at 110° C. for 16 hours. LC/MS showed disappearance of the starting material and the desire compound was formed. The mixture was poured into saturated brine (100 mL) and then extracted with ethyl acetate (50 mL×5). The combined organic layers were dried over anhydrous sodium sulfate, filtered and concentrated in vacuum. The residue was further purified by silica gel column chromatography (petroleum ether: ethyl acetate=15:1 to 5:1) to give tert-butyl 4-[2-(2-ethoxy-2-oxoethoxy)ethyl]piperazine-1-carboxylate (2.40 g, 2.91 mmol, 36% yield, 38% purity) as a colorless oil. LC/MS (ESI) m/z: 317.1 [M+1]$^+$.

Step 2: Preparation of 2-(2-(4-(tert-butoxycarbonyl)piperazin-1-yl)ethoxy)acetic acid

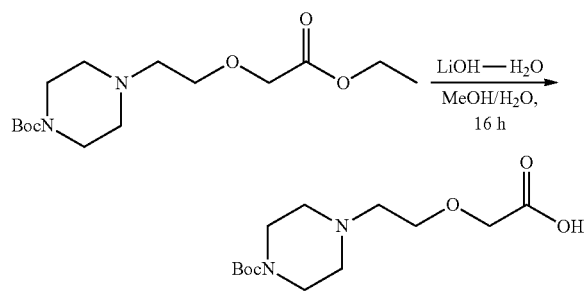

To a solution of tert-butyl 4-[2-(2-ethoxy-2-oxo-ethoxy)ethyl]piperazine-1-carboxylate (750 mg, 2.37 mmol, 1.00 eq) in methanol (5 mL) and water (5 mL) was added lithium hydroxide monohydrate (497 mg, 11.85 mmol, 5.00 eq) at 25° C. The resulting mixture was stirred at 25° C. for 16 hours. LC/MS showed starting material was disappeared and the desired compound was found. Then the reaction mixture was adjusted to pH=(5-6) by hydrochloric acid (2 M, 0.5 mL) and concentrated under reduced pressure to remove methanol. The residue was extracted with ethyl acetate (3 mL×2). The combined organic layers were washed with saturated brine (3 mL×2), dried over anhydrous sodium sulfate, filtered and concentrated in vacuum. 2-[2-(4-tert-butoxycarbonylpiperazin-1-yl)ethoxy]acetic acid (350 mg, 1.21 mmol, 51% yield) was obtain as a colorless oil, which was directly used for next step without further purification. $^1$H NMR (400 MHz, CDCl$_3$) δ: 6.50 (br, 1H), 4.02 (s, 2H), 3.78 (t, J=4.8 Hz, 2H), 3.65-3.62 (m, 4H), 3.47-3.38 (m, 2H), 2.82-2.79 (m, 4H), 1.46 (s, 9H).

Step 3: Preparation of tert-butyl 4-[2-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)ethyl]piperazine-1-carboxylate

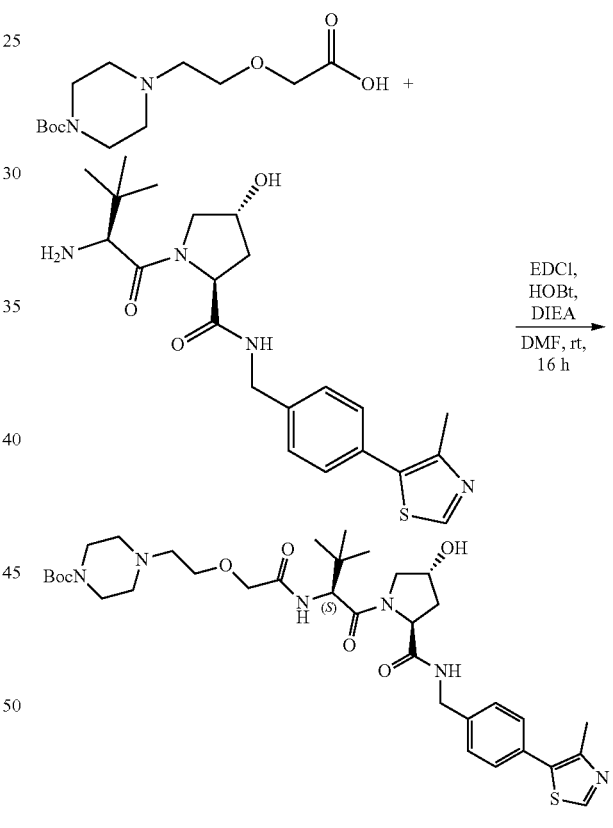

To a solution of 2-[2-(4-tert-butoxycarbonylpiperazin-1-yl)ethoxy]acetic acid (170 mg, 0.59 mmol, 1.00 eq) in N,N-dimethylformamide (6 mL) was added 1-ethyl-3-(3-dimethylaminopropyl)carbodiimide hydrochloride (226 mg, 1.18 mmol, 2.00 eq), 1-hydroxybenzotriazole (119 mg, 0.88 mmol, 1.50 eq), diisopropylethylamine (228 mg, 1.77 mmol, 3.00 eq) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide hydrochloride (275 mg, 0.59 mmol, 1.00 eq) at 25° C. The resulting mixture was stirred at 25° C. for 16 hours. LC/MS showed the disappearance of the starting material and desire compound was found. The mixture was poured into saturated brine (30 mL), and then extracted with ethyl acetate (15 mL×5). The combined organic layers were dried over anhydrous sodium sulfate, filtered and concentrated in vacuum. The residue was further purified by preparative TLC (SiO$_2$, dichloromethane:methanol=10:1) to provide tert-butyl 4-[2-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)ethyl]piperazine-1-carboxylate (320 mg, 0.45 mmol, 77% yield, 99% purity) as a colorless oil. LC/MS (ESI) m/z: 701.2 [M+1]$^+$; $^1$H NMR (400 MHz, CDCl$_3$) δ:8.84 (s, 1H), 7.42-7.39 (m, 5H), 4.54-4.51 (m, 4H), 4.34 (m, 1H), 4.05-3.96 (m, 2H), 3.76-3.70 (m, 2H), 3.67-3.60 (m, 2H), 3.41-3.35 (m, 4H), 2.72-2.66 (m, 2H), 2.57-2.55 (m, 4H), 2.53 (s, 3H), 2.27-2.19 (m, 1H), 2.13-2.05 (m, 1H), 1.38 (s, 9H), 1.00 (s, 9H).

Step 4: Preparation of (2S,4R)- 1-[(2S)-3,3-dimethyl-2-({2-[2-(piperazin-1-yl)ethoxy]acetamido}butanoyl]-4-hydroxy-N-{[4-(4-methyl-1,3-thiazol-5-yl)phenyl]methyl}pyrrolidine-2-carboxamide To a solution of tert-butyl 4-[2-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)ethyl]piperazine-1-carboxylate (110 mg, 0.16 mmol, 1.00 eq) in ethyl acetate (3 mL) was added hydrochloric acid/ethyl acetate (4.0 M, 3 mL) at 25° C. The resulting mixture was stirred at 25° C. for 0.5 hours. LC/MS showed the disappearance of the starting material and desire compound was found. The mixture was concentrated under reduced pressure. (2S,4R)- 1-[(2S)-3,3-dimethyl-2-[[2-(2-piperazin-1-ylethoxy)acetyl]amino]butanoyl]-4-hydroxy-N-[[4-(4-methylthiazol-5-yl)phenyl]methyl]pyrrolidine-2-carboxamide hydrochloride (100 mg, 0.12 mmol, 77% yield, 77% purity) was obtained as a yellow solid. LC/MS (ESI) m/z: 601.2 [M+1]$^+$; $^1$H NMR (400 MHz, METHANOL-d$_4$) δ:7.56-7.50 (m, 5H), 4.63-4.51 (m, 5H), 4.45-4.38 (m, 1H), 4.24 (s, 2H), 3.99-3.91 (m, 4H), 3.84-3.78 (m, 2H), 3.71-3.61 (m, 4H), 3.56-3.50 (m, 2H), 2.57 (m, 4H), 2.32-2.24 (m, 1H), 2.15-2.04 (m, 1H), 1.07 (s, 9H).

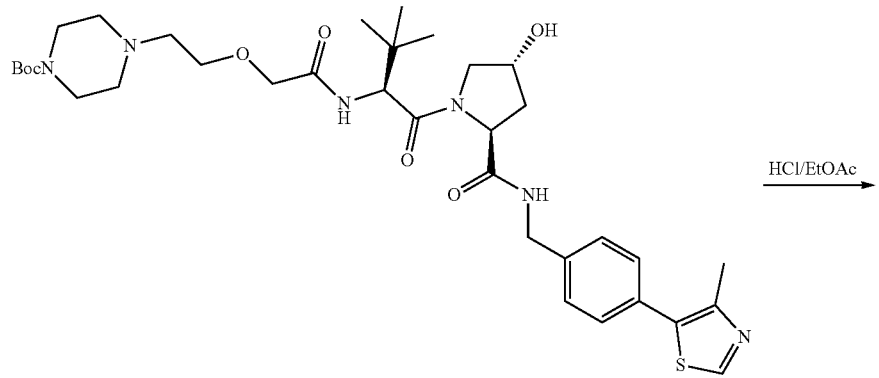

HCl/EtOAc →

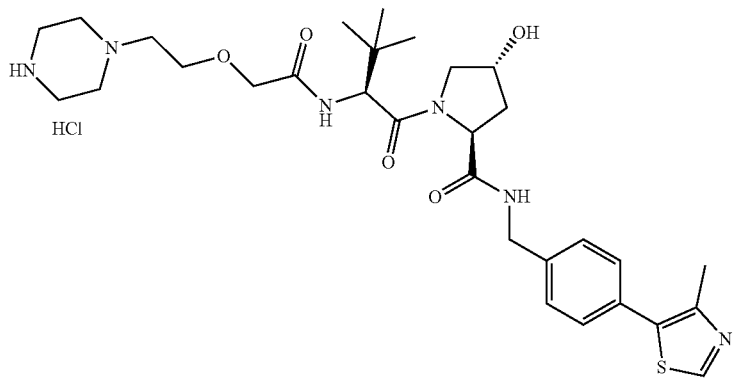

Step 5: Preparation of 7-benzyloxy-4-[4-(2,2-diethoxyethoxy)phenyl]-1,2-dihydronaphthalene

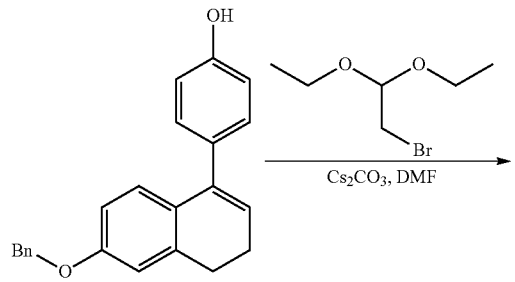

Step 6: Preparation of 7-(benzyloxy)-3-bromo-4-(4-(2,2-diethoxyethoxy)phenyl)-1,2-dihydronaphthalene

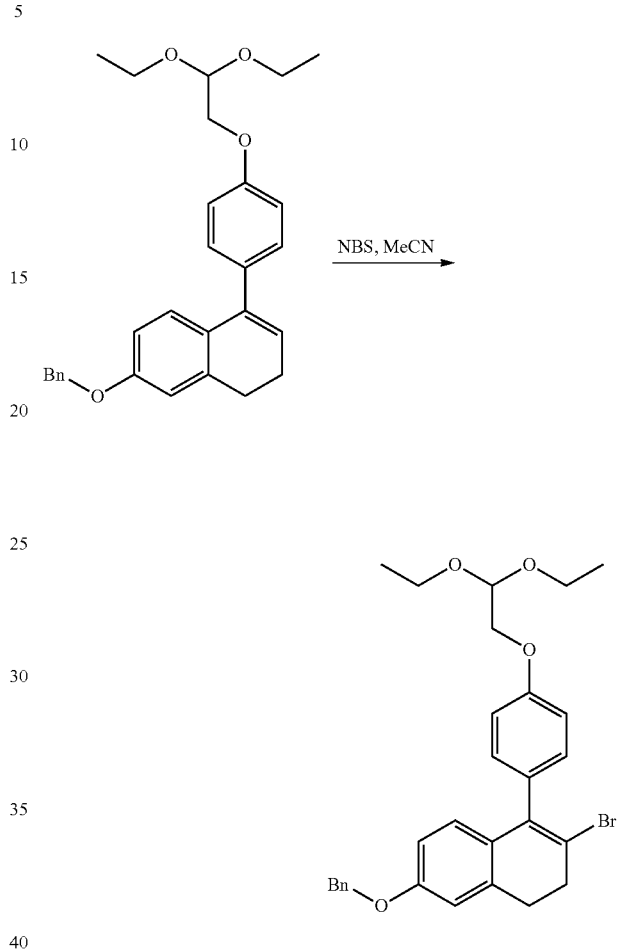

To a solution of 4-(6-benzyloxy-3,4-dihydronaphthalen-1-yl)phenol (22 g, 66.99 mmol, 1.00 eq, prepared according to procedures in step 1-3 described for Exemplary Compound 62) in N,N-dimethylformamide (200 mL) was added cesium carbonate (43.65 g, 133.98 mmol, 2.00 eq) and 2-bromo-1,1-diethoxy-ethane (26.4 g, 133.98 mmol, 20 mL, 2.00 eq). The reaction mixture was stirred at 100° C. for 2 hours. TLC (petroleum ether:ethyl acetate=10:1) showed most of the starting material was consumed. Ethyl acetate (600 mL) and water (300 mL) was added to the mixture. The organic phase was separated. The combined organic phase was washed with brine (300 mL×3), dried over sodium sulfate, filtered and concentrated in vacuum. The residue was purified by silica gel chromatography (petroleum ether:ethyl acetate=1:0 to 25:1) to give 7-benzyloxy-4-[4-(2,2-diethoxyethoxy)phenyl]-1,2-dihydronaphthalene (21 g, 47.24 mmol, 70% yield) as a yellow oil. $^1$H-NMR (400 MHz, CDCl$_3$) δ 7.46-7.31 (m, 5H), 7.29-7.24 (m, 2H), 6.96-6.91 (m, 3H), 6.86 (d, J=2.4 Hz, 1H), 6.71 (dd, J=8.4, 2.8 Hz, 1H), 5.92 (t, J=4.8 Hz, 1H), 5.07 (s, 2H), 4.88 (t, J=5.2 Hz, 1H), 4.05 (d, J=5.2 Hz, 2H), 2.83-3.76 (m, 2H), 3.71-3.63 (m, 2H), 2.82 (t, J=8.0 Hz, 2H), 2.40-2.35 (m, 2H), 1.28 (t, J=6.8 Hz, 6H).

To a solution of 7-benzyloxy-4-[4-(2,2-diethoxyethoxy)phenyl]-1,2-dihydronaphthalene (20 g, 44.99 mmol, 1.00 eq) in acetonitrile (480 mL) was added N-bromosuccinimide (8.41 g, 47.24 mmol, 1.05 eq). The reaction mixture was stirred at 20° C. for 3 hours. TLC (petroleum ether:ethyl acetate=10:1) and LC/MS showed desired product was formed. Saturated sodium bicarbonate solution (500 mL) was added to the mixture, the resulting mixture was extracted with ethyl acetate (400 mL×3). The combined organic phase was washed with brine (80 mL), dried over sodium sulfate, filtered and concentrated in vacuum. The residue was purified by silica gel chromatography (petroleum ether:ethyl acetate=1:0 to 30:1) to give 7-(benzyloxy)-3-bromo-4-(4-(2,2-diethoxyethoxy)phenyl)-1,2-dihydronaphthalene (12.4 g, 23.69 mmol, 53% yield) as a light yellow solid. LC/MS (ESI) m/z: 545.2, 547.2 [M+23, M+25]$^+$; $^1$H-NMR (400 MHz, CDCl$_3$) δ 7.44-7.31 (m, 5H), 7.16-7.13 (m, 2H), 7.01-6.97 (m, 2H), 6.80 (d, J=2.4 Hz, 1H), 6.63 (dd, J=8.4, 2.8 Hz, 1H), 6.59 (t, J=8.8 Hz, 1H), 5.04 (s, 2H), 4.89 (t, J=5.2 Hz, 1H), 4.07 (d, J=5.2 Hz, 2H), 3.83-3.77 (m, 2H), 3.72-3.66 (m, 2H), 3.02-2.93 (m, 4H), 1.28 (t, J=6.8 Hz, 6H).

999

Step 7: Preparation of 7-benzyloxy-4-[4-(2,2-diethoxyethoxy)phenyl]-3-phenyl-1,2-dihydronaphthalene

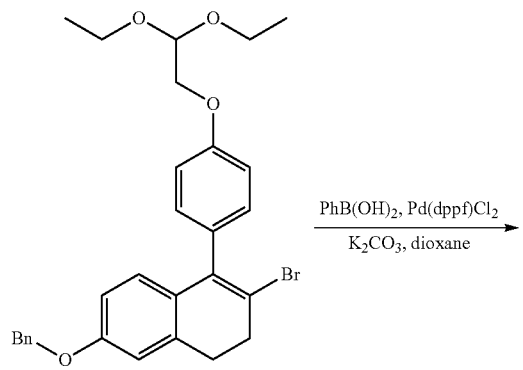

To a solution of 7-benzyloxy-3-bromo-4-[4-(2,2-diethoxyethoxy)phenyl]-1,2-dihydronaphthalene (12.4 g, 23.69 mmol, 1.00 eq), phenylboronic acid (2.89 g, 23.69 mmol, 1.00 eq) in dioxane (100 mL) and water (20 mL) was added potassium carbonate (6.55 g, 47.38 mmol, 2.00 eq) and (1,1'-bis(diphenylphosphino)ferrocene)palladium(II) dichloride (1.73 g, 2.37 mmol, 0.10 eq) under nitrogen. The reaction mixture was stirred at 100° C. for 3 hours. LC/MS showed most of the starting material was consumed. Water (300 mL) was added to the mixture, the resulting mixture was extracted with ethyl acetate (150 mL×3). The combined organic phase was washed with brine (200 mL×2), dried over sodium sulfate, filtered and concentrated in vacuum. The residue was purified by silica gel chromatography (petroleum ether:ethyl acetate=1:0 to 30:1) to give 7-benzyloxy-4-[4-(2,2-diethoxyethoxy)phenyl]-3-phenyl-1,2-dihydronaphthalene (10.4 g, 19.97 mmol, 84% yield) as a white solid. LC/MS (ESI) m/z: 521.3 [M+1]$^+$; $^1$H NMR (400 MHz, CDCl$_3$) δ 7.46-7.32 (m, 5H), 7.14-6.95 (m, 7H), 6.87 (d, J=2.4 Hz, 1H), 6.79 (d, J=8.8 Hz, 2H), 6.72 (d, J=8.4 Hz, 1H), 6.67 (dd, J=8.4, 2.8 Hz, 1H), 5.08 (s, 2H), 4.83 (t, J=5.2 Hz, 1H), 3.99 (d, J=5.2 Hz, 2H), 3.82-3.74 (m, 2H), 3.67-3.63 (m, 2H), 2.97-2.93 (m, 2H), 2.81-2.77 (m, 2H), 1.26 (t, J=6.8 Hz, 6H).

1000

Step 8: Preparation of 5,6-cis-5-(4-(2,2-diethoxyethoxy)phenyl)-6-phenyl-5,6,7,8-tetrahydronaphthalen-2-ol

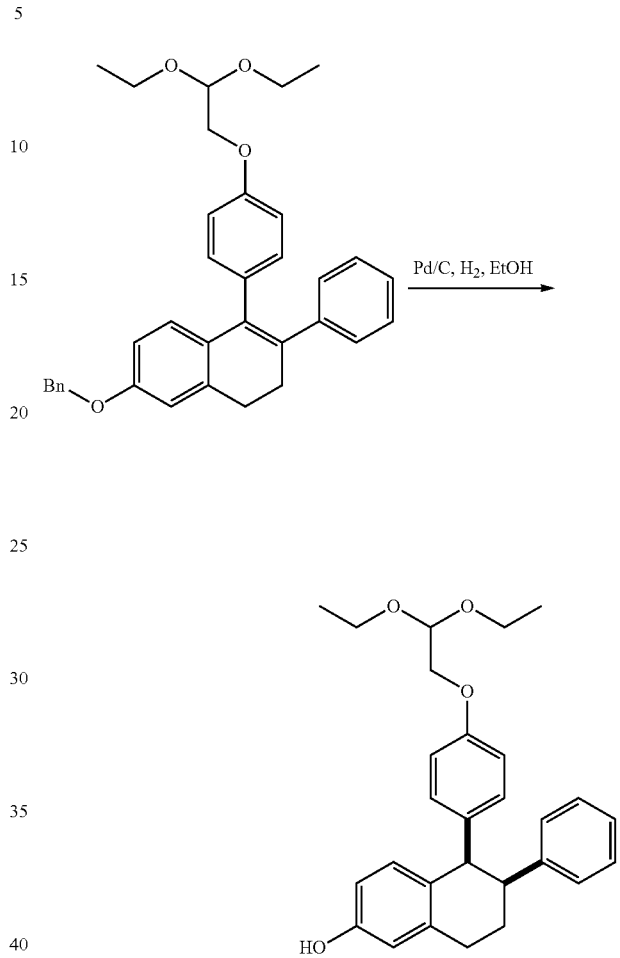

To a solution of 7-benzyloxy-4-[4-(2,2-diethoxyethoxy)phenyl]-3-phenyl-1,2-dihydronaphthalene (4 g, 7.68 mmol, 1.00 eq) in ethyl alcohol (150 mL) and tetrahydrofuran (30 mL) was added palladium/carbon (400 mg, 10% Pd) under nitrogen. The reaction mixture was stirred at 20° C. under hydrogen (50 0si) for 24 hours. TLC (petroleum ether:ethyl acetate=3:1) and LC/MS detected most of the starting material was consumed. The mixture was filtered and the filter was concentrated in vacuum to give 5,6-cis-5-(4-(2,2-diethoxyethoxy)phenyl)-6-phenyl-5,6,7,8-tetrahydronaphthalen-2-ol (3.3 g, 7.09 mmol, 92% yield, 93% purity) as a yellow oil. LC/MS (ESI) m/z: 455.3 [M+23]; $^1$H-NMR (400 MHz, CDCl$_3$) 7.19-7.12 (m, 3H), 6.83-6.79 (m, 3H), 6.71 (d, J=8.4 Hz, 1H), 6.59-6.53 (m, 3H), 6.31 (d, J=8.4 Hz, 2H), 4.81-4.77 (m, 2H), 4.23 (d, J=4.8 Hz, 1H), 3.90 (dd, J=4.8, 1.6 Hz, 2H), 3.78-3.71 (m, 2H), 3.65-3.58 (m, 2H), 3.38-3.33 (m, 1H), 3.10-2.96 (m, 2H), 2.23-2.16 (m, 1H), 1.84-1.79 (m, 1H), 1.24 (t, J=6.8 Hz, 6H).

1001

Step 9: Preparation of (1R,2S)-1-[4-(2,2-diethoxy-ethoxy)phenyl]-2-phenyl-tetralin-6-ol

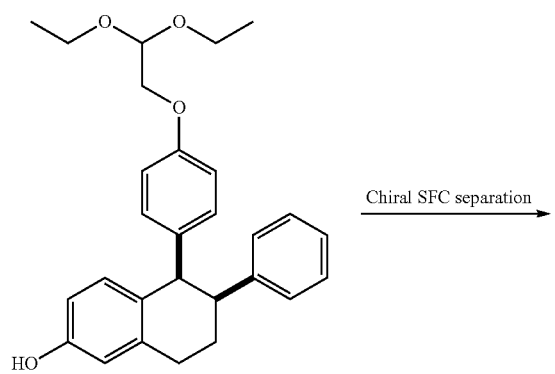

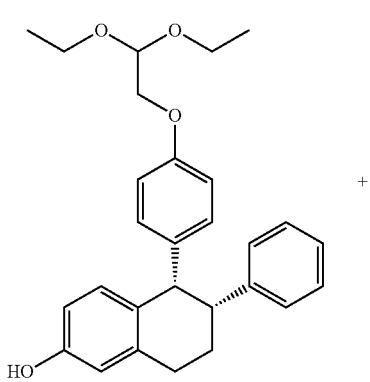

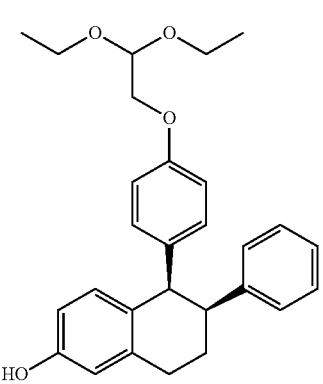

1,2-cis-1-[4-(2,2-diethoxyethoxy)phenyl]-2-phenyl-tetralin-6-ol (6.6 g, 15.26 mmol, 1.00 eq) was purified by SFC using a chiral column (column: AD, 250 mm×30 mm, 10 um; mobile phase: 0.1% ammonium hydroxide in methanol; B %: 25%-25%, 3.5 min). (1S, 2R)-1-[4-(2,2-diethoxy-ethoxy)phenyl]-2-phenyl-tetralin-6-ol (2.5 g, 5.18 mmol, 68% yield) was obtained as the first fraction and (1R,2S)-

1002

1-[4-(2,2-diethoxyethoxy)phenyl]-2-phenyl-tetralin-6-ol (2.5 g, 5.18 mmol, 68% yield) was obtained as the second fraction. Both fractions were light yellow oil.

Step 10: Preparation of 2-[4-[(1R,2S)-6-hydroxy-2-phenyl-tetralin-1-yl]phenoxy]acetaldehyde

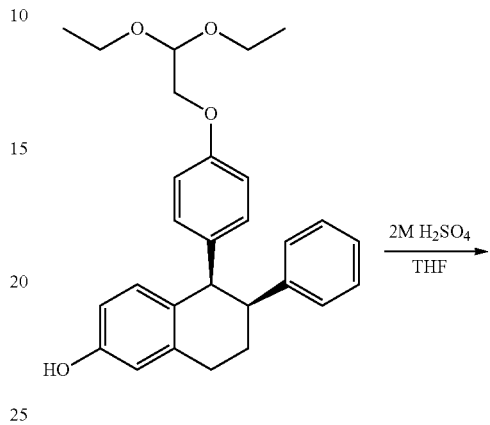

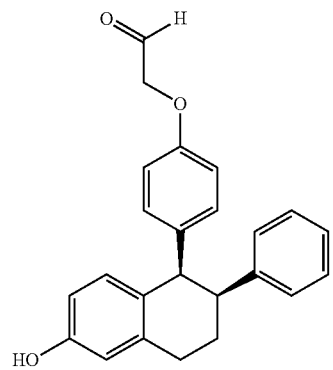

To a solution of (1R, 2S)-1-[4-(2,2-diethoxyethoxy)phenyl]-2-phenyl-tetralin-6-ol (1.5 g, 3.47 mmol, 1.00 eq) in tetrahydrofuran (70 mL) was added sulfuric acid solution (2 M, 70 mL, 40.00 eq). The reaction mixture was stirred at 70° C. for 2 hours. TLC (petroleum ether: ethyl acetate=1:1) showed most of the starting material was consumed. Water (100 mL) was added to the mixture, the resulting mixture was extracted with ethyl acetate (100 mL×3). The combined organic phase was washed with brine (100 mL×2), dried over sodium sulfate, filtered and concentrated in vacuum to give 2-[4-[(1R,2S)-6-hydroxy-2-phenyl-tetralin-1-yl]phenoxy]acetaldehyde (1.17 g, 3.26 mmol, 94% yield) as a light yellow solid.

Step 11: Preparation of (2S,4R)-4-hydroxy-1-[(2S)-2-(2-{2-[4-(2-{4-[(1R,2S)-6-hydroxy-2-phenyl-1,2,3,4-tetrahydronaphthalen-1-yl]phenoxy}ethyl)piperazin-1-yl]ethoxy}acetamido)-3,3-dimethylbutanoyl]-N-{[4-(4-methyl-1,3-thiazol-5-yl)phenyl]methyl}pyrrolidine-2-carboxamide (Exemplary Compound 1)

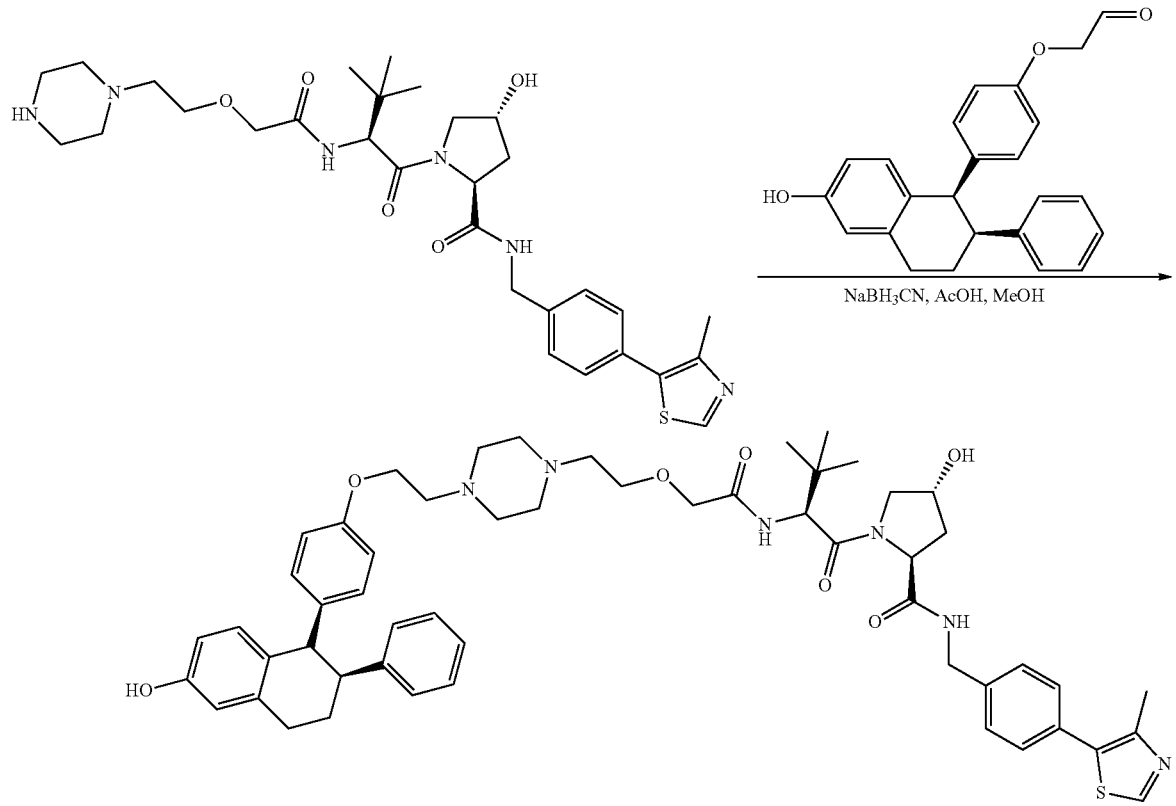

To a solution of (2S,4R)-1-[(2S)-3,3-dimethyl-2-[[2-(2-piperazin-1-ylethoxy)acetyl]amino]butanoyl]-4-hydroxy-N-[[4-(4-methylthiazol-5-yl)phenyl]methyl]pyrrolidine-2-carboxamide hydrochloride (45 mg, 0.07 mmol, 1.00 eq) in dichloromethane (3 mL) and methanol (1.5 mL) was added sodium acetate (12 mg, 0.14 mmol, 2.00 eq) at 25° C. The mixture was stirred for half an hour, and then 2-[4-[(1R,2S)-6-hydroxy-2-phenyl-tetralin-1-yl]phenoxy]acetaldehyde (28 mg, 0.08 mmol, 1.10 eq) was added, followed by sodium cyanoborohydride (9 mg, 141 umol, 2.00 eq). The resulting mixture was stirred at 25° C. for 16 hours. LC/MS showed almost complete disappearance of the starting material and the desire compound was found. The mixture was concentrated in vacuum. The residue was added into saturated brine (10 mL) and then extracted with dichloromethane (10 mL×5). The combined organic layers were dried over anhydrous sodium sulfate, filtered and concentrated in vacuum. The residue was further purified by preparative TLC (SiO$_2$, dichloromethane:methanol=10:1) to provide (2S,4R)-4-hydroxy-1-[(2S)-2-[[2-[2-[4-[2-[4-[(1R,2S)-6-hydroxy-2-phenyl -oxy-2-phenyl-tetralin-1-yl]phenoxy]ethyl]piperazin-1-yl]ethoxy]acetyl]amino]-3,3-dimethyl-butanoyl]-N-[[4-(4-methylthiazol-5-yl)phenyl]methyl]pyrrolidine-2-carboxamide (8 mg, 0.009 mmol, 12% yield, 98% purity) as a white solid. LC/MS (ESI) m/z: 943.1

[M+1]$^+$; $^1$H NMR (400 MHz, DMSO-d$_6$) δ: 9.36-9.10 (br, 1H), 8.95 (s, 1H), 8.60 (t, J=5.6 Hz, 1H), 7.39 (m, 5H), 7.16-7.12 (m, 3H), 6.82 (d, J=7.2 Hz, 2H), 6.64-6.61 (m, 2H), 6.51-6.34 (m, 3H), 6.26-6.24 (m, 2H), 5.25-5.10 (m, 1H), 4.59-4.51 (m, 1H), 4.48-4.32 (m, 3H), 4.29-4.15 (m, 2H), 3.80-3.70 (m, 4H), 3.63-3.55 (m, 3H), 3.34-3.26 (m, 8H), 3.05-2.84 (m, 2H), 2.48-2.43 (m, 9H), 2.11-2.01 (m, 2H), 1.95-1.85 (m, 1H), 1.75-1.65 (m, 1H), 0.93 (s, 9H).

Synthesis of (2S,4R)-4-hydroxy-1-[(2S)-2-{2-[2-(4-{2-[4-(6-hydroxy-2-phenyl-1,2,3,4-tetrahydroisoquinolin-1-yl)phenoxy]ethyl}piperazin-1-yl)ethoxy]acetamido}-3,3-dimethylbutanoyl]-N-[(1 S)-1-[4-(4-methyl-1,3-thiazol-5-yl)phenyl]ethyl]pyrrolidine-2-carboxamide (Exemplary Compound 6)

Step 1: Preparation of 2-(3-benzyloxyphenyl)acetic acid

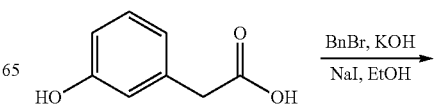

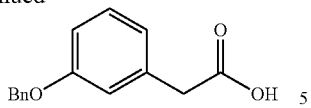

To a solution of 2-(3-hydroxyphenyl)acetic acid (20 g, 131.45 mmol, 1.00 eq) in ethanol (300 mL) was added potassium hydroxide (18.44 g, 328.62 mmol, 2.50 eq), sodium iodide (492 mg, 3.29 mmol, 0.03 eq) and bromomethylbenzene (23.61 g, 138.02 mmol, 1.05 eq). The resulting mixture was stirred at 90° C. for 16 hours. LCMS indicated the reaction was completed. The reaction mixture was concentrated to remove the solvent. The residue was diluted with water (100 mL), and neutralized with concentrated hydrochloric acid to pH=3, then filtrated and the solid was collected. The desired product 2-(3-benzyloxyphenyl)acetic acid (16 g, 66.04 mmol, 50% yield) was obtained as a white solid. $^1$H-NMR (400 MHz, DMSO-$d_6$) δ 7.47-7.35 (m, 5H), 7.23 (t, J=7.8 Hz, 1H), 6.92-6.83 (m, 3H), 5.08 (s, 2H), 3.54 9S, 2H).

Step 2: Preparation of 4-allyloxybenzoic acid

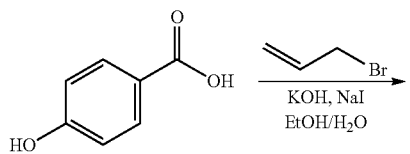

4-Hydroxybenzoic acid (14 g, 101.36 mmol, 1.00 eq) was dissolved in ethanol (200 mL), then aqueous solution (50 mL) containing potassium hydroxide (14.22 g, 253.40 mmol, 2.50 eq) and sodium iodide (456 mg, 3.04 mmol, 0.03 eq) was added at 20° C. and the mixture was stirred at 20° C. for 2 hours. Then 3-bromoprop-1-ene (12.88 g, 106.43 mmol, 1.05 eq) was added dropwise. The resulting mixture was stirred at 90° C. for 16 hours. The desired product was detected by LC/MS. The reaction mixture was concentrated to remove the ethanol, the residue was neutralized with concentrated hydrochloric acid to pH around 3, and then extracted with ethyl acetate (300 mL×2), the combined organic phase was washed with brine (100 mL), dried over sodium sulfate and concentrated. The residue was purified by silica gel column chromatography (dichloromethane:methanol=1:0 to 30:1). The desired product 4-allyloxybenzoic acid (6 g, 33.67 mmol, 33% yield) was obtained as a white solid. LC/MS (ESI) m/z: 179.0 [M+1]$^+$; $^1$H NMR (400 MHz, DMSO-$d_6$) δ 12.65 (br, 1H), 7.89 (d, J=8.8 Hz, 2H), 7.03 (d, J=8.8 Hz, 2H), 6.10-6.00 (m, 1H), 5.43 (d, J=17.2, 1.2 Hz, 1H), 5.28 (dd, J=10.4, 1.2 Hz, 1H), 4.64 (d, J=5.2 Hz, 2H).

Step 3: Preparation of 2-[3-(benzyloxy)phenyl]-N-phenylacetamide

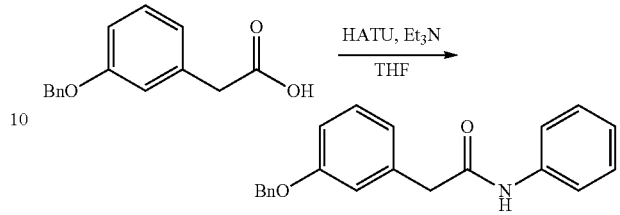

To a solution of 2-(3-benzyloxyphenyl)acetic acid (16 g, 66.04 mmol, 1.00 eq) in tetrahydrofuran (200 mL) was added aniline (6.77 g, 72.64 mmol, 6.64 mL, 1.10 eq), HATU (30.13 g, 79.25 mmol, 1.20 eq), and triethylamine (13.37 g, 132.08 mmol, 18 mL, 2.00 eq). The resulting mixture was stirred at 20° C. for 1 hour. TLC (petroleum ether:ethyl acetate=3:1) indicated the reaction was completed. The reaction mixture was concentrated. The residue was dissolved in ethyl acetate (500 mL), washed with IN hydrochloric acid (100 mL), brine (200 mL), dried over sodium sulfate and then concentrated. The residue was triturated with petroleum ether:ethyl acetate=3:1 (200 mL) and then filtrated. The desired product 2-(3-benzyloxyphenyl)-N-phenyl-acetamide (19.50 g, 59.47 mmol, 90% yield, 97% purity) was obtained as a white solid. LC/MS (ESI) m/z: 318.0 [M+1]$^+$.

Step 4: Preparation of N-[2-(3-benzyloxyphenyl)ethyl]aniline

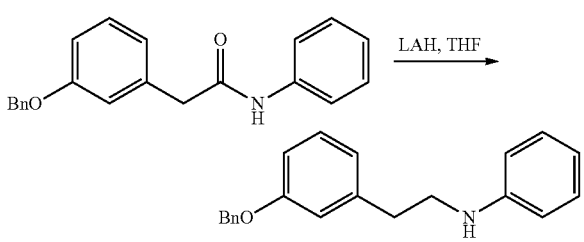

To a solution of 2-(3-benzyloxyphenyl)-N-phenyl-acetamide (12 g, 37.81 mmol, 1.00 eq) in tetrahydrofuran (200 mL) was added lithium aluminum hydride (2.15 g, 56.72 mmol, 1.50 eq) at 0° C. dropwise. The resulting mixture was stirred at 0° C. for additional 2 hours. TLC (petroleum ether:ethyl acetate=3:1) indicated the reaction was completed. Then 2 mL of water and 2 mL of 15% sodium hydroxide aqueous solution was added to quench the reaction, the resulting mixture was stirred for additional 30 minutes, then filtrated and the filtrated cake was further washed with ethyl acetate (500 mL). The filtrate was concentrated. The residue was purified by silica gel column chromatography (petroleum ether:ethyl acetate=20:1 to 10:1). The desired product N-[2-(3-benzyloxyphenyl)ethyl]aniline (6 g, 19.78 mmol, 52% yield) was obtained as a yellow oil. $^1$H-NMR (400 MHz, CDCl$_3$) δ 7.48-7.34 (m, 5H), 7.28-7.19 (m, 3H), 6.90-6.88 (m, 3H), 6.74 (t, J=7.2 Hz, 1H), 6.64 (dd, J=8.4, 0.8 Hz, 2H), 5.09 (s, 2H), 3.71 (br, 1H), 3.43 (t, J=7.2 Hz, 2H), 2.92 (t, J=7.2 Hz, 2H).

1007

Step 5: Preparation of 4-(allyloxy)-N-(3-(benzyloxy)phenethyl)-N-phenylbenzamide

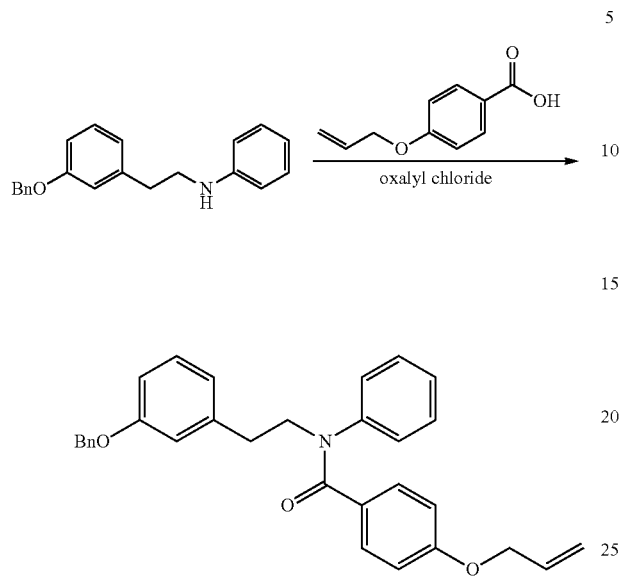

To a solution of 4-allyloxybenzoic acid (4.58 g, 25.71 mmol, 1.30 eq) in dichloromethane (200 mL) was added oxalyl dichloride (5.02 g, 39.56 mmol, 3.46 mL, 2.00 eq). The resulting mixture was stirred at 20° C. for 2 hours. Then the mixture was concentrated to remove the solvent. The residue was dissolved in toluene (100 mL) and N-[2-(3-benzyloxyphenyl)ethyl]aniline (6 g, 19.78 mmol, 1.00 eq) and sodium carbonate (6.29 g, 59.34 mmol, 3.00 eq) was added. The resulting mixture was stirred at 100° C. for 2 hours. TLC (petroleum ether:ethyl acetate=3:1) indicated the reaction was complete. The reaction mixture was filtrated to remove the inorganic base, the filtrate was concentrated. The residue was purified by silica gel column chromatography (petroleum ether:ethyl acetate=30:1 to 10:1). The desired product 4-(allyloxy)-N-(3-(benzyloxy)phenethyl)-N-phenylbenzamide (8.00 g, yield: 87%) was obtained as a yellow oil. LC/MS (ESI) m/z: 464.1 [M+1]$^+$; $^1$H-NMR (400 MHz, CDCl$_3$) δ 7.46-7.34 (m, 5H), 7.28-7.15 (m, 6H), 6.92-6.83 (m, 5H), 6.71-6.67 (m, 2H), 6.04-5.97 (m, 1H), 5.41-5.35 (m, 1H), 5.28 (dq, J=10.4, 1.6 Hz, 1H), 5.05 (s, 2H), 4.48 (dt, J=5.2, 1.6 Hz, 2H), 4.15-4.10 (m, 2H), 3.03-2.99 (m, 2H).

Step 6: Preparation of 1-(4-allyloxyphenyl)-6-benzyloxy-2-phenyl-3,4-dihydro-1H-isoquinoline

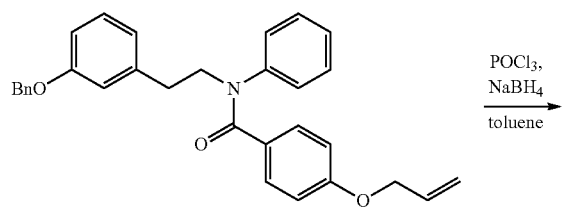

1008

-continued

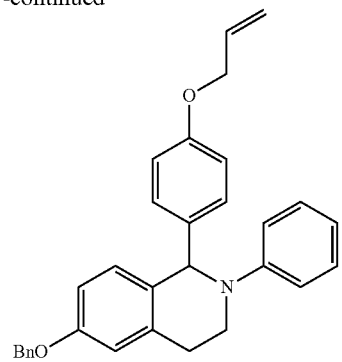

To a solution of 4-allyloxy-N-[2-(3-benzyloxyphenyl)ethyl]-N-phenyl-benzamide (8 g, 17.26 mmol, 1.00 eq) in toluene (80 mL) was added phosphorus oxychloride (52.93 g, 345.20 mmol, 32.08 mL, 20.00 eq). The solution was heated to 120° C. for 16 hours. LC/MS showed starting material was consumed. Sodium borohydride (1.31 g, 34.52 mmol, 2.00 eq) was added to the solution at 20° C. The solution was stirred at 20° C. for 2 hours. LC/MS showed reaction was complete. The solvent was removed and residue was quenched with water (30 mL). The mixture was extracted with ethyl acetate (30 mL×3). The organic layer was dried over sodium sulfate, filtered and concentrated in vacuum to give 1-(4-allyloxyphenyl)-6-benzyloxy-2-phenyl-3,4-dihydro-1H-isoquinoline (5.5 g, 12.29 mmol, 71% yield) as white solid. LC/MS (ESI) m/z: 448.1 [M+1]$^+$.

Step 7: Preparation of 4-(6-(benzyloxy)-2-phenyl-1,2,3,4-tetrahydro isoquinolin-1-yl)phenol

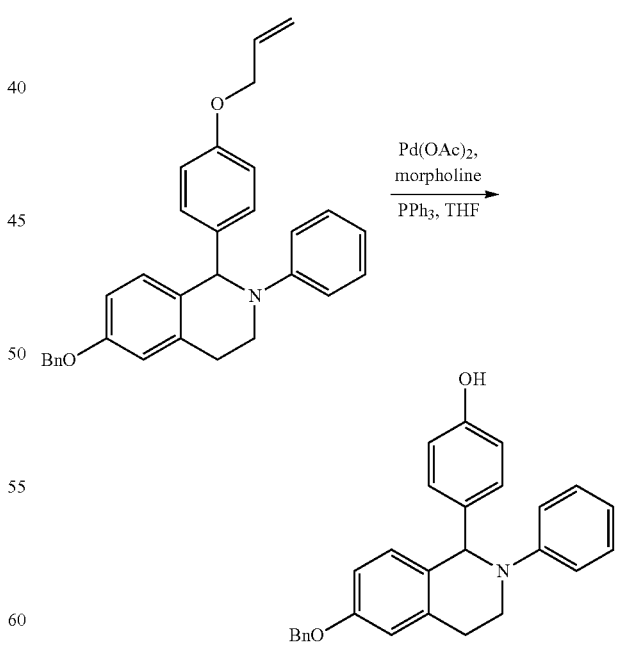

To a solution of 1-(4-allyloxyphenyl)-6-benzyloxy-2-phenyl-3,4-dihydro-1H-isoquinoline (5.5 g, 12.29 mmol, 1.00 eq) in tetrahydrofuran (100 mL) was added triphenylphosphine (4.84 g, 18.43 mmol, 1.50 eq), morpholine (1.28 g, 14.75 mmol, 1.30 mL, 1.20 eq), palladium acetate (276 mg, 1.23 mmol, 0.10 eq). The resulting mixture was stirred at 20° C. for 16 hours. LC/MS indicated the reaction was complete. The reaction mixture was filtered through a pad of Celite and the cake was washed with 100 mL of ethyl acetate. The filtrate was concentrated to remove the solvent. The residue was further purified by semi-preparative reverse phase HPLC (column: Phenomenex Synergi Max-RP 250×50 mm, 10 um; mobile phase: water with 0.1% TFA/acetonitrile; B %: acetonitrile 10%-65%). The collected fraction was concentrated to remove most of acetonitrile. The resulting mixture was extracted with ethyl acetate (250 mL×3). The combined organic phase was washed with brine (400 mL), dried over sodium sulfate, filtered and concentrated in vacuum. The desired product 4-(6-(benzyloxy)-2-phenyl-1,2,3,4-tetrahydroisoquinolin-1-yl)phenol (3.9 g, yield: 78%) was obtained as a yellow solid. LC/MS (ESI) m/z: 408.0 [M+1]$^+$; $^1$H-NMR (400 MHz, CD$_3$OD) δ 7.46-7.44 (m, 2H), 7.40-7.36 (m, 2H), 7.33-7.30 (m, 1H), 7.24 (t, J=8.0 Hz, 2H), 7.06-6.92 (m, 5H), 6.87-6.83 (m, 3H), 6.66-6.63 (m, 2H), 5.79 (s, 1H), 5.07 (s, 2H), 3.72-3.50 (m, 2H), 3.02 (br, 2H).

Step 8: Preparation of tert-butyl 4-[2-[4-(6-benzyloxy-2-phenyl-3,4-dihydro-1H-isoquinolin-1-yl)phenoxy]ethyl]piperazine-1-carboxylate

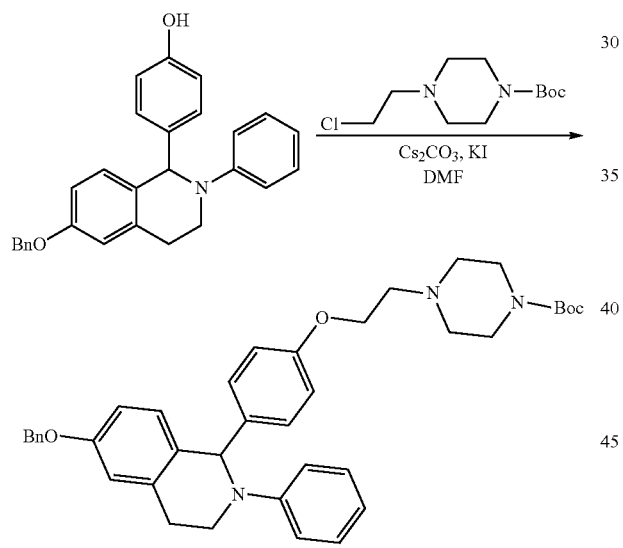

To a solution of 4-(6-benzyloxy-2-phenyl-3,4-dihydro-1H-isoquinolin-1-yl)phenol (2.30 g, 5.64 mmol, 1.00 eq), tert-butyl 4-(2-chloroethyl)piperazine-1-carboxylate (1.68 g, 6.77 mmol, 1.20 eq) in N,N-dimethylformamide (20 mL) was added cesium carbonate (2.76 g, 8.46 mmol, 1.50 eq) and potassium iodide (94 mg, 0.56 mmol, 0.10 eq) under nitrogen atmosphere. The reaction mixture was stirred at 90° C. for 16 hours. LC/MS showed most of the starting material was consumed. Water (150 mL) was added to the mixture, the resulting mixture was extracted with ethyl acetate (50 mL×3). The combined organic phase was washed with brine (100 mL×2), dried over sodium sulfate, filtered and concentrated in vacuum. The residue was purified by silica gel chromatography (petroleum ether/ethyl acetate=20/1 to 1/1) to give tert-butyl 4-[2-[4-(6-benzyloxy-2-phenyl-3,4-dihydro-1H-isoquinolin-1-yl) phenoxy]ethyl]piperazine-1-carboxylate (2.5 g, 3.97 mmol, 70% yield, 98% purity) as a yellow solid. LC/MS (ESI) m/z: 620.3 [M+1]; $^1$H-NMR (400 MHz, DMSO-d$_6$) δ 7.44-7.37 (m, 4H), 7.32-7.28 (m, 2H), 7.17-7.11 (m, 4H), 6.87-6.80 (m, 6H), 6.64 (t, J=7.2 Hz, 1H), 5.84 (s, 1H), 5.07 (s, 2H), 4.06-3.98 (m, 2H), 3.67-3.62 (m, 1H), 3.44-3.40 (m, 1H), 3.29-3.27 (m, 4H), 2.96-2.79 (m, 2H), 2.65 (t, J=5.6 Hz, 2H), 2.39 (t, J=4.8 Hz, 4H), 1.38 (s, 9H).

Step 9: Preparation of 6-(benzyloxy)-2-phenyl-1-(4-(2-(piperazin-1-yl) ethoxy)phenyl)- 1,2,3,4-tetrahydroisoquinoline

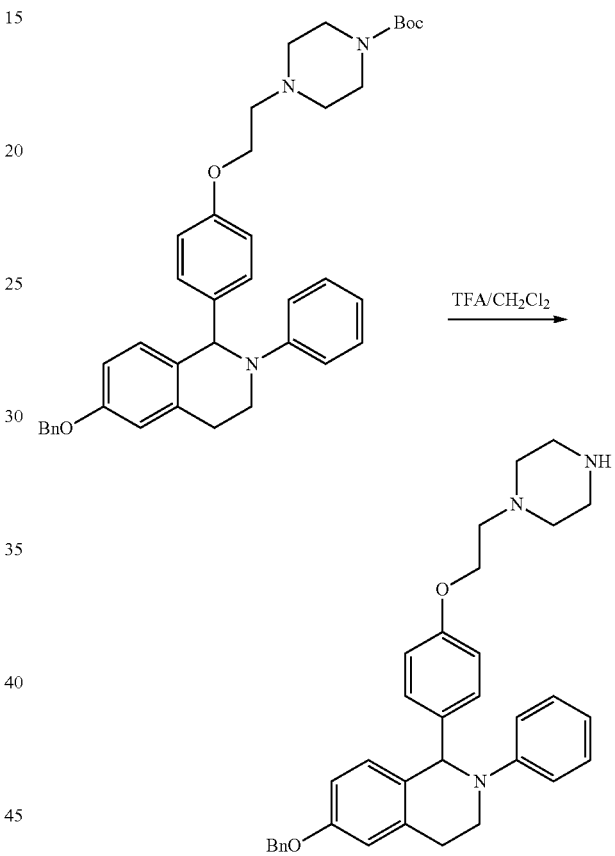

To a solution of tert-butyl-4-[2-[4-(6-benzyloxy-2-phenyl-3,4-dihydro-1H-isoquinolin-1-yl) phenoxy]ethyl]piperazine-1-carboxylate (1.00 g, 1.61 mmol, 1.00 eq) in dichloromethane (40 mL) was added trifluoroacetic acid (10.00 mL) at 25° C. The mixture was stirred at 25° C. for 16 hours. TLC (dichloromethane:methanol=10:1) showed the starting material was consumed completely. The reaction mixture was poured into water (100 mL), and then neutralized with sodium bicarbonate. The resulting mixture was extracted with ethyl acetate (150 mL×3). The combined organic phase was washed with brine (250 mL×2), dried over anhydrous sodium sulfate, filtered and concentrated in vacuum to afford 6-benzyloxy-2-phenyl-1-[4-(2-piperazin-1-ylethoxy)phenyl]-3,4-dihydro-1H-isoquinoline (0.80 g, 1.54 mmol, 95% yield) as a yellow oil. LC/MS (ESI) m/z: 520.3 [M+1]$^+$.

Step 10: Preparation of ethyl 2-(2-(4-(2-(4-(6-(benzyloxy)-2-phenyl-1,2,3,4-tetrahydroisoquinolin-1-yl)phenoxy)ethyl)piperazin-1-yl)ethoxy)acetate

Step 11: Preparation of 2-(2-(4-(2-(4-(6-hydroxy-2-phenyl-1,2,3,4-tetrahydroisoquinolin-1-yl)phenoxy)ethyl)piperazin-1-yl)ethoxy)acetic acid

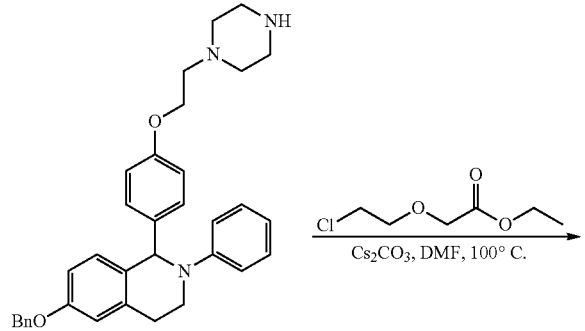

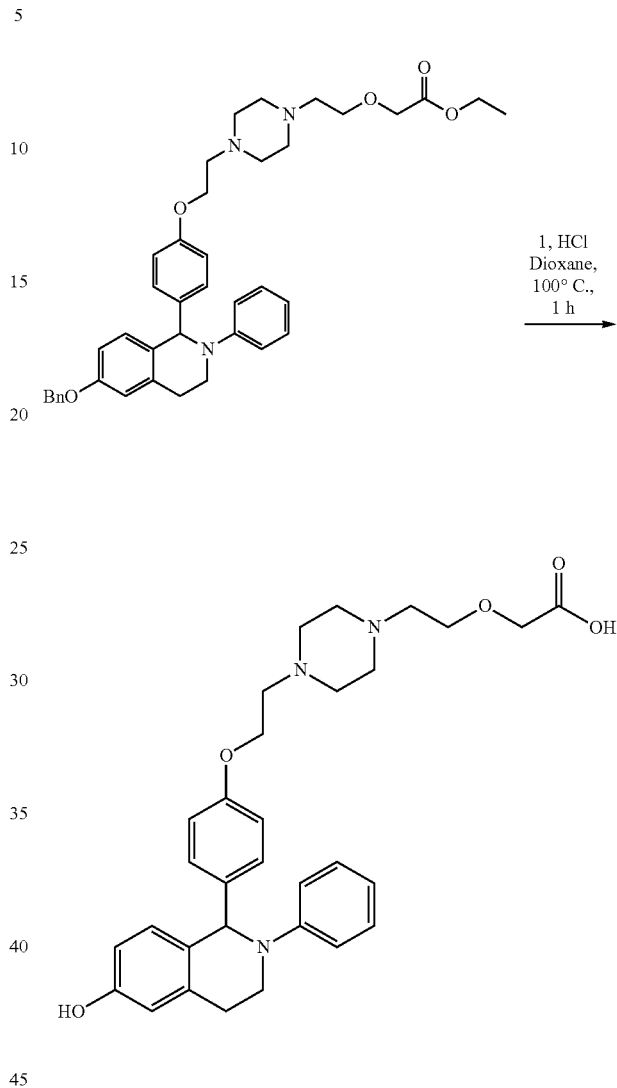

To a solution of ethyl 2-(2-chloroethoxy)acetate (0.24 g, 1.44 mmol, 1.00 eq) and 6-benzyloxy-2-phenyl-1-[4-(2-piperazin-1-ylethoxy)phenyl]-3,4-dihydro-1H-isoquinoline (0.75 g, 1.44 mmol, 1.0 eq) in N,N-dimethylformamide (10 mL) was added sodium iodide (0.22 g, 1.44 mmol, 1.00 eq) and cesium carbonate (0.94 g, 2.88 mmol, 2.00 eq) at 25° C. The mixture was heated to 100° C. and stirred at 100° C. for 16 hours. LC/MS showed the reaction was completed and desired product was formed. The mixture was poured into water (50 ml), and the aqueous phase was extracted with ethyl acetate (50 mL×3). The combined organic phase was washed with brine (100 mL×2), dried over anhydrous sodium sulfate, filtered and concentrated in vacuum. The residue was purified by silica gel column chromatography (dichloromethane:methanol=50:1) to afford ethyl 2-[2-[4-[2-[4-(6-benzyloxy-2-phenyl-3,4-dihydro-1H-isoquinolin-1-yl)phenoxy]ethyl]piperazin-1-yl]ethoxy]acetate (0.58 g, 0.90 mmol, 62% yield) as a yellow oil LC/MS (ESI) m/z: 650.3 [M+1]$^+$.

To a solution of ethyl 2-[2-[4-[2-[4-(6-benzyloxy-2-phenyl-3,4-dihydro-1H-isoquinolin-1-yl) phenoxy]ethyl]piperazin-1-yl]ethoxy]acetate (0.40 g, 0.62 mmol, 1.00 eq) in dioxane (6 mL) was added concentrated hydrochloric acid (11.8 M, 8 mL). The mixture was stirred at 100° C. for 1 hour. LC/MS showed the starting material was consumed and the formation of the desired product. The mixture was cooled to 25° C., and the pH was adjusted to 5 with saturated sodium bicarbonate solution. The aqueous phase was extracted with ethyl acetate (50 mL×5). The combined organic phase was dried with anhydrous sodium sulfate, filtered and concentrated in vacuum to afford 2-[2-[4-[2-[4-(6-hydroxy-2-phenyl-3,4-dihydro-1H-isoquinolin-1-yl)phenoxy]ethyl]piperazin-1-yl]ethoxy]acetic acid (0.32 g, 0.42 mmol, 68% yield, 69% purity) as a yellow oil. The crude product was directly used for the next step without further purification. LC/MS (ESI) m/z: 532.3 [M+1]$^+$.

Step 12: Preparation of (2S,4R)-4-hydroxy-1-((2S)-2-(2-(2-(4-(2-(4-(6-hydroxy-2-phenyl-1,2,3,4-tetrahydroisoquinolin-1-yl)phenoxy)ethyl)piperazin-1-yl)ethoxy)acetamido)-3,3-dimethylbutanoyl)-N-((S)-1-(4-(4-methylthiazol-5-yl)phenyl)ethyl)pyrrolidine-2-carboxamide (Exemplary Compound 6)

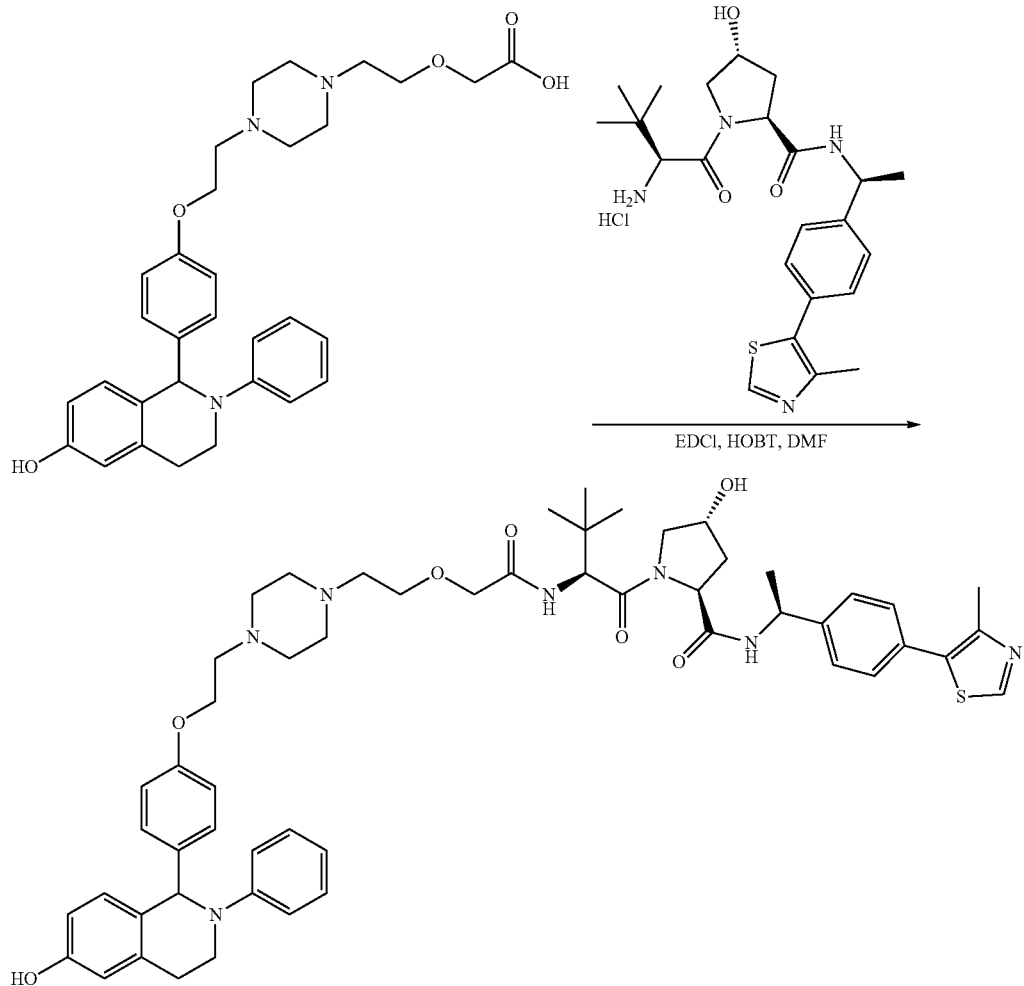

To a solution of 2-[2-[4-[2-[4-(6-hydroxy-2-phenyl-3,4-dihydro-1H-isoquinolin-1-yl) phenoxy]ethyl]piperazin-1-yl]ethoxy] acetic acid (0.16 g, 0.30 mmol, 1.00 eq), 1-hydroxybenzotriazole (0.05 g, 0.36 mmol, 1.20 eq) and 1-(3-dimethylaminopropyl)-3-ethylcarbodiimide hydro chloride (0.09 g, 0.45 mmol, 1.50 eq) in N,N-dimethylformamide (5 mL) was added N,N-diisopropylethylamine (0.19 g, 1.50 mmol, 0.26 mL, 5.00 eq). The mixture was stirred at 25° C. for half an hour, and then (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide (0.14 g, 0.30 mmol, 1.00 eq, HCl salt) was added. The resulting mixture was stirred at 25° C. for 16 hours. LC/MS showed the reaction was completed. The mixture was poured into 100 mL of saturated brine and then extracted with ethyl acetate (50 mL×3). The combined organic layers were dried over anhydrous sodium sulfate, filtered and concentrated in vacuum. The residue was further purified by semi-preparative reverse phase HPLC (column: Phenomenex Synergi C18 150 mm×25 mm, 10 um; mobile phase: water with 0.05% ammonium hydroxide/acetonitrile; B %: 28%-48%, 7.8 min). The collected fraction was concentrated to remove most of acetonitrile and lyophilized to provide (2S,4R)-4-hydroxy-1-[(2S)-2-[[2-[2-[4-[2-[4-(6-hydroxy-2-phenyl-3,4-dihydro-1H-isoquinolin-1-yl)phenoxy]ethyl]piperazin-1-yl]ethoxy]acetyl]amino]-3,3-dimethyl-butanoyl]-N-[(1S)-1-[4-(4-methylthiazol-5-yl)phenyl]ethyl]pyrrolidine-2-carboxamide (25.8 mg, 0.03 mmol, 9% yield, 98% purity) as a gray solid. LC/MS (ESI) m/z: 958.5 [M+1]$^+$; $^1$H-NMR (400 MHz, CD$_3$OD) δ 8.88 (s, 1H), 7.46-7.40 (m, 4H), 7.16 (t, J=8.0 Hz, 2H), 7.09-7.04 (m, 3H), 6.87 (d, J=8.0 Hz, 2H), 6.79 (d, J=8.0 Hz, 2H), 6.72-6.63 (m, 3H), 5.72 (s, 1H), 5.03-4.96 (m, 1H), 4.69 (s, 1H), 4.58 (m, 1H), 4.45 (m, 1H), 4.10-3.97 (m, 4H), 3.86-3.84 (m, 1H), 3.78-3.70 (m, 3H), 3.63-3.58 (m, 1H), 3.45-3.39 (m, 1H), 2.91-2.79 (m, 4H), 2.76-2.51 (m, 9H), 2.49 (s, 3H), 2.23-2.17 (m, 1H), 2.01-1.97 (m, 1H), 1.54 (d, J=7.2, 3H), 1.05 (s, 9H).

Synthesis of 3-{(5-[4-(5-{4-[(1R,2S)-6-hydroxy-2-phenyl-1,2,3,4-tetrahydronaphthalen-1-yl]phenoxy}pentyl)piperazin-1-yl]-1-oxo-2,3-dihydro-H-isoindol-2-yl}piperidine-2,6-dione (Exemplary Compound 62)

Step 1: Preparation of 6-benzyloxytetralin-1-one

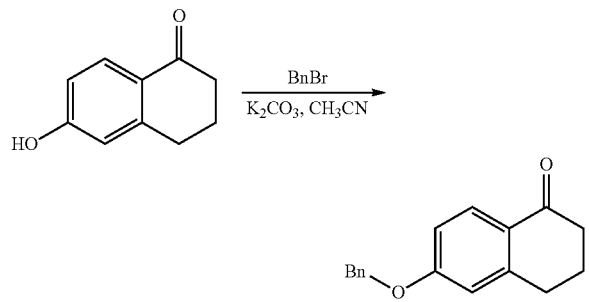

To a solution of 6-hydroxytetralin-1-one (100 g, 616.56 mmol, 1.00 eq) in acetonitrile (1000 mL) was added potassium carbonate (170.43 g, 1.23 mol, 2.00 eq) and benzyl bromide (126.54 g, 739.87 mmol, 88 mL, 1.20 eq). The reaction mixture was stirred at 50° C. for 2 hours. TLC (petroleum ether:ethyl acetate=5:1) showed most of the starting material was consumed. Water (1000 mL) was added to the mixture, the resulting mixture was extracted with ethyl acetate (600 mL×3). The combined organic phase was washed with brine (800 mL), dried over sodium sulfate, filtered and concentrated in vacuum. The residue was triturated with petroleum ether and ethyl acetate (303 mL, petroleum ether:ethyl acetate=100:1, V:V). The mixture was filtered and the filter cake was washed with petroleum ether (50 mL×2), dried in vacuum to give 6-benzyloxytetralin-1-one (146 g, 578.65 mmol, 94% yield) as a brown solid. $^1$H-NMR (400 MHz, CDCl$_3$) δ 8.02 (d, J=8.8 Hz, 1H), 7.45-7.34 (m, 5H), 6.91 (dd, J=8.8, 2.4 Hz, 1H), 6.80 (d, J=2.4 Hz, 1H), 5.12 (s, 2H), 2.93 (t, J=6.0 Hz, 2H), 2.62 (t, J=6.4 Hz, 2H), 2.15-2.09 (m, 2H).

Step 2: Preparation of (6-benzyloxy-3,4-dihydronaphthalen-1-yl) trifluoromethanesulfonate

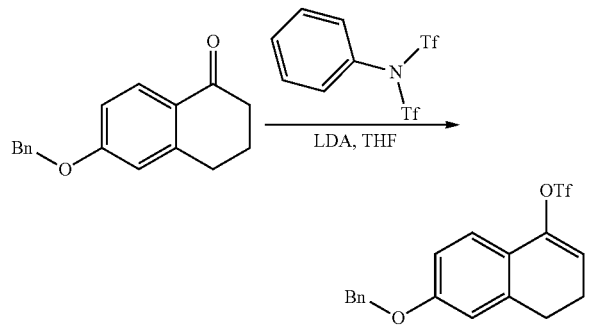

To a solution of 6-benzyloxytetralin-1-one (80 g, 317.07 mmol, 1.00 eq) in tetrahydrofuran (1000 mL) was added lithium diiso-propylamide (2 M, 237.8 mL, 1.50 eq) at −70° C. The mixture was stirred at −70° C. for 1 hour, then 1,1,1-trifluoro-N-phenyl-N-(trifluoromethylsulfonyl)methanesulfonamide (124.6 g, 348.78 mmol, 1.10 eq) in tetrahydrofuran (300 mL) was added dropwise to the mixture. The reaction mixture was stirred at 20° C. for 1 hour. TLC (petroleum ether:ethyl acetate=10:1) showed most of the starting material was consumed. Saturated ammonium chloride (600 mL) was added to the mixture, the organic phase was separated. Ethyl acetate (600 mL) was added to the mixture, the resulting mixture was washed with brine (600 mL×2). The combined organic phase was dried over sodium sulfate, filtered and concentrated in vacuum. The residue was purified by flash silica gel chromatography (petroleum ether:ethyl acetate=1:0 to 50:1) to give (6-benzyloxy-3,4-dihydronaphthalen-1-yl) trifluoromethanesulfonate (88 g, 228.95 mmol, 72% yield) as a light yellow solid. $^1$H NMR (400 MHz, CDCl$_3$) δ 7.46-7.33 (m, 5H), 7.27 (d, J=8.4 Hz, 1H), 6.87-6.83 (m, 2H), 5.88 (t, J=4.8 Hz, 1H), 5.09 (s, 2H), 2.85 (t, J=8.0 Hz, 2H), 2.52-2.47 (m, 2H).

Step 3: Preparation of 4-(6-benzyloxy-3,4-dihydronaphthalen-1-yl)phenol

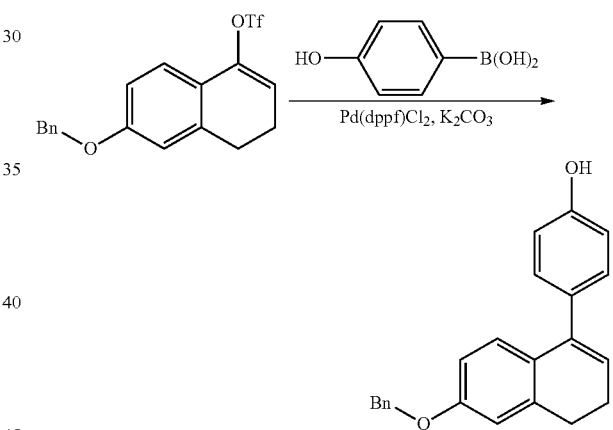

To a solution of (6-benzyloxy-3,4-dihydronaphthalen-1-yl) trifluoromethanesulfonate (80 g, 208.13 mmol, 1.00 eq), (4-hydroxyphenyl)boronic acid (34.45 g, 249.76 mmol, 1.20 eq) in dioxane (700 mL) and water (120 mL) was added potassium carbonate (57.53 g, 416.26 mmol, 2.00 eq) and (1,1'-bis(diphenylphosphino)ferrocene)palladium(II) dichloride (15.23 g, 20.81 mmol, 0.10 eq) under nitrogen. The reaction mixture was stirred at 100° C. for 3 hours. TLC (petroleum ether:ethyl acetate=5:1) showed most of the starting material was consumed. Water (600 mL) was added to the mixture, the resulting mixture was extracted with ethyl acetate (600 mL×3). The combined organic phase was washed with brine (800 mL×2), dried over sodium sulfate, filtered and concentrated in vacuum. The residue was purified by silica gel chromatography (petroleum ether:ethyl acetate=50:1 to 5:1) to give 4-(6-benzyloxy-3,4-dihydronaphthalen-1-yl)phenol (60 g, 182.70 mmol, 88% yield) as a red solid. $^1$H NMR (400 MHz, CDCl$_3$) δ 7.47-7.36 (m, 6H), 7.24-7.22 (m, 2H), 6.97 (t, J=8.8 Hz, 1H), 6.88-6.24 (m, 3H), 6.73 (dd, J=8.4, 2.8 Hz, 1H), 5.93 (t, J=4.8 Hz, 1H), 5.08 (s, 2H), 2.83 (t, J=8.0 Hz, 2H), 2.41-2.36 (m, 2H).

Step 4: Preparation of [4-(6-benzyloxy-3,4-dihydronaphthalen-1-yl)phenyl] acetate

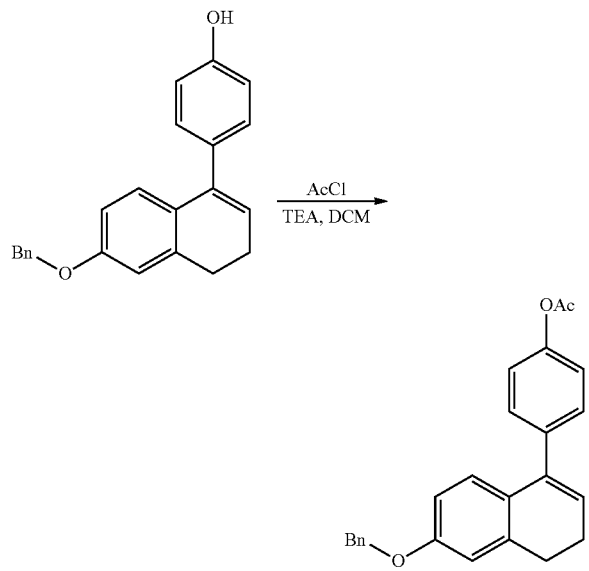

To a solution of 4-(6-benzyloxy-3,4-dihydronaphthalen-1-yl)phenol (60 g, 182.70 mmol, 1.00 eq), triethylamine (46.22 g, 456.76 mmol, 63.3 mL, 2.50 eq) in dichloromethane (400 mL) was added dropwise acetyl chloride (21.51 g, 274.06 mmol, 19.6 mL, 1.50 eq) at 0° C. The reaction mixture was stirred at 20° C. for 1 hour. TLC (petroleum ether:ethyl acetate=5:1) showed most of the starting material was consumed. Water (300 mL) was added to the mixture, the organic phase was separated. The organic phase was washed with brine (200 mL×2), dried over sodium sulfate, filtered and concentrated in vacuum to give [4-(6-benzyloxy-3,4-dihydronaphthalen-1-yl)phenyl] acetate (66 g, crude) as a yellow solid. $^1$H NMR (400 MHz, CDCl$_3$) δ 7.46-7.32 (m, 7H), 7.10 (d, J=8.4 Hz, 2H), 6.96 (d, J=8.4 Hz, 1H), 6.87 (d, J=2.4 Hz, 1H), 6.73 (dd, J=2.4, 8.4 Hz, 1H), 5.97 (t, J=4.4 Hz, 1H), 5.08 (s, 2H), 2.83 (t, J=8.0 Hz, 2H), 2.42-2.37 (m, 2H), 2.34 (s, 3H).

Step 5: Preparation of [4-(6-benzyloxy-2-bromo-3,4-dihydronaphthalen-1-yl)phenyl]acetate

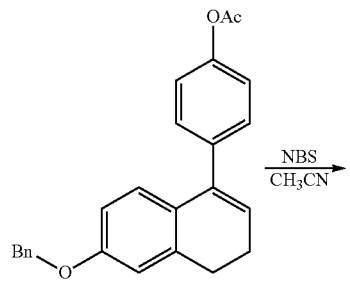

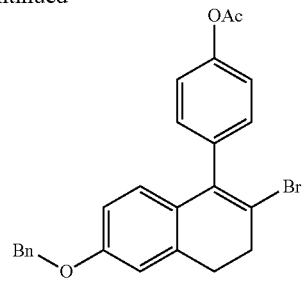

To a solution of [4-(6-benzyloxy-3,4-dihydronaphthalen-1-yl)phenyl] acetate (44 g, 118.78 mmol, 1.00 eq) in acetonitrile (880 mL) was added N-bromosuccinimide (22.20 g, 124.72 mmol, 1.05 eq) in three portions. The reaction mixture was stirred at 20° C. for 2 hours. LC/MS showed most of the starting material was consumed. Saturated sodium bicarbonate (500 mL) was added to the mixture, the resulting mixture was extracted with ethyl acetate (500 mL×3). The combined organic phase was washed with brine (800 mL×2), dried over sodium sulfate, filtered and concentrated in vacuum. The residue was purified by silica gel chromatography (petroleum ether:ethyl acetate=100:1 to 40:1) to give [4-(6-benzyloxy-2-bromo-3,4-dihydronaphthalen-1-yl)phenyl] acetate (33 g, 73.44 mmol, 61.83% yield) as a light yellow solid. LC/MS (ESI) m/z: 449.0, 451.0 [M, M+2]$^+$. $^1$H NMR (400 MHz, CDCl$_3$) 7.33-7.23 (m, 5H), 7.15 (d, J=8.4 Hz, 2H), 7.07 (d, J=8.4 Hz, 2H), 6.71 (s, 1H), 6.55-6.48 (m, 2H), 4.94 (s, 2H), 2.93-2.83 (m, 4H), 2.24 (s, 3H).

Step 6: Preparation of [4-(6-benzyloxy-2-phenyl-3,4-dihydronaphthalen-1-yl)phenyl]acetate

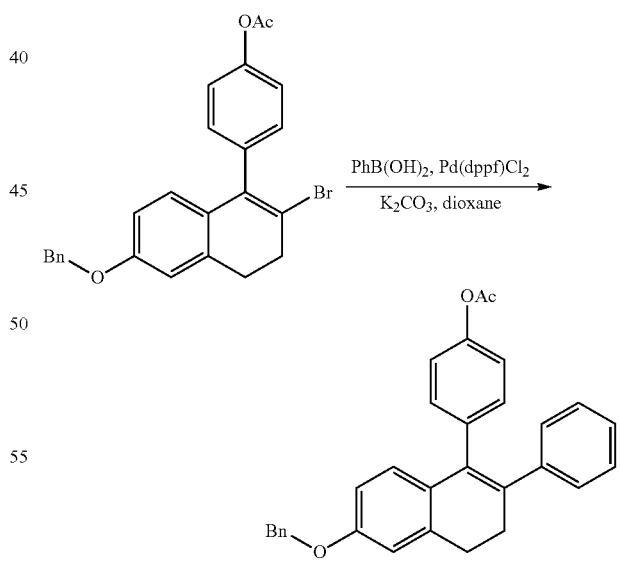

To a solution of [4-(6-benzyloxy-2-bromo-3,4-dihydronaphthalen-1-yl)phenyl]acetate (48 g, 106.82 mmol, 1.00 eq), phenylboronic acid (13.68 g, 112.16 mmol, 1.05 eq) in dioxane (400 mL) and water (60 mL) was added potassium carbonate (29.53 g, 213.64 mmol, 2.00 eq) and (1,1'-bis(diphenylphosphino)ferrocene)palladium(I) dichloride (7.82 g, 10.68 mmol, 0.10 eq) under nitrogen. The reaction

1019 mixture was stirred at 100° C. for 3 hours. TLC (petroleum ether:ethyl acetate=5:1) and LC/MS showed most of the starting material was consumed. Water (400 mL) was added to the mixture, the resulting mixture was extracted with ethyl acetate (300 mL×3). The combined organic phase was washed with brine (500 mL×2), dried over sodium sulfate, filtered and concentrated in vacuum. The residue was purified by trituration with methanol (200 mL). The filter cake was purified by silica gel chromatography (petroleum ether:ethyl acetate=100:1 to 5:1) to give [4-(6-benzyloxy-2-phenyl-3,4-dihydronaphthalen-1-yl)phenyl] acetate (43 g, 96.30 mmol, 90% yield) as a light yellow solid. LC/MS (ESI) m/z: 447.2 [M+1]$^+$. $^1$H NMR (400 MHz, CDCl$_3$) 7.47-7.32 (m, 5H), 7.15-7.04 (m, 5H), 7.03-6.96 (m, 4H), 6.88 (d, J=2.4 Hz, 1H), 6.75 (d, J=8.4 Hz, 1H), 6.69 (dd, J=2.4, 8.4 Hz, 1H), 5.09 (s, 2H), 2.99-2.95 (m, 2H), 2.83-2.79 (m, 2H), 2.30 (s, 3H).

Step 7: Preparation of [4-[(1,2-cis)-6-hydroxy-2-phenyl-tetralin-1-yl]phenyl] acetate

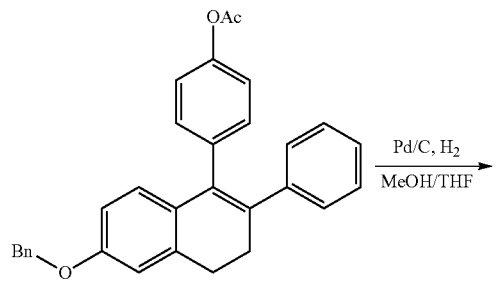

To a solution of [4-(6-benzyloxy-2-phenyl-3,4-dihydronaphthalen-1-yl)phenyl]acetate (17 g, 38.07 mmol, 1.00 eq) in methanol (350 mL) and tetrahydrofuran (70 mL) was added palladium/carbon (2 g, 10%) under nitrogen. The reaction mixture was stirred at 20° C. under hydrogen (50 psi) for 24 hours. TLC (petroleum ether:ethyl acetate=3:1) and LC/MS showed most of the starting material was consumed. The residue was purified by silica gel chromatography (petroleum ether:dichloromethane=10:1 to 0:1) to give [4-[(1,2-cis)-6-hydroxy-2-phenyl-tetralin-1-yl]phenyl] acetate (9.5 g, 26.50 mmol, 70% yield) as a white solid and also extra 4.5 g of crude product. LC/MS (ESI) m/z: 381.0 [M+23]$^+$; $^1$H NMR (400 MHz, CDCl$_3$) δ 7.20-7.15 (m, 3H), 6.83-6.80 (m, 3H), 6.74-6.70 (m, 3H), 6.58 (dd, J=2.4, 8.4 Hz, 1H), 6.43-6.40 (m, 2H), 4.94 (s, 1H), 4.29 (d, J=5.2 Hz, 1H), 3.52-3.37 (m, 1H), 3.11-2.97 (m, 2H), 2.25 (s, 3H), 2.23-2.07 (m, 1H), 1.86-1.81 (m, 1H).

1020

Step 8: Preparation of [4-[(1,2-cis)-6-benzyloxy-2-phenyl-tetralin-1-yl]phenyl]acetate

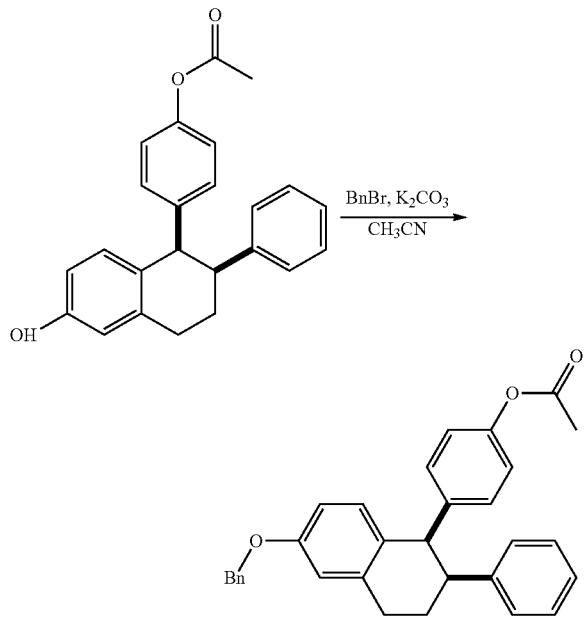

To a solution of [4-[(1,2-cis)-6-hydroxy-2-phenyl-tetralin-1-yl]phenyl] acetate (9.5 g, 26.50 mmol, 1.00 eq) in acetonitrile (100 mL) was added potassium carbonate (7.33 g, 53.01 mmol, 2.00 eq) and benzyl bromide (6.8 g, 39.76 mmol, 4.7 mL, 1.50 eq). The reaction mixture was stirred at 50° C. for 16 hours. TLC (petroleum ether:dichloromethane=2:1) showed most of the starting material was consumed. Water (200 mL) was added to the mixture, the resulting mixture was extracted with ethyl acetate (100 mL×3). The combined organic phase was washed with brine (200 mL), dried over sodium sulfate, filtered and concentrated in vacuum. The residue was purified by silica gel chromatography (petroleum ether:dichloromethane=50:1 to 2:1) to give [4-[(1,2-cis)-6-benzyloxy-2-phenyl-tetralin-1-yl]phenyl]acetate (11 g, 24.52 mmol, 92% yield) as a white solid. $^1$H NMR (400 MHz, CDCl$_3$) δ: 7.48-7.32 (m, 5H), 7.20-7.13 (m, 3H), 6.89-6.86 (m, 2H), 6.84-6.75 (m, 3H), 6.73-6.69 (m, 2H), 6.42-6.40 (m, 2H), 5.07 (s, 2H), 4.30 (d, J=5.2 Hz, 1H), 3.42-3.38 (m, 1H), 3.14-3.01 (m, 2H), 2.24 (s, 3H), 2.22-2.13 (m, 1H), 1.86-1.82 (m, 1H).

Step 9: Preparation of 4-[(1,2)-cis-(6-benzyloxy-2-phenyl-tetralin-1-yl)]phenol

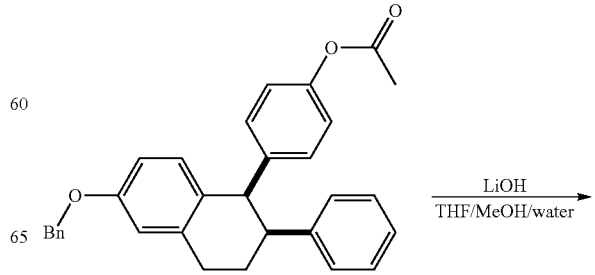

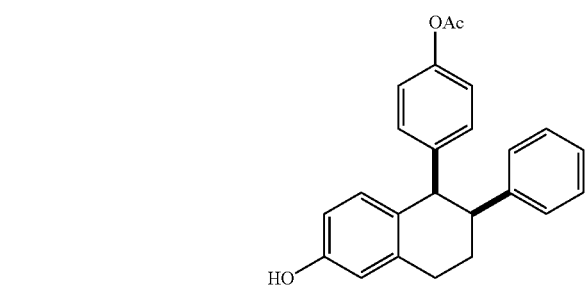

-continued

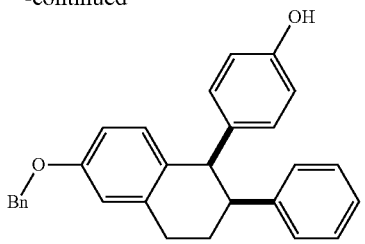

To a solution containing [4-(1,2)-cis-(6-benzyloxy-2-phenyl-tetralin-1-yl)phenyl]acetate (11 g, 24.52 mmol, 1.00 eq) in tetrahydrofuran (30 mL), water (15 mL) and methanol (15 mL) was added lithium hydroxide (5.15 g, 122.62 mmol, 5.00 eq). The reaction mixture was stirred at 20° C. for 1 hour. TLC (petroleum ether:ethyl acetate=3:1) showed most of the starting material was consumed. Hydrochloric acid (2M, 80 mL) and water (50 mL) was added to the mixture to adjust pH ~7, the resulting mixture was extracted with ethyl acetate (100 mL×3). The combined organic phase was washed with brine (150 mL), dried over sodium sulfate, filtered and concentrated in vacuum. The residue was purified by silica gel chromatography (petroleum ether:dichloromethane=10:1 to 0:1) to give 4-[(1,2)-cis-(6-benzyloxy-2-phenyl-tetralin-1-yl)]phenol (9.2 g, 22.63 mmol, 92% yield) as a white solid. $^1$H NMR (400 MHz, CDCl$_3$) δ 7.48-7.33 (m, 5H), 7.21-7.14 (m, 3H), 6.90-6.76 (m, 5H), 6.47 (d, J=5.2 Hz, 1H), 6.30 (d, J=5.2 Hz, 1H), 6.42-6.40 (m, 2H), 5.07 (s, 2H), 4.54 (s, 1H), 4.30 (d, J=5.2 Hz, 1H), 3.42-3.38 (m, 1H), 3.14-3.01 (m, 2H), 2.22-2.13 (m, 1H), 1.86-1.82 (m, 1H).

Step 10: Preparation of (1,2)-cis-6-(benzyloxy)-1-(4-((5-bromopentyl)oxy)phenyl)-2-phenyl-1,2,3,4-tetrahydronaphthalene

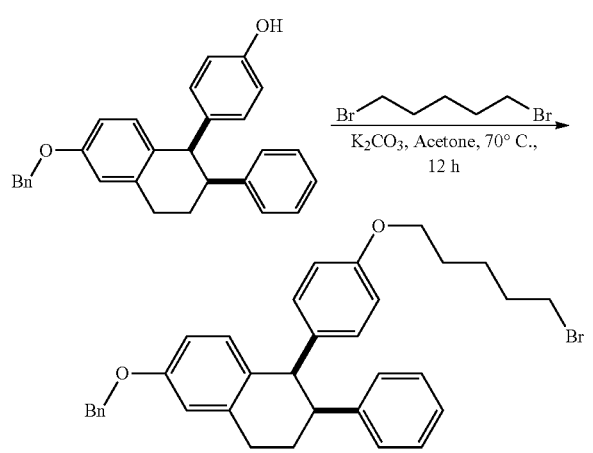

To a solution of 4-(6-benzyloxy-2-phenyl-tetralin-1-yl) phenol (600 mg, 1.48 mmol, 1.00 eq) in acetone (10 mL) was added potassium carbonate (612 mg, 4.43 mmol, 3.00 eq) and 1,5-dibromopentane (1 g, 4.43 mmol, 0.6 mL, 3.00 eq). The mixture was stirred at 70° C. for 12 hours. LC/MS showed the reaction was completed and the desired product was formed. The reaction mixture was diluted with water (30 mL) and extracted with ethyl acetate (20 mL×2). The combined organic phase was washed with brine (10 mL×2), dried with anhydrous sodium sulfate, filtered and concentrated in vacuum. The residue was purified by column chromatography (petroleum ether:ethyl acetate=1:0 to 20:1) to give (1,2)-cis-6-benzyloxy-1-[4-(5-bromopentoxy)phenyl]-2-phenyl-tetralin (620 mg, 1.12 mmol, 75% yield) as a colorless oil. LC/MS (ESI) m/z: 555.2 [M+1]$^+$; $^1$H NMR (400 MHz, DMSO-d$_6$) δ 7.49-7.45 (m, 2H), 7.44-7.39 (m, 2H), 7.37-7.31 (m, 1H), 7.21-7.14 (m, 3H), 6.91-6.85 (m, 2H), 6.82 (dd, J=2.0, 7.2 Hz, 2H), 6.79-6.74 (m, 1H), 6.56-6.50 (m, 2H), 6.33 (d, J=8.4 Hz, 2H), 5.08 (s, 2H), 4.25 (d, J=5.2 Hz, 1H), 3.85 (t, J=6.4 Hz, 2H), 3.43 (t, J=6.4 Hz, 2H), 3.40-3.33 (m, 1H), 3.18-2.98 (m, 2H), 2.28-2.13 (m, 1H), 1.92 (q, J=7.2 Hz, 2H), 1.87-1.80 (m, 1H), 1.80-1.71 (m, 2H), 1.64-1.56 (m, 2H)

Step 11: Preparation of (1R,2S)-6-hydroxy-1-(4-((5-bromopentyl)oxy)phenyl)-2-phenyl-1,2,3,4-tetrahydronaphthalene

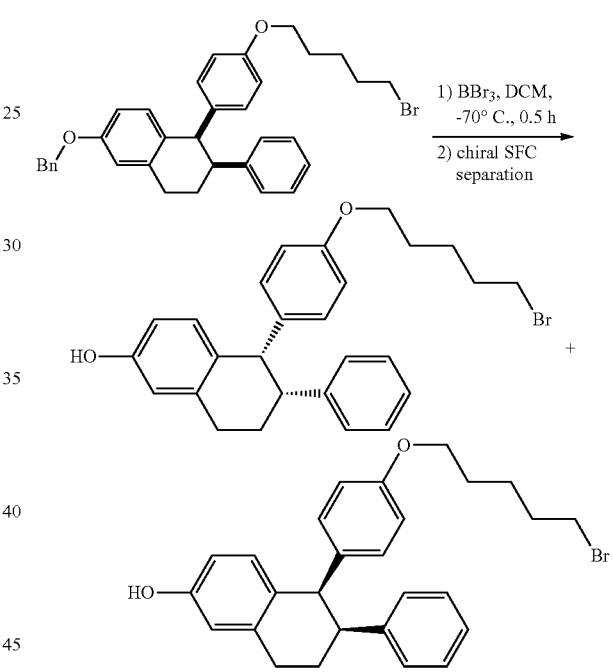

To a solution of (1,2)-cis-6-benzyloxy-1-[4-(5-bromopentoxy)phenyl]-2-phenyl-tetralin (620 mg, 1.12 mmol, 1.00 eq) in dichloromethane (15 mL) was added boron tribromide (1.7 g, 6.72 mmol, 0.65 mL, 6.00 eq) at −70° C. The mixture was stirred at −70° C. for 1 hour. TLC (petroleum ether:ethyl acetate=3:1) showed most of the starting material was consumed and a new spot formed. The reaction mixture was quenched by saturated sodium bicarbonate (5 mL) at −70° C., and then diluted with water (8 mL) and extracted with dichloromethane (5 mL×2). The combined organic phase was washed with saturated brine (5 mL×2), dried with anhydrous sodium sulfate, filtered and concentrated in vacuum. The residue was purified by preparative TLC (petroleum ether:ethyl acetate=3:1) to give desired compound (240 mg, yield 46%, purity 90%) as a white solid, which was further separated by chiral SFC (column: OJ 250 mm×30 mm, 10 um; mobile phase: 0.1% ammonium hydroxide in methanol; B %: 40%-40%, 2.4 min) to give first fraction (1 S,2R)-1-[4-(5-bromopentoxy)phenyl]-2-phenyl-tetralin-6-ol (100 mg, 0.21 mmol, 38% yield) as a white solid and the later fraction (1R,2S)-6-(benzyloxy)-1-(4-((5-bromopentyl)oxy)phenyl)-2-phenyl-1,2,3,4-tetrahydronaphthalene (100 mg, 0.21 mmol, 38% yield) as a white solid.

Step 12: Preparation of tert-butyl 4-(1-oxo-3H-isobenzofuran-5-yl)piperazine-1-carboxylate

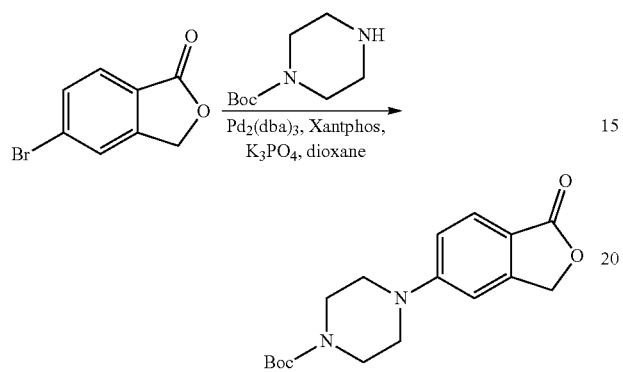

To a solution of 5-bromo-3H-isobenzofuran-1-one (45 g, 211.24 mmol, 1.00 eq) and tert-butyl piperazine-1-carboxylate (39.34 g, 211.24 mmol, 1.00 eq) in dioxane (500 mL) was added tris(dibenzylideneacetone)dipalladium(0) (19.34 g, 21.12 mmol, 0.10 eq), 4,5-bis (diphenylphosphino)-9,9-dimethylxanthene (12.22 g, 21.12 mmol, 0.10 eq) and potassium phosphate (89.68 g, 422.48 mmol, 2.00 eq). The mixture was heated to 100° C. for 16 hours under nitrogen protection. TLC (ethyl acetate: petroleum ether=1:2) showed reaction was complete. The mixture was filtered through a pad of Celite and the filtrate was concentrated in vacuum. The residue was triturated in ethyl acetate: petroleum ether (500 mL, v/v=1:2) to provide tert-butyl 4-(1-oxo-3H-isobenzofuran-5-yl)piperazine-1-carboxylate (50 g, 122.5 mmol, 58% yield, 78% purity) as yellow solid. $^1$H NMR (400 MHz, DMSO) δ 7.62 (d, J=8.8 Hz, 1H), 7.10 (dd, J=8.8 Hz, 2 Hz, 1H), 7.04 (s, 1H), 5.25 (s, 2H), 3.47-3.45 (m, 4H), 3.45-3.38 (m, 4H), 1.42 (s, 9H).

Step 13: Preparation of 4-(4-tert-butoxycarbonylpiperazin-1-yl)-2-(hydroxylmethyl)benzoic acid

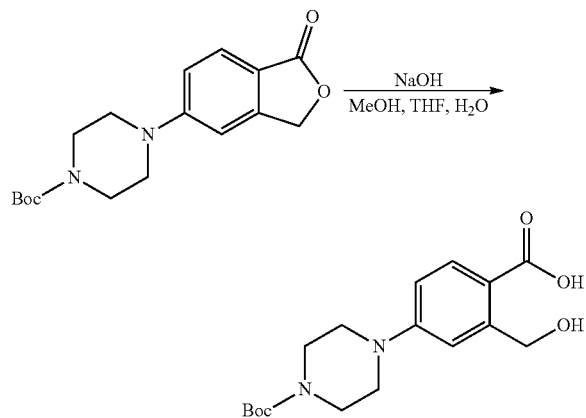

To a mixture of tert-butyl 4-(1-oxo-3H-isobenzofuran-5-yl)piperazine-1-carboxylate (47.8 g, 150.14 mmol, 1.00 eq) in tetrahydrofuran (150 mL), methanol (150 mL) and water (150 mL) was added sodium hydroxide (24 g, 600 mmol, 4.00 eq). The mixture was stirred at 25° C. for 1 hour. TLC (ethyl acetate: petroleum ether=1:2) showed reaction was complete. The solution was adjusted to pH=4-5 with aqueous hydrochloride solution (1M) and extracted with ethyl acetate (100 mL×5). The organic layers were concentrated in vacuum. The crude material was triturated in ethyl acetate: petroleum ether (450 mL, v: v=1:2) to provide 4-(4-tert-butoxycarbonyl piperazin-1-yl)-2-(hydroxymethyl)benzoic acid (40 g, 118.91 mmol, 79% yield) as yellow solid. $^1$H NMR (400 MHz, DMSO) δ 12.36 (s, 1H), 7.78 (d, J=8.8 Hz, 1H), 7.22 (d, J=2 Hz, 1H), 6.81 (dd, J=8.8, 1 Hz), 5.10 (s, 1H), 4.80 (s, 2H), 3.47-3.44 (m, 4H), 3.29-3.27 (m, 4H), 1.42 (s, 9H).

Step 14: Preparation of tert-butyl 4-[3-(hydroxymethyl)-4-methoxy carbonyl-phenyl]piperazine-1-carboxylate

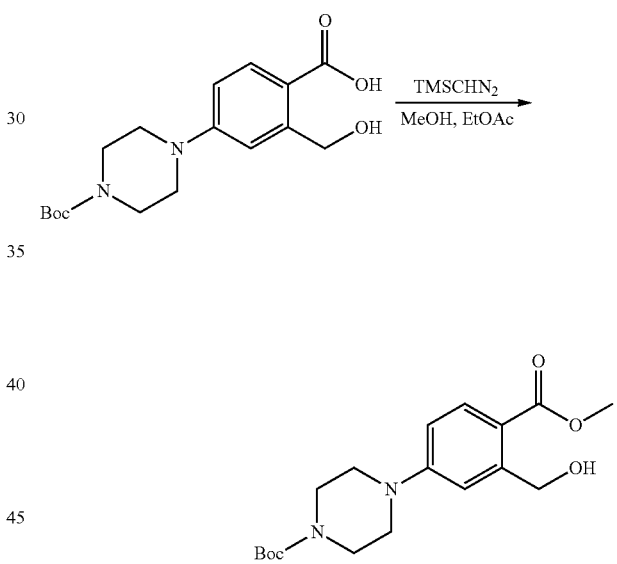

To a solution of 4-(4-tert-butoxycarbonylpiperazin-1-yl)-2-(hydroxymethyl)benzoic acid (20 g, 59.46 mmol, 1.00 eq) in methanol (100 mL) and ethyl acetate (100 mL) was added imino(trimethylsilylmethylene)ammonium (2 M, 89 mL, 3.00 eq) at -10 OC. The solution was stirred at -10° C. for 0.25 hour. TLC (ethyl acetate: petroleum ether=1:2) showed reaction was complete. The solution was quenched with water (300 mL) and extracted with ethyl acetate (150 mL×3). The organic layer was dried over sodium sulfate and filtered. The filtrate was concentrated to provide tert-butyl 4-[3-(hydroxymethyl)-4-methoxycarbonyl-phenyl]piperazine-1- carboxylate (20.84 g, crude) was obtained as brown oil.

Step 15: Preparation of tert-butyl 4-[3-(bromomethyl)-4-methoxycarbonyl-phenyl]piperazine-1-carboxylate

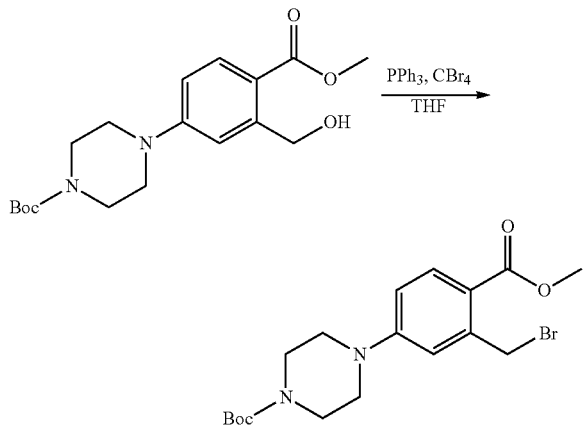

To a solution of tert-butyl 4-[3-(hydroxymethyl)-4-methoxycarbonyl-phenyl]piperazine-1-carboxylate (20.84 g, 59.47 mmol, 1.00 eq) in tetrahydrofuran (200 mL) was added triphenylphosphine (23.4 g, 89.21 mmol, 1.50 eq) and perbromomethane (29.58 g, 89.21 mmol, 1.50 eq). The solution was stirred at 25° C. for 1 hour. TLC (ethyl acetate: petroleum ether=1:3) showed reaction was complete. The solution was quenched with water (200 mL) and extracted with ethyl acetate (100 mL×2). The organic layer was dried over sodium sulfate and filtered. The filtrate was concentrated in vacuum. The residue was purified by silica gel column chromatography (ethyl acetate: petroleum ether=1:50-1:8) to provide tert-butyl 4-[3-(bromomethyl)-4-methoxycarbonyl-phenyl]piperazine-1-carboxylate (12 g, 29.03 mmol, 49% yield) as a pale-yellow oil. $^1$H NMR (300 MHz, CDCl$_3$) δ 7.93 (s, J=9.0 Hz, 1H), 6.88 (d, =2.4 Hz, 1H), 6.78 (dd, J=9.0, 2.4 Hz, 1H), 4.97 (s, 2H), 3.89 (s, 3H), 3.64-3.57 (m, 4H), 3.34-3.30 (m, 4H), 1.42 (s, 9H).

Step 16: Preparation of tert-butyl 4-[2-(2,6-dioxo-3-piperidyl)-1-oxo-isoindolin-5-yl]piperazine-1-carboxylate

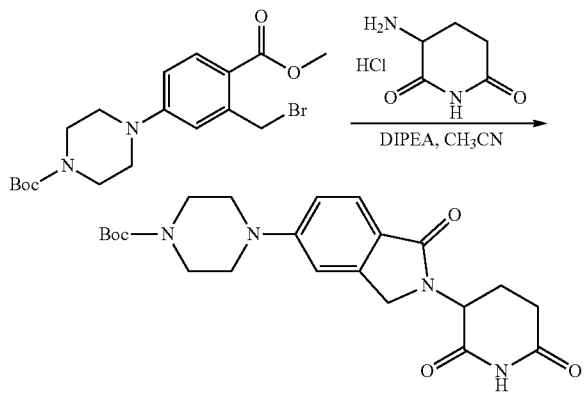

To a solution of tert-butyl 4-[3-(bromomethyl)-4-methoxycarbonyl-phenyl]piperazine-1-carboxylate (12 g, 29.03 mmol, 1.00 eq) in acetonitrile (300 mL) was added 3-aminopiperidine-2,6-dione hydrochloride (7.17 g, 43.55 mmol, 1.50 eq) and N-ethyl-N-isopropylpropan-2-amine (11.26 g, 87.09 mmol, 15 mL, 3.00 eq). The solution was stirred at 80° C. for 16 hours. LC/MS showed reaction was complete. The reaction mixture was cooled to 20° C. and filtered. The solid was washed with acetonitrile (30 mL) to provide tert-butyl 4-[2-(2,6-dioxo-3-piperidyl)-1-oxo-isoindolin-5-yl]piperazine-1-carboxylate (6 g, 14 mmol, 48% yield) as a white solid. $^1$H NMR (400 MHz, DMSO) δ 10.91 (s, 1H), 7.53 (d, J=8.4 Hz, 1H), 7.06-7.04 (m, 2H), 5.03 (dd, 1-13.2, 5.2 Hz, 1H), 4.35-4.19 (m, 2H), 3.48-3.45 (m, 4H), 3.27-3.26 (m, 4H), 2.89-2.87 (m, 1H), 2.60-2.56 (m, 1H), 2.38-2.34 (m, 1H), 1.98-1.96 (m, 1H), 1.42 (s, 9H).

Step 17: Preparation of 3-(1-oxo-5-piperazin-1-yl-isoindolin-2-yl) piperidine-2,6-dione hydrochloride

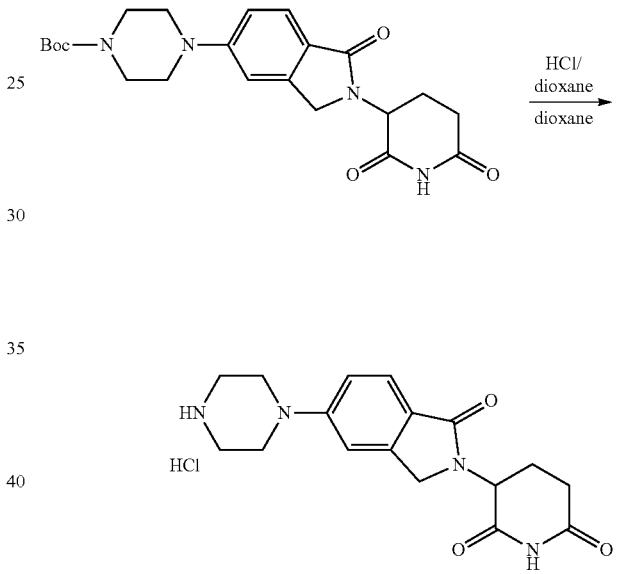

To a mixture of tert-butyl 4-[2-(2,6-dioxo-3-piperidyl)-1-oxo-isoindolin-5-yl]piperazine-1-carboxylate (6 g, 14 mmol, 1.00 eq) in dioxane (70 mL) was added hydrochloride/dioxane (4 M, 100 mL, 28.57 eq). The mixture was stirred at 25° C. for 2 hours. LC/MS showed reaction was complete. The mixture was poured into ethyl acetate (400 mL) and stirred for 30 minutes. The suspension was filtered and solid was collected to provide 3-(1-oxo-5-piperazin-1-yl-isoindolin-2-yl) piperidine-2,6-dione hydrochloride (5 g, 13.71 mmol, 98% yield) as a white solid. $^1$H-NMR (400 MHz, DMSO) δ: 10.95 (s, 1H), 9.49 (s, 2H), 7.57 (d, J=8.4 Hz, 1H), 7.15-7.10 (m, 2H), 5.05 (dd, J=13.2, 5.2 Hz, 1H), 4.37-4.20 (m, 2H), 3.55-3.53 (m, 4H), 3.20-3.19 (m, 4H), 2.90-2.86 (m, 1H), 2.60-2.56 (m, 1H), 2.38-2.34 (m, 1H), 1.98-1.96 (m, 1H).

Step 18: Preparation of 3-(5-[4-(5-{4-[(1R,2S)-6-hydroxy-2-phenyl-1,2,3,4-tetrahydronaphthalen-1-yl]phenoxy}pentyl)piperazin-1-yl]-1-oxo-2,3-dihydro-1H-isoindol-2-yl)piperidine-2,6-dione
(Exemplary Compound 62)

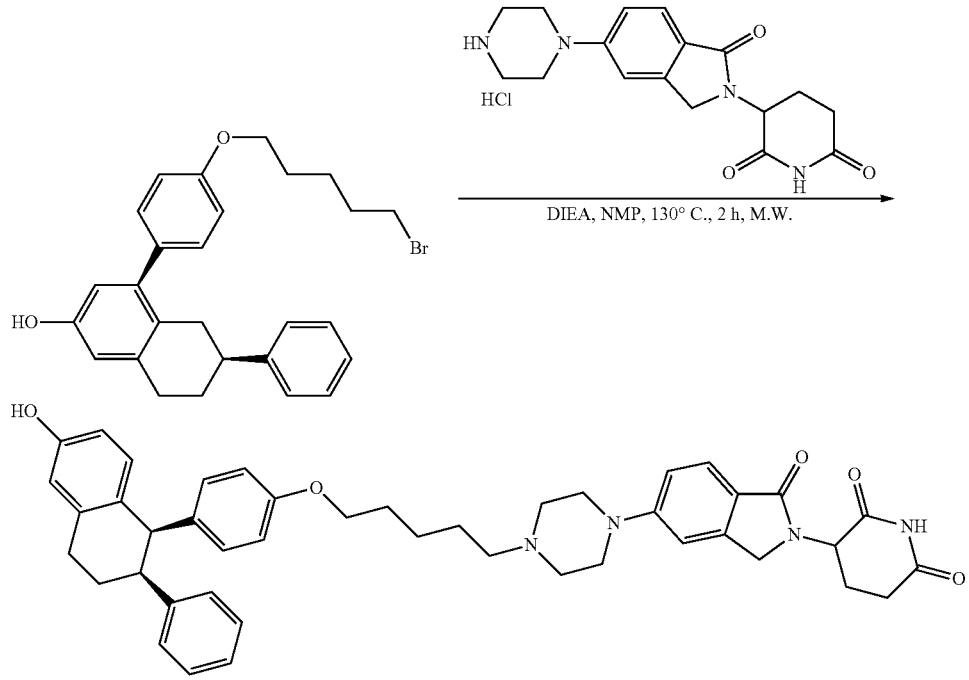

(1R,2S)-1-[4-(5-bromopentoxy)phenyl]-2-phenyl-tetralin-6-ol (50 mg, 0.11 mmol, 1.00 eq), 3-(1-oxo-5-piperazin-1-yl-isoindolin-2-yl)piperidine-2,6-dione hydrochloride (47 mg, 0.13 mmol, 1.20 eq) and diisopropylethylamine (70 mg, 0.53 mmol, 0.1 mL, 5.00 eq) were taken up into a microwave tube in N-methyl-2-pyrrolidinone (3 mL). The sealed tube was heated at 140° C. for 2 hours under microwave. LC/MS showed the reaction was completed and desired product was formed. The reaction mixture was diluted with water (15 mL) and extracted with ethyl acetate (5 mL×2). The combined organic phase was washed with saturated brine (5 mL×2), dried with anhydrous sodium sulfate, filtered and concentrated in vacuum. The residue was purified by preparative TLC (dichloromethane:methanol=10:1) to give 3-{5-[4-(5-(4-[(1R,2S)-6-hydroxy-2-phenyl-1,2,3,4-tetrahydronaphthalen-1-yl]phenoxy) pentyl)piperazin-1-yl]-1-oxo-2,3-dihydro-1H-isoindol-2-yl}piperidine-2,6-dione (16.9 mg, 0.02 mmol, 22% yield, 99.9% purity) as a white solid. This solid was converted to a hydrochloride salt. LC/MS (ESI) m/z: 713.3 [M+1]$^+$; $^1$H-NMR (400 MHz, DMSO-$d_6$) δ: 10.96 (s, 1H), 10.69 (s, 1H), 9.16 (s, 1H), 7.58 (d, J=8.4 Hz, 1H), 7.23-7.08 (m, 5H), 6.83 (d, J=6.4 Hz, 2H), 6.67-6.59 (m, 2H), 6.57-6.45 (m, 3H), 6.27 (d, =8.8 Hz, 2H), 5.06 (dd, J=5.2, 13.2 Hz, 1H), 4.40-4.31 (m, 1H), 4.28-4.14 (m, 2H), 3.99 (d, J=13.2 Hz, 2H), 3.83 (t, J=6.4 Hz, 2H), 3.58-3.51 (m, 2H), 3.34-3.21 (m, 3H), 3.16-3.04 (m, 4H), 3.03-2.84 (m, 3H), 2.62-2.56 (m, 1H), 2.44-2.35 (m, 1H), 2.16-2.02 (m, 1H), 2.01-1.92 (m, 1H), 1.83-1.63 (m, 5H), 1.46-1.35 (m, 2H).

Synthesis of 2-(2,6-dioxopiperidin-3-yl)-5-(4-(5-(4-((1R,2S)-6-hydroxy-2-phenyl-1,2,3,4-tetrahydronaphthalen-1-yl)phenoxy)pentyl)piperazin-1-yl)isoindoline-1,3-dione (Exemplary Compound 69)

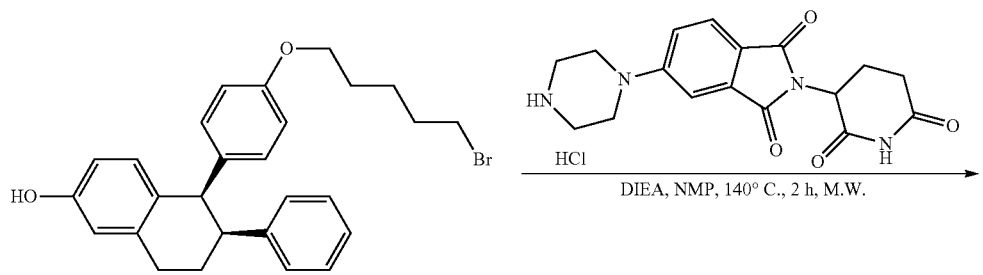

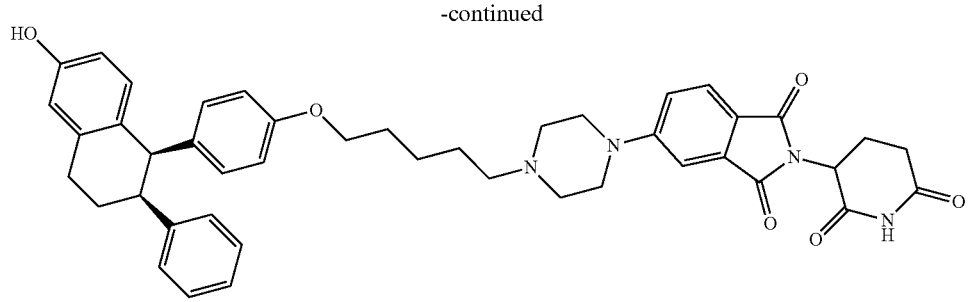

(1R,2S)-1-[4-(5-bromopentoxy)phenyl]-2-phenyl-tetralin-6-ol (50 mg, 0.11 mmol, 1.00 eq, prepared in step 11, Exemplary Compound 62), 2-(2,6-dioxo-3-piperidyl)-5-piperazin-1-yl-isoindoline-1,3-dione (49 mg, 0.13 mmol, 1.20 eq, hydrochloride, prepared in step 3, Exemplary Compound 393) and diisopropylethylamine (70 mg, 0.53 mmol, 0.1 mL, 5.00 eq) were taken up into a microwave tube in 1-methyl-2-pyrrolidinone (3 mL). The sealed tube was heated at 140° C. for 2 hours under microwave. LC-MS showed the reaction was completed and desired MS can be detected. The reaction mixture was diluted with water (15 mL) and extracted with ethyl acetate (5 mL×2). The combined organic phase was washed with saturated brine (5 mL×2), dried with anhydrous sodium sulfate, filtered and concentrated in vacuum. The reaction mixture was filtered and purified by prep-HPLC (column: Phenomenex Synergi C18 150×25 mm, 10 micron; mobile phase: [water (0.225% formic acid)-ACN]; B %: 20%-50%, 10 min). The collected fraction was concentrated to remove most of acetonitrile and hydrochloric acid (1 M, 2 mL) was added. The solution was lyophilized to give 2-(2,6-dioxo-3-piperidyl)-5-[4-[5-[4-[(1R,2S)-6-hydroxy-2-phenyl-tetralin-1-yl]phenoxy]pentyl]piperazin-1-yl]isoindoline-1,3-dione (18.10 mg, 0.02 mmol, 22% yield, 98% purity, hydrochloride) as a yellow solid of hydrochloric acid salt. LC-MS (ESI) m/z: 727.3 [M+1]$^+$. $^1$H NMR (400 MHz, DMSO-d$_6$) δ: 11.10 (s, 1H), 10.14 (s, 1H), 9.14 (s, 1H), 7.76 (d, J=8.4 Hz, 1H), 7.48 (s, 1H), 7.35 (d, J=8.4 Hz, 1H), 7.18-7.09 (m, 3H), 6.83 (d, J=6.8 Hz, 2H), 6.66-6.59 (m, 2H), 6.53 (d, J=8.8 Hz, 2H), 6.48 (dd, J=2.4, 8.4 Hz, 1H), 6.27 (d, J=8.8 Hz, 2H), 5.09 (dd, =5.2, 13.2 Hz, 1H), 4.27-4.15 (m, 3H), 3.83 (t, J=6.4 Hz, 2H), 3.61-3.50 (m, 2H), 3.31-3.24 (m, 3H), 3.17-3.05 (m, 4H), 3.03-2.82 (m, 3H), 2.63-2.57 (m, 2H), 2.17-1.97 (m, 2H), 1.80-1.63 (m, 5H), 1.48-1.35 (m, 2H).

Synthesis of 3-[5-[4-[[1-[4-[(1R,2S)-6-hydroxy-2-phenyl-tetralin-1-yl]phenyl]-4-piperidyl]methyl]piperazin-1-yl]-1-oxo-Isoindolin-2-yl]piperidine-2,6-dione (Exemplary Compound 341)

Step 1: Preparation 6-tert-butoxytetralin-1-one

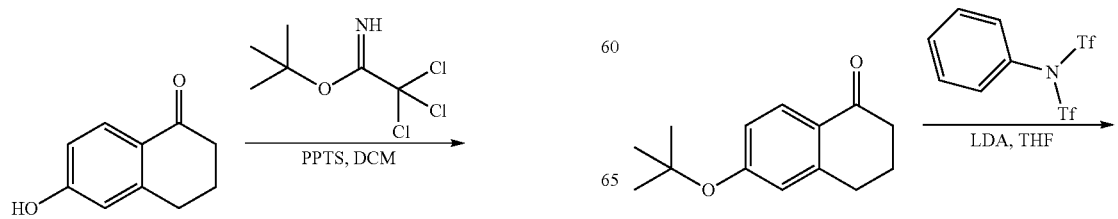

To a stirred solution of 6-hydroxytetralin-1-one (50 g, 308.29 mmol, 1 eq) in anhydrous dichloromethane (2000 mL) at 0° C. was added tert-butyl 2,2,2-trichloroethanimidate (67.36 g, 308.29 mmol, 55 mL, 1 eq) and pyridinium para-toluenesulfonate (7.75 g, 30.83 mmol, 0.1 eq). The reaction mixture was stirred at 10° C. for 3 hours. Additional portion of tert-butyl 2,2,2-trichloroethanimidate (67.36 g, 308.29 mmol, 55 mL, 1 eq) and pyridinium para-toluenesulfonate (7.75 g, 30.83 mmol, 0.1 eq) was added and the reaction mixture was stirred at 10° C. for 15 hours. This process was repeated three times. Thin layer chromatography (petroleum ether:ethyl acetate=3:1, R$_f$=0.8) showed that most of reactant still remained, the reaction mixture was stirred at 10° C. for 72 hours. The reaction mixture was quenched by addition of a solution of sodium hydrogen carbonate (1500 mL) at 15° C., and then extracted with dichloromethane (300 mL×3). The combined organic layers were washed with brine (300 mL×2), dried over anhydrous sodium sulfate, filtered and concentrated under reduced pressure. The residue was purified by silica gel chromatography (petroleum ether:ethyl acetate=100:1 to 50:1) to get 6-tert-butoxytetralin-1-one (21 g, 96.20 mmol, 31% yield) as a yellow oil. $^1$H NMR (400 MHz, CDCl$_3$) δ 7.97 (d, J=8.8 Hz, 1H), 6.91 (dd, J=2.4, 8.8 Hz, 1H), 6.82 (d, J=2.0 Hz, 1H), 2.93-3.90 (t, J=6.0 Hz, 2H), 2.63-2.60 (m, t, J=6.0 Hz, 2H), 2.13 (m, 2H), 1.43 (s, 9H)

Step 2: Preparation of (6-tert-butoxy-3,4-dihydronaphthalen-1-yl) trifluoromethanesulfonate -continued

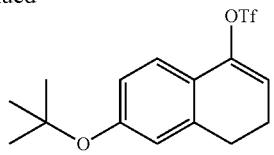

To a solution of 6-tert-butoxytetralin-1-one (40 g, 183.24 mmol, 1 eq) in tetrahydrofuran (500 mL) was added lithium diiso-propylamide (2 M, 137 mL, 1.5 eq) at -70° C. The mixture was stirred at −70° C. for 1 hour, then 1,1,1-trifluoro-N-phenyl-N-(trifluoromethylsulfonyl) methanesulfonamide (72.01 g, 201.56 mmol, 1.1 eq) in tetrahydrofuran (200 mL) was added dropwise to the mixture. The reaction mixture was stirred at 20° C. for 2 hours. Thin layer chromatography (petroleum ether:ethyl acetate=5:1) showed the reaction was completed. Saturated ammonium chloride (300 mL) was added to the mixture, the organic phase was separated. Ethyl acetate (500 mL×3) was added to the mixture, the resulting mixture was washed with brine (1000 mL×2). The combined organic phase was dried over sodium sulfate, filtered and concentrated in vacuum. The residue was purified by silica gel chromatography (petroleum ether:ethyl acetate-1:0 to 50:1) to give (6-tert-butoxy-3,4-dihydronaphthalen-1-yl) trifluoromethanesulfonate (52 g, 144.64 mmol, 78% yield, 97% purity) as a yellow oil. LC-MS (ESI) m/z: 294.9 [M+1-56]$^+$. $^1$H-NMR (400 MHz, CDCl$_3$) δ: 7.30 (d, J=6.4 Hz, 1H), 6.91 (d, J=8.4 Hz, 1H), 6.84 (s, 1H), 5.95 (s, 1H), 2.93-2.78 (m, 2H), 2.59-2.46 (m, 2H), 1.42 (s, 9H).

Step 3: Preparation of 4-(6-tert-butoxy-3,4-dihydronaphthalen-1-yl)phenol

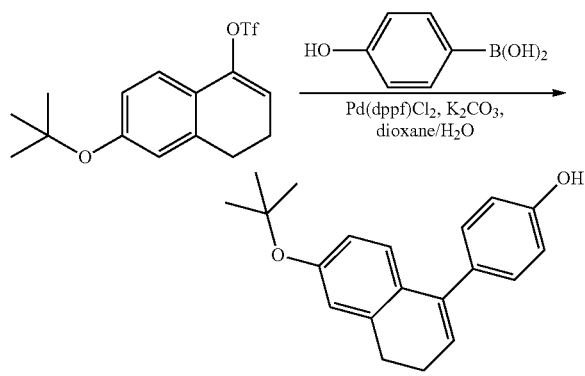

To a solution of (6-tert-butoxy-3,4-dihydronaphthalen-1-yl) trifluoromethanesulfonate (52 g, 148.42 mmol, 1 eq), (4-hydroxyphenyl)boronic acid (24.57 g, 178.11 mmol, 1.2 eq) in dioxane (800 mL) and water (150 mL) was added potassium carbonate (41.03 g, 296.84 mmol, 2 eq) and (1,1'-bis(diphenylphosphino)ferrocene)palladium(II) dichloride (10.86 g, 14.84 mmol, 0.1 eq) under nitrogen. The reaction mixture was stirred at 100° C. for 10 hours. Thin layer chromatography (petroleum ether:ethyl acetate=5:1) showed the reaction was complete. The residue was diluted with water (500 mL) and extracted with ethyl acetate (500 mL×2). The combined organic layers were washed with brine (1000 mL×2), dried with anhydrous sodium sulfate, filtered and concentrated in vacuum. The residue was purified by silica gel chromatography (petroleum ether:tetrahydrofuran=50:1 to 20:1) to give 4-(6-tert-butoxy-3,4-dihydronaphthalen-1-yl)phenol (43 g, 131.46 mmol, 88% yield, 90% purity) as a yellow oil. LCMS (ESI) m/z: 239.1 [M+1-56]; $^1$H-NMR (400 MHz, CDCl$_3$) δ 7.23 (d, J=7.6 Hz, 2H), 6.91 (d, J=8.0 Hz, 1H), 6.87-6.79 (m, 3H), 6.73 (d, J=8.4 Hz, 1H), 5.95 (s, 1H), 4.83-4.75 (m, 1H), 2.87-2.73 (m, 2H), 2.44-2.31 (m, 2H), 1.37 (s, 9H)

Step 4: Preparation of 4-(2-bromo-6-tert-butoxy-3,4-dihydronaphthalen-1-yl)phenol

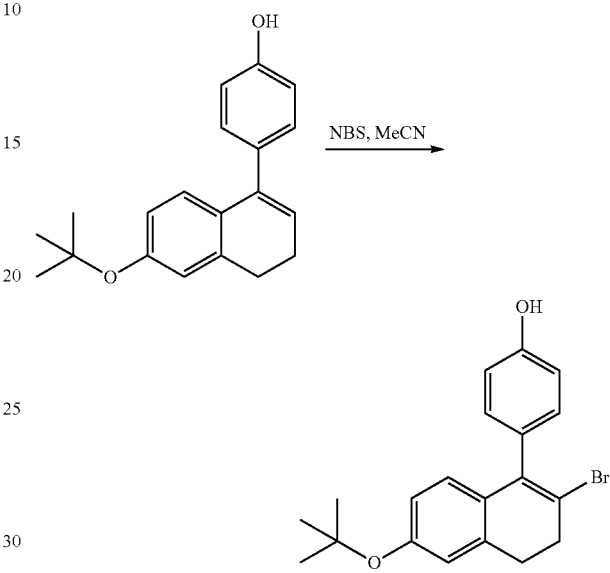

To a solution of 4-(6-tert-butoxy-3,4-dihydronaphthalen-1-yl)phenol (1 g, 3.06 mmol, 1 eq) in acetonitrile (20 mL) was added N-bromosuccinimide (489 mg, 2.75 mmol, 0.9 eq) in three portions. The reaction mixture was stirred at 20° C. for 1.5 hours. LC-MS showed the reaction was completed. The residue was diluted with water (20 mL) and extracted with ethyl acetate (20 mL×2). The combined organic layers were washed with brine (20 mL×2), dried with anhydrous sodium sulfate, filtered and concentrated in vacuum. The residue was purified by silica gel chromatography (petroleum ether:ethyl acetate=1:0 to 20:1) to give 4-(2-bromo-6-tert-butoxy-3,4-dihydronaphthalen-1-yl)phenol (I g, 2.46 mmol, 80% yield, 91% purity) as a yellow oil. LC-MS (ESI) m/z: 316.9 [M+1-56]; $^1$H-NMR (400 MHz, CDCl$_3$) δ 7.12 (d, J=8.4 Hz, 2H), 6.90 (d, J=8.0 Hz, 2H), 6.77 (s, 1H), 6.69-6.62 (m, 1H), 6.60-6.53 (m, 1H), 4.86 (s, 1H), 2.96 (s, 4H), 1.35 (s, 9H).

Step 5: Preparation of 4-(6-tert-butoxy-2-phenyl-3,4-dihydronaphthalen-1-yl)phenol

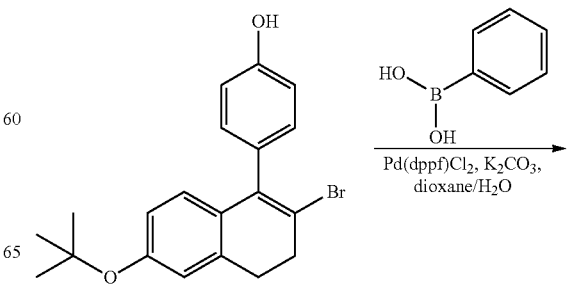

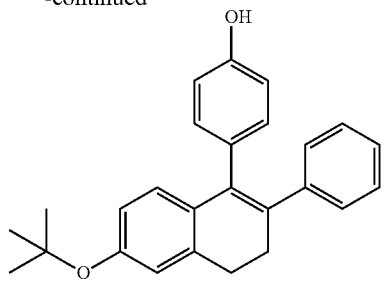

To a solution of 4-(2-bromo-6-tert-butoxy-3,4-dihydronaphthalen-1-yl)phenol (I g, 2.46 mmol, 1 eq), phenylboronic acid (314 mg, 2.58 mmol, 1.05 eq) in dioxane (10 mL) and water (2 mL) was added potassium carbonate (678 mg, 4.91 mmol, 2 eq) and (1,1'-bis(diphenylphosphino)ferrocene)palladium(II) dichloride (179 mg, 0.24 mmol, 0.1 eq) under nitrogen. The reaction mixture was stirred at 100° C. for 12 hours. LC-MS showed the reaction was completed. The residue was diluted with water (20 mL) and extracted with ethyl acetate (20 mL×2). The combined organic layers were washed with brine (20 mL×3), dried with anhydrous sodium sulfate, filtered and concentrated in vacuum. The residue was purified by silica gel chromatography (petroleum ether:ethyl acetate=1:0 to 10:1) to get 4-(6-tert-butoxy-2-phenyl-3,4-dihydronaphthalen-1-yl)phenol (930 mg, 2.35 mmol, 95% yield, 93% purity) as an orange oil. LCMS (ESI) m/z: 314.1 [M+1-56]; $^1$H-NMR (400 MHz, CDCl$_3$) δ 7.16-7.09 (m, 2H), 7.08-6.99 (m, 3H), 6.97-6.89 (m, 2H), 6.86-6.82 (m, 1H), 6.74-6.66 (m, 4H), 4.70 (s, 1H), 2.99-2.89 (m, 2H), 2.84-2.75 (m, 2H), 1.37 (s, 9H)

Step 6: Preparation of 4-(6-tert-butoxy-2-phenyl-tetralin-1-yl)phenol

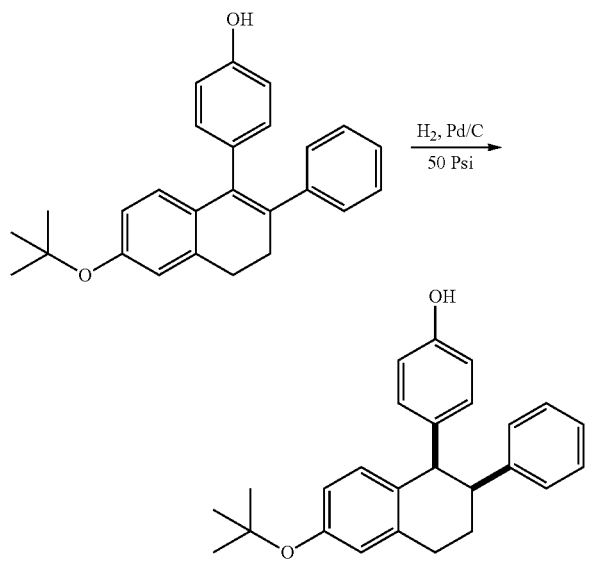

To a solution of 4-(6-tert-butoxy-2-phenyl-3,4-dihydronaphthalen-1-yl)phenol (930 mg, 2.35 mmol, 1 eq) in tetrahydrofuran (20 mL) and methanol (4 mL) was added palladium on activated carbon catalyst (100 mg, 10% purity) under nitrogen. The suspension was degassed under vacuum and purged with hydrogen three times. The mixture was stirred under hydrogen (50 psi) at 30° C. for 36 hours. LC-MS showed the reaction was completed. The reaction mixture was filtered and the solution was concentrated. The resulting material was directly used into the next step without further purification to afford cis-4-(6-tert-butoxy-2-phenyl-tetralin-1-yl)phenol (870 mg, 2.14 mmol, 91% yield, 91% purity) as a white solid. LC-MS (ESI) m/z: 317.0 [M+1-56]$^+$; $^1$H-NMR (400 MHz, CDCl$_3$) δ 7.22-7.12 (m, 3H), 6.89-6.78 (m, 4H), 6.74 (dd, J=2.0, 8.4 Hz, 1H), 6.45 (d, J=8.4 Hz, 2H), 6.27 (d, J=8.4 Hz, 2H), 4.51 (s, 1H), 4.25 (d, J=4.8 Hz, 1H), 3.38 (dd, J=3.2, 12.8 Hz, 1H), 3.08-2.99 (m, 2H), 2.27-2.08 (m, 1H), 1.87-1.76 (m, 1H), 1.37 (s, 9H)

Step 7: Preparation of WX-ARV-HD-012-E1, 4-[(1S,2R)-6-tert-butoxy-2-phenyl-tetralin-1-yl]phenol

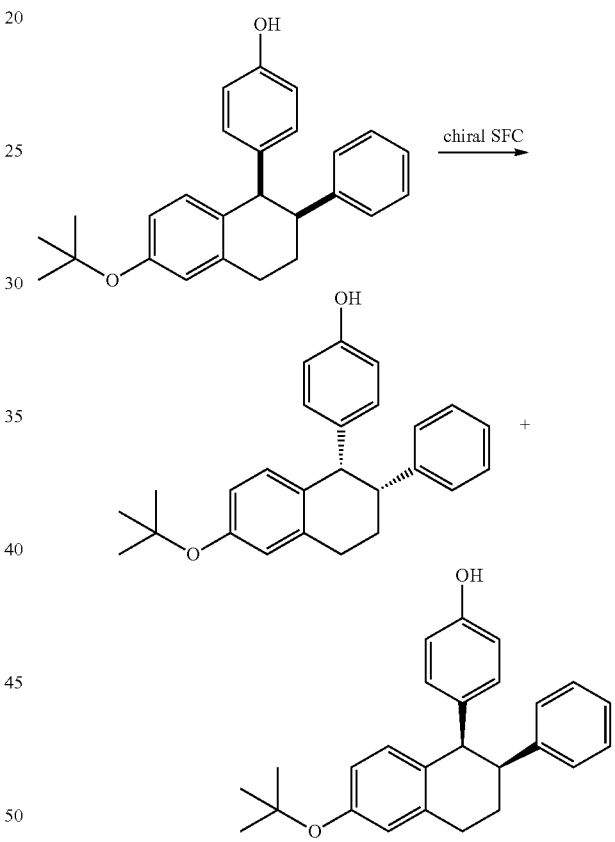

4-(6-tert-butoxy-2-phenyl-tetralin-1-yl)phenol (870 mg, 2.13 mmol, 1 eq) was subjected to supercritical fluid chromatography for chiral separation (column: AD, 250 mm×30 mm, 5 um; mobile phase: 0.1% ammonium hydroxide in methanol, 20%-20%, 4.2 min for each run) to get 4-[(1S,2R)-6-tert-butoxy-2-phenyl-tetralin-1-yl]phenol (420 mg, 1.04 mmol, 97% yield, 92% purity) as the first fraction and 4-[(1R,2S)-6-tert-butoxy-2-phenyl-tetralin-1-yl]phenol (420 mg, 1.04 mmol, 97% yield, 92% purity) as a second fraction. Fraction 1: [α]$_D$=+336.9 (C=0.50 g/100 mL in ethyl acetate, 25° C.), LC-MS (ESI) m/z: 395.1 [M+23]$^+$; $^1$H NMR (400 MHz, DMSO-d$_6$) δ 9.02 (s, 1H), 7.20-7.07 (m, 3H), 6.87-6.79 (m, 3H), 6.79-6.72 (m, 1H), 6.71-6.64 (m, 1H), 6.36 (d, J=8.4 Hz, 2H), 6.15 (d, J=8.4 Hz, 2H), 4.19 (d, J=4.8 Hz, 1H), 3.31-3.26 (m, 1H), 3.09-2.89 (m, 2H), 2.17-2.04 (m, 1H), 1.79-1.65 (m, 1H), 1.29 (s, 9H). Fraction 2: [α]D=−334.1 (C=0.50 g/100 mL in ethyl acetate, 25° C.), LC-MS (ESI) m/z: 395.2 [M+23]+; 1H-NMR (400 MHz, DMSO-d6) δ: 9.02 (s, 1H), 7.21-7.06 (m, 3H), 6.88-6.78 (m, 3H), 6.78-6.72 (m, 1H), 6.71-6.64 (m, 1H), 6.36 (d, J=8.4 Hz, 2H), 6.15 (d, J=8.4 Hz, 2H), 4.19 (d, J=4.8 Hz, 1H), 3.30-3.27 (m, 1H), 3.08-2.90 (m, 2H), 2.16-2.04 (m, 1H), 1.79-1.65 (m, 1H), 1.29 (s, 9H).

Step 8: Preparation of 4-(6-benzyloxy-2-phenyl-3,4-dihydronaphthalen-1-yl)phenyl]1,1,2,2,3,3,4,4,4-nonafluorobutane-1-sulfonate

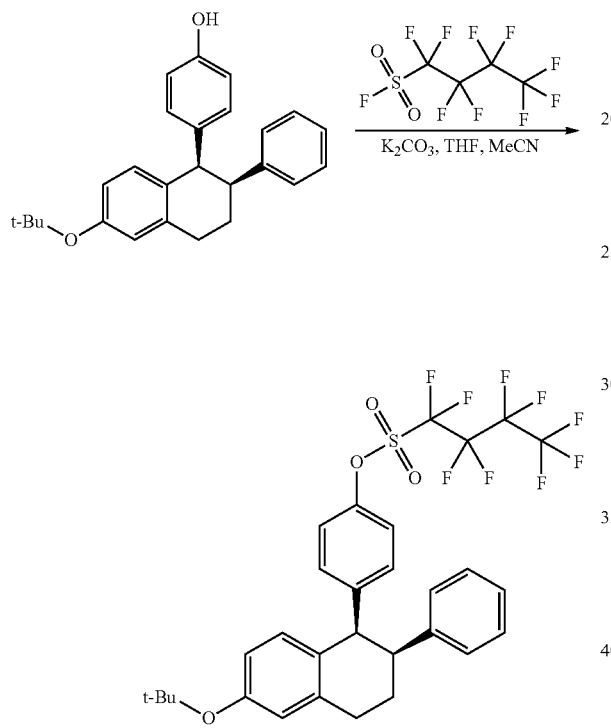

To a solution of 4-[(1R,2S)-6-tert-butoxy-2-phenyl-tetralin-1-yl]phenol (1 g, 2.68 mmol, 1 eq) and 1,1,2,2,3,3,4,4,4-nonafluorobutane-1-sulfonyl fluoride (811 mg, 2.68 mmol, 1 eq) in tetrahydrofuran (5 mL) and acetonitrile (5 mL) was added potassium carbonate (557 mg, 4.03 mmol, 1.5 eq). The reaction mixture was stirred at 25° C. for 16 hours. TLC (petroleum ether:ethyl acetate=10:1) indicated the starting material was consumed completely and one new spot formed. The reaction mixture was concentrated under reduced pressure. The residue was purified by silica gel chromatography (petroleum ether:ethyl acetate=1:0 to 50:1). The desired compound [4-[(1R,2S)-6-tert-butoxy-2-phenyl-tetralin-1-yl]phenyl]1,1,2,2,3,3,4,4,4-nonafluorobutane-1-sulfonate (1.6 g, 2.44 mmol, 91% yield) was obtained as a colorless oil. 1H NMR (400 MHz, CDCl3) 7.21-7.11 (m, 3H), 6.94-6.86 (m, 3H), 6.84-6.73 (m, 4H), 6.46 (d, J=8.8 Hz, 2H), 4.33 (d, J=5.2 Hz, 1H), 3.50-3.40 (m, 1H), 3.16-2.95 (m, 2H), 2.20-2.02 (m, 1H), 1.91-1.79 (m, 1H), 1.38 (s, 9H)

Step 9: Preparation of 1-[4-(6-benzyloxy-2-phenyl-3,4-dihydronaphthalen-1-yl) phenyl]-4-(dimethoxymethyl)piperidine

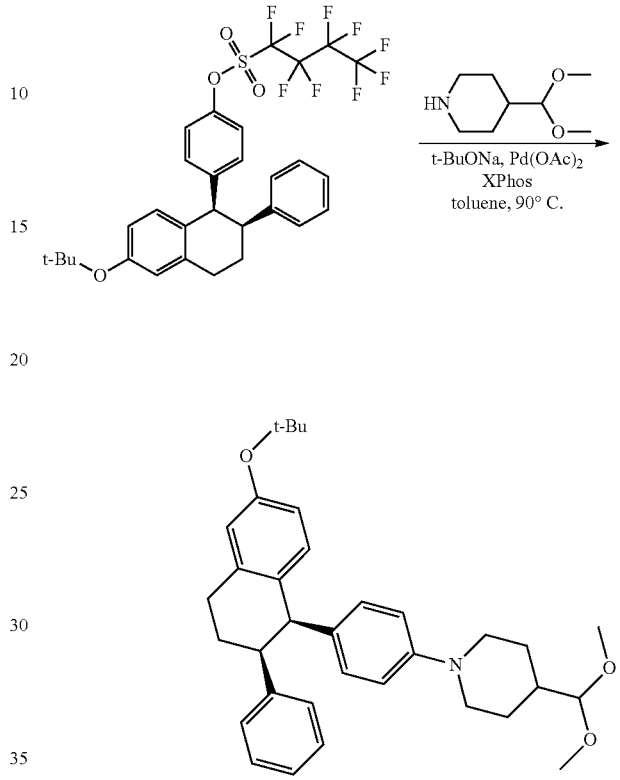

A mixture of [4-[(1R,2S)-6-tert-butoxy-2-phenyl-tetralin-1-yl]phenyl]1,1,2,2,3,3,4,4,4-nonafluorobutane-1-sulfonate (1.6 g, 2.44 mmol, 1 eq), 4-(dimethoxymethyl)piperidine (584 mg, 3.67 mmol, 1.5 eq), sodium tert-butoxide (705 mg, 7.33 mmol, 3 eq), palladium acetate (82 mg, 0.37 mmol, 0.15 eq) and dicyclohexylphosphino -2',4',6'-triisopropylbiphenyl (233 mg, 0.49 mmol, 0.2 eq) in toluene (30 mL) was degassed and purged with nitrogen three times, and then the mixture was stirred at 90° C. for 16 hours under nitrogen atmosphere. LC-MS showed one main peak with desired MS was detected. TLC (petroleum ether:ethyl acetate=10:1) indicated the starting material was consumed completely and one new spot formed. The mixture was cooled, diluted with ethyl acetate (50 mL), filtered on a plug of celite, the filter cake was washed with ethyl acetate (30 mL). The filtrate was concentrated. The residue was purified by silica gel chromatography (petroleum ether:ethyl acetate=100:1 to 10:1). The desired compound 1-[4-[(1R,2S)-6-tert-butoxy-2-phenyl-tetralin-1-yl]phenyl]-4-(dimethoxymethyl)piperidine (1.1 g, 2.14 mmol, 87% yield) was obtained as a white solid. LC-MS (ESI) m/z: 514.3 [M+1]+; 1H NMR (400 MHz, CDCl3) δ 7.21-7.11 (m, 3H), 6.88-6.78 (m, 4H), 6.73 (dd, J=2.4, 8.0 Hz, 1H), 6.57 (d, J=8.4 Hz, 2H), 6.27 (d, J=8.8 Hz, 2H), 4.23 (d, J=4.8 Hz, 1H), 4.06 (d, J=7.2 Hz, 1H), 3.63-3.52 (m, 2H), 3.41-3.30 (m, 7H), 3.13-2.96 (m, 2H), 2.54 (d, J=2.0, 12.0 Hz, 2H), 2.28-2.10 (m, 1H), 1.85-1.63 (m, 4H), 1.49-1.31 (m, 11H).

Step 10: Preparation of 1-[4-[(1R,2S)-6-hydroxy-2-phenyl-tetralin-1-yl]phenyl]piperidine-4-carbaldehyde

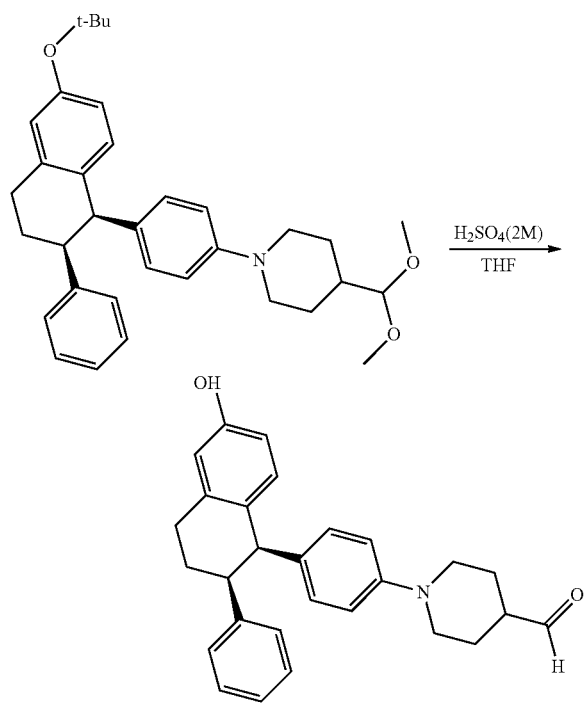

To a solution of 1-[4-[(1R,2S)-6-tert-butoxy-2-phenyl-tetralin-1-yl]phenyl]-4-(dimethoxymethyl)piperidine (1.1 g, 2.14 mmol, 1 eq) in tetrahydrofuran (45 mL) was added sulfuric acid (2 M, 43 mL, 40 eq). The reaction mixture was stirred at 70° C. for 1 hour. LC (petroleum ether:ethyl acetate=3:1) indicated the starting material was consumed completely and one new spot formed. The reaction mixture was quenched by addition of saturated sodium bicarbonate solution to pH=7-8, and extracted with ethyl acetate (20 mL×2). The combined organic layers were washed with brine (20 mL), dried over sodium sulfate, filtered and concentrated under reduced pressure. The residue was used into next step without further purification. The desired compound 1-[4-[(1R,2S)-6-hydroxy-2-phenyl-tetralin-1-yl]phenyl]piperidine-4-carbaldehyde (900 mg, 2.14 mmol, 99% yield, 97% purity) was obtained as light yellow solid. LCMS MS (ESI) m/z: 412.1 [M+1]$^+$ Step 11: Preparation of 3-[5-[4-[[1-[4-[(1R,2S)-6-hydroxy-2-phenyl-tetralin-1-yl]phenyl]-4-piperidyl]methyl]piperazin-1-yl]-1-oxo-isoindolin-2-yl]piperidine-2,6-dione (Exemplary Compound 341)

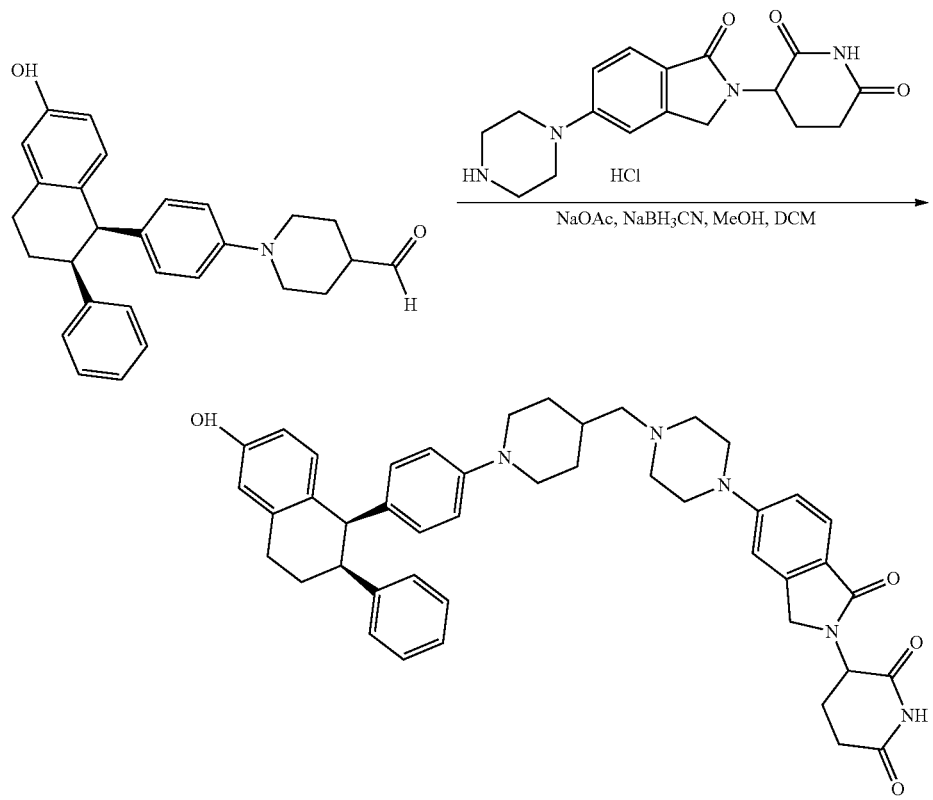

To a solution of 3-(1-oxo-5-piperazin-1-yl-isoindolin-2-yl)piperidine-2,6-dione hydrochloride (319 mg, 0.87 mmol, prepared in Step 17 described for Exemplary Compound 62) in methanol (4 mL) and dichloromethane (4 mL) was added sodium acetate (120 mg, 1.46 mmol, 2 eq). The mixture was stirred at 20° C. for 0.5 h, then to the mixture was added 1-[4-[(1R,2S)-6-hydroxy-2-phenyl-tetralin-1-yl]phenyl]piperidine-4-carbaldehyde (300 mg, 0.73 mmol, 1 eq) and sodium cyanoborohydride (137 mg, 2.19 mmol, 3 eq). The mixture was stirred at 20° C. for 12 h. LC-MS showed the starting material was consumed completely and one main peak with desired MW was detected. The reaction mixture was concentrated under reduced pressure. The residue was purified by prep-HPLC (Phenomenex luna C18 column, 250×50 mm, 10 um; mobile phase: [water (0.05% HCl)-acetonitrile]; B %: acetonitrile 10%-40% in 30 min). The desired compound 3-[5-[4-[[1-[4-[(1R,2S)-6-hydroxy-2-phenyl-tetralin-1-yl]phenyl]-4-piperidyl]methyl]piperazin-1-yl]-1-oxo-isoindolin-2-yl]piperidine-2,6-dione (288.4 mg, 0.37 mmol, 51% yield) was obtained as a white solid of hydrochloride salt. LC-MS (ESI) m/z: 724.4 [M+1]$^+$; $^1$H NMR (400 MHz, DMSO-d$_6$) δ 10.97 (s, 1H), 10.83 (s, 0.9H, HCl), 7.60 (d, J=8.5 Hz, 1H), 7.40 (br s, 2H), 7.22-7.11 (m, 5H), 6.83 (d, J=6.0 Hz, 2H), 6.69-6.63 (m, 2H), 6.58-6.47 (m, 3H), 5.07 (dd, J=5.2, 13.2 Hz, 1H), 4.41-4.30 (m, 2H), 4.28-4.21 (m, 1H), 4.00 (d, J=12.7 Hz, 2H), 3.61 (d, J=11.0 Hz, 2H), 3.54-3.36 (m, 6H), 3.16 (br s, 4H), 3.06-2.84 (m, 3H), 2.76-2.53 (m, 1H), 2.43-2.33 (m, 1H), 2.27 (br s, 1H), 2.16-2.04 (m, 3H), 2.02-1.69 (m, 5H).

Synthesis of 3-[5-[4-[2-[1-[4-[(1R,2S)-6-hydroxy-2-phenyl-tetralin-1-yl]phenyl]-4-piperidyl]ethyl]piperazin-1-yl]-1-oxo-isoindolin-2-yl]piperidine-2,6-dione (Exemplary Compound 343)

Step 1: Preparation of benzyl 4-(2-hydroxyethyl) piperidine-1-carboxylate

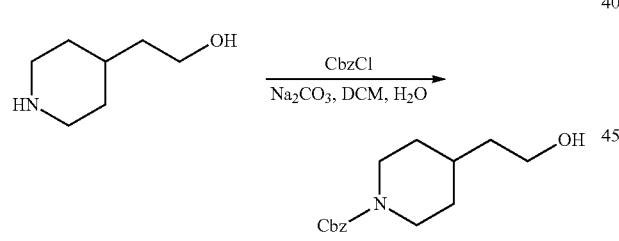

To a solution of 2-(4-piperidyl) ethanol (5 g, 38.70 mmol, 1 eq) in dichloromethane (100 mL) was added sodium carbonate (18.5 g, 174.2 mmol, 4.5 eq) in water (100 mL) at 0*C, and benzyl chloroformate (7.3 g, 42.6 mmol, 6 mL, 1.1 eq) was added dropwise. The mixture was stirred at 20° C. for 12 hours. The mixture was diluted with water (100 mL), extracted with dichloromethane (100 mL×2). The combined organic layers were washed with brine (100 mL×2), dried over sodium sulfate, filtered and concentrated under reduced pressure. The residue was purified by silica gel chromatography (petroleum ether/ethyl acetate=10:1 to 2:1). Benzyl 4-(2-hydroxyethyl) piperidine-1-carboxylate (9.9 g, 37.40 mmol, 48% yield) was obtained as colorless oil. $^1$H NMR (400 MHz, CDCl$_3$) δ 7.43-7.30 (m, 5H), 5.14 (s, 2H), 4.30-4.14 (m, 2H), 3.73 (t, 2H), 2.80 (s, 2H), 1.72 (d, 2H), 1.68-1.61 (m, 1H), 1.54 (m, 2H), 1.30-1.24 (m, 1H), 1.17 (d, 2H).

Step 2: Preparation of 4-(2-oxoethyl) piperidine-1-carboxylate

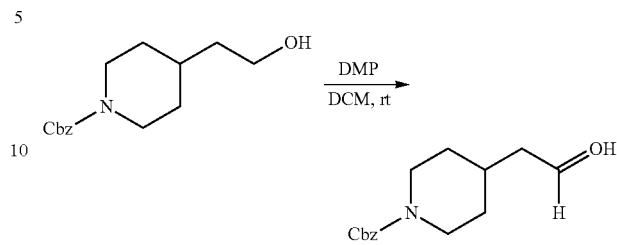

To a solution of benzyl 4-(2-hydroxyethyl) piperidine-1-carboxylate (9 g, 34.20 mmol, 1.0 eq) in dichloromethane (150 mL) was added Dess-Martin reagent (15.9 g, 37.6 mmol, 11.6 mL, 1.1 eq) at 0° C. The mixture was stirred at 20° C. for 3 hours. The reaction mixture was quenched by the addition of saturated sodium bicarbonate (50 mL) at 15° C. and filtered to remove insoluble residue, then diluted with dichloromethane 100 mL. The organic layer was washed with brine 60 mL (20 mL×3), dried over sodium sulfate, filtered and concentrated under reduced pressure. The residue was purified by silica gel chromatography (petroleum ether/ethyl acetate=1/0 to 5:1) to give benzyl 4-(2-oxoethyl) piperidine-1-carboxylate (7.3 g, 28.1 mmol, 82% yield) as a yellow oil. $^1$H NMR (400 MHz, CDCl$_3$) δ=10.12-9.46 (m, 1H), 7.60-7.07 (m, 5H), 5.04 (s, 2H), 4.36-3.89 (m, 2H), 2.74 (s, 2H), 2.40-2.24 (m, 2H), 2.09-1.91 (m, 1H), 1.63 (d, J=12.2 Hz, 2H), 1.30-1.09 (m, 2H).

Step 3: Preparation of benzyl 4-(2,2-dimethoxyethyl) piperidine -1- carboxylate

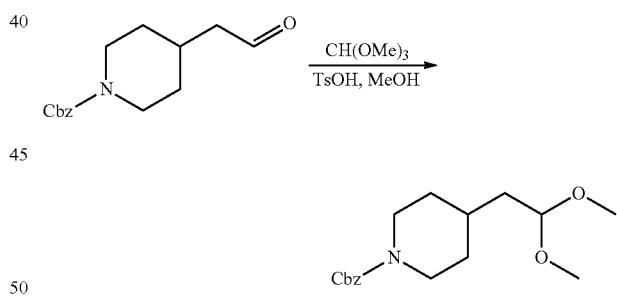

To a solution of benzyl 4-(2-oxoethyl) piperidine-1-carboxylate (8 g, 30.60 mmol, 1 eq) in methyl alcohol (80 mL) was added trimethoxymethane (16.2 g, 153.1 mmol, 16.8 mL, 5 eq) and 4-methylbenzenesulfonic acid (291 mg, 1.5 mmol, 0.05 eq). The mixture was stirred at 15° C. for 1 hour. The reaction mixture was quenched by addition of water (50 mL) at 15° C., and then diluted with dichloromethane 100 mL. The organic layer was washed with brine (20 mL×3), dried over sodium sulfate, filtered and concentrated under reduced pressure to afford benzyl 4-(2,2-dimethoxyethyl) piperidine -1- carboxylate (9.3 g, 30.1 mmol, 98% yield) as a yellow oil. $^1$H NMR (400 MHz, CDCl$_3$) 7.37-7.11 (m, 5H), 5.04 (s, 2H), 4.39 (t, J=5.6 Hz, 1H), 4.07 (s, 2H), 3.31-3.12 (m, 6H), 2.70 (s, 2H), 1.70-1.56 (m, 2H), 1.54-1.41 (m, 3H), 1.19-0.99 (m, 2H).

Step 4: Preparation of 4-(2,2-dimethoxyethyl) piperidine

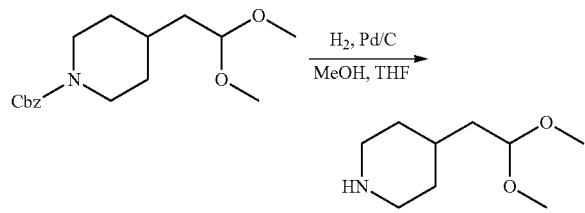

A mixture of benzyl 4-(2,2-dimethoxyethyl)piperidine-1-carboxylate (9.3 g, 30.10 mmol, 1 eq) and palladium on activated carbon catalyst (1 g, 3 mmol, 10% purity, 0.1 eq) in methyl alcohol (130 mL) was degassed and purged with hydrogen 3 times. The mixture was stirred at 15° C. for 15 hours under hydrogen atmosphere at 15 psi. The reaction mixture was filtered and concentrated under reduced pressure to provide 4-(2,2-dimethoxyethyl) piperidine (5 g, 28.9 mmol, 96% yield) as a yellow oil. $^1$H NMR (400 MHz, CDCl$_3$) δ 4.48 (t, J=5.6 Hz, 1H), 3.39-3.26 (m, 6H), 3.05 (d, J=12.0 Hz, 2H), 2.60 (dt, J=2.5, 12.2 Hz, 2H), 1.87 (s, 1H), 1.69 (d, J=12.8 Hz, 2H), 1.59-1.47 (m, 3H), 1.27-1.00 (m, 2H).

Step 5: Preparation of 1,1-[4-(6-benzyloxy-2-phenyl-3,4-dihydronaphthalen-1-yl)phenyl]-4-(2,2-dimethoxyethyl)piperidine

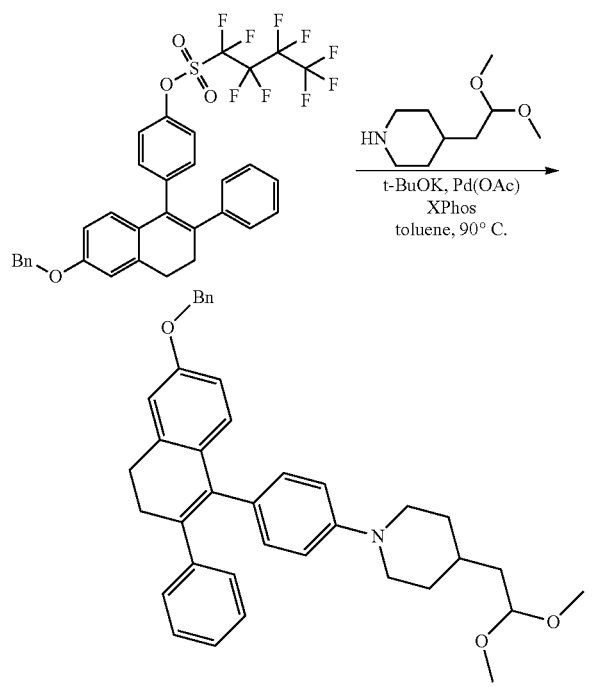

A mixture of [4-(6-benzyloxy-2-phenyl-3,4-dihydronaphthalen-1-yl)phenyl]1,1,2,2,3,3,4,4,4-nonafluorobutane-1-sulfonate (3 g, 4.37 mmol, 1 eq, prepared using the same method as described for Exemplary Compound 341), 4-(2,2-dimethoxyethyl)piperidine (1.14 g, 6.6 mmol, 1.5 eq), palladium acetate (147.15 mg, 0.66 mmol, 0.15 eq), sodium tert-butoxide (1.3 g, 13.1 mmol, 3 eq) and dicyclohexylphosphino-2',4',6'-triisopropylbiphenyl (624.9 mg, 1.3 mmol, 0.3 eq) in toluene (50 mL) was degassed and purged with nitrogen 3 times. The mixture was stirred at 90° C. for 16 hours under nitrogen atmosphere. The reaction mixture was filtered and concentrated under reduced pressure. The residue was purified by silica gel chromatography (petroleum ether/ethyl acetate=1/0 to 15:1) to give 1-[4-(6-benzyloxy-2-phenyl-3,4-dihydronaphthalen-1-yl)phenyl]-4-(2,2-dimethoxyethyl)piperidine (2.2 g, 3.93 mmol, 90% yield) as a white solid. $^1$H NMR (400 MHz, CDCl$_3$) δ=7.47-7.30 (m, 5H), 7.15-7.07 (m, 2H), 7.07-7.00 (m, 3H), 6.92 (d, 0.1=8.5 Hz, 2H), 6.86 (d, J=2.3 Hz, 1H), 6.79 (dd, J=5.6, 8.4 Hz, 3H), 6.67 (dd, J=2.5, 8.5 Hz, 1H), 5.07 (s, 2H), 4.53 (t, J=5.5 Hz, 1H), 3.64 (d, J=12.3 Hz, 2H), 3.34 (s, 6H), 3.02-2.87 (m, 2H), 2.83-2.73 (m, 2H), 2.67 (t, J=11.3 Hz, 2H), 1.83 (d, J=12.5 Hz, 2H), 1.57 (s, 3H), 1.49-1.32 (m, 2H).

Step 6: Preparation of 1-[4-[4-(2,2-dimethoxyethyl)-1-piperidyl]phenyl]-2-phenyl-tetralin-6-ol Hydrogenation of the benzyl ether from step 5 using the same procedure as described for Exemplary Compound 341 provided the desired phenol. $^1$H NMR (400 MHz, CDCl$_3$) δ 7.19-7.12 (m, 3H), 6.85-6.77 (m, 3H), 6.70 (d, J=2.6 Hz, 1H), 6.58 (d, J=8.7 Hz, 2H), 6.53 (dd, J=2.7, 8.3 Hz, 1H), 6.29 (d, J=8.6 Hz, 2H), 4.51 (t, J=5.7 Hz, 1H), 4.20 (d, J=4.9 Hz, 1H), 3.58-3.46 (m, 2H), 3.38-3.34 (m, 1H), 3.33 (s, 6H), 3.11-2.95 (m, 2H), 2.58 (dt, 0.1=2.3, 12.0 Hz, 2H), 2.26-2.10 (m, 1H), 1.89-1.73 (m, 3H), 1.62-1.55 (m, 2H), 1.54-1.46 (m, 1H), 1.42-1.29 (m, 2H).

Step 7: Preparation of (1S,2R)-1-[4-[4-(2,2-dimethoxyethyl)-1-piperidyl]phenyl]-2-phenyl-tetralin-6-ol and (1R,2S)-1-[4-[4-(2,2-dimethoxyethyl)-1-piperidyl]phenyl]-2-phenyl-tetralin-6-ol

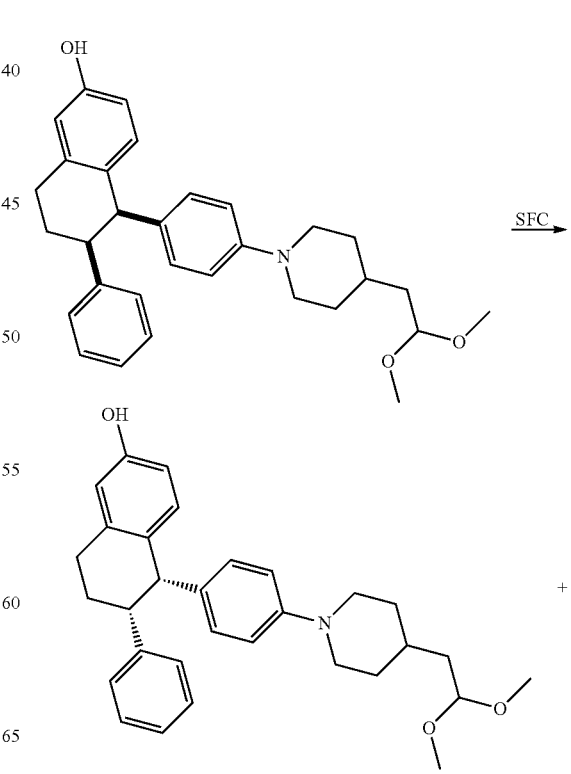

1043
-continued

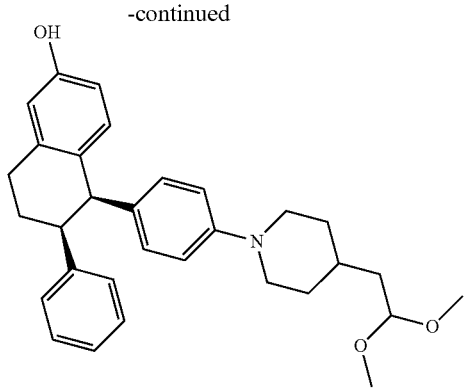

1-[4-[4-(2,2-dimethoxyethyl)-1-piperidyl]phenyl]-2-phenyl-tetralin-6-ol from step 6 (0.5 g, 1.1 mmol, 1 eq) was subjected SFC separation using a chiral column (column: AD, 250 mm×30 mm, 10 um; mobile phase: (0.1% ammonium hydroxide methyl alcohol, 40%-40%, 4.7 min each run) to give the first fraction (1S,2R)-1-[4-[4-(2,2-dimethoxyethyl)-1-piperidyl]phenyl]-2-phenyl-tetralin-6-ol (0.23 g, 0.49 mmol, 92% yield, 100% purity) as a colorless oil, and the second fraction provided (1R,2S)-1-[4-[4-(2,2-dimethoxyethyl)-1-piperidyl] phenyl]-2-phenyl-tetralin-6-ol (0.23 g, 0.49 mmol, 92% yield, 100% purity) as colorless oil. LCMS (ESI) m/z: 472.4 [M+1]$^+$.

Step 8: Preparation of 2-[1-[4-[(1R,2S)-6-hydroxy-2-phenyl-tetralin-1-yl]phenyl]-4-piperidyl] acetaldehyde This aldehyde was prepared using the same method as described for Exemplary Compound 341. $^1$H NMR (400 MHz, CDCl$_3$) δ=9.95-9.73 (m, 1H), 7.18-7.13 (m, 3H), 6.88-6.78 (m, 3H), 6.71 (d, J=2.5 Hz, 1H), 6.58 (dd, J=2.6, 8.2 Hz, 3H), 6.30 (d, J=8.3 Hz, 2H), 4.80-4.52 (m, 1H), 4.21 (d, 0.1=5.1 Hz, 1H), 3.84-3.72 (m, 2H), 3.53 (s, 2H), 3.42-3.27 (m, 1H), 3.05 (d, J=4.5 Hz, 1H), 2.64 (s, 2H), 2.41 (d, J=5.8 Hz, 2H), 2.25-2.11 (m, 1H), 2.08-1.92 (m, 1H), 1.80 (d, J=2.9 Hz, 2H), 1.01-0.66 (m, 1H).

Step 9: Preparation of 3-[5-[4-[2-[1-[4-[(1R,2S)-6-hydroxy-2-phenyl-tetralin-1-yl]phenyl]-4-piperidyl]ethyl]piperazin-1-yl]-1-oxo-isoindolin-2-yl]piperidine-2,6-dione (Exemplary Compound 343)

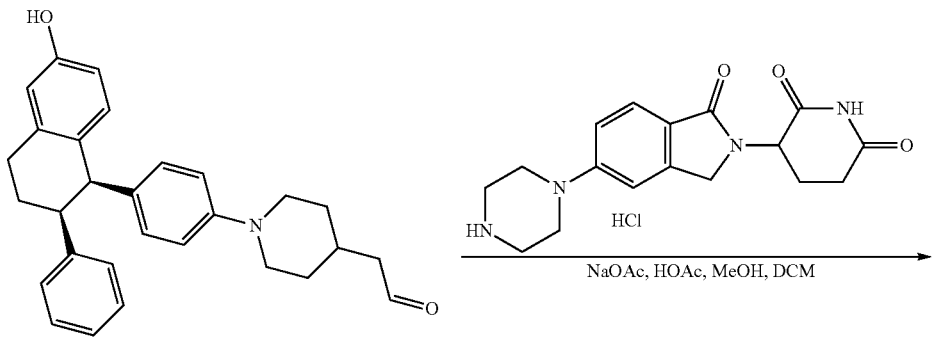

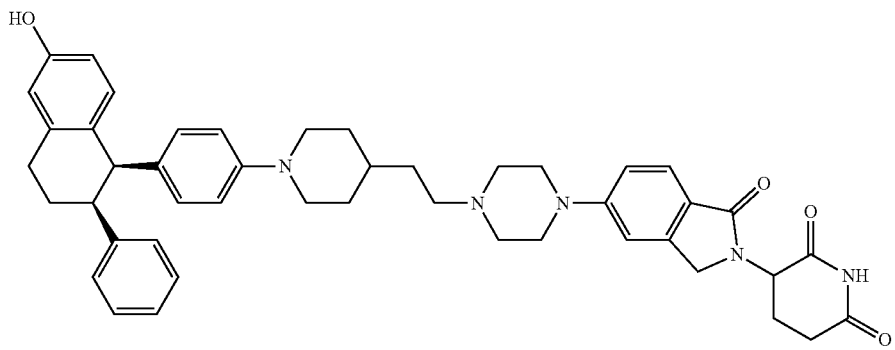

To a solution of 3-(1-oxo-5-piperazin-1-yl-isoindolin-2-yl) piperidine-2,6-dione hydrochloride (85 mg, 0.24 mmol, 1 eq, prepared as described for Exemplary Compound 62) in dichloromethane (1 mL) and methyl alcohol (5 mL) was added sodium acetate (77 mg, 0.94 mmol, 4 eq) in one portion at 25° C. The mixture was stirred at 25° C. for 1 hour and 2-[1-[4-[(1R,2S)-6-hydroxy-2-phenyl-tetralin-1-yl]phenyl]-4-piperidyl]acetaldehyde (100 mg, 0.24 mmol, 1 eq) and acetic acid (525 mg, 8.74 mmol, 37.2 eq) was added, The mixture was stirred at 25° C. for 1 hour. Then sodium cyanoborohydride (29 mg, 0.47 mmol, 2 eq) was added in one portion, the mixture was stirred at 25° C. for 1 hour. The reaction mixture was concentrated under reduced pressure. The residue was purified by preparative HPLC (column: Phenomenex Synergi C18 150×25 mm, 10 um; mobile phase: [water (0.05% hydrochloric acid)-acetonitrile]; B %: 15%-35%, 7.8 min) to give 3-[5-[4- [2-[1-[4-[(1R,2S)-6-hydroxy-2-phenyl-tetralin-1-yl]phenyl]-4-piperidyl]ethyl]piperazin-1-yl]-1-oxo-isoindolin-2-yl]piperidine-2,6-dione (117.7 mg, 64% yield, 99% purity) as an off-white solid of hydrochloride salt. LC-MS (ESI) m/z: 738.3 [M+1]*; $^1$H NMR (400 MHz, DMSO) δ 11.24 (s, 1H), 10.95 (s, 1H), 7.58 (d, J=8.5 Hz, 1H), 7.48 (d, J=6.8 Hz, 2H), 7.20-7.11 (m, 5H), 6.83 (d, J=6.9 Hz, 2H), 6.69-6.61 (m, 2H), 6.53 (d, J=7.3 Hz, 3H), 5.06 (dd, J=4.6, 13.2 Hz, 1H), 4.42-4.18 (m, 3H), 4.00 (d, J=12.8 Hz, 2H), 3.58 (d, J=10.9 Hz, 2H), 3.47-3.27 (m, 6H), 3.23-3.03 (m, 4H), 3.02-2.84 (m, 3H), 2.71-2.52 (m, 1H), 2.39 (d, =13.7 Hz, 2H), 2.10-1.71 (m, 10H).

Synthesis of 2-(2,6-dioxopiperidin-3-yl)-5-(4-((1-(4-((1R,2S)-6-hydroxy-2-phenyl-1,2,3,4-tetrahydrphthalen-1-yl)phenyl)piperidin-4-yl)methyl)piperidin-1-yl)isoindoline-1,3-dione (Exemplary Compound 393)

Step 1: Preparation of 2-(2,6-dioxopiperidin-3-yl)-5-fluoroisoindoline-1,3-dione

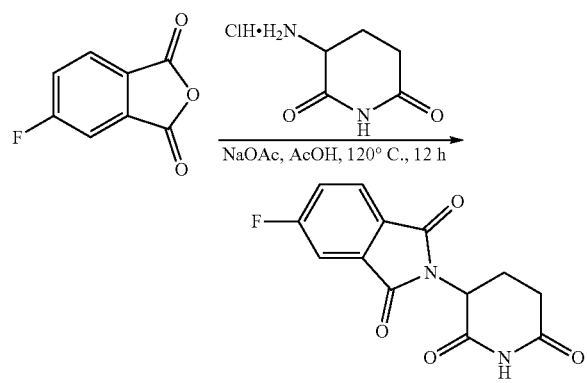

To a solution of 5-fluoroisobenzofuran-1,3-dione (15 g, 90.30 mmol, 1.00 eq) in acetic acid (200 mL) was added sodium acetate (14.8 g, 180.60 mmol, 2.00 eq) and 3-aminopiperidine-2,6-dione hydrochloride (14.9 g, 90.30 mmol, 1.00 eq). The mixture was stirred at 120° C. for 12 hours. The reaction mixture was concentrated under reduced pressure to remove most acetic acid. The residue was poured into water (200 mL) and stirred for 10 minutes. The mixture was filtered. The filtered cake was washed with water (30 mL×2) and dried to give 2-(2,6-dioxo-3-piperidyl)-5-fluoro-isoindoline-1,3-dione (24 g, 86.89 mmol, 96% yield) as an off-white solid. LC-MS (ESI) m/z: 277.1 [M+1]$^+$; $^1$H-NMR (400 MHz, DMSO-d$_6$) δ 11.13 (s, 1H), 8.00 (dd, J=4.4, 8.4 Hz, 1H), 7.84 (dd, J=2.4, 7.2 Hz, 1H), 7.75-7.68 (m, 1H), 5.16 (dd, =5.2, 12.8 Hz, 1H), 2.95-2.84 (m, 1H), 2.66-2.52 (m, 2H), 2.14-2.02 (m, 1H).

Step 2: Preparation of tert-butyl 4-(2-(2,6-dioxopiperidin-3-yl)-1,3-dioxoisoindolin-5-yl)piperazine-1-carboxylate

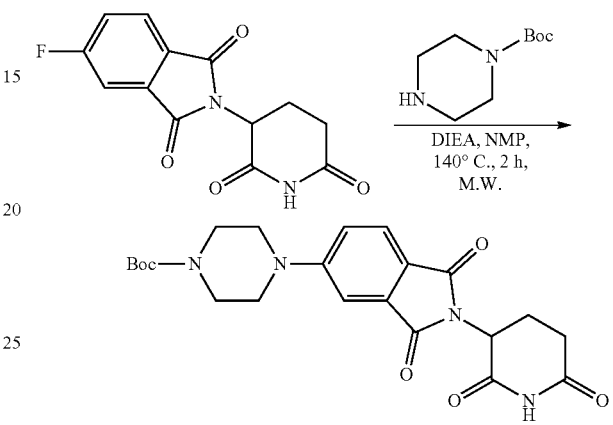

2-(2,6-Dioxo-3-piperidyl)-5-fluoro-isoindoline-1,3-dione (1 g, 3.62 mmol, 1.00 eq), tert-butyl piperazine-1-carboxylate (742 mg, 3.98 mmol, 1.10 eq) and diisopropylethylamine (1.4 g, 10.86 mmol, 1.9 mL, 3.00 eq) were taken up into a microwave tube in 1-methyl-2-pyrrolidinone (15 mL). The sealed tube was heated at 140° C. for 2 hours under microwave conditions (4 batches in parallel). The reaction mixture was diluted with water (120 mL) and extracted with ethyl acetate (50 mL×2). The combined organic phase was washed with saturated brine (30 mL×2), dried with anhydrous sodium sulfate, filtered and concentrated in vacuum. The residue was purified by column chromatography (petroleum ether:ethyl acetate=3:1 to 1:1) to give tert-butyl 4-[2-(2,6-dioxo-3-piperidyl)-1,3-dioxo-isoindolin-5-yl]piperazine-1-carboxylate (4 g, 9.04 mmol, 62% yield) as a yellow solid. LC-MS (ESI) m/z: 343.0 [M-100]$^+$; $^1$H-NMR (400 MHz, CDCl$_3$) δ 8.23 (s, 1H), 7.71 (d, J=8.4 Hz, 1H), 7.28 (d, J=2.4 Hz, 1H), 7.06 (dd, J=2.4, 8.4 Hz, 1H), 4.95 (dd, J=5.2, 12.4 Hz, 1H), 3.66-3.57 (m, 4H), 3.45-3.39 (m, 4H), 2.94-2.85 (m, 1H), 2.80-2.71 (m, 1H), 2.17-2.09 (m, 1H), 2.07-1.98 (m, 1H), 1.49 (s, 9H).

Step 3: Preparation of 2-(2,6-dioxopiperidin-3-yl)-5-(piperazin-1-yl)isoindoline-1,3-dione

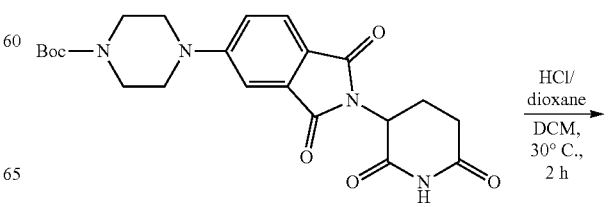

-continued

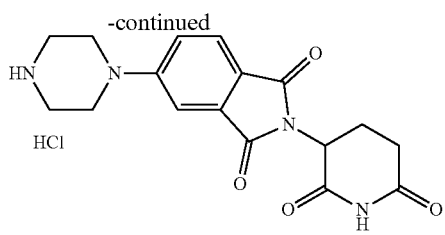

To a solution of tert-butyl 4-[2-(2,6-dioxo-3-piperidyl)-1,3-dioxo-isoindolin-5-yl]piperazine-1-carboxylate (4 g, 9.04 mmol, 1.00 eq) in dichloromethane (20 mL) was added hydrochloric acid/dioxane (4 M, 22 mL, 10.00 eq). The mixture was stirred at 30° C. for 2 hours. The reaction mixture was concentrated under reduced pressure to remove dichloromethane, dioxane and hydrochloric acid to give 2-(2,6-dioxo-3-piperidyl)-5-piperazin-1-yl-isoindoline-1,3-dione (3.2 g, 8.45 mmol, 93% yield, hydrochloride) as a yellow solid. LCMS (ESI) m/z: 343.0 [M+1]$^+$; $^1$H NMR (400 MHz, DMSO-$d_6$) δ 11.10 (s, 1H), 9.56 (s, 2H), 7.74 (d, J=8.4 Hz, 1H), 7.45 (d, J=2.4 Hz, 1H), 7.33 (dd, J=2.4, 8.4 Hz, 1H), 5.09 (dd, J=5.2, 13.2 Hz, 1H), 3.77-3.68 (m, 4H), 3.25-3.15 (m, 4H), 2.96-2.83 (m, 1H), 2.63-2.53 (m, 2H), 2.08-1.99 (m, 1H).

Step 4: Preparation of 2-(2,6-dioxopiperidin-3-yl)-5-(4-((1-(4-((1R,2S)-6-hydroxy-2-phenyl-1,2,3,4-tetrahydronaphthalen-1-yl)phenyl)piperidin-4-yl)methyl)piperazin-1-yl)isoindoline-1,3-dione (Exemplary Compound 393)

To a mixture of 2-(2,6-dioxo-3-piperidyl)-5-piperazin-1-yl-isoindoline-1,3-dione hydrochloride (46 mg, 0.12 mmol, 1 eq) and sodium acetate (15 mg, 0.18 mmol, 1.5 eq) in dichloromethane (2 mL) and methanol (2 mL) was added acetic acid (0.4 mL) at 25° C. under nitrogen. The mixture was stirred at 25° C. for 15 minutes, then 1-(4-((1R,2S)-6-hydroxy-2-phenyl-1,2,3,4-tetrahydronaphthalen-1-yl)phenyl)piperidine-4-carbaldehyde (50 mg, 0.12 mmol, 1 eq, prepared as described for Exemplary Compound 341) was added and the mixture was stirred for 0.5 hours. The resulting mixture was cooled to 0° C., sodium cyanoborohydride (38 mg, 0.61 mmol, 5 eq) was added and the mixture was further stirred at 25° C. for 1 hour. The reaction mixture was concentrated under reduced pressure. The residue was purified by preparative HPLC to afford 2-(2,6-dioxopiperidin-3-yl)-5-(4-((1-(4-((1R,2S)-6-hydroxy-2-phenyl-1,2,3,4-tetrahydronaphthalen-1-yl)phenyl)piperidin-4-yl)methyl)piperazin-1-yl)isoindoline-1,3-dione (59.9 mg, 0.08 mmol, 63% yield) as a yellow solid of formic acid salt. LC-MS (ESI) m/z: 738.4 [M+1]$^+$; $^1$H NMR (400 MHz, DMSO-$d_6$) δ 11.08 (s, 1H), 9.13 (br s, 1H), 8.19 (s, 1H), 7.67 (d, J=8.5 Hz, 1H), 7.33 (s, 1H), 7.25 (br d, J=8.5 Hz, 1H), 7.17-7.08 (m, 3H), 6.83 (br d, J=6.8 Hz, 2H), 6.64 (d, J=8.3 Hz, 1H), 6.60 (d, J=2.3 Hz, 1H), 6.53 (d, J=8.8 Hz, 2H), 6.47 (dd, J=2.4, 8.2 Hz, 1H), 6.19 (d, J=8.7 Hz, 2H), 5.07 (dd, J=5.3, 12.9 Hz, 1H), 4.12 (d, J=4.5 Hz, 1H), 3.50-3.41 (m, 12H), 2.99-2.84 (m, 3H), 2.62-2.53 (m, 3H), 2.23-2.18 (m, 2H), 2.12-1.97 (m, 2H), 1.80-1.61 (m, 4H), 1.23-1.05 (m, 2H).

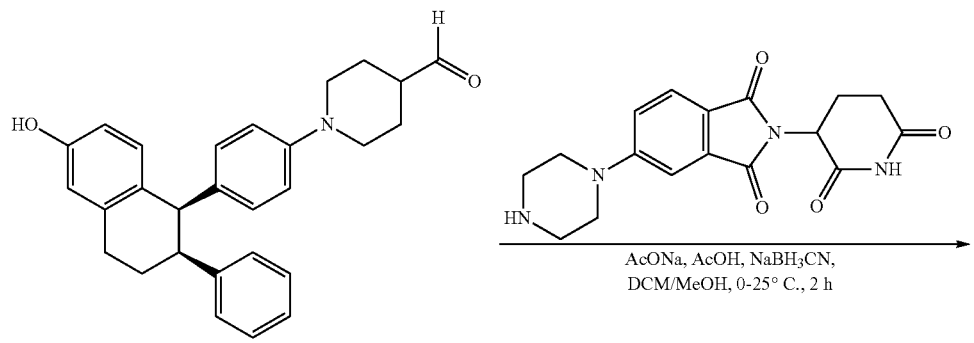

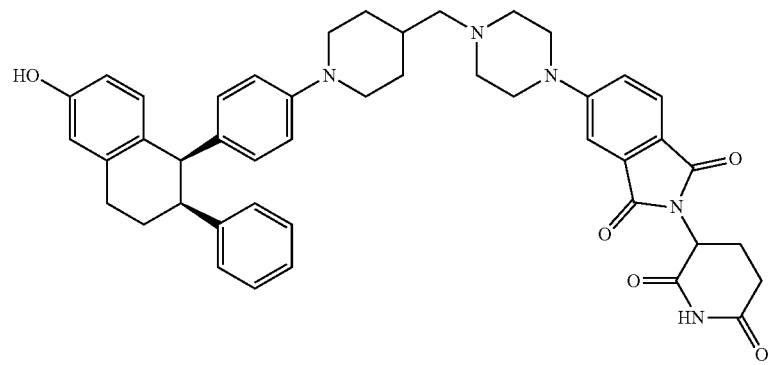

Synthesis of 2-(2,6-dioxopiperidin-3-yl)-5-(4-(2-(1-(4-((1R,2S)-6-hydroxy-2-phenyl-1,2,3,4-tetrahydronaphthalen-1-yl)phenyl)piperidin-4-yl)ethyl)piperazin-1-yl)isoindoline-1,3-dione (Exemplary Compound 395)

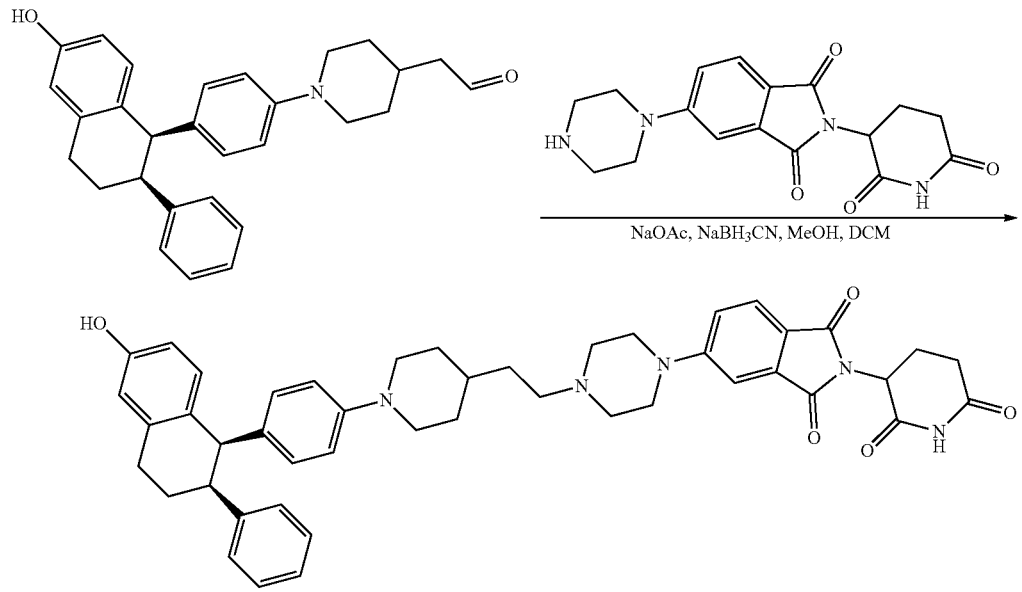

To a solution of 2-(2,6-dioxo-3-piperidyl)-5-piperazin-1-yl-isoindoline-1,3-dione hydrochloride (107 mg, 0.3 mmol, 1.2 eq, prepared as described for Exemplary Compound 393) in dichloromethane (3 mL) and methanol (1 mL) was added sodium acetate (38 mg, 0.5 mmol, 2 eq) at 25° C. After addition, the mixture was stirred at this temperature for 30 min, and then 2-[1-[4-[(1R,2S)-6-hydroxy-2-phenyl-tetralin-1-yl]phenyl]-4-piperidyl]acetaldehyde (100 mg, 0.3 mmol, 1 eq, prepared as described for Exemplary 343) was added at 25° C. The resulting mixture was stirred at 25° C. for 30 minutes. Then sodium cyanoborohydride (29 mg, 0.5 mmol, 2 eq) was added. The resulting mixture was stirred at 25° C. for 1 hour. The reaction mixture was concentrated under reduced pressure to remove solvent. The residue was purified by preparative HPLC (column: Phenomenex Synergi C18 150×25 mm, 10 um; mobile phase: [water (0.225% formic acid) and acetonitrile]; B %: 16%-40% in 8 min) to afford 2-(2,6-dioxo-3-piperidyl)-5-[4-[2-[1-[4-[(1R,2S)-6-hydroxy-2-phenyl-tetralin-1-yl]phenyl]-4-piperidyl]ethyl]piperazin-1-yl]isoindoline-1,3-dione (114.8 mg, 0.2 mmol, 65% yield) as a yellow solid of formic acid salt. LC-MS (ESI) m/z: 752.3 [M+1]; $^1$H-NMR (400 MHz, DMSO-$d_6$) δ 11.08 (s, 1H), 9.10 (s, 1H), 8.15 (s, 1H) 7.68-7.66 (d, 1H), 7.31 (s, 1H), 7.25 (d, 1H), 7.20-7.10 (m, 3H), 6.82 (d, 2H), 6.65-6.58 (m, 2H), 6.52-6.40 (m, 3H), 6.19 (d, 2H), 5.08-5.04 (m, 1H), 4.12-4.11 (d, J=4 Hz, 1H), 3.50-3.41 (m 12H), 2.99-2.83 (m, 3H), 2.60-2.52 (m, 2H), 2.40-2.32 (m, 2H), 2.15-1.95 (m, 2H), 1.71 (m, 3H), 1.40 (m, 3H), 1.17 (m, 2H).

Synthesis of (3S)-3-[5-[4-[[1-[4-(1R,2S)-6-hydroxy-2-phenyl-tetralin-1-yl]phenyl]-4-piperidyl]methyl]piperazin-1-yl]-1-oxo-isoindolin-2-yl]piperidine-2,6-dione (Exemplary Compound 411)

Step 1: Preparation of tert-butyl (4S)-5-amino-4-(benzyloxycarbonyl amino)-5-oxo-pentanoate

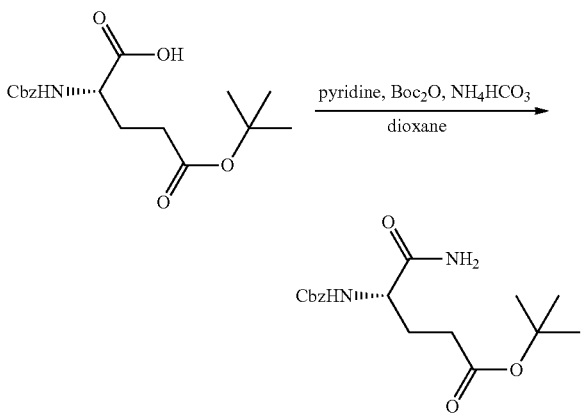

A mixture of (2S)-2-(benzyloxycarbonylamino)-5-tert-butoxy-5-oxo-pentanoic acid (20 g, 59.28 mmol, 1.00 eq), di-tert-butyl dicarbonate (94.85 mmol, 21.79 mL, 1.60 eq) and pyridine (9.38 g, 118.57 mmol, 9.57 mL, 2.00 eq) in 1,4-dioxane (200 mL) was degassed at 0° C. and purged with nitrogen for 3 times, and then the mixture was stirred at 0° C. for 0.5 hour under nitrogen atmosphere. Ammonium bicarbonate (14.06 g, 177.85 mmol, 14.65 mL, 3.00 eq) was added at 0° C. The mixture was stirred at 25° C. for 16 hours. LC-MS showed the desired mass. The volatiles were removed under reduced pressure. The residue was diluted with water (300 mL) and extracted with ethyl acetate (300 mL×1). The combined organic phase was washed with aq. hydrochloric acid (0.5 M, 200 mL×2), saturated sodium bicarbonate (300 mL×3) and brine (500 mL×3), dried with anhydrous sodium sulfate, filtered and concentrated in vacuum to give the crude product. The crude product was triturated (petroleum ether:ethyl acetate=10:1, 300 mL) to provide tert-butyl (4S)-5-amino-4-(benzyloxycarbonylamino)-5-oxo-pentanoate (19 g, 56.08 mmol, 94% yield, 99% purity) as a white solid. LC-MS (ESI) m/z: 359.0 [M+23]$^+$. $^1$H-NMR (400 MHz, CDCl$_3$) δ 7.39-7.29 (m, 5H), 6.38 (s, 1H), 5.74 (d, J=7.2 Hz, 1H), 5.58 (s, 1H), 5.11 (s, 2H), 4.25 (d, J=5.6 Hz, 1H), 2.55-2.41 (m, 1H), 2.39-2.27 (m, 1H), 2.18-2.04 (m, 1H), 2.02-1.85 (m, 1H), 1.45 (s, 9H).

Step 2: Preparation of tert-butyl (4S)-4,5-diamino-5-oxo-pentanoate

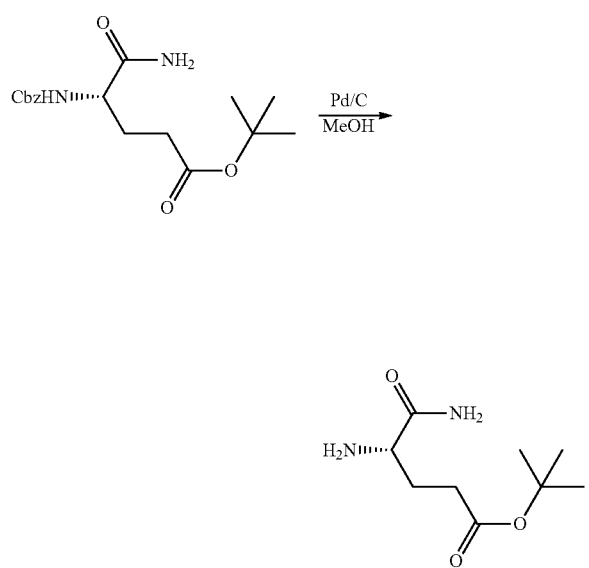

To a solution of tert-butyl (4S)-5-amino-4-(benzyloxycarbonylamino)-5-oxo-pentanoate (19 g, 56.48 mmol, 1.00 eq) in methanol (200 mL) was added palladium on carbon (2 g, 10%) under nitrogen atmosphere. The suspension was degassed and purged with hydrogen 3 times. The mixture was stirred under H2 (50 psi) at 25° C. for 16 hours. Thin layer chromatography (petroleum ether:ethyl acetate=1:2) showed the reaction was completed. The reaction mixture was filtered and the filtrate was concentrated. Compound tert-butyl (4S)-4,5-diamino-5-oxo-pentanoate (11 g, 54.39 mmol, 96% yield) was obtained as a light green oil. $^1$H NMR (400 MHz, CDCl$_3$) δ 7.03 (br s, 1H), 5.55 (br s, 1H), 3.44 (br s, 1H), 2.49-2.31 (m, 2H), 2.11 (dd, J=6.0, 12.8 Hz, 1H), 1.92-1.76 (m, 1H), 1.66 (s, 2H), 1.45 (s, 9H).

Step 3: Preparation of tert-butyl 4-[2-[(1S)-4-tert-butoxy-1-carbamoyl-4-oxo-butyl]-1-oxo-isoindolin-5-yl]piperazine-1-carboxylate

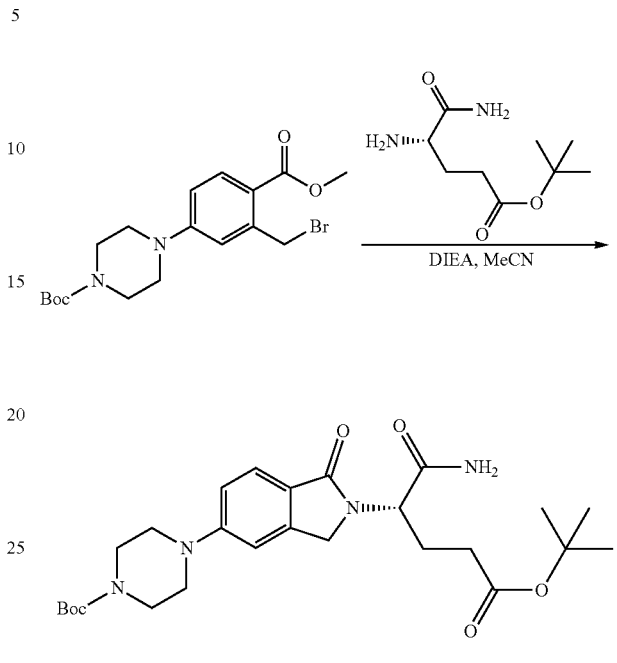

To a solution of tert-butyl 4-[3-(bromomethyl)-4-methoxycarbonyl-phenyl]piperazine-1-carboxylate (1.5 g, 3.63 mmol, 1 eq, prepared in step 15, Exemplary Compound 62) in acetonitrile (30 mL) was added tert-butyl (4S)-4,5-diamino-5-oxo-pentanoate (1.10 g, 5.44 mmol, 1.5 eq) and diisopropylethylamine (1.41 g, 10.89 mmol, 1.90 mL, 3 eq). The mixture was stirred at 80° C. for 12 hours. LC-MS showed the reaction was completed. The mixture was diluted with water (30 mL) and extracted with ethyl acetate (20 mL×3). The combined organic layers was washed with brine (30 mL×2), dried with anhydrous sodium sulfate, filtered and the filtrate was concentrated in vacuum. The residue was purified by preparative reverse phase HPLC (column: Phenomenex Synergi Max-RP 250×50 mm, 10 micron; mobile phase: [water (0.225% formic acid)-acetonitrile]; B %: 40 acetonitrile %-70 acetonitrile % in 30 min) to provide tert-butyl 4-[2-[(1 S)-4-tert-butoxy-1-carbamoyl-4-oxo-butyl]-1-oxo-isoindolin-5-yl]piperazine-1-carboxylate (1.6 g, 2.94 mmol, 81.05% yield, 92% purity) as an off-white solid. LC-MS (ESI) m/z: 503.2 [M+1].

Step 4: Preparation of (3S)-3-(1-oxo-5-piperazin-1-yl-isoindolin-2-yl) piperidine-2,6-dione

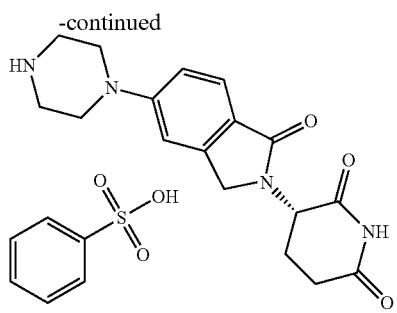

To a solution of tert-butyl 4-[2-[(1S)-4-tert-butoxy-1-carbamoyl-4-oxo-butyl]-1-oxo- isoindolin-5-yl]piperazine-1-carboxylate (700 mg, 1.39 mmol, 1 eq) in acetonitrile (15 mL) was added benzenesulfonic acid (440 mg, 2.79 mmol, 2 eq). The mixture was stirred at 85° C. for 12 hours. LC-MS showed the reaction was completed. The mixture was concentrated in vacuum. The residue was triturated with ethyl acetate (30 mL×3) to get (3S)-3-(1-oxo-5-piperazin-1-yl-isoindolin-2-yl)piperidine-2,6-dione (630 mg, crude) as a gray solid. LC-MS (ESI) m/z: 329.1 [M+1]$^+$; 100% ee from chiral SFC analysis.

Step 5: Preparation of (3S)-3-[5-[4-[[1-[4-[(1R,2S)-6-hydroxy-2-phenyl-tetralin-1-yl]phenyl]-4-piperidyl]methyl]piperazin-1-yl]-1-oxo-isoindolin-2-yl]piperidine-2,6-dione (Exemplary Compound 411)

was added sodium acetate (854 mg, 10.41 mmol, 3 eq) in one portion at 20° C. The mixture was stirred at 20° C. for 10 minutes. Then 1-[4-[(1R,2S)-6-hydroxy-2-phenyl-tetralin-1-yl]phenyl]piperidine-4-carbaldehyde (1 g, 2.43 mmol, 0.7 eq, prepared as described for Exemplary Compound 341) was added. The mixture was stirred at 20° C. for 10 minutes. After that, acetic acid (0.2 mL) and sodium cyanoborohydride (436 mg, 6.94 mmol, 2 eq) was added in one portion. The mixture was stirred at 20° C. for 40 minutes. The mixture was concentrated in vacuum, and 50 mL of tetrahydrofuran and 20 mL of water were added. The mixture was stirred for 20 minutes. Saturated aqueous sodium bicarbonate solution was added to adjust the pH to 8-9. The aqueous phase was extracted with ethyl acetate and tetrahydrofuran (v:v=2:1, 60 mL×3). The combined organic phase was washed with brine (60 mL×1), dried with anhydrous sodium sulfate, filtered and concentrated in vacuum. The residue was purified by preparative reverse phase HPLC (column: Phenomenex luna C18 250×50 mm, 10 micron; mobile phase: [water (0.225% formic acid)-acetonitrile]; B %: 20%-50% in 30 min). The product (3S)-3-[5-[4-[[1-[4-[(1R,2S)-6-hydroxy-2-phenyl-tetralin-1-yl]phenyl]-4-piperidyl]methyl] piperazin-1-yl]-1-oxo-isoindolin-2-yl]piperidine-2,6-dione (964 mg, 1.23 mmol, 35% yield, 98% purity, formate) was obtained as a white solid of formic acid salt after lyophilization. Chiral purity was analyzed by chiral SFC (Chiralcel OJ-3 50×4.6 mm, 3 micron; mobile phase: 50% ethanol (0.05% DEA) in $CO_2$; flow rate: 3 mL/min, wavelength: 220 nm) and observed $t_p$=2.89 min with de over 95%. [α$\square$$_D$=−267.5 (c=0.2 in DMF, 25° C.). LC-MS (ESI)

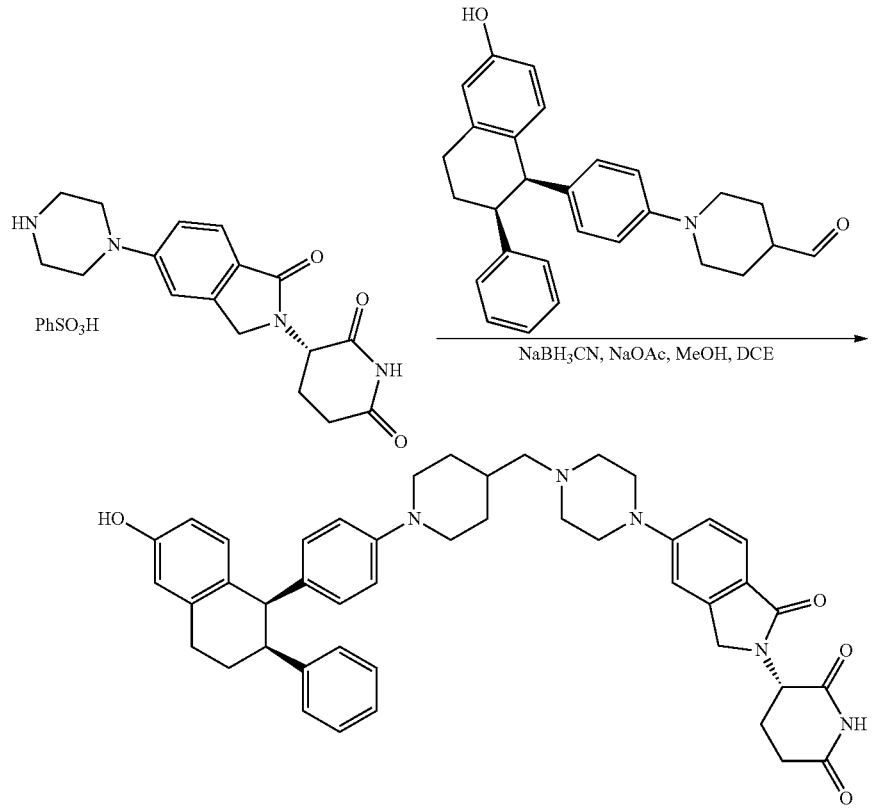

To a mixture of (3S)-3-(1-oxo-5-piperazin-1-yl-isoindolin-2-yl)piperidine-2,6-dione (1.30 g, 3.47 mmol, 1 eq, benzene sulfonate) in dichloromethane (8 mL) and methanol (32 mL) m/z: 724.2 [M+1]$^+$. $^1$H NMR (400 MHz, DMSO-d$_6$) δ10.94 (s, 1H), 8.16 (s, 1H, formate), 7.51 (d, J=8.8 Hz, 1H), 7.21-6.98 (m, 5H), 6.83 (d, J-6.4 Hz, 2H), 6.68-6.57 (m, 2H), 6.56-6.44 (m, 3H), 6.20 (d, J=8.8 Hz, 2H), 5.04 (dd, J=5.2, 13.2 Hz, 1H), 4.32 (d, J=16.8 Hz, 1H), 4.19 (d, J=17.2 Hz, 1H), 4.12 (d, J=4.8 Hz, 1H), 3.51 (br d, J=10.0 Hz, 4H), 3.27 (br s, 8H), 3.03-2.82 (m, 3H), 2.63-2.54 (m, 1H), 2.43-2.28 (m, 2H), 2.19 (d, J=6.8 Hz, 2H), 2.15-2.02 (m, 1H), 2.01-1.89 (m, 1H), 1.83-1.51 (m, 4H), 1.28-1.04 (m, 2H).

The free non-salt form $^1$H-NMR (400 MHz, DMSO-d$_6$) δ 10.93 (s, 1H), 9.09 (s, 1H), 7.51 (d, J=8.8 Hz, 1H), 7.18-7.09 (m, 3H), 7.08-7.02 (m, 2H), 6.83 (d, J=6.4 Hz, 2H), 6.64 (d, J=8.4 Hz, 1H), 6.60 (d, J=2.0 Hz, 1H), 6.53 (d, J=8.8 Hz, 2H), 6.48 (dd, J=2.4, 8.4 Hz, 1H), 6.20 (d, J=8.8 Hz, 2H), 5.04 (dd, J=5.2, 13.2 Hz, 1H), 4.39-4.27 (m, 1H), 4.24-4.15 (m, 1H), 4.12 (d, J=4.8 Hz, 1H), 3.51 (d, J=9.6 Hz, 2H), 3.29-3.24 (m, 5H), 3.03-2.83 (m, 3H), 2.62-2.54 (m, 4H), 2.52 (s, 3H), 2.41-2.36 (m, 1H), 2.19 (d, J=7.2 Hz, 2H), 2.15-2.08 (m, 1H), 2.00-1.89 (m, 1H), 1.81-1.58 (m, 4H), 1.22-1.06 (m, 2H).

Synthesis of (3R)-3-[5-[4-[[4-4[(1R,2S)-6-hydroxy-2-phenyl-tetralin-1-yl]phenyl]-4-piperidyl] methyl] piperazin-1-yl]-1-oxo-isoindolin-2-yl] piperidine-2,6-dione (Exemplary Compound 413)

(1-oxo-5-piperazin-1-yl-isoindolin-2-yl)piperidine-2,6-dione. The chiral purity of the isolated formic acid salt was analyzed by chiral SFC under the same condition as described in compound 411 and observed t$_p$=2.12 min with de 100%. [α]$_D$=−224.1 (c=0.1 in DMF, 25° C.). LC-MS (ESI) m/z: 724.3 [M+1]$^+$; $^1$H NMR (400 MHz, DMSO-d$_6$) δ 10.95 (s, 1H), 9.11 (s, 1H, phenol), 8.15 (s, 0.9H, formate), 7.53 (d, J=8.4 Hz, 1H), 7.19-7.10 (m, 3H), 7.09-7.01 (m, 2H), 6.85 (d, J=7.2 Hz, 2H), 6.69-6.59 (m, 2H), 6.57-6.45 (m, 3H), 6.21 (d, J=8.4 Hz, 2H), 5.05 (dd, J=5.2, 13.2 Hz, 1H), 4.33 (d, J=16.8 Hz, 1H), 4.20 (d, J=16.8 Hz, 1H), 4.14 (d, J=4.4 Hz, 1H), 3.52 (br d, 4H), 3.40-3.25 (br, 8H), 3.05-2.83 (m, 3H), 2.59 (m, 1H), 2.47-2.30 (m, 2H), 2.23 (d, J=6.8 Hz, 2H), 2.16-2.01 (m, 1H), 2.00-1.91 (m, 1H), 1.82-1.62 (m, 4H), 1.25-1.11 (m, 2H).

The free non-salt form $^1$H NMR (400 MHz, DMSO-d$_6$) δ 10.93 (s, 1H), 9.09 (s, 1H), 7.51 (d, J=8.8 Hz, 1H), 7.20-7.08 (m, 3H), 7.08-7.02 (m, 2H), 6.83 (d, J=6.4 Hz, 2H), 6.64 (d, J=8.4 Hz, 1H), 6.60 (d, J=2.4 Hz, 1H), 6.53 (d, J=8.8 Hz, 2H), 6.48 (dd, J=2.4, 8.4 Hz, 1H), 6.20 (d, J=8.8 Hz, 2H), 5.04 (dd, J=5.2, 13.2 Hz, 1H), 4.32 (d, J=17.2 Hz, 1H), 4.19 (d, J=17 Hz, 1H), 4.12 (d, J=4.8 Hz, 1H), 3.51 (br d, J=10.0

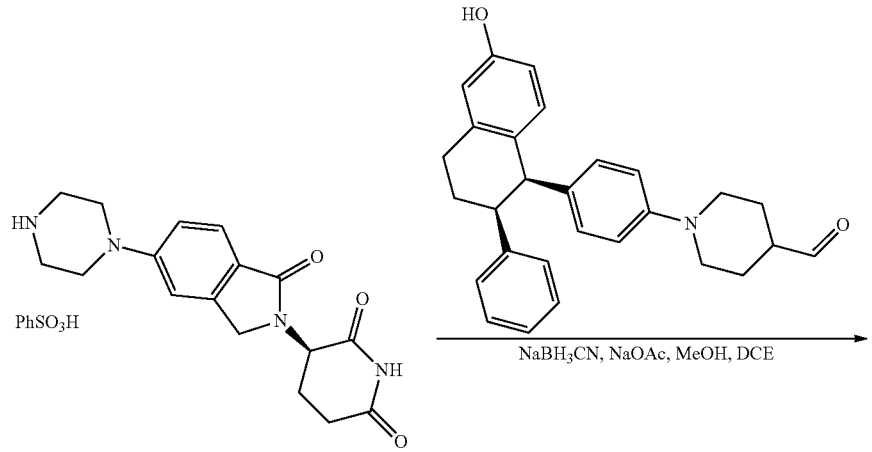

This compound (formic acid salt) was made using the same procedure as described in the preparation of compound 411 except (2R)-2-(benzyloxycarbonylamino)-5-tert-butoxy-5-oxo-pentanoic acid was used in the preparation of (3R)-3-

Hz, 2H), 3.29-3.24 (m, 5H), 3.03-2.83 (m, 3H), 2.62-2.54 (m, 4H), 2.52 (br s, 3H), 2.41-2.36 (m, 1H), 2.19 (d, J=7.2 Hz, 2H), 2.15-2.08 (m, 1H), 2.00-1.89 (m, 1H), 1.81-1.58 (m, 4H), 1.22-1.06 (m, 2H).

Synthesis of 3-[5-[4-[[1-[2-fluoro-4-[(1R,2S)-6-hydroxy-2-phenyl-tetralin-1-yl]phenyl]-4-piperidyl]methyl]piperazin-1-yl]-1-oxo-isoindolin-2-yl] piperidine-2,6-dione (Exemplary Compound 419)
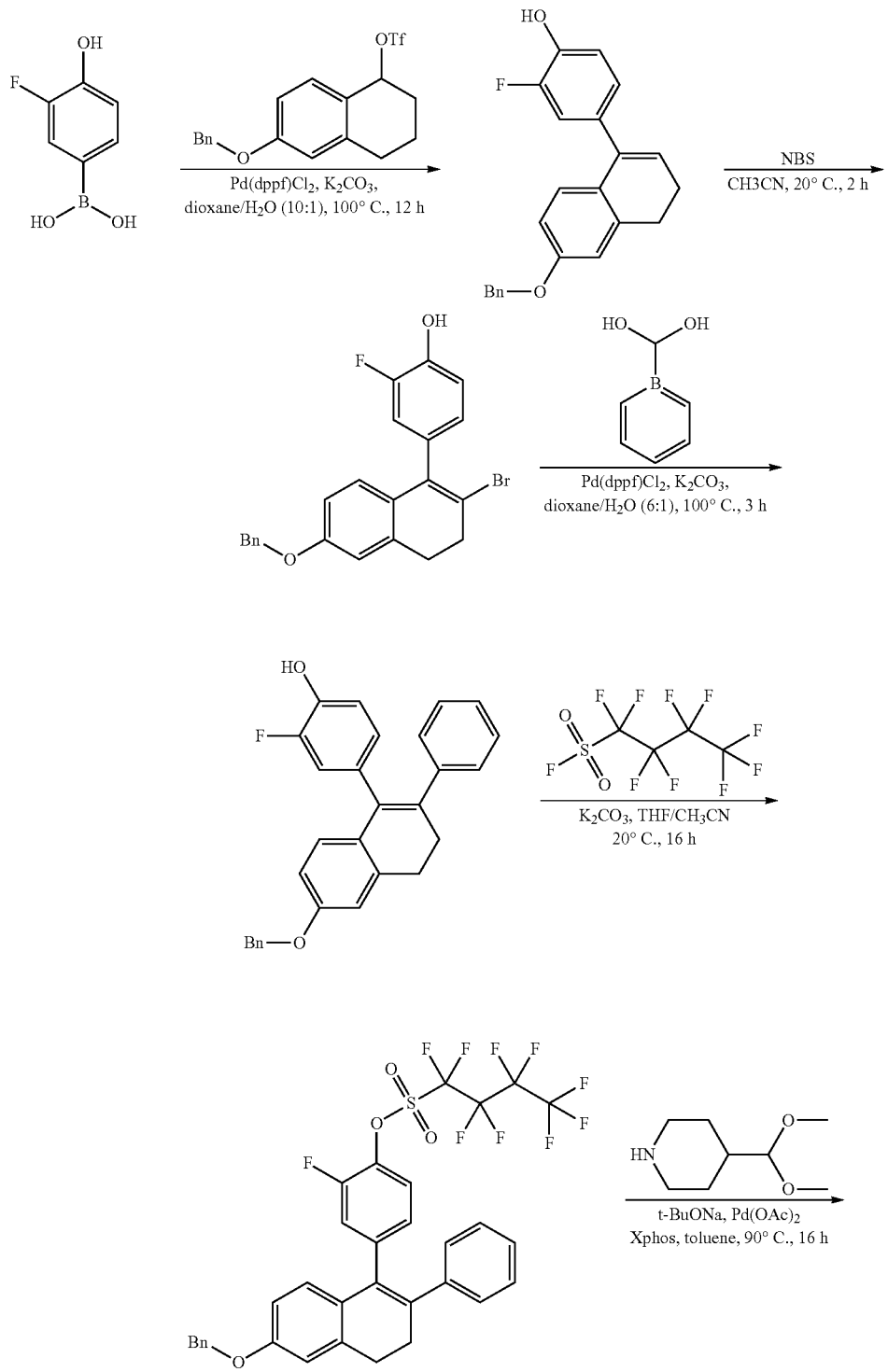

US 10,647,698 B2
1059                                              1060
-continued
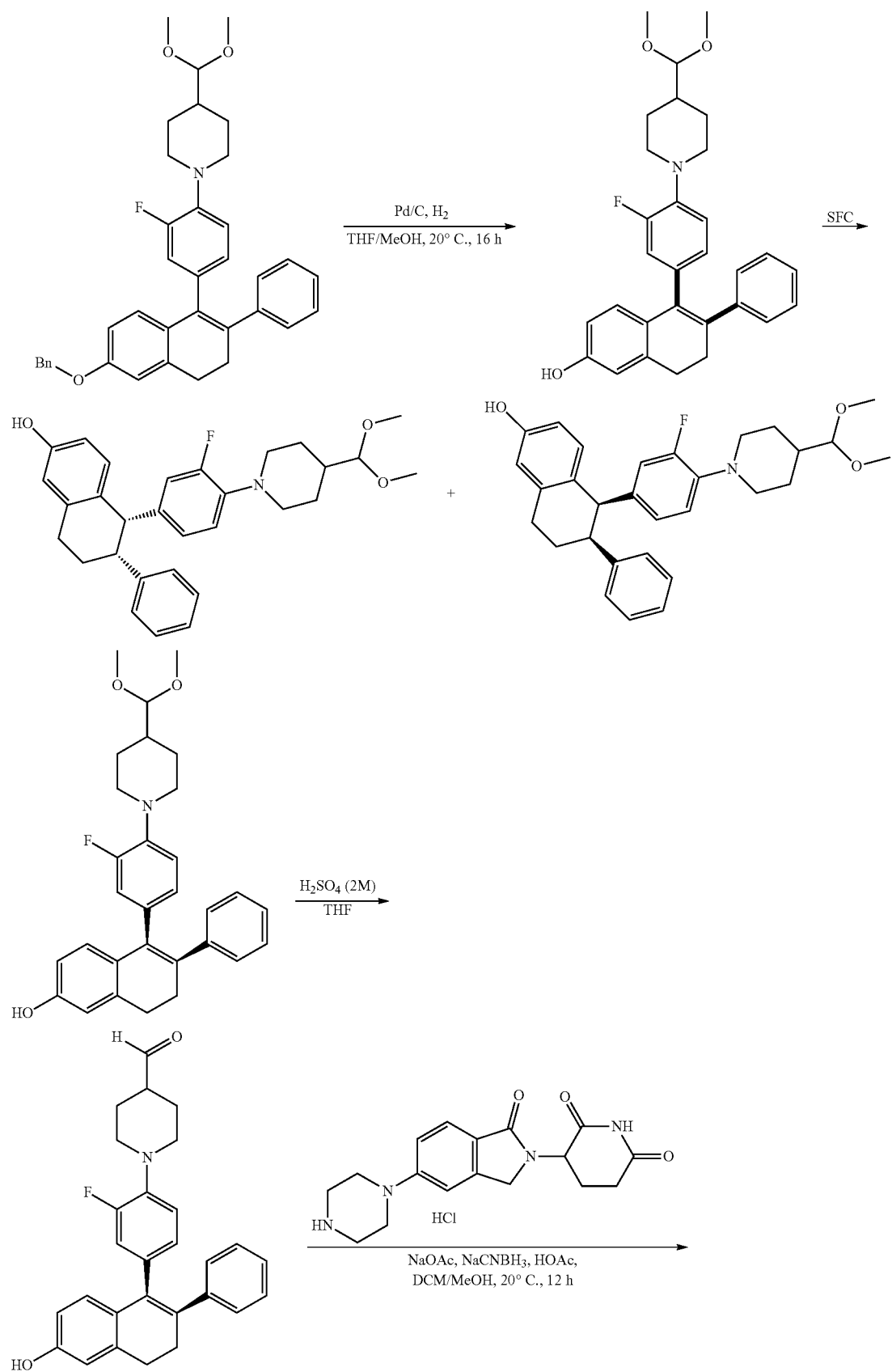

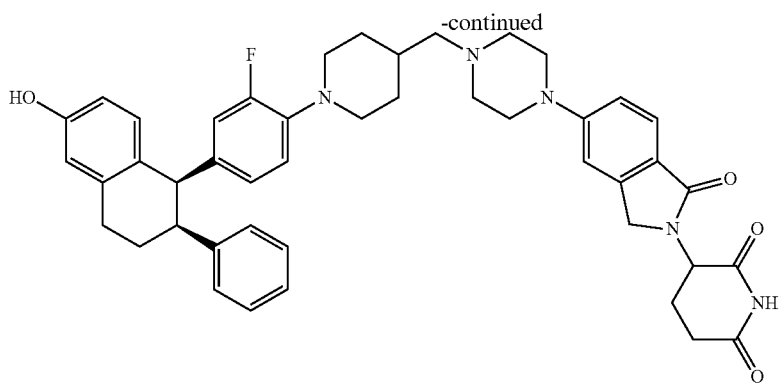

Using the synthetic route described above under the same conditions described for Exemplary Compound 341 (except 3-F-4-hydroxyphenyl boronic acid was used instead of 4-hydroxyphenyl boronic acid), 3-[5-[4-[[1-[2-fluoro-4-[((1R,2S)-6-hydroxy-2-phenyl-tetralin-1-yl]phenyl]-4-piperidyl]methyl]piperazin-1-yl]-1-oxo-isoindolin-2-yl]piperidine-2,6-dione (76.0 mg, 0.09 mmol, 50% yield in the last step) was obtained as a white solid of formic acid salt. LC-MS (ESI) m/z: 742.3 [M+1]+; 1H-NMR (400 MHz, DMSO-d6) δ 10.95 (s, 1H), 8.18 (s, 0.9H, formate), 7.51 (d, J=8.8 Hz, 1H), 7.20-7.12 (m, 3H), 7.06-7.04 (m, 2H), 6.86 (d, J=6.5 Hz, 2H), 6.67-6.61 (m, 3H), 6.49 (dd, J=2.4, 8.4 Hz, 1H), 6.09 (dd, =1.6, 8.0 Hz, 1H), 5.96 (d, J=14.4 Hz, 1H), 5.04 (dd, J=5.2, 13.2 Hz, 1H), 4.32 (d, J=17.2 Hz, 1H), 4.22-4.17 (m, 2H), 3.34-3.11 (m, 13H), 3.00-2.87 (m, 3H), 2.60-2.54 (m, 1H), 2.43-2.35 (m, 1H), 2.20 (d, J=6.8 Hz, 2H), 2.08-1.94 (m, 2H), 1.77-1.55 (m, 4H), 1.25-1.15 (m, 2H).

Synthesis of (3S)-3-15-[4-[[1-[2-fluoro-4-[(1R,2S)-6-hydroxy-2-phenyl-tetralin-1-yl]phenyl]-4-piperidyl]methyl]piperazin-1-yl]-1-oxo-isoindolin-2-yl]piperidine-2,6-dione (Exemplary Compound 524)

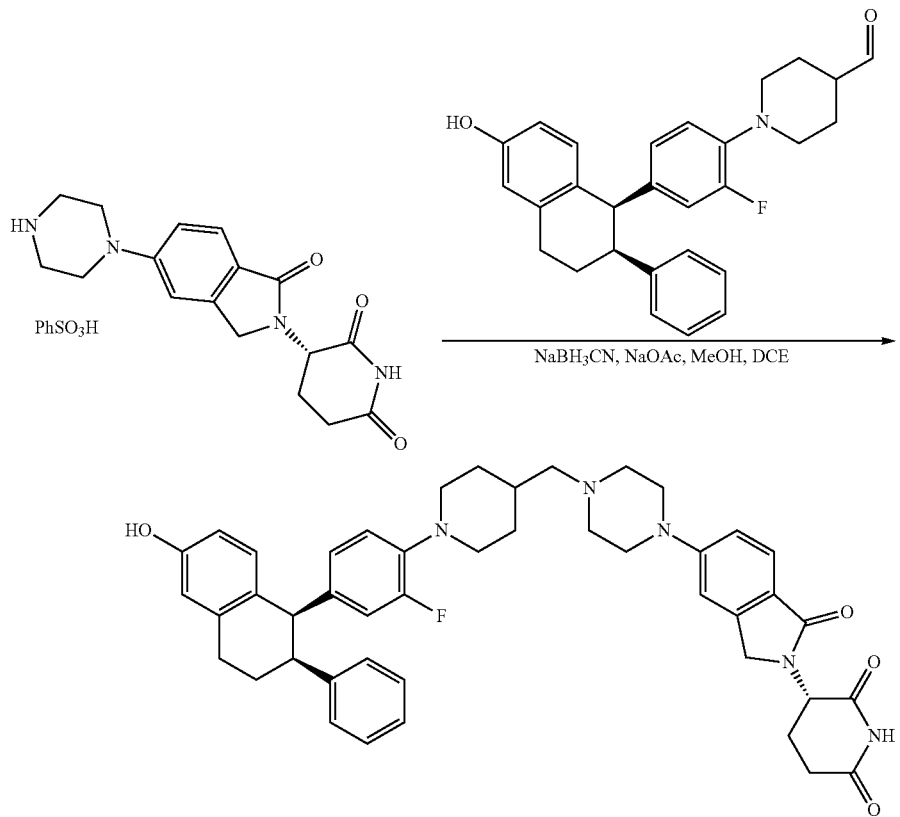

To a mixture of (3S)-3-(1-oxo-5-piperazin-1-yl-isoindolin-2-yl)piperidine-2,6-dione (1.24 g, 3.33 mmol, 1 eq, benzene sulfonate) in dichloromethane (8 mL) and methanol (32 mL) was added sodium acetate (818 mg, 9.98 mmol, 3 eq) in one portion at 20° C. The mixture was stirred at 20° C. for 10 min. 1-[2-Fluoro-4-[(1R,2S)-6-hydroxy-2-phenyl-tetralin-1-yl]phenyl]piperidine-4-carbaldehyde (1 g, 2.33 mmol, 0.7 eq) was added. The mixture was stirred at 20° C. for 10 min. Then acetic acid (0.2 mL) and sodium cyanoborohydride (418 mg, 6.65 mmol, 2 eq) was added in one portion. The mixture was stirred at 20° C. for 40 min. The mixture was concentrated in vacuum. Then 50 mL of tetrahydrofuran and 20 mL of water were added and the mixture was stirred for 20 min. Saturated aqueous sodium bicarbonate solution was added to adjust pH to 8-9. The aqueous phase was extracted with ethyl acetate and tetrahydrofuran (v:v=2:1, 60 mL×3). The combined organic phase was washed with brine (60 mL×1), dried with anhydrous sodium sulfate, filtered and concentrated in vacuum. The residue was purified by preparative reverse phase HPLC (column: Phenomenex luna C18 250×50 mm, 10 micron; mobile phase: [water (0.225% formic acid)-acetonitrile]; B %: 26%-56% in 30 min). The product (3S)-3-[5-[4-[[1-[2-fluoro-4-[(1R,2S)-6-hydroxy-2-phenyl-tetralin-1-yl]phenyl]-4-piperidyl]methyl] piperazin-1-yl]-1-oxo-isoindolin-2-yl]piperidine-2,6-dione (909 mg, 1.12 mmol, 33% yield, 96% purity, formate salt) was obtained as a white solid after lyophilization. Chiral purity was analyzed by chiral SFC (Chiralcel OJ-3, 50×4.6 mm 3 um; mobile phase: 50% ethanol (0.05% DEA) in $CO_2$; flow rate: 3 mL/min; wavelength: 220 nm) and observed $t_p$=2.89 min with diastereomeric purity (de) over 95%. $[\alpha]_D$=−256.8 (c=0.2 in DMF, 25° C.).

LC-MS (ESI) m/z: 742.2 [M+1]$^+$; $^1$H NMR (400 MHz, DMSO-$d_6$) δ 10.94 (s, 1H), 8.15 (s, 0.7H, formate), 7.51 (d, J=8.8 Hz, 1H), 7.24-7.10 (m, 3H), 7.09-6.97 (m, 2H), 6.86 (d, J=6.8 Hz, 2H), 6.72-6.57 (m, 3H), 6.50 (dd, J=2.4, 8.4 Hz, 1H), 6.09 (d, J=8.4 Hz, 1H), 6.01-5.90 (m, 1H), 5.04 (dd, J=5.2, 13.2 Hz, 1H), 4.32 (d, J=17 Hz, 1H), 4.22-4.18 (m, 2H), 3.35-3.23 (m, 9H), 3.19 (d, J=8.4 Hz, 3H), 3.09-2.78 (m, 3H), 2.63-2.54 (m, 1H), 2.42-2.28 (m, 2H), 2.20 (d, J=6.8 Hz, 2H), 2.14-2.00 (m, 1H), 1.99-1.89 (m, 1H), 1.84-1.52 (m, 4H), 1.32-1.10 (m, 2H).

The free non-salt form $^1$H NMR (400 MHz, DMSO-$d_6$) δ 10.94 (s, 1H), 9.15 (s, 1H), 7.51 (d, J=8.4 Hz, 1H), 7.23-7.10 (m, 3H), 7.09-7.01 (m, 2H), 6.86 (d, J=6.8 Hz, 2H), 6.72-6.56 (m, 3H), 6.50 (d, J=7.6 Hz, 1H), 6.09 (d, J=8.0 Hz, 1H), 5.97 (d, J=14.0 Hz, 1H), 5.04 (dd, J=4.8, 13.2 Hz, 1H), 4.38-4.27 (m, 1H), 4.24-4.19 (m, 1H), 4.18 (s, 1H), 3.30-3.23 (m, 5H), 3.23-3.15 (m, 2H), 3.06-2.81 (m, 3H), 2.65-2.54 (m, 4H), 2.52-2.51 (m, 3H), 2.42-2.34 (m, 1H), 2.20 (d, J=7.2 Hz, 2H), 2.13-2.01 (m, 1H), 2.00-1.91 (m, 1H), 1.84-1.70 (m, 3H), 1.68-1.54 (m, 1H), 1.24-1.11 (m, 2H).

Synthesis of (3R)-3-(5-14-[[1-12-fluoro-4-[(1R,2S)-6-hydroxy-2-phenyl-tetralin-1-yl]phenyl]-4-piperidyl]methyl]piperazin-1-yl]-1-oxo-isoindolin-2-yl] piperidine-2,6-dione (Exemplary Compound 525)

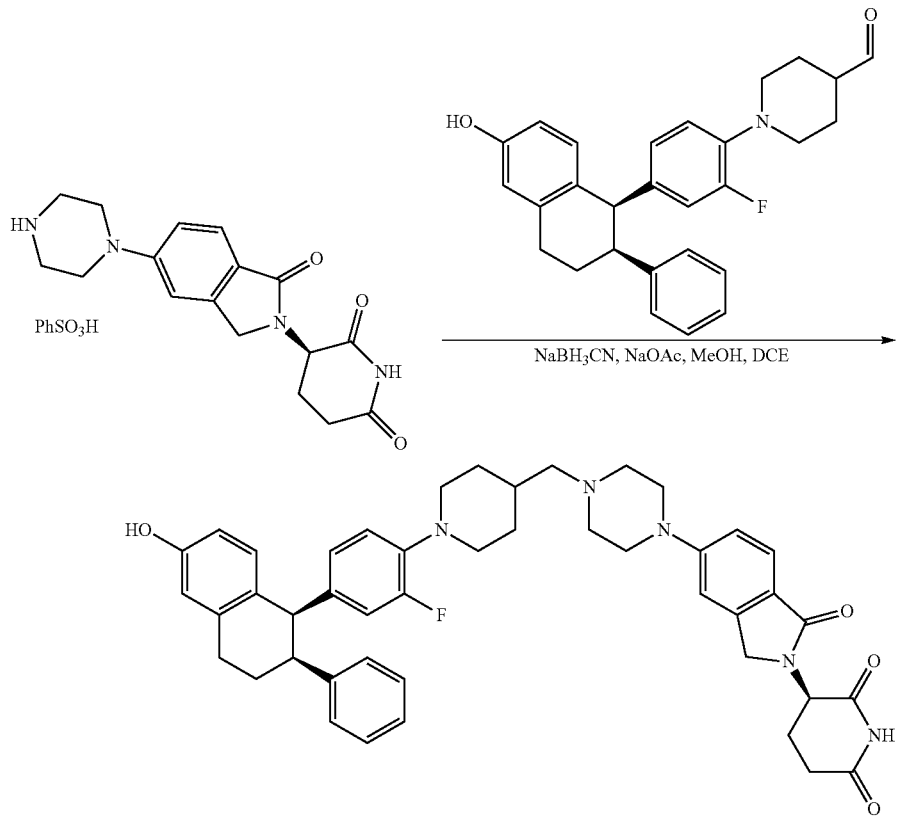

This compound was prepared using the same procedure as described for Exemplary Compound 524 except (3R)-3-(1-oxo-5-piperazin-1-yl-isoindolin-2-yl) piperidine-2,6-dione was used. The purified formic acid salt was analyzed by chiral SFC under the same condition as in compound 524, $t_p$=1.76 min, de 100%). [α]$_D$=−231.6 (c=0.1 in DMF, 25° C.). LC-MS (ESI) m/z: 742.3 [M+1]$^+$; $^1$H NMR (400 MHz, DMSO-d$_6$) δ 10.94 (s, 1H), 9.16 (s, 1H), 8.13 (s, 0.35H, formate), 7.53 (d, J=8.4 Hz, 1H), 7.20-7.10 (m, 3H), 7.08-7.00 (m, 2H), 6.86 (d, J=6.8 Hz, 2H), 6.68-6.60 (m, 3H), 6.50 (m, 1H), 6.09 (d, J=8.4 Hz, 1H), 5.97 (d, J=14.4 Hz, 1H), 5.04 (dd, J=5.2, 13.2 Hz, 1H), 4.33 (d, J=17.2 Hz, 1H), 4.22-4.15 (m, 2H), 3.42-3.35 (m, 6H), 3.20 (br d, J=8.4 Hz, 3H), 3.01-2.81 (m, 4H), 2.76-2.51 (m, 4H), 2.42-2.25 (m, 3H), 2.15-1.88 (m, 2H), 1.80-1.51 (m, 4H), 1.30-1.15 (m, 2H).

The free non-salt form $^1$H NMR (400 MHz, DMSO-d$_6$) δ: 10.93 (s, 1H), 9.15 (s, 1H), 7.51 (d, J=8.8 Hz, 1H), 7.23-7.09 (m, 3H), 7.08-7.01 (m, 2H), 6.86 (d, J=6.4 Hz, 2H), 6.69-6.63 (m, 2H), 6.63-6.60 (m, 1H), 6.50 (dd, J=2.4, 8.4 Hz, 1H), 6.09 (d, J=8.4 Hz, 1H), 5.97 (d, J=14.0 Hz, 1H), 5.04 (dd, J=5.2, 13.2 Hz, 1H), 4.37-4.27 (m, 1H), 4.24-4.19 (m, 1H), 4.18 (s, 1H), 3.30-3.23 (m, 5H), 3.23-3.15 (m, 2H), 3.06-2.81 (m, 3H), 2.65-2.54 (m, 4H), 2.52-2.51 (m, 3H), 2.42-2.34 (m, 1H), 2.20 (d, J=7.2 Hz, 2H), 2.13-2.01 (m, 1H), 2.00-1.91 (m, 1H), 1.84-1.70 (m, 3H), 1.68-1.54 (m, 1H), 1.24-1.11 (m, 2H).

Synthesis of 3-[5-[4-[[1-[3-fluoro-4-[(1S,2S)-6-hydroxy-2-phenyl-tetralin-1-yl]phenyl]-4-piperidyl]methyl]piperazin-1-yl]-1-oxo-isoindolin-2-yl]piperidine-2,6-dione (Exemplary Compound 496)

Step 1: Preparation of [1-(4-bromo-3-fluoro-phenyl)-4-piperidyl]methanol

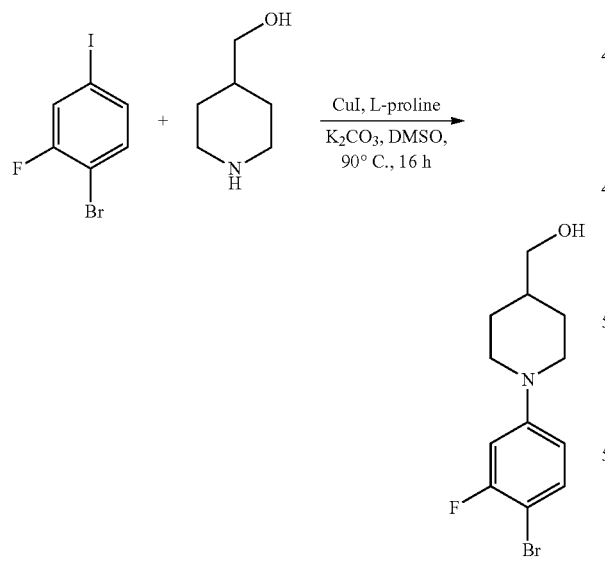

1-Bromo-2-fluoro-4-iodo-benzene (25 g, 83.09 mmol, 1 eq), 4-piperidylmethanol (10.53 g, 91.39 mmol, 1.1 eq), L-proline (3.83 g, 33.23 mmol, 0.4 eq), copper(I) iodide (3.16 g, 16.62 mmol, 0.2 eq) and potassium carbonate (22.97 g, 166.17 mmol, 2 eq) in DMSO (400 mL) was de-gassed and then heated to 90° C. for 10 hours under nitrogen. The mixture was diluted with ethyl acetate (500 mL), washed with saturated ammonium chloride solution (150 mL), dried over anhydrous sodium sulfate and filtered. The filtrate was concentrated in vacuum. The residue was purified by silica gel chromatography (petroleum ether/ethyl acetate=10/1 to 2/1) to afford [1-(4-bromo-3-fluoro-phenyl)-4-piperidyl]methanol (5.02 g, 17.42 mmol, 21% yield) as a yellow solid. $^1$H NMR (400 MHz, METHANOL-d) δ 7.26-7.41 (m, 1H), 6.63-6.83 (m, 2H), 3.68-3.81 (m, 2H), 3.45 (d, J=6.40 Hz, 2H), 3.33 (s, 1H), 2.73 (br t, J=12.23 Hz, 2H), 1.84 (br d, J=12.92 Hz, 2H), 1.64 (br d, J=3.26 Hz, 1H), 1.33 (q, J=12.30 Hz, 2H).

Step 2: Preparation of 1-(4-bromo-3-fluoro-phenyl) piperidine-4-carbaldehyde

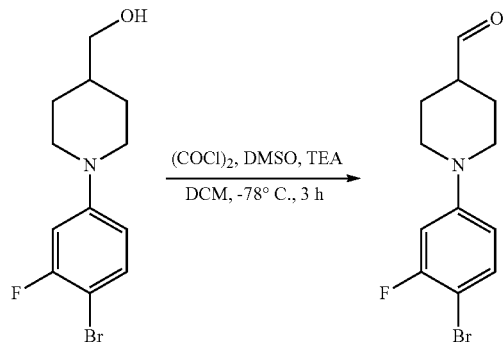 [SMILES: OCC1CCN(c2ccc(Br)c(F)c2)CC1 ; O=CC1CCN(c2ccc(Br)c(F)c2)CC1]

To a mixture of oxalyl dichloride (6.61 g, 52.06 mmol, 4.6 mL, 3 eq) in dichloromethane (50 mL) was added dropwise a solution of DMSO (5.42 g, 69.41 mmol, 5.4 mL, 4 eq) in dichloromethane (50 mL) at −68° C. When the addition was over, the mixture was stirred at −68° C. for 30 minutes. Then a solution of [1-(4-bromo-3-fluoro-phenyl)-4-piperidyl]methanol (5 g, 17.35 mmol, 1 eq) in dichloromethane (50 mL) was added dropwise to the reaction mixture. When the addition was over, the mixture was stirred at −68° C. for 1 hour. Then triethylamine (14.05 g, 138.81 mmol, 19.3 mL, 8 eq) was added dropwise at −68° C. The mixture was stirred □□ 25° C. for 16 hours. The reaction was clean according to TLC. Saturated sodium bicarbonate solution (80 mL) was added. The organic phase was washed with brine (300 mL), dried with anhydrous sodium sulfate, filtered and concentrated in vacuum. The residue was purified by silica gel chromatography (petroleum ether/ethyl acetate=100/1 to 10/1) to afford 1-(4-bromo-3-fluoro-phenyl)piperidine-4-carbaldehyde (4.98 g, crude) as a yellow oil.

Step 3: Preparation of 1-(4-bromo-3-fluoro-phenyl)-4-(dimethoxymethyl)piperidine

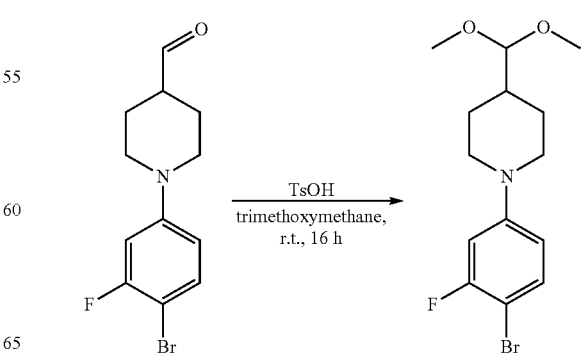

To a solution of 1-(4-bromo-3-fluoro-phenyl)piperidine-4-carbaldehyde (4.9 g, 17.12 mmol, 1 eq) in trimethoxymethane (38.72 g, 364.87 mmol, 40 mL, 21.31 eq) was added para-toluenesulfonic acid (147 mg, 0.85 mmol, 0.05 eq). The mixture was stirred at 25° C. for 16 hours. The reaction mixture was quenched with sodium bicarbonate solution, and then extracted with ethyl acetate 200 mL. The combined organic layers were washed with brine 200 mL, dried over anhydrous sodium sulfate, filtered and concentrated under reduced pressure. The residue was purified by silica gel chromatography (petroleum ether/ethyl acetate=1:0 to 30:1) to afford 1-(4-bromo-3-fluoro-phenyl)-4-(dimethoxymethyl)piperidine (4.6 g, 13.85 mmol, 81% yield) as a yellow oil. LC-MS (ESI) m/z: 331.9 [M+I]$^+$; $^1$H NMR (400 MHz, CDCl$_3$) δ 7.17-7.29 (m, 1H), 6.45-6.68 (m, 2H), 3.99 (d, J=7.03 Hz, 1H), 3.59 (br d, J=12.42 Hz, 2H), 3.30 (s, 6H), 2.62 (td, J=12.39, 2.45 Hz, 2H), 1.62-1.84 (m, 3H), 1.27-1.42 (m, 2H).

Step 4: Preparation of 4-(dimethoxymethyl)-1-[3-fluoro-4-(4,4,5,5-tetramethyl-1,3,2-dioxaborolan-2-yl)phenyl]piperidine

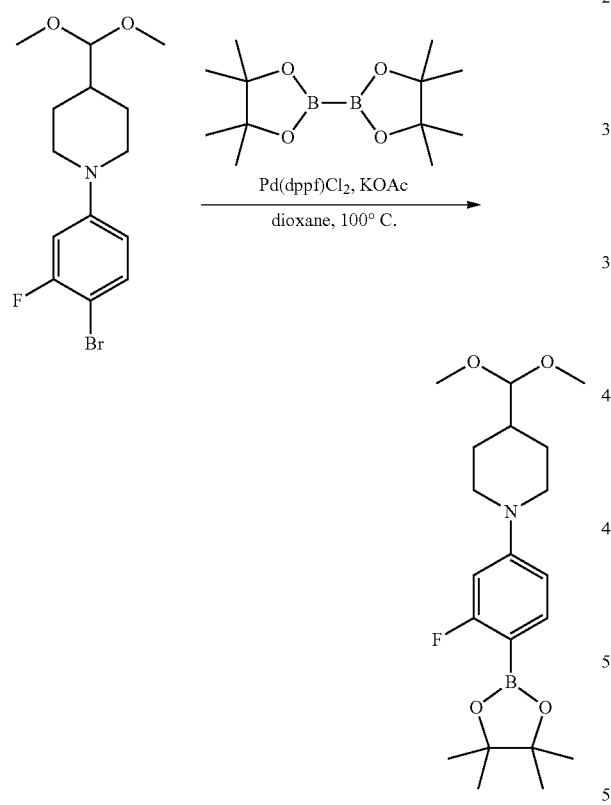

To a solution of 1-(4-bromo-3-fluoro-phenyl)-4-(dimethoxymethyl)piperidine (1 g, 3.01 mmol, 1 eq), 4,4,5,5-tetramethyl-2-(4,4,5,5-tetramethyl-1,3,2-dioxaborolan-2-yl)- 1,3,2-dioxaborolane (1.22 g, 4.82 mmol, 1.6 eq), potassium acetate (590 mg, 6.02 mmol, 2 eq) and 2-di-tert-butylphosphino-2,4,6- triisopropylbiphenyl (287 mg, 0.60 mmol, 0.2 eq) in dioxane (10 mL) was added palladium (II) acetate (81 mg, 0.36 mmol, 0.12 eq) under nitrogen. The mixture was stirred at 100° C. under nitrogen for 3 hours. The reaction mixture was concentrated under reduced pressure. The residue was purified by silica gel chromatography (petroleum ether/ethyl acetate=1:0 to 30:1) to provide 4-(dimethoxymethyl)-1-[3-fluoro-4-(4,4,5,5-tetramethyl-1,3,2-dioxaborolan-2-yl)phenyl]piperidine (800 mg, 2.11 mmol, 70% yield) as a gray solid.

Step 5: Preparation of 1-[4-(6-benzyloxy-3,4-dihydronaphthalen-1-yl)-3-fluoro-phenyl]-4-(dimethoxymethyl)piperidine

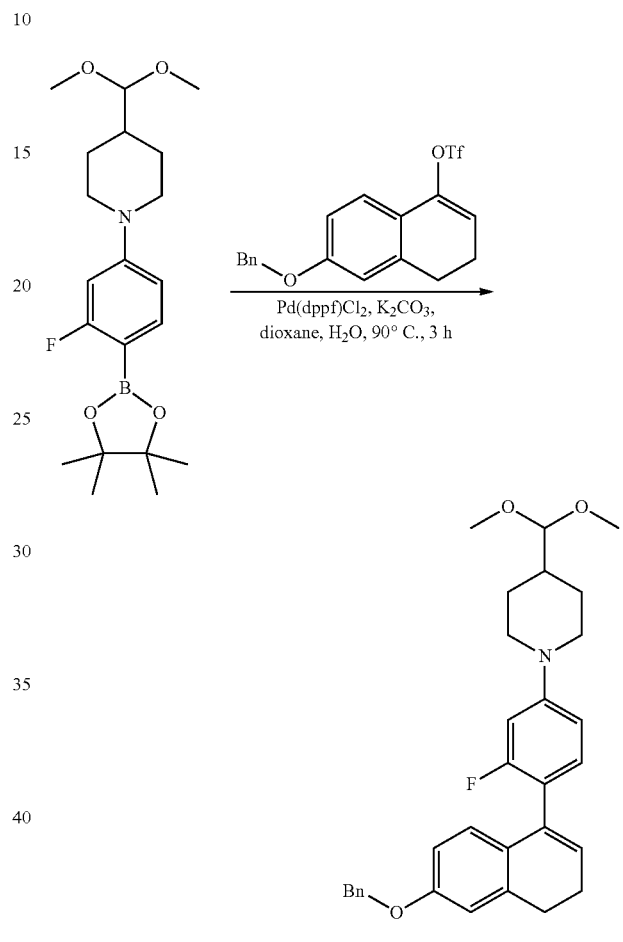

To a solution of 4-(dimethoxymethyl)-1-[3-fluoro-4-(4,4,5,5-tetramethyl-1,3,2-dioxaborolan-2-yl)phenyl]piperidine (700 mg, 1.85 mmol, 1 eq) and (6-benzyloxy-3,4-dihydronaphthalen-1-yl) trifluoromethanesulfonate (709 mg, 1.85 mmol, 1 eq) in dioxane (12 mL) and water (2 mL) was added [1,1'-bis(diphenylphosphino)ferrocene]dichloropalladium (II) (135 mg, 0.18 mmol, 0.1 eq) and potassium carbonate (765 mg, 5.54 mmol, 3 eq) under nitrogen. The mixture was stirred at 90° C. for 3 hours. The reaction mixture was filtered and concentrated under reduced pressure. The residue was purified by silica gel chromatography (petroleum ether/ethyl acetate=1:0 to 30:1) to afford 1-[4-(6-benzyloxy-3,4-dihydronaphthalen-1-yl)-3-fluoro-phenyl]-4-(dimethoxymethyl)piperidine (850 mg, 1.74 mmol, 94% yield) as a yellow solid. LC-MS (ESI) m/z: 488.1 [M+1]$^+$. $^1$H NMR (400 MHz, CDCl$_3$) δ 7.28-7.45 (m, 5H), 7.11 (t, J=8.60 Hz, 1H), 6.77-6.84 (m, 2H), 6.69 (ddd, J=8.60, 6.46, 2.51 Hz, 2H), 6.63 (dd, J=13.36, 2.45 Hz, 1H), 5.93 (t, J=4.52 Hz, 1H), 5.04 (s, 2H), 4.05-4.15 (m, 1H), 3.74 (br d, J=12.55 Hz, 2H), 3.36-3.40 (m, 6H), 2.83 (t, J=7.97 Hz, 2H), 2.72 (td, J=12.33, 2.45 Hz, 2H), 2.39 (td, J=7.91, 4.77 Hz, 2H), 1.71-1.89 (m, 3H), 1.40-1.51 (m, 2H).

Step 6: Preparation of 1-[4-(6-benzyloxy-2-bromo-3,4-dihydronaphthalen-1-yl)-3-fluoro-phenyl]-4-(dimethoxymethyl)piperidine

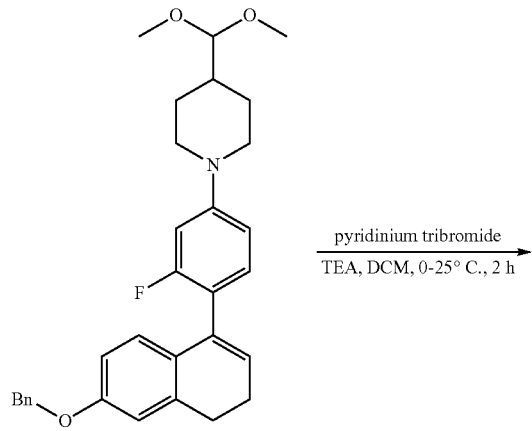

Step 7: Preparation of 1-[4-(6-benzyloxy-2-phenyl-3,4-dihydronaphthalen-1-yl)-3-fluoro-phenyl]-4-(dimethoxymethyl)piperidine

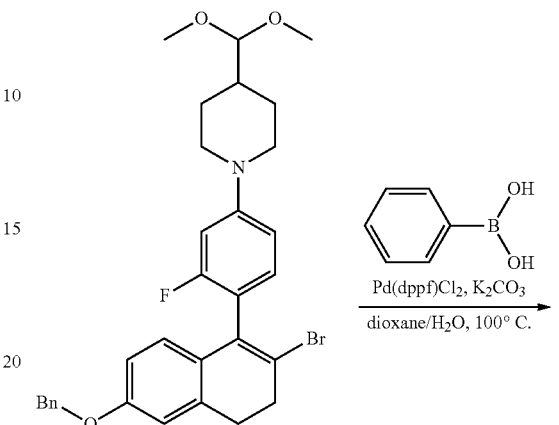

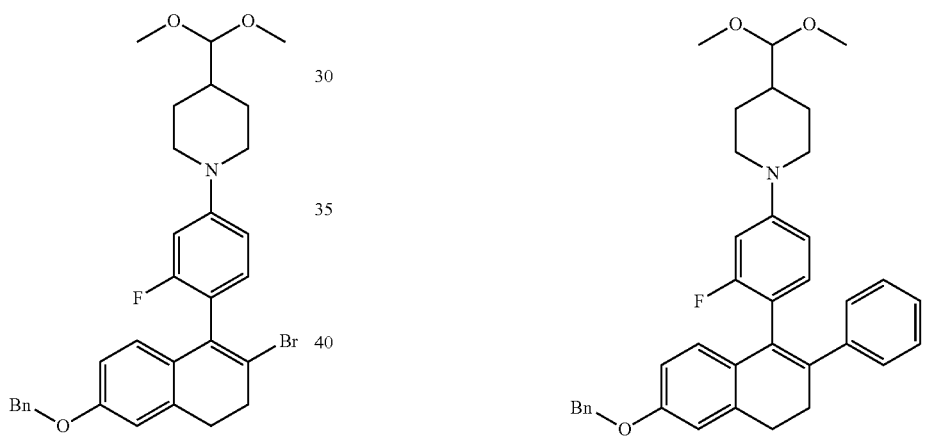

To a solution of 1-[4-(6-benzyloxy-3,4-dihydronaphthalen-1-yl)-3-fluoro-phenyl]-4-(dimethoxymethyl)piperidine (870 mg, 1.78 mmol, 1 eq) and triethylamine (270 mg, 2.68 mmol, 0.3 mL, 1.5 eq) in dichloromethane (20 mL) was added pyridinium tribromide (570 mg, 1.78 mmol, 1 eq) at 0° C. The mixture was stirred at 25° C. for 0.5 hour. The reaction was washed with aqueous sodium sulfite solution (40 mL) and extracted with dichloromethane (120 mL). The combined organic layers were washed with brine (100 mL), dried over sodium sulfate, filtered and concentrated under reduced pressure. The residue was purified by silica gel chromatography (petroleum ether/ethyl acetate=1:0 to 20:1) to give 1-[4-(6-benzyloxy-2-bromo-3,4-dihydronaphthalen-1-yl)-3-fluoro-phenyl]-4-(dimethoxymethyl)piperidine (680 mg, 1.20 mmol, 67% yield) as a yellow solid. LC-MS (ESI) m/z: 568.0 [M+1]$^+$.

To a solution of 1-[4-(6-benzyloxy-2-bromo-3,4-dihydronaphthalen-1-yl)-3-fluoro-phenyl]-4-(dimethoxymethyl)piperidine (680 mg, 1.20 mmol, 1 eq) and phenylboronic acid (146 mg, 1.20 mmol, 1 eq) in dioxane (18 mL) and water (3 mL) was added [1,1'-bis(diphenylphosphino)ferrocene]dichloropalladium (II) (87 mg, 0.12 mmol, 0.1 eq) and potassium carbonate (331 mg, 2.40 mmol, 2 eq). The mixture was stirred at 100° C. for 3 hours. The reaction mixture was filtered and concentrated under reduced pressure. The residue was purified by silica gel chromatography (petroleum ether/ethyl acetate=1:0 to 10:1) to provide 1-[4-(6-benzyloxy-2-phenyl-3,4-dihydronaphthalen-1-yl)-3-fluoro-phenyl]-4-(dimethoxymethyl)-piperidine (600 mg, 1.06 mmol, 88% yield) as a yellow oil. LC-MS (ESI) m/z: 564.2 [M+1]$^+$; $^1$H NMR (400 MHz, CDCl$_3$) δ 7.31-7.48 (m, 5H), 7.04-7.19 (m, 5H), 6.78-6.91 (m, 2H), 6.65-6.76 (m, 2H), 6.49-6.60 (m, 2H), 5.08 (s, 2H), 4.08-4.12 (m, 1H), 3.69 (br d, J=12.42 Hz, 2H), 3.34-3.45 (m, 6H), 2.88-3.08 (m, 2H), 2.73-2.88 (m, 2H), 2.68 (td, J=12.33, 2.32 Hz, 2H), 1.82-1.92 (m, 1H), 1.82-1.92 (m, 1H), 1.72-1.81 (m, 1H), 1.36-1.52 (m, 2H).

1071

Step 8: Preparation of 1-[4-[4-(dimethoxymethyl)-1-piperidyl]-2-fluoro-phenyl]-2-phenyl-tetralin-6-ol

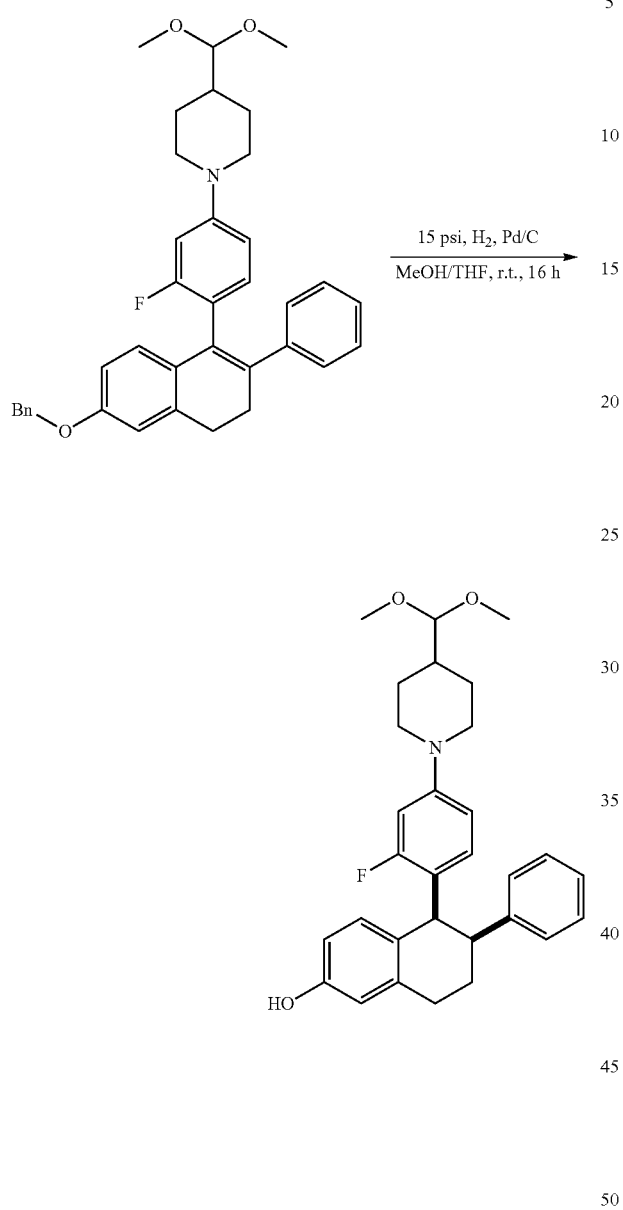

1072

Step 9: Preparation of (IS, 2S)-1-[4-[4-(dimethoxymethyl)-1-piperidyl]-2-fluoro-phenyl]-2-phenyl-tetralin-6-ol

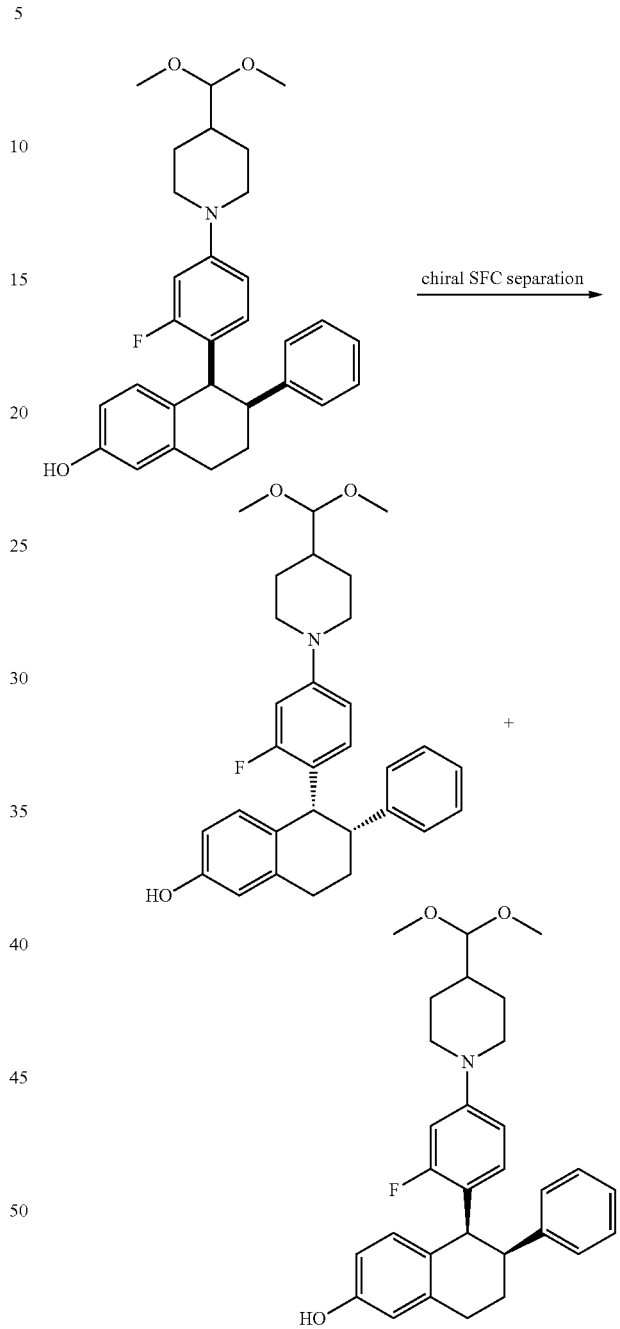

To a solution of 1-[4-(6-benzyloxy-2-phenyl-3,4-dihydronaphthalen-1-yl)-3-fluoro-phenyl]-4-(dimethoxymethyl) piperidine (680 mg, 1.21 mmol, 1 eq) in methanol (10 mL) and tetrahydrofuran (10 mL) was added 10% palladium on activated carbon catalyst under nitrogen. The mixture was stirred at 25° C. for 16 hours under hydrogen (15 psi). The residue was purified by prep-HPLC (column: Phenomenex Synergi C18 150×25 mm, 10 micron, mobile phase: [water (0.225% formic acid)-ACN]; B %: 35%-65% in 10 min). Compound cis-1-[4-[4-(dimethoxymethyl)-1-piperidyl]-2-fluoro-phenyl]-2-phenyl-tetralin-6-ol (450 mg, 0.94 mmol, 78% yield) was obtained as a yellow solid. LC-MS (ESI) m/z: 476.1 [M+1]$^+$.

1-[4-[4-(Dimethoxymethyl)-1-piperidyl]-2-fluoro-phenyl]-2-phenyl-tetralin-6-ol (450 mg, 0.94 mmol, 1 eq) was purified by SFC (column: AD, 250 mm×30 mm, 10 micron); mobile phase: [0.1% ammonium hydroxide in MeOH]; B %: 50%-50% in 3.7 min for each run, total 180 min). Compound (IS, 2S)-1-[4-[4-(dimethoxymethyl)-1-piperidyl]-2-fluoro-phenyl]-2-phenyl-tetralin-6-ol (170 mg, 0.35 mmol, 37% yield) was obtained as a yellow oil.

Step 10 and 11: Preparation of 3-[5-[4-[[1-[3-fluoro-4-[(1 S, 2S)-6-hydroxy-2-phenyl-tetralin-1-yl]phenyl]-4-piperidyl]methyl]piperazin-1-yl]-1-oxo-isoindolin-2-yl]piperidine-2,6-dione (Exemplary Compound 496)

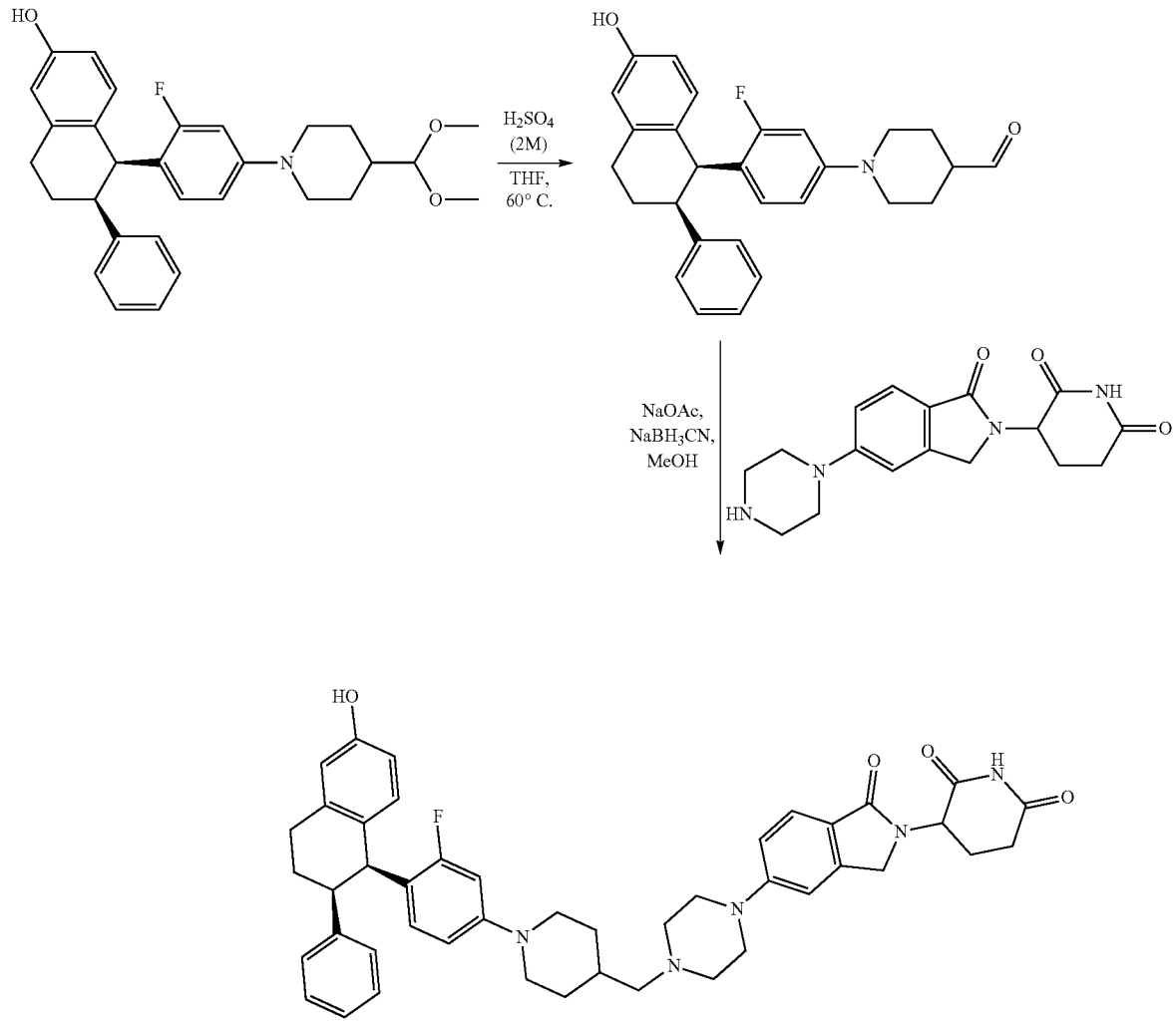

Using the same procedure as described in step 10 and step 11 for Exemplary Compound 341, compound 3-[5-[4-[[1-[3-fluoro-4-[(1 S,2S)-6-hydroxy-2-phenyl-tetralin-1-yl]phenyl]-4-piperidyl]methyl]piperazin-1-yl]-1-oxo-isoindolin-2-yl]piperidine-2,6-dione was obtained as a white solid of formic acid salt. LC-MS (ESI) m/z: 742.2 [M+1]$^+$; $^1$H NMR (400 MHz, DMSO-d$_6$) δ 10.94 (s, 1H, imide), 9.14 (br s, 1H, phenol), 8.20 (s, 0.45H, formate), 7.52 (d, J=8.8 Hz, 1H), 7.08-7.03 (m, 5H), 6.83 (m, 2H), 6.62 (m, 2H), 6.58-6.42 (m, 3H), 6.26 (br d, J=13.68 Hz, 1H), 5.04 (dd, J=13.36, 5.08 Hz, 1H), 4.45 (br d, J=5.02 Hz, 1H), 4.33 (d, J=16.8 Hz, 1H), 4.20 (d, J=16.8 Hz, 1H), 3.63-3.50 (m, 2H), 3.29-3.21 (m, 9H), 3.03-2.84 (m, 3H), 2.60 (br, 3H), 2.40-2.35 (m, 1H), 2.19 (br d, J=6.7 Hz, 3H), 2.01-1.91 (m, 1H), 1.79-1.64 (m, 4H), 1.20-1.07 (m, 2H).

What is claimed is:

1. A compound having the structure:

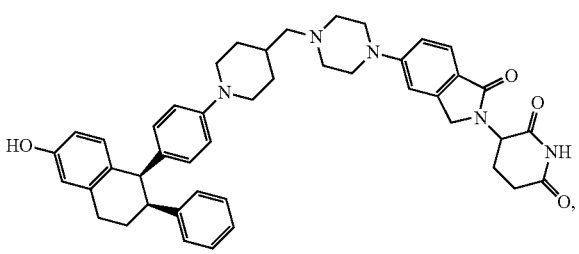

1075
-continued
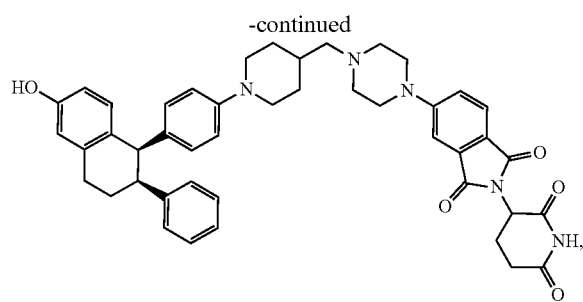
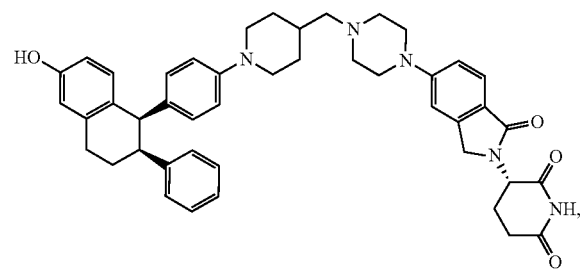
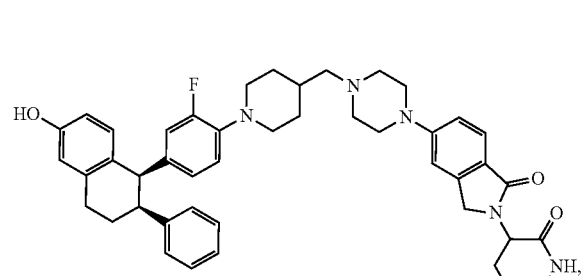
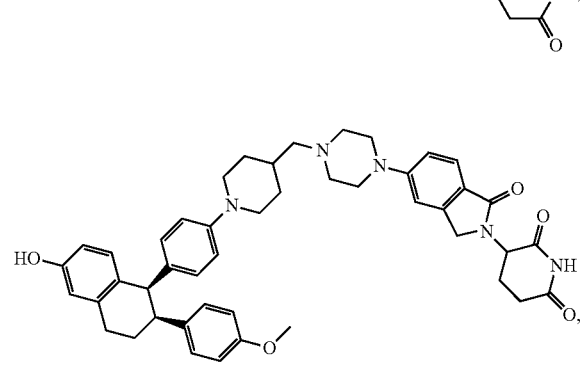
1076
-continued
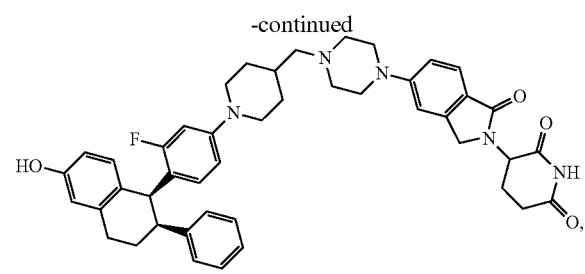
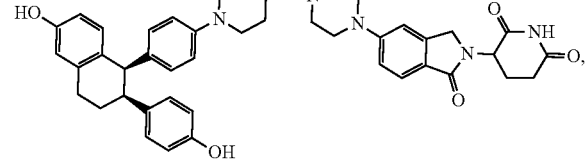
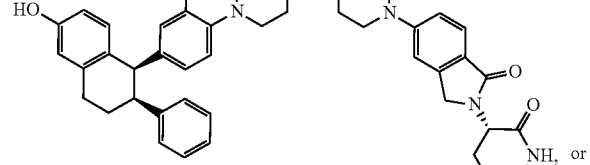
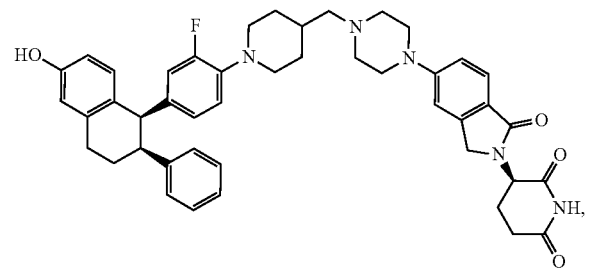
or a pharmaceutically acceptable salt, enantiomer, stereoisomer, isotopic derivative, or prodrug of any of the foregoing.
2. A compound having the structure:
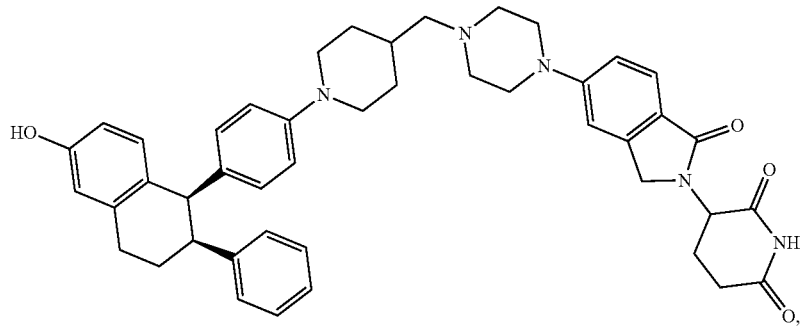 [SMILES: O=C1CCC(N2Cc3cc(N4CCN(CC5CCN(c6ccc([C@@H]7c8ccc(O)cc8CC[C@@H]7c7ccccc7)cc6)CC5)CC4)ccc3C2=O)C(=O)N1]
or a pharmaceutically acceptable salt, enantiomer, or stereoisomer thereof.

3. A compound having the structure:

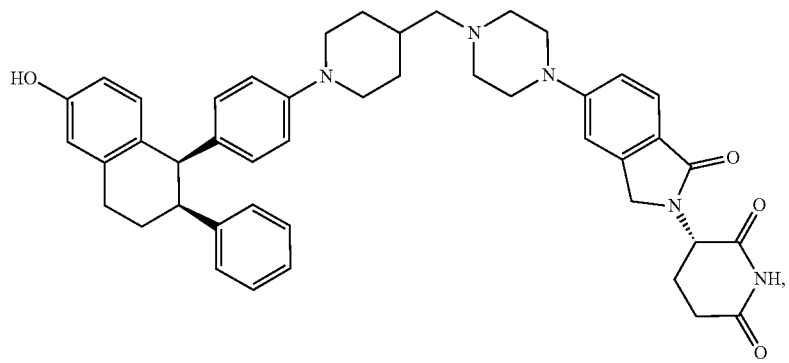 [SMILES: O=C1CC[C@H](N2Cc3cc(N4CCN(CC5CCN(c6ccc([C@@H]7c8ccc(O)cc8CC[C@@H]7c7ccccc7)cc6)CC5)CC4)ccc3C2=O)C(=O)N1]

or a pharmaceutically acceptable salt, enantiomer, or stereoisomer thereof.

4. A compound having the structure:

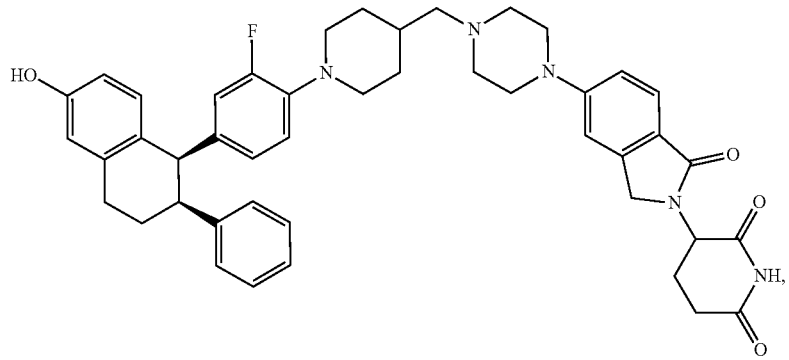 [SMILES: O=C1CCC(N2Cc3cc(N4CCN(CC5CCN(c6ccc([C@@H]7c8ccc(O)cc8CC[C@@H]7c7ccccc7)cc6F)CC5)CC4)ccc3C2=O)C(=O)N1]

or a pharmaceutically acceptable salt, enantiomer, or stereoisomer thereof.

5. A compound having the structure:

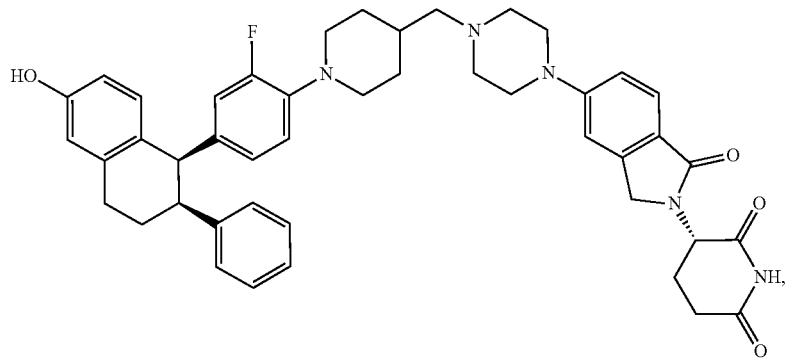 [SMILES: O=C1CC[C@H](N2Cc3cc(N4CCN(CC5CCN(c6ccc([C@@H]7c8ccc(O)cc8CC[C@@H]7c7ccccc7)cc6F)CC5)CC4)ccc3C2=O)C(=O)N1]

or a pharmaceutically acceptable salt, enantiomer, or stereoisomer thereof.

6. A pharmaceutical composition comprising a compound of claim 1 and a pharmaceutically acceptable carrier.

* * * * *